(12) United States Patent
Altmann et al.

(10) Patent No.: US 9,085,555 B2
(45) Date of Patent: Jul. 21, 2015

(54) COMPLEMENT PATHWAY MODULATORS AND USES THEREOF

(75) Inventors: Eva Altmann, Reinach (CH); Ulrich Hommel, Müllheim (DE); Edwige Liliane Jeanne Lorthiois, Niffer (FR); Juergen Klaus Maibaum, Weil-Haltingen (DE); Nils Ostermann, Binzen (DE); Jean Quancard, Huningue (FR); Stefan Andreas Randl, Frankfurt am Main (DE); Olivier Rogel, Hésingue (FR); Véronique Stark-Rogel, legal representative, Hésingue (FR); Oliver Simic, Basel (CH); Anna Vulpetti, Basel (CH)

(73) Assignee: NOVARTIS AG, Basel (CH)

(*) Notice: Subject to any disclaimer, the term of this patent is extended or adjusted under 35 U.S.C. 154(b) by 159 days.

(21) Appl. No.: 13/342,161

(22) Filed: Jan. 2, 2012

(65) Prior Publication Data

US 2012/0295884 A1 Nov. 22, 2012

Related U.S. Application Data

(60) Provisional application No. 61/429,730, filed on Jan. 4, 2011.

(51) Int. Cl.

| C07D 471/04 | (2006.01) |
|---|---|
| C07D 487/04 | (2006.01) |
| A61K 31/437 | (2006.01) |
| A61K 31/404 | (2006.01) |
| C07D 403/12 | (2006.01) |
| C07D 401/14 | (2006.01) |
| C07D 403/14 | (2006.01) |
| C07D 405/14 | (2006.01) |
| C07D 409/14 | (2006.01) |
| C07D 417/12 | (2006.01) |
| C07D 417/14 | (2006.01) |

(52) U.S. Cl.
CPC ............ *C07D 403/12* (2013.01); *A61K 31/404* (2013.01); *A61K 31/437* (2013.01); *C07D 401/14* (2013.01); *C07D 403/14* (2013.01); *C07D 405/14* (2013.01); *C07D 409/14* (2013.01); *C07D 417/12* (2013.01); *C07D 417/14* (2013.01); *C07D 471/04* (2013.01); *C07D 487/04* (2013.01)

(58) Field of Classification Search
CPC .............. C07D 487/04; C07D 471/04; A61K 31/4355; A61K 31/437
USPC .......... 546/113, 118, 119; 548/453, 454, 455, 548/465, 467, 494, 495, 500; 514/300, 303, 514/414
See application file for complete search history.

(56) References Cited

U.S. PATENT DOCUMENTS

| 5,596,000 A | 1/1997 | Esser |
|---|---|---|
| 5,872,135 A | 2/1999 | Desolms |
| 6,274,617 B1 | 8/2001 | Hamilton |
| 6,933,316 B2 | 8/2005 | Hsieh et al. |
| 7,417,063 B2 | 8/2008 | Smallheer et al. |
| 2001/0041733 A1 | 11/2001 | Hamilton |
| 2005/0107319 A1 | 5/2005 | Bansal |
| 2006/0020000 A1 | 1/2006 | Tynebor |
| 2008/0003214 A1 | 1/2008 | Cezanne et al. |

FOREIGN PATENT DOCUMENTS

| DE | 102004045796 | 3/2006 |
|---|---|---|
| EP | 0039051 A2 | 11/1981 |
| EP | 0394989 A2 | 10/1990 |
| FR | 2876692 A1 | 4/2006 |
| WO | 9320099 | 10/1993 |
| WO | 9610035 | 4/1996 |
| WO | 9639137 | 12/1996 |
| WO | 9962484 | 12/1999 |
| WO | 9962487 | 12/1999 |
| WO | 9962879 | 12/1999 |
| WO | 0009112 | 2/2000 |
| WO | 0226697 | 4/2002 |
| WO | 0232879 | 4/2002 |
| WO | 03045912 A1 | 6/2003 |
| WO | 2004034769 A1 | 4/2004 |
| WO | 2004045518 A2 | 6/2004 |
| WO | 2004062601 A2 | 7/2004 |

(Continued)

OTHER PUBLICATIONS

D. Morikis et. al. "Structural aspects and design of low-molecular-mass complement inhibitors" Biochemical Society Transactions (2002) vol. 30, part 6 1026-1036.*

Daniel Ricklin & John D Lambris "Complement-targeted therapeutics" Nature Biotechnology vol. 25 No. 11 Nov. 2007 1265-1275.*

*Primary Examiner* — David K O Dell
(74) *Attorney, Agent, or Firm* — John B. Alexander

(57) ABSTRACT

The present invention provides a compound of formula I:

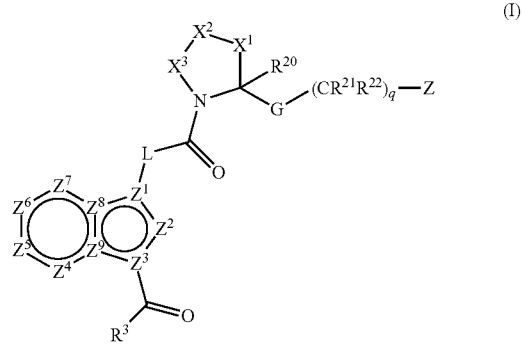

a method for manufacturing the compounds of the invention, and its therapeutic uses. The present invention further provides a combination of pharmacologically active agents and a pharmaceutical composition.

8 Claims, No Drawings

(56) References Cited

FOREIGN PATENT DOCUMENTS

| WO | 2004062607 A2 | 7/2004 |
| WO | 2004065367 A1 | 8/2004 |
| WO | 2004078163 A2 | 9/2004 |
| WO | 2004083174 A2 | 9/2004 |
| WO | 2004087646 A2 | 10/2004 |
| WO | 2005077417 A1 | 8/2005 |
| WO | 2006090192 A1 | 8/2006 |
| WO | 2006127550 A1 | 11/2006 |
| WO | 2006129199 A1 | 12/2006 |
| WO | 2007016589 A2 | 2/2007 |
| WO | 2007044668 A2 | 4/2007 |
| WO | 2007070600 A2 | 6/2007 |
| WO | 2007103549 A2 | 9/2007 |
| WO | 2008036967 A2 | 3/2008 |
| WO | 2008055206 A2 | 5/2008 |
| WO | WO 2008/064218 A2 | 5/2008 |
| WO | 2008132153 | 11/2008 |
| WO | 2008147883 A1 | 12/2008 |
| WO | 2009/106980 A2 | 9/2009 |
| WO | 2010/020675 A1 | 2/2010 |
| WO | WO 2011/082077 A1 | 7/2011 |

* cited by examiner

COMPLEMENT PATHWAY MODULATORS AND USES THEREOF

This application is a U.S. Utility Patent Application which claims priority to U.S. Provisional Application Ser. No. 61/429,730, filed 4 Jan. 2011, the contents of which are incorporated herein by reference in their entirety.

FIELD OF THE INVENTION

The invention relates to the inhibition of the complement alternative pathway and particularly to inhibition of Factor D, in patients suffering from conditions and diseases associated withTo complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor D may be a suitable target for the inhibition of this amplification of the complement pathways because its plasma concentration in humans is very low (about 1.8 µg/mL), and it has been shown to be the limiting enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganlion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H(CFH) (Edwards A O, et al. Complement factor H polymorphism and age-related macular degeneration. Science. 2005 Apr. 15; 308(5720):421-4; Hageman G S, et al A common haplotype in the complement regulatory gene factor H(HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol V is Sci. 2006 August; 47(8): 3242-6; Simonelli F, et al. Polymorphism p. 402Y>H in the complement factor H protein is a risk factor for age related macular degeneration in an Italian population. Br J Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement C2 (Gold B, et al. Variation in factor B (BF) and complement component 2 (C2) genes is associated with age-related macular degeneration. Nat Genet. 2006 April; 38(4):458-62 and Jakobsdottir J, et al. C2 and CFB genes inage-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Mailer J B, et al Variation in complement factor 3 is associated with risk of age-related macular degeneration. Nat Genet. 2007 October; 39(10):1200-1 and Park K H, et al Complement component 3 (C3) haplotypes and risk of advanced age-related macular degeneration. Invest Ophthalmol V is Sci. 2009 July; 50(7): 3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation the alternative complement pathway. In certain embodiments, the present invention provides compounds that modulate, and preferably inhibit, Factor D activity and/or Factor D mediated complement pathway activation. Such Factor D modulators are preferably high affinity Factor D inhibitors that inhibit the catalytic activity of complement Factor D, such as primate Factor D and particularly human Factor D.

The compounds of the present invention inhibit or suppress the amplification of the complement system caused by C3 activation irrespective of the initial mechanism of activation (including for example activation of the classical, lectin or ficolin pathways).

Various embodiments of the invention are described herein. It will be recognized that features specified in each embodiment may be combined with other specified features to provide further embodiments.

Within certain aspects, Factor D modulators provided herein are compounds of Formula I and salts thereof:

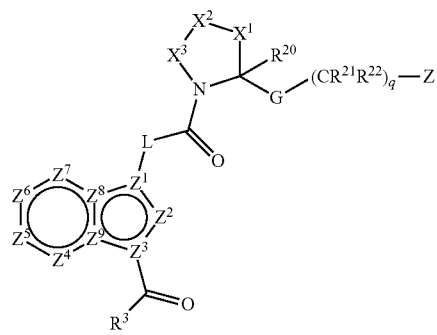

Within certain other aspects, Factor D modulators provided herein are compounds of Formula VII and salts thereof:

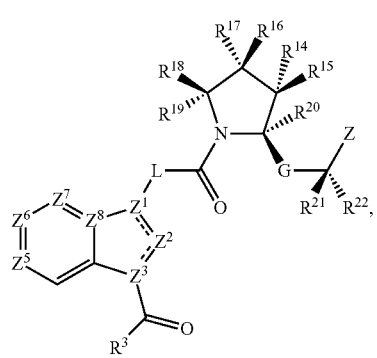

(VII)

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more therapeutically active.

The invention further provides methods of treating or preventing complement mediated diseases, the method comprising the steps of identifying a patient in need of complement modulation therapy and administering a compound of Formula (I) or a subformulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

DETAILED DESCRIPTION OF THE INVENTION

As noted above, the present invention provides compounds that modulate Factor D activation and/or Factor D-mediated signal transduction of the complement system. Such compounds may be used in vitro or in vivo to modulate (preferably inhibit) Factor D activity in a variety of contexts.

In a first embodiment, the invention provides compounds of Formula I and pharmaceutically acceptable salts thereof, which modulate the alternative pathway of the complement system. Compounds of Formula I are represented by the structure:

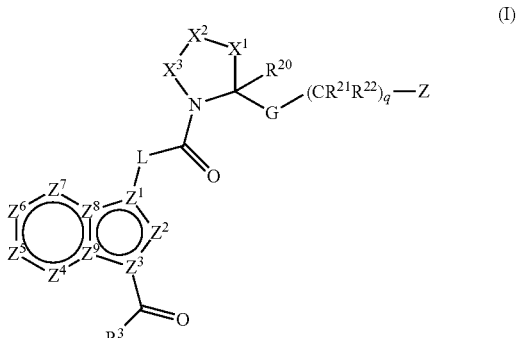

(I)

or a pharmaceutically acceptable salt thereof, wherein
$Z^1$ is C and L is a divalent residue selected from the group consisting of —N(H)— and —C(H)($R^1$)—, or
$Z^1$ is N and L is $CH_2$;
$R^1$ is hydrogen, hydroxy, or amino;
$Z^2$ is C($R^2$) or N;
$Z^3$ is C or N,
$Z^4$ is C($R^4$) or N;
$Z^5$ is C($R^5$) or N, or an N-oxide thereof;
$Z^6$ is C($R^6$) or N, or an N-oxide thereof;
$Z^7$ is C($R^7$) or N, or an N-oxide thereof;
$Z^8$ is C or N;
$Z^9$ is C or N;
wherein one of $Z^1$, $Z^3$, $Z^8$ and $Z^9$ is N and three of $Z^1$, $Z^3$, $Z^8$ and $Z^9$ are C;
wherein 0, 1, or 2 or 3 of $Z^2$, $Z^4$, $Z^5$, $Z^6$ and $Z^7$ are N;

$R^2$ is hydrogen or $C_1$-$C_6$alkyl;

$R^3$ is selected from the group consisting of hydrogen, $C_1$-$C_4$alkyl, hydroxy$C_1$-$C_4$alkyl, $C_1$-$C_4$alkoxy$C_1$-$C_4$alkyl, halo$C_1$-$C_4$alkyl, amino or methylamino;

$R^4$ is selected from the group consisting of hydrogen, halogen, and $C_1$-$C_6$alkyl;

$R^5$ and $R^6$ are independently selected from the group consisting of hydrogen, halogen, hydroxy, $NR^8R^9$, cyano, $CO_2H$, $CONR^{10}R^{11}$ $SO_2C_1$-$C_6$alkyl, and $SO_2NH_2$, $SO_2NR^{10}R^{11}$, $C_1$-$C_6$alkoxycarbonyl, —$C(NR^{10})NR^8R^9$, $C_1$-$C_6$alkyl, halo$C_1$-$C_6$alkyl, $C_2$-$C_6$alkenyl, $C_1$-$C_6$alkoxy, halo$C_1$-$C_6$alkoxy, $C_2$-$C_6$alkenyloxy, wherein each alkyl, alkenyl, alkoxy and alkenyloxy is unsubstituted or substituted with up to 4 substituents independently selected from halogen, hydroxy, tetrazole, $C_1$-$C_4$alkoxy, $C_1$-$C_4$haloalkoxy, $CO_2H$, $C_1$-$C_6$alkoxycarbonyl, $C(O)NR^{10}R^{11}$, $NR^8R^9$, optionally substituted phenyl, heterocycle having 4 to 7 ring atoms and 1, 2, or 3 ring heteroatoms selected from N, O or S, heteroaryl having 5 or 6 ring atoms and 1 or 2 ring heteroatoms selected from N, O or S, and wherein optional phenyl substituents are selected from halogen, hydroxy, $C_1$-$C_4$alkyl, $C_1$-$C_4$alkoxy and $CO_2H$;

$R^5$ and $R^{6,}$ taken in combination with the atoms to which they are attached, form a cycle having 4 to 7 ring atoms and 0, 1 or 2 additional ring N, O or S atoms;

$R^7$ is selected from the group consisting of hydrogen, halogen, $C_1$-$C_6$alkyl, $C_1$-$C_6$alkoxy, haloC-$C_6$alkyl, haloC-$C_6$alkoxy $C_1$-$C_6$alkoxycarbonyl, $CO_2H$ and $C(O)NR^{10}R^{11}$;

$R^8$ and $R^9$ are independently selected from the group consisting of hydrogen, and $C_1$-$C_6$alkyl, halo$C_1$-$C_6$alkyl, $C_1$-$C_6$alkoxy$C_1$-$C_6$alkyl, hydroxy$C_1$-$C_6$alkyl, or $NR^8R^9$, taken in combination, form a heterocycle having 4 to 7 ring atoms and 0 or 1 additional ring N, O or S atoms, which heterocycle is substituted with 0, 1, or 2 substituents independently selected from the group consisting of $C_1$-$C_4$alkyl, halogen, hydroxy, $C_1$-$C_4$alkoxy;

$R^{10}$ and $R^{11}$, are each independently selected from the group consisting of hydrogen and $C_1$-$C_6$alkyl, halo$C_1$-$C_6$alkyl, $C_1$-$C_6$alkoxy$C_1$-$C_6$alkyl, or hydroxy$C_1$-$C_6$alkyl;

$X^1$ is $CR^{14}R^{15}$ or sulfur;

$X^2$ is $CR^{16}R^{17}$, oxygen sulfur, N(H) or N($C_1$-$C_6$alkyl), wherein at least one of $X^1$ and $X^2$ is carbon; or $X^1$ and $X^2$, in combination, forms an olefin of the formula —$C(R^{16})$=$C(H)$— or —$C(R^{16})$=$C(C_1$-$C_4$alkyl)-, wherein the $C(R^{16})$ is attached to $X^3$;

$X^3$ is $(CR^{18}R^{19})$, or N(H) wherein m is 0, 1 or 2, wherein $X^3$ is $CR^{18}R^{19}$ or $(CR^{18}R^{19})_2$ when either $X^1$ or $X^2$ is sulfur or $X^2$ is oxygen; or $X^2$ and $X^3$, taken in combination, are —N=C(H)— or —N=C($C_1$-$C_4$alkyl)- in which the C(H) or C($C_1$-$C_4$alkyl) is attached to $X^1$;

$R^{14}$ is selected from the group consisting of hydrogen, halogen, hydroxy, amino and $C_1$-$C_6$alkyl;

$R^{15}$ is selected from the group consisting of hydrogen, hydroxy, halogen, $C_1$-$C_6$alkyl, halo$C_1$-$C_6$alkyl, $C_2$-$C_6$alkenyl, $C_2$-$C_6$alkynyl, $C_1$-$C_6$alkoxy, halo$C_1$-$C_6$alkoxy, $NR^8R^9$, N(H)C(O)$C_1$-$C_6$alkyl, N(H)C(O)OC$_1$-$C_6$alkyl and $OC(O)NR^{10}R^{11}$ each of alkyl, alkoxy, alkenyl, and alkynyl substituents may be substituted with 0, 1, or 2 groups independently selected at each occurrence from the group consisting of halogen, hydroxy, $C_1$-$C_6$alkyl, $C_1$-$C_6$alkoxy, and $NR^8R^9$;

$R^{16}$ is hydrogen, halogen, hydroxy, azide, cyano, COOH, $C_1$-$C_6$alkoxycarbonyl, $C_1$-$C_6$alkyl, $C_1$-$C_6$alkoxy, $C_1$-$C_6$haloalkyl, $C_1$-$C_6$haloalkoxy, $NR^8R^9$, N(H)C(O)$C_1$-$C_6$alkyl, hydroxy$C_1$-$C_6$alkyl, $C_1$-$C_6$alkoxy$C_1$-$C_6$alkyl, or $C_1$-$C_6$alkyl substituted with $NR^8R^9$, N(H)C(O)H or N(H)C(O)($C_1$-$C_4$alkyl);

$R^{17}$ is hydrogen, halogen, hydroxy, cyano, $C_1$-$C_6$alkyl, $C_1$-$C_6$alkoxy, hydroxy$C_1$-$C_6$alkyl, $C_1$-$C_6$alkoxy$C_1$-$C_6$alkyl, halo$C_1$-$C_6$alkyl, or $C_1$-$C_6$haloalkoxy;

$R^{18}$ is selected from the group consisting of hydrogen, phenyl and $C_1$-$C_6$alkyl, which alkyl group is unsubstituted or substituted with hydroxy, amino, azide, and $NHC(O)C_1$-$C_6$alkyl;

$R^{19}$ and $R^{20}$ are each independently selected from hydrogen and $C_1$-$C_6$alkyl; or $CR^{16}R^{17}$, taken in combination forms a spirocyclic 3 to 6 membered carbocycle which is substituted with 0, 1, or 2 substituents independently selected from the group consisting of halogen and methyl; or $R^{16}$ and $R^{17}$, taken in combination, form an exocyclic methylidene (=$CH_2$);

$R^{15}$ and $R^{16}$ taken in combination form an epoxide ring or a 3 to 6 membered carbocyclic ring system which carbocyclic ring is substituted with 0, 1, or 2 substituents independently selected from the group consisting of halogen, methyl, ethyl, hydroxy$C_1$-$C_4$alkyl, $C_1$-$C_6$alkoxy$C_1$-$C_4$alkyl, $C_1$-$C_4$alkoxycarbonyl, $CO_2H$, and $C_1$-$C_4$alkyl substituted with $NR^8R^9$; or $R^{16}$ and $R^{18}$ or $R^{17}$ and $R^{19}$, taken in combination, form a fused 3 membered carbocyclic ring system which is substituted with 0, 1, or 2 substituents independently selected from the group consisting of halogen, methyl, ethyl, hydroxy$C_1$-$C_4$alkyl, $C_1$-$C_6$alkoxy$C_1$-$C_4$alkyl, $C_1$-$C_4$alkoxycarbonyl, $CO_2H$, and $C_1$-$C_4$alkyl substituted with $NR^8R^9$; or $R^{14}$ and $R^{20}$ taken in combination form a fused 3 carbocyclic ring system;

$R^{14}$ and $R^{19}$ taken in combination form a form 1 to 3 carbon alkylene linker;

$R^{17}$ and $R^{20}$ taken in combination form 1 to 3 carbon alkylene linker;

G is a divalent residue selected from C(O)—N(H), $CH_2$—N(H)—$S(O)_2$—, $CH_2$—N(H)—C(O), $CH_2$—N(H)—C(O)—O, $CH_2N(H)$, $CH_2$—N(H)—C(O)—N(H), $CH_2$—N(H)—C(O)—N(Me), $CH_2N(H)$—$S(O)_2$—N(H)—, and $CH_2N(H)$—$S(O)_2$—N(Me)—, wherein the right most residue is attached to —$(CR^{21}R^{22})_q$;

q is 0, 1, 2, 3 or 4;

$R^{21}$ is independently selected at each occurrence from the group consisting of hydrogen, hydroxy, halogen, $C_1$-$C_6$alkyl, halo$C_1$-$C_6$alkyl, phenyl, $CO_2H$, $C_1$-$C_6$alkoxy carbonyl, C(O)NH$_2$, hydroxy$C_1$-$C_6$alkyl, $C_1$-$C_6$alkoxy$C_1$-$C_6$alkyl, $C_1$-$C_6$alkyl substituted with $NR^8R^9$, imidazoyl$C_1$-$C_6$alkyl heterocycle$C_1$-$C_6$alkyl, where the heterocycle is selected from azetidinyl, pyrrolidinyl, piperidinyl, morpholinyl, 1-oxa-6-aza-spiro[3.3]heptane, 2-oxa-6-aza-spiro[3.3]heptane, piperazinyl, 1,6-diaza-spiro[3.3]heptane, and 2,6-diaza-spiro[3.3]heptane each of which is optionally substituted by 1 or 2 substituent selected from fluoro, hydroxy, $C_1$-$C_4$alkyl or $C_1$-$C_4$alkoxy;

$R^{22}$ is independently selected at each occurrence from hydrogen or $C_1$-$C_6$alkyl; or when q is 1, 2, 3 or 4, $R^{21}$ and a $R^{22}$ substituent, taken in combination with the carbon atoms to which they are attached, form a 3 to 6 membered carbocycle or 4 to 6 membered heterocyle having a ring oxygen or nitrogen; or when q is 2, 3 or 4, two $R^{21}$ or $R^{22}$ residues, located on adjacent carbon atoms, form, together with the carbon atoms to which they are attached, a 3 to 6 membered carbocycle; and Z is $C_1$-$C_6$alkyl, $C_1$-$C_6$haloalkyl, phenyl, phenoxy, naphthyl, naphthyloxy, $C_3$-$C_7$cycloalkyl, indanyl, a 5, 6, 9 or 10 membered saturated or partially unsaturated, monocyclic or bicyclic heterocycle having 1, 2, or 3 ring heteroatoms selected from N, O, or S, or a 5 or 6 membered heteroaryl or heteroaryloxy, which heteroaryl has 1 or 2 ring heteroatoms selected from N, O or S provided that the ring does not have 2 O or S atoms, each residue is unsubstituted or substituted with 1, 2, 3, or 4 substituents which are independently selected from the group consisting of substituted or unsubstituted $C_1$-$C_6$alkyl, $C_1$-$C_6$haloalkyl, halogen, CN, hydroxy, $CO_2H$, tetrazolyl, $C(O)R^{25}$, $S(O)_2R^{26}$, substituted or unsubstituted $C_1$-$C_6$alkoxy, halo$C_1$-$C_6$alkoxy, phenoxy, $NR^{23}R^{24}$, $CH_2NR^{23}R^{24}$, 5 or 6 membered heteroaryl and unsubstituted or substituted phenyl, which substituted phenyl has 1 or 2 substituents independently selected from the group consisting of cyano, halo, $C_1$-$C_6$alkyl or $C_1$-$C_6$haloalkyl, OH, COOH, $COR^{25}$, $S(O)_2R^{26}$, amino, and $CH_2NH_2$, and which substituted alkyl or alkoxy has a substituent selected from hydroxy, $C_1$-$C_4$alkoxy, cyano, $CO_2H$, tetrazole or $NR^{23}R^{24}$;

$R^{23}$ is hydrogen or $C_1$-$C_6$alkyl;

$R^{24}$ is hydrogen, $C_1$-$C_6$alkyl, hydroxy$C_1$-$C_6$alkyl, $C_1$-$C_6$alkoxy$C_1$-$C_6$alkyl, amino$C_1$-$C_6$alkyl, mono- and di-$C_1$-$C_6$alkylamino$C_1$-$C_6$alkyl; or $NR^{23}R^{24}$, taken in combination form a 4, 5 or 6 membered heterocycle having 0 or 1 additional ring heteroatoms selected from the group consisting of N, O or S, and which is substituted with 0, 1 or 2 substituents independently selected from fluoro, hydroxy, $C_1$-$C_4$alkyl or $C_1$-$C_4$alkoxy;

$R^{25}$ is independently selected at each occurrence from the group consisting of $C_1$-$C_6$alkoxy and $NR^{23}R^{24}$; and $R^{26}$ is selected from the group consisting of amino, hydroxy, $C_1$-$C_6$alkyl, and, mono- and di-$C_1$-$C_6$alkylamino.

In certain aspects, the compounds of formula (I) preferably have the stereochemistry of compounds represented by formula (Ia):

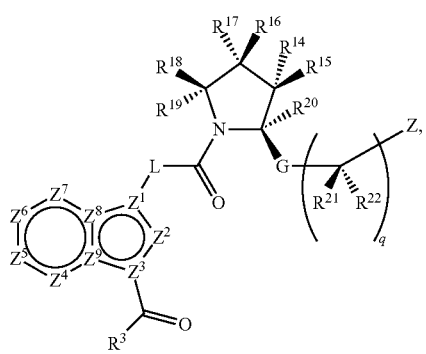

(Ia)

In one aspect, compounds of formula (I) include those compounds represented by formula (II):

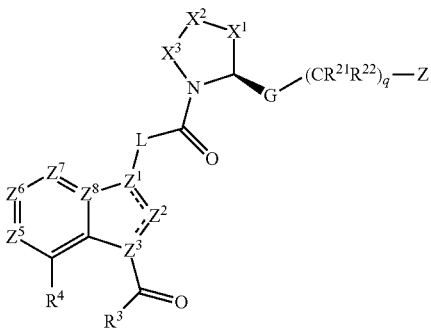

(II)

wherein:
$Z^2$ is CH or N;
$X^1$ is $CHR^{15}$ or S;

$X^2$ is $CR^{16}R^{17}$ or S, wherein at least one of $X^1$ and $X^2$ is not sulfur;

$X^3$ is $CR^{18}R^{19}$ or N(H);

$R^{15}$ is selected from the group consisting of hydrogen, hydroxy, halogen, $C_1$-$C_6$alkyl, halo$C_1$-$C_6$alkyl, $C_1$-$C_6$alkoxy, halo$C_1$-$C_6$alkoxy, $NR^8R^9$, $N(H)C(O)C_1$-$C_4$alkyl, $N(H)C(O)OC_1$-$C_4$alkyl and $OC(O)NR^{10}R^{11}$, each alkyl and alkoxy may be substituted with 0, 1, or 2 groups independently selected at each occurrence from the group consisting of hydroxy, $C_1$-$C_6$alkyl, $C_1$-$C_6$alkoxy, and $NR^8R^9$;

$R^{16}$ is hydrogen, halogen, hydroxy, amino, cyano, $C_1$-$C_4$alkyl, $C_1$-$C_4$alkoxy, $C_1$-$C_4$haloalkyl, $C_1$-$C_4$haloalkoxy, heterocycle$C_0$-$C_4$alkyl, $NR^8R^9$, $N(H)C(O)C_1$-$C_4$ alkyl, hydroxy$C_1$-$C_4$alkyl, $C_1$-$C_4$alkoxy$C_1$-$C_4$alkyl or $C_1$-$C_4$alkyl substituted with $NR^8R^9$;

$R^{17}$ is hydrogen, halogen, hydroxy, $C_1$-$C_4$alkyl, hydroxy$C_1$-$C_4$alkyl or $C_1$-$C_2$alkoxy$C_1$-$C_4$alkyl;

$R^{18}$ is selected from the group consisting of hydrogen, phenyl and $C_1$-$C_6$alkyl, which alkyl group is unsubstituted or substituted with hydroxy, amino, $NHC(O)C_1$-$C_6$alkyl, amide or mono- or di-$C_1$-$C_4$alkyl-amide;

$R^{19}$ is hydrogen; or $CR^{16}R^{17}$, taken in combination, forms a spirocyclic 3 to 6 membered carbocycle; or $R^{15}$ and $R^{16}$, taken in combination, form a cyclopropyl ring which is substituted with 0, 1, or 2 substituents independently selected from the group consisting of halogen, methyl, ethyl, hydroxymethyl, hydroxyethyl, methoxymethyl; or $R^{17}$ and $R^{19}$ taken in combination form a cyclopropyl ring.

In another embodiment, the invention provides compounds of Formula (VII):

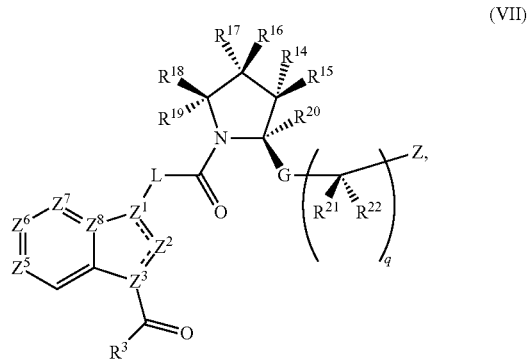

(VII)

or a pharmaceutically acceptable salt thereof, wherein
L is a divalent residue selected from the group consisting of —N(H)— and —C(H)($R^1$)—,
$R^1$ is hydrogen, hydroxy, or amino;
$Z^1$ is C or N;
$Z^2$ is C(H) or N;
$Z^3$ is C or N,
$Z^5$ is C($R^5$), N or an N oxide thereof;
$Z^6$ is C($R^6$), N or an N oxide thereof;
$Z^7$ is C($R^7$), N or an N oxide thereof;
$Z^8$ is C or N
wherein one of $Z^1$ and $Z^3$ is N and the other is C;
wherein 0, 1, 2 or 3 of $Z^2$, $Z^5$, $Z^6$, $Z^7$ and $Z^8$ are N;
$R^3$ is selected from the group consisting of hydrogen, $C_1$-$C_4$alkyl, hydroxy$C_1$-$C_4$alkyl, $C_1$-$C_4$alkoxy$C_1$-$C_4$alkyl, halo$C_1$-$C_4$alkyl, amino or methylamino;
$R^5$ and $R^6$ are independently selected from the group consisting of hydrogen, halogen, hydroxy, $NR^8R^9$, cyano, $CO_2H$, CONR$^{10}$R$^{11}$SO$_2$C$_1$-C$_6$alkyl, and SO$_2$NR$^{10}$R$^{11}$, C$_1$-C$_6$alkoxycarbonyl, C(NR$^8$)NR$^8$R$^9$, C$_1$-C$_6$alkyl, haloC$_1$-C$_6$alkyl, C$_2$-C$_6$alkenyl, C$_1$-C$_6$alkoxy, haloC$_1$-C$_6$alkoxy, C$_2$-C$_6$alkenyloxy, wherein each alkyl, alkenyl, alkoxy and alkenyloxy is unsubstituted or substituted with up to 4 substituents independently selected from halogen, hydroxy, tetrazole, C$_1$-C$_4$alkoxy, C$_1$-C$_4$haloalkoxy, CO$_2$H, C$_1$-C$_6$alkoxycarbonyl, C(O)NR$^{10}$R$^{11}$, NR$^8$R$^9$ optionally substituted phenyl, heterocycle having 4 to 7 ring atoms and 1, 2, or 3 ring heteroatoms selected from N, O or S, heteroaryl having 5 or 6 ring atoms and 1 or 2 ring heteroatoms selected from N, O or S, and wherein optional phenyl substituents are selected from halogen, hydroxy, C$_1$-C$_4$alkyl, C$_1$-C$_4$alkoxy and CO$_2$H;

R$^5$ and R$^{6'}$ taken in combination with the atoms to which they are attached, form a cycle having 4 to 7 ring atoms and 0 or 1 additional ring N, O or S atoms;

R$^7$ is selected from the group consisting of hydrogen, halogen, C$_1$-C$_6$alkyl, C$_1$-C$_6$alkoxy, haloC-C$_6$alkyl, haloC-C$_6$alkoxy C$_1$-C$_6$alkoxycarbonyl, CO$_2$H and C(O)NR$^{10}$R$^{11}$;

R$^8$ and R$^9$ are independently selected from the group consisting of hydrogen, and C$_1$-C$_6$alkyl, haloC$_1$-C$_6$alkyl, C$_1$-C$_6$alkoxyC$_1$-C$_6$alkyl, hydroxyC$_1$-C$_6$alkyl, or NR$^8$R$^9$, taken in combination, form a heterocycle having 4 to 7 ring atoms and 0 or 1 additional ring N, O or S atoms, which heterocycle is substituted with 0, 1, or 2 substituents independently selected from the group consisting of C$_1$-C$_4$alkyl, halogen, hydroxy, C$_1$-C$_4$alkoxy;

R$^8$ and R$^9$ are independently selected from the group consisting of hydrogen, and C$_1$-C$_6$alkyl, haloC$_1$-C$_6$alkyl, C$_1$-C$_6$alkoxyC$_1$-C$_6$alkyl, hydroxyC$_1$-C$_6$alkyl, or NR$^8$R$^9$, taken in combination, form a heterocycle having 4 to 7 ring atoms and 0 or 1 additional ring N, O or S atoms, which heterocycle is substituted with 0, 1, or 2 substituents independently selected from the group consisting of C$_1$-C$_4$alkyl, halogen, hydroxy, C$_1$-C$_4$alkoxy;

R$^{10}$ and R$^{11}$, are each independently selected from the group consisting of hydrogen and C$_1$-C$_6$alkyl, haloC$_1$-C$_6$alkyl, C$_1$-C$_6$alkoxyC$_1$-C$_6$alkyl, or hydroxyC$_1$-C$_6$alkyl;

R$^{14}$ is selected from the group consisting of hydrogen, halogen, hydroxy, amino and C$_1$-C$_6$alkyl;

R$^{15}$ is selected from the group consisting of hydrogen, hydroxy, halogen, C$_1$-C$_6$alkyl, haloC$_1$-C$_6$alkyl, C$_2$-C$_6$alkenyl, C$_2$-C$_6$alkynyl, C$_1$-C$_6$alkoxy, haloC$_1$-C$_6$alkoxy, NR$^8$R$^9$, N(H)C(O)C$_1$-C$_6$alkyl, N(H)C(O)OC$_1$-C$_6$alkyl and OC(O)NR$^{10}$R$^{11}$ each of alkyl, alkoxy, alkenyl, and alkynyl substituents may be substituted with 0, 1, or 2)groups independently selected at each occurrence from the group consisting of halogen, hydroxy, C$_1$-C$_6$alkyl, C$_1$-C$_6$alkoxy, and NR$^{10}$R$^{11}$;

R$^{16}$ is hydrogen, halogen, hydroxy, azide, cyano, COOH, C$_1$-C$_6$alkoxycarbonyl, C$_6$alkyl, C$_1$-C$_6$alkoxy, C$_1$-C$_6$haloalkyl, C$_1$-C$_6$haloalkoxy, NR$^8$R$^9$, N(H)C(O)C$_1$-C$_6$alkyl, hydroxyC$_1$-C$_6$alkyl, C$_1$-C$_6$alkoxyC$_1$-C$_6$alkyl, or C$_1$-C$_6$alkyl substituted with NR$^8$R$^9$, N(H)C(O)H or N(H)C(O)(C$_1$-C$_4$alkyl);

R$^{17}$ is hydrogen, halogen, hydroxy, C$_1$-C$_6$alkyl, C$_1$-C$_4$alkoxy, hydroxyC$_1$-C$_6$alkyl, C$_1$-C$_6$alkoxyC$_1$-C$_6$alkyl, or C$_1$-C$_6$haloalkoxy;

R$^{18}$ is selected from the group consisting of hydrogen, phenyl and C$_1$-C$_6$alkyl, which alkyl group is unsubstituted or substituted with hydroxy, amino, azide, and NHC(O)C$_1$-C$_6$alkyl;

R$^{19}$ and R$^{20}$ are each independently selected from hydrogen and C$_1$-C$_6$alkyl; or CR$^{16}$R$^{17}$, taken in combination, form a spirocyclic 3 to 6 membered carbocycle which is substituted with 0, 1, or 2 substituents independently selected from the group consisting of halogen and methyl; or R$^{16}$ and R$^{17}$, taken in combination, form an exocyclic methylidene (=CH$_2$);

R$^{15}$ and R$^{16}$ or R$^{14}$ and R$^{17}$ taken in combination form an epoxide ring or a 3 to 6 membered carbocyclic ring system which carbocyclic ring is substituted with 0, 1, or 2 substituents independently selected from the group consisting of halogen, methyl, ethyl, hydroxyC$_1$-C$_4$alkyl, C$_1$-C$_6$alkoxyC$_1$-C$_4$alkyl, C$_1$-C$_4$alkoxycarbonyl, CO$_2$H, and C$_1$-C$_4$alkyl substituted with NR$^8$R$^9$; or R$^{17}$ and R$^{19}$ or R$^{16}$ and R$^{18}$, taken in combination, form a fused 3 membered carbocyclic ring system which is substituted with 0, 1, or 2 substituents independently selected from the group consisting of halogen, methyl, ethyl, hydroxyC$_1$-C$_4$alkyl, C$_1$-C$_4$alkoxycarbonyl, CO$_2$H, and C$_1$-C$_4$alkyl substituted with NH$^8$R$^9$; or R$^{14}$ and R$^{20}$ taken in combination form a fused 3 carbocyclic ring system;

R$^{14}$ and R$^{19}$, taken in combination, form a 1 to 3 carbon alkylene linker; or R$^{17}$ and R$^{20}$, taken in combination, form a 1 to 3 carbon alkylene linker;

G is a divalent residue selected from C(O)—N(H), CH$_2$—N(H)—S(O)$_2$—, CH$_2$—N(H)—C(O), CH$_2$—N(H)—C(O)—O, CH$_2$N(H), CH$_2$—N(H)—C(O)—N(H), CH$_2$—N(H)—C(O)—N(Me), CH$_2$N(H)—S(O)$_2$—N(H)—, and CH$_2$N(H)—S(O)$_2$—N(Me)—, wherein the right most residue is attached to —(CR$^{21}$R$^{22}$)$_q$;

q is 0, 1, 2, 3 or 4;

R$^{21}$ is independently selected at each occurrence from the group consisting of hydrogen, hydroxy, halogen, C$_1$-C$_6$alkyl, haloC$_1$-C$_6$alkyl, phenyl, CO$_2$H, C$_1$-C$_6$alkoxy carbonyl, C(O)NH$_2$, hydroxyC$_1$-C$_6$alkyl, C$_1$-C$_6$alkoxyC$_1$-C$_6$alkyl, C$_1$-C$_6$alkyl substituted with NR$^8$R$^9$, imidazoylC$_1$-C$_6$alkyl heterocycleC$_1$-C$_6$alkyl, where the heterocycle is selected from azetidinyl, pyrrolidinyl, piperidinyl, morpholinyl, 1-oxa-6-aza-spiro[3.3]heptane, 2-oxa-6-aza-spiro[3.3]heptane, piperazinyl, 1,6-diaza-spiro[3.3]heptane, and 2,6-diaza-spiro[3.3]heptane each of which is optionally substituted by 1 or 2 substituent selected from fluoro, hydroxy, C$_1$-C$_4$alkyl or C$_1$-C$_4$alkoxy;

R$^{22}$ is independently selected at each occurrence from hydrogen or C$_1$-C$_6$alkyl; or when q is 1, 2, 3 or 4, R$^{21}$ and a R$^{22}$ substituent, taken in combination with the carbon atoms to which they are attached, form a 3 to 6 membered carbocycle or 4 to 6 membered heterocyle having a ring oxygen or nitrogen; or when q is 2, 3 or 4, two R$^{21}$ or R$^{22}$ residues, located on adjacent carbon atoms, form, together with the carbon atoms to which they are attached, a 3 to 6 membered carbocycle; and Z is C$_1$-C$_6$alkyl, C$_1$-C$_6$haloalkyl, phenyl, phenoxy, naphthyl, naphthyloxy, C$_3$-C$_7$cycloalkyl, indanyl, a 5, 6, 9 or 10 membered saturated or partially unsaturated, monocyclic or bicyclic heterocycle having 1, 2, or 3 ring heteroatoms selected from N, O, or S, or a 5 or 6 membered heteroaryl or heteroaryloxy, which heteroaryl has 1 or 2 ring heteroatoms selected from N, O or S provided that the ring does not have 2 O or S atoms, each residue is unsubstituted or substituted with 1, 2, 3, or 4 substituents which are independently selected from the group consisting of substituted or unsubstituted C$_1$-C$_6$alkyl, C$_1$-C$_6$haloalkyl, halogen, CN, hydroxy, CO$_2$H, tetrazolyl, C(O)R$^{25}$, S(O)$_2$R$^{26}$, substituted or unsubstituted C$_1$-C$_6$alkoxy, haloC$_1$-C$_6$alkoxy, phenoxy, NR$^{23}$R$^{24}$, CH$_2$NR$^{23}$R$^{24}$, 5 or 6 membered heteroaryl and unsubstituted or substituted phenyl, which substituted phenyl has 1 or 2 substituents independently selected from the group consisting of cyano, halo, $C_1$-$C_6$alkyl or $C_1$-$C_6$haloalkyl, OH, COOH, $COR^{26}$, $S(O)_2R^{26}$, amino, and $CH_2NH_2$, and which substituted alkyl or alkoxy has a substituent selected from hydroxy, $C_1$-$C_4$alkoxy, cyano, $CO_2H$, tetrazole or $NR^{23}R^{24}$;

$R^{23}$ is hydrogen or $C_1$-$C_6$alkyl;

$R^{24}$ is hydrogen, $C_1$-$C_6$alkyl, hydroxy$C_1$-$C_6$alkyl, $C_1$-$C_6$alkoxy$C_1$-$C_6$alkyl, amino$C_1$-$C_6$alkyl, mono- and di-$C_1$-$C_6$alkylamino$C_1$-$C_6$alkyl; or $NR^{23}R^{24}$, taken in combination form a 4, 5 or 6 membered heterocycle having 0 or 1 additional ring heteroatoms selected from the group consisting of N, O or S, and which is substituted with 0, 1 or 2 substituents independently selected from fluoro, hydroxy, $C_1$-$C_4$alkyl or $C_1$-$C_4$alkoxy;

$R^{25}$ is independently selected at each occurrence from the group consisting of $C_1$-$C_6$alkoxy and $NR^{23}R^{24}$; and $R^{26}$ is selected from the group consisting of amino, hydroxy, $C_1$-$C_6$alkyl, and, mono- and di-$C_1$-$C_6$alkylamino.

In another aspect, compounds of formula (I) or (II) are provided in which $X^1$ is $CHR^{15}$; and $R^{15}$ is hydrogen, fluoro, hydroxy, amino, $C_1$-$C_4$alkyl, $C_1$-$C_6$alkoxy, $OCH_2CH_2OMe$, or $C_2$-$C_4$alkoxy substituted with $NR^8R^9$;

$X^2$ is $CR^{16}R^{17}$;

$R^{16}$ is hydrogen, halogen, hydroxy, $C_1$-$C_4$alkyl, $C_1$-$C_4$alkoxy, $C_1$-$C_4$haloalkyl, $C_1$-$C_4$haloalkoxy, $NR^8R^9$, hydroxy$C_1$-$C_4$alkyl, $C_1$-$C_4$alkoxy$C_1$-$C_4$alkyl, $C_1$-$C_4$alkyl substituted with $NR^8R^9$ or $C_2$-$C_4$alkoxy substituted with $NR^8R^9$;

$R^{17}$ is hydrogen, halogen, hydroxy or $C_1$-$C_4$alkyl; or $R^{15}$ and $R^{16}$ taken in combination form a cyclopropyl ring; or $R^{17}$ and $R^{19}$ taken in combination form a cyclopropyl ring.

In yet another aspect, compounds of formula (I) or (II) are provided in which $X^1$ is S; and $X^2$ and $X^3$ are $CH_2$; or $X^1$ is $CHR^{15}$, wherein $R^{15}$ is hydrogen, fluoro, methyl, hydroxy, methoxy, ethoxy, methoxyethoxy or amino; $X^3$ is $CH_2$; and $X^2$ is $CR^{16}R^{17}$, wherein $R^{16}$ is fluoro, amino, hydroxymethyl, methoxymethyl, aminomethyl or methyl and $R^{17}$ is hydrogen or fluoro; or $X^1$ is $CHR^{15}$, $X^2$ is $CR^{16}R^{17}$, and $X^3$ is $CHR^{19}$, wherein $R^{17}$ and $R^{19}$, taken in combination form a cyclopropyl ring, and $R^{16}$ is hydrogen, hydroxymethyl, or methoxymethyl, and $R^{15}$ is hydrogen; or $X^1$ is $CHR^{15}$, $X^2$ is $CR^{16}R^{17}$, and $X^3$ is $CHR^{19}$, wherein $R^{15}$ and $R^{16}$, taken in combination form a cyclopropyl ring, $R^{17}$ and $R^{19}$ are hydrogen; or $X^1$ and $X^2$ are $CH_2$, and $X^3$ is N(H).

Other compounds of formula (I) or (II) provided herein include those compounds in which the heterocyclic ring of the formula:

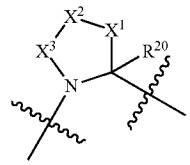

Is selected from the group consisting of:

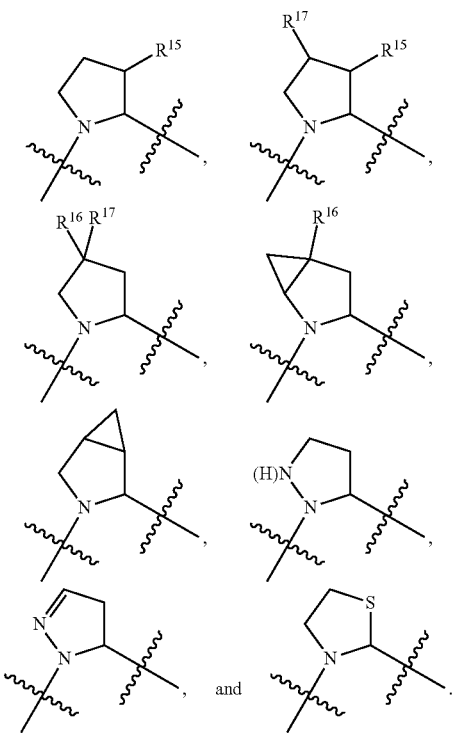

In certain embodiments, the heterocyclic ring of the compounds of formula (I) and formula (II) of the formula:

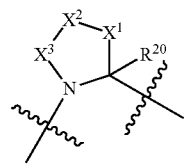

Is a 4-fluoro pyrrolidine, e.g., a heterocyle of the formula:

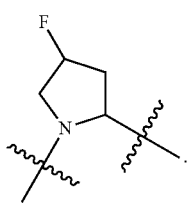 [SMILES: *C1CC(F)CN1*]

In certain aspects, compounds of formula (I) or (II) include compounds in which the heterocyclic ring of the formula:

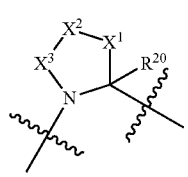

is selected from the group consisting of:

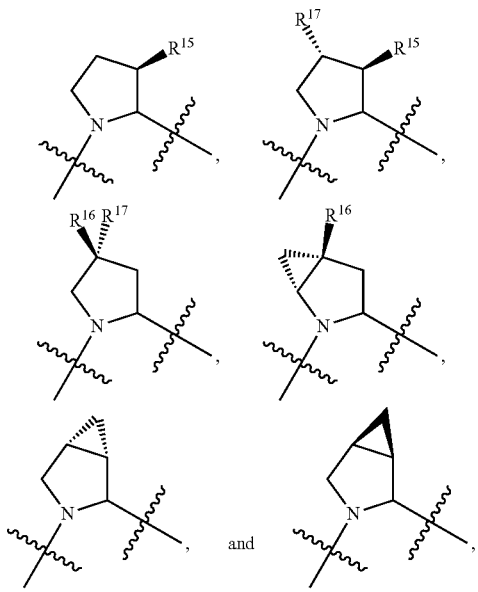

In certain aspects, compounds of formula (VII) include compounds in which the heterocyclic ring of the formula:

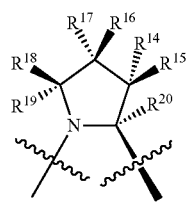

is selected from the group consisting of:

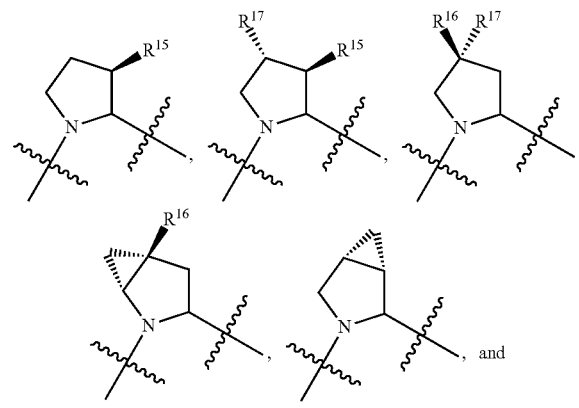

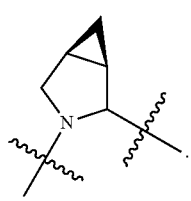

Other compounds of formula (I) provided herein include those compounds in which the bicyclic ring system of the formula:

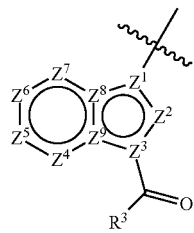

is selected from the group consisting of:

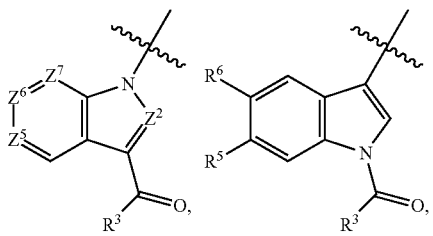

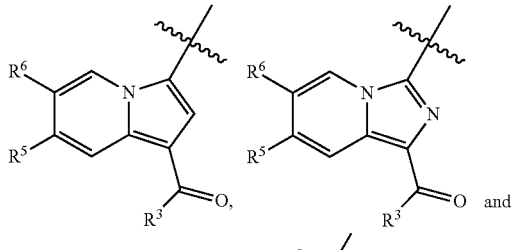

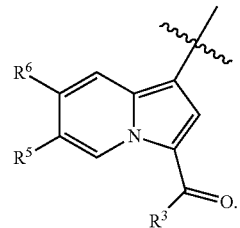

Certain other compounds of formula (I) provided herein include those compounds in which the bicyclic ring system of the formula:

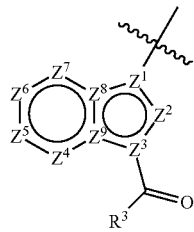

is selected from the group consisting of:

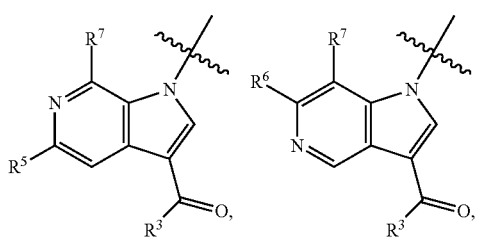

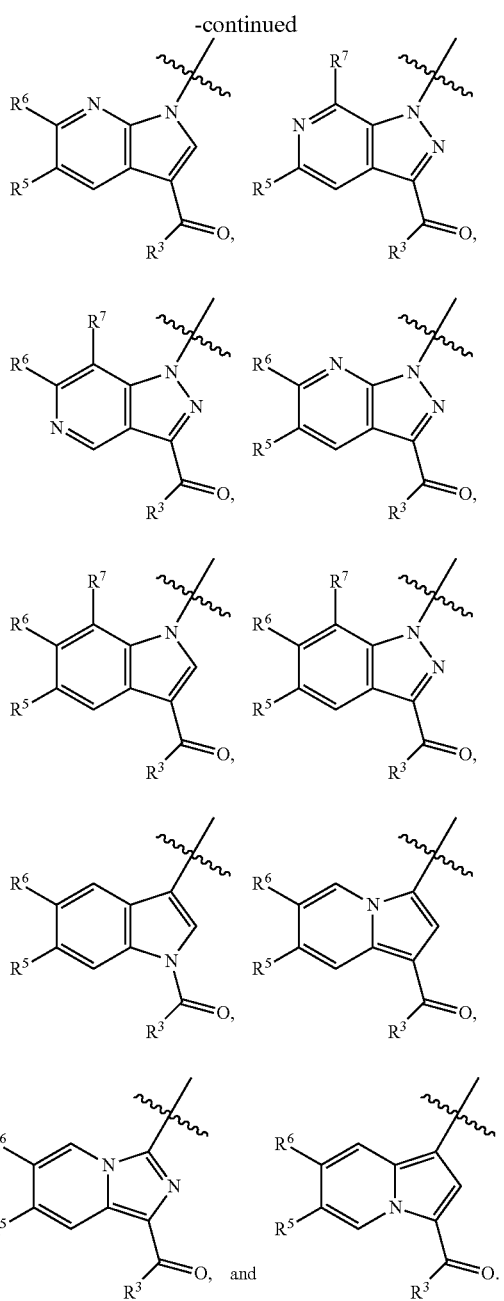

Other compounds of formula (II) or formula (VII) provided herein include those compounds in which the bicyclic ring system of formula (II) or formula (VII)

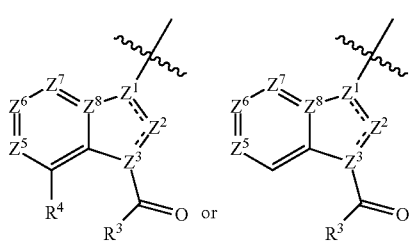

is selected from the group consisting of:

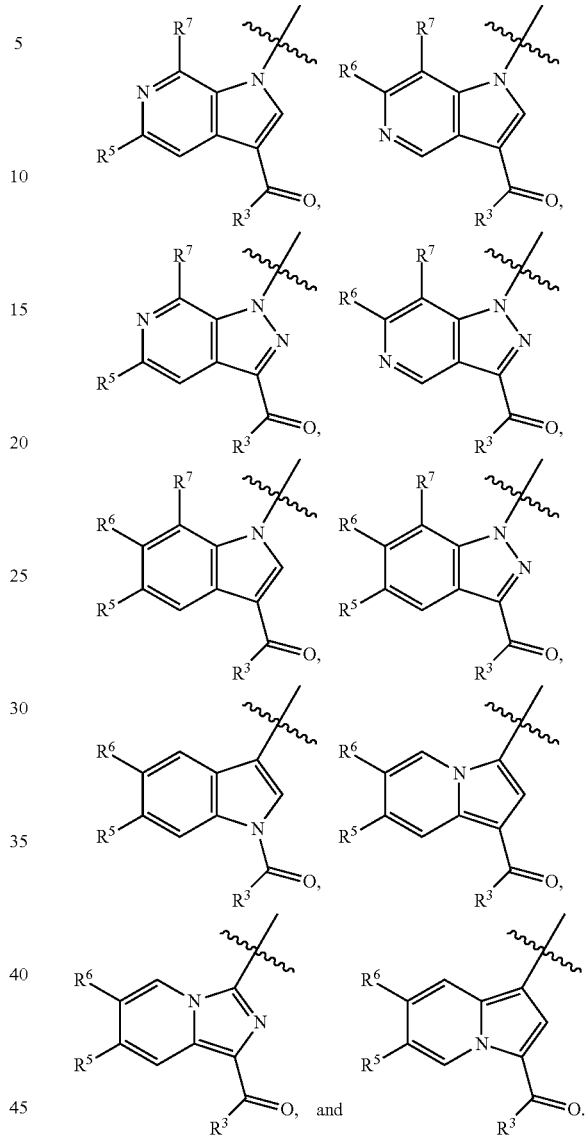

Certain preferred compounds of formula (I), (Ia), (II), (VII) or any subformula thereof provided herein include those compounds in which L is —N(H)— or —CH$_2$—. Certain other preferred compounds of formula (I), (Ia), (II), (VII) or any subformula thereof provided herein include those compounds in which G is —C(O)—N(H)—.

Still other preferred compounds of formula (I), (Ia), (II) or (VII) or any subformula thereof provided herein include those compounds in which q is 0 or 1;

$R^{21}$ is selected from the group consisting of hydrogen, $C_1$-$C_6$alkyl, hydroxy$C_1$-$C_6$alkyl, $C_1$-$C_6$alkoxy$C_1$-$C_6$alkyl and $C_1$-$C_6$alkyl substituted with NR$^8$R$^9$;

$R^{22}$ is hydrogen; or $CR^{21}R^{22}$, taken in combination, form a cyclopropyl ring;

Z is phenyl, pyridyl, oxazolyl, isoxazolyl, thiazolyl, pyrazolyl, thienyl, each of which is unsubstituted or substituted with 1, 2 or 3 substituents, each of which is independently selected from the group consisting of:

halogen, hydroxy, $C_1$-$C_4$alkyl, $C_1$-$C_4$alkoxy, halo$C_1$-$C_4$alkyl, halo$C_1$-$C_4$alkoxy, NR$^{23}$R$^{24}$, CO$_2$H, C(O)NR$^{23}$R$^{24}$, CO$_2$(C$_1$-

$C_4$alkyl), tetrazole, piperidinyl, piperazinyl, morpholino, and alkyl substituted with $C_1$-$C_4$alkoxy or $NR^{23}R^{24}$.

In still other preferred compounds of formula (I), (Ia), (II), or (VII), or any subformulae thereof provided herein, q is 2;

$R^{21}$ is selected, at each occurrence, from the group consisting of hydrogen, $C_1$-$C_6$alkyl, hydroxy$C_1$-$C_6$alkyl, $C_1$-$C_6$alkoxy$C_1$-$C_6$alkyl and $C_1$-$C_6$alkyl substituted with $NR^8R^9$;

$R^{22}$ is hydrogen; or $CR^{21}R^{22}CR^{21}R^{22}$, taken in combination, forms a cis or trans cyclopropane ring;

Z is phenyl, pyridyl, oxazolyl, isoxazolyl, thiazolyl, pyrazolyl, thienyl, each of which is unsubstituted or substituted with 1, 2 or 3 substituents, each of which is independently selected from the group consisting of:

halogen, hydroxy, $C_1$-$C_4$alkyl, $C_1$-$C_4$alkoxy, halo$C_1$-$C_4$alkyl, halo$C_1$-$C_4$alkoxy, $NR^{23}R^{24}$, $CO_2H$, $C(O)NR^{23}R^{24}$, $C_4$alkyl), tetrazole, piperidinyl, piperazinyl, morpholino, and alkyl substituted with $C_1$-$C_4$alkoxy or $NR^{23}R^{24}$.

Still other preferred compounds of formula (I), (Ia), (II) or (VII) or any subformula thereof provided herein include those compounds in which q is 0 or 1;

$R^{21}$ is selected from the group consisting of hydrogen, $C_1$-$C_6$alkyl, hydroxy$C_1$-$C_6$alkyl, $C_1$-$C_6$alkoxy$C_1$-$C_6$alkyl, amino$C_1$-$C_6$alkyl, and mono- and di-$C_1$-$C_4$alkylamino$C_1$-$C_6$alkyl;

$R^{22}$ is hydrogen; or $CR^{21}R^{22}$, taken in combination, form a cyclopropyl ring; and Z is phenyl which is unsubstituted or substituted with 1, 2, or 3 substituents, each of which is independently selected from the group consisting of halogen, hydroxy, $C_1$-$C_4$alkyl, $C_1$-$C_4$alkoxy, halo$C_1$-$C_4$alkyl, halo$C_1$-$C_4$alkoxy, $CO_2H$, $C(O)NH_2$, $CO_2(C_1$-$C_4$alkyl), amino, and mono- and di-$C_1$-$C_4$alkylamino, wherein each N-alkyl residue is substituted with 0 or 1 residues selected from the group consisting of hydroxy, $C_1$-$C_4$alkoxy, amino, or mono- or di-$C_1$-$C_2$alkylamino.

Still other preferred compounds of formula (I), (Ia), (II) or (VII) or any subformula thereof provided herein include those compounds in which q is 0, 1 or 2;

$R^{21}$ is hydrogen;

$R^{22}$ is hydrogen, methyl, or ethyl, which methyl and ethyl are unsubstituted or substituted with hydroxy, methoxy, amino, or mono- or di-methyl amino; or $CR^{21}R^{22}$, taken in combination, form a cyclopropane ring; when q is 2, $CR^{21}R^{22}CR^{21}R^{22}$, taken in combination form a cis- or trans-cyclopropane ring;

Z is phenyl which is unsubstituted or substituted with 1, 2, or 3 residues selected from the group consisting of fluoro, chloro, bromo, methyl, trifluoromethyl, methoxy, trifluoromethoxy, amino, mono- and di-$C_1$-$C_2$alkylamino, tetrazole or $CO_2H$; or Z is pyridyl or thienyl, each of which is unsubstituted or substituted with 1 or 2 substitutents selected from the group consisting of fluoro, chloro, bromo, methyl, trifluoromethyl, methoxy, or trifluoromethoxy.

In another aspect, the invention provides compounds of formula (I) or formula (II) in which the compounds are represented by formulae (III), (IV) or (V):

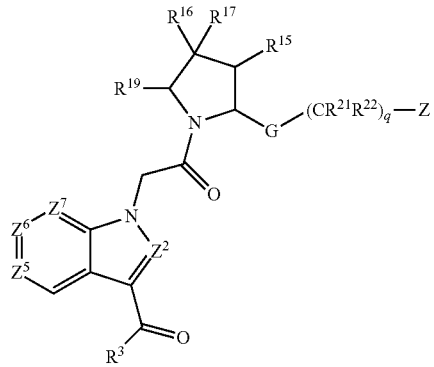

(III)

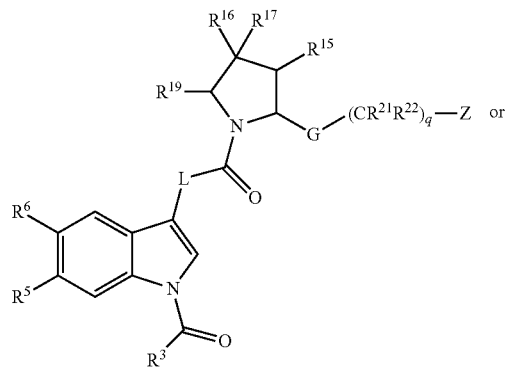

(IV)

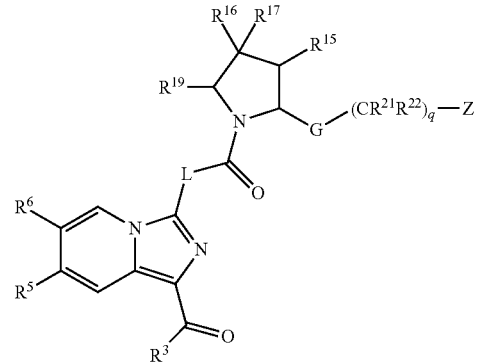

(V)

wherein $Z^2$ is CH or N;

$Z^5$ is $CR^5$ or N;

$Z^6$ is $CR^6$ or N;

$Z^7$ is CH or N, wherein 0, 1 or 2 of $Z^5$, $Z^6$ and $Z^7$ is N;

$R^3$ is hydrogen, methyl, ethyl, iPr, amino, hydroxymethyl, CH2OMe, or mono-, di- and tri-fluoromethyl, NHMe;

$R^5$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, tetrazole, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, tetrazole, $C_1$-$C_4$alkoxy, $CO_2H$, $C_1$-$C_4$alkoxycarbonyl, optionally substituted phenyl, pyridyl and pyrimidinyl, and wherein the phenyl is unsubstituted or substituted with 1 or 2 substituents independently selected from halogen, hydroxy, methyl, methoxy and $CO_2H$;

$R^6$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, $NR^{10}R^{11}$, tetrazole, cyano, imidazolyl, $C_1$-$C_4$alkoxy, $CO_2H$, $C_1$-$C_4$alkoxycarbonyl, optionally substituted phenyl, pyrrolyl, morpholino, piperidino, piperazino, and pyridyl, and wherein the phenyl is unsubstituted or substituted with 1 or 2 substituents independently selected from halogen, hydroxy, methyl, methoxy, mono- and dimethyl amino, and $CO_2H$;

L is $CH_2$ or NH;

$R^{15}$ is hydrogen, fluoro, methyl, hydroxy, methoxy, ethoxy and $OCH_2CH_2OMe$, $OCH_2CH_2N(CH_3)_2$, amino or $OCH_2CH_2$pyrrolyl;

$R^{16}$ is hydrogen, fluoro, methyl, amino, hydroxymethyl, methoxymethyl, or aminomethyl;

$R^{17}$ is hydrogen, fluoro or methyl;

$R^{19}$ is hydrogen or $R^{19}$ and $R^{17}$, taken in combination, form a cyclopropyl ring; or $R^{15}$ and $R^{16}$, taken in combination, form a cyclopropyl ring;

G is —C(O)N(H)—; and q is 0, 1, or 2;

$R^{21}$ is hydrogen, methyl, or ethyl, which methyl and ethyl are unsubstituted or substituted with hydroxy, methoxy, amino, mono- or di-methyl amino, morpholinomethyl, optionally substituted azetidinomethyl, which azetidino ring is substituted with 0 or 1 fluoro or methoxy; or $R^{22}$ is hydrogen;

$CR^{21}R^{22}$, taken in combination, form a cyclopropane ring; or when q is 2, $CR^{21}R^{22}CR^{21}R^{22}$, taken in combination form a cis- or trans-cyclopropane ring;

Z is phenyl, pyridyl, or thienyl, each of which is unsubstituted or substituted with 1, 2, or 3 residues independently selected at each occurrence from the group consisting of halogen, methyl, methoxy, hydroxy, trifluoromethyl, trifluoromethoxy, $CO_2H$, tetrazole, and $NR^{23}R^{24}$.

Certain compounds of Formula (III) provided by the invention include compounds represented by formula (IIIa):

(IIIa)

wherein $R^3$ is hydrogen, methyl, ethyl, iPr, amino, hydroxymethyl, $CH_2OMe$, or mono-, di- and tri-fluoromethyl, NHMe;

$R^5$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, tetrazole, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, tetrazole, $C_1$-$C_4$alkoxy, $CO_2H$, $C_1$-$C_4$alkoxycarbonyl, optionally substituted phenyl, pyridyl and pyrimidinyl, and wherein the phenyl is unsubstituted or substituted with 1 or 2 substituents independently selected from halogen, hydroxy, methyl, methoxy and $CO_2H$;

$R^6$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, $NR^{10}R^{11}$, tetrazole, cyano, imidazolyl, $C_1$-$C_4$alkoxy, $CO_2H$, $C_1$-$C_4$alkoxycarbonyl, optionally substituted phenyl, pyrrolyl, morpholino, piperidino, piperazino, and pyridyl, and wherein the phenyl is unsubstituted or substituted with 1 or 2 substituents independently selected from halogen, hydroxy, methyl, methoxy, mono- and dimethyl amino, and $CO_2H$;

$R^7$ is hydrogen or methyl;

$R^{15}$ is hydrogen, fluoro, methyl, hydroxy, methoxy, ethoxy and $OCH_2CH_2OMe$, $OCH_2CH_2N(CH_3)_2$, amino or $OCH_2CH_2$pyrrolyl;

$R^{16}$ is hydrogen, fluoro, methyl, amino, hydroxymethyl, methoxymethyl, or aminomethyl;

$R^{17}$ is hydrogen, fluoro or methyl;

$R^{19}$ is hydrogen or $R^{19}$ and $R^{17}$, taken in combination, form a cyclopropyl ring; or $R^{15}$ and $R^{16}$, taken in combination, form a cyclopropyl ring;

G is —C(O)N(H)—; and q is 0 or 1;

Z is pyridyl, pyrazinyl, or thienyl, each of which is unsubstituted or substituted with 1, 2, or 3 residues independently selected at each occurrence from the group consisting of halogen, methyl, methoxy, hydroxy, trifluoromethyl, trifluoromethoxy, $CO_2H$, tetrazole, and $NR^{23}R^{24}$.

In another embodiment, compounds of the first embodiment include those compounds represented by one of the formulae (IIIb) or (IVb):

(IIIb)

-continued

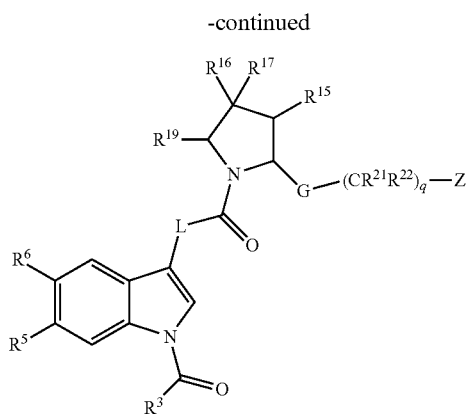

(IVb)

wherein
Z² is CH or N;
Z⁵ is CR⁵ or N;
Z⁶ is CR⁶ or N;
Z⁷ is CH, C(CH₃) or N, wherein 0 or 1 or 2 of Z⁵, Z⁶ and Z⁷ is N;
R³ is hydrogen, methyl, ethyl, iPr, amino, hydroxymethyl, CH2OMe, or mono-, di- and tri-fluoromethyl, NHMe;
R⁵ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, tetrazole, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, cyano, tetrazole, $C_1$-$C_4$alkoxy, $CO_2H$, $C_1$-$C_4$alkoxycarbonyl, tetrahydrofuranyl, optionally substituted phenyl, pyridyl and pyrimidinyl, and wherein the phenyl is unsubstituted or substituted with 1 or 2 substituents independently selected from halogen, hydroxy, methyl, methoxy and $CO_2H$;
R⁶ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, NR¹⁰R¹¹, tetrazole, cyano, imidazolyl, $C_1$-$C_4$alkoxy, $CO_2H$, $C_1$-$C_4$alkoxycarbonyl, optionally substituted phenyl, pyrrolyl, morpholino, piperidino, piperazino, and pyridyl, and wherein the phenyl is unsubstituted or substituted with 1 or 2 substituents independently selected from halogen, hydroxy, methyl, methoxy, mono- and dimethyl amino, and $CO_2H$;
L is $CH_2$ or NH;
R¹⁵ is hydrogen, fluoro, methyl, hydroxy, methoxy, ethoxy and $OCH_2CH_2OMe$, $OCH_2CH_2N(CH_3)_2$, amino or $OCH_2CH_2$pyrrolyl;
R¹⁶ is hydrogen, fluoro, methyl, amino, hydroxymethyl, methoxymethyl, or aminomethyl;
R¹⁷ is hydrogen, fluoro or methyl;
R¹⁹ is hydrogen or R¹⁹ and R¹⁷, taken in combination, form a cyclopropyl ring; or
R¹⁵ and R¹⁶, taken in combination, form a cyclopropyl ring;
G is —C(O)N(H)—; and
q is 0 or 1;
R²¹ is hydrogen, methyl, or ethyl, which methyl and ethyl are unsubstituted or substituted with hydroxy, methoxy, cyano, amino, mono- or di-methyl amino, morpholinomethyl, optionally substituted azetidinomethyl, which azetidino ring is substituted with 0 or 1 fluoro or methoxy; or
R²² is hydrogen;

CR²¹R²², taken in combination, form a cyclopropane ring;
Z is phenyl, pyridyl, pyrazinyl or thienyl, each of which is unsubstituted or substituted with 1, 2, or 3 residues independently selected at each occurrence from the group consisting of halogen, methyl, cyclopropyl, methoxy, hydroxy, trifluoromethyl, trifluoromethoxy, $SF_5$, $CO_2H$, tetrazole, and NR²³R²⁴, unsubstituted or substituted phenyl and unsubstituted or substituted pyridinyl, which substituted phenyl and pyridinyl has 1 or 2 substituents independently selected from the group consisting of halogen and methyl.

Certain compounds, or salts thereof, provided by formula (I) or formula (II) include those compounds which are represented by formula (VI):

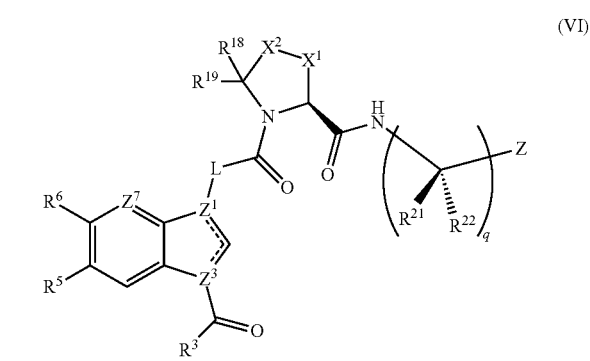

(VI)

wherein
q is 0, 1 or 2;
R²¹ is hydrogen;
R²² is hydrogen, methyl, or ethyl, which methyl and ethyl are unsubstituted or substituted with hydroxy, methoxy, amino, or mono- or di-methyl amino; or
CR²¹R²², taken in combination, form a cyclopropane ring;
when q is 2, CR²¹R²²CR²¹R²², taken in combination form a cis- or trans-cyclopropane ring;
Z is phenyl which is unsubstituted or substituted with 1, 2, or 3 residues selected from the group consisting of fluoro, chloro, bromo, methyl, trifluoromethyl, methoxy, trifluoromethoxy, NR²³R²⁴, tetrazole or $CO_2H$; or
Z is pyridyl or thienyl, each of which is unsubstituted or substituted with 1 or 2 substitutents selected from the group consisting of fluoro, chloro, bromo, methyl, trifluoromethyl, methoxy, or trifluoromethoxy.

In certain aspects, the compound of formula (I) is represented by the structure of formula (VI):

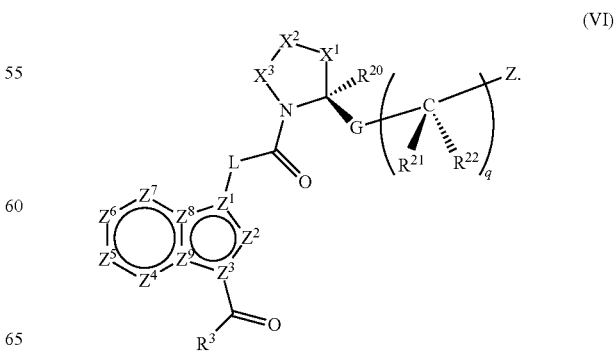

(VI)

In another embodiment, individual compounds according to the invention are those listed in the Examples section below. In certain aspects the compound is selected from the group consisting of:

- (2S,4R)-4-Fluoro-pyrrolidine-1,2-dicarboxylic acid 1-[(1-carbamoyl-1H-indol-3-yl)-amide]2-(3-chloro-2-fluoro-benzylamide);
- (2S,4R)-4-Fluoro-pyrrolidine-1,2-dicarboxylic acid 2-benzylamide 1-[(1-carbamoyl-1H-indol-3-yl)-amide];
- (2S,4R)-4-Fluoro-pyrrolidine-1,2-dicarboxylic acid 1-[(1-carbamoyl-1H-indol-3-yl)-amide]2-[(pyridin-3-ylmethyl)-amide];
- (2S,4R)-4-Fluoro-pyrrolidine-1,2-dicarboxylic acid 1-[(1-carbamoyl-1H-indol-3-yl)-amide]2-(3-chloro-2-fluoro-5-{[(2-methoxy-ethyl)-methyl-amino]-methyl}-benzylamide);
- (2S,4R)-4-Fluoro-pyrrolidine-1,2-dicarboxylic acid 1-[(1-carbamoyl-1H-indol-3-yl)-amide]2-{[(S)-1-(3-chloro-2-fluoro-phenyl)-2-hydroxy-ethyl]-amide};
- (2S,4R)-4-Fluoro-pyrrolidine-1,2-dicarboxylic acid 1-[(1-carbamoyl-1H-indol-3-yl)-amide]2-[(pyridin-4-ylmethyl)-amide];
- (2S,4R)-4-Fluoro-pyrrolidine-1,2-dicarboxylic acid 1-[(1-carbamoyl-1H-indol-3-yl)-amide]2-[3-chloro-2-fluoro-5-(4-methyl-piperazin-1-yl)-benzylamide];
- (2S,4R)-4-Fluoro-pyrrolidine-1,2-dicarboxylic acid 1-[(1-carbamoyl-1H-indol-3-yl)-amide]2-(3-chloro-benzylamide);
- (2S,4R)-4-Fluoro-pyrrolidine-1,2-dicarboxylic acid 1-[(1-carbamoyl-1H-indol-3-yl)-amide]2-(3-hydroxy-benzylamide);
- (2S,4R)-4-Fluoro-pyrrolidine-1,2-dicarboxylic acid 1-[(1-carbamoyl-1H-indol-3-yl)-amide]2-[3-chloro-2-fluoro-5-(4-methyl-piperazin-1-ylmethyl)-benzylamide];
- (2S,4R)-4-Fluoro-pyrrolidine-1,2-dicarboxylic acid 1-[(1-carbamoyl-1H-indol-3-yl)-amide]2-[(5-chloro-thiophen-2-ylmethyl)-amide];
- (2S,4R)-4-Fluoro-pyrrolidine-1,2-dicarboxylic acid 1-[(1-carbamoyl-1H-indol-3-yl)-amide]2-(3-chloro-5-diethylamino-methyl-2-fluoro-benzyl-amide);
- (2S,4R)-4-Fluoro-pyrrolidine-1,2-dicarboxylic acid 1-[(1-carbamoyl-1H-indol-3-yl)-amide]2-[((S)-2-hydroxy-1-phenyl-ethyl)-amide];
- (2S,4R)-4-Fluoro-pyrrolidine-1,2-dicarboxylic acid 1-[(1-carbamoyl-1H-indol-3-yl)-amide]2-(2,3-difluoro-benzylamide);
- (2S,3S)-2-{[(2S,4R)-1-(1-Carbamoyl-1H-indol-3-ylcarbamoyl)-4-fluoro-pyrrolidine-2-carbonyl]-amino}-3-methyl-pentanoic acid tert-butyl ester;
- (2S,4R)-4-Fluoro-pyrrolidine-1,2-dicarboxylic acid 1-[(1-carbamoyl-1H-indol-3-yl)-amide]2-[3-chloro-2-fluoro-5-(4-methoxy-piperidin-1-yl)-benzylamide];
- (2S,4R)-4-Fluoro-pyrrolidine-1,2-dicarboxylic acid 1-[(1-carbamoyl-1H-indol-3-yl)-amide]2-(3-chloro-5-{[(2-dimethylamino-ethyl)-methyl-amino]-methyl}-2-fluoro-benzylamide);
- (2S,4R)-4-Fluoro-pyrrolidine-1,2-dicarboxylic acid 1-[(1-carbamoyl-1H-indol-3-yl)-amide]2-(3-chloro-2-fluoro-5-morpholin-4-ylmethyl-benzylamide);
- (2S,4R)-4-Fluoro-pyrrolidine-1,2-dicarboxylic acid 1-[(1-carbamoyl-1H-indol-3-yl)-amide]2-(3-chloro-2-fluoro-5-morpholin-4-yl-benzylamide);
- (2S,4R)-4-Fluoro-pyrrolidine-1,2-dicarboxylic acid 1-[(1-carbamoyl-1H-indol-3-yl)-amide]2-[3-chloro-2-fluoro-5-(4-methoxy-piperidin-1-ylmethyl)-benzylamide];
- (2S,4R)-4-Fluoro-pyrrolidine-1,2-dicarboxylic acid 1-[(1-carbamoyl-1H-indol-3-yl)-amide]2-{3-chloro-2-fluoro-5-[(2-methoxy-ethyl)-methyl-amino]-benzylamide};
- (2S,4R)-4-Fluoro-pyrrolidine-1,2-dicarboxylic acid 1-[(1-carbamoyl-1H-indol-3-yl)-amide]2-{3-chloro-5-[(2-dimethylamino-ethylamino)-methyl]-2-fluoro-benzylamide};
- 2-({[(2S,4R)-1-(1-Carbamoyl-1H-indol-3-ylcarbamoyl)-4-fluoro-pyrrolidine-2-carbonyl]-amino}-methyl)-benzoic acid;
- 2-({[(2S,4R)-1-(1-Carbamoyl-1H-indol-3-ylcarbamoyl)-4-fluoro-pyrrolidine-3-carbonyl]-amino}-methyl)-benzoic acid;
- (2S,3S)-2-{[(2S,4R)-1-(1-Carbamoyl-1H-indol-3-ylcarbamoyl)-4-fluoro-pyrrolidine-2-carbonyl]-amino}-3-methyl-pentanoic acid;
- (2S,4S)-4-Amino-pyrrolidine-1,2-dicarboxylic acid 1-[(1-carbamoyl-1H-indol-3-yl)-amide]2-(3-chloro-2-fluoro-benzylamide);
- (2S,4S)-4-Amino-pyrrolidine-1,2-dicarboxylic acid 1-[(1-carbamoyl-1H-indol-3-yl)-amide]2-phenylamide;
- (2S,4S)-4-Amino-pyrrolidine-1,2-dicarboxylic acid 2-benzylamide 1-[(1-carbamoyl-1H-indol-3-yl)-amide];
- (2S,4S)-4-Amino-pyrrolidine-1,2-dicarboxylic acid 1-[(1-carbamoyl-1H-indol-3-yl)-amide]2-(3-chloro-benzylamide) as a formate salt;
- (2S,4S)-4-Amino-pyrrolidine-1,2-dicarboxylic acid 1-[(1-carbamoyl-1H-indol-3-yl)-amide]2-(3-methyl-benzylamide);
- (2S,4S)-4-Amino-pyrrolidine-1,2-dicarboxylic acid 1-[(1-carbamoyl-1H-indol-3-yl)-amide]2-(3-trifluoromethyl-benzylamide);
- (2S,4S)-4-Amino-pyrrolidine-1,2-dicarboxylic acid 1-[(1-carbamoyl-1H-indol-3-yl)-amide]2-(3-fluoro-benzylamide);
- (2S,4S)-4-Amino-pyrrolidine-1,2-dicarboxylic acid 1-[(1-carbamoyl-1H-indol-3-yl)-amide]2-(3-cyano-benzylamide);
- (2S,4S)-4-Amino-pyrrolidine-1,2-dicarboxylic acid 2-(3-bromo-benzylamide) 1-[(1-carbamoyl-1H-indol-3-yl)-amide];
- (2S,4S)-4-Amino-pyrrolidine-1,2-dicarboxylic acid 1-[(1-carbamoyl-1H-indol-3-yl)-amide]2-(3-hydroxy-benzylamide);
- (2S,4S)-4-Amino-pyrrolidine-1,2-dicarboxylic acid 1-[(1-carbamoyl-1H-indol-3-yl)-amide]2-(3-methoxy-benzylamide);
- (2S,4S)-4-Amino-pyrrolidine-1,2-dicarboxylic acid 1-[(1-carbamoyl-1H-indol-3-yl)-amide]2-(3-trifluoromethoxy-benzylamide);
- (2S,4S)-4-Amino-pyrrolidine-1,2-dicarboxylic acid 1-[(1-carbamoyl-1H-indol-3-yl)-amide]2-(3-phenoxy-benzylamide);
- (2S,4S)-4-Amino-pyrrolidine-1,2-dicarboxylic acid 2-[(biphenyl-3-ylmethyl)-amide]1-[(1-carbamoyl-1H-indol-3-yl)-amide] as a formate salt;
- (2S,4S)-4-Amino-pyrrolidine-1,2-dicarboxylic acid 1-[(1-carbamoyl-1H-indol-3-yl)-amide]2-(3-pyrrol-1-yl-benzylamide);
- (2S,4S)-4-Amino-pyrrolidine-1,2-dicarboxylic acid 1-[(1-carbamoyl-1H-indol-3-yl)-amide]2-[3-(5-chloro-thiophen-2-yl)-benzylamide];
- (2S,4S)-4-Amino-pyrrolidine-1,2-dicarboxylic acid 1-[(1-carbamoyl-1H-indol-3-yl)-amide]2-[(5'-chloro-[2,2']bithiophenyl-5-ylmethyl)-amide];
- (2S,4S)-4-Amino-pyrrolidine-1,2-dicarboxylic acid 1-[(1-carbamoyl-1H-indol-3-yl)-amide]2-(4-methyl-benzylamide);

(2S,4S)-4-Amino-pyrrolidine-1,2-dicarboxylic acid 1-[(1-carbamoyl-1H-indol-3-yl)-amide]2-(4-chloro-benzylamide);

(2S,4S)-4-Amino-pyrrolidine-1,2-dicarboxylic acid 1-[(1-carbamoyl-1H-indol-3-yl)-amide]2-(4-trifluoromethyl-benzylamide);

(2S,4S)-4-Amino-pyrrolidine-1,2-dicarboxylic acid 1-[(1-carbamoyl-1H-indol-3-yl)-amide]2-(4-trifluoromethoxy-benzylamide);

(2S,4S)-4-Amino-pyrrolidine-1,2-dicarboxylic acid 1-[(1-carbamoyl-1H-indol-3-yl)-amide]2-(4-hydroxy-benzylamide);

(2S,4S)-4-Amino-pyrrolidine-1,2-dicarboxylic acid 1-[(1-carbamoyl-1H-indol-3-yl)-amide]2-(2-hydroxy-benzylamide);

(2S,4S)-4-Amino-pyrrolidine-1,2-dicarboxylic acid 1-[(1-carbamoyl-1H-indol-3-yl)-amide]2-(2-fluoro-benzylamide);

(2S,4S)-4-Amino-pyrrolidine-1,2-dicarboxylic acid 1-[(1-carbamoyl-1H-indol-3-yl)-amide]2-(2-chloro-benzylamide);

(2S,4S)-4-Amino-pyrrolidine-1,2-dicarboxylic acid 2-[(biphenyl-2-ylmethyl)-amide]1-[(1-carbamoyl-1H-indol-3-yl)-amide];

(2S,4S)-4-Amino-pyrrolidine-1,2-dicarboxylic acid 1-[(1-carbamoyl-1H-indol-3-yl)-amide]2-(2,3-difluoro-benzylamide);

(2S,4S)-4-Amino-pyrrolidine-1,2-dicarboxylic acid 1-[(1-carbamoyl-1H-indol-3-yl)-amide]2-(5-chloro-2-methoxy-benzylamide);

(2S,4S)-4-Amino-pyrrolidine-1,2-dicarboxylic acid 1-[(1-carbamoyl-1H-indol-3-yl)-amide]2-(3-chloro-4-methoxy-benzylamide);

(2S,4S)-4-Amino-pyrrolidine-1,2-dicarboxylic acid 1-[(1-carbamoyl-1H-indol-3-yl)-amide]2-(5-chloro-2-fluoro-benzylamide);

(2S,4S)-4-Amino-pyrrolidine-1,2-dicarboxylic acid 1-[(1-carbamoyl-1H-indol-3-yl)-amide]2-(3-chloro-4-fluoro-benzylamide);

(2S,4S)-4-Amino-pyrrolidine-1,2-dicarboxylic acid 1-[(1-carbamoyl-1H-indol-3-yl)-amide]2-(3-chloro-2-methyl-benzylamide);

(2S,4S)-4-Amino-pyrrolidine-1,2-dicarboxylic acid 1-[(1-carbamoyl-1H-indol-3-yl)-amide]2-(5-chloro-2-methyl-benzylamide);

(2S,4S)-4-Amino-pyrrolidine-1,2-dicarboxylic acid 1-[(1-carbamoyl-1H-indol-3-yl)-amide]2-(3-chloro-4-methyl-benzylamide);

(2S,4S)-4-Amino-pyrrolidine-1,2-dicarboxylic acid 1-[(1-carbamoyl-1H-indol-3-yl)-amide]2-(3,5-dichloro-benzylamide);

(2S,4S)-4-Amino-pyrrolidine-1,2-dicarboxylic acid 1-[(1-carbamoyl-1H-indol-3-yl)-amide]2-(3,4-dichloro-benzylamide);

(2S,4S)-4-Amino-pyrrolidine-1,2-dicarboxylic acid 1-[(1-carbamoyl-1H-indol-3-yl)-amide]2-(3-chloro-2,6-difluoro-benzylamide);

(2S,4S)-4-Amino-pyrrolidine-1,2-dicarboxylic acid 1-[(1-carbamoyl-1H-indol-3-yl)-amide]2-[(naphthalen-2-ylmethyl)-amide];

(2S,4S)-4-Amino-pyrrolidine-1,2-dicarboxylic acid 1-[(1-carbamoyl-1H-indol-3-yl)-amide]2-[(naphthalen-1-ylmethyl)-amide];

(2S,4S)-4-Amino-pyrrolidine-1,2-dicarboxylic acid 1-[(1-carbamoyl-1H-indol-3-yl)-amide]2-[(5-methyl-thiazol-2-ylmethyl)-amide];

(2S,4S)-4-Amino-pyrrolidine-1,2-dicarboxylic acid 1-[(1-carbamoyl-1H-indol-3-yl)-amide]2-[(5-chloro-thiophen-2-ylmethyl)-amide];

(2S,4S)-4-Amino-pyrrolidine-1,2-dicarboxylic acid 1-[(1-carbamoyl-1H-indol-3-yl)-amide]2-[(4-methyl-pyridin-2-ylmethyl)-amide];

(2S,4S)-4-Amino-pyrrolidine-1,2-dicarboxylic acid 1-[(1-carbamoyl-1H-indol-3-yl)-amide]2-{[(S)-1-(3-chloro-phenyl)-ethyl]-amide} as a formate salt;

(2S,4S)-4-Amino-pyrrolidine-1,2-dicarboxylic acid 1-[(1-carbamoyl-1H-indol-3-yl)-amide]2-{[(R)-1-(3-chloro-phenyl)-ethyl]-amide} as a formate salt;

(2S,4S)-4-Amino-pyrrolidine-1,2-dicarboxylic acid 1-[(1-carbamoyl-1H-indol-3-yl)-amide]2-{[1-(3,5-dichloro-phenyl)-2-hydroxy-ethyl]-amide};

(2S,4S)-4-Amino-pyrrolidine-1,2-dicarboxylic acid 1-[(1-carbamoyl-1H-indol-3-yl)-amide]2-{[1-(3-chloro-phenyl)-3-hydroxy-propyl]-amide};

(2S,4S)-4-Amino-pyrrolidine-1,2-dicarboxylic acid 1-[(1-carbamoyl-1H-indol-3-yl)-amide]2-[(1-phenyl-cyclopropyl)-amide];

(2S,4S)-4-Amino-pyrrolidine-1,2-dicarboxylic acid 2-benzhydryl-amide 1-[(1-carbamoyl-1H-indol-3-yl)-amide] as a formate salt;

(2S,4S)-4-Amino-pyrrolidine-1,2-dicarboxylic acid 1-[(1-carbamoyl-1H-indol-3-yl)-amide]2-cyclohexylmethyl-amide;

(2S,4S)-4-Amino-pyrrolidine-1,2-dicarboxylic acid 1-[(1-carbamoyl-1H-indol-3-yl)-amide]2-[((1R,2S)-2-hydroxy-cyclohexylmethyl)-amide];

(2S,4S)-4-Amino-pyrrolidine-1,2-dicarboxylic acid 1-[(1-carbamoyl-1H-indol-3-yl)-amide]2-[((1S,2S)-2-hydroxy-cyclohexylmethyl)-amide];

(2S,4S)-4-Amino-pyrrolidine-1,2-dicarboxylic acid 1-[(1-carbamoyl-1H-indol-3-yl)-amide]2-cyclohexylamide;

(2S,4S)-4-Amino-pyrrolidine-1,2-dicarboxylic acid 1-[(1-carbamoyl-1H-indol-3-yl)-amide]2-[(3,4,5,6-tetrahydro-2H-[1,2']bipyridinyl-3-yl)amide];

(2S,4S)-4-Amino-pyrrolidine-1,2-dicarboxylic acid 1-[(1-carbamoyl-1H-indol-3-yl)-amide]2-[(6-chloro-indan-1-yl)amide];

(2S,4S)-4-Amino-pyrrolidine-1,2-dicarboxylic acid 1-[(1-carbamoyl-1H-indol-3-yl)-amide]2-[(6-chloro-chroman-4-yl)-amide];

(2S,4S)-4-Amino-pyrrolidine-1,2-dicarboxylic acid 1-[(1-carbamoyl-1H-indol-3-yl)-amide]2-(phenethyl-amide);

(2S,4S)-4-Amino-pyrrolidine-1,2-dicarboxylic acid 1-[(1-carbamoyl-1H-indol-3-yl)-amide]2-[(2-hydroxy-2-phenyl-ethyl)-amide];

(2S,4S)-4-Amino-pyrrolidine-1,2-dicarboxylic acid 1-[(1-carbamoyl-1H-indol-3-yl)-amide]2-[((1R,2S)-2-phenyl-cyclopropyl)-amide];

(2S,4S)-4-Amino-pyrrolidine-1,2-dicarboxylic acid 1-[(1-carbamoyl-1H-indol-3-yl)-amide]2-[((R)-2-phenyl-propyl)-amide];

(2S,4S)-4-Amino-pyrrolidine-1,2-dicarboxylic acid 1-[(1-carbamoyl-1H-indol-3-yl)-amide]2-[((S)-2-phenyl-propyl)-amide];

(2S,4S)-4-Amino-pyrrolidine-1,2-dicarboxylic acid 1-[(1-carbamoyl-1H-indol-3-yl)-amide]2-{[2-(3-chloro-phenyl)-ethyl]-amide};

(2S,4S)-4-Amino-pyrrolidine-1,2-dicarboxylic acid 1-[(1-carbamoyl-1Hindol-3-yl)-amide]2-{[2-(2-chloro-phenyl)-ethyl]-amide};

(2S,4S)-4-Amino-pyrrolidine-1,2-dicarboxylic acid 1-[(1-carbamoyl-1Hindol-3-yl)-amide]2-{[2-(2-fluoro-phenyl)-ethyl]-amide};

(2S,4S)-4-Amino-pyrrolidine-1,2-dicarboxylic acid 1-[(1-carbamoyl-1Hindol-3-yl)-amide]2-{[2-(3-fluoro-phenyl)-ethyl]-amide};

(2S,4S)-4-Amino-pyrrolidine-1,2-dicarboxylic acid 1-[(1-carbamoyl-1H-indol-3-yl)-amide]2-{[2-(3-chloro-5-fluoro-phenyl)-ethyl]-amide};

(2S,4S)-4-Amino-pyrrolidine-1,2-dicarboxylic acid 1-[(1-carbamoyl-1H-indol-3-yl)-amide]2-[(2-phenoxy-ethyl)-amide];

(2S,3S)-2-{[(2S,4S)-4-Amino-1-(1-carbamoyl-1H-indol-3-ylcarbamoyl)-pyrrolidine-2-carbonyl]-amino}-3-methyl-pentanoic acid methyl ester;

(S)-2-{[(2S,4S)-4-Amino-1-(1-carbamoyl-1H-indol-3-yl-carbamoyl)-pyrrolidine-2-carbonyl]-amino}-pentanoic acid methyl ester;

(R)-2-{[(2S,4S)-4-Amino-1-(1-carbamoyl-1H-indol-3-yl-carbamoyl)-pyrrolidine-2-carbonyl]-amino}-3-methyl-butyric acid methyl ester;

(S)-2-{[(2S,4S)-4-Amino-1-(1-carbamoyl-1H-indol-3-yl-carbamoyl)-pyrrolidine-2-carbonyl]-amino}-4-methyl-pentanoic acid methyl ester;

(S)-2-{[(2S,4S)-4-Amino-1-(1-carbamoyl-1H-indol-3-yl-carbamoyl)-pyrrolidine-2-carbonyl]-amino}-3-tert-butoxy-propionic acid methyl ester;

(S)-2-{[(2S,4S)-4-Amino-1-(1-carbamoyl-1H-indol-3-yl-carbamoyl)-pyrrolidine-2-carbonyl]-amino}-3-phenyl-propionic acid methyl ester;

(S)-{[(2S,4S)-4-Amino-1-(1-carbamoyl-1H-indol-3-ylcarbamoyl)-pyrrolidine-2-carbonyl]-amino}-phenyl-acetic acid methyl ester;

(2S,4S)-4-Amino-pyrrolidine-1,2-dicarboxylic acid 1-[(1-carbamoyl-1H-indol-3-yl)-amide]2-[((1S,2S)-1-carbamoyl-2-methyl-butyl)-amide];

(2S,4S)-4-Amino-pyrrolidine-1,2-dicarboxylic acid 1-[(1-carbamoyl-1H-indol-3-yl)-amide]2-(3-ethyl-benzylamide);

(2S,4S)-4-Amino-pyrrolidine-1,2-dicarboxylic acid 1-[(1-carbamoyl-1H-indol-3-yl)-amide]2-[((1S,2S)-1-hydroxymethyl-2-methyl-butyl)-amide];

(2S,4S)-4-Amino-pyrrolidine-1,2-dicarboxylic acid 1-[(1-carbamoyl-1H-indol-3-yl)-amide]2-[(3-isopropyl-phenyl)-amide];

(2S,4S)-4-Amino-pyrrolidine-1,2-dicarboxylic acid 2-biphenyl-3-ylamide 1-[(1-carbamoyl-1H-indol-3-yl)-amide];

3-{[(2S,4R)-2-(Benzenesulfonylamino-methyl)-4-fluoro-pyrrolidine-1-carbonyl]-amino}-indole-1-carboxylic acid amide;

3-({(2S,4R)-4-Fluoro-2-[(3-fluoro-benzenesulfonylamino)-methyl]-pyrrolidine-1-carbonyl}-amino)-indole-1-carboxylic acid amide;

3-({(2S,4R)-4-Fluoro-2-[(3-chloro-benzenesulfonylamino)-methyl]-pyrrolidine-1-carbonyl}-amino)-indole-1-carboxylic acid amide;

3-({(2S,4R)-4-Fluoro-2-[(3-bromo-benzenesulfonylamino)-methyl]-pyrrolidine-1-carbonyl}-amino)-indole-1-carboxylic acid amide;

3-({(2S,4R)-4-Fluoro-2-[(3-trifluoromethoxy-benzenesulfonylamino)-methyl]-pyrrolidine-1-carbonyl}-amino)-indole-1-carboxylic acid amide;

3-({(2S,4R)-2-[(3-Chloro-2-fluoro-benzenesulfonylamino)-methyl]-4-fluoro-pyrrolidine-1-carbonyl}-amino)-indole-1-carboxylic acid amide;

3-({(2S,4R)-2-[(5-Chloro-thiophene-2-sulfonylamino)-methyl]-4-fluoro-pyrrolidine-1-carbonyl}-amino)-indole-1-carboxylic acid amide;

3-({(S)-2-[(3-Chloro-benzenesulfonylamino)-methyl]-pyrrolidine-1-carbonyl}-amino)-indole-1-carboxylic acid amide;

3-{[(2S,4R)-4-Fluoro-2-(phenylacetylamino-methyl)-pyrrolidine-1-carbonyl]-amino}-indole-1-carboxylic acid amide;

[(2S,4R)-1-(1-Carbamoyl-1H-indol-3-ylcarbamoyl)-4-fluoro-pyrrolidin-2-ylmethyl]-carbamic acid phenyl ester;

[(1R,3S,5R)-2-(1-Carbamoyl-1H-indol-3-ylcarbamoyl)-2-aza-bicyclo[3.1.0]hex-3-ylmethyl]-carbamic acid 3-chloro-2-fluoro-phenyl ester;

3-({(2S,4R)-2-[(3-Chloro-2-fluoro-benzylamino)-methyl]-4-fluoro-pyrrolidine-1-carbonyl}-amino)-indole-1-carboxylic acid amide;

3-({(S)-2-[(3-Trifluoromethoxy-phenylamino)-methyl]-pyrrolidine-1-carbonyl}-amino)-indole-1-carboxylic acid amide;

1-{2-Oxo-2-[(S)-2-(3-trifluoromethoxy-phenylcarbamoyl)-pyrrolidin-1-yl]ethyl}-1H-indole-3-carboxylic acid amide;

(S)-1-[2-(1-Acetyl-1H-indol-3-yl)-acetyl]-pyrrolidine-2-carboxylic acid (3-trifluoromethoxy-phenyl)-amide;

(2S,4R)-1-[2-(1-Acetyl-1H-indol-3-yl)-2-amino-acetyl]-4-fluoro-pyrrolidine-2-carboxylic acid 3-chloro-2-fluoro-benzylamide;

(S)-Pyrrolidine-1,2-dicarboxylic acid 1-[(3-carbamoyl-indolizin-1-yl)-amide]2-[(3-trifluoromethoxy-phenyl)-amide];

(2S,4R)-4-Fluoro-pyrrolidine-1,2-dicarboxylic acid 1-[(3-carbamoyl-indolizin-1-yl)-amide]2-[(3-trifluoromethoxy-phenyl)-amide];

(S)-Pyrrolidine-1,2-dicarboxylic acid 1-[(1-carbamoyl-indolizin-3-yl)-amide]2-[(3-trifluoromethoxy-phenyl)-amide];

(S)-pyrrolidine-1,2-dicarboxylic acid 1-[(1-carbamoyl-1H-indol-3-yl)-amide]2-[(3-trifluoromethoxy-phenyl)-amide];

(2S,4S)-4-Cyano-pyrrolidine-1,2 dicarboxylic acid 1-[(1-carbamoyl-1H-indol-3-yl)-amide]2-[(3-trifluoromethoxy-phenyl)-amide];

(2S,3R)-3-Methyl-pyrrolidine-1,2-dicarboxylic acid 1-[(1-carbamoyl-1H-indol-3-yl)-amide]2-(3-chloro-2-fluoro-benzylamide);

(1-Carbamoyl-3-{[(1R,3S,5R)-3-(3-chloro-2-fluoro-benzyl-carbamoyl)-2-aza-bicyclo[3.1.0]hexane-2-carbonyl]-amino}-1H-indol-6-yl)-acetic acid tert-butyl ester;

(2S,4S)-4-Methoxy-pyrrolidine-1,2-dicarboxylic acid 1-[(1-carbamoyl-1H-indol-3-yl)-amide]2-[(3-trifluoromethoxy-phenyl)-amide];

(1R,3S,5R)-2-Azabicyclo[3.1.0]hexane-2,3-dicarboxylic acid 2-[(1-acetyl-1H-indol-3-yl)-amide]3-{[(S)-1-(3-chloro-2-fluoro-phenyl)-2hydroxy-ethyl]amide};

(1R,3S,5R)-2-Azabicyclo[3.1.0]hexane-2,3-dicarboxylic acid 3-(3-chloro-2-fluoro-benzylamide) 2-[(1-methylcarbamoyl-1H-indol-3-yl)-amide];

(2S,4R)-4-Hydroxy-pyrrolidine-1,2-dicarboxylic acid 1-[(1-carbamoyl-1H-indol-3-yl)-amide]2-[(3-trifluoromethoxy-phenyl)-amide];

(2S,4R)-4-Fluoro-4-methyl-pyrrolidine-1,2-dicarboxylic acid 1-{[1-carbamoyl-5-(2-methoxy-ethoxy)-1H-indol-3-yl]-amide}2-(3-chloro-2-fluoro-benzylamide);

(1-Carbamoyl-3-{[(1R,3S,5R)-3-(3-chloro-2-fluoro-benzyl-carbamoyl)-2-aza-bicyclo[3.1.0]hexane-2-carbonyl]-amino}-1H-indol-5-yloxy)-acetic acid methyl ester;

(1S,3S,5S)-2-Aza-bicyclo[3.1.0]hexane-2,3-dicarboxylic acid 2-[(1-carbamoyl-1H-indol-3-yl)-amide]3-[(3-trifluoromethoxy-phenyl)-amide];

(1S,2S,5R)-3-Aza-bicyclo[3.1.0]hexane-2,3-dicarboxylic acid 3-[(1-carbamoyl-1H-indol-3-yl)-amide]2-(3-chloro-2-fluoro-benzylamide);

2-Aza-bicyclo[2.1.1]hexane-1,2-dicarboxylic acid 2-[(1-carbamoyl-1H-indol-3-yl)-amide]1-(3-chloro-2-fluoro-benzylamide);

(2S,4S)-4-Methyl-pyrrolidine-1,2-dicarboxylic acid 1-[(1-carbamoyl-1H-indol-3-yl)-amide]2-[(3-trifluoromethoxy-phenyl)-amide];

(2S,4R)-4-Fluoro-pyrrolidine-1,2-dicarboxylic acid 2-(3-bromo-2-fluoro-benzylamide) 1-[(1-carbamoyl-1H-indol-3-yl)-amide];

(2S,5R)-5-(Acetylamino-methyl)-pyrrolidine-1,2-dicarboxylic acid 1-[(1-carbamoyl-1H-indol-3-yl)-amide]2-[(3-trifluoromethoxy-phenyl)-amide];

(R)-Pyrrolidine-1,2-dicarboxylic acid 1-[(1-carbamoyl-1H-indol-3-yl)-amide]2-[(3-trifluoromethoxy-phenyl)-amide];

(1S,2S,5R)-3-Aza-bicyclo[3.1.0]hexane-2,3-dicarboxylic acid 3-[(1-carbamoyl-1H-indol-3-yl)-amide]2-[(3-trifluoromethoxy-phenyl)-amide];

(S)-Thiazolidine-2,3-dicarboxylic acid 3-[(1-carbamoyl-1H-indol-3-yl)-amide]2-[(2-fluoro-3-trifluoromethoxy-phenyl)-amide];

3-Chloro-5-{[(2S,4R)-1-(1-carbamoyl-1H-indol-3-ylcarbamoyl)-4-fluoro-pyrrolidine-2-carbonyl]-amino}-benzoic acid methyl ester;

3-({[(2S,4R)-1-(1-Carbamoyl-1H-indol-3-ylcarbamoyl)-4-fluoro-pyrrolidine-2-carbonyl]-amino}-methyl)-5-chloro-4-fluoro-benzoic acid;

(S)-2,5-Dihydro-pyrrole-1,2-dicarboxylic acid 1-[(1-carbamoyl-1H-indol-3-yl)-amide]2-[(3-trifluoromethoxy-phenyl)-amide];

(1R,2S,5S)-6-Oxa-3-aza-bicyclo[3.1.0]hexane-2,3-dicarboxylic acid 3-[(1-carbamoyl-1H-indol-3-yl)-amide]2-(3-chloro-2-fluoro-benzylamide);

(2S,4S)-4-Trifluoromethyl-pyrrolidine-1,2-dicarboxylic acid 1-[(1-carbamoyl-1H-indol-3-yl)-amide]2-(3-chloro-2-fluoro-benzylamide);

(1R,3S,5R)-2-Aza-bicyclo[3.1.0]hexane-2,3-dicarboxylic acid 3-[(3-bromo-phenyl)-amide]2-[(1-carbamoyl-1H-indol-3-yl)-amide];

(1S,5R)-2-Aza-bicyclo[3.1.0]hexane-1,2-dicarboxylic acid 2-[(1-carbamoyl-1H-indol-3-yl)-amide]1-(3-chloro-2-fluoro-benzylamide);

(2S,4R)-4-Fluoro-pyrrolidine-1,2-dicarboxylic acid 2-[(3-bromo-phenyl)-amide]1-[(1-carbamoyl-1H-indol-3-yl)-amide];

(R)-2,2-Dimethyl-thiazolidine-3,4-dicarboxylic acid 3-[(1-carbamoyl-1H-indol-3-yl)amide]-4-[(3-trifluoromethoxy-phenyl)-amide];

(S)-Pyrrolidine-1,2-dicarboxylic acid 1-[(1-carbamoyl-1H-indol-3-yl)-amide]2-[(4'-cyano-biphenyl-3-yl)-amide];

3-Bromo-5-{[(2S,4R)-1-(1-carbamoyl-1H-indol-3-ylcarbamoyl)-4-fluoro-pyrrolidine-2-carbonyl]-amino}-benzoic acid methyl ester;

(2S,4R)-4-Fluoro-pyrrolidine-1,2-dicarboxylic acid 1-[(1-carbamoyl-1H-indol-3-yl)-amide]2-[3-chloro-5-(2-dimethylamino-ethylcarba-moyl)-2-fluoro-benzylamide];

(1R,3S,5R)-2-Aza-bicyclo[3.1.0]hexane-2,3-dicarboxylic acid 2-[(1-carbamoyl-1H-indol-3-yl)-amide]3-[(5-chloro-thiophen-2-ylmethyl)-amide];

2-Bromo-4-{[(2S,4R)-1-(1-carbamoyl-1H-indol-3-ylcarbamoyl)-4-fluoro-pyrrolidine-2-carbonyl]-amino}-benzoic acid methyl ester;

(2S,4R)-4-Methyl-pyrrolidine-1,2-dicarboxylic acid 1-[(1-carbamoyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(1-carbamoyl-1H-indol-3-yl)-amide]3-[(6-ethyl-pyridin-2-yl)-amide];

3-Bromo-5-{[(2S,4R)-1-(1-carbamoyl-1H-indol-3-ylcarbamoyl)-4-fluoro-pyrrolidine-2-carbonyl]-amino}-benzoic acid;

(S)-Pyrrolidine-1,2-dicarboxylic acid 2-[(4-tert-butyl-thiazol-2-yl)amide]1-[(1-carbamoyl-1H-indol-3-yl)-amide];

(R)-Thiazolidine-3,4-dicarboxylic acid 3-[(1-carbamoyl-1H-indol-3-yl)-amide]4-[(3-trifluoromethoxy-phenyl)-amide];

(1R,3S,5R)-2-Aza-bicyclo[3.1.0]hexane-2,3-dicarboxylic acid 2-{[1-carbamoyl-5-(2-methoxy-ethoxy)-1H-indol-3-yl]-amide}3-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(6-ethyl-pyridin-2-yl)-amide];

(2S,4S)-4-Hydroxy-4-methyl-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(5-bromo-4-methyl-pyridin-3-yl)-amide];

(1R,3S,5R)-2-Aza-bicyclo[3.1.0]hexane-2,3-dicarboxylic acid 2-[(1-carbamoyl-1H-indol-3-yl)-amide]3-(3-chloro-2-fluoro-benzylamide);

(1R,2S,5S)-3-Aza-bicyclo[3.1.0]hexane-2,3-dicarboxylic acid 3-[(1-carbamoyl-1H-indol-3-yl)-amide]2-(3-chloro-benzylamide);

(2S,4R)-4-Fluoro-pyrrolidine-1,2-dicarboxylic acid 2-[(5-bromo-2-methyl-pyridin-3-yl)-amide]1-[(1-carbamoyl-1H-indol-3-yl)-amide];

(S)-Thiazolidine-2,3-dicarboxylic acid 3-[(1-carbamoyl-1H-indol-3-yl)-amide]2-(2,3-difluoro-benzylamide);

(S)-Pyrrolidine-1,2-dicarboxylic acid 1-[(1-carbamoyl-1H-indol-3-yl)-amide]2-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-[(5-bromo-pyridin-3-yl)-amide];

(1R,3S,5R)-2-Aza-bicyclo[3.1.0]hexane-2,3-dicarboxylic acid 2-[(1-carbamoyl-1H-indol-3-yl)-amide]3-[(3-fluoro-pyridin-2-yl)-amide];

(1R,3S,5R)-2-Azabicyclo[3.1.0]hexane-2,3-dicarboxylic acid 2-[(1-carbamoyl-1H-indol-3-yl)-amide]3-(2-fluoro-benzylamide);

(S)-Thiazolidine-2,3-dicarboxylic acid 3-[(1-carbamoyl-1H-indol-3-yl)-amide]2-(3-chloro-benzylamide);

(1R,3S,5R)-2-Aza-bicyclo[3.1.0]hexane-2,3-dicarboxylic acid 2-[(1-carbamoyl-1H-indol-3-yl)-amide]3-[(2-fluoro-3-trifluoromethoxy-phenyl)-amide];

(1R,3S,5R)-2-Aza-bicyclo[3.1.0]hexane-2,3-dicarboxylic acid 2-[(1-carbamoyl-1H-indol-3-yl)-amide]3-[(3-chloro-2-fluoro-phenyl)-amide];

(2S,3R)-3-Hydroxy-pyrrolidine-1,2-dicarboxylic acid 1-[(1-carbamoyl-1H-indol-3-yl)-amide]2-(3-chloro-benzylamide);

(S)-Thiazolidine-2,3-dicarboxylic acid 3-[(1-carbamoyl-1H-indol-3-yl)-amide]2-(3-chloro-2-fluoro-benzylamide);

(2S,5R)-5-Azidomethyl-pyrrolidine-1,2-dicarboxylic acid 1-[(1-carbamoyl-1H-indol-3-yl)-amide]2-[(3-trifluoromethoxy-phenyl)-amide];

(S)-5-Aza-spiro[2.4]heptane-5,6-dicarboxylic acid 5-[(1-carbamoyl-1H-indol-3-yl)-amide]6-(3-chloro-benzylamide);

(2S,4R)-4-Fluoro-4-hydroxymethyl-pyrrolidine-1,2-dicarboxylic acid 1-[(1-carbamoyl-1H-indol-3-yl)-amide]2-(3-chloro-2-fluoro-benzylamide);

(2S,4S)-4-Methyl-pyrrolidine-1,2-dicarboxylic acid 1-[(1-carbamoyl-1H-indol-3-yl)-amide]2-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-(3-chloro-benzylamide);

(1R,3S,5S)-5-Methoxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-[(3-fluoro-pyridin-4-yl)-amide];

(2S,3R)-3-Methoxy-pyrrolidine-1,2-dicarboxylic acid 1-[(1-carbamoyl-1H-indol-3-yl)-amide]2-(3-chloro-2-fluoro-benzylamide);

(S)-Piperidine-1,2-dicarboxylic acid 1-[(1-carbamoyl-1H-indol-3-yl)-amide]2-[(3-trifluoromethoxy-phenyl)-amide];

(2S,4S)-4-Cyano-pyrrolidine-1,2-dicarboxylic acid 1-[(1-carbamoyl-1H-indol-3-yl)-amide]2-[(2-fluoro-3-trifluoromethoxy-phenyl)-amide];

(2R,3S,4R)-4-Dimethylamino-3-fluoro-pyrrolidine-1,2-dicarboxylic acid 1-[(1-carbamoyl-1H-indol-3-yl)-amide]2-(3-chloro-2-fluoro-benzylamide);

(2R,3R)-3-Fluoro-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(3-trifluoromethoxy-phenyl)-amide];

(S)-2-Methyl-pyrrolidine-1,2-dicarboxylic acid 1-[(1-carbamoyl-1H-indol-3-yl)-amide]2-[(3-trifluoromethoxy-phenyl)-amide];

(2S,4R)-4-Fluoro-pyrrolidine-1,2-dicarboxylic acid 1-[(1-carbamoyl-1H-indol-3-yl)-amide]2-[(5-chloro-pyridin-3-yl)-amide];

(2S,4R)-4-Fluoro-pyrrolidine-1,2-dicarboxylic acid 1-[(1-carbamoyl-1H-indol-3-yl)-amide]2-[(5-bromo-pyridin-3-yl)-amide];

(1R,3S,5R)-2-Aza-bicyclo[3.1.0]hexane-2,3-dicarboxylic acid 2-[(1-carbamoyl-1H-indol-3-yl)-amide]3-(2,3-difluoro-benzylamide);

(2S,4R)-4-Hydroxy-4-hydroxymethyl-pyrrolidine-1,2-dicarboxylic acid 1-[(1-carbamoyl-1H-indol-3-yl)-amide]2-(3-chloro-2-fluoro-benzylamide);

(1S,2S,5R)-6-Oxa-3-aza-bicyclo[3.1.0]hexane-2,3-dicarboxylic acid 3-[(1-carbamoyl-1H-indol-3-yl)-amide]2-(3-chloro-2-fluoro-benzylamide);

3-Bromo-5-{[(S)-3-(1-carbamoyl-1H-indol-3-ylcarbamoyl)-thiazolidine-2-carbonyl]-amino}-benzoic acid methyl ester;

(S)-Pyrrolidine-1,2-dicarboxylic acid 1-[(1-carbamoyl-1H-indol-3-yl)-amide]2-[(2-methyl-5-phenyl-2H-pyrazol-3-yl)-amide];

(3S,5S)-1-(1-Carbamoyl-1H-indol-3-ylcarbamoyl)-5-(3-chloro-2-fluoro-benzylcarbamoyl)-pyrrolidine-3-carboxylic acid methyl ester;

4,5-Dihydro-pyrazole-1,5-dicarboxylic acid 1-[(1-carbamoyl-1H-indol-3-yl)-amide]5-(3-chloro-2-fluoro-benzylamide);

(2S,4S)-4-Hydroxy-4-hydroxymethyl-pyrrolidine-1,2-dicarboxylic acid 1-[(1-carbamoyl-1H-indol-3-yl)-amide]2-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-{[(S)-1-(3-chloro-2-fluoro-phenyl)-2-hydroxy-ethyl]-amide};

(2S,3S,4S)-4-Fluoro-3-methoxy-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-4-methyl-pyrrolidine-1,2-dicarboxylic acid 1-[(1-carbamoyl-1H-indol-3-yl)-amide]2-(3-chloro-2-fluoro-benzylamide);

(2S,3S,4S)-3-Acetylamino-4-fluoro-pyrrolidine-1,2-dicarboxylic acid 1-[(1-carbamoyl-1H-indol-3-yl)-amide]2-(3-chloro-2-fluoro-benzylamide);

(1S,2S,5R)-3-Azabicyclo[3.1.0]hexane-2,3-dicarboxylic acid 3-[(1-carbamoyl-1H-indol-3-yl)-amide]2-{[(S)-1-(3-chloro-2-fluoro-phenyl)-2-hydroxy-ethyl]-amide};

(2R,3S)-3-Fluoro-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-4-morpholin-4-ylmethyl-pyrrolidine-1,2-dicarboxylic acid 1-[(1-carbamoyl-1H-indol-3-yl)-amide]2-(3-chloro-2-fluoro-benzylamide);

(1R,2S,5S)-3-Aza-bicyclo[3.1.0]hexane-2,3-dicarboxylic acid 3-[(1-carbamoyl-1H-indol-3-yl)-amide]2-(3-chloro-2-fluoro-benzylamide);

(2R,3S,4R)-4-Acetylamino-3-fluoro-pyrrolidine-1,2-dicarboxylic acid 1-[(1-carbamoyl-1H-indol-3-yl)-amide]2-(3-chloro-2-fluoro-benzylamide);

(1R,2S,5S)-3-Azabicyclo[3.1.0]hexane-2,3-dicarboxylic acid 3-[(1-carbamoyl-1H-indol-3-yl)-amide]2-{[(S)-1-(3-chloro-2-fluoro-phenyl)-2-hydroxy-ethyl]-amide};

(2S,3R)-3-Hydroxy-pyrrolidine-1,2-dicarboxylic acid 1-[(1-carbamoyl-1H-indol-3-yl)-amide]2-(3-chloro-2-fluoro-benzylamide);

(1S,3S,5R)-5-Methoxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(5-fluoro-pyridin-3-ylmethyl)-amide];

(1R,3S,5R)-2-Aza-bicyclo[3.1.0]hexane-2,3-dicarboxylic acid 2-[(1-carbamoyl-6-methoxy-1H-indol-3-yl)-amide]3-(3-chloro-2-fluoro-benzylamide);

(1R,3S,5R)-2-Azabicyclo[3.1.0]hexane-2,3-dicarboxylic acid 3-{[(S)-1-(3-bromo-phenyl)-2-hydroxy-ethyl]-amide}2-[(1-carbamoyl-1H-indol-3-yl)-amide];

(1R,3S,5R)-2-Aza-bicyclo[3.1.0]hexane-2,3-dicarboxylic acid 2-[(1-carbamoyl-1H-indol-3-yl)-amide]3-[(2-fluoro-3-trifluoromethyl-phenyl)-amide];

3-{[(S)-1-(1-Carbamoyl-1H-indol-3-ylcarbamoyl)-pyrrolidine-2-carbonyl]-amino}-benzoic acid methyl ester;

(S)-Piperidine-1,2-dicarboxylic acid 1-[(1-carbamoyl-1H-indol-3-yl)-amide]2-(3-chloro-2-fluoro-benzylamide);

(2S,4S)-4-(Acetylamino-methyl)-4-fluoro-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-(2-fluoro-3-trifluoromethyl-benzylamide);

(1R,3S,5R)-2-Azabicyclo[3.1.0]hexane-2,3-dicarboxylic acid 2-[(1-carbamoyl-1H-indol-3-yl)-amide]3-{[(R)-1-(3-chloro-2-fluoro-phenyl)-3-hydroxy-propyl]-amide};

(2S,4S)-4-Fluoro-pyrrolidine-1,2-dicarboxylic acid 1-[(1-carbamoyl-1H-indol-3-yl)amide]2-[(3-trifluoromethoxy-phenyl)-amide];

(S)-Thiazolidine-2,3-dicarboxylic acid 3-[(1-carbamoyl-1H-indol-3-yl)-amide]2-(2,3-difluoro-4-methoxy-benzylamide);

(1R,3S,5R)-2Azabicyclo[3.1.0]hexane-2,3-dicarboxylic acid 2-[(1-carbamoyl-1H-indol-3-yl)amide]3-[(pyridin-3-ylmethyl)-amide];

(2S,3S)-3-Methyl-pyrrolidine-1,2-dicarboxylic acid 1-[(1-carbamoyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(1-carbamoyl-1H-indol-3-yl)-amide]3-[(5-chloropyridin-3-ylmethyl)-amide];

(2S,4R)-4-Fluoro-4-methyl-pyrrolidine-1,2-dicarboxylic acid 1-[(1-carbamoyl-1H-indol-3-yl)-amide]2-{[(R)-1-(3-chloro-2-fluoro-phenyl)-3-hydroxy-propyl]-amide};

(2S,4R)-4-Fluoro-pyrrolidine-1,2-dicarboxylic acid 1-[(1-carbamoyl-1H-indol-3-yl)-amide]2-[(3-fluoro-pyridin-4-ylmethyl)-amide];

(1R,2S,5S)-3-Aza-bicyclo[3.1.0]hexane-2,3-dicarboxylic acid 3-[(1-carbamoyl-1H-indol-3-yl)-amide]2-{[(S)-1-(3-chloro-2-fluoro-phenyl)-2-methoxy-ethyl]-amide};

(2S,4R)-4-Fluoro-pyrrolidine-1,2-dicarboxylic acid 1-[(1-carbamoyl-1H-indol-3-yl)-amide]2-[(3-fluoro-2-trifluoromethyl-pyridin-4-ylmethyl)-amide];

(S)-Pyrrolidine-1,2-dicarboxylic acid 1-[(1-carbamoyl-1H-indol-3-yl)-amide]2-[(3-sulfamoyl-phenyl)-amide];

(1R,3S,5R)-2-Aza-bicyclo[3.1.0]hexane-2,3-dicarboxylic acid 2-[(1-carbamoyl-1H-indol-3-yl)-amide]3-[(3-difluoromethoxy-phenyl)-amide];

(S)-Thiazolidine-2,3-dicarboxylic acid 3-[(1-carbamoyl-1H-indol-3-yl)-amide]2-(2,3-difluoro-5-methoxy-benzylamide);

(1R,3S,5R)-2-Aza-bicyclo[3.1.0]hexane-2,3-dicarboxylic acid 2-[(1-carbamoyl-1H-indol-3-yl)-amide]3-{[(S)-1-(3-chloro-2-fluoro-phenyl)-2-methoxy-ethyl]-amide};

(2S,4R)-4-Fluoro-pyrrolidine-1,2-dicarboxylic acid 1-[(1-carbamoyl-1H-indol-3-yl)-amide]2-[(5-chloro-pyridin-3-ylmethyl)-amide];

(S)-Pyrrolidine-1,2-dicarboxylic acid 1-[(1-carbamoyl-1H-indol-3-yl)-amide]2-[(6-ethyl-pyridin-2-yl)-amide];

(2S,4R)-4-Fluoro-4-methyl-pyrrolidine-1,2-dicarboxylic acid 1-[(1-carbamoyl-1H-indol-3-yl)-amide]2-{[(S)-1-(3-chloro-2-fluoro-phenyl)-2-hydroxy-ethyl]-amide};

(2S,4R)-4-Fluoro-pyrrolidine-1,2-dicarboxylic acid 1-[(1-carbamoyl-1H-indol-3-yl)-amide]2-(3-chloro-2-fluoro-5-methylcarbamoyl-benzylamide);

(2S,4S)-4-Fluoro-4-fluoromethyl-pyrrolidine-1,2-dicarboxylic acid 1-[(1-carbamoyl-1H-indol-3-yl)-amide]2-(3-chloro-2-fluoro-benzylamide);

1R,3S,5R)-2-Aza-bicyclo[3.1.0]hexane-2,3-dicarboxylic acid 2-[(1-carbamoyl-1H-indol-3-yl)-amide]3-[(3-fluoropyridin-2-ylmethyl)-amide];

(2S,4S)-4-Fluoro-4-morpholin-4-ylmethyl-pyrrolidine-1,2-dicarboxylic acid 1-[(1-carbamoyl-1H-indol-3-yl)-amide] 2-(3-chloro-2-fluoro-benzylamide);

3-({[(2S,4R)-1-(1-Carbamoyl-1H-indol-3-ylcarbamoyl)-4-fluoro-pyrrolidine-2-carbonyl]-amino}-methyl)-5-chloro-4-fluoro-benzoic acid methyl ester;

(1S,2S,5R)-3-Aza-bicyclo[3.1.0]hexane-2,3-dicarboxylic acid 3-[(1-carbamoyl-1H-indol-3-yl)-amide]2-{[(S)-1-(3-chloro-2-fluoro-phenyl)-2-methoxy-ethyl]-amide};

{[(2S,4R)-1-(1-Carbamoyl-1H-indol-3-ylcarbamoyl)-4-fluoro-pyrrolidine-2-carbonyl]-amino}-(3-chloro-phenyl)-acetic acid;

(1R,3S,5R)-2-Aza-bicyclo[3.1.0]hexane-2,3-dicarboxylic acid 2-[(1-carbamoyl-1H-indol-3-yl)-amide]3-[(5-chloropyridin-3-yl)-amide];

(2S,4R)-4-Fluoro-pyrrolidine-1,2-dicarboxylic acid 1-[(1-carbamoyl-1H-indol-3-yl)-amide]2-{[(S)-1-(3-chloro-2-fluoro-phenyl)-2-dimethylamino-ethyl]-amide};

(2S,4S)-4-Hydroxy-pyrrolidine-1,2-dicarboxylic acid 1-[(1-carbamoyl-1H-indol-3-yl)-amide]2-[(3-trifluoromethoxy-phenyl)-amide];

(2S,4R)-4-Fluoro-pyrrolidine-1,2-dicarboxylic acid 1-[(1-carbamoyl-1H-indol-3-yl)-amide]2-[3-chloro-2-fluoro-5-(morpholine-4-carbonyl)-benzylamide];

(1R,3S,5R)-2-Aza-bicyclo[3.1.0]hexane-2,3-dicarboxylic acid 2-[(1-carbamoyl-1H-indol-3-yl)-amide]3-[(3-methoxy-phenyl)-amide];

(2S,4R)-4-Fluoro-pyrrolidine-1,2-dicarboxylic acid 1-[(1-carbamoyl-1H-indol-3-yl)-amide]2-(3-chloro-5-diethylamino-2-fluoro-benzylamide);

(S)-Thiazolidine-2,3-dicarboxylic acid 3-[(1-carbamoyl-1H-indol-3-yl)-amide]2-{[(S)-1-(3-chloro-2-fluoro-phenyl)-2-hydroxy-ethyl]-amide};

(1R,3S,5R)-2-Aza-bicyclo[3.1.0]hexane-2,3-dicarboxylic acid 2-[(1-carbamoyl-1H-indol-3-yl)-amide]3-[(3-chlorophenyl)-amide];

(2S,4R)-4-Fluoro-pyrrolidine-1,2-dicarboxylic acid 1-[(1-carbamoyl-1H-indol-3-yl)-amide]2-[3-chloro-2-fluoro-5-(3-methoxy-azetidine-1-carbonyl)-benzylamide];

(2S,4R)-4-Cyano-pyrrolidine-1,2-dicarboxylic acid 1-[(1-carbamoyl-1H-indol-3-yl)-amide]2-[(3-trifluoromethoxy-phenyl)-amide];

(2S,3S)-3-Hydroxy-pyrrolidine-1,2-dicarboxylic acid 1-[(1-carbamoyl-1H-indol-3-yl)-amide]2-(3-chloro-benzylamide);

(1R,3S,5R)-2-Aza-bicyclo[3.1.0]hexane-2,3-dicarboxylic acid 3-benzylamide 2-[(1-carbamoyl-1H-indol-3-yl)-amide];

(2S,3R)-3-Hydroxy-pyrrolidine-1,2-dicarboxylic acid 1-[(1-carbamoyl-1H-indol-3-yl)-amide]2-[(5-chloro-thiophen-2-ylmethyl)-amide];

(2S,4S)-4-Hydroxymethyl-pyrrolidine-1,2-dicarboxylic acid 1-[(1-acetyl-1H-indol-3-yl)-amide]2-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-(2-fluoro-3-trifluoromethyl-benzylamide);

(S)-Thiazolidine-2,3-dicarboxylic acid 3-[(1-carbamoyl-1H-indol-3-yl)-amide]2-(2,3-difluoro-6-methoxy-benzylamide);

(S)-Thiazolidine-2,3-dicarboxylic acid 3-[(1-carbamoyl-1H-indol-3-yl)-amide]2-[(2-chloro-thiazol-5-ylmethyl)-amide];

(S)-Thiazolidine-2,3-dicarboxylic acid 3-[(1-carbamoyl-5-fluoro-1H-indol-3-yl)-amide]2-(3-chloro-2-fluoro-benzylamide);

(1R,3S,5S)-5-Hydroxymethyl-2-aza-bicyclo[3.1.0]hexane-2,3-dicarboxylic acid 3-(3-chloro-2-fluoro-benzylamide) 2-[(1-methylcarbamoyl-1H-indol-3-yl)-amide];

(S)-4-Methylene-pyrrolidine-1,2-dicarboxylic acid 1-[(1-carbamoyl-1H-indol-3-yl)-amide]2-[(3-trifluoromethoxy-phenyl)-amide];

(S)-Thiazolidine-2,3-dicarboxylic acid 3-[(1-carbamoyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(5-allyloxy-1-carbamoyl-1H-indol-3-yl)-amide]3-(3-chloro-2-fluoro-benzylamide);

S)-Pyrrolidine-1,2-dicarboxylic acid 1-[(1-carbamoyl-6-methyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 3-{[(S)-1-(3-chloro-2-fluoro-phenyl)-2-methoxy-ethyl]-amide}2-[(1-methylcarbamoyl-1H-indol-3-yl)-amide];

(S)-Pyrrolidine-1,2-dicarboxylic acid 1-[(1-acetyl-1H-indol-3-yl)-amide]2-[(3-trifluoromethoxy-phenyl)-amide];

3-Bromo-5-{[(1R,3S,5R)-2-(1-carbamoyl-1H-indol-3-yl-carbamoyl)-2-aza-bicyclo[3.1.0]hexane-3-carbonyl]-amino}-benzoic acid methyl ester;

(2S,5R)-5-Phenyl-pyrrolidine-1,2-dicarboxylic acid 1-[(1-carbamoyl-1H-indol-3-yl)-amide]2-[(3-trifluoromethoxy-phenyl)-amide;

(2S,4R)-4-Fluoro-pyrrolidine-1,2-dicarboxylic acid 1-[(1-carbamoyl-1H-indol-3-yl)-amide]2-[(2-fluoro-3-trifluoromethoxy-phenyl)-amide];

(1R,3S,5S)-5-Hydroxymethyl-2-aza-bicyclo[3.1.0]hexane-2,3-dicarboxylic acid 2-[(1-acetyl-1H-indol-3-yl)-amide] 3-(3-chloro-2-fluoro-benzylamide);

(1-Carbamoyl-3-{[(1R,3S,5R)-3-(3-trifluoromethoxy-phenylcarbamoyl)-2-aza-bicyclo[3.1.0]hexane-2-carbonyl]-amino}-1H-indol-6-yloxy)-acetic acid methyl ester;

(2S,4R)-4-Fluoro-pyrrolidine-1,2-dicarboxylic acid 1-[(1-carbamoyl-1H-indol-3-yl)-amide]2-(3-chloro-5-dimethylcarbamoyl-2-fluoro-benzylamide);

2-Bromo-4-{[(2S,4R)-1-(1-carbamoyl-1H-indol-3-ylcarbamoyl)-4-fluoro-pyrrolidine-2-carbonyl]-amino}-benzoic acid;

(S)-Pyrrolidine-1,2-dicarboxylic acid 2-[(5-tert-butyl-2-methyl-2H-pyrazol-3-yl)-amide]1-[(1-carbamoyl-1H-indol-3-yl)-amide];

(2S,4R)-4-Fluoro-pyrrolidine-1,2-dicarboxylic acid 1-[(6-allyloxy-1-carbamoyl-1H-indol-3-yl)-amide]2-(3-chloro-2-fluoro-benzylamide);

(1R,3S,5R)-2-Aza-bicyclo[3.1.0]hexane-2,3-dicarboxylic acid 2-[(1-acetyl-1H-indol-3-yl)-amide]3-{[(S)-1-(3-chloro-2-fluoro-phenyl)-2-dimethylamino-ethyl]-amide};

(S)-Pyrrolidine-1,2-dicarboxylic acid 1-[(1-methylcarbamoyl-1H-indol-3-yl)-amide]2-[(3-trifluoromethoxy-phenyl)-amide];

(2S,3R)-3-Hydroxy-pyrrolidine-1,2-dicarboxylic acid 1-[(1-carbamoyl-1H-indol-3-yl)-amide]2-[(2-chloro-thiazol-5-ylmethyl)-amide];

(1R,3S,5S)-5-Methoxymethyl-2-aza-bicyclo[3.1.0]hexane-2,3-dicarboxylic acid 3-(3-chloro-2-fluoro-benzylamide) 2-[(1-methylcarbamoyl-1H-indol-3-yl)-amide];

(1R,3S,5R)-2-Aza-bicyclo[3.1.0]hexane-2,3-dicarboxylic acid 2-[(1-carbamoyl-1H-indol-3-yl)-amide]3-[(3-isopropyl-phenyl)-amide];

(S)-Pyrrolidine-1,2-dicarboxylic acid 1-[(6-bromo-1-carbamoyl-1H-indol-3-yl)-amide]2-[(3-trifluoromethoxy-phenyl)-amide];

(1R,3S,5R)-2-Azabicyclo[3.1.0]hexane-2,3-dicarboxylic acid 3-{[(S)-1-(3-chloro-2-fluoro-phenyl)-2-hydroxy-ethyl]-amide}2-[(1-methylcarbamoyl-1H-indol-3-yl)-amide];

(S)-Pyrrolidine-1,2-dicarboxylic acid 1-[(1-carbamoyl-6-ethyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 3-{[(S)-1-(3-chloro-2-fluoro-phenyl)-2-dimethylamino-ethyl]-amide}2-[(1-methylcarbamoyl-1H-indol-3-yl)-amide];

(S)-Pyrrolidine-1,2-dicarboxylic acid 1-[(1-carbamoyl-6-trifluoromethyl-1H-indol-3-yl)-amide]2-[(3-trifluoromethoxy-phenyl)-amide];

(S)-Pyrrolidine-1,2-dicarboxylic acid 1-[(1-carbamoyl-6-chloro-1H-indol-3-yl)-amide]2-[(3-trifluoromethoxy-phenyl)-amide];

(2S,4R)-4-Fluoro-pyrrolidine-1,2-dicarboxylic acid 1-[(1-carbamoyl-5-methoxy-1H-indol-3-yl)-amide]2-(3-chloro-2-fluoro-benzylamide);

(S)-Thiazolidine-2,3-dicarboxylic acid 3-[(1-carbamoyl-1H-indol-3-yl)-amide]2-[(5-chloro-thiophen-2-ylmethyl)-amide];

(1R,3S,5R)-2-Aza-bicyclo[3.1.0]hexane-2,3-dicarboxylic acid 2-[(1-carbamoyl-5-fluoro-1H-indol-3-yl)-amide]3-(3-chloro-2-fluoro-benzylamide);

(1R,3S,5R)-2-Aza-bicyclo[3.1.0]hexane-2,3-dicarboxylic acid 2-[(1-carbamoyl-1H-indol-3-yl)-amide]3-[(2-chloro-thiazol-5-ylmethyl)-amide];

(2S,4R)-4-Fluoro-pyrrolidine-1,2-dicarboxylic acid 1-[(1-carbamoyl-1H-indol-3-yl)-amide]2-{[(S)-1-(3-chloro-phenyl)-2,2,2-trifluoro-ethyl]amide};

(1R,3S,5R)-2-Aza-bicyclo[3.1.0]hexane-2,3-dicarboxylic acid 2-[(1-carbamoyl-6-fluoro-1H-indol-3-yl)-amide]3-[(3-trifluoromethoxy-phenyl)-amide];

(2S,4R)-4-Fluoro-pyrrolidine-1,2-dicarboxylic acid 1-[(1-carbamoyl-5-methoxy-1H-indol-3-yl)-amide]2-[(2-fluoro-3-trifluoromethoxy-phenyl)-amide];

(S)-Azetidine-1,2-dicarboxylic acid 1-[(1-carbamoyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(1-carbamoyl-5-methoxy-1H-indol-3-yl)-amide] 3-(3-chloro-2-fluoro-benzylamide);

(S)-4,4-Difluoro-pyrrolidine-1,2-dicarboxylic acid 1-[(1-carbamoyl-1H-indol-3-yl)-amide]2-(3-chloro-2-fluoro-benzylamide);

(S)-5,5-Dimethyl-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-pyrrolidine-1,2-dicarboxylic acid 1-{[1-carbamoyl-5-(2-methoxy-ethoxy)-1H-indol-3-yl]-amide}2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(3-fluoro-4-methyl-pyridin-2-ylmethyl)-amide];

(2S,4R)-4-Fluoro-pyrrolidine-1,2-dicarboxylic acid 1-[(1-carbamoyl-1H-indol-3-yl)-amide]2-[(5-trifluoromethyl-pyridin-3-ylmethyl)-amide];

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yl)-acetic acid ethyl ester;

(1S,5R)-2-Aza-bicyclo[3.1.0]hexane-1,2-dicarboxylic acid 2-[(1-carbamoyl-1H-indol-3-yl)-amide]1-[(3-trifluoromethoxy-phenyl)amide];

(2S,4R)-4-Fluoro-pyrrolidine-1,2-dicarboxylic acid 1-[(1-carbamoyl-6-difluoromethoxy-1H-indol-3-yl)-amide]2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-[(2-methoxy-pyridin-4-yl)-amide];

(S)-Thiazolidine-2,3-dicarboxylic acid 3-[(1-carbamoyl-1H-indol-3-yl)-amide]2-[(5-chloro-pyridin-3-yl)-amide];

(1R,3S,5R)-2-Aza-bicyclo[3.1.0]hexane-2,3-dicarboxylic acid 2-[(6-allyloxy-1-carbamoyl-1H-indol-3-yl)-amide]3-(3-chloro-2-fluoro-benzylamide);

(2S,4S)-4-Hydroxymethyl-pyrrolidine-1,2-dicarboxylic acid 1-[(1-carbamoyl-1H-indol-3-yl)-amide]2-(3-chloro-2-fluoro-benzylamide);

(S)-Pyrrolidine-1,2-dicarboxylic acid 1-[(6-benzyloxy-1-carbamoyl-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(1-carbamoyl-1H-indol-3-yl)-amide]3-{[(S)-1-(3-chloro-2-fluoro-phenyl)-2-dimethylamino-ethyl]-amide};

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid ethyl ester;

(2S,4R)-4-Methoxy-pyrrolidine-1,2-dicarboxylic acid 1-[(1-carbamoyl-1H-indol-3-yl)-amide]2-[(3-trifluoromethoxy-phenyl)-amide];

(2S,4R)-4-Fluoro-pyrrolidine-1,2-dicarboxylic acid 2-[(2-tert-butyl-pyridin-4-yl)-amide]1-[(1-carbamoyl-1H-indol-3-yl)-amide];

(1-Carbamoyl-3-{[(2S,4R)-2-(3-chloro-2-fluoro-benzylcarbamoyl)-4-fluoro-4-methyl-pyrrolidine-1-carbonyl]-amino}-1H-indol-5-yloxy)-acetic acid methyl ester;

(2S,4R)-4-Fluoro-pyrrolidine-1,2-dicarboxylic acid 1-[(1-carbamoyl-1H-indol-3-yl)-amide]2-{[(R)-1-(3-chloro-phenyl)-2,2,2-trifluoro-ethyl]amide};

(1R,3S,5R)-2-Aza-bicyclo[3.1.0]hexane-2,3-dicarboxylic acid 2-[(1-carbamoyl-1H-indol-3-yl)-amide]3-{[(S)-1-(3-chloro-phenyl)-2-hydroxy-ethyl]-amide};

(S)-Thiazolidine-2,3-dicarboxylic acid 3-[(1-carbamoyl-1H-indol-3-yl)-amide]2-[(5-bromo-pyridin-3-yl)-amide];

(2S,4R)-4-Fluoro-pyrrolidine-1,2-dicarboxylic acid 1-[(1-carbamoyl-1H-indol-3-yl)-amide]2-[3-chloro-2-fluoro-5-(4-methyl-piperazine-1-carbonyl)-benzylamide];

(2S,4R)-4-Fluoro-pyrrolidine-1,2-dicarboxylic acid 1-[(1-carbamoyl-1H-indol-3-yl)-amide]2-[(3-fluoro-pyridin-4-yl)-amide];

(S)-Pyrrolidine-1,2-dicarboxylic acid 1-[(1-carbamoyl-1H-indol-3-yl)-amide]2-[(3-carbamoyl-phenyl)-amide];

(S)-Pyrrolidine-1,2-dicarboxylic acid 1-[(1-carbamoyl-1H-indol-3-yl)-amide]2-[(3-methanesulfonyl-phenyl)-amide];

(2S,4R)-4-Fluoro-pyrrolidine-1,2-dicarboxylic acid 1-[(1-carbamoyl-1H-indol-3-yl)-amide]2-[(6-chloro-chroman-4-yl)-amide] (mixture of 2 diastereoisomers);

(2S,4R)-4-Fluoro-pyrrolidine-1,2-dicarboxylic acid 1-[(1-carbamoyl-1H-indol-3-yl)-amide]2-[(3-fluoro-pyridin-2-yl)-amide];

(2S,4S)-4-Dimethylaminomethyl-4-fluoro-pyrrolidine-1,2-dicarboxylic acid 1-[(1-carbamoyl-1H-indol-3-yl)-amide]2-(3-chloro-2-fluoro-benzylamide);

(2S,4R)-4-Fluoro-pyrrolidine-1,2-dicarboxylic acid 1-[(1-carbamoyl-1H-indol-3-yl)-amide]2-{3-chloro-5-[(2-dimethylamino-ethyl)-methyl-amino]-2-fluoro-benzylamide};

(1R,3S,5R)-2-Aza-bicyclo[3.1.0]hexane-2,3-dicarboxylic acid 3-[(3-tert-butyl-phenyl)-amide]2-[(1-carbamoyl-1H-indol-3-yl)-amide];

(2S,4S)-4-Hydroxy-pyrrolidine-1,2-dicarboxylic acid 1-[(1-carbamoyl-1H-indol-3-yl)-amide]2-(3-chloro-2-fluoro-benzylamide);

(S)-4,4-Difluoro-pyrrolidine-1,2-dicarboxylic acid 1-[(1-carbamoyl-1H-indol-3-yl)-amide]2-[(3-trifluoromethoxy-phenyl)-amide];

3-Bromo-5-{[(2S,4R)-1-(1-carbamoyl-1H-indol-3-ylcarbamoyl)-4-fluoro-pyrrolidine-2-carbonyl]-amino}-4-fluoro-benzoic acid ethyl ester;

(1R,3S,5R)-2-Aza-bicyclo[3.1.0]hexane-2,3-dicarboxylic acid 2-[(1-carbamoyl-1H-indol-3-yl)-amide]3-[(3-trifluoromethoxy-phenyl)-amide];

(S)-Pyrrolidine-1,2-dicarboxylic acid 1-[(5-allyloxy-1-carbamoyl-1H-indol-3-yl)-amide]2-[(3-trifluoromethoxy-phenyl)-amide];

(2S,5R)-5-Methyl-pyrrolidine-1,2-dicarboxylic acid 1-[(1-carbamoyl-1H-indol-3-yl)-amide]2-[(3-trifluoromethoxy-phenyl)-amide];

(2S,5S)-5-Methyl-pyrrolidine-1,2-dicarboxylic acid 1-[(1-carbamoyl-1H-indol-3-yl)-amide]2-[(3-trifluoromethoxy-phenyl)-amide];

(2S,5R)-5-Ethyl-pyrrolidine-1,2-dicarboxylic acid 1-[(1-carbamoyl-1H-indol-3-yl)-amide]2-[(3-trifluoromthoxy-phenyl)-amide];

3-Chloro-5-{[(2S,4R)-1-(1-carbamoyl-1H-indol-3-ylcarbamoyl)-4-fluoro-pyrrolidine-2-carbonyl]-amino}-benzoic acid;

3-Bromo-5-{[(1R,3S,5R)-2-(1-carbamoyl-1H-indol-3-ylcarbamoyl)-2-aza-bicyclo[3.1.0]hexane-3-carbonyl]-amino}-benzoic acid;

3-Bromo-5-{[(S)-3-(1-carbamoyl-1H-indol-3-ylcarbamoyl)-thiazolidine-2-carbonyl]-amino}-benzoic acid;

3-Bromo-5-{[(1R,3S,5R)-2-(1-carbamoyl-5-methoxy-1H-indol-3-ylcarbamoyl)-2-aza-bicyclo[3.1.0]hexane-3-carbonyl]-amino}-benzoic acid;

3-Bromo-5-{[(2S,4R)-1-(1-carbamoyl-1H-indol-3-ylcarbamoyl)-4-fluoro-pyrrolidine-2-carbonyl]-amino}-4-fluoro-benzoic acid;

(1R,3S,5R)-2-Aza-bicyclo[3.1.0]hexane-2,3-dicarboxylic acid 3-{[3-bromo-5-(1H-tetrazol-5-yl)-phenyl]-amide}2-[(1-carbamoyl-1H-indol-3-yl)-amide];

(1R,3S,5R)-2-Aza-bicyclo[3.1.0]hexane-2,3-dicarboxylic acid 3-{[3-bromo-5-(1-tert-butyl-1H-tetrazol-5-yl)-phenyl]-amide}2-[(1-carbamoyl-1H-indol-3-yl)-amide];

(2S,4R)-4-Fluoro-pyrrolidine-1,2-dicarboxylic acid 1-[(1-carbamoyl-1H-indol-3-yl)-amide]2-[3-chloro-2-fluoro-5-(1H-tetrazol-5-yl)-benzylamide];

(2S,4R)-4-Fluoro-pyrrolidine-1,2-dicarboxylic acid 2-[5-(1-tert-butyl-1H-tetrazol-5-yl)-3-chloro-2-fluoro-benzylamide]1-[(1-carbamoyl-1H-indol-3-yl)-amide];

(2R,3S)-3-Fluoro-pyrrolidine-1,2-dicarboxylic acid 1-[(1-carbamoyl-1H-indol-3-yl)-amide]2-(3-chloro-benzylamide);

(2R,3R)-3-Fluoro-pyrrolidine-1,2-dicarboxylic acid 1-[(1-carbamoyl-1H-indol-3-yl)-amide]2-(3-chloro-benzylamide);

(2S,5R)-5-Methyl-pyrrolidine-1,2-dicarboxylic acid 1-[(1-carbamoyl-1H-indol-3-yl)-amide]2-(3-chloro-2-fluoro-benzylamide);

(2S,5R)-5-Ethyl-pyrrolidine-1,2-dicarboxylic acid 1-[(1-carbamoyl-1H-indol-3-yl)-amide]2-(3-chloro-2-fluoro-benzylamide);

(2S,4R)-4-Hydroxymethyl-pyrrolidine-1,2-dicarboxylic acid 1-[(1-carbamoyl-1H-indol-3-yl)-amide]2-(3-chloro-2-fluoro-benzylamide);

(3S,5S)-1-(1-Carbamoyl-1H-indol-3-ylcarbamoyl)-5-(3-chloro-2,6-difluoro-benzylcarbamoyl)-pyrrolidine-3-carboxylic acid methyl ester;

(3S,5S)-1-(1-Carbamoyl-1H-indol-3-ylcarbamoyl)-5-(3-chloro-2,6-difluoro-benzylcarbamoyl)-pyrrolidine-3-carboxylic acid;

(2S,4S)-4-Hydroxymethyl-pyrrolidine-1,2-dicarboxylic acid 2-(3-bromo-2-fluoro-benzylamide) 1-[(1-carbamoyl-1H-indol-3-yl)-amide];

(2S,4S)-4-Fluoro-4-hydroxymethyl-pyrrolidine-1,2-dicarboxylic acid 1-[(1-carbamoyl-1H-indol-3-yl)-amide]2-(3-chloro-2-fluoro-benzylamide);

(1S,3S,5R)-5-Hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide);

(1R,3S,5S)-5-Hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide);

(2S,4S)-4-Difluoromethyl-pyrrolidine-1,2-dicarboxylic acid 1-[(1-carbamoyl-1H-indol-3-yl)-amide]2-(3-chloro-2-fluoro-benzylamide);

(2S,5R)-5-Hydroxymethyl-pyrrolidine-1,2-dicarboxylic acid 1-[(1-carbamoyl-1H-indol-3-yl)-amide]2-[(3-trifluoromethoxy-phenyl)-amide];

4,5-Dihydro-pyrazole-1,5-dicarboxylic acid 1-[(1-carbamoyl-1H-indol-3-yl)-amide]5-(3-chloro-benzylamide);

(S)-4,5-Dihydro-pyrazole-1,5-dicarboxylic acid 1-[(1-carbamoyl-1H-indol-3-yl)-amide]5-(3-chloro-2-fluoro-benzylamide);

(R)-4,5-Dihydro-pyrazole-1,5-dicarboxylic acid 1-[(1-carbamoyl-1H-indol-3-yl)-amide]5-(3-chloro-2-fluoro-benzylamide);

(2S,3R)-3-Hydroxy-pyrrolidine-1,2-dicarboxylic acid 1-[(1-carbamoyl-1H-indol-3-yl)-amide]2-{[(R)-1-(3-chloro-2-fluoro-phenyl)-ethyl]-amide};

(2S,3R)-3-Hydroxy-pyrrolidine-1,2-dicarboxylic acid 1-[(1-carbamoyl-1H-indol-3-yl)-amide]2-{[(S)-1-(3-chloro-2-fluoro-phenyl)-ethyl]-amide};

(S)-Pyrrolidine-1,2-dicarboxylic acid 1-{[1-(2-hydroxy-acetyl)-1H-indol-3-yl]amide}2-[(3-trifluoromethoxy-phenyl)-amide];

(S)-Pyrrolidine-1,2-dicarboxylic acid 1-[(1-acetyl-6-cyano-1H-indol-3-yl)-amide]2-[(3-trifluoromethoxy-phenyl)-amide];

(2S,4R)-4-Fluoro-pyrrolidine-1,2-dicarboxylic acid 1-[(1-acetyl-6-difluoromethoxy-1H-indol-3-yl)-amide]2-(3-chloro-2-fluoro-benzylamide);

(S)-Pyrrolidine-1,2-dicarboxylic acid 1-[(1-carbamoyl-6-hydroxy-1H-indol-3-yl)-amide]2-[(3-trifluoromethoxy-phenyl)-amide];

(S)-Pyrrolidine-1,2-dicarboxylic acid 1-[(1-carbamoyl-5-hydroxy-1H-indol-3-yl)-amide]2-[(3-trifluoromethoxy-phenyl)-amide];

(1R,3S,5R)-2-Aza-bicyclo[3.1.0]hexane-2,3-dicarboxylic acid 2-[(1-carbamoyl-5-hydroxy-1H-indol-3-yl)-amide]3-(3-chloro-2-fluoro-benzylamide);

(1R,3S,5R)-2-Aza-bicyclo[3.1.0]hexane-2,3-dicarboxylic acid 2-[(1-carbamoyl-5-hydroxy-1H-indol-3-yl)-amide]3-(2-fluoro-benzylamide);

(1R,3S,5R)-2-Aza-bicyclo[3.1.0]hexane-2,3-dicarboxylic acid 2-[(1-carbamoyl-5-cyanomethoxy-1H-indol-3-yl)-amide]3-(3-chloro-2-fluoro-benzylamide);

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-acetic acid;

(1-Carbamoyl-3-{[(2S,4R)-2-(3-chloro-2-fluoro-benzylcarbamoyl)-4-fluoro-4-methyl-pyrrolidine-1-carbonyl]-amino}-1H-indol-5-yloxy)-acetic acid;

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yloxy)-acetic acid;

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yl)-acetic acid;

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid;

(1R,3S,5R)-2-Aza-bicyclo[3.1.0]hexane-2,3-dicarboxylic acid 2-{[1-carbamoyl-5-(2-hydroxy-ethoxy)-1H-indol-3-yl]-amide}3-(3-chloro-2-fluoro-benzylamide);

(S)-Thiazolidine-2,3-dicarboxylic acid 3-{[1-carbamoyl-5-(2-hydroxy-ethoxy)-1H-indol-3-yl]-amide}2-(3-chloro-2-fluoro-benzylamide);

(1R,3S,5R)-2-Aza-bicyclo[3.1.0]hexane-2,3-dicarboxylic acid 2-{[1-carbamoyl-5-(2-hydroxy-ethoxy)-1H-indol-3-yl]-amide}3-[(3-trifluoromethoxy-phenyl)-amide];

(1S,2S,5R)-3-Aza-bicyclo[3.1.0]hexane-2,3-dicarboxylic acid 3-{[1-carbamoyl-5-(2-hydroxy-ethoxy)-1H-indol-3-yl]-amide}2-(3-chloro-2-fluoro-benzylamide);

(2S,4R)-4-Fluoro-4-methyl-pyrrolidine-1,2-dicarboxylic acid 1-{[1-carbamoyl-5-(2-hydroxy-ethoxy)-1H-indol-3-yl]-amide}2-(3-chloro-2-fluoro-benzylamide);

(1R,3S,5R)-2-Aza-bicyclo[3.1.0]hexane-2,3-dicarboxylic acid 2-{[1-carbamoyl-6-(2-hydroxy-ethyl)-1H-indol-3-yl]-amide}3-(3-chloro-2-fluoro-benzylamide);

(1R,3S,5R)-2-Aza-bicyclo[3.1.0]hexane-2,3-dicarboxylic acid 2-{[1-carbamoyl-5-(2-hydroxy-ethyl)-1H-indol-3-yl]-amide}3-(3-chloro-2-fluoro-benzylamide);

(1R,3S,5R)-2-Aza-bicyclo[3.1.0]hexane-2,3-dicarboxylic acid 2-{[1-carbamoyl-5-(2-hydroxy-2-methyl-propoxy)-1H-indol-3-yl]-amide}3-(3-chloro-2-fluoro-benzylamide);

(1R,3S,5R)-2-Aza-bicyclo[3.1.0]hexane-2,3-dicarboxylic acid 2-{[1-carbamoyl-5-(2-dimethylamino-ethoxy)-1H-indol-3-yl]-amide}3-(3-chloro-2-fluoro-benzylamide);

(1R,3S,5R)-2-Aza-bicyclo[3.1.0]hexane-2,3-dicarboxylic acid 2-{[1-carbamoyl-5-(2-pyrrolidin-1-yl-ethoxy)-1H-indol-3-yl]-amide}3-(3-chloro-2-fluoro-benzylamide);

(1R,3S,5R)-2-Aza-bicyclo[3.1.0]hexane-2,3-dicarboxylic acid 2-{[1-carbamoyl-5-(2-imidazol-1-yl-ethoxy)-1H-indol-3-yl]-amide}3-(3-chloro-2-fluoro-benzylamide);

(1-Carbamoyl-3-{[(1R,3S,5R)-3-(2-fluoro-benzylcarbamoyl)-2-aza-bicyclo[3.1.0]hexane-2-carbonyl]-amino}-1H-indol-5-yloxy)-acetic acid tert-butyl ester;

(1-Carbamoyl-3-{[(1R,3S,5R)-3-(2-fluoro-benzylcarbamoyl)-2-aza-bicyclo[3.1.0]hexane-2-carbonyl]-amino}-1H-indol-5-yloxy)-acetic acid;

(1R,3S,5R)-2-Aza-bicyclo[3.1.0]hexane-2,3-dicarboxylic acid 2-[(1-carbamoyl-6-hydroxy-1H-indol-3-yl)-amide]3-(3-chloro-2-fluoro-benzylamide);

(2S,4R)-4-Fluoro-pyrrolidine-1,2-dicarboxylic acid 1-[(1-carbamoyl-6-hydroxy-1H-indol-3-yl)-amide]2-(3-chloro-2-fluoro-benzylamide);

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yloxy)-acetic acid methyl ester;

(1R,3S,5R)-2-Aza-bicyclo[3.1.0]hexane-2,3-dicarboxylic acid 2-{[1-carbamoyl-6-(2-hydroxy-ethoxy)-1H-indol-3-yl]-amide}3-(3-chloro-2-fluoro-benzylamide);

(2S,4S)-4-Amino-pyrrolidine-1,2-dicarboxylic acid 1-[(1-carbamoyl-1H-indol-3-yl)-amide]2-[(3-trifluoromethoxy-phenyl)-amide];

(2S,3S,4R)-4-Amino-3-methoxy-pyrrolidine-1,2-dicarboxylicacid 1-[(1-carbamoyl-1H-indol-3-yl)-amide]2-(3-chloro-2-fluoro-benzylamide);

(2S,4S)-4-Amino-pyrrolidine-1,2-dicarboxylic acid 1-[(6-benzyloxy-1-carbamoyl-1H-indol-3-yl)-amide]2-[(3-trifluoromethoxy-phenyl)-amide];

(S)-piperazine-1,2-dicarboxylic acid 1-[(1-carbamoyl-1H-indol-3-yl)-amide]2-(3-chloro-benzylamide);

(S)-Pyrrolidine-1,2-dicarboxylic acid 2-[(4'-aminomethyl-biphenyl-3-yl)-amide]1-[(1-carbamoyl-1H-indol-3-yl)-amide];

(S)-Pyrrolidine-1,2-dicarboxylic acid 2-[(4'-aminomethyl-2'-fluoro-biphenyl-3-yl)-amide]1-[(1-carbamoyl-1H-indol-3-yl)-amide];

(2S,5R)-5-Aminomethyl-pyrrolidine-1,2-dicarboxylic acid 1-[(1-carbamoyl-1H-indol-3-yl)-amide]2-[(3-trifluoromethoxy-phenyl)-amide];

(2S,4R)-4-Aminomethyl-pyrrolidine-1,2-dicarboxylic acid 1-[(1-carbamoyl-1H-indol-3-yl)-amide]2-[(3-trifluoromethoxy-phenyl)-amide];

(2S,4S)-4-Aminomethyl-pyrrolidine-1,2-dicarboxylic acid 1-[(1-carbamoyl-1H-indol-3-yl)-amide]2-[(3-trifluoromethoxy-phenyl)-amide];

(2S,4R)-4-Aminomethyl-pyrrolidine-1,2-dicarboxylic acid 1-[(1-carbamoyl-1H-indol-3-yl)-amide]2-(3-chloro-2-fluoro-benzylamide);

(2S,4R)-4-Dimethylaminomethyl-pyrrolidine-1,2-dicarboxylic acid 1-[(1-carbamoyl-1H-indol-3-yl)-amide]2-(3-chloro-2-fluoro-benzylamide);

(2S,4S)-4-Aminomethyl-4-hydroxy-pyrrolidine-1,2-dicarboxylic acid 1-[(1-carbamoyl-1H-indol-3-yl)-amide]2-(3-chloro-2-fluoro-benzylamide);

(2S,4R)-4-Aminomethyl-4-fluoro-pyrrolidine-1,2-dicarboxylic acid 1-[(1-carbamoyl-1H-indol-3-yl)-amide]2-(3-chloro-2-fluoro-benzylamide);

(2S,4S)-4-Aminomethyl-4-fluoro-pyrrolidine-1,2-dicarboxylic acid 1-[(1-carbamoyl-1H-indol-3-yl)-amide]2-(3-chloro-2-fluoro-benzylamide);

(2S,4S)-4-Fluoro-4-formylaminomethyl-pyrrolidine-1,2-dicarboxylic acid 1-[(1-carbamoyl-1H-indol-3-yl)-amide]2-(3-chloro-2-fluoro-benzylamide);

(2S,4S)-4-Aminomethyl-4-fluoro-pyrrolidine-1,2-dicarboxylic acid 1-[(1-carbamoyl-1H-indol-3-yl)-amide]2-(3-chloro-2,6-difluoro-benzylamide);

(2S,4S)-4-Aminomethyl-4-fluoro-pyrrolidine-1,2-dicarboxylic acid 1-[(1-acetyl-1H-indol-3-yl)-amide]2-(3-chloro-2-fluoro-benzylamide);

(2S,4S)-4-Aminomethyl-4-fluoro-pyrrolidine-1,2-dicarboxylic acid 2-{[(S)-1-(3-bromo-phenyl)-2-fluoro-ethyl]-amide}1-[(1-carbamoyl-1H-indol-3-yl)-amide];

(2S,4S)-4-Aminomethyl-4-fluoro-pyrrolidine-1,2-dicarboxylic acid 1-[(1-carbamoyl-1H-indol-3-yl)-amide]2-[(3-trifluoromethoxy-phenyl)-amide];

(2S,3S,4S)-3-Amino-4-fluoro-pyrrolidine-1,2-dicarboxylic acid 1-[(1-acetyl-1H-indol-3-yl)-amide]2-(3-chloro-2-fluoro-benzylamide);

(2S,3R,4S)-4-Amino-3-hydroxy-pyrrolidine-1,2-dicarboxylic acid 1-[(1-carbamoyl-1H-indol-3-yl)-amide]2-(3-chloro-2-fluoro-benzylamide);

(2S,3R)-3-Amino-pyrrolidine-1,2-dicarboxylic acid 1-[(1-carbamoyl-1H-indol-3-yl)-amide]2-(3-chloro-2-fluoro-benzylamide);

(2S,3R)-3-Amino-pyrrolidine-1,2-dicarboxylic acid 1-[(1-acetyl-1H-indol-3-yl)-amide]2-(3-chloro-2-fluoro-benzylamide);

(2S,3R)-3-Amino-pyrrolidine-1,2-dicarboxylic acid 1-[(1-carbamoyl-1H-indol-3-yl)-amide]2-{[(S)-1-(3-chloro-2-fluoro-phenyl)-2,2,2-trifluoro-ethyl]-amide};

(2S,3S)-3-Amino-pyrrolidine-1,2-dicarboxylic acid 1-[(1-carbamoyl-1H-indol-3-yl)-amide]2-(3-chloro-2-fluoro-benzylamide);

(2S,3S)-3-Amino-pyrrolidine-1,2-dicarboxylic acid 1-[(1-carbamoyl-1H-indol-3-yl)-amide]2-(3-chloro-benzylamide);

(2S,3R)-3-Acetylamino-pyrrolidine-1,2-dicarboxylic acid 1-[(1-carbamoyl-1H-indol-3-yl)-amide]2-(3-chloro-2-fluoro-benzylamide);

(2S,3R)-3-(2-Methoxy-ethylamino)-pyrrolidine-1,2-dicarboxylic acid 1-[(1-carbamoyl-1H-indol-3-yl)-amide]2-(3-chloro-2-fluoro-benzylamide);

(2S,4S)-4-Fluoro-4-methylaminomethyl-pyrrolidine-1,2-dicarboxylic acid 1-[(1-carbamoyl-1H-indol-3-yl)-amide]2-(3-chloro-2-fluoro-benzylamide);

(2S,4S)-4-Methylamino-pyrrolidine-1,2-dicarboxylic acid 1-[(1-carbamoyl-1H-indol-3-yl)-amide]2-(3-chloro-2-fluoro-benzylamide);

(2S,4S)-4-(2-Methoxy-ethylamino)-pyrrolidine-1,2-dicarboxylic acid 1-[(1-carbamoyl-1H-indol-3-yl)-amide]2-(3-chloro-2-fluoro-benzylamide);

(2S,4S)-4-Dimethylamino-pyrrolidine-1,2-dicarboxylic acid 1-[(1-carbamoyl-1H-indol-3-yl)-amide]2-(3-chloro-2-fluoro-benzylamide);

(S)-4,4-Dimethoxy-pyrrolidine-1,2-dicarboxylic acid 1-[(1-carbamoyl-1H-indol-3-yl)-amide]2-(3-chloro-2-fluoro-benzylamide);

(2S,3S,4R)-4-Amino-3-hydroxy-pyrrolidine-1,2-dicarboxylic acid 1-[(1-carbamoyl-1H-indol-3-yl)-amide]2-(3-chloro-2-fluoro-benzylamide);

(2R,3S,4R)-4-Amino-3-fluoro-pyrrolidine-1,2-dicarboxylic acid 1-[(1-carbamoyl-1H-indol-3-yl)-amide]2-(3-chloro-2-fluoro-benzylamide);

(2S,3S,4S)-3-Amino-4-fluoro-pyrrolidine-1,2-dicarboxylic acid 1-[(1-carbamoyl-1H-indol-3-yl)-amide]2-(3-chloro-2-fluorobenzylamide);

3-{2-[(S)-5-(3-Chloro-2-fluoro-benzylcarbamoyl)-pyrazolidin-1-yl]-2-oxo-ethyl}-indole-1-carboxylic acid amide;

3-{2-[(R)-5-(3-Chloro-2-fluoro-benzylcarbamoyl)-pyrazolidin-1-yl]-2-oxo-ethyl}-indole-1-carboxylic acid amide;

Pyrazolidine-1,5-dicarboxylic acid 1-[(1-carbamoyl-1H-indol-3-yl)-amide]5-(3-chloro-benzylamide);

(3S,5S)-1-(1-Carbamoyl-1H-indol-3-ylcarbamoyl)-5-(2-fluoro-3-trifluoromethoxy-phenylcarbamoyl)-pyrrolidine-3-carboxylic acid methyl ester;

(2S,4S)-4-Hydroxymethyl-pyrrolidine-1,2-dicarboxylic acid 1-[(1-carbamoyl-1H-indol-3-yl)-amide]2-(3-chloro-2,6-difluoro-benzylamide);

(2S,4R)-4-Fluoro-pyrrolidine-1,2-dicarboxylic acid 2-[(3-bromo-5-carbamoyl-phenyl)-amide]1-[(1-carbamoyl-1H-indol-3-yl)-amide];

(2S,4R)-4-Fluoro-pyrrolidine-1,2-dicarboxylic acid 1-[(1-carbamoyl-1H-indol-3-yl)-amide]2-[3-chloro-2-fluoro-5-(2-methoxy-ethylcarbamoyl)-benzylamide];

(S)-Pyrrolidine-1,2-dicarboxylic acid 1-[(1-carbamoyl-1H-indol-3-yl)-amide]2-[(3-isopropyl-isoxazol-5-yl)-amide];

(S)-Pyrrolidine-1,2-dicarboxylic acid 1-[(1-carbamoyl-1H-indol-3-yl)-amide]2-[(3-phenyl-isoxazol-5-yl)-amide];

3-{2-[(S)-2-(3-trifluoromethoxy-phenylcarbamoyl)-pyrrolidin-1-yl]-2-oxo-ethyl}-indole-1-carboxylic acid amide;

3-{2-[(2S,4R)-4-Fluoro-2-(2-fluoro-3-trifluoromethoxy-phenylcarbamoyl)-pyrrolidin-1-yl]-2-oxo-ethyl}-indole-1-carboxylic acid amide;

3-{2-[(1S,2S,5R)-2-[(S)-1-(3-Chloro-2-fluoro-phenyl)-2-hydroxy-ethylcarbamoyl]-3-azabicyclo[3.1.0]hex-3-yl]-2-oxo-ethyl}-indole-1-carboxylic acid amide;

3-{2-[(2S,3R)-2-(3-Chloro-2-fluoro-benzylcarbamoyl)-3-hydroxy-pyrrolidin-1-yl]-2-oxo-ethyl}-indole-1-carboxylic acid amide;

3-{2-[(2S,4S)-2-(3-Chloro-2-fluoro-benzylcarbamoyl)-4-dimethylaminomethyl-4-fluoro-pyrrolidin-1-yl]-2-oxo-ethyl}-indole-1-carboxylic acid amide;

3-{2-[(1R,3S,5R)-3-(3-Chloro-2-fluoro-benzylcarbamoyl)-2-aza-bicyclo[3.1.0]hex-2-yl]-2-oxo-ethyl}-indole-1-carboxylic acid amide;

3-(2-{(2S,4R)-2-[(R)-1-(3-Chloro-2-fluoro-phenyl)-3-hydroxy-propylcarbamoyl]-4-fluoro-4-methyl-pyrrolidin-1-yl]-2-oxo-ethyl)-indole-1-carboxylic acid amide;

3-{2-[(2S,4R)-2-(3-Chloro-2-fluoro-benzylcarbamoyl)-4-fluoro-pyrrolidin-1-yl]-2-oxo-ethyl}-indole-1-carboxylic acid amide;

3-(2-{(1R,3S,5R)-3-[(S)-1-(3-Chloro-2-fluoro-phenyl)-2-hydroxy-ethyl carbamoyl]-2-aza-bicyclo[3.1.0]hex-2-yl}-2-oxo-ethyl)-indole-1-carboxylic acid amide;

3-{2-[(S)-2-(3-Chloro-2-fluoro-benzylcarbamoyl)-thiazolidin-3-yl]-2-oxo-ethyl}-indole-1-carboxylic acid amide;

3-{2-[(2S,4R)-2-(3-Chloro-2-fluoro-benzylcarbamoyl)-4-fluoro-4-hydroxymethyl-pyrrolidin-1-yl]-2-oxo-ethyl}-indole-1-carboxylic acid amide;

3-{2-[(1R,3S,5R)-3-(3-Chloro-2-fluoro-benzylcarbamoyl)-2-aza-bicyclo[3.1.0]hex-2-yl]-2-oxo-ethyl}-5-methoxy-indole-1-carboxylic acid amide;

3-{2-[(1R,3S,5R)-3-(3-Chloro-2-fluoro-benzylcarbamoyl)-2-aza-bicyclo[3.1.0]hex-2-yl]-2-oxo-ethyl}-5-(2-hydroxy-ethoxy)-indole-1-carboxylic acid amide;

3-{2-[(1R,3S,5S)-3-(3-Chloro-2-fluoro-benzylcarbamoyl)-5-methoxymethyl-2-aza-bicyclo[3.1.0]hex-2-yl]-2-oxo-ethyl}-indole-1-carboxylic acid amide;

5-(2-Hydroxy-ethoxy)-3-{2-oxo-2-[(1R,3S,5R)-3-(3-trifluoromethoxy-phenylcarbamoyl)-2-aza-bicyclo[3.1.0]hex-2-yl]ethyl}-indole-1-carboxylic acid amide;

3-(2-{(1R,3S,5R)-3-[(5-Chloro-thiophen-2-ylmethyl)-carbamoyl]-2-aza-bicyclo[3.1.0]hex-2-yl]-2-oxo-ethyl)-indole-1-carboxylic acid amide;

3-(2-{(1R,3S,5R)-3-[(R)-1-(3-Chloro-2-fluoro-phenyl)-3-hydroxy-propylcarbamoyl]-2-azabicyclo[3.1.0]hex-2-yl]-2-oxo-ethyl)-indole-1-carboxylic acid amide;

3-(2-{(1R,3S,5R)-3-[(S)-1-(3-Chloro-2-fluoro-phenyl)-2-dimethylamino-ethylcarbamoyl]-2-aza-bicyclo[3.1.0]hex-2-yl]-2-oxo-ethyl)-indole-1-carboxylic acid amide;

3-{2-[(2S,4R)-2-(3-Chloro-2-fluoro-benzylcarbamoyl)-4-fluoro-4-methyl-pyrrolidin-1-yl]-2-oxo-ethyl}-5-(2-hydroxy-ethoxy)-indole-1-carboxylic acid amide;

3-{2-[(2S,4R)-2-(3-Chloro-2-fluoro-benzylcarbamoyl)-4-fluoro-pyrrolidin-1-yl]-2-oxo-ethyl}-5-fluoro-indole-1-carboxylic acid amide;

3-{2-[(1R,3S,5R)-3-(3-Chloro-2-fluoro-benzylcarbamoyl)-2-aza-bicyclo[3.1.0]hex-2-yl]-2-oxo-ethyl}-2-methyl-indole-1-carboxylic acid amide;

3-{2-[(S)-2-(3-Chloro-2-fluoro-benzylcarbamoyl)-thiazolidin-3-yl]-2-oxo-ethyl}-5-(2-hydroxy-ethoxy)-indole-1-carboxylic acid amide;

3-(2-{(1R,2S,5S)-2-[(S)-1-(3-Chloro-2-fluoro-phenyl)-2-hydroxy-ethylcarbamoyl]-3-azabicyclo[3.1.0]hex-3-yl]-2-oxo-ethyl)-indole-1-carboxylic acid amide;

3-(2-{(1R,3S,5R)-3-[(S)-1-(3-Chloro-2-fluoro-phenyl)-2-methoxy-ethylcarbamoyl]-2-aza-bicyclo[3.1.0]hex-2-yl]-2-oxo-ethyl)-indole-1-carboxylic acid amide;

3-{2-[(1S,2S,5R)-2-(3-Chloro-2-fluoro-benzylcarbamoyl)-3-aza-bicyclo[3.1.0]hex-3-yl]-2-oxo-ethyl}-5-(2-hydroxy-ethoxy)-indole-1-carboxylic acid amide;

3-{2-[(2S,3S,4S)-3-Amino-2-(3-chloro-2-fluoro-benzylcarbamoyl)-4-fluoro-pyrrolidin-1-yl]-2-oxo-ethyl}-indole-1-carboxylic acid amide;

3-{2-[(1R,3S,5S)-3-(3-Chloro-2-fluoro-benzylcarbamoyl)-5-hydroxymethyl-2-aza-bicyclo[3.1.0]hex-2-yl]-2-oxo-ethyl}-indole-1-carboxylic acid amide;

3-{2-[(2S,4S)-4-Amino-2-(3-chloro-2-fluoro-benzylcarbamoyl)-pyrrolidin-1-yl]-2-oxo-ethyl}-indole-1-carboxylic acid amide;

3-{2-[5-(3-Chloro-benzylcarbamoyl)-pyrazolidin-1-yl]-2-oxo-ethyl}-indole-1-carboxylic acid amide;

3-{2-[(2S,4S)-4-Aminomethyl-2-(3-chloro-2-fluoro-benzylcarbamoyl)-4-fluoro-pyrrolidin-1-yl]-2-oxo-ethyl}-indole-1-carboxylic acid amide;

3-{2-[(2S,4S)-4-Aminomethyl-2-(3-chloro-2,6-difluoro-benzylcarbamoyl)-4-fluoro-pyrrolidin-1-yl]-2-oxo-ethyl}-indole-1-carboxylic acid amide;

3-{2-[(1R,3S,5R)-3-(3-Chloro-2-fluoro-benzylcarbamoyl)-2-aza-bicyclo[3.1.0]hex-2-yl]-2-oxo-ethyl}-5-(2-dimethylamino-ethoxy)-indole-1-carboxylic acid amide;

(1-Carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid;

3-{2-[(1R,3S,5R)-3-(3-Chloro-2-fluoro-benzylcarbamoyl)-2-aza-bicyclo[3.1.0]hex-2-yl]-2-oxo-ethyl}-6-(2-hydroxy-ethyl)-indole-1-carboxylic acid amide;

1-{2-[(1R,3S,5R)-3-(3-Chloro-2-fluoro-benzylcarbamoyl)-2-aza-bicyclo[3.1.0]hex-2-yl]-2-oxo-ethyl}-1H-indole-3-carboxylic acid amid;

1-{2-[(2S,4R)-2-(3-Chloro-2-fluoro-benzylcarbamoyl)-4-fluoro-pyrrolidin-1-yl]-2-oxo-ethyl}-1H-indole-3-carboxylic acid amide;

1-{2-[(2S,4R)-2-(3-Chloro-2-fluoro-benzylcarbamoyl)-4-fluoro-pyrrolidin-1-yl]-2-oxo-ethyl}-7-methoxy-1H-indole-3-carboxylic acid amide;

(S)-1-[2-(3-Acetyl-indol-1-yl)acetyl]-piperidine-2-carboxylic acid 3-chloro-2-fluoro-benzylamide;

6-Bromo-1-{2-[(2S,4R)-2-(3-chloro-2-fluoro-benzylcarbamoyl)-4-fluoro-pyrrolidin-1-yl]-2-oxo-ethyl}-5-fluoro-1H-indole-3-carboxylic acid amide;

3-[({(1R,3S,5R)-2-[2-(3-Acetyl-indol-1-yl)-acetyl]-2-aza-bicyclo[3.1.0]hexane-3-carbonyl}-amino)-methyl]-5-chloro-4-fluoro-benzoic acid methyl ester;

1-{2-[(2S,4R)-2-(3-Bromo-2-fluoro-benzylcarbamoyl)-4-fluoro-pyrrolidin-1-yl]-2-oxo-ethyl}-1H-indole-3-carboxylic acid amide;

(2S,4R)-1-[2-(3-Acetyl-pyrrolo[2,3-c]pyridin-1-yl)-acetyl]-4-fluoro-4-methyl-pyrrolidine-2-carboxylic acid 3-chloro-2-fluoro-benzylamide;

(1R,3S,5R)-2-[2-(3-Acetyl-pyrrolo[2,3-b]pyridin-1-yl)-acetyl]-2-aza-bicyclo[3.1.0]hexane-3-carboxylic acid 3-chloro-2-fluoro-benzylamide;

(1R,3S,5R)-2-[2-(3-Acetyl-pyrrolo[2,3-b]pyridin-1-yl)-acetyl]-2-aza-bicyclo[3.1.0]hexane-3-carboxylic acid (5-chloro-thiophen-2-ylmethyl)-amide;

(2S,3S,4S)-1-[2-(3-Acetyl-5-methoxy-indol-1-yl)-acetyl]-4-fluoro-3-methoxy-pyrrolidine-2-carboxylic acid 3-chloro-2-fluoro-benzylamide;

1-{2-[(2S,4R)-2-(3-Chloro-2-fluoro-phenylcarbamoyl)-4-fluoro-pyrrolidin-1-yl]-2-oxo-ethyl}-1H-indole-3-carboxylic acid amide;

(2S,3S,4S)-1-[2-(3-Acetyl-6-methoxy-indol-1-yl)-acetyl]-4-fluoro-3-methoxy-pyrrolidine-2-carboxylic acid 3-chloro-2-fluoro-benzylamide;

5-Chloro-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide;

7-Chloro-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide;

(1R,3S,5S)-2-[2-(3-Acetyl-pyrrolo[2,3-b]pyridin-1-yl)-acetyl]-5-methoxymethyl-2-aza-bicyclo[3.1.0]hexane-3-carboxylic acid 3-chloro-2-fluoro-benzylamide;

6-Chloro-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide;

1-{2-[(2S,4R)-2-(3-Chloro-2-fluoro-benzylcarbamoyl)-4-fluoro-pyrrolidin-1-yl]-2-oxo-ethyl}-5,6-difluoro-1H-indole-3-carboxylic acid amide;

1-{2-[(2S,4R)-2-(3-Chloro-2-fluoro-benzylcarbamoyl)-4-fluoro-pyrrolidin-1-yl]-2-oxo-ethyl}-6-trifluoromethoxy-1H-indole-3-carboxylic acid amide;

(1R,3S,5R)-2-[2-(3-Acetyl-5-methoxy-pyrrolo[2,3-b]pyridin-1-yl)-acetyl]-2-aza-bicyclo[3.1.0]hexane-3-carboxylic acid 3-chloro-2-fluoro-benzylamide;

(1R,3S,5R)-2-{2-[3-(2,2,2-Trifluoro-acetyl)-indol-1-yl]-acetyl}-2-aza-bicyclo[3.1.0]hexane-3-carboxylic acid 3-chloro-2-fluoro-benzylamide;

1-{2-[(2S,4R)-2-(3-Chloro-2-fluoro-benzylcarbamoyl)-4-fluoro-4-methyl-pyrrolidin-1-yl]-2-oxo-ethyl}-1H-indole-3-carboxylic acid amide;

1-{2-[(2S,4R)-2-(3-Chloro-2-fluoro-benzylcarbamoyl)-4-fluoro-pyrrolidin-1-yl]-2-oxo-ethyl}-5-methoxy-1H-indole-3-carboxylic acid amide;

(2S,4R)-1-[2-(3-Acetyl-indol-1-yl)-acetyl]-4-fluoro-pyrrolidine-2-carboxylic acid 3-chloro-5-cyano-2-fluoro-benzylamide;

1-{2-[(2S,4R)-2-(3-Chloro-2-fluoro-benzylcarbamoyl)-4-fluoro-pyrrolidin-1-yl]-2-oxo-ethyl}-6-methoxy-1H-indole-3-carboxylic acid amide;

(2S,4R)-1-[2-(3-Acetyl-6-methoxy-indol-1-yl)-acetyl]-4-fluoro-pyrrolidine-2-carboxylic acid 3-chloro-2-fluoro-benzylamide;

(S)-1-[2-(3-Acetyl-5-methoxy-indol-1-yl)-acetyl]-piperidine-2-carboxylic acid 3-chloro-2-fluoro-benzylamide;

(2S,4R)-1-[2-(3-Acetyl-pyrrolo[3,2-c]pyridin-1-yl)-acetyl]-4-fluoro-4-methyl-pyrrolidine-2-carboxylic acid 3-chloro-2-fluoro-benzylamide;

5-Benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide;

(1R,3S,5R)-2-[2-(3-Acetyl-indol-1-yl)-acetyl]-2-aza-bicyclo[3.1.0]hexane-3-carboxylic acid [(R)-1-(3-chloro-2-fluoro-phenyl)-3-hydroxy-propyl]-amide;

(2S,3S,4S)-1-[2-(3-Acetyl-indol-1-yl)-acetyl]-4-fluoro-3-methoxy-pyrrolidine-2-carboxylic acid 3-chloro-2-fluoro-benzylamide;

(1R,2S,5S)-3-[2-(3-Acetyl-pyrrolo[2,3-c]pyridin-1-yl)-acetyl]-3-aza-bicyclo[3.1.0]hexane-2-carboxylic acid 3-chloro-2-fluoro-benzylamide;

(2S,4R)-1-[2-(3-Acetyl-indol-1-yl)-acetyl]-4-fluoro-pyrrolidine-2-carboxylic acid 3-chloro-2-fluoro-benzylamide;

(2S,4R)-1-[2-(3-Acetyl-5-benzyloxy-indol-1-yl)-acetyl]-4-fluoro-pyrrolidine-2-carboxylic acid 3-chloro-2-fluoro-benzylamide;

(2S,4R)-1-[2-(3-Acetyl-6-trifluoromethoxy-indol-1-yl)-acetyl]-4-fluoro-pyrrolidine-2-carboxylic acid 3-chloro-2-fluoro-benzylamide;

(1R,3S,5R)-2-[2-(3-Acetyl-indol-1-yl)-acetyl]-2-aza-bicyclo[3.1.0]hexane-3-carboxylic acid 3-chloro-2-fluoro-benzylamide;

(2S,4R)-1-[2-(3-Acetyl-indol-1-yl)-acetyl]-4-fluoro-4-methyl-pyrrolidine-2-carboxylic acid 3-chloro-2-fluoro-benzylamide;

(1R,3S,4S)-2-[2-(3-Acetyl-indol-1-yl)-acetyl]-2-aza-bicyclo[2.2.1]heptane-3-carboxylic acid 3-chloro-2-fluoro-benzylamide;

(S)-3-[2-(3-Acetyl-pyrrolo[2,3-b]pyridin-1-yl)-acetyl]-thiazolidine-2-carboxylic acid 3-chloro-2-fluoro-benzylamide;

(2S,4R)-1-[2-(3-Acetyl-indol-1-yl)-acetyl]-4-fluoro-pyrrolidine-2-carboxylic acid (2-fluoro-3-trifluoromethoxy-phenyl)-amide;

(1R,3S,5R)-2-[2-(3-Acetyl-indol-1-yl)-acetyl]-2-aza-bicyclo[3.1.0]hexane-3-carboxylic acid [3-bromo-5-(2H-tetrazol-5-yl)-phenyl]amide;

(2S,4R)-1-[2-(3-Acetyl-indol-1-yl)-acetyl]-4-fluoro-pyrrolidine-2-carboxylic acid 3-bromo-2-fluoro-benzylamide;

1-{2-[(2S,4R)-4-Fluoro-2-(2-fluoro-3-trifluoromethyl-phenylcarbamoyl)-pyrrolidin-1-yl]-2-oxo-ethyl}-1H-indole-3-carboxylic acid amide;

(2S,4R)-1-[2-(3-Acetyl-indol-1-yl)-acetyl]-4-fluoro-pyrrolidine-2-carboxylic acid [(S)-1-(3-chloro-2-fluoro-phenyl)-2-hydroxy-ethyl]-amide;

1-{2-[(2S,4R)-2-(3-Chloro-2-fluoro-benzylcarbamoyl)-4-fluoro-pyrrolidin-1-yl]-2-oxo-ethyl}-1H-indole-3-carboxylic acid methylamide;

(2S,3S,4S)-1-[2-(3-Acetyl-pyrrolo[2,3-b]pyridin-1-yl)-acetyl]-4-fluoro-3-methoxy-pyrrolidine-2-carboxylic acid 3-chloro-2-fluoro-benzylamide;

(2S,4R)-1-[2-(3-Acetyl-indol-1-yl)-acetyl]-4-fluoro-pyrrolidine-2-carboxylic acid 3-chloro-2-fluoro-5-(1H-tetrazol-5-yl)-benzylamide;

(1R,3S,5R)-2-[2-(3-Acetyl-indol-1-yl)-acetyl]-2-aza-bicyclo[3.1.0]hexane-3-carboxylic acid [(S)-1-(3-chloro-2-fluoro-phenyl)-2-dimethylamino-ethyl]amide;

3-[({(2S,4R)-1-[2-(3-Acetyl-indol-1-yl)-acetyl]-4-fluoro-pyrrolidine-2-carbonyl}-amino)-methyl]-5-chloro-4-fluoro-benzoic acid methyl ester;

(1R,3S,5R)-2-[2-(3-Acetyl-pyrrolo[3,2-c]pyridin-1-yl)-acetyl]-2-aza-bicyclo[3.1.0]hexane-3-carboxylic acid 3-chloro-2-fluoro-benzylamide;

(1R,3S,5R)-2-[2-(3-Acetyl-indol-1-yl)-acetyl]-2-aza-bicyclo[3.1.0]hexane-3-carboxylic acid 3-chloro-2-fluoro-5-(1H-tetrazol-5-yl)-benzylamide;

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-6-carboxylic acid methyl ester;

(1R,3S,5R)-2-[2-(3-Acetyl-indol-1-yl)-acetyl]-2-aza-bicyclo[3.1.0]hexane-3-carboxylic acid 3-chloro-5-cyano-2-fluoro-benzylamide;

1-{2-[(2S,4R)-2-(3-Chloro-2-fluoro-benzylcarbamoyl)-4-fluoro-pyrrolidin-1-yl]-2-oxo-ethyl}-6-difluoromethoxy-1H-indole-3-carboxylic acid amide;

6-Benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide;

(2S,4R)-1-[2-(3-Acetyl-pyrrolo[2,3-b]pyridin-1-yl)-acetyl]-4-fluoro-4-methyl-pyrrolidine-2-carboxylic acid 3-chloro-2-fluoro-benzylamide;

(2S,4R)-1-[2-(3-Acetyl-6-chloro-indol-1-yl)-acetyl]-4-fluoro-pyrrolidine-2-carboxylic acid 3-chloro-2-fluoro-benzylamide;

(1R,3S,5R)-2-[2-(3-Acetyl-6-cyano-pyrrolo[2,3-b]pyridin-1-yl)-acetyl]-2-aza-bicyclo[3.1.0]hexane-3-carboxylic acid 3-chloro-2-fluoro-benzylamide;

(1R,3S,5R)-2-[2-(3-Acetyl-pyrrolo[2,3-b]pyridin-1-yl)-acetyl]-2-aza-bicyclo[3.1.0]hexane-3-carboxylic acid [(S)-1-(3-chloro-2-fluoro-phenyl)-2-methoxy-ethyl]-amide;

(2S,4R)-1-[2-(3-Acetyl-6-benzyloxy-indol-1-yl)-acetyl]-4-fluoro-pyrrolidine-2-carboxylic acid 3-chloro-2-fluoro-benzylamide;

(1R,3S,5R)-2-[2-(3-Acetyl-pyrrolo[2,3-c]pyridin-1-yl)-acetyl]-2-aza-bicyclo[3.1.0]hexane-3-carboxylic acid [(S)-1-(3-chloro-2-fluoro-phenyl)-2-methoxy-ethyl]-amide;

(1R,3S,5R)-2-[2-(3-Acetyl-6-benzyloxy-indol-1-yl)-acetyl]-2-aza-bicyclo[3.1.0]hexane-3-carboxylic acid 3-chloro-2-fluoro-benzylamide;

(1R,2S,5S)-3-[2-(3-Acetyl-pyrrolo[3,2-c]pyridin-1-yl)-acetyl]-3-aza-bicyclo[3.1.0]hexane-2-carboxylic acid 3-chloro-2-fluoro-benzylamide;

(1R,2S,5S)-3-[2-(3-Acetyl-pyrrolo[2,3-b]pyridin-1-yl)-acetyl]-3-aza-bicyclo[3.1.0]hexane-2-carboxylic acid 3-chloro-2-fluoro-benzylamide;

(2S,4R)-1-[2-(3-Acetyl-5-trifluoromethoxy-indol-1-yl)-acetyl]-4-fluoro-pyrrolidine-2-carboxylic acid 3-chloro-2-fluoro-benzylamide;

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboxylic acid methyl ester;

3-Acetyl-1-{2-[(1R,3S,5R)-3-(3-chloro-2-fluorobenzylcarbamoyl)-2-aza-bicyclo[3.1.0]hex-2-yl]-2-oxo-ethyl}-1H-indole-7-carboxylic acid methyl ester;

3-Acetyl-1-{2-[(2S,4R)-2-(3-chloro-2-fluoro-benzylcarbamoyl)-4-fluoro-pyrrolidin-1-yl]-2-oxo-ethyl}-1H-indole-6-carboxylic acid methyl ester;

(2S,4R)-4-Fluoro-1-{2-[3-(2-hydroxy-acetyl)-indol-1-yl]-acetyl}-4-methyl-pyrrolidine-2-carboxylic acid 3-chloro-2-fluoro-benzylamide;

(1S,2S,5R)-3-[2-(3-Acetyl-pyrrolo[2,3-c]pyridin-1-yl)-acetyl]-3-aza-bicyclo[3.1.0]hexane-2-carboxylic acid 3-chloro-2-fluoro-benzylamide;

(3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid methyl ester;

(2S,4R)-4-Fluoro-1-{2-[3-(2,2,2-trifluoro-acetyl)-indol-1-yl]-acetyl}-pyrrolidine-2-carboxylic acid 3-bromo-2-fluoro-benzylamide;

(2S,4R)-1-[2-(3-Acetyl-pyrrolo[2,3-b]pyridin-1-yl)-acetyl]-4-fluoro-pyrrolidine-2-carboxylic acid 3-chloro-2-fluoro-benzylamide;

3-Acetyl-1-{2-[(2S,4R)-2-(3-chloro-2-fluoro-benzylcarbamoyl)-4-fluoro-4-methyl-pyrrolidin-1-yl]-2-oxo-ethyl}-1H-indole-6-carboxylic acid methyl ester;

(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yl)-acetic acid methyl ester;

(1R,3S,5R)-2-[2-(3-Acetyl-pyrrolo[2,3-c]pyridin-1-yl)-acetyl]-2-aza-bicyclo[3.1.0]hexane-3-carboxylic acid 3-chloro-2-fluorobenzylamide;

(2S,4R)-4-Fluoro-1-{2-[3-(2-hydroxy-acetyl)-indol-1-yl]-acetyl}-pyrrolidine-2-carboxylic acid [(S)-1-(3-bromo-phenyl)-2-fluoro-ethyl]amide;

(2S,4R)-1-[2-(3-Acetyl-pyrrolo[2,3-c]pyridin-1-yl)-acetyl]-4-fluoro-pyrrolidine-2-carboxylic acid 3-chloro-2-fluoro-benzylamide;

(1R,3S,5R)-2-[2-(3-Acetyl-pyrrolo[3,2-b]pyridin-1-yl)-acetyl]-2-aza-bicyclo[3.1.0]hexane-3-carboxylic acid 3-chloro-2-fluoro-benzylamide;

(2S,4R)-4-Fluoro-4-methyl-1-{2-[3-(2,2,2-trifluoro-acetyl)-indol-1-yl]-acetyl}-pyrrolidine-2-carboxylic acid 3-chloro-2-fluoro-benzylamide;

(2R,3S,4R)-1-[2-(3-Acetyl-indol-1-yl)-acetyl]-4-dimethylamino-3-fluoro-pyrrolidine-2-carboxylic acid 3-chloro-2-fluoro-benzylamide;

(1R,3S,5R)-2-{2-[3-(2-Hydroxy-acetyl)-indol-1-yl]-acetyl}-2-aza-bicyclo[3.1.0]hexane-3-carboxylic acid 3-chloro-2-fluoro-benzylamide;

(1R,3S,5R)-2-[2-(3-Acetyl-pyrrolo[2,3-b]pyridin-1-yl)-acetyl]-2-aza-bicyclo[3.1.0]hexane-3-carboxylic acid [(R)-1-(3-chloro-2-fluoro-phenyl)-3-hydroxy-propyl]-amide;

(1R,3S,5R)-2-[2-(3-Acetyl-pyrrolo[2,3-b]pyridin-1-yl)-acetyl]-2-aza-bicyclo[3.1.0]hexane-3-carboxylic acid (3-trifluoromethoxy-phenyl)-amide;

(S)-1-[2-(3-Formyl-indol-1-yl)-acetyl]-pyrrolidine-2-carboxylic acid (3-trifluoromethoxy-phenyl)-amide;

(2S,4R)-4-Fluoro-1-[2-(3-formyl-5-methoxy-indol-1-yl)-acetyl]-pyrrolidine-2-carboxylic acid 3-chloro-2-fluoro-benzylamide;

(2S,4R)-4-Fluoro-1-{2-[3-(2,2,2-trifluoro-acetyl)-indol-1-yl]-acetyl}-pyrrolidine-2-carboxylic acid 3-chloro-2-fluoro-benzylamide;

(1R,3S,5R)-2-[2-(3-Acetyl-pyrrolo[2,3-b]pyridin-1-yl)-acetyl]-2-aza-bicyclo[3.1.0]hexane-3-carboxylic acid (2-fluoro-3-trifluoromethoxy-phenyl)-amide;

(2S,4R)-4-Fluoro-1-{2-[3-(2-hydroxy-acetyl)-indol-1-yl]-acetyl}-pyrrolidine-2-carboxylic acid 3-chloro-2-fluoro-benzylamide;

(2S,4R)-4-Fluoro-1-{2-[3-(2-hydroxy-acetyl)-indol-1-yl]-acetyl}-pyrrolidine-2-carboxylic acid 3-bromo-2-fluoro-benzylamide;

(2S,4R)-4-Fluoro-1-{2-[3-(2-methoxy-acetyl)-indol-1-yl]-acetyl}-pyrrolidine-2-carboxylic acid 3-chloro-2-fluoro-benzylamide;

1-{2-[(2S,4R)-2-(3-Chloro-2-fluoro-benzylcarbamoyl)-4-fluoro-4-hydroxymethyl-pyrrolidin-1-yl]-2-oxo-ethyl}-1H-indole-3-carboxylic acid amide;

1-{2-[(S)-2-(3-Chloro-2-fluoro-benzylcarbamoyl)-thiazolidin-3-yl]-2-oxo-ethyl}-1H-indole-3-carboxylic acid amide;

(1R,3S,5R)-2-[2-(3-Acetyl-indol-1-yl)-acetyl]-2-aza-bicyclo[3.1.0]hexane-3-carboxylic acid [(S)-1-(3-chloro-2-fluoro-phenyl)-2-methoxy-ethyl]-amide;

(2S,3S,4S)-1-[2-(3-Acetyl-indol-1-yl)-acetyl]-4-fluoro-3-ethoxy-pyrrolidine-2-carboxylic acid 3-chloro-2-fluoro-benzylamide;

(2S,3S,4S)-1-[2-(3-Acetyl-indol-1-yl)-acetyl]-4-fluoro-3-methoxy-pyrrolidine-2-carboxylic acid [(R)-1-(3-chloro-2-fluoro-phenyl)-ethyl]-amide;

(2S,3S,4S)-1-[2-(3-Acetyl-indol-1-yl)-acetyl]-4-fluoro-3-methoxy-pyrrolidine-2-carboxylic acid [(S)-1-(3-chloro-2-fluoro-phenyl)-ethyl]-amide;

(2S,3S,4S)-1-[2-(3-Acetyl-indol-1-yl)-acetyl]-4-fluoro-3-methoxy-pyrrolidine-2-carboxylic acid [1-(3-chloro-phenyl)cyclopropyl]-amide;

(2S,3S,4S)-1-[2-(3-Acetyl-indol-1-yl)-acetyl]-4-fluoro-3-methoxy-pyrrolidine-2-carboxylic acid [1-(4-chloro-phenyl)cyclopropyl]-amide;

1-{2-[(2S,3S,4S)-3-Amino-2-(3-chloro-2-fluoro-benzylcarbamoyl)-4-fluoro-pyrrolidin-1-yl]-2-oxo-ethyl}-1H-indole-3-carboxylic acid amide;

(2S,3S,4S)-1-[2-(3-Acetyl-indol-1-yl)-acetyl]-3-amino-4-fluoro-pyrrolidine-2-carboxylic acid 3-chloro-2-fluoro-benzylamide;

(2R,3S,4R)-1-[2-(3-Acetyl-indol-1-yl)-acetyl]-4-amino-3-fluoro-pyrrolidine-2-carboxylic acid 3-chloro-2-fluoro-benzylamide;

1-{2-[(2S,4R)-2-(3-Chloro-2-fluoro-benzylcarbamoyl)-4-fluoro-pyrrolidin-1-yl]-2-oxo-ethyl}-5-hydroxy-1H-indole-3-carboxylic acid amide;

1-{2-[(2S,4R)-2-(3-Chloro-2-fluoro-benzylcarbamoyl)-4-fluoro-pyrrolidin-1-yl]-2-oxo-ethyl}-6-hydroxy-1H-indole-3-carboxylic acid amide;

(2S,4R)-1-[2-(3-Acetyl-5-hydroxy-indol-1-yl)-acetyl]-4-fluoro-pyrrolidine-2-carboxylic acid 3-chloro-2-fluoro-benzylamide;

(2S,4R)-1-[2-(3-Acetyl-5-hydroxy-indol-1-yl)-acetyl]-4-fluoro-4-methyl-pyrrolidine-2-carboxylic acid 3-chloro-2-fluoro-benzylamide;

(1R,3S,5R)-2-[2-(3-Acetyl-5-hydroxy-indol-1-yl)-acetyl]-2-aza-bicyclo[3.1.0]hexane-3-carboxylic acid 3-chloro-2-fluoro-benzylamide;

(2S,4R)-1-[2-(3-Acetyl-6-hydroxy-indol-1-yl)-acetyl]-4-fluoro-4-methyl-pyrrolidine-2-carboxylic acid 3-chloro-2-fluoro-benzylamide;

(2S,4R)-1-[2-(3-Acetyl-6-hydroxy-indol-1-yl)-acetyl]-4-fluoro-pyrrolidine-2-carboxylic acid 3-chloro-2-fluoro-benzylamide;

(1R,3S,5R)-2-[2-(3-Acetyl-6-hydroxy-indol-1-yl)-acetyl]-2-aza-bicyclo[3.1.0]hexane-3-carboxylic acid 3-chloro-2-fluoro-benzylamide;

1-{2-[(2S,4R)-2-(3-Chloro-2-fluoro-benzylcarbamoyl)-4-fluoro-pyrrolidin-1-yl]-2-oxo-ethyl}-6-(1H-tetrazol-5-ylmethoxy)-1H-indole-3-carboxylic acid amide;

(2S,4R)-1-{2-[3-Acetyl-6-(1H-tetrazol-5-ylmethoxy)-indol-1-yl]-acetyl}-4-fluoro-yrrolidine-2-carboxylic acid 3-chloro-2-fluoro-benzylamide;

(2S,4R)-1-[2-(3-Acetyl-5-methoxy-indol-1-yl)-acetyl]-4-fluoro-pyrrolidine-2-carboxylic acid 3-chloro-2-fluoro-benzylamide;

(2S,4R)-1-{2-[3-Acetyl-5-(pyridin-2-ylmethoxy)-indol-1-yl]-acetyl}-4-fluoro-pyrrolidine-2-carboxylic acid 3-chloro-2-fluoro-benzylamide;

(2S,4R)-1-{2-[3-Acetyl-5-(pyrimidin-2-ylmethoxy)-indol-1-yl]-acetyl}-4-fluoro-pyrrolidine-2-carboxylic acid 3-chloro-2-fluoro-benzylamide;

1-{2-[(2S,4R)-2-(3-Chloro-2-fluoro-benzylcarbamoyl)-4-fluoro-pyrrolidin-1-yl]-2-oxo-ethyl}-6-(2-methoxy-ethoxy)-1H-indole-3-carboxylic acid amide;

(3-Carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid methyl ester;

(3-Carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid;

1-{2-[(2S,4R)-2-(3-Chloro-2-fluoro-benzylcarbamoyl)-4-fluoro-pyrrolidin-1-yl]-2-oxo-ethyl}-6-(2-hydroxy-ethoxy)-1H-indole-3-carboxylic acid amide;

(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yl)-acetic acid;

(3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid;

3-Acetyl-1-{2-[(2S,4R)-2-(3-chloro-2-fluoro-benzylcarbamoyl)-4-fluoro-pyrrolidin-1-yl]-2-oxo-ethyl}-1H-indole-6-carboxylic acid;

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-6-carboxylic acid;

3-Acetyl-1-{2-[(2S,4R)-2-(3-chloro-2-fluoro-benzylcarbamoyl)-4-fluoro-4-methyl-pyrrolidin-1-yl]-2-oxo-ethyl}-1H-indole-6-carboxylic acid;

(2S,3S,4S)-4-Fluoro-3-methoxy-pyrrolidine-1,2-dicarboxylic acid 1-[(1-carbamoyl-1H-indol-3-yl)-amide]2-(3-chloro-2-fluoro-benzylamide);

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-7-carboxylic acid;

4-(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yloxymethyl)-benzoic acid;

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboxylic acid;

(2S,4R)-1-[2-(3-Acetyl-6-hydroxymethyl-indol-1-yl)-acetyl]-4-fluoro-pyrrolidine-2-carboxylic acid 3-chloro-2-fluoro-benzylamide;

3-[({(2S,4R)-1-[2-(3-Acetyl-indol-1-yl)-acetyl]-4-fluoro-pyrrolidine-2-carbonyl}-amino)-methyl]-5-chloro-4-fluoro-benzoic acid;

3-[({(1R,3S,5R)-2-[2-(3-Acetyl-indol-1-yl)-acetyl]-2-aza-bicyclo[3.1.0]hexane-3-carbonyl}-amino)-methyl]-5-chloro-4-fluoro-benzoic acid;

(2S,4S)-1-[2-(3-Acetyl-indol-1-yl)-acetyl]-4-aminomethyl-4-fluoro-pyrrolidine-2-carboxylic acid 3-chloro-2-fluoro-benzylamide;

(2S,4S)-1-[2-(3-Acetyl-indol-1-yl)-acetyl]-4-methylamino-pyrrolidine-2-carboxylic acid 3-chloro-2-fluoro-benzylamide;

(2S,4S)-1-[2-(3-Acetyl-indol-1-yl)-acetyl]-4-(2-methoxy-ethylamino)-pyrrolidine-2-carboxylic acid 3-chloro-2-fluoro-benzylamide;

(1R,3S,5S)-2-[2-(3-Acetyl-pyrrolo[2,3-b]pyridin-1-yl)-acetyl]-5-hydroxymethyl-2-aza-bicyclo[3.1.0]hexane-3-carboxylic acid 3-chloro-2-fluoro-benzylamide;

(1R,3S,5S)-2-[2-(3-Acetyl-indol-1-yl)-acetyl]-5-hydroxymethyl-2-aza-bicyclo[3.1.0]hexane-3-carboxylic acid 3-chloro-2-fluoro-benzylamide;

(1S,2S,5R)-3-[2-(3-Acetyl-indol-1-yl)-acetyl]-3-aza-bicyclo[3.1.0]hexane-2-carboxylic acid [(S)-1-(3-chloro-2-fluoro-phenyl)-2hydroxy-ethyl]amide;

(1R,3S,5R)-2-[2-(3-Acetyl-pyrrolo[2,3-b]pyridin-1-yl)-acetyl]-2-aza-bicyclo[3.1.0]hexane-3-carboxylic acid [(S)-1-(3-chloro-2-fluoro-phenyl)-2-hydroxy-ethyl]-amide;

(2S,4R)-1-[2-(3-Acetyl-pyrrolo[2,3-b]pyridin-1-yl)-acetyl]-4-fluoro-4-methyl-pyrrolidine-2-carboxylic acid [(S)-1-(3-chloro-2-fluoro-phenyl)-2-hydroxy-ethyl]-amide;

(1R,3S,5R)-2-{2-[3-Acetyl-5-(N,N-dimethyl-carbamimidoyl)-indol-1-yl]-acetyl}-2-aza-bicyclo[3.1.0]hexane-3-carboxylic acid 3-chloro-2-fluoro-benzylamide;

(1R,3S,5R)-2-{2-[3-Acetyl-6-(N,N-dimethyl-carbamimidoyl)-indol-1-yl]-acetyl}-2-aza-bicyclo[3.1.0]hexane-3-carboxylic acid 3-chloro-2-fluoro-benzylamide;

(2S,4R)-1-{2-[3-Acetyl-6-(1H-tetrazol-5-yl)-indol-1-yl]-acetyl}-4-fluoro-pyrrolidine-2-carboxylic acid 3-chloro-2-fluoro-benzylamide;

(1R,3S,5R)-2-{2-[3-Acetyl-6-(1H-tetrazol-5-yl)-indol-1-yl]-acetyl}-2-aza-bicyclo[3.1.0]hexane-3-carboxylic acid 3-chloro-2-fluoro-benzylamide;

(2S,3S,4S)-1-[2-(3-Acetyl-d3-indol-1-yl)-acetyl]-4-fluoro-3-methoxy-pyrrolidine-2-carboxylic acid 3-chloro-2-fluoro-benzylamide;

(2S,3S,4S)-1-[2-(3-Acetyl-indol-1-yl)-acetyl]-4-fluoro-3-methoxy-d3-pyrrolidine-2-carboxylic acid 3-chloro-2-fluoro-benzylamide;

(1R,3S,5R)-2-[2-(1-Acetyl-imidazo[1,5-a]pyridin-3-yl)-acetyl]-2-aza-bicyclo[3.1.0]hexane-3-carboxylic acid 3-chloro-2-fluoro-benzylamide; and {(1R,3S,5R)-2-[2-(3-Acetyl-indol-1-yl)-acetyl]-2-aza-bicyclo[3.1.0]hex-3-ylmethyl}-carbamic acid 3-chloro-2-fluoro-phenyl ester.

In another embodiment, pharmaceutical compositions are provided which comprise one or more pharmaceutically acceptable carriers and a therapeutically effective amount of a compound of any one of formulae (I), (Ia), (II), (III), (IV), (V), (VI), (VII), or a subformulae thereof.

In another embodiment, combinations, in particular pharmaceutical combinations, are provided which comprise a therapeutically effective amount of the compound of any one of formulae (I), (Ia), (II), (III), (IV), (V), (VI), (VII), or a subformulae thereof.

In another embodiment, methods of modulating complement alternative pathway activity in a subject are provided which methods comprise administering to the subject a therapeutically effective amount of the compound of any one of formulae (I), (Ia), (II), (III), (IV), (V), (VI), (VII), or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae (I), (Ia), (II), (III), (IV), (V), (VI), (VII), or a subformulae thereof.

In another embodiment, methods of treating age related macular degeneration in a subject are provided which methods comprise administering to the subject a therapeutically effective amount of the compound of any one of formulae (I), (Ia), (II), (III), (IV), (V), (VI), (VII), or a subformulae thereof.

In another aspect, the invention provides for the use of compounds of any one of formulae (I), (Ia), (II), (III), (IV), (V), (VI), (VII), or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according to any one of formulae (I), (Ia), (II), (III), (IV), (V), (VI), (VII), or a subformulae thereof in the treatment of age-related macular degeneration.

In another embodiment, compounds which are synthetic intermediates in the preparation of compounds according to any one of formulae (I), (Ia), (II), (III), (IV), (V), (VI), (VII), or a subformulae thereof are provided. In particular, compounds provided herein as synthetic intermediates include the compounds of the formulae:

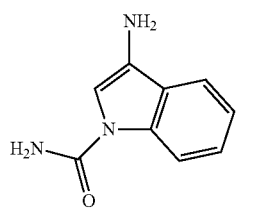
3-amino-1H-indole-1-carboxamide

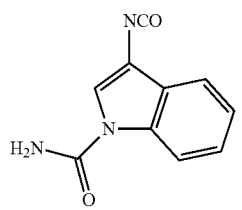
3-isocyanato-1H-indole-1-carboxamide

1-(3-isocyanato-1H-indol-1-yl)ethanone

-continued

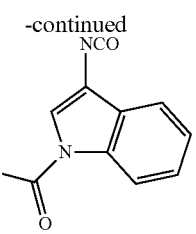
3-isocyanato-N-methyl-1H-indole-1-carboxamide

In one embodiment, the invention provides a combination, in particular a pharmaceutical combination, comprising a therapeutically effective amount of the compound according to the definition of formula (I), (Ia), (II), (VII) or subformulae thereof or any one of the specifically disclosed compounds of the invention and one or more therapeutically active agents (preferably selected from those listed infra).

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S-, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an 0-O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
- (a) alkyl;
- (b) hydroxy (or protected hydroxy);
- (c) halo;
- (d) oxo, i.e., =O;
- (e) amino, alkylamino or dialkylamino;
- (f) alkoxy;
- (g) cycloalkyl;
- (h) carboxyl;
- (i) heterocyclooxy, wherein heterocyclooxy denotes a heterocyclic group bonded through an oxygen bridge;
- (j) alkyl-O—C(O)—;
- (k) mercapto;
- (l) nitro;
- (m) cyano;
- (n) sulfamoyl or sulfonamido;
- (o) aryl;
- (p) alkyl-C(O)—O—;
- (q) aryl-C(O)—O—;
- (r) aryl-S—;
- (s) aryloxy;
- (t) alkyl-S—;
- (u) formyl, i.e., HC(O)—;
- (v) carbamoyl;
- (w) aryl-alkyl-; and
- (x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
- (a) alkyl;
- (b) hydroxy (or protected hydroxy);
- (c) halo;
- (d) oxo, i.e., =O;
- (e) amino, alkylamino or dialkylamino;
- (f) alkoxy;
- (g) cycloalkyl;
- (h) carboxyl;
- (i) heterocyclooxy, wherein heterocyclooxy denotes a heterocyclic group bonded through an oxygen bridge;
- (j) alkyl-O—C(O)—;
- (k) mercapto;
- (l) nitro;
- (m) cyano;
- (n) sulfamoyl or sulfonamido;
- (o) aryl;
- (p) alkyl-C(O)—O—;
- (q) aryl-C(O)—O—;
- (r) aryl-S—;
- (s) aryloxy;
- (t) alkyl-S—;
- (u) formyl, i.e., HC(O)—;
- (v) carbamoyl;
- (w) aryl-alkyl-; and
- (x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as 2H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include deuteration of $R^3$, when $R^3$ is alkanoyl, e.g., $C(O)CD_3$. In other embodiments, certain substitutents on the pyrrole ring are selectively deuterated. For example, when any of $R^{14}$, $R^{15}$, $R^{16}$, $R^{17}$, $R^{18}$, $R^{19}$, or $R^{20}$ are methoxy or ethoxy, the alkyl residue is preferably deuterated, e.g., $OCD_3$ or $OC_2D_5$. In certain other compounds, when two substituents of the pyrrole ring are combined to form a cyclopropyl ring, the unsubstituted methylene carbon is selectively deuterated. Certain preferred deuterated compounds are provided in Examples 619 and 620 infra.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor D, or (ii) associated with Factor D activity, or (iii) characterized by activity (normal or abnormal) of the complement alternative pathway; or (2) reducing or inhibiting the activity of Factor D; or (3) reducing or inhibiting the expression of Factor D; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor D and/or the complement alternative pathway; or at least partially reducing or inhibiting the expression of Factor D and/or the complement alternative pathway. The meaning of the term "a therapeutically effective amount" as illustrated in the above embodiment for Factor D and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds of formula (I) can be prepared according to the Schemes provided infra.

A compound of the formula IV or V can, for example, be prepared from a corresponding N-protected aminoacid as described below:

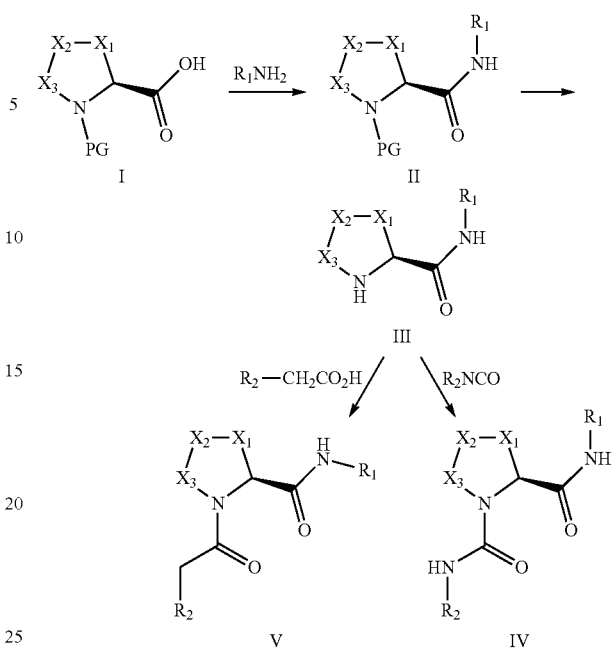

By reacting an N-protected aminoacid I wherein PG is a protecting group or a reactive derivative thereof with an amino compound, under condensation conditions to obtain a compound of the formula II. Removing the protecting group and reacting the compound of the formula III with an isocyanate to obtain a compound of the formula IV or with an acid or a reactive derivative thereof under condensation conditions to obtain a compound of the formula V.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and ophthalmic administration, etc. In addition, the pharmaceutical compositions of the present invention can be made up in a solid form (including without limitation capsules, tablets, pills, granules, powders or suppositories), or in a liquid form (including without limitation solutions, suspensions, emulsions, each of which may be suitable for ophthalmic administration). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ophthalmic application, e.g., for the treatment of eye diseases e.g., for therapeutic or prophylactic use in treating age related macular degeneration and other complement mediated ophthalmic disorders. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor D modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing compelment mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor D, wherein the other therapeutic agent is prepared for administration with a compound of formula (I). The invention also provides a compound of formula (I) for use in a method of treating a disease or condition mediated by the complement alternative pathway and/or Factor D, wherein the compound of formula (I) is administered with another therapeutic agent. The invention also provides another therapeutic agent for use in a method of treating a disease or condition mediated by the complement alternative pathway and/or Factor D, wherein the other therapeutic agent is administered with a compound of formula (I).

The invention also provides the use of a compound of formula (I) for treating a disease or condition mediated by the complement alternative pathway and/or Factor D, wherein the patient has previously (e.g. within 24 hours) been treated with another therapeutic agent. The invention also provides the use of another therapeutic agent for treating a disease or condition mediated by the complement alternative pathway and/or Factor D wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor D, wherein the method comprises administering to the subject a therapeutically effective amount of the compound according to the definition of Formula (I).

In one embodiment, the invention provides a compound according to the definition of formula (I), (Ia), (VII) or any subformulae thereof, for use as a medicament.

In one embodiment, the invention provides the use of a compound according to the definition of formula (I), (Ia), (VII) or any subformulae thereof, for the treatment of a disorder or disease in a subject mediated by complement activation. In particular, the invention provides the use of a compound according to the definition of formula (I), (Ia), (VII) or any subformulae thereof, for the treatment of a disorder or disease mediated by activation of the complement alternative pathway.

In one embodiment, the invention provides the use of a compound according to the definition of formula (I), (Ia), in the manufacture of a medicament for the treatment of a disorder or disease in a subject characterized by activation of the complement system. More particularly in the manufacture of a medicament for the treatment of a disease or disorder in a subject characterized by over activiation of the complement alternative pathway.

In one embodiment, the invention provides the use of a compound according to the definition of formula (I), (Ia), or subformulae thereof for the treatment of a disorder or disease in a subject characterized by activation of the complement system. More particularly, the invention provides uses of the compounds provided herein in the treatment of a disease or disorder characterized by over activiation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing compelment mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macuar degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

The following examples are intended to illustrate the invention and are not to be construed as being limitations thereon. Temperatures are given in degrees centrigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the Following In Vitro Tests May be Used
Human complement factor D assay: Method 1

Recombinant human factor D (expressed in *E. coli* and purified using standard methods) at 10 nM concentration is incubated with test compound at various concentrations for 1 hour at room temperature in 0.1 M Hepes buffer, pH 7.5, containing 1 mM $MgCl_2$, 1 M NaCl and 0.05% CHAPS. A synthetic substrate Z-Lys-thiobenzyl and 2,4-dinitrobenzenesulfonyl-fluoresceine are added to final concentrations of 200 µM and 25 µM, respectively. The increase in fluorescence is recorded at excitation of 485 nm and emission at 535 nm in a microplate spectrofluorimeter. $IC_{50}$ values are calculated from percentage of inhibition of complement factor D-activity as a function of test compound concentration.

Human Complement Factor D Assay: Method 2

Recombinant human factor D (expressed in *E. coli* and purified using standard methods) at a 10 nM concentration is incubated with test compound at various concentrations for 1 hour at room temperature in 0.1 M PBS pH 7.4 containing 7.5 mM $MgCl_2$ and 0.075% (w/v) CHAPS. Cobra venom factor and human complement factor B substrate complex is added to a final concentration of 200 nM. After 1 hour incubation at room temperature, the enzyme reaction was stopped by addition of 0.1 M sodium carbonate buffer pH 9.0 containing 0.15 M NaCl and 40 mM EDTA. The product of the reaction, Ba, was quantified by means of an enzyme-linked-immunosorbent assay. $IC_{50}$ values are calculated from percentage of inhibition of factor D-activity as a function of test compound concentration.

The following Examples, while representing preferred embodiments of the invention, serve to illustrate the invention without limiting its scope.

ABBREVIATIONS abs. Absolute
Ac acetyl
EtOAc ethyl acetate
AcOH acetic acid
aq aqueous
cc concentrated
c-hexane cyclohexane
CSA Camphor sulfonic acid
DIPEA N,N-diisopropylethylamine
DBU 1,8-diazabicyclo[5.4.0]undec-7-ene
DCC N,N'-dicyclohexylcarbodiimide
DIBALH diisobutylaluminium hydride
DMF dimethylformamide
DMSO dimethylsulfoxide
DPPA diphenylphosphoryl azide
EDCl 1-(3-dimethylaminopropyl)-3-ethylcarbodiimide hydrochloride
Ether diethylether
$Et_3N$ triethylamine
$Et_2O$ diethylether
EtOH ethanol
Flow flow rate
h hour(s)
HMPA hexamethylphosphoroamide
HOBt 1-hydroxybenzotriazole
HBTU 2-(1H-benzotriazol-1-yl)-1,1,3,3-tetramethyluronium tetrafluoroborate
HPLC High Performance Liquid Chromatography
iPrOH isopropanol
L liter(s)
KHMDS potassium hexamethyldisilazane
LC-MS Liquid Chromatography/Mass Spectrometry
LDA lithium diisopropylamine
Me methyl
MeI methyl iodide
MeOH methanol
MesCl Mesyl Chloride
min minute(s)
mL milliliter
MS Mass Spectrometry
NBS N-Bromo succinimide
NMM 4-methylmorpholine
NMR Nuclear Magnetic Resonance
Pd/C palladium on charcoal
Ph phenyl
PyBOP (benzotriazol-1-yloxy)-tripyrrolidinophosphonium-Hexafluorophosphate
SEM-Cl 2-(Trimethylsilyl)ethoxymethyl chloride
RT room temperature
TBAF tetra-butylammonium fluoride
TBDMS-Cl tert-butyldimethylsilyl chloride
TBDMS tert-butyldimethylsilyl
TBME tert-Butylmethylether
TEA triethylamine
TMEDA tetramethylethylenediamine
TEMPO 2,2,6,6,-tetramethyl-1-piperidinyloxy free radical
TFA trifluoroacetic acid
THF tetrahydrofurane
$T_3P$ Propylphosphonic anhydride
RP reverse phase
Prep Preparative
TLC Thin Layer Chromatography
$t_r$ retention time
Trademarks
Celite=Celite® (The Celite Corporation)=filtering aid based on diatomaceous earth
$NH_2$ Isolute (=Isolute® $NH_2$, Isolute® is registered for Argonaut Techno-logies, Inc.)=ion exchange with amino groups based on silica gel
Nucleosil=Nucleosil®, trademark of Machery & Nagel, Düren, FRG for HPLC materials
PTFE membrane=Chromafil O-45/15MS Polytetrafluoroethylene Machereynagel)
PL Thiol Cartridge=Stratosphere® SPE, PL-Thiol MP SPE+, 500 mg per 6 mL tube, 1.5 mmol (nominal)
Temperatures are measured in degrees Celsius. Unless otherwise indicated, the reactions take place at RT.
Phase Separator: Biotage—Isolute Phase separator (Part Nr: 120-1908-F for 70 mL and Part Nr: 120-1909-J for 150 mL)
TLC conditions: $R_f$ values for TLC are measured on 5×10 cm TLC plates, silica gel $F_{254}$, Merck, Darmstadt, Germany.
HPLC Conditions:
HPLC were performed using an Agilent 1100 or 1200 series instrument. Mass spectra and LC/MS were determined using an Agilent 1100 series instrument.
a: Waters Symmetry C18, 3.5 um, 2.1×50 mm, 20-95% $CH_3CN/H_2O/3.5$ min, 95% $CH_3CN/2$ min, $CH_3CN$ and $H_2O$ containing 0.1% TFA, flow: 0.6 mL/min
b: Agilent Eclipse XDB-C18; 1.8 um; 4.6×50 mm 20-100% $CH_3CN/H_2O/6$ min, 100% $CH_3CN/1.5$ min, $CH_3CN$ and $H_2O$ containing 0.1% of TFA, flow: 1 mL/min
c. Agilent Eclipse XDB-C18, 1.8 um, 4.6×50 mm, 5-100% $CH_3CN/H_2O/6$ min, 100% $CH_3CN/1.5$ min, $CH_3CN$ and $H_2O$ containing 0.1% TFA, flow: 1 mL/min
d. Waters XBridge C18, 2.5 um, 3×30 mm, 10-95% $CH_3CN/H_2O/1.7$ min/flow: 1.4 mL/min, 95% $CH_3CN$/flow: 0.7 min/1.6 mL/min, $CH_3CN$ containing 0.05% TFA, $H_2O$ containing 0.05% TFA and 5% $CH_3CN$
e. Waters XBridge C18, 2.5 um, 3×30 mm, 1% $CH_3CN/H_2O/0.5$ min/flow: 1.4 mL/min, 1-95% $CH_3CN/H_2O/1.7$ min/flow: 1.4 mL/min, 95% $CH_3CN$/flow: 0.7 min/1.6 mL/min, $CH_3CN$ containing 0.05% TFA, $H_2O$ containing 0.05% TFA and 5% $CH_3CN$
f. Waters Sunfire C18, 2.5 um, 3×30 mm, 10-98% in 2.5 min, $CH_3CN$ and $H_2O$ containing 0.1% TFA, flow: 1.4 mL/min
g. Waters Sunfire C18, 2.5 um, 3×30 mm, 0-10% in 0.5 min, 10-98% in 2.5 min, $CH_3CN$ and $H_2O$ containing 0.1% TFA, flow: 1.4 mL/min
h. Waters Sunfire C18, 2.5 um, 3×30 mm, 10-98% in 4.5 min, $CH_3CN$ and $H_2O$ containing 0.1% TFA, flow: 1.4 mL/min
i. Waters Sunfire C18, 5 um, 21×50 mm, 20-95% $CH_3CN/H_2O/3.5$ min, 95% $CH_3CN/2$ min, $CH_3CN$ and $H_2O$ containing 0.1% HCOOH, flow: 0.6 mL/min
j. Waters Atlantis; 2.1×30 mm, 20-95% $CH_3CN/H_2O/2.5$ min, 95% $CH_3CN/H_2O/0.05$ min, 20-95-20% $CH_3CN/H_2O/0.45$ min $CH_3CN$ and $H_2O$ containing 0.1% of HCOOH, flow: 0.6 mL/min
k. Agilent Eclipse XDB-C18; 1.8 um; 2.1×30 mm 5-100% $CH_3CN/H_2O/3$ min, 100% $CH_3CN/0.75$ min, $CH_3CN$ and $H_2O$ containing 0.1% of TFA, flow: 0.6 mL/min l. Agilent Eclipse XDB-C18; 1.8 um; 2.1×30 mm 20-100% CH$_3$CN/H$_2$O/3 min, 100% CH$_3$CN/0.75 min, CH$_3$CN and H$_2$O containing 0.1% of TFA, flow: 0.6 mL/min UPLC Conditions:

m. UPLC/MS: Waters Acquity; UPLC column: Waters Acquility HSS T3; 1.8 um; 2.1×50 mm 10-95% CH$_3$CN/H$_2$O/1.5 min, H$_2$O containing 0.05% HCOOH and CH$_3$CN containing 0.04% HCOOH+3.75 mM NH$_4$OAc, flow 1.2 mL/min The asterisk (*) indicated in the name of a compound designate a racemic mixture.

Part A

Synthesis of Substituted Aromatic or Heteroromatic Building Blocks

Scheme A1: general protocol for the preparation of various isocyanate building blocks

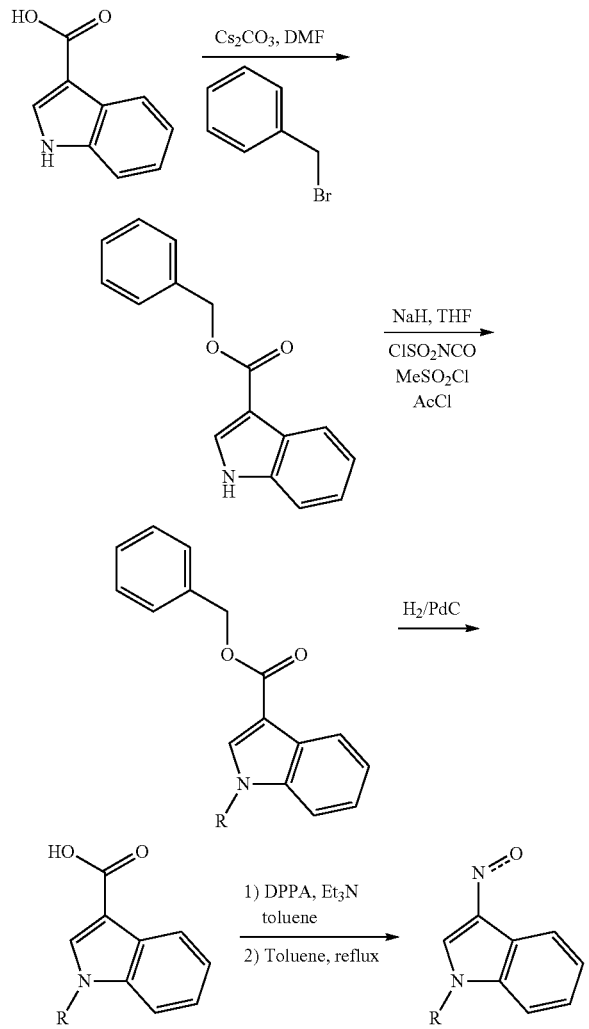

R = CONH$_2$, COMe 3-isocyanato-indole-1-carboxylic acid amide

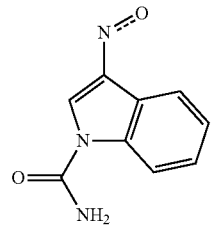

A. 1H-Indole-3-carboxylic acid benzyl ester

To a solution of 1H-indole-3-carboxylic acid (5 g, 31 mmol) in DMF (70 mL) under nitrogen atmosphere at 0° C. was added cesium carbonate (11 g, 31 mmol) and benzyl bromide (4.05 mL, 34.1 mmol). The reaction mixture was stirred at RT for 48 h and poured into water. EtOAc was added and the layers were separated, the aqueous one being back extracted three times with EtOAc. The combined organic layers were washed with water, dried over Na$_2$SO$_4$, filtered and concentrated. The residue was taken up in Et$_2$O and the resulting precipitate was filtered-off to give the title compound. TLC, R$_f$ (c-hexane/EtOAc 1:1)=0.55; MS (LC-MS): 252.1 [M+H]+, 274.0 [M+Na]+, 525.1 [2M+Na]+, 250.1 [M−H]−; t$_R$ (HPLC conditions a) 3.77 min.

B. 1-Carbamoyl-1H-indole-3-carboxylic acid benzyl ester

To a solution of 1H-indole-3-carboxylic acid benzyl ester (3.5 g, 13.9 mmol) in THF (70 mL) at 5° C., was added NaH (60% in mineral oil, 557 mg, 13.9 mmol). The mixture was stirred at 5° C. for 30 min before slow dropwise addition of chlorosulfonyl isocyanate (2.42 mL, 27.9 mmol) maintaining the temperature between 5° C. and 10° C. The pale yellow solution was further stirred at RT for 3.5 h. Acetic acid (22.5 mL) was added (exothermic), and the resulting solution was stirred at RT for 1.5 h before addition of ice cubes and water (100 mL). The white thick suspension was stirred at RT for 30 min and the precipitate was filtered-off, taken up in MeOH and filtered-off again to afford the desired compound. 1H-NMR (400 MHz, DMSO): δ (ppm) 8.64 (s, 1H), 8.29 (d, 1H), 8.04 (d, 1H), 7.90 (m, 2H), 7.50 (d, 2H), 7.42 (t, 2H), 7.36-7.30 (m, 3H), 5.38 (s, 2H).

C. 1-carbamoyl-1H-indole-3-carboxylic acid

1-Carbamoyl-1H-indole-3-carboxylic acid benzyl ester (1.33 g, 4.52 mmol) was dissolved in a mixture of DMF/THF 1:1 (28 mL), Pd/C (10%, 250 mg) was added and the solution was degassed 3 times replacing air by nitrogen and finally nitrogen by hydrogen. The reaction mixture was further stirred under hydrogen atmosphere overnight and the catalyst was removed through a pad of Celite and washed with THF. The solvents were concentrated under high vacuum to give a yellowish solid which was taken up in Et$_2$O and filtered-off to afford the title compound. 1H-NMR (400 MHz, DMSO): δ (ppm) 12.6 (m, 1H), 8.54 (bs, 1H), 8.28 (d, 1H), 8.05 (d, 1H), 7.85 (m, 2H), 7.34-7.27 (m, 2H).

D. 3-isocyanato-indole-1-carboxylic acid amide

To a suspension of 1-carbamoyl-1H-indole-3-carboxylic acid (1.31 g, 6.42 mmol) in toluene (30 mL, CH$_2$Cl$_2$ can also be used instead of toluene) under nitrogen was added Et₃N (893 μl, 6.42 mmol). After 15 min DPPA (1.54 mL, 6.42 mmol) was added and the reaction mixture was further stirred at RT overnight. Toluene was concentrated, the residue was taken up in CH₂Cl₂ and the precipitate was filtered-off to give the acyl azide intermediate (565 mg). Toluene (20 mL) was added and the suspension refluxed for 1.5 h under nitrogen atmosphere until no more acyl azide could be detected by TLC. Toluene was concentrated under vacuum and the desired isocyanate was directly used in the next step without further purification. 1H-NMR (400 MHz, CDCl3): δ (ppm) 8.18 (d, 1H), 7.61 (d, 1H), 7.44 (t, 1H), 7.35 (t, 1H), 7.23 (s, 1H), 5.39 (bs, 2H).

3-Isocyanato-6-methoxy-indole-1-carboxylic acid amide

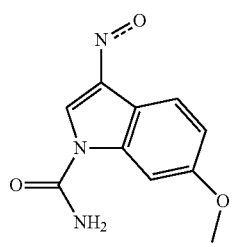

was prepared from 6-methoxy-indole-3-carboxylic acid using the protocol described for the preparation of 3-isocyanato-indole-1-carboxylic acid amide scheme A1.

1-(3-Isocyanato-indol-1-yl)-ethanone

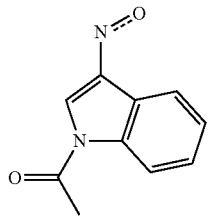

A. 1-Acetyl-1H-indole-3-carboxylic acid benzyl ester

To a solution of 1H-indole-3-carboxylic acid benzyl ester (600 mg, 2.39 mmol) in THF (10 mL) at 0° C. under nitrogen was added NaH (60% in mineral oil, 191 mg, 4.78 mmol). The mixture was stirred for 20 min at 0° C., acetyl chloride (339 μl, 4.78 mmol) was added and the resulting suspension was stirred at RT for 48 h. The solvent was concentrated and the residue poured in water and extracted twice with CH₂Cl₂. The Combined organic layers were dried over Na₂SO₄, filtered and concentrated. The crude residue was purified by flash column chromatography on silica gel (c-hexane to c-hexane/EtOAc 75:25) to give the desired product as a white solid. TLC, R$_f$ (c-hexane/EtOAc 3:1)=0.38; MS (LC-MS): 294.1 [M+H]+, 316.0 [M+Na]+; t$_R$ (HPLC conditions a): 4.69 min.

B. 1-Acetyl-1H-indole-3-carboxylic acid

1-Acetyl-1H-indole-3-carboxylic acid benzyl ester (300 mg, 1.02 mmol) was dissolved in MeOH (10 mL), Pd/C 10% (60 mg) was added and the solution was degassed 3 times replacing air by nitrogen and finally nitrogen by hydrogen. The reaction mixture was further stirred under hydrogen atmosphere 2 h and the catalyst was removed through a pad of Celite and washed with MeOH. The solvent was concentrated under vacuum to give a mixture of 1-acetyl-1H-indole-3-carboxylic acid and 1-acetyl-2,3-dihydro-1H-indole-3-carboxylic acid benzyl ester in a 7:3 ratio as measured by NMR. The desired compound was not purified at this stage but was used directly in the next step. 1-Acetyl-1H-indole-3-carboxylic acid: TLC, R$_f$ (CH₂Cl₂/MeOH 9:1)=0.31; MS (LC-MS): 204.1 [M+H]+, 202.1 [M−H]−; t$_R$ (HPLC conditions a): 3.14 min. 1-Acetyl-2,3-dihydro-1H-indole-3-carboxylic acid benzyl ester: MS (LC-MS): 206.1 [M+H]+, 228.1 [M+Na]+, 433.0 [2M+Na]+, 204.1 [M−H]−; t$_R$ (HPLC conditions a): 1.93 min.

C. 1-(3-Isocyanato-indol-1-yl)-ethanone

To a suspension of 1-acetyl-1H-indole-3-carboxylic acid (containing ca 30% of 1-acetyl-2,3-dihydro-1H-indole-3-carboxylic acid benzyl ester, 194 mg) in toluene (5 mL) was added Et₃N (130 μl, 0.935 mmol) and the resulting solution was stirred at RT under nitrogen for 15 min. DPPA (225 μl, 0.935 mmol) was added and the reaction mixture was further stirred at RT overnight. Toluene was concentrated under vacuum and the residue was purified by flash column chromatography on silica gel (c-hexane to c-hexane/EtOAc 1:1) to give the desired acyl azide intermediate as a white powder (96 mg; t$_R$ HPLC conditions a: 3.86 min). Toluene (3 mL) was added and the mixture was refluxed for 1.5 h until completion of the reaction. Toluene was concentrated under vacuum to give the desired isocyanate. TLC, R$_f$ (c-hexane/EtOAc 1:2)= 0.58; t$_R$ (HPLC conditions a): 3.92 min. 1H-NMR (400 MHz, CDCl₃): δ (ppm): 8.44 (m, 1H), 7.56 (d, 1H), 7.44 (t, 1H), 7.36 (t, 1H), 7.23 (d, 1H), 2.60 (s, 3H).

Scheme A2: preparation of 3-Isocyanato-indole-1-carboxylic acid methylamide

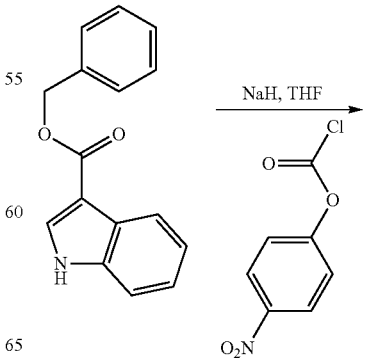

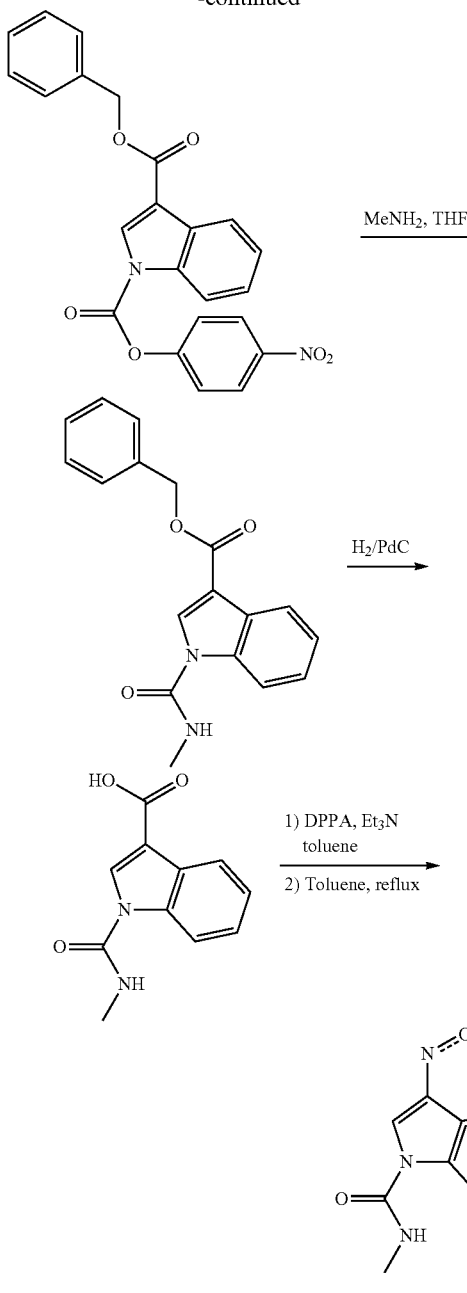

A. Indole-1,3-dicarboxylic acid 3-benzyl ester 1-(4-nitro-phenyl) ester

To a solution of 1H-indole-3-carboxylic acid benzyl ester (100 mg, 0.398 mmol) in dry THF (2 mL) at 0° C. under nitrogen was added NaH (60% in mineral oil, 32 mg, 0.796 mmol). The resulting solution was stirred at 0° C. for 10 min, and added dropwise to a stirred solution of 4-nitrophenyl chloroformate (160 mg, 0.796 mmol) in dry THF (2 mL) cooled at 0° C. The resulting solution was stirred at RT under nitrogen for 48 h. The mixture was poured into water and extracted twice with $CH_2Cl_2$. The combined organic layers were dried over $Na_2SO_4$, filtered and concentrated. The crude residue was successively purified by flash column chromatography on silica gel (c-hexane to c-hexane/EtOAc 7:3) and by preparative HPLC (Waters SunFire C18-ODB, 5 μm, 19×50 mm, 20% $CH_3CN/H_2O$ 2.5 min, 20-100% $CH_3CN/H_2O$ in 10 min, $CH_3CN/H_2O$ containing 0.1% HCOOH flow: 20 mL/min) to give after extraction of the pure fractions the desired compound. TLC, $R_f$ (c-hexane/EtOAc 1:1)=0.8; MS (LC/MS): 439.0 [M+Na]+; $t_R$ (HPLC conditions a): 4.58 min.

B. 1-Methylcarbamoyl-1H-indole-3-carboxylic acid benzyl ester

To a solution of indole-1,3-dicarboxylic acid 3-benzyl ester 1-(4-nitro-phenyl)ester (45 mg, 0.108 mmol) in dry THF (1 mL) was added methylamine (2 M in THF, 270 μl, 0.54 mmol) and the reaction was stirred at RT for 15 min. The mixture was concentrated and the residue was taken up in $Et_2O$ and filtered to give the desired compound. TLC, $R_f$ (c-hexane/EtOAc 1:1)=0.52; MS (LC/MS): 309.1 [M+H]+, 331.1 [M+Na]+, 639.2 [2M+Na]+, 353.2 [M+HCOO]−; $t_R$ (HPLC conditions a): 3.86 min.

C. 1-Methylcarbamoyl-1H-indole-3-carboxylic acid

To 1-Methylcarbamoyl-1H-indole-3-carboxylic acid benzyl ester (115 mg, 0.373 mmol) dissolved in a mixture of $MeOH/CH_2Cl_2$ 1-1 (4 mL), Pd/C 10% (20 mg) was added and the solution was degassed 3 times replacing air by nitrogen and finally nitrogen by hydrogen. The reaction mixture was further stirred under hydrogen atmosphere for 1 h. The mixture was placed under a nitrogen atmosphere and the catalyst was removed through a pad of Celite and washed with MeOH. Solvents were concentrated under vacuum to give the desired compound. MS (LC/MS): 219.1 [M+H]+; $t_R$ (HPLC conditions a): 2.54 min.

D. 3-Isocyanato-indole-1-carboxylic acid methylamide

A solution of 1-methylcarbamoyl-1H-indole-3-carboxylic acid (80 mg, 0.367 mmol) and $Et_3N$ (51 μl, 0.367 mmol) in a mixture of toluene/THF 1/1 (4 mL) was stirred at RT under nitrogen for 30 min. DPPA (90%, 88 μl, 0.367 mmol) was added and the reaction mixture was further stirred at RT under nitrogen overnight. Solvents were concentrated under vacuum and the residue was purified by flash column chromatography on silica gel (c-hexane/EtOAc 1-1) to give the acyl azide intermediate as white crystals (83 mg, $t_R$ (HPLC conditions a): 3.40 min). The acyl azide intermediate was refluxed in toluene (2 mL) for 1 h to give after concentration of the solvent the desired isocyanate. The compound was used directly in the next step without further purification.

Scheme A3: preparation of 6-ethyl-3-isocyanato-indole-1-carboxylic acid amide

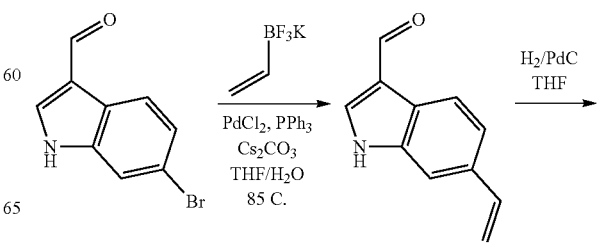

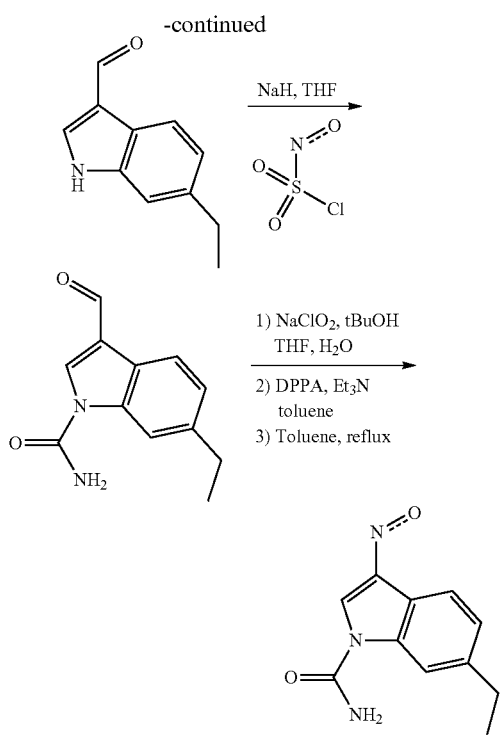

A. 6-Vinyl-1H-indole-3-carbaldehyde 6-bromoindole-3-carboxaldehyde (5 g, 22.3 mmol), potassium vinyltrifluoroborate (4.48 g, 33.5 mmol), PdCl$_2$ (396 mg, 2.23 mmol), PPh$_3$ (1.75 mg, 6.7 mmol) and Cs$_2$CO$_3$ (2.18 mg, 66.9 mmol) were combined in a 500 mL flask placed under a nitrogen atmosphere. THF (135 mL) and H$_2$O (15 mL) were added and the yellow solution was heated at 85° C. for 2 days. The reaction was allowed to cool to RT, water was added and the mixture was extracted twice with CH$_2$Cl$_2$. The combined organic layers were dried over Na$_2$SO$_4$, filtered and concentrated. The crude residue was purified by flash column chromatography on silica gel (c-hexane to c-hexane/EtOAc 1:1) to give the title compound. TLC, R$_f$ (c-hexane/EtOAc 1:1)=0.4; MS (LC/MS): 172.0 [M+H]+ 170.1 [M−H]−; t$_R$ (HPLC conditions a): 2.95 min.

B. 6-Ethyl-1H-indole-3-carbaldehyde

6-Vinyl-1H-indole-3-carbaldehyde (1.5 g, 8.76 mmol) was dissolved in THF (45 mL), Pd/C 10% (300 mg) was added and the solution was degassed 3 times replacing air by nitrogen and finally nitrogen by hydrogen. The reaction mixture was further stirred under hydrogen atmosphere 4 h and the catalyst was removed through a pad of Celite and washed with THF. The solvent was concentrated under and the crude residue was purified by flash column chromatography on silica gel (c-hexane to c-hexane/EtOAc 1:1) to give the desired compound. TLC, R$_f$ (c-hexane/EtOAc 1:1)=0.40; MS (LC/MS): 174.1 [M+H]+, 196.1 [M+Na]+, 172.1 [M−H]−; t$_R$ (HPLC conditions a): 3.05 min.

C. 6-Ethyl-3-formyl-indole-1-carboxylic acid amide

To a solution of NaH (60% in mineral oil, 259 mg, 6.47 mmol) in THF (10 mL) cooled to 5° C. under nitrogen a solution of 6-ethyl-1H-indole-3-carbaldehyde (1.12 g, 6.47 mmol) in THF (20 mL) was slowly added and the mixture was stirred at 5° C. for 30 min. While maintaining the internal temperature between 5° C. and 10° C., chlorosulfonyl isocyanate (1.12 mL, 12.9 mmol) was added dropwise and the solution was further stirred at RT overnight. Acetic acid (15 mL) was added (slightly exothermic) and the solution was stirred at RT for 1.5 h. Ice cubes and water (25 mL) were added, and the solution was further stirred at RT for 30 min. Water was added and the mixture was extracted with EtOAc. The aqueous layer was back-extracted twice with EtOAc. The combined organic layers were dried (Na$_2$SO$_4$), filtered and concentrated. The crude residue was purified by flash column chromatography on silica gel (c-hexane to EtOAc) to give the desired compound. LC/MS: 290.0 [M+H]+, 312.0 [M+Na]+; t$_R$ (HPLC conditions a): 3.02 min.

D. 1-Carbamoyl-6-ethyl-1H-indole-3-carboxylic acid

6-Ethyl-3-formyl-indole-1-carboxylic acid amide (720 mg, 3.33 mmol) was dissolved in a mixture of THF (60 mL) and t-butanol (18 mL). 2-methyl-2-butene (2 M solution in THF, 66.6 mL, 133 mmol) was added, followed by a water (16 mL) solution of NaClO$_2$ (80%, 3.76 g, 33.3 mmol) and NaH$_2$PO$_4$ (3.20 g, 26.6 mmol). The resulting solution was stirred at RT for 4 h and THF was concentrated. EtOAc was added and the layers separated. The aqueous layer was acidified by addition of HCl 1N and extracted twice with EtOAc. The combined organic extracts were dried (Na$_2$SO$_4$), filtered and concentrated. The crude residue was purified by flash column chromatography on silica gel (eluent: c-hexane to EtOAc to CH$_2$Cl$_2$/MeOH 8:2) to give the desired compound. t$_R$ (HPLC conditions a): 2.17 min. 1H-NMR (400 MHz, CDCl$_3$): δ (ppm): 12.9 (m, 1H), 8.81 (s, 1H), 8.66 (bs, 1H), 8.23 (d, 1H),), 8.09 (m, 2H), 7.70 (dd, 1H).

E. 6-Ethyl-3-isocyanato-indole-1-carboxylic acid amide

To a solution of 1-carbamoyl-6-ethyl-1H-indole-3-carboxylic acid (330 mg, 1.42 mmol) in toluene (8 mL) was added triethylamine (0.198 mL, 1.42 mmol) and the resulting suspension was stirred at RT under nitrogen for 15 min. DPPA (0.34 mL, 1.42 mmol) was added and the reaction mixture was further stirred at RT for 3 h. TLC indicated completion of the reaction. The mixture was concentrated, CH$_2$Cl$_2$ was added and the suspension was filtered to give the acyl azide intermediate. Toluene (4 mL) was added and the reaction mixture was refluxed for 3 h. The crude compound was directly used in the next step.

Scheme A4: general protocol described for the preparation of 5-allyloxy-3-isocyanato-indole-1-carboxylic acid amide

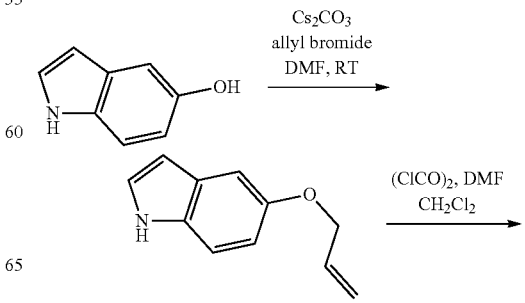

-continued

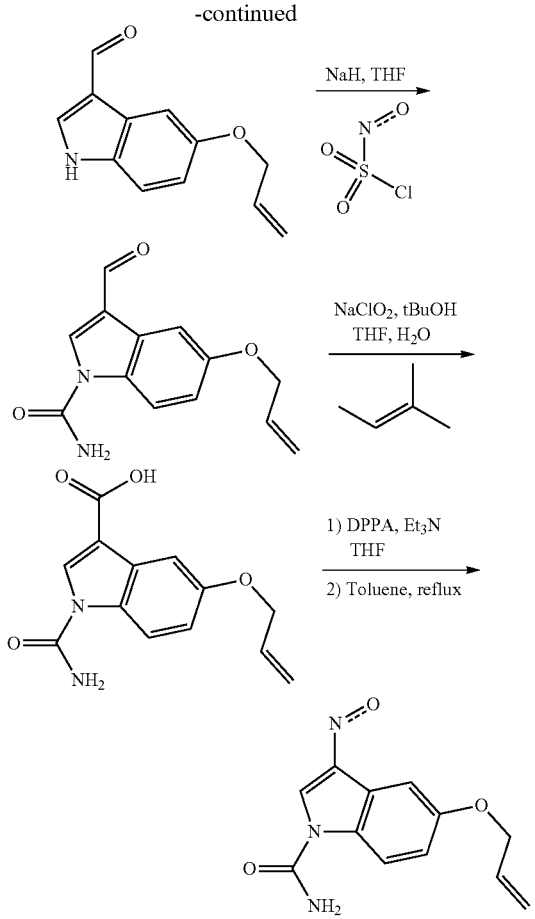

A. 5-Allyloxy-1H-indole

To a suspension of 5-hydroxyindole (1.23 g, 9.24 mmol) and cesium carbonate (3.01 g, 9.24 mmol) in DMF (40 mL) under nitrogen atmosphere at 0° C. was added allylbromide (879 µl, 10.16 mmol). The reaction mixture was stirred at RT for 2 h and poured into water and extracted with EtOAc (×3). The combined organic layers were washed twice with water, dried over $Na_2SO_4$, filtered and concentrated. The crude residue was purified by flash column chromatography on silica gel (c-hexane to c-hexane/EtOAc 9:1) to give the desired compound. TLC, $R_f$ (c-hexane/EtOAc 1:1)=0.76; $t_R$ (conditions a): 3.46 min.

B. 5-Allyloxy-1H-indole-3-carbaldehyde

To a solution of oxalyl chloride (1.22 mL, 14.1 mmol) in dry $CH_2Cl_2$ (20 mL) was added at 0° C. under nitrogen a solution of dry DMF (1.3 mL) in dry $CH_2Cl_2$ (20 mL). The mixture was stirred at 0° C. for 30 min and a solution of 5-allyloxy-1H-indole (1.25 g, 7.22 mmol) in $CH_2Cl_2$ (10 mL) was added. The resulting solution was allowed to reach RT and stirred for 4 h. The solvent was concentrated and the residue dissolved in THF (35 mL) and 20% aqueous ammonium acetate (48 mL) and heated at reflux for 30 min, cooled, treated with an aqueous saturated solution of $NaHCO_3$, and extracted twice with EtOAc. The combined organic layers were dried over $Na_2SO_4$, filtered and concentrated. The crude solid was taken up in $CH_2Cl_2$ and filtered-off to give the desired compound. TLC, $R_f$ (c-hexane/EtOAc 1:2)=0.56; MS (LC/MS): 202.0 [M+H]+, 224.1 [M+Na]+, 200.1 [M−H]−, 159.1 [M−H-allyl]−; $t_R$ (HPLC conditions a): 2.89 min.

C. 5-Allyloxy-3-formyl-indole-1-carboxylic acid amide

To a suspension of NaH (60% in mineral oil, 352 mg, 8.79 mmol) in THF (12 mL) under nitrogen atmosphere at 5° C. was added a solution of 5-allyloxy-1H-indole-3-carbaldehyde (1.18 g, 5.86 mmol) in THF (28 mL) and the resulting mixture was stirred at 5° C. for 30 min before slow addition of chlorosulfonyl isocyanate (11.02 mL, 11.7 mmol) while maintaining the temperature between 5° C. and 10° C. The solution was further stirred at RT for 4 h, acetic acid (11 mL) was added and the solution was stirred at RT for 1 h. Ice cubes and water (100 mL) were added and the mixture was stirred at RT for 30 min. The solution was extracted twice with EtOAc and the combined organic extracts were dried over $Na_2SO_4$, filtered and concentrated. The crude residue was purified by flash column chromatography on silica gel (100% c-hexane to 100% EtOAc) to give the title compound. TLC, $R_f$ (c-hexane/EtOAc 1:2)=0.36; MS (LC/MS): 245.1 [M+H]+, 267.0 [M+Na]+, 200.1 [M−$CONH_2$]−; $t_R$ (HPLC conditions a): 2.95 min.

D. 5-Allyloxy-1-carbamoyl-1H-indole-3-carboxylic acid

5-Allyloxy-3-formyl-indole-1-carboxylic acid amide (530 mg, 2.17 mmol) was dissolved in a mixture of THF (38 mL) and t-butanol (12 mL). 2-methyl-2-butene 2 M solution in THF (40 mL, 80 mmol) was added, followed by a water (9.5 mL) solution of $NaClO_2$ (80%, 2.45 g, 21.7 mmol) and $NaH_2PO_4$ (2.08 g, 17.4 mmol). The resulting solution was stirred at RT for 1 h, until consumption of the starting material. HCl 1N (3 mL) was added, and the organic solvents were concentrated. The remaining aqueous layer was filtered and the resulting precipitate was washed with water and $Et_2O$ to give the desired compound. TLC, $R_f$ (c-hexane/EtOAc 1:2)= 0.08; LC/MS: 261.1 [M+H]+, 259.0 [M−H]−, 216.1 [M−$CONH_2$]−, 519.1 [2M−H]−; $t_R$ (HPLC conditions a): 2.8 min.

E. 5-Allyloxy-3-isocyanato-indole-1-carboxylic acid amide

To a suspension of 5-allyloxy-1-carbamoyl-1H-indole-3-carboxylic acid (500 mg, 1.92 mmol) in THF (10 mL) was added $Et_3N$ (267 µl, 1.92 mmol) and the resulting solution was stirred at RT under nitrogen for 15 min. DDPA (462 µl, 1.92 mmol) was added and the reaction was further stirred at RT under nitrogen for 1 h. TLC indicated consumption of the starting material. THF was concentrated and the residue was taken up in $CH_2Cl_2$ and filtered-off to give the crude acyl azide intermediate (TLC, $R_f$ (c-hexane/EtOAc 1:2)=0.65; $t_R$ (HPLC conditions a): 3.50 min). The acyl azide intermediate was suspended in toluene (7 mL) and refluxed under nitrogen for 2 h until completion of the reaction. The crude isocyanate was used as was in the next step.

6-Allyloxy-3-isocyanato-indole-1-carboxylic acid amide

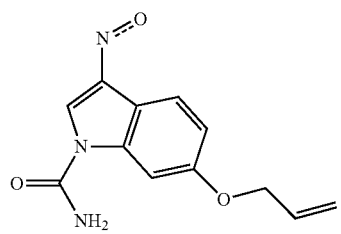

was prepared from 6-hydroxy-indole using the protocol described for the preparation of 5-allyloxy-3-isocyanato-indole-1-carboxylic acid amide in Scheme A4.

6-Methyl-3-isocyanato-indole-1-carboxylic acid amide

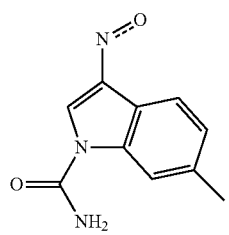

was prepared from 6-methyl-1H-indole-3-carbaldehyde using the protocol described for steps C, D and E in scheme A4 for the preparation of 5-allyloxy-3-isocyanato-indole-1-carboxylic acid amide.

6-Bromo-3-isocyanato-indole-1-carboxylic acid amide

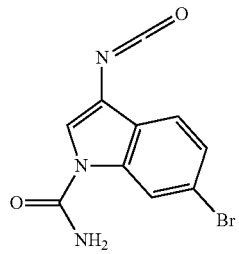 [SMILES: NC(=O)n1cc(N=CC=O)c2ccc(Br)cc21]

was prepared from 6-bromo-1H-indole-3-carbaldehyde using the protocol described for steps C, D and E in scheme A4 for the preparation of 5-allyloxy-3-isocyanato-indole-1-carboxylic acid amide.

6-Chloro-3-isocyanato-indole-1-carboxylic acid amide

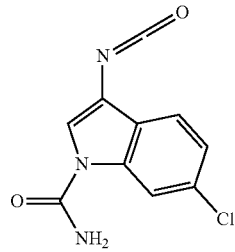 [SMILES: NC(=O)n1cc(N=CC=O)c2ccc(Cl)cc21]

was prepared from 6-chloroindole using the protocol described for steps B-E in scheme A4 for the preparation of 5-allyloxy-3-isocyanato-indole-1-carboxylic acid amide.

6-Trifluoromethyl-3-isocyanato-indole-1-carboxylic acid amide

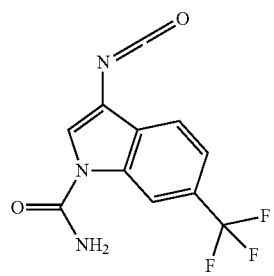 [SMILES: NC(=O)n1cc(N=CC=O)c2ccc(C(F)(F)F)cc21]

was prepared from 6-trifluoromethylindole using the protocol described for steps B-E in scheme A4 for the preparation of 5-allyloxy-3-isocyanato-indole-1-carboxylic acid amide except that the acyl azide intermediate was prepared in 1,2 dimethoxyethane instead of toluene.

5-Fluoro-3-isocyanato-indole-1-carboxylic acid amide

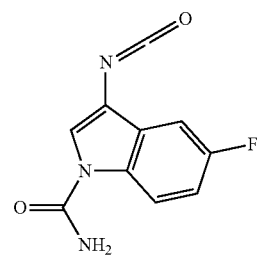 [SMILES: NC(=O)n1cc(N=CC=O)c2cc(F)ccc21]

was prepared from 5-fluoro-1H-indole-3-carbaldehyde using the protocol described for steps C, D and E in scheme A4 for the preparation of 5-allyloxy-3-isocyanato-indole-1-carboxylic acid amide.

6-Fluoro-3-isocyanato-indole-1-carboxylic acid amide

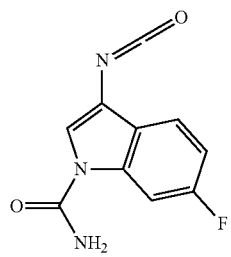 [SMILES: NC(=O)n1cc(N=CC=O)c2ccc(F)cc21]

was prepared from 6-fluoro-1H-indole-3-carbaldehyde [2795-41-7] using the protocol described for steps C, D and E in scheme A4 for the preparation of 5-allyloxy-3-isocyanato-indole-1-carboxylic acid amide.

3-Isocyanato-5-methoxy-indole-1-carboxylic acid amide

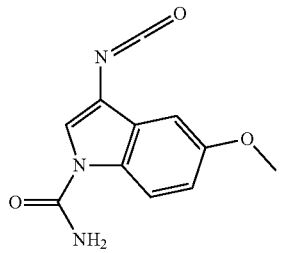 [SMILES: COc1ccc2c(c1)c(N=CC=O)cn2C(N)=O]

was prepared from 5-methoxy-1H-indole-3-carbaldehyde using the protocol described for steps C, D and E in scheme A4 for the preparation of 5-allyloxy-3-isocyanato-indole-1-carboxylic acid amide.

6-Benzyloxy-3-isocyanato-indole-1-carboxylic acid amide

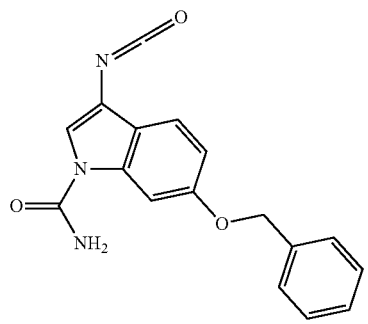 [SMILES: NC(=O)n1cc(N=CC=O)c2ccc(OCc3ccccc3)cc21]

was prepared from 6-benzyloxyindole using the protocol described for steps B-E in scheme A4 for the preparation of 5-allyloxy-3-isocyanato-indole-1-carboxylic acid amide.

6-Difluoromethoxy-3-isocyanato-indole-1-carboxylic acid amide

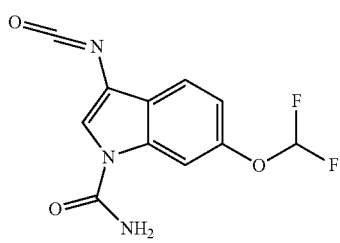 [SMILES: NC(=O)n1cc(N=C=O)c2ccc(OC(F)F)cc21]

was prepared from 6-difluoromethoxy-1H-indole [200207-21-2] using the protocol described for steps B-E in Scheme A4 for the preparation of 5-allyloxy-3-isocyanato-indole-1-carboxylic acid amide.

6-Difluoromethoxy-3-isocyanato-1H-indole

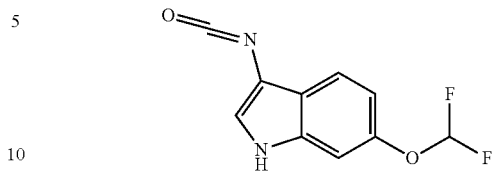

To a suspension of 1-carbamoyl-6-difluoromethoxy-1H-indole-3-carboxylic acid (180 mg, 0.66 mmol) in THF (6 mL) was added Et$_3$N (111 µl, 0.8 mmol) and the resulting solution was stirred at RT under nitrogen for 10 min. DDPA (220 µl, 0.8 mmol) was added and the reaction was further stirred at RT under nitrogen for 3 h. TLC indicated consumption of the starting material. The reaction mixture was concentrated and the crude residue was purified by flash column chromatography on silica gel (c-hexane/EtOAc 4:1 to 1:1) to give 6-difluoromethoxy-1H-indole-3-carbonyl azide (MS: 251 [M−H]−; t$_R$ (HPLC conditions k): 3.57 min) and 1-carbamoyl-6-difluoromethoxy-1H-indole-3-carbonyl azide (MS: 251 [M−CONH$_2$]−; 268 [M−N$_2$]+; t$_R$ (HPLC conditions k): 3.46 min). 6-Difluoromethoxy-1H-indole-3-carbonyl azide intermediate was suspended in toluene (6 mL) and refluxed under nitrogen for 3 h until completion of the reaction. The crude isocyanate was used as was in the next step.

1-Carbamoyl-6-difluoromethoxy-1H-indole-3-carboxylic acid was prepared from 6-difluoromethoxy-1H-indole [200207-21-2] using the protocol described for steps B-D in Scheme A4 for the preparation of 5-allyloxy-3-isocyanato-indole-1-carboxylic acid amide.

3-Isocyanato-5-(2-methoxy-ethoxy)-indole-1-carboxylic acid amide

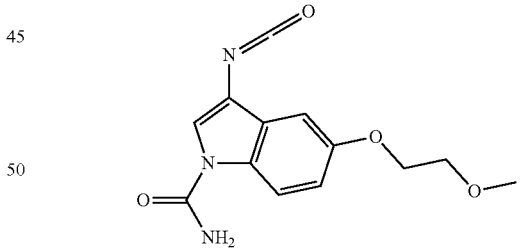

was prepared from 5-(2-methoxy-ethoxy)-1H-indole using the protocol described for steps B-E in scheme A4 for the preparation of 5-allyloxy-3-isocyanato-indole-1-carboxylic acid amide.

5-(2-Methoxy-ethoxy)-1H-indole 5-hydroxyindole (5 g, 15 mmol) was dissolved in acetone (75 mL), cesium carbonate (5.38 g, 16.5 mmol) and 2-bromoethyl methyl ether (1.55 mL, 16.5 mmol) were added and the reaction mixture was stirred at reflux under nitrogen overnight. Acetone was concentrated. The residue was dissolved in water and extracted twice with EtOAc. The combined organic layers were dried over Na₂SO₄, filtered and concentrated. The crude residue was purified by flash column chromatography on silica gel (c-hexane to c-hexane/EtOAc 7/3) to give the desired material. TLC, $R_f$ (c-hexane/EtOAc 1:1)= 0.6; MS (LC-MS): 192.1 [M+H]+, 214.0 [M+Na]+, 405.1 [2M+Na]+; tR (HPLC conditions f): 1.56 min.

(1-Carbamoyl-3-isocyanato-1H-indol-5-yloxy)-acetic acid methyl ester

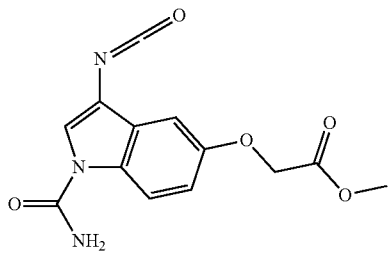 [SMILES: COC(=O)COc1ccc2c(c1)c(N=CC=O)cn2C(N)=O]

was prepared from (1H-indol-5-yloxy)-acetic acid methyl ester using the protocol described for steps B-E in scheme A4 for the preparation of 5-allyloxy-3-isocyanato-indole-1-carboxylic acid amide.

(1H-Indo)-5-yloxy)-acetic acid methyl ester

A solution of 5-hydroxyindole (5.07 g, 38.1 mmol) and cesium carbonate (12.4 g, 38.1 mmol) in acetone (150 mL) was cooled to 0° C. and methyl bromoacetate (3.96 mL, 41.9 mmol) was added. The reaction mixture was then stirred at RT under nitrogen for 2 h. The reaction mixture was concentrated. The residue was diluted with water and extracted twice with CH₂Cl₂. The combined organic layers were dried over Na₂SO₄, filtered and concentrated. The resulting solid was taken up in Et₂O and filtered-off to the desired material. TLC, $R_f$ (c-hexane/EtOAc 1:1)=0.55; MS (LC-MS): 206.1 [M+H]+, 433.0 [2M+Na]+; $t_R$ (HPLC conditions f): 1.64 min.

(1-Carbamoyl-3-isocyanato-1H-indol-6-yloxy)-acetic acid methyl ester

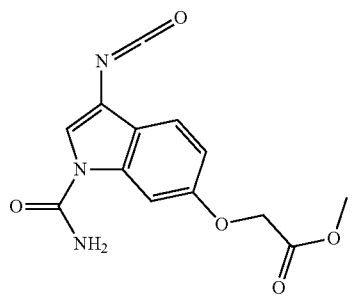 [SMILES: COC(=O)COc1ccc2c(N=CC=O)cn(C(N)=O)c2c1]

was prepared from (1H-indol-6-yloxy)-acetic acid methyl ester using the protocol described for the preparation of (1-carbamoyl-3-isocyanato-1H-indol-5-yloxy)-acetic acid methyl ester.

(1-Carbamoyl-3-isocyanato-1H-indol-6-yl)-acetic acid ethyl ester

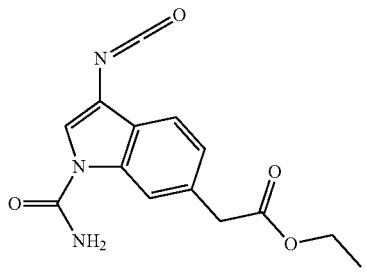 [SMILES: CCOC(=O)Cc1ccc2c(N=CC=O)cn(C(N)=O)c2c1]

was prepared from (1H-indol-6-yl)-acetic acid ethyl ester using the protocol described for steps B-E in scheme A4 for the preparation of 5-allyloxy-3-isocyanato-indole-1-carboxylic acid amide.

(1H-Indol-6-yl)-acetic acid ethyl ester

To a solution of 6-ethoxycarbonylmethyl-indole-1-carboxylic acid methyl ester (965 mg, 3.25 mmol) in EtOH (10 mL) was added dimethylamine (~5.6 M in EtOH, 24.4 mL, 48.8 mmol) and the solution was stirred at RT overnight. EtOH was concentrated and the crude residue was purified by flash column chromatography on silica gel (c-hexane to c-hexane/EtOAc 85:15) to give the desired material. MS (UPLC): 204.2 [M+H]+, 221.2 [M+NH₄]+, 248.2 [M+HCOO]−; $t_R$ (HPLC conditions f): 1.87 min.

6-Ethoxycarbonylmethyl-indole-1-carboxylic acid methyl ester

A mixture of 6-bromo-indole-1-carboxylic acid methyl ester (1.12 g, 4.43 mmol), ethyl acetoacetate (1.23 mL, 9.74 mmol), palladium acetate (20 mg, 0.089 mmol), 2-di-tert-butylphosphino-2'-methylbiphenyl (55 mg, 0.177 mmol) and K₃PO₄ (2.58 g, 12.2 mmol) in toluene (6 mL) was heated at 100° C. under nitrogen overnight. The reaction was poured into water and extracted twice with EtOAc. The combined organic layers were dried over Na₂SO₄, filtered and concentrated. The crude material was purified by flash column chromatography on silica gel (c-hexane to c-hexane/EtOAc 93:7) to give the desired material. TLC, $R_f$ (c-hexane/EtOAc 4:1)= 0.3; MS (UPLC): 262.2 [M+H]+, 279.2 [M+NH₄]+, 284.2 [M+Na]+, 523.3 [M+Na]+, 545.3 [2M+Na]+; $t_R$ (HPLC conditions f): 2.11 min.

6-Bromo-indole-1-carboxylic acid methyl ester

To a solution of 6-bromoindole (1.46 g, 7.44 mmol) in DMF (35 mL) under nitrogen atmosphere, was added NaH (60% in mineral oil, 327 mg, 8.19 mmol), followed by methyl chloroformate (652 µL, 8.19 mmol) and the resulting solution was stirred at RT overnight. The mixture was poured into water and extracted twice with EtOAc. The combined organic layers were washed again with water, dried over Na₂SO₄, filtered and concentrated. The crude residue was purified by flash column chromatography on silica gel (c-hexane to c-hexane/EtOAc 88:12) to give the desired material. TLC, $R_f$ (EtOAc)=0.75; MS (UPLC): 254.2/255.2 [M+H]+; $t_R$ (HPLC conditions f): 2.32 min.

(1-Carbamoyl-3-isocyanato-1H-indol-5-yl)-acetic acid ethyl ester

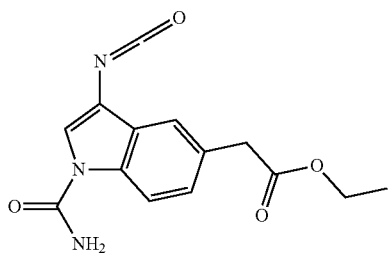 [SMILES: CCOC(=O)Cc1ccc2c(c1)c(N=CC=O)cn2C(N)=O]

was prepared from 5-bromoindole as described for the synthesis of (1-carbamoyl-3-isocyanato-1H-indol-6-yl)-acetic acid ethyl ester.

(1-Carbamoyl-3-isocyanato-1H-indol-6-yl)-acetic acid tert-butyl ester

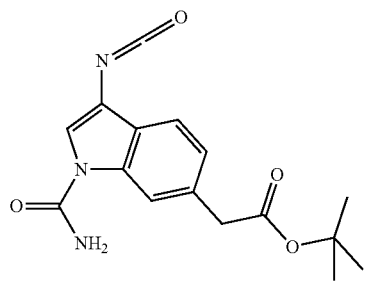 [SMILES: CC(C)(C)OC(=O)Cc1ccc2c(N=CC=O)cn(C(N)=O)c2c1]

was prepared from (1H-indol-6-yl)-acetic acid tert-butyl ester using the protocol described for steps B-E in scheme A4 for the preparation of 5-allyloxy-3-isocyanato-indole-1-carboxylic acid amide.

(1H-Indol-6-yl)-acetic acid tert-butyl ester

To a solution of 6-bromoindole (2 g, 10.2 mmol) in THF (20 mL) under nitrogen atmosphere was added KH (30% in mineral oil de-greased with pentane, 1.5 g, 11.22 mmol) and the mixture was stirred at RT for 30 min before addition of [P(t-Bu)$_3$PdBr]$_2$ (40 mg, 0.051 mmol) diluted in THF (20 mL). The resulting mixture was added to a solution of 2-tert-butoxy-2-oxoethylzinc chloride (0.5 M in Et$_2$O, 22.4 mL, 11.2 mmol) stirred under nitrogen atmosphere and the mixture was further stirred at RT for 24 h. The reaction mixture was diluted with EtOAc, and washed with a saturated aqueous solution of NaHCO$_3$, then with water. The organic layer was dried over Na$_2$SO$_4$, filtered and concentrated. The crude residue was purified by flash column chromatography on silica gel (c-hexane to c-hexane/EtOAc 94:6 to c-hexane/EtOAc 8:2) to give the desired material. TLC, $R_f$ (c-hexane/EtOAc 4:1)=0.3; MS (UPLC): 232.2 [M+H]+, 176.1 [MH−tBu]+, 249.2 [M+NH$_4$]+, 463.4 [2M+H]+, 273.3 [M+HCOO]−.

3-Isocyanato-1H-indole-6-carbonitrile

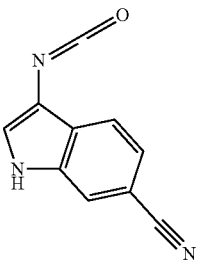 [SMILES: N#Cc1ccc2c(N=CC=O)c[nH]c2c1]

To a solution of 1-carbamoyl-6-cyano-1H-indole-3-carboxylic acid (210 mg, 0.916 mmol) in toluene (6 mL) was added Et$_3$N (128 µl, 0.916 mmol) and the resulting yellow suspension was stirred at RT under nitrogen 15 min before addition of DDPA (220 µl, 0.916 mmol). The reaction mixture was further stirred at RT overnight. The crude reaction mixture was concentrated and purified by flash column chromatography (c-hexane to c-hexane/EtOAc 1:1) to give 6-cyano-1H-indole-3-carbonyl azide (TLC, $R_f$(EtOAc)=1); $t_R$ (HPLC conditions a): 3.29 min; 1H-NMR (400 MHz, DMSO): δ (ppm): 12.7 (bs, 1H), 8.45 (s, 1H), 8.20 (d, 1H), 8.04 (bs, 1H), 7.62 (dd, 1H). Toluene (4 mL) was added and the reaction mixture was refluxed for 3 h to generate the corresponding isocynate, which was used without purification in the next step.

1-Carbamoyl-6-cyano-1H-indole-3-carboxylic acid was prepared from 6-cyano-indole using the protocol described for steps B-E in scheme A4 for the preparation of 5-allyloxy-3-isocyanato-indole-1-carboxylic acid amide.

Scheme A5: preparation of 2-benzyloxy-1-(3-isocyanato-indol-1-yl)-ethanone

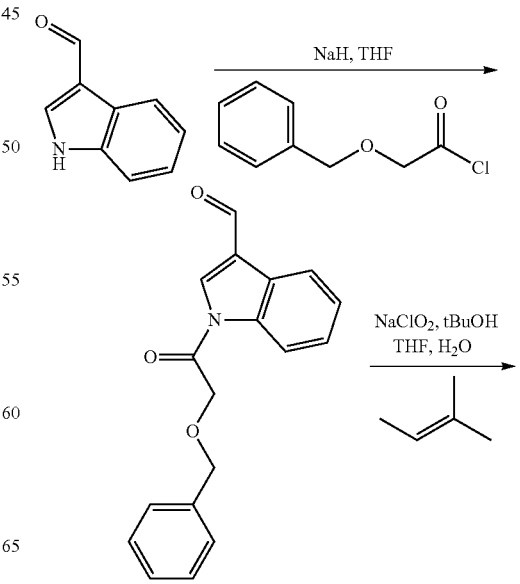

-continued

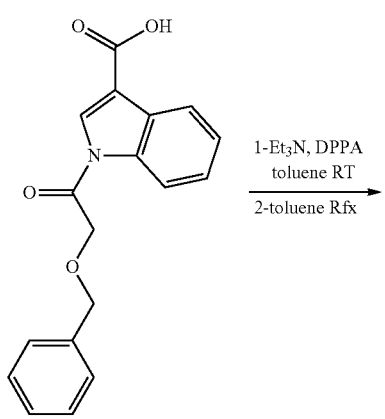

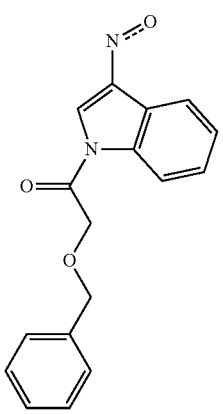

A.
1-(2-Benzyloxy-acetyl)-1H-indole-3-carbaldehyde

To a solution of indole-3-carboxaldehyde (2 g, 13.8 mmol) in THF (70 mL) at 5° C., was added NaH (60% in mineral oil, 551 mg, 13.8 mmol) under nitrogen atmosphere. The mixture was stirred at 5° C. for 30 min before dropwise addition of benzyloxyacetyl chloride (2.6 mL, 16.53 mmol) over 20 min maintaining the internal temperature between 5° C. and 10° C. The resulting dark solution was further stirred at RT for 1 h. As the reaction was not completed benzyloxyacetyl chloride (1 mL, 6.44 mmol, 0.5 eq) and NaH (60% in mineral oil, 551 mg, 13.8 mmol) were added and the mixture was further stirred at RT for 3 days. The reaction mixture was concentrated, and the residue taken up in $CH_2Cl_2$ and washed with water. The organic layer was dried over $Na_2SO_4$, filtered, and concentrated. The crude material was purified by flash column chromatography on silica gel (c-hexane to c-hexane/EtOAc 4-1) corresponding to the desired compound. TLC, $R_f$ (c-hexane/EtOAc 1:1)=0.61; MS (LC/MS): 294.1 [M+H]+, 316.1 [M+Na]+; $t_R$ (HPLC conditions a): 3.87 min.

B. 1-(2-Benzyloxy-acetyl)-1H-indole-3-carboxylic acid

To a solution of 1-(2-benzyloxy-acetyl)-1H-indole-3-carbaldehyde (1.53 g, 5.22 mmol) in a mixture of THF (80 mL) and t-butanol (24 mL). A 2 M 2-methyl-2-butene solution in THF (104 mL, 209 mmol) was added, followed by a water (20 mL) solution of $NaClO_2$ (80%, 5.9 g, 52.2 mmol) and $NaH_2PO_4$ (5 g, 41.7 mmol). The resulting yellow solution was stirred at RT for 2 h. The solvents were concentrated and the aqueous layer was filtered and the resulting precipitate was washed with $Et_2O$ to give the desired compound. LC/MS: 310.1 [M−H]−, 332.0 [M+Na]+, 308.0 [M−H]−, 617.0 [2M−H]−; $t_R$ (HPLC conditions a): 3.62 min.

C.
2-Benzyloxy-1-(3-isocyanato-indol-1-yl)-ethanone

A solution of 1-(2-benzyloxy-acetyl)-1H-indole-3-carboxylic acid (200 mg, 0.647 mmol) and $Et_3N$ (90 µl, 0.647 mmol) in toluene (3 mL) was stirred at RT under nitrogen for 15 min. DDPA (90%, 155 µl, 0.647 mmol) was added and the reaction mixture was further stirred at RT for 3 h. Toluene was concentrated to give the acyl azide intermediate (TLC-$R_f$ (c-hexane/EtOAc 1:1)=0.73; $t_R$ (HPLC conditions a)=4.26 min). The crude azide was refluxed in toluene (3 mL) for 1 h and toluene was concentrated to give the desired isocyanate which was used in the next step without further purification.

Scheme A6: preparation of 1-isocyanato-indolizine-3-carboxylic acid benzyl ester

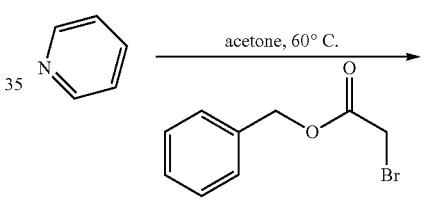

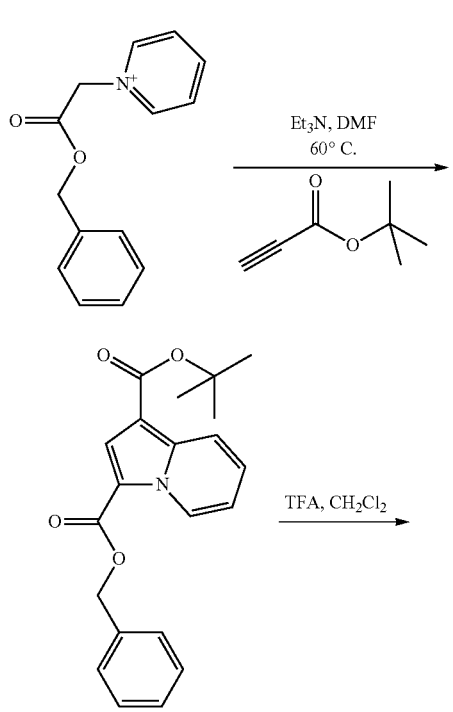

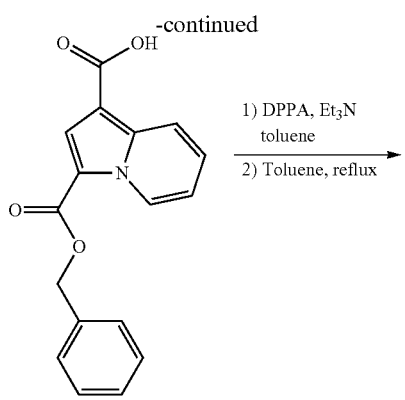

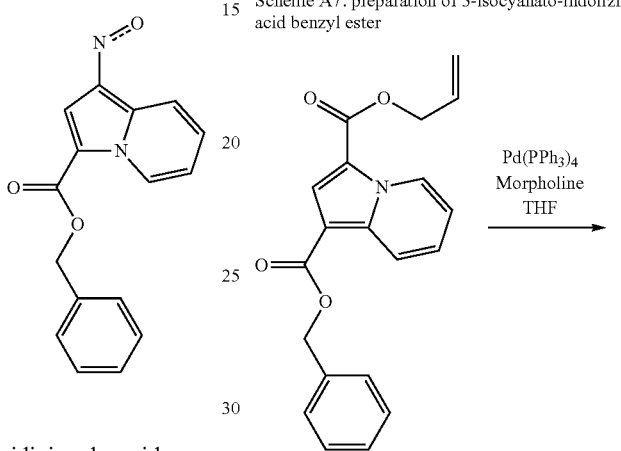

A. 1-Benzyloxycarbonylmethyl-pyridinium bromide

To a solution of benzyl bromoacetate (10 g, 43.7 mmol) in acetone (200 mL) was added a solution of pyridine (3.51 mL, 43.7 mmol) in acetone (20 mL) and the resulting mixture was stirred at 60° C. under nitrogen over the week-end. Then allowed to cool to RT and concentrated to give the desired material. MS (LC/MS): 228.1 [MH]+.

B. Indolizine-1,3-dicarboxylic acid 3-benzyl ester 1-tert-butyl ester

To a suspension of 1-benzyloxycarbonylmethyl-pyridinium bromide (1.50 g, 9.74 mmol) and tert-butyl propiolate (1.34 mL, 9.74 mmol) in DMF (80 mL) was added a solution of triethylamine (4.1 mL, 29.2 mmol) in DMF (10 mL). The mixture was vigourously stirred 4 h at 60° C. under air atmosphere. The solution was allowed to cool to RT, poured into water and extracted with EtOAc (2x). The combined organic extracts were dried over $Na_2SO_4$, filtered and concentrated. The crude residue was purified by flash column chromatography on silica gel (c-hexane to c-hexane/EtOAc 8:2) to give the desired material. TLC, $R_f$ (c-hexane/EtOAc 8:2)=0.6; MS (LC/MS): 725.3 [2M+Na]+; $t_R$ (HPLC conditions a): 4.84 min.

C. Indolizine-1,3-dicarboxylic acid 3-benzyl ester

A solution of indolizine-1,3-dicarboxylic acid 3-benzyl ester 1-tert-butyl ester (400 mg, 1.14 mmol) and TFA (872 µl, 11.4 mmol) in $CH_2Cl_2$ (10 mL) was stirred at RT overnight. The reaction mixture was concentrated and the crude solid was taken-up in a mixture of MeOH and $CH_2Cl_2$, the precipitate was filtered-off and washed with a minimum of MeOH to give the desired compound as a white powder. The filtrate was concentrated and purified by flash column chromatography on silica gel ($CH_2Cl_2$ to $CH_2Cl_2$/MeOH 95:5) to give again the desired compound. TLC, $R_f$ ($CH_2Cl_2$/MeOH 9:1)=0.6; MS (LC/MS): 296.0 [M+H]+ 294.1 [M−H]−; $t_R$ (HPLC conditions a): 3.64 min.

D. 1-Isocyanato-indolizine-3-carboxylic acid benzyl ester was prepared from indolizine-1,3-dicarboxylic acid 3-benzyl ester using the protocol described in step E scheme A4 for the preparation of 5-allyloxy-3-isocyanato-indole-1-carboxylic acid amide.

Scheme A7: preparation of 3-isocyanato-indolizine-1-carboxylic acid benzyl ester

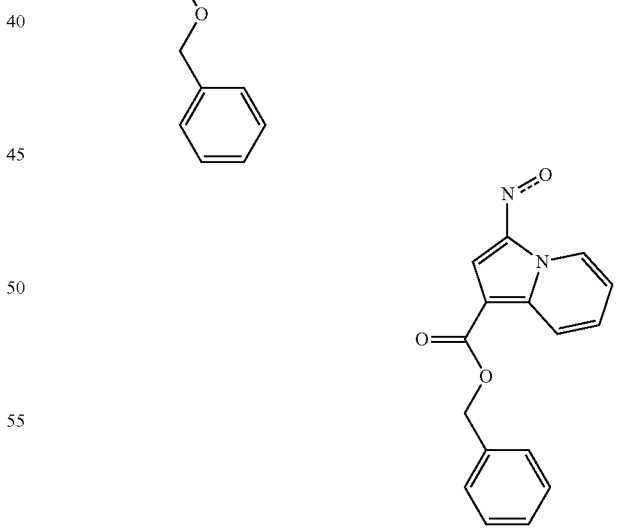

Indolizine-1,3-dicarboxylic acid 3-allyl ester 1-benzyl ester

The title compound was prepared using the protocol described in steps A and B for the preparation of 1-isocyanato-indolizine-3-carboxylic acid benzyl ester scheme A6 using bromo-acetic acid allyl ester in step A and propionic acid benzyl ester in step B. TLC, $R_f$(c-hexane/EtOAc 1:1)= 0.8; MS (LC/MS): 336.1 [M+H]+, 358.1 [M+Na]+, 693.2 [2M+Na]+; $t_R$ (HPLC conditions a): 4.55 min.

A. Indolizine-1,3-dicarboxylic acid 1-benzyl ester

To a solution of indolizine-1,3-dicarboxylic acid 3-allyl ester 1-benzyl ester (300 mg, 0.895 mmol) in THF (6 mL) were added Pd(PPh$_3$)$_4$ (34.5 mg, 0.09 mmol) and morpholine (260 mg, 8.95 mmol). The reaction mixture was stirred at RT under nitrogen atmosphere for 30 min. The reaction mixture was diluted in EtOAC, extracted twice with HCl 1N and the combined organic extracts were washed with brine, dried over Na$_2$SO$_4$, filtered and concentrated to give the desired compound which was used without further purification in the next step TLC, $R_f$(CH$_2$Cl$_2$/MeOH 9:1)=0.4: MS (LC/MS): 294.0 [M−H]−; $t_R$ (HPLC conditions a): 3.62 min.

B. 3-Isocyanato-indolizine-1-carboxylic acid benzyl ester

The title compound was prepared from indolizine-1,3-dicarboxylic acid 1-benzyl ester using the protocol described in step E scheme A4 for the preparation of 5-allyloxy-3-isocyanato-indole-1-carboxylic acid amide.

Scheme A8: preparation of (1-carbamoyl-1H-indol-3-yl)-acetic acid

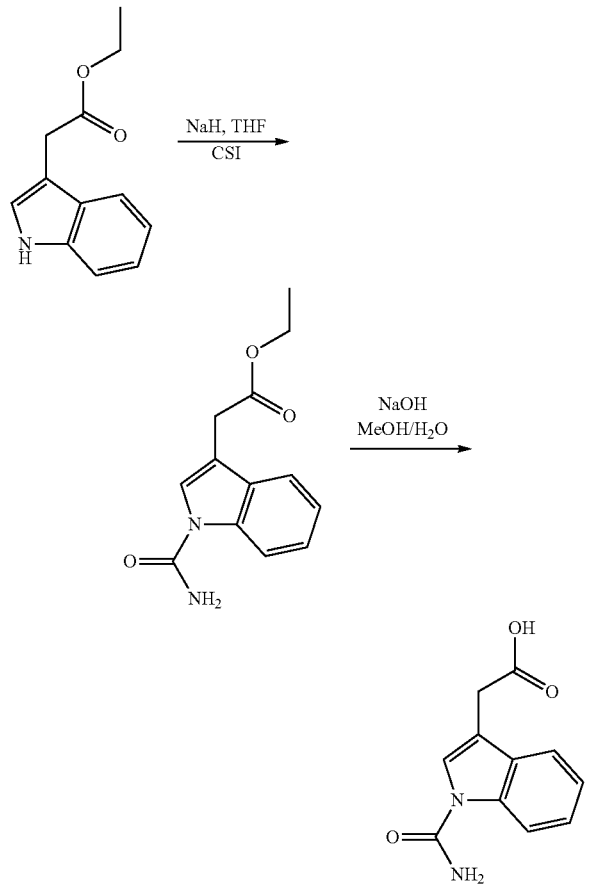

A. (1-Carbamoyl-1H-indol-3-yl)-acetic acid ethyl ester

To a solution of (1H-indol-3-yl)-acetic acid ethyl ester (2.5 g, 12.30 mmol) in THF (58 mL) at 0° C. was added sodium hydride (60% in mineral oil, 0.354 g, 14.8 mmol) portionwise under argon. The dark brown solution was stirred at 0° C. for 45 min before dropwise addition of chlorosulfonylisocyanate (2.14 mL, 24.6 mmol). The reaction mixture was allowed to warm to RT overnight under stirring. Acetic acid (3 mL) was then added to the mixture which was stirred at RT for 20 min. Ice was added to mixture which was stirred for 60 min then diluted with water and extracted with EtOAc (3×). The combined organic extracts were washed with brine, dried (Phase separator) and concentrated in vacuo. The residual oil was purified via flash column chromatography on silica gel (EtOAc/cyclohexane 1:3 to 2:3) to give the desired material. TLC, $R_f$(EtOAc/cyclohexane 1:1)=0.35; MS: 247 [M+H]+, 493 [2M+H]+; $t_R$ (HPLC conditions b) 3.51 min.

B. (1-Carbamoyl-1H-indol-3-yl)-acetic acid

To a suspension of (1-carbamoyl-1H-indol-3-yl)-acetic acid ethyl ester in methanol (61 mL) and water (6.1 mL) was added an 1N aqueous solution of NaOH (12.2 mL, 12.2 mmol) and the resulting yellow solution was stirred at RT for 4 h. The reaction mixture was concentrated under reduced pressure and the residue was suspended in HCl 1N. The aqueous mixture was extracted with EtOAC (3×), the combined organic extracts were dried (phase separator) and concentrated in vacuo. The crude product was used directly in the next step without any further purification. MS: 219 [M+H]+, 437 [2M+H]+; $t_R$ (HPLC conditions b) 2.16 min.

(1-Carbamoyl-2-methyl-1H-indol-3-yl)-acetic acid

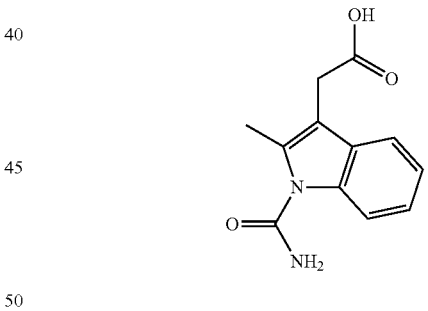

was prepared in a similar manner as described in Scheme A8 Step B for (1-carbamoyl-1H-indol-3-yl)-acetic acid starting from (1-carbamoyl-2-methyl-1H-indol-3-yl)-acetic acid ethyl ester. The crude product (brownish solid) obtained after extractive work-up was used directly in the next step without purification. MS: 233 [M+H]+; $t_R$ (HPLC conditions b) 3.26 min.

(1-Carbamoyl-2-methyl-1H-indol-3-yl)-acetic acid ethyl ester

The title compound was prepared in a similar manner as described in Scheme A8 Step A starting from (2-methyl-1H-indol-3-yl)-acetic acid ethyl ester [21909-49-9] (1.20 g, 5.52 mmol), NaH (60% in mineral oil, 331 mg, 8.28 mmol) and chlorosulfonylisocyanate (0.959 mL, 11.1 mmol). Purification by flash column chromatography on silica gel (EtOAc/ c-hexane 1:4 to 1:1) afforded a yellowish solid. TLC, R$_f$ (EtOAc/c-hexane 1:1)=0.31; MS: 261 [M+H]+; t$_R$ (HPLC conditions b) 3.54 min.

(1-Carbamoyl-5-fluoro-1H-indol-3-yl)-acetic acid

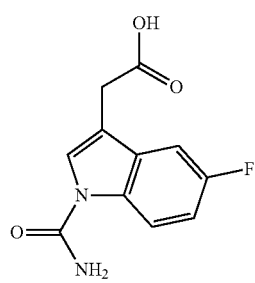 [SMILES: NC(=O)n1cc(CC(=O)O)c2cc(F)ccc21]

was prepared in a similar manner as described in Scheme A8 Step B for (1-carbamoyl-1H-indol-3-yl)-acetic acid starting from (1-carbamoyl-5-fluoro-1H-indol-3-yl)-acetic acid ethyl ester. The crude product (yellowish solid) obtained after extractive work-up was used directly in the next step without purification. MS: 236.9 [M+H]+; t$_R$ (HPLC conditions b) 2.4 min.

(1-Carbamoyl-5-fluoro-1H-indol-3-yl)-acetic acid ethyl ester

The title compound was prepared in a similar manner as described in Scheme A8 Step A starting from (5-fluoro-1H-indol-3-yl)-acetic acid methyl ester [497258-29-4] (150 mg, 0.724 mmol), NaH (60% in mineral oil, 37.4 mg, 0.869 mmol) and chlorosulfonylisocyanate (0.126 mL, 1.45 mmol). Purification by flash column chromatography on silica gel (EtOAc/c-hexane gradient 1:3 to 2:3) afforded the title compound. TLC, R$_f$ (EtOAc/c-hexane 1:1)=0.16; MS: 261 [M+H]+, 501 [2M+H]+; t$_R$ (HPLC conditions b) 3.2 min.

(1-Carbamoyl-5-methoxy-1H-indol-3-yl)-acetic acid

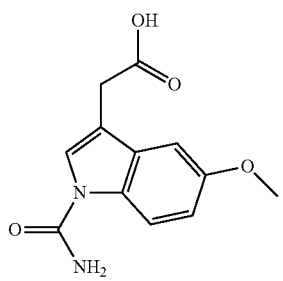 [SMILES: COc1ccc2c(c1)c(CC(=O)O)cn2C(N)=O]

was prepared from 5-methoxy-3-indolylacetic acid methyl ester according to the protocol described scheme A8 for the preparation of (1-carbamoyl-1H-indol-3-yl)-acetic acid. Rf, TLC (EtOAC)=0.2; MS (LC/MS): 248.9 [M+H]+, 271.0 [M+Na]+, 247.1 [M−H]−, 495.1 [2M−H]−, 204.1 [M−CONH$_2$]−; t$_R$ (HPLC conditions f): 1.54 min.

5-methoxy-3-indolylacetic acid methyl ester

To a suspension of 5-methoxy-3-indolylacetic acid (500 mg, 2.44 mmol) in CH$_2$Cl$_2$ (7 mL) were added DCC (553 mg, 2.68 mmol), DMAP (30 mg, 0.244 mmol) and methanol (99 µL, 2.44 mmol). The resulting white suspension was stirred at RT under nitrogen for 2.5 h. The mixture was filtered and the filtrate concentrated to give a brown oil which was purified by flash column chromatography on silica gel (c-hexane to c-hexane/EtOAc 8-2) to afford the desired material as a brown oil. TLC, Rf (EtOAc)=0.82; MS (LC-MS): 220.0 [M+H]+, 242.1 [M+Na]+, 461.0 [2M+Na]+, 218.1 [M−H]−; t$_R$ (HPLC conditions f) 3.2 min.

Scheme A9: [1-carbamoyl-5-(2-hydroxy-ethoxy)-1H-indol-3-yl]-acetic acid

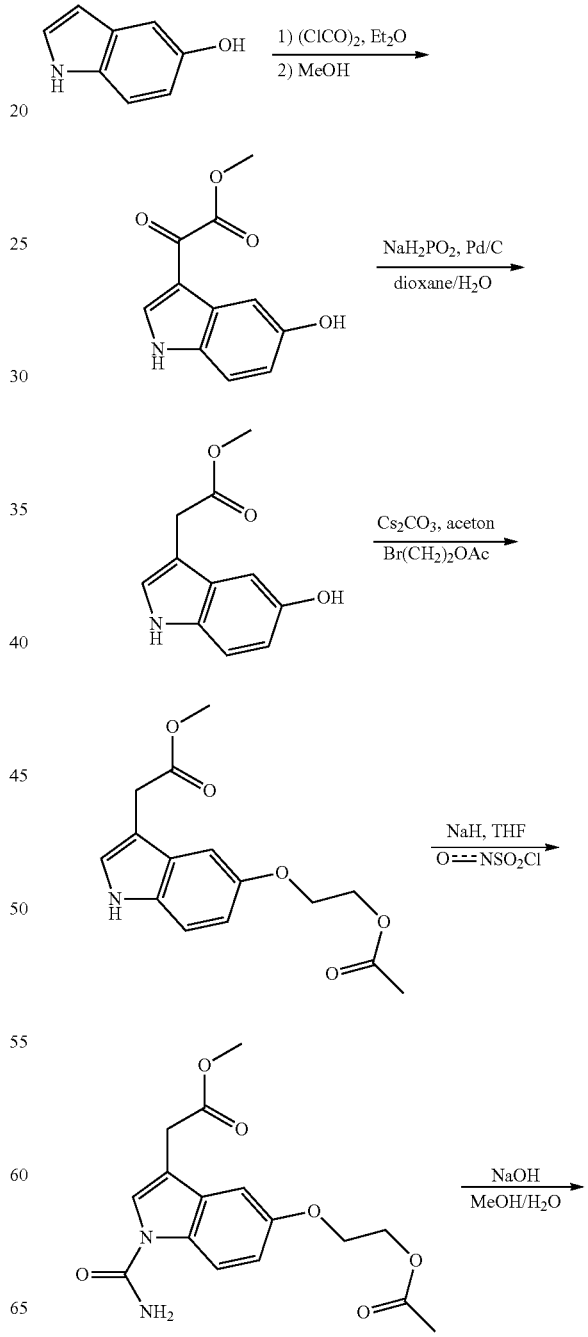

-continued

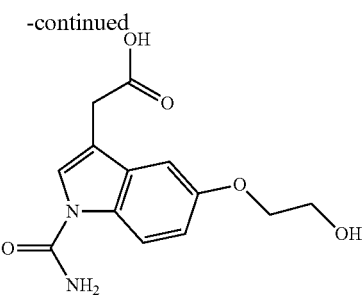

A. (5-Hydroxy-1H-indol-3-yl)-oxo-acetic acid methyl ester

To a solution of oxalyl chloride (3.18 mL, 37.6 mmol) in dry ether (50 mL) was added 5-hydroxyindole (2.5 g, 18.8 mmol) in small portions over 15 min at −5° C. under nitrogen, and the resulting mixture was stirred at RT for 30 min. The suspension was filtered and the residue was washed with $Et_2O$. Dry MeOH (60 mL) was carefully added, and the resulting mixture was stirred at RT for 1 h. The suspension was filtered and successively washed with MeOH and $Et_2O$ to afford the desired material. TLC, $R_f$ (EtOAc)=0.75; MS (LC-MS): 220.0 [M+H]+, 242.1 [M+Na]+, 461.0 [2M+Na]+, 218.1 [M−H]−; $t_R$ (HPLC conditions f): 1.02 min.

B. (5-Hydroxy-1H-indol-3-yl)-acetic acid methyl ester

To a suspension of (5-hydroxy-1H-indol-3-yl)-oxo-acetic acid methyl ester (1 g, 4.56 mmol) in dioxane (14 mL) was added Pd/C 10% (400 mg) and a solution of $NaH_2PO_2.H_2O$ (4.84 g, 45.6 mmol) in water (2.35 mL). The reaction mixture was stirred and heated to reflux for 1.5 h. After completion the reaction mixture was cooled to RT, and the catalyst removed by filtration through a pad of Celite and washed with MeOH. Solvents were concentrated, and the residue was dissolved in $CH_2Cl_2$ and washed with water. The organic layer was dried over $Na_2SO_4$, filtered and concentrated to give the desired material. TLC, $R_f$ (EtOAc)=0.85; MS (LC-MS): 206.1 [M+H]+. 1H-NMR (400 MHz, DMSO): δ (ppm): 10.64 (bs, 1H), 8.64 (s, 1H), 7.14 (m, 2H), 6.78 (d, 1H), 6.60 (dd, 1H), 3.65 (s, 3H), 3.58 (s, 2H).

C. [5-(2-Acetoxy-ethoxy)-1H-indol-3-yl]-acetic acid methyl ester

To a solution of (5-hydroxy-1H-indol-3-yl)-acetic acid methyl ester (670 mg, 3.26 mmol) in acetone (15 mL) was added cesium carbonate (1.17 g, 3.59 mmol) and 2-bromoethyl acetate (395 μL, 3.59 mmol). The suspension was refluxed overnight under nitrogen. Acetone was concentrated and the residue was dissolved in water and extracted twice with EtOAc. The combined organic layers were dried over $Na_2SO_4$, filtered and concentrated. The crude residue was purified by flash column chromatography on silica gel (c-hexane to c-hexane/EtOAc 6:4) to give the desired material. TLC, $R_f$ (c-hexane/EtOAc 1:1)=0.45; MS (LC-MS): 292.1 [M+H]+, 314.0 [M+Na]+, 290.0 [M−H]−; $t_R$ (HPLC conditions f): 1.70 min.

D. 5-(2-Acetoxy-ethoxy)-1-carbamoyl-1H-indol-3-yl]-acetic acid methyl ester

A suspension of NaH (60% in mineral oil, 43 mg, 1.06 mmol) in THF (2.5 mL) under nitrogen atmosphere was cooled to 5° C. and a solution of [5-(2-acetoxy-ethoxy)-1H-indol-3-yl]-acetic acid methyl ester (249 mg, 0.71 mmol) in THF (2.5 mL) was added. The mixture was stirred 30 min before slow addition of chlorosulfonyl isocyanate (123 μL, 1.42 mmol) at 5° C. The resulting solution was then stirred overnight allowing the temperature to slowly reach RT. Acetic acid (1.3 mL) was added, and the solution was stirred at RT for 1 h, before addition of ice and water (16 mL). The mixture was further stirred at RT for 30 min and was extracted twice with EtOAc. The combined organic layers were washed with water, dried over $Na_2SO_4$, filtered and concentrated. The crude residue was purified by flash column chromatography on silica gel (100% c-hexane to 100% EtOAc) to afford the desired material. TLC, $R_f$(EtOAc)=0.7; MS (LC-MS): 335.0 [M+H]+, 357.1 [M+Na]+, 333.1 [M−H]−, 290.0 [M−$CONH_2$]−, 379.0 [M+HCOO]−; $t_R$ (HPLC conditions f): 1.63 min.

E. [1-Carbamoyl-5-(2-hydroxy-ethoxy)-1H-indol-3-yl]acetic acid 5-(2-Acetoxy-ethoxy)-1-carbamoyl-1H-indol-3-yl]-acetic acid methyl ester (54 mg, 0.153 mmol) was dissolved in MeOH (1.3 mL) and H2O (130 μL). NaOH 1N (307 μL, 0.307 mmol) was added and the mixture was stirred at RT for 1 h. The reaction mixture was concentrated, the crude poured into HCl 1N and extracted twice with $CH_2Cl_2$. A precipitate formed in the aqueous layer and was filtered-off to give the desired material. TLC, $R_f$ (EtOAc)=0.15; MS (LC/MS): 279.1 [M+H]+, 301.0 [M+Na]+, 277.0 [M−H]−, 233.9 [M−$CONH_2$]−; 1H-NMR (400 MHz, DMSO): δ (ppm): 12.4 (bs, 1H), 8.13 (d, 1H), 7.73 (s, 1H), 7.43 (bs, 2H), 7.05 (d, 1H), 6.89 (dd, 1H), 4.0 (t, 2H), 3.74 (t, 2H), 3.64 (d, 2H).

(6-tert-Butoxycarbonylmethyl-1-carbamoyl-1H-indol-3-yl)-acetic acid

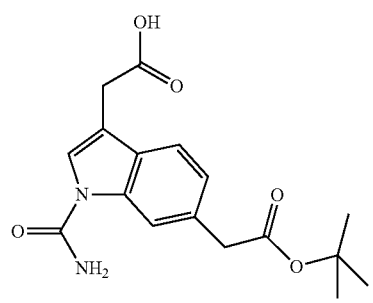 [SMILES: CC(C)(C)OC(=O)Cc1ccc2c(CC(=O)O)cn(C(N)=O)c2c1]

was prepared from (1H-indol-6-yl)-acetic acid tert-butyl ester (described for the preparation of (1-carbamoyl-3-isocyanato-1H-indol-6-yl)-acetic acid tert-butyl ester) according to the protocol described scheme A9 steps A, B, D, E for the preparation of [1-carbamoyl-5-(2-hydroxy-ethoxy)-1H-indol-3-yl]-acetic acid. MS (LC/MS): 350.2/352.2 [M+$NH_4$]+, 687.2/689.2 [2M+Na]+, 277.0/279.0 [MH−tBu]+, 288.0/290.0 [M−$CONH_2$]−, 376.9/378.8 [M+HCOO]−, 662.8/664.7 [2M−H]−; $t_R$ (HPLC conditions f): 1.79 min.

1-Carboxymethyl-1H-indole-3-carboxylic acid ethyl ester

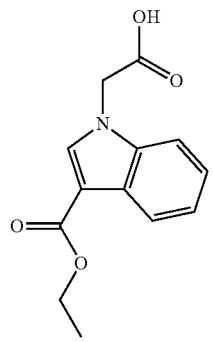 [SMILES: CCOC(=O)c1cn(CC(=O)O)c2ccccc12]

1-tert-Butoxycarbonylmethyl-1H-indole-3-carboxylic acid ethyl ester (700 mg, 2.31 mmol) was dissolved in CH$_2$Cl$_2$ (12 mL), TFA (2.65 mL, 34.6 mmol) was added and the solution was stirred at RT over week end. CH$_2$Cl$_2$ and water were added, the layers were separated and the aqueous one re-extracted with CH$_2$Cl$_2$ (2×). The combined organic layers were dried with Na$_2$SO$_4$, filtered and concentrated to give the desired compound. TLC, R$_f$(EtOAc)=0.62; MS (LC/MS): 248.1 [M+H]+, 246.0 [M−H]−; t$_R$ (HPLC conditions a): 3.03 min.

1-tert-Butoxycarbonylmethyl-1H-indole-3-carboxylic acid ethyl ester

To a suspension of 1H-indole-3-carboxylic acid ethyl ester (800 mg, 4.23 mmol) and potassium carbonate (1.34 g, 9.72 mmol) in CH$_3$CN (21 mL) under nitrogen was added tert-butyl bromoacetate (875 μL, 5.92 mmol) and the reaction mixture was heated at reflux overnight. The reaction mixture was allowed to cool to RT, EtOAc and water were added and the layers were separated, the aqueous one being re-extracted with EtOAc. The organic layers were washed with brine, dried (Na$_2$SO$_4$), filtered and concentrated. The crude residue was purified by flash column chromatography (c-hexane to c-hexane/EtOAc 1:1) to afford the desired compound. TLC, R$_f$ (EtOAc)=0.77; MS (LC/MS): 304.1 [M+H]+, 302.0 [M−H]−; t$_R$ (HPLC conditions a): 4.01 min.

Scheme A10: preparation of (3-carbamoyl-6-methoxy-indol-1-yl)-acetic acid

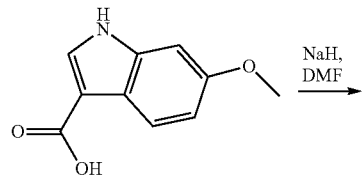

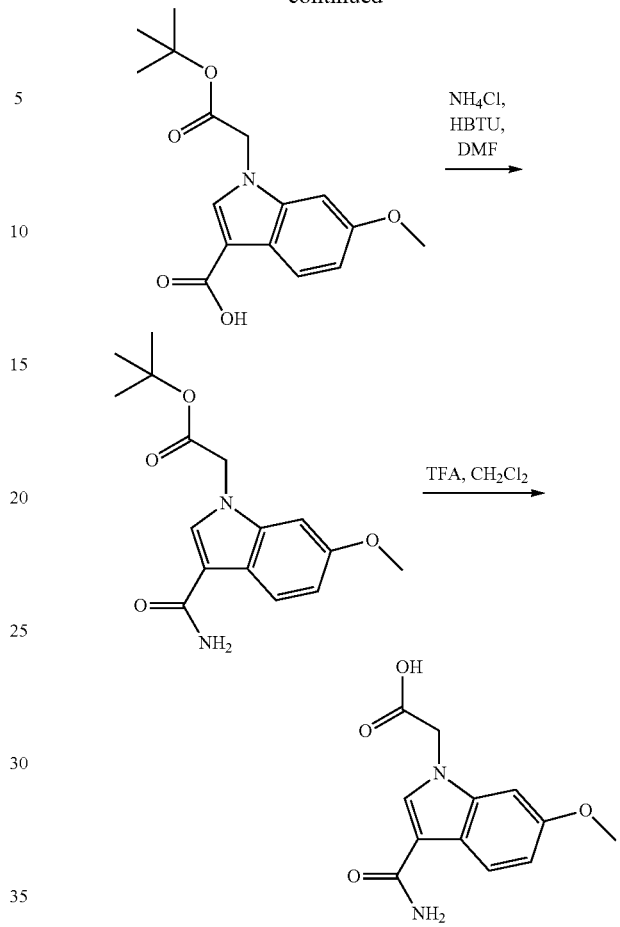

A. 1-tert-Butoxycarbonylmethyl-6-methoxy-1H-indole-3-carboxylic acid

To an ice-cooled suspension of 6-methoxy-1H-indole-3-carboxylic acid (1 g, 5.23 mmol) in DMF (35 mL) was added NaH (60% suspension in oil; 0.523 g, 13.1 mmol) in one portion, and the mixture was stirred at 0° C. for 30 min. Tert-butyl-2-bromoacetate (0.85 mL, 5.75 mmol) was then added dropwise, and stirring was continues at RT overnight. The reaction mixture was neutralized by addition of saturated NH$_4$Cl, and the solution was then adjusted to pH=2-3 by addition of 0.1N HCl. The aqueous layer was repeatedly extracted with CH$_2$Cl$_2$, the combined organics were washed with brine, dried (phase separator) and concentrated in vacuo. The residue was dissolved in a small volume of methanol, followed by addition of water until a solid precipitated. The precipitate was filtered off, washed with water and dried in vacuo to afford the title compound as a white solid. MS (LC/MS): 306 [M+H]+, 328 [M+Na]+; t$_R$ (HPLC conditions c): 4.67 min.

B. (3-Carbamoyl-6-methoxy-indol-1-yl)-acetic acid tert-butyl ester

To a mixture of 1-tert-butoxycarbonylmethyl-6-methoxy-1H-indole-3-carboxylic acid (500 mg, 1.28 mmol) in DMF (6 mL) were added successively NH$_4$Cl (137 mg, 2.55 mmol), HBTU (1.21 g, 3.19 mmol) and DIPEA (0.90 mL, 5.11 mmol), and stirring was continued at RT for 16 h. Additional aliquots of NH₄Cl (2 equiv) and DIPEA (4 equiv) were added to the reaction mixture. After stirring for 16 h, water was added and the aqueous layer was extracted repeatedly with EtOAc. The combined organics were washed with saturated aqueous NaHCO₃ solution and brine, dried (phase separator) and concentrated in vacuo. Purification by preparative HPLC (Macherey Nagel, VP250/40, C18 nucleosil 100-10, eluent: 20-100% CH₃CN/H₂O/20 min, 100% CH₃CN/2 min, CH₃CN and H₂O containing 0.1% TFA, flow: 40 mL/min) and lyophilization of the purified fractions afforded the title compound as a beige solid. MS: 305 [M+H]+, 609 [2M+H]+; $t_R$ (HPLC conditions c): 4.26 min.

C. (3-Carbamoyl-6-methoxy-indol-1-yl)-acetic acid

To a solution of (3-carbamoyl-6-methoxy-indol-1-yl)-acetic acid tert-butyl ester (300 mg, 0.99 mmol) in CH₂Cl₂ (9 mL) was added TFA (4.5 mL) at RT, and stirring was continued for 2 h. Methanol was then added to the reaction mixture, and volatiles were removed in vacuo. The residue was taken up in methanol and concentrated under reduced pressure to afford the title compound as a grey solid: MS: 249 [M+H]+, 497 [2M+H]+; $t_R$ (HPLC conditions c): 2.86 min. The material thus obtained was used in the next reaction step without further purification.

Scheme A11: preparation of (3-carbamoyl-5-chloro-indol-1-yl)-acetic acid

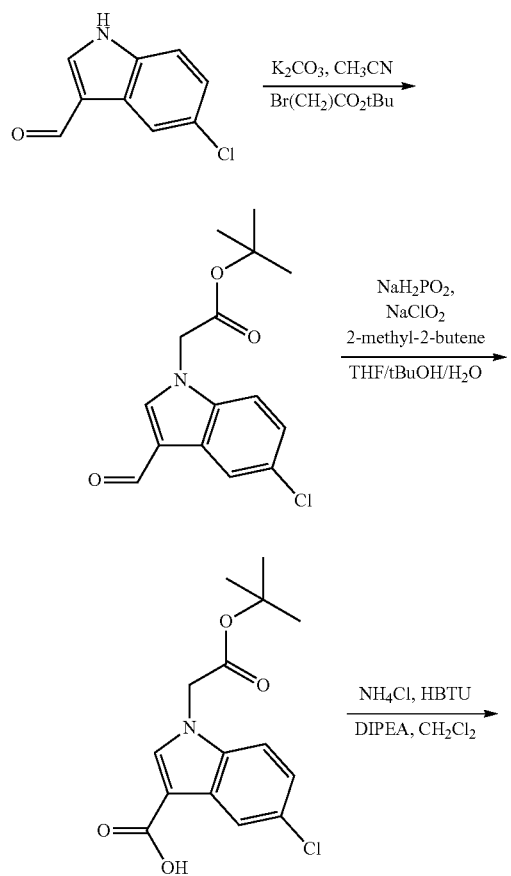

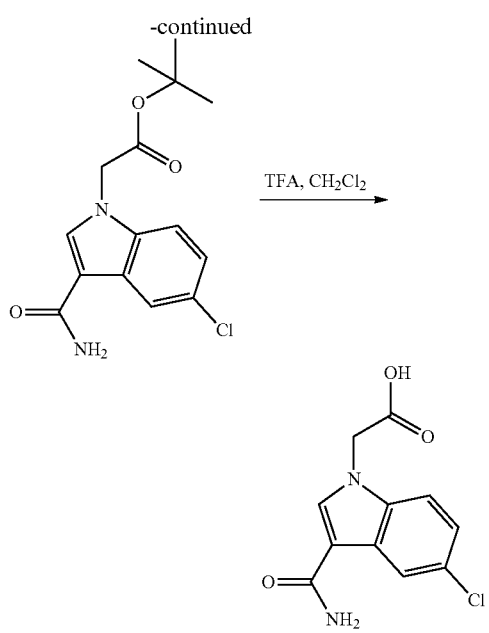

A. (5-Chloro-3-formyl-indol-1-yl)-acetic acid tert-butyl ester

To a suspension of 5-chloro-1H-indole-3-carbaldehyde [827-01-0] (500 mg, 2.78 mmol) and K₂CO₃ (885 mg, 6.40 mmol) in (14 mL) was added tert-butyl 2-bromoacetate (0.576 mL, 3.90 mmol) dropwise at RT. The resulting mixture was then heated to reflux for 18 h. After cooling to RT, the mixture was diluted with EtOAc and water. The organic layer was separated, subsequently washed with water (1×) and brine (1×), dried (Phase separator) and concentrated in vacuo to give the crude title compound. MS (LC/MS): 294 [M+H]+; $t_R$ (HPLC conditions b): 5.45 min. The product was used in the next reaction step without further purification.

B. 1-tert-Butoxycarbonylmethyl-5-chloro-1H-indole-3-carboxylic acid

To a solution of (5-chloro-3-formyl-indol-1-yl)-acetic acid tert-butyl ester (902 mg, 2.92 mmol) in THF (12 mL) and tert-butanol (4.80 mL) were added successively 2-methyl-2-butene (9.27 mL, 88.0 mmol), a solution of NaClO₂ (2.64 g, 29.2 mmol) and sodium dihydrogen phosphate (2.80 g, 23.3 mmol) in water (4.80 mL), followed by stirring at RT for 18 h. The reaction mixture was acidified with 0.1N HCl (pH 2 to 3) and extracted with EtOAc (3×). The combined organics were dried (Phase separator) and concentrated in vacuo. The residue was triturated with diethyl ether, the solid was filtered off, washed with diethyl ether and dried in vacuo to afford the title compound as a white solid. MS (LC/MS): 310 [M+H]+; $t_R$ (HPLC conditions b): 5.16 min.

C. (3-Carbamoyl-5-chloro-indol-1-yl)-acetic acid tert-butyl ester

To a mixture of 1-tert-butoxycarbonylmethyl-5-chloro-1H-indole-3-carboxylic acid (400 mg, 1.29 mmol) in CH₂Cl₂ (6 mL) were added successively NH₄Cl (138 mg, 2.58 mmol), HBTU (1.22 g, 3.23 mmol) and DIPEA (0.902 mL, 5.17 mmol). Stirring was continued at RT for 16 h. Additional aliquots of NH₄Cl (2 equiv) and DIPEA (4 equiv) were added to the reaction mixture. After stirring for 4 h, the reaction mixture was diluted with $CH_2Cl_2$ and the solution was washed with water (2×), 0.1N aqueous HCl (2×), saturated aqueous $NaHCO_3$ (2×) and brine, dried (Phase separator) and concentrated in vacuo. The residue was purified by flash column chromatography on silica gel (EtOAc/c-hexane gradient 2:1 to 1:0) to give the title compound as a white solid. TLC $R_f$ (EtOAc/c-hexane 2:1)=0.20; MS (LC/MS): 309 [M+H]+, 617 [2M+H]+; $t_R$ (HPLC conditions b): 4.75 min.

D. (3-Carbamoyl-5-chloro-indol-1-yl)-acetic acid

To a solution of (3-carbamoyl-5-chloro-indol-1-yl)-acetic acid tert-butyl ester (455 mg, 0.973 mmol) in $CH_2Cl_2$ (6.0 mL) was added TFA (3.0 mL) at RT and stirring was continued for 2 h. Methanol was then added to the reaction mixture and volatiles were removed in vacuo. The residue was taken up in methanol and concentrated again under reduced pressure. The residue was dissolved in 1N aqueous NaOH and washed with $CH_2Cl_2$ (3×). The water phase was acidified to pH 2 by adding 6N aqueous HCl to form a white suspension. The precipitate was filtered off, washed with water and dried in vacuo to afford the crude title compound as a white solid. MS (LC/MS): 253 [M+H]+, 505 [2M+H]+; $t_R$ (HPLC conditions b): 3.99 min. The product was used in the next reaction step without further purification.

(3-Carbamoyl-7-chloro-indol-1-yl)-acetic acid

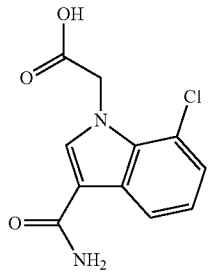 [SMILES: NC(=O)c1cn(CC(=O)O)c2c(Cl)cccc12]

was prepared from 7-chloro-1H-indole-3-carbaldehyde [1008-07-7] using similar protocols as described in Scheme A11 for the preparation of (3-carbamoyl-5-chloro-indol-1-yl)-acetic acid. White solid. MS (LC/MS): 253 [M+H]+, 505 [2M+H]+; $t_R$ (HPLC conditions b): 3.32 min.

(6-Benzyloxy-3-carbamoyl-indol-1-yl)-acetic acid

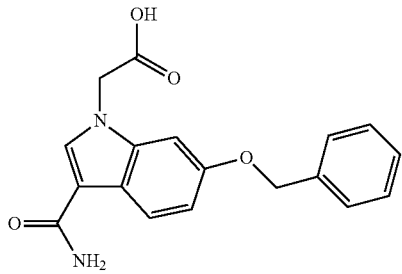 [SMILES: NC(=O)c1cn(CC(=O)O)c2cc(OCc3ccccc3)ccc12]

was prepared from 6-benzyloxy-1H-indole-3-carbaldehyde [92855-64-6] using similar protocols as described in Scheme A11 for the preparation of (3-carbamoyl-5-chloro-indol-1-yl)-acetic acid. White solid. MS (LC/MS): 325 [M+H]+, 649 [2M+H]+; $t_R$ (HPLC conditions b): 4.06 min.

(5-Benzyloxy-3-carbamoyl-indol-1-yl)-acetic acid

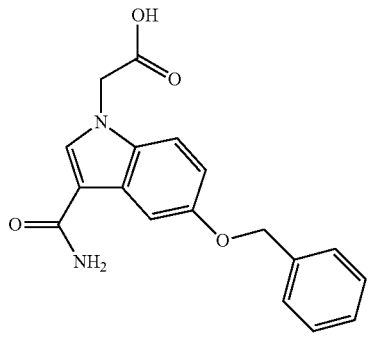 [SMILES: NC(=O)c1cn(CC(=O)O)c2ccc(OCc3ccccc3)cc12]

was prepared from 5-benzyloxy-1H-indole-3-carbaldehyde [6953-22-6] using similar protocols as described in Scheme A11 for the preparation of (3-carbamoyl-5-chloro-indol-1-yl)-acetic acid. White solid. MS (LC/MS): 325 [M+H]+, 649 [2M+H]+; $t_R$ (HPLC conditions b): 4.04 min.

(3-Carbamoyl-7-methoxy-indol-1-yl)-acetic acid

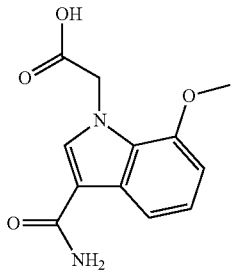 [SMILES: COc1cccc2c(C(N)=O)cn(CC(=O)O)c12]

was prepared from 7-methoxy-1H-indole-3-carbaldehyde [109021-59-2] in a similar manner as described in Scheme A11 for the preparation of (3-carbamoyl-5-chloro-indol-1-yl)-acetic acid. White solid. MS (LC/MS): 249 [M+H]+, 497 [2M+H]+; $t_R$ (HPLC conditions c): 3.05 min.

(3-carbamoyl-5,6-difluoro-indol-1-yl)-acetic acid

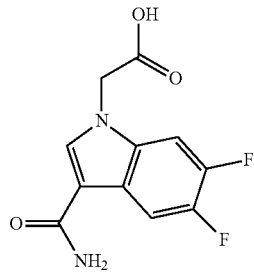 [SMILES: NC(=O)c1cn(CC(=O)O)c2cc(F)c(F)cc12]

was prepared from 5,6-difluoro-1H-indole-3-carbaldehyde in a similar manner as described in Scheme A11 for the preparation of (3-carbamoyl-5-chloro-indol-1-yl)-acetic acid. The title compound was obtained as a white solid: MS (LC/MS): 255.0 [M+H]+, 509.0 [2M+H]+; $t_R$ (HPLC conditions k): 2.58 min.

5,6-Difluoro-1H-indole-3-carbaldehyde

To an ice-cooled solution of oxalyl chloride (1.21 mL, 13.8 mmol) in CH$_2$Cl$_2$ (40 mL) was added a solution of DMF (2.02 mL) in CH$_2$Cl$_2$ (40.0 mL). The reaction was stirred for 30 min, then 5,6-difluoro-1H-indole [169674-01-5] (2.00 g, 13.1 mmol) was added in one portion. The reaction mixture was allowed to warm to RT overnight. Volatiles were evaporated, and the residue was taken up in THF (20 mL) and 20% aqueous ammonium acetate solution (20 mL). The resulting mixture was heated to reflux for 30 min. After cooling, the mixture was treated with saturated aqueous NaHCO$_3$ solution and extracted three times with EtOAc. The combined organic layers were dried (phase separator) and evaporated in vacuo to afford the title compound as a beige solid: MS (LC/MS): 182.0 [M+H]+; $t_R$ (HPLC conditions c): 3.94 min. The material thus obtained was used in the next step without further purification.

(3-Carbamoyl-6-trifluoromethoxy-indol-1-yl)-acetic acid

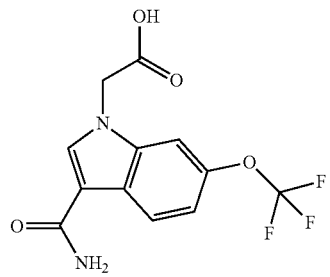 [SMILES: NC(=O)c1cn(CC(=O)O)c2cc(OC(F)(F)F)ccc12]

was prepared from 6-trifluoromethoxy-1H-indole [467451-91-8] in a similar manner as described for the preparation of (3-carbamoyl-5,6-difluoro-indol-1-yl)-acetic acid. White solid. MS (LC/MS): 303.0 [M+H]+, 605.0 [2M+H]+; $t_R$ (HPLC conditions k): 2.75 min.

(6-Bromo-3-carbamoyl-5-fluoro-indol-1-yl)-acetic acid

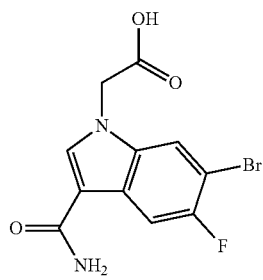 [SMILES: NC(=O)c1cn(CC(=O)O)c2cc(Br)c(F)cc12]

was prepared from 6-bromo-5-fluoro-1H-indole [259860-08-7] in a similar manner as described for the preparation of (3-carbamoyl-5,6-difluoro-indol-1-yl)-acetic acid. White solid. MS (LC/MS): 315.0 [M+H]+, 631.0 [2M+H]+; $t_R$ (HPLC conditions k): 2.79 min.

(3-Carbamoyl-6-difluoromethoxy-indol-1-yl)-acetic acid

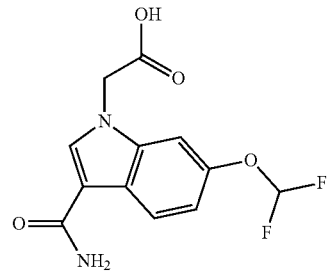 [SMILES: NC(=O)c1cn(CC(=O)O)c2cc(OC(F)F)ccc12]

was prepared from 6-difluoromethoxy-1H-indole [200207-21-2] in a similar manner as described for the preparation of (3-carbamoyl-5,6-difluoro-indol-1-yl)acetic acid. White solid. MS (LC/MS): 285 [M+H]+, 569 [2M+H]+; $t_R$ (HPLC conditions k): 2.64 min.

(3-Methylcarbamoyl-indol-1-yl)-acetic acid

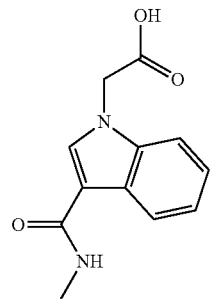 [SMILES: CNC(=O)c1cn(CC(=O)O)c2ccccc12]

was prepared from 1H-indole-3-carbaldehyde using similar protocols as described in Scheme A11 for the preparation of (3-carbamoyl-5-chloro-indol-1-yl)-acetic acid (using methylamine hydrochloride in step C). MS (LC/MS): 233 [M+H]+; 465 [M+H]+; 231 [M−H]−; 463 [M+H]−; $t_R$ (HPLC conditions b): 1.8 min.

Scheme A12: Preparation of (3-Carbamoyl-5-methoxy-indol-1-yl)-acetic acid

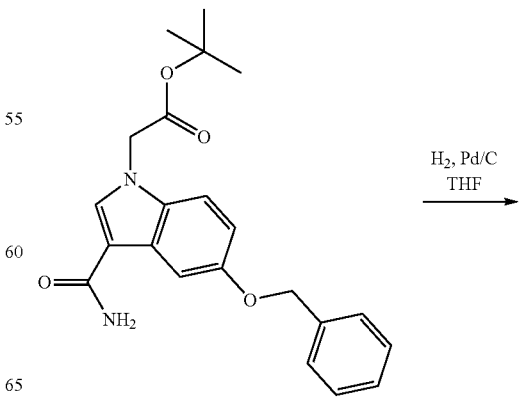

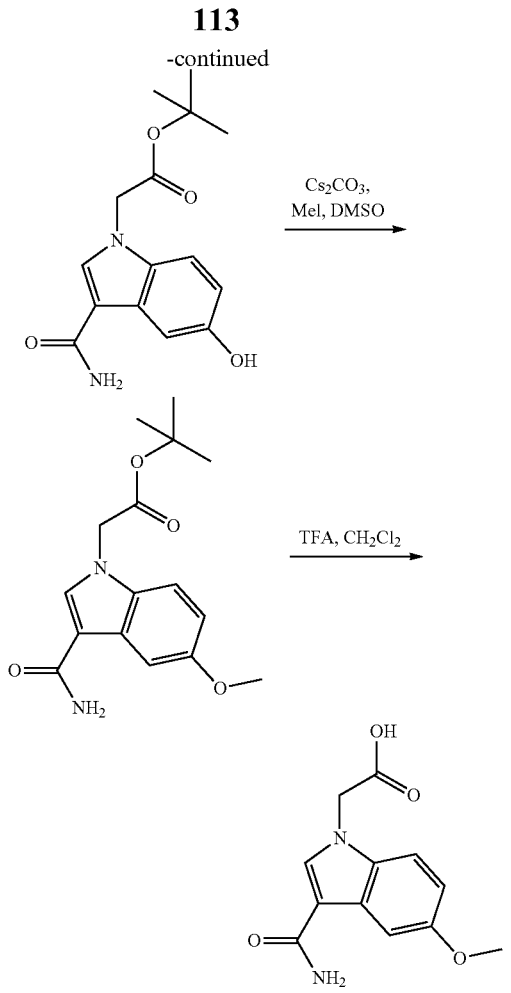

A. (5-Benzyloxy-3-carbamoyl-indol-1-yl)-acetic acid tert-butyl ester

The title compound was prepared from 5-benzyloxy-1H-indole-3-carbaldehyde [6953-22-6] in a similar manner as described in Scheme A11 for steps A to C.

B. (3-Carbamoyl-5-hydroxy-indol-1-yl)-acetic acid tert-butyl ester (5-Benzyloxy-3-carbamoyl-indol-1-yl)-acetic acid tert-butyl ester (250 mg, 0.657 mmol) was suspended in THF (13 mL). Air was removed from the flask and replaced with nitrogen three times. Pd/C 10% (25 mg) was added to the solution which was again degassed, placed under a hydrogen atmosphere and stirred at RT overnight. The catalyst was removed through a 0.45 microns filter and concentrated in vacuo. The crude material was purified by preparative HPLC (SunFire C18-ODB, 5 µm, 30×100 mm, eluent: 5-100% $CH_3CN/H_2O$/ 20 min, 100% $CH_3CN$/2 min, $CH_3CN$ and $H_2O$ containing 0.1% TFA, flow: 40 mL/min) to give after lyophilization of the purified fractions the desired compound as a white solid. MS: 291 [M+H]+, 313 [M+Na]+, 581 [2M+H]+, 603 [2M+Na]+; $t_R$ (HPLC conditions c): 3.75 min.

C. (3-Carbamoyl-5-methoxy-indol-1-yl)-acetic acid tert-butyl ester

To a solution of (3-carbamoyl-5-hydroxy-indol-1-yl)-acetic acid tert-butyl ester (50 mg, 0.172 mmol) in DMSO (1.7 mL) was added $Cs_2CO_3$ (336 mg, 1.03 mmol). The mixture was stirred at RT for 5 min, followed by addition of methyl iodide (0.048 mL, 0.774 mmol), and stirring was continued at RT for 3 days. The reaction mixture was partitioned between water and $CH_2Cl_2$, the layers were separated and the aqueous phase was extracted twice with $CH_2Cl_2$. The combined organics were washed twice with brine, dried (phase separator) and concentrated in vacuo to afford the title compound as a yellow solid: MS (LC/MS): 305 [M+H]+, 327 [M+Na]+, 609 [2M+H]+; $t_R$ (HPLC conditions c): 4.31 min. The material thus obtained was used in the next reaction step without further purification.

D. (3-Carbamoyl-5-methoxy-indol-1-yl)-acetic acid

To a solution of (3-carbamoyl-5-methoxy-indol-1-yl)-acetic acid tert-butyl ester (45.0 mg, 0.118 mmol) in $CH_2Cl_2$ (2.0 mL) was added TFA (1.0 mL) at RT, and stirring was continued for 3 h. Methanol was then added to the reaction mixture and volatiles were removed in vacuo. The residue was taken up in methanol and concentrated again under reduced pressure to afford the title compound as a beige solid: MS (LC/MS): 249 [M+H]+, 277 [M+Na]+; $t_R$ (HPLC conditions c): 2.93 min. The material thus obtained was used in the next reaction step without further purification.

Scheme A13: Preparation of (3-acetyl-5-trifluoromethoxy-indol-1-yl)-acetic acid

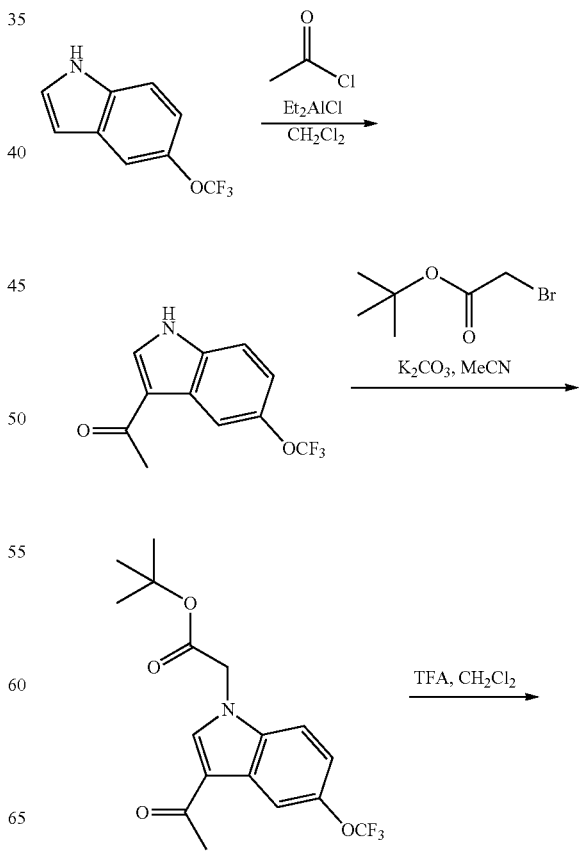

A. 1-(5-Trifluoromethoxy-1H-indol-3-yl)-ethanone

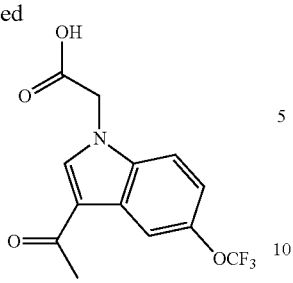

To a solution of 5-(trifluoromethoxy)-1H-indole [262593-63-5] (1.00 g, 4.97 mmol) in CH$_2$Cl$_2$ (20 mL), cooled to 0° C., was added dropwise diethylaluminum chloride (1M solution in hexane; 7.46 mL, 7.46 mmol), and stirring was continued for 30 min. A solution of acetyl chloride (0.532 mL, 7.46 mmol) in CH$_2$Cl$_2$ (20 mL) was subsequently added, and the reaction mixture was stirred at 0° C. for 1 h. A 5% aqueous citric acid solution (100 mL) was then added at 0° C., and the mixture was stirred for 15 min at RT. The mixture (two phases) was filtered, and the precipitate was dried at 50° C. in vacuo for 1 h to afford the title compound. Beige solid. MS: 244.0 [M+H]+; t$_R$ (HPLC conditions c): 4.60 min. The material thus obtained was used directly in the next step without further purification

B. (3-Acetyl-5-trifluoromethoxy-indol-1-yl)-acetic acid tert-butyl ester

To a solution of 1-(5-trifluoromethoxy-1H-indol-3-yl)-ethanone (0.50 g, 2.06 mmol) in CH$_3$CN (10 mL) was added K$_2$CO$_3$ (0.313 g, 2.26 mmol) and tert-butyl 2-bromoacetate (0.334 mL, 2.26 mmol). The reaction mixture was stirred at 90° C. overnight. The reaction mixture was filtered, and the filtrate was diluted with CH$_2$Cl$_2$. The organics were washed with 1M aqueous HCl solution (5 mL) and saturated aqueous NaHCO$_3$ solution (5 mL). The organic layer was dried (phase separator) and evaporated in vacuo to afford the title compound as a yellowish oil: MS: 358.0 [M+H]+; t$_R$ (HPLC conditions c): 5.66 min. The material thus obtained was used directly in the next step without further purification.

C. (3-Acetyl-5-trifluoromethoxy-indol-1-yl)-acetic acid

To a solution of (3-acetyl-5-trifluoromethoxy-indol-1-yl)-acetic acid tert-butyl ester (680 mg, 1.90 mmol) in CH$_2$Cl$_2$ (10 mL) was added TFA (1.47 mL, 19.0 mmol), and stirring was continued at RT overnight. The reaction mixture was then diluted with CH$_2$Cl$_2$ and MeOH, and volatiles were evaporated under reduced pressure. The residue was taken up in MeOH and then evaporated again. The crude material was taken up in 1M aqueous NaOH solution (5 mL), and the water layer was washed with CH$_2$Cl$_2$ and subsequently acidified to pH=1 by addition of a 6M HCl solution. The precipitate was filtered and dried at 50° C. in vacuo for 1 h to afford the title compound as a off-white solid: MS: 302.0 [M+H]+; t$_R$ (HPLC conditions c): 4.40 min. The material thus obtained was used directly in the next step without further purification.

(3-Acetyl-6-trifluoromethoxy-indol-1-yl)-acetic acid

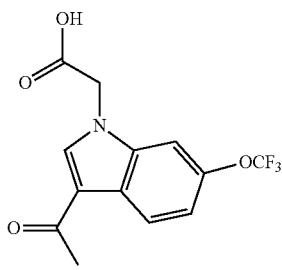 [SMILES: CC(=O)c1cn(CC(=O)O)c2cc(OC(F)(F)F)ccc12]

was prepared from 6-trifluoromethoxy-1H-indole [467451-91-8] in a similar manner as described in Scheme A13 for the preparation of (3-ccetyl-5-trifluoromethoxy-indol-1-yl)-acetic acid. MS: 302.0 [M+H]+; t$_R$ (HPLC conditions c): 4.39 min.

(3-Acetyl-6-methoxy-indol-1-yl)-acetic acid

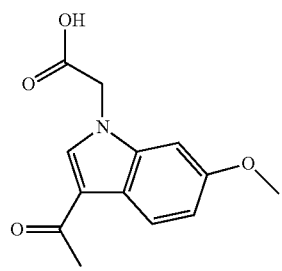 [SMILES: COc1ccc2c(C(C)=O)cn(CC(=O)O)c2c1]

was prepared from 1-(6-methoxy-1H-indol-3-yl)-ethanone [99532-52-2] in a similar manner as described in step B and C of Scheme A13 for the preparation of (3-acetyl-5-trifluoromethoxy-indol-1-yl)-acetic acid. Brown solid. MS: 248 [M+H]+, 517 [2M+Na]+; t$_R$ (HPLC conditions k): 2.30 min.

(3-Acetyl-6-chloro-indol-1-yl)-acetic acid

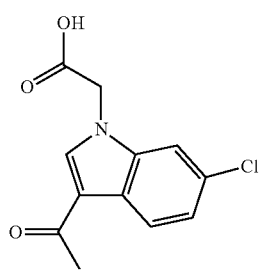 [SMILES: CC(=O)c1cn(CC(=O)O)c2cc(Cl)ccc12]

was prepared from 6-chloro-1H-indole in a similar manner as described in Scheme A13 for the preparation of (3-acetyl-5-trifluoromethoxy-indol-1-yl)-acetic acid. Brown solid. MS: 252 [M+H]+, 274 [M+Na]+; t$_R$ (HPLC conditions k): 2.89 min.

117

(3-Acetyl-6-cyano-indol-1-yl)-acetic acid

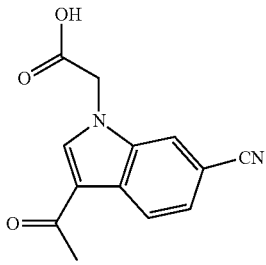 [SMILES: CC(=O)c1cn(CC(=O)O)c2cc(C#N)ccc12]

was prepared from 1H-indole-6-carbonitrile in a similar manner as described in Scheme A13 for the preparation of (3-acetyl-5-trifluoromethoxy-indol-1-yl)-acetic acid. MS: 243 [M+H]+; $t_R$ (HPLC conditions k): 2.72 min.

(3-Acetyl-5-cyano-indol-1-yl)-acetic acid

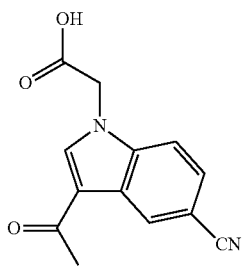 [SMILES: CC(=O)c1cn(CC(=O)O)c2ccc(C#N)cc12]

was prepared from 1H-indole-5-carbonitrile in a similar manner as described in Scheme A13 for the preparation of (3-acetyl-5-trifluoromethoxy-indol-1-yl)-acetic acid. MS (LC/MS): 241.2 [M−H]−; 243.2 [M+H]+; $t_R$ (HPLC conditions a): 2.62 min.

(3-Acetyl-5-benzyloxy-indol-1-yl)-acetic acid

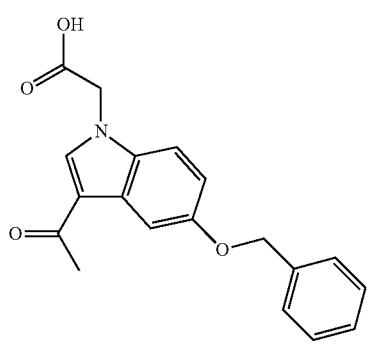 [SMILES: CC(=O)c1cn(CC(=O)O)c2ccc(OCc3ccccc3)cc12]

was prepared from 5-benzyloxy-1H-indole in a similar manner as described in Scheme A13 for the preparation of (3-acetyl-5-trifluoromethoxy-indol-1-yl)acetic acid. MS: 324 [M+H]+, 346 [M+Na]+; $t_R$ (HPLC conditions k): 3.34 min.

118

(3-Acetyl-6-benzyloxy-indol-1-yl)-acetic acid

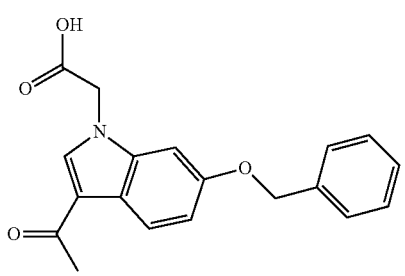 [SMILES: CC(=O)c1cn(CC(=O)O)c2cc(OCc3ccccc3)ccc12]

was prepared from 6-benzyloxy-1H-indole in a similar manner as described in Scheme A13 for the preparation of (3-acetyl-5-trifluoromethoxy-indol-1-yl)acetic acid. MS: 324 [M+H]+, 647 [2M+1]+; $t_R$ (HPLC conditions k): 3.38 min.

3-Acetyl-1-carboxymethyl-1H-indole-5-carboxylic acid methyl ester

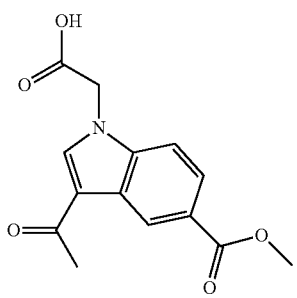 [SMILES: COC(=O)c1ccc2c(c1)c(C(C)=O)cn2CC(=O)O]

was prepared from 1H-indole-5-carboxylic acid methyl ester in a similar manner as described in Scheme A13 for the preparation of (3-acetyl-5-trifluoromethoxy-indol-1-yl)-acetic acid. MS: 276 [M+H]+; $t_R$ (HPLC conditions k): 2.84 min.

3-Acetyl-1-carboxymethyl-1H-indole-7-carboxylic acid methyl ester

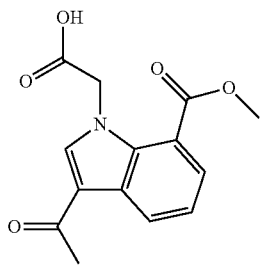 [SMILES: COC(=O)c1cccc2c(C(C)=O)cn(CC(=O)O)c12]

was prepared from 1H-indole-7-carboxylic acid methyl ester in a similar manner as described in Scheme A13 for the preparation of (3-acetyl-5-trifluoromethoxy-indol-1-yl)-acetic acid. MS: 276 [M+H]+; $t_R$ (HPLC conditions k): 2.89 min.

3-Acetyl-1-carboxymethyl-1H-indole-6-carboxylic acid methyl ester

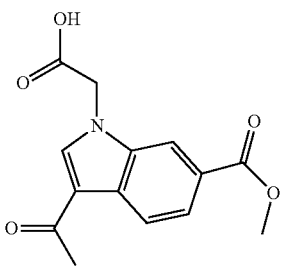 [SMILES: COC(=O)c1ccc2c(C(C)=O)cn(CC(=O)O)c2c1]

was prepared from 3-acetyl-1H-indole-6-carboxylic acid methyl ester [106896-61-1] in a similar manner as described in step B and C of Scheme A13 for the preparation of (3-acetyl-5-trifluoromethoxy-indol-1-yl)-acetic acid. Colored solid. MS: 276 [M+H]+; $t_R$ (HPLC conditions k): 2.80 min.

(3-Acetyl-6-methoxycarbonylmethyl-indol-1-yl)-acetic acid

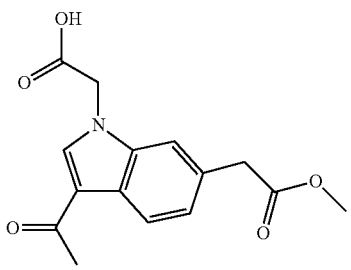 [SMILES: COC(=O)Cc1ccc2c(C(C)=O)cn(CC(=O)O)c2c1]

was prepared from (3-acetyl-1H-indol-6-yl)-acetic acid methyl ester in a similar manner as described in Scheme A13 for the preparation of (3-acetyl-5-trifluoromethoxy-indol-1-yl)-acetic acid. Brown solid. MS: 290 [M+H]+; $t_R$ (HPLC conditions k): 2.83 min.

(3-Acetyl-1H-indol-6-yl)-acetic acid methyl ester

To a stirred solution of (3-acetyl-1H-indol-6-yl)-acetic acid [39689-58-2] (500 mg, 2.85 mmol) in MeOH (14 mL), cooled to at 0° C., was added (trimethylsilyl)diazomethane (2M solution in Et$_2$O; 6.00 mL, 12.0 mmol). After stirring at RT for 30 min, the reaction mixture was concentrated in vacuo to afford the title compound as a yellow wax. MS: 190 [M+H]+; $t_R$ (HPLC conditions k): 3.20 min. The material thus obtained was used directly in the next step without further purification.

(3-Acetyl-pyrrolo[2,3-b]pyridin-1-yl)-acetic acid

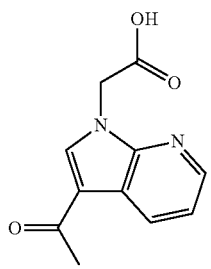 [SMILES: CC(=O)c1cn(CC(=O)O)c2ncccc12]

was prepared in a similar manner as described in step B and C of Scheme A13 for the preparation of (3-acetyl-5-trifluoromethoxy-indol-1-yl)-acetic acid from 1-(1H-pyrrolo[2,3-b]pyridin-3-yl)-ethanone [83393-46-8]. MS (UPLC/MS): 219.2 [M+H]+, 217.2 [M−H]−, 263.3 [M+HCOO]−, 435.3 [2M−H]−; $t_R$ (HPLC conditions f): 1.16 min. 1H-NMR (400 MHz, DMSO): δ (ppm): 8.55 (bs, 1H), 8.49 (dd, 1H), 8.36 (dd, 1H), 7.31 (dd, 1H), 5.12 (s, 2H), 2.48 (s, 3H).

(3-Acetyl-pyrrolo[3,2-b]pyridin-1-yl)-acetic acid

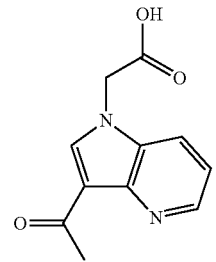 [SMILES: CC(=O)c1cn(CC(=O)O)c2cccnc12]

was prepared in a similar manner as described in step B and C of Scheme A13 for the preparation of (3-acetyl-5-trifluoromethoxy-indol-1-yl)-acetic acid from 1-(1H-pyrrolo[3,2-b]pyridin-3-yl)-ethanone (prepared according to *J. Org. Chem.* 2002, 67, 6226). MS (UPLC/MS): 219.2 [M+H]+, 217.3 [M−H]−, 435.3 [2M−H]−; $t_R$ (HPLC conditions f): 1.16 min. 1H-NMR (400 MHz, DMSO): δ (ppm): 8.79 (bs, 1H), 8.64 (m, 2H), 7.64 (m, 1H), 5.33 (s, 2H), 2.67 (s, 3H).

[3-(2,2,2-Trifluoro-acetyl)-indol-1-yl]-acetic acid

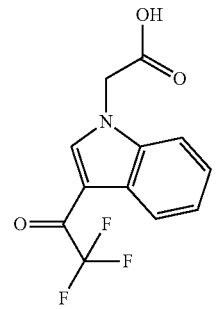 [SMILES: O=C(O)Cn1cc(C(=O)C(F)(F)F)c2ccccc21]

was prepared from 2,2,2-trifluoro-1-(1H-indol-3-yl)-ethanone in a similar manner as described in Scheme A13 (step B and C) for the preparation of (3-acetyl-5-trifluoromethoxy-indol-1-yl)-acetic acid. White solid. MS: 272.0 [M+H]+; $t_R$ (HPLC conditions c): 4.59 min.

[3-(2-Hydroxy-acetyl)-indol-1-yl]-acetic acid

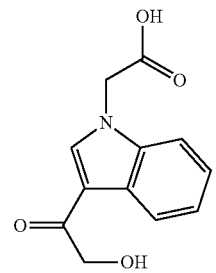 [SMILES: O=C(O)Cn1cc(C(=O)CO)c2ccccc21]

was prepared from 2-hydroxy-1-(1H-indol-3-yl)-ethanone [2400-51-3] in a similar manner as described in Scheme A13

(step B and C) for the preparation of (3-acetyl-5-trifluoromethoxy-indol-1-yl)-acetic acid. Colored solid. MS: 234.0 [M+H]+, 489.0 [2M+Na]+; $t_R$ (HPLC conditions c): 3.11 min.

[3-(2-Methoxy-acetyl)-indol-1-yl]-acetic acid

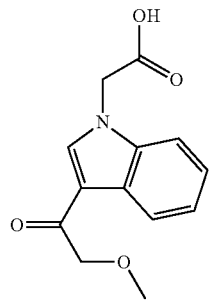 [SMILES: COCC(=O)c1cn(CC(=O)O)c2ccccc12]

was prepared from 1H-indole in a similar manner as described in Scheme A13 (in step A, 2-methoxyacetyl chloride was used instead of acetyl chloride) for the preparation of (3-acetyl-5-trifluoromethoxy-indol-1-yl)-acetic acid. Brown solid. MS: 248.0 [M+H]+; $t_R$ (HPLC conditions c): 3.42 min.

3-Acetyl-1-carboxymethyl-1H-pyrrolo[2,3-b]pyridine-6-carboxylic acid methyl ester

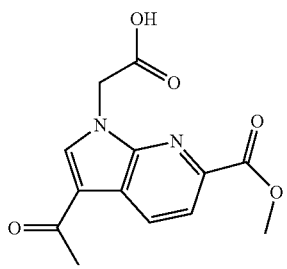 [SMILES: COC(=O)c1ccc2c(C(C)=O)cn(CC(=O)O)c2n1]

was prepared from methyl 3-acetyl-1H-pyrrolo[2,3-b]pyridine-6-carboxylate using a similar protocol as described in Scheme A13, Steps C and D: MS (LC/MS): 277 [M+H]+; $t_R$ (HPLC conditions k): 2.68 min.

Methyl 3-acetyl-1H-pyrrolo[2,3-b]pyridine-6-carboxylate was prepared from methyl 1H-pyrrolo[2,3-b]pyridine-6-carboxylate using a similar protocol as described in Scheme A17, Step A: MS (LC/MS): 219 [M+H]+; $t_R$ (HPLC conditions k): 2.58 min.

Methyl 1H-pyrrolo[2,3-b]pyridine-6-carboxylate

To a stirred solution of 1H-pyrrolo[2,3-b]pyridine-6-carboxylic acid [898746-35-5] (500 mg, 3.08 mmol) in MeOH was added a 2M solution of trimethylsilyldiazomethane in Et$_2$O at 0° C., and the reaction mixture was stirred at RT for 30 min. The reaction mixture was concentrated in vacuo to give the title compound. MS (LC/MS): 177 [M+H]+, 375 [2M+H]+; $t_R$ (HPLC conditions k): 2.71

Scheme A14: preparation of (3-acetyl-5-triisopropylsilanyloxymethyl-indol-1-yl)-acetic acid

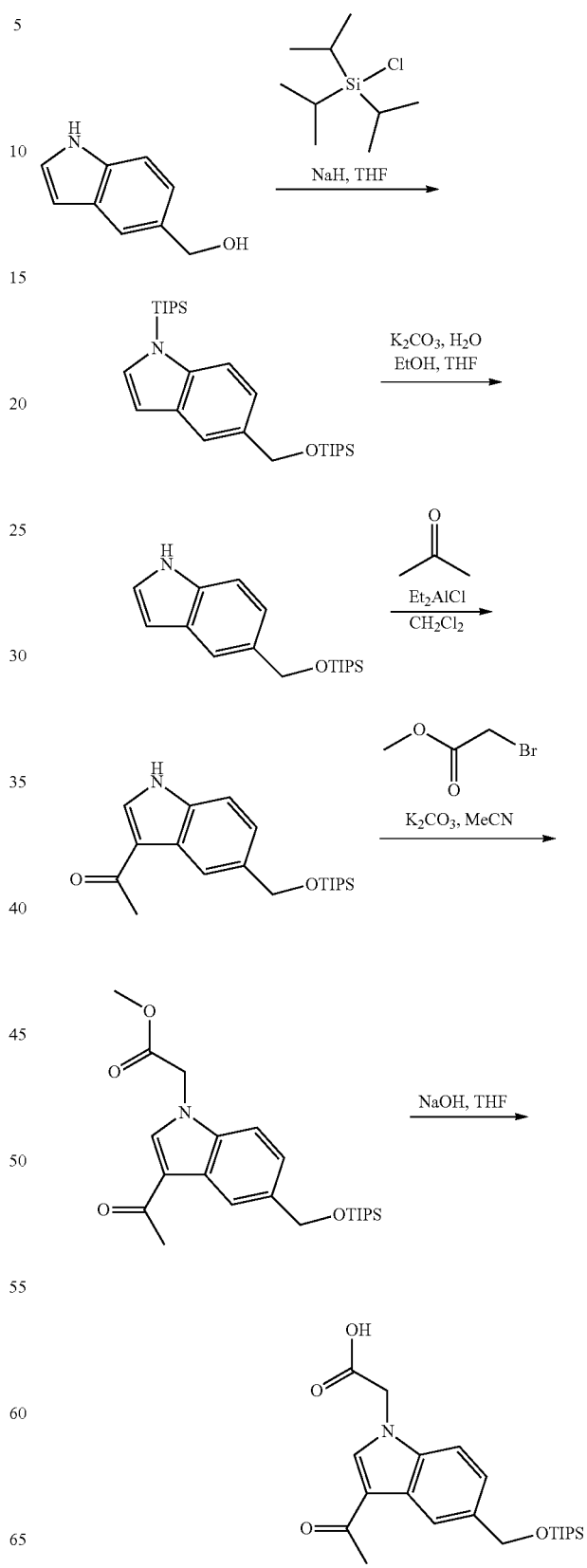

A. 1-Triisopropylsilanyl-5-triisopropylsilanyloxymethyl-1H-indole

To a solution of (1H-indol-5-yl)-methanol (1.00 g, 6.79 mmol) in THF (60 mL), cooled to 0° C., was added sodium hydride (60% in mineral oil; 1.36 g, 34.0 mmol) portionwise. After stirring for 5 min, triisopropylsilyl chloride (2.88 mL, 13.6 mmol) was added, and the resulting solution was stirred at RT for 2 h. The reaction was quenched by addition of a saturated aqueous NaHCO$_3$ solution at 0° C. The aqueous layer was repeatedly extracted with EtOAc, and the combined organics were washed with H$_2$O (1×) and brine (1×), dried (phase separator) and concentrated in vacuo. Purification by flash column chromatography on silica gel (eluent gradient: c-hexane to c-hexane/EtOAc 9:1) afforded the title compound as a white solid. TLC, R$_f$ (c-hexane/EtOAc 9:1)=0.72. 1H-NMR (400 MHz, DMSO-d$_6$): 5 ppm 7.61 (s, 1H), 7.49 (d, 1H), 7.32 (d, 1H), 6.93 (d, 1H), 6.57 (d, 1H), 4.92 (s, 2H), 1.60-1.85 (m, 3H), 1.01-1.12 (m, 39H).

B. 5-Triisopropylsilanyloxymethyl-1H-indole

To a suspension of 1-triisopropylsilanyl-5-triisopropylsilanyloxymethyl-1H-indole (2.80 g, 6.09 mmol) in EtOH (30 mL)/THF (10 mL)/water (10 mL) was added K$_2$CO$_3$ (4.21 g, 30.4 mmol), and the reaction mixture was heated at 85° C. for 16 h. The reaction was quenched with 1N HCl at 0° C. The aqueous layer was extracted with CH$_2$Cl$_2$ (2×) and the combined organic layers were washed with brine, dried (phase separator) and concentrated under reduced pressure. The oily residue was purified by flash column chromatography on silica gel (eluent gradient: c-hexane to c-hexane/EtOAc 9:1) to afford the title compound as a yellow oil. TLC, R$_f$ (c-hexane/EtOAc 9:1)=0.29. t$_R$ (HPLC conditions k): 5.02 min. MS (LC/MS): 304 [M+H]+.

C. 1-(5-Triisopropylsilanyloxymethyl-1H-indol-3-yl)-ethanone

The title compound was prepared from 5-triisopropylsilanyloxymethyl-1H-indole in a similar manner as described in step A of Scheme A13 for the preparation of (3-acetyl-5-trifluoromethoxy-indol-1-yl)-acetic acid. Brown solid. MS: 346 [M+H]+; t$_R$ (HPLC conditions c): 6.86 min.

D. (3-Acetyl-5-triisopropylsilanyloxymethyl-indol-1-yl)-acetic acid methyl ester The title compound was prepared from 1-(5-triisopropylsilanyloxymethyl-1H-indol-3-yl)-ethanone in a similar manner as described in step B of Scheme A13 for the preparation of (3-acetyl-5-trifluoromethoxy-indol-1-yl)-acetic acid. MS: 418 [M+H]+; t$_R$ (HPLC conditions k): 4.75 min.

E. (3-Acetyl-5-triisopropylsilanyloxymethyl-indol-1-yl)-acetic acid

To a solution of (3-acetyl-5-triisopropylsilanyloxymethyl-indol-1-yl)-acetic acid methyl ester (109 mg, 0.138 mmol) in THF (5 mL) and water (0.5 mL) was added 1N NaOH (0.69 mL, 0.69 mmol), and stirring was continued at RT for 16 h. The reaction mixture was partitioned between EtOAc and saturated aqueous NaHCO$_3$. The aqueous layer was extracted with EtOAC (2×), the combined organics were dried (phase separator) and concentrated in vacuo to afford the title compound as a yellow wax. MS (LC/MS): 404 [M+H]+; t$_R$ (HPLC conditions k): 4.35 min.

Scheme A15: Preparation of (3-acetyl-pyrrolo[2,3-c]pyridin-1-yl)-acetic acid trifluoroacetate

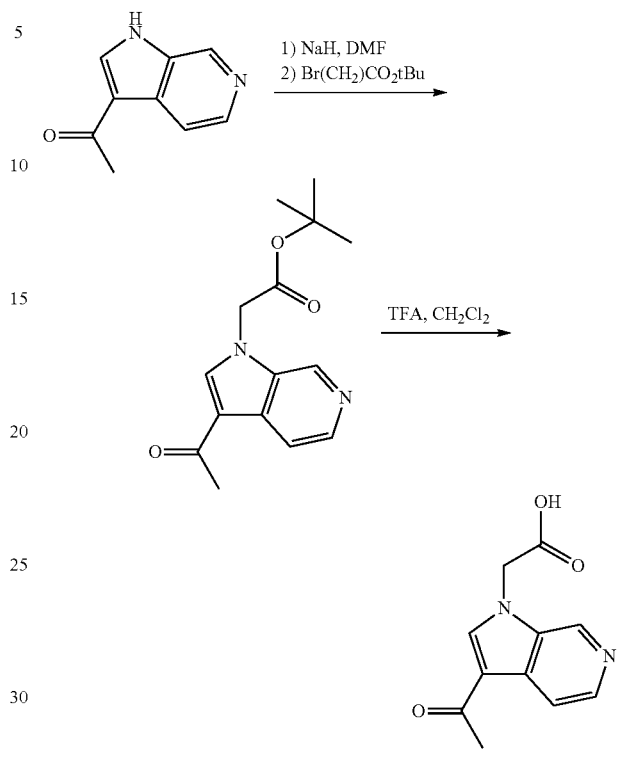

A. (3-Acetyl-pyrrolo[2,3-c]pyridin-1-yl)-acetic acid tert-butyl ester

To a suspension of NaH (60% in mineral oil, 90 mg, 2.25 mmol) in DMF (4.2 mL) cooled at 0° C. was added a solution of 1-(1H-pyrrolo[2,3-c]pyridin-3-yl)-ethanone (prepared according to J. Org. Chem. 2002, 67, 6226) (300 mg, 1.87 mmol) in DMF (4.2 mL) and the resulting suspension was stirred at 0° C. under nitrogen atmosphere for 30 min before slow addition of tert-butyl bromoacetate (277 µL, 1.87 mmol). The reaction mixture was allowed to reach RT and further stirred at RT for 1.5 h. After completion of the reaction, the mixture was purified first by catch-release on SiliaPrep Tosic Acid-(2×10 g) (Varian) (eluent: MeOH (50 mL) by 2 M ammonia in MeOH (50 mL)) to give a mixture of regioisomers: (3-acetyl-pyrrolo[2,3-c]pyridin-1-yl)-acetic acid tert-butyl ester and (3-acetyl-pyrrolo[2,3-c]pyridin-6-yl)-acetic acid tert-butyl ester followed by flash column chromatography on silica gel (CH$_2$Cl$_2$ to CH$_2$Cl$_2$/MeOH 85-15) to give (3-acetyl-pyrrolo[2,3-c]pyridin-1-yl)-acetic acid tert-butyl ester as a yellow powder. TLC, R$_f$ (CH$_2$Cl$_2$/MeOH 9-1)=0.50; MS (UPLC/MS): 275.3 [M+H]+, 319.2 [M+HCOO]−; t$_R$ (HPLC conditions f): 1.28 min; 1H-NMR (400 MHz, DMSO-d$_6$): δ (ppm): 8.88 (s, 1H), 8.50 (s, 1H), 8.33 (d, 1H), 8.06 (d, 1H), 5.27 (s, 2H), 2.48 (s, 3H), 1.45 (s, 9H).

B. (3-Acetyl-pyrrolo[2,3-c]pyridin-1-yl)-acetic acid trifluoroacetate

A solution of (3-acetyl-pyrrolo[2,3-c]pyridin-1-yl)-acetic acid tert-butyl ester (230 mg, 0.8 mmol) and TFA (0.915 mL, 11.95 mmol) in CH$_2$Cl$_2$ (3.1 mL) was stirred at RT overnight.

The reaction mixture was concentrated and the residue was dried under high vacuum. The resulting solid was taken-up in Et$_2$O and filtered to give the desired compound (TFA salt) as beige powder which was used in the next step without purification. MS (UPLC/MS): 219.2 [M+H]+, 217.2 [M–H]–; 1H-NMR (400 MHz, DMSO): δ (ppm): 9.50 (s, 1H), 9.03 (s, 1H), 8.54 (d, 1H), 8.51 (d, 1H), 5.40 (s, 2H), 2.57 (s, 3H).

(3-Acetyl-pyrrolo[3,2-c]pyridin-1-yl)-acetic acid trifluoroacetate

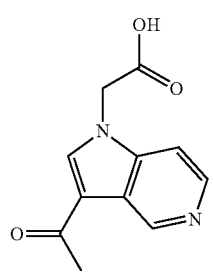 [SMILES: CC(=O)c1cn(CC(=O)O)c2ccncc12]

was prepared using similar procedures as described for the synthesis of (3-acetyl-pyrrolo[2,3-c]pyridin-1-yl)-acetic acid in Scheme A15 from 1-(1H-pyrrolo[3,2-c]pyridin-3-yl)-ethanone (prepared according to *J. Org. Chem.* 2002, 67, 6226). MS (UPLC/MS): 219.1 [M+H]+, 217.2 [M–H]–, 435.3 [2M–H]–; 1H-NMR (400 MHz, DMSO): δ (ppm): 9.54 (s, 1H), 8.89 (s, 1H), 8.66 (d, 1H), 8.30 (d, 1H), 5.38 (s, 2H), 2.58 (s, 3H).

(3-Acetyl-6-methoxy-pyrrolo[2,3-b]pyridin-1-yl)-acetic acid

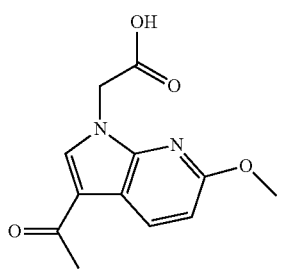 [SMILES: COc1ccc2c(C(C)=O)cn(CC(=O)O)c2n1]

was prepared using similar procedures as described for the synthesis of (3-acetyl-pyrrolo[2,3-c]pyridin-1-yl)-acetic acid in Scheme A15 from 1-(6-methoxy-1H-pyrrolo[2,3-b]pyridin-3-yl)-ethanone. MS (UPLC/MS): 249.2 [M+H]+, 497.3 [2M+H]+, 519.3 [2M+Na]+, 247.1 [M–H]–, 293.2 [M+HCOO]–, 495.3 [2M+HCOO]–; t$_R$ (HPLC conditions f): 1.55 min. 1H-NMR (400 MHz, DMSO): δ (ppm): 12.3 (bs, 1H), 8.33 (d, 1H), 8.21 (s, 1H), 6.70 (d, 1H), 3.89 (s, 3H), 3.32 (s, 2H), 2.43 (s, 3H).

1-(6-methoxy-1H-pyrrolo[2,3-b]pyridin-3-yl)-ethanone

To a suspension of AlCl$_3$ (1.37 g, 10.3 mmol) in CH$_2$Cl$_2$ (40 mL) was added 6-methoxy-7-azaindole (315 mg, 2.07 mmol) and the mixture was stirred at RT for 30 min under nitrogen. Acetyl chloride (736 μL, 10.3 mmol) was added dropwise and the resulting mixture stirred at RT overnight. MeOH (8 mL) was added cautiously to quench the reaction and the solvents were removed under vacuum. The residue was purified by flash column chromatography on silica gel (CH$_2$Cl$_2$ to CH$_2$Cl$_2$/MeOH 93-7) and by preparative HPLC (Waters Sunfire C18-ODB, 5 μm, 30×100 mm, 5% to 100% CH$_3$CN in H$_2$O in 25 min, CH$_3$CN and H$_2$O containing 0.1% TFA, flow: 40 mL/min) to give after neutralization (aqueous saturated NaHCO$_3$) and extraction (CH$_2$Cl$_2$) of the purified fractions the desired compound TLC, R$_f$ (CH$_2$Cl$_2$/MeOH 9:1)=0.55; MS (UPLC/MS): 191.2 [M+H]+, 189.1 [M–H]–, 379.2 [2M–H]–; t$_R$ (HPLC conditions f): 1.45 min. 1H-NMR (400 MHz, DMSO): δ (ppm): 8.35 (d, 1H), 8.29 (s, 1H), 6.75 (d, 1H), 5.04 (s, 2H), 3.89 (s, 3H), 2.44 (s, 3H).

(3-Acetyl-5-methoxy-pyrrolo[2,3-b]pyridin-1-yl)-acetic acid trifluoroacetate

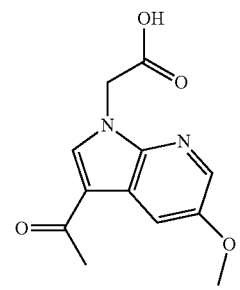 [SMILES: COc1cnc2c(c1)c(C(C)=O)cn2CC(=O)O]

was prepared using similar procedures as described for the synthesis of (3-acetyl-6-methoxy-pyrrolo[2,3-b]pyridin-1-yl)-acetic acid in Scheme A15 from 1H-pyrrolo[2,3-b]pyridine-6-carbonitrile. TLC, R$_f$(CH$_2$Cl$_2$/MeOH 4:1)=0.50; MS (UPLC/MS): 191.2 [M+H]+, 189.1 [M–H]–; t$_R$ (HPLC conditions f): 1.23 min.

(3-Acetyl-6-cyano-pyrrolo[2,3-b]pyridin-1-yl)-acetic acid

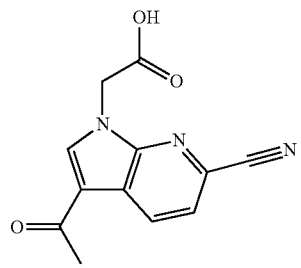 [SMILES: CC(=O)c1cn(CC(=O)O)c2nc(C#N)ccc12]

was prepared using similar procedures as described for the synthesis of (3-acetyl-6-methoxy-pyrrolo[2,3-b]pyridin-1-yl)-acetic acid in Scheme A15 from 1H-pyrrolo[2,3-b]pyridine-6-carbonitrile. MS (UPLC/MS): 244.1 [M+H]+, 242.1 [M–H]–; t$_R$ (HPLC conditions f): 1.42 min.

(3-Acetyl-5-methyl-pyrrolo[2,3-c]pyridin-1-yl)-acetic acid trifluoroacetate

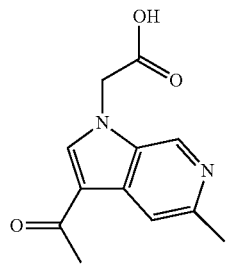 [SMILES: CC(=O)c1cn(CC(=O)O)c2cnc(C)cc12]

was prepared using similar procedures as described for the synthesis of (3-acetyl-pyrrolo[2,3-c]pyridin-1-yl)-acetic acid in Scheme A15 from 1-(5-methyl-1H-pyrrolo[2,3-c]pyridin-3-yl)-ethanone (prepared according to *J. Org. Chem.* 2002, 67, 6226). MS (UPLC/MS): 233.2 [M+H]+, 231.2 [M−H]−.

(5-Acetyl-pyrrolo[2,3-c]pyridazin-7-yl)-acetic acid

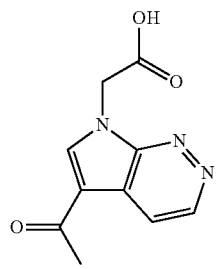 [SMILES: CC(=O)c1cn(CC(=O)O)c2nnccc12]

was prepared using similar procedures as described for the synthesis of (3-acetyl-pyrrolo[2,3-c]pyridin-1-yl)-acetic acid in Scheme A15 from 1-(7H-pyrrolo[2,3-c]pyridazin-5-yl)-ethanone (prepared according to *J. Org. Chem.* 2002, 67, 6226). MS (UPLC/MS): 220.1 [M+H]+, 178.0 [MH−CH$_3$CO]+, 218.1 [M−H]−, 437.2 [2M−H]−.

(3-Propionyl-pyrrolo[2,3-c]pyridin-1-yl)-acetic acid trifluoroacetate

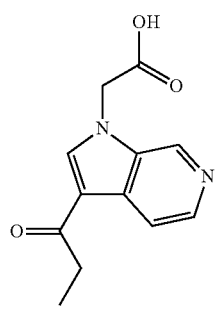 [SMILES: CCC(=O)c1cn(CC(=O)O)c2cnccc12]

was prepared using similar procedures as described for the synthesis of (3-acetyl-6-methoxy-pyrrolo[2,3-b]pyridin-1-yl)-acetic acid in Scheme A15 from 1-(1H-pyrrolo[2,3-c]pyridin-3-yl)-propan-1-one. 1H-NMR (400 MHz, DMSO-d$_6$): δ (ppm): 9.56 (s, 1H), 9.09 (s, 1H), 8.58 (m, 2H), 5.42 (s, 2H), 3.0 (q, 2H), 1.15 (t, 3H).

1-(1H-Pyrrolo[2,3-c]pyridin-3-yl)-propan-1-one

6-Azaindole (500 mg, 4.23 mmol) was added to a suspension of AlCl$_3$ (2.82 g, 21.16 mmol) in CH$_2$Cl$_2$ (100 mL) under argon atmosphere. The mixture was stirred at RT for 30 min and propionyl chloride (1.84 mL, 21.16 mmol) was added dropwise. The reaction mixture was stirred for 2.5 h and quenched by cautious addition of MeOH (20 mL). The solvents were removed under reduced pressure and the crude residue was purified by flash column chromatography on silica gel (CH$_2$Cl$_2$ to CH$_2$Cl$_2$/MeOH 87:13). TLC, R$_f$ (CH$_2$Cl$_2$/MeOH 9:1)=0.35; MS (UPLC/MS): 175.2 [M+H]+, 173.1 [M−H]−, 347.3 [2M−H]−, 219.1 [M+HCOO]−; t$_R$ (HPLC conditions f): 0.42 min.

Scheme A16: Preparation of (5-Acetyl-pyrrolo[2,3-d]pyrimidin-7-yl)-acetic acid trifluoroacetate

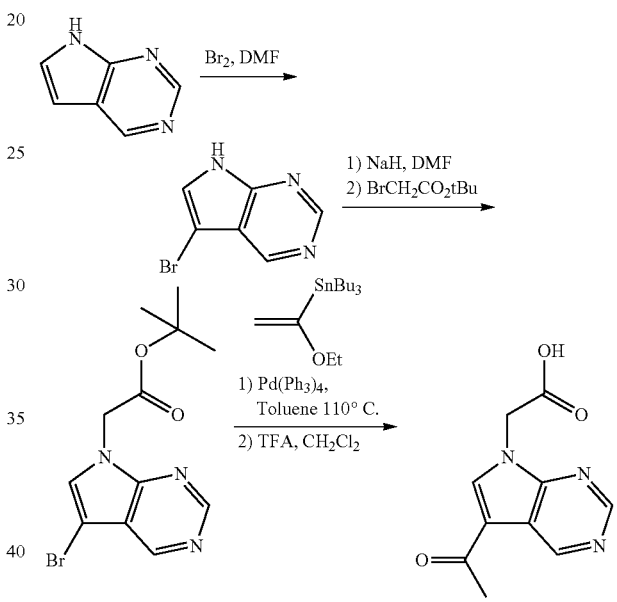

A. 5-Bromo-7H-pyrrolo[2,3-d]pyrimidine

A solution of bromine (0.086 mL, 1.68 mmol) in DMF (5.5 mL) was added to a solution of 7H-pyrrolo[2,3-d]pyrimidine (200 mg, 1.68 mmol) in DMF (5.5 mL). The reaction mixture was stirred at RT for 4 h and poured into a mixture of ice and water containing Na$_2$S$_2$O$_3$. A saturated aqueous solution of NaHCO$_3$ was added (until basic pH), the layers were separated and the aqueous layer was extracted twice with EtOAc. The combined organic extracts were washed with brine, dried (Na$_2$SO$_4$), filtered and concentrated. The material thus obtained was used without further purification in the next step. TLC, R$_f$ (CH$_2$Cl$_2$/MeOH 9:1)=0.45; MS (UPLC/MS): 198.1/200.1 [M+H]+, 196.1/198.1 [M−H]−.

B. (5-Bromo-pyrrolo[2,3-d]pyrimidin-7-yl)-acetic acid tert-butyl ester

To suspension of NaH (60% in mineral oil, 34 mg, 0.85 mmol) in DMF (1.5 mL) at 0° C. under nitrogen atmosphere was added a solution of 5-bromo-7H-pyrrolo[2,3-d]pyrimidine (140 mg, 0.71 mmol) in DMF (1.5 mL). The reaction mixture was stirred at 0° C. for 30 min and tert-butyl bromoacetate (104 µL, 0.71 mmol) was slowly added. The mixture was further stirred at RT for 30 min, then poured into water and extracted with EtOAc (×3). The combined organic extracts were washed with water, dried (Na$_2$SO$_4$), filtered and concentrated. MS (UPLC/MS): 312.3/314.2 [M+H]+.

C. (5-Acetyl-pyrrolo[2,3-d]pyrimidin-7-yl)-acetic acid tert-butyl ester

A solution of (5-bromo-pyrrolo[2,3-d]pyrimidin-7-yl)-acetic acid tert-butyl ester (220 mg, 0.71 mmol), tri-butyl(1-ethoxyvinyl)tin (285 µL, 0.85 mmol) and tetrakis(triphenylphosphine) palladium (16.28 mg, 14.1 µmol) in toluene (7 mL) was heated at 110° C. for 72 h under argon atmosphere. The mixture was allowed to cool to RT, poured into water and extracted with EtOAc (×2). The combined organic layers were dried (Na$_2$SO$_4$), filtered and concentrated. The crude residue was purified by flash column chromatography on silica gel (CH$_2$Cl$_2$ to CH$_2$Cl$_2$/MeOH 94:6). TLC, Rf (CH$_2$Cl$_2$/MeOH 9:1)=0.54; MS (UPLC/MS): 276.3 [M+H]+, 320.4 [M+HCOO]−; t$_R$ (HPLC conditions f): 1.40 min.

D. (5-Acetyl-pyrrolo[2,3-d]pyrimidin-7-yl)-acetic acid

A solution of (5-acetyl-pyrrolo[2,3-d]pyrimidin-7-yl)-acetic acid tert-butyl ester (146 mg, 0.53 mmol) and TFA (0.814 mL, 10.62 mmol) in CH$_2$Cl$_2$ (2.5 mL) was stirred at RT for 24 h. Solvents were removed under reduced pressure and the material thus obtained was used without further purification in the next step. 1H-NMR (400 MHz, DMSO): δ (ppm): 9.45 (s, 1H), 9.0 (s, 1H), 8.68 (s, 1H), 7.66-7.56 (m, 2H), 5.16 (s, 2H), 2.53 (s, 3H).

3-Acetyl-1-carboxymethyl-1H-indazole-6-carboxylic acid benzyl ester

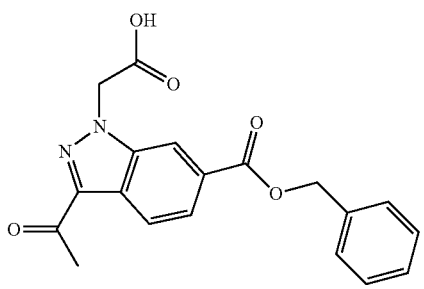 [SMILES: CC(=O)c1nn(CC(=O)O)c2cc(C(=O)OCc3ccccc3)ccc12]

was prepared using similar protocols as described in Scheme A16 Step C and D from 3-bromo-1-tert-butoxycarbonylmethyl-1H-indazole-6-carboxylic acid benzyl ester. MS (UPLC/MS): 553.4 [M+H]+, 351.4 [M−H]−, 703.6 [2M−H]−; t$_R$ (HPLC conditions f): 2.10 min.

3-Bromo-1-tert-butoxycarbonylmethyl-1H-indazole-6-carboxylic acid benzyl ester was prepared using similar protocol as described in Scheme A20 Step C from 3-bromo-1H-indazole-6-carboxylic acid benzyl ester. MS (UPLC/MS): 445.4/447.3 [M+H]+; t$_R$ (UPLC conditions m): 1.45 min.

3-Bromo-1H-indazole-6-carboxylic acid benzyl ester

A solution of 3-bromo-indazole-1,6-dicarboxylic acid 6-benzyl ester 1-tert-butyl ester (2.05 g, 4.75 mmol) and TFA (3.66 mL, 47.5 mmol) in CH$_2$Cl$_2$ (30 mL) was stirred at RT for 16 h. A saturated aqueous solution of NaHCO$_3$ was added, the layers were separated and the aqueous layer was extracted with CH$_2$Cl$_2$ (×3). The combined organic extracts were dried (Na$_2$SO$_4$), filtered and concentrated and the material thus obtained was used without further purification in the next step. MS (UPLC/MS): 331.2/333.2 [M+H]+, 329.3/331.2 [M−H]−; t$_R$ (UPLC conditions m): 1.18 min.

3-Bromo-indazole-1,6-dicarboxylic acid 6-benzyl ester 1-tert-butyl ester

A solution containing 3-bromo-indazole-1,6-dicarboxylic acid 1-tert-butyl ester (1.80 g, 5.28 mmol), benzylbromide (0.753 mL, 6.33 mmol), Cs$_2$CO$_3$ (1.89 g, 5.80 mmol) and sodium iodide (0.095 g, 0.633 mmol) in DMF (30 mL) was stirred 16 h at RT. The mixture was diluted with water and extracted with EtOAc (×3). The combined organic extracts were dried (Na$_2$SO$_4$), filtered and concentrated in vacuo. The residue was purified by flash column chromatography on silica gel (EtOAc/c-hexane 1:4). MS (UPLC/MS): 431.2/433.2 [M+H]+; t$_R$ (UPLC conditions f): 2.77 min.

3-Bromo-indazole-1,6-dicarboxylic acid 1-tert-butyl ester

A solution containing 3-bromo-1H-indazole-6-carboxylic acid (1.40 g, 5.81 mmol), triethylamine (0.89 ml, 6.39 mmol), DMAP (0.071 g, 0.58 mmol) and (Boc)$_2$O (1.90 g, 8.71 mmol) in CH$_2$Cl$_2$ (60 mL) was stirred 16 h at 25° C. Volatils were removed under reduced pressure, water and Et$_2$O were added. The aqueous layer was acidified by addition of KHSO$_4$ (10% in water) and extracted with EtOAc (×3). The combined organic extracts were dried (Na$_2$SO$_4$), filtered and concentrated in vacuo. The material thus obtained was used without further purification in the next step. MS (UPLC/MS): 441.2/443.2 [M+H]+.

3-Bromo-1H-indazole-6-carboxylic acid

Bromine (0.385 mL, 7.48 mmol) was added dropwise to a solution of 1H-indazole-6-carboxylic acid (1 g, 5.98 mmol) in acetic acid (30 mL) and the reaction mixture was stirred for 16 h at 25° C. in the dark. The reaction was quenched by addition of a saturated aqueous solution of Na$_2$SO$_3$ (12 mL) and brine (25 mL) and extracted with EtOAc (×3). The combined organic extracts were washed with brine, dried (Na$_2$SO$_4$), filtered and concentrated. The material thus obtained was used without further purification in the next step. MS (UPLC/MS): 239.1/241.1 [M−H]−, 481.3/483.3 [2M−H]−; t$_R$ (UPLC conditions f): 1.59 min.

Scheme A17: (3-Acetyl-6-amino-pyrrolo[2,3-b]pyridin-1-yl)-acetic acid

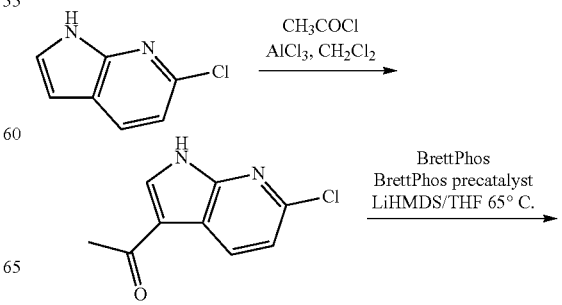

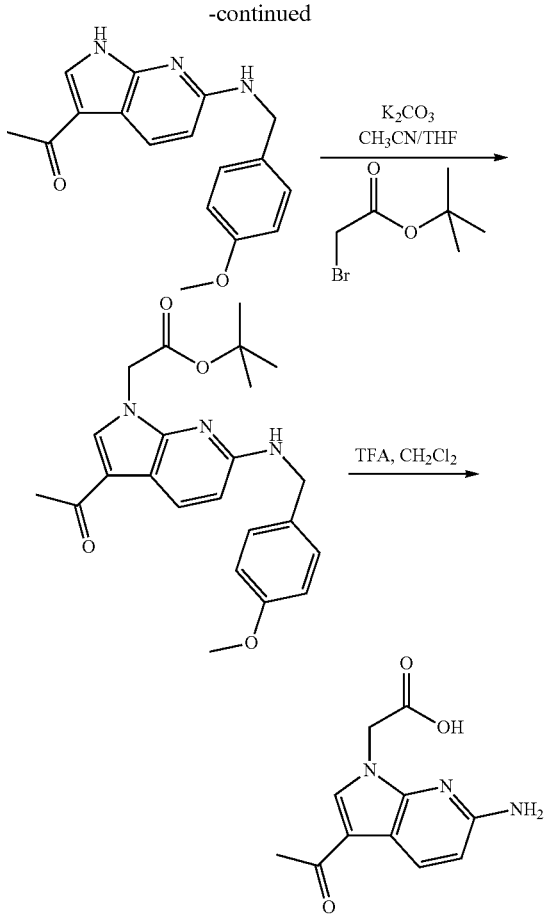

A. 1-(6-Chloro-1H-pyrrolo[2,3-b]pyridin-3-yl)-ethanone

6-Chloro-7-azaindole (1 g, 6.55 mmol) was added to a suspension of AlCl₃ (4.37 g, 32.8 mmol) in CH₂Cl₂ (150 mL) under nitrogen atmosphere. The mixture was stirred at RT for 30 min, and acetyl chloride (2.34 mL, 32.8 mmol) was added dropwise. The resulting mixture was further stirred at RT for 2 h. After completion, MeOH (40 mL) was added cautiously and volatils were removed under reduced pressure. The residue was diluted in CH₂Cl₂ and neutralized by addition of a saturated aqueous solution of NaHCO₃. The layers were separated and the organic extracts were dried (Na₂SO₄), filtered and concentrated. The crude residue was purified twice by flash column chromatography on silica gel (CH₂Cl₂ to CH₂Cl₂/MeOH 95-5). TLC, R$_f$ (CH₂Cl₂/MeOH 9:1)=0.5; MS (UPLC/MS): 195.1/197.1 [M+H]+, 193.1/195.1 [M−H]−; t$_R$ (HPLC conditions f): 1.54 min.

B. 1-[6-(4-Methoxy-benzylamino)-1H-pyrrolo[2,3-b]pyridin-3-yl]-ethanone

The reaction was performed according to the protocol described in *Org. Lett.,* 2010, 12(20), 4438-4441. A vial containing 1-(6-chloro-1H-pyrrolo[2,3-b]pyridin-3-yl)-ethanone (100 mg, 0.49 mmol), BrettPhos (2.62 mg, 4.88 μmol) and BrettPhos precatalyst (3.9 mg, 4.88 μmol) and a magnetic stir bar was sealed with a teflon screw-cap, evacuated and backfilled with argon. A balloon of argon was placed on top of the vial, to allow a pressure balance and LiHMDS (1 M in THF, 1172 μL, 1.17 mmol) was added, followed by 4-methoxybenzylamine (76 μL, 0.59 mmol). The reaction mixture was stirred and heated at 65° C. for 22 h, then allowed to cool to RT, quenched by the addition of 1 M HCl (1 mL) diluted with EtOAc and poured into a saturated aqueous solution of NaHCO₃. After extracting twice with EtOAc, the combined organic layers were washed with brine, dried (Na₂SO₄), filtered and concentrated. The crude was purified by flash column chromatography on silica gel (c-hexane to EtOAc). TLC, R$_f$ (EtOAc)=0.75; MS (UPLC/MS): 296.2 [M+H]+, 591.3 [2M+H]+, 613.2 [2M+Na]+; t$_R$ (HPLC conditions f): 1.5 min.

C. [3-Acetyl-6-(4-methoxy-benzylamino)-pyrrolo[2,3-b]pyridin-1-yl]-acetic acid tert-butyl ester Tert-butyl bromoacetate (27 μL, 0.18 mmol) was added to a suspension of 1-[6-(4-methoxy-benzylamino)-1H-pyrrolo[2,3-b]pyridin-3-yl]-ethanone (0.17 mmol) and potassium carbonate (27.5 mg, 0.20 mmol) in CH₃CN (0.33 mL) and THF (0.33 mL). The reaction mixture was stirred at RT for 7 h. Potassium carbonate (27.5 mg, 0.20 mmol) and tert-butyl bromoacetate (27 μL, 0.18 mmol) were added again and stirring was continued overnight, this operation was repeated the next day. The suspension was filtered, the filtrate concentrated under reduced pressure and the crude residue was purified by flash column chromatography on silica gel (CH₂Cl₂ to CH₂Cl₂/MeOH 98:2). TLC, R$_f$ (CH₂Cl₂/MeOH 9:1)=0.9; MS (UPLC/MS): 410.2 [M+H]+, 819.4 [2M+H]+, 841.3 [2M+Na]+, 454.1 [M+HCOO]−; t$_R$ (HPLC conditions f): 2.30 min.

D. (3-Acetyl-6-amino-pyrrolo[2,3-b]pyridin-1-yl)-acetic acid trifluoroacetate A solution of [3-acetyl-6-(4-methoxy-benzylamino)-pyrrolo[2,3-b]pyridin-1-yl]-acetic acid tert-butyl ester (51 mg, 0.125 mmol) and TFA (191 μL, 2.49 mmol) in CH₂Cl₂ (0.6 mL) was stirred at RT for 24 h. Volatils were removed under reduced pressure and the brown solid thus obtained was used without further purification in the next step. MS (UPLC/MS): 234.1 [M+H]+, 232.1 [M−H]−. 1H-NMR (400 MHz, DMSO): δ (ppm): 8.08 (d, 1H), 8.02 (s, 1H), 6.83 (m, 2H), 6.44 (d, 1H), 4.90 (s, 2H), 2.38 (s, 3H).

Scheme A18: Preparation of (3-acetyl-5-methoxy-indol-1-yl)-acetic acid

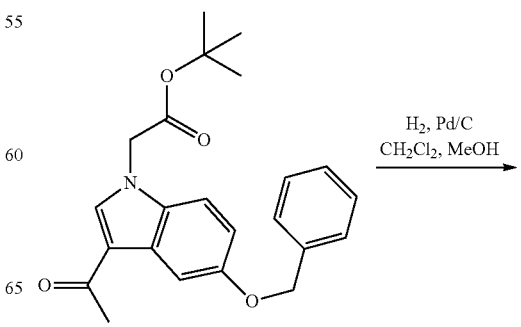

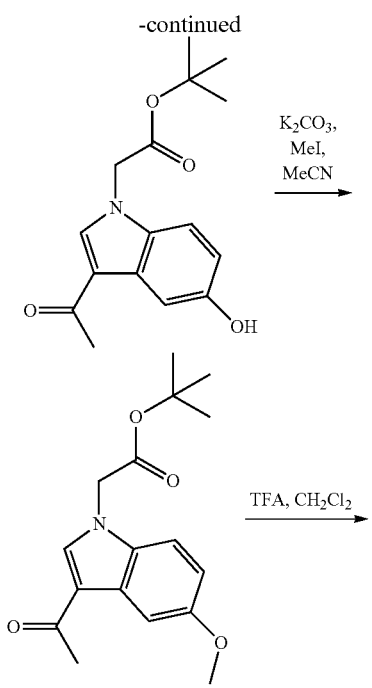

A. (3-Acetyl-5-hydroxy-indol-1-yl)-acetic acid tert-butyl ester

To a solution of (3-acetyl-5-benzyloxy-indol-1-yl)-acetic acid tert-butyl ester (MS: 380.0 [M+H]+; $t_R$ (HPLC conditions c): 5.72 min; prepared from 5-benzyloxy-1H-indole [1215-59-4] in a similar manner as described in Scheme A13 (step A and B)) (3.3 g, 8.70 mmol) in $CH_2Cl_2$/MeOH (80 mL) was added Pd/C (0.093 g, 0.870 mmol). The reaction mixture was stirred at RT for 5 h under $H_2$ atmosphere. The reaction mixture was filtered over a pad of Celite and washed with $CH_2Cl_2$ and MeOH. Volatiles were evaporated, and the crude mixture was purified by flash chromatography on silica gel (gradient c-hexane/EtOAc 2:1 to 100% EtOAc). TLC, $R_f$ (c-hexane/EtOAc 1:1)=0.35; MS: 312.0 [M+Na]+; $t_R$ (HPLC conditions c): 4.27 min.

B. (3-Acetyl-5-methoxy-indol-1-yl)-acetic acid tert-butyl ester

To a solution of (3-acetyl-5-hydroxy-indol-1-yl)-acetic acid tert-butyl ester (500 mg, 1.73 mmol) in $CH_3CN$ (15 mL) was added $K_2CO_3$ (358 mg, 2.59 mmol) and iodomethane (0.162 mL, 2.59 mmol). The reaction mixture was stirred at 50° C. overnight. Additional $K_2CO_3$ (716 mg, 5.18 mmol) and iodomethane (0.324 mL, 5.18 mmol) were added and heating was continued for an additional 2 days. Volatiles were evaporated, the reaction mixture was taken up in water and extracted twice with AcOEt. The combined organic phases were dried (Phase separator) and evaporated to give the title compound. MS (LC/MS): 304.0 [M+H]+, 629.0 [2M+Na]+; $t_R$ (HPLC conditions c): 4.92 min.

C. (3-Acetyl-5-methoxy-indol-1-yl)-acetic acid

To (3-acetyl-5-methoxy-indol-1-yl)-acetic acid tert-butyl ester (520 mg, 1.71 mmol) in $CH_2Cl_2$ (15 mL) was added TFA (1.32 mL, 17.1 mmol). The reaction mixture was stirred at RT overnight. Volatiles were evaporated, then the crude material was taken up in 5 mL of 1M aqueous NaOH solution and washed with $CH_2Cl_2$ which was discarded. The water phase was acidified to pH=1 by adding a 6M aqueous HCl solution, and then was extracted twice with AcOEt. The combined organic phases were dried (Phase separator) and evaporated to give the title compound. MS (LC/MS): 248.1 [M+H]+, 246.1 [M−H]−; $t_R$ (HPLC conditions c): 3.47 min.

Scheme A19: Preparation of (3-acetyl-5-trifluoromethoxy-indol-1-yl)-acetic acid

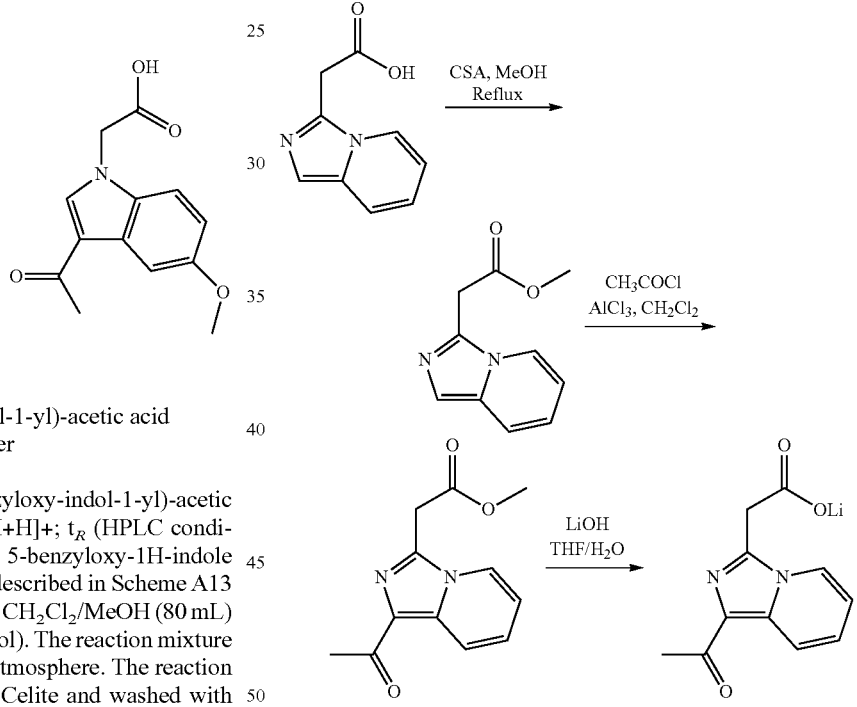

A. Imidazo[1,5-a]pyridin-3-yl-acetic acid methyl ester

A suspension of imidazo[1,5-a]pyridin-3-ylacetic acid (Ellanovalabs, 2 g, 11.35 mmol) and camphorsulfonic acid (2.9 g, 12.49 mmol) in MeOH (120 mL) was refluxed for 4 h. Then allowed to cool to RT and concentrated under reduced pressure. The crude residue was diluted in $CH_2Cl_2$ and the organic layer was washed with a saturated aqueous solution of $NaHCO_3$. The organics were dried ($Na_2SO_4$), filtered and concentrated. The material thus obtained was used in the next step without further purification: TLC, $R_f$ ($CH_2Cl_2$/MeOH 9:1)=0.55; MS (UPLC/MS): 191.1 [M+H]+; $t_R$ (HPLC conditions f): 0.4 min.

B. (1-Acetyl-imidazo[1,5-a]pyridin-3-yl)-acetic acid methyl ester

A solution of imidazo[1,5-a]pyridin-3-yl-acetic acid methyl ester (1.38 g, 7.26 mmol) in $CH_2Cl_2$ (50 mL) was added to a suspension of $AlCl_3$ (2.9 g, 21.77 mmol) in $CH_2Cl_2$ (115 mL) and the mixture was stirred at RT for 30 min under nitrogen atmosphere. Acetyl chloride (1.55 mL, 21.77 mmol) was subsequently added dropwise and the mixture was further stirred overnight. $AlCl_3$ (1.94 g, 14.51 mmol) and 15 min later acetyl chloride (1.04 mL, 14.51 mmol) were added and stirring was continued overnight to complete the reaction. The reaction mixture was cooled with at 0° C. and carefully quenched by cautious addition of MeOH (35 mL). Solvents were evaporated under reduced pressure and the crude residue was purified by flash column chromatography on silica gel (eluent: $CH_2Cl_2$ to $CH_2Cl_2$/MeOH 94:6). TLC, $R_f$ ($CH_2Cl_2$/MeOH 9:1)=0.60; MS (UPLC/MS): 233.1 [M+H]+, 255.1 [M+Na]+, 487.1 [2M+Na]+; $t_R$ (HPLC conditions f): 1.27 min.

C. Lithium (1-acetyl-imidazo[1,5-a]pyridin-3-yl)-acetate

To a solution of (1-acetyl-imidazo[1,5-a]pyridin-3-yl)-acetic acid methyl ester (1.12 g, 4.82 mmol) in THF (15 mL) and water (7.5 mL) was added $LiOH.H_2O$ (202 mg, 4.82 mmol). The reaction was stirred at RT for 5.5 h until completion of the reaction. The mixture was concentrated under reduced pressure and the material thus obtained was used in the next step without further purification: MS (UPLC/MS): 219.2 [M+H]+, 241.2 [M+Na]+, 217.2 [M−H]−; $t_R$ (HPLC conditions f): 1.03 min.

Scheme A20: Preparation of (3-Acetyl-5-methyl-pyrazolo[3,4-c]pyridin-1-yl)-acetic acid trifluoroacetate

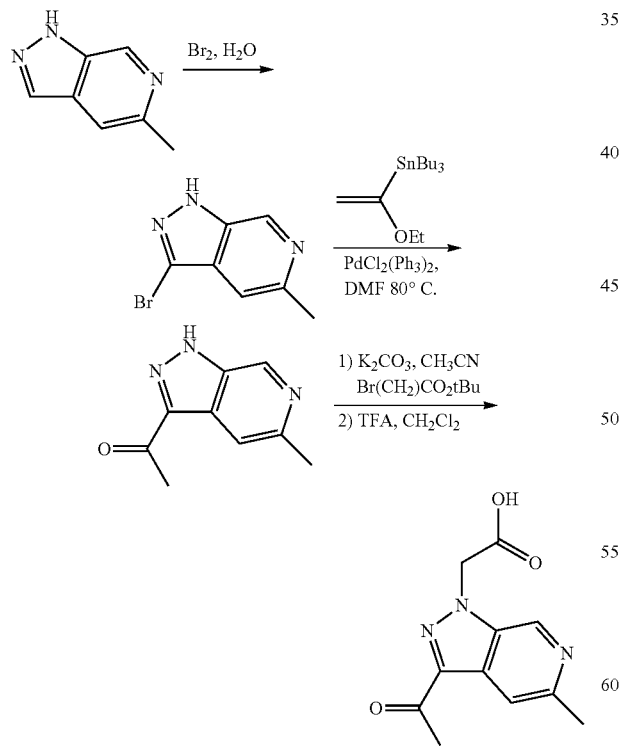

A. 3-Bromo-5-methyl-1H-pyrazolo[3,4-c]pyridine

5-Methyl-1H-pyrazolo[3,4-c]pyridine (2 g, 15.02 mmol) and bromine (0.774 mL, 15.02 mmol) in water (71.5 mL) were stirred at RT for 1 h. The reaction mixture was neutralized with NaOH (20% in water), the precipitate was filtered, washed with water and dried under high vacuum. Yellow powder, MS (UPLC/MS): 212/214 [M+H]+, 210/212 [M−H]−; $t_R$ (HPLC conditions f): 0.74 min.

B. 1-(5-Methyl-1H-pyrazolo[3,4-c]pyridin-3-yl)-ethanone

A solution of 3-bromo-5-methyl-1H-pyrazolo[3,4-c]pyridine (2.13 g, 10.04 mmol), tri-butyl(1-ethoxyvinyl)tin (6.78 mL, 20.09 mmol) and $PdCl_2(PPh_3)_2$ (0.705 mg, 1 mmol) in DMF (12.6 mL) was heated at 80° C. overnight under argon atmosphere. Then concentrated under reduced pressure and diluted with EtOAc. HCl (2N) was added, the layers were separated and the aqueous layer was basified by addition of $NaHCO_3$ (1N in water) and extracted with EtOAc (3×). The combined organic extracts were dried ($Na_2SO_4$), filtered and concentrated. The yellow oil thus obtained was used without further purification in the next step. TLC, Rf (c-hexane/EtOAC 1:1)=0.05; MS (UPLC/MS): 176 [M+H]+, 174 [M−H]−.

C. (3-Acetyl-5-methyl-pyrazolo[3,4-c]pyridin-1-yl)-acetic acid tert-butyl ester To a solution of 1-(5-methyl-1H-pyrazolo[3,4-c]pyridin-3-yl)-ethanone (1 g, 5.71 mmol) in $CH_3CN$ (30 mL) were added potassium carbonate (1.81 g, 13.13 mmol) and tert-butyl bromoacetate (0.927 mL, 6.28 mmol). The reaction mixture was stirred at reflux for 1 h, then poured into water and extracted with EtOAc (×3). The combined organic extracts were dried ($Na_2SO_4$), filtered and concentrated. The crude residue was purified by flash column chromatography on silica gel (c-hexane/EtOAc 1:0 to 3:2). TLC, Rf (c-hexane/EtOAC 1:1)=0.25; MS (UPLC/MS): 290 [M+H]+; $t_R$ (HPLC conditions f): 1.50 min.

D. (3-Acetyl-5-methyl-pyrazolo[3,4-c]pyridin-1-yl)-acetic acid

A solution of (3-acetyl-5-methyl-pyrazolo[3,4-c]pyridin-1-yl)-acetic acid tert-butyl ester (126 mg, 0.37 mmol) and TFA (0.171 mL, 2.22 mmol) in $CH_2Cl_2$ (5 mL) was stirred at RT for 24 h. Solvents were removed under reduced pressure, $Et_2O$ was added and the precipitate was filtered, washed with $Et_2O$ and dried under high vacuum. The material thus obtained was used without further purification in the next step. MS (UPLC/MS): 234 [M+H]+, 232 [M−H]−, 465 [2M−H]−; $t_R$ (HPLC conditions f): 0.53 min.

(3-Acetyl-pyrazolo[4,3-c]pyridin-1-yl)-acetic acid trifluoroacetate

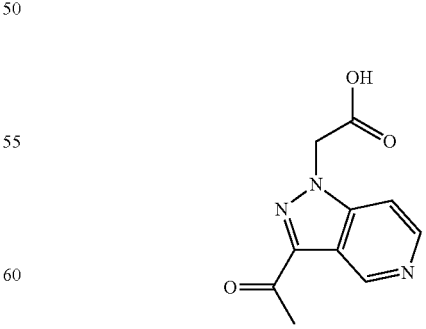

was prepared using similar procedures as described for the synthesis of (3-acetyl-5-methyl-pyrazolo[3,4-c]pyridin-1-yl)-acetic acid in Scheme A20 from 1-(1H-pyrazolo[4,3-c]pyridin-3-yl)-ethanone (Sphinx Scientific laboratory LLC, catalog number: PPY-CS0001). 1H-NMR (400 MHz, DMSO): δ (ppm): 9.57 (s, 1H), 8.52 (m, 1H), 8.08 (m, 1H), 5.56 (s, 2H), 2.69 (s, 3H).

(3-Acetyl-pyrazolo[3,4-c]pyridin-1-yl)-acetic acid trifluoroacetate

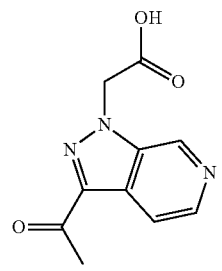 [SMILES: CC(=O)c1nn(CC(=O)O)c2cnccc12]

was prepared using similar procedures as described for the synthesis of (3-acetyl-5-methyl-pyrazolo[3,4-c]pyridin-1-yl)-acetic acid in Scheme A20 from 1-(1H-pyrazolo[3,4-c]pyridin-3-yl)-ethanone (Sphinx Scientific laboratory LLC, catalog number: PPY-1-CS01). MS (UPLC/MS): 220 [M+H]+; $t_R$ (HPLC conditions I): 0.69 min.

(3-Acetyl-pyrazolo[3,4-b]pyridin-1-yl)-acetic acid trifluoroacetate

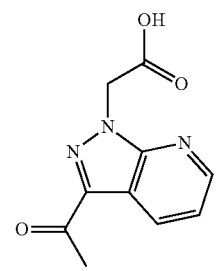 [SMILES: CC(=O)c1nn(CC(=O)O)c2ncccc12]

was prepared using similar procedures as described for the synthesis of (3-acetyl-5-methyl-pyrazolo[3,4-c]pyridin-1-yl)-acetic acid in Scheme A20 from 1-(1H-pyrazolo[3,4-b]pyridin-3-yl)-ethanone (Sphinx Scientific laboratory LLC, [889451-31-4], PYP-3-0043). MS (UPLC/MS): 220 [M+H]+, 218.2 [M−H]−; $t_R$ (HPLC conditions k): 2.51 min.

Scheme A21: Preparation of 2-(3-acetyl-6-(methoxycarbonyl)-1H-indazol-1-yl)acetic acid

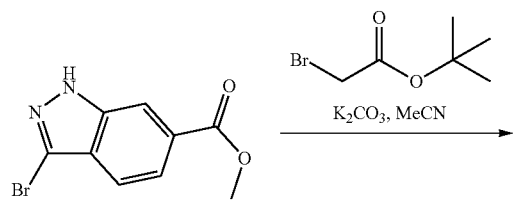

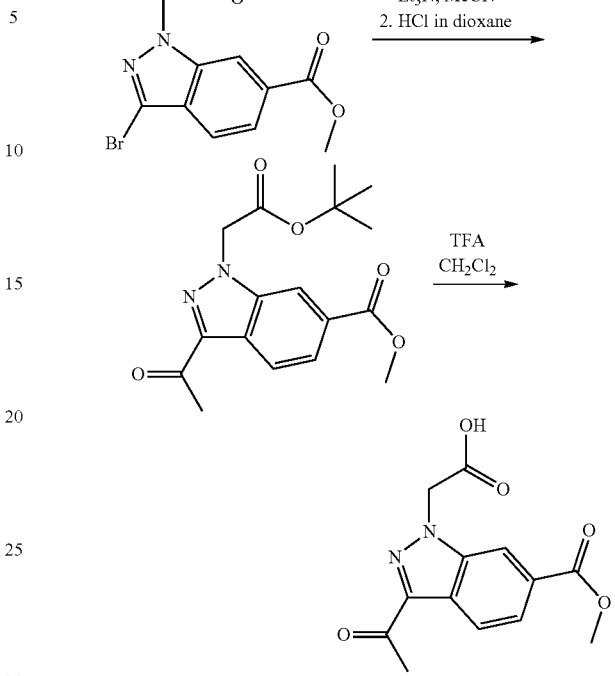

A. Methyl 3-bromo-1-(2-tert-butoxy-2-oxoethyl)-1H-indazole-6-carboxylate

The title compound was prepared from methyl 3-bromo-1H-indazole-6-carboxylate [192945-56-5] in a similar manner as described in step B of Scheme A13 for the preparation of (3-acetyl-5-trifluoromethoxy-indol-1-yl)acetic acid. MS: 392 [M+Na]+, 313 [M−tBu]+; $t_R$ (HPLC conditions k): 4.08 min.

B. Methyl 3-acetyl-1-(2-tert-butoxy-2-oxoethyl)-1H-indazole-6-carboxylate

A solution of methyl 3-bromo-1-(2-tert-butoxy-2-oxoethyl)-1H-indazole-6-carboxylate (1.00 g, 2.71 mmol), n-butyl vinylether (1.75 mL, 13.5 mmol), palladium acetate (61 mg, 0.27 mmol), triphenylphosphine (142 mg, 0.54 mmol) and triethylamine (0.45 mL, 3.25 mmol) in dry CH$_3$CN (10 mL) was heated at 100° C. under microwave irradiation for 7 h. Then, the mixture was further heated at 120° C. for 5 h under microwave irradiation. The solvent was evaporated, and the residue was then treated with 4N HCl/dioxane with stirring at RT for 16 h. Volatiles were evaporated and the residue was purified by preparative HPLC (Waters Sunfire, C18-ODB, 5 μm, 30×100 mm, flow: 40 mL/min, eluent: 5-100% CH$_3$CN/H$_2$O/20 min, 100% CH$_3$CN/2 min, CH$_3$CN and H$_2$O containing 0.1% TFA) to give after lyophilization of the pure fractions the title compound. MS (LC-MS): 333 [M+H]+, 355 [M+Na]; $t_R$ (HPLC conditions k): 3.83 min.

C. 2-(3-Acetyl-6-(methoxycarbonyl)-1H-indazol-1-yl)acetic acid

The title compound was prepared from methyl 3-acetyl-1-(2-tert-butoxy-2-oxoethyl)-1H-indazole-6-carboxylate in a similar manner as described in step C of Scheme A13 for the preparation of (3-acetyl-5-trifluoromethoxy-indol-1-yl)acetic acid. MS: 277 [M+H]+; $t_R$ (HPLC conditions k): 2.95 min.

Scheme A22: Preparation of 2-(3-(2-yydroxyacetyl)-1H-indazol-1-yl) acetic acid

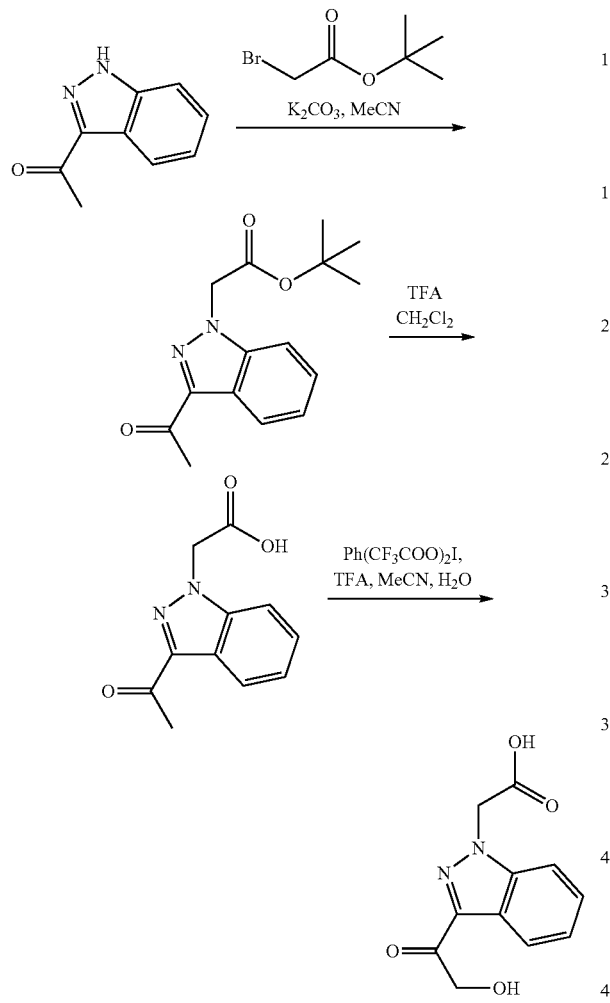

A. Tert-butyl 2-(3-acetyl-1H-indazol-1-yl)acetate

The title compound was prepared from 1-(1H-indazol-3-yl]ethanone [4498-72-0] in a similar manner as described in step B of Scheme A13 for the preparation of (3-acetyl-5-trifluoromethoxy-indol-1-yl)-acetic acid. MS: 275 [M+H]+; $t_R$ (HPLC conditions k): 3.78 min.

B. 2-(3-Acetyl-1H-indazol-1-yl)acetic acid

The title compound was prepared from tert-butyl 2-(3-acetyl-1H-indazol-1-yl)acetate in a similar manner as described in step C of Scheme A13 for the preparation of (3-acetyl-5-trifluoromethoxy-indol-1-yl)-acetic acid. MS: 219 [M+H]+; $t_R$ (HPLC conditions k): 2.78 min.

C. 2-(3-(2-Hydroxyacetyl)-1H-indazol-1-yl)acetic acid

The title compound was prepared in a similar manner as described by N. Yoshikawa et al., *J. Org. Chem.*, 2002, 67, 2556-2565: A mixture of 2-(3-acetyl-1H-indazol-1-yl)acetic acid (100 mg, 0.46 mmol), TFA (0.71 mL, 0.92 mmol) and bis-(trifluoroacetoxy)-iodobenzene (394 mg, 0.92 mmol) in $CH_3CN$ (4 mL) and water (0.6 mL) was heated to reflux (90° C.) for 16 h. Solvents were evaporated and the crude product was purified by preparative HPLC (Waters Sunfire, C18-ODB, 5 μm, 30×100 mm, flow: 40 mL/min, eluent: 5-100% $CH_3CN/H_2O/20$ min, 100% $CH_3CN/2$ min, $CH_3CN$ and $H_2O$ containing 0.1% TFA) to give after lyophilization of the purified fractions the title compound. MS (LC-MS): 233 [M+H]+; $t_R$ (HPLC conditions k): 2.41 min.

Scheme A23: Preparation of 2-(3-acetyl-5,6-dimethoxy-1H-indazol-1-yl) acetic acid

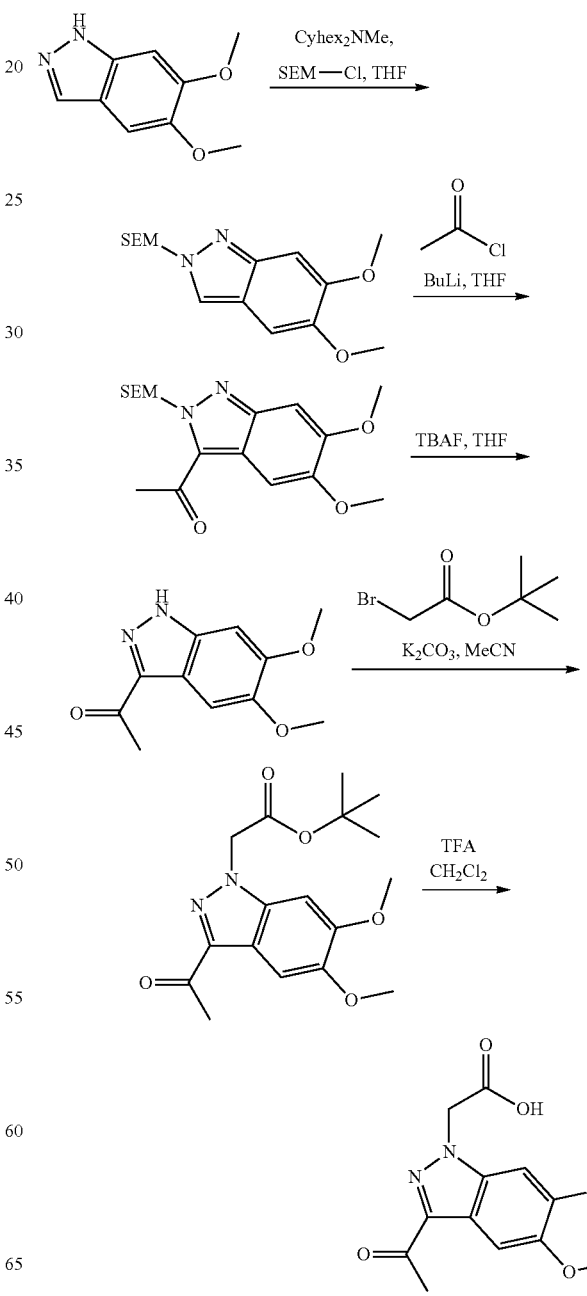

A. 5,6-Dimethoxy-2-((2-(trimethylsilyl)ethoxy)methyl)-2H-indazole

The title compound was prepared in a similar manner as described by G. Luo et al., *J. Org. Chem.* 2006, 71, 5392-5395: To a solution of 5,6-dimethoxyindazole [7746-30-7] (356 mg, 2.00 mmol) in THF (20 mL) was added dicyclohexylmethylamine (0.51 mL, 2.40 mmol) followed by SEM-Cl (0.43 mL, 2.40 mmol). The mixture was stirred at RT for 24 h, followed by dilution with EtOAc and quench with 1N aqueous NaOH solution. The layers were separated and the organic layer was washed with water and brine, then dried (Phase separator) and evaporated. The residue was purified by flash column chromatography on silica gel (c-hexane/EtOAc 4:1 to 1:1) to separate from the regioisomer 5,6-dimethoxy-1-((2-(trimethylsilyl)ethoxy)methyl)-1H-indazole and to provide the title compound. TLC, $R_f$ (c-hexane/EtOAc 1:1)= 0.37; MS (LC/MS): 309 [M+H; $t_R$ (HPLC conditions k): 3.70 min.

B. 1-(5,6-Dimethoxy-2-((2-(trimethylsilyl)ethoxy)methyl)-2H-indazol-3-yl)ethanone The title compound was prepared in a similar manner as described by G. Luo et al., *J. Org. Chem.* 2006, 71, 5392-5395: To a solution of 5,6-dimethoxy-2-((2-(trimethylsilyl)ethoxy)methyl)-2H-indazole (200 mg, 0.65 mmol) in THF (5 mL) at −78° C. was added dropwise a 2.5 M solution of n-BuLi in hexanes (0.29 mL, 0.71 mmol). The reaction mixture was stirred at −78° C. for 20 min. Acetyl chloride (0.07 mL, 0.97 mmol) was then added dropwise, and the mixture was stirred at RT for 16 h. Saturated aqueous NH$_4$Cl solution was added to the reaction mixture, followed by stirring for 30 min. The aqueous phase was extracted twice with EtOAc and the combined organics were washed with brine, dried (Phase separator) and evaporated to give the crude title compound which was used directly in the next step without further purification.

C. 1-(5,6-Dimethoxy-1H-indazol-3-yl)ethanone

The title compound was prepared in a similar manner as described by G. Luo et al., *J. Org. Chem.* 2006, 71, 5392-5395: To a solution of 1-(5,6-dimethoxy-2-((2-(trimethylsilyl)ethoxy)methyl)-2H-indazol-3-yl]ethanone (200 mg, 0.57 mmol) in THF (6 mL) was added a 1M solution in THF of TBAF (2.85 mL, 2.85 mmol), and the mixture was heated to reflux for 16 h. The reaction mixture was then diluted with EtOAc and successively washed with water and brine, then dried (Phase separator) and evaporated. The crude product was purified by preparative HPLC (Waters Sunfire, C18-ODB, 5 μm, 30×100 mm, flow: 40 mL/min, eluent: 5-100% CH$_3$CN/H$_2$O/20 min, 100% CH$_3$CN/2 min, CH$_3$CN and H$_2$O containing 0.1% TFA) to give after lyophilization of the purified fractions the title compound. MS (LC-MS): 221 [M+H]+; $t_R$ (HPLC conditions k): 2.61 min.

D. Tert-butyl 2-(3-acetyl-5,6-dimethoxy-1H-indazol-1-yl)acetate

The title compound was prepared from 1-(5,6-dimethoxy-1H-indazol-3-yl]ethanone in a similar manner as described in step B of Scheme A13 for the preparation of (3-acetyl-5-trifluoromethoxy-indol-1-yl)-acetic acid. MS: 335 [M+H]+; $t_R$ (HPLC conditions k): 3.58 min.

E. 2-(3-Acetyl-5,6-dimethoxy-1H-indazol-1-yl)acetic acid

The title compound was prepared from tert-butyl 2-(3-acetyl-5,6-dimethoxy-1H-indazol-1-yl)acetate in a similar manner as described in step C of Scheme A13 for the preparation of (3-acetyl-5-trifluoromethoxy-indol-1-yl)-acetic acid. MS: 279 [M+H]+; $t_R$ (HPLC conditions k): 2.73 min.

Scheme A24: Preparation of 2-(3-acetyl-5-(pyrimidin-2-ylmethoxy)-1H-indazol-1-yl)acetic acid

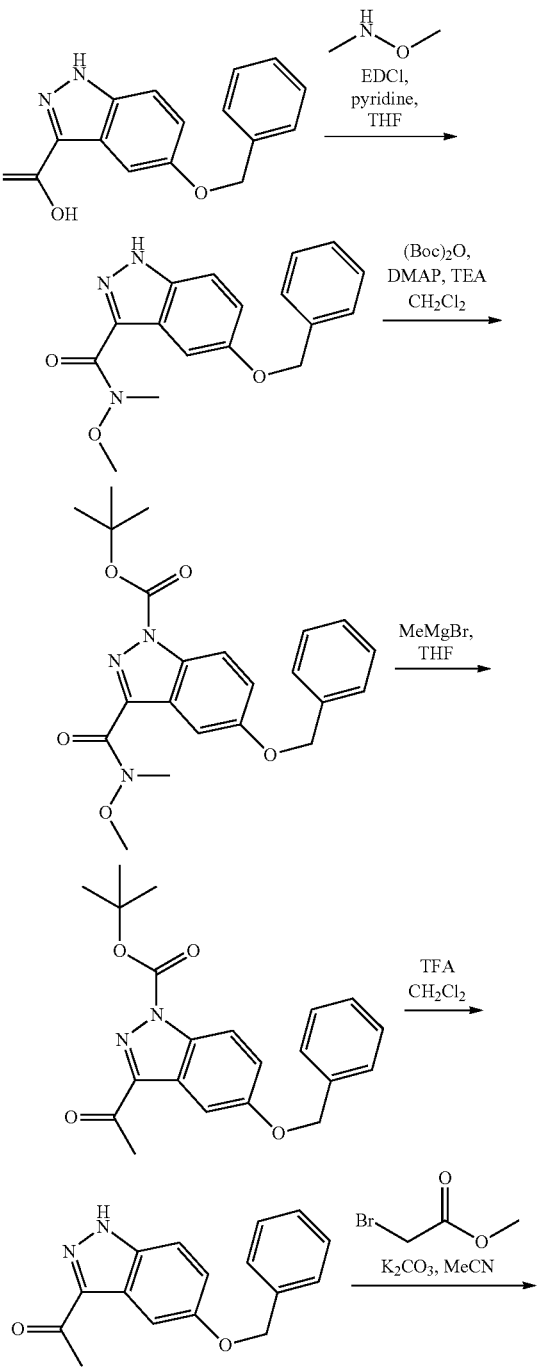

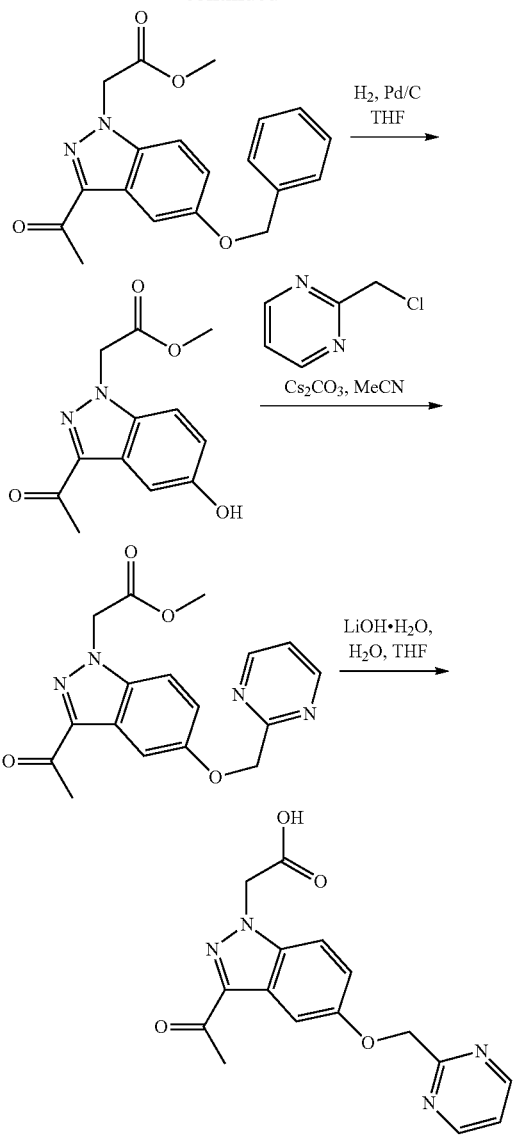

A. 5-(Benzyloxy)-N-methoxy-N-methyl-1H-indazole-3-carboxamide

The title compound was prepared in a similar manner as described by F. Crestey et al., *Tetrahedron* 2007, 63, 419-428: To 5-(benzyloxy)-1H-indazole-3-carboxylic acid [177941-16-1] (3.50 g, 13.1 mmol) in THF (70 mL) was added N,O-dimethylhydroxylamine (1.40 g, 14.4 mmol). The mixture was cooled to 0° C. before the addition of pyridine (2.30 mL, 28.7 mmol). The solution was stirred at 0° C. for 1.5 h, and then at RT for 1 h. Pyridine (2.10 mL, 26.1 mmol) and EDCl (5.00 g, 26.1 mmol) were added and the mixture was stirred at RT overnight. Water was added to the reaction mixture followed by extraction (×3) with $CH_2Cl_2$. The combined organics were washed with saturated aqueous $NaHCO_3$ solution, then dried (Phase separator) and evaporated to give the title compound. MS (LC/MS): 312.0 [M+H]+, 334.0 [M+Na]+, 645.1 [2M+Na]+, 310.0 [M−H]−; $t_R$ (HPLC conditions c): 4.44 min.

B. Tert-butyl 5-(benzyloxy)-3-(methoxy(methyl)carbamoyl)-1H-indazole-1-carboxylate The title compound was prepared in a similar manner as described by F. Crestey et al., *Tetrahedron* 2007, 63, 419-428: To a solution of 5-(benzyloxy)-N-methoxy-N-methyl-1H-indazole-3-carboxamide (3.40 g, 10.9 mmol) in $CH_2Cl_2$ (70 mL) was added DMAP (0.13 g, 1.09 mmol), TEA (1.67 mL, 12.0 mmol) and Boc-anhydride (3.80 mL, 16.4 mmol) at 0° C. The reaction mixture was stirred at 0° C. for 1 h and allowed to return to RT overnight. The reaction mixture was diluted with $CH_2Cl_2$ and washed with 50 mL of 0.1 M aqueous HCl solution and water. The organic phase was dried (Phase separator) and evaporated to give the title compound. MS (LC/MS): 434.0 [M+Na]+, 845.0 [2M+Na]+; $t_R$ (HPLC conditions c): 5.79 min.

C. Tert-butyl 3-acetyl-5-(benzyloxy)-1H-indazole-1-carboxylate and 1-(5-(benzyloxy)-1H-indazol-3-yl)ethanone The title compound was prepared in a similar manner as described by F. Crestey et al., *Tetrahedron* 2007, 63, 419-428: To tert-butyl 5-(benzyloxy)-3-(methoxy(methyl)carbamoyl)-1H-indazole-1-carboxylate (4.70 g, 11.4 mmol) in THF (60 mL), cooled to −78° C., was added a 3 M solution of MeMgBr (22.9 mL, 68.5 mmol) in $Et_2O$. The reaction mixture was stirred at −78° C. for 1 h. A saturated aqueous $NH_4Cl$ solution was added to the reaction mixture and temperature was allowed to raise to RT. The mixture was extracted twice with $CH_2Cl_2$, the combined organics were dried (Phase separator) and evaporated to give the title mixture which was used without purification in the next step.

D. 1-(5-(Benzyloxy)-1H-indazol-3-yl)ethanone

To the mixture of tert-butyl 3-acetyl-5-(benzyloxy)-1H-indazole-1-carboxylate and 1-(5-(benzyloxy)-1H-indazol-3-yl)ethanone (3.80 g, 10.4 mmol) in $CH_2Cl_2$ (50 mL) was added TFA (7.99 mL, 104 mmol). The reaction mixture was stirred at RT overnight. The reaction mixture was diluted with $CH_2Cl_2$ and washed with 100 mL of 2N aqueous NaOH solution. The basic phase was extracted twice with $CH_2Cl_2$, then the combined organic phases were dried (Phase separator) and evaporated to give the title compound. MS (LC/MS): 267.0 [M+H]+, 289.0 [M+Na]+, 265.1 [M−H]−; $t_R$ (HPLC conditions c): 4.71 min.

E. Methyl 2-(3-acetyl-5-(benzyloxy)-1H-indazol-1-yl)acetate

To 1-(5-(benzyloxy)-1H-indazol-3-yl)ethanone (3.50 g, 13.1 mmol) in $CH_3CN$ (100 mL) was added $K_2CO_3$ (4.54 g, 32.9 mmol) and methyl 2-bromoacetate (1.33 mL, 14.5 mmol). The reaction mixture was stirred at 90° C. for 90 min. The reaction mixture was filtered and the solid was washed with $CH_3CN$. Volatiles were evaporated and then the crude mixture was purified by flash column chromatography on silica gel (gradient: c-hexane/EtOAc 1:1 to 1:3). TLC, $R_f$ (c-hexane/EtOAc 1:3)=0.64; MS (LC/MS): 339.0 [M+H]+, 361.0 [M+Na]+; $t_R$ (HPLC conditions c): 5.09 min.

F. Methyl 2-(3-acetyl-5-hydroxy-1H-indazol-1-yl)acetate

To methyl 2-(3-acetyl-5-(benzyloxy)-1H-indazol-1-yl)acetate (3.70 g, 10.9 mmol) in THF (80 mL) was added Pd/C (10%, 400 mg). The reaction mixture was stirred at 50° C. overnight under a H₂ atmosphere. The reaction mixture was filtered over a pad of Celite and washed with CH₂Cl₂, then volatiles were evaporated to give the title compound. MS (LC/MS): 248.9 [M+H]+, 271.0 [M+Na]+; t_R (HPLC conditions c): 3.36 min.

G. Methyl 2-(3-acetyl-5-(pyrimidin-2-ylmethoxy)-1H-indazol-1-yl)acetate

To methyl 2-(3-acetyl-5-hydroxy-1H-indazol-1-yl)acetate (1.80 g, 7.25 mmol) in CH₃CN (75 mL) was added 2-(chloromethyl)pyrimidine hydrochloride salt (1.32 g, 7.98 mmol) and Cs₂CO₃ (5.91 g, 18.13 mmol). The reaction mixture was stirred at 70° C. for 2 h. The reaction mixture was filtered and washed with CH₃CN. Solvent was evaporated and the crude mixture was purified by flash column chromatography on silica gel (gradient: c-hexane/EtOAc 1:1 to 1:3). TLC, R_f (c-hexane/EtOAc 1:3)=0.35; MS (LC/MS): 340.9 [M+H]+, 363.0 [M+Na]+; t_R (HPLC conditions c): 3.64 min.

H. 2-(3-Acetyl-5-(pyrimidin-2-ylmethoxy)-1H-indazol-1-yl)acetic acid

To methyl 2-(3-acetyl-5-(pyrimidin-2-ylmethoxy)-1H-indazol-1-yl)acetate (1.93 g, 5.67 mmol) in THF (15 mL) and water (15 mL) was added LiOH.H₂O (0.25 g, 5.95 mmol). The reaction mixture was stirred at RT for 1.5 h. Volatiles were evaporated and the residue was freeze-dried overnight to give the title compound. MS (LC/MS): 327.0 [M+H]+, 325.1 [M+H]+; t_R (HPLC conditions c): 3.24 min.

(3-Acetyl-5-benzyloxy-indazol-1-yl)-acetic acid

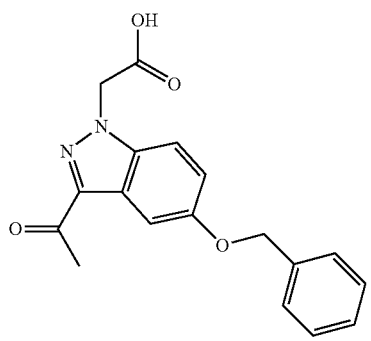 [SMILES: CC(=O)c1nn(CC(=O)O)c2ccc(OCc3ccccc3)cc12]

To a solution of (3-acetyl-5-benzyloxy-indazol-1-yl)-acetic acid methyl ester (prepared as described in Scheme A24, 1.50 g, 4.43 mmol) in MeOH (40 mL) was added a 10% aqueous solution of NaOH (5.32 mL, 13.30 mmol) and the resulting mixture was stirred at RT for 16 h. The mixture was concentrated, diluted in water and acidified to pH=2 with 6N HCl. The mixture was then extracted with EtOAc and the organic layer was dried (Na₂SO₄), filtered and concentrated. The product was used in the next step without further purification. MS (UPLC-MS): 325 [M+H]+; t_R (UPLC conditions m): 0.90 min.

Scheme A25: Preparation of (3-carbamaoyl-indazol-1-yl)-acetic acid

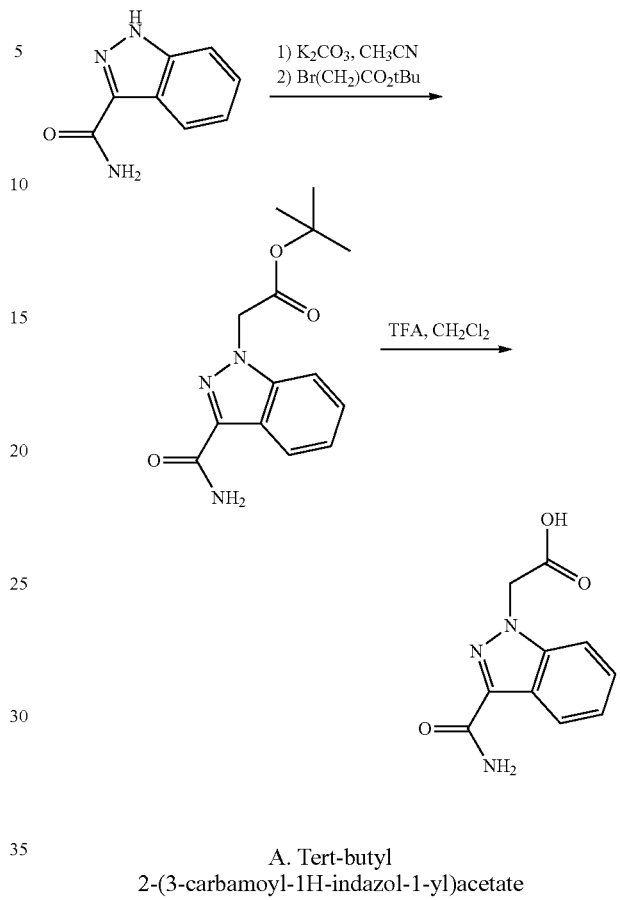

A. Tert-butyl 2-(3-carbamoyl-1H-indazol-1-yl)acetate

To a suspension of 1H-indazole-3-carboxamide [90004-04-9] (2.00 g, 12.4 mmol) and potassium carbonate (4.12 g, 29.8 mmol) in CH₃CN (60 mL) was added tert-butyl bromoacetate (2.20 mL, 14.9 mmol) dropwise at RT, and the resulting mixture was heated to reflux for 16 h. The mixture was then cooled to RT and filtered, the solid was washed with CH₃CN and the filtrate was concentrated under vacuum. The residual oil was used directly in the next reaction step without further purification. MS (LC/MS): 276.0 [M+H]+; t_R (HPLC conditions k): 3.22 min.

B. (3-Carbamoyl-indazol-1-yl)-acetic acid

To a solution of tert-butyl 2-(3-carbamoyl-1H-indazol-1-yl)acetate (3.42 g, 12.4 mmol) in CH₂Cl₂ (20 mL) was added TFA (10 mL, 130 mmol) and the resulting mixture was stirred at RT for 16 h. The reaction mixture was concentrated in vacuo, the residual solid was suspended in methanol and concentrated again in vacuo to give the title compound. MS (LC/MS): 220 [M+H]+; t_R (HPLC conditions k): 1.79 min.

Scheme A26: Preparation of 2-(3-carbamaoyl-1H-pyrazolo[3,4-c]pyridin-1-yl)acetic acid

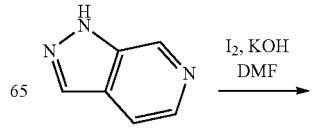

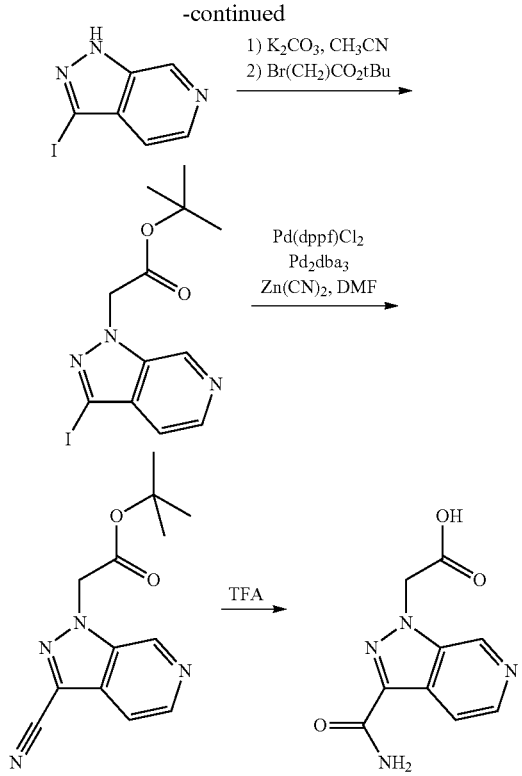

A. 3-Iodo-1H-pyrazolo[3,4-c]pyridine

To a solution of 1H-pyrazolo[3,4-c]pyridine [27]-47-6] (4.00 g, 33.6 mmol) in DMF (50 mL) were added iodine (12.8 g, 50.4 mmol) and potassium hydroxide (4.70 g, 84.0 mmol). The reaction mixture was stirred at RT for 16 h. The mixture was diluted with 10% sodium thiosulfate and water, then extracted (3×) with EtOAc. The combined organic extracts were washed with brine, then dried (Phase separator) and concentrated under vacuum. MS (LC/MS): 246.0 [M+H]+; $t_R$ (HPLC conditions k): 0.48 min.

B. Tert-butyl 2-(3-iodo-1H-pyrazolo[3,4-c]pyridin-1-yl)acetate

To a suspension of 3-iodo-1H-pyrazolo[3,4-c]pyridine (6.24 g, 22.9 mmol) and potassium carbonate (7.29 g, 52.7 mmol) in acetonitrile (50 mL) was added tert-butyl bromoacetate (4.06 mL, 27.5 mmol) dropwise at RT and the resulting mixture was heated to reflux for 2 h. The mixture was cooled to RT and filtered, the solid was washed with CH₃CN and the filtrate was concentrated under vacuum. The residual oil was purified by flash column chromatography on silica gel (gradient EtOAc/c-hexane 1:4, then 1:2, then 1:1). MS (LC/MS): 360.0 [M+H]+; $t_R$ (HPLC conditions k): 2.93 min.

C. Tert-butyl 2-(3-cyano-1H-pyrazolo[3,4-c]pyridin-1-yl)acetate

A mixture of tert-butyl 2-(3-iodo-1H-pyrazolo[3,4-c]pyridin-1-yl)acetate (3.76 g, 10.5 mmol), Zn(CN)₂ (1.35 g, 11.5 mmol), Pd(dppf)Cl₂ (855 mg, 1.05 mmol), Pd₂(dba)₃ (959 mg, 1.05 mmol), water (4 mL) and DMF (30 mL) was stirred at 100° C. for 16 h under argon. The reaction mixture was diluted with EtOAc and then was successively washed with water, sat. aq. NaHCO₃ (2×) and brine, dried (Phase separator) and concentrated under vacuum. The residual oil was purified by flash column chromatography on silica gel (EtOAc/c-hexane 1:1 then 100% EtOAc). MS (LC/MS): 259.0 [M+H]+; $t_R$ (HPLC conditions k): 3.10 min. Further elution of the column with CH₂Cl₂/MeOH 8:2 and subsequent purification by preparative HPLC (Macherey-Nagel Nucleosil 100-10 C18, 5 µm, 40×250 mm, flow: 40 mL/min, eluent: 5-100% CH₃CN/H₂O/20 min, 100% CH₃CN/2 min, CH₃CN and H₂O containing 0.1% TFA) afforded tert-butyl 2-(3-carbamoyl-1H-pyrazolo[3,4-c]pyridin-1-yl)acetate as a side-product. MS (LC/MS): 277.0 [M+H]+; $t_R$ (HPLC conditions k): 2.39 min.

D. 2-(3-Carbamoyl-1H-pyrazolo[3,4-c]pyridin-1-yl)acetic acid

A solution of tert-butyl 2-(3-cyano-1H-pyrazolo[3,4-c]pyridin-1-yl)acetate (663 mg, 2.40 mmol) in TFA (6 mL) was subjected to microwave irradiation at 140° C. for 90 min. The reaction mixture was concentrated in vacuo, the residual solid was suspended in MeOH and volatiles were removed again in vacuo. MS: 221.0 [M+H]+; $t_R$ (HPLC conditions k): 0.23 min.

From tert-butyl 2-(3-carbamoyl-1H-pyrazolo[3,4-c]pyridin-1-yl)acetate:

To a solution of tert-butyl 2-(3-carbamoyl-1H-pyrazolo[3,4-c]pyridin-1-yl)acetate (663 mg, 2.40 mmol) in CH₂Cl₂ (20 mL) was added TFA (10 mL, 130 mmol), and the resulting mixture was stirred at RT for 6 h. The reaction mixture was concentrated in vacuo, the residual solid was suspended in methanol and volatiles were removed again in vacuo to give the title compound.

(3-Carbamoyl-5-ethyl-pyrazolo[3,4-c]pyridin-1-yl)-acetic acid

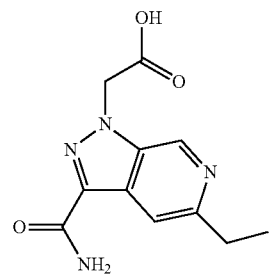 [SMILES: CCc1cc2c(C(N)=O)nn(CC(=O)O)c2cn1]

was prepared from 5-ethyl-1H-pyrazolo[3,4-c]pyridine by using the same procedures as for the preparation of 2-(3-carbamoyl-1H-pyrazolo[3,4-c]pyridin-1-yl)acetic acid (Scheme A26). MS (LC-MS): 249 [M+H]+, $t_R$ (HPLC conditions k): 0.49 min.

5-Ethyl-1H-pyrazolo[3,4-c]pyridine

Triethylaluminum (21.7 mL, 40.4 mmol, 25 wt % solution in toluene) was added to a vigorously stirred solution of 5-bromo-1H-pyrazolo[3,4-c]pyridine [929617-35-6] (4.00 g, 20.2 mmol) and Pd(PPh₃)₄ (1.17 g, 1.01 mmol) in THF (100 mL) under argon. The reaction mixture was stirred at 65° C. for 60 h. The mixture was cooled to RT and poured into sat. aq. NH₄Cl. The resulting suspension was filtered, the solid was washed with water and discarded. The filtrate and combined washings were extracted with EtOAc (3×). The combined organic extracts were washed with brine, then dried (Phase separator) and concentrated under reduced pressure. The residual oil was purified by flash column chromatography on silica gel (EtOAc/c-hexane 50:50, then 75:25, then 100:0). TLC, $R_f$(c-hexane/EtOAc 1:3)=0.22; MS (LC-MS): 148 [M+H]+, $t_R$ (HPLC conditions k): 0.71 min.

(3-Carbamoyl-7-methyl-pyrazolo[3,4-c]pyridin-1-yl)-acetic acid

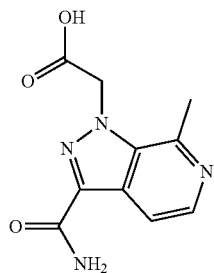 [SMILES: Cc1nccc2c(C(N)=O)nn(CC(=O)O)c12]

was prepared using the same procedure as for the preparation of 2-(3-carbamoyl-1H-pyrazolo[3,4-c]pyridin-1-yl)acetic acid starting from 7-methyl-1H-pyrazolo[3,4-c]pyridine (Scheme A26). MS (LC-MS): 235 [M+H]+, $t_R$ (HPLC conditions k): 0.6 min.

7-Methyl-1H-pyrazolo[3,4-c]pyridine

Trimethylaluminum (23.9 mL, 47.8 mmol, 2M sol. in toluene) was added to a vigorously stirred solution of 7-chloro-1H-pyrazolo[3,4-c]pyridine (3.67 g, 23.9 mmol) and Pd(PPh$_3$)$_4$ (1.38 g, 1.19 mmol) in THF (109 mL) under argon. The reaction mixture was stirred at 65° C. for 16 h. The mixture was cooled to RT and poured into sat. aq. NH$_4$Cl. The resulting suspension was filtered, the solid washed with water and discarded. The filtrate and the combined washings were extracted with EtOAc (3×). The combined organic extracts were washed with brine then dried (Phase separator) and concentrated under reduced pressure to give 7-methyl-1H-pyrazolo[3,4-c]pyridine as a solid. MS (LC-MS): 134 [M+H]+, $t_R$ (HPLC conditions k): 0.25 min.

7-Chloro-1H-pyrazolo[3,4-c]pyridine

A solution of 2-chloro-4-methylpyridin-3-amine [133627-45-9] (3.0 g, 21.0 mmol) in acetic acid (300 mL) was treated with a solution of sodium nitrite (1.45 g, 21.0 mmol) in water (2.5 mL). The reaction mixture was stirred at rt for 15 min then allowed to stand at ambient temperature for 24 h. An additional solution of sodium nitrite (500 mg, 7.25 mmol) in water (1 mL) was added to the mixture which was allowed to stand at rt for 3 h. Acetic acid was evaporated under reduced pressure and the residual aqueous solution was partitioned between EtOAc and sat. aq. NaHCO$_3$. The insoluble solid was filtered off (dried under vacuum; batch 1) and the organic filtrate was washed with water and brine, then dried (Phase separator) and concentrated under vacuum (batch 2). The two batches were combined to give 7-chloro-1H-pyrazolo[3,4-c]pyridine as a solid. MS (LC-MS): 153 [M+H]+, $t_R$ (HPLC conditions k): 0.9 min.

(3-Carbamoyl-5,7-dimethyl-pyrazolo[3,4-c]pyridin-1-yl)-acetic acid

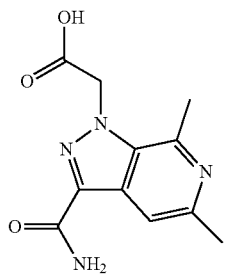 [SMILES: Cc1cc2c(C(N)=O)nn(CC(=O)O)c2c(C)n1]

was prepared from 5,7-dimethyl-1H-pyrazolo[3,4-c]pyridine by using the same procedures as described for the preparation of 2-(3-carbamoyl-1H-pyrazolo[3,4-c]pyridin-1-yl)acetic acid (Scheme A26). MS (LC-MS): 249 [M+H]+, $t_R$ (HPLC conditions c): 0.9 min.

5,7-Dimethyl-1H-pyrazolo[3,4-c]pyridine

To a vigorously stirred solution of 7-bromo-5-methyl-1H-pyrazolo[3,4-c]pyridine (3.65 g, 14.6 mmol) and Pd(PPh$_3$)$_4$ (845 mg, 0.73 mmol) in THF (65 mL) was added trimethylaluminum (14.6 mL, 29.3 mmol; 2 M sol. in toluene) under argon. The reaction mixture was stirred at 65° C. for 60 h, and then was cooled to RT and poured into a sat. aq. NH$_4$Cl solution. The resulting suspension was filtered, the solid was washed with water and discarded. The filtrate and the combined washings were extracted with EtOAc (3×). The combined organics were washed with brine, then dried (Phase separator) and concentrated under reduced pressure to give 5,7-dimethyl-1H-pyrazolo[3,4-c]pyridine as a solid. MS (LC-MS): 148 [M+H]+, $t_R$ (HPLC conditions k): 0.50 min.

7-Bromo-5-methyl-1H-pyrazolo[3,4-c]pyridine

A solution of 2-bromo-4,6-dimethylpyridin-3-amine [104829-98-3] (4.00 g, 19.9 mmol) in acetic acid (300 mL) was treated with a solution of sodium nitrite (1.37 g, 19.9 mmol) in water (2.5 mL). The reaction mixture was stirred at RT for 15 min and was then allowed to stand at ambient temperature for 24 h. An additional solution of sodium nitrite (500 mg, 7.25 mmol) in water (1 mL) was added to the mixture which was allowed to stand at RT for 16 h. Acetic acid was evaporated under reduced pressure and the residual aqueous solution was partitioned between EtOAc and sat. aq. NaHCO$_3$. The precipitate was filtered off, washed and discarded. The combined filtrates were washed with water and brine, then dried (Phase separator) and concentrated under vacuum to give 7-bromo-5-methyl-1H-pyrazolo[3,4-c]pyridine as a solid. MS (LC-MS): 212 [M+H]+, $t_R$ (HPLC conditions k): 2.49 min.

(3-Carbamoyl-5-cyclopropyl-1H-pyrazolo[3,4-c]pyridin-1-yl)acetic acid

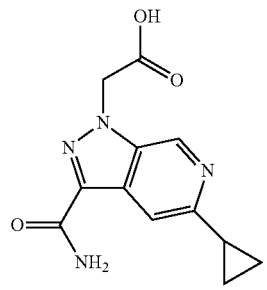 [SMILES: NC(=O)c1nn(CC(=O)O)c2cnc(C3CC3)cc12]

was prepared by using the same procedure as described for the preparation of 2-(3-carbamoyl-1H-pyrazolo[3,4-c]pyridin-1-yl)acetic acid and by starting from 5-cyclopropyl-1H-pyrazolo[3,4-c]pyridine (Scheme A26). MS (LC-MS): 261 [M+H]+, $t_R$ (HPLC conditions c): 1.84 min.

5-Cyclopropyl-1H-pyrazolo[3,4-c]pyridine

A solution of 6-cyclopropyl-4-methylpyridin-3-amine (130 mg, 0.88 mmol) in AcOH (10 mL) was treated with a solution of sodium nitrite (61 mg, 0.88 mmol) in water (0.5 mL). The reaction mixture was stirred at RT for 15 min and then was allowed to stand at RT for 24 h. AcOH was evaporated under reduced pressure and the residual aqueous solution was partitioned between EtOAc and sat. aq. NaHCO$_3$. The organic solution was washed with water and brine, then dried (Phase separator) and concentrated under. MS (LC-MS): 160 [M+H]+, $t_R$ (HPLC conditions c): 2.07 min.

6-Cyclopropyl-4-methylpyridin-3-amine

To a solution of 2-cyclopropyl-4-methyl-5-nitropyridine (201 mg, 0.96 mmol) in MeOH (5 mL) were added 3N aqueous HCl (9.6 mL, 28.8 mmol) and Zn powder (376 mg, 5.75 mmol). The mixture was stirred 18 h at RT. The solution was neutralized with a sat. aq. NaHCO$_3$ solution and extracted with CH$_2$Cl$_2$ (3×). The combined organics were dried (Phase Separator) and concentrated under reduced pressure. MS (LC-MS): 149 [M+H]+, $t_R$ (HPLC conditions c): 2.22 min.

2-Cyclopropyl-4-methyl-5-nitropyridine

Potassium cyclopropyltrifluoroborate (857 mg, 5.79 mmol), 2-chloro-4-methyl-5-nitropyridine (500 mg, 2.90 mmol), Pd(OAc)$_2$ (26 mg, 0.12 mmol), Cs$_2$CO$_3$ (2.83 g, 8.69 mmol), and n-butyl-di-adamantylphosphine (62 mg, 0.17 mmol) were charged into a capped vial. The vial was purged with argon and then sealed with a septum cap. Toluene/H$_2$O 10:1 (11 mL) was added by syringe and the mixture was heated at 100° C. for 16 h. More potassium cyclopropyltrifluoroborate (857 mg, 5.79 mmol) was added to the mixture which was further heated at 100° C. for 72 h. The mixture was diluted with CH$_2$Cl$_2$ and filtered through a pad of Celite. The filtrate was dried (Phase separator) and concentrated under reduced pressure. The residue was purified by preparative HPLC (Waters Sunfire, C18-ODB, 5 µm, 30×100 mm, flow: 40 mL/min, eluent: 5-100% CH$_3$CN/H$_2$O/30 min, 100% CH$_3$CN/3 min, CH$_3$CN and H$_2$O containing 0.1% TFA). MS (LC-MS): 179 [M+H]+, $t_R$ (HPLC conditions c): 4.26 min.

(3-Carbamoyl-5-(trifluoromethyl)-1H-pyrazolo[3,4-c]pyridin-1-yl)acetic acid

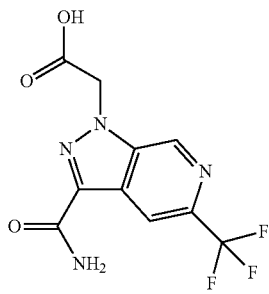 [SMILES: NC(=O)c1nn(CC(=O)O)c2cnc(C(F)(F)F)cc12]

was prepared by using the same procedure as described for the preparation of 2-(3-carbamoyl-1H-pyrazolo[3,4-c]pyridin-1-yl)acetic acid and by starting from 5-trifluoromethyl-1H-pyrazolo[3,4-c]pyridine (Scheme A26). MS (LC-MS): 289 [M+H]+, $t_R$ (HPLC conditions c): 2.93 min.

5-Trifluoromethyl-1H-pyrazolo[3,4-c]pyridine

A solution of 4-methyl-6-(trifluoromethyl)pyridin-3-amine [944317-54-8] (1.00 g, 5.68 mmol) in acetic acid (75 mL) was treated with a solution of sodium nitrite (392 mg, 5.68 mmol) in water (1 mL). The reaction mixture was stirred at RT for 15 min and then was allowed to stand at ambient temperature for 48 h. Acetic acid was evaporated under reduced pressure and the residual aqueous solution was partitioned between EtOAc and sat. aq. NaHCO$_3$. The organic solution was washed with water and brine, then dried (Phase separator) and concentrated under vacuum. MS (LC-MS): 188 [M+H]+, $t_R$ (HPLC conditions k): 2.49 min.

(3-Carbamoyl-5-methoxy-pyrazolo[3,4-c]pyridin-1-yl)-acetic acid

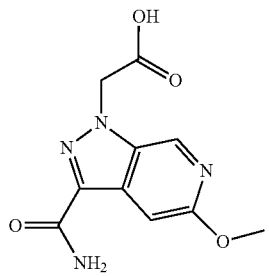

was prepared from 5-methoxy-1H-pyrazolo[3,4-c]pyridine [76006-07-0] by using the same procedures as described for the preparation of 2-(3-carbamoyl-1H-pyrazolo[3,4-c]pyridin-1-yl)acetic acid (Scheme A26). MS (LC-MS): 251 [M+H]+, $t_R$ (HPLC conditions k): 0.62 min.

Scheme A27: Preparation of (3-carbamoyl-5-methyl-pyrazolo[3,4-c]pyridin-1-yl)-acetic acid

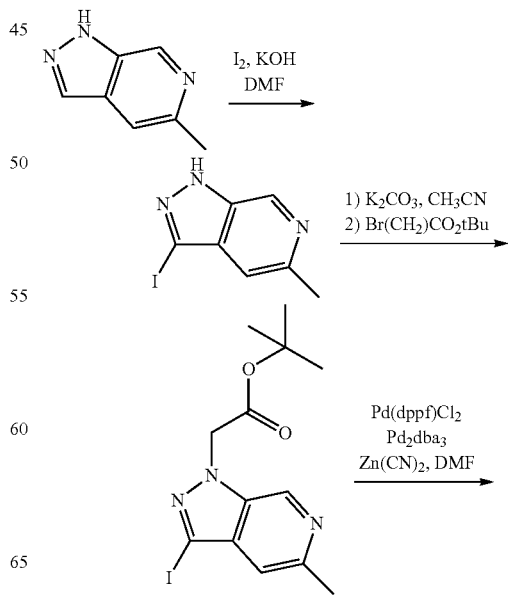

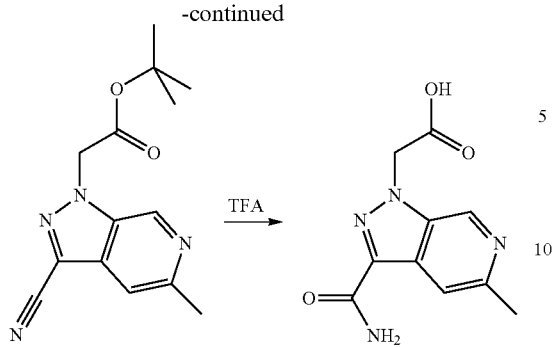

A. 3-Iodo-5-methyl-1H-pyrazolo[3,4-c]pyridine

To a solution of 5-methyl-1H-pyrazolo[3,4-c]pyridine [76006-06-9] (1.00 g, 7.51 mmol) in DMF (15 mL) were added iodine (2.86 g, 11.3 mmol) and potassium hydroxide (1.05 g, 18.8 mmol). The reaction mixture was stirred at RT for 60 h. The mixture was diluted with 10% sodium thiosulfate and water, the resulting suspension was filtered. The solid was washed with water and then dried under vacuum. MS (LC/MS): 260.0 [M+H]+; $t_R$ (HPLC conditions k): 0.28 min.

B. Tert-butyl 2-(3-iodo-5-methyl-1H-pyrazolo[3,4-c]pyridin-1-yl)acetate

To a suspension of 3-iodo-5-methyl-1H-pyrazolo[3,4-c]pyridine (1.00 g, 3.86 mmol), and potassium carbonate (1.28 g, 9.26 mmol) in acetonitrile (40 mL) was added tert-butyl bromoacetate (0.685 mL, 4.63 mmol) dropwise at RT and the resulting mixture was heated to reflux for 16 h. The mixture was cooled to RT and filtered, the solid was washed with acetonitrile and the filtrate was concentrated under vacuum. The residual oil was used directly in the next step without further purification. MS (LC/MS): 374.0 [M+H]+; $t_R$ (HPLC conditions k): 2.96 min.

C. Tert-butyl 2-(3-cyano-5-methyl-1H-pyrazolo[3,4-c]pyridin-1-yl)acetate

A mixture of tert-butyl 2-(3-iodo-5-methyl-1H-pyrazolo[3,4-c]pyridin-1-yl)acetate (1.00 g, 2.55 mmol), Zn(CN)$_2$ (329 mg, 2.55 mmol), Pd(dppf)Cl$_2$ (208 mg, 0.25 mmol), Pd$_2$(dba)$_3$ (233 mg, 0.25 mmol), water (2.7 mL) and DMF (20 mL) was subjected to microwave irradiation at 120° C. for 30 min under argon. The reaction mixture was filtered through a pad of Celite and the filtrate was diluted with water and EtOAc. The phases were separated and the aqueous layer was extracted with EtOAc. The combined organic extracts were washed with brine, then dried (Phase separator) and concentrated under vacuum. The residual oil was purified by flash chromatography on silica gel (EtOAc/c-hexane 1:2 then 1:1). MS (LC/MS): 273.0 [M+H]+; $t_R$ (HPLC conditions k): 3.04 min.

D. (3-Carbamoyl-5-methyl-pyrazolo[3,4-c]pyridin-1-yl)-acetic acid

A solution of tert-butyl 2-(3-cyano-5-methyl-1H-pyrazolo[3,4-c]pyridin-1-yl)acetate (250 mg, 0.92 mmol) in TFA (4 mL) was subjected to microwave irradiation at 140° C. for 90 min. The reaction mixture was concentrated in vacuo, the residual solid was suspended in methanol and concentrated again in vacuo. MS: 235.0 [M+H]+; $t_R$ (HPLC conditions k): 0.24 min.

(3-Carbamoyl-pyrazolo[3,4-b]pyridin-1-yl)-acetic acid

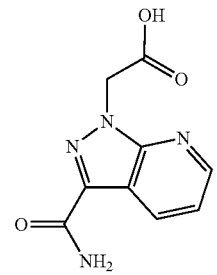 [SMILES: NC(=O)c1nn(CC(=O)O)c2ncccc12]

was prepared from 1H-pyrazolo[3,4-b]pyridine [271-73-8] by using the same procedures as described for the preparation of (3-carbamoyl-5-methyl-pyrazolo[3,4-c]pyridin-1-yl)-acetic acid (Scheme A27). MS (LC-MS): 221 [M+H]+, $t_R$ (HPLC conditions k): 0.87 min.

(3-Carbamoyl-pyrazolo[4,3-c]pyridin-1-yl)-acetic acid

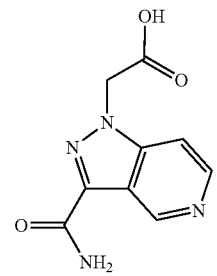 [SMILES: NC(=O)c1nn(CC(=O)O)c2ccncc12]

was prepared from 1H-pyrazolo[4,3-c]pyridine [271-52-3] by using the same procedures as for the preparation of (3-carbamoyl-5-methyl-pyrazolo[3,4-c]pyridin-1-yl)-acetic acid (Scheme A27). MS (LC-MS): 221 [M+H]+, $t_R$ (HPLC conditions k): 0.19 min.

(3-Carbamoyl-6-methyl-pyrazolo[4,3-c]pyridin-1-yl)-acetic acid

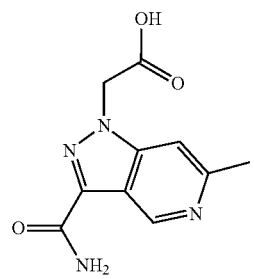 [SMILES: Cc1cc2c(cn1)c(C(N)=O)nn2CC(=O)O]

was prepared from 6-methyl-1H-pyrazolo[4,3-c]pyridine by using the same procedures as for the preparation of (3-carbamoyl-5-methyl-pyrazolo[3,4-c]pyridin-1-yl)-acetic acid (Scheme A27). MS (LC-MS): 235 [M+H]+, $t_R$ (HPLC conditions k): 0.29 min.

6-Methyl-1H-pyrazolo[4,3-c]pyridine

A solution of 4-chloro-6-methyl-1H-pyrazolo[4,3-c]pyridine [1159828-70-2] (750 mg, 4.48 mmol) in a mixture of ethanol (25 mL) and THF (10 mL) was hydrogenated over 10% Pd/C (75 mg, 0.07 mmol) at RT for 24 h. The reaction mixture was filtered, the catalyst was washed with ethanol and the filtrate was concentrated under vacuum. MS (LC-MS): 134 [M+H]+, $t_R$ (HPLC conditions k): 0.23 min.

Scheme A28: Preparation of 2-(3-carbamoyl-1H-pyrazolo[3,4-c]pyridazin-1-yl)acetic acid

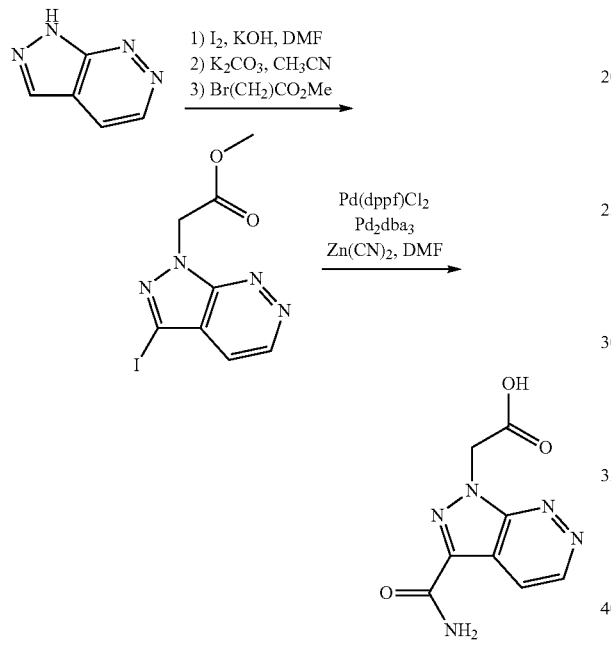

A. Methyl 2-(3-iodo-1H-pyrazolo[3,4-c]pyridazin-1-yl)acetate

To a solution of 1H-pyrazolo[3,4-c]pyridazine [271-75-0] (450 mg, 3.75 mmol) in DMF (10 mL) was added iodine (951 mg, 3.75 mmol) and KOH (525 mg, 9.37 mmol). The mixture was stirred at RT for 16 h until completion of the reaction. Methyl 2-bromoacetate (0.380 mL, 4.12 mmol) was then added to the reaction mixture and stirring was continued at RT for 2 h. The mixture was diluted with EtOAc and washed with water (10 mL), the organic phase was dried (Na₂SO₄) and evaporated under vacuum. The crude mixture was purified by flash column chromatography on silica gel (c-Hex/EtOAc 66:33) to afford the title compound as a brown solid. TLC, $R_f$ (c-Hex/EtOAc 1:1)=0.40; MS (LC/MS): 318.9 [M+H]+; $t_R$ (HPLC conditions c): 3.35 min.

B. 2-(3-Carbamoyl-1H-pyrazolo[3,4-c]pyridazin-1-yl)acetic acid

To a solution of methyl 2-(3-iodo-1H-pyrazolo[3,4-c]pyridazin-1-yl)acetate (675 mg, 2.12 mmol) in DMF (7.5 mL) and water (1.5 mL) was added Zn(CN)₂ (274 mg, 2.33 mmol), Pd₂dba₃ (194 mg, 0.21 mmol) and PdCl₂(dppf).CH₂Cl₂ adduct (173 mg, 0.21 mmol). The reaction mixture was stirred at 100° C. for 16 h. The resulting suspension was filtered and the filtrate was evaporated under vacuum. The residue was suspended in CH₃CN/MeOH 1:1, the solid was filtered off and the filtrate was purified by preparative HPLC (Macherey Nagel, VP250/40, C18 Nucleosil 100-10, flow: 40 mL/min, eluent: 5-100% CH₃CN/H₂O/20 min, 100% CH₃CN/2 min, CH₃CN and H₂O containing 0.1% TFA) to give the title compound after lyophilisation. MS (LC/MS): 222.1 [M+H]+; $t_R$ (HPLC conditions c): 1.34 min.

Part B

Synthesis of Various 5-Membered Heterocycles

Scheme B1: Preparation of (2S,5R) and (2S,5S)-5-Methyl-pyrrolidine-1,2-dicarboxylic acid 1-tert-butyl ester in a (7:1) ratio following a similar procedure as described in *J. Org. Chem.* 2003, 60, 7219.

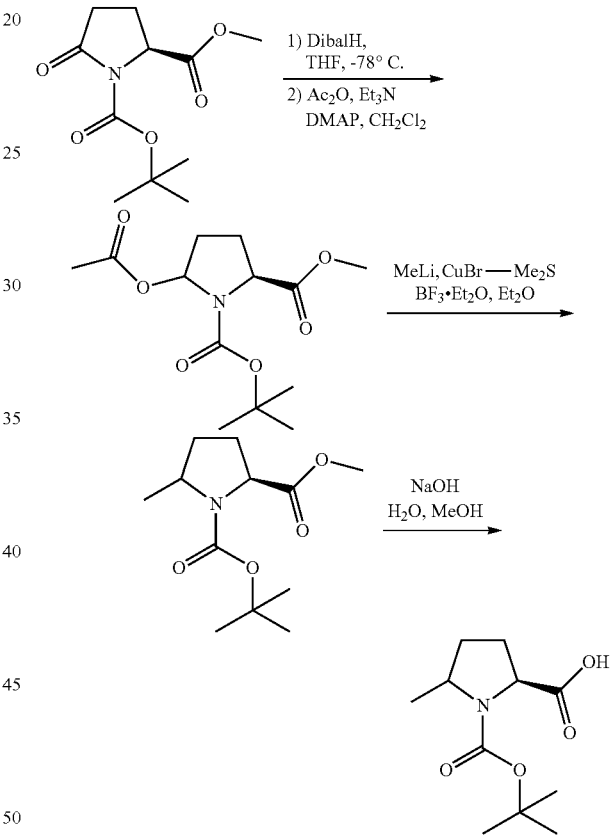

A. (S)-5-Acetoxy-pyrrolidine-1,2-dicarboxylic acid 1-tert-butyl ester 2-methyl ester To a solution of (S)-5-oxo-pyrrolidine-1,2-dicarboxylic acid 1-tert-butyl ester 2-methyl ester (prepared according to *J. Org. Chem.* 2003, 60, 7219) (1.9 g, 7.8 mmol) in THF (25 mL), cooled to −78° C., was slowly added DibalH (1 M in toluene; 11.0 mL, 11.0 mmol) under an argon atmosphere, followed by stirring of the solution at −78° C. for 1 h. The reaction was quenched by addition of a saturated aqueous solution of NH₄Cl (30 mL). The mixture was allowed to warm up to RT, and a 10% aqueous Na₂CO₃ solution (20 mL) and CH₂Cl₂ (70 mL) were subsequently added. The layers were separated and the aqueous phase was extracted with CH₂Cl₂ (2×50 mL). The combined organics were dried (Na₂SO₄) and concentrated in vacuo. The residue was dissolved in CH₂Cl₂ (25 mL), acetic anhydride (2.21 mL, 23.4 mmol), NEt₃ (3.26 mL, 23.4 mmol) and 4-dimethylaminopyridine (0.2 g, 1.6 mmol) were subsequently added and the reaction mixture was stirred at RT overnight. The organics were washed with a saturated aqueous NaHCO₃ solution (10 mL) and 1M aqueous HCl, dried (Phase separator) and concentrated in vacuo. The residue was purified by flash column chromatography on silica gel (c-hexane/EtOAc gradient 3:1 to 1:1) to give the title compound. TLC, $R_f$ (c-hexane/EtOAc 1:1)=0.5; MS: 310.0 [M+Na]+, 597.3 [2M+Na]+.

B. (2S,5R)- and (2S,5S)-5-Methyl-pyrrolidine-1,2-dicarboxylic acid 1-tert-butyl ester 2-methyl ester To a suspension of copper bromide-dimethylsulfide complex (1.09 g, 5.32 mmol) in Et₂O (30 mL), cooled to −40° C., was added methyl lithium (1.6M in Et₂O; 3.32 mL, 5.32 mmol) dropwise under an argon atmosphere. The solution was stirred for 45 min, then cooled to −78° C., and boron trifluoride etherate was added dropwise (0.67 mL, 5.32 mmol). After 15 min, a solution of (S)-5-acetoxy-pyrrolidine-1,2-dicarboxylic acid 1-tert-butyl ester 2-methyl ester (0.51 g, 1.77 mmol) in Et₂O (5 mL) was added dropwise. The reaction mixture was stirred for 15 min and was, after warming up to RT over 1 h, quenched by addition of a 1:1 (v/v) mixture of an aqueous saturated NH₄Cl solution and a 25% aqueous NH₄OH solution (10 mL). After stirring for 30 min, the two layers were separated and the aqueous phase was extracted with Et₂O (2×50 mL). The combined organics were dried (Na₂SO₄) and concentrated under reduced pressure. The residue was purified by flash column chromatography on silica gel (c-hexane/EtOAc 8:2) to give the title compound as a (trans:cis) mixture of diastereoisomers in a 7:1 ratio. TLC, $R_f$ (c-hexane/EtOAc 3:1)=0.42; MS: 266.0 [M+Na]+, 509.2 [2M+Na]+.

C. (2S,5R)- and (2S,5S)-5-Methyl-pyrrolidine-1,2-dicarboxylic acid 1-tert-butyl ester To a solution of (2S,5R)- and (2S,5S)-5-methyl-pyrrolidine-1,2-dicarboxylic acid 1-tert-butyl ester 2-methyl ester (0.33 g, 1.35 mmol; trans:cis ratio 7:1) in MeOH (2 mL) was added 1N NaOH (2 mL) and the reaction mixture was stirred at RT overnight. An additional aliquot of 1N NaOH (2 mL) was added and the mixture was heated at 50° C. for 5 h. Volatiles were removed under reduced pressure, and the aqueous phase was acidified to pH 1 by addition of 6N HCl, followed by extraction with CH₂Cl₂ (2×25 mL). The combined organics were dried (Phase separator) and concentrated to afford the title compound a (trans:cis) mixture of diastereoisomers in a 7:1 ratio. TLC, $R_f$ (CH₂Cl₂/MeOH (10% AcOH) 9:1)=0.41; MS (LC/MS): 227.9 [M−H]−.

(2S,5S)-5-Ethyl-pyrrolidine-1,2-diarboxylic acid 1-tert-butyl ester

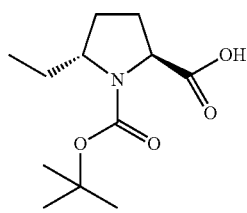 [SMILES: CC[C@@H]1CC[C@@H](C(=O)O)N1C(=O)OC(C)(C)C]

A. (2S,5R)-5-Ethyl-pyrrolidine-1,2-dicarboxylic acid 1-tert-butyl ester 2-methyl ester To a stirred suspension of copper bromide-dimethylsulfide complex (2.15 g, 10.4 mmol) in dry Et₂O (40 mL), cooled to −40° C., was added dropwise ethyl magnesium chloride (2M in Et₂O; 5.22 mL, 10.4 mmol; Aldrich 300330) under an argon atmosphere. After stirring for 45 min, the mixture was cooled to −78° C., followed by dropwise addition of boron trifluoride etherate (1.32 mL, 10.4 mmol) and stirring for 15 min. Then, a solution of (S)-5-acetoxy-pyrrolidine-1,2-dicarboxylic acid 1-tert-butyl ester 2-methyl ester (1.00 g, 3.48 mmol, prepared as described in Scheme B1) in dry Et₂O (10 mL) was added dropwise to result in a black suspension. The reaction mixture was stirred for 15 min and subsequently was allowed to warm up to RT over a period of 1 h. The reaction was quenched by addition of a (1:1)-mixture of a saturated aqueous NH₄Cl solution and a concentrated aqueous NH₃ solution (10 mL), followed by stirring for 30 min. The organic layer was separated, and the aqueous phase was extracted with Et₂O (2×50 mL). The combined organics were dried (Na₂SO₄) and evaporated under reduced pressure. The residue was purified by flash column chromatography on silica gel (EtOAc/c-hexane 2:8) to afford the title compound (contained less than 10% of the minor (2S,5S)-diastereoisomer according to 1H-NMR). TLC $R_f$ (EtOAc/c-hexane 1:3)=0.48.

B. (2S,5S)-5-Ethyl-pyrrolidine-1,2-diarboxylic acid 1-tert-butyl ester

To a solution of (2S,5R)-5-ethyl-pyrrolidine-1,2-dicarboxylic acid 1-tert-butyl ester 2-methyl ester (containing <10% of the minor (2S,5R)-diastereomer) (340 mg, 1.32 mmol) in MeOH (15 mL) was added a 2N aqueous NaOH solution (1.32 mL, 2.64 mmol), followed by stirring the reaction mixture at 50° C. overnight. An additional aliquot of NaOH (2 equiv) was added and stirring was continued at 50° C. for 6 h. Volatiles were removed under reduced pressure and the residue was taken up in water. The aqueous layer was acidified (pH 1) by adding 6N aqueous HCl, followed by extraction with CH₂Cl₂ (2×20 mL). The combined organics were dried (Phase separator) and evaporated in vacuo to afford the title compound (contained less than 10% of the minor (2S,5S)-diastereoisomer). TLC, $R_f$ (CH₂Cl₂/MeOH (2% AcOH): 9:1)=0.40.

Scheme B2: preparation of (2S,4R) and (2S,4S)-2-(3-Trifluoromethoxy-phenylcarbamoyl)-4-methyl-pyrrolidine-1-carboxylic acid tert-butyl ester

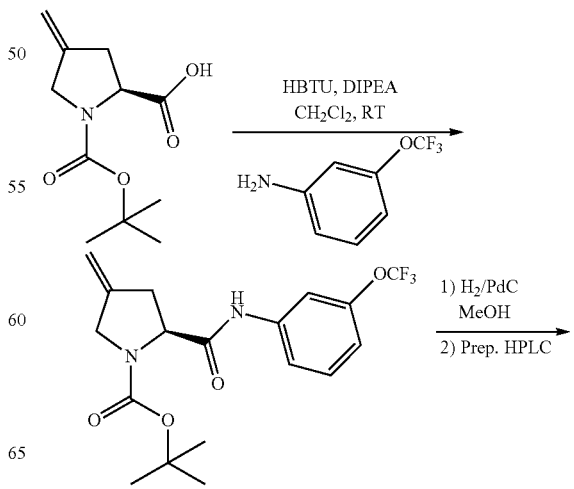

A. (S)-2-(3-Trifluoromethoxy-phenylcarbamoyl)-4-methylene-pyrrolidine-1-carboxylic acid tert-butyl ester To a suspension of N-Boc-4-methylene-L-proline (1 g, 4.4 mmol) in CH₂Cl₂ (40 mL) was added 3-(trifluoromethoxy)aniline (0.71 mL, 5.28 mmol), HBTU (1.14 g, 6.6 mmol) and diisopropylethylamine (1.51 mL, 8.8 mmol). The reaction mixture was stirred at RT for 2 days. The mixture was successively washed with 30 mL of a saturated aqueous NaHCO₃ solution and an HCl 1M solution. The organic layers were dried (phase separator) and concentrated under vacuum. The crude residue was purified by flash column chromatography on silica gel (eluent: c-hexane/EtOAc:65/35) to give the title compound. TLC, R$_f$ (c-hexane/EtOAc: 1:1)=0.55; MS (LC/MS): 287.0 [M-Boc]+, 385.0 [M-H]-.

B. (2S,4R) and (2S,4S)-2-(3-Trifluoromethoxy-phenylcarbamoyl)-4-methyl-pyrrolidine-1-carboxylic acid tert-butyl ester

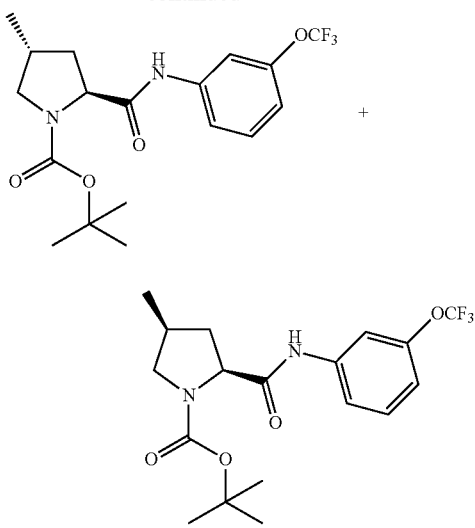

To a solution of (S)-2-(3-trifluoromethoxy-phenylcarbamoyl)-4-methylene-pyrrolidine-1-carboxylic acid tert-butyl ester (0.5 g, 1.29 mmol) in EtOAc (15 mL) was added Pd/C (10%) and the reaction mixture was placed under hydrogen atmosphere overnight. The reaction mixture was filtered on a pad of Celite, the catalyst residue was washed with EtOAc and the solvent was concentrated. The crude material was purified by preparative HPLC (waters SunFire C18-ODB, 5 μm, 30×100 mm, eluent: 20-100% CH₃CN/H₂O/20 min, 100% CH₃CN/2 min, CH₃CN and H₂O containing 0.1% TFA, flow: 40 mL/min, loading 150 mg per run) to give after lyophilization of the purified fractions the desired compounds: (2S,4S)-2-(3-trifluoromethoxy-phenylcarbamoyl)-4-methyl-pyrrolidine-1-carboxylic acid tert-butyl ester: t$_R$ (HPLC conditions b): 5.34 min; LC/MS: 387.0 [M-H]-; (2S,4R)-2-(3-trifluoromethoxy-phenylcarbamoyl)-4-methyl-pyrrolidine-1-carboxylic acid tert-butyl ester: t$_R$ (HPLC conditions b): 5.53 min; MS (LC/MS): 387.0 [M-H]-.

(2S,3R)-3-Methyl-pyrrolidine-1,2-dicarboxylic acid 1-tert-butyl ester

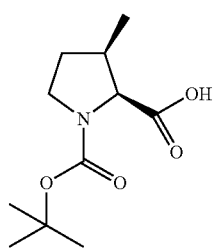 [SMILES: C[C@@H]1CCN(C(=O)OC(C)(C)C)[C@@H]1C(=O)O]

A. (2S,3R)-3-Methyl-1-((S)-1-phenyl-ethyl)-pyrrolidine-2-carboxylic acid benzyl ester was prepared following the procedure described in Tet. Lett. 1997, 38 (1), 89-92 starting from [but-3-enyl-((S)-1-phenyl-ethyl)-amino]-acetic acid benzyl ester.

B. (2S,3R)-3-Methyl-pyrrolidine-1,2-dicarboxylic acid 1-tert-butyl ester (2S,3R)-3-Methyl-1-((S)-1-phenyl-ethyl)-pyrrolidine-2-carboxylic acid benzyl ester (245 mg, 0.758 mmol) and Boc₂O (165 mg, 0.758 mmol) were dissolved in MeOH (3.5 mL). Air was removed from the flask and replaced with nitrogen three times. Pd/C 10% (76 mg) was added and the solution was again degassed and placed under a hydrogen atmosphere. The mixture was stirred at RT for 1.5 h, filtered through a pad of Celite and the solvent was concentrated in vacuo. The residue was dissolved in EtOAc and an aqueous saturated solution of NaHCO₃ was added. The layers were separated and the aqueous one acidified with HCl 1N (pH=1) and extracted twice with EtOAc. The combined organic layers were dried over Na₂SO₄, filtered and concentrated to give the desired compound which was used without further purification in the next step. 1H-NMR (400 MHz, DMSO): δ (ppm): 12.5 (bs, 1H), 4.02 (d, 1H), 3.47 (q, 1H), 3.19 (m, 1H), 2.4 (m, 1H), 1.92 (m, 1H), 1.54 (m, 1H), 1.40 and 1.35 (2s, 9H), 0.96 (d, 3H).

(3S,5S)-5-(3-Chloro-2-fluoro-benzylcarbamoyl)-pyrrolidine-1,3-dicarboxylic acid 1-tert-butyl ester 3-methyl ester

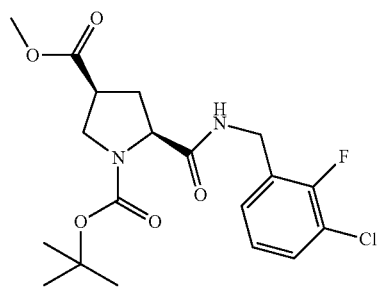 [SMILES: COC(=O)[C@H]1C[C@@H](C(=O)NCc2cccc(Cl)c2F)N(C(=O)OC(C)(C)C)C1]

A. (2S,4S)-4-Cyano-pyrrolidine-1,2-dicarboxylic acid 1-tert-butyl ester

A solution of N-boc-cis-4-cyano-L-proline methyl ester (800 mg, 3.15 mmol) in MeOH (27 mL) was cooled to 0° C. and LiOH.H₂O (792 mg, 18.9 mmol) was added. The colorless solution was allowed to reach RT and stirred for 4 h. LiOH.H₂O (792 mg, 18.9 mmol) was added and the reaction further stirred at for 1 hour to complete the reaction. MeOH was concentrated and the residue diluted in $CH_2Cl_2$ and treated with aqueous 1M HCl adjusting the pH to 1. The layers were separated and the aqueous one re-extracted with $CH_2Cl_2$ (×2). The combined organic extracts were dried ($Na_2SO_4$), filtered and concentrated to give the desired compound which was used in the next step without further purification. MS (LC/MS): 263.0 [M+Na]+, 503.2 [2M+Na]+, 239.1 [M−H]−.

B. (2S,4S)-2-(3-Chloro-2-fluoro-benzylcarbamoyl)-4-cyano-pyrrolidine-1-carboxylic acid tert-butyl ester To a mixture of (2S,4S)-4-cyano-pyrrolidine-1,2-dicarboxylic acid 1-tert-butyl ester (700 mg, 2.91 mmol), 3-chloro-2-fluorobenzylamine (558 mg, 3.50 mmol), HBTU (1.66 g, 4.37 mmol) in DMF (15 mL) was added DIPEA (1.5 mL, 8.74 mmol) and the resolution mixture was stirred at RT under nitrogen for 48 h. The mixture was poured in water and extracted with EtOAc (2×). The combined organic extracts were washed with water (1×), dried ($Na_2SO_4$), filtered and concentrated. The crude material was purified by flash column chromatography (c-hexane to c-hexane/EtOAc 1:1) to give the desired compound. TLC, $R_f$ (c-hexane/EtOAc 1:1)= 0.40; MS: 404.0 [M+Na]+, 380.0 [M−H]−, $t_R$ (HPLC conditions a): 3.45 min.

C. (3S,5S)-5-(3-Chloro-2-fluoro-benzylcarbamoyl)-pyrrolidine-1,3-dicarboxylic acid 1-tert-butyl ester 3-methyl ester Chlorotrimethylsilane (5.66 mL, 44.8 mmol) was added dropwise to dry MeOH (7.6 mL) at 0° C. followed by a solution of (2S,4S)-2-(3-chloro-2-fluoro-benzylcarbamoyl)-4-cyano-pyrrolidine-1-carboxylic acid tert-butyl ester (900 mg, 2.36 mmol) in dry $CH_2Cl_2$ (6.7 mL) and the resulting mixture was stirred at RT for 5 h. The mixture was cooled to 0° C., quenched with a saturated aqueous solution of $NaHCO_3$ and extracted with $CH_2Cl_2$ (×3). To the organic extracts was added di-tert-butyl dicarbonate (514 mg, 2.36 mmol) at RT and the resulting solution was stirred overnight. The reaction mixture was concentrated in vacuo and the crude material purified by flash column chromatography (c-hexane to c-hexane/EtOAc 1:1) to give the expected compound. $t_R$ (HPLC conditions a): 3.50 min.

(2S,4S)-2-(3-Chloro-2-fluoro-benzylcarbamoyl)-4-hydroxymethyl-pyrrolidine-1-carboxylic acid tert-butyl ester

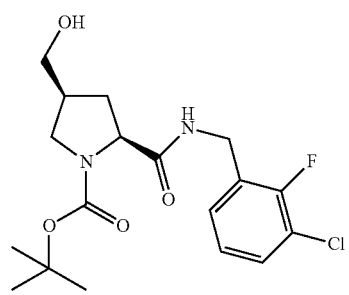 [SMILES: CC(C)(C)OC(=O)N1C[C@@H](CO)C[C@H]1C(=O)NCc1cccc(Cl)c1F]

To a solution (3S,5S)-5-(3-chloro-2-fluoro-benzylcarbamoyl)-pyrrolidine-1,3-dicarboxylic acid 1-tert-butyl ester 3-methyl ester (550 mg, 1.33 mmol) in THF (6 mL) was added lithium borohydride (2 M in THF, 1.46 mL, 2.92 mmol) at RT and the mixture was further stirred for 2 h under $N_2$ atmosphere. After completion brine and $CH_2Cl_2$ were added, the layers were separated and the aqueous one re-extracted with $CH_2Cl_2$. The combined organic layers were dried ($MgSO_4$), filtered and concentrated. The crude was purified by flash column chromatography on silica gel (eluent: EtOAc) to give the desired material. MS (LC/MS): 409.1 [M+Na]+, 287.0 [MH−Boc]+, 385.1 [M−H]−; $t_R$ (HPLC conditions f): 1.82 min.

(2S,3R)-2-(3-Chloro-2-fluoro-benzylcarbamoyl)-3-methoxy-pyrrolidine-1-carboxylic acid tert-butyl ester

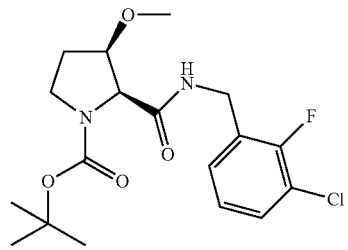 [SMILES: CO[C@@H]1CCN(C(=O)OC(C)(C)C)[C@@H]1C(=O)NCc1cccc(Cl)c1F]

A. (2S,3R)-3-Methoxy-pyrrolidine-1,2-dicarboxylic acid 1-tert-butyl ester 2-methyl ester To a solution of (2S,3R)-3-hydroxy-pyrrolidine-1,2-dicarboxylic acid 1-tert-butyl ester [186132-96-7] (500 mg, 2.16 mmol; Chem-Impex International, Inc.) in acetone (10 mL) were added successively $Ag_2O$ (1.65 g, 7.14 mmol) and MeI (0.473 mL, 7.57 mmol), followed by stirring at RT overnight. The reaction mixture was filtered, the filtrate was evaporated and the residue was taken up again in acetone (10 mL). To this solution was added $Ag_2O$ (1.65 g, 7.14 mmol) and MeI (0.473 mL, 7.57 mmol) and the reaction mixture was stirred for 60 h. Solids were then removed by filtration, the filtrate was concentrated under reduced pressure and the residue was purified by flash column chromatography on silica gel (EtOAC/c-hexane gradient 1:2 to 1:1) to afford the title compound as a colorless oil. MS (LC/MS): 282 [M+Na]+; 160 [M−BOC]+; $t_R$ (HPLC conditions b): 3.37 min.

B. (2S,3R)-3-Methoxy-pyrrolidine-1,2-dicarboxylic acid 1-tert-butyl ester

To a solution of (2S,3R)-3-methoxy-pyrrolidine-1,2-dicarboxylic acid 1-tert-butyl ester 2-methyl ester (150 mg, 0.578 mmol) in THF (4 mL) and water (2.0 mL) was added LiOH (69.3 mg, 2.89 mmol) and the reaction mixture was stirred at RT for 40 h. Another aliquot of LiOH was added (69.3 mg, 2.89 mmol). Stirring was continued at RT for 60 h and subsequently at 50° C. for 16 h to complete the reaction. Water was added and volatiles were removed under reduced pressure. The aqueous phase was adjusted to pH 2 to 3 by addition of 1N aqueous HCl, followed by extraction with EtOAC (3×). The combined organics were dried (Phase separator) and concentrated in vacuo to give the title compound as a white solid. MS (LC/MS): 262 [M+Na]+, 190 [MH−tBu]+, 146 [MH−Boc]+, $t_R$ (HPLC conditions b): 3.51 min.

C. (2S,3R)-2-(3-Chloro-2-fluoro-benzylcarbamoyl)-3-methoxy-pyrrolidine-1-carboxylic acid tert-butyl ester The mixture of (2S,3R)-3-methoxy-pyrrolidine-1,2-dicarboxylic acid 1-tert-butyl ester (60.0 mg, 0.245 mmol), (3-chloro-2-fluorophenyl)methanamine (0.034 mL, 0.269 mmol), HBTU (139 mg, 0.367 mmol) and DIPEA (0.085 mL, 0.489 mmol) in CH$_2$Cl$_2$ (5 mL) was stirred for 20 h at RT. The reaction mixture was then diluted with CH$_2$Cl$_2$, and the organics were washed subsequently with 0.1N aqueous HCl (3×), aqueous NaHCO$_3$ solution (2×) and brine. The organic layers were dried (Phase separator), concentrated in vacuo and the residue was purified by preparative HPLC (Waters Sunfire, C18-ODB, 5 μm, 30×100 mm; flow: 40 mL/min; eluent: 5-100% CH$_3$CN/H$_2$O for 20 min, 100% CH$_3$CN for 2 min, CH$_3$CN and H$_2$O containing 0.1% TFA) to afford the title compound as a white solid. MS (LC/MS): 387 [M+H]+, 331 [MH−tBu]+, 287 [MH−Boc]+; t$_R$ (HPLC conditions b): 4.26 min.

(2R,3S)-2-(3-chloro-2-fluoro-benzylcarbamoyl)-3-fluoro-pyrrolidine-1-carboxylic acid tert-butyl ester

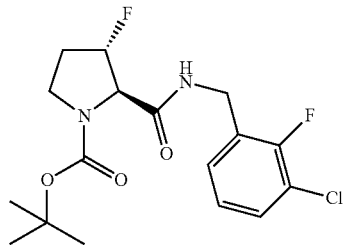 [SMILES: CC(C)(C)OC(=O)N1CC[C@H](F)[C@H]1C(=O)NCc1cccc(Cl)c1F]

A. (2S,3R)-3-Hydroxy-pyrrolidine-1,2-dicarboxylic acid 2-benzyl ester 1-tert-butyl ester To a solution of (2S,3R)-3-hydroxy-pyrrolidine-1,2-dicarboxylic acid 1-tert-butyl ester [186132-96-7] (500 mg, 2.162 mmol; Chem-Impex International, Inc.) in MeOH (9.0 mL), cooled to 0° C., was added with stirring a solution of Cs$_2$CO$_3$ (704 mg, 2.162 mmol) in water (6.0 mL). The mixture was concentrated by rotary evaporation and the residue was suspended in DMF (17.0 mL). The suspension was cooled to 0° C., followed by addition of benzylbromide (0.514 mL, 4.32 mmol) and stirring overnight at RT. The reaction mixture was filtered, the filtrate was concentrated under reduced pressure and the residue was dissolved in EtOAc. The organics were washed with aqueous NaHCO$_3$ (2×) and water (2×), dried (Phase separator) and concentrated in vacuo. The residue was purified by flash column chromatography on silica gel (EtOAc/c-hexane 2:3) to give the title compound as an oil. MS (LC/MS): 322 [M+H]+, 665 [2M+Na]+; t$_R$ (HPLC conditions b): 4.12 min.

B. (2R,3S)-3-Fluoro-pyrrolidine-1,2-dicarboxylic acid 2-benzyl ester 1-tert-butyl ester The title compound was prepared in a similar manner as described by J. A. Hodges et al., *J. Amer. Chem. Soc.* 2005, 127, 15923-15932: To a solution of (2S,3R)-3-hydroxy-pyrrolidine-1,2-dicarboxylic acid 2-benzyl ester 1-tert-butyl ester (490 mg, 1.53 mmol) in CH$_2$Cl$_2$ (30 mL), cooled to −78° C., was added dropwise DAST (1.01 mL, 7.62 mmol). The reaction mixture was stirred at −78° C. for 5 h, and then was allowed to warm to RT and stirred overnight. After cooling to 0° C., the reaction was quenched with MeOH, followed by addition of aqueous NaHCO$_3$ solution. Volatiles were removed under reduced pressure and the residue was taken up in EtOAc. The organics were washed with aqueous NaHCO$_3$ (3×), water and brine, dried (Phase separator) and concentrated in vacuo. The residue was purified by flash column chromatography on silica gel (EtOAc/c-hexane 1:9) to give the title compound (89% purity by HPLC/215 nm). MS (LC/MS): 346 [M+Na]+, 268 [MH−tBu]+, 224 [MH−Boc]+; t$_R$ (HPLC conditions b): 5.31 min.

C. (2R,3S)-3-Fluoro-pyrrolidine-1,2-dicarboxylic acid 1-tert-butyl ester

A solution of (2R,3S)-3-fluoro-pyrrolidine-1,2-dicarboxylic acid 2-benzyl ester 1-tert-butyl ester (252 mg, 0.778 mmol; 72% purity by HPLC/215 nm) in MeOH (20 mL) was hydrogenated at RT (1 atm) over Pd/C 10% (35 mg, 10% w/w) for 24 h. The reaction mixture was filtered through a 0.45 microns filter and concentrated under reduced pressure to give the crude title compound (70% purity by HPLC/215 nm) as a white solid. This material was used in the next reaction step without further purification. MS (LC/MS): 232 [M−H]+; t$_R$ (HPLC conditions b): 2.78 min.

D. (2R,3S)-2-(3-Chloro-2-fluoro-benzylcarbamoyl)-3-fluoro-pyrrolidine-1-carboxylic acid tert-butyl ester To a solution of (2R,3S)-3-fluoro-pyrrolidine-1,2-dicarboxylic acid 1-tert-butyl ester (120 mg, 0.514 mmol) in CH$_2$Cl$_2$ (5 mL) were added successively 3-chloro-2-fluorobenzylamine (0.065 mL, 0.514 mmol), HBTU (293 mg, 0.772 mmol) and DIPEA (0.18 mL, 1.03 mmol), and stirring was continued at RT for 20 h. The reaction mixture was then diluted with CH$_2$Cl$_2$, and the organics were washed with 0.1N aqueous HCl (2×), aqueous NaHCO$_3$ (2×) and brine (1×), dried (Phase separator) and concentrated in vacuo. The residue was purified by flash column chromatography on silica gel (EtOAc/c-hexane gradient 1:4 to 1:3) to afford the title compound as a white foam. TLC R$_f$ (EtOAc/c-hexane 1:1)= 0.62; MS (LC/MS): 397 [M+Na]+, 319 [MH−tBu]+, 275 [MH−Boc]+; t$_R$ (HPLC conditions b): 4.72 min.

(2R,3R)-2-(3-Chloro-2-fluoro-benzylcarbamoyl)-3-fluoro-pyrrolidine-1-carboxylic acid tert-butyl ester

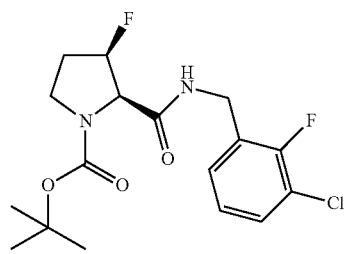 [SMILES: CC(C)(C)OC(=O)N1CC[C@@H](F)[C@H]1C(=O)NCc1cccc(Cl)c1F]

A. (2S,3R)-3-Hydroxy-pyrrolidine-1,2-dicarboxylic acid 2-benzyl ester 1-tert-butyl ester To a solution of (2S,3S)-3-hydroxy-pyrrolidine-1,2-dicarboxylic acid 1-tert-butyl ester [187039-57-2] (500 mg, 2.16 mmol) in MeOH (9.0 mL), cooled to 0° C., was added with stirring a solution of Cs$_2$CO$_3$ (704 mg, 2.162 mmol) in water (6.0 mL). The mixture was concentrated by rotary evaporation and the residue was suspended in DMF (17.0 mL). The suspension was cooled to 0° C., followed by addition of benzylbromide (0.514 mL, 4.32 mmol) and stirring overnight at RT. The reaction mixture was filtered, the filtrate was concentrated under reduced pressure and the residue was dissolved in EtOAc. The organics were washed with aqueous NaHCO$_3$ (2×) and water (2×), dried (Phase separator) and concentrated in vacuo. The residue was purified by flash column chromatography on silica gel (EtOAc/c-hexane 2:3) to give the title compound as a white solid. MS (LC/MS): 665 [2M+Na]+, 266 [MH−tBu]+, 222 [MH−Boc]+; $t_R$ (HPLC conditions b): 4.18 min.

B. (2R,3R)-3-Fluoro-pyrrolidine-1,2-dicarboxylic acid 2-benzyl ester 1-tert-butyl ester The title compound was prepared in a similar manner as described by L. Demange et al., *Tetrahedron Letters* 2001, 42, 651-653: To a solution of (2S,3R)-3-hydroxy-pyrrolidine-1,2-dicarboxylic acid 2-benzyl ester 1-tert-butyl ester (360 mg, 1.12 mmol) in CH$_2$Cl$_2$ (30 mL), cooled to −78° C., was added dropwise DAST (0.740 mL, 5.60 mmol). The reaction mixture was stirred at −78° C. for 5 h, and then was allowed to warm to RT and stirred overnight. After cooling to 0° C., the reaction was quenched with MeOH, followed by addition of aqueous NaHCO$_3$ solution. Volatiles were removed under reduced pressure and the residue was taken up in EtOAc. The organics were washed with aqueous NaHCO$_3$ (3×), water and brine, dried (Phase separator) and concentrated in vacuo. The residue was purified by flash column chromatography on silica gel (EtOAc/c-hexane 1:9) to give the title compound (99% purity by HPLC/215 nm). TLC R$_f$ (EtOAc/c-hexane 1:4)=0.2; MS (LC/MS): 346 [M+Na]+, 268 [MH−tBu]+, 224 [MH−Boc]+; $t_R$ (HPLC conditions b): 5.01 min.

C. (2R,3R)-3-Fluoro-pyrrolidine-1,2-dicarboxylic acid 1-tert-butyl ester

A solution of (2R,3R)-3-fluoro-pyrrolidine-1,2-dicarboxylic acid 2-benzyl ester 1-tert-butyl ester (70.0 mg, 0.216 mmol) in MeOH (10 mL) was hydrogenated at RT (1 atm) over Pd/C 10% (35 mg, 50% w/w) for 48 h. The reaction mixture was filtered through a 0.45 microns filter and concentrated under reduced pressure to give the crude title compound (>95% purity by 1H-NMR) as a white solid. MS (LC/MS): 232 [M−H]+; $t_R$ (HPLC conditions b): 2.26 min. This material was used in the next reaction step without further purification.

D. (2R,3R)-2-(3-Chloro-2-fluoro-benzylcarbamoyl)-3-fluoro-pyrrolidine-1-carboxylic acid tert-butyl ester To a solution of (2R,3R)-3-fluoro-pyrrolidine-1,2-dicarboxylic acid 1-tert-butyl ester (45.0 mg, 0.193 mmol) in CH$_2$Cl$_2$ (5 mL) were added successively 3-chloro-2-fluorobenzylamine (0.024 mL, 0.193 mmol), HBTU (110 mg, 0.289 mmol) and DIPEA (0.067 mL, 0.386 mmol), and stirring was continued at RT for 20 h. The reaction mixture was then diluted with CH$_2$Cl$_2$, and the organics were washed with 0.1N aqueous HCl (2×), aqueous NaHCO$_3$ (2×) and brine (1×), dried (Phase separator) and concentrated in vacuo. The residue was purified by flash column chromatography on silica gel (eluent: EtOAc/c-hexane gradient 1:4 to 1:3) to afford the title compound. TLC R$_f$ (EtOAc/c-hexane 1:1)= 0.31; MS (LC/MS): 397 [M+Na]+, 319 [MH−tBu]+, 275 [MH−Boc]+; $t_R$ (HPLC conditions b): 4.37 min.

Procedure 1 for the preparation of (2S,3R)-3-Azido-pyrrolidine-2-carboxylic acid 3-chloro-2-fluoro-benzylamide trifluoroacetate

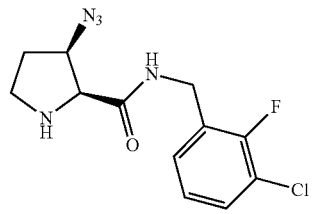 [SMILES: [N-]=[N+]=N[C@@H]1CCN[C@@H]1C(=O)NCc1cccc(Cl)c1F]

A. (2S,3R)-3-Azido-pyrrolidine-1,2-dicarboxylic acid 1-tert-butyl ester

To a solution of (2S,3R)-3-azido-pyrrolidine-1,2-dicarboxylic acid 1-tert-butyl ester 2-methyl ester [361367-97-7] (210 mg, 0.777 mmol; Sunshine Ltd) in THF (6 mL) was added a solution of LiOH (55.8 mg, 2.33 mmol) in water (3 mL), followed by stirring at RT for 20 h. The reaction mixture was concentrated under reduced pressure and the residual aqueous phase was washed with EtOAc (3×). The water phase was adjusted to pH 2 to 3 by adding 1N aqueous HCl, followed by extraction with EtOAc (3×). The combined organics were dried (Phase separator) and concentrated in vacuo to give the crude title compound as a colorless oil. The crude product was used in the next reaction step without further purification. MS (LC/MS): 279 [M+Na]+, 200 [MH−tBu]+, 157 [MH−Boc]+; $t_R$ (HPLC conditions b): 2.77 min.

B. (2S,3R)-3-Azido-2-(3-chloro-2-fluoro-benzylcarbamoyl)-pyrrolidine-1-carboxylic acid tert-butylester To (2S,3R)-3-azido-pyrrolidine-1,2-dicarboxylic acid 1-tert-butyl ester (170 mg, 0.663 mmol) in CH$_2$Cl$_2$ (12 mL) were added successively 3-chloro-2-fluorobenzylamine (0.092 mL, 0.730 mmol), HBTU (377 mg, 0.995 mmol) DIPEA (0.232 mL, 1.33 mmol) and stirring was continued at RT for 20 h. The reaction mixture was diluted with CH$_2$Cl$_2$ and the organics were washed with 1N aqueous HCl (2×), aqueous 1N NaOH 1N (2×) and brine, dried (Phase separator) and concentrated in vacuo. The crude product was purified in two steps: first by preparative HPLC (Macherey-Nagel Nucleosil 100-10 C18, 5 µm, 40×250 mm; flow: 20 mL/min; eluent: 20-100% CH$_3$CN/H$_2$O for 20 min, 100% CH$_3$CN for 2 min, CH$_3$CN and H$_2$O containing 0.1% TFA) and subsequently by flash column chromatography on silica (EtOAc/c-hexane gradient 1:3 to 1:1) to afford the title compound as a colorless wax. TLC R$_f$ (EtOAc/c-hexane 1:1)=0.41; MS (LC/MS): 420 [M+Na]+, 342 [MH−tBu]+, 298 [MH−Boc]+; $t_R$ (HPLC conditions b): 4.66 min.

C. (2S,3R)-3-Azido-pyrrolidine-2-carboxylic acid 3-chloro-2-fluoro-benzylamide trifluoroacetate To a solution of (2S,3R)-3-azido-2-(3-chloro-2-fluoro-benzylcarbamoyl)-pyrrolidine-1-carboxylic acid tert-butylester (87 mg, 0.22 mmol) in CH$_2$Cl$_2$ (6 mL) was added TFA at RT, and stirring was continued overnight at RT. Methanol was added to the reaction mixture and volatiles were removed under reduced pressure. The residue was taken up in MeOH and concentrated in vacuo to afford the crude title compound as a colorless wax. The product was used in the next reaction step without further purification. MS (LC/MS): 298 [M+H]+; $t_R$ (HPLC conditions b): 2.71 min.

(2S,3S)-3-Azido-pyrrolidine-2-carboxylic acid 3-chloro-2-fluoro-benzylamide trifluoroacetate

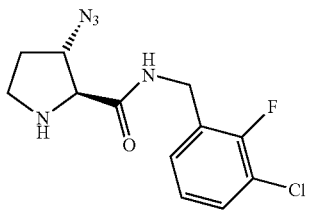

was prepared in a similar manner as described in procedure 1 for (2S,3R)-3-azido-pyrrolidine-2-carboxylic acid 3-chloro-2-fluoro-benzylamide trifluoroacetate from (2S,3S)-3-azido-pyrrolidine-1,2-dicarboxylic acid 1-tert-butyl ester 2-methyl ester [361367-99-9]. MS (LC/MS): 298 [M+H]+; $t_R$ (HPLC conditions b): 2.68 min.

Alternative procedure 2 for the preparation of (2S,3R)-3-Azido-pyrrolidine-2-carboxylic acid 3-chloro-2-fluoro-benzylamide trifluoroacetate

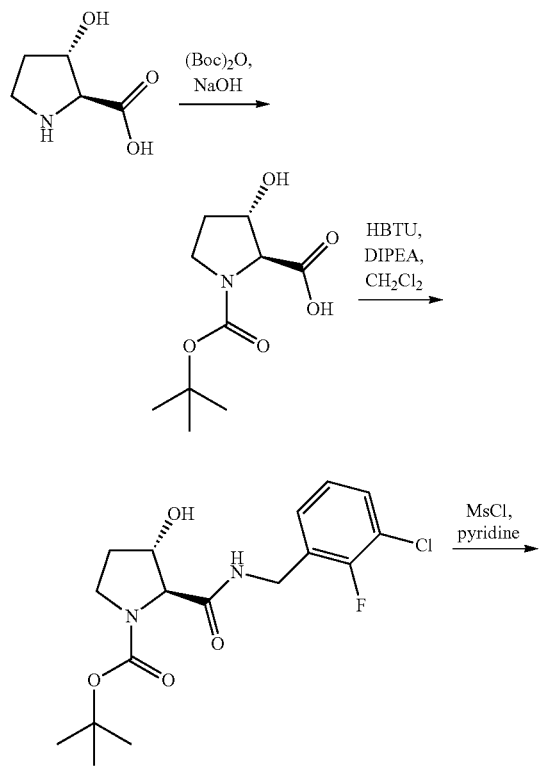

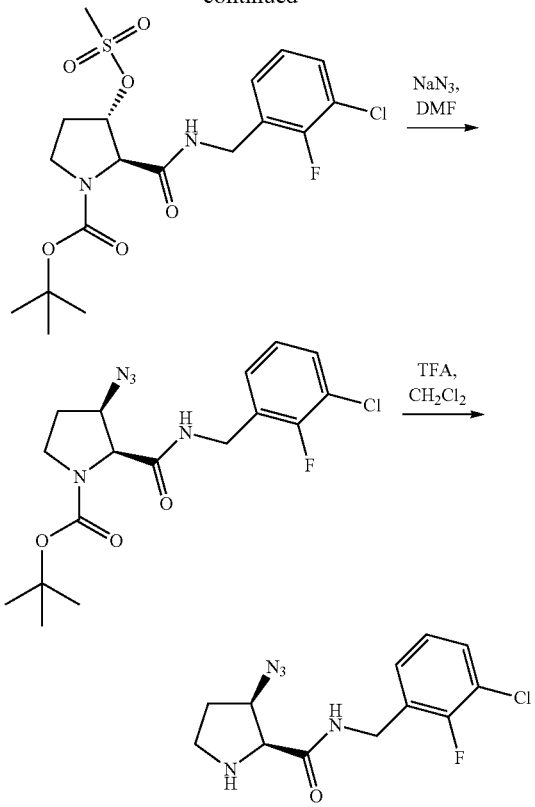

A. (2S,3S)-2-(3-Chloro-2-fluoro-benzylcarbamoyl)-3-hydroxy-pyrrolidine-1-carboxylic acid tert-butyl ester To a solution of (2S,3S)-3-hydroxy-pyrrolidine-1,2-dicarboxylic acid 1-tert-butyl ester (800 mg, 3.46 mmol; prepared according to *J. Amer. Chem. Soc.* 2005, 127, 15923-15932) in CH$_2$Cl$_2$ (35 mL) were added successively 3-chloro-2-fluorobenzylamine (0.435 mL, 3.46 mmol), HBTU (1.97 g, 5.19 mmol), DIPEA (1.21 mL, 6.92 mmol). After stirring at RT for 18 h, the reaction mixture was diluted with CH$_2$Cl$_2$ and the organics were washed with water (2×), 0.1N aqueous HCl (2×), aqueous NaHCO$_3$ solution (2×) and brine, dried (phase separator) and concentrated in vacuo. The crude product was purified by flash column chromatography on silica gel (EtOAc/c-hexane 1:2 to 4:1 then EtOAc) to afford the title compound as a colorless wax. TLC $R_f$(EtOAc/c-hexane 1:1)= 0.32; MS (LC/MS): 373 [M+H]+, 395 [M+Na]+, 767 [2M+Na]+; $t_R$ (HPLC conditions C): 4.42 min.

B. (2S,3S)-2-(3-Chloro-2-fluoro-benzylcarbamoyl)-3-methanesulfonyloxy-pyrrolidine-1-carboxylic acid tert-butyl ester To an ice-cooled solution of (2S,3S)-2-(3-chloro-2-fluoro-benzylcarbamoyl)-3-hydroxy-pyrrolidine-1-carboxylic acid tert-butyl ester (0.98 g, 2.64 mmol) in dry pyridine (13 mL) was added methanesulfonyl chloride (0.31 mL, 3.96 mmol). The reaction was stirred at 0° C. for 2 h and then at RT for 72 h. The volatiles were evaporated in vacuo and the residue was partitioned between water and EtOAc. The aqueous layer was repeatedly extracted with EtOAc, the combined organics were washed with 0.1N HCl and brine, dried (phase separator) and concentrated in vacuo to afford the title compound. Brown oil. MS (LC-MS): 451 [M+H]+, 395 [MH−tBu]+, 351 [MH−Boc]+; $t_R$ (HPLC conditions c): 5.08 min. The material thus obtained was used without any purification.

C. (2S,3R)-3-Azido-2-(3-chloro-2-fluoro-benzylcarbamoyl)-pyrrolidine-1-carboxylic acid tert-butyl ester A mixture of (2S,3S)-2-(3-chloro-2-fluoro-benzylcarbamoyl)-3-methanesulfonyloxy-pyrrolidine-1-carboxylic acid tert-butyl ester (1.60 g, 2.35 mmol) and NaN$_3$ (0.370 g, 5.67 mmol) in dry DMF (12 mL) was stirred at 110° C. for 60 h. The mixture was partitioned between water and EtOAc. The aqueous layer was extracted with EtOAc (3×), the combined organics were washed with brine, dried (phase separator) and concentrated in vacuo. The crude product was purified by flash column chromatography on silica gel (EtOAc/c-hexane 1:4 to 1:2) to afford the title compound as a colorless foam. MS (LC-MS): 398 [M+H]+, 342 [MH−tBu]+, 298 [MH−Boc]+; $t_R$ (HPLC conditions c): 5.15 min.

D. (2S,3R)-3-Azido-pyrrolidine-2-carboxylic acid 3-chloro-2-fluoro-benzylamide trifluoroacetate To a solution of (2S,3R)-3-azido-2-(3-chloro-2-fluoro-benzylcarbamoyl)-pyrrolidine-1-carboxylic acid tert-butyl ester (560 mg, 1.41 mmol) in CH$_2$Cl$_2$ (8 mL) was added TFA (4 mL), and the solution was stirred at RT for 2 h. Methanol was added then added, and volatiles were removed under reduced pressure. The residue was taken up in methanol and concentrated in vacuo to afford the crude title compound as a yellow resin. MS (LC/MS): 298.0 [M+H]+; $t_R$ (HPLC conditions c): 3.59 min. The product was used directly in the next step without further purification.

Scheme B3: preparation of -(2S,5R)-5-Azidomethyl-pyrrolidine-2-carboxylic acid (3-trifluoromethoxy-phenyl)-amide

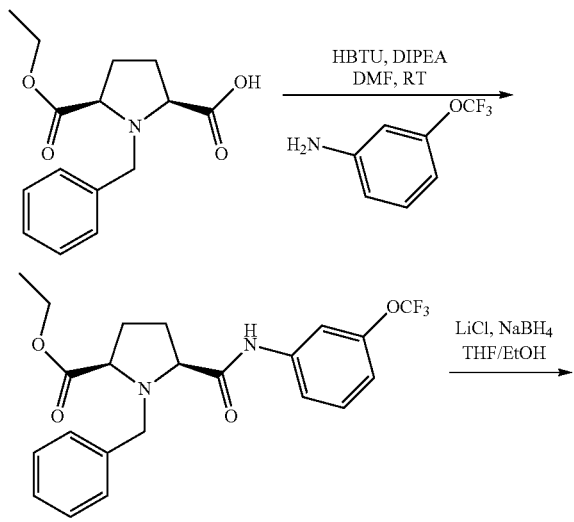

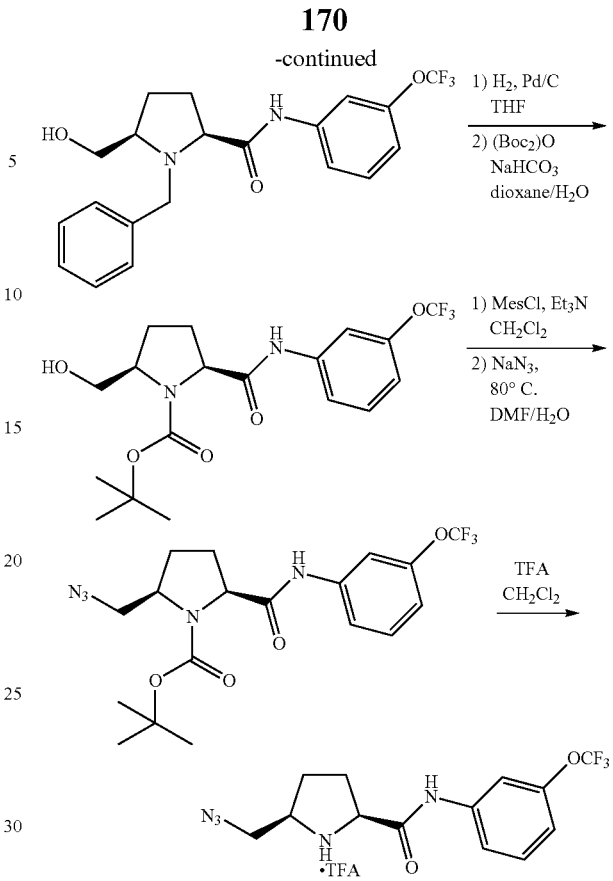

(2R,5S)-1-Benzyl-pyrrolidine-2,5-dicarboxylic acid monoethyl ester

The title compound was prepared according to the procedure described in *Gazzetta Chimica Italiana*, 1996, 126, 543-554 from (2R,5S)-1-benzyl-pyrrolidine-2,5-dicarboxylic acid diethyl ester prepared from benzylamine and diethyl meso-dibromoadipate according to the procedure described in *J. Med. Chem.* 2006, 49, 11, 3068-3076.

A. (2R,5S)-1-Benzyl-5-(3-trifluoromethoxy-phenylcarbamoyl)-pyrrolidine-2-carboxylic acid ethyl ester To a suspension of (2R,5S)-1-benzyl-pyrrolidine-2,5-dicarboxylic acid monoethyl ester (2 g, 7.21 mmol) in DMF (25 mL) was added 3-(trifluoromethoxy)aniline (1.53 mL, 8.65 mmol), HBTU (4.19 g, 10.8 mmol) and diisopropylethylamine (3.78 mL, 21.6 mmol). The reaction mixture was stirred at RT overnight. EtOAc and 1N HCl were added, the layers were separated and the aqueous one was back-extracted with EtOAc (×3). The combined organic extracts were washed with an aqueous solution containing 5% of NaHCO$_3$, dried over Na$_2$SO$_4$, filtered and concentrated. The crude residue was purified by flash column chromatography on silica gel (c-hexane/EtOAc gradient 100:0 to 80:20) to give the title compound. MS (LC/MS): 437.2 [M+H]+; $t_R$ (HPLC conditions b) 5.50 min.

B. (2S,5R)-1-Benzyl-5-hydroxymethyl-pyrrolidine-2-carboxylic acid (3-trifluoromethoxy-phenyl)-amide To a solution of (2R,5S)-1-benzyl-5-(3-trifluoromethoxy-phenylcarbamoyl)-pyrrolidine-2-carboxylic acid ethyl ester (2.5 g, 5.73 mmol) in a mixture of THF (40 mL) and EtOH (20 mL) was added LiCl (486 mg, 11.5 mmol) followed by NaBH$_4$ (451 mg, 11.5 mmol) and the mixture was stirred at RT overnight. The crude reaction mixture was concentrated, EtOAc and 1N HCl were added, the layers were separated and the aqueous one back-extracted with EtOAc. The combined organic extracts were washed with brine, dried over Na$_2$SO$_4$, filtered and concentrated. The crude residue was used without further purification in the next step. MS (LC/MS): 395 [M+H]+; $t_R$ (HPLC conditions b): 3.66 min.

C. (2S,5R)-5-Hydroxymethyl-pyrrolidine-2-carboxylic acid (3-trifluoromethoxy-phenyl)-amide To a solution of (2S,5R)-1-benzyl-5-hydroxymethyl-pyrrolidine-2-carboxylic acid (3-trifluoromethoxy-phenyl)-amide (500 mg, 1.27 mmol) in THF (5 mL) containing 5 drops of MeOH was added Pd/C (10%, 27 mg). The solution was degassed 3 times replacing air by nitrogen and finally nitrogen by hydrogen. The reaction mixture was further stirred under hydrogen atmosphere overnight. The catalyst was removed through a pad of Celite and washed with THF. Solvents were concentrated and the resulting material was used without purification in the next step. MS (LC/MS): 305 [M+H]+; $t_R$ (HPLC conditions b): 2.89 min.

D. (2S,5R)-5-Hydroxymethyl-2-(3-trifluoromethoxy-phenylcarbamoyl)-pyrrolidine-1-carboxylic acid tert-butyl ester A mixture of (2S,5R)-5-hydroxymethyl-pyrrolidine-2-carboxylic acid (3-trifluoromethoxy-phenyl)-amide (422 mg, 1.27 mmol), (Boc)$_2$O (420 mg, 1.91 mmol) and NaHCO$_3$ (161 mg, 1.91 mmol) in water/dioxane (2.5/2.5 mL) was stirred for 48 h. CH$_2$Cl$_2$ and HCl 0.1N were added, the layers were separated and the aqueous one re-extracted with CH$_2$Cl$_2$. The crude organic extracts were washed with brine, dried over Na$_2$SO$_4$, filtered and concentrated. The crude residue was purified by flash column chromatography on silica gel (c-hexane/EtOAc gradient 100:0 to 1:1) to give the desired compound. MS (LC-MS): 403 [M–H]–; $t_R$ (HPLC conditions b) 4.76 min.

E. (2R,5S)-2-Methanesulfonyloxymethyl-5-(3-trifluoromethoxy-phenylcarbamoyl)-pyrrolidine-1-carboxylic acid tert-butyl ester To a solution of (2S,5R)-5-hydroxymethyl-2-(3-trifluoromethoxy-phenylcarbamoyl)-pyrrolidine-1-carboxylic acid tert-butyl ester (390 mg, 0.97 mmol) in CH$_2$Cl$_2$ (3.5 mL) was added at 0° C. under nitrogen atmosphere Et$_3$N (296 µl, 2.12 mmol) and mesylchloride (167 µl, 2.12 mmol) and the mixture was further stirred at RT for 3 h. CH$_2$Cl$_2$ and HCl 0.1N were added, the layers were separated and the aqueous one re-extracted with CH$_2$Cl$_2$. The crude organic extracts were washed with brine dried over Na$_2$SO$_4$, filtered and concentrated. The crude material was used without purification in the next step. MS (LC-MS): 383 [MH–Boc]+; $t_R$ (HPLC conditions b) 5.1 min.

F. (2R,5S)-2-Azidomethyl-5-(3-trifluoromethoxyphenylcarbamoyl)-pyrrolidine-1-carboxylic acid tert-butyl ester To a solution of (2R,5S)-2-methanesulfonyloxymethyl-5-(3-trifluoromethoxy-phenylcarbamoyl)-pyrrolidine-1-carboxylic acid tert-butyl ester (465 mg, 0.97 mmol) in DMF (3 mL) was added a solution of sodium azide (313 mg, 4.82 mmol) in water (0.5 mL) and the mixture was stirred at 80° C. under nitrogen atmosphere overnight. EtOAc and a saturated aqueous solution of NaHCO$_3$ were added, the layers were separated and the aqueous one back-extracted with EtOAc. The combined organic extracts were washed with brine, dried over Na$_2$SO$_4$, filtered and concentrated. The crude residue was purified by flash column chromatography on silica gel (c-hexane/EtOAc gradient 100:0 to 1:1) to give the desired compound. MS (LC-MS): 330 [MH–Boc]+; $t_R$ (HPLC conditions b) 5.75 min.

G. (2S,5R)-5-Azidomethyl-pyrrolidine-2-carboxylic acid (3-trifluoromethoxy-phenyl)-amide (2R,5S)-2-Azidomethyl-5-(3-trifluoromethoxy-phenylcarbamoyl)-pyrrolidine-1-carboxylic acid tert-butyl ester (100 mg, 0.233 mmol) was dissolved in CH$_2$Cl$_2$ (0.2 mL), TFA (0.18 mL, 2.33 mmol) was added and the solution was stirred at RT 3 h. The solution was concentrated under high vacuum to give the desired TFA salt. MS (LC/MS): 328 [M–H]–; $t_R$ (HPLC conditions b): 3.45 min.

(2S,5R)-5-(tert-Butyl-dimethyl-silanyloxymethyl)-pyrrolidine-2-carboxylic acid (3-trifluoromethoxyphenyl)-amide

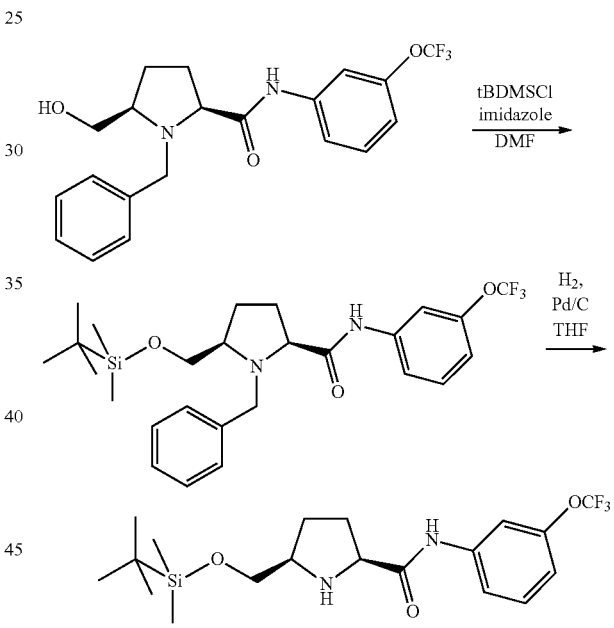

A. (2S,5R)-1-Benzyl-5-(tert-butyl-dimethyl-silanyloxymethyl)-pyrrolidine-2-carboxylic acid (3-trifluoromethoxy-phenyl)-amide A mixture containing (2S,5R)-1-benzyl-5-hydroxymethyl-pyrrolidine-2-carboxylic acid (3-trifluoromethoxyphenyl)-amide (300 mg, 0.76 mmol)(prepared as described in Scheme B3), TBDMSCl (129 mg, 0.84 mmol) and imidazole (57 mg, 0.84 mmol) in DMF (3 mL) was stirred at RT overnight. The mixture was concentrated and the residue taken-up in CH$_2$Cl$_2$, 1N aqueous HCl was added, the layers were separated and the aqueous one back-extracted with CH$_2$Cl$_2$. The organic extracts were washed with brine, dried over Na$_2$SO$_4$, filtered and concentrated. The crude residue was purified by flash column chromatography on silica gel (c-hexane/EtOAc gradient 100:0 to 1:1) to give the title compound. MS (LC/MS): 509.2 [M+H]+; $t_R$ (HPLC conditions b): 5.99 min.

B. (2S,5R)-5-(tert-Butyl-dimethyl-silanyloxymethyl)-pyrrolidine-2-carboxylic acid (3-trifluoromethoxy-phenyl)-amide To a solution of (2S,5R)-1-benzyl-5-(tert-butyl-dimethyl-silanyloxymethyl)-pyrrolidine-2-carboxylic acid (3-trifluoromethoxy-phenyl)-amide (97 mg, 0.19 mmol) in THF (1 mL) was added Pd/C (10%, 20 mg). The solution was degassed 3 times replacing air by nitrogen and finally nitrogen by hydrogen. The reaction mixture was further stirred under hydrogen atmosphere overnight. The catalyst was removed through a pad of Celite and washed with THF. Solvent was concentrated and the crude residue was purified by preparative HPLC (Waters SunFire C18-ODB 5 μm, 19×50, 5-100% $CH_3CN/H_2O$ in 17 min, 100% $CH_3CN$ for 3 min, $CH_3CN$ and $H_2O$ containing 0.1% TFA, flow: 20 mL/min) to give the desired compound. MS (LC/MS): 419 [M+H]+; $t_R$ (HPLC conditions b): 5.28 min.

Scheme B4: preparation of (2S,5R)-5-(acetylamino-methyl)-pyrrolidine-2-carboxylic acid(3-trifluoromethoxy-phenyl)-amide

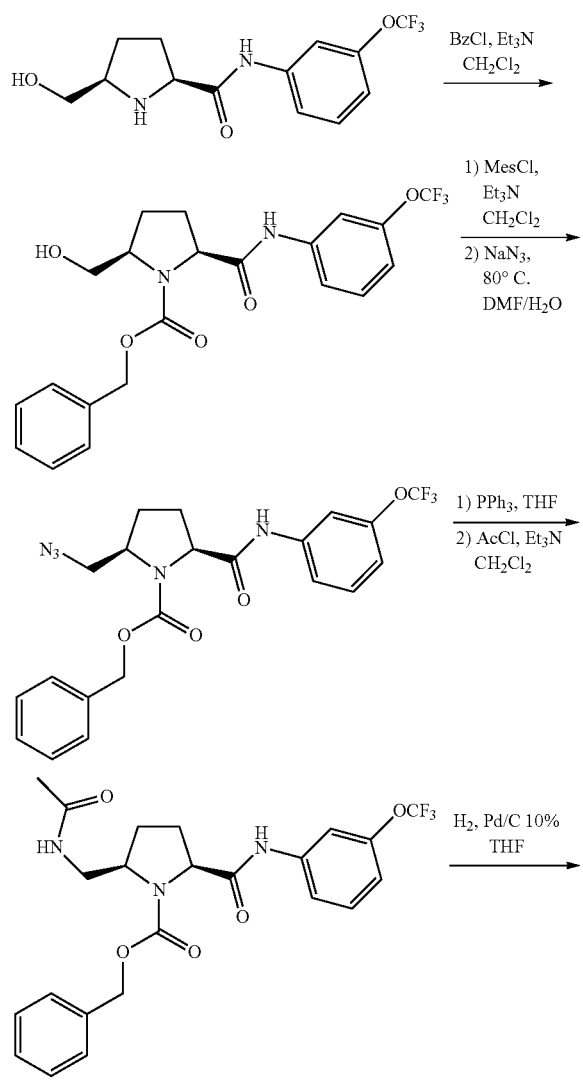

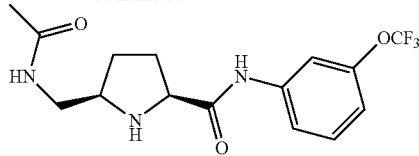

A. (2R,5S)-2-Hydroxymethyl-5-(3-trifluoromethoxy-phenylcarbamoyl)-pyrrolidine-1-carboxylic acid benzyl ester To a solution of (2S,5R)-5-hydroxymethyl-pyrrolidine-2-carboxylic acid (3-trifluoromethoxy-phenyl)-amide (797 mg, 2.62 mmol) (prepared as described in Scheme B3) in $CH_2Cl_2$ (10 mL) was added under nitrogen atmosphere $Et_3N$ (440 μl, 3.14 mmol) and benzylchloroformate (406 μl, 2.88 mmol) and the mixture was further stirred at RT overnight. $CH_2Cl_2$ and HCl 0.1N were added, the layers were separated and the aqueous one re-extracted with $CH_2Cl_2$. The crude organic extracts were washed with brine dried over $Na_2SO_4$, filtered and concentrated. The crude material was purified by flash column chromatography on silica gel (c-hexane/EtOAc gradient 100:0 to 1:1) to give the title compound. MS (LC-MS): 439 [M+H]+; $t_R$ (HPLC conditions b) 4.88 min.

B. (2R,5S)-2-Methanesulfonyloxymethyl-5-(3-trifluoromethoxy-phenylcarbamoyl)-pyrrolidine-1-carboxylic acid benzyl ester To a solution of (2R,5S)-2-hydroxymethyl-5-(3-trifluoromethoxy-phenylcarbamoyl)-pyrrolidine-1-carboxylic acid benzyl ester (500 mg, 1.14 mmol) in $CH_2Cl_2$ (5 mL) was added at 0° C. under nitrogen atmosphere $Et_3N$ (350 μl, 2.5 mmol) and mesylchloride (197 μl, 2.5 mmol) and the mixture was further stirred at RT for 3 h. $CH_2Cl_2$ and HCl 0.1N were added, the layers were separated and the aqueous one re-extracted with $CH_2Cl_2$. The crude organic extracts were washed with brine dried over $Na_2SO_4$, filtered and concentrated. The crude material was used without further purification in the next step. MS (LC-MS): 517 [MH−Boc]+; $t_R$ (HPLC conditions b) 5.15 min.

C. (2R,5S)-2-Azidomethyl-5-(3-trifluoromethoxy-phenylcarbamoyl)-pyrrolidine-1-carboxylic acid benzyl ester To a solution of (2R,5S)-2-methanesulfonyloxymethyl-5-(3-trifluoromethoxy-phenylcarbamoyl)-pyrrolidine-1-carboxylic acid benzyl ester (589 mg, 1.14 mmol) in DMF (4.5 mL) was added a solution of sodium azide (371 mg, 5.7 mmol) in water (0.5 mL) and the mixture was stirred at 80° C. under nitrogen atmosphere overnight. EtOAc and a water were added, the layers were separated and the aqueous one back-extracted with EtOAc. The combined organic extracts were washed with brine, dried over $Na_2SO_4$, filtered and concentrated. The crude residue was purified by flash column chromatography on silica gel (c-hexane/EtOAc gradient 100:0 to 6:5) to give the desired compound. MS (LC-MS): 464 [MH−Boc]+; $t_R$ (HPLC conditions b) 5.73 min.

D. (2R,5S)-2-Aminomethyl-5-(3-trifluoromethoxy-phenylcarbamoyl)-pyrrolidine-1-carboxylic acid benzyl ester A mixture of (2R,5S)-2-azidomethyl-5-(3-trifluoromethoxy-phenylcarbamoyl)-pyrrolidine-1-carboxylic acid benzyl ester (460 mg, 0.99 mmol) and triphenylphosphine (312 mg, 1.19 mmol) in THF (4 mL) was stirred at RT overnight. After completion of the reaction, THF was removed and the crude reaction mixture was purified by preparative HPLC (Waters SunFire C18-ODB 5 μm, 19×50, 5-100% CH$_3$CN/H$_2$O in 17 min, 100% CH$_3$CN for 3 min, CH$_3$CN and H$_2$O containing 0.1% TFA, flow: 20 mL/min) to give the title compound. MS: 438 [M+H]+; $t_R$ (HPLC conditions b): 3.8 min.

E. (2R,5S)-2-(Acetylamino-methyl)-5-(3-trifluoromethoxy-phenylcarbamoyl)-pyrrolidine-1-carboxylic acid benzyl ester To a solution of (2R,5S)-2-aminomethyl-5-(3-trifluoromethoxy-phenylcarbamoyl)-pyrrolidine-1-carboxylic acid benzyl ester (200 mg), and Et$_3$N (77 μL, 0.55 mmol) in CH$_2$Cl$_2$ (3 mL) was added under nitrogen atmosphere at 0° C. acetyl chloride (39 μL, 0.55 mmol) and the mixture was stirred at 0° C. for 1 h. CH$_2$Cl$_2$ and 1N aqueous HCl were added, the layers were separated and the aqueous one back-extracted with CH$_2$Cl$_2$. The combined organic extracts were washed with brine, dried over Na$_2$SO$_4$, filtered and concentrated. The crude residue was purified by flash column chromatography on silica gel (c-hexane/EtOAc gradient 100:0 to 0:100) to give the title compound. MS (LC/MS): 480.1 [M+H]+; $t_R$ (HPLC conditions b): 4.69 min.

F. (2S,5R)-5-(Acetylamino-methyl)-pyrrolidine-2-carboxylic acid (3-trifluoromethoxy-phenyl)-amide To a solution of (2R,5S)-2-(acetylamino-methyl)-5-(3-trifluoromethoxy-phenylcarbamoyl)-pyrrolidine-1-carboxylic acid benzyl ester (48 mg, 0.1 mmol) in THF (0.3 mL) was added Pd/C (10%, 2.1 mg). The solution was degassed 3 times replacing air by nitrogen and finally nitrogen by hydrogen. The reaction mixture was further stirred under hydrogen atmosphere for 5 h. The catalyst was removed through a pad of Celite and washed with THF. Solvents were concentrated and the resulting residue was used without further purification in the next step. MS (LC/MS): 346 [M+H]+; $t_R$ (HPLC conditions b): 2.94 min.

Scheme B5: preparation of 3,4-dihydro-2H-pyrazole-3-carboxylic acid 3-chloro-2-fluoro-benzylamide

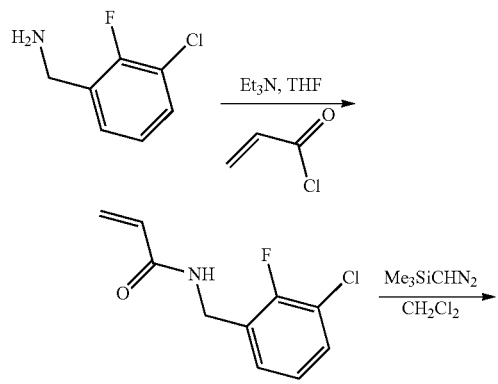

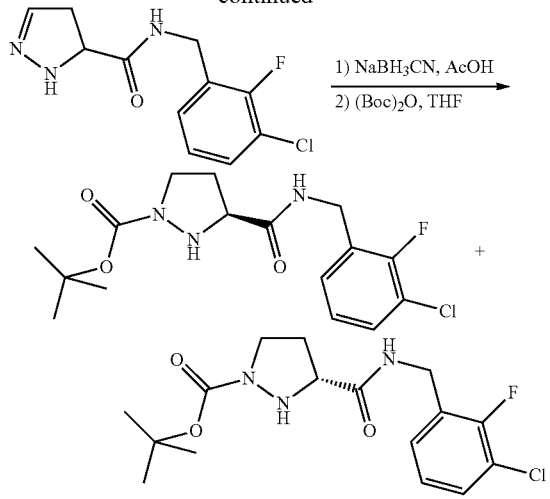

A. N-(3-Chloro-2-fluoro-benzyl)-acrylamide

To a solution of 2-fluoro-3-chlorobenzylamine (1 g, 6.27 mmol) and TEA (1.05 mL, 7.52 mmol) in THF (20.9 mL) was added acryloyl chloride (0.61 mL, 7.52 mmol) dropwise and the reaction mixture was stirred at 23° C. for 2 h. The reaction mixture was diluted in EtOAc, HCl 1N was added and the layers separated. The aqueous layer was extracted again with EtOAc and the combined organic layers were dried, filtered and concentrated to dryness. The crude residue was purified by flash column chromatography on silica gel (xyclohexane/EtOAc gradient 100:0 to 1:1) to give the desired material. TLC, R$_f$ (c-hexane/EtOAc 5:5)=0.41; MS (LC/MS): 214.0 [M+H]+; $t_R$ (HPLC conditions b): 3.35 min.

B. (S)-3,4-Dihydro-2H-pyrazole-3-carboxylic acid 3-chloro-2-fluoro-benzylamide To a solution of N-(3-chloro-2-fluoro-benzyl)-acrylamide (1.25 g, 5.85 mmol) in 1/1 mixture of toluene (58.5 mL)/hexane (58.5 mL) was added trimethylsilyldiazomethane (5.85 mL, 11.7 mmol, 2M in hexane). The reaction was stirred at 23° C. for 20 h until completion. Solvents were removed in vacuo then CH$_2$Cl$_2$ (58.5 mL) was added followed by TFA (0.49 mL, 6.44 mmol) and the reaction mixture was further stirred at 23° C. for 1 h. The reaction mixture was quenched with NaHCO$_3$ 5% aqueous solution and extracted with CH$_2$Cl$_2$. The combined organic layers were dried, filtered and evaporated to dryness. The crude residue was purified by flash column chromatography on silica gel (c-hexane/EtOAc gradient 100:0 to 0:100) followed by preparative HPLC (Waters SunFire C180 DB, 5 μm, 30×100, eluent: 20% CH$_3$CN/80% H$_2$O to 100% CH$_3$CN in 20 min, CH$_3$CN and H$_2$O containing 0.1% of TFA, flow 40 mL/min) to give the desired material after lyophilization of the purified fractions. TLC, R$_f$ (Et OAc)=0.23; MS (LC-MS): 256.0 [M+H]+; $t_R$ (HPLC conditions b): 2.53 min.

C. (S)-3-(3-Chloro-2-fluoro-benzylcarbamoyl)-pyrazolidine-1-carboxylic acid tert-butyl ester and (R)-3-(3-Chloro-2-fluoro-benzylcarbamoyl)-pyrazolidine-1-carboxylic acid tert-butyl ester To a solution of pyrazolidine-3-carboxylic acid 3-chloro-2-fluoro-benzylamide (600 mg, 2.35 mmol) in acetic acid glacial (10.4 mL) was added NaCNBH₃ (369 mg, 5.87 mmol) and the reaction mixture was stirred at 23° C. for 2 h. The reaction mixture was diluted with EtOAc and quenched with a saturated aqueous K₂CO₃ solution. The layers were separated and the aqueous one extracted again with EtOAc. The combined organic layers were dried, filtered and evaporated to dryness to give the desired material which was used in the next step without purification. The residue was dissolved in THF (9.4 mL), Boc₂O (0.817 mL, 3.52 mmol), TEA (0.654 mL, 4.69 mmol) and DMAP (28.7 mg, 0.235 mmol) were added and the reaction mixture was stirred at 23° C. for 2 h. The crude was concentrated and purified by flash column chromatography on silica gel (c-hexane/EtOAc gradient 100:0 to 0:100) to give the desired racemic material. TLC, $R_f$ (EtOAc)=0.4; MS (LC/MS): 380 [M+Na]+, 258 [MH–Boc]+; $t_R$ (HPLC conditions b): 4.22 min.

The racemic mixture was purified by chiral preparative HPLC (Chiralpak AD 00SC-JF004, 5×50 cm, heptane/isopropanol 90/10, flow 35 mL/min, detection 210 nM) to give peak 1 ($t_R$: 61.43 min) and peak 2 ($t_R$: 99.77 min). Peak 1: (R$^§$)-3-(3-chloro-2-fluoro-benzylcarbamoyl)-pyrazolidine-1-carboxylic acid tert-butyl ester, MS: 258.0 [MH+–boc], 379.9 [MNa+]; $t_R$ (HPLC, Chiralpak AD, 250 mm×4.6 mm, heptane/isopropanol 91/10, flow 1 mL/min, detection 220 nM): 14.1 min. Peak 2: (S)-3-(3-chloro-2-fluoro-benzylcarbamoyl)-pyrazolidine-1-carboxylic acid tert-butyl ester, MS: 258.0 [MH+–boc] [MH+], 379.9 [MNa+]; $t_R$ (HPLC, Chiralpak AD, 250 mm×4.6 mm, heptane/isopropanol 91/10, flow 1 mL/min, detection 220 nM): 22.37 min. The absolute stereochemistry has been assigned tentatively based on the test results for the final compounds Example 432 and Example 433 in the biological assay.

Scheme B6: preparation of ((2S,4S)-4-[Methyl-(2,2,2-trichloro-ethoxycarbonyl)-amino]-pyrrolidine-1,2-dicarboxylic acid tert-butyl ester

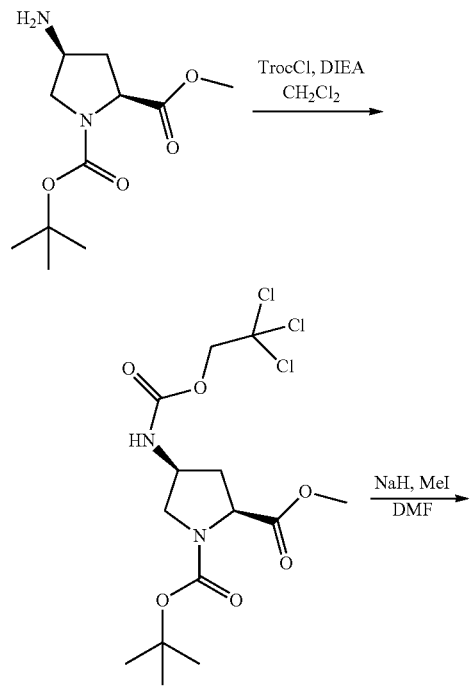

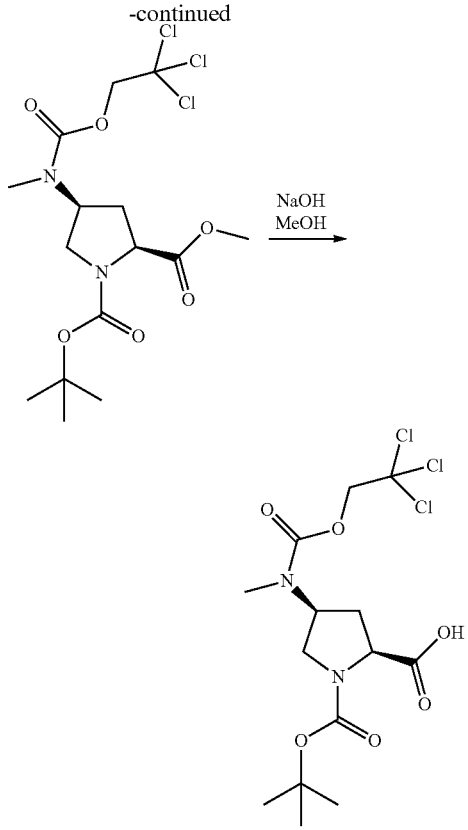

A. (2S,4S)-4-(2,2,2-Trichloro-ethoxycarbony-lamino)-pyrrolidine-1,2-dicarboxylic acid 1-tert-butyl ester 2-methyl ester To a solution of (2S,4S)-1-tert-butyl 2-methyl 4-aminopyrrolidine-1,2-dicarboxylate (4.6 g, 10.7 mmol) in CH₂Cl₂ (100 mL) were added 2,2,2-trichloroethyl carbonochloridate (1.73 mL, 12.88 mmol) and DIPEA (2.81 mL, 16.1 mmol). The reaction mixture was stirred at RT for 2 h then was poured into water. The desired compound was extracted with EtOAc (2×100 mL), the organic phases were joined, washed with 1N HCl then brine, dried over Na₂SO₄, filtered and concentrated. The crude residue was purified by flash column chromatography on silica gel (c-hexane to c-hexane/EtOAc 1:1). MS (UPLC): 421 [M+H]+, 419 [M–H]–; $t_R$ (HPLC conditions f): 1.11 min.

B. (2S,4S)-4-[Methyl-(2,2,2-trichloro-ethoxycarbonyl)-amino]-pyrrolidine-1,2-dicarboxylic acid 1-tert-butyl ester 2-methyl ester To a solution of (2S,4S)-4-(2,2,2-trichloro-ethoxycarbonylamino)-pyrrolidine-1,2-dicarboxylic acid 1-tert-butyl ester 2-methyl ester (420 mg, 1 mmol) and methyl iodide (0.18 mL, 3 mmol) in DMF (10 mL) cooled at 0° C. under argon was added sodium hydride (44 mg, 1.1 mmol). The reaction mixture was stirred at RT for 2 h then was poured into water. The desired compound was extracted with EtOAc (2×25 mL), the organic phases were joined, washed with 1N HCl then brine, dried over Na₂SO₄, filtered and concentrated. The crude residue was purified by flash column chromatography on silica gel (c-hexane to c-hexane/EtOAc 1:1). MS (UPLC): 436 [M+H]+, 434 [M–H]–; $t_R$ (HPLC conditions f): 2.35 min.

C. (2S,4S)-4-[Methyl-(2,2,2-trichloro-ethoxycarbonyl)-amino]-pyrrolidine-1,2-dicarboxylic acid 1-tert-butyl ester To a solution of ((2S,4S)-4-[methyl-(2,2,2-trichloro-ethoxycarbonyl)-amino]-pyrrolidine-1,2-dicarboxylic acid 1-tert-butyl ester 2-methyl ester (360 mg, 0.83 mmol) in MeOH (20 mL) was added aq. 1N NaOH (1.66 mL, 1.66 mmol). The reaction was stirred at RT for 16 h then was concentrated. The residue was acidified with aq 2N HCl to pH 3, extracted with EtOAc (2×25 mL). The organic phases were joined, dried over $Na_2SO_4$, filtered and concentrated. The crude residue was used without further purification in the next step. MS (UPLC): 421 [M+H]+, 419 [M–H]–; $t_R$ (HPLC conditions f): 1.00 min.

Scheme B7: preparation of (2S,4R)-2-(3-Bromo-5-carboxy-phenylcarbamoyl)-4-fluoro-pyrrolidine-1-carboxylic acid tert-butyl ester

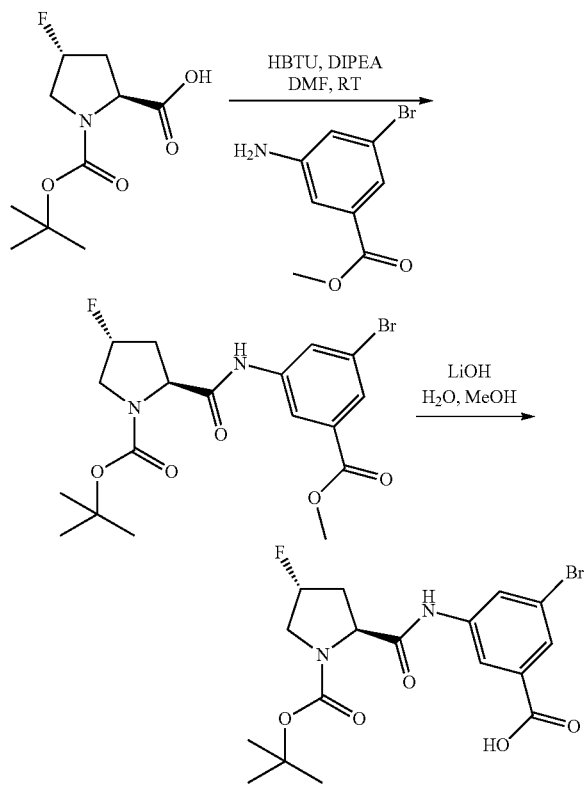

A. (2S,4R)-2-(3-Bromo-5-methoxycarbonyl-phenylcarbamoyl)-4-fluoro-pyrrolidine-1-carboxylic acid tert-butyl ester To a mixture of N-Boc-trans-4-fluoro-L-proline (500 mg, 2.14 mmol), methyl 3-amino-5-bromobenzoate (592 mg, 2.57 mmol) and HBTU (1.22 g, 3.22 mmol) in DMF (6 mL) was added DIPEA (734 μl, 4.29 mmol) and the resulting solution was stirred at RT under nitrogen overnight. The mixture was poured into water and extracted three times with EtOAc. The combined organic layers were washed twice with water, dried over $Na_2SO_4$, filtered and concentrated. The crude residue was purified by flash column chromatography on silica gel (c-hexane 100% to c-hexane/EtOAc 70:30) to give the desired material. TLC, $R_f$(c-hexane/EtOAc 1:2)=0.8; MS (LC/MS): 467.0/469.0 [M+Na]+, 345.1/347.0 [MH–Boc]+, 443.1/445.1 [M–H]–; tR (HPLC conditions a): 3.77 min.

B. (2S,4R)-2-(3-Bromo-5-carboxy-phenylcarbamoyl)-4-fluoro-pyrrolidine-1-carboxylic acid tert-butyl ester To a solution of (2S,4R)-2-(3-bromo-5-methoxycarbonyl-phenylcarbamoyl)-4-fluoro-pyrrolidine-1-carboxylic acid tert-butyl ester (480 mg, 1.08 mmol) in MeOH (10 mL), cooled to 0° C. was added $LiOH.H_2O$ (271 mg, 6.47 mmol) and the resulting solution was allowed to reach RT and stirred for 5 h. MeOH was concentrated and the residue was diluted in $CH_2Cl_2$, HCl 1 M was added (pH=1) and the layers were separated. The aqueous layer was back extracted twice with $CH_2Cl_2$ and the combined organic layers were dried over $Na_2SO_4$, filtered and concentrated to give the desired material which was used without further purification in the next step. MS (LC-MS): 453.0/455.0 [M+Na]+, 375.1/377.1 [MH–tBu]+, 331.1/333.1 [MH–Boc]+, 429.0/431.0 [M–H]–; $t_R$ (HPLC conditions a): 3.27 min.

(2S,4R)-2-(3-Bromo-4-carboxy-phenylcarbamoyl)-4-fluoro-pyrrolidine-1-carboxylic acid tert-butyl ester

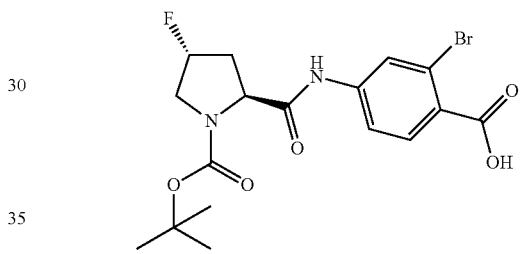

A. (2S,4R)-2-(3-Bromo-4-methoxycarbonyl-phenylcarbamoyl)-4-fluoro-pyrrolidine-1-carboxylic acid tert-butyl ester A mixture of (2S,4R)-4-fluoro-pyrrolidine-1,2-dicarboxylic acid 1-tert-butyl ester (355 mg, 1.52 mmol), and 4-amino-2-bromo-benzoic acid methyl ester (prepared as described in Part C) (350 mg, 1.52 mmol), HBTU (865 mg, 2.282 mmol) and DIPEA (0.531 mL, 3.04 mmol) in $CH_2Cl_2$ (15 mL) was stirred at RT for 60 h. Additional aliquots of (2S,4R)-4-fluoro-pyrrolidine-1,2-dicarboxylic acid 1-tert-butyl ester (180 mg), HBTU (580 mg) and DIPEA (0.265 mL) were added to the mixture, and stirring was continued at RT for 20 h and subsequently at 40° C. for 24 h. The reaction mixture was diluted with $CH_2Cl_2$ and the organic layer was washed with water, 1N aqueous HCl (3×), aqueous $NaHCO_3$ solution (2×) and brine, dried (Phase separator) and concentrated in vacuo. The residue was purified by flash column chromatography on silica gel (eluent: EtOAc/c-hexane gradient 1:3 to 1:2) to afford the title compound as a white foam. TLC $R_f$ (EtOAc/c-hexane 1:2)=0.24; MS (LC/MS): 468 [M+Na]+, 388/390 [MH–tBu]+, 345/347 [MH–Boc]+; $t_R$ (HPLC conditions b): 4.36 min.

B. (2S,4R)-2-(3-Bromo-4-carboxy-phenylcarbamoyl)-4-fluoro-pyrrolidine-1-carboxylic acid tert-butyl ester To a solution of (2S,4R)-2-(3-bromo-4-methoxycarbonyl-phenylcarbamoyl)-4-fluoro-pyrrolidine-1-carboxylic acid tert-butyl ester (400 mg, 0.898 mmol) in MeOH (9 mL) was added a 2N aqueous NaOH solution (1.78 mL, 3.59 mmol). The reaction mixture was stirred at RT for 20 h and then evaporated under reduced pressure. The residue was taken up in water and the aqueous phase was acidified (pH 2 to 3) by adding 0.1N aqueous HCl. The resulting suspension was extracted with EtOAc (4×) and the combined organics were concentrated under reduced pressure to afford the crude title compound as a pale yellow solid. This product was used in the next reaction step without further purification. MS (LC/MS): 454 [M+Na]+, 374 [MH−tBu]+, 330 [MH−Boc]+; $t_R$ (HPLC conditions b): 3.41 min.

(2S,4R)-2-{[carboxy-(3-chloro-phenyl)-methyl]-carbamoyl}-4-fluoro-pyrrolidine-1-carboxylic acid tert-butyl ester

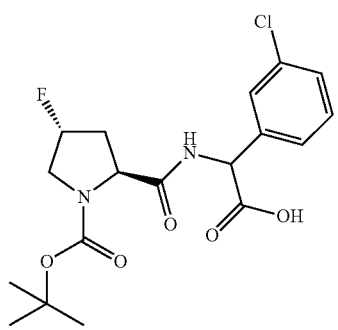 [SMILES: CC(C)(C)OC(=O)N1C[C@H](F)C[C@H]1C(=O)NC(C(=O)O)c1cccc(Cl)c1]

(2S,4R)-2-{[(3-Chloro-phenyl)-methoxycarbonyl-methyl]-carbamoyl}-4-fluoro-pyrrolidine-1-carboxylic acid tert-butyl ester To a mixture of N-Boc-trans-4-fluoro-L-proline (200 mg, 0.86 mmol), amino-(3-chloro-phenyl)-acetic acid methyl ester (233 mg, 0.94 mmol) and HBTU (488 mg, 1.29 mmol) in DMF (2.5 mL) was added DIPEA (294 µl, 1.72 mmol) and the mixture was stirred at RT under nitrogen overnight. Then poured into water and extracted twice with EtOAc. The combined organic layers were washed again with water, dried over Na$_2$SO$_4$, filtered and concentrated. The crude residue was purified by flash column chromatography on silica gel (CH$_2$Cl$_2$ to CH$_2$Cl$_2$/MeOH 9:1) to give the desired material. TLC, $R_f$ (CH$_2$Cl$_2$/MeOH 4:1)=0.3; MS (LC/MS): 437.0 [M+Na]+, 315.1 [MH−Boc]+, 413.0 [M−H]−; $t_R$ (HPLC conditions a): 3.59 min.

(2S,4R)-2-{[carboxy-(3-chloro-phenyl)-methyl]-carbamoyl}-4-fluoro-pyrrolidine-1-carboxylic acid tert-butyl ester To a solution of (2S,4R)-2-{[(3-chloro-phenyl)-methoxycarbonyl-methyl]-carbamoyl}-4-fluoro-pyrrolidine-1-carboxylic acid tert-butyl ester (diastereomeric mixture, 365 mg, 0.88 mmol) in MeOH (8 mL) was added LiOH.H$_2$O (222 mg, 5.28 mmol) at 0° C. The solution was slowly allowed to reach RT and stirred for 1 h. MeOH was concentrated and the residue was diluted in CH$_2$Cl$_2$ and acidified by addition of HCl 1N. The layers were separated and the aqueous one extracted twice with CH$_2$Cl$_2$. The combined organic layers were dried over Na$_2$SO$_4$, filtered and concentrated to give the desired material. TLC, $R_f$(EtOAc)=0.1; MS (LC-MS): 301.0/303.0 [MH−Boc]+; $t_R$ (HPLC conditions a): 3.20 min.

3-Chloro-4-fluoro-5-{[((2S,4R)-4-fluoro-pyrrolidine-2-carbonyl)-amino]-methyl}-benzoic acid

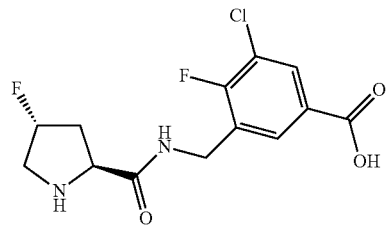 [SMILES: O=C(O)c1cc(Cl)c(F)c(CNC(=O)[C@@H]2C[C@@H](F)CN2)c1]

(2S,4R)-2-(3-Chloro-2-fluoro-5-methoxycarbonyl-benzylcarbamoyl)-4-fluoro-pyrrolidine-1-carboxylic acid tert-butyl ester To a mixture of N-boc-trans-4-fluoro-L-proline (143 mg, 0.61 mmol), 3-aminomethyl-5-chloro-4-fluoro-benzoic acid methyl ester (prepared as described in Part C, 275 mg, 0.61 mmol) and HATU (0.35 g, 0.92 mmol) in DMF (4 mL) was added DIPEA (430 µl, 2.45 mmol) and the resulting solution was stirred overnight at ambient temperature. The reaction mixture was splitted in two batches and the crude product was purified without aqueous workup by RP-preparative HPLC (Waters Sunfire, C18-ODB, 5 µm, 30×100 mm, 5-100% CH$_3$CN/H$_2$O/20 min, 100% CH$_3$CN/2 min, CH$_3$CN and H$_2$O containing 0.1% TFA, flow: 40 ml/min) to give the title compound. MS (LC-MS): 333.0 [M−100]+; $t_R$ (HPLC conditions c): 5.05 min.

(2S,4R)-2-(5-Carboxy-3-chloro-2-fluoro-benzylcarbamoyl)-4-fluoro-pyrrolidine-1-carboxylic acid tert-butyl ester To a mixture of (2S,4R)-2-(3-chloro-2-fluoro-5-methoxycarbonyl-benzylcarbamoyl)-4-fluoro-pyrrolidine-1-carboxylic acid tert-butyl ester (140 mg, 0.3 mmol) in THF/MeOH/H$_2$O 2:1:1 (4 mL) was added LiOH (7 mg, 0.3 mmol). The reaction mixture was stirred for 4 h at ambient temperature and the solvent was removed in vacuo to give the title compound which was used without further purification. MS (LC/MS): 319.0 [M−100]+. $t_R$ (HPLC conditions c): 4.40 min.

3-Chloro-4-fluoro-5-{[((2S,4R)-4-fluoro-pyrrolidine-2-carbonyl)-amino]-methyl}-benzoic acid To a mixture of (2S,4R)-2-(5-carboxy-3-chloro-2-fluoro-benzylcarbamoyl)-4-fluoro-pyrrolidine-1-carboxylic acid tert-butyl ester (146 mg, 0.3 mmol) in CH$_2$Cl$_2$ (4 mL) was added TFA (1 mL). The reaction mixture was stirred for 1 h at ambient temperature and the solvent was removed in vacuo to give the title compound which was used without further purification. $t_R$ (HPLC conditions c): 3.11 min.

Scheme B8: preparation of (1R,3S,5R)-2-aza-bicyclo[3.1.0]hexane-3-carboxylic acid [3-bromo-5-(1H-tetrazol-5-yl)-phenyl]-amide and (1R,3S,5R)-2-aza bicyclo[3.1.0]hexane-3-carboxylic acid [3-bromo-5-(1-tert-butyl-1H-tetrazol-5-yl)-phenyl]-amide

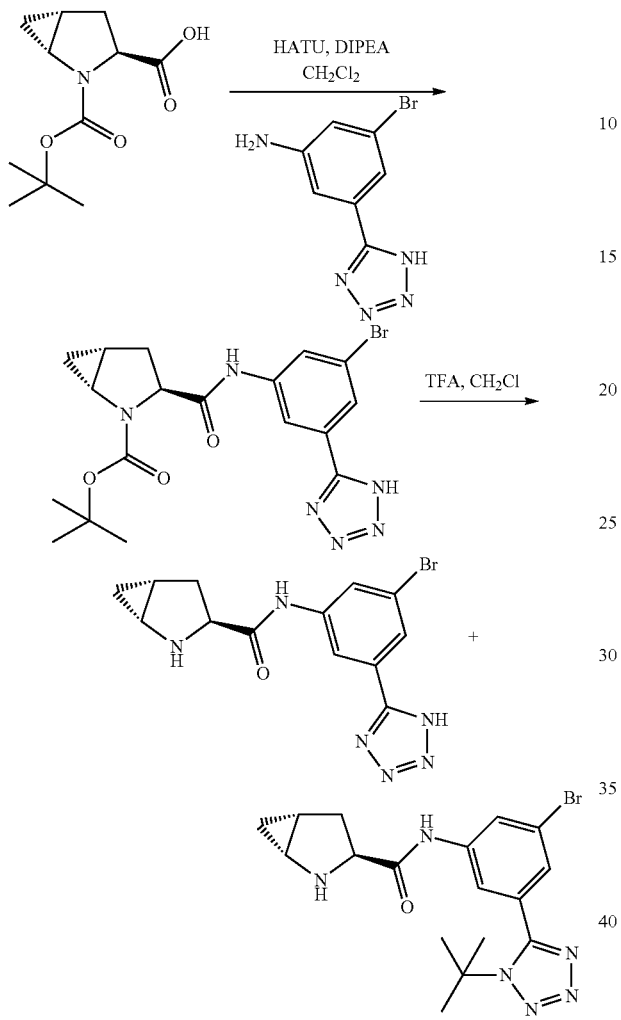

A. (1R,3S,5R)-3-[3-Bromo-5-(1H-tetrazol-5-yl)-phenylcarbamoyl]-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (250 mg, 1.1 mmol) in CH$_2$Cl$_2$ (6 mL) was added 3-bromo-5-(1H-tetrazol-5-yl)-phenylamine dihydrochloride (prepared as described in Part C, 365 mg, 1.32 mmol), HBTU (626 mg, 1.65 mmol) and DIPEA (0.576 ml, 3.3 mmol). The reaction mixture was stirred at RT overnight. The reaction mixture was diluted with CH$_2$Cl$_2$ and successively washed with 1 M aqueous HCl solution (30 mL) and a saturated aqueous NaHCO$_3$ solution. The organic phase was dried (phase separator) and evaporated under vacuum. The crude mixture was purified by preparative HPLC (C18 Nucleosil 100-10, flow: 40 ml/min, eluent: 5-100% CH$_3$CN/H$_2$O/20 min, 100% CH$_3$CN/2 min, CH$_3$CN and H$_2$O containing 0.1% TFA). After combination of the purified fractions, CH$_3$CN was removed under vacuum and lyophilization gave the desired compound. MS (LC/MS): 447.1 [M−H]−; t$_R$ (HPLC conditions k): 4.62 min.

B. (1R,3S,5R)-2-Aza-bicyclo[3.1.0]hexane-3-carboxylic acid [3-bromo-5-(1H-tetrazol-5-yl)-phenyl]-amide and (1R,3S,5R)-2-Aza-bicyclo[3.1.0]hexane-3-carboxylic acid [3-bromo-5-(1-tert-butyl-1H-tetrazol-5-yl)-phenyl]-amide To a solution of (1R,3S,5R)-3-[3-bromo-5-(1H-tetrazol-5-yl)-phenylcarbamoyl]-2-aza-bicyclo[3.1.0]hexane-2-carboxylic acid tert-butyl ester (200 mg, 0.445 mmol) in CH$_2$Cl$_2$ (2 mL) was added TFA (0.686 ml, 8.9 mmol). The reaction mixture was stirred at RT for 4 h. After completion the reaction mixture was diluted with CH$_2$Cl$_2$ and MeOH and the volatiles were removed under vacuum. MeOH was added and the reaction mixture concentrated again under vacuum. This operation was repeated twice to afford a mixture in a 2/3 ratio of (1R,3S,5R)-2-aza-bicyclo[3.1.0]hexane-3-carboxylic acid [3-bromo-5-(1H-tetrazol-5-yl)-phenyl]-amide: MS (LC/MS): 349.2 [M+H]+; t$_R$ (HPLC conditions k): 3.06 min and (1R,3S,5R)-2-aza-bicyclo[3.1.0]hexane-3-carboxylic acid [3-bromo-5-(1-tert-butyl-1H-tetrazol-5-yl)-phenyl]-amide: MS (LC/MS): 405.3 [M+H]+; t$_R$ (HPLC conditions k): 4.46 min.

(2S,4R)-4-Fluoro-pyrrolidine-2-carboxylic acid 3-chloro-2-fluoro-5-(2H-tetrazol-5-β-benzylamide and (2S,4R)-4-Fluoro-pyrrolidine-2-carboxylic acid 5-(1-tert-butyl-1H-tetrazol-5-yl)-3-chloro-2-fluoro-benzylamide

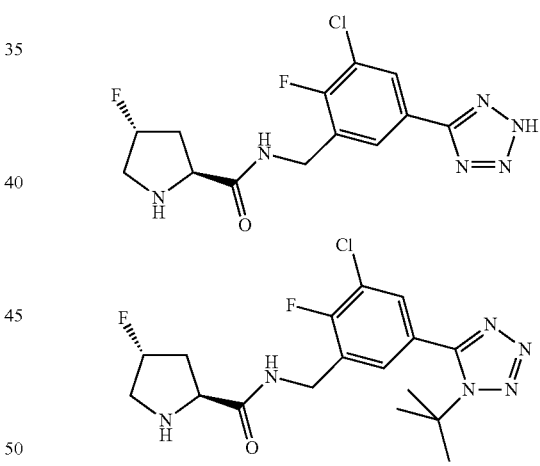

To a solution of a 1:2 mixture of (2S,4R)-2-[5-(1-tert-butyl-1H-tetrazol-5-yl)-3-chloro-2-fluoro-benzylcarbamoyl]-4-fluoro-pyrrolidine-1-carboxylic acid tert-butyl ester and (2S,4R)-2-[3-chloro-2-fluoro-5-(2H-tetrazol-5-yl)-benzylcarbamoyl]-4-fluoro-pyrrolidine-1-carboxylic acid tert-butyl ester (86 mg, 0.19 mmol) in CH$_2$Cl$_2$ (3 mL) was added TFA (1 mL) and the reaction mixture was stirred for 2 h at ambient temperature. The solvent was removed in vacuo to give the title compounds which were used without separation in the next step. (2S,4R)-4-Fluoro-pyrrolidine-2-carboxylic acid 3-chloro-2-fluoro-5-(2H-tetrazol-5-yl)-benzylamide: MS (LC-MS): 343.0 [M]+; t$_R$ (HPLC conditions c): 2.47 min and (2S,4R)-4-fluoro-pyrrolidine-2-carboxylic acid 5-(1-tert-butyl-1H-tetrazol-5-yl)-3-chloro-2-fluoro-benzylamide: MS (LC-MS): 399.0 [M]+; t$_R$ (HPLC conditions c): 3.16 min.

(2S,4R)-2-[3-Chloro-2-fluoro-5-(2H-tetrazol-5-yl)-benzylcarbamoyl]-4-fluoro-pyrrolidine-1-carboxylic acid tert-butyl ester and (2S,4R)-2-[5-(1-tert-Butyl-1H-tetrazol-5-yl)-3-chloro-2-fluoro-benzylcarbamoyl]-4-fluoro-pyrrolidine-1-carboxylic acid tert-butyl ester To a mixture of N-boc-trans-4-fluoro-L-proline (107 mg, 0.46 mmol) and HATU (260 mg, 0.69 mmol) in DMF (2 mL) was added a 1:2 mixture of 5-(1-tert-butyl-1H-tetrazol-5-yl)-3-chloro-2-fluoro-benzylamine and 3-chloro-2-fluoro-5-(2H-tetrazol-5-yl)-benzylamine (preparation described in Part C, 220 mg, 0.46 mmol) and DIPEA (319 µl, 1.8 mmol) and the resulting solution was stirred overnight at ambient temperature. The reaction mixture was purified without aqueous workup by RP-preparative HPLC (Waters Sunfire, C18-ODB, 5 µm, 30×100 mm, 5-100% $CH_3CN/H_2O/20$ min, 100% $CH_3CN/2$ min, $CH_3CN$ and $H_2O$ containing 0.1% TFA, flow: 40 ml/min) to give the title compounds (2S,4R)-2-[3-chloro-2-fluoro-5-(2H-tetrazol-5-yl)-benzylcarbamoyl]-4-fluoro-pyrrolidine-1-carboxylic acid tert-butyl ester: MS (LC-MS): 343.0 [M−100]+; $t_R$ (HPLC conditions c): 3.27 min and (2S,4R)-2-[5-(1-tert-butyl-1H-tetrazol-5-yl)-3-chloro-2-fluoro-benzylcarbamoyl]-4-fluoro-pyrrolidine-1-carboxylic acid tert-butyl ester: MS (LC-MS): 499.0 [M]+; $t_R$ (HPLC conditions c): 4.02 min.

Scheme B9: preparation of (1R,3S,5R)-3-[(S)-1-(3-Chloro-2-fluoro-phenyl)-2-methoxy-ethylcarbamoyl]-2-aza-bicyclo[3.1.0]hexane-2-carboxylic acid tert-butyl ester

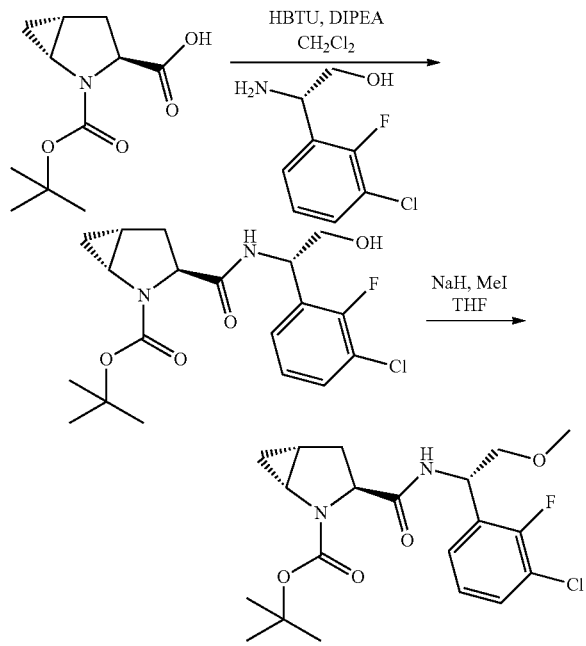

A. (1R,3S,5R)-3-[(S)-1-(3-Chloro-2-fluoro-phenyl)-2-hydroxy-ethylcarbamoyl]-2-aza-bicyclo[3.1.0]hexane-2-carboxylic acid tert-butyl ester To a mixture of (1R,3S,5R)-2-aza-bicyclo[3.1.0]hexane-2,3-dicarboxylic acid 2-tert-butyl ester (750 mg, 3.30 mmol), (2S)-2-amino-2-(3-chloro-2-fluorophenyl)ethan-1-ol (746 mg, 3.30 mmol) and HBTU (1.75 g, 4.62 mmol) in $CH_2Cl_2$ (30 mL) was added under nitrogen DIPEA (2.31 mL, 13.20 mmol). The reaction mixture was stirred at RT overnight. $CH_2Cl_2$ and water were added, the layers were separated and the aqueous one back-extracted with $CH_2Cl_2$ (×3). The combined organic extracts were dried ($Na_2SO_4$), filtered and concentrated. The crude material was purified by flash column chromatography on silica gel (c-hexane/EtOAc 1:1 to EtOAc) to give the desired compound as a colorless oil. MS (UPLC/MS): 399.3/401.3 [M+H]+, 443.4/445.3 [M+HCOO]−; $t_R$ (HPLC conditions a): 3.28 min.

B. (1R,3S,5R)-3-[(S)-1-(3-Chloro-2-fluoro-phenyl)-2-methoxy-ethylcarbamoyl]-2-aza-bicyclo[3.1.0]hexane-2-carboxylic acid tert-butyl ester To a suspension of NaH (60% in mineral oil, 25.7 mg, 0.64 mmol) in THF (3 mL) cooled at 0° C. under Argon was added (1R,3S,5R)-3-[(S)-1-(3-chloro-2-fluoro-phenyl)-2-hydroxy-ethylcarbamoyl]-2-aza-bicyclo[3.1.0]hexane-2-carboxylic acid tert-butyl ester (270 mg, 0.64 mmol). The reaction mixture was stirred at 0° C. for 30 min and iodomethane (0.06 mL, 0.97 mmol) was added. After 1 h the reaction mixture was poured into saturated $NaHCO_3$ aqueous solution. $CH_2Cl_2$ was added, the layers were separated and the aqueous one back-extracted with $CH_2Cl_2$ (×3). The combined organic extracts were dried ($Na_2SO_4$), filtered and concentrated. The crude material was purified by flash column chromatography on silica gel (c-hexane to c-hexane/EtOAc 20:80) the desired compound as a colorless oil. TLC, $R_f$ (EtOAc)=0.65; MS (UPLC/MS): 413.4/415.4 [M+H]+, 457.4/459.4 [M+HCOO]−; $t_R$ (HPLC conditions a): 3.67 min.

(1R,3S,5R)-3-[(R)-1-(3-Chloro-2-fluoro-phenyl)-3-methoxy-propylcarbamoyl]-2-aza-bicyclo[3.1.0]hexane-2-carboxylic acid tert-butyl ester

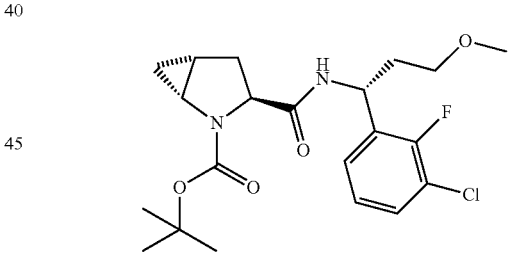

was prepared according to Scheme B9 (Step B) from (1R,3S,5R)-3-[(R)-1-(3-chloro-2-fluoro-phenyl)-3-hydroxy-propylcarbamoyl]-2-aza-bicyclo[3.1.0]hexane-2-carboxylic acid tert-butyl ester. TLC, $R_f$ (EtOAc)=0.82; MS (UPLC/MS): 427.4/429.4 [M+H]+, 471.4 [M+HCOO]−; $t_R$ (HPLC conditions a): 3.71 min.

(1R,3S,5R)-3-[(R)-1-(3-Chloro-2-fluoro-phenyl)-3-hydroxy-propylcarbamoyl]-2-aza-bicyclo[3.1.0]hexane-2-carboxylic acid tert-butyl ester was prepared according to Scheme B9 (Step A) using (3R)-3-amino-3-(3-chloro-2-fluorophenyl)propan-1-ol. TLC, $R_f$ (EtOAc)=0.55; MS (UPLC/MS): 413.4/415.4 [M+H]+, 457.5 [M+HCOO]−; $t_R$ (HPLC conditions a): 3.33 min.

(2S,4R)-2-[(S)-1-(3-Chloro-2-fluoro-phenyl)-2-methoxy-ethylcarbamoyl]-4-fluoro-4-methyl-pyrrolidine-1-carboxylic acid tert-butyl ester

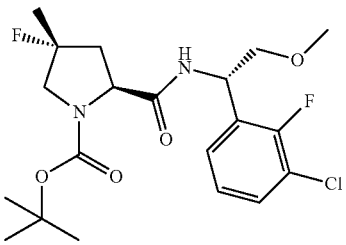 [SMILES: COC[C@@H](NC(=O)[C@@H]1C[C@@](C)(F)CN1C(=O)OC(C)(C)C)c1cccc(Cl)c1F]

was prepared according to Scheme B9 (Step B) from (2S,4R)-2-[(S)-1-(3-chloro-2-fluoro-phenyl)-2-hydroxy-ethylcarbamoyl]-4-fluoro-4-methyl-pyrrolidine-1-carboxylic acid tert-butyl ester. TLC, $R_f$ (EtOAc)=0.90; MS (UPLC-MS): 433.4/435.4 [M+H]+, 477.4 [M+HCOO]−; $t_R$ (HPLC conditions a): 3.73 min.

(2S,4R)-2-[(S)-1-(3-Chloro-2-fluoro-phenyl)-2-hydroxy-ethylcarbamoyl]-4-fluoro-4-methyl-pyrrolidine-1-carboxylic acid tert-butyl ester was prepared according to Scheme B9 (Step A) from (2S,4R)-4-fluoro-4-methyl-pyrrolidine-1,2-dicarboxylic acid 1-tert-butyl ester (prepared as described Scheme B18). TLC, $R_f$ (EtOAc)=0.8; MS (UPLC-MS): 419.3 [M+H]+, 463.2 [M+HCOO]−; $t_R$ (HPLC conditions A): 3.35 min.

(2S,4R)-2-[(R)-1-(3-Chloro-2-fluoro-phenyl)-3-hydroxy-propylcarbamoyl]-4-fluoro-4-methyl-pyrrolidine-1-carboxylic acid tert-butyl ester

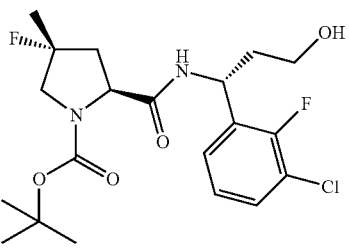 [SMILES: CC(C)(C)OC(=O)N1C[C@](C)(F)C[C@H]1C(=O)N[C@H](CCO)c1cccc(Cl)c1F]

was prepared according to Scheme B9 (Step A) from (2S,4R)-4-fluoro-4-methyl-pyrrolidine-1,2-dicarboxylic acid 1-tert-butyl ester (prepared as described Scheme B18) and (R)-3-amino-3-(3-chloro-2-fluoro-phenyl)-propan-1-ol. TLC, $R_f$ (EtOAc)=0.55; MS (UPLC/MS): 433.3 [M+H]+, 477.3 [M+HCOO]−; $t_R$ (HPLC conditions a): 3.26 min.

(1S,2S,5R)-2-[(S)-1-(3-Chloro-2-fluoro-phenyl)-2-methoxy-ethylcarbamoyl]-3-aza-bicyclo[3.1.0]hexane-3-carboxylic acid tert-butyl ester

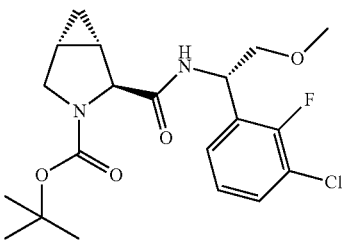 [SMILES: COC[C@@H](NC(=O)[C@@H]1[C@H]2C[C@H]2CN1C(=O)OC(C)(C)C)c1cccc(Cl)c1F]

was prepared according to Scheme B9 (Step B) from (1S,2S,5R)-2-[(S)-1-(3-chloro-2-fluoro-phenyl)-2-hydroxy-ethylcarbamoyl]-3-aza-bicyclo[3.1.0]hexane-3-carboxylic acid tert-butyl ester. TLC, $R_f$ (EtOAc): 0.65; MS (UPLC/MS): 413.4/415.4 [M+H]+, 457.4/459.4 [M+HCOO]−; $t_R$ (HPLC conditions a): 3.67 min.

(1S,2S,5R)-2-[(S)-1-(3-Chloro-2-fluoro-phenyl)-2-hydroxy-ethylcarbamoyl]-3-aza-bicyclo[3.1.0]hexane-3-carboxylic acid tert-butyl ester was prepared according to Scheme B9 (Step A) from (1S,2S,5R)-3-aza-bicyclo[3.1.0]hexane-2,3-dicarboxylic acid 3-tert-butyl ester (Enamine, EN-400-12629). TLC, $R_f$ (EtOAc)=0.65; MS (UPLC/MS): 399.3/401.3 [M+H]+, 443.4/445.4 [M+HCOO]−; $t_R$ (HPLC conditions a): 3.28 min.

(1R,2S,5S)-2-[(S)-1-(3-Chloro-2-fluoro-phenyl)-2-methoxy-ethylcarbamoyl]-3-aza-bicyclo[3.1.0]hexane-3-carboxylic acid tert-butyl ester

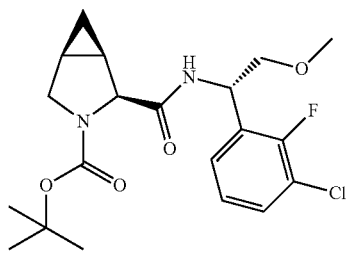 [SMILES: COC[C@@H](NC(=O)[C@@H]1[C@@H]2C[C@@H]2CN1C(=O)OC(C)(C)C)c1cccc(Cl)c1F]

was prepared according to Scheme B9 (Step B) from (1R,2S,5S)-2-[(S)-1-(3-chloro-2-fluoro-phenyl)-2-hydroxy-ethylcarbamoyl]-3-aza-bicyclo[3.1.0]hexane-3-carboxylic acid tert-butyl ester. TLC, $R_f$ (EtOAc): 0.45; MS (UPLC/MS): 413.3/415.3 [M+H]+, 457.3 [M+HCOO]−; $t_R$ (HPLC conditions a): 3.64 min.

(1R,2S,5S)-2-[(S)-1-(3-Chloro-2-fluoro-phenyl)-2-hydroxy-ethylcarbamoyl]-3-aza-bicyclo[3.1.0]hexane-3-carboxylic acid tert-butyl ester was prepared according to Scheme B9 (Step A) from racemic (1R*,2S*,5S*)-3-aza-bicyclo[3.1.0]hexane-2,3-dicarboxylic acid 3-tert-butyl ester. Diastereoisomers were separated by chiral HPLC (Chiralpak ADOOCM-EL001, 5×50 cm, mobile phase: n-heptane/IPA 75/25, Flow: 50 ml/min, detection: 220 nm) to give (1S,2R,5R)-2-[(S)-1-(3-chloro-2-fluoro-phenyl)-2-hydroxy-ethylcarbamoyl]-3-aza-bicyclo[3.1.0]hexane-3-carboxylic acid tert-butyl ester: $t_R$ (HPLC, Chiralpak (20 μm) 046×25 cm, n-Heptan/IPA 80:20, flow: 1 ml/min): 7.25 min; TLC, $R_f$ (EtOAc)=0.58; MS (UPLC/MS): 399.4 [M+H]+, 443.3 [M+HCOO]− and (1R,2S,5S)-2-[(S)-1-(3-chloro-2-fluoro-phenyl)-2-hydroxy-ethylcarbamoyl]-3-aza-bicyclo[3.1.0]hexane-3-carboxylic acid tert-butyl ester: $t_R$ (HPLC, Chiralpak (20 μm) 046×25 cm, n-Heptan/IPA 80:20, flow: 1 ml/min): 8.37 min; TLC, $R_f$(EtOAc)=0.58; MS (UPLC/MS): 399.3 [M+H]+, 443.3 [M+HCOO]−. The absolute stereochemistry of the diastereoisomers was assigned based on the test results for the final compound Example 212 in the biological assay.

(1R*,2S*,5S*)-3-aza-bicyclo[3.1.0]hexane-2,3-dicarboxylic acid 3-tert-butyl ester To a solution of racemic (1R*,2S*,5S*)-3-aza-bicyclo[3.1.0]hexane-2-carboxylic acid (10 g, 79 mmol) (ABCR [22255-16-19]) in a mixture of THF (84 mL) and water (42 mL) was added a solution of NaOH (4.18 g, 105 mmol) in water (42 mL, 10% w/v) and a solution of Boc$_2$O (27.4 mL, 118 mmol) in THF (84 mL) and water (42 mL). The resulting biphasic mixture was stirred at RT overnight. The mixture was concentrated under vacuum and the resulting aqueous layer was extracted EtOAc (×5), then acidified to pH 2-3 by addition of HCl 1N, saturated with NaCl and extracted with CHCl$_3$/EtOH 2:1 (×3). The combined organic layers were dried (Na$_2$SO$_4$), filtered and concentrated to give the desired material which was used without further purification in the next step. MS (UPLC/MS): 226.2 [M–H]–; 1H-NMR (400 MHz, DMSO): δ (ppm) 12.4 (m, 1H), 4.19 (m, 1H), 3.46 (m, 1H), 3.38 (m, 1H), 1.88 (m, 1H), 1.64 (m, 1H), 1.35 (1, 9H), 0.65 (m, 1H), 0.54 (m, 1H).

Scheme B10: preparation of (2S,4S)-4-(9H-fluoren-9-ylmethoxycarbonylamino)-1-(R-carbamoyl) pyrrolidine-2-carboxylic acid

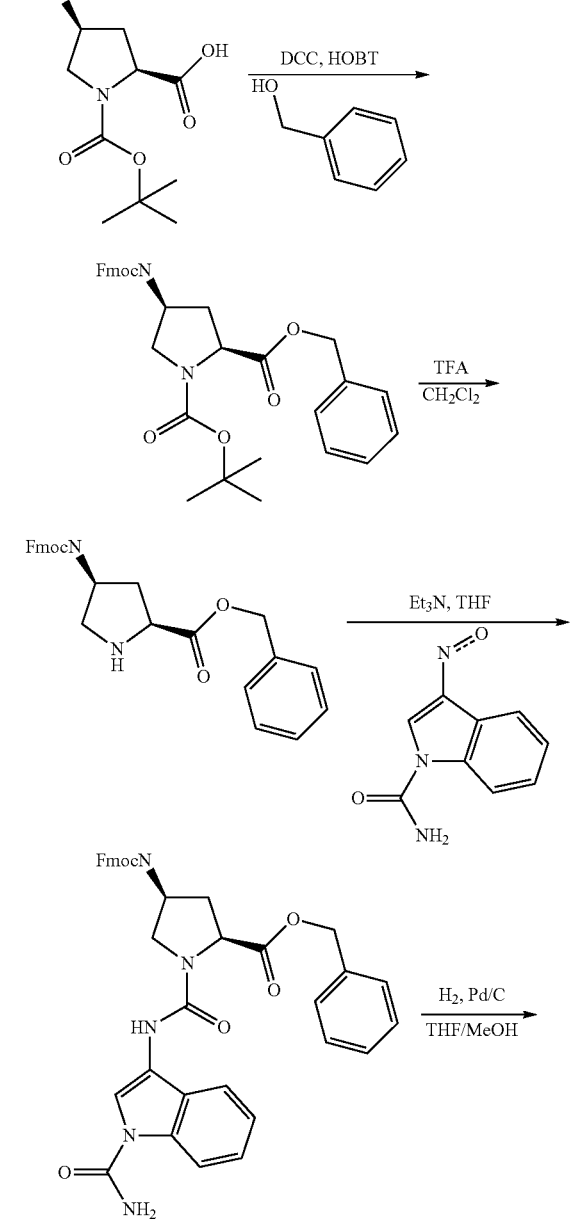

-continued

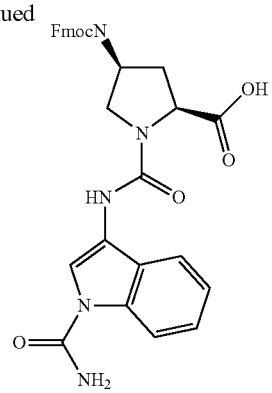

A. (2S,4S)-4-(9H-fluoren-9-ylmethoxycarbonylamino)-pyrrolidine-1,2-dicarboxylic acid 2-benzyl ester 1-tert-butyl ester To a suspension of (2S,4S)-Fmoc-4-amino-1-boc-pyrrolidine-2-carboxylic acid (7.7 g, 17.1 mmol) in CH$_2$Cl$_2$ (50 mL) were added DCC (4.2 g, 20.5 mmol), DMAP (0.2 g, 1.7 mmol) and benzyl alcohol (1.7 mL, 17.08 mmol). The resulting white suspension was stirred at RT overnight under nitrogen. TLC indicated completion of the reaction. The mixture was filtered, and the filtrate was concentrated to give the crude residue which was purified by flash column chromatography on silica gel (c-hexane to c-hexane/EtOAc 4:1) to afford the title compound. TLC, R$_f$ (c-hexane/EtOAc 3:1)=0.25; MS (LC/MS): 565.3 [M+Na]+, 443.2 [MH–Boc]+; t$_R$ (HPLC conditions a): 4.5 min; 1H-NMR (400 MHz, DMSO): δ (ppm) 7.91 (d, 2H,), 7.70 (d, 2H), 7.53 (d, 1H), 7.45-7.32 (m, 9H), 5.23-5.06 (m, 2H), 4.35-4.22 (m, 4H), 4.05 (q, 1H), 3.72-3.65 (m, 1H), 3.11-3.06 (m, 1H), 1.86-1.81 (m, 1H), 1.41 (s, 4H), 1.28 (s, 5H).

B. (2S,4S)-4-(9H-fluoren-9-ylmethoxycarbonylamino)-pyrrolidine-2-carboxylic acid benzyl ester To a solution of (2S,4S)-4-(9H-fluoren-9-ylmethoxycarbonylamino)-pyrrolidine-1,2-dicarboxylic acid 2-benzyl ester 1-tert-butyl ester (7.3 g, 13.49 mmol) in CH$_2$Cl$_2$ (45 mL) was added TFA (5.1 mL, 67.5 mmol). The solution was stirred at RT overnight. The solvent was concentrated and the residue co-evaporated three times with CH$_2$Cl$_2$ to remove the excess of TFA. The crude residue was taken-up in diethylether and the resulting precipitate filtered-off to give the title compound as a white powder. MS (LC/MS): 443.2 [MH]+; t$_R$ (HPLC conditions a): 3.3 min; 1H-NMR (400 MHz, DMSO): δ (ppm) 9.84 (s, 1H), 9.14 (s, 1H), 7.90 (d, 2H), 7.68 (d, 2H), 7.62 (d, 1H), 7.45-7.33 (m, 9H), 5.28-5.21 (m, 2H), 4.59-4.54 (m, 1H), 4.41 (d, 2H), 4.26-4.16 (m, 2H), 3.46-3.41 (m, 1H), 3.16-3.11 (m, 1H), 2.64-2.58 (m, 1H).

C. (2S,4S)-1-(1-Carbamoyl-1H-indol-3-ylcarbamoyl)-4-(9H-fluoren-9-ylmethoxy carbonylamino)-pyrrolidine-2-carboxylic acid benzyl ester To a solution of (2S,4S)-4-(9H-fluoren-9-ylmethoxycarbonylamino)-pyrrolidine-2-carboxylic acid benzyl ester (3.03 g, 5.45 mmol) and Et$_3$N (1.1 mL, 8.2 mmol) in dry THF (60 mL) was added a solution of 3-isocyanato-indole-1-carboxylic acid amide (1.1 g, 5.4 mmol, prepared as described in Scheme A1) in dry THF (60 mL). The resulting solution was stirred at RT under nitrogen for 20 min. The mixture was poured into water and extracted twice with EtOAc. The combined organic layers were dried over $Na_2SO_4$, filtered and concentrated under high vacuum (the temperature of the water bath of the rotary evaporator was kept to RT) to give the title compound. $R_f$ (c-hexane/EtOAc 1:3)=0.39; MS (LCMS): 644.2 [M+H]+, 666.2 [M+Na]+; $t_R$ (HPLC conditions a): 4.0 min.

D. (2S,4S)-1-(1-Carbamoyl-1H-indol-3-ylcarbamoyl)-4-(9H-fluoren-9-ylmethoxy carbonylamino)-1-(R-carbamoyl)pyrrolidine-2-carboxylic acid (2S,4S)-4-(9H-Fluoren-9-ylmethoxycarbonylamino)-1-(R-carbamoyl)pyrrolidine-2-carboxylic acid benzyl ester (2.83 g, 4.4 mmol) was dissolved in a mixture of MeOH/THF (1:1) (60 mL). Air was removed from the flask and replaced with nitrogen three times. Then Pd/C 10% (425 mg) was added to the solution which was once again degassed and refilled with nitrogen three times. The mixture was placed under a hydrogen atmosphere, and stirred at RT for 2 h. The catalyst was removed through a pad of Celite and washed with THF. The filtrate was concentrated, the residue was taken up in diethylether and the resulting precipitate filtered-off to give the title compound. MS (LC/MS): 554.2 [M+H]+, 552.1 [M−H]−; $t_R$ (HPLC conditions a): 3.5 min.

(2S,4R)-1-(1-Carbamoyl-1H-indol-3-ylcarbamoyl)-4-fluoro-pyrrolidine-2-carboxylic acid

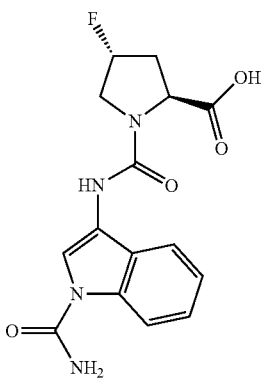 [SMILES: NC(=O)n1cc(NC(=O)N2C[C@H](F)C[C@H]2C(=O)O)c2ccccc21]

A. (2S,4R)-4-Fluoro-pyrrolidine-1,2-dicarboxylic acid 2-benzyl ester 1-tert-butyl ester To a suspension of N-Boc-trans-4-fluoro-L-proline (4.5 g, 19.29 mmol) in $CH_2Cl_2$ (68 mL) were added DCC (4.78 g, 23.15 mmol), DMAP (0.236 g, 1.93 mmol) and benzyl alcohol (2 mL, 19.29 mmol). The resulting white suspension was stirred at RT for 48 h and filtered. The filtrate was concentrated to give a colorless oil which was purified by flash column chromatography on silica gel (c-hexane to c-hexane/EtOAc 4-1) to give the desired compound. TLC, $R_f$(c-hexane/EtOAc 3:1)=0.3; MS: 346.0 [M+Na]+; $t_R$ (HPLC conditions a): 3.85 min.

B. (2S,4R)-4-Fluoro-pyrrolidine-2-carboxylic acid benzyl ester (2S,4R)-4-Fluoro-pyrrolidine-1,2-dicarboxylic acid 2-benzyl ester 1-tert-butyl ester (3.16 g, 9.76 mmol) was dissolved in $CH_2Cl_2$ (50 mL), TFA (7.47 mL, 98 mmol) was added and the solution was stirred at RT 16 h. The solution was concentrated under high vacuum to give the desired TFA salt as a brown oil which was used without further purification in the next step. MS (LC/MS): 224.1 [M+H]+.

C. (2S,4R)-1-(1-Carbamoyl-1H-indol-3-ylcarbamoyl)-4-fluoro-pyrrolidine-2-carboxylic acid benzyl ester To a solution of (2S,4R)-4-fluoro-pyrrolidine-2-carboxylic acid benzyl ester TFA salt (4.45 g, 13.2 mmol), 3-isocyanato-indole-1-carboxylic acid amide (2.65 g, 13.2 mmol) (prepared as described in Scheme A1) and THF (66 mL) was added triethylamine (5.51 mL, 39.6 mmol). The resulting solution was stirred at RT under nitrogen for 1 h until completion of the reaction. The mixture was poured in water and extracted with EtOAc. The organic layer was washed with an aqueous saturated solution of $NaHCO_3$, dried over $Na_2SO_4$, filtered and concentrated. The crude material was purified by flash column chromatography on silica gel (c-hexane/EtOAc 9:1 to pure EtOAc) to give the desired compound. TLC, $R_f$ ($CH_2Cl_2$/MeOH 9:1)=0.40; MS: 425.2 [M+H]+; $t_R$ (HPLC conditions a): 3.6 min.

D. (2S,4R)-1-(1-Carbamoyl-1H-indol-3-ylcarbamoyl)-4-fluoro-pyrrolidine-2-carboxylic acid To a solution of (2S,4R)-1-(1-carbamoyl-1H-indol-3-ylcarbamoyl)-4-fluoro-pyrrolidine-2-carboxylic acid benzyl ester (2.5 g, 5.89 mmol) in THF (40 mL) was added Pd/C 10% (500 mg). Air was removed from the flask under high vacuum and replaced with nitrogen, this operation was repeated three times and finally nitrogen was removed and replaced with hydrogen. The mixture was stirred under a hydrogen atmosphere for 16 h. Hydrogen was removed under vacuum and replaced with nitrogen and the catalyst was removed by filtration over a pad of Celite and washed with THF. Solvents were concentrated to give the title product. MS (LC/MS): 335.0 [M+H]+, 691.2 [2M+Na]+, 333.1 [M−H]−; $t_R$ (HPLC conditions a): 2.22 min.

{1-(1-Acetyl-1H-indol-3-yl)-2-[(2S,4R)-2-(3-chloro-2-fluoro-benzylcarbamoyl)-4-fluoro-pyrrolidin-1-yl]-2-oxo-ethyl}-carbamic acid tert-butyl ester

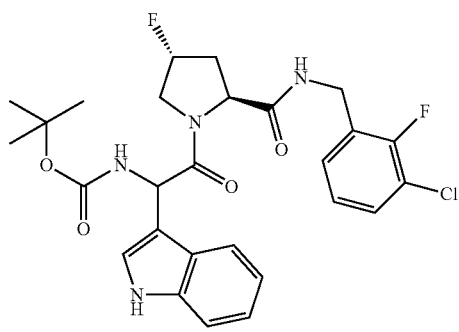 [SMILES: CC(C)(C)OC(=O)NC(C(=O)N1C[C@H](F)C[C@H]1C(=O)NCc1cccc(Cl)c1F)c1c[nH]c2ccccc12]

To a solution of (2S,4R)-4-fluoro-pyrrolidine-2-carboxylic acid 3-chloro-2-fluoro-benzylamide. TFA salt (600 mg, 1.54 mmol), N-Boc-2-(indole-3-yl)-DL-glycine (538 mg, 1.85 mmol) and HBTU (878 mg, 2.32 mmol) in DMF (5.14 mL) was added DIPEA (809 µL, 4.63 mmol) and the reaction mixture was stirred at 23° C. for 24 h. The mixture was diluted with EtOAc and successively washed with HCl 1N and aqueous NaHCO$_3$ 5%. The organic layer was dried (Na$_2$SO$_4$), filtered and concentrated. The crude residue was purified by flash column chromatography on silica gel (Cyclohexane/EtOAc gradient 100:0 to 1:1) to give two fractions P1 and P2 containing each one diastereosiomer. P1: TLC, R$_f$ (c-hexane/EtOAc 1:1)=0.25; MS (LC/MS): 545.2 [M−H]−; t$_R$ (HPLC conditions b): 4.89 min. P2: TLC, R$_f$ (c-hexane/EtOAc 1:1)= 0.15; MS (LC/MS): 545.2 [M−H]−; t$_R$ (HPLC conditions b): 4.96 min.

(2S,4R)-4-fluoro-pyrrolidine-2-carboxylic acid 3-chloro-2-fluoro-benzylamide

The title compound was prepared as a TFA salt according to Scheme D5 (steps A and B) from 3-chloro-2-fluoro-benzylamine and (2S,4R)-4-fluoro-pyrrolidine-1,2-dicarboxylic acid 1-tert-butyl ester. MS (LC-MS): 274.9 [M+H]+; t$_R$ (HPLC conditions b): 2.23 min.

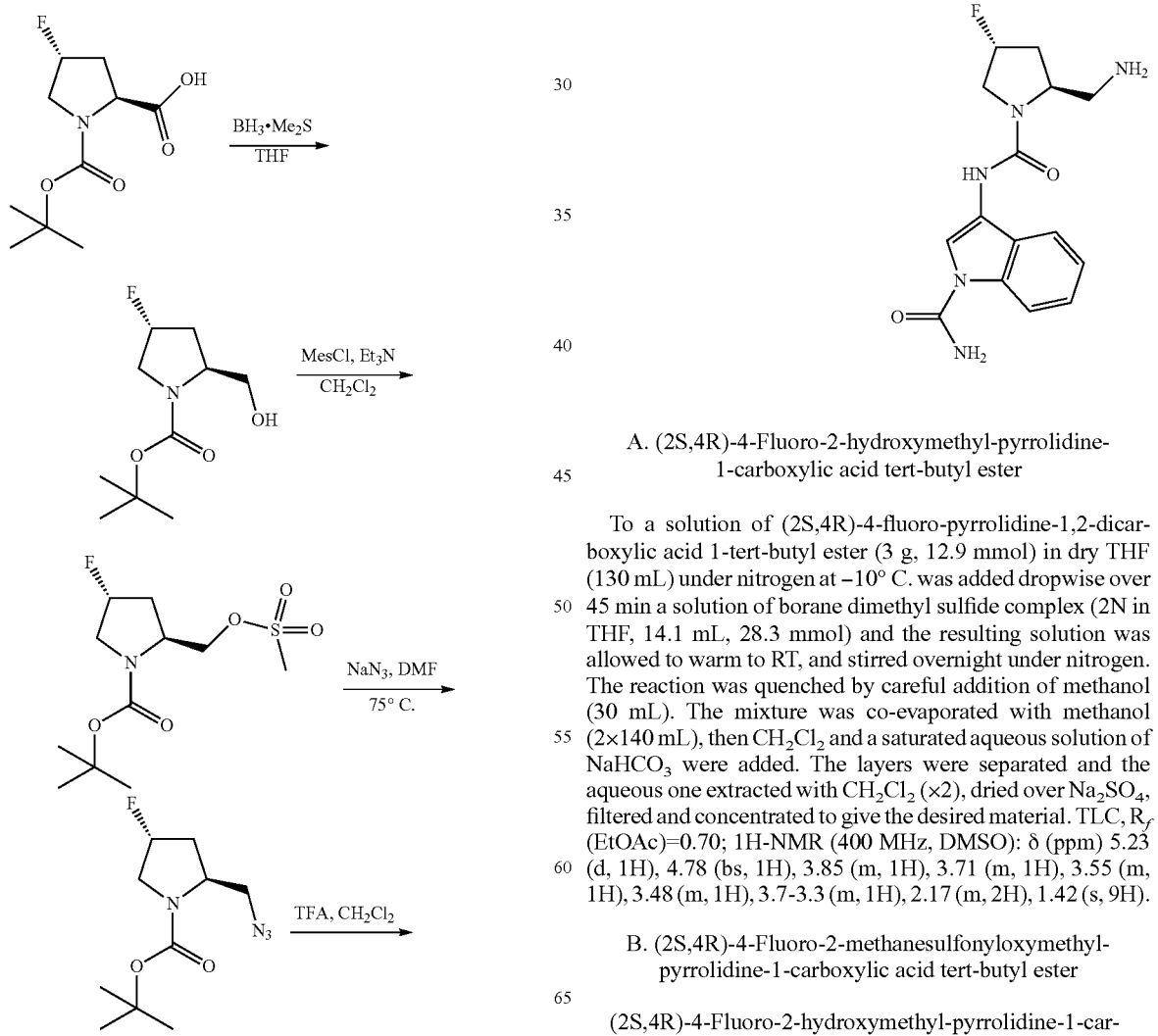

A. (2S,4R)-4-Fluoro-2-hydroxymethyl-pyrrolidine-1-carboxylic acid tert-butyl ester To a solution of (2S,4R)-4-fluoro-pyrrolidine-1,2-dicarboxylic acid 1-tert-butyl ester (3 g, 12.9 mmol) in dry THF (130 mL) under nitrogen at −10° C. was added dropwise over 45 min a solution of borane dimethyl sulfide complex (2N in THF, 14.1 mL, 28.3 mmol) and the resulting solution was allowed to warm to RT, and stirred overnight under nitrogen. The reaction was quenched by careful addition of methanol (30 mL). The mixture was co-evaporated with methanol (2×140 mL), then CH$_2$Cl$_2$ and a saturated aqueous solution of NaHCO$_3$ were added. The layers were separated and the aqueous one extracted with CH$_2$Cl$_2$ (×2), dried over Na$_2$SO$_4$, filtered and concentrated to give the desired material. TLC, R$_f$ (EtOAc)=0.70; 1H-NMR (400 MHz, DMSO): δ (ppm) 5.23 (d, 1H), 4.78 (bs, 1H), 3.85 (m, 1H), 3.71 (m, 1H), 3.55 (m, 1H), 3.48 (m, 1H), 3.7-3.3 (m, 1H), 2.17 (m, 2H), 1.42 (s, 9H).

B. (2S,4R)-4-Fluoro-2-methanesulfonyloxymethyl-pyrrolidine-1-carboxylic acid tert-butyl ester (2S,4R)-4-Fluoro-2-hydroxymethyl-pyrrolidine-1-carboxylic acid tert-butyl ester (2.87 g, 13.1 mmol) was dissolved in 45 mL of CH$_2$Cl$_2$. The mixture was cooled down to 0° C., and methanesulfonyl chloride (2.55 mL, 32.8 mmol) and triethylamine (4.56 mL, 32.8 mmol) were added. The mixture was allowed to warm to RT and stirred for 1.5 h. The mixture was quenched with a saturated aqueous solution of NaHCO$_3$, extracted twice with CH$_2$Cl$_2$, dried over Na$_2$SO$_4$ and concentrated. The crude residue was purified by flash column chromatography on silica gel (c-hexane to c-hexane/ EtOAC 3:7) to afford the desired material. TLC, R$_f$(c-hexane/ EtOAc 1:1)=0.4; MS: 320.0 [M+Na]+, 198.1 [MH−Boc]+, 617.2 [2M+Na]+.

C. (2S,4R)-2-Azidomethyl-4-fluoro-pyrrolidine-1-carboxylic acid tert-butyl ester A mixture of (2S,4R)-4-fluoro-2-methanesulfonyloxymethyl-pyrrolidine-1-carboxylic acid tert-butyl ester (3.3 g, 11.1 mmol) and NaN$_3$ (721 mg, 11.1 mmol) in DMF (50 mL) was stirred at 75° C. under nitrogen overnight. The mixture was diluted with water and extracted with EtOAc (×3). The combined organic extracts were washed with water (×3), dried over Na$_2$SO$_4$, and concentrated. The crude residue was purified by flash column chromatography on silica gel (c-hexane/EtOAc 100/0 to 0/100) to give the desired material. 1H-NMR (400 MHz, DMSO): δ (ppm) 5.25 (d, 1H), 4.03 (m, 1H), 3.92-3.70 (m, 2H), 3.5-3.25 (m, 2H), 2.27 (m, 1H), 2.2-1.8 (m, 1H), 1.43 (s, 9H).

D. (2S,4R)-2-Azidomethyl-4-fluoro-pyrrolidine

To a solution of (2S,4R)-2-azidomethyl-4-fluoro-pyrrolidine-1-carboxylic acid tert-butyl ester (600 mg, 2.45 mmol) in CH$_2$Cl$_2$ (2.5 mL) was added TFA (1.88 mL, 24.6 mmol) and the solution was stirred at RT for 2 h. CH$_2$Cl$_2$ was concentrated and the crude was dried under high vacuum to give the desired material which was used without further purification in the next step.

E. 3-[((2S,4R)-2-Azidomethyl-4-fluoro-pyrrolidine-1-carbonyl)-amino]-indole-1-carboxylic acid amide To a solution of (2S,4R)-2-azidomethyl-4-fluoro-pyrrolidine (2.46 mmol) and Et$_3$N (1.7 mL, 12.3 mmol) in THF (8 mL) was added a solution of 3-isocyanato-indole-1-carboxylic acid amide (543 mg, 2.70 mmol) in THF (4 mL) and the resulting solution was stirred at RT under nitrogen for 20 min. The mixture was poured into water and extracted twice with EtOAc. The combined organic layers were dried over Na$_2$SO$_4$, filtered and concentrated. The crude residue was purified by flash column chromatography on silica gel (c-hexane to c-hexane/EtOAc 1:4 to 100% EtOAc) to give the desired material. TLC, R$_f$(EtOAc)=0.7; MS (LC-MS): 346.1 [M+H]+, 368.0 [M+Na]+, 344.0 [M−H]−; t$_R$ (HPLC conditions f): 1.61 min.

F. 3-[((2S,4R)-2-Aminomethyl-4-fluoro-pyrrolidine-1-carbonyl)-amino]-indole-1-carboxylic acid amide 3-[((2S,4R)-2-Azidomethyl-4-fluoro-pyrrolidine-1-carbonyl)-amino]-indole-1-carboxylic acid amide (500 mg, 2.84 mmol) was suspended in THF (5 mL). Air was removed from the flask and replaced with nitrogen three times. Pd/C 10% (100 mg) was added to the solution which was again degassed, placed under a hydrogen atmosphere, and stirred at RT for 1.5 h. The catalyst was removed through a pad of Celite and washed with THF and MeOH to give the desired material which was used in the next step without further purification. MS (LC-MS): 320.2 [M+H]+, 639.2 [2M+H]+, 661.3 [2M+Na]+, 318.1 [M−H]−; t$_R$ (HPLC conditions f): 0+1.02+1.61 min.

Scheme B12: preparation of (2S,4R)-2-(3-chloro-2-fluoro-benzylcarbamoyl)-4-fluoro-4-hydroxymethyl-pyrrolidine-1-carboxylic acid tert-butyl-ester

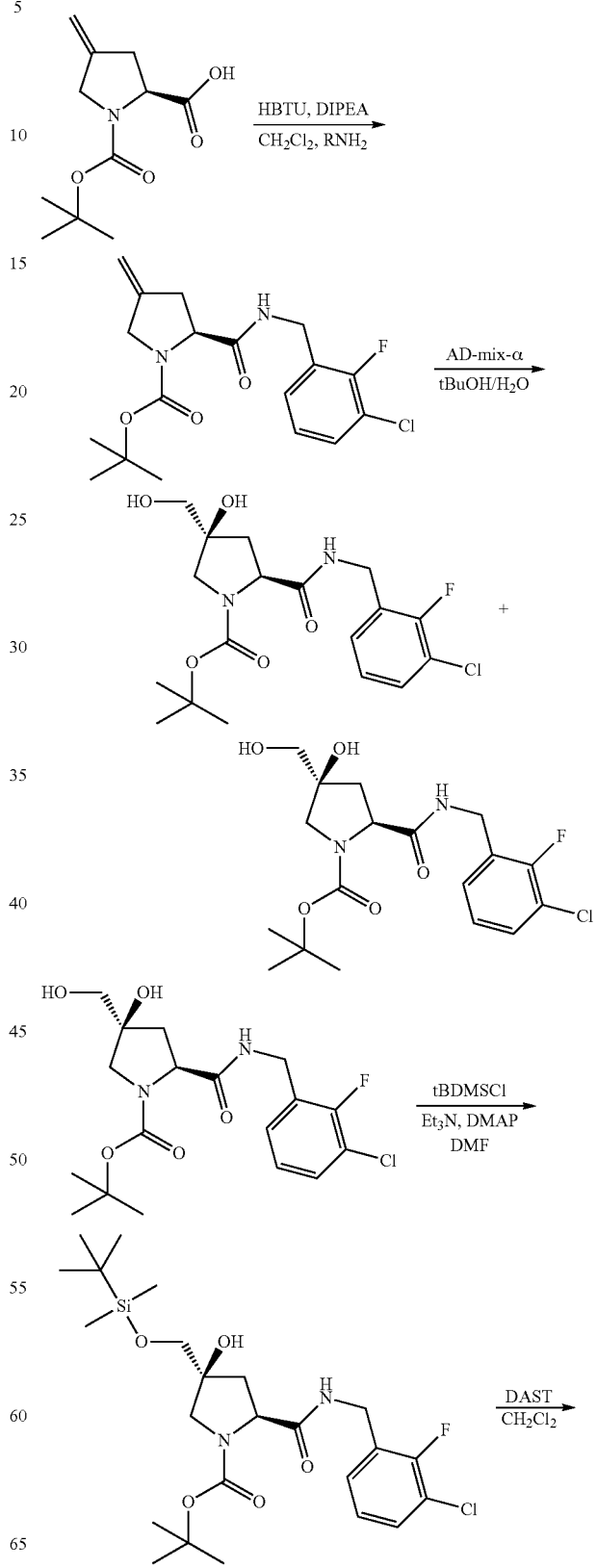

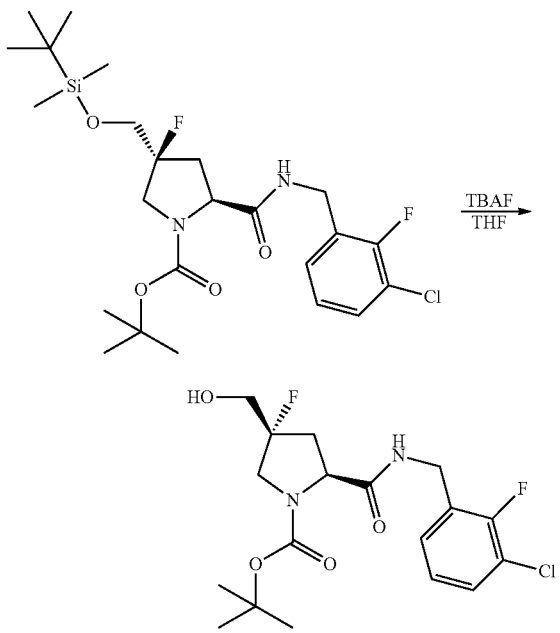

A. (S)-2-(3-Chloro-2-fluoro-benzylcarbamoyl)-4-methylene-pyrrolidine-1-carboxylic acid tert-butyl ester To a solution of N-Boc-4-methylene-L-proline (5.3 g, 22.6 mmol) in CH$_2$Cl$_2$ (25 mL) was added a solution of 3-chloro-2-fluorobenzylamine (3.61 g, 22.6 mmol) in CH$_2$Cl$_2$ (25 mL) followed by HBTU (10.3 g, 27.1 mmol) and DIPEA (5.81 mL, 33.9 mmol) and the resulting solution was stirred at RT under nitrogen for 2 h. The mixture was poured into HCl 1N and extracted twice with CH$_2$Cl$_2$. The combined organic layers were neutralized with an aqueous saturated solution of NaHCO$_3$, dried (Na$_2$SO$_4$), filtered and concentrated. The crude residue was purified by flash column chromatography on silica gel (c-hexane to c-hexane/EtOAc 85:15 to c-hexane/EtOAc 50:50) to give the desired material. TLC, R$_f$(EtOAc)= 0.75; MS (LC-MS): 391.0/393.1 [M+Na]+, 313.0/315.0 [MH−tBu]+, 413.0/415.0 [M+HCOO]−; t$_R$ (HPLC conditions f): 2.12 min.

B. (2S,4S)-2-(3-Chloro-2-fluoro-benzylcarbamoyl)-4-hydroxy-4-hydroxymethyl-pyrrolidine-1-carboxylic acid tert-butyl ester and (2S,4R)-2-(3-Chloro-2-fluoro-benzylcarbamoyl)-4-hydroxy-4-hydroxymethyl-pyrrolidine-1-carboxylic acid tert-butyl ester A flask was charged with t-butanol (13 mL), water (13 mL), and AD-mix-α (3.8 g). The mixture was stirred at RT until both phases were clear, and then cooled to 0° C. (S)-2-(3-Chloro-2-fluoro-benzylcarbamoyl)-4-methylene-pyrrolidine-1-carboxylic acid tert-butyl ester (1 g, 2.71 mmol) was added at once, and the heterogeneous slurry was stirred vigorously from 0° C. to RT overnight. The reaction was quenched at 0° C. by addition of sodium sulfite (4 g) and then warmed to RT and stirred for 45 min. The reaction mixture was extracted with CH$_2$Cl$_2$ (×3). The combined organic layers were dried (Na$_2$SO$_4$), filtered and concentrated to give a mixture of diastereosiomers in a 2:1 ratio. The crude mixture was purified by flash column chromatography on silica gel (c-hexane/EtOAc 1-1 to 100% EtOAc, and then from CH$_2$Cl$_2$ to CH$_2$Cl$_2$/MeOH 8:2) to give (2S,4S)-2-(3-chloro-2-fluoro-benzylcarbamoyl)-4-hydroxy-4-hydroxymethyl-pyrrolidine-1-carboxylic acid tert-butyl ester (major isomer): TLC, R$_f$(EtOAc)=0.3; MS (LC-MS): 403.1/405.1 [M+H]+, 425.0/427.1 [M+Na]+, 827.2/829.2 [2M+Na]+, 347.0/349.0 [MH−tBu]+, 401.0/403.0 [M−H]−, 447.1/449.0 [M+HCOO]−; t$_R$ (HPLC conditions f): 1.71 min and (2S,4R)-2-(3-chloro-2-fluoro-benzylcarbamoyl)-4-hydroxy-4-hydroxymethyl-pyrrolidine-1-carboxylic acid tert-butyl ester (minor isomer): TLC, R$_f$(EtOAc)=0.2; MS (LC-MS): 425.0/427.1 [M+Na]+, 827.2/829.2 [2M+Na]+, 347.0/349.0 [MH−tBu]+, 447.1/449.0 [M+HCOO]−; t$_R$ (HPLC conditions f): 1.66 min.

C. (2S,4S)-4-(tert-Butyl-dimethyl-silanyloxymethyl)-2-(3-chloro-2-fluoro-benzyl carbamoyl)-4-hydroxy-pyrrolidine-1-carboxylic acid tert-butyl ester To a solution of (2S,4S)-2-(3-chloro-2-fluoro-benzylcarbamoyl)-4-hydroxy-4-hydroxymethyl-pyrrolidine-1-carboxylic acid tert-butyl ester (200 mg, 0.5 mmol) in DMF (2 mL) was added tert-butyldimethylsilyl chloride (75 mg, 0.5 mmol), triethylamine (69 μL, 0.5 mmol) and DMAP (6 mg, 0.05 mmol). The mixture was stirred at RT under nitrogen overnight. Tert-butyldimethylsilyl chloride (75 mg, 0.5 mmol), and triethylamine (69 μL, 0.5 mmol) were again added and the mixture further stirred at RT for 2.5 h. The mixture was poured into an aqueous saturated NaHCO$_3$ solution, and extracted with EtOAc (×3). The combined organic layers were washed with water, dried (Na$_2$SO$_4$), filtered and concentrated. The crude mixture was purified by flash column chromatography on silica gel (eluent: EtOAc) to afford the desired material. TLC, R$_f$ (c-hexane/EtOAc 1:1)=0.50; MS (LC-MS): 518.2/520.2 [M+H]+, 540.2/542.2 [M+Na]+, 462.0/464.0 [MH−tBu]+, 516.0/518.2 [M−H]−; t$_R$ (HPLC conditions f): 2.72 min.

D. (2S,4R)-4-(tert-Butyl-dimethyl-silanyloxymethyl)-2-(3-chloro-2-fluoro-benzyl carbamoyl)-4-fluoro-pyrrolidine-1-carboxylic acid tert-butyl ester To a solution of (2S,4S)-4-(tert-butyl-dimethyl-silanyloxymethyl)-2-(3-chloro-2-fluoro-benzyl carbamoyl)-4-hydroxy-pyrrolidine-1-carboxylic acid tert-butyl ester (200 mg, 0.35 mmol) in CH$_2$Cl$_2$ (10 mL) under N$_2$ atmosphere at −78° C. was added DAST (92 μL, 0.7 mmol). The reaction mixture was then allowed to reach RT and further stirred for 1.5 h then poured into an aqueous saturated solution of NaHCO$_3$ and extracted twice with CH$_2$Cl$_2$. The combined organic layers were dried (Na$_2$SO$_4$), filtered and concentrated to give the desired material which was used without further purification in the next step. TLC, R$_f$ (c-hexane/EtOAc 1:1)=0.75; MS (LC/MS): 541.2/543.1 [M+Na]+, 463.1/465.1 [MH−tBu]+, 419.0/421.1 [MH−Boc]+; t$_R$ (HPLC conditions f): 2.81 min.

E. (2S,4R)-2-(3-Chloro-2-fluoro-benzylcarbamoyl)-4-fluoro-4-hydroxymethyl-pyrrolidine-1-carboxylic acid tert-butyl ester A solution of (2S,4S)-4-(tert-butyl-dimethyl-silanyloxymethyl)-2-(3-chloro-2-fluoro-benzyl carbamoyl)-4-hydroxy-pyrrolidine-1-carboxylic acid tert-butyl ester (180 mg, 0.34 mmol) in THF (1.5 mL) and TBAF (680 µL, 0.680 mmol, 1M solution in THF) was stirred at RT under nitrogen for 30 min. After completion of the reaction, the mixture was poured in water and extracted twice with EtOAc. The combined organic layers were washed with water, dried over Na₂SO₄, filtered and concentrated. The crude material was purified by flash column chromatography on silica gel (c-hexane/EtOAc gradient 1:1 to EtOAc) to give the desired material. TLC, R$_f$ (EtOAc)=0.45; MS (LC-MS): 427.0 [M+Na]+, 349.0 [MH−tBu]+, 305.0 [MH−Boc]+, 403.1/405.1 [M−H]−, 449.2/451.1 [M+HCOO]−; t$_R$ (HPLC conditions f): 1.91 min.

(2S,4S)-2-(3-chloro-2-fluoro-benzylcarbamoyl)-4-fluoro-4-fluoromethyl-pyrrolidine-1-carboxylic acid tert-butyl ester

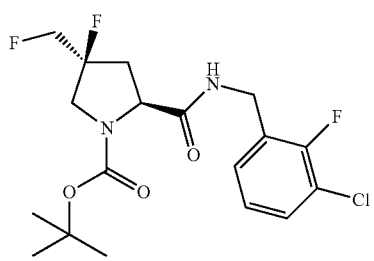 [SMILES: CC(C)(C)OC(=O)N1C[C@](F)(CF)C[C@H]1C(=O)NCc1cccc(Cl)c1F]

To a solution of (2S,4S)-2-(3-chloro-2-fluoro-benzylcarbamoyl)-4-fluoro-4-hydroxymethyl-pyrrolidine-1-carboxylic acid tert-butyl ester (80 mg, 0.19 mmol) (prepared using the same protocol as described in Scheme B12 for (2S,4S)-2-(3-chloro-2-fluoro-benzylcarbamoyl)-4-fluoro-4-hydroxymethyl-pyrrolidine-1-carboxylic acid tert-butyl ester) in CH₂Cl₂ (5 mL) at −78° C. under nitrogen was added DAST (50 µL, 0.375 mmol) and the solution was allowed to reach RT and stirred for 2 h. The reaction mixture was poured into an aqueous saturated solution of NaHCO₃ and extracted twice with CH₂Cl₂. The combined organic layers were dried (Na₂SO₄), filtered and concentrated. The crude residue was purified by flash column chromatography on silica gel (c-hexane/EtOAc gradient 2:1 to 1:3) to give the desired material. TLC, R$_f$ (EtOAc)=0.72; MS (LC-MS): 429.1/431.0 [M+Na]+, 351.0/353.0 [MH−tBu]−, 451.1/453.1 [M+HCOO]−; t$_R$ (HPLC conditions f): 2.14 min.

Scheme B13: preparation of (2S,4R)-2-(3-Chloro-2-fluoro-benzylcarbamoyl)-4-fluoro-4-methyl-pyrrolidine-1-carboxylic acid tert-butyl ester

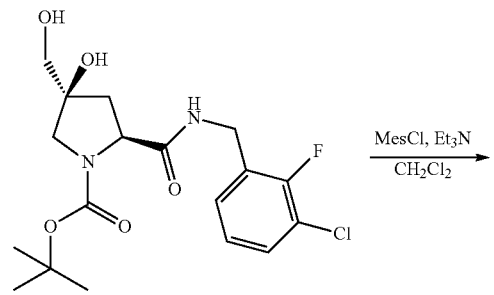

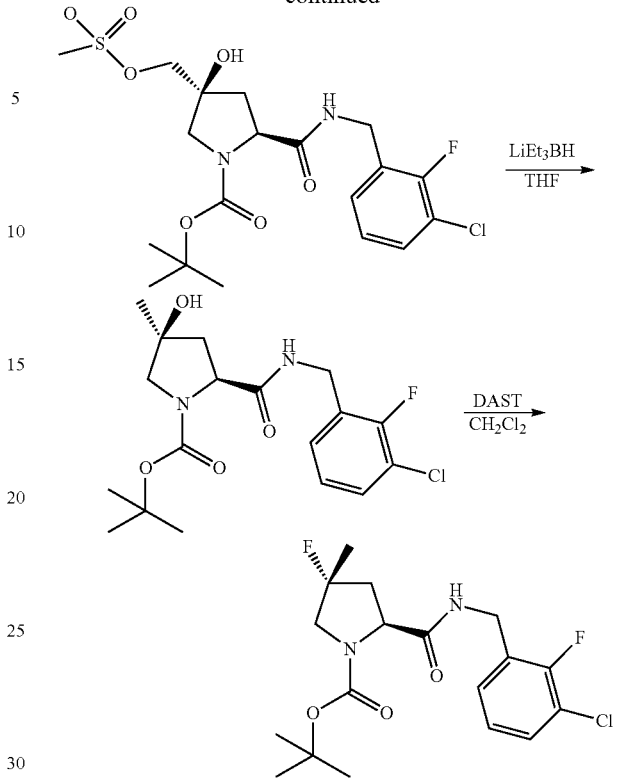

A. (2S,4S)-2-(3-Chloro-2-fluoro-benzylcarbamoyl)-4-hydroxy-4-methanesulfonyloxy methyl-pyrrolidine-1-carboxylic acid tert-butyl ester To a solution of (2S,4S)-2-(3-chloro-2-fluoro-benzylcarbamoyl)-4-hydroxy-4-hydroxymethyl-pyrrolidine-1-carboxylic acid tert-butyl ester (3.53 g, 8.76 mmol) (prepared as described Scheme B12) and Et₃N (1.46 mL, 10.5 mmol) in CH₂Cl₂ (90 mL) at 0° C. under nitrogen, was added methanesulfonyl chloride (819 µL, 10.52 mmol) dropwise. The resulting solution was stirred at 0° C. for 1.5 h and quenched with a saturated aqueous solution of NaHCO₃, extracted twice with CH₂Cl₂, dried (Na₂SO₄), filtered and concentrated. The crude material was purified by flash column chromatography on silica gel (c-hexane to c-hexane/EtOAc 4:6) to give the desired material. TLC, R$_f$ (EtOAc)=0.7, MS (UPLC/MS): 481.3/483.3 [M+H]+, 381.2/383.2 [MH−Boc]+, 425.2/427.2 [MH−tBu]+, 479.3/481.3 [M−H]−, 525.3/527.3 [M+HCOO]−; t$_R$ (HPLC conditions f): 2.04 min.

B. (2S,4S)-2-(3-Chloro-2-fluoro-benzylcarbamoyl)-4-hydroxy-4-methyl-pyrrolidine-1-carboxylic acid tert-butyl ester (2S,4S)-2-(3-Chloro-2-fluoro-benzylcarbamoyl)-4-hydroxy-4-methanesulfonyloxy methyl-pyrrolidine-1-carboxylic acid tert-butyl ester (1 g, 2.08 mmol) was dissolved in THF (21 mL) under nitrogen atmosphere before addition of lithium triethylborohydride (1 M in THF, 20.8 mL, 20.8 mmol). The solution was stirred at RT for 15 min, then poured into cold water and extracted with EtOAc (×2). The combined organic layers were dried (Na₂SO₄), filtered and concentrated. The crude material was purified by flash column chromatography on silica gel (c-hexane/EtOAc 1:1) to give the desired material. TLC, $R_f$ (EtOAc)=0.7; MS (UPLC/MS): 387.3/389.3 [M+H]+, 409.3/411.3 [M+Na]+, 331.2/333.2 [MH–tBu]+, 287.2/289.2 [MH–Boc]+, 795.5/797.6 [2M+Na]+, 385.3/387.2 [M–H]–, 431.3/433.3 [M+HCOO]–.

C. (2S,4R)-2-(3-Chloro-2-fluoro-benzylcarbamoyl)-4-fluoro-4-methyl-pyrrolidine-1-carboxylic acid tert-butyl ester To a solution of (2S,4S)-2-(3-chloro-2-fluoro-benzylcarbamoyl)-4-hydroxy-4-methyl-pyrrolidine-1-carboxylic acid tert-butyl ester (865 mg, 2.1 mmol) in CH$_2$Cl$_2$ (60 mL) under nitrogen at –78° C. was added DAST (550 µL, 4.16 mmol) and the solution was slowly allowed to reach RT and stirred for 1 h. The reaction mixture was poured into cold aqueous saturated NaHCO$_3$ solution and extracted with CH$_2$Cl$_2$ (×2). The combined organic layers were dried (Na$_2$SO$_4$), filtered and concentrated to give the desired material which was used in the next step without further purification. TLC, $R_f$ (EtOAc)=0.75; MS (UPLC/MS): 389.3/391.3 [M+H]+, 411.3/413.2 [M+Na]+, 333.2/335. [MH–tBu]+, 289.2/291.2 [MH–Boc]+, 387.2/389.4 [M–H]–, 433./435.2 [M+HCOO]–; $t_R$ (HPLC conditions f): 2.2 min.

Scheme B14: preparation of (2S,4S)-2-(3-Chloro-2-fluoro-benzylcarbamoyl)-4-fluoro-4-morpholin-4-ylmethylpyrrolidine-1-carboxylic acid tert-butyl ester

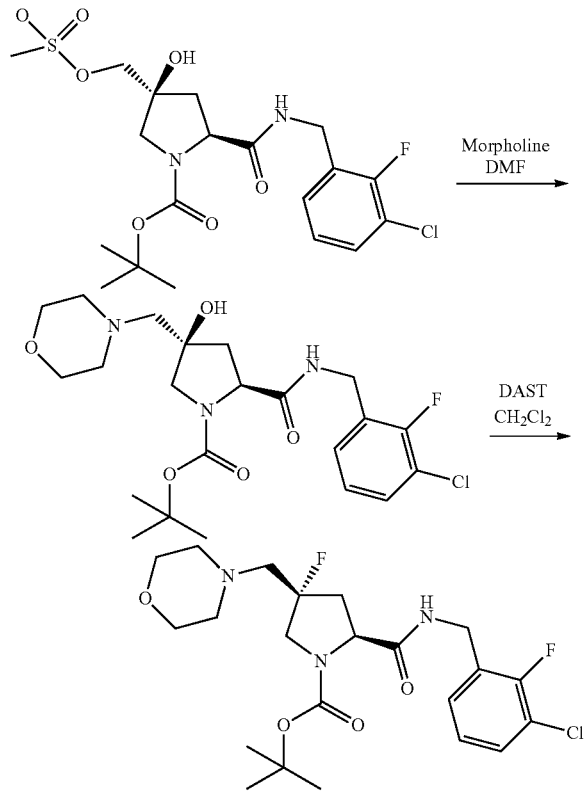

A. (2S,4R)-2-(3-Chloro-2-fluoro-benzylcarbamoyl)-4-hydroxy-4-morpholin-4-ylmethyl-pyrrolidine-1-carboxylic acid tert-butyl ester To a solution of (2S,4S)-2-(3-chloro-2-fluoro-benzylcarbamoyl)-4-hydroxy-4-methanesulfonyloxy methyl-pyrrolidine-1-carboxylic acid tert-butyl ester (200 mg, 0.416 mmol) (prepared as described Scheme B13) in DMF (10 mL) was added morpholine (181 mL, 2.079 mmol) and the solution was stirred for 16 h at 80° C. The reaction mixture was diluted with EtOAc, washed with a saturated aqueous solution of NaHCO$_3$ (3 times). The organic layers were dried (Na$_2$SO$_4$), filtered and concentrated. The crude material was purified by flash column chromatography on silica gel (CH$_2$Cl$_2$/MeOH 8:2) to give the desired material. MS (LC/MS): 472.1/474.1 [M+H]+, 470.0/472.1 [M–H]–; $t_R$ (HPLC conditions f): 1.58 min; $^{19}$F NMR (100 MHz, DMSO-d$_6$) δ (ppm): –120.

B. (2S,4S)-2-(3-Chloro-2-fluoro-benzylcarbamoyl)-4-fluoro-4-morpholin-4-ylmethyl pyrrolidine-1-carboxylic acid tert-butyl ester To a solution of (2S,4R)-2-(3-chloro-2-fluoro-benzylcarbamoyl)-4-hydroxy-4-morpholin-4-ylmethyl-pyrrolidine-1-carboxylic acid tert-butyl ester (85 mg, 0.18 mmol) in CH$_2$Cl$_2$ (10 mL) under N$_2$ atmosphere at –78° C. was added DAST (47 µL, 0.359 mmol). The reaction mixture was then allowed to reach RT and further stirred for 1.5 h then poured into an aqueous saturated solution of NaHCO$_3$ and extracted twice with CH$_2$Cl$_2$. The combined organic layers were dried (Na$_2$SO$_4$), filtered and concentrated. The crude material was purified by flash column chromatography on silica gel (CH$_2$Cl$_2$/MeOH 8:2) to give the desired material. MS (LC/MS): 474.1/476.2 [M+H]+, 472.1 [M–H]–; $t_R$ (HPLC conditions f): 1.59 min.

(2S,4R)-2-(3-Chloro-2-fluoro-benzylcarbamoyl)-4-fluoro-4-morpholin-4-ylmethyl-pyrrolidine-1-carboxylic acid tert-butyl ester

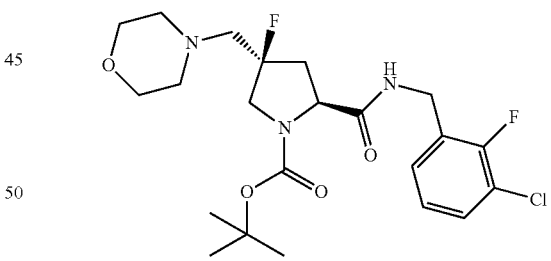

was obtained using the same protocols as described in Scheme B14 for the preparation of (2S,4S)-2-(3-chloro-2-fluoro-benzylcarbamoyl)-4-fluoro-4-morpholin-4-ylmethylpyrrolidine-1-carboxylic acid tert-butyl ester starting from starting from (2S,4R)-2-(3-chloro-2-fluoro-benzyl carbamoyl)-4-hydroxy-4-methanesulfonyloxymethyl-pyrrolidine-1-carboxylic acid tert-butyl ester (prepared from (2S,4R)-2-(3-chloro-2-fluoro-benzylcarbamoyl)-4-hydroxy-4-hydroxymethyl-pyrrolidine-1-carboxylic acid tert-butyl ester as described scheme B13). MS (LC/MS): 474.1/476.2 [M+H]+, 472.1 [M–H]–; $t_R$ (HPLC conditions f): 1.62 min.

Scheme B15: (2S,4S)-2-(3-Chloro-2-fluoro-benzylcarbamoyl)-4-dimethylaminomethyl-4-fluoro-pyrrolidine-1-carboxylic acid tert-butyl ester

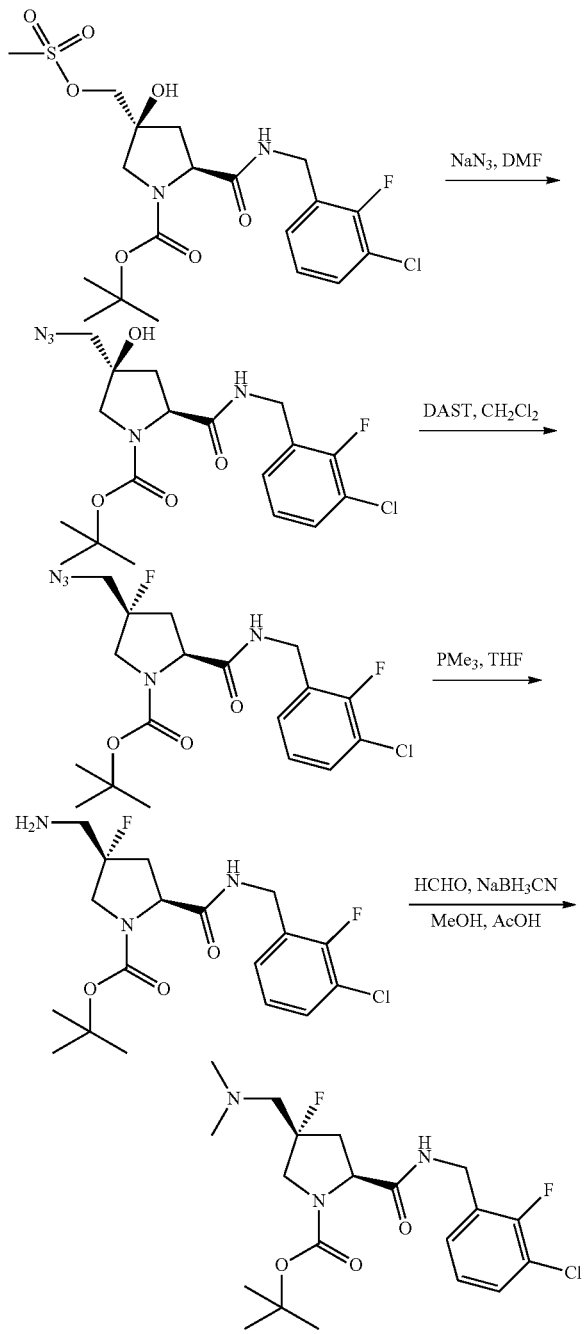

A. (2S,4S)-4-azidomethyl-2-(3-chloro-2-fluoro-benzylcarbamoyl)-4-hydroxy-pyrrolidine-1-carboxylic acid tert-butyl ester To a solution of (2S,4S)-2-(3-chloro-2-fluoro-benzylcarbamoyl)-4-hydroxy-4-methanesulfonyloxy methyl-pyrrolidine-1-carboxylic acid tert-butyl ester (580 mg, 1.21 mmol) (prepared as described Scheme B13) in DMF (20 mL) was added sodium azide (392 mL, 6.03 mmol) and the solution was stirred for 16 h at 80° C. The reaction mixture was diluted with EtOAc, washed with a saturated aqueous solution of NaHCO$_3$ (3 times). The organic layers were dried (Na$_2$SO$_4$), filtered and concentrated. The crude material was purified by flash column chromatography on silica gel (c-hexane/EtOAc 1:1) to give the desired material. MS (LC/MS): 430.1/432.1 [M+H]+, 374.1 [MH−tBu]+, 332 [MH−Boc]+; t$_R$ (HPLC conditions f): 2.22 min.

B. (2S,4R)-4-azidomethyl-2-(3-chloro-2-fluoro-benzylcarbamoyl)-4-fluoro-pyrrolidine-1-carboxylic acid tert-butyl ester To a solution of (2S,4S)-4-azidomethyl-2-(3-chloro-2-fluoro-benzylcarbamoyl)-4-hydroxy-pyrrolidine-1-carboxylic acid tert-butyl ester (430 mg, 1.0 mmol) in CH$_2$Cl$_2$ (25 mL) under N$_2$ atmosphere at −78° C. was added DAST (266 µL, 2.01 mmol). The reaction mixture was allowed to warm up to RT and further stirred for 1.5 h. The reaction mixture was poured into an aqueous saturated solution of NaHCO$_3$ and extracted twice with CH$_2$Cl$_2$. The combined organic layers were dried (Na$_2$SO$_4$), filtered and concentrated. The crude material was purified by flash column chromatography on silica gel (c-hexane/EtOAc 1:1) to give the desired material. MS (LC/MS): 474.1/476.2 [M+H]+, 472.1 [M−H]−; t$_R$ (HPLC conditions f): 2.23 min, 19F NMR (100 MHz, DMSO-d$_6$) δ (ppm): −120, −150.

C. (2S,4S)-4-aminomethyl-2-(3-chloro-2-fluoro-benzylcarbamoyl)-4-fluoro-pyrrolidine-1-carboxylic acid tert-butyl ester To a solution of (2S,4R)-4-azidomethyl-2-(3-chloro-2-fluoro-benzylcarbamoyl)-4-fluoro-pyrrolidine-1-carboxylic acid tert-butyl ester (380 mg, 0.884 mmol) in THF (25 mL) under N$_2$ atmosphere at RT was added 1M PMe$_3$ in THF (1.06 mL, 1.06 mmol). The reaction mixture was stirred for 16 h then quenched with water and extracted twice with EtOAc. The combined organic layers were dried (Na$_2$SO$_4$), filtered and concentrated. The crude material was purified by flash column chromatography on silica gel (CH$_2$Cl$_2$/MeOH 8:2) to give the desired material. MS (LC/MS): 404/406 [M+H]+, 402 [M−H]−; t$_R$ (HPLC conditions f): 1.57 min, $^{19}$F NMR (100 MHz, DMSO-d$_6$) δ (ppm): −120, −154.

D. (2S,4S)-2-(3-chloro-2-fluoro-benzylcarbamoyl)-4-dimethylaminomethyl-4-fluoro-pyrrolidine-1-carboxylic acid tert-butyl ester To a solution of (2S,4S)-4-aminomethyl-2-(3-chloro-2-fluoro-benzylcarbamoyl)-4-fluoro-pyrrolidine-1-carboxylic acid tert-butyl ester (245 mg, 0.607 mmol) in MeOH (2 mL) were added formaldehyde (836 µL, 6.07 mmol), sodium cyanoborohydride (126 mg, 2.0 mmol) and acetic acid (69.5 µL, 1.21 mmol). The reaction mixture was stirred for 16 h at RT then concentrated. The crude material was purified by flash column chromatography on silica gel (CH$_2$Cl$_2$/MeOH 8:2) to give the desired material. MS (LC/MS): 432.1/434.1 [M+H]+, 430.1 [M−H]−; t$_R$ (HPLC conditions f): 1.62 min, $^{19}$F NMR (100 MHz, DMSO-d$_6$) δ (ppm): −121, −149.

205

(2S,4R)-4-Azidomethyl-2-(3-chloro-2-fluoro-benzylcarbamoyl)-4-hydroxy-pyrrolidine-1-carboxylic acid tert-butyl ester

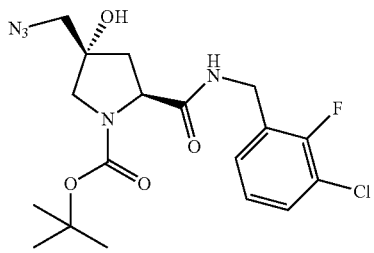 [SMILES: CC(C)(C)OC(=O)N1C[C@@](O)(CN=[N+]=[N-])C[C@H]1C(=O)NCc1cccc(Cl)c1F]

was obtained using the same protocols as described in Scheme B15 step A for the preparation of (2S,4R)-4-azidomethyl-2-(3-chloro-2-fluoro-benzylcarbamoyl)-4-fluoro-pyrrolidine-1-carboxylic acid tert-butyl ester starting from (2S,4R)-2-(3-chloro-2-fluoro-benzylcarbamoyl)-4-hydroxy-4-methanesulfonyloxy methyl-pyrrolidine-1-carboxylic acid tert-butyl ester (prepared from (2S,4R)-2-(3-chloro-2-fluoro-benzylcarbamoyl)-4-hydroxy-4-hydroxymethyl-pyrrolidine-1-carboxylic acid tert-butyl ester as described scheme B13). MS (UPLC/MS): 450/452 [M+Na]+, 472/474 [M+HCOO]−; $t_R$ (HPLC conditions f): 2.08 min.

(2S,4S)-4-Azidomethyl-2-(3-chloro-2-fluoro-benzylcarbamoyl)-4-fluoro-pyrrolidine-1-carboxylic acid tert-butyl ester

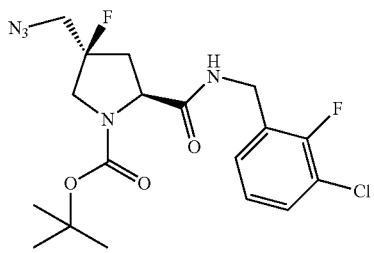 [SMILES: CC(C)(C)OC(=O)N1C[C@](F)(CN=[N+]=[N-])C[C@H]1C(=O)NCc1cccc(Cl)c1F]

was obtained using the same protocols as described in Scheme B15 step A and B for the preparation of (2S,4R)-4-azidomethyl-2-(3-chloro-2-fluoro-benzylcarbamoyl)-4-fluoro-pyrrolidine-1-carboxylic acid tert-butyl ester starting from (2S,4R)-2-(3-chloro-2-fluoro-benzylcarbamoyl)-4-hydroxy-4-methanesulfonyloxy methyl-pyrrolidine-1-carboxylic acid tert-butyl ester (prepared from (2S,4R)-2-(3-chloro-2-fluoro-benzylcarbamoyl)-4-hydroxy-4-hydroxymethyl-pyrrolidine-1-carboxylic acid tert-butyl ester as described scheme B13). MS (LC/MS): 474.1/476.2 [M+H]+, 472.1 [M−H]−; $t_R$ (HPLC conditions f): 2.180 min, $^{19}$F NMR (100 MHz, DMSO-d$_6$) δ (ppm): −120, −150.

206

(2S,4S)-4-(Acetylamino-methyl)-2-(3-chloro-2-fluoro-benzylcarbamoyl)-4-fluoro-pyrrolidine-1-carboxylic acid tert-butyl ester

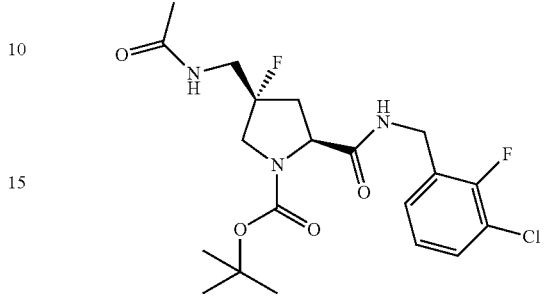

To a solution of (2S,4S)-4-aminomethyl-2-(3-chloro-2-fluoro-benzylcarbamoyl)-4-fluoro-pyrrolidine-1-carboxylic acid tert-butyl ester (179 mg, 0.51 mmol) in MeOH (5 ml) was added acetic anhydride (0.52 mL, 5.1 mmol). The reaction mixture was stirred at RT for 16 hours then quenched with 6N NaOH. After extraction with CH$_2$Cl$_2$ (3×30 mL), the organic phases were joined and dried on Na2SO4, filtered and concentrated. Purification by flash column chromatography on silica gel (c-hexane/EtOAc 1:1).]. MS (UPLC/MS): 395 [M+H]+; $t_R$ (HPLC conditions f): 2.02 min.

Scheme B16: preparation of (2S,4R)-4-Azidomethyl-2-[(S)-1-(3-bromo-phenyl)-2-fluoro-ethylcarbamoyl]-4-fluoro-pyrrolidine-1-carboxylic acid tert-butyl ester

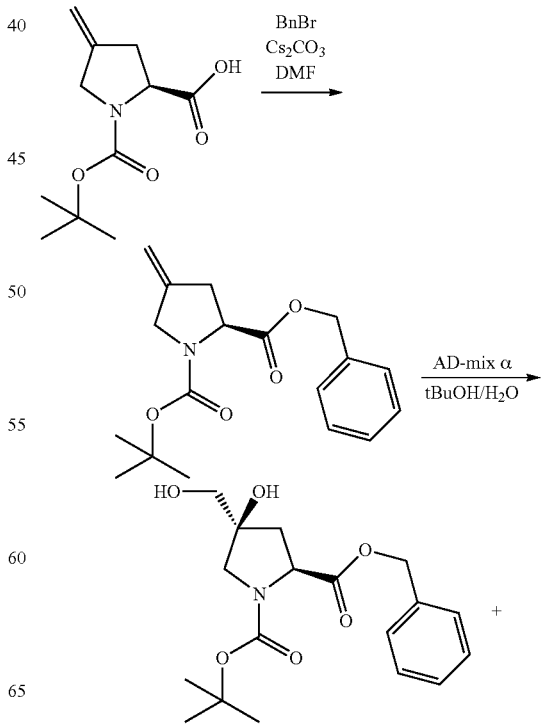

-continued

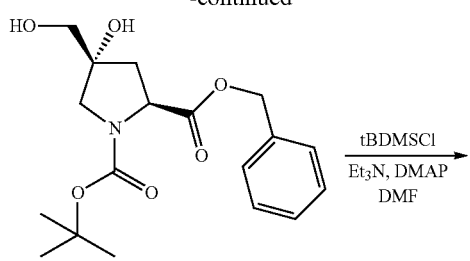

tBDMSCl
Et₃N, DMAP
DMF

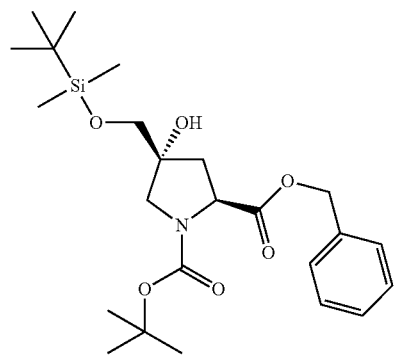

+

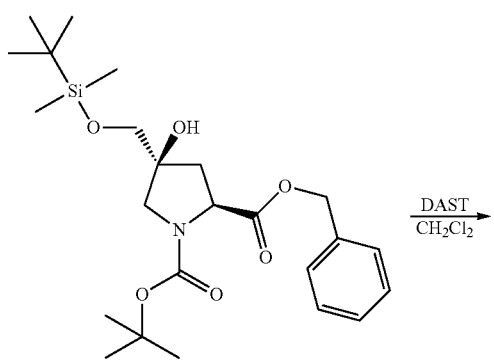

DAST
CH₂Cl₂

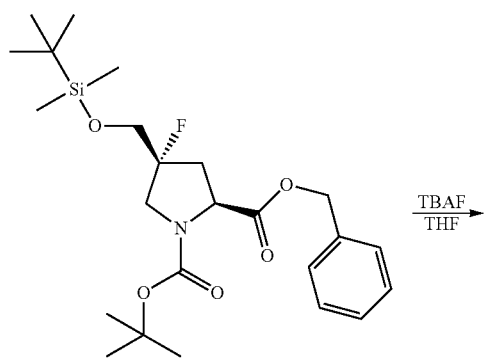

TBAF
THF

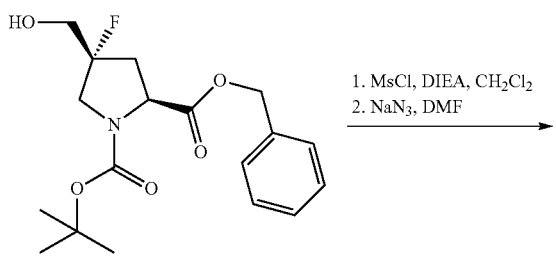

1. MsCl, DIEA, CH₂Cl₂
2. NaN₃, DMF

-continued

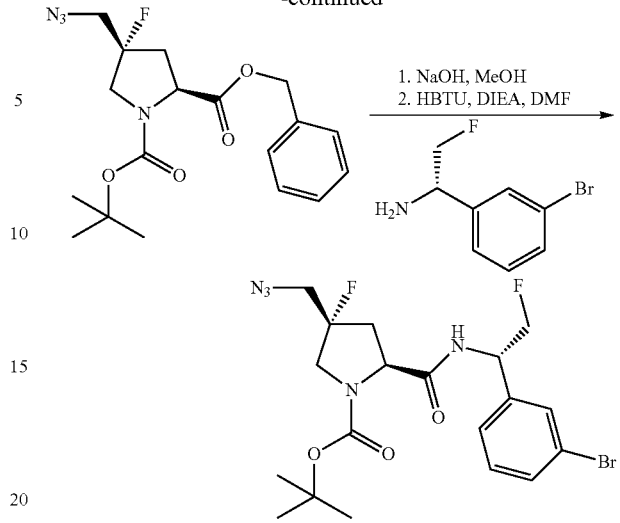

1. NaOH, MeOH
2. HBTU, DIEA, DMF

A. (S)-4-Methylene-pyrrolidine-1,2-dicarboxylic acid 2-benzyl ester 1-tert-butyl ester To (S)-1-(tert-butoxycarbonyl)-4-methylenepyrrolidine-2-carboxylic acid (4 g, 17.60 mmol) dissolved in DMF (100 mL) at 0° C. were added benzyl bromide (2.51 mL, 21.12 mmol) and cesium carbonate (6.31 g, 19.36 mmol). The solution was stirred 16 h at RT then was concentrated. Purification by flash column chromatography on silica gel (c-hexane/EtOAc 1:1). MS (UPLC/MS): 218 [MH−tBu]+, $t_R$ (HPLC conditions f): 2.44 min.

B. (2S,4S)-4-Hydroxy-4-hydroxymethyl-pyrrolidine-1,2-dicarboxylic acid 2-benzyl ester 1-tert-butyl ester and (2S,4S)-4-Hydroxy-4-hydroxymethyl-pyrrolidine-1,2-dicarboxylic acid 2-benzyl ester 1-tert-butyl ester A solution of AD-mix-alpha (30 g, 21.43 mmol) in tBuOH (120 mL) and Water (120 mL) was stirred until both phases were clear and then cooled to 0° C. (S)-4-Methylene-pyrrolidine-1,2-dicarboxylic acid 2-benzyl ester 1-tert-butyl ester (6.48 g, 20.42 mmol) was added and the reaction mixture was stirred at RT for 16 h. The reaction mixture was quenched at 0° C. by addition of sodium sulfite (14.5 g) and then allowed to reach RT and stirred for 1 h. After extraction with CH₂Cl₂ (3×100 mL), the organic phases were joined, dried with Na₂SO₄, filtered and concentrated. Purification by flash column chromatography on silica gel (c-hexane/EtOAc 1:1) gave the desired compounds as an unseparable mixture. MS (UPLC/MS): 352 [M+H]+, $t_R$ (HPLC conditions f): 1.50 min.

C. (2S,4R)-4-(tert-Butyl-dimethyl-silanyloxymethyl)-4-hydroxy-pyrrolidine-1,2-dicarboxylic acid 2-benzyl ester 1-tert-butyl ester and (2S,4S)-4-(tert-Butyl-dimethyl-silanyloxymethyl)-4-hydroxy-pyrrolidine-1,2-dicarboxylic acid 2-benzyl ester 1-tert-butyl ester To a solution of (2S,4S)-4-hydroxy-4-hydroxymethyl-pyrrolidine-1,2-dicarboxylic acid 2-benzyl ester 1-tert-butyl ester and (2S,4S)-4-hydroxy-4-hydroxymethyl-pyrrolidine-1,2-dicarboxylic acid 2-benzyl ester 1-tert-butyl ester (5.46 g, 15.54 mmol) in DMF (80 mL) were added tert-butyl dimethylchlorosilane (2.45 g, 16.32 mmol), triethylamine (2.16 mL, 15.54 mmol) and DMAP (0.19 g, 1.55 mmol). The solution was stirred for 16 h at RT then was washed with sat NaHCO$_3$ (2×100 mL). The organic layer was dried with Na$_2$SO$_4$, filtered and concentrated. Purification by flash column chromatography on silica gel (c-hexane/EtOAc 9:1) gave (2S,4R)-4-(tert-butyl-dimethyl-silanyloxymethyl)-4-hydroxy-pyrrolidine-1,2-dicarboxylic acid 2-benzyl ester 1-tert-butyl ester: MS (UPLC/MS): 466 [M+H]+]+, 510 [M+HCOO]−; $t_R$ (HPLC conditions f): 2.83 min and (2S,4S)-4-(tert-butyl-dimethyl-silanyloxymethyl)-4-hydroxy-pyrrolidine-1,2-dicarboxylic acid 2-benzyl ester 1-tert-butyl ester: MS (UPLC/MS): 466 [M+H]+, 510 [M+HCOO]−; $t_R$ (HPLC conditions f): 2.95 min.

D. (2S,4R)-4-(tert-Butyl-dimethyl-silanyloxymethyl)-4-fluoro-pyrrolidine-1,2-dicarboxylic acid 2-benzyl ester 1-tert-butyl ester To a solution of (2S,4S)-4-(tert-butyl-dimethyl-silanyloxymethyl)-4-hydroxy-pyrrolidine-1,2-dicarboxylic acid 2-benzyl ester 1-tert-butyl ester (5.20 g, 11.17 mmol) in CH$_2$Cl$_2$ (100 mL) at −78° C. was added DAST (2.21 mL, 16.75 mmol). The solution was stirred for 16 hours at RT then was washed with sat NaHCO$_3$ (2×100 mL). The organic layer was dried with Na$_2$SO$_4$, filtered and concentrated. Purification by flash column chromatography on silica gel (c-hexane/EtOAc 9:1). MS (UPLC/MS): 468 [M+H]+, 512 [M+HCOO]−; $t_R$ (HPLC conditions f): 3.00 min.

E. (2S,4R)-4-Fluoro-4-hydroxymethyl-pyrrolidine-1,2-dicarboxylic acid 2-benzyl ester 1-tert-butyl ester To a solution of (2S,4R)-4-(tert-butyl-dimethyl-silanyloxymethyl)-4-fluoro-pyrrolidine-1,2-dicarboxylic acid 2-benzyl ester 1-tert-butyl ester (4.10 g, 8.77 mmol) in THF (80 mL) at RT was added 1M TBAF in THF (17.53 mL, 17.53 mmol). The reaction was stirred at RT for 30 min then poured into water and extracted with EtOAc. The organic layer was dried with Na$_2$SO$_4$, filtered and concentrated. Purification by flash column chromatography on silica gel (c-hexane/EtOAc 3:2). MS (UPLC/MS): 354 [M+H]+, 398 [M+HCOO]−; $t_R$ (HPLC conditions f): 2.07 min.

F. (2S,4R)-4-Azidomethyl-4-fluoro-pyrrolidine-1,2-dicarboxylic acid 2-benzyl ester 1-tert-butyl ester To a solution of (2S,4R)-4-fluoro-4-hydroxymethyl-pyrrolidine-1,2-dicarboxylic acid 2-benzyl ester 1-tert-butyl ester (1.76 g, 4.98 mmol) in CH$_2$Cl$_2$ (30 mL) and few drops of NEt$_3$ was stirred at RT for 10 min then methanesulfonyl chloride (0.39 mL, 5.03 mmol) was added. The reaction was stirred at RT for 30 min then poured into water and extracted with EtOAc. The organic layer was dried with Na$_2$SO$_4$, filtered and concentrated. The residue (2.25 g, 4.21 mmol) was dissolved in DMF (50 mL) and sodium azide (1.69 g, 26.1 mmol) was added. The solution was stirred for 16 hours at 80° C. then was cooled to RT, poured into water and extracted with EtOAc. The organic layer was dried with Na$_2$SO$_4$, filtered and concentrated. Purification by flash column chromatography on silica gel (c-hexane/EtOAc 1:1). MS (UPLC/MS): 379 [M+H]+; $t_R$ (HPLC conditions f): 2.44 min.

G. (2S,4R)-4-Azidomethyl-2-[(S)-1-(3-bromo-phenyl)-2-fluoro-ethylcarbamoyl]-4-fluoro-pyrrolidine-1-carboxylic acid tert-butyl ester To a solution of (2S,4R)-4-azidomethyl-4-fluoro-pyrrolidine-1,2-dicarboxylic acid 2-benzyl ester 1-tert-butyl ester (500 mg, 1.32 mmol) in methanol (20 mL), 1M sodium hydroxide (2.64 mL, 2.64 mmol) was added. The solution was stirred for 2 hours at RT then was diluted with water, the methanol was removed under reduced pressure. The aqueous layer was washed with Et$_2$O (2×100 mL). The aqueous layer was acidified until pH 3 with 2N HCl and extracted with EtOAc (2×100 mL), dried with Na$_2$SO$_4$, filtered and concentrated. To the residue (100 mg, 0.34 mmol), (S)-1-(3-bromo-phenyl)-2-fluoro-ethylamine (described in Part C) (83 mg, 0.38 mmol) and HBTU (197 mg, 0.52 mmol) in DMF (5 mL) was added DIPEA (0.12 mL, 0.69 mmol). The reaction mixture was stirred for 16 h at RT then poured into water and extracted with EtOAc. The organic layer was dried with Na$_2$SO$_4$, filtered and concentrated. Purification by flash column chromatography on silica gel (c-hexane/EtOAc 1:1). MS (UPLC/MS): 488 [M+H]+, 532 [M+HCOO]−; $t_R$ (HPLC conditions f): 2.32 min.

Scheme B17: preparation of (2S,4S)-4-Fluoro-4-{[methyl-(2,2,2-trichloro-ethoxycarbonyl)-amino]-methyl}-pyrrolidine-1,2-dicarboxylic acid 2-benzyl ester 1-tert-butyl ester

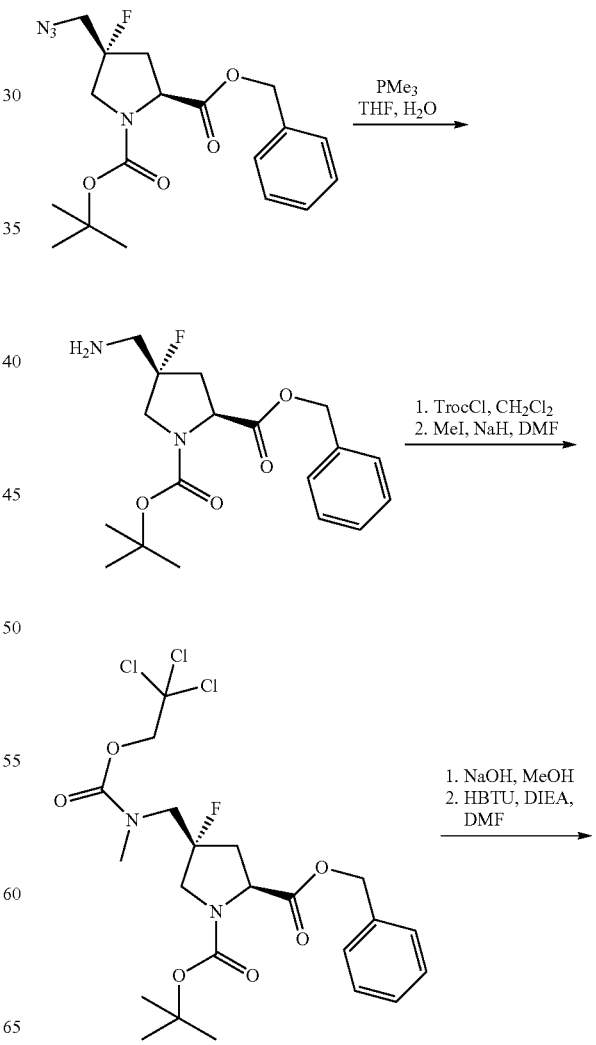

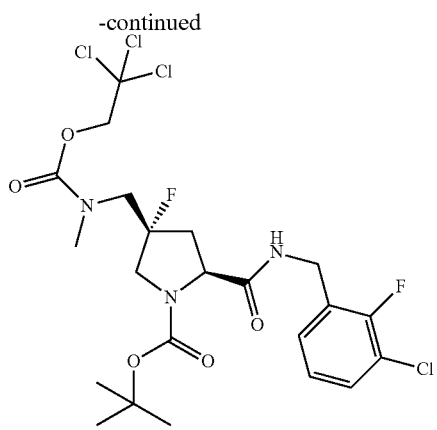

A. (2S,4S)-4-Aminomethyl-4-fluoro-pyrrolidine-1,2-dicarboxylic acid 2-benzyl ester 1-tert-butyl ester A solution of (2S,4R)-4-azidomethyl-4-fluoro-pyrrolidine-1,2-dicarboxylic acid 2-benzyl ester 1-tert-butyl ester (prepared as described in Scheme B16) (1 g, 2.64 mmol), trimethylphosphine in THF (3.17 mL, 3.17 mmol) and water (0.10 mL, 5.29 mmol) in THF (40 mL) was stirred for 16 h at RT. The reaction mixture was quenched with water, extracted with EtOAc, washed with brine, dried over $Na_2SO_4$, filtered and concentrated. Purification by flash column chromatography on silica gel ($CH_2Cl_2$/MeOH 9:1). MS (UPLC/MS): 353 [M+H]+, 411 [M+HCOO]−; $t_R$ (HPLC conditions f): 1.62 min.

B. (2S,4S)-2-(3-Chloro-2-fluoro-benzylcarbamoyl)-4-fluoro-4-{[methyl-(2,2,2-trichloro-ethoxycarbonyl)-amino]-methyl}-pyrrolidine-1-carboxylic acid tert-butyl ester To a solution of (2S,4S)-4-aminomethyl-4-fluoro-pyrrolidine-1,2-dicarboxylic acid 2-benzyl ester 1-tert-butyl ester (100 mg, 0.28 mmol) in $CH_2Cl_2$ (10 mL) was added Troc-Cl (0.05 mL, 0.34 mmol). The reaction mixture was stirred for 16 h at RT. The reaction mixture was quenched with water, extracted with EtOAc, washed with brine, dried over $Na_2SO_4$, filtered, concentrated and purified by flash column chromatography on silica gel (c-hexane/EtOAc 1:1). To a solution of (2S,4S)-4-Fluoro-4-[(2,2,2-trichloro-ethoxycarbonylamino)-methyl]-pyrrolidine-1,2-dicarboxylic acid 2-benzyl ester 1-tert-butyl ester (50 mg, 0.09 mmol) and methyl iodide (0.02 mL, 0.28 mmol) in DMF (5 mL) at 0° C. was added sodium hydride (2.50 mg, 0.10 mmol) in portions. The reaction mixture was stirred 90 min at 0° C. and 16 h at RT. The reaction mixture was quenched with water, extracted with EtOAc, washed with brine, dried over $Na_2SO_4$, filtered and concentrated. Purification by flash column chromatography on silica gel (c-hexane/EtOAc 1:1). MS (UPLC/MS): 541/543 [M+H]+, 586/587 [M+HCOO]−; $t_R$ (HPLC conditions f): 2.66 min.

C. (2S,4S)-4-Fluoro-4-{[methyl-(2,2,2-trichloro-ethoxycarbonyl)-amino]-methyl}-pyrrolidine-1,2-dicarboxylic acid 2-benzyl ester 1-tert-butyl ester To a solution of (2S,4S)-2-(3-chloro-2-fluoro-benzylcarbamoyl)-4-fluoro-4-{[methyl-(2,2,2-trichloro-ethoxycarbonyl)-amino]-methyl}-pyrrolidine-1-carboxylic acid tert-butyl ester (110 mg, 0.20 mmol) in methanol (5 mL), 1M sodium hydroxide 0.40 mL, 0.40 mmol) was added. The solution was stirred for 2 h at RT then was diluted with water, the methanol was removed under reduced pressure. The aqueous layer was washed with $Et_2O$ (2×25 mL). The aqueous layer was acidified until pH 3 with 2N HCl and extracted with EtOAc (2×25 mL), dried with $Na_2SO_4$, filtered and concentrated. To the residue (80 mg, 0.17 mmol), (3-chloro-2-fluorophenyl)methanamine (33.9 mg, 0.21 mmol) and HBTU (101 mg, 0.26 mmol) dissolved in DMF (5 mL) was added DIPEA (0.06 mL, 0.35 mmol). The reaction mixture was stirred for 16 h at RT. The reaction mixture was quenched with water, extracted with EtOAc, washed with brine, dried over $Na_2SO_4$, filtered and concentrated. Purification by flash column chromatography on silica gel (c-hexane/EtOAc 1:1). MS (UPLC/MS): 592/594 [M+H]+, 636/638 [M+HCOO]−; $t_R$ (HPLC conditions f): 2.49 min.

Scheme B18: preparation of (R)-4-Fluoro-4-methyl-pyrrolidine-1,2-dicarboxylic acid 1-tert-butyl ester

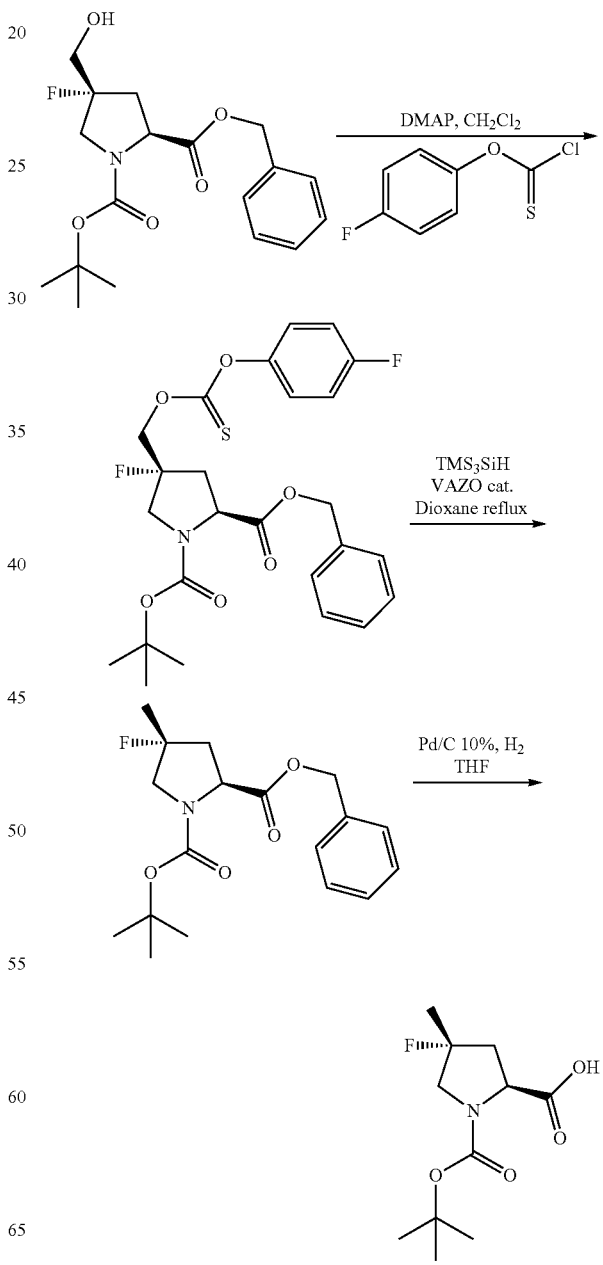

A. (2S,4R)-4-Fluoro-4-(4-fluoro-phenoxythiocarbonyloxymethyl)-pyrrolidine-1,2-dicarboxylic acid 2-benzyl ester 1-tert-butyl ester To a solution of (2S,4R)-4-fluoro-4-hydroxymethyl-pyrrolidine-1,2-dicarboxylic acid 2-benzyl ester 1-tert-butyl ester (synthesis described in Scheme B16) (300 mg, 0.85 mmol) in CH$_2$Cl$_2$ (10 mL) was added 4-fluorophenylthiono chloro formate (0.18 mL, 1.27 mmol) and DMAP (311 mg, 2.55 mmol). The reaction mixture was stirred at RT for 2 days then was diluted with CH$_2$Cl$_2$ (40 mL), washed with aq 0.5 HCl (50 mL), water (50 mL) and brine, dried over Na$_2$SO$_4$, filtered and concentrated. Purification by flash column chromatography on silica gel (c-hexane/EtOAc 3:1) gave the desired compound. MS (UPLC/MS): 508 [M+H]+; t$_R$ (HPLC conditions f): 2.73 min.

B. (2S,4R)-4-Fluoro-4-methyl-pyrrolidine-1,2-dicarboxylic acid 2-benzyl ester 1-tert-butyl ester To a solution of (2S,4R)-4-fluoro-4-(4-fluoro-phenoxythiocarbonyloxymethyl)-pyrrolidine-1,2-dicarboxylic acid 2-benzyl ester 1-tert-butyl ester (290 mg, 0.57 mmol) in dioxane (5 mL) were added VAZO (69 mg, 0.28 mmol) and tris(trimethylsilyl)silane (0.24 mL, 0.77 mmol). The reaction mixture was refluxed for 30 min then was stirred for 16 h at RT and concentrated. Purification by flash column chromatography on silica gel (c-hexane/EtOAc 4:1). MS (UPLC/MS): 338 [M+H]+; t$_R$ (HPLC conditions f): 2.38 min.

C. (2S,4R)-4-Fluoro-4-methyl-pyrrolidine-1,2-dicarboxylic acid 1-tert-butyl ester A solution containing (2S,4R)-4-fluoro-4-methyl-pyrrolidine-1,2-dicarboxylic acid 2-benzyl ester 1-tert-butyl ester (700 mg, 2.075 mmol) and Pd/C 10% (221 mg, 2.075 mmol) in THF (6 mL) was placed under a nitrogen atmosphere and stirred for 5 h. The catalyst was removed through a pad of celite and washed with MeOH. Solvents were removed under vacuum to give the desired material as a colorless oil which was used without further purification in the next step. MS (UPLC/MS): 246.2 [M−H]−, 292.2 [M+HCOO−]−, 493.4 [2M−H]−.

Scheme B19: preparation of (2R,3R,4R)-4-Azido-3-fluoro-pyrrolidine-2-carboxylic acid 3-chloro-2-fluoro-benzylamide and (2S,3S,4S)-3-azido-4-fluoro-pyrrolidine-2-carboxylic acid 3-chloro-2-fluoro-benzylamide

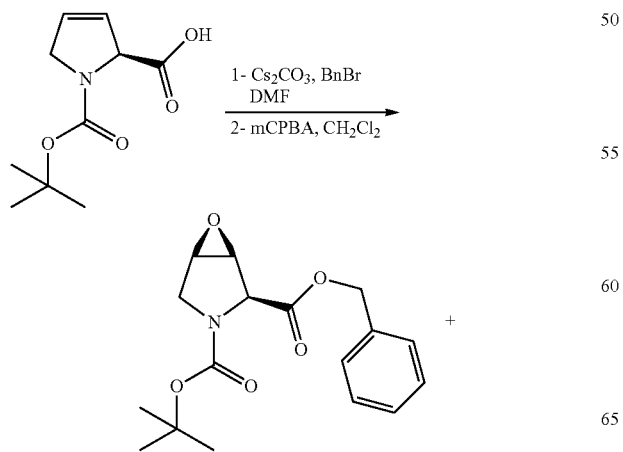

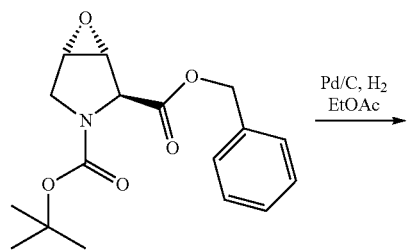

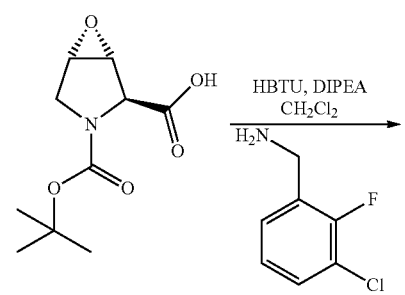

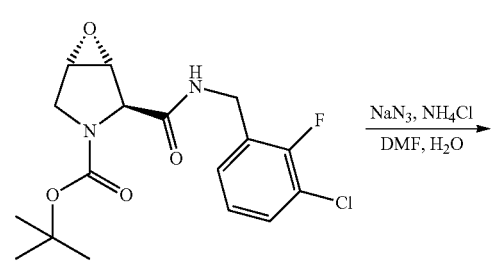

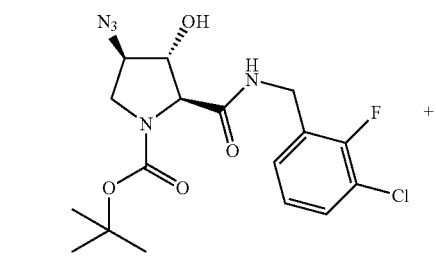

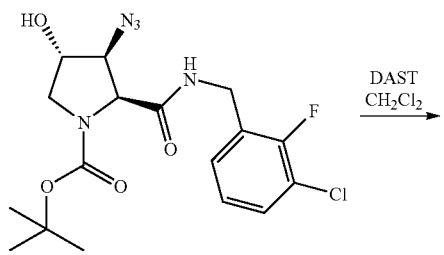

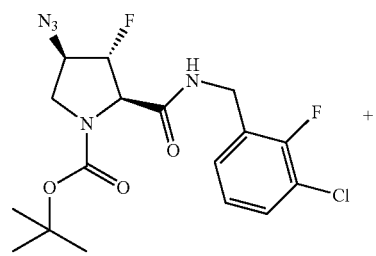

-continued

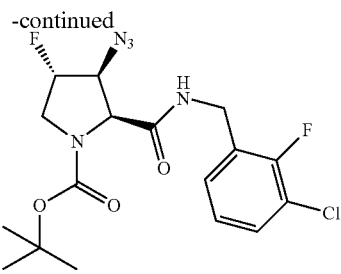

A. (S)-2,5-Dihydro-pyrrole-1,2-dicarboxylic acid 2-benzyl ester 1-tert-butyl ester To a solution of (S)-1-(tert-butoxycarbonyl)-2,5-dihydro-1H-pyrrole-2-carboxylic acid (10 g, 46.9 mmol) in DMF (249 mL) cooled at 0° C. were added cesium carbonate (16.8 g, 51.6 mmol) then benzyl bromide (6.69 mL, 56.3 mmol) and the mixture was allowed to warm up to RT overnight. The reaction mixture was quenched with water (500 mL) and extracted with ethyl acetate (3×200 mL). The organic layers were combined and washed with brine, dried ($Na_2SO_4$), filtered and concentrated. The crude residue was purified by flash column chromatography on silica gel (c-hexane to c-hexane/EtOAc 4:1) to give the desired material. TLC, $R_f$ (c-hexane/EtOAc 4:1)=0.25; MS (UPLC): 326 [M+Na]+, 204 [MH−Boc]+; $t_R$ (HPLC conditions f): 2.35 min.

B. (1R,2S,5S)-6-Oxa-3-aza-bicyclo[3.1.0]hexane-2,3-dicarboxylic acid 2-benzyl ester 3-tert-butyl ester and (1S,2S,5R)-6-oxa-3-aza-bicyclo[3.1.0]hexane-2,3-dicarboxylic acid 2-benzyl ester 3-tert-butyl ester To a solution of (S)-2,5-dihydro-pyrrole-1,2-dicarboxylic acid 2-benzyl ester 1-tert-butyl ester (6.14 g, 20.2 mmol) were added 3-chloroperbenzoic acid (6.99 g, 40.5 mmol) and 4,4' thiobis(6-tert-butyl-m cresol) (0.726 g, 2.02 mmol). The mixture was refluxed under nitrogen atmosphere overnight then an additional batch of 3-chloroperbenzoic acid (6.99 g, 40.5 mmol) and 4,4' thiobis(6-tert-butyl-m cresol) (0.726 g, 2.02 mmol) was added. Refluxing was continued for 24 h. The reaction mixture was diluted with $CH_2Cl_2$, washed with sodium metabisulphite aqueous (5%), saturated aqueous $NaHCO_3$, brine, dried over $Na_2SO_4$, filtered and concentrated. The diastereomeric epoxides in a ratio of 65/35 (determined by NMR on the crude mixture) were separated by flash column chromatography (c-hexane to c-hexane/EtOAc 4:1) to give (1R,2S,5S)-6-oxa-3-aza-bicyclo[3.1.0]hexane-2,3-dicarboxylic acid 2-benzyl ester 3-tert-butyl ester: TLC, $R_f$ (c-hexane/EtOAc 4:1)=0.20; MS (LC/MS): 220 [MH−Boc]+, 342 [M+Na]+; $t_R$ (HPLC conditions f): 2.14 min and (1S,2S,5R)-6-oxa-3-aza-bicyclo[3.1.0]hexane-2,3-dicarboxylic acid 2-benzyl ester 3-tert-butyl ester: TLC, $R_f$(c-hexane/EtOAc 4:1)=0.15; MS (LC/MS): 220 [MH−Boc]+, 342 [M+Na]+; $t_R$ (HPLC conditions f): 2.03 min.

C. (1R,2S,5S)-6-Oxa-3-aza-bicyclo[3.1.0]hexane-2,3-dicarboxylic acid 3-tert-butyl ester A solution (1R,2S,5S)-6-oxa-3-aza-bicyclo[3.1.0]hexane-2,3-dicarboxylic acid 2-benzyl ester 3-tert-butyl ester (2.62 g, 8.21 mmol) in ethyl acetate (32 mL) was hydrogenated under $H_2$ with palladium hydroxide on carbon (1.15 g, 8.21 mmol) for 1 night. The reaction mixture was filtered over a glass fiber filter, quenched with $Na_2CO_3$ saturated aqueous solution and was extracted twice with EtOAc. The aqueous layer was acidified with HCl 1N to pH=2 and extracted 4 times with ethyl acetate, washed with brine, dried over $Na_2SO_4$, filtered and concentrated to give the desired material which was used in the next step without further purification. MS (UPLC): 230 [M+H]+, 228 [M−H]−.

D. (1R,2S,5S)-2-(3-Chloro-2-fluoro-benzylcarbamoyl)-6-oxa-3-aza-bicyclo[3.1.0]hexane-3-carboxylic acid tert-butyl ester To a mixture of (1R,2S,5S)-6-oxa-3-aza-bicyclo[3.1.0] hexane-2,3-dicarboxylic acid 3-tert-butyl ester (1.55 g, 6.79 mmol), (3-chloro-2-fluoro)benzylamine (1.63 g, 10.19 mmol) and HBTU (3.86 g, 10.2 mmol) in $CH_2Cl_2$ (17 mL) was added diisopropylethylamine (1.78 mL, 10.19 mmol). The resulting solution was stirred overnight at RT under nitrogen then poured into an aqueous saturated $NaHCO_3$ solution and extracted with $CH_2Cl_2$ (×3). The organic layers were combined, washed with brine, dried over $Na_2SO_4$, filtered and concentrated. The crude residue was purified by flash column chromatography on silica gel (c-hexane to c-hexane/EtOAc 1:1). TLC, $R_f$ (EtOAc)=0.65; MS (UPLC): 371 [M+H]+, 271 [MH−Boc]+; $t_R$ (HPLC conditions f): 2.04 min.

E. (2S,3R,4R)-4-Azido-2-(3-chloro-2-fluoro-benzylcarbamoyl)-3-hydroxy-pyrrolidine-1-carboxylic acid tert-butyl ester and (2S,3S,4S)-3-Azido-2-(3-chloro-2-fluoro-benzylcarbamoyl)-4-hydroxy-pyrrolidine-1-carboxylic acid tert-butyl ester A solution of (1R,2S,5S)-2-(3-chloro-2-fluoro-benzylcarbamoyl)-6-oxa-3-aza-bicyclo[3.1.0]hexane-3-carboxylic acid tert-butyl ester (2.3 g, 5.95 mmol), sodium azide (2.32 g, 35.7 mmol) and $NH_4Cl$ (0.637 g, 11.9 mmol) in DMF (23 mL) with $H_2O$ (3.22 mL, 179 mmol) was heated at 100° C. for 1 h. The reaction mixture was poured into ice, extracted with $CH_2Cl_2$, washed with water and brine, dried over $Na_2SO_4$, filtered and concentrated. The crude residue was purified by flash column chromatography on silica gel (c-hexane to c-hexane/EtOAc 1:1) to give a mixture of unseparable regioisomers (2S,3R,4R)-4-azido-2-(3-chloro-2-fluoro-benzylcarbamoyl)-3-hydroxy-pyrrolidine-1-carboxylic acid tert-butyl ester and (2S,3S,4S)-3-azido-2-(3-chloro-2-fluoro-benzylcarbamoyl)-4-hydroxy-pyrrolidine-1-carboxylic acid tert-butyl ester in a ratio 3:2 (absolute stereochemistry was assigned by NMR). TLC, $R_f$(c-hexane/EtOAc 1:1)=0.3; MS (UPLC): 414 [M+H]+, 315 [MH−Boc]+, 412 [M−H]−; $t_R$ (HPLC conditions f): 2.06 min.

F. (2R,3R,4R)-4-Azido-2-(3-chloro-2-fluoro-benzylcarbamoyl)-3-fluoro-pyrrolidine-1-carboxylic acid tert-butyl ester and (2S,3S,4S)-3-Azido-2-(3-chloro-2-fluoro-benzylcarbamoyl)-4-fluoro-pyrrolidine-1-carboxylic acid tert-butyl ester To a solution of (2S,3R,4R)-4-azido-2-(3-chloro-2-fluoro-benzylcarbamoyl)-3-hydroxy-pyrrolidine-1-carboxylic acid tert-butyl ester and (2S,3S,4S)-3-azido-2-(3-chloro-2-fluoro-benzylcarbamoyl)-4-hydroxy-pyrrolidine-1-carboxylic acid tert-butyl ester (ratio 3/2, 1.14 g, 2.75 mmol) in $CH_2Cl_2$ (55 mL) was added DAST (1.456 mL, 11.02 mmol) at −78° C. and the reaction mixture was stirred overnight at RT. The reaction mixture was carefully quenched with a saturated aqueous solution of $NaHCO_3$, extracted with $CH_2Cl_2$, dried over $Na_2SO_4$, filtered and concentrated. The crude residue was purified by flash column chromatography on silica gel (c-hexane to c-hexane/EtOAc 9:1) to give a mixture of the two regioisomers, which were separated by preparative HPLC (Sunfire prep C18-ODB, 5 µm, 30×100 mm, 30% CH₃CN/H₂O 1.5 min, 30-100% CH₃CN/H₂O in 58.5 min, CH₃CN/H₂O containing 0.1% TFA flow: 20 mL/min) to give after lyophilization of the purified fractions: (2R,3R,4R)-4-azido-2-(3-chloro-2-fluoro-benzylcarbamoyl)-3-fluoro-pyrrolidine-1-carboxylic acid tert-butyl ester; TLC, R$_f$ (c-hexane/EtOAc 4:1)=0.23; MS (LC/MS): 416 [M+H]+, 316 [MH−Boc]+; 414 [M−H]−, t$_R$ (HPLC conditions h): 3.11 min and (2S,3S,4S)-3-azido-2-(3-chloro-2-fluoro-benzyl carbamoyl)-4-fluoro-pyrrolidine-1-carboxylic acid tert-butyl ester; R$_f$ (c-hexane/EtOAc 4:1)=0.13; MS (LC/MS): 416 [M+H]+, 316 [MH−Boc]+; 414 [M−H]−; t$_R$ (HPLC conditions h): 3.02 min.

Scheme B20: preparation of (2R,3S,4R)-2-(3-Chloro-2-fluoro-benzylcarbamoyl)-4-dimethylamino-3-fluoro-pyrrolidine-1-carboxylic acid tert-butyl ester

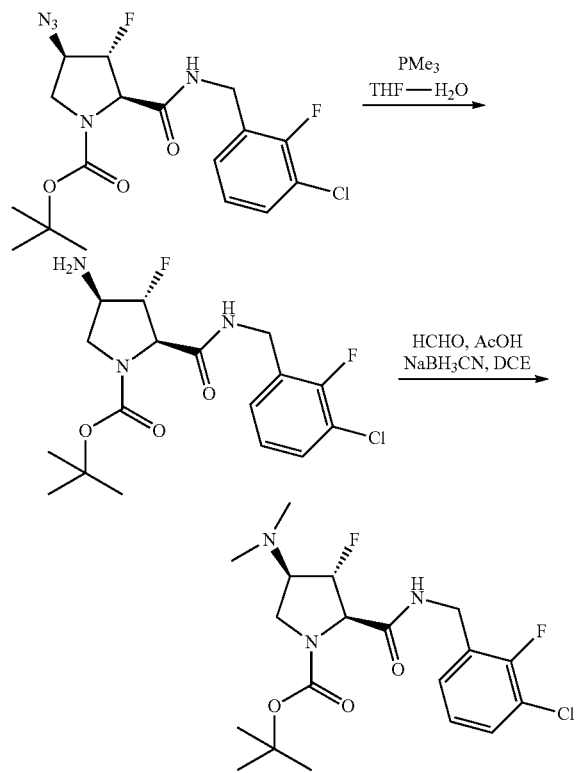

A. (2R,3S,4R)-4-Amino-2-(3-chloro-2-fluoro-benzylcarbamoyl)-3-fluoro-pyrrolidine-1-carboxylic acid tert-butyl ester A solution of (2R,3R,4R)-4-azido-2-(3-chloro-2-fluoro-benzylcarbamoyl)-3-fluoro-pyrrolidine-1-carboxylic acid tert-butyl ester (described in Scheme B19) (485 mg, 1.16 mmol), trimethylphosphine in THF (2.33 mL, 2.33 mmol) and water (0.04 mL, 2.33 mmol) in THF (20 mL) was stirred for 16 h at RT. The reaction mixture was quenched with water and extracted twice with EtOAc. The organic phase was washed with brine, dried over Na₂SO₄, filtered and concentrated. Purification by flash column chromatography on silica gel (CH₂Cl₂/MeOH 95:5). MS (UPLC/MS): 390/392 [M+H]+, 434/436 [M+HCOO]−; t$_R$ (HPLC conditions f): 1.64 min.

B. (2R,3S,4R)-2-(3-Chloro-2-fluoro-benzylcarbamoyl)-4-dimethylamino-3-fluoro-pyrrolidine-1-carboxylic acid tert-butyl ester To a solution of (2R,3S,4R)-4-amino-2-(3-chloro-2-fluoro-benzylcarbamoyl)-3-fluoro-pyrrolidine-1-carboxylic acid tert-butyl ester (190 mg, 0.48 mmol) in MeOH (2 mL) was added formaldehyde (134 µl, 4.87 mmol). The reaction mixture was stirred 30 min at RT before addition of sodium cyanoborohydride (101 mg, 1.60 mmol) and acetic acid (56 µl, 0.97 mmol). After stirring for 30 min, the solution was concentrated. Purification by flash column chromatography on silica gel (c-hexane/EtOAc 1:1) gave the desired compound. MS (UPLC/MS): 418/420 [M+H]+, 462/464 [M+HCOO]−; t$_R$ (HPLC conditions f): 1.61 min.

Scheme B21: preparation of [(3R,4S,5S)-1-tert-Butylcarbamoyl-5-(3-chloro-2-fluoro-benzylcarbamoyl)-4-methoxy-pyrrolidin-3-yl]-carbamic acid 9H-fluoren-9-ylmethyl ester

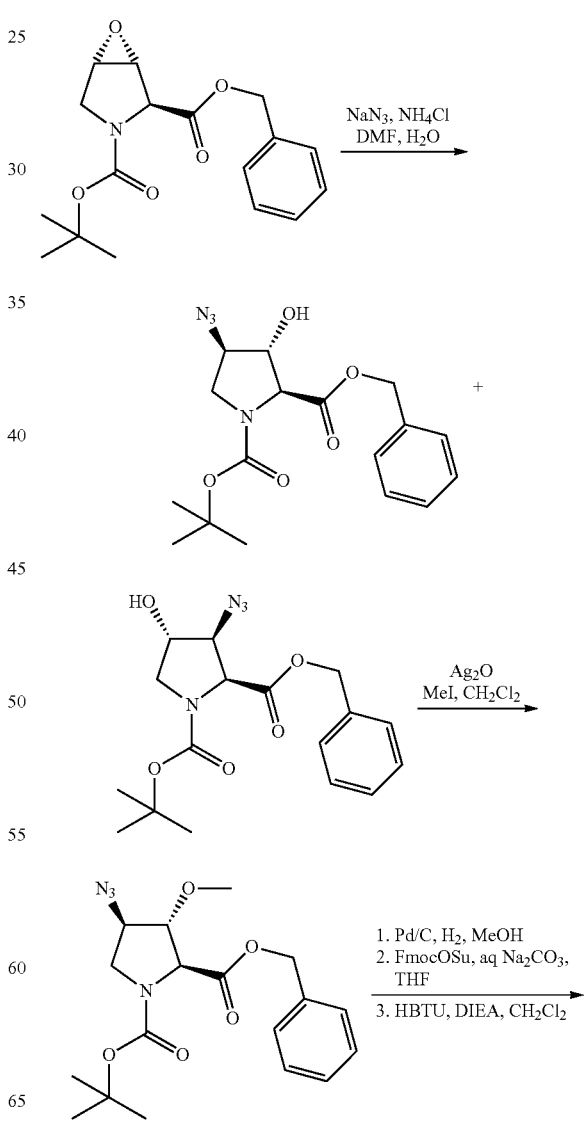

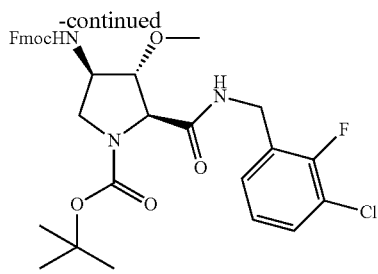

A. (2S,3R,4R)-4-Azido-2-benzylcarbamoyl-3-hydroxy-pyrrolidine-1-carboxylic acid tert-butyl ester and (2S,3S,4S)-3-azido-2-benzylcarbamoyl-4-hydroxy-pyrrolidine-1-carboxylic acid tert-butyl ester A solution of (1R,2S,5S)-6-oxa-3-aza-bicyclo[3.1.0]hexane-2,3-dicarboxylic acid 2-benzyl ester 3-tert-butyl ester (described in Scheme B19) (5.43 g, 11.90 mmol), sodium azide (4.64 g, 71.4 mmol) and NH$_4$Cl (1.27 g, 23.80 mmol) in DMF (74 mL) with H$_2$O (6.43 mL, 357 mmol) was heated at 100° C. for 1 h. The reaction mixture was poured into ice, extracted with CH$_2$Cl$_2$ (3×250 mL), washed with water and brine, dried over Na$_2$SO$_4$, filtered and concentrated. Purification by flash column chromatography on silica gel (c-hexane/EtOAc 1:1) gave the desired compounds as an unseparable mixture. MS (UPLC/MS): 307 [MH−tBu]+, 407 [M+HCOO]−; t$_R$ (HPLC conditions f): 1.04 min.

B. (2S,3R,4R)-4-Azido-3-methoxy-pyrrolidine-1,2-dicarboxylic acid 2-benzyl ester 1-tert-butyl ester A solution of (2S,3R,4R)-4-azido-2-benzylcarbamoyl-3-hydroxy-pyrrolidine-1-carboxylic acid tert-butyl ester and (2S,3S,4S)-3-azido-2-benzylcarbamoyl-4-hydroxy-pyrrolidine-1-carboxylic acid tert-butyl ester (517 mg, 1.42 mmol) in CH$_2$Cl$_2$ (10 mL), silver oxide (1.32 g, 5.71 mmol) and methyl iodide (0.35 mL, 5.71 mmol) was heated in a sealed tube for 1 week at 40° C. in the dark. The reaction mixture was filtered over celite pad and concentrated. Purification by flash column chromatography on silica gel (c-hexane/EtOAc 4:1) gave only (2S,3R,4R)-4-azido-3-methoxy-pyrrolidine-1,2-dicarboxylic acid 2-benzyl ester 1-tert-butyl ester. MS (UPLC/MS): 321 [MH−tBu]+, 421 [M+HCOO]−; t$_R$ (HPLC conditions f): 2.40 min.

C. (2S,3S,4S)-2-(3-Chloro-2-fluoro-benzylcarbamoyl)-4-(9H-fluoren-9-ylmethoxy carbonylamino)-3-methoxy-pyrrolidine-1-carboxylic acid tert-butyl ester A solution of (2S,3R,4R)-4-azido-3-methoxy-pyrrolidine-1,2-dicarboxylic acid 2-benzyl ester 1-tert-butyl ester (440 mg, 1.16 mmol) in methanol (3 mL) was hydrogenated with palladium on carbon 10% (124 mg, 1.16 mmol) overnight. The reaction mixture was filtered over a glass fiber filter, washed with methanol and evaporated in vacuo. The residue was dissolved in THF (2 mL) and a 10% aqueous Na$_2$CO$_3$ (3.09 mL, 1.11 mmol) solution was added. The reaction mixture was cooled at 0° C. then FmocOSu dissolved in THF (7 mL) was added and stirred for 2 h at RT. The reaction mixture was concentrated in vacuo to leave a residue which was dissolved in EtOAc (10 mL) and treated with saturated aq. NH$_4$Cl solution. The mixture was extracted with EtOAc (3×20 mL) and the organic layers were collected, dried over MgSO$_4$, filtered and concentrated. The residue was dissolved in DMF (3 mL) then 3-chloro-2-fluoro benzylamine (267 mg, 1.67 mmol) and HBTU (526 mg, 1.38 mmol), DIPEA (292 µl, 1.67 mmol) were added. The resulting orange solution was stirred overnight at RT. Purification by flash column chromatography on silica gel (c-hexane/EtOAc 3:2) afforded the title compound. MS (UPLC/MS): 624/626 [M+H]+, 668/670 [M+HCOO]−; t$_R$ (HPLC conditions f): 2.65 min.

Scheme B22: preparation of (2R,3S,4R)-2-(3-chloro-2-fluoro-benzylcarbamoyl)-4-(9H-fluoren-9-ylmethoxycarbonylamino)-3-fluoro-pyrrolidine-1-carboxylic acid tert-butyl ester and (2S,3S,4S)-2-(3-chloro-2-fluoro-benzylcarbamoyl)-3-(9H-fluoren-9-ylmethoxycarbonylamino)-4-fluoro-pyrrolidine-1-carboxylic acid tert-butyl ester

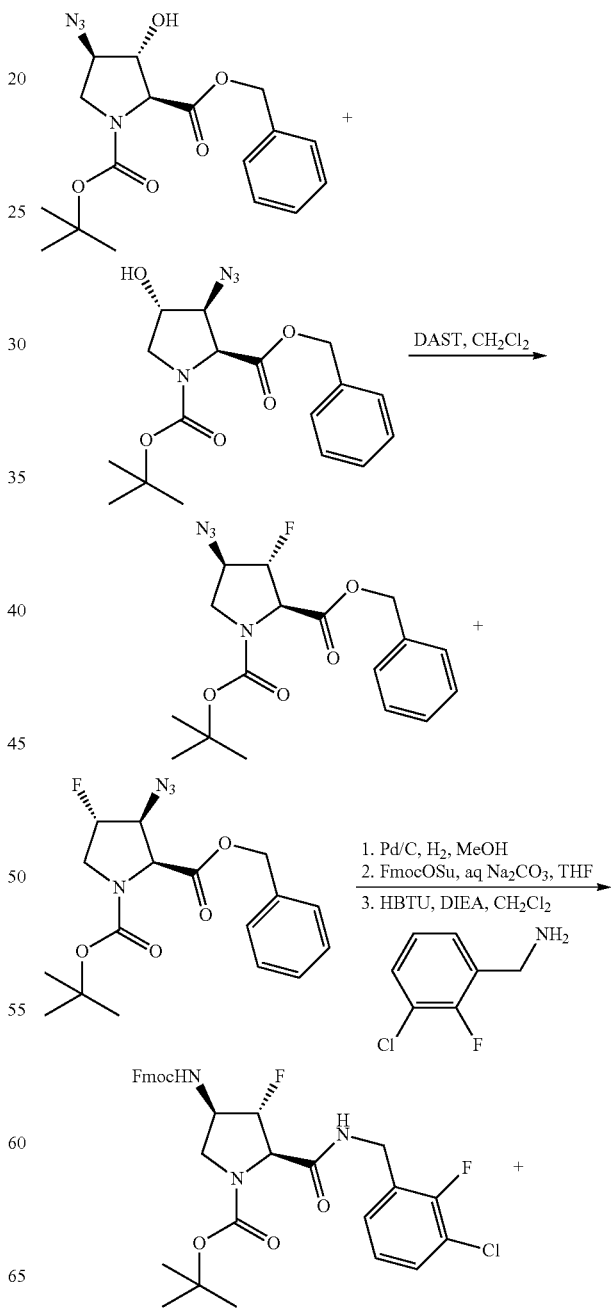

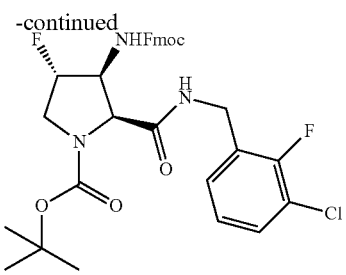

A. (2R,3R,4R)-4-Azido-3-fluoro-pyrrolidine-1,2-dicarboxylic acid 2-benzyl ester 1-tert-butyl ester and (2S,3S,4S)-3-azido-4-fluoro-pyrrolidine-1,2-dicarboxylic acid 2-benzyl ester 1-tert-butyl ester A solution of (2S,3R,4R)-4-azido-3-hydroxy-pyrrolidine-1,2-dicarboxylic acid 2-benzyl ester 1-tert-butyl ester and (2S,3S,4S)-3-azido-4-hydroxy-pyrrolidine-1,2-dicarboxylic acid 2-benzyl ester 1-tert-butyl ester (described in Scheme B21) (3.95 g, 10 mmol) in CH$_2$Cl$_2$ (100 mL) was cooled under Argon at −78° C. then DAST (6.62 mL) was added. The reaction mixture was stirred for 16 h at RT, carefully quenched with sat. aq. NaHCO$_3$ (100 mL) and stirred for 30 min at 0° C., extracted twice with CH$_2$Cl$_2$, dried over Na$_2$SO$_4$, filtered and concentrated. Purification by flash column chromatography on silica gel (c-hexane/EtOAc 1:1). MS (UPLC/MS): 365 [M+H]+; t$_R$ (HPLC conditions f): 2.40 min.

B. (2R,3S,4R)-2-(3-Chloro-2-fluoro-benzylcarbamoyl)-4-(9H-fluoren-9-ylmethoxy carbonylamino)-3-fluoro-pyrrolidine-1-carboxylic acid tert-butyl ester and (2S,3S,4S)-2-(3-Chloro-2-fluoro-benzylcarbamoyl)-3-(9H-fluoren-9-ylmethoxycarbonylamino)-4-fluoro-pyrrolidine-1-carboxylic acid tert-butyl ester A solution of (2R,3R,4R)-4-azido-3-fluoro-pyrrolidine-1,2-dicarboxylic acid 2-benzyl ester 1-tert-butyl ester and (2S,3S,4S)-3-azido-4-fluoro-pyrrolidine-1,2-dicarboxylic acid 2-benzyl ester 1-tert-butyl ester (2.78 g, 7.63 mmol) in methanol (25 mL) was hydrogenated with palladium on carbon 10% (812 mg, 0.76 mmol) overnight. The reaction mixture was filtered over a glass fiber filter, washed with methanol and concentrated. 200 mg (0.084 mmol) of the residue was dissolved in THF (2 mL) and a 10% aqueous Na$_2$CO$_3$ (1 mL, 1 mmol) solution was added. The reaction mixture was cooled at 0° C. then FmocOSu (284 mg, 0.084 mmol) dissolved in THF (7 mL) was added and stirred for 2 h at RT. The reaction mixture was concentrated in vacuo to give a residue which was dissolved in EtOAc (10 mL) and treated with saturated aq NH$_4$Cl solution. The mixture was extracted with EtOAc (3×20 mL) and the organic layers were collected, dried over MgSO$_4$, filtered and concentrated. The residue was dissolved in DMF (3 mL) then 3-chloro-2 fluoro benzylamine (192 mg, 1.2 mmol) and HBTU (456 mg, 1.2 mmol), DIPEA (210 µl, 1.2 mmol) were added. The resulting solution was stirred overnight at RT. Purification by flash column chromatography on silica gel (c-hexane/EtOAc 4:1). MS (UPLC/MS): 612/614 [M+H]+, 656/658 [M+HCOO]−; t$_R$ (HPLC conditions f): 0.75/0.76 min.

Scheme B23: preparation of (2R,3S,4R)-4-Acetylamino-2-(3-chloro-2-fluoro-benzylcarbamoyl)-3-fluoro-pyrrolidine-1-carboxylic acid tert-butyl ester and (2S,3S,4S)-3-acetylamino-2-(3-chloro-2-fluoro-benzylcarbamoyl)-4-fluoro-pyrrolidine-1-carboxylic acid tert-butyl ester

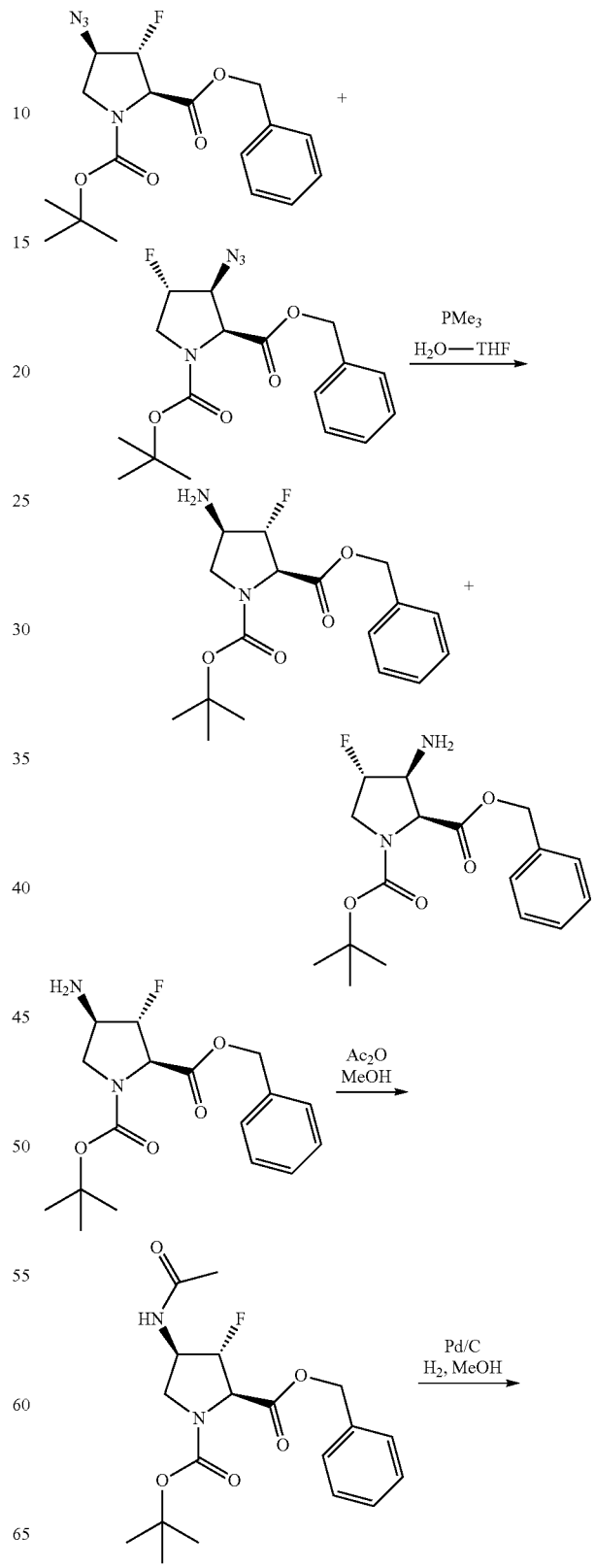

223

-continued

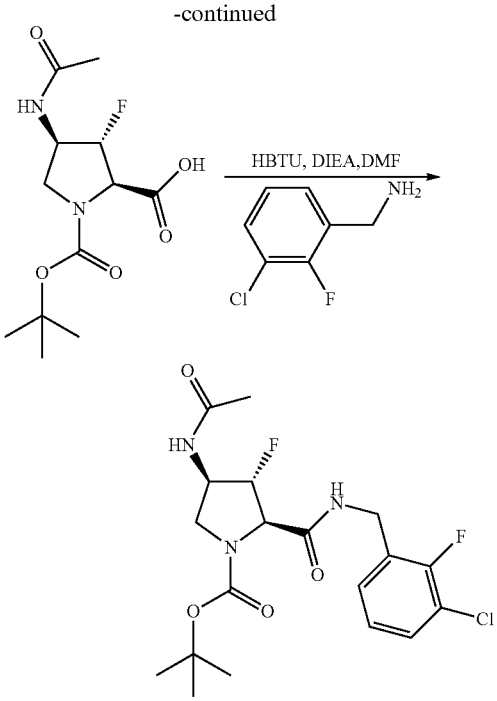

A. (2S,3S,4S)-3-Amino-4-fluoro-pyrrolidine-1,2-dicarboxylic acid 2-benzyl ester 1-tert-butyl ester and (2R,3S,4R)-4-amino-3-fluoro-pyrrolidine-1,2-dicarboxylic acid 2-benzyl ester 1-tert-butyl ester A mixture of (2R,3R,4R)-4-azido-2-benzylcarbamoyl-3-fluoro-pyrrolidine-1-carboxylic acid tert-butyl ester and (2S,3S,4S)-3-azido-2-benzylcarbamoyl-4-fluoro-pyrrolidine-1-carboxylic acid tert-butyl ester (3.52 g, 8.98 mmol) (described in Scheme B22), trimethylphosphine in THF (17.97 mL, 17.97 mmol) and water (0.32 mL, 17.97 mmol) in THF (100 mL) was stirred for 16 h at RT. The reaction mixture was quenched with water and extracted twice with EtOAc. The organic phases were joined, washed with brine, dried over Na$_2$SO$_4$, filtered and concentrated. Purification by flash column chromatography on silica gel (c-hexane/EtOAc 1:1) gave (2S,3S,4S)-3-amino-4-fluoro-pyrrolidine-1,2-dicarboxylic acid 2-benzyl ester 1-tert-butyl ester: MS (UPLC/MS): 339 [M+H]+; t$_R$ (HPLC conditions f): 1.59 min and (2R,3S,4R)-4-amino-3-fluoro-pyrrolidine-1,2-dicarboxylic acid 2-benzyl ester 1-tert-butyl ester: MS (UPLC/MS): 339 [M+H]+; t$_R$ (HPLC conditions f): 1.62 min.

B. (2R,3S,4R)-4-Acetylamino-3-fluoro-pyrrolidine-1,2-dicarboxylic acid 2-benzyl ester 1-tert-butyl ester To a solution of (2S,3S,4S)-3-amino-4-fluoro-pyrrolidine-1,2-dicarboxylic acid 2-benzyl ester 1-tert-butyl ester (762 mg, 2.25 mmol) in methanol (20 mL) was added acetic anhydride (3.19 mL, 33.8 mmol) under argon. The reaction mixture was stirred for 16 h at RT. After concentration, the residue was purified by flash column chromatography on silica gel (c-hexane/EtOAc 3:1). MS (UPLC/MS): 381 [M+H]+, 281 [MH−Boc]−; t$_R$ (HPLC conditions f): 2.00 min.

C. (2R,3S,4R)-4-Acetylamino-3-fluoro-pyrrolidine-1,2-dicarboxylic acid 1-tert-butyl ester A solution of (2R,3S,4R)-4-acetylamino-3-fluoro-pyrrolidine-1,2-dicarboxylic acid 2-benzyl ester 1-tert-butyl ester (315 mg, 0.82 mmol) in methanol (2 mL) was hydrogenated with palladium on carbon 10% (88 mg, 0.82 mmol) overnight. The reaction mixture was filtered over glass fiber and was concentrated. The residue was used as was for the next step.

D. (2R,3S,4R)-4-Acetylamino-2-(3-chloro-2-fluoro-benzylcarbamoyl)-3-fluoro-pyrrolidine-1-carboxylic acid tert-butyl ester To a mixture of (2R,3S,4R)-4-acetylamino-3-fluoro-pyrrolidine-1,2-dicarboxylic acid 1-tert-butyl ester (245 mg, 0.84 mmol), (3-chloro-2-fluoro)benzylamine (202 mg, 1.26 mmol) and HBTU (480 mg, 1.26 mmol) in DMF (7.5 mL) was added DIPEA (0.22 mL, 1.26 mmol). The resulting solution was stirred overnight at RT. The reaction mixture was poured into aq. sat. NaHCO$_3$ and was extracted with CH$_2$Cl$_2$ (3×20 mL). The organic phases were joined, washed with brine, dried over Na$_2$SO$_4$, filtered and concentrated. Purification by flash column chromatography on silica gel (c-hexane/EtOAc 1:1). MS (UPLC/MS): 376 [MH−tBu]+, 476 [M+HCOO]−; t$_R$ (HPLC conditions f): 1.93 min.

(2S,3S,4S)-3-Acetylamino-2-(3-chloro-2-fluoro-benzylcarbamoyl)-4-fluoro-pyrrolidine-1-carboxylic acid tert-butyl ester

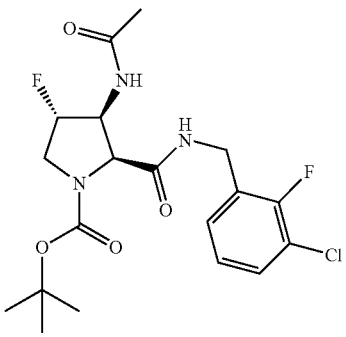 [SMILES: CC(=O)N[C@H]1[C@@H](C(=O)NCc2cccc(Cl)c2F)N(C(=O)OC(C)(C)C)C[C@@H]1F]

The title compound was prepared in a similar manner as described above from (2R,3S,4R)-4-amino-3-fluoro-pyrrolidine-1,2-dicarboxylic acid 2-benzyl ester 1-tert-butyl ester. MS (UPLC/MS): 432 [M+H]+, 476 [M+HCOO]−; t$_R$ (HPLC conditions f): 1.96 min.

Scheme B24: preparation of (2S,3S,4S)-4-Fluoro-3-methoxy-pyrrolidine-2-carboxylic acid 3-chloro-2-fluoro-benzylamide trifluoroacetate

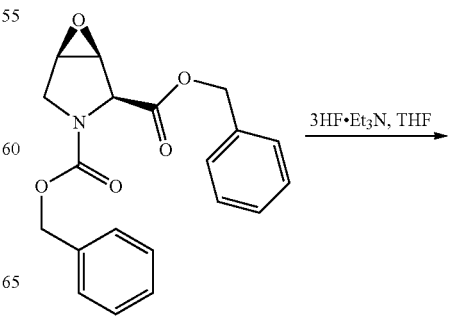

3HF·Et$_3$N, THF

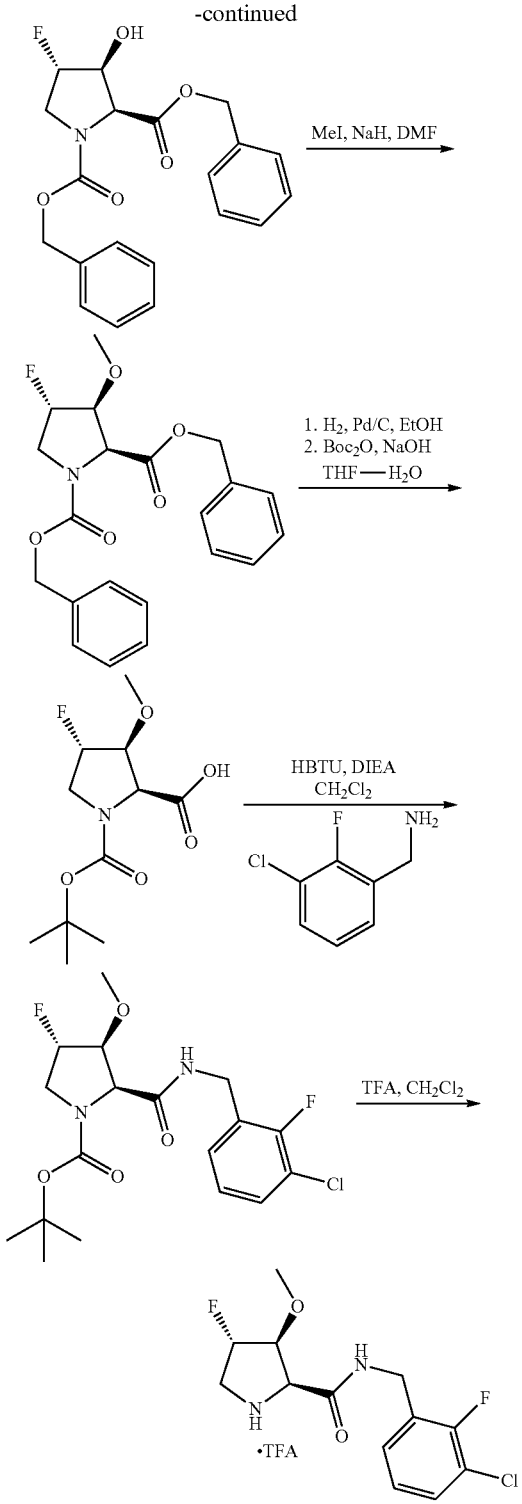

A. (2S,3S,4S)-4-fluoro-3-hydroxy-pyrrolidine-1,2-dicarboxylic acid dibenzyl ester To a solution of (1S,2S,5R)-6-oxa-3-aza-bicyclo[3.1.0] hexane-2,3-dicarboxylic acid dibenzyl ester (prepared as described Scheme B19, 4 g, 11.3 mmol) in THF (3 mL) was added 3HF.Et$_3$N (18.5 mL, 113 mmol). The reaction mixture was microwaved at 130° C. (6×40 min) then was poured into a saturated solution of Na$_2$CO$_3$ and stirred for 30 min. The mixture was extracted with EtOAc (2×100 mL), the organic phases were joined, washed with brine, dried over Na$_2$SO$_4$, filtered and concentrated. The crude residue was purified by flash column chromatography on silica gel (c-hexane/EtOAc 7:3) to give a mixture containing (2S,3S,4S)-4-fluoro-3-hydroxy-pyrrolidine-1,2-dicarboxylic acid dibenzyl ester as the major isomer. MS (UPLC): 374 [M+H]+; $t_R$ (HPLC conditions f): 2.13 min.

B. (2S,3S,4S)-4-Fluoro-3-methoxy-pyrrolidine-1,2-dicarboxylic acid dibenzyl

To a solution of (2S,3S,4S)-4-fluoro-3-hydroxy-pyrrolidine-1,2-dicarboxylic acid dibenzyl ester (531 mg, 1.42 mmol) cooled with an ice-bath and under argon was added NaH (60% in mineral oil, 62 mg, 1.52 mmol). The reaction mixture was stirred for 30 min then MeI (0.26 mL, 4.27 mmol) was added. The reaction mixture was stirred for 30 min then was quenched with water. After extraction with EtOAc (2×25 mL), the organic phases were joined, washed with brine, dried over Na$_2$SO$_4$, filtered and concentrated. The crude residue was purified by flash column chromatography on silica gel (c-hexane to c-hexane/EtOAc 7:3). MS (UPLC): 388 [M+H]+; $t_R$ (HPLC conditions f): 2.36 min.

C. (2S,3S,4S)-4-Fluoro-3-methoxy-pyrrolidine-1,2-dicarboxylic acid 1-tert-butyl ester To a solution of (2S,3S,4S)-4-fluoro-3-methoxy-pyrrolidine-1,2-dicarboxylic acid dibenzyl ester (430 mg, 1.11 mmol) in MeOH (25 mL) was added Pd/C 10% (100 mg). The reaction was placed under hydrogen atmosphere and was stirred for 2 h then was filtered over glass-fiber, rinsed with MeOH (25 mL) and water (25 mL). After concentration, the residue was lyophilized overnight. The powder obtained was dissolved in THF/Water 1/1 (20 mL) then aq. 1N NaOH (0.755 mL) and Boc anhydride (412 mg, 2.22 mmol) were added and the reaction mixture was stirred at RT overnight. After concentration, the crude residue was purified by flash column chromatography on silica gel (c-hexane/EtOAc 1:1+ 0.5% AcOH). MS (UPLC): 264 [M+H]+; $t_R$ (HPLC conditions f): 0.65 min.

D. (2S,3S,4S)-2-(3-Chloro-2-fluoro-benzylcarbamoyl)-4-fluoro-3-methoxy-pyrrolidine-1-carboxylic acid tert-butyl ester To a solution of (2S,3S,4S)-4-fluoro-3-methoxy-pyrrolidine-1,2-dicarboxylic acid 1-tert-butyl ester (500 mg, 1.90 mmol) in DMF (20 mL) were added 3-chloro-2-fluoro-benzylamine (330 mg, 2.1 mmol), HBTU (1.4 g, 3.8 mmol) and DIPEA (1.32 mL, 7.6 mmol). The reaction mixture was stirred at RT for 2 h then was poured into water (50 mL). After extraction with ETOAc (3×30 mL), the organic phases were joined, washed with brine, dried over Na$_2$SO$_4$, filtered and concentrated. The crude residue was purified by flash column chromatography on silica gel (c-hexane to c-hexane/EtOAc 1:1) to give (2S,3S,4S)-2-(3-chloro-2-fluoro-benzylcarbamoyl)-4-fluoro-3-methoxy-pyrrolidine-1-carboxylic acid tert-butyl ester: $R_f$ TLC (c-hexane/EtOAc 1:1)=0.37; MS (UPLC): 405.1/407.2 [M+H]+, 349.1/351.1 [MH−tBu]+, 449.2/451.2 [M+HCOO]−; $t_R$ (HPLC conditions f): 2.12 min. 1H NMR (400 MHz, DMSO-d$_6$) δ (ppm): 8.59 (m, 1H), 7.48 (m, 1H), 7.37 (m, 1H), 7.20 (m, 1H), 5.20 (br.d, 1H), 4.47-4.26 (m, 3H), 4.19 (ddd, 1H), 3.81-3.65 (m, 1H), 3.54-3.40 (m, 1H), 3.36 (s, 3H), 1.42 and 1.27 (2 s, 9H).

E. (2S,3S,4S)-4-Fluoro-3-methoxy-pyrrolidine-2-carboxylic acid 3-chloro-2-fluoro-benzylamide trifluoroacetate TFA (0.86 mL, 11.12 mmol) was added to a solution of (2S,3S,4S)-2-(3-chloro-2-fluoro-benzylcarbamoyl)-4- fluoro-3-methoxy-pyrrolidine-1-carboxylic acid tert-butyl ester (450 mg, 1.12 mmol) in CH₂Cl₂ (20 mL). The reaction mixture was stirred overnight then was concentrated. The residue was triturated with Et₂O (10 mL) to give a precipitate which was filtered off, washed with Et₂O (10 mL) then dried under high vacuum. The absolute stereochemistry was confirmed by X-ray. $t_R$ (HPLC conditions f): 0.40 min; MS (UPLC): 349 [M+HCOO]−, 305 [M+H]+.

Scheme B25: Alternative for the preparation of (2S,3S,4S)-2-(3-chloro-2-fluoro-benzylcarbamoyl)-4-fluoro-3-methoxy-pyrrolidine-1-carboxylic acid tert-butyl ester

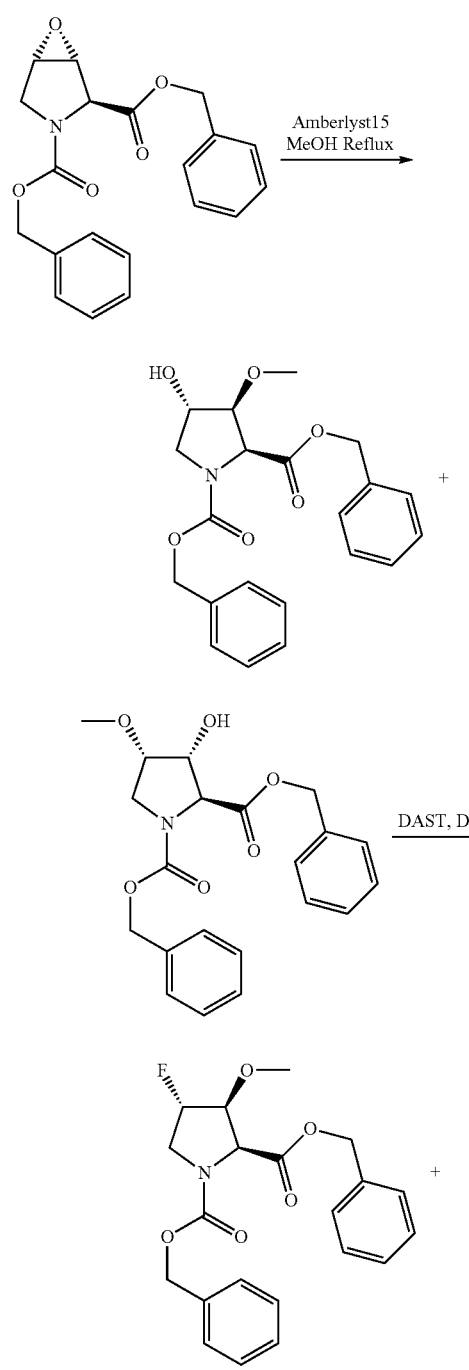

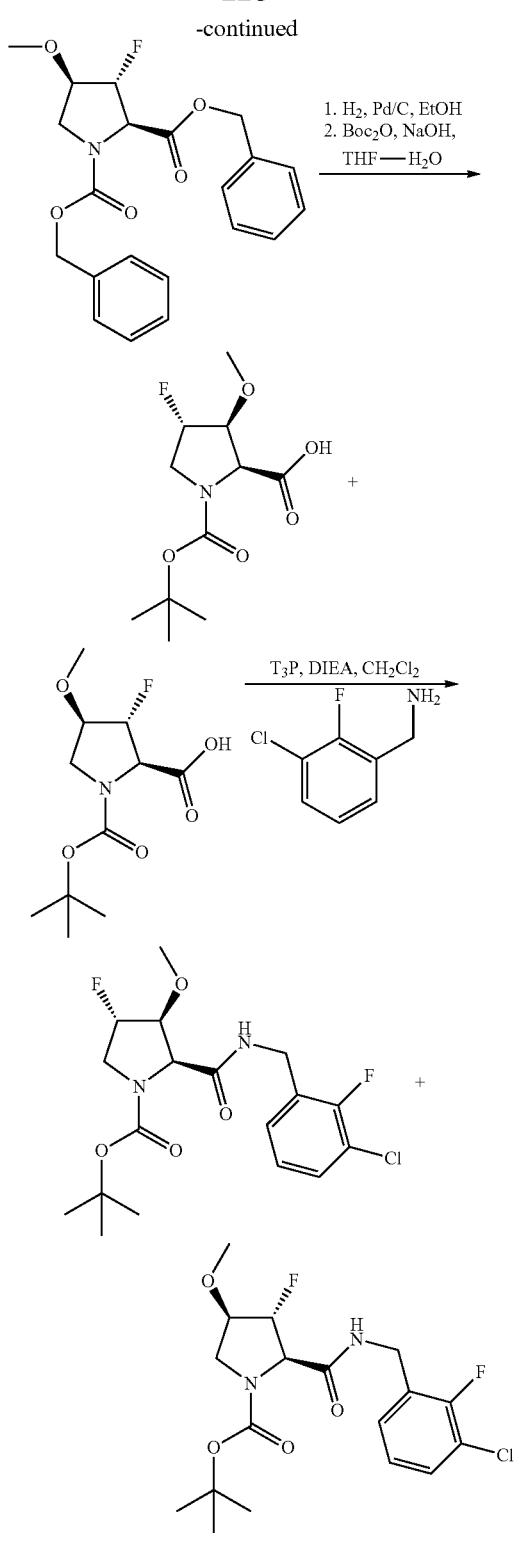

A. (2S,3S,4S)-4-Hydroxy-3-methoxy-pyrrolidine-1,2-dicarboxylic acid dibenzyl ester and (2S,3R,4R)-3-hydroxy-4-methoxy-pyrrolidine-1,2-dicarboxylic acid dibenzyl ester To a solution of (1R,2S,5S)-6-Oxa-3-aza-bicyclo[3.1.0]hexane-2,3-dicarboxylic acid dibenzyl ester (prepared as described Scheme B19, 30 g, 85 mmol) in MeOH (150 mL) was added Amberlyst 15 (30 g). The reaction mixture was heated overnight at 65° C., then allowed to cool to RT and filtered. Amberlyst 15 residue was washed with MeOH. The combined filtrates were combined and concentrated. The crude residue was purified by flash column chromatography on silica gel (c-hexane 100% to EtOAc 100%) to give a mixture of the 2 regioisomers as a yellow oil. $R_f$, TLC (c-hexane/EtOAc 1:1)=0.5; MS (UPLC): 386.2 [M+H]+, 430.2 [M+HCOO]−; $t_R$ (HPLC conditions a): 1.93 min.

B. (2S,3S,4S)-4-Fluoro-3-methoxy-pyrrolidine-1,2-dicarboxylic acid dibenzyl ester and (2R,3R,4R)-3-fluoro-4-methoxy-pyrrolidine-1,2-dicarboxylic acid dibenzyl ester A solution of (2S,3S,4S)-4-hydroxy-3-methoxy-pyrrolidine-1,2-dicarboxylic acid dibenzyl ester and (2S,3R,4R)-3-hydroxy-4-methoxy-pyrrolidine-1,2-dicarboxylic acid dibenzyl ester (17.8 g, 46.2 mmol) in $CH_2Cl_2$ (250 mL) was cooled under Argon at −78° C. then DAST (12.2 mL, 92 mmol) was added dropwise. The reaction mixture was allowed to reach RT and further stirred for 16 h. The reaction mixture was diluted with $CH_2Cl_2$ and carefully quenched with sat. aq. $NaHCO_3$. The layers were separated, the aqueous layer extracted twice with $CH_2Cl_2$, the combined organic layers were dried over $Na_2SO_4$, filtered and concentrated. Purification by flash column chromatography on silica gel (c-hexane/EtOAc 100:0 to 0:100) gave a mixture of the 2 regioisomers as a yellow solid. MS (UPLC/MS): 388.3 [M+H]+, 405.3 [M+NH$_4$]+; $t_R$ (HPLC conditions f): 2.34 min.

C. (2S,3S,4S)-4-Fluoro-3-methoxy-pyrrolidine-1,2-dicarboxylic acid 1-tert-butyl ester and (2R,3R,4R)-3-Fluoro-4-methoxy-pyrrolidine-1,2-dicarboxylic acid 1-tert-butyl ester were obtained as a mixture using the protocol described in Scheme B24 step C. $R_f$, TLC (EtOAc)=0.1.

D. (2S,3S,4S)-2-(3-Chloro-2-fluoro-benzylcarbamoyl)-4-fluoro-3-methoxy-pyrrolidine-1-carboxylic acid tert-butyl ester and (2R,3R,4R)-2-(3-Chloro-2-fluoro-benzylcarbamoyl)-3-fluoro-4-methoxy-pyrrolidine-1-carboxylic acid tert-butyl ester To a solution of (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester (1.55 g, 5.89 mmol) in $CH_2Cl_2$ (50 mL) were added 3-chloro-2-fluoro-benzylamine (1.03 g, 6.48 mmol), propylphosphonic anhydride (50% in EtOAc, 5.20 mL, 8.83 mmol) and DIPEA (3.08 mL, 17.7 mmol). The reaction mixture was stirred at RT for 2 h and concentrated. The crude residue was purified by flash column chromatography on silica gel (c-hexane/EtOAc 7:3) to give (2S,3S,4S)-2-(3-chloro-2-fluoro-benzylcarbamoyl)-4-fluoro-3-methoxy-pyrrolidine-1-carboxylic acid tert-butyl ester: $R_f$, TLC (c-hexane/EtOAc 1:1)=0.35; MS (UPLC): 405.1/407.2 [M+H]+, 349.1/351.1 [MH−tBu]+, 449.2/451.2 [M+HCOO]−; $t_R$ (HPLC conditions f): 2.12 min and (2R,3R,4R)-2-(3-chloro-2-fluoro-benzylcarbamoyl)-3-fluoro-4-methoxy-pyrrolidine-1-carboxylic acid tert-butyl ester: $R_f$, TLC (c-hexane/EtOAc 1:1)=0.5; MS (UPLC): 405.1/407.2 [M+H]+, 349.0/351.1 [MH−tBu]+, 449.2/451.2 [M+HCOO]−; $t_R$ (HPLC conditions f): 2.20 min.

(2S,3S,4S)-2-[(R)-1-(3-Chloro-2-fluoro-phenyl)-ethylcarbamoyl]-4-fluoro-3-methoxy-pyrrolidine-1-carboxylic acid tert-butyl ester

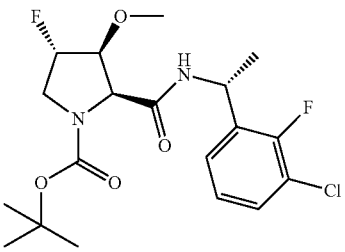 [SMILES: CO[C@H]1[C@@H](C(=O)N[C@H](C)c2cccc(Cl)c2F)N(C(=O)OC(C)(C)C)C[C@@H]1F]

was prepared according to the same protocols described in Scheme B25 using (R)-1-(3-chloro-2-fluoro-phenyl)-ethylamine in Step D. Separation of two regioisomers was performed by flash column chromatography on silica gel (c-hexane/EtOAc 6:4) to give ((2S,3S,4S)-2-[(R)-1-(3-chloro-2-fluoro-phenyl)-ethylcarbamoyl]-4-fluoro-3-methoxy-pyrrolidine-1-carboxylic acid tert-butyl ester. MS (UPLC): 405/407 [M+H]+; $t_R$ (HPLC conditions f): 2.14 min.

(2S,3S,4S)-2-[1-(3-Chloro-2-fluoro-phenyl)-cyclopropylcarbamoyl]-4-fluoro-3-methoxy-pyrrolidine-1-carboxylic acid tert-butyl ester

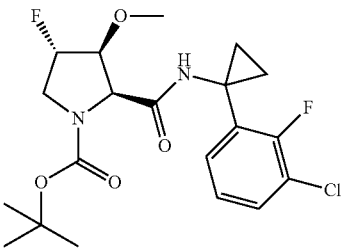 [SMILES: CO[C@H]1[C@@H](C(=O)NC2(c3cccc(Cl)c3F)CC2)N(C(=O)OC(C)(C)C)C[C@@H]1F]

was prepared according to the same protocols described in Scheme B25 using 1-(3-chloro-2-fluoro-phenyl)-cyclopropylamine in Step D. 1-(3-chloro-2-fluoro-phenyl)-cyclopropylamine is prepared as described in Part C. Separation of two regioisomers was performed by flash column chromatography on silica gel (c-hexane/EtOAc 1:1) to give (2S,3S,4S)-2-[1-(3-chloro-2-fluoro-phenyl)-cyclopropylcarbamoyl]-4-fluoro-3-methoxy-pyrrolidine-1-carboxylic acid tert-butyl ester. MS (UPLC): 431/433 [M+H]+; $t_R$ (HPLC conditions f): 2.21 min.

(2S,3S,4S)-2-(3-Chloro-2-fluoro-benzylcarbamoyl)-3-ethoxy-4-fluoro-pyrrolidine-1-carboxylic acid tert-butyl ester

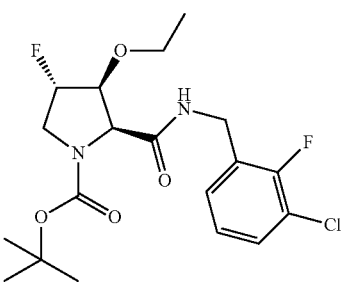 [SMILES: CCO[C@H]1[C@@H](C(=O)NCc2cccc(Cl)c2F)N(C(=O)OC(C)(C)C)C[C@@H]1F]

was prepared according to the same protocols described in Scheme B25 using EtOH instead of MeOH in Step A. Separation of two regioisomers was performed by flash column chromatography on silica gel (c-hexane/EtOAc 6:4) to give (2S,3S,4S)-2-(3-chloro-2-fluoro-benzylcarbamoyl)-3-ethoxy-4-fluoro-pyrrolidine-1-carboxylic acid tert-butyl ester. MS (UPLC): 419/421 [M+H]+; $t_R$ (HPLC conditions f): 2.23 min.

(2S,3S,4S)-4-Fluoro-2-(2-fluoro-3-trifluoromethoxy-phenylcarbamoyl)-3-methoxy-pyrrolidine-1-carboxylic acid tert-butyl ester

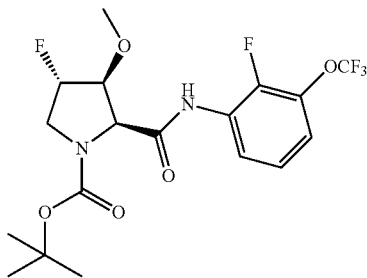 [SMILES: CO[C@H]1[C@@H](C(=O)Nc2cccc(OC(F)(F)F)c2F)N(C(=O)OC(C)(C)C)C[C@@H]1F]

To a solution of (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester (prepared as described in Scheme B25, 1.00 g, 3.80 mmol) in $CH_2Cl_2$ (10 mL) at 0° C. under nitrogen atmosphere was added 1-chloro-N,N,2-trimethylprop-1-en-1-amine (609 mg, 4.56 mmol) and the mixture was stirred at this temperature for 1 h. 2-Fluoro-3-(trifluoromethoxy) aniline (0.815 mg, 4.18 mmol) was then added, followed by DIPEA (1.327 mL, 7.60 mmol) and the mixture was stirred at RT for 1 h. The crude residue was purified by flash column chromatography on silica gel (c-hexane/EtOAc 1:0 to 1:1) to give (2S,3S,4S)-4-fluoro-2-(2-fluoro-3-trifluoromethoxy-phenylcarbamoyl)-3-methoxy-pyrrolidine-1-carboxylic acid tert-butyl ester. 1H NMR (400 MHz, DMSO-$d_6$) 2:1 mixture of rotamers δ (ppm): 10.15 (m, 1H), 7.87 (m, 1/3H), 7.77 (m, 2/3H), 7.31 (m, 2H), 5.29-5.11 (m, 1H), 4.76 (d, 1/3H), 4.70 (d, 2/3H), 4.29 (m, 1H), 3.80-3.53 (m, 2H), 3.39 (m, 3H), 1.39 (s, 3H), 1.31 (s, 6H). MS (UPLC-MS): 441 [M+H]+; $t_R$ (HPLC conditions f): 2.14 min.

(2S,3S,4S)-2-(3-Bromo-2-fluoro-phenylcarbamoyl)-4-fluoro-3-methoxy-pyrrolidine-1-carboxylic acid tert-butyl ester

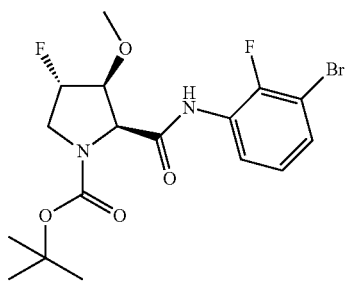 [SMILES: CO[C@H]1[C@@H](C(=O)Nc2cccc(Br)c2F)N(C(=O)OC(C)(C)C)C[C@@H]1F]

To a solution of (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester (prepared as described in Scheme B25, 100 mg, 0.380 mmol) in $CH_2Cl_2$ (2.4 mL) at 0° C. under nitrogen atmosphere was added 1-chloro-N,N,2-trimethylprop-1-en-1-amine (50.8 mg, 0.38 mmol) and the mixture was stirred at this temperature for 2 h. 3-Bromo-2-fluoroaniline (144 mg, 0.76 mmol) was then added, followed by DIPEA (0.265 mL, 1.52 mmol) and the mixture was stirred at RT for 1 h. The reaction mixture was concentrated and the crude residue was purified by preparative HPLC (Waters Sunfire C18-ODB, 5 µm, 30×100 mm, eluent: 0-0.5 min 5% $CH_3CN$ in $H_2O$ Flow: 5 mL/min, 0.5-18.5 min 5 to 100% $CH_3CN/H_2O$ Flow: 40 mL/min, 18.5-20 min 100% $CH_3CN$, $CH_3CN$ and $H_2O$ both containing 0.1% TFA). The purified HPLC fractions were neutralized by addition of a saturated aqueous solution of $Na_2CO_3$, the layer were separated and the aqueous layer was extracted with $CH_2Cl_2$ (×2). The combined organic extracts were dried ($Na_2SO_4$), filtered and concentrated. White solid. $R_f$, TLC (c-hexane/EtOAc 1:1)=0.75; MS (UPLC): 435.1/437.1 [M+H]+, 433.1/435.1 [M–H]–; $t_R$ (HPLC conditions f): 2.06 min.

(2S,3S,4S)-2-(6-Bromo-pyridin-2-ylcarbamoyl)-4-fluoro-3-methoxy-pyrrolidine-1-carboxylic acid tert-butyl ester

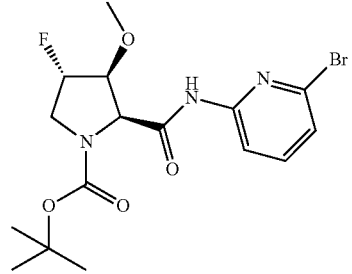 [SMILES: CO[C@H]1[C@@H](C(=O)Nc2cccc(Br)n2)N(C(=O)OC(C)(C)C)C[C@@H]1F]

was prepared according to the same protocols described for the synthesis of (2S,3S,4S)-2-(3-bromo-2-fluoro-phenylcarbamoyl)-4-fluoro-3-methoxy-pyrrolidine-1-carboxylic acid tert-butyl ester. White solid. $R_f$, TLC (EtOAc)=0.8; 418.1/420.1 [M+H]+, 416.2/418.1 [M–H]–; $t_R$ (HPLC conditions f): 2.0 min.

Scheme B26: Preparation of (2S,3S,4S)-2-(3-chloro-2-fluoro-benzylcarbamoyl)-3-(2-dimethylamino-ethoxy)-4-fluoro-pyrrolidine-1-carboxylic acid tert-butyl ester

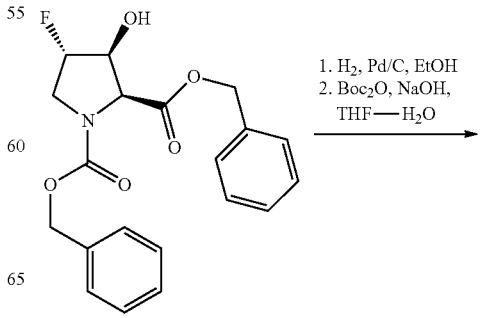

1. $H_2$, Pd/C, EtOH
2. $Boc_2O$, NaOH, THF—$H_2O$

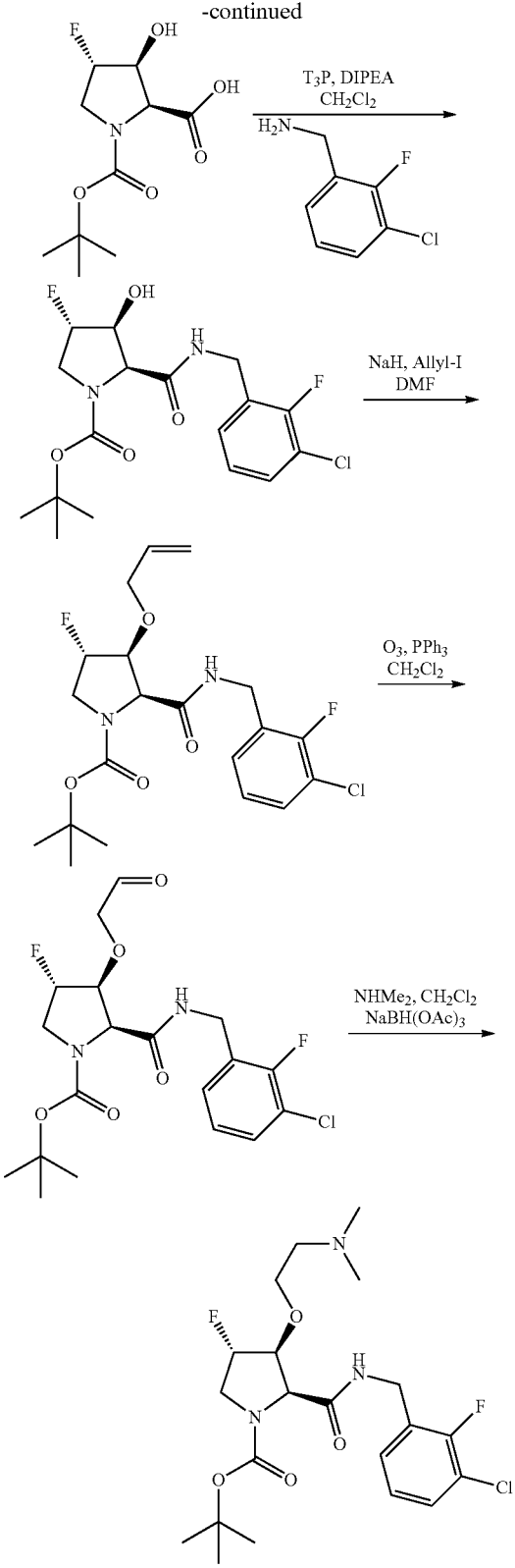

A. (2S,3S,4S)-4-fluoro-3-hydroxy-pyrrolidine-1,2-dicarboxylic acid 1-tert-butyl ester To a solution of (2S,3S,4S)-4-fluoro-3-hydroxy-pyrrolidine-1,2-dicarboxylic acid dibenzyl ester (390 mg, 1.04 mmol) in MeOH (10 mL) was added Pd/C 10% (39 mg). The reaction was placed under hydrogen atmosphere and stirred 2 h then was filtered over glass-fiber and rinsed with water. After concentration, the residue was dissolved in THF/Water 2/1 (30 mL), aqueous NaOH (1N, 2.09 mL, 2.09 mmol) and Boc anhydride (456 mg, 2.09 mmol) were added and the reaction mixture was stirred 16 h at RT. THF was removed under reduced pressure and the aqueous layer was extracted with $Et_2O$ (×2), acidified by addition of $KHSO_4$ (10% in water) and extracted with EtOAc (×2). The combined EtOAc extracts were dried ($Na_2SO_4$), filtered and concentrated. The material thus obtained was used in the next step without further purification.

B. (2S,3S,4S)-2-(3-chloro-2-fluoro-benzylcarbamoyl)-4-fluoro-3-hydroxy-pyrrolidine-1-carboxylic acid tert-butyl ester To a solution of (2S,3S,4S)-4-fluoro-3-hydroxy-pyrrolidine-1,2-dicarboxylic acid 1-tert-butyl ester (195 g, 0.782 mmol) in $CH_2Cl_2$ (10 mL) were added 3-chloro-2-fluoro-benzylamine (150 mg, 0.94 mmol), propylphosphonic anhydride (50% in EtOAc, 0.346 mL, 1.17 mmol) and DIPEA (0.41 mL, 2.35 mmol). The reaction mixture was stirred 1 h at RT, then quenched by addition of a saturated aqueous solution of $NaHCO_3$ and extracted with $CH_2Cl_2$ (×2). The combined organic extracts were dried ($Na_2SO_4$), filtered and concentrated. The crude residue was purified by flash column chromatography on silica gel (c-hexane/EtOAc 1:1). MS (UPLC): 391.3/393.1 [M+H]+, 435.4/437.4 [M+HCOO]−; $t_R$ (HPLC conditions f): 1.95 min.

C. (2S,3S,4S)-3-allyloxy-2-(3-chloro-2-fluoro-benzylcarbamoyl)-4-fluoro-pyrrolidine-1-carboxylic acid tert-butyl ester To a solution of NaH (60% in mineral oil, 8.6 mg, 0.215 mmol) in DMF (5 mL) cooled with an ice-bath and under argon was added (2S,3S,4S)-2-(3-chloro-2-fluoro-benzylcarbamoyl)-4-fluoro-3-hydroxy-pyrrolidine-1-carboxylic acid tert-butyl ester (70 mg, 0.179 mmol). The reaction mixture was stirred for 20 min before addition of allyl iodide (0.025 mL, 0.269 mmol) at 0° C. The reaction mixture was stirred for 30 min then quenched by addition of water and extracted with EtOAc (×2). The organic extracts were combined, washed with brine, dried ($Na_2SO_4$), filtered and concentrated. The crude residue was purified by flash column chromatography on silica gel (c-hexane/EtOAc 3:2). MS (UPLC): 431.4/433.1 [M+H]+, 475.5/577.5 [M+HCOO]−; $t_R$ (HPLC conditions f): 2.29 min.

D. (2S,3S,4S)-2-(3-Chloro-2-fluoro-benzylcarbamoyl)-4-fluoro-3-(2-oxo-ethoxy)-pyrrolidine-1-carboxylic acid tert-butyl ester Ozone was bubbled through a solution of (2S,3S,4S)-3-allyloxy-2-(3-chloro-2-fluoro-benzylcarbamoyl)-4-fluoro-pyrrolidine-1-carboxylic acid tert-butyl ester (59 mg, 0.137 mmol) in $CH_2Cl_2$ (20 mL) at −78° C. When the solution turned blue, ozone addition was stopped and nitrogen was passed through the solution until the blue color was discharged. Triphenylphosphine (35.9 mg, 0.137 mmol) was added to the ozonide solution at −78° C. and the reaction mixture was allowed to slowly reach RT. The reaction mixture was concentrated and the material thus obtained used without further purification in the next step. MS (UPLC): 433.4/435.4 [M+H]+, 477.4/579.5 [M+HCOO]−.

E. (2S,3S,4S)-2-(3-Chloro-2-fluoro-benzylcarbamoyl)-3-(2-dimethylamino-ethoxy)-4-fluoro-pyrrolidine-1-carboxylic acid tert-butyl ester To a solution of the crude material obtained in the previous step and dimethylamine (2 N in MeOH, 173 μl, 0.347 mmol) in MeOH (3 mL) at 25° C. were successively added AcOH (100 μL) and sodium triacetoxyborohydride (73.5 mg, 0.347 mmol). The reaction mixture was stirred 2 h and concentrated. The crude residue was purified by preparative HPLC ((Waters Sunfire, C18-ODB, 5 μm, 30×100 mm, 5-100% $CH_3CN/H_2O$/20 min, 100% $CH_3CN$/2 min, $CH_3CN$ and $H_2O$ containing 0.1% TFA, flow: 40 mL/min). MS (UPLC): 462.4/464.4 [M+H]+, 506.5/508.5 [M+HCOO]−; $t_R$ (UPLC conditions m): 0.70 min.

Scheme B27: Preparation of (2S,3S,4S)-2-[1-(3-Chloro-2-fluoro-phenyl)-cyclopropylcarbamoyl]-4-fluoro-3-hydroxy-pyrrolidine-1-carboxylic acid tert-butyl ester

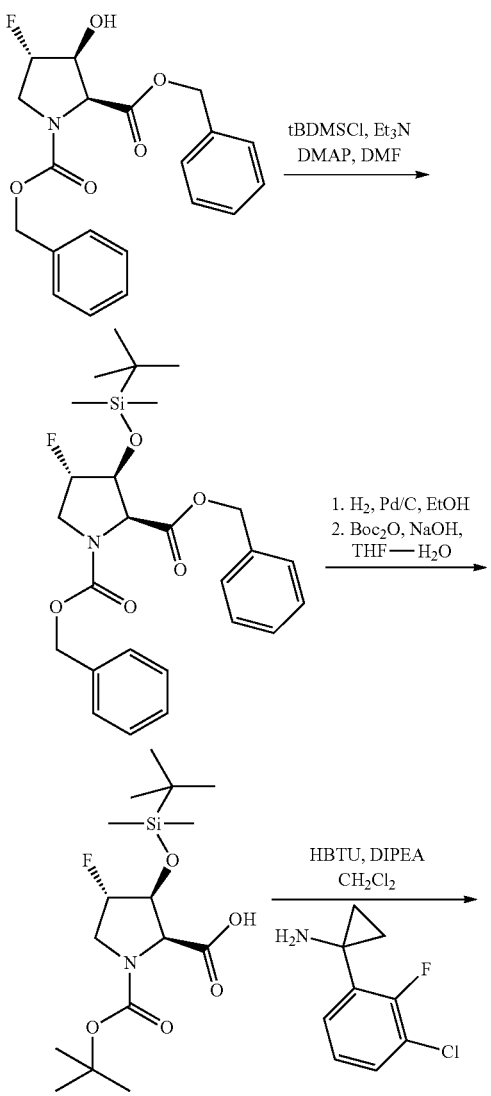

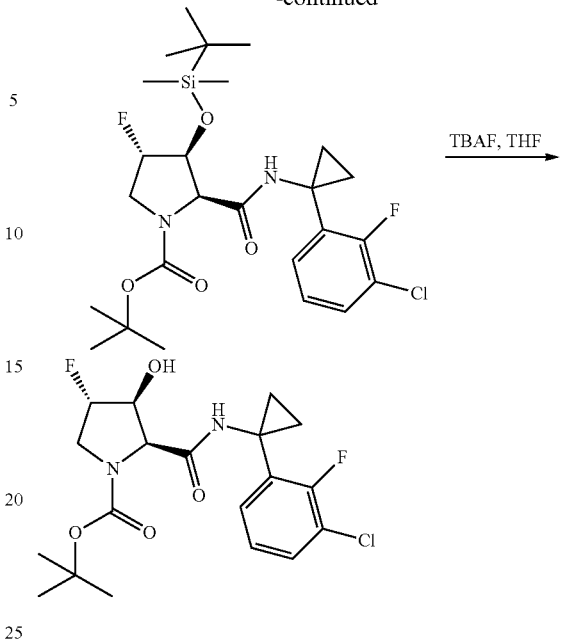

A. (2S,3S,4S)-3-(tert-Butyl-dimethyl-silanyloxy)-4-fluoro-pyrrolidine-1,2-dicarboxylic acid dibenzyl ester To a solution of (2S,3S,4S)-4-fluoro-3-hydroxy-pyrrolidine-1,2-dicarboxylic acid dibenzyl ester (1.90 g, 5.09 mmol) in DMF (40 mL) were added tert-butyldimethylchlorosilane (0.844 g, 5.60 mmol), triethylamine (0.709 ml, 5.09 mmol) and DMAP (0.062 g, 0.509 mmol). The reaction mixture was stirred 25° C. for 1 week. Then quenched by addition of a saturated aqueous solution of $NaHCO_3$. The layers were separated and the organic extract was dried ($Na_2SO_4$), filtered and concentrated. The crude residue was purified by flash column chromatography on silica gel (c-hexane/EtOAc 9:1). MS (UPLC): 588.4 [M+H]+, 505.5 [M+NH$_4$]+, 510.4 [M+Na]+; $t_R$ (HPLC conditions f): 2.90 min.

B. (2S,3S,4S)-3-(tert-Butyl-dimethyl-silanyloxy)-4-fluoro-pyrrolidine-1,2-dicarboxylic acid 1-tert-butyl ester was prepared from (2S,3S,4S)-3-(tert-butyl-dimethyl-silanyloxy)-4-fluoro-pyrrolidine-1,2-dicarboxylic acid dibenzyl ester according to the protocol described in Scheme B26 step A. $t_R$ (UPLC conditions m): 1.21 min.

C. (2S,3S,4S)-3-(tert-Butyl-dimethyl-silanyloxy)-2-[1-(3-chloro-2-fluoro-phenyl)-cyclopropyl carbamoyl]-4-fluoro-pyrrolidine-1-carboxylic acid tert-butyl ester To a solution of (2S,3S,4S)-3-(tert-butyl-dimethyl-silanyloxy)-4-fluoro-pyrrolidine-1,2-dicarboxylic acid 1-tert-butyl ester (300 mg, 0.825 mmol), 1-(3-chloro-2-fluoro-phenyl)-cyclopropylamine (prepared as described in Part C, 272 mg, 0.908 mmol) and HBTU (376 mg, 0.99 mmol) in DMF (10 mL) was added DIPEA (0.432 ml, 2.476 mmol) under nitrogen atmosphere. The reaction mixture was stirred 2 h at 25° C. Then quenched by addition of a saturated aqueous solution of $NaHCO_3$ and extracted with EtOAc (×2). The combined organic extracts were dried ($Na_2SO_4$), filtered and concentrated. The crude residue was purified by flash column chromatography on silica gel (c-hexane/EtOAc 1:1). MS (UPLC): 531.5/533.5 [M+H]+, 505.5 [M+NH4]+, 510.4 [M+Na]+; $t_R$ (UPLC conditions m): 1.55 min.

(2S,3S,4S)-2-[1-(3-Chloro-2-fluoro-phenyl)-cyclopropylcarbamoyl]-4-fluoro-3-hydroxy-pyrrolidine-1-carboxylic acid tert-butyl ester TBAF (1N in THF, 0.547 ml, 0.547 mmol) was added to a solution of (2S,3S,4S)-3-(tert-butyl-dimethyl-silanyloxy)-2-[1-(3-chloro-2-fluoro-phenyl)-cyclopropyl carbamoyl]-4-fluoro-pyrrolidine-1-carboxylic acid tert-butyl ester (242 mg, 0.456 mmol) in THF (10 mL) and the reaction mixture was stirred 30 min at 25° C. Then poured into water, extracted with EtOAc (×2), dried (Na2SO4), filtered and concentrated. The material thus obtained was used without further purification in the next step. MS (UPLC): 417.5/419.5 [M+H]+, 461.5/463.5 [M+HCOO]−; $t_R$ (HPLC conditions f): 2.04 min.

Scheme B28: preparation of (1R,3S,5S) and (1S,3S,5R)-3-(3-Chloro-2-fluoro-benzylcarbamoyl)-5-hydroxymethyl-2-aza-bicyclo [3.1.0] hexane-2-carboxylic acid tert-butyl ester

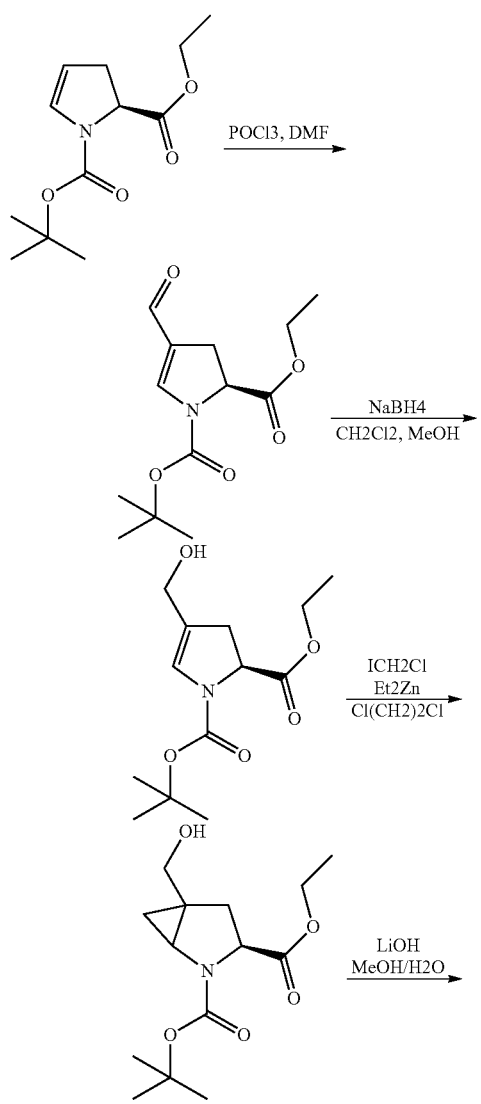

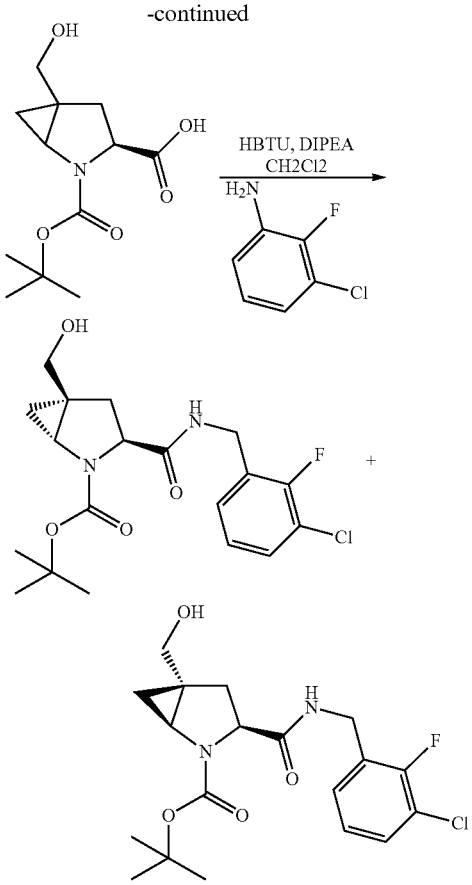

A. (S)-4-Formyl-2,3-dihydro-pyrrole-1,2-dicarboxylic acid 1-tert-butyl ester 2-ethyl ester POCl3 (7.59 mL, 83 mmol) was added in 25 min at 0° C. under N2 atmosphere to DMF (6.39 mL, 83 mmol) and the mixture was stirred at RT for 20 min. Dry CH2Cl2 (150 mL) was added at 0° C., followed by a solution of (S)-2,3-dihydro-pyrrole-1,2-dicarboxylic acid 1-tert-butyl ester 2-ethyl ester (10 g, 41.4 mmol) in CH2Cl2 (50 mL). The mixture was stirred 30 min at RT until completion. The mixture was slowly poured into an ice cold aqueous solution of NaOH 10 N (150 mL) and extracted with CH2Cl2 (×3). The combined organic extracts were washed with brine (×2), with water, dried (Na2SO4), filtered and concentrated. The crude residue was purified by flash column chromatography on silica gel (c-hexane to c-hexane/EtOAc 9:1) to give the desired material as a yellow oil. $R_f$, TLC (c-hexane/EtOAc 4:1)=0.2; MS (UPLC-MS): 270 [M+H]+, 170 [M−Boc]−; $t_R$ (HPLC conditions f): 1.93 min.

B. (S)-4-Hydroxymethyl-2,3-dihydro-pyrrole-1,2-dicarboxylic acid 1-tert-butyl ester 2-ethyl ester A solution of (S)-4-formyl-2,3-dihydro-pyrrole-1,2-dicarboxylic acid 1-tert-butyl ester 2-ethyl ester (3.32 g, 12.3 mmol) in CH2Cl2 (51.4 mL) was cooled at −78° C. under nitrogen atmosphere, solid NaBH4 (1 g, 24.7 mmol) was added portionwise maintaining the temperature at −78° C. MeOH (25.7 mL) was added dropwise and the reaction mixture was allowed to reach 0° C. and was stirred 1 h30 at 0° C. The reaction was quenched with an aqueous saturated solution of NH4Cl and extracted with CH2Cl2 (×3). The combined organic layers were washed with brine, dried (Na2SO4), filtered and concentrated. The crude residue was purified by flash column chromatography on silica gel (c-hexane to c-hexane/EtOAc 1:1 to EtOAc) to give the desired material as a yellow oil. R$_f$ TLC (c-hexane/EtOAc 1:1)=0.30; MS (UPLC-MS): 272.2 [M+H]+, 316 [M+HCOO]−; t$_R$ (HPLC conditions f): 1.74 min.

C. (1R,3S,5S) and (1S,3S,5R)-5-Hydroxymethyl-2-aza-bicyclo[3.1.0]hexane-2,3-dicarboxylic acid 2-tert-butyl ester 3-ethyl ester To a solution of (S)-4-hydroxymethyl-2,3-dihydro-pyrrole-1,2-dicarboxylic acid 1-tert-butyl ester 2-ethyl ester (1.12 g, 4.13 mmol) in CH$_2$Cl$_2$ (115 mL) under argon at −20° C. were slowly added diethylzinc (1M in hexanes, 8.26 mL, 8.26 mmol) and diiodomethane (0.73 mL, 9.08 mmol) and the reaction mixture was further stirred at −10° C. for 2 h. Diethylzinc (1M in hexanes, 8.26 mL, 8.26 mmol) and diiodomethane (0.73 mL, 9.08 mmol) were again added and the reaction mixture was further stirred at −10° C. for 2 h to complete the reaction. A saturated aqueous solution of NH$_4$Cl was added slowly (exothermic) at −20° C. followed by CH$_2$Cl$_2$. The layers were separated and the aqueous layer was extracted with CH$_2$Cl$_2$ (×2). To the combined organic layers were added few crystals of Na$_2$S and water (ratio CH$_2$Cl$_2$/H$_2$O 20:1) and the biphasic mixture was stirred for 30 min. Water was added, the layers were separated, dried (Na$_2$SO$_4$), filtered and concentrated to give a mixture of diastereoisomers. The crude residue was purified by flash column chromatography on silica gel (c-hexane/EtOAc 1:1) to give a mixture of diastereoisomers (4:6 (1R,3S,5S)/(1S,3S,5R)). The absolute stereochemistry of the diastereoisomers was determined by NMR. R$_f$ TLC (c-hexane/EtOAc 1:1)=0.25; MS (UPLC-MS): 186.1 [MH−Boc]+, 230.2 [MH−tBu]+, 286.3 [MH+H]+, 308.2 [MH+Na]+, 330.3 [M+HCOO]−; t$_R$ (HPLC conditions f): 1.75 min.

Alternatively (1R,3S,5S) and (1S,3S,5R)-5-hydroxymethyl-2-aza-bicyclo[3.1.0]hexane-2,3-dicarboxylic acid 2-tert-butyl ester 3-ethyl ester were prepared according to the procedure below derived from *J. Amer. Chem. Soc.*, 1998, 120, 46, 11943.

To a solution of dry DME (198 µL, 1.91 mmol) in dry CH$_2$Cl$_2$ (4 mL) under argon atmosphere and cooled at −10° C. was added diethylzinc (1 M in hexanes, 2.05 mL, 2.05 mmol) followed by chloroiodomethane (330 µL, 4.1 mmol) over a 15-20 min period while maintaining the internal temperature at −10° C. The solution was stirred for an additional 10 min at −10° C. and a solution of butylboronic acid N,N,N',N'-tetramethyl-D-tartaric acid diamide ester (346 µL, 1.36 mmol) in anhydrous CH$_2$Cl$_2$ (1 mL) was added over a 5 min period immediately followed by the addition of a solution of (S)-4-hydroxymethyl-2,3-dihydro-pyrrole-1,2-dicarboxylic acid 1-tert-butyl ester 2-ethyl ester (185 mg, 0.68 mmol) in dry CH$_2$Cl$_2$ (1 mL). The reaction mixture was stirred at −10° C. The reaction was quenched with 1 mL of a saturated aqueous NH$_4$Cl and 10% KHSO$_4$ (3 mL), EtOAc was added, the layers were separated and the aqueous layer back-extracted with EtOAc (×2). To the combined organic layers was added a solution containing 6 mL of 2 N aqueous NaOH and 1 mL of 30% aqueous H$_2$O$_2$ and the resulting biphasic solution was vigorously stirred for 5 min. The two layers were separated and the organic layer was successively washed with saturated aqueous Na$_2$SO$_3$, NaHCO$_3$ and brine, dried over Na$_2$SO$_4$, filtered and concentrated. The crude material was purified by flash column chromatography on silica gel (c-hexane to c-hexane/EtOAc 6-4) to give a mixture of diastereoisomers (approximately 70/30 (1R,3S,5S)/(1S,3S,5R)).

D. (1R,3S,5S) and (1S,3S,5R)-5-Hydroxymethyl-2-aza-bicyclo[3.1.0]hexane-2,3-dicarboxylic acid 2-tert-butyl ester To a diastereoisomeric mixture of (1R,3S,5S) and (1S,3S,5R)-5-hydroxymethyl-2-aza-bicyclo[3.1.0]hexane-2,3-dicarboxylic acid 2-tert-butyl ester 3-ethyl ester (ratio 4:6, 100 mg, 0.31 mmol) in THF (1.5 mL) and H$_2$O (0.15 mL) at 0° C. was added NaOH (1 M in water, 0.63 mL, 0.63 mmol). The solution was stirred 1 h at RT and poured into 10% KHSO$_4$ (until pH 1), EtOAc was added and the layers were separated (×3). The combined organic layers were dried (Na$_2$SO$_4$), filtered and concentrated. The crude residue was used without further purification in the next step. MS (HPLC/MS): 256.2 [M−H]−, 258.3 [M+H]+, 280.3 [M+Na]+, 200.2 [MH−tBu]+, 515.54 [2M+H]+, 537.4 [2M+Na]+; t$_R$ (HPLC conditions f): 1.28 min.

E. (1R,3S,5S) and (1S,3S,5R)-3-(3-Chloro-2-fluorobenzylcarbamoyl)-5-hydroxymethyl-2-aza-bicyclo[3.1.0]hexane-2-carboxylic acid tert-butyl ester To a diastreoisomeric mixture of (1R,3S,5S) and (1S,3S,5R)-5-hydroxymethyl-2-aza-bicyclo[3.1.0]hexane-2,3-dicarboxylic acid 2-tert-butyl ester (312 mg, 1.21 mmol), 3-chloro-2-fluorobenzylamine (232 mg, 1.46 mmol), HBTU (690 mg, 1.82 mmol) in CH$_2$Cl$_2$ (6 mL) was added DIPEA (0.623 mL, 3.64 mmol). The resulting solution was stirred at RT under nitrogen overnight. DIPEA (0.21 mL, 1.21 mmol), HBTU (230 mg, 0.6 mmol) and 3-chloro-2-fluorobenzylamine (97 mg, 0.606 mmol) were added and the mixture was further stirred overnight at RT under N2. The mixture was poured into an aqueous solution of HCl 1N (pH-1) and extracted with CH$_2$Cl$_2$ (2×). The combined organic layers were washed with brine, dried (Na$_2$SO$_4$), filtered and concentrated. The crude residue was purified by flash column chromatography on silica gel (c-hexane to c-hexane/EtOAc 40:60) to give (1S,3S,5R)-3-(3-chloro-2-fluoro-benzylcarbamoyl)-5-hydroxymethyl-2-aza-bicyclo[3.1.0]hexane-2-carboxylic acid tert-butyl ester: TLC, R$_f$ (EtOAc)=0.55 (stained with ninhydrine); MS (UPLC-MS): 399.2/401.2 [M+H]+, 299.2/301.2 [MH−Boc]+, 343.2/345.2 [MH−tBu]+, 443.2/445.3 [M+HCOO]−; t$_R$ (HPLC conditions f): 1.95 min, and (1R,3S,5S)-3-(3-chloro-2-fluoro-benzylcarbamoyl)-5-hydroxymethyl-2-aza-bicyclo[3.1.0]hexane-2-carboxylic acid tert-butyl ester: TLC, R$_f$ (EtOAc)=0.45 (stained with ninhydrine); MS (UPLC-MS): 399.2/401.2 [M+H]+, 299.2/301.2 [MH−Boc]+, 343.2/345.2 [MH−tBu]+, 443.2/445.3 [M+HCOO]−; t$_R$ (HPLC conditions f): 1.89 min.

(1R,3S,5S)-5-Hydroxymethyl-2-aza-bicyclo[3.1.0]hexane-2,3-dicarboxylic acid 2-tert-butyl ester

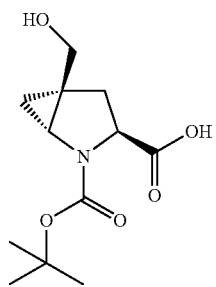 [SMILES: CC(C)(C)OC(=O)N1[C@H](C(=O)O)C[C@@]2(CO)C[C@@H]12]

was obtained using the same protocols as described in Scheme B28 step D from (1R,3S,5S)-5-hydroxymethyl-2-aza-bicyclo[3.1.0]hexane-2,3-dicarboxylic acid 2-tert-butyl ester 3-ethyl ester. 1H NMR (400 MHz, DMSO-d$_6$) δ (ppm): 12.5 (m, 1H), 4.71 (m, 1H), 3.92 (m, 1H), 3.42-3.35 (m, 2H), 3.17 (m, 1H), 2.31 (m, 1H), 2.08 (m, 1H), 1.41 and 1.33 (2 s, 9H), 0.79 (m, 1H), 0.67 (m, 1H).

(1R,3S,5S)-5-Hydroxymethyl-2-aza-bicyclo[3.1.0] hexane-2,3-dicarboxylic acid 2-tert-butyl ester 3-ethyl ester The mixture of (1R,3S,5S) and (1S,3S,5R)-5-hydroxymethyl-2-aza-bicyclo[3.1.0]hexane-2,3-dicarboxylic acid 2-tert-butyl ester 3-ethyl ester (360 g) was separated into its diastereoisomers by preparative chiral HPLC column: 8 SMB columns Chiralpak AD, 20 um, 250×30 mm; eluent: heptane-EtOH 80:20) to give (1R,3S,5S)-5-hydroxymethyl-2-aza-bicyclo[3.1.0]hexane-2,3-dicarboxylic acid 2-tert-butyl ester 3-ethyl ester: $t_R$ (Chiralpak AD-prep, 20 uM, 250×4.6 mm, n-heptane/EtOH 80/20, flow rate 1 mL/min, detection: UV at 210 nm): 6.94 min and (1S,3S,5R)-5-hydroxymethyl-2-aza-bicyclo[3.1.0]hexane-2,3-dicarboxylic acid 2-tert-butyl ester 3-ethyl ester: $t_R$ (Chiralpak AD-prep, 20 uM, 250×4.6 mm, n-heptane/EtOH 80/20, flow rate 1 mL/min, detection: UV at 210 nm): 4.20 min.

(1R,3S,5S) and (1S,3S,5R)-3-(3-Chloro-2-fluoro-benzylcarbamoyl)-5-methoxymethyl-2-aza-bicyclo [3.1.0]hexane-2-carboxylic acid tert-butyl ester

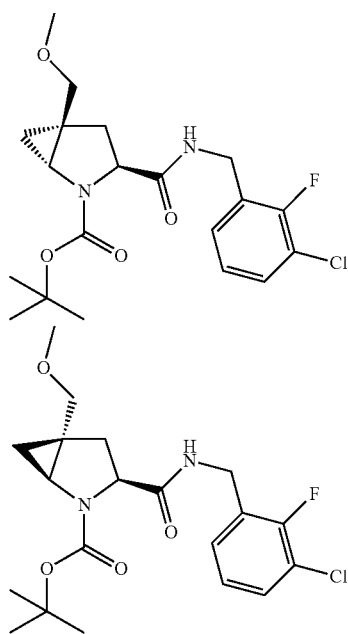

were obtained using the same protocols as described in Scheme B28 steps D and E for the preparation of (1R,3S,5S) and (1S,3S,5R)-3-(3-chloro-2-fluoro-benzylcarbamoyl)-5-hydroxymethyl-2-aza-bicyclo[3.1.0]hexane-2-carboxylic acid tert-butyl ester starting from (1R,3S,5S) and (1S,3S,5R)-5-methoxymethyl-2-aza-bicyclo[3.1.0]hexane-2,3-dicarboxylic acid 2-tert-butyl ester 3-ethyl ester. NaOH was replaced by LiOH.H$_2$O in step D. The diastereoisomers were separated by flash column chromatography on silica gel (c-hexane/EtOAc 1:1 to EtOAc) to give (1S,3S,5R)-3-(3-chloro-2-fluoro-benzylcarbamoyl)-5-methoxymethyl-2-aza-bicyclo[3.1.0]hexane-2-carboxylic acid tert-butyl ester as a colorless oil: TLC, $R_f$ (c-hexane/EtOAc 1:1)=0.50; MS (UPLC/MS): 413.3/415.2 [M+H]+, 457.3/459.3 [M+HCOO]−; $t_R$ (HPLC conditions a): 3.74 min and (1R,3S,5S)-3-(3-chloro-2-fluoro-benzylcarbamoyl)-5-methoxymethyl-2-aza-bicyclo[3.1.0]hexane-2-carboxylic acid tert-butyl ester as a colorless oil: TLC, $R_f$ (c-hexane/EtOAc 1:1)= 0.30; MS (UPLC/MS): 413.2/415.3 [M+H]+, 457.3/459.3 [M+HCOO]−; $t_R$ (HPLC conditions a): 3.57 min.

(1R,3S,5S) and (1S,3S,5R)-5-Methoxymethyl-2-aza-bicyclo[3.1.0]hexane-2,3-dicarboxylic acid 2-tert-butyl ester 3-ethyl ester (1R,3S,5S) and (1S,3S,5R)-5-hydroxymethyl-2-aza-bicyclo[3.1.0]hexane-2,3-dicarboxylic acid 2-tert-butyl ester 3-ethyl ester as mixture of diastereoisomers (35:65 (1R,3S,5S)/(1S,3S,5R)) (840 mg, 2.94 mmol) were slowly added at 0° C. under Argon to a suspension of NaH (60% in mineral oil, 141 mg, 3.53 mmol) in THF (9 mL). The reaction mixture was stirred at 0° C. for 30 min and iodomethane (0.28 mL, 4.42 mmol) was added slowly at 0° C. The reaction mixture was further stirred at RT overnight. Saturated NaHCO$_3$ and CH$_2$Cl$_2$ were added, the layers were separated and the aqueous one back-extracted twice with CH$_2$Cl$_2$. The combined organic extracts were dried (Na$_2$SO$_4$), filtered and concentrated. The crude material was purified by flash column chromatography on silica gel (c-hexane to c-hexane/EtOAc 2:8) to give the title compound as an unseparable mixture of diastereosisomers. TLC, $R_f$ (c-hexane/EtOAc 1:1)=0.70; MS (UPLC/MS): 300.3 [M+H]+, 599.5 [2M+H]+; $t_R$ (HPLC conditions a): 3.45 min. The absolute stereochemistry of the diastereoisomers was tentatively assigned by NMR and based on the test results for the final compounds Example 214 and Example 184 in the biological assay.

(1R,3S,5R)-3-(3-Chloro-2-fluoro-benzylcarbamoyl)-5-methyl-2-aza-bicyclo[3.1.0]hexane-2-carboxylic acid tert-butyl ester

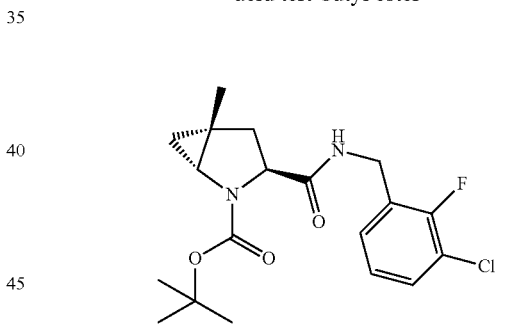

Lithium triethylborohydride (1N in THF, 2.06 mL, 2.06 mmol) was added at 0° C. to a solution of (1R,3S,5S)-3-(3-chloro-2-fluoro-benzylcarbamoyl)-5-methanesulfonyloxymethyl-2-aza-bicyclo[3.1.0]hexane-2-carboxylic acid tert-butyl ester (385 mg, 0.67 mmol) in THF (6.8 mL) under argon atmosphere. The solution was stirred 10 min at 0° C., then poured into cold water and extracted with EtOAc (×2). The combined organic extracts were dried (Na$_2$SO$_4$), filtered and concentrated. The crude residue was purified by flash column chromatography on silica gel (c-hexane to c-hexane/EtOAc 75:25). TLC, $R_f$ (c-hexane/EtOAc 1:1)=0.55; MS (UPLC/MS): 383.3/385.3 [M+H]+, 427.5/429.4 [M+HCOO]−; $t_R$ (HPLC conditions f): 2.24 min.

(1R,3S,5S)-3-(3-Chloro-2-fluoro-benzylcarbamoyl)-5-methanesulfonyloxymethyl-2-aza-bicyclo[3.1.0] hexane-2-carboxylic acid tert-butyl ester To a solution of (1R,3S,5S)-3-(3-chloro-2-fluoro-benzylcarbamoyl)-5-hydroxymethyl-2-aza-bicyclo[3.1.0]hexane- 2-carboxylic acid tert-butyl ester (290 mg, 0.72 mmol) and Et₃N (144 µL, 1.04 mmol) in CH₂Cl₂ (6.5 mL) at 0° C. under nitrogen atmosphere was added methanesulfonyl chloride (81 µL, 1.04 mmol) and the mixture was stirred at RT for 1 h. Et₃N (48 µL, 0.35 mmol) and methanesulfonyl chloride (27 µL, 0.35 mmol) were again added and the mixture was further stirred for 0.5 h to complete the reaction. A saturated aqueous solution of NaHCO₃ was added, the layers were separated and the aqueous layer extracted with CH₂Cl₂ (×2), dried (Na₂SO₄), filtered and concentrated. The material thus obtained was used in the next step without further purification. TLC, R$_f$ (EtOAc)=0.65; MS (UPLC/MS): 477.3/479.3 [M+H]+, 521.3/523.3 [M+HCOO]—

(1R,3S,5R)-5-Methyl-2-aza-bicyclo[3.1.0]hexane-2,3-dicarboxylic acid 2-tert-butyl ester

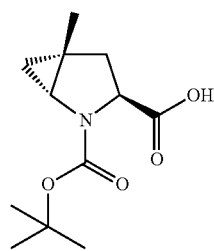 [SMILES: CC(C)(C)OC(=O)N1[C@H](C(=O)O)C[C@@]2(C)C[C@@H]12]

To a solution of (1R,3S,5R)-5-methyl-2-aza-bicyclo[3.1.0]hexane-2,3-dicarboxylic acid 2-tert-butyl ester 3-ethyl ester (185 mg, 0.69 mmol) in MeOH (1.1 mL), THF (1.1 mL) and H₂O (1.1 mL) was added KOH (77 mg, 1.37 mmol). The solution was stirred 2.5 h at RT, HCl (0.1N) was added (until pH 1), CH₂Cl₂ was added and the layers were separated (×2). The combined organic layers were dried (Na₂SO₄), filtered and concentrated. The material (yellow oil) thus obtained was used without further purification in the next step. 1H NMR (400 MHz, DMSO-d₆) δ (ppm): 12.46 (m, 1H), 3.86 (m, 1H), 3.06 (m, 1H), 2.40 (dd, 1H), 1.86 (m, 1H), 1.37 (m, 9H), 1.18 (s, 3H) 0.65 (m, 2H).

(1R,3S,5R)-5-Methyl-2-aza-bicyclo[3.1.0]hexane-2,3-dicarboxylic acid 2-tert-butyl ester 3-ethyl ester To a solution of (1R,3S,5S)-5-methanesulfonyloxymethyl-2-aza-bicyclo[3.1.0]hexane-2,3-dicarboxylic acid 2-tert-butyl ester (100 mg, 0.24 mmol) in DME (2.6 mL) were successively added NaI (355 mg, 2.37 mmol) and zinc powder (155 mg, 2.37 mmol). The reaction mixture was refluxed 30 min under argon atmosphere, cooled to RT and quenched by addition of a saturated aqueous solution of NH₄Cl (1.6 mL). CH₂Cl₂ (1.6 mL) and few Na₂S crystals were added and the biphasic mixture was stirred at RT for 1 h. The layers were separated, the organic extracts were washed with brine, dried (Na₂SO₄), filtered and concentrated under reduced pressure. The crude residue was purified by flash column chromatography on silica gel (eluent: c-hexane to c-hexane/EtOAc). TLC, R$_f$(c-hexane/EtOAc 2:1)=0.60; MS (UPLC/MS): 270.3 [M+H]+, 214.2 [MH−tBu]+, 170.2 [MH−Boc]+; 1H NMR (400 MHz, DMSO-d₆) δ (ppm): 4.11 (m, 2H), 3.95 (m, 1H), 3.10 (m, 1H), 2.42 (m, 1H), 1.84 (m, 1H), 1.38 (m, 9H), 1.20 (t, 3H) 1.18 (s, 3H) 0.69 (dd, 1H), 0.64 (m, 1H).

(1R,3S,5S)-5-methanesulfonyloxymethyl-2-aza-bicyclo[3.1.0]hexane-2,3-dicarboxylic acid 2-tert-butyl ester To a solution of (1R,3S,5S)-5-hydroxymethyl-2-aza-bicyclo[3.1.0]hexane-2,3-dicarboxylic acid 2-tert-butyl ester 3-ethyl ester (500 mg, 1.75 mmol) and Et₃N (366 µL, 2.63 mmol) in CH₂Cl₂ (16 mL) was added methanesulfonyl chloride (205 µL, 2.63 mmol) at 0° C. under nitrogen atmosphere. The reaction mixture was slowly allowed to reach RT and stirred 1 h. The reaction was quenched by addition of a saturated aqueous solution of NaHCO₃, the layers were separated and the aqueous layer extracted twice with CH₂Cl₂. The combined organic extracts were dried (Na₂SO₄), filtered and concentrated. The material thus obtained was used without further purification in the next step. Yellow oil, TLC, R$_f$ (EtOAc)=0.80.

Scheme B29: Preparation of (1R,3S,5S)-5-Hydroxymethyl-2-aza-bicyclo[3.1.0]hexane-3-carboxylic acid (2-fluoro-3-trifluoromethoxyphenyl-amide hydrochloride

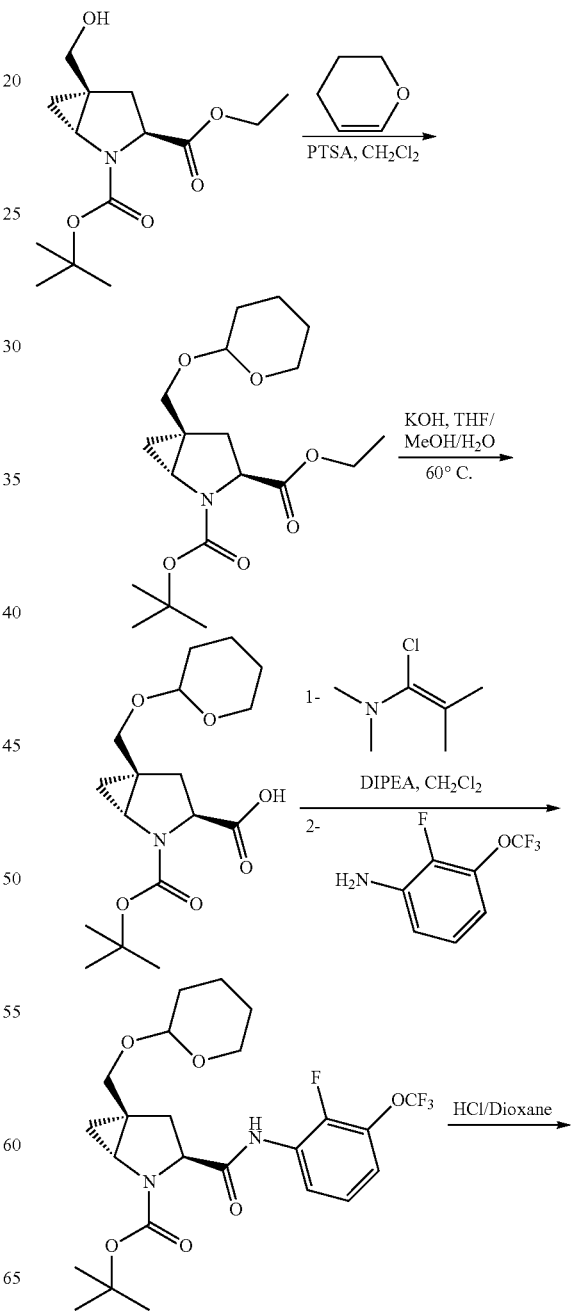

-continued

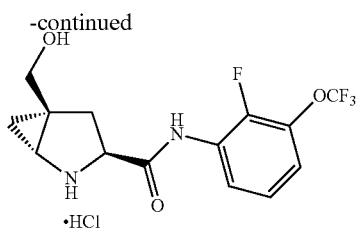

A. (1R,3S,5S)-5-(Tetrahydro-pyran-2-yloxymethyl)-2-aza-bicyclo[3.1.0]hexane-2,3-dicarboxylic acid 2-tert-butyl ester 3-ethyl ester A mixture of (1R,3S,5S)-5-hydroxymethyl-2-aza-bicyclo[3.1.0]hexane-2,3-dicarboxylicacid 2-tert-butyl ester 3-ethyl ester (500 mg, 1.75 mmol), 3,4-dihydro-2H-pyran (176 µL, 1.93 mmol) and TsOH.H$_2$O (33 mg, 0.17 mmol) in CH$_2$Cl$_2$ (6 mL) was stirred 3 h at RT. Then poured into a saturated aqueous solution of NaHCO$_3$ and extracted with CH$_2$Cl$_2$ (×2). The combined organic extracts were dried (Na$_2$SO$_4$), filtered and concentrated. The crude residue was purified by flash column chromatography on silica gel (c-hexane to c-hexane/EtOAc 1:1). Colorless oil. TLC, R$_f$(EtOAc)=0.85; MS (UPLC/MS): 370.4 [M+H]+, 387.4 [M+H$_2$O]+; t$_R$ (HPLC conditions f): 2.28 min.

B. (1R,3S,5S)-5-(Tetrahydro-pyran-2-yloxymethyl)-2-aza-bicyclo[3.1.0]hexane-2,3-dicarboxylic acid 2-tert-butyl ester To a solution of (1R,3S,5S)-5-(tetrahydro-pyran-2-yloxymethyl)-2-aza-bicyclo[3.1.0]hexane-2,3-dicarboxylic acid 2-tert-butyl ester 3-ethyl ester (510 mg, 1.38 mmol) in MeOH (2.3 mL), THF (2.3 mL) and water (2.3 mL) was added KOH (155 mg, 2.76 mmol). The reaction was stirred at 60° C. for 45 min. Then allowed to cool to RT and diluted with EtOAc. The layers were separated, the aqueous layer was acidified by addition of HCl (0.1N, until pH 1) and extracted with EtOAc (×2). The organics were dried (Na$_2$SO$_4$), filtered and concentrated. MS (UPLC/MS): 359.4 [M+NH$_4$]+, 340.4 [M−H]−, 386.4 [M+HCOO]−, 681.5 [2M−H]−; t$_R$ (HPLC conditions f): 1.84 min.

C. (1R,3S,5S)-3-(2-Fluoro-3-trifluoromethoxy-phenylcarbamoyl)-5-(tetrahydro-pyran-2-yloxymethyl)-2-aza-bicyclo[3.1.0]hexane-2-carboxylic acid tert-butyl ester To a solution of (1R,3S,5S)-5-(tetrahydro-pyran-2-yloxymethyl)-2-aza-bicyclo[3.1.0]hexane-2,3-dicarboxylic acid 2-tert-butyl ester (100 mg, 0.29 mmol) in dry CH$_2$Cl$_2$ (1 mL) under argon at 0° C. was added 1-chloro-N,N,2-trimethylpropenylamine (58 µL, 0.44 mmol) and the reaction mixture was stirred at 0° C. for 1.5 h. 2-Fluoro-3-(trifluoromethoxy)aniline (86 mg, 0.44 mmol) was added, followed by DIPEA (100 µL, 0.59 mmol) and the mixture was stirred at RT overnight. Then poured into water and extracted with CH$_2$Cl$_2$ (×2), the organics were dried (Na$_2$SO$_4$), filtered and concentrated. The crude residue was purified by flash column chromatography on silica gel (eluent: c-hexane to c-hexane/EtOAc 85:15). TLC, R$_f$ (c-hexane/EtOAc 2:1)=0.45; MS (UPLC/MS): 519.3 [M+H]+, 536.3 [M+NH$_4$]+, 517.4 [M−H]−, 563.3 [M−HCOO]−; t$_R$ (HPLC conditions f): 2.51 min.

D. (1R,3S,5S)-5-Hydroxymethyl-2-aza-bicyclo[3.1.0]hexane-3-carboxylic acid (2-fluoro-3-trifluoromethoxy-phenyl)-amide hydrochloride To a solution of (1R,3S,5S)-3-(2-fluoro-3-trifluoromethoxy-phenylcarbamoyl)-5-(tetrahydro-pyran-2-yloxymethyl)-2-aza-bicyclo[3.1.0]hexane-2-carboxylic acid tert-butyl ester (105 mg, 0.19 mmol) in dioxane (0.5 mL) was added HCl (4 N in dioxane, 481 µL, 1.92 mmol). The mixture was stirred at RT for 4 h, solvent was removed under reduced pressure and the material thus obtained was used without further purification in the next step. MS (UPLC/MS): 335.2 [M+H]+, 333.2 [M−H]−, 379.6 [M+HCOO]−.

(1R,3S,5R)-3-[3-(3-Chloro-2-fluoro-phenyl)-oxetan-3-ylcarbamoyl]-2-aza-bicyclo[3.1.0]hexane-2-carboxylic acid tert-butyl ester

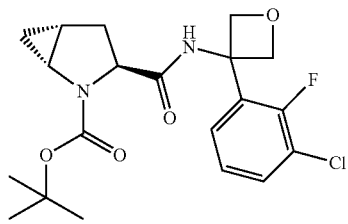 [SMILES: CC(C)(C)OC(=O)N1[C@@H]2C[C@@H]2C[C@H]1C(=O)NC1(c2cccc(Cl)c2F)COC1]

To a solution of (1R,3S,5R)-2-aza-bicyclo[3.1.0]hexane-2,3-dicarboxylic acid 2-tert-butyl ester (220 mg, 0.968 mmol), propylphosphonic anhydride (50% in EtOAc, 0.856 ml, 1.45 mmol) and 3-(3-chloro-2-fluoro-phenyl)-oxetan-3-ylamine (prepared as described in Part C, 358 mg, 1.06 mmol) in CH$_2$Cl$_2$ (10 mL) was added DIPEA (0.507 ml, 2.90 mmol) under nitrogen atmosphere. The reaction mixture was stirred 2 h at RT and concentrated. The crude residue was purified by flash column chromatography on silica gel (c-hexane/EtOAc 3:2). MS (LC/MS): 411.2/413.2 [M+H]+, 455.2/457.2 [M+HCOO]−; t$_R$ (HPLC conditions f): 2.02 min.

Scheme B30: Preparation of (1R,3S,5R)-2-[2-(3-Acetyl-pyrazolo[3,4-b]pyridin-1-yl)-acetyl]-2-azabicyclo[3.1.0]-hexane-3-carboxylic acid

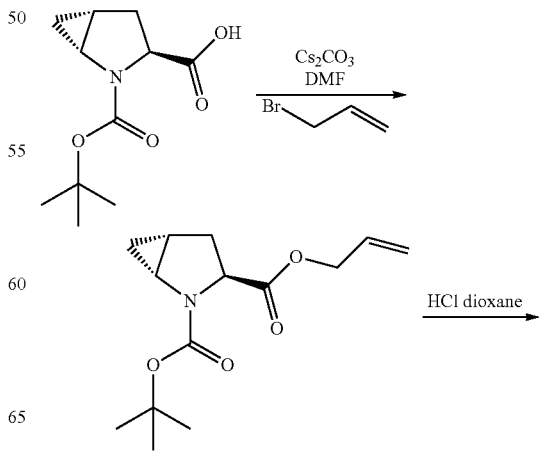

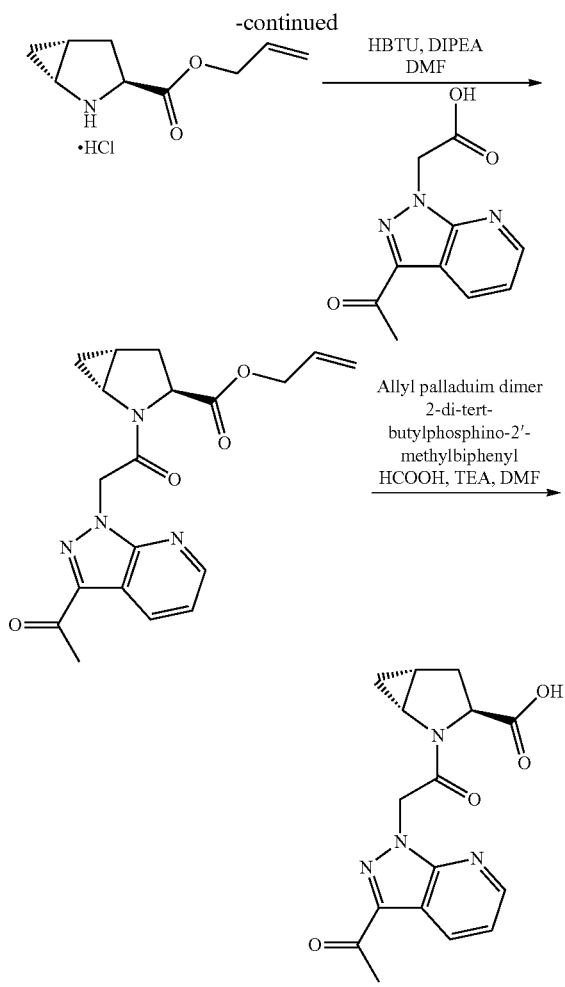

A. (1R,3S,5R)-2-Azabicyclo[3.1.0]hexane-2,3-dicarboxylic acid 3-allyl ester 2-tert-butyl ester To a solution of (1R,3S,5R)-2-azabicyclo[3.1.0]hexane-2,3-dicarboxylic acid 2-tert-butyl ester (1.5 g, 3.6 mmol) and Cs$_2$CO$_3$ (2.26 g, 6.9 mmol) in DMF (20 mL) allyl bromide (0.6 mL, 3.9 mmol) was added. The reaction mixture was stirred for 40 h at RT. DMF was evaporated. The residue was dissolved in EtOAc and washed with HCl 1N, dried over Na$_2$SO$_4$, filtered and concentrated. The crude residue was purified by flash column chromatography on silica gel (c-hexane to c-hexane/EtOAc 4:6). MS (LCMS):167.9 [MH−Boc]+, 290.0 [M+Na]+.

B. (1R,3S,5R)-2-Azabicyclo[3.1.0]hexane-3-carboxylic acid allyl ester hydrochloride To (1R,3S,5R)-2-azabicyclo[3.1.0]hexane-2,3-dicarboxylic acid 3-allyl ester 2-tert-butyl ester (1.69 g, 6.32 mmol) was added HCl 4N in dioxane (15.8 mL, 63.2 mmol). The reaction mixture was stirred for 6 h at RT and subsequently lyophilized. MS: 168.0 [M+H]+.

C. (1R,3S,5R)-2-[2-(3-Acetyl-pyrazolo[3,4-b]pyridin-1-yl)-acetyl]-2-aza-bicyclo[3.1.0]hexane-3-carboxylic acid allyl ester To a solution of (1R,3S,5R)-2-azabicyclo[3.1.0]hexane-2,3-dicarboxylic acid 3-allyl ester hydrochloride (1.03 g, 6.43 mmol), (3-acetyl-pyrazolo[3,4-b]pyridin-1-yl)acetic acid (prepared as described in Part A, 1.3 g, 5.93 mmol) and HBTU (2.70 g, 7.12 mmol) in DMF (19.7 mL) was added DIPEA (3.11 mL, 17.8 mmol). The reaction mixture was stirred for 16 h at RT. DMF was evaporated. The residue was poured into NH$_4$Cl (saturated aqueous solution) and extracted with EtOAc (3×50 mL). The organic phases were combined, dried over Na$_2$SO$_4$, filtered and concentrated. The crude residue was purified by flash column chromatography on silica gel (c-hexane to c-hexane/EtOAc 0:10). R$_f$, TLC (EtOAc)=0.6; MS (LCMS): 369.0 [M+H]+, 391.0 [MH+Na]+; t$_R$ (HPLC conditions k): 2.78 min.

D. (1R,3S,5R)-2-[2-(3-Acetyl-pyrazolo[3,4-b]pyridin-1-yl)-acetyl]-2-aza-bicyclo[3.1.0]hexane-3-carboxylic acid Allyl palladium chloride dimer (0.084 g, 0.231 mmol) and 2-di-tert-butylphosphino-2'-methylbiphenyl (0.288 g, 0.923 mmol) were dissolved in DMF (7.69 mL) under argon atmosphere. The reaction mixture was stirred at RT for 10 min. After cooling the reaction mixture to 10° C., formic acid (0.513 mL, 13.38 mmol) was added followed by TEA (1.865 mL, 13.38 mmol) and a solution of (1R,3S,5R)-2-[2-(3-acetyl-pyrazolo[3,4-b]pyridin-1-yl)acetyl]-2-azabicyclo[3.1.0]hexane-3-carboxylic acid allyl ester (1 g, 2.3 mmol) in DMF (15.38 mL). The reaction mixture was stirred at 10° C. during 1 h. DMF was evaporated. The residue was poured into NH$_4$Cl (saturated aqueous solution) and extracted with EtOAc (3×50 mL). The organic phases were combined, dried over Na$_2$SO$_4$, filtered and concentrated. The residue was dissolved in MeOH and filtered over a PL-Thiol cartridge. The filtrate was concentrated. The crude residue was purified by preparative HPLC (Waters Sunfire C18-OBD, 5 µm, 30×100 mm, flow: 40 mL/min, eluent: 5% to 80% CH$_3$CN in H$_2$O in 20 min, CH$_3$CN and H$_2$O containing 0.1% TFA) and the pure fractions were combined and lyophilized. White solid. MS (LCMS): 328.9 [M+H]+; 351.0 [MH+Na]; t$_R$ (HPLC conditions I): 1.84 min. 1H NMR (400 MHz, DMSO-d$_6$): (ppm) 8.66 (dd, J=4.52, 1.59 Hz, 1H), 8.58 (m, J=6.36 Hz, 1H), 7.35-7.50 (m, 1H), 8.54-8.61 (m, 1H), 5.88 (d, J=16.87 Hz, 1H), 5.55 (d, J=17.12 Hz, 1H), 4.14-4.24 (m, 1H), 3.75-3.83 (m, 1H), 2.64 (s, 3H), 2.26-2.36 (m, 1H), 2.10-2.23 (m, 1H), 1.80-1.95 (m, 1H), 0.95-1.07 (m, 1H), 0.67-0.81 (m, 1H).

Scheme B31: Preparation of (1R,3S,5R)-2-[2-(3-Carbamoyl-indazol-1-yl)-acetyl]-2-aza-bicyclo[3.1.0]hexane-3-carboxylic acid

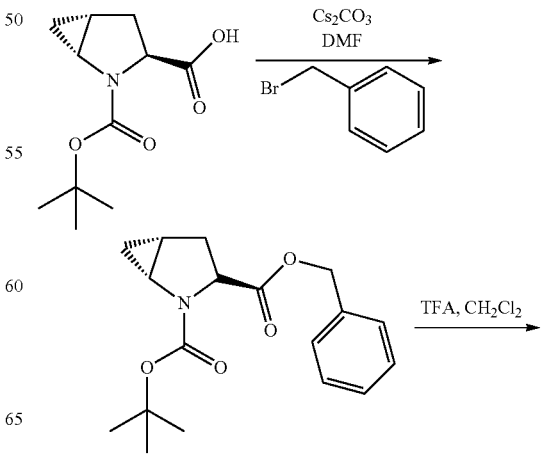

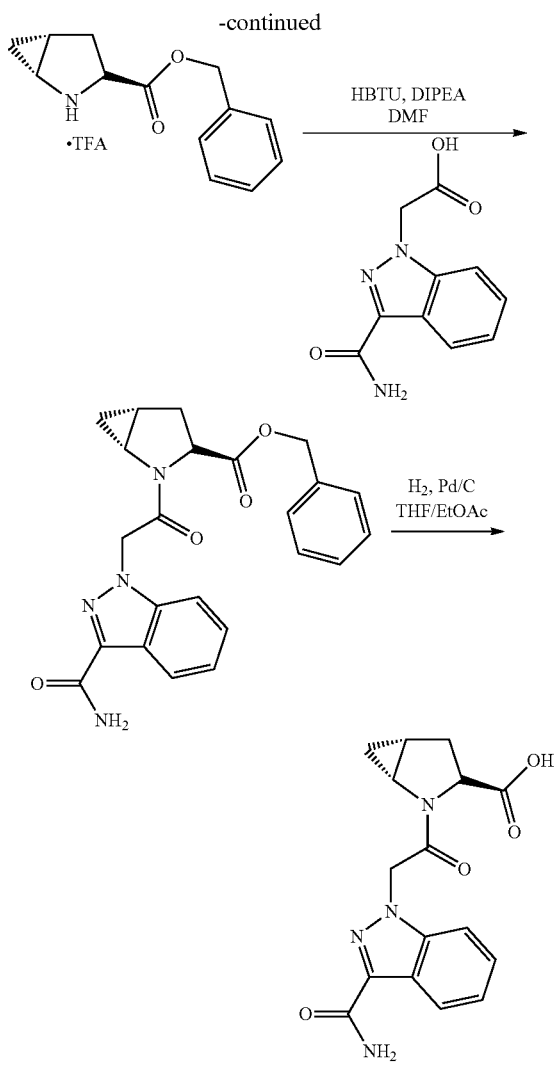

A. (1R,3S,5R)-2-Aza-bicyclo[3.1.0]hexane-2,3-dicarboxylic acid 3-benzyl ester 2-tert-butyl ester To a solution of (1R,3S,5R)-2-azabicyclo[3.1.0]hexane-2,3-dicarboxylic acid 2-tert-butyl ester (2.5 g, 11.0 mmol) and $Cs_2CO_3$ (3.94 g, 12.1 mmol) in DMF (50 mL) at 0° C. benzylbromide (2.26 g, 13.2 mmol) was added dropwise. The reaction mixture was stirred overnight at RT. DMF was evaporated. The residue was dissolved in EtOAc and washed with a saturated aqueous solution of $NaHCO_3$, the layers were separated and the aqueous phase was extracted with EtOAc (×2). The combined organic extracts were dried over $Na_2SO_4$, filtered and concentrated. The crude residue was purified by flash column chromatography on silica gel (c-hexane/EtOAc 100:0 to 0:100) to give the desired material as a colorless oil. MS (LCMS): 318.2 [M+H]+; $t_R$ (HPLC conditions f): 2.23 min.

B. (1R,3S,5R)-2-Aza-bicyclo[3.1.0]hexane-3-carboxylic acid benzyl ester trifluoroacetate To (1R,3S,5R)-2-aza-bicyclo[3.1.0]hexane-2,3-dicarboxylic acid 3-benzyl ester 2-tert-butyl ester (3.27 g, 9.79 mmol) in $CH_2Cl_2$ (50 mL) was added was added TFA (7.54 mL, 98 mmol). The reaction mixture was stirred overnight at RT and subsequently concentrated under reduced pressure to give the desired material as a yellow oil. MS (UPLC): 218.1 [M+H]+; $t_R$ (HPLC conditions f): 1.24 min.

C. (1R,3S,5R)-2-[2-(3-Carbamoyl-indazol-1-yl)-acetyl]-2-aza-bicyclo[3.1.0]hexane-3-carboxylic acid benzyl ester To a solution of (1R,3S,5R)-2-aza-bicyclo[3.1.0]hexane-3-carboxylic acid benzyl ester trifluoroacetate (3.9 g, 9.77 mmol), (3-carbamoyl-indazol-1-yl)-acetic acid (prepared as described in Scheme A25, 2.26 g, 9.77 mmol), HBTU (5.56 g, 14.66 mmol) in $CH_2Cl_2$ (60 mL) was added DIPEA (5.12 mL, 29.3 mmol). The reaction mixture was stirred for 48 h at RT. The reaction mixture was poured into water and extracted with $CH_2Cl_2$ (×3). The combined organic extracts were dried over $Na_2SO_4$, filtered and concentrated. The crude residue was purified by flash column chromatography on silica gel (c-hexane/EtOAc 10:0 to 0:10). $R_f$, TLC (EtOAc)=0.85; MS (UPLC): 436.3 [M+$NH_4$]+, 463.2 [M+HCOO]−; $t_R$ (HPLC conditions f): 1.82 min.

D. (1R,3S,5R)-2-[2-(3-Carbamoyl-indazol-1-yl)-acetyl]-2-aza-bicyclo[3.1.0]hexane-3-carboxylic acid (1R,3S,5R)-2-[2-(3-carbamoyl-indazol-1-yl)-acetyl]-2-aza-bicyclo[3.1.0]hexane-3-carboxylic acid benzyl ester (3.9 g, 8.85 mmol) was dissolved in THF (120 mL) and EtOAc (120 mL). Air was removed from the flask and replaced with nitrogen three times. Pd/C 10% (390 mg) was added to the solution which was again degassed, placed under a hydrogen atmosphere, and stirred at RT for 4 h. The catalyst was removed through a pad of Celite and washed with EtOAc. Solvents were removed under reduced pressure and the foam thus obtained was used without further purification in the next step. MS (LCMS): 346.2 [M+$NH_4$]+, 327.1 [M−H]−; $t_R$ (HPLC conditions f): 1.12 min.

Scheme B32: (1R,3S,5R)-3-aminomethyl-2-aza-bicyclo[3.1.0]hexane-2-carboxylic acid tert-butyl ester

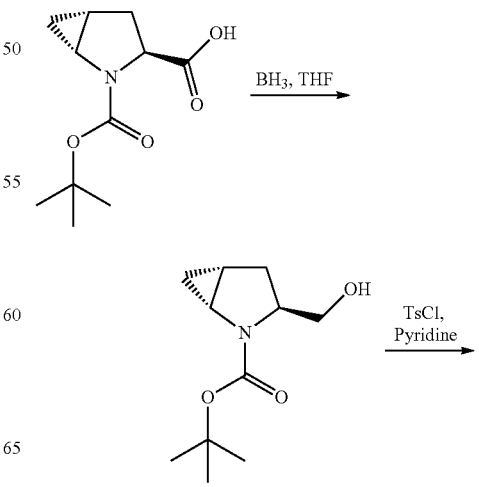

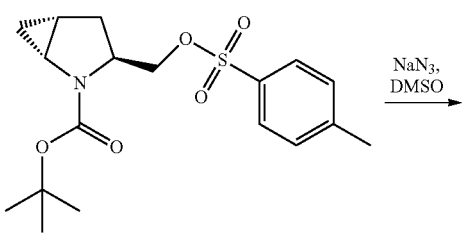

NaN₃, DMSO →

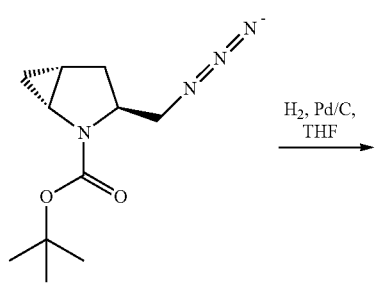

H₂, Pd/C, THF →

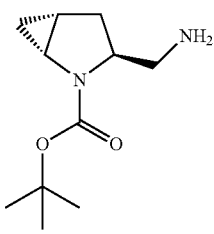

A. (1R,3S,5R)-3-Hydroxymethyl-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (0.5 g, 2.2 mmol) in dry THF (10 mL), cooled to 0° C., was added under an argon atmosphere dropwise a 1M solution of boran-tetrahydrofuran-complex (4.40 mL, 4.40 mmol). The reaction mixture was kept at 0° C. for an additional 2 h and then allowed to warm up to RT overnight. The reaction was quenched by careful addition of water and subsequently EtOAc. The organic layer was subsequently washed with saturated aqueous solutions of NaCl, NaHCO₃, water and NaCl. The organic phase was dried (phase separator) and concentrated to give the title compound as a colorless oil. MS (LC-MS): 214.0 [M+H]+; $t_R$ (HPLC conditions k): 2.99 min. The material thus obtained was used in the next step without further purification.

B. (1R,3S,5R)-3-(Toluene-4-sulfonyloxymethyl)-2-aza-bicyclo[3.1.0]hexane-2-carboxylic acid tert-butyl ester To an ice-cooled solution of (1R,3S,5R)-3-hydroxymethyl-2-aza-bicyclo[3.1.0]hexane-2-carboxylic acid tert-butyl ester (0.480 g, 2.15 mmol) in pyridine (5 mL) was added 4-toluenesulfonyl chloride (0.490 g, 2.58 mmol). The reaction mixture was stirred at RT for 6 h and then diluted with Et₂O. The organic phase was washed with 1N HCl (3×), aqueous NaHCO₃ (3×) and NaCl, then dried (phase separator) and concentrated under reduced pressure. The residue was purified by flash column chromatography on silica gel (eluent gradient: c-hexane to c-hexane/EtOAc 4:1) to afford the title compound as a colorless wax. TLC, $R_f$ (c-hexane/EtOAc 4:1)=0.2. MS (LC-MS): 390.0 [M+Na]+, 757.0 [2M+H]+. $t_R$ (HPLC conditions k): 4.07 min.

C. (1R,3S,5R)-3-Azidomethyl-2-aza-bicyclo[3.1.0]hexane-2-carboxylic acid tert-butyl ester A mixture of (1R,3S,5R)-3-(toluene-4-sulfonyloxymethyl)-2-aza-bicyclo[3.1.0]hexane-2-carboxylic acid tert-butyl ester (0.400 g, 1.08 mmol) and NaN₃ (0.420 g, 6.47 mmol) in dry DMSO (8 mL) was stirred at 65° C. overnight. After cooling, the mixture was diluted with Et₂O and washed with water (×3) and brine (×2). The organics were dried (phase separator) and concentrated in vaccuo to give the title compound as a colorless oil. MS (LC-MS): 239.0 [M+H]+; $t_R$ (HPLC conditions k): 3.78 min. The material thus obtained was used in the next step without further purification.

D. (1R,3S,5R)-3-Aminomethyl-2-aza-bicyclo[3.1.0]hexane-2-carboxylic acid tert-butyl ester (1R,3S,5R)-3-azidomethyl-2-aza-bicyclo[3.1.0]hexane-2-carboxylic acid tert-butyl ester (195 mg, 0.82 mmol) was suspended in THF (10 mL). Air was removed from the flask and replaced with nitrogen three times. Pd/C 10% (20 mg) was added to the solution which was again degassed, placed under a hydrogen atmosphere, and stirred at RT overnight. The catalyst was removed through a 0.45 microns filter, and the filtrate was concentrated in vacuo to give the title compound. MS (LC-MS): 213.0 [M+H]+; $t_R$ (HPLC conditions k): 2.51 min. The material thus obtained was used in the next step without further purification.

Part C

Synthesis of Aniline and Benzylamine Intermediates

4-Amino-2-bromo-benzoic acid methyl ester

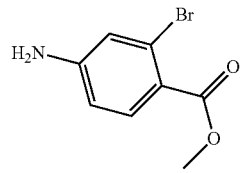

To a suspension of 2-bromo-4-nitro-benzoic acid methyl ester [100959-22-6] (350 mg, 1.35 mmol) in MeOH (60 mL) were subsequently added tin powder (1.6 g, 13.5 mmol) and 3N aqueous HCl (27.8 mL, 83 mmol). The mixture was stirred overnight at RT. The liquid phase was decanted from the excess tin and neutralized by adding a saturated aqueous NaHCO₃ solution. An equal amount of water by volume was added and the water phase was extracted with EtOAc (3×). The combined organics were dried (Phase Separator) and concentrated in vacuo. The residue was purified by flash column chromatography on silica gel (eluent: EtOAc/c-hexane 1:4) to give the title compound as yellow solid. MS (LC/MS): 230 [M+H]+; $t_R$ (HPLC conditions b): 2.89 min.

3'-Amino-2-fluoro-biphenyl-4-carbonitrile

3-Aminophenylboronic acid (200 mg, 1.29 mmol), 3-fluoro-4-iodobenzonitrile (319 mg, 1.29 mmol), TBACl (35.9 mg, 0.129 mmol) and Pd(PPh$_3$)$_4$ (74.6 mg, 0.064 mmol) were suspended in a mixture of toluene (4 mL) and K$_2$CO$_3$ 1M in water (4 mL). The biphasic mixture was vigorously stirred under argon at 90° C. for 20 h. The organic layer was separated and the aqueous phase was extracted with toluene (×2). The organic layers were combined, washed with water, dried over Na$_2$SO$_4$, filtered and concentrated. The crude residue was purified by column chromatography (c-hexane/EtOAc 3:1) to give the desired material. MS (LC/MS) [M+H]+=213; t$_R$ (HPLC, Waters Atlantis, 2.1×30 mm, flow 0.6 mL/min, CH$_3$CN/H$_2$O 5 to 95% in 2.5 min, 95% CH$_3$CN 2 min, 95 to 5% CH$_3$CN, H$_2$O and CH$_3$CN both containing 0.1% HCOOH): 2.84 min.

2-Fluoro-3-(trifluoromethoxy)aniline hydrochloride

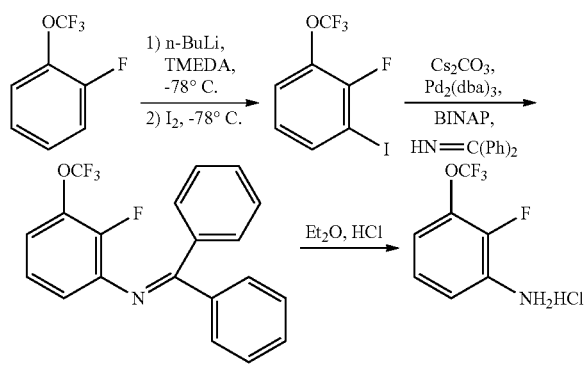

A. 2-Fluoro-1-iodo-3-(trifluoromethoxy)benzene

To a solution of 1-fluoro-2-(trifluoromethoxy)benzene [2106-18-5] (20.0 g, 111 mmol) in dry THF (200 mL), cooled to −78° C., was added dropwise n-BuLi (2.5 M solution in n-hexane; 65 mL, 160 mmol) and subsequently TMEDA (60 mL). The reaction mixture was stirred for additional 60 min at −78° C., followed by addition of a solution of iodine (30.2 g, 120 mmol) in dry THF (50 mL). The resulting mixture was stirred for 1 h and then quenched by addition of a saturated aqueous NH$_4$Cl solution (20 mL). The organic layer was washed with 1N HCl, water and brine, and dried over MgSO$_4$. Volatiles were removed in vacuo to afford the title compound as yellow oil. The product was used in the next reaction step without further purification. MS (LC/MS): 306.0 [M+H]+.

B. Benzhydrylidene-(2-fluoro-3-trifluoromethoxyphenyl)-amine

To a solution of 2-fluoro-1-iodo-3-(trifluoromethoxy)benzene (25 g, 81 mmol) in dry toluene (200 mL) was added Cs$_2$CO$_3$ (38.7 g, 120 mmol), Pd$_2$(dba)$_3$ (7.42 g, 8.1 mmol), BINAP (10.8 g, 16.2 mmol) and benzhydrylideneamine (19.6 g, 108 mmol). The reaction mixture was refluxed for 8 h with stirring and then cooled to RT. The organic layer was washed with water and brine and then dried over MgSO$_4$. After removal of solvent in vacuo, the residue was purified by column chromatography on silica gel (solvent gradient from 100% n-hexane to n-hexane/EtOAc 20:1) to afford the title compound as a pale yellow oil. $^1$H NMR (CDCl$_3$, 400 MHz): δ 7.72 (s, 1H, ArH,), 7.70 (s, 1H, ArH), 7.45-7.42 (m, 1H, ArH,), 7.37-7.33 (m, 2H, ArH), 7.25-7.17 (m, 3H, ArH), 7.06 (s, 1H, ArH), 7.05 (s, 1H, ArH,), 6.84 (t, 1H, J=8 Hz, ArH), 6.78 (t, 1H, J=8 Hz, ArH), 6.67-6.64 (m, 1H, ArH).

C. 2-Fluoro-3-(trifluoromethoxy)aniline hydrochloride

To a mixture of benzhydrylidene-(2-fluoro-3-trifluoromethoxy-phenyl)-amine (7.5 g, 20 mmol) in Et$_2$O (40 mL) was added 3N aqueous HCl (10 mL). The reaction mixture was stirred for 4 h at RT, followed by addition of water. The aqueous layer was extracted with Et$_2$O (2×10 mL), the combined organic layers were washed with brine and then dried over MgSO$_4$. After removal of solvent in vacuo, the residue was purified by preparative HPLC (stationary phase: Gimini 300×50 mm, particle size 10 μm; solvent: A H$_2$O+BCH$_3$CN, pressure: 60-70 bar). The product was extracted with Et$_2$O as the free base from the combined fractions. HCl gas was bubbled through the organic phase, and the solvent was removed under vacuum to afford the title compound. Recrystallisation from EtOH/diisopropylether gave a white solid. $^1$H NMR (D$_2$O, 400 MHz): δ 7.40-7.35 (m, 1H, ArH), 7.32-7.27 (m, 1H, ArH), 7.27-7.19 (m, 1H, ArH). HRMS: 196.03801 [M]+ (calcd. 196.03800 for C$_7$H$_5$F$_4$NO); Anal. Calcd. for C$_7$H$_5$F$_4$NO: C, 36.31; H, 2.61; N, 6.05; Cl, 15.31; F, 32.82. Found: C, 35.78; H, 2.63; N, 6.14; Cl, 15.69; F, 31.99.

3-Difluoromethoxy-2-fluoro-phenylamine

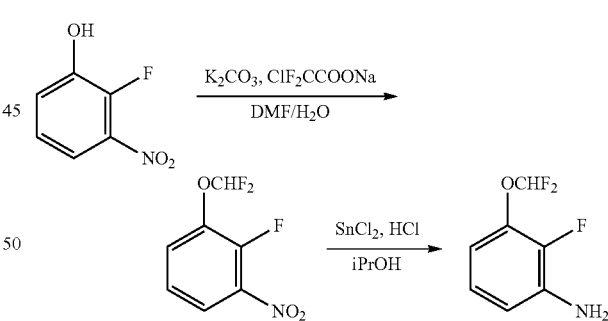

A. 1-Difluoromethoxy-2-fluoro-3-nitro-benzene

To a mixture of sodium 2-chloro-2,2-difluoroacetate (7.14 g, 46.8 mmol) and potassium carbonate (3.50 g, 25.3 mmol) in DMF (10 mL) and water (2.5 mL) at 110° C. was added a solution of 2-fluoro-3-nitrophenol (2 g, 12.65 mmol) in DMF (10 mL) and the mixture was stirred at 110° C. for 6 h. After cooling down, the mixture was quenched with water and extracted with EtOAc. The organic layer was then washed with water, brine and dried over Na$_2$SO$_4$, filtered and concentrated. The crude material was purified by flash column chromatography on silica gel (c-hexane to c-hexane/EtOAc 1:1).

1H NMR (400 MHz, DMSO-d$_6$) δ (ppm): 7.79 (td, 1H), 7.45 (t, 1H), 5.15 (m, 1H), 7.44 (m, 1H). t$_R$ (HPLC conditions f): 2.09 min.

B. 3-Difluoromethoxy-2-fluoro-phenylamine

To a mixture of 1-difluoromethoxy-2-fluoro-3-nitro-benzene (2.16 g, 10.43 mmol) and tin(II) chloride (6.92 g, 36.5 mmol) in 2-propanol (100 ml) was added carefully HCl (37%, 10.28 ml, 125 mmol) and the mixture was stirred for 30 min at 110° C. The reaction mixture was cooled to RT, diluted with water and the pH adjusted to 10 by addition of 2N NaOH. The mixture was extracted with EtOAc and the organic layer was dried over Na$_2$SO$_4$, filtered and concentrated to afford the titled compound. 1H NMR (400 MHz, DMSO-d$_6$) δ (ppm): 7.06 (t, 1H), 6.95 (m, 1H), 6.87 (m, 1H), 6.55 (td, 1H), 5.04 (bs, 2H). t$_R$ (HPLC conditions f): 1.93 min.

3-Cyclopropyl-2-fluoro-phenylamine

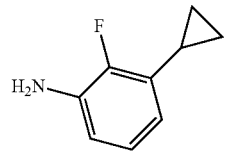 [SMILES: Nc1cccc(C2CC2)c1F]

To a solution of 3-bromo-2-fluoroaniline (200 mg, 1.05 mmol), cyclopropylboronic acid (118 mg, 1.37 mmol), potassium phosphate (782 mg, 3.68 mmol), and tricyclohexylphosphine (29.5 mg, 0.105 mmol) in toluene (2.4 mL) and water (120 µL) was added Pd(OAc)$_2$ (11.8 mg, 0.05 mmol). The reaction mixture was degassed by repeating alternating application of vacuum and positive nitrogen pressure (3×), and then heated at 100° C. under nitrogen overnight. The mixture was cooled to RT, diluted with water, and extracted twice with EtOAc. The combined organic layers were dried (Na$_2$SO$_4$), filtered and concentrated. The crude residue was purified by flash column chromatography on silica gel (c-hexane to c-hexane/EtOAc 93-7). TLC, R$_f$ hexane/EtOAc 2:1)=0.7; MS (UPLC/MS): 152.0 [M+H]+.

2,3-Difluoro-5-methoxy-benzylamine

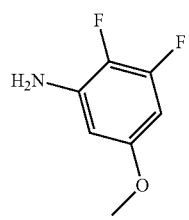

A. 2,3-Difluoro-5-methoxy-benzoic acid methyl ester

To a solution of 2,3-difluoro-5-hydroxy-benzoic acid [749230-51-1] (1.00 g, 5.74 mmol; Melford Laboratories Ltd) in DMF (20 mL) was added K$_2$CO$_3$ (1.99 g, 14.4 mmol) and MeI (0.79 mL, 12.6 mmol), followed by stirring at RT overnight. The reaction mixture was diluted with EtOAc, the organics were washed with a saturated aqueous NH$_4$Cl solution (50 mL) and a saturated aqueous NaHCO$_3$ solution, dried (Phase separator) and evaporated under reduced pressure. The residue was purified by flash column chromatography on silica gel (c-hexane/EtOAc 3:1) to afford the title compound as a colorless oil. TLC, R$_f$ (c-hexane/EtOAc 3:1)=0.37; MS (LC/MS): 203.0 [M+H]+; t$_R$ (HPLC conditions c): 4.72 min.

B. (2,3-Difluoro-5-methoxy-phenyl)-methanol

To a solution of 2,3-difluoro-5-methoxy-benzoic acid methyl ester (925 mg, 4.58 mmol) in THF (25 mL), cooled to 0° C., was added a solution of LiBH$_4$ (199 mg, 9.15 mmol) in THF (5 mL). The reaction mixture was stirred at RT for overnight. An additional aliquot of LiBH$_4$ (4 equiv) was added and stirring was continued at RT for 6 h, and subsequently at 60° C. overnight. The mixture was diluted with EtOAc, the organics were washed with 1N aqueous NaOH solution (50 mL), dried (Phase separator) and evaporated in vacuo to afford the title compound as a white solid. TLC R$_f$ (c-hexane/EtOAc 1:1)=0.57; MS (LC/MS): 198.0 [M+Na]+; t$_R$ (HPLC conditions c): 3.74 min.

C. 1-Azidomethyl-2,3-difluoro-5-methoxy-benzene

To a solution of (2,3-difluoro-5-methoxy-phenyl)-methanol (715 mg, 4.11 mmol) in toluene (10 mL) was added DPPA (1.04 mL, 4.93 mmol) and DBU (0.805 mL, 5.34 mmol), followed by stirring at RT for 1 h. The reaction mixture was diluted with EtOAc, the organics were washed with diluted brine (20 mL), dried (Phase separator) and evaporated in vacuo. The residue was purified by flash column chromatography on silica gel (c-hexane/EtOAc 9:1) to afford the title compound as a colorless oil. TLC R$_f$ (c-hexane/EtOAc 3:1)= 0.55; MS (LC/MS): 208.0 [M+NH$_4$]+; t$_R$ (HPLC conditions c): 5.46 min.

D. 2,3-Difluoro-5-methoxy-benzylamine

To a solution of 1-azidomethyl-2,3-difluoro-5-methoxy-benzene (710 mg, 3.57 mmol) in EtOH (20 mL) was added Pd/C 10% (70 mg) and the reaction mixture was stirred at RT overnight under an H$_2$ atmosphere. The reaction mixture was filtered through Celite, followed by washing with EtOH and CH$_2$Cl$_2$. The combined filtrates were evaporated in vacuo and the residue was purified by flash column chromatography on silica gel (CH$_2$Cl$_2$/acetone 9:1, then CH$_2$Cl$_2$/MeOH 9:1) to afford the title compound as a yellowish oil. TLC R$_f$ (CH$_2$Cl$_2$/MeOH 9:1)=0.32; MS (LC/MS): 174.0 [M+H]+; t$_R$ (HPLC conditions c): 2.30 min.

3-Amino-5-bromo-4-fluoro-benzoic acid ethyl ester

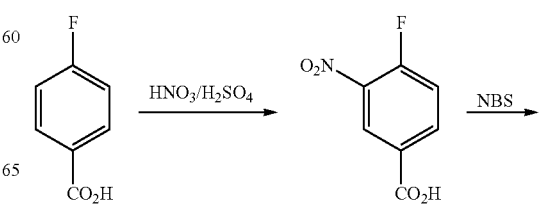

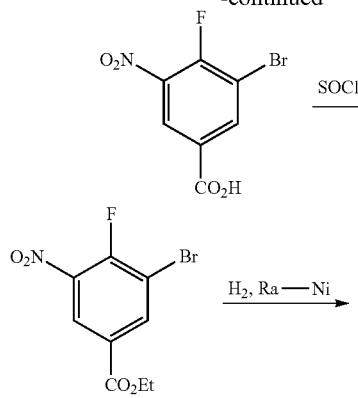

A. 4-Fluoro-3-nitro-benzoic acid

Conc. HNO$_3$ (79 mL) was dropwise added to a solution of 4-fluoro-benzoic acid (70 g, 0.5 mol) in conc. H$_2$SO$_4$ (500 mL) at 0° C. The mixture was stirred for 4 h at RT and then poured into ice-water (3.0 L). The precipitate was filtered off, washed twice with water (0.5 L) and dried to give the title compound as a white solid. 1H-NMR (300 MHz, CDCl$_3$): δ (ppm) 11.0 (s, br, 1H), 8.86 (m, 1H), 8.42 (m, 1H), 7.47 (m, 1H).

B. 3-Bromo-4-fluoro-5-nitro-benzoic acid

NBS (47.9 g, 0.268 mol) was added portion-wise to a solution of 4-fluoro-3-nitro-benzoic acid (41.5 g, 0.224 mol) in conc. H$_2$SO$_4$ (0.35 L). The reaction mixture was stirred for 5 h at 65° C. and then poured into ice-water (1.5 L). The precipitate was filtered off, washed twice with water (300 mL) and dried to give the title compound as a white solid. 1H-NMR (300 MHz, CDCl$_3$): δ (ppm) 10.7 (s, br, 1H), 8.76 (m, 1H), 8.62 (m, 1H).

C. 3-Bromo-4-fluoro-5-nitro-benzoic acid ethyl ester

SOCl$_2$ (33.7 g, 0.283 mol) was added dropwise to a solution of 3-bromo-4-fluoro-5-nitro-benzoic acid (37.4 g, 0.142 mol) in EtOH (300 mL). The reaction mixture was refluxed overnight, cooled to RT and subsequently concentrated under reduced pressure. The residue was dissolved in EtOAc (300 mL), washed twice with water (50 mL), dried (Na$_2$SO$_4$) and concentrated to give the title compound as yellow solid. 1H-NMR (300 MHz, CDCl$_3$): δ (ppm) 8.65 (m, 1H), 8.53 (m, 1H), 4.46 (m, 2H), 1.45 (m, 3H).

D. 3-Amino-5-bromo-4-fluoro-benzoic acid ethyl ester

A mixture of 3-bromo-4-fluoro-5-nitro-benzoic acid ethyl ester (20 g, 2.2 mol) and 3 g of Raney-Ni in EtOH (250 mL) was hydrogenated at RT (1 atm) overnight. The reaction mixture was filtered, the filtrate was concentrated under reduced pressure and the residue was washed with petrol ether to afford the title compound as a white solid. (400 MHz, DMSO-d$_6$): δ (ppm) 7.38 (dd, 1H), 7.26 (dd, 1H), 5.81 (s, 2H), 4.26 (q, 2H), 1.29 (t, 3H).

3-Bromo-5-(1H-tetrazol-5-yl)-phenylamine dihydrochloride

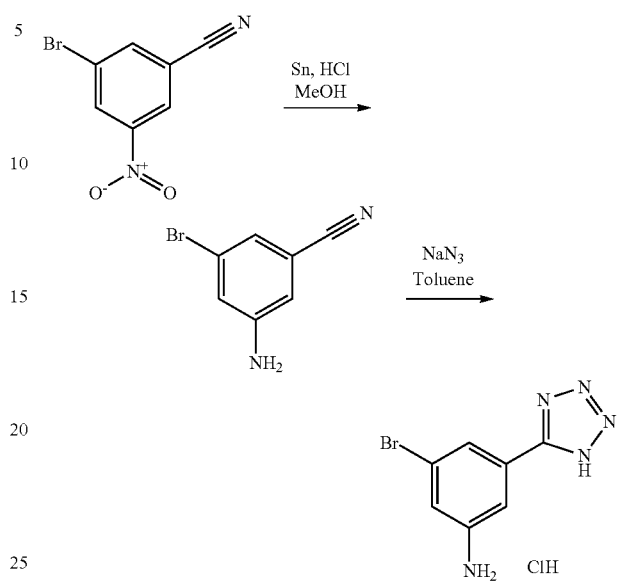

A. 3-Amino-5-bromo-benzonitrile

To a solution of 3-bromo-5-nitrobenzonitrile (1 g, 4.4 mmol) in MeOH (50 mL) was added tin (5.23 g, 44 mmol) and 3N HCl (44 mL, 132 mmol). The reaction mixture was stirred at RT for 2 h, the filtered off and washed with MeOH. The filtrate was concentrated in vacuo, and the remaining water phase was basified to pH=12 by addition of 4N NaOH. The aqueous layer was extracted twice with EtOAc (100 mL), the combined organics were dried (Na$_2$SO$_4$) and evaporated in vacuo to afford the title compound as a yellowish solid. MS (LC/MS): 197.0 [M+H]+; t$_R$ (HPLC conditions c): 4.30 min.

B. 3-Bromo-5-(1H-tetrazol-5-yl)-phenylamine hydrochloride

To a solution of 3-amino-5-bromo-benzonitrile (200 mg, 1.02 mmol) in toluene (2 mL) was added 6N HCl (0.220 mL, 1.32 mmol), triethylamine (0.184 mL, 1.32 mmol) and sodium azide (86.0 mg, 1.32 mmol). The reaction mixture was stirred at 100° C. for 30 min in a microwave apparatus (Personal Chemistry, Biotage), and after cooling to RT was then diluted with CH$_2$Cl$_2$/MeOH (4:1) and washed with 10 mL of water. The organic phase was discarded, and the water phase was acidified to pH=1 by adding 12N HCl. The aqueous layer was freeze-dried overnight to afford the title compound as a yellowish solid. MS (LC/MS): 239.3 [M+H]+; t$_R$ (HPLC conditions c): 3.23 min.

3-Bromo-2-fluoro-benzylamine, hydrochloride

A mixture of 3-bromo-2-fluoro-benzonitrile (1.0 g, 5.0 mmol) and Raney-Ni in EtOH (4% NH$_3$) (30 mL) was stirred under a hydrogen atmosphere (1 atm) at RT for 6.5 h. The reaction mixture was filtered through Celite, rinsed down with CH$_2$Cl$_2$, and the filtrate was concentrated under reduced pressure. The crude mixture was taken up in 1M aqueous HCl, the organic layer was separated, and the water phase was freeze-dried overnight to afford the title compound as a white solid. MS (LC/MS): 206.0 [M+H]+; t$_R$ (HPLC conditions c): 2.21 min.

C-(3-Fluoro-pyridin-4-yl)-methylamine

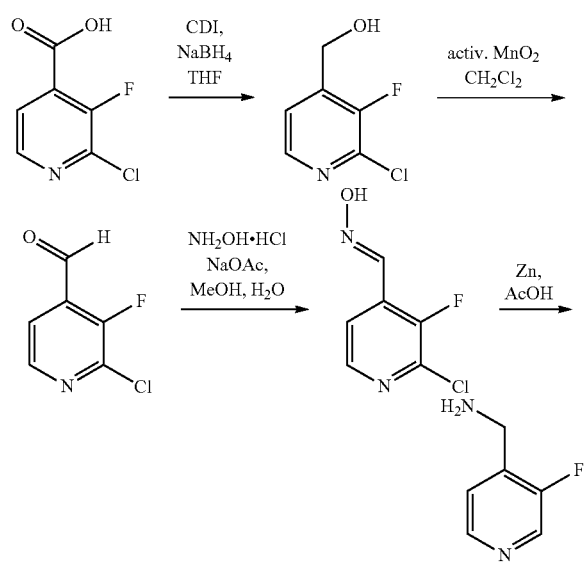

A. (2-Chloro-3-fluoro-pyridin-4-yl)-methanol

Carbonyldiimidazole (1.80 g, 11.1 mmol) was added to a solution of 2-chloro-3-fluoro-isonicotinic acid (1.3 g, 7.41 mmol) in THF (21.2 mL). The reaction mixture was stirred at RT overnight and was then added to a cold (0° C.) solution of NaBH$_4$ (1.40 g, 37 mmol) in water (52.9 mL). The mixture was stirred for 10 min at 0° C., and 1M HCl was then added carefully to quench the reaction (caution: H$_2$ evolving). Volatiles were removed via rotary evaporation and the residue was dissolved in saturated aqueous NaHCO$_3$. The mixture was extracted repeatedly with CH$_2$Cl$_2$, the combined organics were dried (phase separator) and concentrated in vaccuo. Purification by flash column chromatography on silica gel (eluent gradient: c-hexane/EtOAc 4:1 to 2:1) afforded the title compound as a white solid. TLC, R$_f$(c-hexane/EtOAc 1:1)= 0.37; MS (LC/MS): 162.0 [M+H]+; t$_R$ (HPLC conditions b): 1.60 min.

B. 2-Chloro-3-fluoro-pyridine-4-carbaldehyde

A mixture of (2-chloro-3-fluoro-pyridin-4-yl)-methanol (0.9 g, 5.76 mmol) and activated MnO$_2$ (5.76 g, 66.2 mmol) in CH$_2$Cl$_2$ was stirred at RT overnight. The solid was filtered off and washed with CH$_2$Cl$_2$, and the filtrate was concentrated under mildly reduced pressure to afford the title compound as a colorless liquid. MS (LC/MS): 191.0 [M+MeOH]+; t$_R$ (HPLC conditions b): 2.02 min.

C. 2-Chloro-3-fluoro-pyridine-4-carbaldehyde oxime

To a solution of 2-chloro-3-fluoro-pyridine-4-carbaldehyde (1.20 g, 5.64 mmol) in MeOH (48 mL) and water (8 mL) were added hydroxylamine hydrochloride (0.59 g, 8.46 mmol) and ammonium acetate (1.30 g, 16.9 mmol), and stirring was continued at RT overnight. The reaction mixture was concentrated in vacuo, and the residue was suspended in CH$_2$Cl$_2$/MeOH 9:1. The precipitate was filtered off, washed with CH$_2$Cl$_2$ and dried to afford the title compound as a white solid. MS (LC/MS): 175.0 [M+H]+; t$_R$ (HPLC conditions b): 2.78 min.

D. C-(3-Fluoro-pyridin-4-yl)-methylamine

Zinc dust (2.52 g, 38.6 mmol) was added at RT to a solution of 2-chloro-3-fluoro-pyridine-4-carbaldehyde oxime (1.34 g, 6.29 mmol) in acetic acid (30 mL). The reaction mixture was stirred at RT for 2 h, then concentrated in vacuo. The colored oily residue was partitioned between CH$_2$Cl$_2$ and 1N HCl. The layers were separated and the aqueous phase was extracted twice with CH$_2$Cl$_2$. The pH of the aqueous layer was then adjusted to pH=9 with 1N NaOH, and the resulting white suspension was extracted repeatedly with CH$_2$Cl$_2$. The combined organics were dried (phase separator) and concentrated in vacuo to afford the title compound as a yellow oil. MS (LC/MS): 127.0 [M+H]+; t$_R$ (HPLC conditions c): 0.50 min.

C-(3-Fluoro-2-trifluoromethyl-pyridin-4-yl)-methylamine

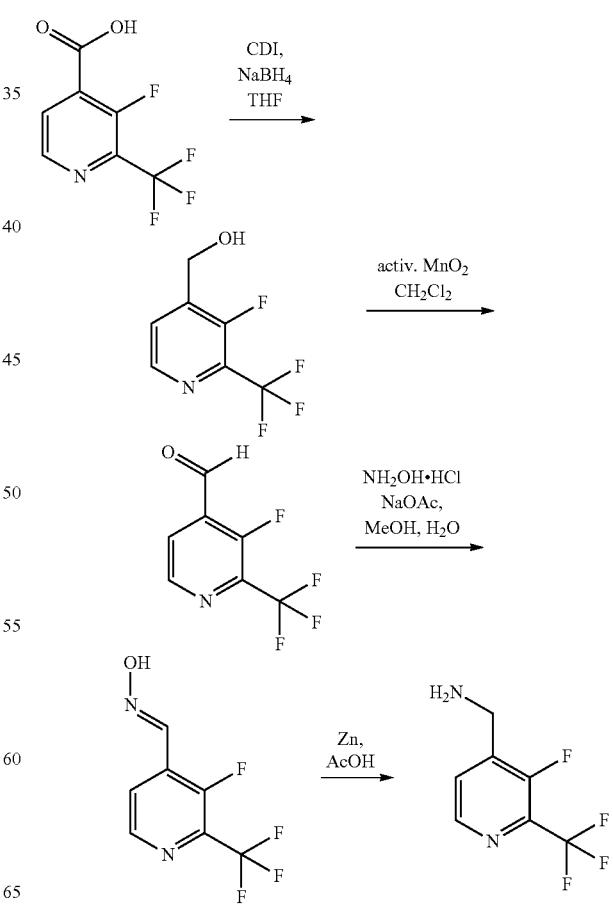

A.
(3-Fluoro-2-trifluoromethyl-pyridin-4-yl)-methanol

Carbonyldiimidazole (1.16 g, 7.17 mmol) was added to a solution of 3-fluoro-2-trifluoromethyl-isonicotinic acid (1.00 g, 4.78 mmol) in THF (13.7 mL). The reaction mixture was stirred at RT overnight and was then added to a cold (0° C.) solution of $NaBH_4$ (0.905 g, 23.9 mmol) in water (34.2 mL). The mixture was stirred for 10 min at 0° C., and 1M HCl was then added carefully (caution: $H_2$ evolving). Volatiles were removed under reduced pressure, and the residue was dissolved in saturated aqueous $NaHCO_3$. The mixture was extracted repeatedly with $CH_2Cl_2$, the combined organics were dried (phase separator) and concentrated in vacuo. Purification by flash column chromatography on silica gel (eluent gradient: c-hexane/EtOAc 1:1 to 0:1) afforded the title compound as a yellow oil. TLC, $R_f$(c-hexane/EtOAc 1:1)=0.27; MS (LC/MS): 196.0 [M+H]+; $t_R$ (HPLC conditions b): 2.62 min.

B.
3-Fluoro-2-trifluoromethyl-pyridine-4-carbaldehyde

A mixture of (3-fluoro-2-trifluoromethyl-pyridin-4-yl)-methanol (0.620 g, 3.18 mmol) and activated $MnO_2$ (3.20 g, 36.5 mmol) in $CH_2Cl_2$ was stirred at RT overnight. The solid was filtered off, washed with $CH_2Cl_2$, and the filtrate was concentrated under mildly reduced pressure to afford the title compound as a yellow liquid. MS (LC/MS): 212.0 [M+$NH_4$]+, 226.0 [M+MeOH]+. $t_R$ (HPLC conditions c): 3.26 min.

C.
3-Fluoro-2-trifluoromethyl-pyridine-4-carbaldehyde oxime

To a solution of 3-fluoro-2-trifluoromethyl-pyridine-4-carbaldehyde (0.495 g, 2.05 mmol) in MeOH (17.6 mL) and water (2.9 mL) were added hydroxylamine hydrochloride (0.214 g, 3.08 mmol) and ammonium acetate (0.474 g, 6.15 mmol), and the resulting mixture was stirred at RT overnight. Volatile were removed in vacuo, and the residue was suspended in $CH_2Cl_2$/MeOH 9:1. The precipitate was filtered off, washed with $CH_2Cl_2$ and dried to afford the title compound as a white solid. MS (LC/MS): 209.0 [M+H]+; $t_R$ (HPLC conditions c): 4.28 min.

D. C-(3-Fluoro-2-trifluoromethyl-pyridin-4-yl)-methylamine

Zinc dust (0.63 g, 9.62 mmol) was added at RT to a solution of 3-fluoro-2-trifluoromethyl-pyridine-4-carbaldehyde oxime (0.460 g, 1.57 mmol) in acetic acid (8 mL). The reaction mixture was stirred at RT for 3 h, then filtered through a 0.45 microns filter, and the filtrate was concentrated in vacuo. The colored oily residue was partitioned between $CH_2Cl_2$ and 1N HCl, the layers were separated and the aqueous phase was extracted twice with $CH_2Cl_2$. The pH of the aqueous layer was then adjusted to pH=9 by adding a saturated aqueous $NaHCO_3$ solution, and the resulting white suspension was extracted four times with $CH_2Cl_2$. The combined organics were dried (phase separator) and concentrated in vacuo to afford the title compound as a yellow oil. MS (LC/MS): 195.0 [M+H]+; $t_R$ (HPLC conditions c): 2.47 min.

3-Aminomethyl-5-chloro-4-fluoro-benzoic acid methyl ester

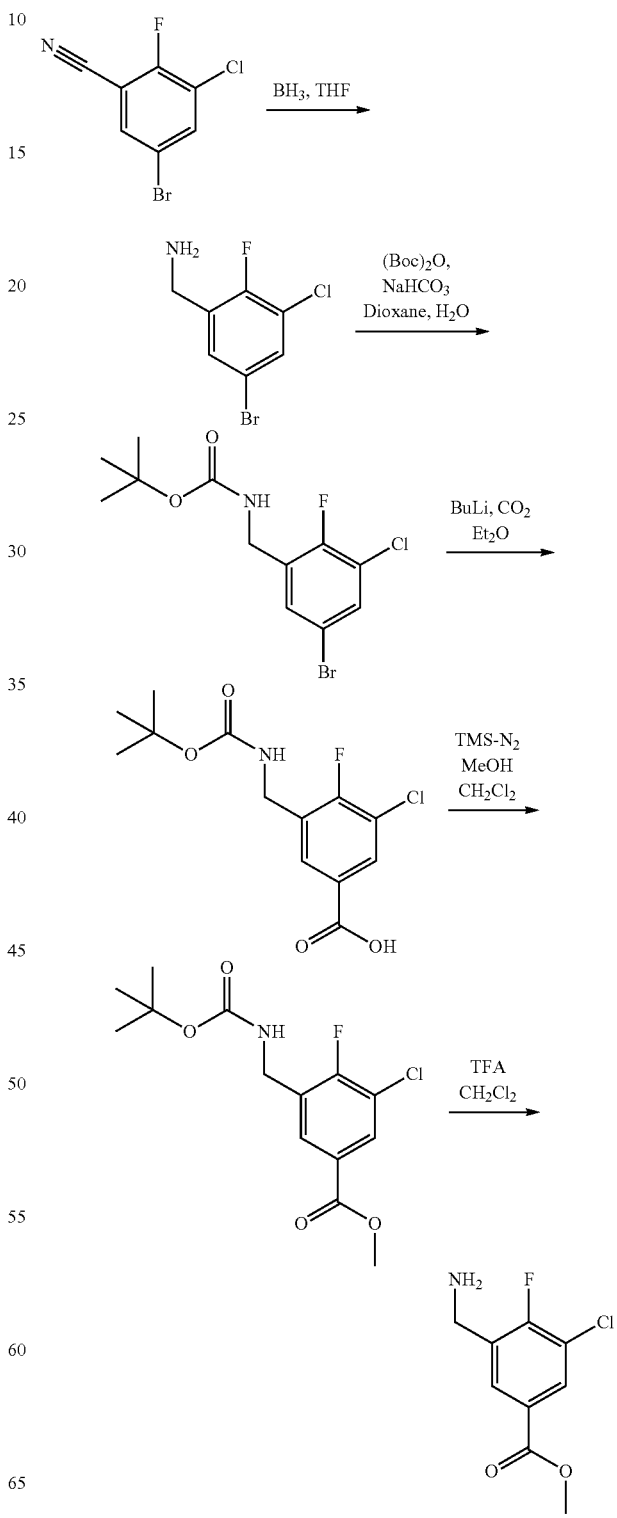

A. 5-Bromo-3-chloro-2-fluoro-benzylamine

To a solution of 5-bromo-3-chloro-2-fluorobenzonitrile (13.2 g, 56.3 mmol) in THF (200 mL) was added under an argon atmosphere a 1M solution of boran-tetrahydrofuran-complex (70.4 mL, 70.4 mmol) dropwise over 30 min. The reaction mixture was then heated at 65° C. for 1.5 h. After cooling to RT, a 2N HCl solution (70.4 mL, 141 mmol) was added dropwise over 30 min. The reaction mixture was then again heated at 65° C. for 1 h and subsequently cooled to RT. Volatiles were evaporated and the residue was taken up in 1M aqueous HCl solution, followed by extraction with EtOAc (3×150 mL). The combined organics were washed with 1M aqueous HCl solution. The combined acid phases were basified to pH=12 by addition of 4M aqueous NaOH solution and then extracted with EtOAc (3×150 mL). The organics were dried ($Na_2SO_4$), filtered and evaporated in vacuo to afford the title compound as a yellowish oil. MS (LC/MS): 238.0 [M+H]+; $t_R$ (HPLC conditions c): 3.25 min. The material thus obtained was used directly in the next step without further purification

B. (5-Bromo-3-chloro-2-fluoro-benzyl)-carbamic acid tert-butyl ester

To a solution of 5-bromo-3-chloro-2-fluoro-benzylamine (10.6 g, 44.3 mmol) in dioxane/$H_2O$ 3:1 (280 mL) was added $Boc_2O$ (10.3 mL, 44.3 mmol) and $NaHCO_3$ (11.2 g, 133 mmol). The reaction mixture was stirred at RT for 60 h. Volatiles were then removed under reduced pressure, the residue was taken up in water, and the aqueous layer was extracted twice with EtOAc (200 mL). The organics were dried ($Na_2SO_4$), filtered and evaporated in vacuo to afford the title compound as a white solid. MS (LC/MS): 284.0 [M+H]+; $t_R$ (HPLC conditions c): 5.98 min. The material thus obtained was used directly in the next step without further purification.

C. 3-(tert-Butoxycarbonylamino-methyl)-5-chloro-4-fluoro-benzoic acid

To a solution of (5-bromo-3-chloro-2-fluoro-benzyl)-carbamic acid tert-butyl ester (8 g, 23.6 mmol) in $Et_2O$ (300 mL), cooled to −78° C., was added under an argon atmosphere n-BuLi (1.6M in hexane; 37.5 mL, 60.1 mmol) dropwise over 30 min. The reaction mixture was stirred at −78° C. for 15 min, then $CO_2$ gas was bubbled through the mixture over 1 min. After stirring for 15 min, a saturated solution of $NH_4Cl$ (50 mL) added dropwise over 15 min, and the reaction mixture was allowed to warm up to RT. The aqueous phase was basified to pH=12 by addition of a 4M aqueous NaOH solution and then washed with EtOAc (100 mL). The aqueous layer was acidified to pH=1 by addition of a 4M aqueous HCl solution and extracted with EtOAc (3×200 mL). The combined organics were dried ($Na_2SO_4$) and concentrated under vacuo to give the title compound as an off-white solid. MS (LC/MS): 302.0 [M−H]−; $t_R$ (HPLC conditions c): 4.79 min.

D. 3-(tert-Butoxycarbonylamino-methyl)-5-chloro-4-fluoro-benzoic acid methyl ester To a solution of 3-(tert-butoxycarbonylamino-methyl)-5-chloro-4-fluoro-benzoic acid (4.00 g, 13.2 mmol) in $CH_2Cl_2$ (100 mL) were added MeOH (6.94 mL, 171 mmol) and subsequently trimethylsilyldiazomethane (8.56 mL, 17.1 mmol) in a dropwise manner over 15 min. Stirring was continued at RT for 4.5 h. Volatiles were then evaporated under reduced pressure to afford the title compound as a colorless oil, which was used directly in the next step without further purification. TLC $R_f$ (c-hexane/EtOAc 6:1)=0.40; $t_R$ (HPLC conditions c): 5.56 min.

E. 3-Aminomethyl-5-chloro-4-fluoro-benzoic acid methyl ester

To a solution of 3-(tert-butoxycarbonylamino-methyl)-5-chloro-4-fluoro-benzoic acid methyl ester (4.25 g, 13.4 mmol) in $CH_2Cl_2$ (70 mL) was added TFA (10.3 mL, 134 mmol), and stirring was continued at RT overnight. Methanol was then added to the reaction mixture, and volatiles were removed in vacuo. The residue was taken up in methanol and concentrated again under reduced pressure to afford the title compound as a beige solid. MS (LC/MS): 218.0 [M+H]+; $t_R$ (HPLC conditions c): 3.10 min. The material thus obtained was used in the next reaction step without further purification.

3-Chloro-2-fluoro-5-(2H-tetrazol-5-yl)-benzylamine

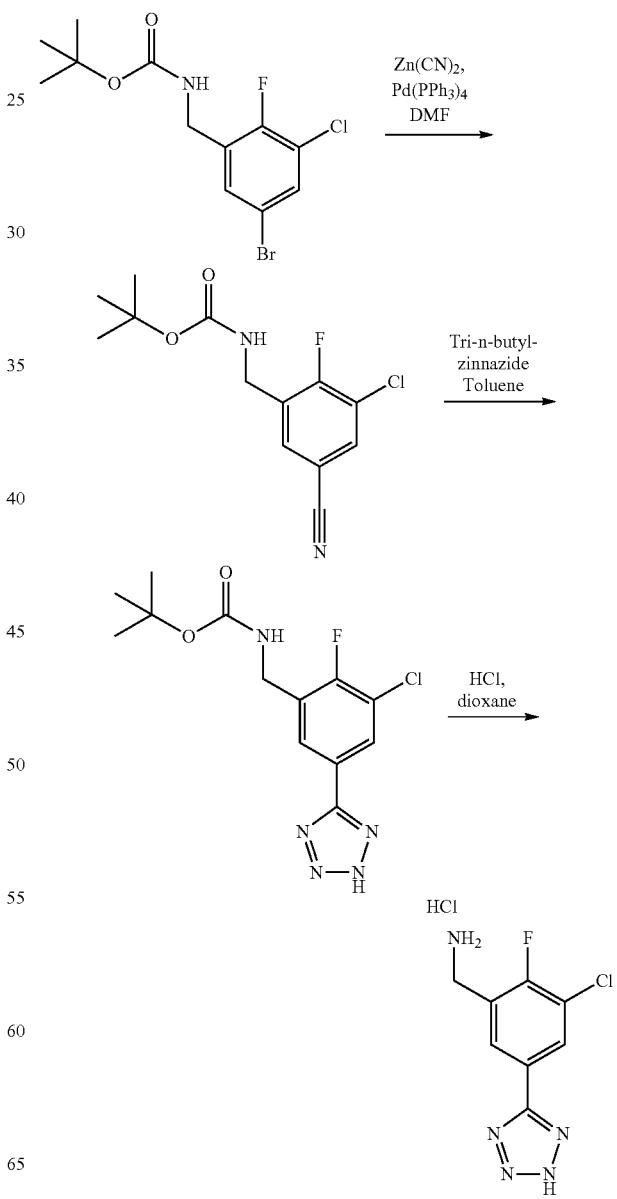

A. (3-Chloro-5-cyano-2-fluoro-benzyl)-carbamic acid tert-butyl ester

To a solution of (5-bromo-3-chloro-2-fluoro-benzyl)-carbamic acid tert-butyl ester (3 g, 8.86 mmol) in DMF (45 mL) was added zinc cyanide (1.04 g, 8.86 mmol) and Pd(Ph₃P)₄ (1.02 g, 0.886 mmol). The reaction mixture was stirred at 120° C. for 15 min in a microwave apparatus (Personal Chemistry, Biotage). After cooling to RT, the mixture was filtered through Celite and rinsed down with EtOAc. The filtrate was washed with saturated aqueous NH₄Cl solution (4×75 mL), dried (Na₂SO₄) and evaporated in vacuo. Purification by flash column chromatography on silica gel (eluent gradient: c-hexane/EtOAc 9:1 to 3:1) afforded the title compound as white solid. TLC R_f (c-hexane/EtOAc 3:1)=0.35; t_R (HPLC conditions c): 5.28 min.

B. [3-Chloro-2-fluoro-5-(2H-tetrazol-5-yl)-benzyl]-carbamic acid tert-butyl ester To a solution of (3-chloro-5-cyano-2-fluoro-benzyl)-carbamic acid tert-butyl ester (1.30 g, 4.57 mmol) in toluene (35 mL) was added tri-n-butyl-tinazide (6.26 mL, 22.8 mmol). The reaction mixture was stirred at 135° C. for 90 min in a microwave (Personal Chemistry, Biotage). After cooling to RT, the mixture was diluted with EtOAc and washed with saturated aqueous NH₄Cl solution (3×100 mL). After washing the organic phase with 70 mL of a 1M aqueous NaOH solution and separation of the phases, three layers were obtained: the upper organic phase was discarded, the middle oily layer was isolated and diluted with EtOAc. The water phase was acidified with 4M aqueous HCl solution, extracted twice with EtOAc (50 mL). All organics were combined, dried (phase separator) and evaporated in vacuo to afford the title compound. Yellowish solid. MS (LC/MS): 328.0 [M+H]+, 349.9 [M+Na]+, 271.9 [MH−tBu]+; t_R (HPLC conditions c): 4.74 min. The material thus obtained was used in the next reaction step without further purification.

C. 3-Chloro-2-fluoro-5-(2H-tetrazol-5-yl)-benzylamine, hydrochloride

To a solution of [3-chloro-2-fluoro-5-(2H-tetrazol-5-yl)-benzyl]-carbamic acid tert-butyl ester (1.06 g, 3.23 mmol) in dioxane (20 mL) was added a 4M HCl solution in dioxane (8.09 mL, 32.3 mmol). The reaction mixture was stirred at RT for 72 h and then freeze-dried overnight to afford the title compound as a white solid. MS (LC/MS): 228.0 [M+H]+; t_R (HPLC conditions c): 2.68 min.

5-(1-tert-Butyl-1H-tetrazol-5-yl)-3-chloro-2-fluoro-benzylamine

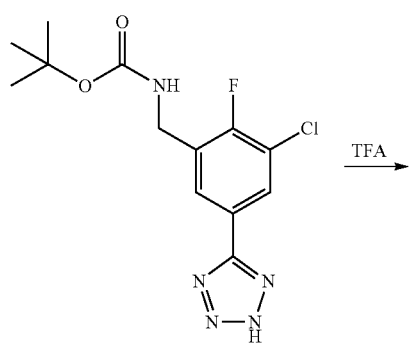

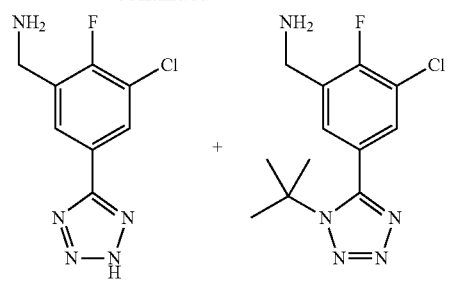

To a solution of [3-chloro-2-fluoro-5-(2H-tetrazol-5-yl)-benzyl]-carbamic acid tert-butyl ester (0.15 g, 0.46 mmol) in CH₂Cl₂ (4 mL) was added TFA (1.5 mL). The reaction mixture was stirred at RT for 2 h and the solvent was removed in vacuo to give the title compound as a 2:1 mixture of 5-(1-tert-butyl-1H-tetrazol-5-yl)-3-chloro-2-fluoro-benzylamine and 3-chloro-2-fluoro-5-(2H-tetrazol-5-yl)-benzylamine which was used in the next steps without separation. MS (LC/MS): 228.0 and 284.0 [M+H]+. t_R (HPLC conditions c): 2.16 and 2.99 min.

3-Aminomethyl-5-chloro-4-fluoro-benzonitrile

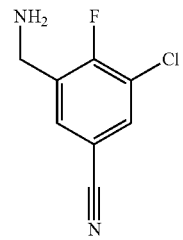 [SMILES: N#Cc1cc(Cl)c(F)c(CN)c1]

To a solution of (3-chloro-5-cyano-2-fluoro-benzyl)-carbamic acid tert-butyl ester (645 mg, 2.27 mmol) in CH₂Cl₂ (15 mL) was added TFA (1.75 mL, 22.7 mmol), and stirring was continued at RT overnight. Volatiles were removed under reduce pressure, water was added and the mixture was washed with EtOAc. The aqueous layer was basified to pH=12 by addition of 4M NaOH solution and extracted twice with EtOAc. The combined organics were dried (phase separator) and evaporated to afford the title compound as a beige solid. MS (LC/MS): 185.0 [M+H]+; t_R (HPLC conditions c): 2.62 min.

Scheme C1: preparation of (3-Aminomethyl-5-chloro-4-fluoro-phenyl)-(2-methoxy-ethyl)-methyl-amine

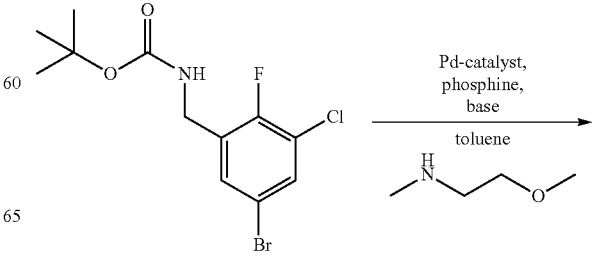

-continued

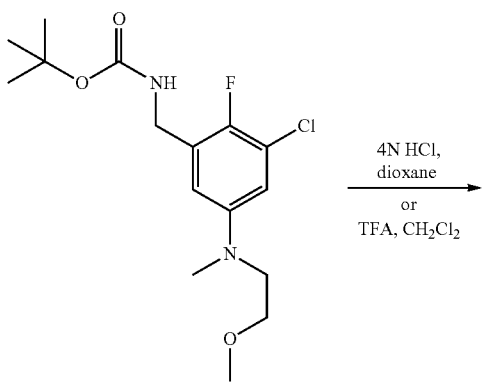

A. {3-Chloro-2-fluoro-5-[(2-methoxy-ethyl)-methyl-amino]-benzyl}-carbamic acid tert-butyl ester A suspension of (5-bromo-3-chloro-2-fluoro-benzyl)-carbamic acid tert-butyl ester (250 mg, 0.7 mmol), N-methoxy-ethyl-methylamine (99 mg, 1.1 mmol), sodium tert-butoxide (142 mg, 1.5 mmol) and di-µ-bromobis(tri-tert-butylphosphino)dipalladium (I) [CAS 185812-86-6] (29 mg, 0.04 mmol) in toluene (5 mL) was sealed in a microwave vial and heated for 30 min at 140° C. (Emrys Optimizer; personal chemistry). The reaction mixture was quenched by addition of saturated aqueous NaHCO₃, extracted with EtOAc, dried (Na₂SO₄) and evaporated in vacuo. The crude product was purified by RP-preparative HPLC (Waters Sunfire, C18-ODB, 5 µm, 30×100 mm, 5-100% CH₃CN/H₂O/20 min, 100% CH₃CN/2 min, CH₃CN and H₂O containing 0.1% TFA, flow: 40 mL/min) to give the title compound after lyophilization. MS (LC/MS): 347.0 [M]+. $t_R$ (HPLC conditions c): 5.23 min.

B. (3-Aminomethyl-5-chloro-4-fluoro-phenyl)-(2-methoxy-ethyl)-methyl-amine

To a mixture of {3-chloro-2-fluoro-5-[(2-methoxy-ethyl)-methyl-amino]-benzyl}-carbamic acid tert-butyl ester (60 mg, 0.17 mmol) in MeOH (2 mL) was added a solution of 4N HCl in dioxane (2 mL). The reaction mixture was stirred for 1 h at ambient temperature and the solvent was removed in vacuo to give the title compound. MS (LC/MS): 247.0 [M]+. $t_R$ (HPLC conditions c): 3.15 min.

N-(3-Aminomethyl-5-chloro-4-fluoro-phenyl)-N',N',N'-trimethyl-ethane-1,2-diamine

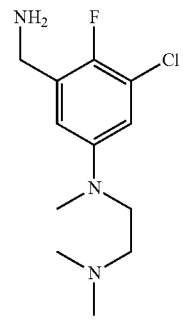 [SMILES: CN(C)CCN(C)c1cc(Cl)c(F)c(CN)c1]

was prepared according to Scheme C1 (step B) from {3-chloro-5-[(2-dimethylamino-ethyl)-methyl-amino]-2-fluoro-benzyl}-carbamic acid tert-butyl ester and 4N HCl in dioxane. MS (LC-MS): 260.0 [M]+

{3-Chloro-5-[(2-dimethylamino-ethyl)-methyl-amino]-2-fluoro-benzyl}-carbamic acid tert-butyl ester was prepared according to Scheme C1 (step A) from (5-bromo-3-chloro-2-fluoro-benzyl)-carbamic acid tert-butyl ester (300 mg, 0.89 mmol), N,N,N'-trimethyl-ethylenediamine (136 mg, 1.3 mmol), sodium tert-butoxide (170 mg, 1.8 mmol) and di-µ-bromobis(tri-tert-butylphosphino)dipalladium (I) [CAS 185812-86-6] (34 mg, 0.04 mmol). MS (LC-MS): 360.3 [M]+; $t_R$ (HPLC conditions c): 4.15 min.

(3-Aminomethyl-5-chloro-4-fluoro-phenyl)-diethyl-amine

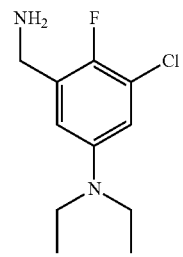

was prepared according to Scheme C1 (step B) from (3-chloro-5-diethylamino-2-fluoro-benzyl)-carbamic acid tert-butyl ester and TFA in CH₂Cl₂. MS (LC-MS): 231.0 [M]+; $t_R$ (HPLC conditions c): 2.29 min.

(3-Chloro-5-diethylamino-2-fluoro-benzyl)-carbamic acid tert-butyl ester was prepared according to Scheme C1 (step A) from (5-bromo-3-chloro-2-fluoro-benzyl)-carbamic acid tert-butyl ester (300 mg, 0.89 mmol), diethylamine (0.14 mL, 1.3 mmol), sodium tert-butoxide (170 mg, 1.8 mmol) and di-µ-bromobis(tri-tert-butylphosphino)dipalladium (I) [CAS 185812-86-6] (34 mg, 0.04 mmol). MS (LC-MS): 331.2 [M]+; $t_R$ (HPLC conditions c): 4.08 min.

3-Chloro-2-fluoro-5-(4-methyl-piperazin-1-yl)-benzylamine

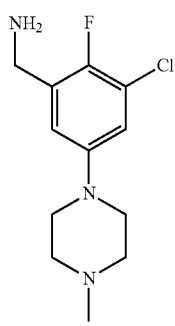 [SMILES: CN1CCN(c2cc(Cl)c(F)c(CN)c2)CC1]

was prepared according to Scheme C1 (step B) from [3-chloro-2-fluoro-5-(4-methyl-piperazin-1-yl)-benzyl]-carbamic acid tert-butyl ester and 4N HCl in dioxane. MS (LC-MS): 258.0 [M]+; $t_R$ (HPLC conditions f): 0.74 min.

[3-Chloro-2-fluoro-5-(4-methyl-piperazin-1-yl)-benzyl]-carbamic acid tert-butyl ester was prepared according to Scheme C1 (step A) from (5-bromo-3-chloro-2-fluoro-benzyl)-carbamic acid tert-butyl ester (200 mg, 0.59 mmol), 1-methylpiperazine (71 mg, 0.71 mmol), caesium carbonate (269 mg, 0.83 mmol), palladium (II) acetate (6.6 mg, 0.03 mmol) and 4,5-bis(diphenylphosphino)-9,9-dimethylxanthene (24 mg, 0.04 mmol). MS (LC-MS): 358.0 [M]+; $t_R$ (HPLC conditions c): 3.98 min.

3-Chloro-2-fluoro-5-(4-methoxy-piperidin-1-yl)-benzylamine

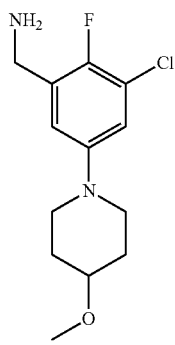 [SMILES: COC1CCN(c2cc(Cl)c(F)c(CN)c2)CC1]

was prepared according to Scheme C1 (step B) from [3-chloro-2-fluoro-5-(4-methyl-piperazin-1-yl)-benzyl]-carbamic acid tert-butyl ester and 4N HCl in dioxane. MS (LC-MS): 273.0 [M]+; $t_R$ (HPLC conditions c): 2.97 min.

[3-Chloro-2-fluoro-5-(4-methoxy-piperidin-1-yl)-benzyl]-carbamic acid tert-butyl ester was prepared according to Scheme C1 (step A) from (5-bromo-3-chloro-2-fluoro-benzyl)-carbamic acid tert-butyl ester (250 mg, 0.74 mmol), 1-methoxypiperidine (102 mg, 0.89 mmol), caesium carbonate (337 mg, 1.0 mmol), palladium (II) acetate (8.3 mg, 0.04 mmol) and 4,5-bis(diphenylphosphino)-9,9-dimethylxanthene (30 mg, 0.05 mmol). MS (LC-MS): 373.0 [M]+; $t_R$ (HPLC conditions c): 4.68 min.

3-Chloro-2-fluoro-5-morpholin-4-yl-benzylamine

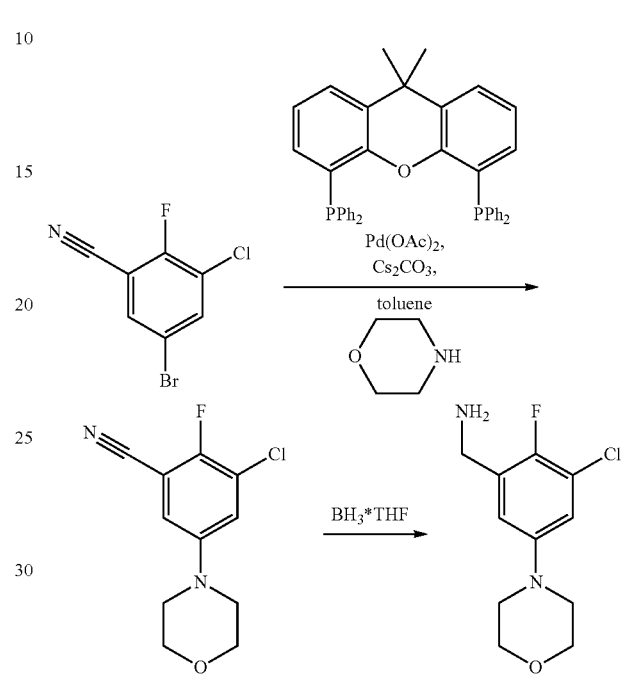

A. 3-Chloro-2-fluoro-5-morpholin-4-yl-benzonitrile

A suspension of 5-Bromo-3-chloro-2-fluoro-benzonitrile (200 mg, 0.85 mmol), morpholine (74 mg, 0.85 mmol), caesium carbonate (389 mg, 1.2 mmol), palladium(II) acetate (10 mg, 0.04 mmol) and 4,5-bis(diphenylphosphino)-9,9-dimethylxanthene (35 mg, 0.06 mmol) in toluene (5 mL) was sealed in a microwave vial and heated for 30 min at 140° C. (Emrys Optimizer; personal chemistry). The reaction mixture was quenched by addition of saturated aqueous NaHCO$_3$, extracted with EtOAc, dried (Na$_2$SO$_4$) and the solvent was removed in vacuo to give the title compound which was used without further purification in the next step. TLC R$_f$(hexane/EtOAc 1:1)=0.60; $t_R$ (HPLC conditions c): 5.28 min.

B. 3-Chloro-2-fluoro-5-morpholin-4-yl-benzylamine

To a solution of 3-Chloro-2-fluoro-5-morpholin-4-yl-benzonitrile (215 mg, 0.85 mmol) in THF (2 mL) was added dropwise a solution of BH$_3$-THF. The reaction mixture was heated under reflux for several hours, cooled to ambient temperature and quenched carefully by addition of methanol. The solvent was removed in vacuo and the crude product was purified by RP-preparative HPLC (Waters Sunfire, C18-ODB, 5 μm, 30×100 mm, 5-100% CH$_3$CN/H$_2$O/20 min, 100% CH$_3$CN/2 min, CH$_3$CN and H$_2$O containing 0.1% TFA, flow: 40 mL/min) to give the title compound. MS (LC/MS): 244.9 [M]+; $t_R$ (HPLC conditions c): 3.02 min.

Scheme C2: preparation of (3-Aminomethyl-5-chloro-4-fluoro-benzyl)-diethyl-amine

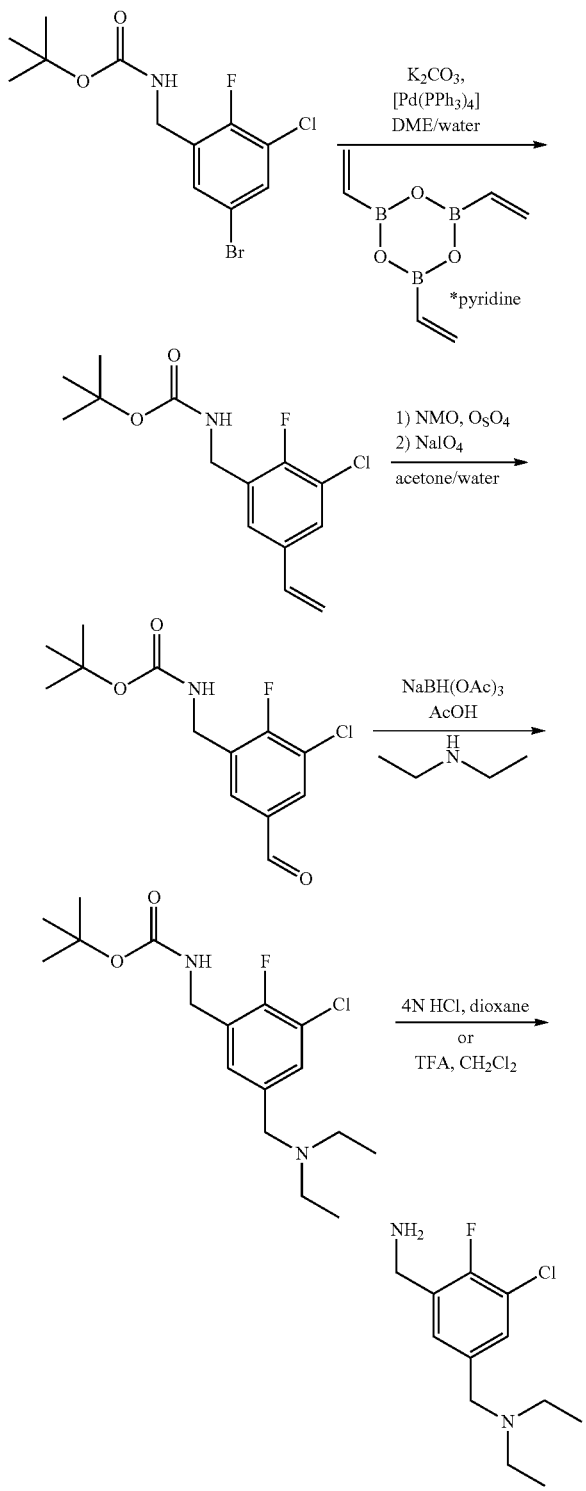

A. (3-Chloro-2-fluoro-5-vinyl-benzyl)-carbamic acid tert-butyl ester

To a solution of (5-bromo-3-chloro-2-fluoro-benzyl)-carbamic acid tert-butyl ester (6 g, 17.7 mmol) in DME (100 mL) was added Pd(Ph$_3$)$_4$ (1.0 g, 0.9 mmol) under argon atmosphere and the mixture was stirred for 30 min at ambient temperature. After addition of vinyl boronic anhydride pyridine complex (4.3 g, 17.7 mmol), water (25 mL) and K$_2$CO$_3$ (2.45 g, 17.7 mmol) the reaction was heated under reflux for 7 h. The reaction mixture was concentrated in vacuo to half of the volume, quenched by addition of saturated aqueous NaHCO$_3$ and extracted with EtOAc. After drying (Na$_2$SO$_4$) the solvent was removed in vacuo and the residue was purified by flash column chromatography on silica gel (eluent: hexane/EtOAc 9:1 to 4:1) to afford the title compound as a colorless oil. 1H-NMR (500 MHz, DMSO): δ (ppm) 7.62 (d, 1H), 7.45 (m, 1H, —NH), 7.35 (d, 1H), 6.68 (dd, 1H), 5.82 (d, 1H), 5.32 (d, 1H), 4.18 (d, 2H), 1.39 (s, 9H).

B. (3-Chloro-2-fluoro-5-formyl-benzyl)-carbamic acid tert-butyl ester

To a solution of (3-chloro-2-fluoro-5-vinyl-benzyl)-carbamic acid tert-butyl ester (2.7 g, 9.5 mmol) in acetone (20 mL) was added N-methylmorpholine-N-oxide monohydrate (1.5 g, 11 mmol) and a solution of 4% aq. osmiumtetraoxide (3.7 mL, 0.5 mmol). The reaction was stirred for 1 h, saturated aqueous Na$_2$S$_2$O$_3$-solution was added and stirring was continued for one hour. After extraction with EtOAc and removal of the solvent in vacuo, the residue was dissolved in acetone/water (3:1, 40 mL) and NaIO$_4$ (4.0 g, 19 mmol) was added. After stirring for 2 h at ambient temperature, the reaction mixture was filtered, washed with EtOAc, extracted with EtOAc, dried (Na$_2$SO$_4$) and the solvent was removed in vacuo to give the title compound which was used without further purification. t$_R$ (HPLC conditions c): 5.22 min.

C. (3-Chloro-5-diethylaminomethyl-2-fluoro-benzyl)-carbamic acid tert-butyl ester A solution of (3-chloro-2-fluoro-5-formyl-benzyl)-carbamic acid tert-butyl ester (200 mg, 0.7 mmol), diethylamine (51 mg, 0.7 mmol) and acetic acid (0.06 mL) in THF (mL) was stirred for 30 min at ambient temperature. After addition of sodium triacetoxyborohydride (368 mg, 1.7 mmol) the reaction was stirred overnight, quenched by addition of saturated aqueous NaHCO$_3$ and extracted with EtOAc. The solvent was removed in vacuo and the residue was purified by RP-preparative HPLC (Waters Sunfire, C18-ODB, 5 μm, 30×100 mm, 5-100% CH$_3$CN/H$_2$O/20 min, 100% CH$_3$CN/2 min, CH$_3$CN and H$_2$O containing 0.1% TFA, flow: 40 mL/min) to give the title compound. MS (LC-MS): 345.0 [M]+; t$_R$ (HPLC conditions c): 4.09 min.

D. (3-Aminomethyl-5-chloro-4-fluoro-benzyl)-diethyl-amine

To a mixture of (3-chloro-5-diethylaminomethyl-2-fluoro-benzyl)-carbamic acid tert-butyl ester (115 mg, 0.33 mmol) in MeOH (1 mL) was added a solution of 4N HCl in dioxane (3 mL). The reaction mixture was stirred for 2 h at ambient temperature and the solvent was removed in vacuo to give the title compound. MS (LC/MS): 245.0 [M]+; t$_R$ (HPLC conditions c): 2.13 min.

273

3-Chloro-2-fluoro-5-morpholin-4-ylmethyl-benzylamine

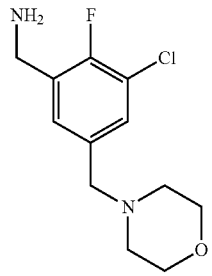 [SMILES: NCc1cc(CN2CCOCC2)cc(Cl)c1F]

was prepared according to Scheme C2 (step D) from (3-chloro-2-fluoro-5-morpholin-4-ylmethyl-benzyl)-carbamic acid tert-butyl ester (231 mg, 0.64 mmol) and 4N HCl in dioxane. MS (LC-MS): 259.0 [M]+.

(3-Chloro-2-fluoro-5-morpholin-4-ylmethyl-benzyl)-carbamic acid tert-butyl ester was prepared according to Scheme C2 (step C) from (3-chloro-2-fluoro-5-formyl-benzyl)-carbamic acid tert-butyl ester (220 mg, 0.65 mmol), morpholine (57 mg, 0.65 mmol), acetic acid (0.056 mL, 0.9 mmol) and sodium triacetoxyborohydride (344 mg, 1.6 mmol) in THF (8 mL). TLC, $R_f$(EtOAc)=0.44; MS (LC-MS): 359.0 [M]+.

3-Chloro-2-fluoro-5-(4-methyl-piperazin-1-ylmethyl)-benzylamine

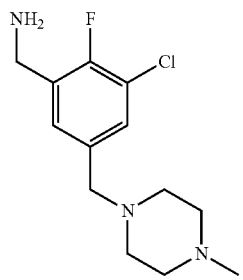 [SMILES: CN1CCN(Cc2cc(Cl)c(F)c(CN)c2)CC1]

was prepared according to Scheme C2 (step D) from [3-chloro-2-fluoro-5-(4-methyl-piperazin-1-ylmethyl)-benzyl]-carbamic acid tert-butyl ester (225 mg, 0.61 mmol) and 4N HCl in dioxane. MS (LC-MS): 272.0 [M]+; $t_R$ (HPLC conditions c): 2.07 min.

[3-Chloro-2-fluoro-5-(4-methyl-piperazin-1-ylmethyl)-benzyl]-carbamic acid tert-butyl ester was prepared according to Scheme C2 (step C) from (3-chloro-2-fluoro-5-formyl-benzyl)-carbamic acid tert-butyl ester (200 mg, 0.59 mmol), 1-methylpiperazine (59 mg, 0.59 mmol), acetic acid (0.053 mL, 0.89 mmol) and sodium triacetoxyborohydride (313 mg, 1.5 mmol) in THF (8 mL). MS (LC-MS): 372.0 [M]+; $t_R$ (HPLC conditions c): 3.64 min.

274

3-Chloro-2-fluoro-5-(4-methoxy-piperidin-1-ylmethyl)-benzylamine

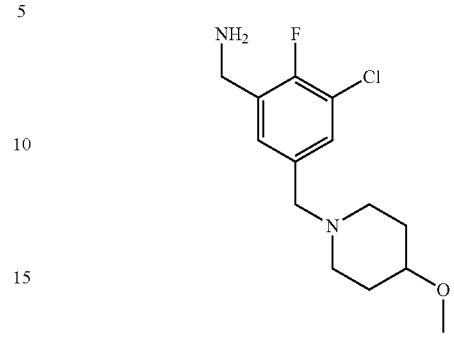

was prepared according to Scheme C2 (step D) from [3-chloro-2-fluoro-5-(4-methoxy-piperidin-1-ylmethyl)-benzyl]-carbamic acid tert-butyl ester (225 mg, 0.61 mmol) and 4N HCl in dioxane. MS (LC-MS): 287.0 [M]+; $t_R$ (HPLC conditions c): 2.34 min.

[3-Chloro-2-fluoro-5-(4-methoxy-piperidin-1-ylmethyl)-benzyl]-carbamic acid tert-butyl ester was prepared according to Scheme C2 (step C) from (3-chloro-2-fluoro-5-formyl-benzyl)-carbamic acid tert-butyl ester (200 mg, 0.59 mmol), 1-methoxypiperidine (68 mg, 0.59 mmol), acetic acid (0.051 mL, 0.89 mmol) and sodium triacetoxyborohydride (313 mg, 1.5 mmol) in THF (8 mL). MS (LC-MS): 387.0 [M]+

(3-Aminomethyl-5-chloro-4-fluoro-benzyl)-(2-methoxy-ethyl)-methyl-amine

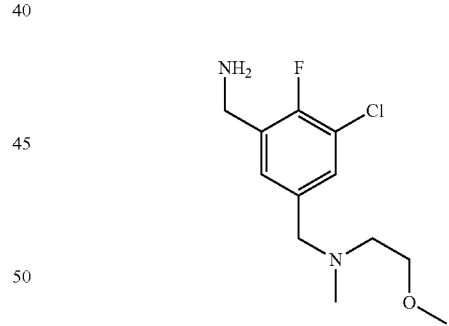

was prepared according to Scheme C2 (step D) from (3-chloro-2-fluoro-5-{[(2-methoxy-ethyl)-methyl-amino]-methyl}-benzyl)-carbamic acid tert-butyl ester (222 mg, 0.47 mmol) and 4N HCl in dioxane. MS (LC-MS): 261.0 [M]+.

(3-Chloro-2-fluoro-5-{[(2-methoxy-ethyl)-methyl-amino]-methyl}-benzyl)-carbamic acid tert-butyl ester was prepared according to Scheme C2 (step C) from (3-chloro-2-fluoro-5-formyl-benzyl)-carbamic acid tert-butyl ester (200 mg, 0.59 mmol), N-methoxyethyl-methylamine (74 mg, 0.83 mmol), acetic acid (0.06 mL, 1.0 mmol) and sodium triacetoxyborohydride (368 mg, 1.7 mmol) in THF (8 mL). MS (LC-MS): 362.3 [M+H]+; $t_R$ (HPLC conditions c): 4.04 min.

N-(3-Aminomethyl-5-chloro-4-fluoro-benzyl)-N,N',N'-trimethyl-ethane-1,2-diamine

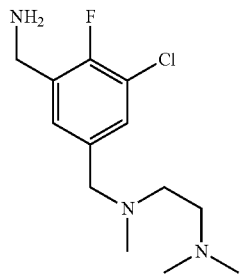 [SMILES: CN(C)CCN(C)Cc1cc(Cl)c(F)c(CN)c1]

was prepared according to Scheme C2 (step D) from (3-chloro-5-{[(2-dimethylamino-ethyl)-methyl-amino]-methyl}-2-fluoro-benzyl)-carbamic acid tert-butyl ester (228 mg, 0.51 mmol) and 4N HCl in dioxane. MS (LC-MS): 274.0 [M]+.

(3-Chloro-5-{[(2-dimethylamino-ethyl)-methyl-amino]-methyl}-2-fluoro-benzyl)-carbamic acid tert-butyl ester was prepared according to Scheme C2 (step C) from (3-chloro-2-fluoro-5-formyl-benzyl)-carbamic acid tert-butyl ester (200 mg, 0.59 mmol), N,N,N'-trimethyl-ethylendiamine (71 mg, 0.70 mmol), acetic acid (0.06 mL, 1.0 mmol) and sodium triacetoxyborohydride (368 mg, 1.7 mmol) in THF (8 mL). MS (LC-MS): 374.0 [M]+; $t_R$ (HPLC conditions c): 3.53 min.

N-(3-Aminomethyl-5-chloro-4-fluoro-benzyl)-N',N'-dimethyl-ethane-1,2-diamine

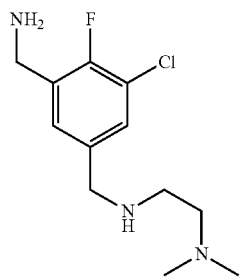

was prepared according to Scheme C2 (step D) from (3-chloro-5-{[(2-dimethylamino-ethyl)-methyl-amino]-methyl}-2-fluoro-benzyl)-carbamic acid tert-butyl ester (165 mg, 0.46 mmol) and 4N HCl in dioxane (3 mL). MS (LC-MS): 260.0 [M]+.

{3-Chloro-5-[(2-dimethylamino-ethylamino)-methyl]-2-fluoro-benzyl}-carbamic acid tert-butyl ester was prepared according to Scheme C2 (step C) from (3-chloro-2-fluoro-5-formyl-benzyl)-carbamic acid tert-butyl ester (200 mg, 0.70 mmol), N,N-dimethyl-ethylendiamine (67 mg, 0.77 mmol), acetic acid (0.06 mL, 1.0 mmol) and sodium triacetoxyborohydride (368 mg, 1.7 mmol) in THF (8 mL). MS (LC-MS): 360.3 [M+H]+; $t_R$ (HPLC conditions c): 3.49 min.

Scheme C3: preparation of 3-Aminomethyl-5-chloro-4-fluoro-N,N-dimethyl-benzamide

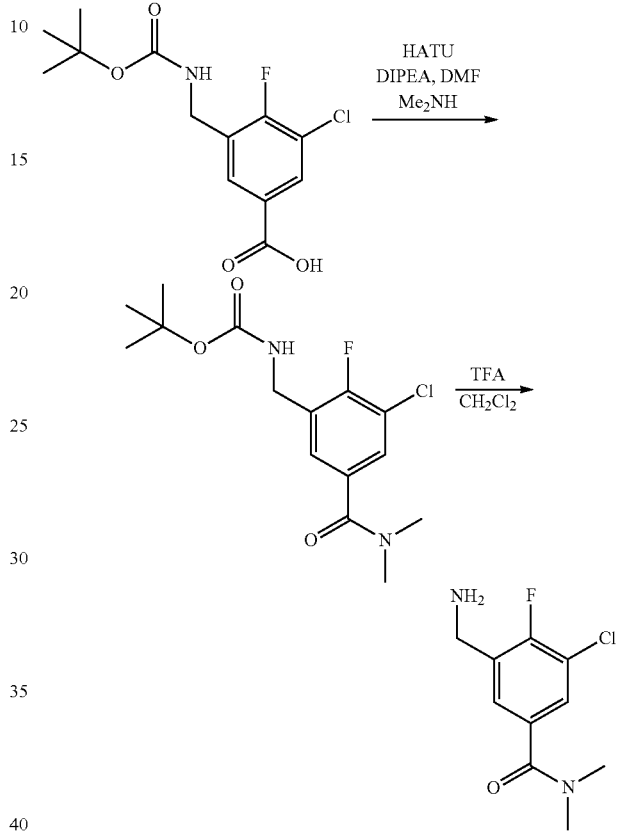

A. (3-Chloro-5-dimethylcarbamoyl-2-fluoro-benzyl)-carbamic acid tert-butyl ester A mixture of 3-(tert-butoxycarbonylamino-methyl)-5-chloro-4-fluoro-benzoic acid (100 mg, 0.3 mmol), HATU (188 mg, 0.5 mmol), dimethylamine (0.2 mL, 2M in THF) and DIPEA (0.23 mL, 1.3 mmol) in DMF (2 mL) was stirred for 16 h at ambient temperature. The crude product was purified without aqueous workup by RP-preparative HPLC (Waters Sunfire, C18-ODB, 5 µm, 30×100 mm, 5-100% $CH_3CN/H_2O$/20 min, 100% $CH_3CN$/2 min, $CH_3CN$ and $H_2O$ containing 0.1% TFA, flow: 40 ml/min) to give the title compound. MS (LC-MS): 275.0 [M−55]+; $t_R$ (HPLC conditions c): 4.68 min.

B. 3-Aminomethyl-5-chloro-4-fluoro-N,N-dimethyl-benzamide

To a mixture of (3-chloro-5-dimethylcarbamoyl-2-fluoro-benzyl)-carbamic acid tert-butyl ester (115 mg, 0.33 mmol) in $CH_2Cl_2$ (4 mL) was added TFA (1 mL). The reaction mixture was stirred for 1 h at ambient temperature and the solvent was removed in vacuo to give the title compound. MS (LC/MS): 231.0 [M]+. $t_R$ (HPLC conditions c): 2.59 min.

3-Aminomethyl-5-chloro-4-fluoro-N-methyl-benzamide

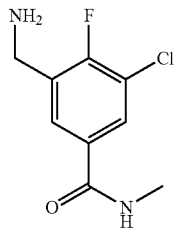

was prepared according to Scheme C3 (step B) from (3-chloro-2-fluoro-5-methylcarbamoyl-benzyl)-carbamic acid tert-butyl ester (99 mg, 0.3 mmol) and TFA (0.5 mL) in CH$_2$Cl$_2$. MS (LC-MS): 217.0 [M]+; $t_R$ (HPLC conditions c): 2.39 min.

(3-Chloro-2-fluoro-5-methylcarbamoyl-benzyl)-carbamic acid tert-butyl ester was prepared according to Scheme C3 (step A) from 3-(tert-butoxycarbonylamino-methyl)-5-chloro-4-fluoro-benzoic acid (125 mg, 0.41 mmol), HATU (235 mg, 0.6 mmol), methylamine (0.25 mL, 2M in THF) and DIPEA (0.29 mL, 1.6 mmol) in DMF (2 mL). MS (LC-MS): 633.0 [2M]+; $t_R$ (HPLC conditions c): 4.55 min.

(3-Aminomethyl-5-chloro-4-fluoro-phenyl)-(3-methoxy-azetidin-1-yl)-methanone

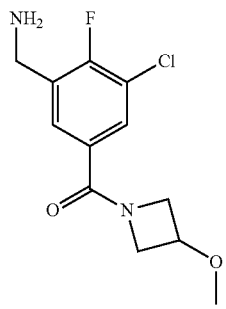 [SMILES: COC1CN(C(=O)c2cc(Cl)c(F)c(CN)c2)C1]

was prepared according to Scheme C3 (step B) from [3-chloro-2-fluoro-5-(3-methoxy-azetidine-1-carbonyl)-benzyl]-carbamic acid tert-butyl ester (99 mg, 0.3 mmol) and TFA (0.5 mL) in CH$_2$Cl$_2$. MS (LC-MS): 273.0 [M]+; $t_R$ (HPLC conditions c): 2.73 min.

[3-Chloro-2-fluoro-5-(3-methoxy-azetidine-1-carbonyl)-benzyl]-carbamic acid tert-butyl ester was prepared according to Scheme C3 (step A) from 3-(tert-butoxycarbonylamino-methyl)-5-chloro-4-fluoro-benzoic acid (116 mg, 0.38 mmol), HATU (218 mg, 0.46 mmol), 3-methoxy-azetidine (57 mg, 0.57 mmol) and DIPEA (0.27 mL, 1.5 mmol) in DMF (2 mL). MS (LC-MS): 373.0 [M]+

3-Aminomethyl-5-chloro-N-(2-dimethylamino-ethyl)-4-fluoro-benzamide

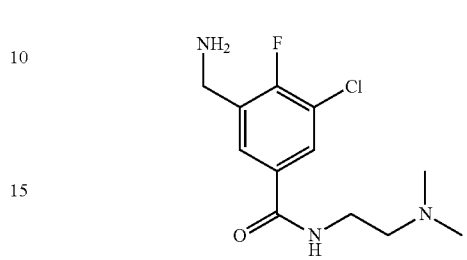

was prepared according to Scheme C3 (step B) from [3-chloro-5-(2-dimethylamino-ethylcarbamoyl)-2-fluoro-benzyl]-carbamic acid tert-butyl ester (120 mg, 0.3 mmol) and TFA (1 mL) in CH$_2$Cl$_2$. MS (LC-MS): 274.0 [M]+; $t_R$ (HPLC conditions c): 2.17 min.

[3-Chloro-5-(2-dimethylamino-ethylcarbamoyl)-2-fluoro-benzyl]-carbamic acid tert-butyl ester was prepared according to Scheme C3 (step A) from 3-(tert-butoxycarbonylamino-methyl)-5-chloro-4-fluoro-benzoic acid (116 mg, 0.38 mmol), HATU (218 mg, 0.46 mmol), N,N-dimethylethylenediamine (40 mg, 0.46 mmol) and DIPEA (0.2 mL, 1.1 mmol) in DMF (2 mL). MS (LC-MS): 374.2 [M]+; $t_R$ (HPLC conditions c): 3.87 min.

(3-Aminomethyl-5-chloro-4-fluoro-phenyl)-morpholin-4-yl-methanone

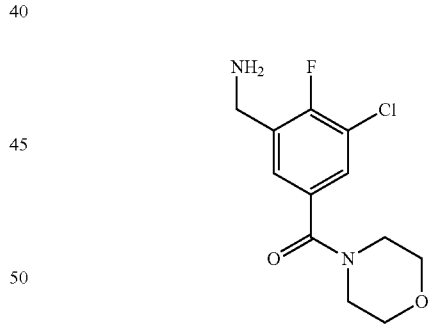

was prepared according to Scheme C3 (step B) from [3-chloro-2-fluoro-5-(morpholine-4-carbonyl)-benzyl]-carbamic acid tert-butyl ester (72 mg, 0.19 mmol) and TFA (1 mL) in CH$_2$Cl$_2$. MS (LC-MS): 273.0 [M]+; $t_R$ (HPLC conditions c): 2.64 min.

[3-Chloro-2-fluoro-5-(morpholine-4-carbonyl)-benzyl]-carbamic acid tert-butyl ester was prepared according to Scheme C3 (step A) from 3-(tert-butoxycarbonylamino-methyl)-5-chloro-4-fluoro-benzoic acid (125 mg, 0.41 mmol), HATU (235 mg, 0.62 mmol), morpholine (43 mg, 0.49 mmol) and DIPEA (0.22 mL, 1.2 mmol) in DMF (2 mL). MS (LC-MS): 317.0 [M−55]+; $t_R$ (HPLC conditions c): 4.65 min.

(3-Aminomethyl-5-chloro-4-fluoro-phenyl)-(4-methyl-piperazin-1-yl)-methanone

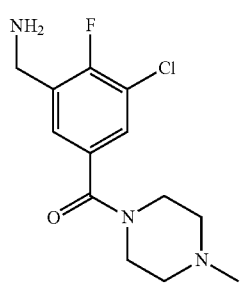 [SMILES: CN1CCN(C(=O)c2cc(Cl)c(F)c(CN)c2)CC1]

was prepared according to Scheme C3 (step B) from [3-chloro-2-fluoro-5-(4-methyl-piperazine-1-carbonyl)-benzyl]-carbamic acid tert-butyl ester (165 mg, 0.43 mmol) and TFA (2 mL) in CH$_2$Cl$_2$. MS (LC-MS): 286.0 [M]+; $t_R$ (HPLC conditions c): 1.47 min.

[3-Chloro-2-fluoro-5-(4-methyl-piperazine-1-carbonyl)-benzyl]-carbamic acid tert-butyl ester was prepared according to Scheme C3 (step A) from 3-(tert-butoxycarbonylamino-methyl)-5-chloro-4-fluoro-benzoic acid (150 mg, 0.49 mmol), HATU (282 mg, 0.74 mmol), 4-methylpiperazine (59 mg, 0.59 mmol) and DIPEA (0.26 mL, 1.5 mmol) in DMF (2 mL). MS (LC-MS): 386.0 [M]+; $t_R$ (HPLC conditions c): 3.77 min.

(S)-1-(3-Bromo-phenyl)-2-fluoro-ethylamine hydrochloride

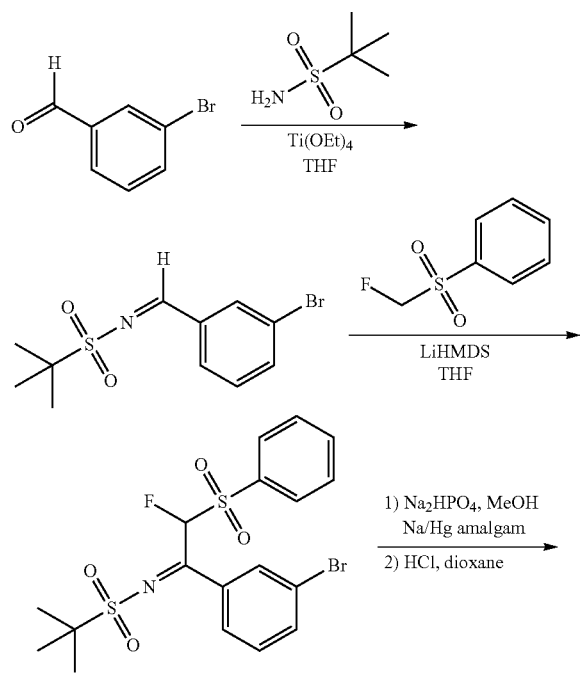

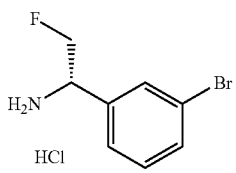

A. 2-Methyl-propane-2-sulfonic acid 1-(3-bromo-phenyl)-meth-(Z)-ylideneamide To a solution of 3-bromo-benzaldehyde (1.27 mL, 10.8 mmol) in THF (50 mL) were added titanium(IV) ethoxide (0.786 mL, 21.6 mmol) and tert-butylsulfonamide (1.31 g, 10.8 mmol), and stirring was continued for 16 h at 65° C. After cooling to RT, volatiles were evaporated, and the residue was purified by flash column chromatography on silica gel (c-hexane/EtOAc 3:1) to afford the title compound. MS (LC/MS): 289 [M+H]+; $t_R$ (HPLC conditions f): 2.35 min.

B. 2-Methyl-propane-2-sulfonic acid [2-benzenesulfonyl-1-(3-bromo-phenyl)-2-fluoro-eth-(Z)-ylidene]-amide To a mixture of 2-methyl-propane-2-sulfonic acid 1-(3-bromo-phenyl)-meth-(Z)-ylideneamide (2.16 g, 7.49 mmol) and (fluoromethylsulfonyl)benzene (1.31 g, 7.49 mmol) in THF (50 mL), cooled to −78° C., was added LiHMDS (1M in THF; 7.87 mL, 7.87 mmol). The reaction mixture was stirred for 40 min at −78° C., followed by quenching saturated aqueous NH$_4$Cl (10 mL) at −78° C. The mixture was extracted with EtOAc (3×), dried over Na$_2$SO$_4$, filtered and concentrated in vacuo. Purification by flash column chromatography on silica gel (c-hexane/EtOAc 3:1) afforded the title compound. MS (LC/MS): 462/464 [M+H]+; $t_R$ (HPLC conditions f): 2.20 min.

C. (S)-1-(3-Bromo-phenyl)-2-fluoro-ethylamine hydrochloride

To a mixture of 2-methyl-propane-2-sulfonic acid [2-benzenesulfonyl-1-(3-bromo-phenyl)-2-fluoro-eth-(Z)-ylidene]-amide (1.74 g, 3.76 mmol) and sodium phosphate dibasic (4.27 g, 30.1 mmol) in methanol (50 mL), cooled to −20° C., was added Na/Hg amalgam (6.92 g, 30.1 mmol). The reaction mixture was stirred for 1 h at −20° C., followed by filtration. To the filtrate was added a 4N HCl solution in dioxane (9.41 mL, 37.6 mmol), followed by stirring for 30 min at 25° C. After evaporation of volatiles, Et$_2$O was added to the residue and the resulting precipitate was filtered off. The title compound thus obtained was used in the next reaction step without further purification. MS (LC/MS): 218/220 [M+H]+; $t_R$ (HPLC conditions f): 1.05 min.

Scheme C4: preparation of (S)-1-(3-Chloro-2-fluoro-phenyl)N*2*,N*2*-dimethyl-ethane-1,2-diamine

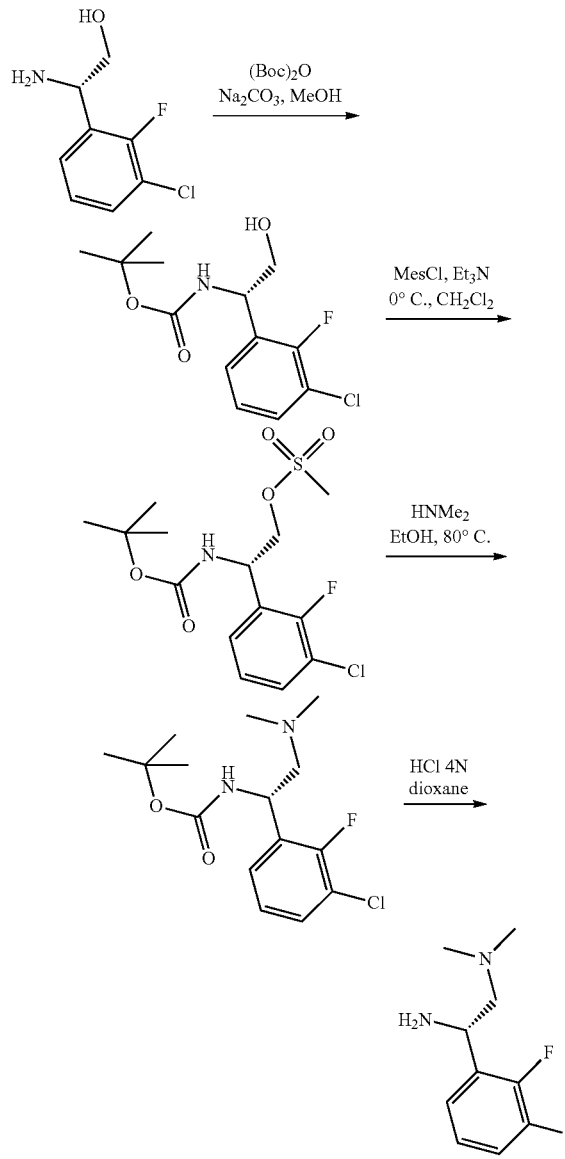

A. [(S)-1-(3-Chloro-2-fluoro-phenyl)-2-hydroxy-ethyl]-carbamic acid tert-butyl ester To a solution of (2S)-2-amino-2-(3-chloro-2-fluorophenyl)ethan-1-ol (517 mg, 2.29 mmol) in MeOH (35 mL) were added (Boc)$_2$O (0.54 mL, 2.31 mmol) and sodium carbonate (970 mg, 9.15 mmol) and the reaction mixture was stirred at RT overnight. Organic volatiles were removed and the crude material was purified by flash column chromatography on silica gel (c-hexane to c-hexane/EtOAc 1:1). TLC, R$_f$(c-hexane/EtOAc 1:1): 0.55; MS (UPLC/MS): 290.2/292.2 [M+H]+, 334.2/336.3 [M+HCOO]−; t$_R$ (HPLC conditions a): 3.36 min.

B. Methanesulfonic acid (S)-2-tert-butoxycarbonylamino-2-(3-chloro-2-fluoro-phenyl)-ethyl ester To a solution of [(S)-1-(3-chloro-2-fluoro-phenyl)-2-hydroxy-ethyl]-carbamic acid tert-butyl ester (550 mg, 1.9 mmol) and triethylamine (0.29 mL, 2.09 mmol) in CH$_2$Cl$_2$ (5.5 mL) cooled at −10° C. was added under nitrogen atmosphere mesylchloride (0.16 mL, 2.09 mmol) and the reaction mixture was stirred at 0° C. for 1.5 h. The reaction mixture was quenched with ice and water then extracted twice with EtOAc. The combined organic layers were washed with water, dried (Na$_2$SO$_4$), filtered and concentrated. The crude material was used without purification in the next step. MS (UPLC/MS): 412.3/414.3 [M+HCOO]−; t$_R$ (HPLC conditions a): 3.66 min.

C. [(S)-1-(3-Chloro-2-fluoro-phenyl)-2-dimethylamino-ethyl]-carbamic acid tert-butyl ester A solution of methanesulfonic acid (S)-2-tert-butoxycarbonylamino-2-(3-chloro-2-fluoro-phenyl)-ethyl ester (690 mg, 1.88 mmol) in 33% dimethylamine in EtOH (5.6 M, 7.5 mL, 42 mmol) was heated at 80° C. for 2 h in a sealed tube. The reaction mixture was concentrated and the crude material was purified by flash column chromatography on silica gel (c-hexane/EtOAc 1:1 to EtOAc) to give a pale yellow oil. TLC, R$_f$ (EtOAc): 0.60; MS (UPLC/MS): 317.3/319.3 [M+H]+; t$_R$ (HPLC conditions a): 3.19 min.

D. (S)-1-(3-Chloro-2-fluoro-phenyl)-N*2*,N*2*-dimethyl-ethane-1,2-diamine

To a solution of [(S)-1-(3-chloro-2-fluoro-phenyl)-2-dimethylamino-ethyl]-carbamic acid tert-butyl ester (315 mg, 0.99 mmol) in dioxane (6 mL) was added HCl 4N in dioxane (9.94 mL, 39.8 mmol). The reaction mixture was stirred at RT for 1 h and concentrated to give the desired material as a HCL salt which was used without further purification in the next step. MS (UPLC/MS): 217.2/219.2 [M+H]+; 1H NMR (400 MHz, DMSO-d$_6$) δ (ppm): 9.17 (bs, 2H), 7.75 (m, 2H), 7.40 (t, 1H), 5.16 (m, 1H), 3.85 (m, 1H), 3.60 (m, 1H), 2.87 (s, 3H).

(R)-1-(3-Chloro-2-fluoro-phenyl)-N*3*,N*3*-dimethyl-propane-1,3-diamine

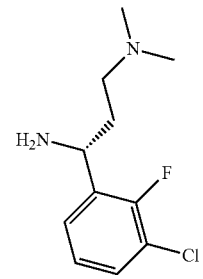

was prepared using similar procedures as described for the synthesis of (3-acetyl-pyrrolo[2,3-c]pyridin-1-yl)-acetic acid in Scheme C4 from (R)-3-amino-3-(3-chloro-2-fluoro-phenyl)-propan-1-ol. 1H-NMR (400 MHz, DMSO): δ (ppm): 8.89 (m, 2H), 7.73 (m, 2H), 7.39 (t, 1H), 4.69 (m, 1H), 3.13 (m, 1H), 2.98 (m, 1H), 2.73 (s, 6H), 2.47 (m, 1H), 2.34 (1H).

1-(3-chloro-phenyl)-cyclopropylamine

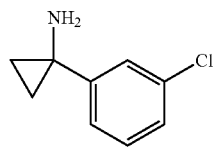 [SMILES: NC1(c2cccc(Cl)c2)CC1]

To a solution of 3-chlorobenzonitrile (1 g, 7.27 mmol) and titanium (IV) isopropoxide (2.34 mL, 8 mmol) in Et$_2$O (35 mL) at −78° C. was added ethyl magnesium chloride in THF (5.71 mL, 15.99 mmol). The solution was stirred for 10 min at −78° C. then at 25° C. for 1 h. BF$_3$.Et$_2$O (1.82 mL, 14.54 mmol) was added and the solution was stirred for 1 h at 25° C. The reaction mixture was quenched with 1N HCl (22 mL) Et$_2$O was added (100 mL). Then 10% aq. NaOH (70 mL) was added and the layers were separated. The organic layer was dried over Na$_2$SO$_4$, filtered and concentrated. The crude residue was purified by preparative HPLC (Waters SunFire C18-ODB, 5 μm, 19×50 mm, 5% CH$_3$CN/H$_2$O 2.5 min, 5-100% CH$_3$CN/H$_2$O in 10 min, CH$_3$CN/H$_2$O containing 0.1% HCOOH flow: 20 mL/min) to give after lyophilization of the purified fractions the title compound. MS (UPLC-MS): 170 [M+H]+, 168 [M−H]−; $t_R$ (HPLC conditions f): 1.22 min.

1-(4-chloro-phenyl)-cyclopropylamine

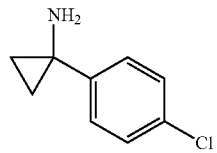 [SMILES: NC1(c2ccc(Cl)cc2)CC1]

was prepared using the same procedure as for the preparation of 1-(3-chloro-phenyl)-cyclopropylamine starting from 4-chlorobenzonitrile. MS (UPLC-MS): 170 [M+H]+, 168 [M−H]; $t_R$ (HPLC conditions f): 1.21 min.

1-(3-Chloro-2-fluoro-phenyl)-cyclopropylamine

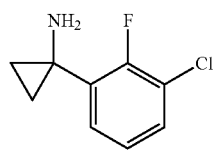

was prepared using the same procedure as for the preparation of 1-(3-chloro-phenyl)-cyclopropylamine starting from 3-chloro-2-fluororo-benzonitrile. MS (UPLC-MS): 186/188 [M+H]+; $t_R$ (HPLC conditions f): 1.13 min.

3-(3-Chloro-2-fluoro-phenyl)-oxetan-3-ylamine hydrochloride

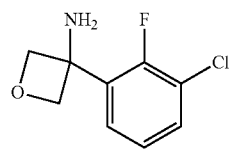 [SMILES: NC1(c2cccc(Cl)c2F)COC1]

A solution of 2-methyl-propane-2-sulfinic acid [3-(3-chloro-2-fluoro-phenyl)-oxetan-3-yl]-amide (940 mg, 2.46 mmol) and hydrochloric acid (4 N in dioxane, 0.922 ml, 3.69 mmol) in MeOH (5 mL) was stirred 30 min at 0° C. and concentrated. The material thus obtained was used without further purification in the next step. MS (UPLC-MS): 202/204 [M+H]+; $t_R$ (HPLC conditions f): 0.86 min.

2-methyl-propane-2-sulfinic acid [3-(3-chloro-2-fluoro-phenyl)-oxetan-3-yl]-amide To a solution of 1-bromo-3-chloro-2-fluorobenzene (896 mg, 4.28 mmol) in THF (100 mL) was added at −78° C. under nitrogen atmosphere n-butyllithium (1.6 N in hexanes, 2.67 ml, 4.28 mmol). The reaction mixture was stirred 1 h at −78° C. and a solution of 2-methyl-N-(oxetan-3-ylidene)propane-2-sulfinamide (500 mg, 2.85 mmol) in THF (17.5 ml) was added dropwise. The reaction mixture was further stirred 1 h at −78° C. then allowed to reach RT and quenched by slow addition of a saturated aqueous solution of NH$_4$Cl, extracted with EtOAc (×2). The combined organic extracts were washed with water and brine, dried (Na$_2$SO$_4$), filtered and concentrated. The material thus obtained was used without further purification in the next step. MS (UPLC-MS): 306.1/308.1 [M+H]+; $t_R$ (HPLC conditions f): 1.85 min.

Scheme C5: Preparation of 2,2'-difluoro-biphenyl-3-ylamine

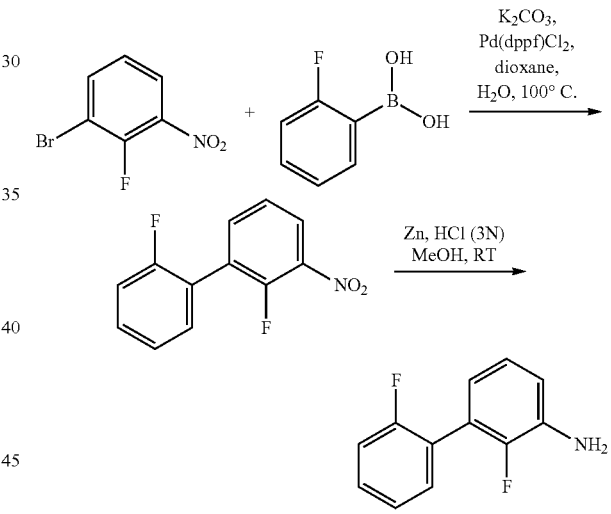

A. 2,2'-Difluoro-3-nitro-biphenyl

To a solution of 1-bromo-2-fluoro-3-nitrobenzene [58534-94-4] (150 mg, 0.68 mmol) and 2-fluorophenylboronic acid [1193-03-9] (191 mg, 1.36 mmol) in dioxane (4 mL) and water (1 mL) was added potassium carbonate (236 mg, 1.70 mmol) and Pd(dppf)Cl$_2$CH$_2$Cl$_2$ adduct (55.7 mg, 0.068 mmol). The solution was heated for 30 min at 100° C. under microwave irradiation. The reaction mixture was diluted with CH$_2$Cl$_2$ and the resulting solution was washed successively with saturated aqueous NaHCO$_3$ solution, 1N HCl solution and brine, then dried (Phase separator) and concentrated under reduced pressure. The residue was purified by preparative HPLC (Waters Sunfire, C18-ODB, 5 μm, 30×100 mm, flow: 40 mL/min, eluent: 20-100% CH$_3$CN/H$_2$O/20 min, 100% CH$_3$CN/2 min, CH$_3$CN and H$_2$O containing 0.1% TFA) to give after lyophilization of the purified fractions the title compound. MS (LC-MS): 236 [M+H]+; $t_R$ (HPLC conditions k): 3.81 min.

B. 2,2'-Difluoro-biphenyl-3-ylamine

To a suspension of 2,2'-difluoro-3-nitro-biphenyl (100 mg, 0.36 mmol) in methanol (5 mL) were added a 3N aqueous HCl solution (7.23 mL, 21.7 mmol) and Zn powder (426 mg, 6.51 mmol). The mixture was stirred 4 h at RT. The reaction mixture was concentrated and neutralized with saturated aqueous $NaHCO_3$ solution, then diluted with an equal volume of water and extracted (×3) with $CH_2Cl_2$. The combined organics were dried (Phase Separator) and concentrated in vacuo to give the title compound. MS (LC-MS): 206 $[M+H]+$; $t_R$ (HPLC conditions k): 3.30 min.

7-Chloro-2-fluoro-biphenyl-3-ylamine

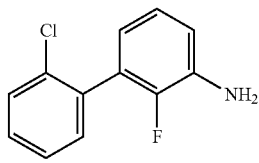 [SMILES: Nc1cccc(-c2ccccc2Cl)c1F]

was prepared by using the same procedures as described for the preparation of 2,2'-difluoro-biphenyl-3-ylamine in Scheme C5, starting from 2-chlorophenylboronic acid [1679-18-1]. MS (LC-MS): 222 $[M+H]+$; $t_R$ (HPLC conditions k): 3.42 min.

Scheme C6: Preparation of 3-(3-chloro-pyridin-2-yl)-2-fluoro-phenylamine

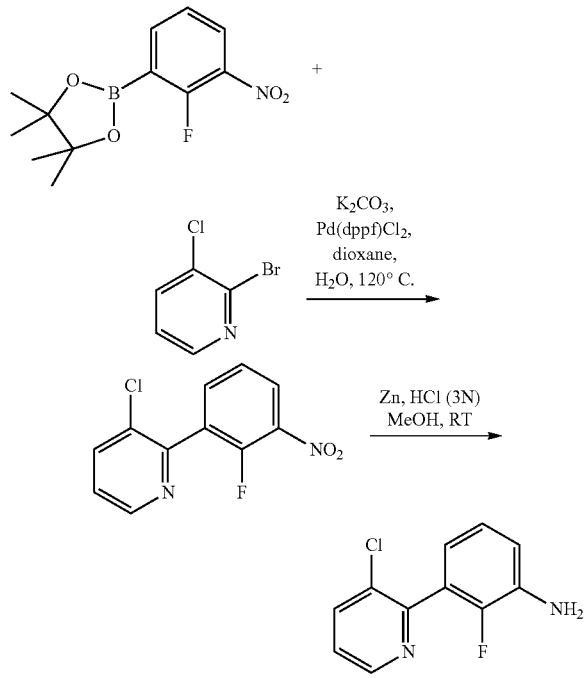

A. 3-Chloro-2-(2-fluoro-3-nitro-phenyl)-pyridine

To a solution of 2-bromo-3-chloropyridine [96424-68-9] (144 mg, 0.75 mmol) and 2-fluoro-3-nitrophenylboronic acid pinacol ester [1189042-70-3] (200 mg, 0.75 mmol) in diox- ane (4 mL) and water (1 mL) was added potassium carbonate (259 mg, 1.87 mmol) and $Pd(dppf)Cl_2CH_2Cl_2$ adduct (61.2 mg, 0.075 mmol). The solution was heated for 60 min at 120° C. under microwave irradiation. The reaction mixture was diluted with EtOAc and the resulting solution was washed successively with saturated aqueous $NaHCO_3$ solution and brine, then dried (Phase separator) and concentrated under reduced pressure. The residue was purified by flash chromatography on silica gel (c-hexane/EtOAc 4:1) to give the title compound. MS (LC-MS): 253 $[M+H]+$; $t_R$ (HPLC conditions k): 3.45 min.

B. 3-(3-Chloro-pyridin-2-yl)-2-fluoro-phenylamine was prepared by using the same procedure as described for the preparation of 2,2'-difluoro-biphenyl-3-ylamine in Scheme C5 step B. MS (LC-MS): 223 $[M+H]+$; $t_R$ (HPLC conditions k): 2.63 min.

2-Fluoro-3-(3-methyl-pyridin-2-yl)-phenylamine

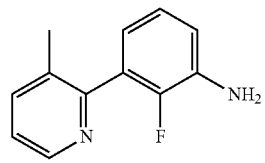

was prepared by using the same procedures as described for the preparation of 3-(3-chloro-pyridin-2-yl)-2-fluoro-phenylamine in Scheme C6, starting from 2-bromo-3-methylpyridine [3430-17-9]. MS (LC-MS): 203 $[M+H]+$; $t_R$ (HPLC conditions k): 1.36 min.

2-Fluoro-3-(3-fluoro-pyridin-2-yl)-phenylamine

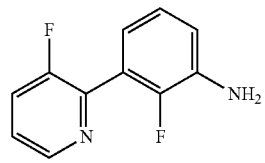 [SMILES: Nc1cccc(-c2ncccc2F)c1F]

was prepared by using the same procedures as described for the preparation of 3-(3-chloro-pyridin-2-yl)-2-fluoro-phenylamine in Scheme C6, starting from 2-bromo-3-fluoropyridine [40273-45-8] and 2-fluoro-3-nitrophenylboronic acid [1150114-29-6]. MS (LC-MS): 207 $[M+H]+$; $t_R$ (HPLC conditions k): 2.39 min.

6-(2,6-difluoro-phenyl)-pyridin-2-ylamine

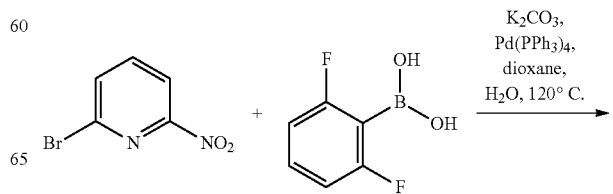

-continued

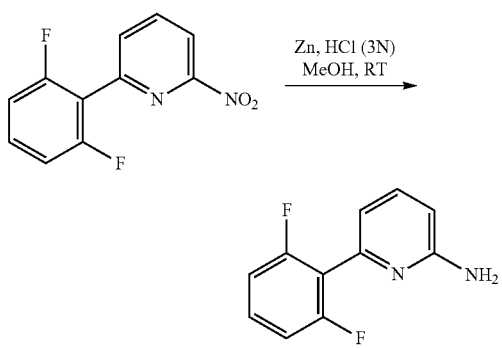

A. 2-(2,6-Difluoro-phenyl)-6-nitro-pyridine

To a solution of 2-bromo-6-nitropyridine [21203-78-1] (200 mg, 0.99 mmol) and 2,6-difluorophenylboronic acid [162101-25-9] (311 mg, 1.97 mmol) in dioxane (4 mL) and water (1 mL) was added potassium carbonate (340 mg, 2.46 mmol) and Pd(PPh$_3$)$_4$ (114 mg, 0.099 mmol). The solution was heated for 60 min at 120° C. under microwave irradiation. More 2,6-difluorophenylboronic acid (622 mg, 3.94 mmol) was added to the mixture followed by heating at 120° C. for 120 min under microwave irradiation. The reaction mixture was then diluted with EtOAc and the resulting solution was washed successively with saturated aqueous NaHCO$_3$ solution and brine, the organics were then dried (Phase separator) and concentrated under reduced pressure. The residue was purified by flash column chromatography on silica gel (c-hexane/EtOAc 9:1) to give the title compound. MS (LC-MS): 237 [M+H]+, 259 [M+Na]+; t$_R$ (HPLC conditions k): 3.44 min.

B. 6-(2,6-Difluoro-phenyl)-pyridin-2-ylamine was prepared by using the same procedure as described for the preparation of 2,2'-difluoro-biphenyl-3-ylamine in Scheme C5 step B. MS (LC-MS): 207 [M+H]+; t$_R$ (HPLC conditions k): 2.39 min.

2'-chloro-6'-fluorobiphenyl-3-amine

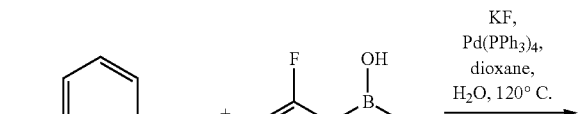

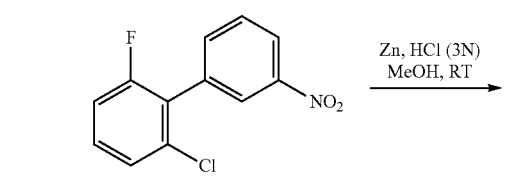

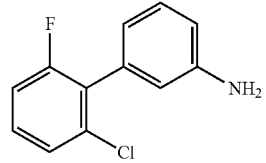

A. 2-Chloro-6-fluoro-3'-nitro-1,1'-biphenyl

To a solution of 1-bromo-3-nitrobenzene [585-79-5] (400 mg, 1.98 mmol) and 2-chloro-6-fluorophenylboronic acid [313545-32-3] (414 mg, 2.37 mmol) in dioxane (12 mL) and water (3 mL) was added potassium fluoride (460 mg, 7.92 mmol) and Pd(PPh$_3$)$_4$ (229 mg, 0.20 mmol). The solution was heated for 60 min at 120° C. under microwave irradiation. More 2-chloro-6-fluorophenylboronic acid (414 mg, 2.37 mmol) was added to the mixture followed by heating at 120° C. for 45 min under microwave irradiation. The reaction mixture was then diluted with EtOAc and the resulting solution was washed successively with saturated aqueous NaHCO$_3$ solution and brine, the organics were then dried (Phase separator) and concentrated under reduced pressure. The residue was purified by preparative HPLC (Waters Sunfire, C18-ODB, 5 μm, 30×100 mm, flow: 50 mL/min, eluent: 20-100% CH$_3$CN/H$_2$O/20 min, 100% CH$_3$CN/2 min, CH$_3$CN and H$_2$O containing 0.1% TFA) to give the title compound. t$_R$ (HPLC conditions c): 5.42 min.

B. 2'-Chloro-6'-fluorobiphenyl-3-amine was prepared by using the same procedure as described for the preparation of 2,2'-difluoro-biphenyl-3-ylamine in Scheme C5 step B. MS (LC-MS): 222 [M+H]+; t$_R$ (HPLC conditions c): 3.58 min.

Part D

Synthesis of Examples 1 to 773

1H NMR and HRMS Data for Selected Compounds can be Found at the End of Part D.

Scheme D1: general protocol described for the preparation of Example 1: (2S,4R)-4-Fluoro-pyrrolidine-1,2-dicarboxylic acid 1-[(1-carbamoyl-1H-indol-3-yl)-amide]2-(3-chloro-2-fluoro-benzylamide)

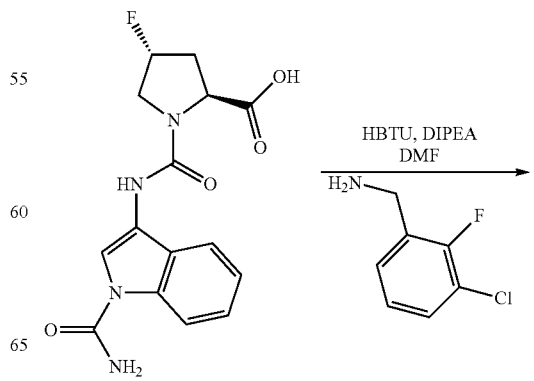

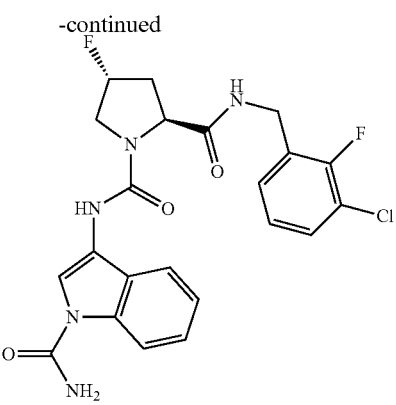

(2S,4R)-1-(1-Carbamoyl-1H-indol-3-ylcarbamoyl)-4-fluoro-pyrrolidine-2-carboxylic acid (80 mg, 0.24 mmol, prepared as described in Part B), 3-chloro-2-fluorobenzylamine (76 mg, 0.48 mmol) and HBTU (136 mg, 0.36 mmol) were dissolved in DMF (7.98 mL). DIPEA (125 μl, 0.718 mmol) was added and the reaction mixture was stirred at 25° C. for 1 h. The crude reaction mixture was diluted with EtOAc and successively washed with HCl 1N and NaHCO$_3$ (5% in water). The organic layer was dried (Na$_2$SO$_4$), filtered and concentrated. The crude material was purified by preparative HPLC (Waters Sunfire C18-ODB, 5 um, 19×50 mm, flow: 20 mL/min, gradient: 0-2.5 min 20% CH$_3$CN, 2.5-12.5 min 20 to 100% CH$_3$CN, 12.5-15 min 100% CH$_3$CN, H$_2$O and CH$_3$CN containing 0.1% HCOOH) the pure fractions were combined, extracted with EtOAc and concentrated. The residue was finally taken up in Et$_2$O and the desired compound was obtained after filtration. MS: 475.9 [M+H]+, 498 [M+Na]+; $t_R$ (HPLC conditions b): 3.64 min.

The examples below were prepared according to the general procedures described in Scheme D1 for Example 1 using commercially available building blocks, if not otherwise stated (see notes at the end of table 1):

TABLE 1

| Example | Structure | Name | Characterization (end-table notes), TLC, R$_f$ (eluent); MS (LC/MS); $t_R$ (HPLC conditions) |
|---|---|---|---|
| 2 | 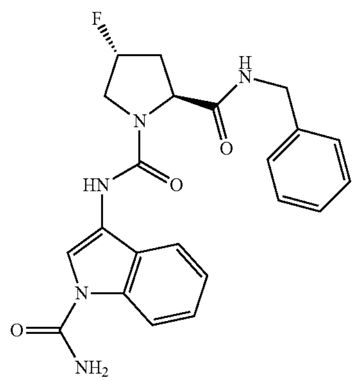 [SMILES: NC(=O)n1cc(NC(=O)N2C[C@H](F)C[C@H]2C(=O)NCc2ccccc2)c2ccccc21] | (2S,4R)-4-Fluoro-pyrrolidine-1,2-dicarboxylic acid 2-benzylamide 1-[(1-carbamoyl-1H-indol-3-yl)-amide] | 424 [M + H]+; $t_R$ (b): 3.15 min. |
| 3 | 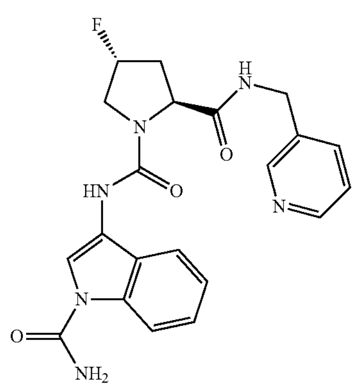 [SMILES: NC(=O)n1cc(NC(=O)N2C[C@H](F)C[C@H]2C(=O)NCc2cccnc2)c2ccccc21] | (2S,4R)-4-Fluoro-pyrrolidine-1,2-dicarboxylic acid 1-[(1-carbamoyl-1H-indol-3-yl)-amide] 2-[(pyridin-3-ylmethyl)-amide] | 425.0 [M + H]+, 423.1 [M − H]−; $t_R$ (a): 1.05 min. |

TABLE 1-continued

| Example | Name | Characterization (end-table notes), TLC, R$_f$(eluent); MS (LC/MS); t$_R$ (HPLC conditions) |
|---|---|---|
| 4 | (2S,4R)-4-Fluoro-pyrrolidine-1,2-dicarboxylic acid 1-[(1-carbamoyl-1H-indol-3-yl)-amide] 2-(3-chloro-2-fluoro-5-{[(2-methoxy-ethyl)-methyl-amino]-methyl}-benzylamide) | (1[C2]) 577.3 [M]+; t$_R$ (c): 3.67 min. |
| 5 | (2S,4R)-4-Fluoro-pyrrolidine-1,2-dicarboxylic acid 1-[(1-carbamoyl-1H-indol-3-yl)-amide] 2-{[(S)-1-(3-chloro-2-fluoro-phenyl)-2-hydroxy-ethyl]-amide} | 506.4 [M + H]+, 504.3 [M − H]−; t$_R$ (a): 2.87 min. |
| 6 | (2S,4R)-4-Fluoro-pyrrolidine-1,2-dicarboxylic acid 1-[(1-carbamoyl-1H-indol-3-yl)-amide] 2-[(pyridin-4-ylmethyl)-amide] | 425.2 [M + H]+, 447.1 [M + Na]+, 871.3 [2M + Na]+, 423.1 [M − H]−, 380 [M − CONH$_2$]−; t$_R$ (a): 1.27 min. |

TABLE 1-continued

| Example | Structure | Name | Characterization (end-table notes), TLC, R$_f$ (eluent); MS (LC/MS); t$_R$ (HPLC conditions) |
|---------|-----------|------|--------------------------------------------------------------------------------------------|
| 7 | 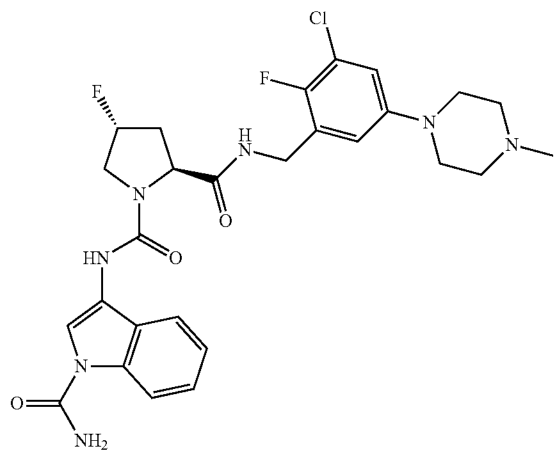 [SMILES: CN1CCN(c2cc(Cl)c(F)c(CNC(=O)[C@@H]3C[C@@H](F)CN3C(=O)Nc3cn(C(N)=O)c4ccccc34)c2)CC1] | (2S,4R)-4-Fluoro-pyrrolidine-1,2-dicarboxylic acid 1-[(1-carbamoyl-1H-indol-3-yl)-amide] 2-[3-chloro-2-fluoro-5-(4-methyl-piperazin-1-yl)-benzylamide] | (1[C1]) 574.2/577.3 [M + H]+; t$_R$ (c): 3.63 min. |
| 8 | 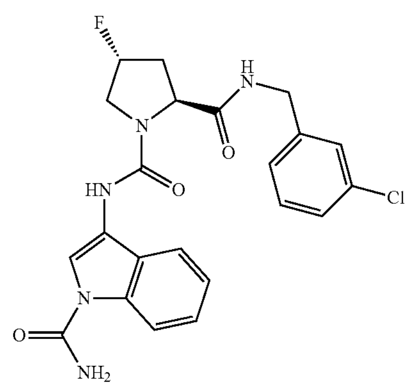 [SMILES: NC(=O)n1cc(NC(=O)N2C[C@H](F)C[C@H]2C(=O)NCc2cccc(Cl)c2)c2ccccc21] | (2S,4R)-4-Fluoro-pyrrolidine-1,2-dicarboxylic acid 1-[(1-carbamoyl-1H-indol-3-yl)-amide] 2-(3-chloro-benzylamide) | 458.2 [M + H]+ 456.1 [M − H]−; t$_R$ (a): 3.05 min; t$_R$ (b): 3.34 min. |
| 9 | 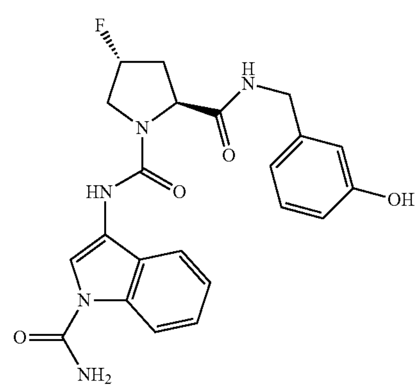 [SMILES: NC(=O)n1cc(NC(=O)N2C[C@H](F)C[C@H]2C(=O)NCc2cccc(O)c2)c2ccccc21] | (2S,4R)-4-Fluoro-pyrrolidine-1,2-dicarboxylic acid 1-[(1-carbamoyl-1H-indol-3-yl)-amide] 2-(3-hydroxy-benzylamide) | 440 [M + H]+; t$_R$ (b): 2.66 min. |

| Example | Structure | Name | Characterization (end-table notes), TLC, $R_f$ (eluent); MS (LC/MS); $t_R$ (HPLC conditions) |
|---|---|---|---|
| 10 | 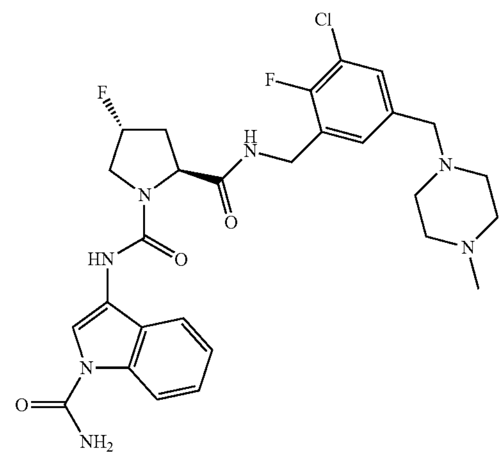 [SMILES: CN1CCN(Cc2cc(Cl)c(F)c(CNC(=O)[C@@H]3C[C@@H](F)CN3C(=O)Nc3cn(C(N)=O)c4ccccc34)c2)CC1] | (2S,4R)-4-Fluoro-pyrrolidine-1,2-dicarboxylic acid 1-[(1-carbamoyl-1H-indol-3-yl)-amide] 2-[3-chloro-2-fluoro-5-(4-methyl-piperazin-1-ylmethyl)-benzylamide] | (1[C2]) 588 [M + H]+; $t_R$ (c): 3.31 min. |
| 11 | 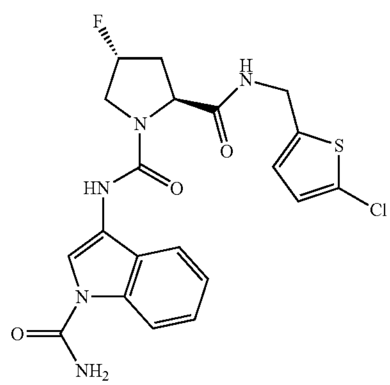 [SMILES: NC(=O)n1cc(NC(=O)N2C[C@H](F)C[C@H]2C(=O)NCc2ccc(Cl)s2)c2ccccc21] | (2S,4R)-4-Fluoro-pyrrolidine-1,2-dicarboxylic acid 1-[(1-carbamoyl-1H-indol-3-yl)-amide] 2-[(5-chloro-thiophen-2-ylmethyl)-amide] | 463.9 [M + H]+; $t_R$ (b): 3.55 min. |
| 12 | 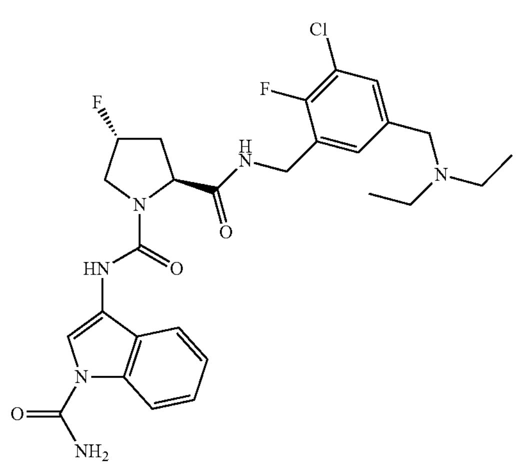 [SMILES: CCN(CC)Cc1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-(3-chloro-5-diethylamino-methyl-2-fluoro-benzyl-amide) | (1[C2]) 561.3 [M]+; $t_R$ (c): 3.72 min. |

TABLE 1-continued

| Example | Structure | Name | Characterization (end-table notes), TLC, R$_f$(eluent); MS (LC/MS); t$_R$ (HPLC conditions) |
|---|---|---|---|
| 13 | 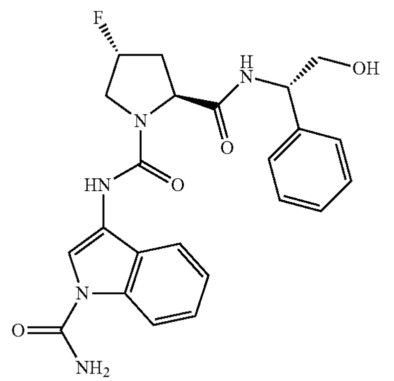 [SMILES: NC(=O)n1cc(NC(=O)N2C[C@H](F)C[C@H]2C(=O)N[C@H](CO)c2ccccc2)c2ccccc21] | (2S,4R)-4-Fluoro-pyrrolidine-1,2-dicarboxylic acid 1-[(1-carbamoyl-1H-indol-3-yl)-amide] 2-[((S)-2-hydroxy-1-phenyl-ethyl)-amide] | 454.3 [M + H]+, 452.3 [M − H]−; t$_R$ (a): 2.63 min. |
| 14 | 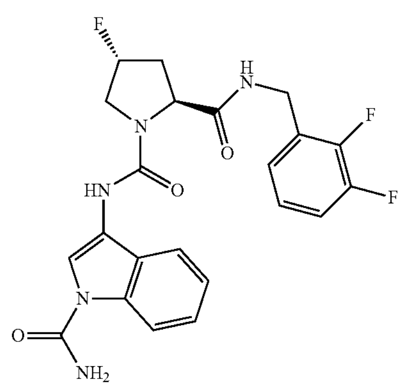 [SMILES: NC(=O)n1cc(NC(=O)N2C[C@H](F)C[C@H]2C(=O)NCc2cccc(F)c2F)c2ccccc21] | (2S,4R)-4-Fluoro-pyrrolidine-1,2-dicarboxylic acid 1-[(1-carbamoyl-1H-indol-3-yl)-amide] 2-(2,3-difluoro-benzylamide) | 460.1 [M + H]+; 415 [M − CONH$_2$]−; t$_R$ (a): 2.95 min. |
| 15 | 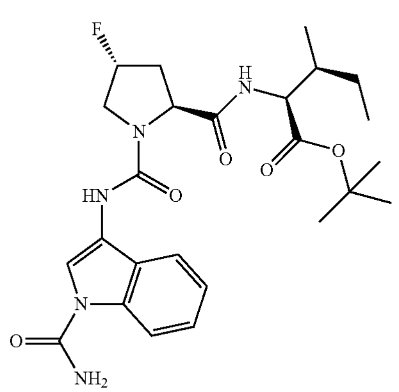 [SMILES: CC[C@H](C)[C@H](NC(=O)[C@@H]1C[C@@H](F)CN1C(=O)Nc1cn(C(N)=O)c2ccccc12)C(=O)OC(C)(C)C] | (2S,3S)-2-{[(2S,4R)-1-(1-Carbamoyl-1H-indol-3-ylcarbamoyl)-4-fluoro-pyrrolidine-2-carbonyl]-amino}-3-methyl-pentanoic acid tert-butyl ester | R$_f$(EtOAc) = 0.7; 504.3 [M + H]+, 526.3 [M + Na]+, 448.1 [MH − tBu]+, 502.2 [M − H]−, 459.2 [M − CONH$_2$]−; t$_R$ (a): 3.42 min. |

TABLE 1-continued

| Example | Structure | Name | Characterization (end-table notes), TLC, $R_f$(eluent); MS (LC/MS); $t_R$ (HPLC conditions) |
|---|---|---|---|
| 16 | 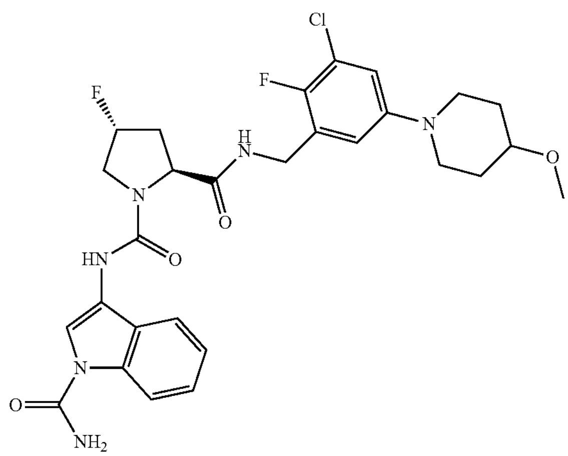 [SMILES: COC1CCN(c2cc(Cl)c(F)c(CNC(=O)[C@@H]3C[C@@H](F)CN3C(=O)Nc3cn(C(N)=O)c4ccccc34)c2)CC1] | (2S,4R)-4-Fluoro-pyrrolidine-1,2-dicarboxylic acid 1-[(1-carbamoyl-1H-indol-3-yl)-amide] 2-[3-chloro-2-fluoro-5-(4-methoxy-piperidin-1-yl)-benzylamide] | (1[C1]) 589.3/592.3 [M + H]+, $t_R$ (c): 3.76 min. |
| 17 | 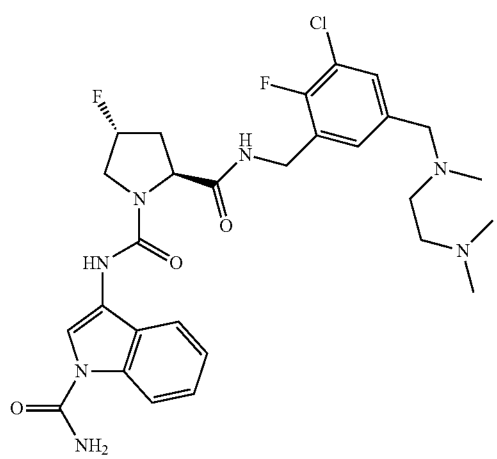 [SMILES: CN(C)CCN(C)Cc1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-(3-chloro-5-{[(2-dimethylamino-ethyl)-methyl-amino]-methyl}-2-fluoro-benzylamide) | (1[C2]) 590.2 [M]+; $t_R$ (c): 3.25 min. |
| 18 | 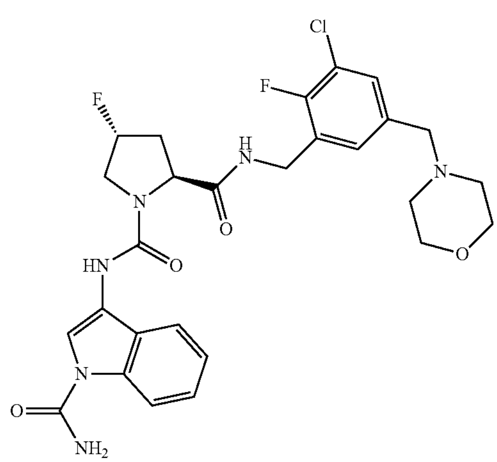 [SMILES: NC(=O)n1cc(NC(=O)N2C[C@H](F)C[C@H]2C(=O)NCc2cc(CN3CCOCC3)cc(Cl)c2F)c2ccccc21] | (2S,4R)-4-Fluoro-pyrrolidine-1,2-dicarboxylic acid 1-[(1-carbamoyl-1H-indol-3-yl)-amide] 2-(3-chloro-2-fluoro-5-morpholin-4-ylmethyl-benzylamide) | (1[C2]) 575.2 [M]+; $t_R$ (c): 3.57 min. |

TABLE 1-continued

| Example | Structure | Name | Characterization (end-table notes), TLC, R_f (eluent); MS (LC/MS); t_R (HPLC conditions) |
|---|---|---|---|
| 19 | 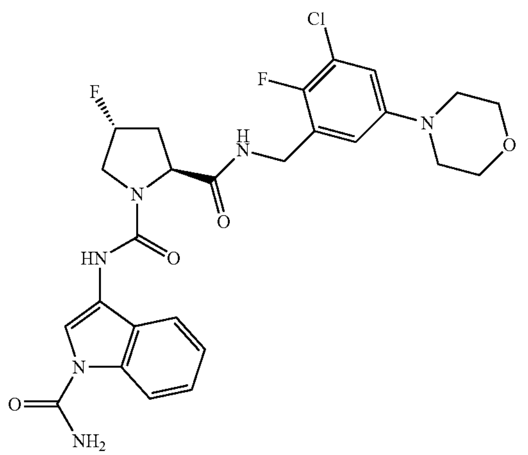 [SMILES: NC(=O)n1cc(NC(=O)N2C[C@H](F)C[C@H]2C(=O)NCc2cc(N3CCOCC3)cc(Cl)c2F)c2ccccc21] | (2S,4R)-4-Fluoro-pyrrolidine-1,2-dicarboxylic acid 1-[(1-carbamoyl-1H-indol-3-yl)-amide] 2-(3-chloro-2-fluoro-5-morpholin-4-yl-benzylamide) | (1) 561.3/564 [M + H]+, t_R (c): 4.26 min. |
| 20 | 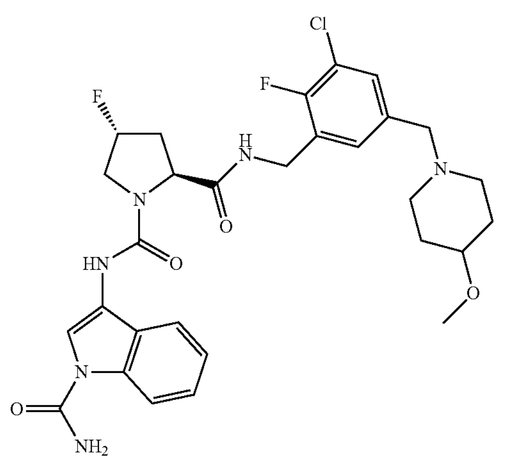 [SMILES: COC1CCN(Cc2cc(Cl)c(F)c(CNC(=O)[C@@H]3C[C@@H](F)CN3C(=O)Nc3cn(C(N)=O)c4ccccc34)c2)CC1] | (2S,4R)-4-Fluoro-pyrrolidine-1,2-dicarboxylic acid 1-[(1-carbamoyl-1H-indol-3-yl)-amide] 2-(3-chloro-2-fluoro-5-(4-methoxy-piperidin-1-ylmethyl)-benzylamide] | (1[C2]) 603 [M + H]+; t_R (c): 3.72 min. |
| 21 | 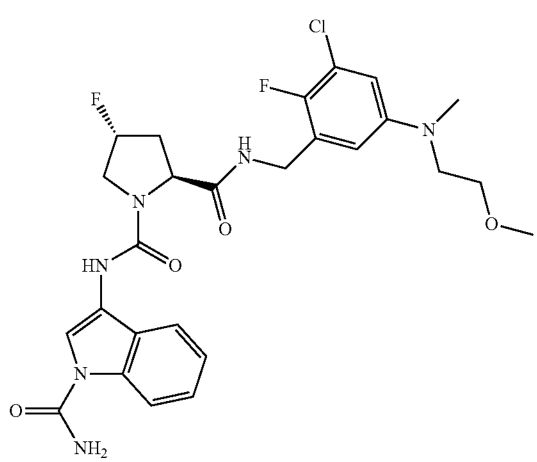 [SMILES: COCCN(C)c1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-{3-chloro-2-fluoro-5-[(2-methoxy-ethyl)-methyl-amino]-benzylamide} | (1[C1]) 563.3/566.3 [M + H]+, t_R (c): 3.99 min. |

TABLE 1-continued

| Example | Structure | Name | Characterization (end-table notes), TLC, $R_f$(eluent); MS (LC/MS); $t_R$ (HPLC conditions) |
|---|---|---|---|
| 22 | 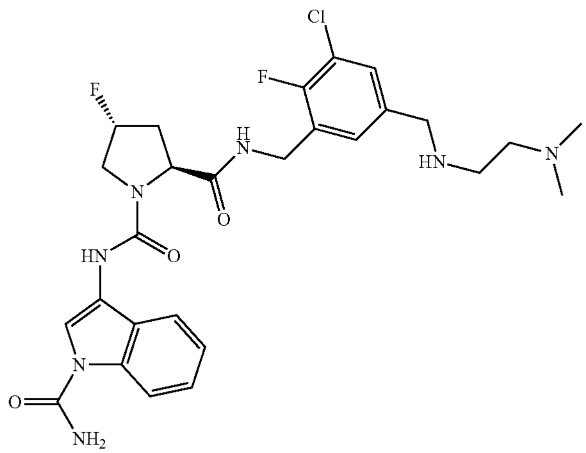 [SMILES: CN(C)CCNCc1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-{3-chloro-5-[(2-dimethylamino-ethylamino)-methyl]-2-fluoro-benzylamide} | (1[C2]) 576.2/579.2 [M + H]+, $t_R$ (c): 3.27 min. |

(1) The substituted benzylamine or aniline derivative used in step A was prepared as described in Part C [Scheme].

Example 23

2-({[(2S,4R)-1-(1-Carbamoyl-1H-indol-3-ylcarbamoyl)-4-fluoro-pyrrolidine-2-carbonyl]-amino}-methyl)-benzoic acid

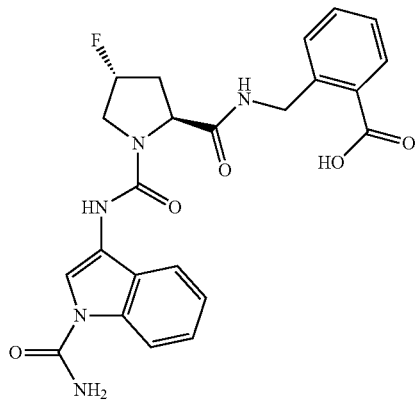 [SMILES: NC(=O)n1cc(NC(=O)N2C[C@H](F)C[C@H]2C(=O)NCc2ccccc2C(=O)O)c2ccccc21]

To a solution of 2-({[(2S,4R)-1-(1-carbamoyl-1H-indol-3-ylcarbamoyl)-4-fluoro-pyrrolidine-2-carbonyl]-amino}-methyl)-benzoic acid tert-butyl ester (prepared according to Scheme D1 using 2-aminomethyl-benzoic acid tert-butyl ester) (76 mg, 0.145 mm) in CH$_2$Cl$_2$ (1 mL) was added TFA (168 µl, 2.18 mmol) and the resulting solution was stirred at RT overnight. The crude mixture was concentrated to give a solid which was suspended in Et$_2$O and filtered to give the desired material. MS (LC-MS): 468.1 [M+H]+, 490.1 [M+Na]+, 957.2 [2M+Na]+, 466.1 [M–H]–, 423.1 [M–CONH$_2$]–, $t_R$ (HPLC conditions a): 2.64 min.

Example 24

2-({[(2S,4R)-1-(1-Carbamoyl-1H-indol-3-ylcarbamoyl)-4-fluoro-pyrrolidine-3-carbonyl]-amino}-methyl)-benzoic acid

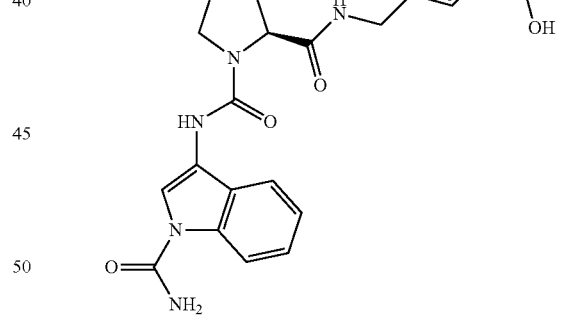

To a solution of 3-({[(2S,4R)-1-(1-carbamoyl-1H-indol-3-ylcarbamoyl)-4-fluoro-pyrrolidine-2-carbonyl]-amino}-methyl)-benzoic acid tert-butyl ester (prepared according to Scheme D1 using 3-aminomethyl-benzoic acid tert-butyl ester) (21 mg, 0.04 mmol) in CH$_2$Cl$_2$ (0.5 mL) was added TFA (31 µl, 0.4 mmol) and the solution was stirred at RT for 24 h. The solvent was concentrated and the crude residue was purified by preparative HPLC (C18-ODB, 5 µm, 19×50 mm, waters, eluent: CH$_3$CN/H$_2$O+0.1% HCOOH flow: 20 mL/min, standard 20% method) to give after lyophilization of the purified fractions the desired material. MS (LC-MS): 468 [M+H]+, 490 [M+Na]+, 466 [M–H]–, 423.0 [M–CONH$_2$]–; $t_R$ (HPLC conditions a): 2.57 min.

Example 25

(2S,3S)-2-{[(2S,4R)-1-(1-Carbamoyl-1H-indol-3-ylcarbamoyl)-4-fluoro-pyrrolidine-2-carbonyl]-amino}-3-methyl-pentanoic acid

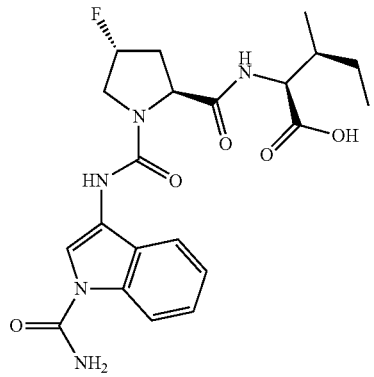 [SMILES: CC[C@H](C)[C@H](NC(=O)[C@@H]1C[C@@H](F)CN1C(=O)Nc1cn(C(N)=O)c2ccccc12)C(=O)O]

To a suspension of (2S,3S)-2-{[(2S,4R)-1-(1-carbamoyl-1H-indol-3-ylcarbamoyl)-4-fluoro-pyrrolidine-2-carbonyl]-amino}-3-methyl-pentanoic acid tert-butyl ester Example 15 (64 mg, 0.127 mmol) in CH$_2$Cl$_2$ (1 mL) was added TFA (97 µl, 1.27 mmol) and the resulting solution was stirred at RT for 20 h. TFA (1.27 mmol) was added again to ensure completion of the reaction. CH$_2$Cl$_2$ was concentrated and the crude residue was purified by preparative HPLC (C18-ODB, 5 µm, 19×50 mm, waters, eluent: CH$_3$CN/H$_2$O+0.1% HCOOH flow: 20 mL/min, standard 20% method) to give after lyophilization of the purified fractions the desired material which was dissolved in CH$_3$CN and was purified again on trimethylaminopropyl cartridge (Mega Bond Elut-SAX, 1 g, from Varian, conditioned with 20 mL of CH$_3$CN). The column was eluted with CH$_3$CN and the compound was finally released with 10 mL of HCl 0.1N in CH$_3$CN, concentration led to a residue which was taken up in Et$_2$O and filtered-off to give the desired material. MS (LC-MS): 448.1 [M+H]+, 446 [M−H]−; t$_R$ (HPLC conditions a): 2.67 min.

Scheme D2: general protocol described for the preparation of Example 26: (2S,4S)-4-Amino-pyrrolidine-1,2-dicarboxylic acid 1-[(1-carbamoyl-1H-indol-3-yl)-amide] 2-(3-chloro-2-fluoro-benzylamide)

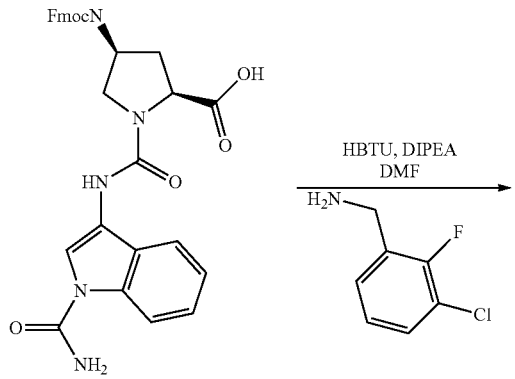

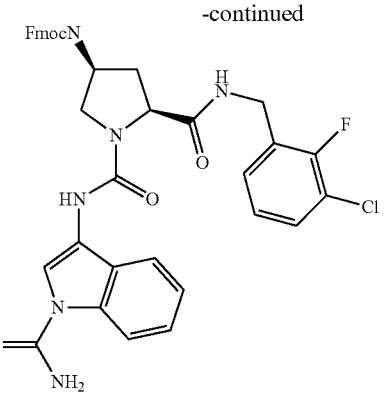

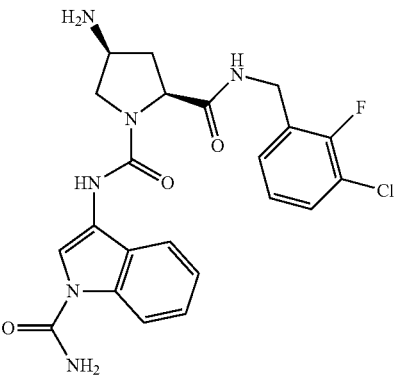

A. (2S,4S)-4-(9H-fluoren-9-ylmethoxycarbonylamino)-pyrrolidine-1,2-dicarboxylic acid 1-[(1-carbamoyl-1H-indol-3-yl)-amide]2-(3-chloro-2-fluoro-benzylamide)

(2S,4S)-1-[(1-carbamoyl-1H-indol-3-yl)-amide]-4-(9H-fluoren-9-ylmethoxycarbonylamino)-pyrrolidine-2-carboxylic acid (400 mg, 0.723 mmol, prepared as described in Scheme B10), 3-chloro-2-fluorobenzylamine (230 mg, 1.45 mmol) and HBTU (411 mg, 1.08 mmol) were dissolved in DMF (2.5 mL). DIPEA (0.378 mL, 2.18 mmol) was added and the reaction mixture was stirred at 25° C. for 16 h. The reaction mixture was diluted in EtOAc and successively washed with HCl 1N and NaHCO$_3$ (5% in water). The combined organic extracts were dried (Na$_2$SO$_4$), filtered and concentrated to dryness. The crude residue was purified by preparative HPLC (Waters Sunfire C18-ODB, 5 um, 30×100 mm, 20% CH$_3$CN/2 min, 20-100% CH$_3$CN/H$_2$O/18 min, 100% CH$_3$CN/2 min, CH$_3$CN and H$_2$O containing 0.1% TFA, flow: 40 mL/min) to give the desired compound. MS (LC/MS): 695 [M+H]+, 717 [M+Na]+; t$_R$ (HPLC conditions b): 5.16 min.

Alternative Protocol:

(2S,4S)-1-[(1-carbamoyl-1H-indol-3-yl)-amide]-4-(9H-fluoren-9-ylmethoxycarbonylamino)-pyrrolidine-2-carboxylic acid (40 mg, 0.072 mmol, prepared as described in Scheme B10) and amine (0.08 mmol) were dissolved in NMP (0.7 mL). DIPEA (0.025 mL, 0.143 mmol) and HBTU (40.6 mg, 0.107 mmol) were added and the reaction mixture was stirred at 25° C. for 90 min. The reaction mixture was diluted with MeOH (1 mL) and filtered over a PTFE membrane (0.45 um). The resulting filtrate was purified by preparative HPLC (Waters Sunfire C18-ODB, 5 um, 30×150 mm, 45% CH$_3$CN/3.0 min, 45-70% CH$_3$CN/H$_2$O/12 min, 70-95% CH$_3$CN/2 min, CH$_3$CN and H$_2$O containing 0.1% TFA, flow: 50 mL/min) to give the desired compound.

Alternative Protocol 2:

(2S,4S)-1-[(1-carbamoyl-1H-indol-3-yl)-amide]-4-(9H-fluoren-9-ylmethoxycarbonylamino)-pyrrolidine-2-carboxylic acid (70 mg, 0.126 mmol, prepared as described in Scheme B10), amine (0.253 mmol) and HBTU (100 mg, 0.264 mmol) were dissolved in DMF (2 mL). DIPEA (0.066 mL, 0.379 mmol) was added and the reaction mixture was stirred at 25° C. for 90 min. The reaction mixture was diluted with MeOH (2 mL), filtered over a PTFE membrane (0.45 um) and washed with MeOH. The resulting filtrate was purified by preparative HPLC (Waters Sunfire C18-ODB, 5 um, 30×150 mm, 20% $CH_3CN$/1.5 min, 20-88% $CH_3CN$/9 min, 88-100% $CH_3CN$/3 min, $H_2O$ containing 0.1% TFA, flow: 50 mL/min) to give the desired compound.

B. (2S,4S)-4-Amino-pyrrolidine-1,2-dicarboxylic acid 1-[(1-carbamoyl-1H-indol-3-yl)-amide]2-(3-chloro-2-fluoro-benzylamide)

To a solution of (2S,4S)-4-(9H-fluoren-9-ylmethoxycarbonylamino)-pyrrolidine-1,2-dicarboxylic acid 1-[(1-carbamoyl-1H-indol-3-yl)-amide]2-(3-chloro-2-fluoro-benzylamide) (209 mg, 0.3 mmol) in DMF (15 mL) was added piperazine polymer bound (Aldrich CAS 526290, loading=1.5 mmol/g, 2 g, 3.01 mmol) and the reaction mixture was stirred at 25° C. for 16 h. The reaction mixture was filtered, the polymer was washed with $CH_2Cl_2$ and the filtrate was concentrated to dryness. The crude residue was purified by preparative HPLC (Waters Sunfire C18-ODB, 5 um, 30×100 mm, 20% $CH_3CN$/2 min, 20-100% $CH_3CN$/$H_2O$/18 min, 100% $CH_3CN$/2 min, $CH_3CN$ and $H_2O$ containing 0.1% HCOOH, flow: 40 mL/min) to give the title compound as a formate salt. MS (LC/MS): 473 [M+H]+; $t_R$ (HPLC conditions b): 2.52 min.

Alternative Protocol:

Alternatively the crude residue can be purified by catch release using silicaPrep Tosic Acid-1 g column (SPE-R60530B-06S from Silicycle). The column was conditioned with MeOH (10 mL), and the crude residue dissolved in MeOH was added. The column was washed MeOH (10 mL) and the compound released by elution with 2M ammonia in MeOH (10 mL).

Alternative Protocol 2:

To solutions of (2S,4S)-4-(9H-fluoren-9-ylmethoxycarbonylamino)-pyrrolidine-1,2-dicarboxylic acid 1-[(1-carbamoyl-1H-indol-3-yl)-amide] amides in DMF (2.0 mL) was added piperazine polymer bound (Aldrich CAS 526290, loading=1.5 mmol/g, 2 g, 3.01 mmol), the reaction vessels were flushed with argon and the reaction mixtures were stirred at 25° C. for 48 h. The resulting solutions were poured onto cartridges containing 500 mg of silicaPrep Tosic Acid (SPE-R60530B-06S from Silicycle), conditioned with MeOH (10 mL). The columns were washed with MeOH (20 mL) and the compounds were then released by elution with 2M ammonia in MeOH (10 mL).

The examples below were prepared according to the general procedure described for Example 26 Scheme D2, using various amines in step A:

TABLE 2

| Example | Structure | Name | Characterization (end-table notes), TLC, $R_f$(eluent); MS (LC/MS); $t_R$ (HPLC conditions) |
|---|---|---|---|
| 27 | 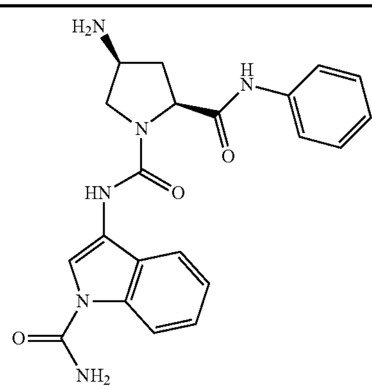 | (2S,4S)-4-Amino-pyrrolidine-1,2-dicarboxylic acid 1-[(1-carbamoyl-1H-indol-3-yl)-amide] 2-phenylamide | (1) 407 [M + H]+; $t_R$ (d): 0.6 min. |
| 28 | 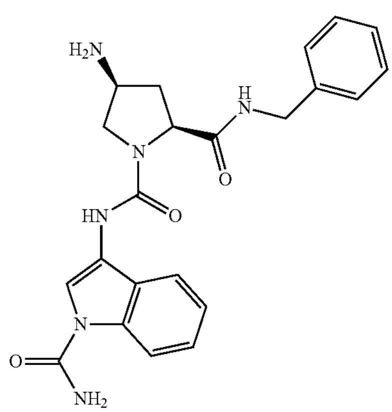 [SMILES: NC(=O)n1cc(NC(=O)N2C[C@@H](N)C[C@H]2C(=O)NCc2ccccc2)c2ccccc21] | (2S,4S)-4-Amino-pyrrolidine-1,2-dicarboxylic acid 2-benzylamide 1-[(1-carbamoyl-1H-indol-3-yl)-amide] | (2) 421.3 [M + H]+; $t_R$ (d): 0.62 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 29 | 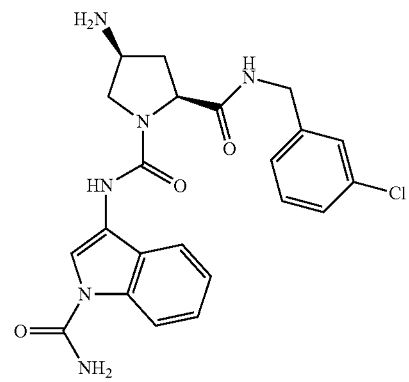 | (2S,4S)-4-Amino-pyrrolidine-1,2-dicarboxylic acid 1-[(1-carbamoyl-1H-indol-3-yl)-amide] 2-(3-chloro-benzylamide) as a formate salt | (1) 454/456.1 [M + H]+, 932.2 [2M + Na]+, 453.1 [M − H]−; $t_R$ (d): 2.51 min. |
| 30 | 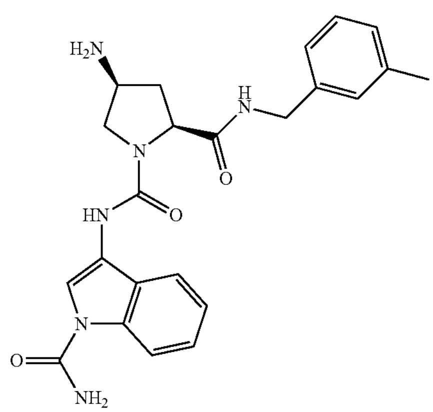 [SMILES: Cc1cccc(CNC(=O)[C@@H]2C[C@H](N)CN2C(=O)Nc2cn(C(N)=O)c3ccccc23)c1] | (2S,4S)-4-Amino-pyrrolidine-1,2-dicarboxylic acid 1-[(1-carbamoyl-1H-indol-3-yl)-amide] 2-(3-methyl-benzylamide) | (1) 435 [M + H]+; $t_R$ (b): 2.62 min. |
| 31 | 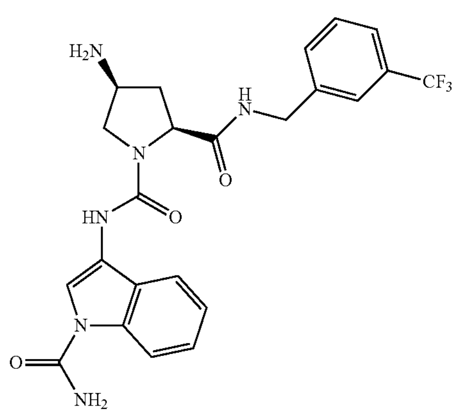 [SMILES: NC(=O)n1cc(NC(=O)N2C[C@@H](N)C[C@H]2C(=O)NCc2cccc(C(F)(F)F)c2)c2ccccc21] | (2S,4S)-4-Amino-pyrrolidine-1,2-dicarboxylic acid 1-[(1-carbamoyl-1H-indol-3-yl)-amide] 2-(3-trifluoromethyl-benzylamide) | (1) 489 [M + H]+; $t_R$ (b): 2.95 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 32 | 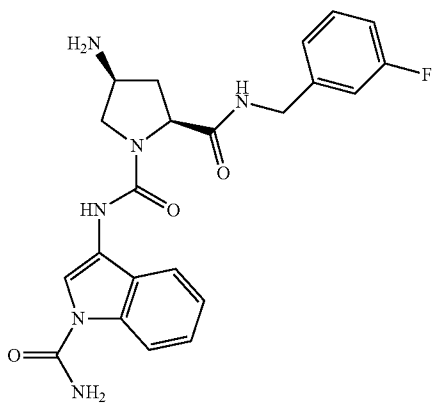 [SMILES: NC(=O)n1cc(NC(=O)N2C[C@@H](N)C[C@H]2C(=O)NCc2cccc(F)c2)c2ccccc21] | (2S,4S)-4-Amino-pyrrolidine-1,2-dicarboxylic acid 1-[(1-carbamoyl-1H-indol-3-yl)-amide] 2-(3-fluoro-benzylamide) | (2) 439.1 [M + H]+; $t_R$ (d): 0.75 min. |
| 33 | 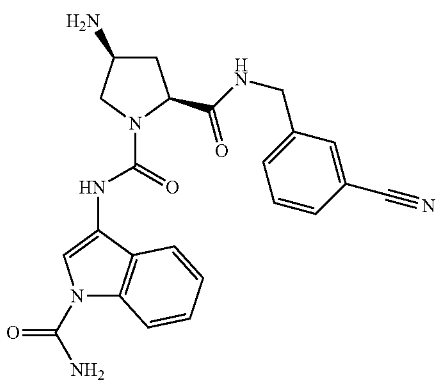 [SMILES: N#Cc1cccc(CNC(=O)[C@@H]2C[C@H](N)CN2C(=O)Nc2cn(C(N)=O)c3ccccc23)c1] | (2S,4S)-4-Amino-pyrrolidine-1,2-dicarboxylic acid 1-[(1-carbamoyl-1H-indol-3-yl)-amide] 2-(3-cyano-benzylamide) | (1) 446 [M + H]+; $t_R$ (b): 2.09 min. |
| 34 | 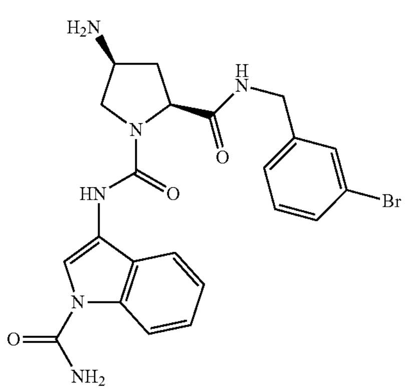 [SMILES: NC(=O)n1cc(NC(=O)N2C[C@@H](N)C[C@H]2C(=O)NCc2cccc(Br)c2)c2ccccc21] | (2S,4S)-4-Amino-pyrrolidine-1,2-dicarboxylic acid 2-(3-bromo-benzylamide) 1-[(1-carbamoyl-1H-indol-3-yl)-amide] | (1) 499/501 [M + H]+; $t_R$ (b): 2.78 min. |

TABLE 2-continued

| Example | Structure | Name | Characterization (end-table notes), TLC, R_f (eluent); MS (LC/MS); t_R (HPLC conditions) |
|---|---|---|---|
| 35 | 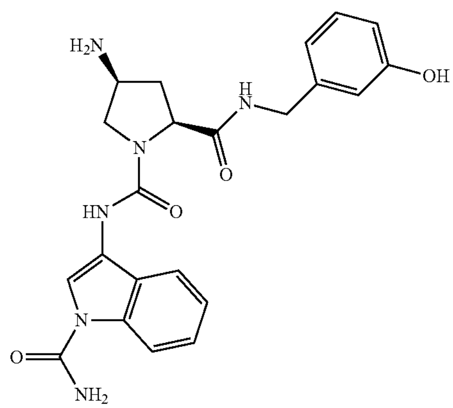 [SMILES: NC(=O)n1cc(NC(=O)N2C[C@@H](N)C[C@H]2C(=O)NCc2cccc(O)c2)c2ccccc21] | (2S,4S)-4-Amino-pyrrolidine-1,2-dicarboxylic acid 1-[(1-carbamoyl-1H-indol-3-yl)-amide] 2-(3-hydroxy-benzylamide) | (2) 437.1 [M + H]+; t_R (d): 0.52 min. |
| 36 | 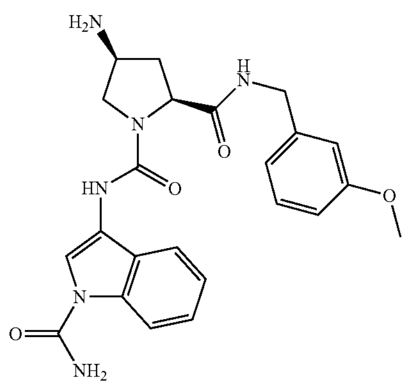 [SMILES: COc1cccc(CNC(=O)[C@@H]2C[C@H](N)CN2C(=O)Nc2cn(C(N)=O)c3ccccc23)c1] | (2S,4S)-4-Amino-pyrrolidine-1,2-dicarboxylic acid 1-[(1-carbamoyl-1H-indol-3-yl)-amide] 2-(3-methoxy-benzylamide) | (1) 451 [M + H]+; t_R (b): 2.36. |
| 37 | 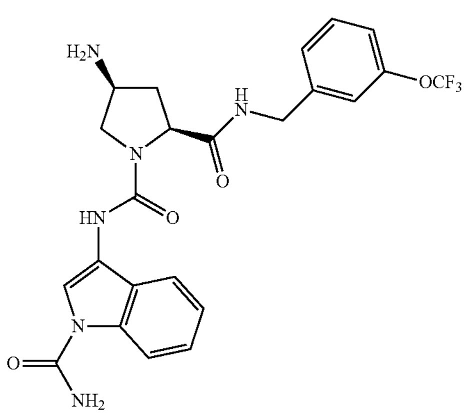 [SMILES: NC(=O)n1cc(NC(=O)N2C[C@@H](N)C[C@H]2C(=O)NCc2cccc(OC(F)(F)F)c2)c2ccccc21] | (2S,4S)-4-Amino-pyrrolidine-1,2-dicarboxylic acid 1-[(1-carbamoyl-1H-indol-3-yl)-amide] 2-(3-trifluoromethoxy-benzylamide) | (2) 505.1 [M + H]+; t_R (d): 0.90 min. |

TABLE 2-continued

| Example | Structure | Name | Characterization (end-table notes), TLC, R$_f$ (eluent); MS (LC/MS); t$_R$ (HPLC conditions) |
|---|---|---|---|
| 38 | 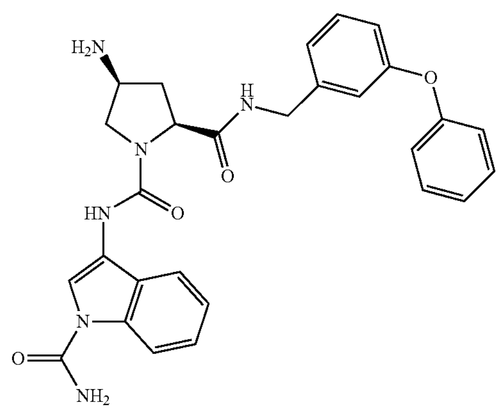 [SMILES: NC(=O)n1cc(NC(=O)N2C[C@@H](N)C[C@H]2C(=O)NCc2cccc(Oc3ccccc3)c2)c2ccccc21] | (2S,4S)-4-Amino-pyrrolidine-1,2-dicarboxylic acid 1-[(1-carbamoyl-1H-indol-3-yl)-amide] 2-(3-phenoxy-benzylamide) | (2) 513.2 [M + H]+; t$_R$ (d): 0.95 min. |
| 39 | 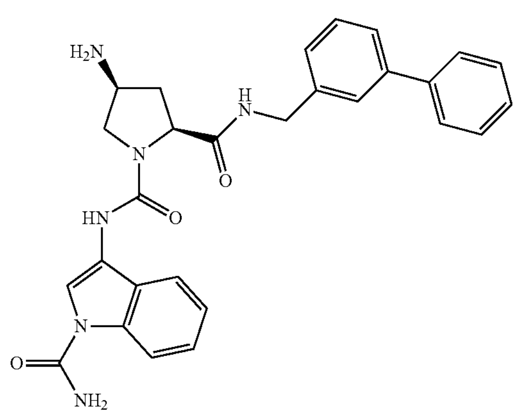 [SMILES: NC(=O)n1cc(NC(=O)N2C[C@@H](N)C[C@H]2C(=O)NCc2cccc(-c3ccccc3)c2)c2ccccc21] | (2S,4S)-4-Amino-pyrrolidine-1,2-dicarboxylic acid 2-[(biphenyl-3-ylmethyl)-amide] 1-[(1-carbamoyl-1H-indol-3-yl)-amide] as a formate salt | (1) 497.2 [M + H]+, 495.2 [M − H]−; t$_R$ (a): 2.8 min. |
| 40 | 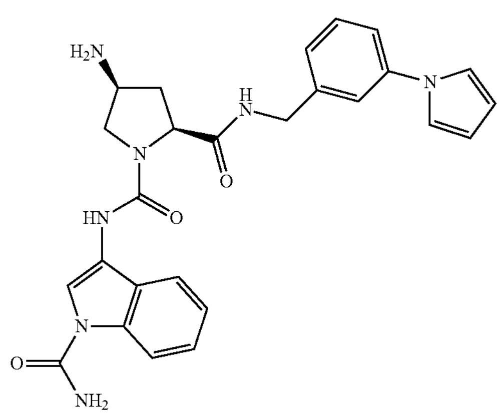 [SMILES: NC(=O)n1cc(NC(=O)N2C[C@@H](N)C[C@H]2C(=O)NCc2cccc(-n3cccc3)c2)c2ccccc21] | (2S,4S)-4-Amino-pyrrolidine-1,2-dicarboxylic acid 1-[(1-carbamoyl-1H-indol-3-yl)-amide] 2-(3-pyrrol-1-yl-benzylamide) | (2) 486.2 [M + H]+; t$_R$ (d): 0.87 min. |

TABLE 2-continued

| Example | Name | Characterization (end-table notes), TLC, $R_f$ (eluent); MS (LC/MS); $t_R$ (HPLC conditions) |
|---|---|---|
| 41 | (2S,4S)-4-Amino-pyrrolidine-1,2-dicarboxylic acid 1-[(1-carbamoyl-1H-indol-3-yl)-amide] 2-[3-(5-chloro-thiophen-2-yl)-benzylamide] | (1) $R_f$(MeOH) = 0.25; 537.1/539.2 [M + H]+, 536/538 [M − H]−; $t_R$ (a): 2.92 min. |
| 42 | (2S,4S)-4-Amino-pyrrolidine-1,2-dicarboxylic acid 1-[(1-carbamoyl-1H-indol-3-yl)-amide] 2-[(5'-chloro-[2,2']bithiophenyl-5-ylmethyl)-amide] | (1) $R_f$(MeOH) = 0.28; 543.1/545 [M + H]+, 541/543.2 [M − H]−; $t_R$ (a): 2.90 min. |
| 43 | (2S,4S)-4-Amino-pyrrolidine-1,2-dicarboxylic acid 1-[(1-carbamoyl-1H-indol-3-yl)-amide] 2-(4-methyl-benzylamide) | (3) 435.2 [M + H]+; $t_R$ (d): 0.87 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 44 | 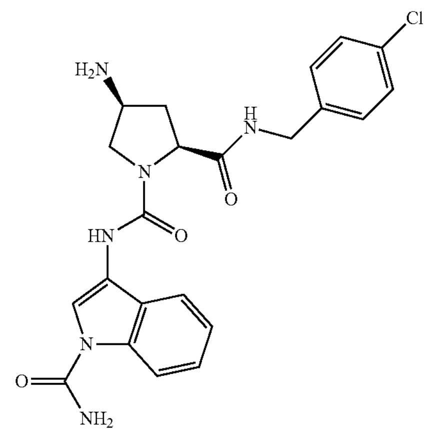 [SMILES: NC(=O)n1cc(NC(=O)N2C[C@@H](N)C[C@H]2C(=O)NCc2ccc(Cl)cc2)c2ccccc21] | (2S,4S)-4-Amino-pyrrolidine-1,2-dicarboxylic acid 1-[(1-carbamoyl-1H-indol-3-yl)-amide] 2-(4-chloro-benzylamide) | (2) 445 [M + H]+; $t_R$ (d): 0.82 min. |
| 45 | 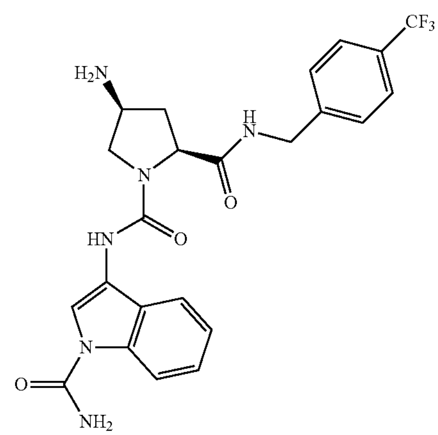 [SMILES: NC(=O)n1cc(NC(=O)N2C[C@@H](N)C[C@H]2C(=O)NCc2ccc(C(F)(F)F)cc2)c2ccccc21] | (2S,4S)-4-Amino-pyrrolidine-1,2-dicarboxylic acid 1-[(1-carbamoyl-1H-indol-3-yl)-amide] 2-(4-trifluoromethyl-benzylamide) | (2) 489.1 [M + H]+; $t_R$ (d): 0.88 min. |
| 46 | 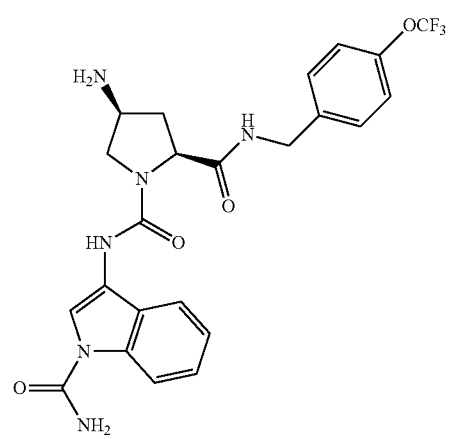 [SMILES: NC(=O)n1cc(NC(=O)N2C[C@@H](N)C[C@H]2C(=O)NCc2ccc(OC(F)(F)F)cc2)c2ccccc21] | (2S,4S)-4-Amino-pyrrolidine-1,2-dicarboxylic acid 1-[(1-carbamoyl-1H-indol-3-yl)-amide] 2-(4-trifluoromethoxy-benzylamide) | (2) 505.1 [M + H]+; $t_R$ (d): 0.91 min. |

| Example | Structure | Name | Characterization (end-table notes), TLC, $R_f$ (eluent); MS (LC/MS); $t_R$ (HPLC conditions) |
|---|---|---|---|
| 47 | 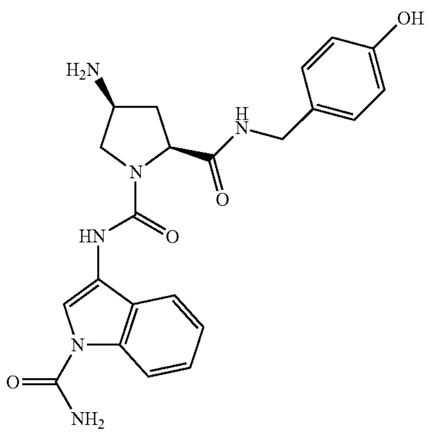 [SMILES: NC(=O)n1cc(NC(=O)N2C[C@@H](N)C[C@H]2C(=O)NCc2ccc(O)cc2)c2ccccc21] | (2S,4S)-4-Amino-pyrrolidine-1,2-dicarboxylic acid 1-[(1-carbamoyl-1H-indol-3-yl)-amide] 2-(4-hydroxy-benzylamide) | (2) 437.1 [M + H]+; $t_R$ (d): 0.52 min. |
| 48 | 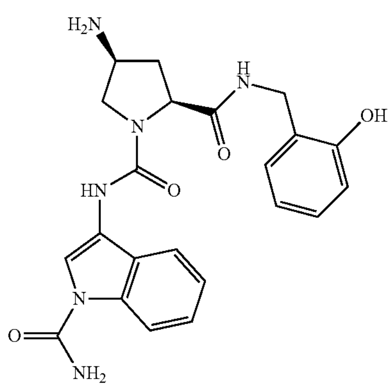 [SMILES: NC(=O)n1cc(NC(=O)N2C[C@@H](N)C[C@H]2C(=O)NCc2ccccc2O)c2ccccc21] | (2S,4S)-4-Amino-pyrrolidine-1,2-dicarboxylic acid 1-[(1-carbamoyl-1H-indol-3-yl)-amide] 2-(2-hydroxy-benzylamide) | (3) 437.1 [M + H]+; $t_R$ (d): 0.72 min. |
| 49 | 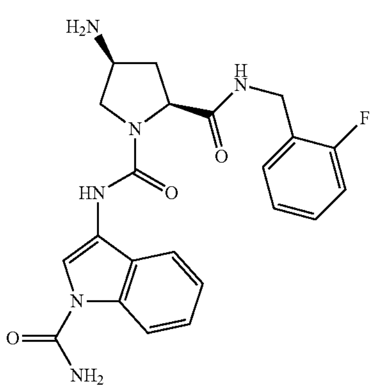 [SMILES: NC(=O)n1cc(NC(=O)N2C[C@@H](N)C[C@H]2C(=O)NCc2ccccc2F)c2ccccc21] | (2S,4S)-4-Amino-pyrrolidine-1,2-dicarboxylic acid 1-[(1-carbamoyl-1H-indol-3-yl)-amide] 2-(2-fluoro-benzylamide) | (1) 439.3 [M + H]+; $t_R$ (b): 2.12 min. |

TABLE 2-continued

| Example | Structure | Name | Characterization (end-table notes), TLC, R_f (eluent); MS (LC/MS); t_R (HPLC conditions) |
|---|---|---|---|
| 50 | 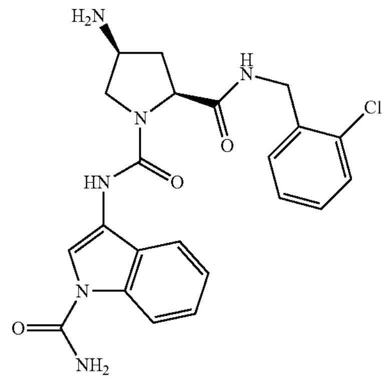 [SMILES: NC(=O)n1cc(NC(=O)N2C[C@@H](N)C[C@H]2C(=O)NCc2ccccc2Cl)c2ccccc21] | (2S,4S)-4-Amino-pyrrolidine-1,2-dicarboxylic acid 1-[(1-carbamoyl-1H-indol-3-yl)-amide] 2-(2-chloro-benzylamide) | (3) 455.1 [M + H]+; t_R (d): 0.88 min. |
| 51 | 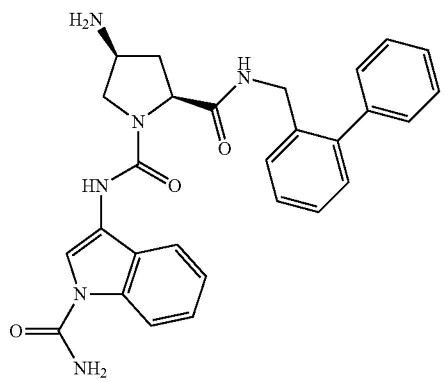 [SMILES: NC(=O)n1cc(NC(=O)N2C[C@@H](N)C[C@H]2C(=O)NCc2ccccc2-c2ccccc2)c2ccccc21] | (2S,4S)-4-Amino-pyrrolidine-1,2-dicarboxylic acid 2-[(biphenyl-2-ylmethyl)-amide] 1-[(1-carbamoyl-1H-indol-3-yl)-amide] | (3) 497.1 [M + H]+; t_R (d): 1.02 min. |
| 52 | 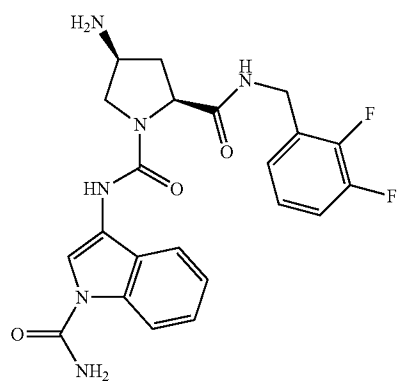 [SMILES: NC(=O)n1cc(NC(=O)N2C[C@@H](N)C[C@H]2C(=O)NCc2cccc(F)c2F)c2ccccc21] | (2S,4S)-4-Amino-pyrrolidine-1,2-dicarboxylic acid 1-[(1-carbamoyl-1H-indol-3-yl)-amide] 2-(2,3-difluoro-benzylamide) | (1) 457.2 [M + H]+; t_R (b): 2.24 min. |
| 53 | 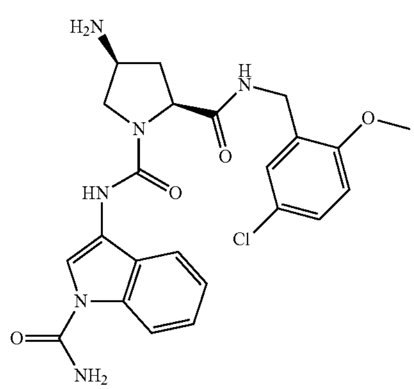 [SMILES: COc1ccc(Cl)cc1CNC(=O)[C@@H]1C[C@H](N)CN1C(=O)Nc1cn(C(N)=O)c2ccccc12] | (2S,4S)-4-Amino-pyrrolidine-1,2-dicarboxylic acid 1-[(1-carbamoyl-1H-indol-3-yl)-amide] 2-(5-chloro-2-methoxy-benzylamide) | (1) 485 [M + H]+; t_R (b): 2.80 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 54 | 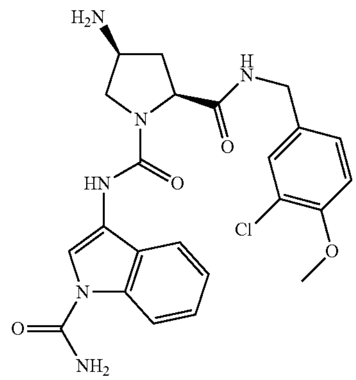 [SMILES: COc1ccc(CNC(=O)[C@@H]2C[C@H](N)CN2C(=O)Nc2cn(C(N)=O)c3ccccc23)cc1Cl] | (2S,4S)-4-Amino-pyrrolidine-1,2-dicarboxylic acid 1-[(1-carbamoyl-1H-indol-3-yl)-amide] 2-(3-chloro-4-methoxy-benzylamide) | (1) 485 [M + H]+; $t_R$ (b): 2.67 min. |
| 55 | 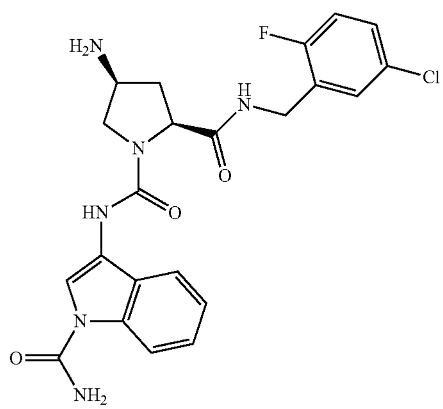 [SMILES: NC(=O)n1cc(NC(=O)N2C[C@@H](N)C[C@H]2C(=O)NCc2cc(Cl)ccc2F)c2ccccc21] | (2S,4S)-4-Amino-pyrrolidine-1,2-dicarboxylic acid 1-[(1-carbamoyl-1H-indol-3-yl)-amide] 2-(5-chloro-2-fluoro-benzylamide) | (1) 473 [M + H]+; $t_R$ (b): 2.68 min. |
| 56 | 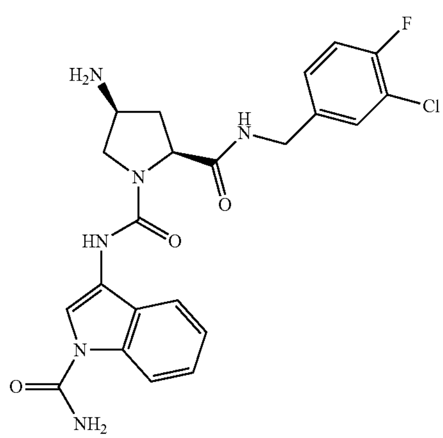 [SMILES: NC(=O)n1cc(NC(=O)N2C[C@@H](N)C[C@H]2C(=O)NCc2ccc(F)c(Cl)c2)c2ccccc21] | (2S,4S)-4-Amino-pyrrolidine-1,2-dicarboxylic acid 1-[(1-carbamoyl-1H-indol-3-yl)-amide] 2-(3-chloro-4-fluoro-benzylamide) | (1) 473 [M + H]+; $t_R$ (b): 2.77 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 57 | 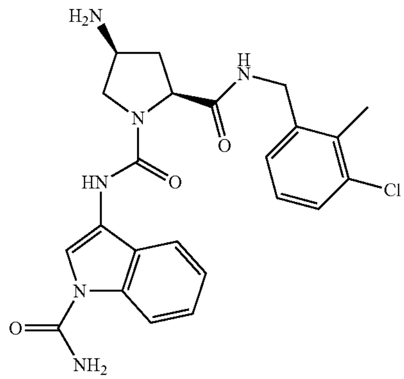 [SMILES: Cc1c(Cl)cccc1CNC(=O)[C@@H]1C[C@H](N)CN1C(=O)Nc1cn(C(N)=O)c2ccccc12] | (2S,4S)-4-Amino-pyrrolidine-1,2-dicarboxylic acid 1-[(1-carbamoyl-1H-indol-3-yl)-amide] 2-(3-chloro-2-methyl-benzylamide) | (1) 469 [M + H]+; $t_R$ (b): 2.82 min. |
| 58 | 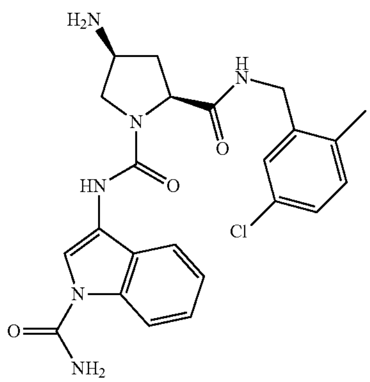 [SMILES: Cc1ccc(Cl)cc1CNC(=O)[C@@H]1C[C@H](N)CN1C(=O)Nc1cn(C(N)=O)c2ccccc12] | (2S,4S)-4-Amino-pyrrolidine-1,2-dicarboxylic acid 1-[(1-carbamoyl-1H-indol-3-yl)-amide] 2-(5-chloro-2-methyl-benzylamide) | (1) 469 [M + H]+; $t_R$ (b): 2.84 min. |
| 59 | 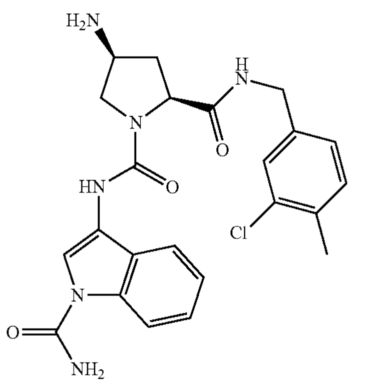 [SMILES: Cc1ccc(CNC(=O)[C@@H]2C[C@H](N)CN2C(=O)Nc2cn(C(N)=O)c3ccccc23)cc1Cl] | (2S,4S)-4-Amino-pyrrolidine-1,2-dicarboxylic acid 1-[(1-carbamoyl-1H-indol-3-yl)-amide] 2-(3-chloro-4-methyl-benzylamide) | (1) 469 [M + H]+; $t_R$ (b): 2.93 min. |
| 60 | 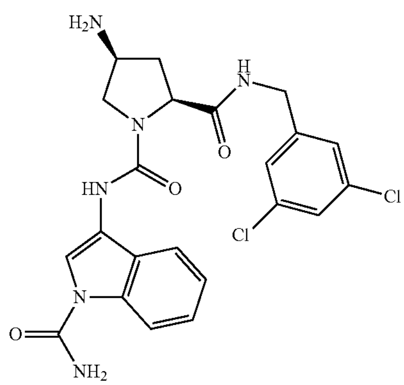 [SMILES: NC(=O)n1cc(NC(=O)N2C[C@@H](N)C[C@H]2C(=O)NCc2cc(Cl)cc(Cl)c2)c2ccccc21] | (2S,4S)-4-Amino-pyrrolidine-1,2-dicarboxylic acid 1-[(1-carbamoyl-1H-indol-3-yl)-amide] 2-(3,5-dichloro-benzylamide) | (3) 489.1 [M + H]+; $t_R$ (d): 0.96 min. |

TABLE 2-continued

| Example | Structure | Name | Characterization (end-table notes), TLC, R$_f$ (eluent); MS (LC/MS); t$_R$ (HPLC conditions) |
|---|---|---|---|
| 61 | 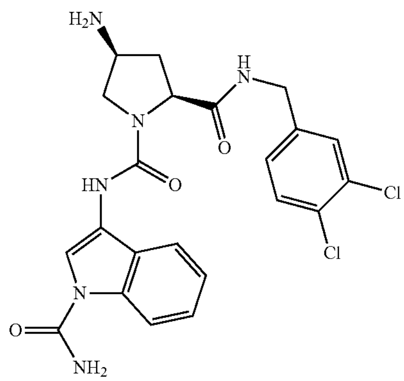 [SMILES: NC(=O)n1cc(NC(=O)N2C[C@@H](N)C[C@H]2C(=O)NCc2ccc(Cl)c(Cl)c2)c2ccccc21] | (2S,4S)-4-Amino-pyrrolidine-1,2-dicarboxylic acid 1-[(1-carbamoyl-1H-indol-3-yl)-amide] 2-(3,4-dichloro-benzylamide) | (3) 489.1 [M + H]+; t$_R$ (d): 0.96 min. |
| 62 | 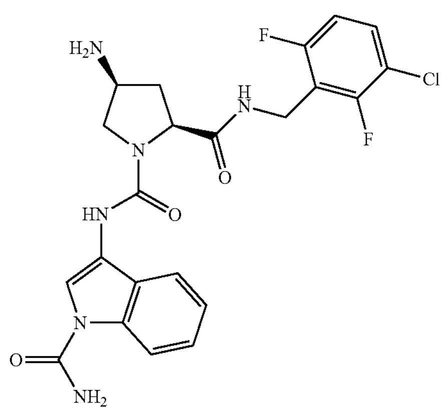 [SMILES: NC(=O)n1cc(NC(=O)N2C[C@@H](N)C[C@H]2C(=O)NCc2c(F)ccc(Cl)c2F)c2ccccc21] | (2S,4S)-4-Amino-pyrrolidine-1,2-dicarboxylic acid 1-[(1-carbamoyl-1H-indol-3-yl)-amide] 2-(3-chloro-2,6-difluoro-benzylamide) | (3) 491.1 [M + H]+; t$_R$ (d): 0.88 min. |
| 63 | 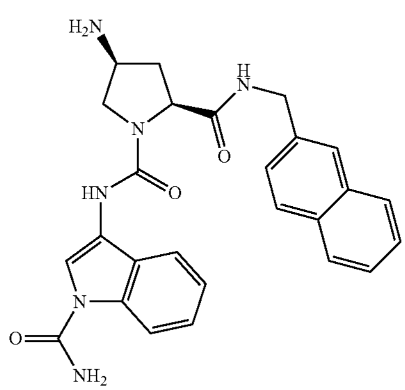 [SMILES: NC(=O)n1cc(NC(=O)N2C[C@@H](N)C[C@H]2C(=O)NCc2ccc3ccccc3c2)c2ccccc21] | (2S,4S)-4-Amino-pyrrolidine-1,2-dicarboxylic acid 1-[(1-carbamoyl-1H-indol-3-yl)-amide] 2-[(naphthalen-2-ylmethyl)-amide] | (3) 471.2 [M + H]+; t$_R$ (d): 0.95 min. |

TABLE 2-continued

| Example | Name | Characterization (end-table notes), TLC, $R_f$ (eluent); MS (LC/MS); $t_R$ (HPLC conditions) |
|---|---|---|
| 64 | (2S,4S)-4-Amino-pyrrolidine-1,2-dicarboxylic acid 1-[(1-carbamoyl-1H-indol-3-yl)-amide] 2-[(naphthalen-1-ylmethyl)-amide] | (3) 471.2 [M + H]+; $t_R$ (d): 0.94 min. |
| 65 | (2S,4S)-4-Amino-pyrrolidine-1,2-dicarboxylic acid 1-[(1-carbamoyl-1H-indol-3-yl)-amide] 2-[(5-methyl-thiazol-2-ylmethyl)-amide] | (3,4) 442.1 [M + H]+; $t_R$ (d): 0.60 min. |
| 66 | (2S,4S)-4-Amino-pyrrolidine-1,2-dicarboxylic acid 1-[(1-carbamoyl-1H-indol-3-yl)-amide] 2-[(5-chloro-thiophen-2-ylmethyl)-amide] | (1) 461 [M + H]+; $t_R$ (b): 2.37 min. |
| 67 | (2S,4S)-4-Amino-pyrrolidine-1,2-dicarboxylic acid 1-[(1-carbamoyl-1H-indol-3-yl)-amide] 2-[(4-methyl-pyridin-2-ylmethyl)-amide] | (3,4) 436.2 [M + H]+; $t_R$ (e): 1.13 min. |

TABLE 2-continued

| Example | Structure | Name | Characterization (end-table notes), TLC, R$_f$ (eluent); MS (LC/MS); t$_R$ (HPLC conditions) |
|---|---|---|---|
| 68 | 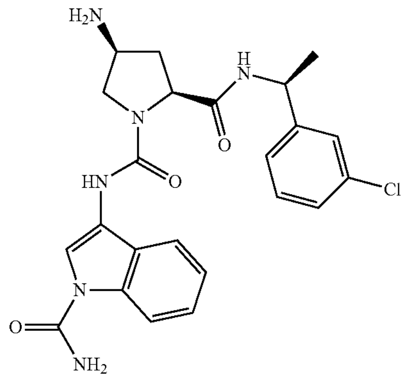 [SMILES: C[C@H](NC(=O)[C@@H]1C[C@H](N)CN1C(=O)Nc1cn(C(N)=O)c2ccccc12)c1cccc(Cl)c1] | (2S,4S)-4-Amino-pyrrolidine-1,2-dicarboxylic acid 1-[(1-carbamoyl-1H-indol-3-yl)-amide] 2-{[(S)-1-(3-chloro-phenyl)-ethyl]-amide} as a formate salt | (1) 469/471 [M + H]+, 424/426 [M − CONH$_2$]−; t$_R$ (a): 2.57 min. |
| 69 | 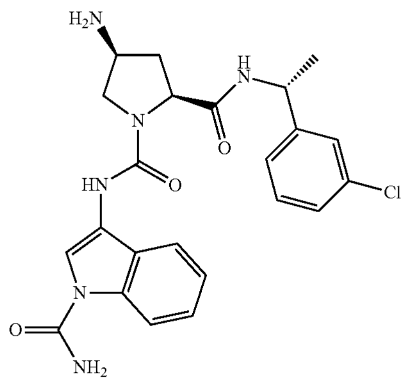 [SMILES: C[C@@H](NC(=O)[C@@H]1C[C@H](N)CN1C(=O)Nc1cn(C(N)=O)c2ccccc12)c1cccc(Cl)c1] | (2S,4S)-4-Amino-pyrrolidine-1,2-dicarboxylic acid 1-[(1-carbamoyl-1H-indol-3-yl)-amide] 2-{[(R)-1-(3-chloro-phenyl)-ethyl]-amide} as a formate salt | (1) 469/471 [M + H]+, 424/426 [M − CONH$_2$]−; t$_R$ (a): 2.59 min. |
| 70 | 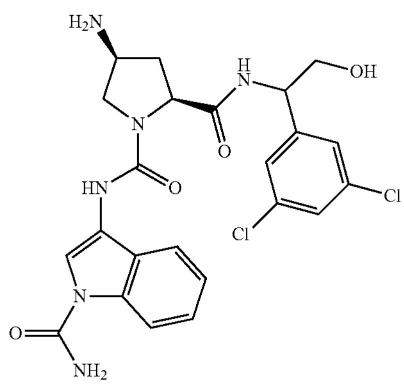 [SMILES: NC(=O)n1cc(NC(=O)N2C[C@@H](N)C[C@H]2C(=O)NC(CO)c2cc(Cl)cc(Cl)c2)c2ccccc21] | (2S,4S)-4-Amino-pyrrolidine-1,2-dicarboxylic acid 1-[(1-carbamoyl-1H-indol-3-yl)-amide] 2-{[1-(3,5-dichloro-phenyl)-2-hydroxy-ethyl]-amide} | (1) mixture of 2 diastereomers. 519 [M + H]+; t$_R$ (b): 2.72/2.76 min. |
| 71 | 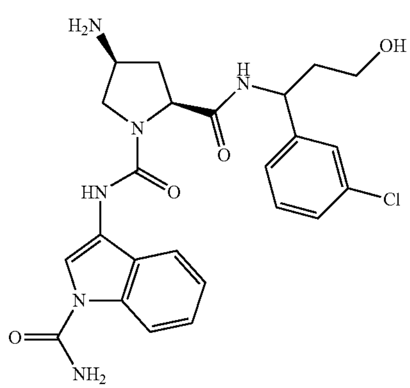 [SMILES: NC(=O)n1cc(NC(=O)N2C[C@@H](N)C[C@H]2C(=O)NC(CCO)c2cccc(Cl)c2)c2ccccc21] | (2S,4S)-4-Amino-pyrrolidine-1,2-dicarboxylic acid 1-[(1-carbamoyl-1H-indol-3-yl)-amide] 2-{[1-(3-chloro-phenyl)-3-hydroxy-propyl]-amide} | (3) 499.1 [M + H]+; t$_R$ (d): 0.82 min. |

| Example | Structure | Name | Characterization (end-table notes), TLC, $R_f$ (eluent); MS (LC/MS); $t_R$ (HPLC conditions) |
|---|---|---|---|
| 72 | 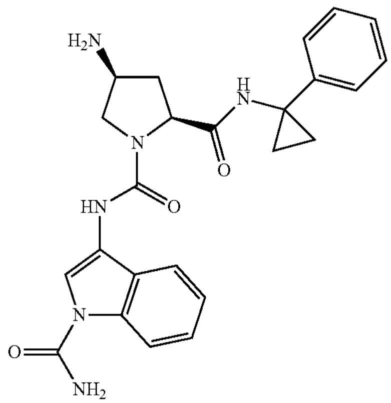 [SMILES: NC(=O)n1cc(NC(=O)N2C[C@@H](N)C[C@H]2C(=O)NC2(c3ccccc3)CC2)c2ccccc21] | (2S,4S)-4-Amino-pyrrolidine-1,2-dicarboxylic acid 1-[(1-carbamoyl-1H-indol-3-yl)-amide] 2-[(1-phenyl-cyclopropyl)-amide] | (2) 447.1 [M + H]+; $t_R$ (d): 0.77 min. |
| 73 | 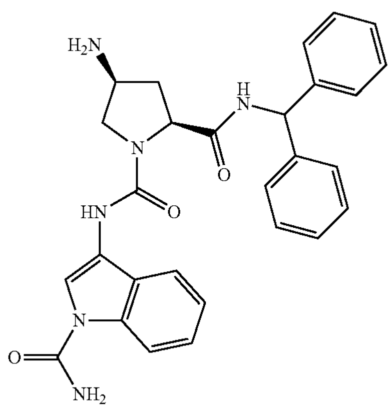 [SMILES: NC(=O)n1cc(NC(=O)N2C[C@@H](N)C[C@H]2C(=O)NC(c2ccccc2)c2ccccc2)c2ccccc21] | (2S,4S)-4-Amino-pyrrolidine-1,2-dicarboxylic acid 2-benzhydryl-amide 1-[(1-carbamoyl-1H-indol-3-yl)-amide] as a formate salt | (1) 497.2 [M + H]+, 495.2 [M − H]−; $t_R$ (a): 2.80 min. |
| 74 | 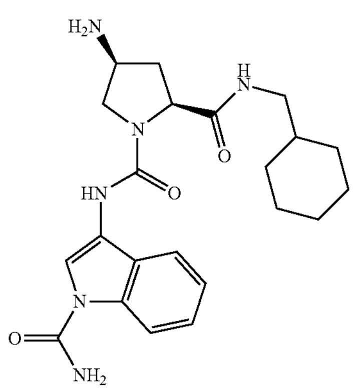 [SMILES: NC(=O)n1cc(NC(=O)N2C[C@@H](N)C[C@H]2C(=O)NCC2CCCCC2)c2ccccc21] | (2S,4S)-4-Amino-pyrrolidine-1,2-dicarboxylic acid 1-[(1-carbamoyl-1H-indol-3-yl)-amide] 2-cyclohexylmethyl-amide | (2) 427.1 [M + H]+, $t_R$ (d): 0.83 min. |

TABLE 2-continued

| Example | Name | Characterization (end-table notes), TLC, R_f (eluent); MS (LC/MS); t_R (HPLC conditions) |
|---|---|---|
| 75 | (2S,4S)-4-Amino-pyrrolidine-1,2-dicarboxylic acid 1-[(1-carbamoyl-1H-indol-3-yl)-amide] 2-[((1R*,2S*)-2-hydroxy-cyclohexylmethyl)-amide] | (2) mixture of trans diastereomers: 443.2 [M + H]+, 465.2 [M + Na]+, 441.2 [M − H]−; t_R (a): 1.84/1.36 min. |
| 76 | (2S,4S)-4-Amino-pyrrolidine-1,2-dicarboxylic acid 1-[(1-carbamoyl-1H-indol-3-yl)-amide] 2-[((1S,2S)-2-hydroxy-cyclohexylmethyl)-amide] | (3) 443.2 [M + H]+; t_R (d): 0.70 min. |
| 77 | (2S,4S)-4-Amino-pyrrolidine-1,2-dicarboxylic acid 1-[(1-carbamoyl-1H-indol-3-yl)-amide] 2-cyclohexylamide | (2) 413.1 [M + H]+, t_R (d): 0.75 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 78 | 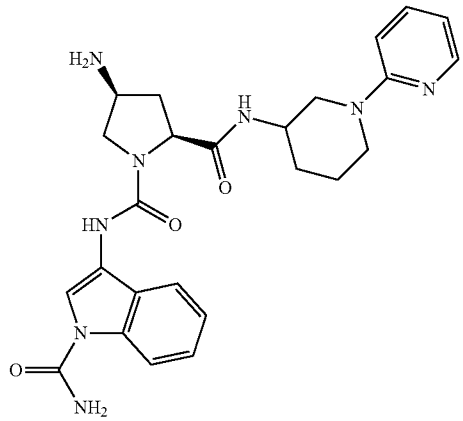 [SMILES: NC(=O)n1cc(NC(=O)N2C[C@@H](N)C[C@H]2C(=O)NC2CCCN(c3ccccn3)C2)c2ccccc21] | (2S,4S)-4-Amino-pyrrolidine-1,2-dicarboxylic acid 1-[(1-carbamoyl-1H-indol-3-yl)-amide] 2-[(3,4,5,6-tetrahydro-2H-[1,2']bipyridinyl-3-yl)-amide] | (2) Mixture of diastereomers 491.2 [M + H]+, $t_R$ (e): 1.12/1.19 min. |
| 79 | 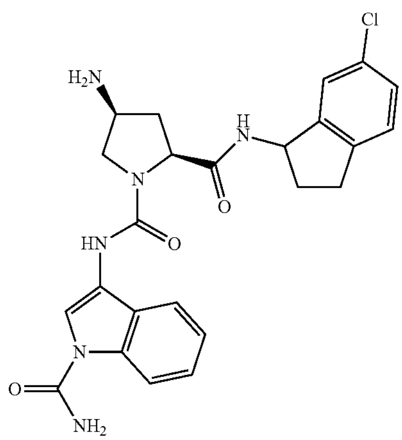 [SMILES: NC(=O)n1cc(NC(=O)N2C[C@@H](N)C[C@H]2C(=O)NC2CCc3ccc(Cl)cc32)c2ccccc21] | (2S,4S)-4-Amino-pyrrolidine-1,2-dicarboxylic acid 1-[(1-carbamoyl-1H-indol-3-yl)-amide] 2-[(6-chloro-indan-1-yl)-amide] | (3) 481.1 [M + H]+; $t_R$ (d): 0.94 min. |
| 80 | 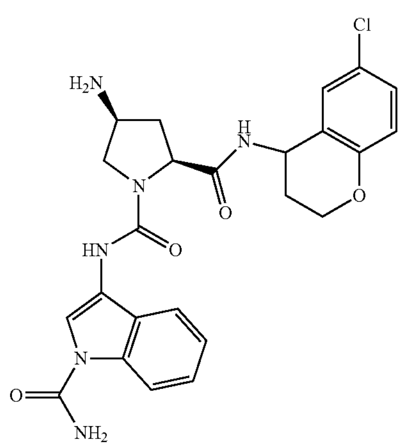 [SMILES: NC(=O)n1cc(NC(=O)N2C[C@@H](N)C[C@H]2C(=O)NC2CCOc3ccc(Cl)cc32)c2ccccc21] | (2S,4S)-4-Amino-pyrrolidine-1,2-dicarboxylic acid 1-[(1-carbamoyl-1H-indol-3-yl)-amide] 2-[(6-chloro-chroman-4-yl)-amide] | (3) 497.1 [M + H]+; $t_R$ (d): 0.92 min. |

TABLE 2-continued

| Example | Structure | Name | Characterization (end-table notes), TLC, R$_f$ (eluent); MS (LC/MS); t$_R$ (HPLC conditions) |
|---|---|---|---|
| 81 | 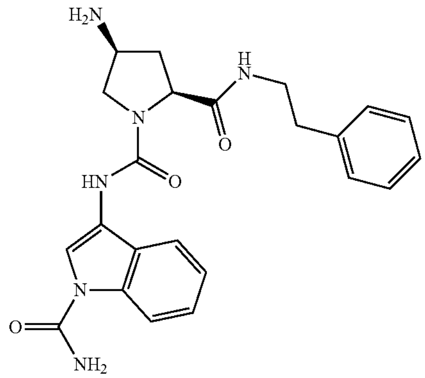 [SMILES: NC(=O)n1cc(NC(=O)N2C[C@@H](N)C[C@H]2C(=O)NCCc2ccccc2)c2ccccc21] | (2S,4S)-4-Amino-pyrrolidine-1,2-dicarboxylic acid 1-[(1-carbamoyl-1H-indol-3-yl)-amide] 2-(phenethyl-amide) | (2) 435.1 [M + H]+, t$_R$ (d): 0.77 min. |
| 82 | 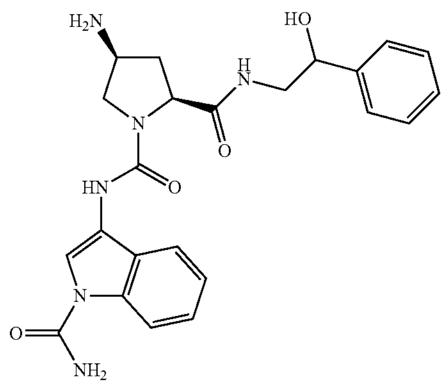 [SMILES: NC(=O)n1cc(NC(=O)N2C[C@@H](N)C[C@H]2C(=O)NCC(O)c2ccccc2)c2ccccc21] | (2S,4S)-4-Amino-pyrrolidine-1,2-dicarboxylic acid 1-[(1-carbamoyl-1H-indol-3-yl)-amide] 2-[(2-hydroxy-2-phenyl-ethyl)-amide] | (3) 451.2 [M + H]+; t$_R$ (d): 0.71 min. |
| 83 | 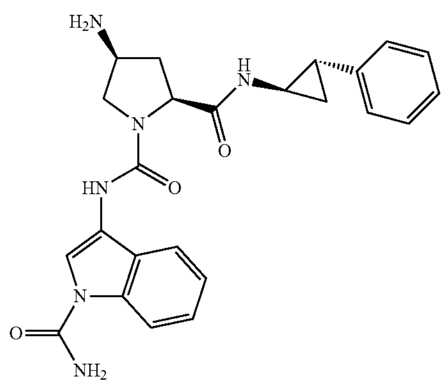 [SMILES: NC(=O)n1cc(NC(=O)N2C[C@@H](N)C[C@H]2C(=O)N[C@@H]2C[C@H]2c2ccccc2)c2ccccc21] | (2S,4S)-4-Amino-pyrrolidine-1,2-dicarboxylic acid 1-[(1-carbamoyl-1H-indol-3-yl)-amide] 2-[((1R,2S)-2-phenyl-cyclopropyl-amide] | (3) 447.2 [M + H]+; t$_R$ (d): 0.90 min. |
| 84 | 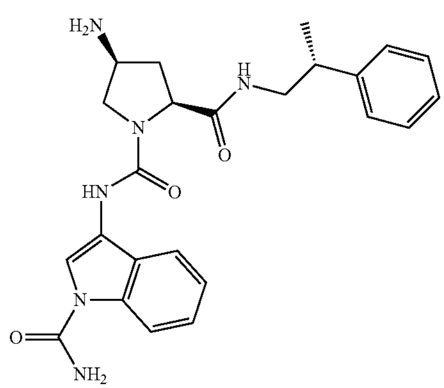 [SMILES: C[C@@H](CNC(=O)[C@@H]1C[C@H](N)CN1C(=O)Nc1cn(C(N)=O)c2ccccc12)c1ccccc1] | (2S,4S)-4-Amino-pyrrolidine-1,2-dicarboxylic acid 1-[(1-carbamoyl-1H-indol-3-yl)-amide] 2-[((R)-2-phenyl-propyl)-amide] | (3) 449.2 [M + H]+; t$_R$ (d): 0.90 min. |

TABLE 2-continued

| Example | Structure | Name | Characterization (end-table notes), TLC, R$_f$ (eluent); MS (LC/MS); t$_R$ (HPLC conditions) |
|---|---|---|---|
| 85 | 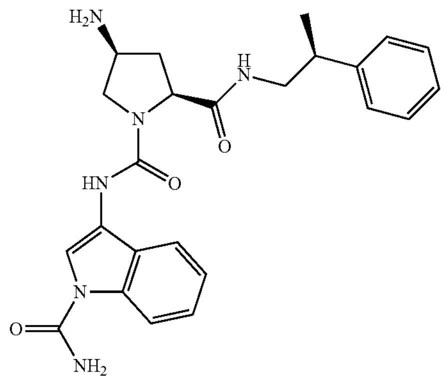 [SMILES: C[C@H](CNC(=O)[C@@H]1C[C@H](N)CN1C(=O)Nc1cn(C(N)=O)c2ccccc12)c1ccccc1] | (2S,4S)-4-Amino-pyrrolidine-1,2-dicarboxylic acid 1-[(1-carbamoyl-1H-indol-3-yl)-amide] 2-[((S)-2-phenyl-propyl)-amide] | (3) 449.2 [M + H]+; t$_R$ (d): 0.90 min. |
| 86 | 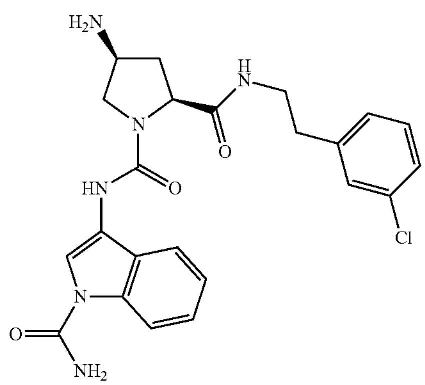 [SMILES: NC(=O)n1cc(NC(=O)N2C[C@@H](N)C[C@H]2C(=O)NCCc2cccc(Cl)c2)c2ccccc21] | (2S,4S)-4-Amino-pyrrolidine-1,2-dicarboxylic acid 1-[(1-carbamoyl-1H-indol-3-yl)-amide] 2-{[2-(3-chloro-phenyl)-ethyl]-amide} | (3) 469.1 [M + H]+; t$_R$ (d): 0.91 min. |
| 87 | 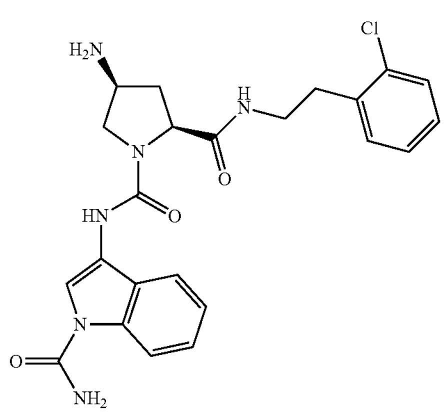 [SMILES: NC(=O)n1cc(NC(=O)N2C[C@@H](N)C[C@H]2C(=O)NCCc2ccccc2Cl)c2ccccc21] | (2S,4S)-4-Amino-pyrrolidine-1,2-dicarboxylic acid 1-[(1-carbamoyl-1Hindol-3-yl)-amide] 2-{[2-(2-chloro-phenyl)-ethyl]-amide} | (3) 469.1 [M + H]+; t$_R$ (d): 0.91 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 88 | 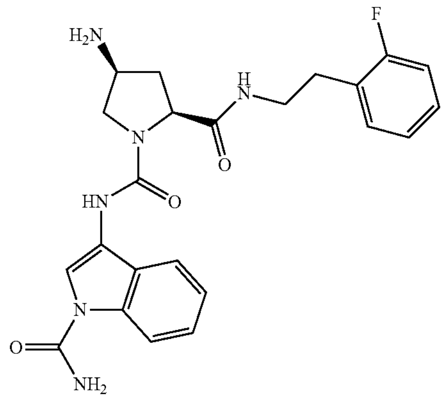 | (2S,4S)-4-Amino-pyrrolidine-1,2-dicarboxylic acid 1-[(1-carbamoyl-1Hindol-3-yl)-amide] 2-{[2-(2-fluoro-phenyl)-ethyl]-amide} | (3) 453.1 [M + H]+; $t_R$ (d): 0.86 min. |
| 89 | 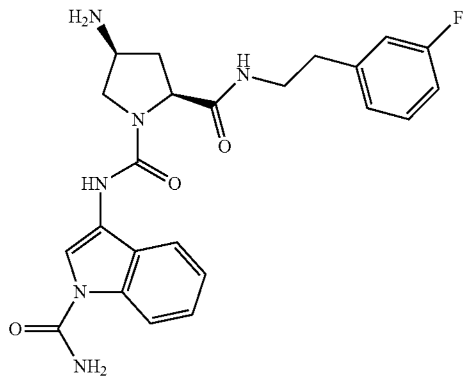 [SMILES: NC(=O)n1cc(NC(=O)N2C[C@@H](N)C[C@H]2C(=O)NCCc2cccc(F)c2)c2ccccc21] | (2S,4S)-4-Amino-pyrrolidine-1,2-dicarboxylic acid 1-[(1-carbamoyl-1Hindol-3-yl)-amide] 2-{[2-(3-fluoro-phenyl)-ethyl]-amide} | (3) 453.1 [M + H]+; $t_R$ (d): 0.86 min. |
| 90 | 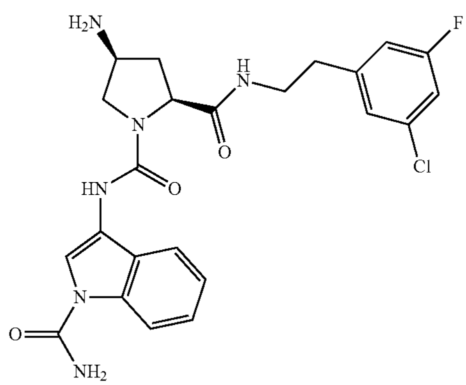 [SMILES: NC(=O)n1cc(NC(=O)N2C[C@@H](N)C[C@H]2C(=O)NCCc2cc(F)cc(Cl)c2)c2ccccc21] | (2S,4S)-4-Amino-pyrrolidine-1,2-dicarboxylic acid 1-[(1-carbamoyl-1H-indol-3-yl)-amide] 2-{[2-(3-chloro-5-fluoro-phenyl)-ethyl]-amide} | (3) 473.1 [M + H]+; $t_R$ (d): 0.90 min. |
| 91 | 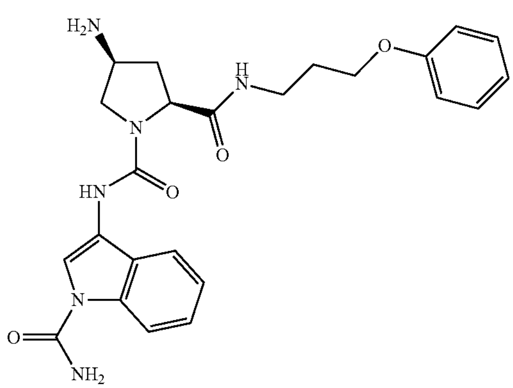 [SMILES: NC(=O)n1cc(NC(=O)N2C[C@@H](N)C[C@H]2C(=O)NCCCOc2ccccc2)c2ccccc21] | (2S,4S)-4-Amino-pyrrolidine-1,2-dicarboxylic acid 1-[(1-carbamoyl-1H-indol-3-yl)-amide] 2-[(2-phenoxy-ethyl)-amide] | (2) 451.1 [M + H]+, $t_R$ (d): 0.78 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 92 | 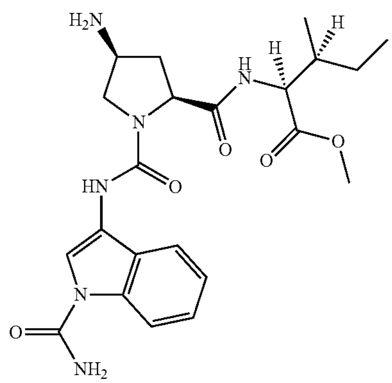 [SMILES: CC[C@H](C)[C@H](NC(=O)[C@@H]1C[C@H](N)CN1C(=O)Nc1cn(C(N)=O)c2ccccc12)C(=O)OC] | (2S,3S)-2-{[(2S,4S)-4-Amino-1-(1-carbamoyl-1H-indol-3-ylcarbamoyl)-pyrrolidine-2-carbonyl]-amino}-3-methyl-pentanoic acid methyl ester | (2) 459.1 [M + H]+, $t_R$ (d): 0.79 min. |
| 93 | 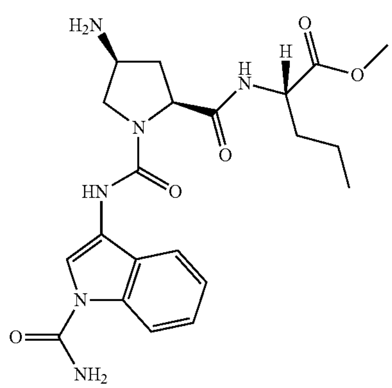 [SMILES: CCC[C@H](NC(=O)[C@@H]1C[C@H](N)CN1C(=O)Nc1cn(C(N)=O)c2ccccc12)C(=O)OC] | (S)-2-{[(2S,4S)-4-Amino-1-(1-carbamoyl-1H-indol-3-ylcarbamoyl)-pyrrolidine-2-carbonyl]-amino}-pentanoic acid methyl ester | (3) 445.2 [M + H]+; $t_R$ (d): 0.80 min. |
| 94 | 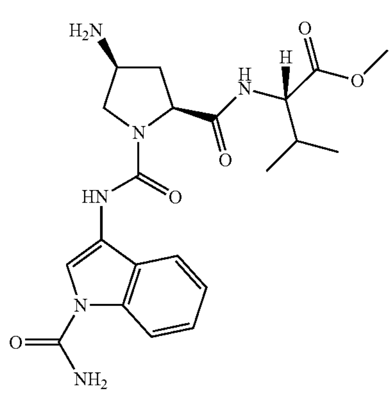 [SMILES: COC(=O)[C@@H](NC(=O)[C@@H]1C[C@H](N)CN1C(=O)Nc1cn(C(N)=O)c2ccccc12)C(C)C] | (R)-2-{[(2S,4S)-4-Amino-1-(1-carbamoyl-1H-indol-3-ylcarbamoyl)-pyrrolidine-2-carbonyl]-amino}-3-methyl-butyric acid methyl ester | (3) 445.2 [M + H]+; $t_R$ (d): 0.76 min. |

TABLE 2-continued

| Example | Structure | Name | Characterization (end-table notes), TLC, $R_f$ (eluent); MS (LC/MS); $t_R$ (HPLC conditions) |
|---|---|---|---|
| 95 | 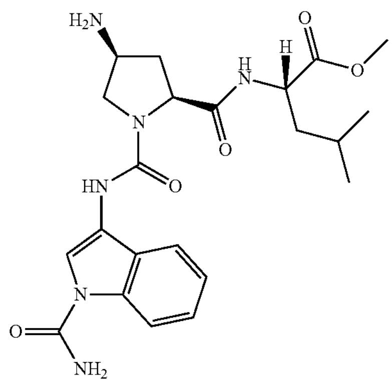 [SMILES: COC(=O)[C@H](CC(C)C)NC(=O)[C@@H]1C[C@H](N)CN1C(=O)Nc1cn(C(N)=O)c2ccccc12] | (S)-2-{[(2S,4S)-4-Amino-1-(1-carbamoyl-1H-indol-3-ylcarbamoyl)-pyrrolidine-2-carbonyl]-amino}-4-methyl-pentanoic acid methyl ester | (3) 459.2 [M + H]+; $t_R$ (d): 0.87 min. |
| 96 | 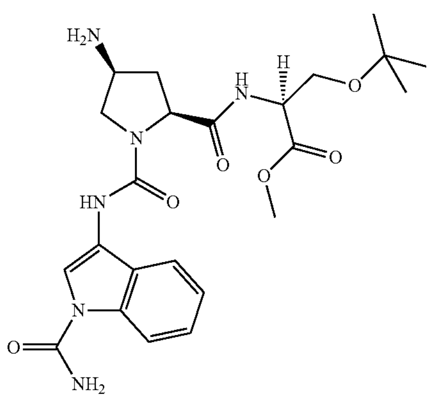 [SMILES: COC(=O)[C@H](COC(C)(C)C)NC(=O)[C@@H]1C[C@H](N)CN1C(=O)Nc1cn(C(N)=O)c2ccccc12] | (S)-2-{[(2S,4S)-4-Amino-1-(1-carbamoyl-1H-indol-3-ylcarbamoyl)-pyrrolidine-2-carbonyl]-amino}-3-tert-butoxy-propionic acid methyl ester | (3) 489.2 [M + H]+; $t_R$ (d): 0.87 min. |
| 97 | 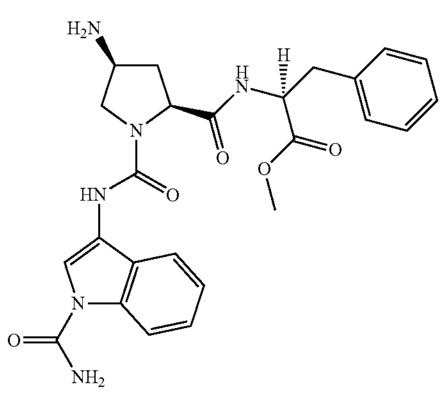 [SMILES: COC(=O)[C@H](Cc1ccccc1)NC(=O)[C@@H]1C[C@H](N)CN1C(=O)Nc1cn(C(N)=O)c2ccccc12] | (S)-2-{[(2S,4S)-4-Amino-1-(1-carbamoyl-1H-indol-3-ylcarbamoyl)-pyrrolidine-2-carbonyl]-amino}-3-phenyl-propionic acid methyl ester | (3) 493.2 [M + H]+; $t_R$ (d): 0.88 min. |

TABLE 2-continued

| Example | Structure | Name | Characterization (end-table notes), TLC, R_f (eluent); MS (LC/MS); t_R (HPLC conditions) |
|---|---|---|---|
| 98 | 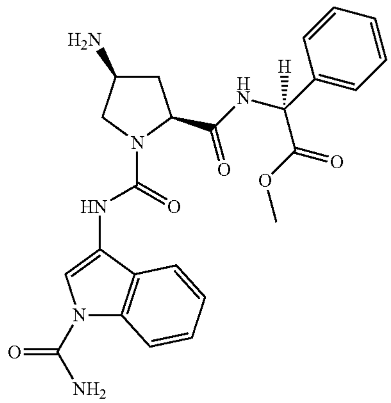 [SMILES: COC(=O)[C@@H](NC(=O)[C@@H]1C[C@H](N)CN1C(=O)Nc1cn(C(N)=O)c2ccccc12)c1ccccc1] | (S)-{[(2S,4S)-4-Amino-1-(1-carbamoyl-1H-indol-3-ylcarbamoyl)-pyrrolidine-2-carbonyl]-amino}-phenyl-acetic acid methyl ester | (3) 479.1 [M + H]+; t_R (d): 0.84 min. |
| 99 | 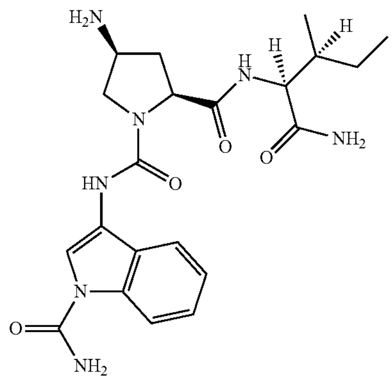 [SMILES: CC[C@H](C)[C@H](NC(=O)[C@@H]1C[C@H](N)CN1C(=O)Nc1cn(C(N)=O)c2ccccc12)C(N)=O] | (2S,4S)-4-Amino-pyrrolidine-1,2-dicarboxylic acid 1-[(1-carbamoyl-1H-indol-3-yl)-amide] 2-[((1S,2S)-1-carbamoyl-2-methyl-butyl)-amide] | (2) 444.1 [M + H]+, t_R (d): 0.61 min. |
| 100 | 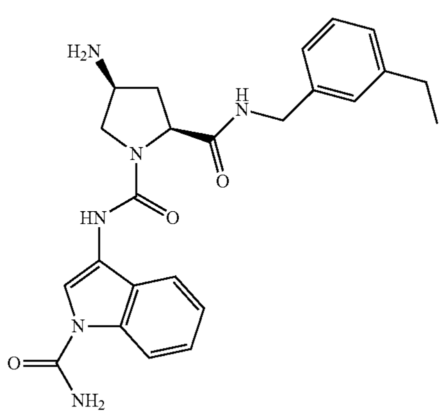 [SMILES: CCc1cccc(CNC(=O)[C@@H]2C[C@H](N)CN2C(=O)Nc2cn(C(N)=O)c3ccccc23)c1] | (2S,4S)-4-Amino-pyrrolidine-1,2-dicarboxylic acid 1-[(1-carbamoyl-1H-indol-3-yl)-amide] 2-(3-ethyl-benzylamide) | (2) 449.1 [M + H]+; t_R (d): 0.86 min. |

TABLE 2-continued

| Example | Structure | Name | Characterization (end-table notes), TLC, R_f (eluent); MS (LC/MS); t_R (HPLC conditions) |
|---|---|---|---|
| 101 | 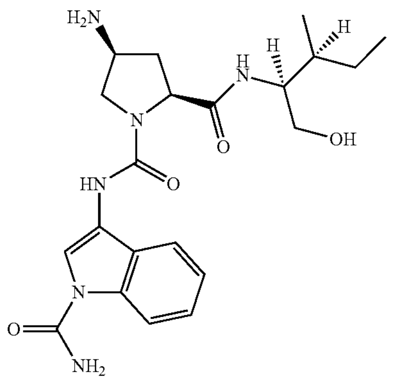 [SMILES: CC[C@H](C)[C@@H](CO)NC(=O)[C@@H]1C[C@H](N)CN1C(=O)Nc1cn(C(N)=O)c2ccccc12] | (2S,4S)-4-Amino-pyrrolidine-1,2-dicarboxylic acid 1-[(1-carbamoyl-1H-indol-3-yl)-amide] 2-[((1S,2S)-1-hydroxymethyl-2-methyl-butyl)-amide] | (2) 431.1 [M + H]+, t_R (d): 0.69 min. |

(1) Compound prepared according to the general procedure described for Example 26 Scheme D2; (2) Compound prepared according to the alternative protocol described for step A and using silica gel derivatized piperazine (SPE-R60530B-06S from Silicycle) in step B; (3) Compound prepared using the alternative protocols 2 for both step A and B; (4) in Step B stirring was continued at 60° C. for additional 30 h.

Example 102

(2S,4S)-4-Amino-pyrrolidine-1,2-dicarboxylic acid 1-[(1-carbamoyl-1H-indol-3-yl)-amide]2-[(3-isopropyl-phenyl)-amide]

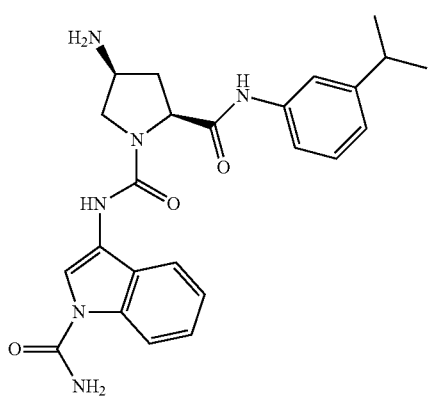 [SMILES: CC(C)c1cccc(NC(=O)[C@@H]2C[C@H](N)CN2C(=O)Nc2cn(C(N)=O)c3ccccc23)c1]

was prepared according to the general procedure described in Scheme D2 using 5 equivalents of 3-isopropylaniline in step A and silica gel derivatized piperazine (Silicycle, loading=0.9 mmol/g, cat. Number: SPE-R60030B) in step B. MS (LC/MS): 449.2 [M+H]+, 920.3 [2M+Na]+, 447.3 [M–H]–; t_R (HPLC conditions a): 2.74 min.

Example 103

(2S,4S)-4-Amino-pyrrolidine-1,2-dicarboxylic acid 2-biphenyl-3-ylamide 1-[(1-carbamoyl-1H-indol-3-yl)-amide]

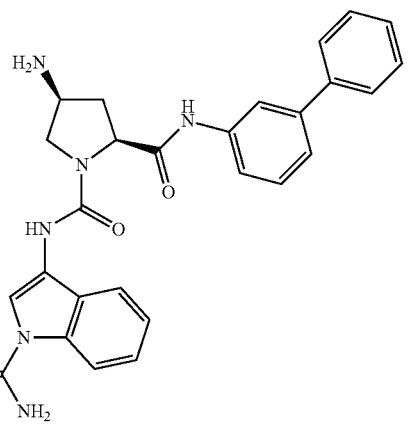

was prepared according to the general procedures described in Scheme D2 using 10 equivalents of biphenyl-3-ylamine in step A. MS (LC/MS): 483.3 [M+H]+, 481.2 [M–H]–; t_R (HPLC conditions a): 2.83 min.

Scheme D3

General Protocol Described for the Preparation Example 104

3-({(2S,4R)-4-Fluoro-2-[(2-fluoro-benzenesulfonylamino)-methyl]-pyrrolidine-1-carbonyl}-amino)-indole-1-carboxylic acid amide

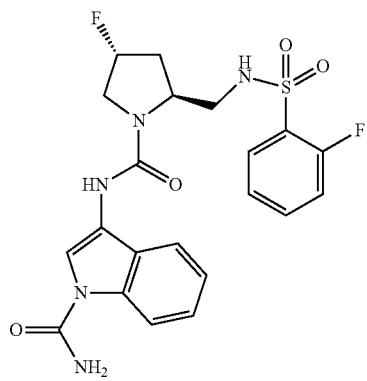 [SMILES: NC(=O)n1cc(NC(=O)N2C[C@H](F)C[C@H]2CNS(=O)(=O)c2ccccc2F)c2ccccc21]

To a mixture of 3-[((2S,4R)-2-aminomethyl-4-fluoro-pyrrolidine-1-carbonyl)-amino]-indole-1-carboxylic acid amide (52 mg, 0.163 mmol) (prepared as described Scheme B11) and 2-fluorobenzenesulfonyl chloride (24 μL, 0.179 mmol) in $CH_2Cl_2$ (0.5 mL), was added triethylamine (25 μL, 0.179 mmol) and the resulting suspension was stirred at RT under nitrogen overnight. The mixture was poured into water and extracted twice with $CH_2Cl_2$. The combined organic layers were dried over $Na_2SO_4$, filtered and concentrated. The crude residue was purified by preparative HPLC (Waters Sunfire, C18-ODB, 5 μm, 19×50 mm, eluent: 20% to 100% $CH_3CN$ in $H_2O$ in 15 min, $CH_3CN$ and $H_2O$ containing 0.1% HCOOH, flow: 20 mL/min) to give after lyophilization of the purified fractions the desired material. $R_f$, TLC (EtOAc)=0.55; MS (LC-MS): 478.1 [M+H]+, 500 [M+Na]+, 516 [M+K]+, 977.2 [2M+Na]+, 476 [M−H]−; $t_R$ (HPLC conditions f): 1.73 min.

The examples below were prepared according to the procedure described in Scheme D3 for Example 104, using various sulfonyl chlorides:

TABLE 3

| Example | Structure | Name | Characterization TLC, $R_f$ (eluent); MS (LC/MS); $t_R$ (HPLC conditions) |
|---|---|---|---|
| 105 | 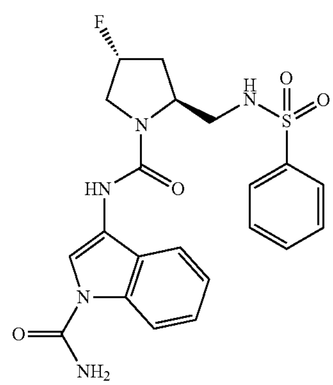 [SMILES: NC(=O)n1cc(NC(=O)N2C[C@H](F)C[C@H]2CNS(=O)(=O)c2ccccc2)c2ccccc21] | 3-{[(2S,4R)-2-(Benzenesulfonylaminomethyl)-4-fluoro-pyrrolidine-1-carbonyl]-amino}-indole-1-carboxylic acid amide | $R_f$(EtOAc) = 0.65; 460 [M + H]+, 482 [M + Na]+, 919 [2M + H]+, 941 [2M + Na], 458.2 [M − H]−; $t_R$ (f): 1.71 min. |
| 106 | 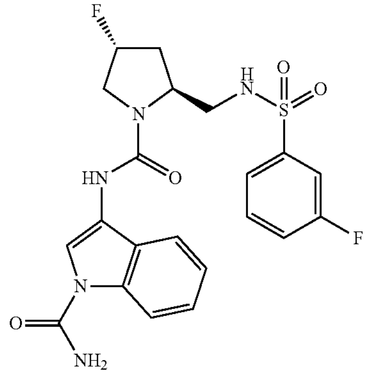 [SMILES: NC(=O)n1cc(NC(=O)N2C[C@H](F)C[C@H]2CNS(=O)(=O)c2cccc(F)c2)c2ccccc21] | 3-({(2S,4R)-4-Fluoro-2-[(3-fluoro-benzenesulfonylamino)-methyl]-pyrrolidine-1-carbonyl}-amino)-indole-1-carboxylic acid amide | $R_f$(EtOAc) = 0.7; 478 [M + H]+, 476 [M − H]−; $t_R$ (f): 1.79 min. |

| Example | Structure | Name | Characterization TLC, R$_f$ (eluent); MS (LC/MS); t$_R$ (HPLC conditions) |
|---|---|---|---|
| 107 | 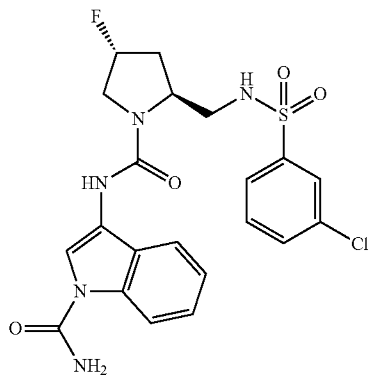 [SMILES: NC(=O)n1cc(NC(=O)N2C[C@H](F)C[C@H]2CNS(=O)(=O)c2cccc(Cl)c2)c2ccccc21] | 3-({(2S,4R)-4-Fluoro-2-[(3-chloro-benzenesulfonylamino)-methyl]-pyrrolidine-1-carbonyl}-amino)-indole-1-carboxylic acid amide | R$_f$ (EtOAc) = 0.7; 494/496 [M + H]+, 516.1/518.2 [M + Na]+, 492/494 [M − H]−; t$_R$ (f): 1.99 min. |
| 108 | 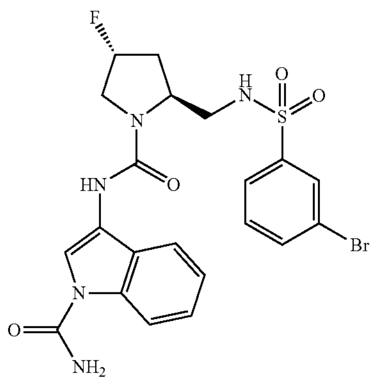 [SMILES: NC(=O)n1cc(NC(=O)N2C[C@H](F)C[C@H]2CNS(=O)(=O)c2cccc(Br)c2)c2ccccc21] | 3-({(2S,4R)-4-Fluoro-2-[(3-bromo-benzenesulfonylamino)-methyl]-pyrrolidine-1-carbonyl}-amino)-indole-1-carboxylic acid amide | R$_f$ (EtOAc) = 0.70; 537.9/539.9 [M + H]+, 559.9/561.8 [M + Na]+, 356/538 [M − H]−; t$_R$ (f): 1.89 min. |
| 109 | 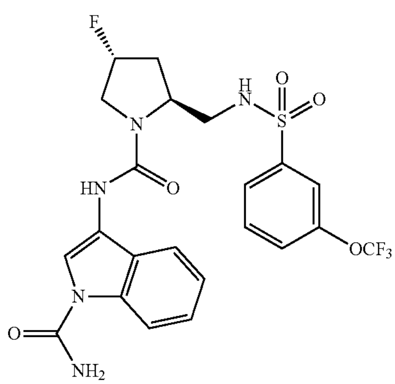 [SMILES: NC(=O)n1cc(NC(=O)N2C[C@H](F)C[C@H]2CNS(=O)(=O)c2cccc(OC(F)(F)F)c2)c2ccccc21] | 3-({(2S,4R)-4-Fluoro-2-[(3-trifluoromethoxy-benzenesulfonylamino)-methyl]-pyrrolidine-1-carbonyl}-amino)-indole-1-carboxylic acid amide | R$_f$ (EtOAc) = 0.75; 544.2 [M + H]+, 566 [M + Na]+, 542 [M − H]−; t$_R$ (f): 2.08 min. |
| 110 | 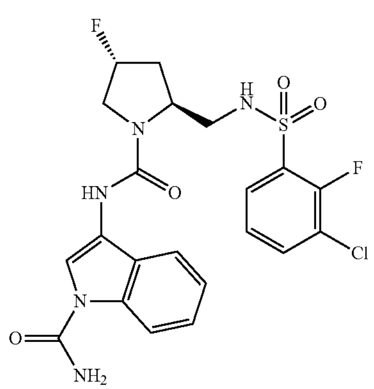 [SMILES: NC(=O)n1cc(NC(=O)N2C[C@H](F)C[C@H]2CNS(=O)(=O)c2cccc(Cl)c2F)c2ccccc21] | 3-({(2S,4R)-2-[(3-Chloro-2-fluoro-benzenesulfonylamino)-methyl]-4-fluoro-pyrrolidine-1-carbonyl}-amino)-indole-1-carboxylic acid amide | 512/514 [M + H]+, 534.1/536 [M + Na]+, 510/512 [M − H]−; t$_R$ (f): 1.92 min. |

TABLE 3-continued

| Example | Structure | Name | Characterization TLC, $R_f$ (eluent); MS (LC/MS); $t_R$ (HPLC conditions) |
|---|---|---|---|
| 111 | 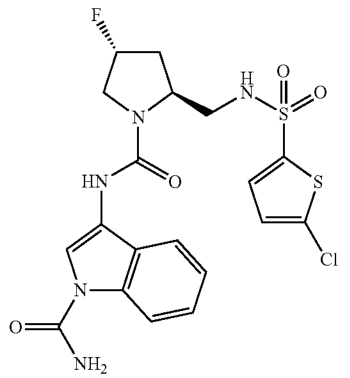 [SMILES: NC(=O)n1cc(NC(=O)N2C[C@H](F)C[C@H]2CNS(=O)(=O)c2ccc(Cl)s2)c2ccccc21] | 3-({(2S,4R)-2-[(5-Chloro-thiophene-2-sulfonylamino)-methyl]-4-fluoro-pyrrolidine-1-carbonyl}-amino)-indole-1-carboxylic acid amide | $R_f$(EtOAc) = 0.7; 500/502 [M + H]+, 522/524 [M + Na]+, 498/500 [M − CONH$_2$]−; $t_R$ (f): 1.88 min. |
| 112 | 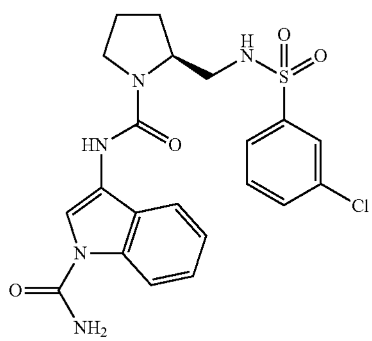 [SMILES: NC(=O)n1cc(NC(=O)N2CCC[C@H]2CNS(=O)(=O)c2cccc(Cl)c2)c2ccccc21] | 3-({(S)-2-[(3-Chloro-benzenesulfonylamino)-methyl]-pyrrolidine-1-carbonyl}-amino)-indole-1-carboxylic acid amide | 476.0 [M + H]+, 474.1 [M − H]−; $t_R$ (a): 3.34 min. |

Example 113

3-{[(2S,4R)-4-Fluoro-2-(phenylacetylamino-methyl)-pyrrolidine-1-carbonyl]-amino}-indole-1-carboxylic acid amide

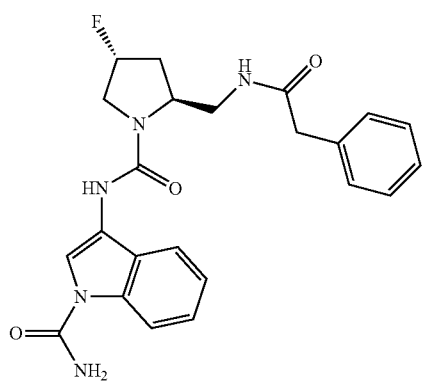 [SMILES: NC(=O)n1cc(NC(=O)N2C[C@H](F)C[C@H]2CNC(=O)Cc2ccccc2)c2ccccc21]

To a mixture of 3-[((2S,4R)-2-aminomethyl-4-fluoro-pyrrolidine-1-carbonyl)-amino]-indole-1-carboxylic acid amide (50 mg, 0.16 mmol, prepared as described in Scheme B11) and phenylacetyl chloride (23 µL, 0.17 mmol) in CH$_2$Cl$_2$ (0.5 mL), was added triethylamine (24 µL, 0.17 mmol) and the resulting suspension was stirred at RT under N$_2$ overnight. The mixture was poured into water and extracted with CH$_2$Cl$_2$ (×2). The combined organic layers were dried (Na$_2$SO$_4$), filtered and concentrated. The crude residue was purified by preparative HPLC (Waters Sunfire, C18-ODB, 5 µm, 19×50 mm, eluent: 20% to 100% CH$_3$CN in H$_2$O in 15 min, CH$_3$CN and H$_2$O containing 0.1% HCOOH, flow: 20 mL/min) to give after lyophilization of the purified fractions the desired material. $R_f$, TLC (EtOAc)=0.1; MS (LC-MS): 438.1 [M+H]+, 897.2 [2M+Na]+, 393.1 [M−CONH$_2$]−; $t_R$ (HPLC conditions f): 1.70 min.

Example 114

[(2S,4R)-1-(1-Carbamoyl-1H-indol-3-ylcarbamoyl)-4-fluoro-pyrrolidin-2-ylmethyl]-carbamic acid phenyl ester

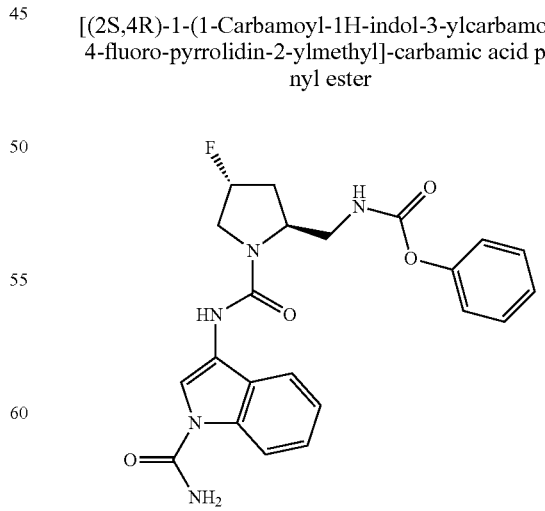

To a mixture of 3-[((2S,4R)-2-aminomethyl-4-fluoro-pyrrolidine-1-carbonyl)-amino]-indole-1-carboxylic acid amide (50 mg, 0.157 mmol, prepared as described in Scheme B11)

and phenyl chloroformate (22 µL, 0.17 mmol) in CH$_2$Cl$_2$ (0.5 mL), was added triethylamine (24 µL, 0.17 mmol) and the resulting suspension was stirred at RT under nitrogen overnight. The mixture was poured into water and extracted with CH$_2$Cl$_2$ (×2). The combined organic layers were dried (Na$_2$SO$_4$), filtered and concentrated. The crude residue was purified by preparative HPLC (Waters Sunfire, C18-ODB, 5 µm, 19×50 mm, eluent: 20% to 100% CH$_3$CN in H$_2$O in 15 min, CH$_3$CN and H$_2$O containing 0.1% HCOOH, flow: 20 mL/min) to give after lyophilization of the purified fractions the desired material. R$_f$, TLC (EtOAc)=0.45; MS (LC-MS): 440 [M+H]+, 901.3 [2M+Na]+; t$_R$ (HPLC conditions f): 1.77 min.

Example 115

[(1R,3S,5R)-2-(1-Carbamoyl-1H-indol-3-ylcarbamoyl)-2-aza-bicyclo[3.1.0]hex-3-ylmethyl]-carbamic acid 3-chloro-2-fluoro-phenyl ester

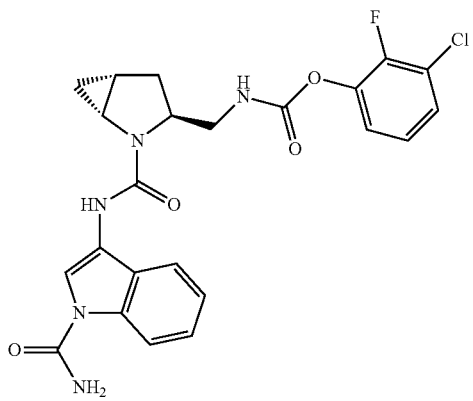 [SMILES: NC(=O)n1cc(NC(=O)N2[C@H](CNC(=O)Oc3cccc(Cl)c3F)C[C@H]3C[C@H]32)c2ccccc21]

To a solution of [(1R,3S,5R)-1-(2-aza-bicyclo[3.1.0]hex-3-yl)methyl]-carbamic acid 3-chloro-2-fluoro-phenyl ester, trifluoroacetate (60.0 mg, 0.211 mmol) and Et$_3$N (88 µl, 0.62 mmol) in THF (5 mL) was added 3-isocyanato-indole-1-carboxylic acid amide (43.0 mg, 0.211 mmol; prepared as described in Scheme A1). The solution was stirred at RT under a nitrogen atmosphere for 3 days. Purified by preparative HPLC (Waters Sunfire, C18-ODB, 5 µm, 30×100 mm, eluent: 5-100% CH$_3$CN/H$_2$O/20 min, 100% CH$_3$CN/2 min, CH$_3$CN and H$_2$O containing 0.1% TFA, flow: 40 mL/min) afforded after lyophilization of the purified HPLC fractions the title compound. MS (LC/MS): 486.0 [M+H]+; t$_R$ (HPLC conditions k): 3.57 min.

(1R,3S,5R)-3-[(3-Chloro-2-fluoro-phenoxycarbonylamino)-methyl]-2-aza-bicyclo[3.1.0]-hexane-2-carboxylic acid tert-butyl ester To a solution of 3-chloro-2-fluorophenol (180 mg, 1.20 mmol) in dry CH$_2$Cl$_2$ (10 mL), cooled to at 0° C., was added triphosgene (120 mg, 0.4 mmol) followed by dropwise addition of a solution of DIPEA (210 µL, 1.20 mmol) in CH$_2$Cl$_2$ (5 mL). The mixture was allowed to warm to RT and stirring was continued for 1 h. The reaction mixture was then added dropwise to a solution of (1R,3S,5R)-3-aminomethyl-2-aza-bicyclo[3.1.0]hexane-2-carboxylic acid tert-butyl ester (170 mg, 0.80 mmol) (prepared as described in Part B) and DIPEA (168 µL, 0.96 mmol) in CH$_2$Cl$_2$ (10 mL) at RT. After stirring for 2 h, the reaction was quenched by addition of methanol (2 mL) and water with vigorous stirring. The mixture was extracted with CH$_2$Cl$_2$ (2×), the combined organics were washed with brine, dried (phase separator) and concentrated under reduced pressure. Purification by flash column chromatography on silica gel (eluent gradient: c-hexane/EtOAc 9:1 to c-hexane/EtOAc 1:1) afforded the title compound as a colorless wax. MS (LC/MS): 385.0 [M+H]+; t$_R$ (HPLC conditions k): 4.03 min.

[(1R,3S,5R)-1-(2-Aza-bicyclo[3.1.0]hex-3-yl)methyl]-carbamic acid 3-chloro-2-fluoro-phenyl ester, trifluoroacetate To a solution of (1R,3S,5R)-3-[(3-chloro-2-fluoro-phenoxycarbonylamino)-methyl]-2-azabicyclo[3.1.0]hexane-2-carboxylic acid tert-butyl ester (130 mg, 0.34 mmol) in CH$_2$Cl$_2$ (4 mL) was added TFA (2 mL, 26 mmol) and solution was stirred at RT for 2 h. Methanol was then added and volatiles were removed under reduced pressure. The residue was taken up in MeOH and concentrated in vacuo to afford the crude title compound as a colorless wax. MS (LC/MS): 285.0 [M+H]+; t$_R$ (HPLC conditions k): 2.66 min. The material thus obtained was used directly in the next step without further purification.

Example 116

3-({(2S,4R)-2-[(3-Chloro-2-fluoro-benzylamino)-methyl]-4-fluoro-pyrrolidine-1-carbonyl}-amino)-indole-1-carboxylic acid amide

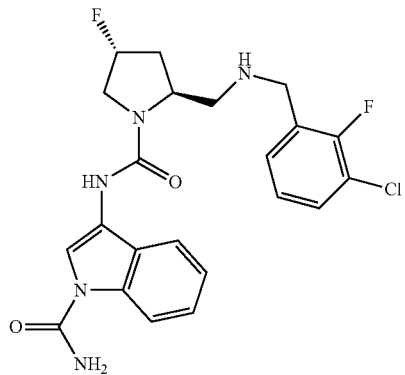 [SMILES: NC(=O)n1cc(NC(=O)N2C[C@H](F)C[C@H]2CNCc2cccc(Cl)c2F)c2ccccc21]

3-[((2S,4R)-2-Aminomethyl-4-fluoro-pyrrolidine-1-carbonyl)-amino]-indole-1-carboxylic acid amide (50 mg, 0.157 mmol) and 3-chloro-2-fluorobenzaldehyde (25 mg, 0.157 mmol, prepared as described in Scheme B11) were mixed in dichloroethane (1 mL), sodium triacetoxyborohydride (46.5 mg, 0.22 mmol) was added and the mixture was stirred at RT under nitrogen for 2 days. 3-Chloro-2-fluorobenzaldehyde (25 mg, 0.157 mmol) and triacetoxyborohydride (46.5 mg, 0.219 mmol) were added to complete the reaction. The reaction mixture was poured into a saturated aqueous solution of NaHCO$_3$ and extracted with CH$_2$Cl$_2$. The combined organic extracts were dried (Na$_2$SO$_4$), filtered and concentrated. The crude residue diluted in MeOH was purified by SiliaPrep Tosic Acid-1 g (SPE-R60530B-06S from Silicycle), the column was washed with 10 mL of MeOH and the compound released with 10 mL of 2M ammonia in MeOH to give after concentration the desired material which was further purified by preparative HPLC (Waters Sunfire, C18-ODB, 5 µm, 19×50 mm, eluent: 20% to 100% $CH_3CN$ in $H_2O$ in 15 min, $CH_3CN$ and $H_2O$ containing 0.1% HCOOH, flow: 20 mL/min) to give after lyophilization of the purified fractions the desired material as a formic acid salt. MS (LC-MS): 462.1/464 [M+H]+, 460/462 [M−H]−; $t_R$ (HPLC, conditions f): 1.54 min.

Example 117

3-({(S)-2-[(3-Trifluoromethoxy-phenylamino)-methyl]-pyrrolidine-1-carbonyl}-amino)-indole-1-carboxylic acid amide

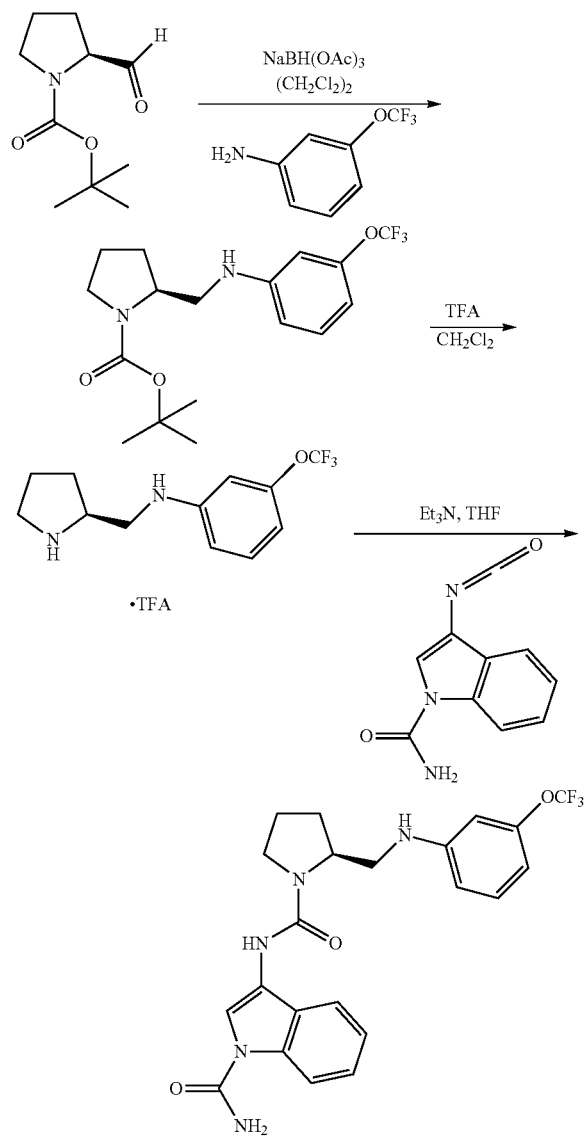

A. (S)-2-[(3-Trifluoromethoxy-phenylamino)-methyl]-pyrrolidine-1-carboxylic acid tert-butyl ester N-(tert-Butoxycarbonyl)-L-prolinal (200 mg, 1.00 mmol) and 3-trifluoromethoxy-phenylamine (186.8 mg, 1.05 mmol) were mixed in 1,2-dichloroethane (10 mL) and treated with sodium triacetoxyborohydride (314 mg, 1.41 mmol). The mixture was stirred at RT under nitrogen overnight, then quenched by addition of water, extracted with $CH_2Cl_2$, dried over $Na_2SO_4$, filtered and concentrated. The crude oil was purified by flash column chromatography on silica gel (c-hexane to c-hexane/EtOAc 1:1) to give the desired material. MS (LC/MS): 361.1 [M+H]+.

B. (S)-1-Pyrrolidin-2-ylmethyl-(3-trifluoromethoxy-phenyl)-amine

A solution of (S)-2-[(3-trifluoromethoxy-phenylamino)-methyl]-pyrrolidine-1-carboxylic acid tert-butyl ester (100 mg, 0.277 mmol) and TFA (1 mLl) in $CH_2Cl_2$ (2 mL) was stirred at RT for 2 h. Solvent was concentrated and the residue was co-evaporated twice with $CH_2Cl_2$ and dried under high vacuum overnight to give the crude title compound as a TFA salt. MS: 261.1 [MH−Boc]+, $t_R$ (HPLC conditions a): 2.61 min.

C. 3-({(S)-2-[(3-Trifluoromethoxy-phenylamino)-methyl]-pyrrolidine-1-carbonyl}-amino)-indole-1-carboxylic acid amide To a solution of (S)-1-pyrrolidin-2-ylmethyl-(3-trifluoromethoxy-phenyl)-amine (49 mg, 0.131 mmol) and $Et_3N$ (55 µl, 0.393 mmol) in THF (1.5 mL) was added a solution of 3-isocyanato-1-methyl-1H-indole (26 mg, 0.393 mmol, prepared as described in Scheme A1) in THF (1.5 mL). The resulting solution was stirred at RT under nitrogen for 1 h. The mixture was poured into water and extracted twice with EtOAc. The combined organic layers were dried ($Na_2SO_4$), filtered and concentrated. The crude residue was purified by preparative HPLC (Waters C18-ODB, 5 µm, 19×50 mm, eluent: $CH_3CN/H_2O$+0.1% HCOOH, flow: 20 ml/min) to give after lyophilisation of the purified fraction the title compound. TLC, $R_f$ (c-hexane/EtOAc 1:2)=0.23; MS (LC/MS): 462.1 [M+H]+, 484.1 [M+Na]+; $t_R$ (HPLC conditions a): 3.75 min.

Example 118

1-{2-oxo-2-[(S)-2-(3-trifluoromethoxy-phenylcarbamoyl)-pyrrolidin-1-yl]-ethyl}-1H-indole-3-carboxylic acid amide

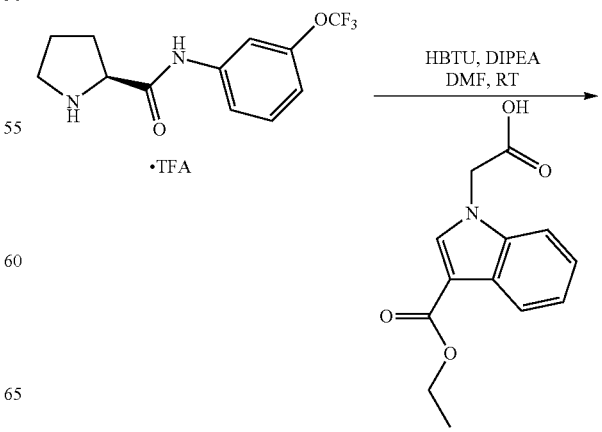

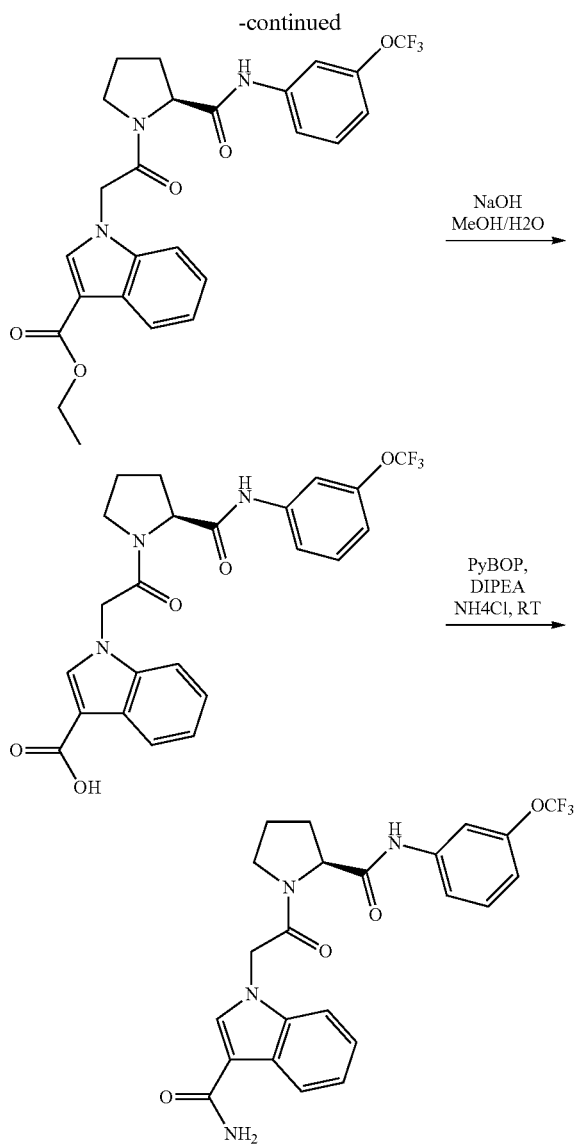

A. 1-{2-Oxo-2-[(S)-2-(3-trifluoromethoxy-phenyl-carbamoyl)-pyrrolidin-1-yl]-ethyl}-1H-indole-3-carboxylic acid ethyl ester The title compound was prepared according to the general procedure described in Scheme D6 using 1-carboxymethyl-1H-indole-3-carboxylic acid ethyl ester (prepared as described in Part A) and DMF as solvent. TLC, $R_f$(EtOAc)=0.56; MS (LC/MS): 526 [M+Na]+, 502 [M−H]−; $t_R$ (HPLC conditions a): 3.90 min.

B. 1-{2-Oxo-2-[(S)-2-(3-trifluoromethoxy-phenyl-carbamoyl)-pyrrolidin-1-yl]-ethyl}-1H-indole-3-carboxylic acid To a solution of 1-{2-oxo-2-[(S)-2-(3-trifluoromethoxy-phenylcarbamoyl)-pyrrolidin-1-yl]ethyl}-1H-indole-3-carboxylic acid ethyl ester (314 mg, 0.62 mmol) in MeOH (12 mL) and water (1.2 mL) was added NaOH 1N (1.87 mL, 1.87 mmol) and the mixture was heated at 80° C. for 6 h. MeOH was concentrated, HCl 1N was added and the residue was extracted with EtOAc. The organic extracts were dried with $Na_2SO_4$, filtered and concentrated. The crude residue was purified by preparative HPLC (Interchrom C18-ODB, 10 µm, 28×250 mm, 20% $CH_3CN$ in $H_2O$ 2.5 min, then 20% to 100% $CH_3CN$ in $H_2O$ in 32.5 min, $CH_3CN$ and $H_2O$ containing 0.1% HCOOH; flow: 40 mL/min) to give after lyophilization of the purified fractions the desired compound. TLC, $R_f$ (EtOAc)=0.05; MS (LC/MS): 498.1 [M+Na]+, 474.1 [M−H]−; $t_R$ (HPLC conditions a): 3.48 min.

C. Example 118

1-{2-Oxo-2-[(S)-2-(3-trifluoromethoxy-phenylcar-bamoyl)-pyrrolidin-1-yl]-ethyl}-1H-indole-3-carboxylic acid amide 1-{2-oxo-2-[(S)-2-(3-trifluoromethoxy-phenylcarbam-oyl)-pyrrolidin-1-yl]-ethyl}-1H-indole-3-carboxylic acid (11 mg, 0.023 mmol), was treated with PyBOP (12 mg, 0.023 mmol), HOBt (3.54 mg, 0.023 mmol), DIPEA (16 µL, 0.092 mmol), and $NH_4Cl$ (1 mg, 0.069 mmol) in DMF (1 mL) and the reaction mixture was stirred at RT under nitrogen for 3 h, then poured into an aqueous saturated solution of $NaHCO_3$, EtOAc (20 mL) was added and the layers were separated. The aqueous layer was back-extracted twice with EtOAc and the combined organic extracts were dried ($Na_2SO_4$), filtered and concentrated. The crude residue was purified by preparative HPLC (Waters SunFire C18-ODB, 5 µm, 19×50 mm, 20% $CH_3CN/H_2O$ 2.5 min, 20-100% $CH_3CN/H_2O$ in 10 min, $CH_3CN/H_2O$ containing 0.1% HCOOH flow: 20 mL/min) to give after lyophilization of the purified fractions the desired compound. TLC, $R_f$ ($CH_2Cl_2$/MeOH 95:5)=0.17; MS (LC/MS): 473.2 [M−H]−; $t_R$ (HPLC conditions a): 3.24 min.

Example 119

(S)-1-[2-(1-Acetyl-1H-indol-3-yl)-acetyl]-pyrroli-dine-2-carboxylic acid (3-trifluoromethoxy-phenyl)-amide

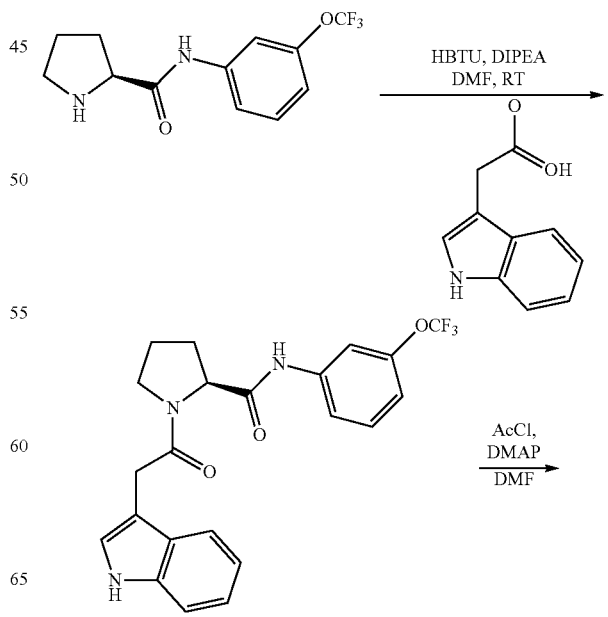

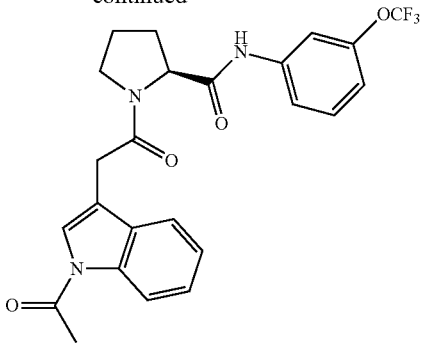

A. (S)-1-(2-1H-Indol-3-yl-acetyl)-pyrrolidine-2-carboxylic acid (3-trifluoromethoxy-phenyl)-amide The title compound was prepared according to the general procedure described in Scheme D6 using (1H-indol-3-yl)-acetic acid using DMF as solvent. TLC, $R_f$(c-hexane/EtOAc 1:1)=0.14; MS (LC/MS): 432.3 [M+H]+, 454.1 [M+Na]+; $t_R$ (HPLC conditions a): 3.68 min.

B. Example 119

(S)-1-[2-(1-Acetyl-1H-indol-3-yl)-acetyl]-pyrrolidine-2-carboxylic acid (3-trifluoromethoxy-phenyl)-amide To a solution of (S)-1-(2-1H-Indol-3-yl-acetyl)-pyrrolidine-2-carboxylic acid (3-trifluoromethoxy-phenyl)-amide (100 mg, 0.232 mmol) in DMF (1.5 mL) under nitrogen atmosphere were added acetyl chloride (148 µl, 2.09 mmol) followed by DMAP (85 mg, 0.7 mmol) and the reaction mixture was heated at 80° C. for 18 h. After completion of the reaction, the mixture was poured into citric acid (10% solution), and extracted three times with EtOAc. The combined organic layers were washed twice with water, dried over $Na_2SO_4$, filtered and concentrated. The crude material was purified by preparative HPLC (Waters SunFire C18-ODB, 5 µm, 19×50 mm, 20% $CH_3CN/H_2O$ 2.5 min, 20-100% $CH_3CN/H_2O$ in 10 min, $CH_3CN/H_2O$ containing 0.1% HCOOH flow: 20 mL/min) to give after lyophilization of the purified fractions the desired compound.

TLC, $R_f$(c-hexane/EtOAC 3:7)=0.16; MS (LC/MS): 474.1 [M+H]+, 496 [M+Na]+, 472 [M–H]–; $t_R$ (HPLC conditions a): 3.80 min.

Example 120

(2S,4R)-1-[2-(1-Acetyl-1H-indol-3-yl)-2-amino-acetyl]-4-fluoro-pyrrolidine-2-carboxylic acid 3-chloro-2-fluoro-benzylamide

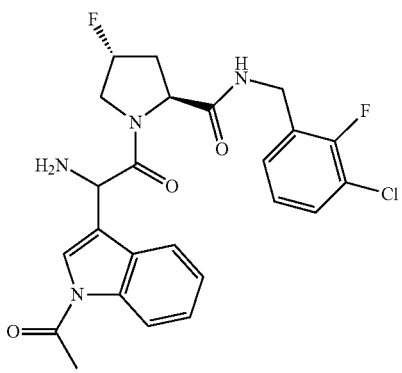 [SMILES: CC(=O)n1cc(C(N)C(=O)N2C[C@H](F)C[C@H]2C(=O)NCc2cccc(Cl)c2F)c2ccccc21]

A solution of {1-(1-acetyl-1H-indol-3-yl)-2-[(2S,4R)-2-(3-chloro-2-fluoro-benzylcarbamoyl)-4-fluoro-pyrrolidin-1-yl]-2-oxo-ethyl}-carbamic acid tert-butyl ester (102 mg, 0.173 mmol) and TFA (66.7 µL, 0.866 mmol) in $CH_2Cl_2$ (0.58 mL) was stirred at 23° C. overnight. TFA (66.7 µL, 0.866 mmol) was again added and the reaction mixture was stirred at 23° C. for an additional 4 h to complete the reaction. Solvents were removed in vacuo and the crude residue was purified by preparative HPLC (Waters SunFire C180 DB, 5 µm, 19×50, eluent: 5% $CH_3CN/95\%\ H_2O$ to 100% $CH_3CN$ in 17 min, $CH_3CN$ and $H_2O$ containing 0.1% of TFA, flow 20 mL/min) to give after lyophilization of the purified fractions the desired material. MS (LC-MS): 487.1 [M–H]–; $t_R$ (HPLC conditions b): 3.19 min.

{1-(1-Acetyl-1H-indol-3-yl)-2-[(2S,4R)-2-(3-chloro-2-fluoro-benzylcarbamoyl)-4-fluoro-Pyrrolidin-1-yl]-2-oxo-ethyl}-carbamic acid tert-butyl ester To a solution of [2-[(2S,4R)-2-(3-chloro-2-fluoro-benzyl-carbamoyl)-4-fluoro-pyrrolidin-1-yl]-1-(1H-indol-3-yl)-2-oxo-ethyl]-carbamic acid tert-butyl ester diastereosiomer P2 (prepared as described in Part B) (150 mg, 0.274 mmol) in dry THF (1.37 mL) was added under argon and at 0° C., tBuOK (40 mg, 0.356 mmol). The reaction mixture was stirred 5 min at 0° C. then acetyl chloride (25.3 µL, 0.356 mmol) was added and the reaction mixture was allowed to warm up to 23° C. and stirred overnight. The mixture was quenched by addition of an aqueous saturated solution of $NaHCO_3$ and extracted with EtOAc (×3). The organic layers were dried ($Na_2SO_4$), filtered and concentrated. The crude residue was purified by flash column chromatography on silica gel (c-hexane/EtOAc gradient 100:0 to 0:100) to give the desired material. TLC, $R_f$ (EtOAc)=0.65; MS (LC-MS): 587.2 [M–H]–, 611 [M+Na]+; $t_R$ (HPLC conditions b): 5.18 min.

Scheme D4: preparation of Example 121: (S)-Pyrrolidine-1,2-dicarboxylic acid 1-[(3-carbamoyl-indolizin-1-yl)-amide] 2-[(3-trifluoromethoxy-phenyl)-amide]

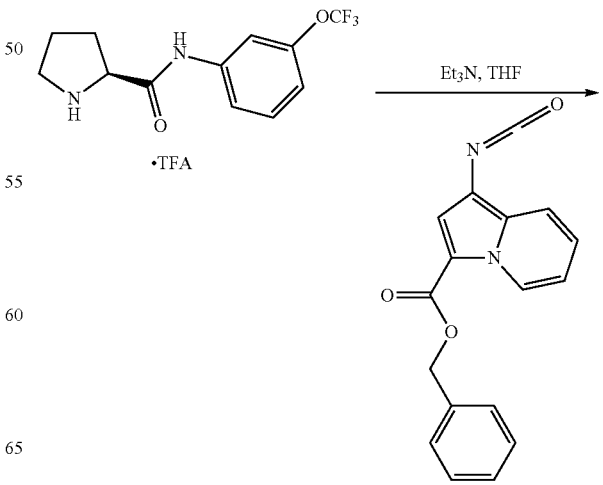

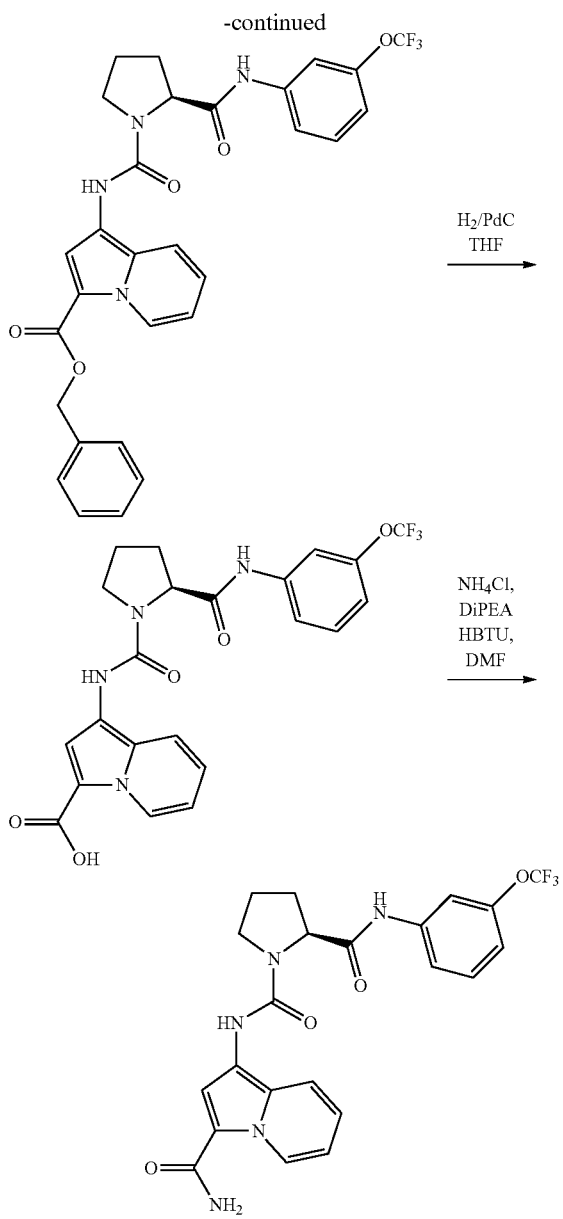

B. 1-{[(S)-2-(3-Trifluoromethoxy-phenylcarbamoyl)-pyrrolidine-1-carbonyl]-amino}-indolizine-3-carboxylic acid To 1-{[(S)-2-(3-Trifluoromethoxy-phenylcarbamoyl)-pyrrolidine-1-carbonyl]-amino}-indolizine-3-carboxylic acid benzyl ester (100 mg, 0.177 mmol) dissolved in THF (3 mL) was added Pd/C 10% (20 mg). Air was removed from the flask under vacuum and replaced with nitrogen three times, finally nitrogen was removed and replaced with hydrogen and the mixture was stirred at RT for 5 h. Hydrogen was removed and replaced by nitrogen, the catalyst was removed by filtration through a pad of Celite and washed with THF. Solvents were concentrated to give a mixture containing the desired compound contaminated with 20% of the decarboxylated analog. The mixture was used without further purification in the next step. LC/MS: 475 [M−H]−; $t_R$ (HPLC conditions a): 3.41 min.

C. Example 121

(S)-Pyrrolidine-1,2-dicarboxylic acid 1-[(3-carbamoyl-indolizin-1-yl)-amide]2-[(3-trifluoromethoxy-phenyl)-amide]

To a solution of 1-{[(S)-2-(3-trifluoromethoxy-phenylcarbamoyl)-pyrrolidine-1-carbonyl]-amino}-indolizine-3-carboxylic acid containing 20% of the decarboxylated analog (65 mg, 0.136 mmol), $NH_4Cl$ (8.80 mg, 0.164 mmol) and HBTU (78 mg, 0.205 mmol) in DMF (2.5 mL) was added DIPEA (49 μl, 0.287 mmol) and the resulting solution was stirred at RT under nitrogen overnight. After completion of the reaction, the mixture was poured into HCl 1N and extracted with EtOAc (×3). The combined organic extracts were washed with water (×2), dried ($Na_2SO_4$), filtered and concentrated. The crude residue was purified by preparative HPLC (Waters SunFire C18-ODB, 5 μm, 19×50 mm, 20% $CH_3CN/H_2O$ 2.5 min, 20-100% $CH_3CN/H_2O$ in 10 min, $CH_3CN/H_2O$ containing 0.1% HCOOH flow: 20 mL/min) to give after lyophilization of the purified fractions the desired compound as a powder. TLC, $R_f$($CH_2Cl_2$/MeOH 9:1)=0.4; MS (LC/MS): 476 [M+H]+, 498.1 [M+Na]+, 474.1 [M−H]−; $t_R$ (HPLC conditions a): 3.30 min.

Example 122

(2S,4R)-4-Fluoro-pyrrolidine-1,2-dicarboxylic acid 1-[(3-carbamoyl-indolizin-1-yl)-amide]2-[(3-trifluoromethoxy-phenyl)-amide]

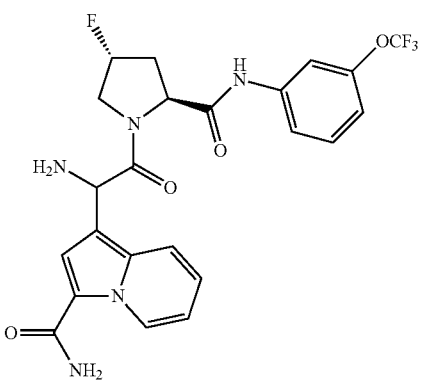 [SMILES: NC(=O)c1cc(C(N)C(=O)N2C[C@H](F)C[C@H]2C(=O)Nc2cccc(OC(F)(F)F)c2)c2ccccn12]

The title compound was prepared according to the same procedure as described in Scheme D4 starting from (S)-pyrrolidine-1,2-dicarboxylic acid 1-[(3-carbamoyl-indolizin-1-

A. 1-{[(S)-2-(3-Trifluoromethoxy-phenylcarbamoyl)-pyrrolidine-1-carbonyl]-amino}-indolizine-3-carboxylic acid benzyl ester To a solution of (S)-pyrrolidine-2-carboxylic acid (3-trifluoromethoxy-phenyl)-amide TFA salt (328 mg, 0.845 mmol) and triethylamine (353 μl, 2.54 mmol) in THF (10 mL) was added the crude 1-isocyanato-indolizine-3-carboxylic acid benzyl ester (247 mg, 0.845 mmol, prepared as described in Scheme A6). The resulting mixture was stirred at RT under nitrogen over the week-end then poured into HCl 1N and extracted with EtOAc (×3). The combined organic extracts were washed with an aqueous saturated solution of $NaHCO_3$, dried ($Na_2SO_4$), filtered and concentrated. The crude mixture was purified by flash column chromatography on silica gel (c-hexane/EtOAc 1:1 to c-hexane/EtOAc 3:7) to afford the desired compound. TLC, $R_f$(c-hexane/EtOAc 1:1)=0.3; MS (LC/MS): 567.3 [M+H]+ 565.2 [M−H]−; $t_R$ (HPLC conditions a): 4.16 min.

yl)-amide]2-[(3-trifluoro methoxy-phenyl)-amide]. MS: 494 [M+H]+, 492.1 [M−H]−; $t_R$ (HPLC conditions a): 1.87 min.

Example 123

(S)-Pyrrolidine-1,2-dicarboxylic acid 1-[(1-carbamoyl-indolizin-3-yl)-amide]2-[(3-trifluoromethoxy-phenyl)-amide]

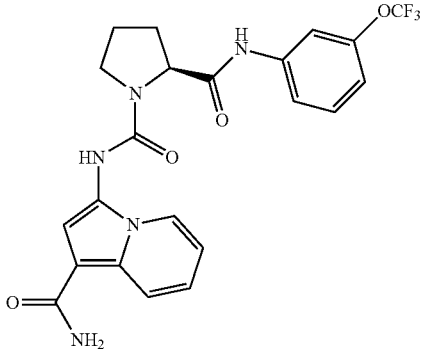 [SMILES: NC(=O)c1cc(NC(=O)N2CCC[C@H]2C(=O)Nc2cccc(OC(F)(F)F)c2)n2ccccc12]

The title compound was prepared from 3-isocyanato-indolizine-1-carboxylic acid benzyl ester (prepared as described in Scheme A7) using the protocol described in Scheme D4. TLC, $R_f$ (CH$_2$Cl$_2$/MeOH 9:1)=0.4; MS (LC/MS): 476 [M+H]+, 498.1 [M+Na]+, 474.1 [M−H]−; $t_R$ (HPLC conditions a): 3.13 min.

Scheme D5: general protocol described for the preparation of Example 124: (S)-pyrrolidine-1,2-dicarboxylic acid 1-[(1-carbamoyl-1H-indol-3-yl)-amide] 2-[(3-trifluoromethoxy-phenyl)-amide]

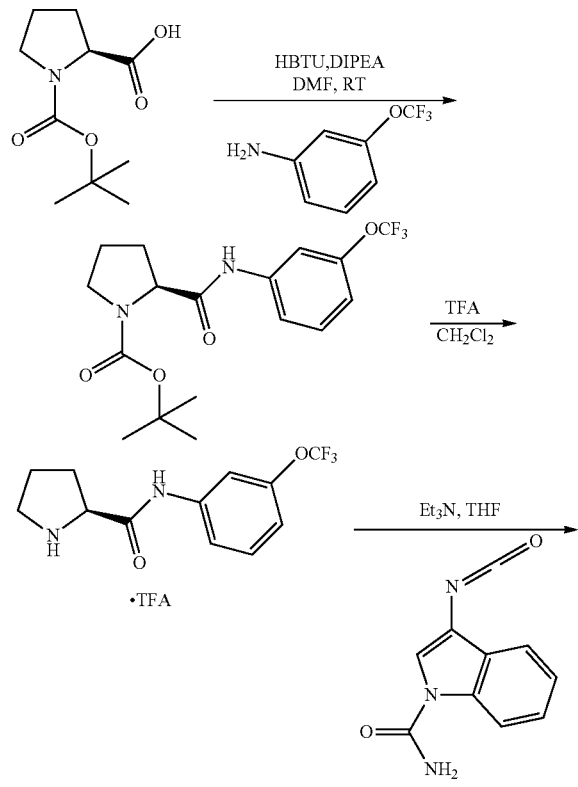

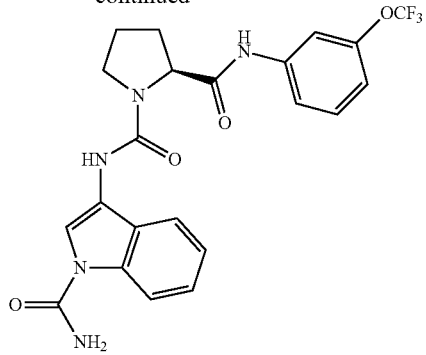

A. (S)-2-(3-Trifluoromethoxy-phenylcarbamoyl)-pyrrolidine-1-carboxylic acid tert-butyl ester To a mixture of Boc-L-proline (5 g, 23.23 mmol), 3-(trifluoromethoxy)aniline (3.73 mL, 27.88 mmol) and HBTU (13.2 g, 34.8 mmol) in DMF (60 mL) was added DIPEA (7.95 mL, 46.5 mmol) and the resulting yellow solution was stirred at RT under nitrogen. The solvent was concentrated under vacuum and the residue dissolved in EtOAc and washed with HCl 1N. The combined organic layers were neutralized by addition of an aqueous saturated solution of NaHCO$_3$. The layers were separated and the aqueous one back-extracted twice with CH$_2$Cl$_2$. The combined organic extracts were dried (Na$_2$SO$_4$), filtered and concentrated. The crude residue was purified by flash column chromatography on silica gel (c-hexane/EtOAc 3:1 to 2:1) to give the desired compound. TLC, $R_f$ (c-hexane/EtOAc 1:1)=0.57; MS (LC/MS): 397.1 [M+Na]+, 275.2 [MH−Boc]+, 373.3 [M−H]−; $t_R$ (HPLC conditions a) 3.81 min.

Dichloromethane can also be used instead of DMF.

B. (S)-Pyrrolidine-2-carboxylic acid (3-trifluoromethoxy-phenyl)-amide

To a solution of (S)-2-(3-trifluoromethoxy-phenylcarbamoyl)-pyrrolidine-1-carboxylic acid tert-butyl ester (8.52 g, 22.6 mmol) in CH$_2$Cl$_2$ (50 mL) was added TFA (8.65 mL, 113 mmol) and solution was stirred at RT for 12 h. The crude reaction mixture was concentrated under vacuum, Et$_2$O was added and the white precipitate was filtered off to give the desired compound as a TFA salt. MS (LC/MS): 275.2 [M+H]+, 273.3 [M−H]−; $t_R$ (HPLC conditions a) 2.47 min.

C. Example 124

(S)-Pyrrolidine-1,2-dicarboxylic acid 1-[(1-carbamoyl-1H-indol-3-yl)-amide]2-[(3-trifluoromethoxy-phenyl)-amide]

To a solution of (S)-pyrrolidine-2-carboxylic acid (3-trifluoromethoxy-phenyl)-amide trifluoroacetate (328 mg, 0.845 mmol) and Et$_3$N (353 μl, 2.53 mmol) in THF (7.5 mL) was added a suspension of 3-isocyanato-indole-1-carboxylic acid amide (170 mg, 0.845 mmol, prepared as described in Scheme A1) in THF (7.5 mL). The resulting solution was stirred at RT under nitrogen for 1 h, poured into water and the mixture was extracted twice with EtOAc. The combined organic layers were dried over Na$_2$SO$_4$, filtered and concentrated. The crude residue was purified by preparative HPLC (Waters SunFire C18-ODB, 5 μm, 19×50 mm, 20% CH$_3$CN/H$_2$O 2.5 min, 20-100% CH$_3$CN/H$_2$O in 10 min, CH$_3$CN/H$_2$O containing 0.1% HCOOH flow: 20 mL/min) to give after lyophilization of the purified HPLC fractions the title compound. TLC, $R_f$ (c-hexane/EtOAc 1:2)=0.11; MS (LC/MS): 476.2 [M+H]+, 973.2 [2M+Na]+.

The examples below were prepared according to the general procedures described in Scheme D5 for the preparation of Example 124 from commercially available building blocks, if not otherwise stated (see notes at the end of table 4):

TABLE 4

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 125 | 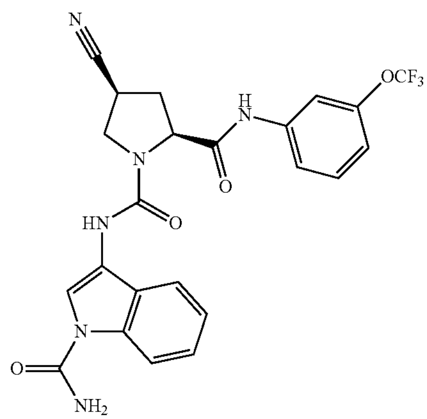 [SMILES: N#C[C@H]1C[C@@H](C(=O)Nc2cccc(OC(F)(F)F)c2)N(C(=O)Nc2cn(C(N)=O)c3ccccc23)C1] | (2S,4S)-4-Cyano-pyrrolidine-1,2 dicarboxylic acid 1-[(1-carbamoyl-1H-indol-3-yl)-amide] 2-[(3-trifluoromethoxy-phenyl)-amide] | 501.1 [M + H]+; $t_R$ (b): 4.07 min. |
| 126 | 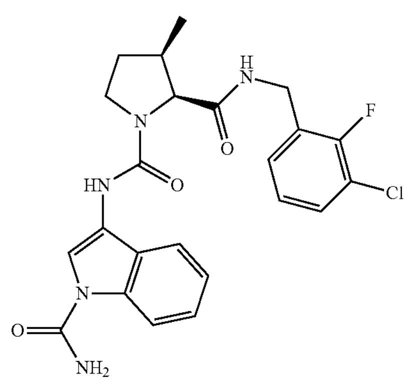 [SMILES: C[C@@H]1CCN(C(=O)Nc2cn(C(N)=O)c3ccccc23)[C@@H]1C(=O)NCc1cccc(Cl)c1F] | (2S,3R)-3-Methyl-pyrrolidine-1,2-dicarboxylic acid 1-[(1-carbamoyl-1H-indol-3-yl)-amide] 2-(3-chloro-2-fluoro-benzylamide) | (7) $R_f$ (EtOAc) = 0.5; 472.1/474.2 [M + H]+, 427/429 [M − CONH$_2$]−; $t_R$ (a): 3.24 min. |
| 127 | 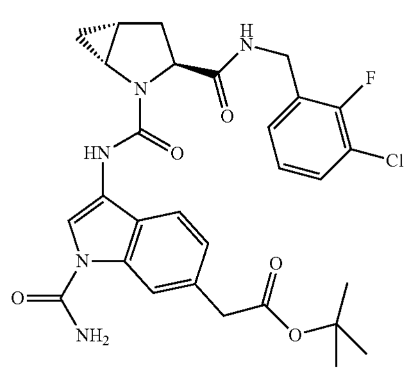 [SMILES: CC(C)(C)OC(=O)Cc1ccc2c(NC(=O)N3[C@@H]4C[C@@H]4C[C@H]3C(=O)NCc3cccc(Cl)c3F)cn(C(N)=O)c2c1] | (1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid tert-butyl ester | (9) $R_f$ (EtOAc) = 0.44; 584.4/586.4 [M + H]+, 582.7/584.4 [M − H]−, 539.4/541.4 [M − CONH$_2$]−, 628.4/630.4 [M + HCOO]−; $t_R$ (f): 2.20 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 128 | 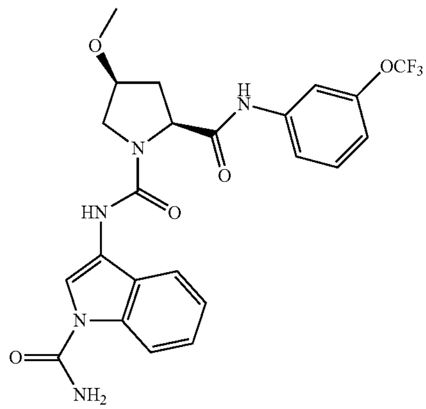 [SMILES: CO[C@H]1C[C@@H](C(=O)Nc2cccc(OC(F)(F)F)c2)N(C(=O)Nc2cn(C(N)=O)c3ccccc23)C1] | (2S,4S)-4-Methoxy-pyrrolidine-1,2-dicarboxylic acid 1-[(1-carbamoyl-1H-indol-3-yl)-amide] 2-[(3-trifluoromethoxy-phenyl)-amide] | 506.2 [M + H]+, 504.1 [M − H]−; t$_R$ (a): 3.43 min. |
| 129 | 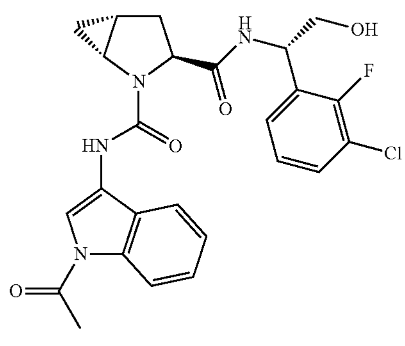 [SMILES: CC(=O)n1cc(NC(=O)N2[C@@H]3C[C@@H]3C[C@H]2C(=O)N[C@H](CO)c2cccc(Cl)c2F)c2ccccc21] | (1R,3S,5R)-2-Azabicyclo[3.1.0]hexane-2,3-dicarboxylic acid 2-[(1-acetyl-1H-indol-3-yl)-amide] 3-{[(S)-1-(3-chloro-2-fluoro-phenyl)-2hydroxy-ethyl]-amide} | (5,8[B9],9[A1]) R$_f$ (EtOAc) = 0.45; 499.4/501.3 [M + H]+, 521.3/523.4 [M + Na]+, 543.3/545.4 [M + HCOO]−, 497.5/499.8 [M − H]−; t$_R$ (a): 1.95 min. |
| 130 | 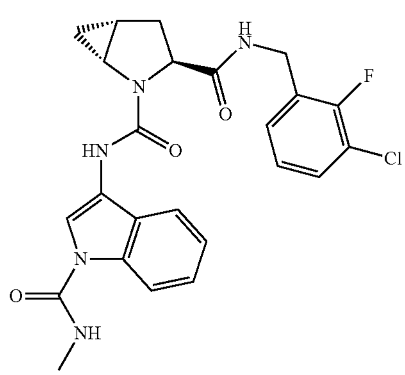 [SMILES: CNC(=O)n1cc(NC(=O)N2[C@@H]3C[C@@H]3C[C@H]2C(=O)NCc2cccc(Cl)c2F)c2ccccc21] | (1R,3S,5R)-2-Azabicyclo[3.1.0]hexane-2,3-dicarboxylic acid 3-(3-chloro-2-fluoro-benzylamide) 2-[(1-methylcarbamoyl-1H-indol-3-yl)-amide] | (9[A2]) R$_f$ (EtOAc) = 0.3; 484.4 [M + H]+, 484.4 [M + HCOO]−; t$_R$ (a): 3.34 min. |

TABLE 4-continued

| Example | Name | Characterization (end-table notes), TLC, R$_f$ (eluent); MS (LC/MS); t$_R$ (HPLC conditions); 19F NMR (100 MHz, solvent) δ (ppm): |
|---|---|---|
| 131 | (2S,4R)-4-Hydroxy-pyrrolidine-1,2-dicarboxylic acid 1-[(1-carbamoyl-1H-indol-3-yl)-amide] 2-[(3-trifluoromethoxy-phenyl)-amide] | 492.1 [M + H]+, 490.1 [M − H]−; t$_R$ (a): 3.08 min. |
| 132 | (2S,4R)-4-Fluoro-methyl-pyrrolidine-1,2-dicarboxylic acid 1-{[1-carbamoyl-5-(2-methoxy-ethoxy)-1H-indol-3-yl]-amide} 2-(3-chloro-2-fluoro-benzylamide) | (8[B13],9) R$_f$ (EtOAc) = 0.35; 550.5/552.4 [M + H]+, 572.3/574.5 [M + Na]+, 548.4/550.4 [M − H]−, 594.4/596.4 [M + HCOO]−; t$_R$ (f): 1.82 min. |
| 133 | (1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-acetic acid methyl ester | (9) R$_f$ (EtOAc) = 0.2; 558.1/560.2 [M + H]+, 580/582.1 [M + Na]+, 513.1/515 [M − CONH$_2$]−; t$_R$ (f): 1.87 min. |
| 134 | (1S,3S,5R)-2-Aza-bicyclo[3.1.0]hexane-2,3-dicarboxylic acid 2-[(1-carbamoyl-1H-indol-3-yl)-amide] 3-[(3-trifluoromethoxy-phenyl)-amide] | R$_f$ (c-hexane/EtOAc 1:2) = 0.15, 488.2 [M + H]+, 486.1 [M − H]−; t$_R$ (a): 3.59 min. |

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 135 | 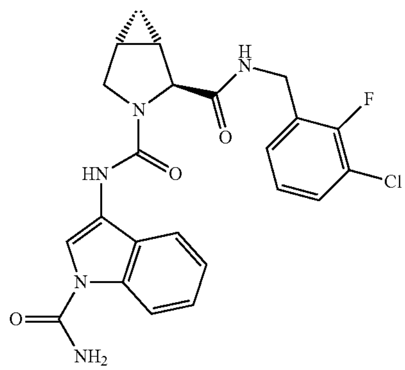 | (1S,2S,5R)-3-Aza-bicyclo[3.1.0]hexane-2,3-dicarboxylic acid 3-[(1-carbamoyl-1H-indol-3-yl)-amide] 2-(3-chloro-2-fluoro-benzylamide) | 470 [M + H]+, 425 [M − CONH₂] −; t_R (f): 1.84 min. |
| 136 | 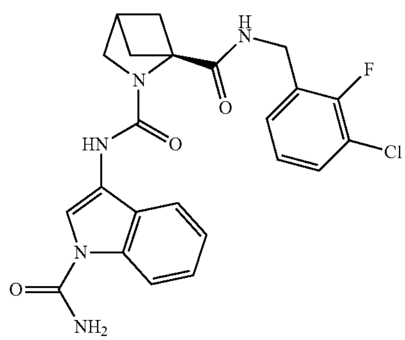 | 2-Aza-bicyclo[2.1.1]hexane-1,2-dicarboxylic acid 2-[(1-carbamoyl-1H-indol-3-yl)-amide] 1-(3-chloro-2-fluoro-benzylamide) | (1) White solid. R_f (EtOAc) = 0.2; 470/473 [M]+; t_R (c): 4.51 min. |
| 137 | 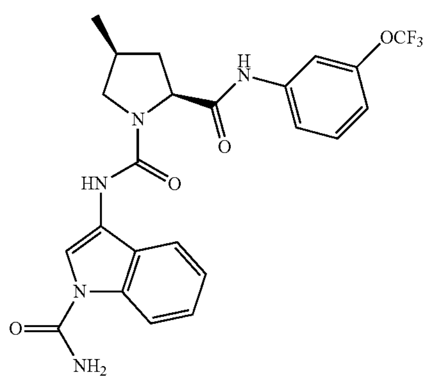 [SMILES: C[C@H]1C[C@@H](C(=O)Nc2cccc(OC(F)(F)F)c2)N(C(=O)Nc2cn(C(N)=O)c3ccccc23)C1] | (2S,4S)-4-Methyl-pyrrolidine-1,2-dicarboxylic acid 1-[(1-carbamoyl-1H-indol-3-yl)-amide] 2-[(3-trifluoromethoxy-phenyl)-amide] | (8[B2]) R_f (c-hexane/EtOAc 1:3) = 0.44; 487.9 [M − H]−, 446.0 [M − CONH₂]−; t_R (c): 4.51 min. |
| 138 | 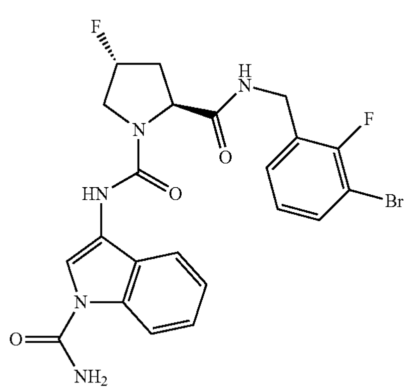 [SMILES: NC(=O)n1cc(NC(=O)N2C[C@H](F)C[C@H]2C(=O)NCc2cccc(Br)c2F)c2ccccc21] | (2S,4R)-4-Fluoro-pyrrolidine-1,2-dicarboxylic acid 2-(3-bromo-2-fluoro-benzylamide) 1-[(1-carbamoyl-1H-indol-3-yl)-amide] | (1,6) 522.0 [M + H]+; t_R (c): 4.38 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 139 | 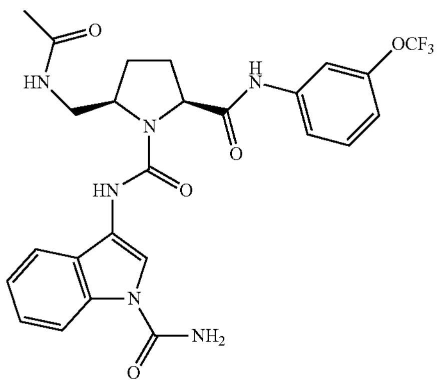 [SMILES: CC(=O)NC[C@H]1CC[C@@H](C(=O)Nc2cccc(OC(F)(F)F)c2)N1C(=O)Nc1cn(C(N)=O)c2ccccc12] | (2S,5R)-5-(Acetylamino-methyl)-pyrrolidine-1,2-dicarboxylic acid 1-[(1-carbamoyl-1H-indol-3-yl)-amide] 2-[(3-trifluoromethoxy-phenyl)-amide] | (8[B4]) 547 [M + H]+; t$_R$ (b): 4.05 min. |
| 140 | 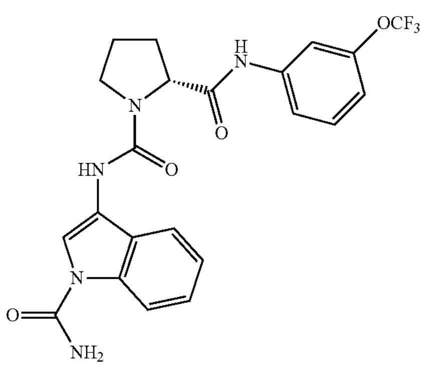 [SMILES: NC(=O)n1cc(NC(=O)N2CCC[C@@H]2C(=O)Nc2cccc(OC(F)(F)F)c2)c2ccccc21] | (R)-Pyrrolidine-1,2-dicarboxylic acid 1-[(1-carbamoyl-1H-indol-3-yl)-amide] 2-[(3-trifluoromethoxy-phenyl)-amide] | 476.1 [M + H]+, 498.1 [M + Na]+, 474.1 [M − H]−; t$_R$ (a): 3.47 min. |
| 141 | 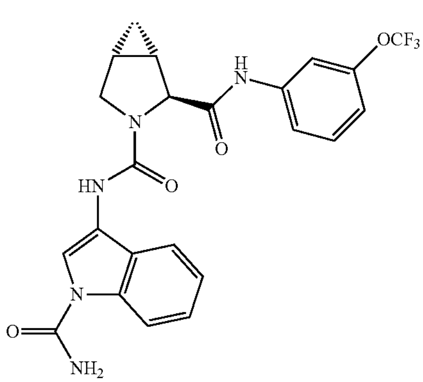 | (1S*,2S*,5R*)-3-Aza-bicyclo[3.1.0]hexane-2,3-dicarboxylic acid 3-[(1-carbamoyl-1H-indol-3-yl)-amide] 2-[(3-trifluoromethoxy-phenyl)-amide] | 488.2 [M + H]+, 510.1 [M + Na]+; t$_R$ (a): 3.52 min |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 142 | 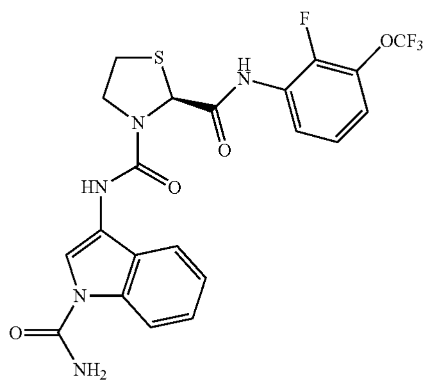 [SMILES: NC(=O)n1cc(NC(=O)N2CCS[C@H]2C(=O)Nc2cccc(OC(F)(F)F)c2F)c2ccccc21] | (S)-Thiazolidine-2,3-dicarboxylic acid 3-[(1-carbamoyl-1H-indol-3-yl)-amide] 2-[(2-fluoro-3-trifluoromethoxy-phenyl)-amide] | (1,6) White solid. 510 [M + H]+; t_R (b) 4.36 min. |
| 143 | 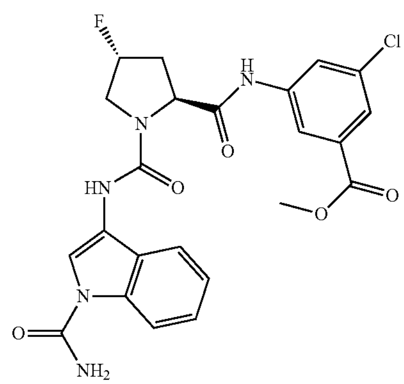 [SMILES: COC(=O)c1cc(Cl)cc(NC(=O)[C@@H]2C[C@@H](F)CN2C(=O)Nc2cn(C(N)=O)c3ccccc23)c1] | 3-Chloro-5-{[(2S,4R)-1-(1-carbamoyl-1H-indol-3-ylcarbamoyl)-4-fluoro-pyrrolidine-2-carbonyl]-amino}-benzoic acid methyl ester | (1) 500 [M + H]+; t_R (b): 3.96 min. |
| 144 | 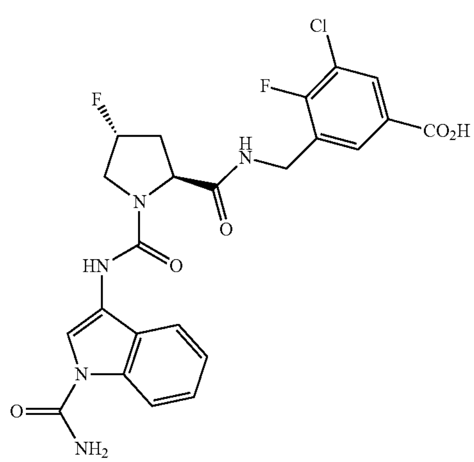 [SMILES: NC(=O)n1cc(NC(=O)N2C[C@H](F)C[C@H]2C(=O)NCc2cc(C(=O)O)cc(Cl)c2F)c2ccccc21] | 3-({[(2S,4R)-1-(1-Carbamoyl-1H-indol-3-ylcarbamoyl)-4-fluoro-pyrrolidine-2-carbonyl]-amino}-methyl)-5-chloro-4-fluoro-benzoic acid | (8) 520.0 [M]+; t_R (c): 3.05 min |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 145 | 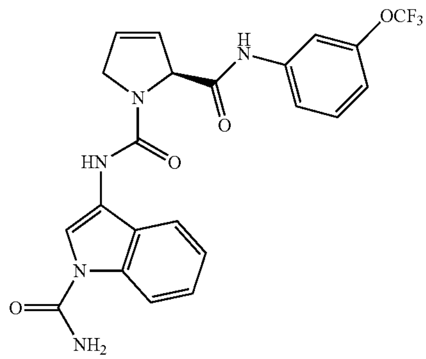 | (S)-2,5-Dihydro-pyrrole-1,2-dicarboxylic acid 1-[(1-carbamoyl-1H-indol-3-yl)-amide] 2-[(3-trifluoromethoxy-phenyl)-amide] | 474.1 [M + H]+, 969.2 [2MH + Na]+, 472.1 [M + H]−; t$_R$ (a): 3.38 min. |
| 146 | 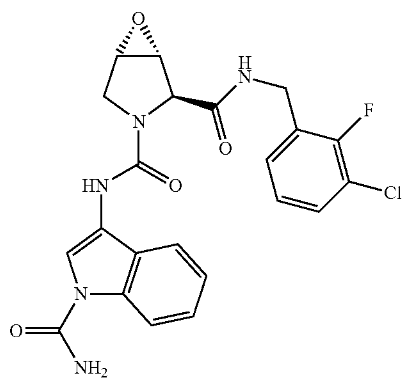 | (1R,2S,5S)-6-Oxa-3-aza-bicyclo[3.1.0]hexane-2,3-dicarboxylic acid 3-[(1-carbamoyl-1H-indol-3-yl)-amide] 2-(3-chloro-2-fluoro-benzylamide) | (8[B19]) 472 [M + H]+; t$_R$ (f): 1.76 min; 19F NMR (CD$_3$OD): −124. |
| 147 | 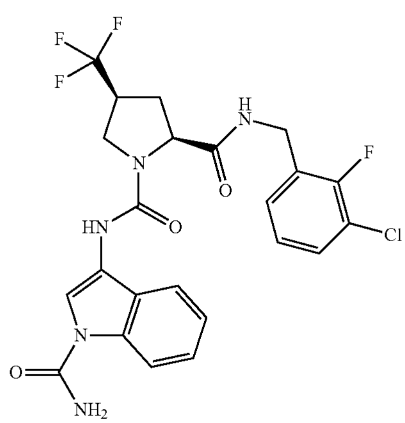 [SMILES: NC(=O)n1cc(NC(=O)N2C[C@@H](C(F)(F)F)C[C@H]2C(=O)NCc2cccc(Cl)c2F)c2ccccc21] | (2S,4S)-4-Trifluoromethyl-pyrrolidine-1,2-dicarboxylic acid 1-[(1-carbamoyl-1H-indol-3-yl)-amide] 2-(3-chloro-2-fluoro-benzylamide) | (1) Off-white solid. R$_f$ (EtOAc) = 0.30; 526.0 [M + H]+; t$_R$ (c): 4.88 min. |

TABLE 4-continued

| Example | Name | Characterization (end-table notes), TLC, R$_f$ (eluent); MS (LC/MS); t$_R$ (HPLC conditions); 19F NMR (100 MHz, solvent) δ (ppm): |
|---|---|---|
| 148 | (1R,3S,5R)-2-Aza-bicyclo[3.1.0]hexane-2,3-dicarboxylic acid 3-[(3-bromo-phenyl)-amide] 2-[(1-carbamoyl-1H-indol-3-yl)-amide] | (1) 481.9/483.0 [M + H]+, 481.9/482.8 [M − H]−, 436.9/438.9 [M − CONH$_2$]−; t$_R$ (b) 4.20 min. |
| 149 | (1S,5R)-2-Aza-bicyclo[3.1.0]hexane-1,2-dicarboxylic acid 2-[(1-carbamoyl-1H-indol-3-yl)-amide] 1-(3-chloro-2-fluoro-benzylamide) | (1) White solid. R$_f$ (EtOAc) = 0.43; 470 [M + H]+; t$_R$ (c): 4.49 min. |
| 150 | (2S,4R)-4-Fluoro-pyrrolidine-1,2-dicarboxylic acid 2-[(3-bromo-phenyl)-amide] 1-[(1-carbamoyl-1H-indol-3-yl)-amide] | (1) 487/489 [M + H]+; t$_R$ (b): 3.64 min. |
| 151 | (R)-2,2-Dimethyl-thiazolidine-3,4-dicarboxylic acid 3-[(1-carbamoyl-1H-indol-3-yl)-amide] 4-[(3-trifluoromethoxy-phenyl)-amide] | R$_f$ (c-hexane/EtOAc 1:3) = 0.51; 522.1 [M + H]+, 520.2 [M − H]−; t$_R$ (c): 5.39 min. |

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 152 | 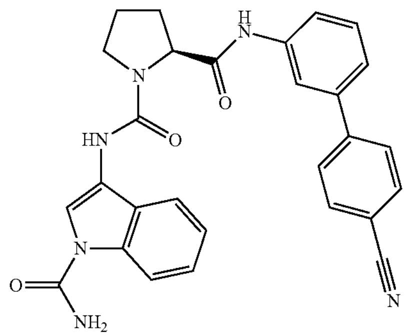 [SMILES: N#Cc1ccc(-c2cccc(NC(=O)[C@@H]3CCCN3C(=O)Nc3cn(C(N)=O)c4ccccc34)c2)cc1] | (S)-Pyrrolidine-1,2-dicarboxylic acid 1-[(1-carbamoyl-1H-indol-3-yl)-amide] 2-[(4'-cyano-biphenyl-3-yl)-amide] | 493 [M + H]+; $t_R$ (j) 2.90 min. |
| 153 | 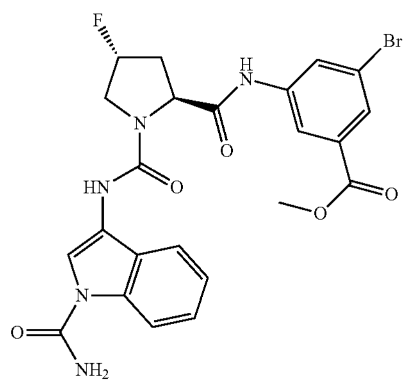 [SMILES: COC(=O)c1cc(Br)cc(NC(=O)[C@@H]2C[C@@H](F)CN2C(=O)Nc2cn(C(N)=O)c3ccccc23)c1] | 3-Bromo-5-{[(2S,4R)-1-(1-carbamoyl-1H-indol-3-ylcarbamoyl)-4-fluoro-pyrrolidine-2-carbamoyl]-amino}-benzoic acid methyl ester | $R_f$ (EtOAc) = 0.75; 546.1/548.1 [M + H]+, 568.1/570 [M + Na]+, 544/546 [M − H]−, 500/502 [M − CONH$_2$]−; $t_R$ (a): 3.33 min. |
| 154 | 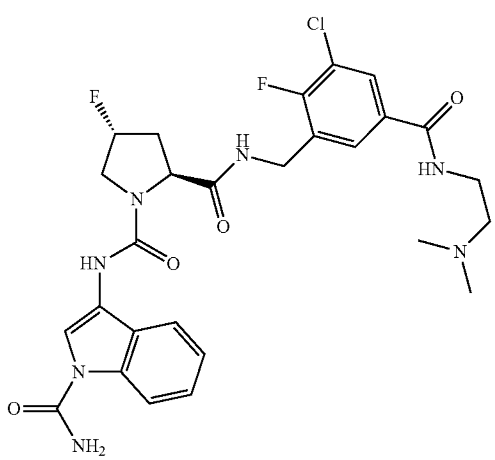 [SMILES: CN(C)CCNC(=O)c1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-[3-chloro-5-(2-dimethylamino-ethyl-carbamoyl)-2-fluoro-benzylamide] | (3,6[C3]) 590.2 [M]+; $t_R$ (c): 3.59 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 155 | 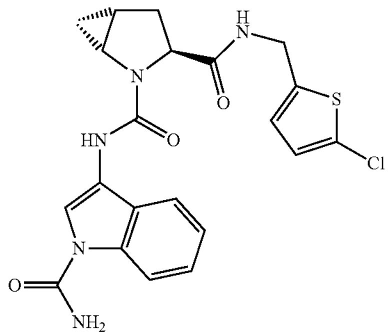 | (1R,3S,5R)-2-Aza-bicyclo[3.1.0]hexane-2,3-dicarboxylic acid 2-[(1-carbamoyl-1H-indol-3-yl)-amide] 3-[(5-chloro-thiophen-2-ylmethyl)-amide] | 458 [M + H]+, 456 [M − H]−, 413 [M − CONH$_2$]; t$_R$ (f): 1.99 min. |
| 156 | 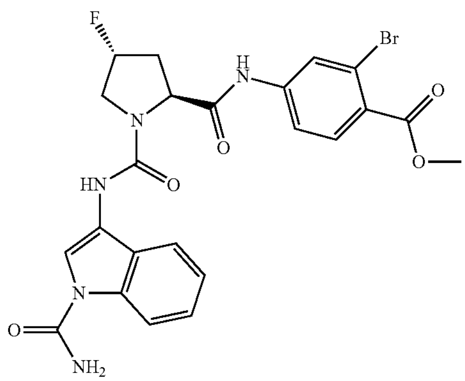 [SMILES: COC(=O)c1ccc(NC(=O)[C@@H]2C[C@@H](F)CN2C(=O)Nc2cn(C(N)=O)c3ccccc23)cc1Br] | 2-Bromo-4-{[(2S,4R)-1-(1-carbamoyl-1H-indol-3-ylcarbamoyl)-4-fluoro-pyrrolidine-2-carbonyl]-amino}-benzoic acid methyl ester | (1) 546/548 [M + H]+; t$_R$ (b): 3.55 min. |
| 157 | 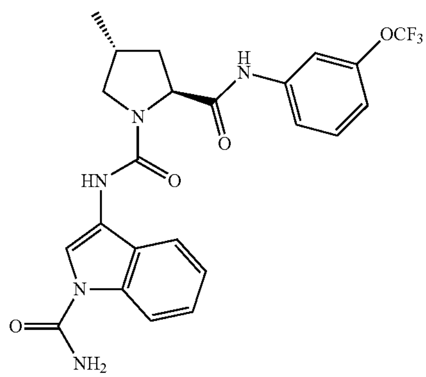 [SMILES: C[C@@H]1C[C@@H](C(=O)Nc2cccc(OC(F)(F)F)c2)N(C(=O)Nc2cn(C(N)=O)c3ccccc23)C1] | (2S,4R)-4-Methyl-pyrrolidine-1,2-dicarboxylic acid 1-[(1-carbamoyl-1H-indol-3-yl)-amide] 2-[(3-trifluoromethoxy-phenyl)-amide] | (8[B2]) R$_f$(c-hexane/EtOAc 1:3) = 0.44; 489.1 [M − H], 445.0 [M − CONH$_2$]−; t$_R$ (c): 4.65 min. |
| 158 | 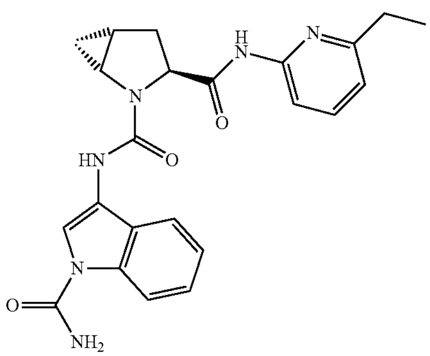 | (1R,3S,5R)-2-Aza-bicyclo[3.1.0]hexane-2,3-dicarboxylic acid 2-[(1-carbamoyl-1H-indol-3-yl)-amide] 3-[(6-ethyl-pyridin-2-yl)-amide] | 433.1 [M + H]+ 432.1 [M − H]−; t$_R$ (a): 2.49 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 159 | 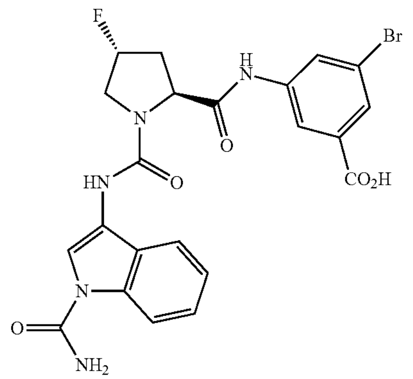 [SMILES: NC(=O)n1cc(NC(=O)N2C[C@H](F)C[C@H]2C(=O)Nc2cc(Br)cc(C(=O)O)c2)c2ccccc21] | 3-Bromo-5-{[(2S,4R)-1-(1-carbamoyl-1H-indol-3-ylcarbamoyl)-4-fluoro-pyrrolidine-2-carbonyl]-amino}-benzoic acid | (8[B7]) $R_f$ (CH$_2$Cl$_2$/MeOH 4:1) = 0.23; 532.0/534.0 [M + H]+, 554.0/556.0 [M + Na]+, 530.2/532.2 [M − H]−, 486.9/489.0 [M − CONH$_2$]−; $t_R$ (a): 2.98 min. |
| 160 | 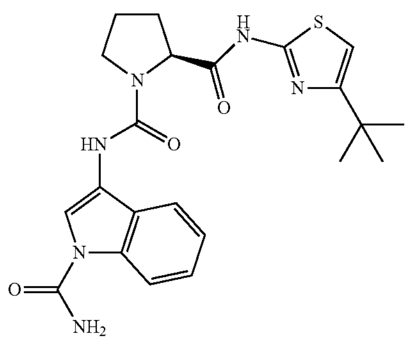 [SMILES: CC(C)(C)c1csc(NC(=O)[C@@H]2CCCN2C(=O)Nc2cn(C(N)=O)c3ccccc23)n1] | (S)-Pyrrolidine-1,2-dicarboxylic acid 2-[(4-tert-butyl-thiazol-2-yl)-amide] 1-[(1-carbamoyl-1H-indol-3-yl)-amide] | $R_f$ (c-hexane/EtOAc 1:2) = 0.32; 455.2 [M + H]+, 909.2 [2M + H]+, 453.1 [M − H]−; $t_R$ (H a): 3.5 min. |
| 161 | 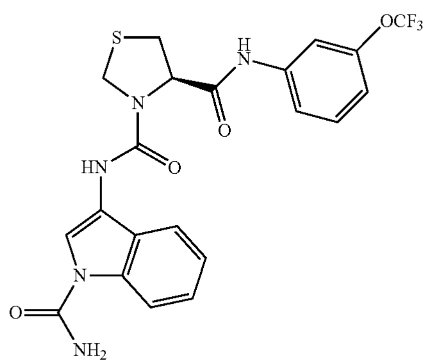 [SMILES: NC(=O)n1cc(NC(=O)N2CSC[C@H]2C(=O)Nc2cccc(OC(F)(F)F)c2)c2ccccc21] | (R)-Thiazolidine-3,4-dicarboxylic acid 3-[(1-carbamoyl-1H-indol-3-yl)-amide] 4-[(3-trifluoromethoxy-phenyl)-amide] | $R_f$ (c-hexane/EtOAc 1:3) = 0.42; 494.0 [M + H]+, 492.1 [M − H]−; $t_R$ (c): 5.03 min. |
| 162 | 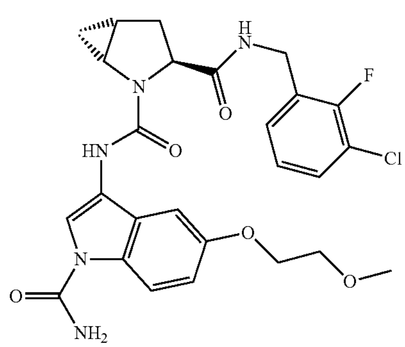 | (1R,3S,5R)-2-Aza-bicyclo[3.1.0]hexane-2,3-dicarboxylic acid 2-{[1-carbamoyl-5-(2-methoxy-ethoxy)-1H-indol-3-yl]-amide} 3-(3-chloro-2-fluoro-benzylamide) | (9) $R_f$ (EtOAc) = 0.3; 544.2/546.1 [M + H]+, 566/568.1 [M + Na]+, 542 [M − H]−, 499.1 [M − CONH$_2$]−; $t_R$ (f): 1.85 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 163 | (2S,4R)-4-Fluoro-pyrrolidine-1,2-dicarboxylic acid 1-[(1-carbamoyl-1H-indol-3-yl)-amide] 2-[(6-ethyl-pyridin-2-yl)-amide] | 439.1 [M + H]+, 899.2 [2M + Na]+, 437.0 [M − H]−; t_R (a): 2.32 min. |
| 164 | (2S,4S)-4-Hydroxy-4-methyl-pyrrolidine-1,2-dicarboxylic acid 1-[(1-carbamoyl-1H-indol-3-yl)-amide] 2-(3-chloro-2-fluoro-benzylamide) | (8[B13]) R_f (EtOAc) = 0.21; 488.2/490.1 [M + H]+, 486.1/488.1 [M − H]−; t_R (f): 1.75 min. |
| 165 | (2S,4R)-4-Fluoro-pyrrolidine-1,2-dicarboxylic acid 1-[(1-carbamoyl-1H-indol-3-yl)-amide] 2-[(5-bromo-4-methyl-pyridin-3-yl)-amide] | (4) R_f (EtOAc) = 0.38; 503/505 [M + H]+; t_R (c): 3.70 min |
| 166 | (1R,3S,5R)-2-Aza-bicyclo[3.1.0]hexane-2,3-dicarboxylic acid 2-[(1-carbamoyl-1H-indol-3-yl)-amide] 3-(3-chloro-2-fluoro-benzylamide) | 470 [M + H]+; t_R (b): 3.87 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 167 | (1R*,2S*,5S*)-3-Azabicyclo[3.1.0]hexane-2,3-dicarboxylic acid 3-[(1-carbamoyl-1H-indol-3-yl)-amide] 2-(3-chloro-benzylamide) | 452.0 [M + H]+, 407.0 [M − CONH$_2$]−; t$_R$ (a): 3.16 min. |
| 168 | (2S,4R)-4-Fluoro-pyrrolidine-1,2-dicarboxylic acid 2-[(5-bromo-2-methyl-pyridin-3-yl)-amide] 1-[(1-carbamoyl-1H-indol-3-yl)-amide] | 505.0 [M + H]+; t$_R$ (c): 3.67 min. |
| 169 | (S)-Thiazolidine-2,3-dicarboxylic acid 3-[(1-carbamoyl-1H-indol-3-yl)-amide] 2-(2,3-difluoro-benzylamide) | 460.1 [M + H]+, 941.2 [2M + Na]+, 415.0 [M − CONH$_2$]−; t$_R$ (a): 3.11 min. |
| 170 | (S)-Pyrrolidine-1,2-dicarboxylic acid 1-[(1-carbamoyl-1H-indol-3-yl)-amide] 2-(3-chloro-2-fluoro-benzylamide) | 458.0 [M + H]+, t$_R$ (b): 3.70 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 171 | 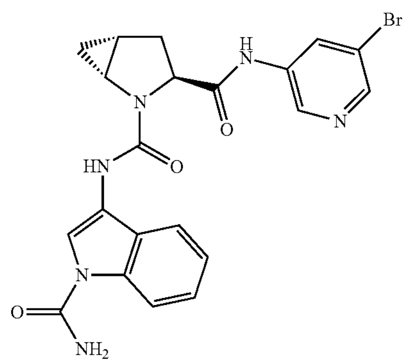 | (1R,3S,5R)-2-Aza-bicyclo[3.1.0]hexane-2,3-dicarboxylic acid 2-[(1-carbamoyl-1H-indol-3-yl)-amide] 3-[(5-bromo-pyridin-3-yl)-amide] | (4) White solid. R$_f$ (EtOAc) = 0.48; 483/485 [M + H]+; t$_R$ (c): 4.08 min. |
| 172 | 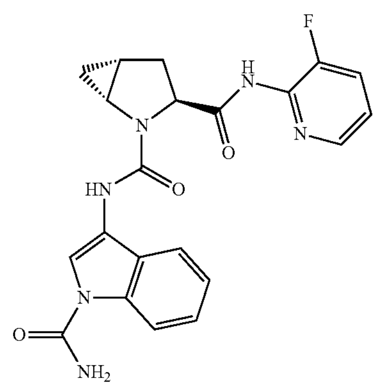 [SMILES: NC(=O)n1cc(NC(=O)N2[C@@H]3C[C@@H]3C[C@H]2C(=O)Nc2ncccc2F)c2ccccc21] | (1R,3S,5R)-2-Aza-bicyclo[3.1.0]hexane-2,3-dicarboxylic acid 2-[(1-carbamoyl-1H-indol-3-yl)-amide] 3-[(3-fluoro-pyridin-2-yl)-amide] | (4) Off-white solid. R$_f$ (CH$_2$Cl$_2$/MeOH 95/5) = 0.21; 423 [M + H]+; t$_R$ (c): 3.59 min. |
| 173 | 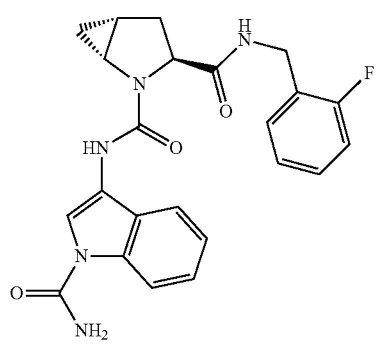 | (1R,3S,5R)-2-Azabicyclo[3.1.0]hexane-2,3-dicarboxylic acid 2-[(1-carbamoyl-1H-indol-3-yl)-amide] 3-(2-fluoro-benzylamide) | R$_f$ (EtOAc) = 0.5; 436.4/438.5 [M + H]+, 871.7/873.7 [2M + H]+, 480.4/482.4 [M + HCOO]−; t$_R$ (f): 1.77 min. |
| 174 | 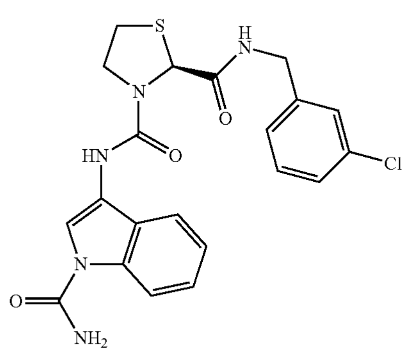 [SMILES: NC(=O)n1cc(NC(=O)N2CCS[C@H]2C(=O)NCc2cccc(Cl)c2)c2ccccc21] | (S)-Thiazolidine-2,3-dicarboxylic acid 3-[(1-carbamoyl-1H-indol-3-yl)-amide] 2-(3-chloro-benzylamide) | 458 [M + H]+; t$_R$ (a): 3.17 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---------|-----------|------|--------------------------------------|
| 175 | 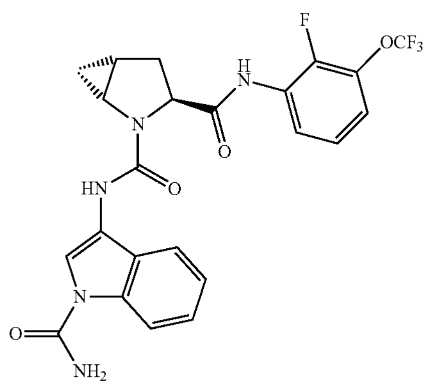 | (1R,3S,5R)-2-Aza-bicyclo[3.1.0]hexane-2,3-dicarboxylic acid 2-[(1-carbamoyl-1H-indol-3-yl)-amide] 3-[(2-fluoro-3-trifluoromethoxy-phenyl)-amide] | (1,6) White solid. 506 [M + H]+; $t_R$ (b) 4.47 min. |
| 176 | 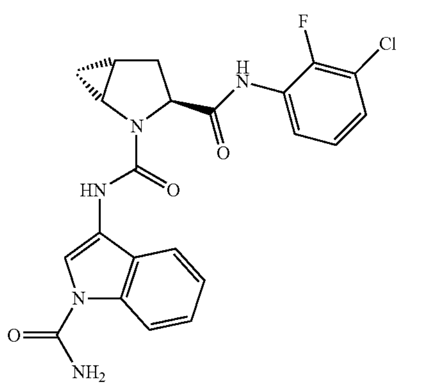 | (1R,3S,5R)-2-Aza-bicyclo[3.1.0]hexane-2,3-dicarboxylic acid 2-[(1-carbamoyl-1H-indol-3-yl)-amide] 3-[(3-chloro-2-fluoro-phenyl)-amide] | (1) White solid. 456 [M + H]+; $t_R$ (b): 4.14 min. |
| 177 | 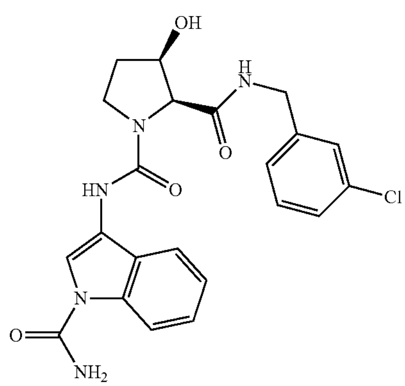 [SMILES: NC(=O)n1cc(NC(=O)N2CC[C@@H](O)[C@H]2C(=O)NCc2cccc(Cl)c2)c2ccccc21] | (2S,3R)-3-Hydroxy-pyrrolidine-1,2-dicarboxylic acid 1-[(1-carbamoyl-1H-indol-3-yl)-amide] 2-(3-chloro-benzylamide) | (1) White solid. 456 [M + H]+; $t_R$ (b): 2.84 min. |

TABLE 4-continued

| Example | Name | Characterization (end-table notes), TLC, $R_f$ (eluent); MS (LC/MS); $t_R$ (HPLC conditions); 19F NMR (100 MHz, solvent) δ (ppm): |
|---|---|---|
| 178 | (S)-Thiazolidine-2,3-dicarboxylic acid 3-[(1-carbamoyl-1H-indol-3-yl)-amide] 2-(3-chloro-2-fluoro-benzylamide) | 475.9 [M + H]+, 498 [M + Na]+; $t_R$ (b): 3.89 min. |
| 179 | (2S,5R)-5-Azidomethyl-pyrrolidine-1,2-dicarboxylic acid 1-[(1-carbamoyl-1H-indol-3-yl)-amide] 2-[(3-trifluoromethoxy-phenyl)-amide] | (8[B3]) 531.1 [M + H]+; $t_R$ (b): 4.85 min. |
| 180 | (S)-5-Aza-spiro[2.4]heptane-5,6-dicarboxylic acid 5-[(1-carbamoyl-1H-indol-3-yl)-amide] 6-(3-chloro-benzylamide) | 466.1 [M + H]+, 421.1 [M − CONH$_2$]−; $t_R$ (a): 3.26 min. |
| 181 | (2S,4R)-4-Fluoro-4-hydroxymethyl-pyrrolidine-1,2-dicarboxylic acid 1-[(1-carbamoyl-1H-indol-3-yl)-amide] 2-(3-chloro-2-fluoro-benzylamide) | (8[B12]) $R_f$ (EtOAc) = 0.15; 506.2/508.1 [M + H]+, 528.1/530.2 [M + Na]+, 504.1/506 [M − H]−; $t_R$ (f): 1.69 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 182 | 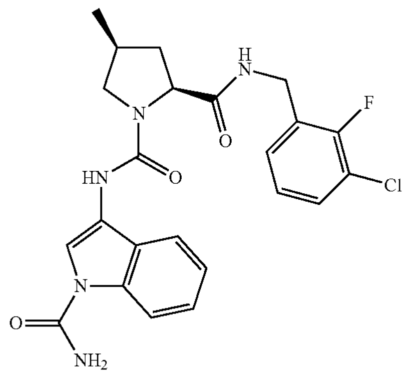 [SMILES: C[C@H]1C[C@@H](C(=O)NCc2cccc(Cl)c2F)N(C(=O)Nc2cn(C(N)=O)c3ccccc23)C1] | (2S,4S)-4-Methyl-pyrrolidine-1,2-dicarboxylic acid 1-[(1-carbamoyl-1H-indol-3-yl)-amide] 2-(3-chloro-2-fluoro-benzylamide) | (1,8[B2]) R$_f$ (EtOAc) = 0.51; 472.0 [M + H]+; t$_R$ (c): 4.62 min. |
| 183 | 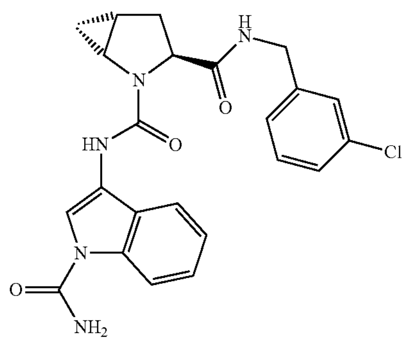 | (1R,3S,5R)-2-Aza-bicyclo[3.1.0]hexane-2,3-dicarboxylic acid 2-[(1-carbamoyl-1H-indol-3-yl)-amide] 3-(3-chloro-benzylamide) | 452/454 [M + H]+; t$_R$ (a): 3.16 min; t$_R$ (b): 3.78 min. |
| 184 | 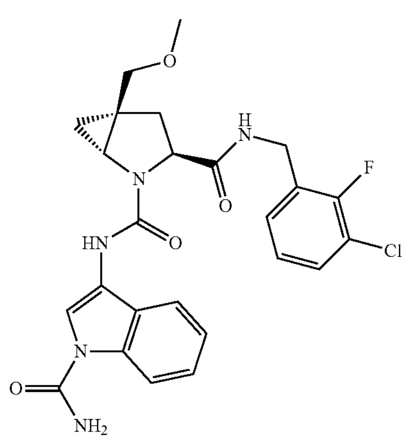 [SMILES: COC[C@@]12C[C@@H](C(=O)NCc3cccc(Cl)c3F)N(C(=O)Nc3cn(C(N)=O)c4ccccc34)[C@@H]1C2] | (1R,3S,5S)-5-Methoxymethyl-2-aza-bicyclo[3.1.0]hexane-2,3-dicarboxylic acid 2-[(1-carbamoyl-1H-indol-3-yl)-amide] 3-(3-chloro-2-fluoro-benzylamide) | (5,8) Rf (EtOAc) = 0.20; 514.4/516.4 [M + H]+, 512.3 [M − H]−; t$_R$ (a): 3.27 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 185 | 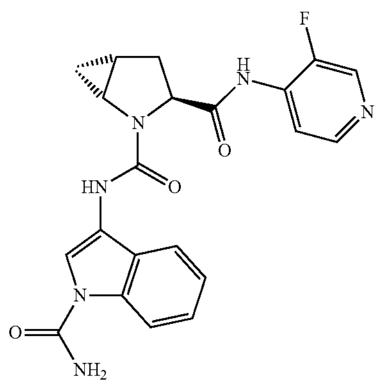 | (1R,3S,5R)-2-Aza-bicyclo[3.1.0]hexane-2,3-dicarboxylic acid 2-[(1-carbamoyl-1H-indol-3-yl)-amide] 3-[(3-fluoro-pyridin-4-yl)-amide] | (4) R$_f$ (EtOAc) = 0.23; 423 [M + H]+; t$_R$ (c): 3.4 min. |
| 186 | 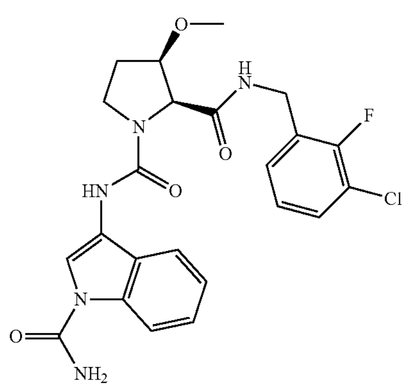 [SMILES: CO[C@@H]1CCN(C(=O)Nc2cn(C(N)=O)c3ccccc23)[C@@H]1C(=O)NCc1cccc(Cl)c1F] | (2S,3R)-3-Methoxy-pyrrolidine-1,2-dicarboxylic acid 1-[(1-carbamoyl-1H-indol-3-yl)-amide] 2-(3-chloro-2-fluoro-benzylamide) | (8) White solid. 488 [M + H]+; t$_R$ (b): 3.61 min. |
| 187 | 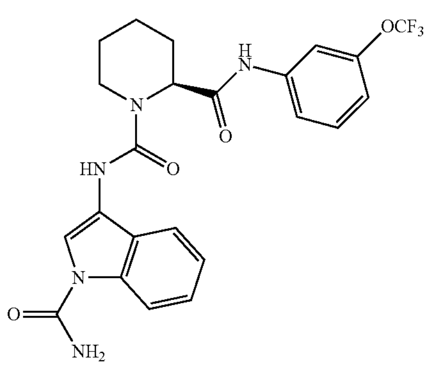 [SMILES: NC(=O)n1cc(NC(=O)N2CCCC[C@H]2C(=O)Nc2cccc(OC(F)(F)F)c2)c2ccccc21] | (S)-Piperidine-1,2-dicarboxylic acid 1-[(1-carbamoyl-1H-indol-3-yl)-amide] 2-[(3-trifluoromethoxy-phenyl)-amide] | R$_f$ (c-hexane-EtOAc 1:2) = 0.21; 490.1 [M + H]+, 1001.2 [2M + Na]+, 488.1 [M − H]−; t$_R$ (a): 3.75 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 188 | 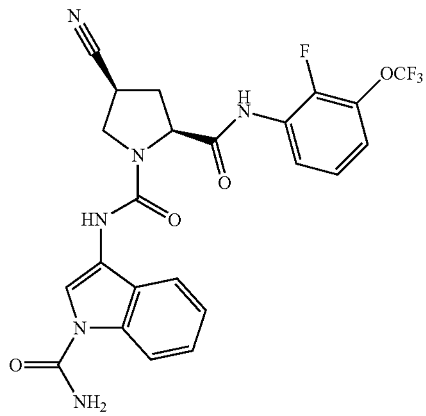 | (2S,4S)-4-Cyano-pyrrolidine-1,2-dicarboxylic acid 1-[(1-carbamoyl-1H-indol-3-yl)-amide] 2-[(2-fluoro-3-trifluoromethoxy-phenyl)-amide] | (2 at 50° C., 3,6) $R_f$(EtOAc) = 0.45; 519.1 [M + H]+, 541.0 [M + Na]+, 517.2 [M − H]−; $t_R$ (f): 1.93. |
| 189 | 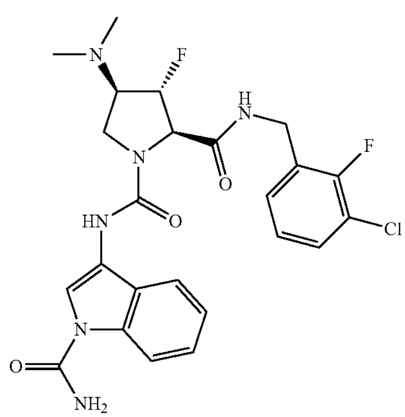 [SMILES: CN(C)[C@@H]1CN(C(=O)Nc2cn(C(N)=O)c3ccccc23)[C@H](C(=O)NCc2cccc(Cl)c2F)[C@H]1F] | (2R,3S,4R)-4-Dimethylamino-3-fluoro-pyrrolidine-1,2-dicarboxylic acid 1-[(1-carbamoyl-1H-indol-3-yl)-amide] 2-(3-chloro-2-fluoro-benzylamide) | (8[B20]) $R_f$ (CH$_2$Cl$_2$/MeOH 95/5) = 0.26; 519 [M + H]+, 563 [M − HCOO]−; $t_R$ (f): 1.51 min. |
| 190 | 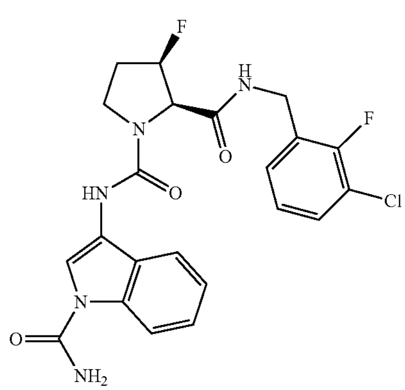 [SMILES: NC(=O)n1cc(NC(=O)N2CC[C@@H](F)[C@H]2C(=O)NCc2cccc(Cl)c2F)c2ccccc21] | (2R,3R)-3-Fluoro-pyrrolidine-1,2-dicarboxylic acid 1-[(1-carbamoyl-1H-indol-3-yl)-amide] 2-(3-chloro-2-fluoro-benzylamide) | (8) White solid. 476 [M + H]+; $t_R$ (b): 3.66 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 191 | 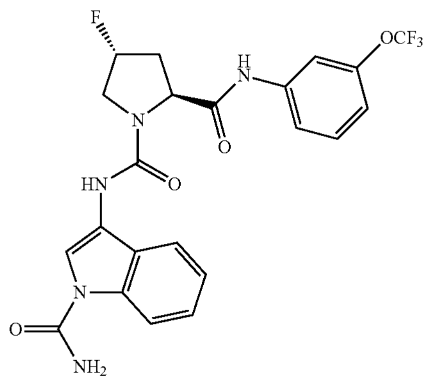 [SMILES: NC(=O)n1cc(NC(=O)N2C[C@H](F)C[C@H]2C(=O)Nc2cccc(OC(F)(F)F)c2)c2ccccc21] | (2S,4R)-4-Fluoro-pyrrolidine-1,2-dicarboxylic acid 1-[(1-carbamoyl-1H-indol-3-yl)-amide] 2-[(3-trifluoromethoxy-phenyl)-amide] | R$_f$ (c-hexane/EtOAc 1:2) = 0.33; 494.0 [M + H]+, 492.1 [M − H]−; t$_R$ (a): 3.41 min. |
| 192 | 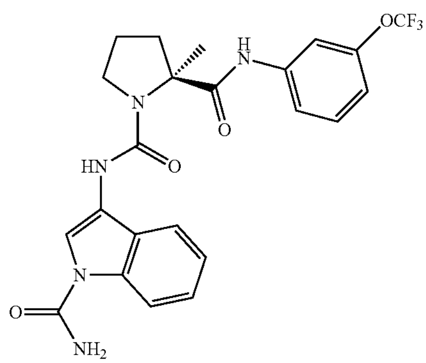 [SMILES: C[C@@]1(C(=O)Nc2cccc(OC(F)(F)F)c2)CCCN1C(=O)Nc1cn(C(N)=O)c2ccccc12] | (S)-2-Methyl-pyrrolidine-1,2-dicarboxylic acid 1-[(1-carbamoyl-1H-indol-3-yl)-amide] 2-[(3-trifluoromethoxy-phenyl)-amide] | 490.1 [M + H]+, 512.2 [M + Na]+; t$_R$ (a): 3.61 min. |
| 193 | 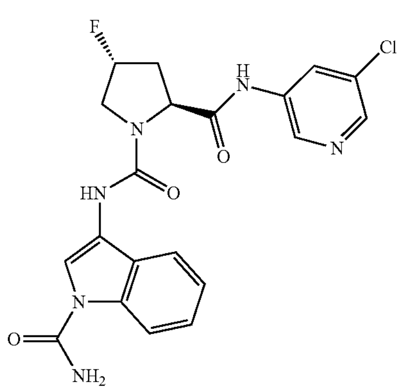 [SMILES: NC(=O)n1cc(NC(=O)N2C[C@H](F)C[C@H]2C(=O)Nc2cncc(Cl)c2)c2ccccc21] | (2S,4R)-4-Fluoro-pyrrolidine-1,2-dicarboxylic acid 1-[(1-carbamoyl-1H-indol-3-yl)-amide] 2-[(5-chloro-pyridin-3-yl)-amide] | (4) R$_f$ (c-hexane/EtOAc 1:3) = 0.12; 445 [M + H]+; t$_R$ (b): 3.79 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 194 | 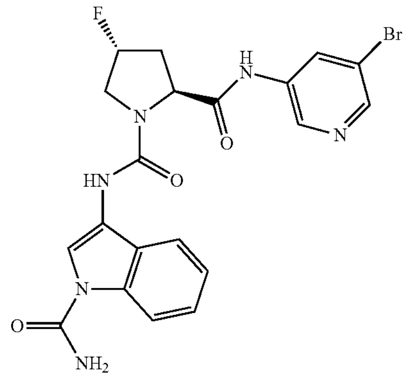 | (2S,4R)-4-Fluoro-pyrrolidine-1,2-dicarboxylic acid 1-[(1-carbamoyl-1H-indol-3-yl)-amide] 2-[(5-bromo-pyridin-3-yl)-amide] | (4) R$_f$ (c-hexane/EtOAc 1:3) = 0.1; 491 [M + H]+; t$_R$ (c): 3.85 min. |
| 195 | 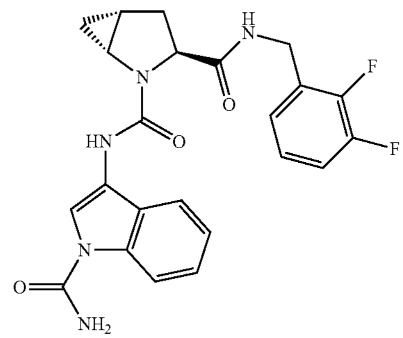 [SMILES: NC(=O)n1cc(NC(=O)N2[C@@H]3C[C@@H]3C[C@H]2C(=O)NCc2cccc(F)c2F)c2ccccc21] | (1R,3S,5R)-2-Aza-bicyclo[3.1.0]hexane-2,3-dicarboxylic acid 2-[(1-carbamoyl-1H-indol-3-yl)-amide] 3-(2,3-difluoro-benzylamide) | 454.1 [M + H]+, 929.3 [2M + Na]+, 409.1 [M − CONH$_2$]−; t$_R$ (a): 3.09 min. |
| 196 | 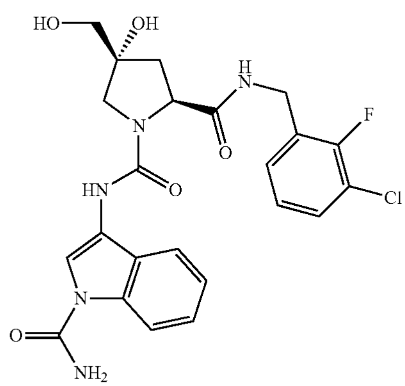 | (2S,4R)-4-Hydroxy-4-hydroxymethyl-pyrrolidine-1,2-dicarboxylic acid 1-[(1-carbamoyl-1H-indol-3-yl)-amide] 2-(3-chloro-2-fluoro-benzylamide) | (8[B12]) 504 [M + H]+, 502 [M − H]−; t$_R$ (f): 1.57 min. |
| 197 | 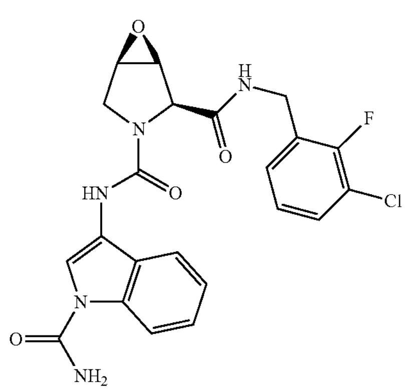 | (1S,2S,5R)-6-Oxa-3-aza-bicyclo[3.1.0]hexane-2,3-dicarboxylic acid 3-[(1-carbamoyl-1H-indol-3-yl)-amide] 2-(3-chloro-2-fluoro-benzylamide) | (8[B19]) 472 [M + H]+; t$_R$ (f): 1.54 min; 19F NMR (CD$_3$OD): −124. |

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 198 | 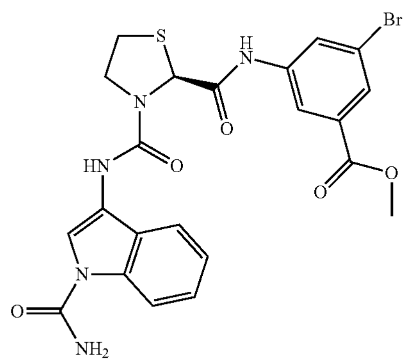 [SMILES: COC(=O)c1cc(Br)cc(NC(=O)[C@@H]2SCCN2C(=O)Nc2cn(C(N)=O)c3ccccc23)c1] | 3-Bromo-5-{[(S)-3-(1-carbamoyl-1H-indol-3-ylcarbamoyl)-thiazolidine-2-carbonyl]-amino}-benzoic acid methyl ester | (1) 544.2/546.2 [M + H]+; $t_R$ (b): 4.26 min. |
| 199 | 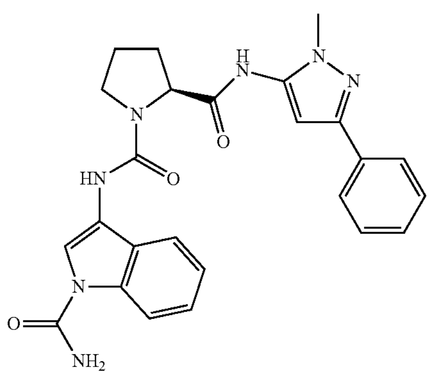 [SMILES: Cn1nc(-c2ccccc2)cc1NC(=O)[C@@H]1CCCN1C(=O)Nc1cn(C(N)=O)c2ccccc12] | (S)-Pyrrolidine-1,2-dicarboxylic acid 1-[(1-carbamoyl-1H-indol-3-yl)-amide] 2-[(2-methyl-5-phenyl-2H-pyrazol-3-yl)-amide] | $R_f$ (EtOAc) = 0.26; 472.1 [M + H]+, 470.2 [M − H]−; $t_R$ (a): 3.07 min. |
| 200 | 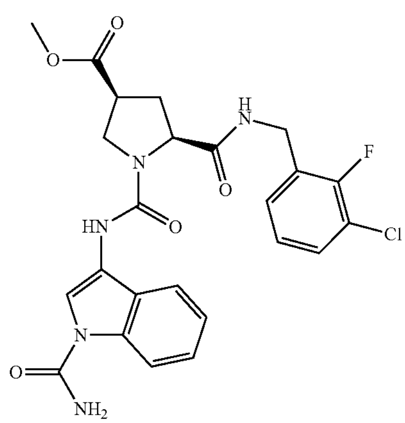 [SMILES: COC(=O)[C@H]1C[C@@H](C(=O)NCc2cccc(Cl)c2F)N(C(=O)Nc2cn(C(N)=O)c3ccccc23)C1] | (3S,5S)-1-(1-Carbamoyl-1H-indol-3-ylcarbamoyl)-5-(3-chloro-2-fluoro-benzylcarbamoyl)-pyrrolidine-3-carboxylic acid methyl ester | (8) 516 [M + H]+, 540 [M + Na]+; $t_R$ (b): 3.37 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 201 | 4,5-Dihydro-pyrazole-1,5-dicarboxylic acid 1-[(1-carbamoyl-1H-indol-3-yl)-amide] 5-(3-chloro-2-fluoro-benzylamide) | (8[B5]) R_f (CH_2Cl_2/acetone 1:1) = 0.53; 457.0 [M + H]+; t_R (b): 3.77 min. |
| 202 | (2S,4S)-4-Hydroxy-4-hydroxymethyl-pyrrolidine-1,2-dicarboxylic acid 1-[(1-carbamoyl-1H-indol-3-yl)-amide] 2-(3-chloro-2-fluoro-benzylamide) | (8[B12]) 504 [M + H]+, 502 [M − H]−; t_R (f): 1.60 min. |
| 203 | (1R,3S,5R)-2-Aza-bicyclo[3.1.0]hexane-2,3-dicarboxylic acid 2-[(1-carbamoyl-1H-indol-3-yl)-amide] 3-{[(S)-1-(3-chloro-2-fluoro-phenyl)-2-hydroxy-ethyl]-amide} | (5,8[B9]) R_f (CH_2Cl_2/MeOH 95:5) = 0.2; 498.1/500.4 [M − H]−, 543.8 [M + HCOO]−, 500.2 [M + H]+, 522/522.7 [M + Na]+; t_R (a): 1.81 min. |
| 204 | (2S,3S,4S)-4-Fluoro-3-methoxy-pyrrolidine-1,2-dicarboxylic acid 1-[(1-carbamoyl-1H-indol-3-yl)-amide] 2-(3-chloro-2-fluoro-benzylamide) | (8[B24]) 506 [M + H]+, 550 [M + HCOO]−; t_R (f): 1.87 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 205 | 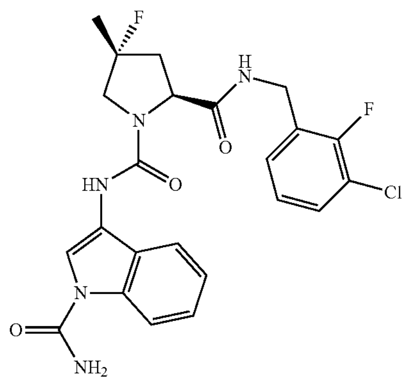 [SMILES: C[C@@]1(F)C[C@@H](C(=O)NCc2cccc(Cl)c2F)N(C(=O)Nc2cn(C(N)=O)c3ccccc23)C1] | (2S,4R)-4-Fluoro-4-methyl-pyrrolidine-1,2-dicarboxylic acid 1-[(1-carbamoyl-1H-indol-3-yl)-amide] 2-(3-chloro-2-fluoro-benzylamide) | (8[B13]) TLC, R_f (EtOAc) = 0.45; 490.1/492.1 [M + H]+, 488/490 [M − H]−, 445/447.1 [M − CONH_2]−; t_R (f): 1.89 min. |
| 206 | 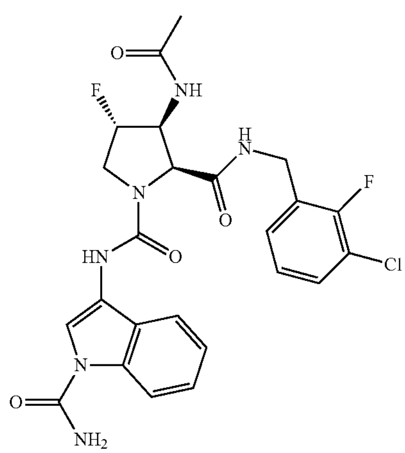 [SMILES: CC(=O)N[C@H]1[C@@H](C(=O)NCc2cccc(Cl)c2F)N(C(=O)Nc2cn(C(N)=O)c3ccccc23)C[C@@H]1F] | (2S,3S,4S)-3-Acetylamino-4-fluoro-pyrrolidine-1,2-dicarboxylic acid 1-[(1-carbamoyl-1H-indol-3-yl)-amide] 2-(3-chloro-2-fluoro-benzylamide) | (8[B23]) R_f (CH_2Cl_2/MeOH 95/5) = 0.26; 531 [M + H]+, 533 [M − H]−; t_R (f): 1.72 min. |
| 207 | 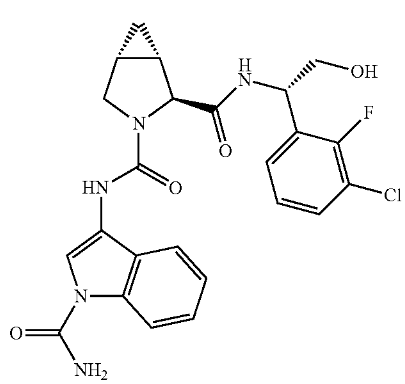 [SMILES: NC(=O)n1cc(NC(=O)N2C[C@@H]3C[C@@H]3[C@H]2C(=O)N[C@H](CO)c2cccc(Cl)c2F)c2ccccc21] | (1S,2S,5R)-3-Azabicyclo[3.1.0]hexane-2,3-dicarboxylic acid 3-[(1-carbamoyl-1H-indol-3-yl)-amide] 2-{[(S)-1-(3-chloro-2-fluoro-phenyl)-2-hydroxy-ethyl]-amide} | (5,8[B9]) R_f (EtOAc) = 0.25; 500.3 [M + H]+, 544.3/546.4 [M + HCOO]−; t_R (a): 2.93 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 208 | 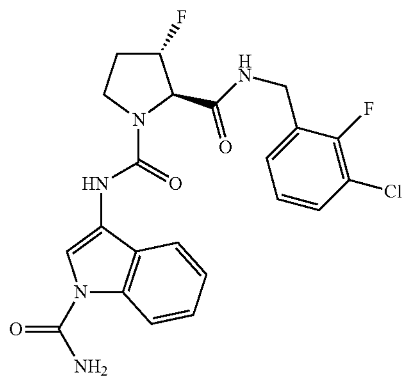 [SMILES: NC(=O)n1cc(NC(=O)N2CC[C@H](F)[C@H]2C(=O)NCc2cccc(Cl)c2F)c2ccccc21] | (2R,3S)-3-Fluoro-pyrrolidine-1,2-dicarboxylic acid 1-[(1-carbamoyl-1H-indol-3-yl)-amide] 2-(3-chloro-2-fluoro-benzylamide) | (8) White solid. 476 [M + H]+; t$_R$ (b): 3.86 min. |
| 209 | 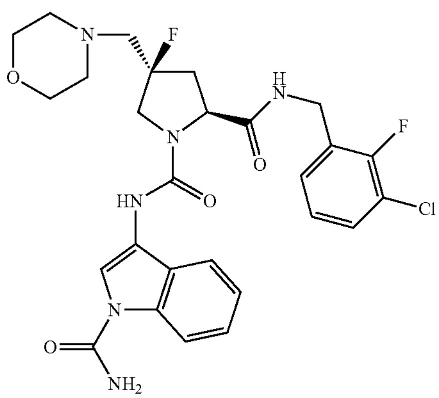 [SMILES: NC(=O)n1cc(NC(=O)N2C[C@](F)(CN3CCOCC3)C[C@H]2C(=O)NCc2cccc(Cl)c2F)c2ccccc21] | (2S,4R)-4-Fluoro-morpholin-4-ylmethyl-pyrrolidine-1,2-dicarboxylic acid 1-[(1-carbamoyl-1H-indol-3-yl)-amide] 2-(3-chloro-2-fluoro-benzylamide) | (8[B14]) 575 [M + H]+, 502 [M − H]−; t$_R$ (f): 1.53 min. |
| 210 | 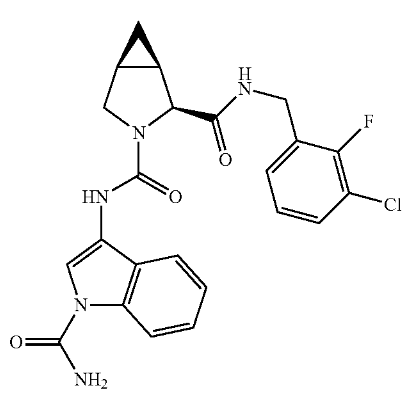 [SMILES: NC(=O)n1cc(NC(=O)N2C[C@H]3C[C@H]3[C@H]2C(=O)NCc2cccc(Cl)c2F)c2ccccc21] | (1R,2S,5S)-3-Aza-bicyclo[3.1.0]hexane-2,3-dicarboxylic acid 3-[(1-carbamoyl-1H-indol-3-yl)-amide] 2-(3-chloro-2-fluoro-benzylamide) | R$_f$ (EtOAc) = 0.45; 470.4/472.4 [M + H]+, 468.3/470.3 [M − H]−, 514.4/516.5 [M + HCOO]−; t$_R$ (a): 3.21 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 211 | 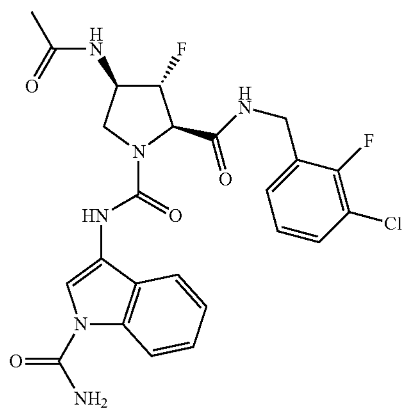 [SMILES: CC(=O)N[C@@H]1CN(C(=O)Nc2cn(C(N)=O)c3ccccc23)[C@H](C(=O)NCc2cccc(Cl)c2F)[C@H]1F] | (2R,3S,4R)-4-Acetylamino-3-fluoro-pyrrolidine-1,2-dicarboxylic acid 1-[(1-carbamoyl-1H-indol-3-yl)-amide] 2-(3-chloro-2-fluoro-benzylamide) | (8[B23]) R$_f$ (EtOAc) = 0.26; 531 [M + H]+, 533 [M − H]−; t$_R$ (f): 1.74 min. |
| 212 | 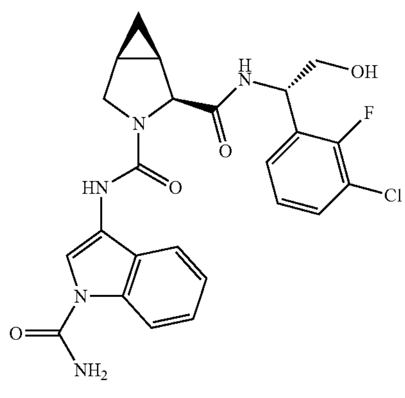 [SMILES: NC(=O)n1cc(NC(=O)N2C[C@H]3C[C@H]3[C@H]2C(=O)N[C@H](CO)c2cccc(Cl)c2F)c2ccccc21] | (1R,2S,5S)-3-Azabicyclo[3.1.0]hexane-2,3-dicarboxylic acid 3-[(1-carbamoyl-1H-indol-3-yl)-amide] 2-{[(S)-1-(3-chloro-2-fluoro-phenyl)-2-hydroxy-ethyl]-amide} | (5,8[B9]) R$_f$ (EtOAc) = 0.3; 520.3 [M + H]+, 564.3/566.3 [M + HCOO]−; t$_R$ (a): 3.0 min. |
| 213 | 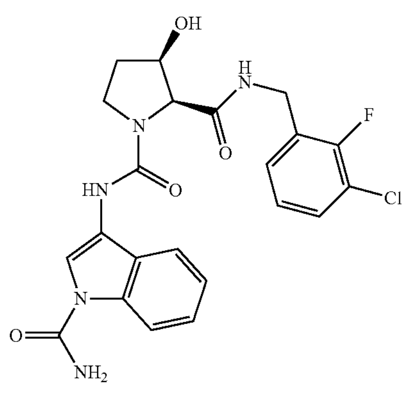 [SMILES: NC(=O)n1cc(NC(=O)N2CC[C@@H](O)[C@H]2C(=O)NCc2cccc(Cl)c2F)c2ccccc21] | (2S,3R)-3-Hydroxy-pyrrolidine-1,2-dicarboxylic acid 1-[(1-carbamoyl-1H-indol-3-yl)-amide] 2-(3-chloro-2-fluoro-benzylamide) | (1) White solid. 474 [M + H]+; t$_R$ (b): 3.11 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 214 | 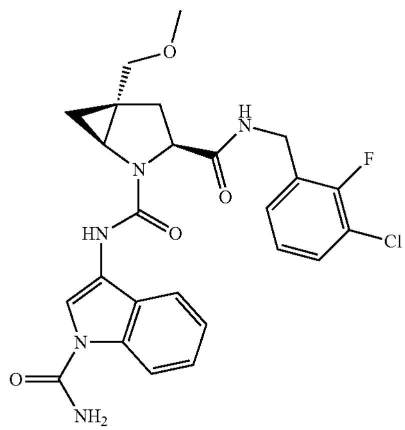 [SMILES: COC[C@@]12C[C@@H]1N(C(=O)Nc1cn(C(N)=O)c3ccccc13)[C@H](C(=O)NCc1cccc(Cl)c1F)C2] | (1S,3S,5R)-5-Methoxymethyl-2-aza-bicyclo[3.1.0]hexane-2,3-dicarboxylic acid 2-[(1-carbamoyl-1H-indol-3-yl)-amide] 3-(3-chloro-2-fluoro-benzylamide) | (5,8) White solid. Rf (EtOAc) = 0.20; 514.4/516.4 [M + H]+, 512.4 [M − H]−, 558.3/560.3 [M + HCOO]−; t$_R$ (a): 3.27 min. |
| 215 | 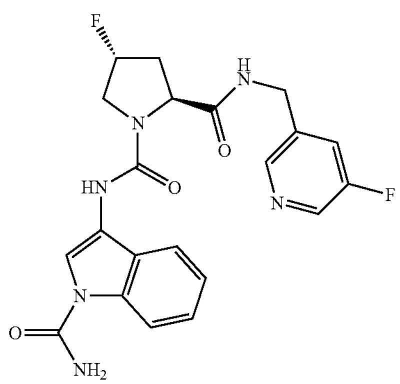 [SMILES: NC(=O)n1cc(NC(=O)N2C[C@H](F)C[C@H]2C(=O)NCc2cncc(F)c2)c2ccccc21] | (2S,4R)-4-Fluoro-pyrrolidine-1,2-dicarboxylic acid 1-[(1-carbamoyl-1H-indol-3-yl)-amide] 2-[(5-fluoro-pyridin-3-ylmethyl)-amide] | (1) White solid. 443 [M + H]+; t$_R$ (b): 3.15 min. |
| 216 | 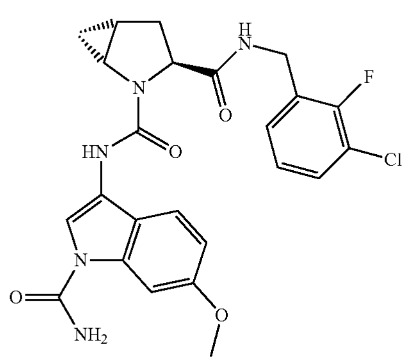 | (1R,3S,5R)-2-Aza-bicyclo[3.1.0]hexane-2,3-dicarboxylic acid 2-[(1-carbamoyl-6-methoxy-1H-indol-3-yl)-amide] 3-(3-chloro-2-fluoro-benzylamide) | (9[A1]) R$_f$ (EtOAc) = 0.45; 500/502.2 [M + H]+, 455.2/457.2 [M − CONH$_2$]−; t$_R$ (f): 1.90 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 217 | 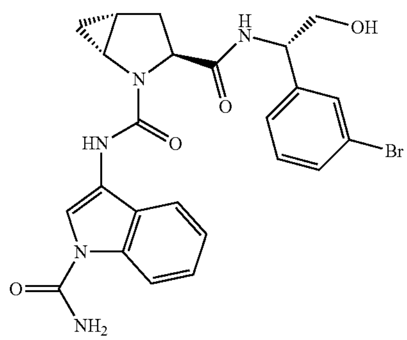 [SMILES: NC(=O)n1cc(NC(=O)N2[C@@H]3C[C@@H]3C[C@H]2C(=O)N[C@H](CO)c2cccc(Br)c2)c2ccccc21] | (1R,3S,5R)-2-Azabicyclo[3.1.0]hexane-2,3-dicarboxylic acid 3-{[(S)-1-(3-bromo-phenyl)-2-hydroxy-ethyl]-amide} 2-[(1-carbamoyl-1H-indol-3-yl)-amide] | (5) $R_f$ (EtOAc) = 0.25; 526.3/528.3 [M + H]+, 570.4/572.4 [M + HCOO]−; $t_R$ (a): 3.1 min. |
| 218 | 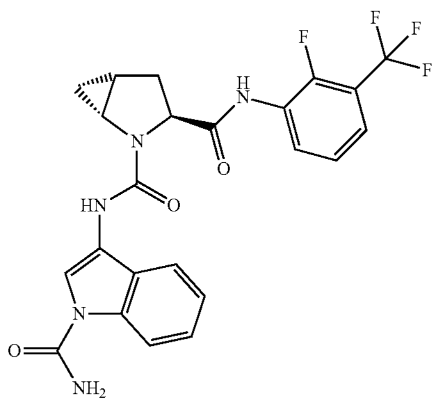 | (1R,3S,5R)-2-Azabicyclo[3.1.0]hexane-2,3-dicarboxylic acid 2-[(1-carbamoyl-1H-indol-3-yl)-amide] 3-[(2-fluoro-3-trifluoromethoxy-phenyl)-amide] | (1) White solid. 490 [M + H]+; $t_R$ (b): 4.39 min. |
| 219 | 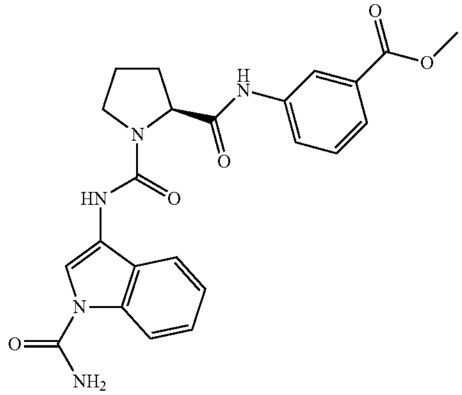 [SMILES: COC(=O)c1cccc(NC(=O)[C@@H]2CCCN2C(=O)Nc2cn(C(N)=O)c3ccccc23)c1] | 3-{[(S)-1-(1-Carbamoyl-1H-indol-3-ylcarbamoyl)-pyrrolidine-2-carbonyl]-amino}-benzoic acid methyl ester | 450.1 [M + H]+, 473.0 [M + Na]+, 899.2 [2M + H]+, 448.1 [M − H]−; $t_R$ (a): 3.03 min. |

TABLE 4-continued

| Example | Name | Characterization (end-table notes), TLC, R$_f$ (eluent); MS (LC/MS); t$_R$ (HPLC conditions); 19F NMR (100 MHz, solvent) δ (ppm): |
|---|---|---|
| 220 | (S)-Piperidine-1,2-dicarboxylic acid 1-[(1-carbamoyl-1H-indol-3-yl)-amide] 2-(3-chloro-2-fluoro-benzylamide) | (1) 472 [M + H]+, 494 [M + Na]+; t$_R$ (c): 4.72 min. |
| 221 | (2S,4S)-4-(Acetylamino-methyl)-4-fluoro-pyrrolidine-1,2-dicarboxylic acid 1-[(1-carbamoyl-1H-indol-3-yl)-amide] 2-(3-chloro-2-fluoro-benzylamide) | (8) 531 [M + H]−, 533 [M + H]+; t$_R$ (f): 0.56 min; 19F NMR (DMSO-d$_6$): −121, −1.50. |
| 222 | (2S,4R)-4-Fluoro-pyrrolidine-1,2-dicarboxylic acid 1-[(1-carbamoyl-1H-indol-3-yl)-amide] 2-(2-fluoro-3-trifluoromethyl-benzylamide) | (1) White solid. 510 [M + H]+; t$_R$ (b): 3.88 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 223 | 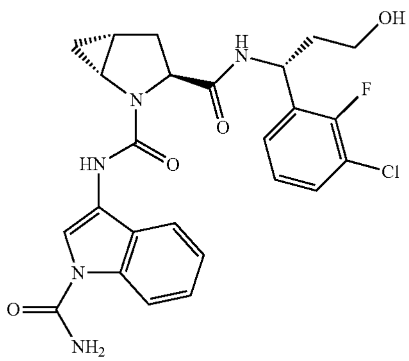 [SMILES: NC(=O)n1cc(NC(=O)N2[C@@H]3C[C@@H]3C[C@H]2C(=O)N[C@H](CCO)c2cccc(Cl)c2F)c2ccccc21] | (1R,3S,5R)-2-Azabicyclo[3.1.0]hexane-2,3-dicarboxylic acid 2-[(1-carbamoyl-1H-indol-3-yl)-amide] 3-{[(R)-1-(3-chloro-2-fluoro-phenyl)-3-hydroxy-propyl]-amide} | (5,8[B9]) R_f (EtOAc) = 0.1; 514.3/516.3 [M + H]+, 558.3/560.2 [M + HCOO]−; t_R (a): 3.15 min. |
| 224 | 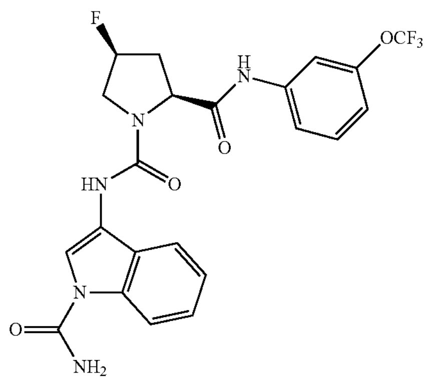 [SMILES: NC(=O)n1cc(NC(=O)N2C[C@@H](F)C[C@H]2C(=O)Nc2cccc(OC(F)(F)F)c2)c2ccccc21] | (2S,4S)-4-Fluoro-pyrrolidine-1,2-dicarboxylic acid 1-[(1-carbamoyl-1H-indol-3-yl)-amide] 2-[(3-trifluoromethoxy-phenyl)-amide] | (1) R_f (c-hexane/EtOAc 1:3) = 0.19; 494 [M + H]+; t_R (c): 4.78 min. |
| 225 | 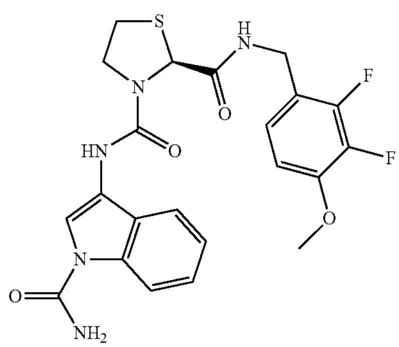 [SMILES: COc1ccc(CNC(=O)[C@@H]2SCCN2C(=O)Nc2cn(C(N)=O)c3ccccc23)c(F)c1F] | (S)-Thiazolidine-2,3-dicarboxylic acid 3-[(1-carbamoyl-1H-indol-3-yl)-amide] 2-(2,3-difluoro-4-methoxy-benzylamide) | (2,3) White solid. R_f (c-hexane/EtOAc 1:3) = 0.33; 490.1 [M + H]+; t_R (c): 4.39 min. |
| 226 | 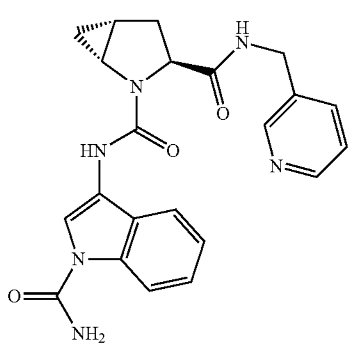 [SMILES: NC(=O)n1cc(NC(=O)N2[C@@H]3C[C@@H]3C[C@H]2C(=O)NCc2cccnc2)c2ccccc21] | (1R,3S,5R)-2Azabicyclo[3.1.0]hexane-2,3-dicarboxylic acid 2-[(1-carbamoyl-1H-indol-3-yl)amide] 3-[(pyridin-3-ylmethyl)-amide] | (1) 419.3 [M + H]+; t_R (a): 1.83 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 227 | 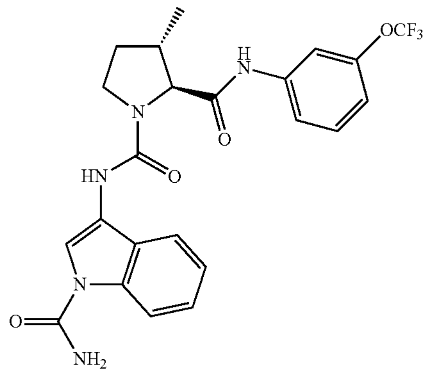 [SMILES: C[C@H]1CCN(C(=O)Nc2cn(C(N)=O)c3ccccc23)[C@@H]1C(=O)Nc1cccc(OC(F)(F)F)c1] | (2S,3S)-3-Methyl-pyrrolidine-1,2-dicarboxylic acid 1-[(1-carbamoyl-1H-indol-3-yl)-amide] 2-[(3-trifluoromethoxy-phenyl)-amide] | 490 [M + H]+; t$_R$ (b): 4.51 min. |
| 228 | 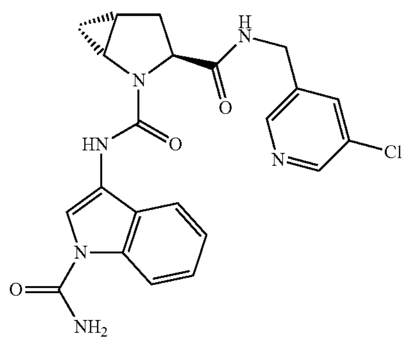 | (1R,3S,5R)-2-Aza-bicyclo[3.1.0]hexane-2,3-dicarboxylic acid 2-[(1-carbamoyl-1H-indol-3-yl)-amide] 3-[(5-chloro-pyridin-3-ylmethyl)-amide] | 453 [M + H]+; t$_R$ (a): 2.70 min. |
| 229 | 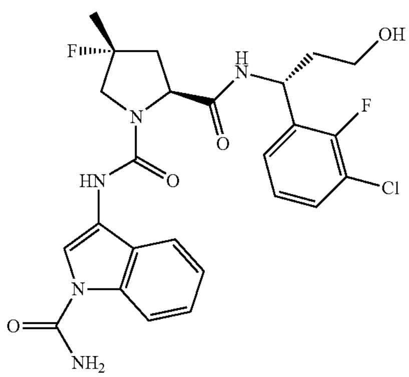 [SMILES: C[C@@]1(F)C[C@@H](C(=O)N[C@H](CCO)c2cccc(Cl)c2F)N(C(=O)Nc2cn(C(N)=O)c3ccccc23)C1] | (2S,4R)-4-Fluoro-4-methyl-pyrrolidine-1,2-dicarboxylic acid 1-[(1-carbamoyl-1H-indol-3-yl)-amide] 2-{[(R)-1-(3-chloro-2-fluoro-phenyl)-3-hydroxy-propyl]-amide} | (5,8[B9]) R$_f$(EtOAc) = 0.1; 514.3/516.3 [M + H]+, 558.3/560.2 [M + HCOO]−; t$_R$ (a): 3.15 min. |
| 230 | 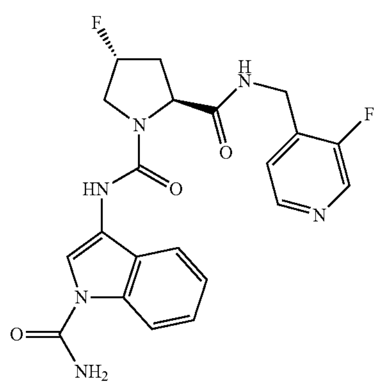 [SMILES: NC(=O)n1cc(NC(=O)N2C[C@H](F)C[C@H]2C(=O)NCc2ccncc2F)c2ccccc21] | (2S,4R)-4-Fluoro-pyrrolidine-1,2-dicarboxylic acid 1-[(1-carbamoyl-1H-indol-3-yl)-amide] 2-[(3-fluoro-pyridin-4-ylmethyl)-amide] | (1,6). 443.0 [M + H]+, t$_R$ (c): 3.05 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 231 | 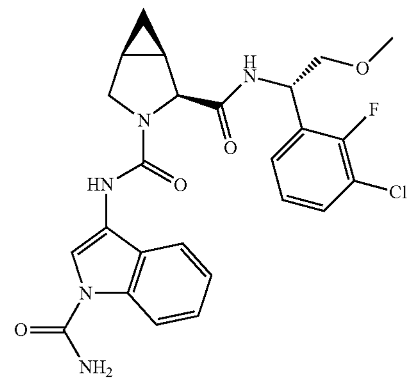 [SMILES: COC[C@@H](NC(=O)[C@@H]1[C@@H]2C[C@@H]2CN1C(=O)Nc1cn(C(N)=O)c2ccccc12)c1cccc(Cl)c1F] | (1R,2S,5S)-3-Aza-bicyclo[3.1.0]hexane-2,3-dicarboxylic acid 3-[(1-carbamoyl-1H-indol-3-yl)-amide] 2-{[(S)-1-(3-chloro-2-fluoro-phenyl)-2-methoxy-ethyl]-amide} | (5,8[B9]) White powder. R$_f$ (CH$_2$Cl$_2$/MeOH 9:1): 0.60; 514.3/516.3 [M + H]+, 558.3/560.3 [M + HCOO]−; t$_R$ (a): 3.31 min. |
| 232 | 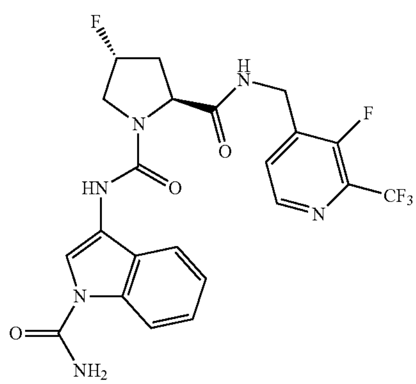 [SMILES: NC(=O)n1cc(NC(=O)N2C[C@H](F)C[C@H]2C(=O)NCc2ccnc(C(F)(F)F)c2F)c2ccccc21] | (2S,4R)-4-Fluoro-pyrrolidine-1,2-dicarboxylic acid 1-[(1-carbamoyl-1H-indol-3-yl)-amide] 2-[(3-fluoro-2-trifluoromethyl-pyridin-4-ylmethyl)-amide] | (1,6). 511.0 [M + H]+; t$_R$ (c): 4.16 min. |
| 233 | 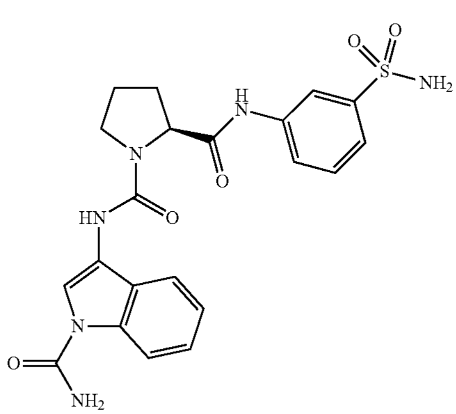 [SMILES: NC(=O)n1cc(NC(=O)N2CCC[C@H]2C(=O)Nc2cccc(S(N)(=O)=O)c2)c2ccccc21] | (S)-Pyrrolidine-1,2-dicarboxylic acid 1-[(1-carbamoyl-1H-indol-3-yl)-amide] 2-[(3-sulfamoyl-phenyl)-amide] | 471.1 [M + H]+, 963.3 [2M + Na]+; t$_R$ (a): 2.58 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 234 | 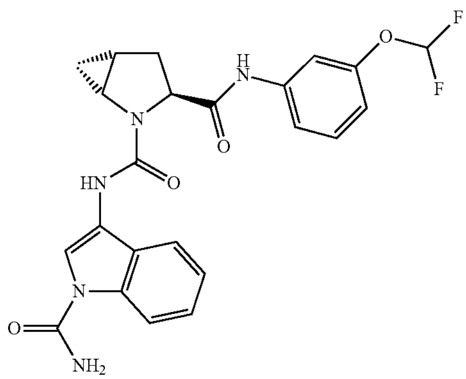 | (1R,3S,5R)-2-Aza-bicyclo[3.1.0]hexane-2,3-dicarboxylic acid 2-[(1-carbamoyl-1H-indol-3-yl)-amide] 3-[(3-difluoromethoxy-phenyl)-amide] | (1) 470.0 [M + H]+, 468.9 [M − H]−, 425.0 [M − CONH$_2$]−; t$_R$ (b) 4.05 min. HCO$_2$ |
| 235 | 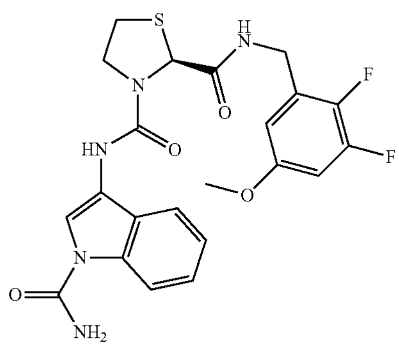 [SMILES: COc1cc(F)c(F)c(CNC(=O)[C@@H]2SCCN2C(=O)Nc2cn(C(N)=O)c3ccccc23)c1] | (S)-Thiazolidine-2,3-dicarboxylic acid 3-[(1-carbamoyl-1H-indol-3-yl)-amide] 2-(2,3-difluoro-5-methoxy-benzylamide) | (2,3,6) Solid. R$_f$ (c-hexane/EtOAc 1:3) = 0.33; 490 [M + H]+; t$_R$ (c): 4.48 min. |
| 236 | 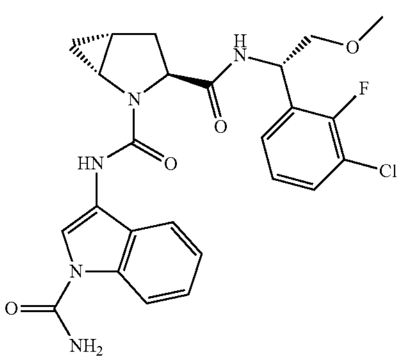 [SMILES: COC[C@@H](NC(=O)[C@@H]1C[C@H]2C[C@H]2N1C(=O)Nc1cn(C(N)=O)c2ccccc12)c1cccc(Cl)c1F] | (1R,3S,5R)-2-Aza-bicyclo[3.1.0]hexane-2,3-dicarboxylic acid 2-[(1-carbamoyl-1H-indol-3-yl)-amide] 3-{[(S)-1-(3-chloro-2-fluoro-phenyl)-2-methoxy-ethyl]-amide} | (5,8[B9]) White powder. 514.4/516.4 [M + H]+, 531.4/533.4 [M + Na]+, 558.4/560.4 [M + HCOO]−; t$_R$ (f): 1.97 min. |
| 237 | 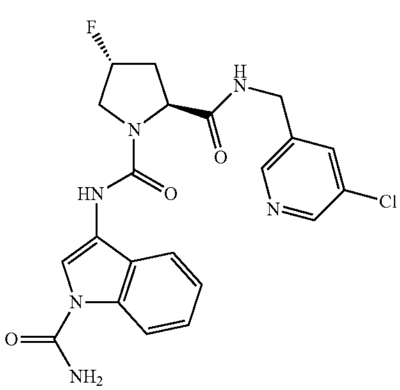 | (2S,4R)-4-Fluoro-pyrrolidine-1,2-dicarboxylic acid 1-[(1-carbamoyl-1H-indol-3-yl)-amide] 2-[(5-chloro-pyridin-3-ylmethyl)-amide] | 459.1/461 [M + H]+; t$_R$ (f): 1.30 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 238 | 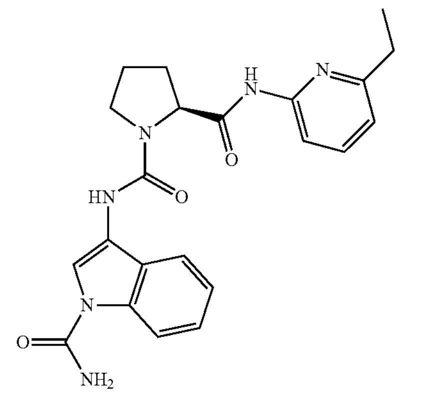 [SMILES: CCc1cccc(NC(=O)[C@@H]2CCCN2C(=O)Nc2cn(C(N)=O)c3ccccc23)n1] | (S)-Pyrrolidine-1,2-dicarboxylic acid 1-[(1-carbamoyl-1H-indol-3-yl)-amide] 2-[(6-ethyl-pyridin-2-yl)-amide] | $R_f$ (CH$_2$Cl$_2$/iPrOH 95:5) = 0.13; 421.1 [M + H]+, 419.2 [M − H]−; $t_R$ (a): 2.42 min. |
| 239 | 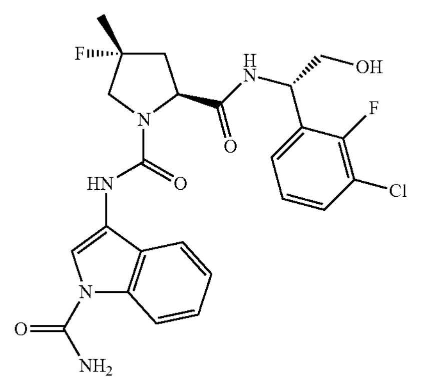 [SMILES: C[C@@]1(F)C[C@@H](C(=O)N[C@H](CO)c2cccc(Cl)c2F)N(C(=O)Nc2cn(C(N)=O)c3ccccc23)C1] | (2S,4R)-4-Fluoro-4-methyl-pyrrolidine-1,2-dicarboxylic acid 1-[(1-carbamoyl-1H-indol-3-yl)-amide] 2-{[(S)-1-(3-chloro-2-fluoro-phenyl)-2-hydroxy-ethyl]-amide} | (5,8[B9]) $R_f$ (CH$_2$Cl$_2$/MeOH 9:1) = 0.3; 500.3/502.4 [M + H]+, 544.2/546.2 [M + HCOO]−; $t_R$ (a): 3.02 min. |
| 240 | 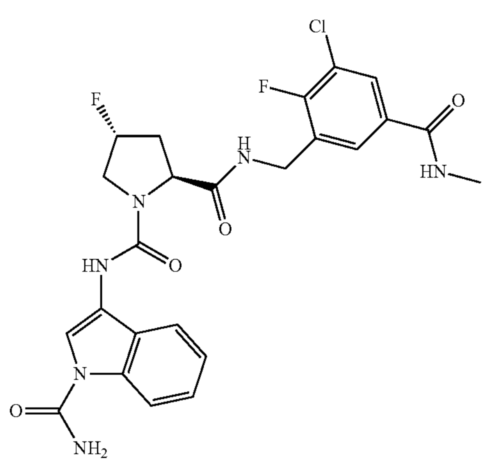 [SMILES: CNC(=O)c1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-(3-chloro-2-fluoro-5-methylcarbamoyl-benzylamide) | (3,6[C3]) 533.0 [M]+; $t_R$ (c): 3.86 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 241 | 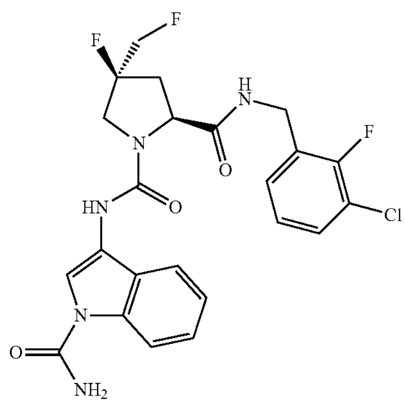 [SMILES: NC(=O)n1cc(NC(=O)N2C[C@](F)(CF)C[C@H]2C(=O)NCc2cccc(Cl)c2F)c2ccccc21] | (2S,4S)-4-Fluoro-4-fluoromethyl-pyrrolidine-1,2-dicarboxylic acid 1-[(1-carbamoyl-1H-indol-3-yl)-amide] 2-(3-chloro-2-fluoro-benzylamide) | (8) $R_f$ (EtOAc) = 0.38; 508/510 [M + H]+, 530/532 [M + Na]+, 506/508 [M − H]−, 463.1/465.1 [M − CONH$_2$]−; $t_R$ (f): 1.92 min. |
| 242 | 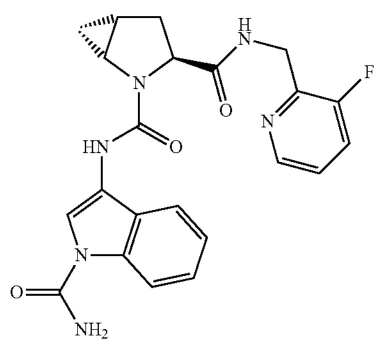 | 1R,3S,5R)-2-Aza-bicyclo[3.1.0]hexane-2,3-dicarboxylic acid 2-[(1-carbamoyl-1H-indol-3-yl)-amide] 3-[(3-fluoro-pyridin-2-ylmethyl)-amide] | 437.2 [M + H]+, 895.3 [2M + Na]+; $t_R$ (a): 2.36 min. |
| 243 | 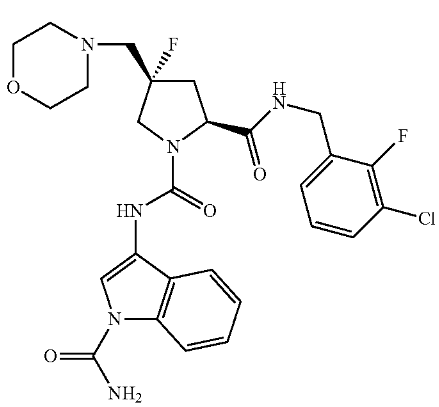 [SMILES: NC(=O)n1cc(NC(=O)N2C[C@@](F)(CN3CCOCC3)C[C@H]2C(=O)NCc2cccc(Cl)c2F)c2ccccc21] | (2S,4S)-4-Fluoro-4-morpholin-4-ylmethyl-pyrrolidine-1,2-dicarboxylic acid 1-[(1-carbamoyl-1H-indol-3-yl)-amide] 2-(3-chloro-2-fluoro-benzylamide) | (8[B14]) 575 [M + H]+, 502 [M − H]−; tR (f): 1.51 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 244 | 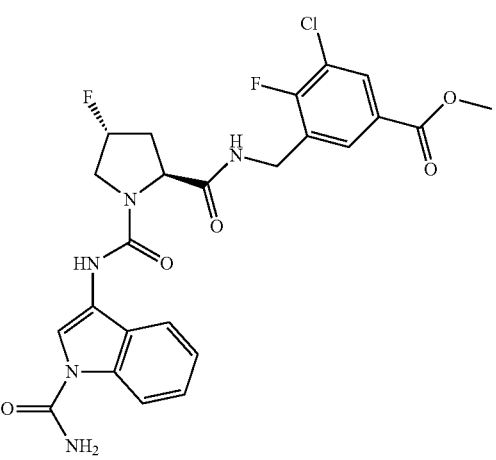 [SMILES: COC(=O)c1cc(Cl)c(F)c(CNC(=O)[C@@H]2C[C@@H](F)CN2C(=O)Nc2cn(C(N)=O)c3ccccc23)c1] | 3-({[(2S,4R)-1-(1-Carbamoyl-1H-indol-3-ylcarbamoyl)-4-fluoro-pyrrolidine-2-carbonyl]-amino}-methyl)-5-chloro-4-fluoro-benzoic acid methyl ester | (3,6) 534.0 [M]+; $t_R$ (c): 3.24 min. |
| 245 | 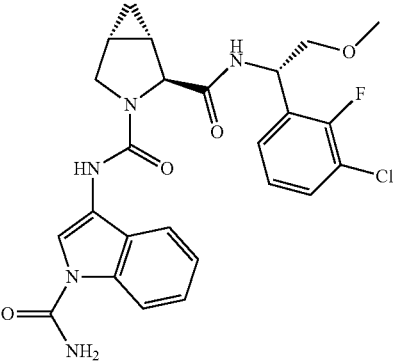 [SMILES: COC[C@@H](NC(=O)[C@@H]1[C@H]2C[C@H]2CN1C(=O)Nc1cn(C(N)=O)c2ccccc12)c1cccc(Cl)c1F] | (1S,2S,5R)-3-Aza-bicyclo[3.1.0]hexane-2,3-dicarboxylic acid 3-[(1-carbamoyl-1H-indol-3-yl)-amide] 2-{[(S)-1-(3-chloro-2-fluoro-phenyl)-2-methoxy-ethyl]-amide} | (5,8[B9]) White powder. $R_f$ (EtOAc): 0.20; 514.4/516.4 [M + H]+, 558.4/560.3 [M + HCOO]−; $t_R$ (a): 3.25 min. |
| 246 | 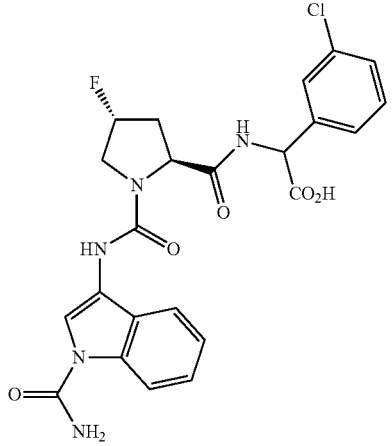 [SMILES: NC(=O)n1cc(NC(=O)N2C[C@H](F)C[C@H]2C(=O)NC(C(=O)O)c2cccc(Cl)c2)c2ccccc21] | {[(2S,4R)-1-(1-Carbamoyl-1H-indol-3-ylcarbamoyl)-4-fluoro-pyrrolidine-2-carbonyl]-amino}-(3-chloro-phenyl)-acetic acid | (8) (mixture of diastereomers) $R_f$(CH$_2$Cl$_2$/MeOH 4:1) = 0.2; 502/504, [M + H]+, 500/502 [M − H]−; $t_R$ (a): 2.86 and 2.92 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 247 | 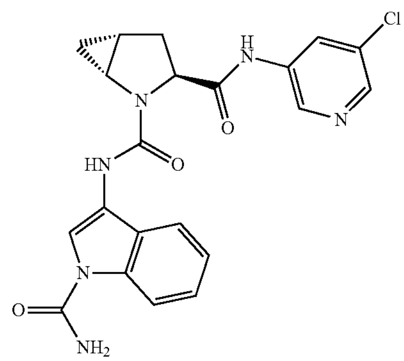 [SMILES: NC(=O)n1cc(NC(=O)N2[C@@H]3C[C@@H]3C[C@H]2C(=O)Nc2cncc(Cl)c2)c2ccccc21] | (1R,3S,5R)-2-Aza-bicyclo[3.1.0]hexane-2,3-dicarboxylic acid 2-[(1-carbamoyl-1H-indol-3-yl)-amide] 3-[(5-chloro-pyridin-3-yl)-amide] | (4) White solid. $R_f$ (EtOAc) = 0.46; 439.0 [M + H]+; $t_R$ (c): 4.01 min. |
| 248 | 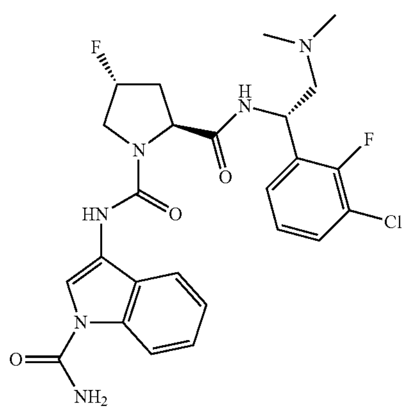 [SMILES: CN(C)C[C@@H](NC(=O)[C@@H]1C[C@@H](F)CN1C(=O)Nc1cn(C(N)=O)c2ccccc12)c1cccc(Cl)c1F] | (2S,4R)-4-Fluoro-pyrrolidine-1,2-dicarboxylic acid 1-[(1-carbamoyl-1H-indol-3-yl)-amide] 2-{[(S)-1-(3-chloro-2-fluoro-phenyl)-2-dimethylamino-ethyl]-amide} | (5,6[C4]) 533.4/535.5 [M + H]+, 577.5/579.4 [M + HCOO]; $t_R$ (a): 2.60 min. |
| 249 | 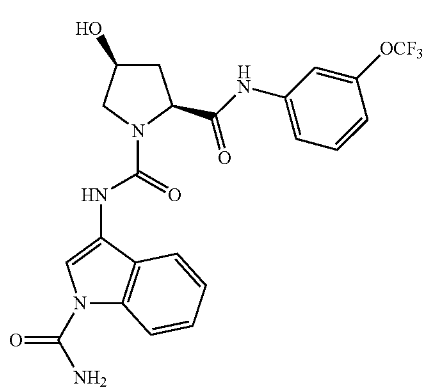 [SMILES: NC(=O)n1cc(NC(=O)N2C[C@@H](O)C[C@H]2C(=O)Nc2cccc(OC(F)(F)F)c2)c2ccccc21] | (2S,4S)-4-Hydroxy-pyrrolidine-1,2-dicarboxylic acid 1-[(1-carbamoyl-1H-indol-3-yl)-amide] 2-[(3-trifluoromethoxy-phenyl)-amide] | 492.1 [M + H]+, 514.2 [M + H]+, 490.1 [M − H]−; $t_R$ (a): 3.19 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 250 | 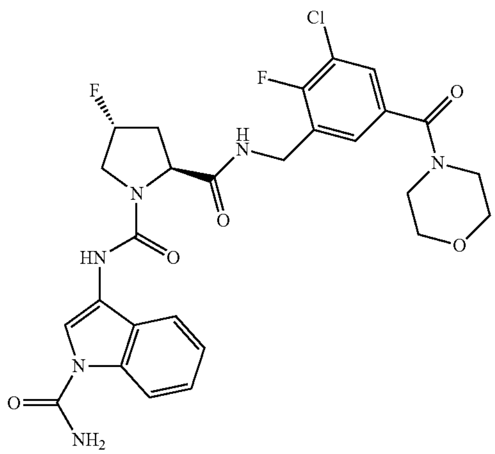 [SMILES: NC(=O)n1cc(NC(=O)N2C[C@H](F)C[C@H]2C(=O)NCc2cc(C(=O)N3CCOCC3)cc(Cl)c2F)c2ccccc21] | (2S,4R)-4-Fluoro-pyrrolidine-1,2-dicarboxylic acid 1-[(1-carbamoyl-1H-indol-3-yl)-amide] 2-[3-chloro-2-fluoro-5-(morpholine-4-carbonyl)-benzylamide] | (3,6[C3]) 589.3 [M]+; t_R (c): 3.96 min. |
| 251 | 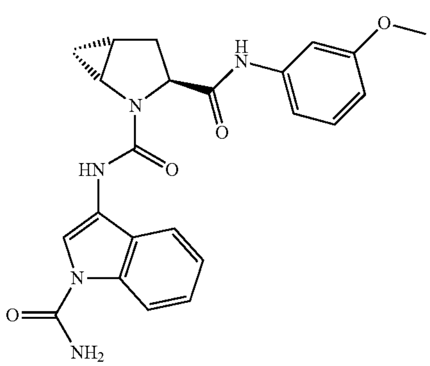 | (1R,3S,5R)-2-Aza-bicyclo[3.1.0]hexane-2,3-dicarboxylic acid 2-[(1-carbamoyl-1H-indol-3-yl)-amide] 3-[(3-methoxy-phenyl)-amide] | (1) 434.0 [M + H]+, 388.9 [M − CONH_2]−; t_R (b) 3.64 min. |
| 252 | 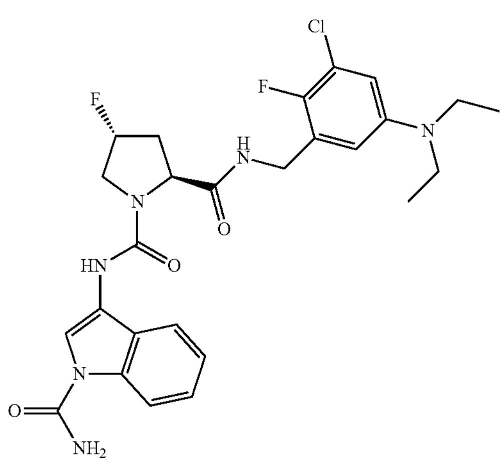 [SMILES: CCN(CC)c1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-(3-chloro-5-diethylamino-2-fluoro-benzylamide) | (3,6[C1]) 547.2 [M]+; t_R (c): 3.67 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 253 | 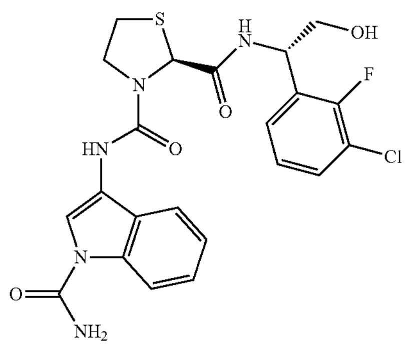 [SMILES: NC(=O)n1cc(NC(=O)N2CCS[C@H]2C(=O)N[C@H](CO)c2cccc(Cl)c2F)c2ccccc21] | (S)-Thiazolidine-2,3-dicarboxylic acid 3-[(1-carbamoyl-1H-indol-3-yl)-amide] 2-{[(S)-1-(3-chloro-2-fluoro-phenyl)-2-hydroxy-ethyl]-amide} | (5) R_f (EtOAc) = 0.2; 506.3/508.2 [M + H]+, 550.2/552.2 [M + HCOO]−; t_R (a): 3.06 min. |
| 254 | 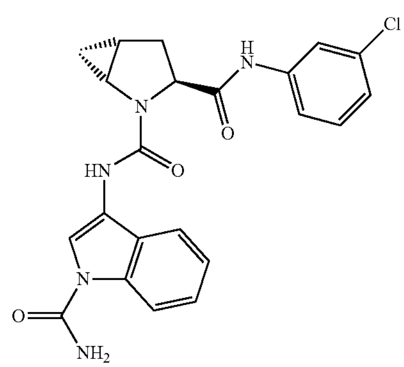 | (1R,3S,5R)-2-Aza-bicyclo[3.1.0]hexane-2,3-dicarboxylic acid 1-[(1-carbamoyl-1H-indol-3-yl)-amide] 3-[(3-chloro-phenyl)-amide] | (1) 438.0/440.0 [M + H]+, 437.8 [M − H]−, 393/395 [M − CONH_2]−; t_R (b) 4.12 min. |
| 255 | 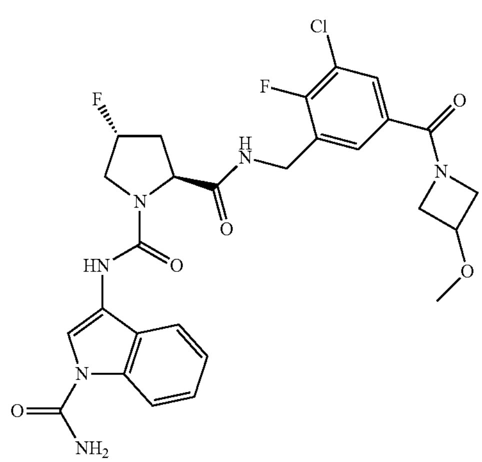 [SMILES: COC1CN(C(=O)c2cc(Cl)c(F)c(CNC(=O)[C@@H]3C[C@@H](F)CN3C(=O)Nc3cn(C(N)=O)c4ccccc34)c2)C1] | (2S,4R)-4-Fluoro-pyrrolidine-1,2-dicarboxylic acid 1-[(1-carbamoyl-1H-indol-3-yl)-amide] 2-[3-chloro-2-fluoro-5-(3-methoxy-azetidine-1-carbonyl)-benzylamide] | (3,6[C3]) 589.3 [M]+; t_R (c): 4.06 min. |

TABLE 4-continued

| Example | Structure | Name | Characterization (end-table notes), TLC, R_f (eluent); MS (LC/MS); t_R (HPLC conditions); 19F NMR (100 MHz, solvent) δ (ppm): |
|---|---|---|---|
| 256 | 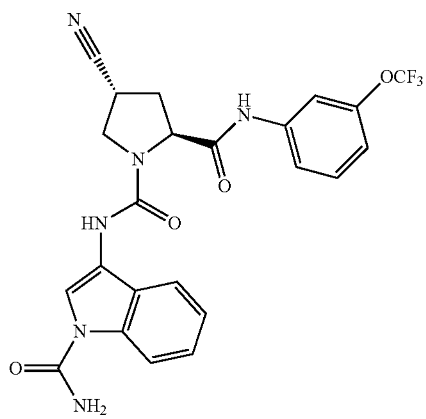 [SMILES: N#C[C@@H]1C[C@@H](C(=O)Nc2cccc(OC(F)(F)F)c2)N(C(=O)Nc2cn(C(N)=O)c3ccccc23)C1] | (2S,4R)-4-Cyano-pyrrolidine-1,2-dicarboxylic acid 1-[(1-carbamoyl-1H-indol-3-yl)-amide] 2-[(3-trifluoromethoxy-phenyl)-amide] | 501.1 [M + H]+; t_R (b): 4.22 min. |
| 257 | 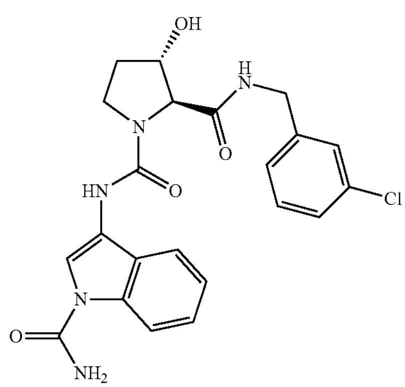 [SMILES: NC(=O)n1cc(NC(=O)N2CC[C@H](O)[C@H]2C(=O)NCc2cccc(Cl)c2)c2ccccc21] | (2S,3S)-3-Hydroxy-pyrrolidine-1,2-dicarboxylic acid 1-[(1-carbamoyl-1H-indol-3-yl)-amide] 2-(3-chloro-benzylamide) | (1) White solid. 456 [M + H]+; t_R (b): 2.99 min. |
| 258 | 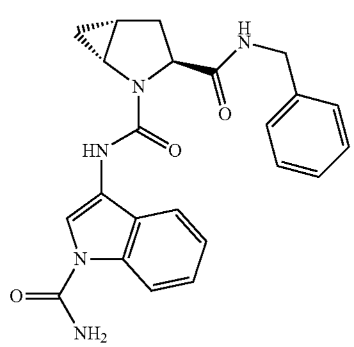 [SMILES: NC(=O)n1cc(NC(=O)N2[C@@H]3C[C@@H]3C[C@H]2C(=O)NCc2ccccc2)c2ccccc21] | (1R,3S,5R)-2-Aza-bicyclo[3.1.0]hexane-2,3-dicarboxylic acid 3-benzylamide 2-[(1-carbamoyl-1H-indol-3-yl)-amide] | 418.3 [M + H]+, 416.3 [M − H]−; t_R (a): 2.94 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 259 | 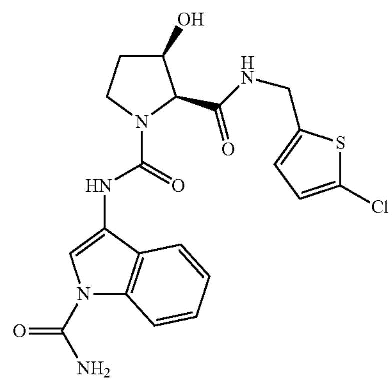 [SMILES: NC(=O)n1cc(NC(=O)N2CC[C@@H](O)[C@H]2C(=O)NCc2ccc(Cl)s2)c2ccccc21] | (2S,3R)-3-Hydroxy-pyrrolidine-1,2-dicarboxylic acid 1-[(1-carbamoyl-1H-indol-3-yl)-amide] 2-[(5-chloro-thiophen-2-ylmethyl)-amide] | (1) White solid. 462/463 [M + H]+; t$_R$ (b): 2.92 min. |
| 260 | 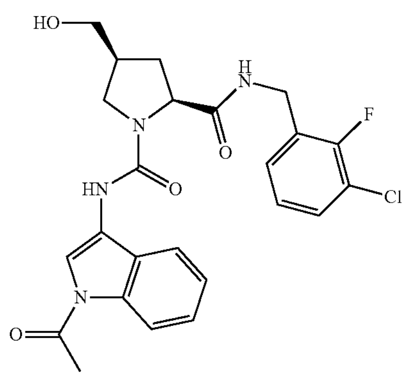 [SMILES: CC(=O)n1cc(NC(=O)N2C[C@@H](CO)C[C@H]2C(=O)NCc2cccc(Cl)c2F)c2ccccc21] | (2S,4S)-4-Hydroxymethyl-pyrrolidine-1,2-dicarboxylic acid 1-[(1-acetyl-1H-indol-3-yl)-amide] 2-(3-chloro-2-fluoro-benzylamide) | (8,9[A1]) R$_f$ (EtOAc) = 0.15; 487.4/489.4 [M + H]+, 485.4/486.4 [M − H]−; t$_R$ (a): 3.11 min. |
| 261 | 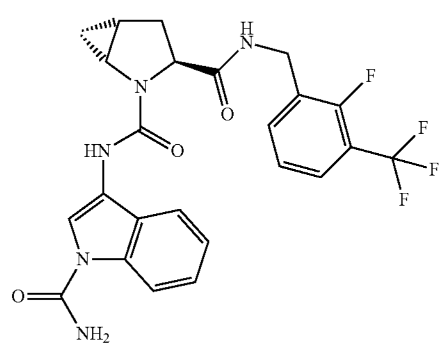 | (1R,3S,5R)-2-Aza-bicyclo[3.1.0]hexane-2,3-dicarboxylic acid 2-[(1-carbamoyl-1H-indol-3-yl)-amide] 3-(2-fluoro-3-trifluoromethyl-benzylamide) | (1) White solid. 504 [M + H]+; t$_R$ (b): 4.08 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 262 | 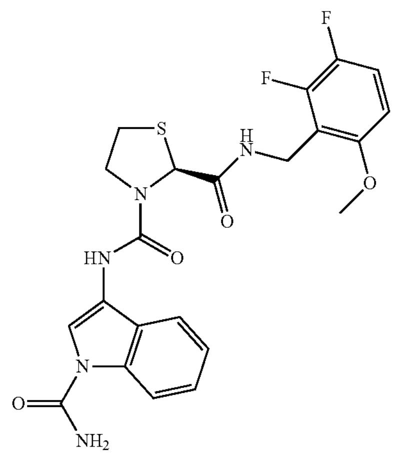 [SMILES: COc1ccc(F)c(F)c1CNC(=O)[C@@H]1SCCN1C(=O)Nc1cn(C(N)=O)c2ccccc12] | (S)-Thiazolidine-2,3-dicarboxylic acid 3-[(1-carbamoyl-1H-indol-3-yl)-amide] 2-(2,3-difluoro-6-methoxy-benzylamide) | (2,3) White solid. R$_f$ (c-hexane/EtOAc 1:3) = 0.19; 490.1 [M + H]+; t$_R$ (c): 4.45 min. |
| 263 | 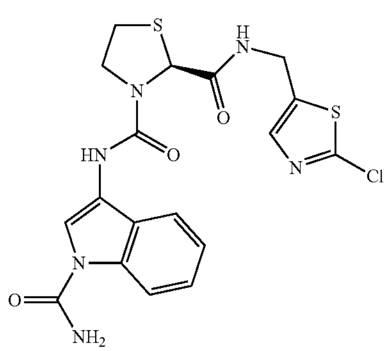 | (S)-Thiazolidine-2,3-dicarboxylic acid 3-[(1-carbamoyl-1H-indol-3-yl)-amide] 2-[(2-chloro-thiazol-5-ylmethyl)-amide] | (1) White solid. 465 [M + H]+; t$_R$ (b): 3.06 min. |
| 264 | 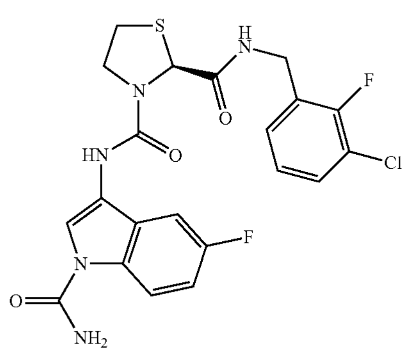 [SMILES: NC(=O)n1cc(NC(=O)N2CCS[C@H]2C(=O)NCc2cccc(Cl)c2F)c2cc(F)ccc21] | (S)-Thiazolidine-2,3-dicarboxylic acid 3-[(1-carbamoyl-5-fluoro-1H-indol-3-yl)-amide] 2-(3-chloro-2-fluoro-benzylamide) | (9[A4]) 494 [M + H]+; t$_R$ (b): 4.01 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 265 | 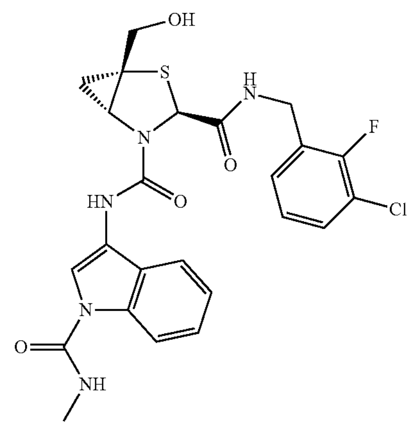 [SMILES: CNC(=O)n1cc(NC(=O)N2[C@H](C(=O)NCc3cccc(Cl)c3F)S[C@@]3(CO)C[C@@H]23)c2ccccc21] | (1R,3S,5S)-5-Hydroxymethyl-2-aza-bicyclo[3.1.0]hexane-2,3-dicarboxylic acid 3-(3-chloro-2-fluoro-benzylamide) 2-[(1-methylcarbamoyl-1H-indol-3-yl)-amide] | (5,8[B28],9[A2]) White solid. R$_f$ (EtOAc) = 0.20; 514.4/516.4 [M + H]+, 558.4/560.3 [M + HCOO]−; t$_R$ (f): 1.80 min. |
| 266 | 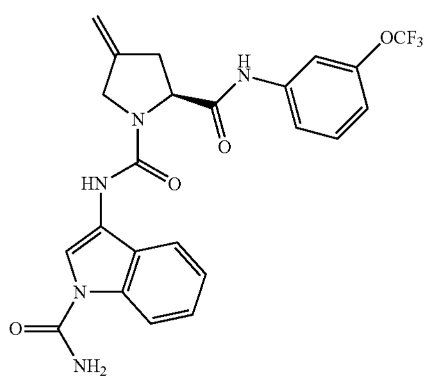 | (S)-4-Methylene-pyrrolidine-1,2-dicarboxylic acid 1-[(1-carbamoyl-1H-indol-3-yl)-amide] 2-[(3-trifluoromethoxy-phenyl)-amide] | (1) R$_f$ (c-hexane/EtOAc 1:3) = 0.38; 486. [M − H]−, 443 [M − CONH$_2$]−; t$_R$ (i): 3.52 min. |
| 267 | 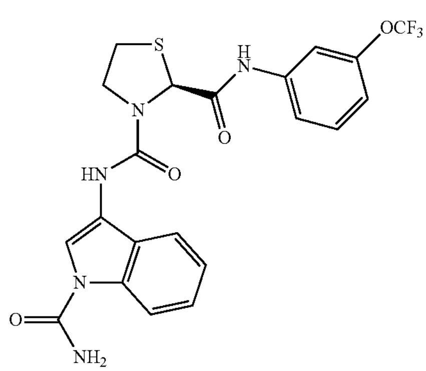 | (S)-Thiazolidine-2,3-dicarboxylic acid 3-[(1-carbamoyl-1H-indol-3-yl)-amide] 2-[(3-trifluoromethoxy-phenyl)-amide] | 494.0 [M + H]+, 492.1 [M − H]−; t$_R$ (a): 3.52 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 268 | 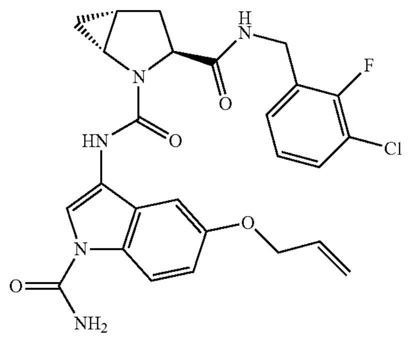 [SMILES: C=CCOc1ccc2c(c1)c(NC(=O)N1[C@@H]3C[C@@H]3C[C@H]1C(=O)NCc1cccc(Cl)c1F)cn2C(N)=O] | (1R,3S,5R)-2-Aza-bicyclo[3.1.0]hexane-2,3-dicarboxylic acid 2-[(5-allyloxy-1-carbamoyl-1H-indol-3-yl)-amide] 3-(3-chloro-2-fluoro-benzylamide) | (9) R$_f$(EtOAc) = 0.47; 526/528 [M + H]+, 481.1/483.3 [M − CONH$_2$]−; t$_R$ (f): 2.01 min. |
| 269 | 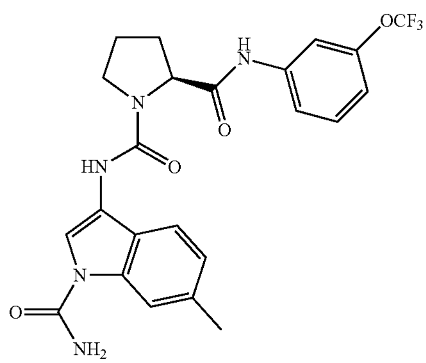 [SMILES: Cc1ccc2c(NC(=O)N3CCC[C@H]3C(=O)Nc3cccc(OC(F)(F)F)c3)cn(C(N)=O)c2c1] | S)-Pyrroldine-1,2-dicarboxylic acid 1-[(1-carbamoyl-6-methyl-1H-indol-3-yl)-amide] 2-[(3-trifluoromethoxy-phenyl)-amide] | (9[A4]) R$_f$(c-hexane/EtOAc 8:2) = 0.4; 490.1 [M + H]+, 488 [M − H]−; t$_R$ (a): 3.57 min. |
| 270 | 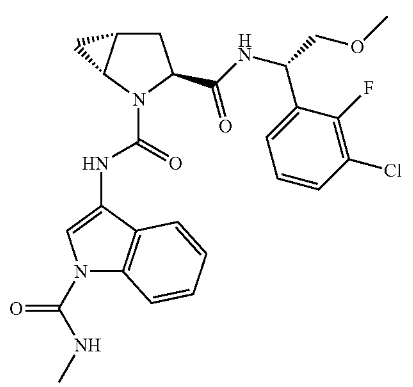 [SMILES: CNC(=O)n1cc(NC(=O)N2[C@@H]3C[C@@H]3C[C@H]2C(=O)N[C@H](COC)c2cccc(Cl)c2F)c2ccccc21] | (1R,3S,5R)-2-Aza-bicyclo[3.1.0]hexane-2,3-dicarboxylic acid 3-{[(S)-1-(3-chloro-2-fluoro-phenyl)-2-methoxy-ethyl]-amide} 2-[(1-methylcarbamoyl-1H-indol-3-yl)-amide] | (5,8[B9],9[A2]) White powder. R$_f$(EtOAc): 0.30; 528.4/530.4 [M + H]+, 572.4 [M + HCOO]−; t$_R$ (a): 3.41 min. |
| 271 | 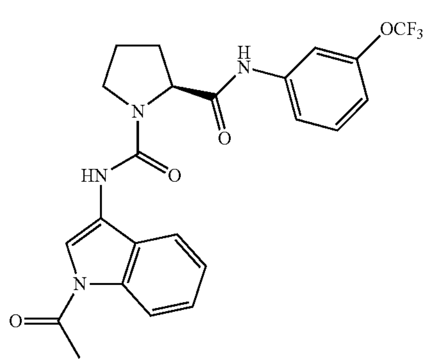 [SMILES: CC(=O)n1cc(NC(=O)N2CCC[C@H]2C(=O)Nc2cccc(OC(F)(F)F)c2)c2ccccc21] | (S)-Pyrrolidine-1,2-dicarboxylic acid 1-[(1-acetyl-1H-indol-3-yl)-amide] 2-[(3-trifluoromethoxy-phenyl)-amide] | (9[A1]) R$_f$(c-hexane/EtOAc 1:2) = 0.35; 475.1 [M + H]+, 473.2 [M − H]−; t$_R$ (a): 3.94 min. |

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 272 | 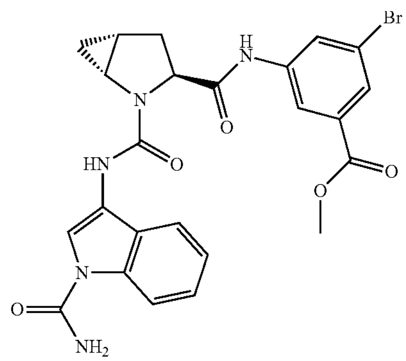 [SMILES: COC(=O)c1cc(Br)cc(NC(=O)[C@@H]2C[C@H]3C[C@H]3N2C(=O)Nc2cn(C(N)=O)c3ccccc23)c1] | 3-Bromo-5-{[(1R,3S,5R)-2-(1-carbamoyl-1H-indol-3-ylcarbamoyl)-2-aza-bicyclo[3.1.0]hexane-3-carbonyl]-amino}-benzoic acid methyl ester | (1) White solid. 538.0 [M + H]+; t$_R$ (b): 4.3 min. |
| 273 | 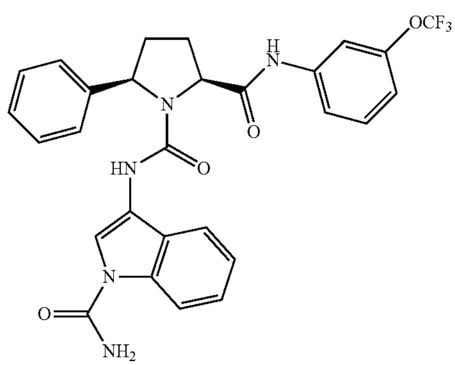 [SMILES: NC(=O)n1cc(NC(=O)N2[C@@H](c3ccccc3)CC[C@H]2C(=O)Nc2cccc(OC(F)(F)F)c2)c2ccccc21] | (2S,5R)-5-Phenyl-pyrrolidine-1,2-dicarboxylic acid 1-[(1-carbamoyl-1H-indol-3-yl)-amide] 2-[(3-trifluoromethoxy-phenyl)-amide] | (1) 552.1 [M + H]+; t$_R$ (c): 5.53 min. |
| 274 | 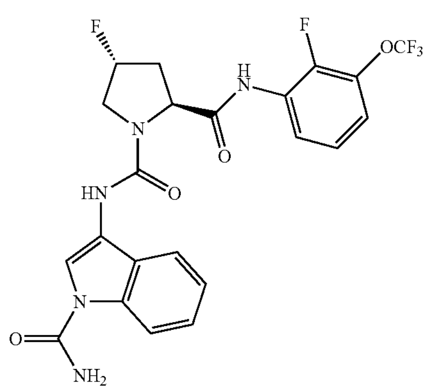 [SMILES: NC(=O)n1cc(NC(=O)N2C[C@H](F)C[C@H]2C(=O)Nc2cccc(OC(F)(F)F)c2F)c2ccccc21] | (2S,4R)-4-Fluoro-pyrrolidine-1,2-dicarboxylic acid 1-[(1-carbamoyl-1H-indol-3-yl)-amide] 2-[(2-fluoro-3-trifluoromethoxy-phenyl)-amide] | (1,6) 512 [M + H]+; t$_R$ (b) 4.15 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 275 | (1R,3S,5S)-5-Hydroxymethyl-2-aza-bicyclo[3.1.0]hexane-2,3-dicarboxylic acid 2-[(1-acetyl-1H-indol-3-yl)-amide] 3-(3-chloro-2-fluoro-benzylamide) | (5,8[B28],9[A1]) White solid. R_f (EtOAc) = 0.25; 499.3/501.3 [M + H]+, 521.3/523.2 [M + Na]+, 497.3/499.3 [M − H]−, 543.2/545.3 [M + HCOO]−; t_R (f): 1.90 min. |
| 276 | (1-Carbamoyl-3-{[(1R,3S,5R)-3-(3-trifluoromethoxy-phenylcarbamoyl)-2-aza-bicyclo[3.1.0]hexane-2-carbonyl]-amino}-1H-indol-6-yloxy)-acetic acid methyl ester | (9) R_f (EtOAc) = 0.6; 576.3 [M + H]+, 574.3 [M − H]−, 620.3 [M + HCOO]−; t_R (f): 2.12 min. |
| 277 | (2S,4R)-4-Fluoro-pyrrolidine-1,2-dicarboxylic acid 1-[(1-carbamoyl-1H-indol-3-yl)-amide] 2-(3-chloro-5-dimethylcarbamoyl-2-fluoro-benzylamide) | (3,6[C3]) 547.2 [M]+; t_R (c): 3.97 min. |

TABLE 4-continued

| Example | Structure | Name | Characterization (end-table notes), TLC, R*f* (eluent); MS (LC/MS); t*R* (HPLC conditions); 19F NMR (100 MHz, solvent) δ (ppm): |
|---|---|---|---|
| 278 | 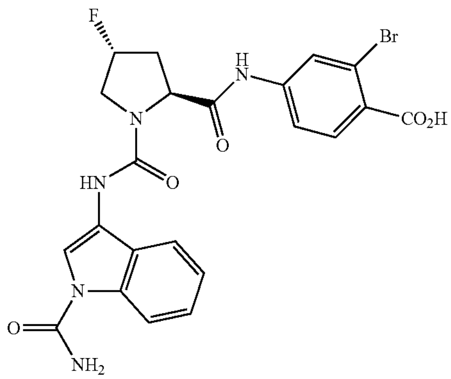 [SMILES: NC(=O)n1cc(NC(=O)N2C[C@H](F)C[C@H]2C(=O)Nc2ccc(C(=O)O)c(Br)c2)c2ccccc21] | 2-Bromo-4-{[(2S,4R)-1-(1-carbamoyl-1H-indol-3-ylcarbamoyl)-4-fluoro-pyrrolidine-2-carbonyl]-amino}-benzoic acid | (8) 530/531 [M + H]+; t*R* (b): 3.0 min. |
| 279 | 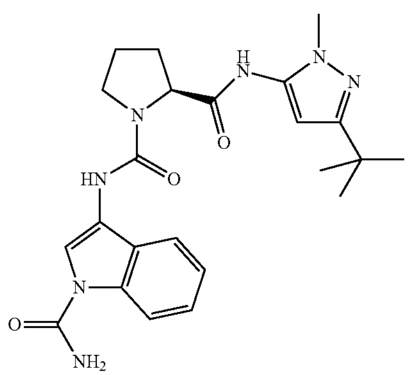 [SMILES: Cn1nc(C(C)(C)C)cc1NC(=O)[C@@H]1CCCN1C(=O)Nc1cn(C(N)=O)c2ccccc12] | (S)-Pyrrolidine-1,2-dicarboxylic acid 2-[(5-tert-butyl-2-methyl-2H-pyrazol-3-yl)-amide] 1-[(1-carbamoyl-1H-indol-3-yl)-amide] | 452.2 [M + H]+, 450.2 [M − H]−; t*R* (a): 2.79 min. |
| 280 | 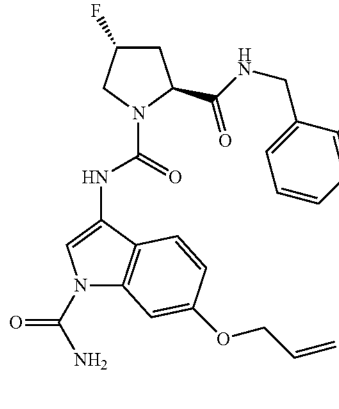 | (2S,4R)-4-Fluoro-pyrrolidine-1,2-dicarboxylic acid 1-[(6-allyloxy-1-carbamoyl-1H-indol-3-yl)-amide] 2-(3-chloro-2-fluoro-benzylamide) | (9[A4]) R*f* (EtOAc) = 0.55; 532 [M + H]+; t*R* (b): 4.08 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 281 | 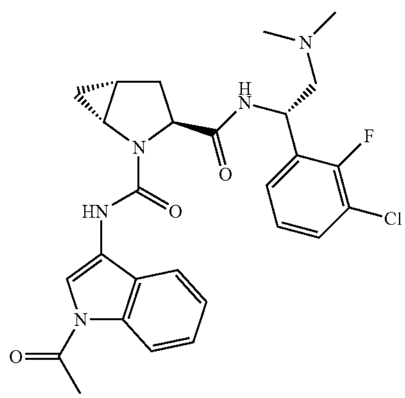 [SMILES: CC(=O)n1cc(NC(=O)N2[C@@H]3C[C@@H]3C[C@H]2C(=O)N[C@H](CN(C)C)c2cccc(Cl)c2F)c2ccccc21] | (1R,3S,5R)-2-Aza-bicyclo[3.1.0]hexane-2,3-dicarboxylic acid 2-[(1-acetyl-1H-indol-3-yl)-amide] 3-{[(S)-1-(3-chloro-2-fluoro-phenyl)-2-dimethylamino-ethyl]-amide} | (5,6[C4],9[A1]) $R_f$ (CH$_2$Cl$_2$/MeOH 9:1) = 0.65; 526.3/528.3 [M + H]+, 570.3/572.3 [M + HCOO]; $t_R$ (a): 3.06 min. |
| 282 | 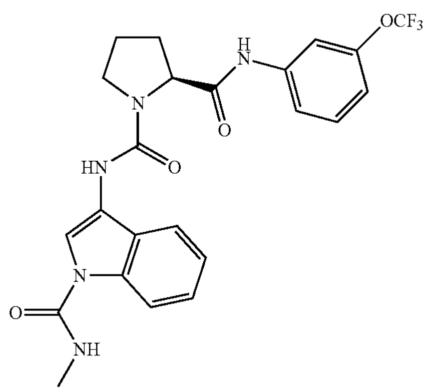 [SMILES: CNC(=O)n1cc(NC(=O)N2CCC[C@H]2C(=O)Nc2cccc(OC(F)(F)F)c2)c2ccccc21] | (S)-Pyrrolidine-1,2-dicarboxylic acid 1-[(1-methylcarbamoyl-1H-indol-3-yl)-amide] 2-[(3-trifluoromethoxy-phenyl)-amide] | (9[A2]) 490.1 [M + H]+, 488.2 [M − H]−; $t_R$ (a): 3.65 min. |
| 283 | 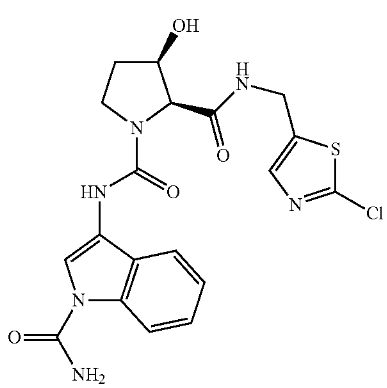 [SMILES: NC(=O)n1cc(NC(=O)N2CC[C@@H](O)[C@H]2C(=O)NCc2cnc(Cl)s2)c2ccccc21] | (2S,3R)-3-Hydroxy-pyrrolidine-1,2-dicarboxylic acid 1-[(1-carbamoyl-1H-indol-3-yl)-amide] 2-[(2-chloro-thiazol-5-ylmethyl)-amide] | (1) White solid. 463 [M + H]+; $t_R$ (b): 2.03 min. |

TABLE 4-continued

| Example | Structure | Name | Characterization (end-table notes), TLC, R$_f$(eluent); MS (LC/MS); t$_R$ (HPLC conditions); 19F NMR (100 MHz, solvent) δ (ppm): |
|---|---|---|---|
| 284 | 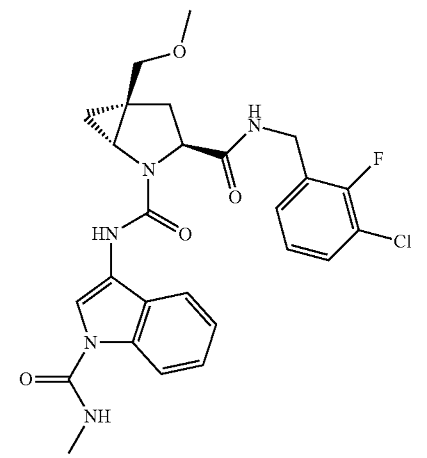 [SMILES: CNC(=O)n1cc(NC(=O)N2[C@H](C(=O)NCc3cccc(Cl)c3F)C[C@@]3(COC)C[C@@H]23)c2ccccc21] | (1R,3S,5S)-5-Methoxymethyl-2-aza-bicyclo[3.1.0]hexane-2,3-dicarboxylic acid 3-(3-chloro-2-fluoro-benzylamide) 2-[(1-methylcarbamoyl-1H-indol-3-yl)-amide] | (5,8,9[A2]) White solid. 528.4 [M + H]+, 526.2 [M + H]−, 572.3 [M + HCOO]−; t$_R$ (a): 3.34 min. |
| 285 | 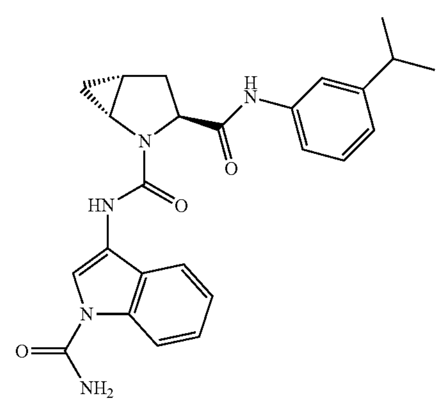 [SMILES: CC(C)c1cccc(NC(=O)[C@@H]2C[C@H]3C[C@H]3N2C(=O)Nc2cn(C(N)=O)c3ccccc23)c1] | (1R,3S,5R)-2-Aza-bicyclo[3.1.0]hexane-2,3-dicarboxylic acid 2-[(1-carbamoyl-1H-indol-3-yl)-amide] 3-[(3-isopropyl-phenyl)-amide] | R$_f$(c-hexane/EtOAc 1:2) = 0.29; 446.2 [M + H]+, 891.3 [2M + H]+, 913.3 [2M + Na]+, 401.2 [M − CONH$_2$]−; t$_R$ (a): 3.54 min. |
| 286 | 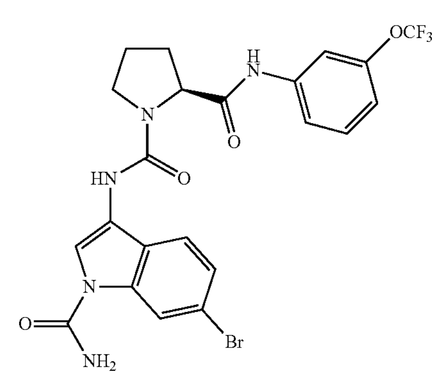 | (S)-Pyrrolidine-1,2-dicarboxylic acid 1-[(6-bromo-1-carbamoyl-1H-indol-3-yl)-amide] 2-[(3-trifluoromethoxy-phenyl)-amide] | (9[A4]) R$_f$(c-hexane/EtOAc 1:1) = 0.5; 554/556 [M + H]+; t$_R$ (a): 3.74 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 287 | 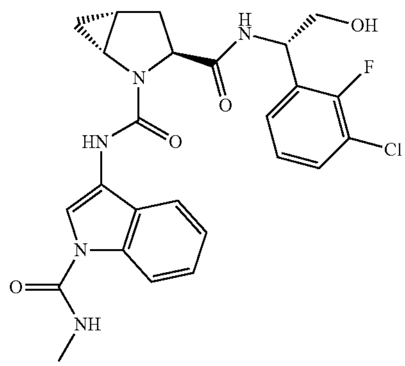 [SMILES: CNC(=O)n1cc(NC(=O)N2[C@@H]3C[C@@H]3C[C@H]2C(=O)N[C@H](CO)c2cccc(Cl)c2F)c2ccccc21] | (1R,3S,5R)-2-Azabicyclo[3.1.0]hexane-2,3-dicarboxylic acid 3-{[(S)-1-(3-chloro-2-fluoro-phenyl)-2-hydroxy-ethyl]-amide}2-[(1-methylcarbamoyl-1H-indol-3-yl)-amide] | (5,8[B9],9[A2]) R$_f$ (EtOAc) = 0.2; 514.4 [M + H]+ 558.4 [M + HCOO]−; t$_R$ (a): 3.12 min. |
| 288 | 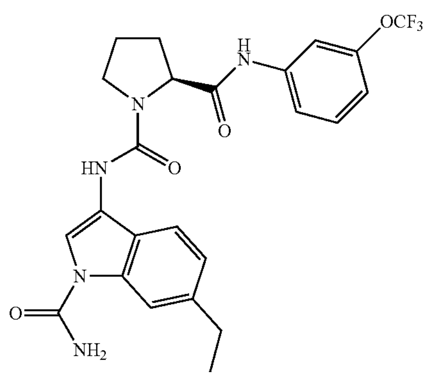 [SMILES: CCc1ccc2c(NC(=O)N3CCC[C@H]3C(=O)Nc3cccc(OC(F)(F)F)c3)cn(C(N)=O)c2c1] | (S)-Pyrrolidine-1,2-dicarboxylic acid 1-[(1-carbamoyl-6-ethyl-1H-indol-3-yl)-amide] 2-[(3-trifluoromethoxy-phenyl)-amide] | (9[A3]) 504.1 [M + H]+, 526.2 [M + Na]+, 502 [M − H]−; t$_R$ (a): 3.68 min. |
| 289 | 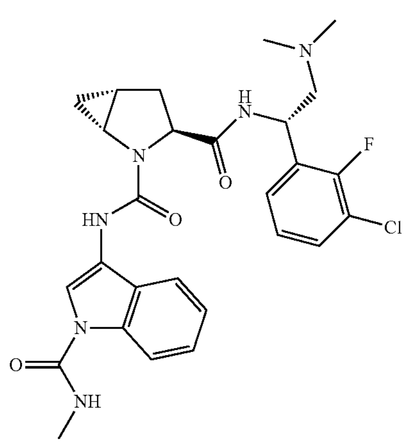 [SMILES: CNC(=O)n1cc(NC(=O)N2[C@@H]3C[C@@H]3C[C@H]2C(=O)N[C@H](CN(C)C)c2cccc(Cl)c2F)c2ccccc21] | (1R,3S,5R)-2-Azabicyclo[3.1.0]hexane-2,3-dicarboxylic acid 3-{[(S)-1-(3-chloro-2-fluoro-phenyl)-2-dimethylamino-ethyl]-amide} 2-[(1-methylcarbamoyl-1H-indol-3-yl)-amide] | (5,6[C4],9[A2]) White solid. R$_f$ (EtOAc) = 0.25; 541.4/543.4 [M + H]+, 585.3/587.2 [M + HCOO]; t$_R$ (a): 2.88 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 290 | (S)-Pyrrolidine-1,2-dicarboxylic acid 1-[(1-carbamoyl-6-trifluoromethyl-1H-indol-3-yl)-amide] 2-[(3-trifluoromethoxy-phenyl)-amide] | (9) 499 [M − H]−; t_R (a): 4.15 min. |
| 291 | (S)-Pyrrolidine-1,2-dicarboxylic acid 1-[(1-carbamoyl-6-chloro-1H-indol-3-yl)-amide] 2-[(3-trifluoromethoxy-phenyl)-amide] | (9[A4]) R_f (c-hexane/ETOAc 1:1) = 0.5; 510.1 [M + H]+, 532 [M + Na]+, 508 [M − H]−; t_R (a): 3.67 min. |
| 292 | (2S,4R)-4-Fluoro-pyrrolidine-1,2-dicarboxylic acid 1-[(1-carbamoyl-5-methoxy-1H-indol-3-yl)-amide] 2-(3-chloro-2-fluoro-benzylamide) | (9[A4]) R_f (EtOAc) = 0.45; 506.0/508.0 [M + H]+, 504.1/506.1 [M − H]−, 461.0/463.0 [M − CONH_2]−; t_R (f): 1.80 min. |
| 293 | (S)-Thiazolidine-2,3-dicarboxylic acid 3-[(1-carbamoyl-1H-indol-3-yl)-amide] 2-[(5-chloro-thiophen-2-ylmethyl)-amide] | 464.0 [M + H]+, 462.0 [M − H]−, 419.0 [M − CONH_2]−; t_R (f): 2.02 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 294 | (1R,3S,5R)-2-Aza-bicyclo[3.1.0]hexane-2,3-dicarboxylic acid 2-[(1-carbamoyl-5-fluoro-1H-indol-3-yl)-amide] 3-(3-chloro-2-fluoro-benzylamide) | (9[A4]) R_f (EtOAc) = 0.47; 488 [M + H]+; t_R (b): 4.01 min. |
| 295 | (1R,3S,5R)-2-Aza-bicyclo[3.1.0]hexane-2,3-dicarboxylic acid 2-[(1-carbamoyl-1H-indol-3-yl)-amide] 3-[(2-chloro-thiazol-5-ylmethyl)-amide] | (1) White solid. 459 [M + H]+; t_R (b): 3.11 min. |
| 296 | (2S,4R)-4-Fluoro-pyrrolidine-1,2-dicarboxylic acid 1-[(1-carbamoyl-1H-indol-3-yl)-amide] 2-{[(S)-1-(3-chloro-phenyl)-2,2,2-trifluoro-ethyl]-amide} | (4) R_f (c-hexane/EtOAc 25/75) = 0.55; 526.0 [M + H]+; t_R (c): 4.80 min. |
| 297 | (1R,3S,5R)-2-Aza-bicyclo[3.1.0]hexane-2,3-dicarboxylic acid 2-[(1-carbamoyl-6-fluoro-1H-indol-3-yl)-amide] 3-[(3-trifluoromethoxy-phenyl)-amide] | (9[A4]) 506 [M + H]+; t_R (b): 4.62 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---------|-----------|------|---------|
| 298 | 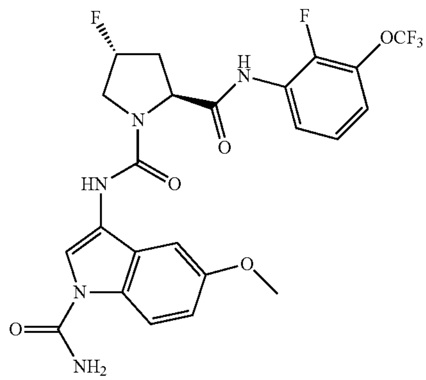 [SMILES: COc1ccc2c(c1)c(NC(=O)N1C[C@H](F)C[C@H]1C(=O)Nc1cccc(OC(F)(F)F)c1F)cn2C(N)=O] | (2S,4R)-4-Fluoro-pyrrolidine-1,2-dicarboxylic acid 1-[(1-carbamoyl-5-methoxy-1H-indol-3-yl)-amide] 2-[(2-fluoro-3-trifluoromethoxy-phenyl)-amide] | (6,9[A4]) 542.0 [M + H]+, 564.0 [M + Na]+; t$_R$ (k): 3.47 min |
| 299 | 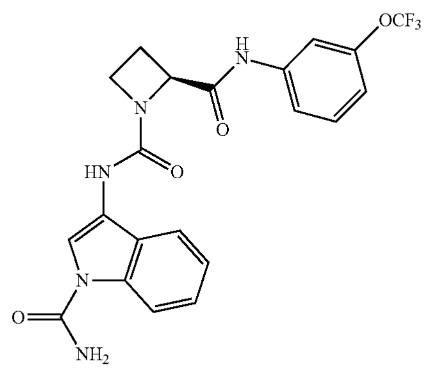 [SMILES: NC(=O)n1cc(NC(=O)N2CC[C@H]2C(=O)Nc2cccc(OC(F)(F)F)c2)c2ccccc21] | (S)-Azetidine-1,2-dicarboxylic acid 1-[(1-carbamoyl-1H-indol-3-yl)-amide] 2-[(3-trifluoromethoxy-phenyl)-amide] | 462.1 [M + H]+, 460.1 [M − H]−; t$_R$ (a): 3.52 min. |
| 300 | 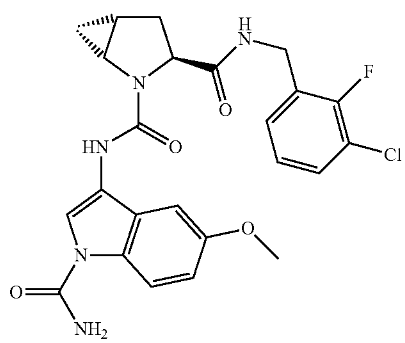 | (1R,3S,5R)-2-Aza-bicyclo[3.1.0]hexane-2,3-dicarboxylic acid 2-[(1-carbamoyl-5-methoxy-1H-indol-3-yl)-amide] 3-(3-chloro-2-fluoro-benzylamide) | (9[A4]) R$_f$ (EtOAc) = 0.45; 500/502.1 [M + H]+, 455/457 [M − CONH$_2$]−; t$_R$ (f): 1.91 min. |
| 301 | 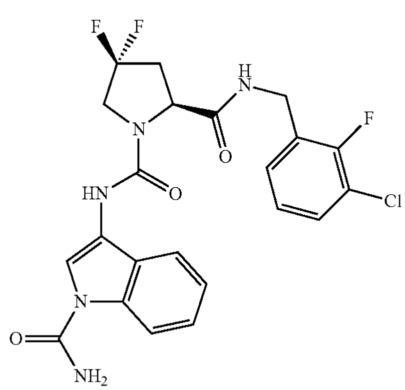 | (S)-4,4-Difluoro-pyrrolidine-1,2-dicarboxylic acid 1-[(1-carbamoyl-1H-indol-3-yl)-amide] 2-(3-chloro-2-fluoro-benzylamide) | R$_f$ (EtOAc) = 0.65; 492 [M + H]+, 494 [M − H]−; t$_R$ (f): 1.96 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 302 | 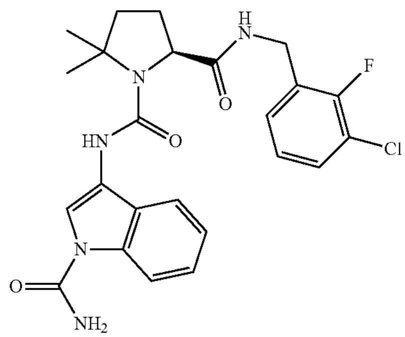 [SMILES: CC1(C)CC[C@@H](C(=O)NCc2cccc(Cl)c2F)N1C(=O)Nc1cn(C(N)=O)c2ccccc12] | (S)-5,5-Dimethyl-pyrrolidine-1,2-dicarboxylic acid 1-[(1-carbamoyl-1H-indol-3-yl)-amide] 2-(3-chloro-2-fluoro-benzylamide) | (1) Off-white solid. R$_f$ (EtOAc) = 0.53; 486.2 [M + H]+; t$_R$ (c): 4.87 min. |
| 303 | 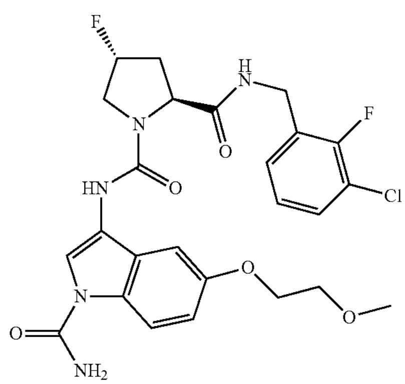 [SMILES: COCCOc1ccc2c(c1)c(NC(=O)N1C[C@H](F)C[C@H]1C(=O)NCc1cccc(Cl)c1F)cn2C(N)=O] | (2S,4R)-4-Fluoro-pyrrolidine-1,2-dicarboxylic acid 1-{[1-carbamoyl-5-(2-methoxy-ethoxy)-1H-indol-3-yl]-amide} 2-(3-chloro-2-fluoro-benzylamide) | (9) R$_f$ (EtOAc) = 0.3; 550.2/552.1 [M + H]+, 572/574.1 [M + Na]+, 548 [M − H]−, 505 [M − CONH$_2$]−; t$_R$ (f): 1.76 min. |
| 304 | 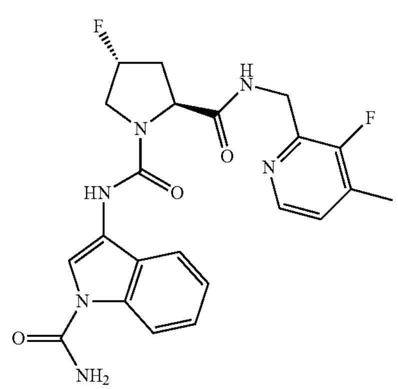 [SMILES: Cc1ccnc(CNC(=O)[C@@H]2C[C@@H](F)CN2C(=O)Nc2cn(C(N)=O)c3ccccc23)c1F] | (2S,4R)-4-Fluoro-pyrrolidine-1,2-dicarboxylic acid 1-[(1-carbamoyl-1H-indol-3-yl)-amide] 2-[(3-fluoro-4-methyl-pyridin-2-ylmethyl)-amide] | (1) 457.0 [M + H]+; t$_R$ (c): 3.20 min. |

TABLE 4-continued

| Example | Name | Characterization (end-table notes), TLC, R_f (eluent); MS (LC/MS); t_R (HPLC conditions); 19F NMR (100 MHz, solvent) δ (ppm): |
|---|---|---|
| 305 | (2S,4R)-4-Fluoro-pyrrolidine-1,2-dicarboxylic acid 1-[(1-carbamoyl-1H-indol-3-yl)-amide] 2-[(5-trifluoromethyl-pyridin-3-ylmethyl)-amide] | (1) White solid. 493 [M + H]+; t_R (b): 3.76 min. |
| 306 | (1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yl)-acetic acid ethyl ester | (9) R_f (EtOAc) = 0.45; 556.3/558.4 [M + H]+, 554.3/556.3 [M − H]−, 511.3/513.3 [M − CONH_2]−; t_R (f): 2.02 min. |
| 307 | (1S,5R)-2-Aza-bicyclo[3.1.0]hexane-1,2-dicarboxylic acid 2-[(1-carbamoyl-1H-indol-3-yl)-amide] 1-[(3-trifluoromethoxy-phenyl)-amide] | R_f (c-hexane-EtOAc 1:2) = 0.15; 488 [M + H]+, 486.1 [M − H]−; t_R (a): 3.51 min. |
| 308 | (2S,4R)-4-Fluoro-pyrrolidine-1,2-dicarboxylic acid 1-[(1-carbamoyl-6-difluoromethoxy-1H-indol-3-yl)-amide] 2-(3-chloro-2-fluoro-benzylamide) | (9[A4]) White solid. 542.0 [M + H]+; 564.0 [M + Na]+; t_R (k): 3.41 min. |

TABLE 4-continued

| Example | Name | Characterization (end-table notes), TLC, R$_f$(eluent); MS (LC/MS); t$_R$ (HPLC conditions); 19F NMR (100 MHz, solvent) δ (ppm): |
|---|---|---|
| 309 | (2S,4R)-4-Fluoro-pyrrolidine-1,2-dicarboxylic acid 1-[(1-carbamoyl-1H-indol-3-yl)-amide] 2-[(2-methoxy-pyridin-4-yl)-amide] | (3,4) Off-white solid. R$_f$(c-hexane/EtOAc 1:1) = 0.42; 441.2 [M + H]+; t$_R$ (c): 3.28 min. |
| 310 | (S)-Thiazolidine-2,3-dicarboxylic acid 3-[(1-carbamoyl-1H-indol-3-yl)-amide] 2-[(5-chloro-pyridin-3-yl)-amide] | (3,4) Off-white solid. R$_f$(EtOAc) = 0.47; 445.0 [M + H]+; t$_R$ (c): 4.03 min. |
| 311 | (1R,3S,5R)-2-Aza-bicyclo[3.1.0]hexane-2,3-dicarboxylic acid 2-[(6-allyloxy-1-carbamoyl-1H-indol-3-yl)-amide] 3-(3-chloro-2-fluoro-benzylamide) | (9[A4]) R$_f$(EtOAc) = 0.4; 526 [M + H]+; t$_R$ (b): 4.33 min. |
| 312 | (2S,4S)-4-Hydroxymethyl-pyrrolidine-1,2-dicarboxylic acid 1-[(1-carbamoyl-1H-indol-3-yl)-amide] 2-(3-chloro-2-fluoro-benzylamide) | (8) 488.2 [M + H]+, 433.0 [M − CONH$_2$]−; t$_R$ (f): 1.63 min. |

TABLE 4-continued

| Example | Structure | Name | Characterization (end-table notes), TLC, R$_f$(eluent); MS (LC/MS); t$_R$ (HPLC conditions); 19F NMR (100 MHz, solvent) δ (ppm): |
|---|---|---|---|
| 313 | 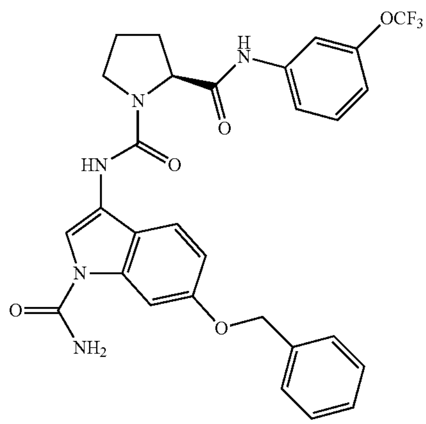 [SMILES: NC(=O)n1cc(NC(=O)N2CCC[C@H]2C(=O)Nc2cccc(OC(F)(F)F)c2)c2ccc(OCc3ccccc3)cc21] | (S)-Pyrrolidine-1,2-dicarboxylic acid 1-[(6-benzyloxy-1-carbamoyl-1H-indol-3-yl)-amide]2-[(3-trifluoromethoxy-phenyl)-amide] | (9[A4]) R$_f$(EtOAc) = 0.44; 582.1 [M + H]+, 580.2 [M − H]−; t$_R$ (a): 3.91 min. |
| 314 | 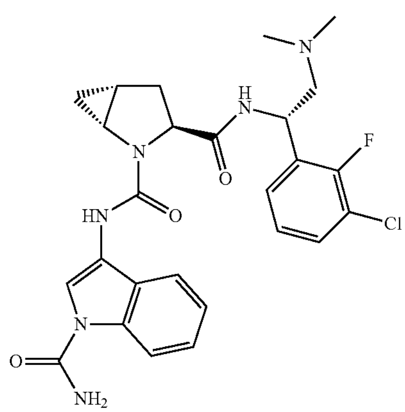 [SMILES: CN(C)C[C@@H](NC(=O)[C@@H]1C[C@H]2C[C@H]2N1C(=O)Nc1cn(C(N)=O)c2ccccc12)c1cccc(Cl)c1F] | (1R,3S,5R)-2-Aza-bicyclo[3.1.0]hexane-2,3-dicarboxylic acid 2-[(1-carbamoyl-1H-indol-3-yl)-amide] 3-{[(S)-1-(3-chloro-2-fluoro-phenyl)-2-dimethylamino-ethyl]-amide} | (5,6[C4]) White solid. R$_f$(EtOAc) = 0.1; 527.3/529.3 [M + H]+, 571.3 [M + HCOO]; t$_R$ (a): 2.84 min. |
| 315 | 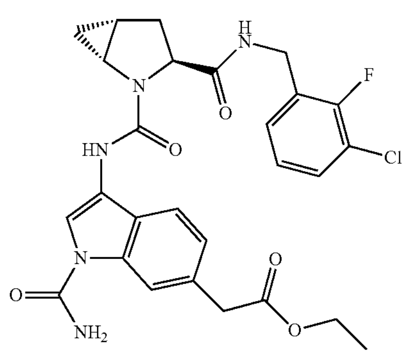 [SMILES: CCOC(=O)Cc1ccc2c(NC(=O)N3[C@@H]4C[C@@H]4C[C@H]3C(=O)NCc3cccc(Cl)c3F)cn(C(N)=O)c2c1] | (1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid ethyl ester | (9) R$_f$(EtOAc) = 0.4; 556.3/558.4 [M + H]+, 573.4/575.2 [M + H$_3$O]+, 1111.7/1113.7 [2M + H]+, 554.3/556.4 [M − H]−, 600.3/602.8 [M + HCOO]−; t$_R$ (f): 2.02 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 316 | 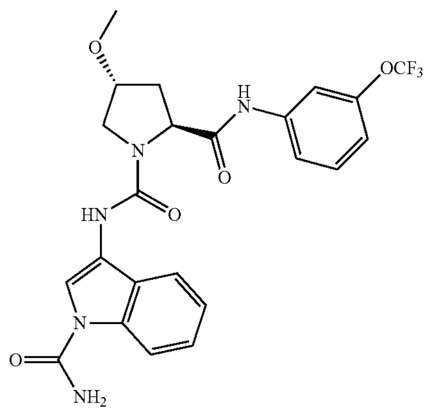 [SMILES: CO[C@@H]1C[C@@H](C(=O)Nc2cccc(OC(F)(F)F)c2)N(C(=O)Nc2cn(C(N)=O)c3ccccc23)C1] | (2S,4R)-4-Methoxy-pyrrolidine-1,2-dicarboxylic acid 1-[(1-carbamoyl-1H-indol-3-yl)-amide] 2-[(3-trifluoromethoxy-phenyl)-amide] | R$_f$(c-hexane/EtOAc 1:2) = 0.1; 506.0 [M + H]+, 504.1 [M − H]; t$_R$ (a): 3.36 min. |
| 317 | 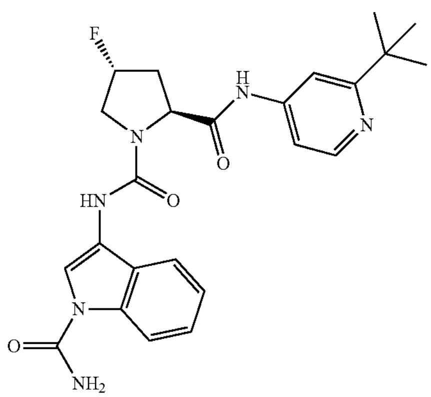 [SMILES: CC(C)(C)c1cc(NC(=O)[C@@H]2C[C@@H](F)CN2C(=O)Nc2cn(C(N)=O)c3ccccc23)ccn1] | (2S,4R)-4-Fluoro-pyrrolidine-1,2-dicarboxylic acid 2-[(2-tert-butyl-pyridin-4-yl)-amide] 1-[(1-carbamoyl-1H-indol-3-yl)-amide] | (4) Off-white solid. R$_f$ (c-hexane/EtOAc 1:1) = 0.42; 467.3 [M + H]+; t$_R$ (c): 3.58 min. |
| 318 | 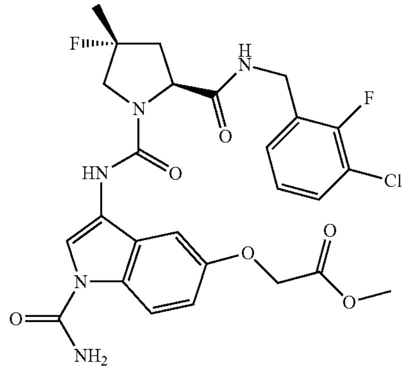 [SMILES: COC(=O)COc1ccc2c(c1)c(NC(=O)N1C[C@](C)(F)C[C@H]1C(=O)NCc1cccc(Cl)c1F)cn2C(N)=O] | (1-Carbamoyl-3-{[(2S,4R)-2-(3-chloro-2-fluoro-benzylcarbamoyl)-4-fluoro-4-methyl-pyrrolidine-1-carbonyl]-amino}-1H-indol-5-yloxy)-acetic acid methyl ester | (8[B13],9) R$_f$(EtOAc) = 0.6; 578.4/580.4 [M + H]+, 576.3/578.2 [M − H]−, 533.5/535.5 [M − CONH$_2$]−; t$_R$ (f): 1.90 min. |

TABLE 4-continued

| Example | Structure | Name | Characterization (end-table notes), TLC, R$_f$(eluent); MS (LC/MS); t$_R$ (HPLC conditions); 19F NMR (100 MHz, solvent) δ (ppm): |
|---|---|---|---|
| 319 | 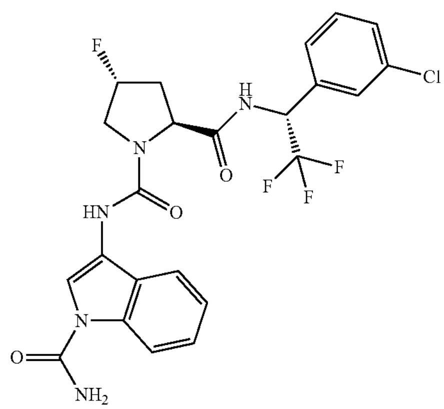 [SMILES: NC(=O)n1cc(NC(=O)N2C[C@H](F)C[C@H]2C(=O)N[C@H](c2cccc(Cl)c2)C(F)(F)F)c2ccccc21] | (2S,4R)-4-Fluoro-pyrrolidine-1,2-dicarboxylic acid 1-[(1-carbamoyl-1H-indol-3-yl)-amide] 2-{[(R)-1-(3-chloro-phenyl)-2,2,2-trifluoro-ethyl]-amide} | (4) R$_f$(c-hexane/EtOAc 1:3) = 0.56; 526.0 [M + H]+; t$_R$ (c): 4.79 min. |
| 320 | 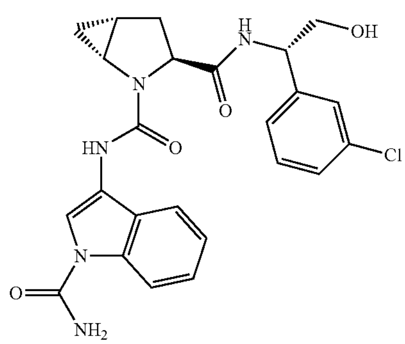 [SMILES: NC(=O)n1cc(NC(=O)N2[C@@H]3C[C@@H]3C[C@H]2C(=O)N[C@H](CO)c2cccc(Cl)c2)c2ccccc21] | (1R,3S,5R)-2-Aza-bicyclo[3.1.0]hexane-2,3-dicarboxylic acid 2-[(1-carbamoyl-1H-indol-3-yl)-amide] 3-{[(S)-1-(3-chloro-phenyl)-2-hydroxy-ethyl]-amide} | (5) 482.4 [M + H]+; t$_R$ (a): 3.05 min. |
| 321 | 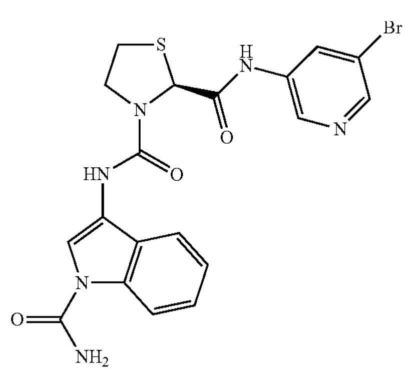 [SMILES: NC(=O)n1cc(NC(=O)N2CCS[C@H]2C(=O)Nc2cncc(Br)c2)c2ccccc21] | (S)-Thiazolidine-2,3-dicarboxylic acid 3-[(1-carbamoyl-1H-indol-3-yl)-amide] 2-[(5-bromo-pyridin-3-yl)-amide] | (3,4) Off-white solid. R$_f$(EtOAc) = 0.38; 489.0 [M + H]+; t$_R$ (c): 4.10 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 322 | 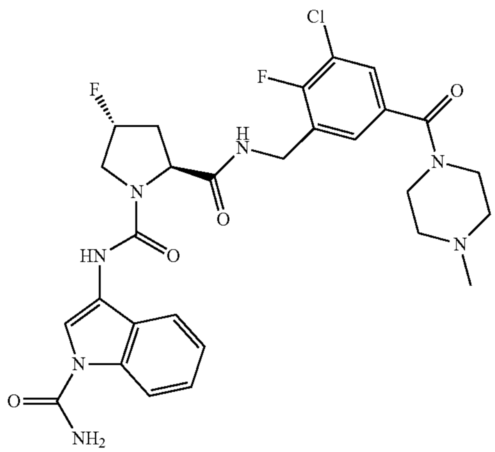 [SMILES: CN1CCN(C(=O)c2cc(Cl)c(F)c(CNC(=O)[C@@H]3C[C@@H](F)CN3C(=O)Nc3cn(C(N)=O)c4ccccc34)c2)CC1] | (2S,4R)-4-Fluoro-pyrrolidine-1,2-dicarboxylic acid 1-[(1-carbamoyl-1H-indol-3-yl)-amide] 2-[3-chloro-2-fluoro-5-(4-methyl-piperazine-1-carbonyl)-benzylamide] | (3,6[C3]) 602.2 [M]+; t$_R$ (c): 3.47 min. |
| 323 | 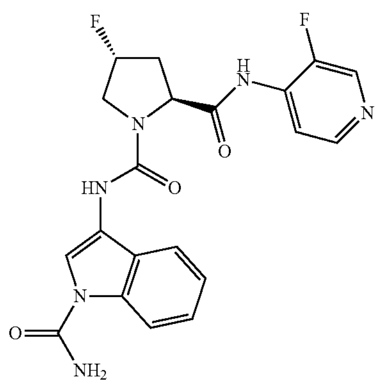 [SMILES: NC(=O)n1cc(NC(=O)N2C[C@H](F)C[C@H]2C(=O)Nc2ccncc2F)c2ccccc21] | (2S,4R)-4-Fluoro-pyrrolidine-1,2-dicarboxylic acid 1-[(1-carbamoyl-1H-indol-3-yl)-amide] 2-[(3-fluoro-pyridin-4-yl)-amide] | (4) White foam. R$_f$ (EtOAc) = 0.18; 429.0 [M + H]+; t$_R$ (c): 3.14 min. |
| 324 | 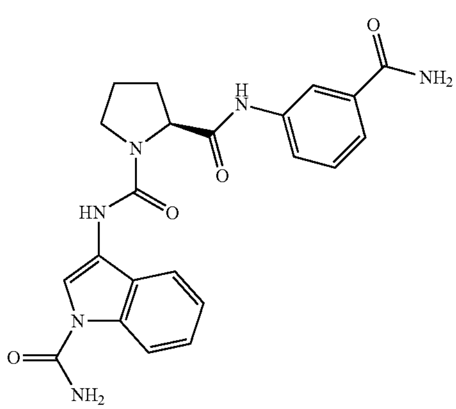 [SMILES: NC(=O)c1cccc(NC(=O)[C@@H]2CCCN2C(=O)Nc2cn(C(N)=O)c3ccccc23)c1] | (S)-Pyrrolidine-1,2-dicarboxylic acid 1-[(1-carbamoyl-1H-indol-3-yl)-amino] 2-[(3-carbamoyl-phenyl)-amide] | 435.1 [M + H]+, 891.3 [2M + Na]+, 433.1 [M − H]−; t$_R$ (a): 2.39 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---------|-----------|------|------|
| 325 | 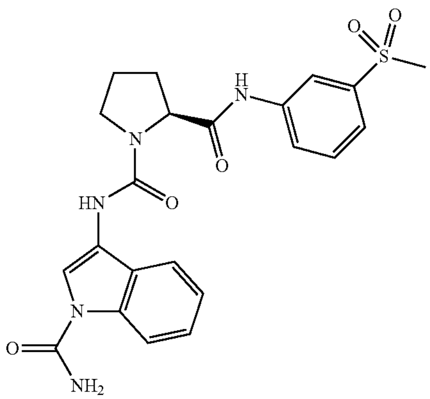 [SMILES: CS(=O)(=O)c1cccc(NC(=O)[C@@H]2CCCN2C(=O)Nc2cn(C(N)=O)c3ccccc23)c1] | (S)-Pyrrolidine-1,2-dicarboxylic acid 1-[(1-carbamoyl-1H-indol-3-yl)-amide] 2-[(3-methanesulfonyl-phenyl)-amide] | 470.0 [M + H]+, 939.1 [2MH]+, 961.2 [2M + Na]+, 468.1 [M − H]−; t$_R$ (a): 2.70 min. |
| 326 | 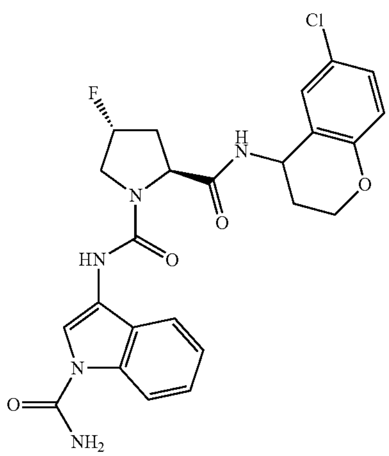 [SMILES: NC(=O)n1cc(NC(=O)N2C[C@H](F)C[C@H]2C(=O)NC2CCOc3ccc(Cl)cc32)c2ccccc21] | (2S,4R)-4-Fluoro-pyrrolidine-1,2-dicarboxylic acid 1-[(1-carbamoyl-1H-indol-3-yl)-amide] 2-[(6-chloro-chroman-4-yl)-amide] (mixture of 2 diastereomers) | (3) 500.0 [M]+; t$_R$ (c): 4.39 min. |
| 327 | 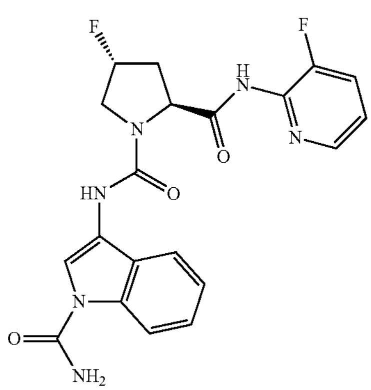 [SMILES: NC(=O)n1cc(NC(=O)N2C[C@H](F)C[C@H]2C(=O)Nc2ncccc2F)c2ccccc21] | (2S,4R)-4-Fluoro-pyrrolidine-1,2-dicarboxylic acid 1-[(1-carbamoyl-1H-indol-3-yl)-amide] 2-[(3-fluoro-pyridin-2-yl)-amide] | (4) White solid. R$_f$ (EtOAc) = 0.25; 429.0 [M + H]+; t$_R$ (c): 3.42 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 328 | 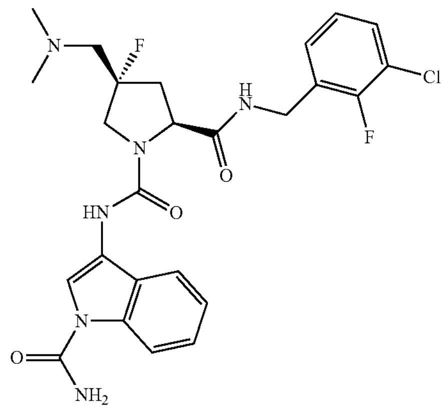 [SMILES: CN(C)C[C@@]1(F)C[C@@H](C(=O)NCc2cccc(Cl)c2F)N(C(=O)Nc2cn(C(N)=O)c3ccccc23)C1] | (2S,4S)-4-Dimethylaminomethyl-4-fluoro-pyrrolidine-1,2-dicarboxylic acid 1-[(1-carbamoyl-1H-indol-3-yl)-amide] 2-(3-chloro-2-fluoro-benzylamide) | (8[B15]) 532 [M + H]+, 530 [M − H]−; t$_R$ (f): 1.62 min, 19F NMR (DMSO-d$_6$): −120, −149. |
| 329 | 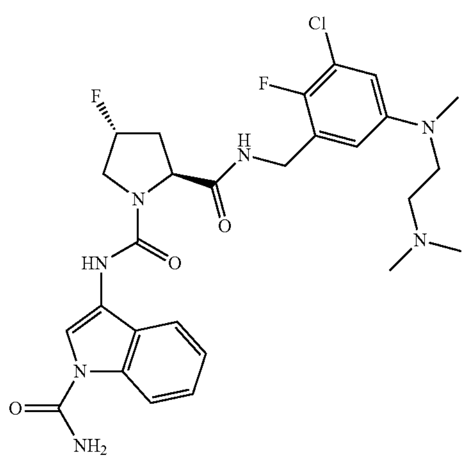 [SMILES: CN(C)CCN(C)c1cc(Cl)c(F)c(CNC(=O)[C@@H]2C[C@@H](F)CN2C(=O)Nc2cn(C(N)=O)c3ccccc23)c1] | (2S,4R)-4-Fluoro-pyrrolidine-1,2-dicarboxylic acid 1-[(1-carbamoyl-1H-indol-3-yl)-amide] 2-{3-chloro-5-[(2-dimethylamino-ethyl)-methyl-amino]-2-fluoro-benzylamide} | (3,6[C1]) 576.2 [M]+; t$_R$ (c): 3.91 min. |
| 330 | 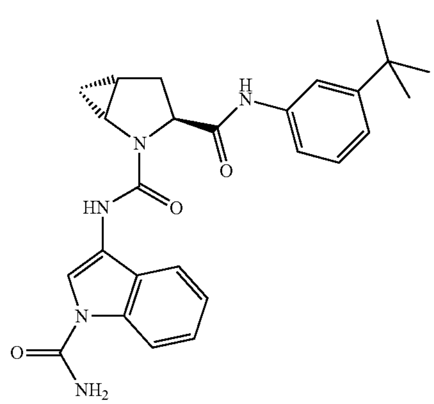 | (1R,3S,5R)-2-Aza-bicyclo[3.1.0]hexane-2,3-dicarboxylic acid 3-[(3-tert-butyl-phenyl)-amide] 2-[(1-carbamoyl-1H-indol-3-yl)-amide] | (1) 460.1 [M + H]+, 415.1 [M − CONH$_2$]−; t$_R$ (b): 4.68 min. |

TABLE 4-continued

| Example | Structure | Name | Characterization (end-table notes), TLC, $R_f$ (eluent); MS (LC/MS); $t_R$ (HPLC conditions); 19F NMR (100 MHz, solvent) δ (ppm): |
|---|---|---|---|
| 331 | 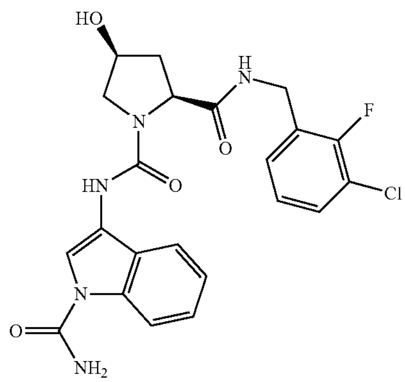 [SMILES: NC(=O)n1cc(NC(=O)N2C[C@@H](O)C[C@H]2C(=O)NCc2cccc(Cl)c2F)c2ccccc21] | (2S,4S)-4-Hydroxy-pyrrolidine-1,2-dicarboxylic acid 1-[(1-carbamoyl-1H-indol-3-yl)-amide] 2-(3-chloro-2-fluoro-benzylamide) | $R_f$ (EtOAc) = 0.2; 474.1/476.2 [M + H]+, 496.1/498 [M + Na]+, 472/474.1 [M − H]−, 429.1/431 [M − CONH$_2$]−; $t_R$ (a): 2.88 min. |
| 332 | 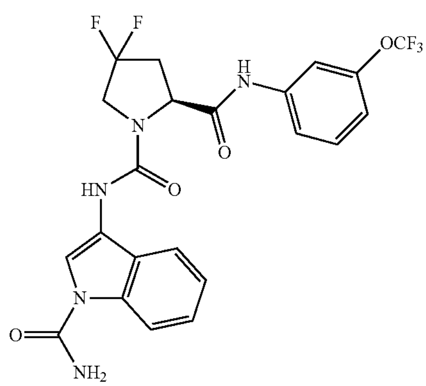 [SMILES: NC(=O)n1cc(NC(=O)N2CC(F)(F)C[C@H]2C(=O)Nc2cccc(OC(F)(F)F)c2)c2ccccc21] | (S)-4,4-Difluoro-pyrrolidine-1,2-dicarboxylic acid 1-[(1-carbamoyl-1H-indol-3-yl)-amide] 2-[(3-trifluoromethoxy-phenyl)-amide] | 512.2 [M + H]+, 501.1 [M − H]−; $t_R$ (a): 3.63 min. |
| 333 | 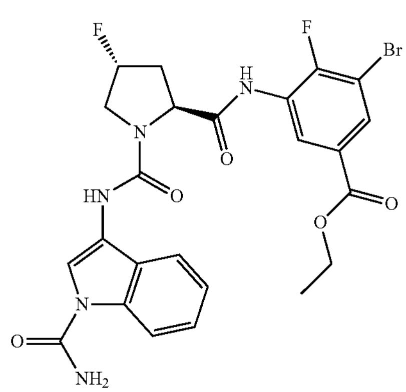 [SMILES: CCOC(=O)c1cc(Br)c(F)c(NC(=O)[C@@H]2C[C@@H](F)CN2C(=O)Nc2cn(C(N)=O)c3ccccc23)c1] | 3-Bromo-5-{[(2S,4R)-1-(1-carbamoyl-1H-indol-3-ylcarbamoyl)-4-fluoro-pyrrolidine-2-carbonyl]-amino}-4-fluoro-benzoic acid ethyl ester | (4,6) 578/580 [M + H]+, 576/578 [M − H]−; $t_R$ (b): 4.3 min. |

TABLE 4-continued

| Example | Structure | Name | Characterization (end-table notes), TLC, R$_f$ (eluent); MS (LC/MS); t$_R$ (HPLC conditions); 19F NMR (100 MHz, solvent) δ (ppm): |
|---|---|---|---|
| 334 | 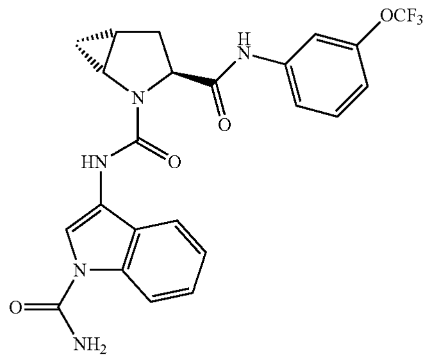 | (1R,3S,5R)-2-Aza-bicyclo[3.1.0]hexane-2,3-dicarboxylic acid 2-[(1-carbamoyl-1H-indol-3-yl)-amide] 3-[(3-trifluoromethoxy-phenyl)-amide] | R$_f$ (c-hexane/EtOAc 1:2) = 0.40; 488 [M + H]+, 997.2 [2M + Na]+, 486.1 [M − H]−, 443.2 [M − CONH$_2$]−; t$_R$ (a): 3.55 min. |
| 335 | 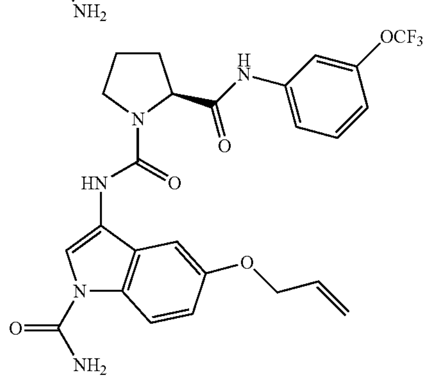 | (S)-Pyrrolidine-1,2-dicarboxylic acid 1-[(5-allyloxy-1-carbamoyl-1H-indol-3-yl)-amide] 2-[(3-trifluoromethoxy-phenyl)-amide] | (9[A4]) R$_f$ (EtOAc) = 0.51; 532.2 [M + H]+, 530 [M − H]−; t$_R$ (a): 3.64 min. |

(1) CH$_2$Cl$_2$ was used instead of DMF in step A; (2) CH$_3$CN was used instead of DMF in step A; (3) HATU was used as the coupling reagent in step A; (4) The reaction mixture in step A was heated at 70° C.; (5) HCl (4 M in dioxane) in dioxane was used instead of TFA in CH$_2$Cl$_2$ in step B; (6) The substituted benzylamine or aniline derivative used in step A was prepared as described in Part C [Scheme]; (7) The substituted proline derivative used in step A was prepared as described in Part B [Scheme]; (8) The title compound was prepared according to the general procedure described in Scheme D5 steps B and C starting from the substituted proline derivative prepared as described in Part B [Scheme]; (9) The isocyanate reagent used in step C was prepared as described in Part A.

Example 336

(2S,5R)-5-Methyl-pyrrolidine-1,2-dicarboxylic acid 1-[(1-carbamoyl-1H-indol-3-yl)-amide]2-[(3-trifluoromethoxy-phenyl)-amide]

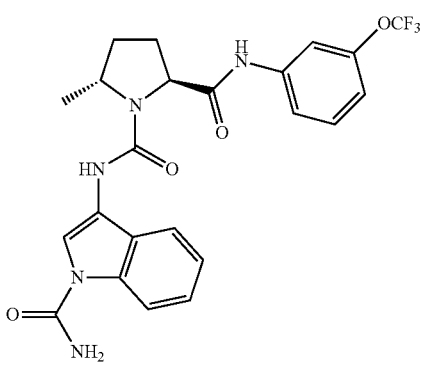 [SMILES: C[C@@H]1CC[C@@H](C(=O)Nc2cccc(OC(F)(F)F)c2)N1C(=O)Nc1cn(C(N)=O)c2ccccc12]

The title compound was prepared according to the general procedure described in Scheme D5 except that CH$_2$Cl$_2$ was used instead of DMF in step A, starting from a mixture of (2S,5R)- and (2S,5S)-5-methyl-pyrrolidine-1,2-dicarboxylic acid 1-tert-butyl ester in a 7:1 ratio (prepared as described in Scheme B1). The diastereoisomers were separated by chiral HPLC (Chiracel OJ, 20 μM, 185×48 mm, flow: 100 mL/min, mobile phase: n-hexane/EtOH 9:1) to give the title compound: TLC, R$_f$ (c-hexane/EtOAc 1:3)=0.45; MS (LC/MS): 490.0 [M+H]+, 488.0 [M−H]−; t$_R$ (HPLC conditions c): 4.99 min.

Example 337

(2S,5S)-5-Methyl-pyrrolidine-1,2-dicarboxylic acid 1-[(1-carbamoyl-1H-indol-3-yl)-amide]2-[(3-trifluoromethoxy-phenyl)-amide]

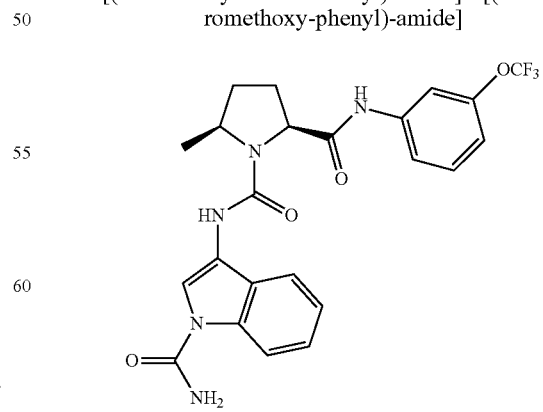

The title compound was prepared according to the general procedure described in Scheme D5 except that CH$_2$Cl$_2$ was used instead of DMF in step A, starting from a (7:1)-mixture of (2S,5R)- and (2S,5S)-5-methyl-pyrrolidine-1,2-dicarboxylic acid 1-tert-butyl ester (prepared as described in Scheme B1). The diastereoisomeric product was separated by chiral HPLC (Chiracel OJ, 20 µM, 185×48 mm, flow: 100 mL/min, mobile phase: n-hexane/EtOH 9:1) to give the title compound. TLC $R_f$ (c-hexane/EtOAc 1:3)=0.45; MS (LC/MS): 490.0 [M+H]+, 488.0 [M−H]−; $t_R$ (HPLC conditions c): 5.21 min.

Example 338

(2S,5R)-5-Ethyl-pyrrolidine-1,2-dicarboxylic acid 1-[(1-carbamoyl-1H-indol-3-yl)-amide]2-[(3-trifluoromthoxy-phenyl)-amide]

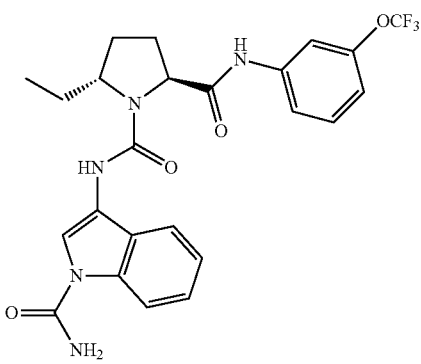 [SMILES: CC[C@@H]1CC[C@@H](C(=O)Nc2cccc(OC(F)(F)F)c2)N1C(=O)Nc1cn(C(N)=O)c2ccccc12]

The title compound was prepared according to the general procedure described in Scheme D5 except that $CH_2Cl_2$ was used instead of DMF in step A, starting from a >9:1 diastereoisomeric mixture of (2S,5R)- and (2S,5S)-5-ethyl-pyrrolidine-1,2-diarboxylic acid 1-tert-butyl ester (prepared as described in Part B). Purification of the product in the final reaction step by chiral preparative HPLC (Chiralcel OJ H 5 µM stationary phase) gave the title compound as single diastereomer. TLC $R_f$ (EtOAc)=0.60; MS (LC/MS): 504.1 [M+H]+; $t_R$ (Chiralcel OJ H 5 µM, column 250×4.0 mm, n-hexane/EtOH 8:2, flow 1.1 mL/min, 25° C., detection 200 nm): 4.73 min; $t_R$ (HPLC conditions c): 5.21 min.

Example 339

3-Chloro-5-{[(2S,4R)-1-(1-carbamoyl-1H-indol-3-ylcarbamoyl)-4-fluoro-pyrrolidine-2-carbonyl]-amino}-benzoic acid

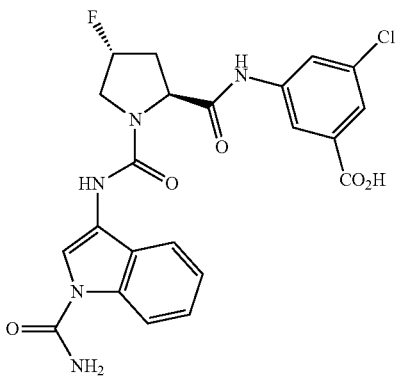 [SMILES: NC(=O)n1cc(NC(=O)N2C[C@H](F)C[C@H]2C(=O)Nc2cc(Cl)cc(C(=O)O)c2)c2ccccc21]

The title compound was prepared according to the general procedure described in Scheme D5 (Steps B and C) starting from (2S,4R)-2-(3-carboxy-5-chloro-phenylcarbamoyl)-4-fluoro-pyrrolidine-1-carboxylic acid tert-butyl ester) (prepared by using similar protocols as described in Scheme B7). White solid. MS (LC/MS): 486 [M−H]+; $t_R$ (HPLC conditions b): 3.31 min.

Example 340

3-Bromo-5-{[(1R,3S,5R)-2-(1-carbamoyl-1H-indol-3-ylcarbamoyl)-2-aza-bicyclo[3.1.0]hexane-3-carbonyl]-amino}-benzoic acid

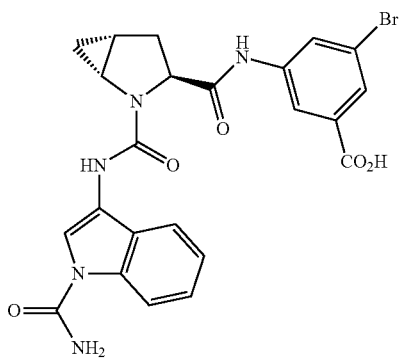 [SMILES: NC(=O)n1cc(NC(=O)N2[C@@H]3C[C@@H]3C[C@H]2C(=O)Nc2cc(Br)cc(C(=O)O)c2)c2ccccc21]

The title compound (White solid) was prepared according to the general procedure described in Scheme D5 (Steps B and C) starting from (1R,3S,5R)-3-(3-bromo-5-carboxy-phenylcarbamoyl)-2-aza-bicyclo[3.1.0]hexane-2-carboxylic acid tert-butyl ester) (prepared by using similar protocols as described in Scheme B7, except that the reaction mixture was heated at 65° C. in step A and dioxane was used instead of MeOH in step B). White solid. MS (LC/MS): 524.3/525.3 [M+H]+; $t_R$ (HPLC conditions b): 3.6 min.

Example 341

3-Bromo-5-{[(S)-3-(1-carbamoyl-1H-indol-3-ylcarbamoyl)-thiazolidine-2-carbonyl]-amino}-benzoic acid

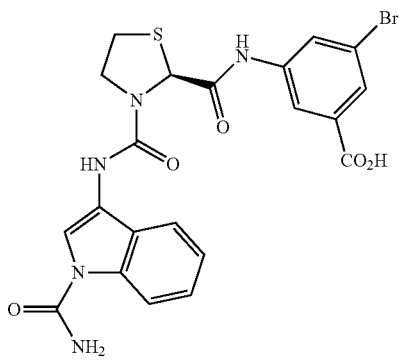 [SMILES: NC(=O)n1cc(NC(=O)N2CCS[C@H]2C(=O)Nc2cc(Br)cc(C(=O)O)c2)c2ccccc21]

The title compound was prepared according to the general procedure described in Scheme D5 (Steps B and C) starting from (S)-2-(3-bromo-5-carboxy-phenylcarbamoyl)-thiazolidine-3-carboxylic acid tert-butyl ester) (prepared by using similar protocols as described in Scheme B7). MS (LC/MS): 530.2/532.2/533.1 [M−H]−; $t_R$ (HPLC conditions b): 3.55 min.

Example 342

3-Bromo-5-{[(1R,3S,5R)-2-(1-carbamoyl-5-methoxy-1H-indol-3-ylcarbamoyl)-2-aza-bicyclo[3.1.0]hexane-3-carbonyl]-amino}-benzoic acid

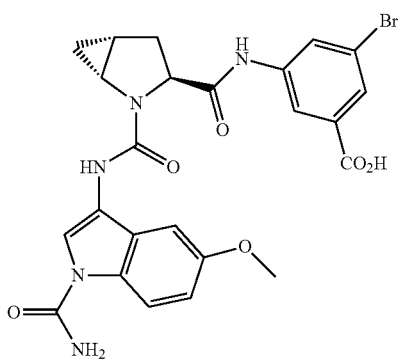 [SMILES: COc1ccc2c(c1)c(NC(=O)N1[C@@H]3C[C@@H]3C[C@H]1C(=O)Nc1cc(Br)cc(C(=O)O)c1)cn2C(N)=O]

The title compound (White solid) was prepared according to the general procedure described in Scheme D5 (Steps B and C) using (1R,3S,5R)-3-(3-bromo-5-carboxy-phenylcarbamoyl)-2-aza-bicyclo[3.1.0]hexane-2-carboxylic acid tert-butyl ester) (prepared by using similar protocols as described in Scheme B7, except that the reaction mixture was heated at 65° C. in step A and dioxane was used instead of MeOH in step B) and 3-Isocyanato-5-methoxy-indole-1-carboxylic acid amide (prepared as described in Scheme A1). MS (LC/MS): 556.0 [M+H]+; $t_R$ (HPLC conditions c): 4.32 min.

Example 343

3-Bromo-5-{[(2S,4R)-1-(1-carbamoyl-1H-indol-3-ylcarbamoyl)-4-fluoro-pyrrolidine-2-carbonyl]-amino}-4-fluoro-benzoic acid

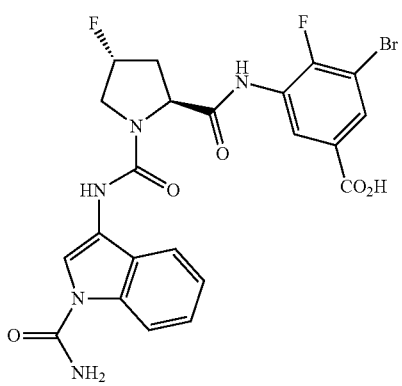 [SMILES: NC(=O)n1cc(NC(=O)N2C[C@H](F)C[C@H]2C(=O)Nc2cc(C(=O)O)cc(Br)c2F)c2ccccc21]

The title compound was prepared according to the general procedure described in Scheme D5 (Steps B and C) starting from (2S,4R)-2-(3-bromo-5-carboxy-2-fluoro-phenylcarbamoyl)-4-fluoro-pyrrolidine-1-carboxylic acid tert-butyl ester (prepared by using similar protocols as described in Scheme B7 starting from 3-amino-5-bromo-4-fluoro-benzoic acid ethyl ester described Part C). MS (LC/MS): 550/552 [M+H]+; $t_R$ (HPLC conditions b): 3.3 min.

Example 344

(1R,3S,5R)-2-Aza-bicyclo[3.1.0]hexane-2,3-dicarboxylic acid 3-{[3-bromo-5-(1H-tetrazol-5-yl)-phenyl]-amide}2-[(1-carbamoyl-1H-indol-3-yl)-amide]

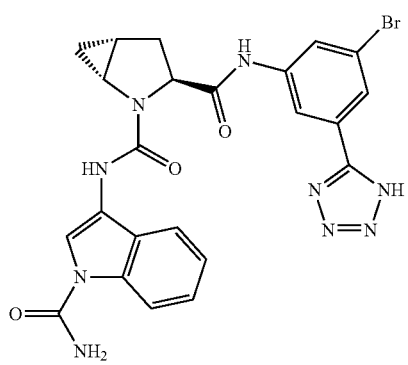 [SMILES: NC(=O)n1cc(NC(=O)N2[C@@H]3C[C@@H]3C[C@H]2C(=O)Nc2cc(Br)cc(-c3nnn[nH]3)c2)c2ccccc21]

The title compound was prepared according to the general procedure described in Scheme D5 step C from a mixture of (1R,3S,5R)-2-aza-bicyclo[3.1.0]hexane-3-carboxylic acid [3-bromo-5-(1H-tetrazol-5-yl)-phenyl]-amide and (1R,3S,5R)-2-aza-bicyclo[3.1.0]hexane-3-carboxylic acid [3-bromo-5-(1-tert-butyl-1H-tetrazol-5-yl)-phenyl]amide (ratio 2:3, prepared as described in Scheme B8). Purification by preparative HPLC (Sunfire, C18-ODB, 5 µm, 30×100 mm, flow: 40 mL/min, eluent: 5-100% $CH_3CN/H_2O$/20 min, 100% $CH_3CN$/2 min, $CH_3CN$ and $H_2O$ containing 0.1% TFA) afforded the title compound (1R,3S,5R)-2-aza-bicyclo[3.1.0]hexane-2,3-dicarboxylic acid 3-{[3-bromo-5-(1H-tetrazol-5-yl)-phenyl]amide}2-[(1-carbamoyl-1H-indol-3-yl)-amide] as a white powder, MS (LC/MS): 550.0 [M+H]+; $t_R$ (HPLC conditions c): 4.35 min.

Example 345

(1R,3S,5R)-2-Aza-bicyclo[3.1.0]hexane-2,3-dicarboxylic acid 3-{[3-bromo-5-(1-tert-butyl-1H-tetrazol-5-yl)-phenyl]-amide}2-[(1-carbamoyl-1H-indol-3-yl)-amide]

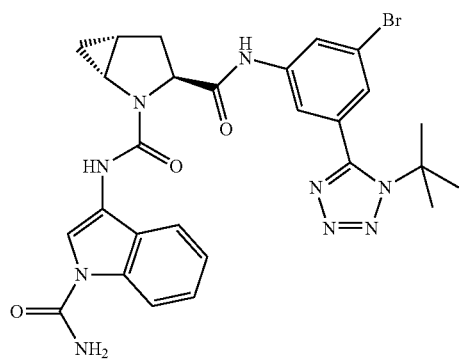 [SMILES: CC(C)(C)n1nnnc1-c1cc(Br)cc(NC(=O)[C@@H]2C[C@H]3C[C@H]3N2C(=O)Nc2cn(C(N)=O)c3ccccc23)c1]

The title compound was prepared according to the general procedure described in Scheme D5 step C from a mixture of (1R,3S,5R)-2-aza-bicyclo[3.1.0]hexane-3-carboxylic acid [3-bromo-5-(1H-tetrazol-5-yl)-phenyl]-amide and (1R,3S,5R)-2-aza-bicyclo[3.1.0]hexane-3-carboxylic acid [3-bromo-5-(1-tert-butyl-1H-tetrazol-5-yl)phenyl]-amide (ratio 2:3, prepared as described in Scheme B8). Purification by preparative HPLC (Sunfire, C18-ODB, 5 μm, 30×100 mm, flow: 40 mL/min, eluent: 5-100% CH$_3$CN/H$_2$O/20 min, 100% CH$_3$CN/2 min, CH$_3$CN and H$_2$O containing 0.1% TFA) afforded the title compound (1R,3S,5R)-2-aza-bicyclo [3.1.0]hexane-2,3-dicarboxylic acid 3-{[3-bromo-5-(1-tert-butyl-1H-tetrazol-5-yl)-phenyl]-amide}2-[(1-carbamoyl-1H-indol-3-yl)-amide] as a white solid. MS (LC/MS): 606.0 [M+H]+; t$_R$ (HPLC conditions c): 5.60 min.

Example 346

(2S,4R)-4-Fluoro-pyrrolidine-1,2-dicarboxylic acid 1-[(1-carbamoyl-1H-indol-3-yl)-amide]2-[3-chloro-2-fluoro-5-(1H-tetrazol-5-yl)-benzylamide]

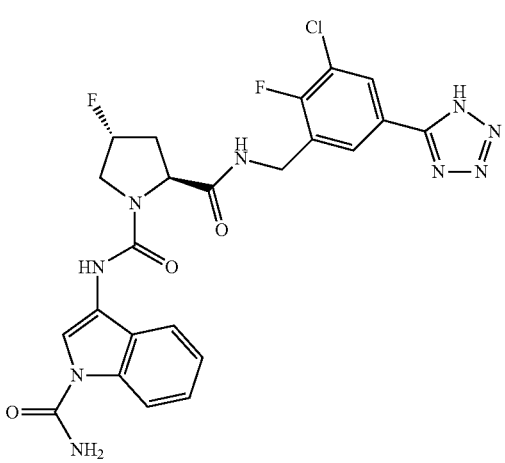 [SMILES: NC(=O)n1cc(NC(=O)N2C[C@H](F)C[C@H]2C(=O)NCc2cc(-c3nnn[nH]3)cc(Cl)c2F)c2ccccc21]

The title compound was prepared according to the general procedure described in Scheme D5 step C from a 2:1 mixture of (2S,4R)-4-fluoro-pyrrolidine-2-carboxylic acid 3-chloro-2-fluoro-5-(2H-tetrazol-5-yl)-benzylamide and (2S,4R)-4-fluoro-pyrrolidine-2-carboxylic acid 5-(1-tert-butyl-1H-tetrazol-5-yl)-3-chloro-2-fluoro-benzylamide (prepared as described in Part B). The crude products were purified without aqueous workup by RP-preparative HPLC (Waters Sunfire, C18-ODB, 5 μm, 30×100 mm, 5-80% CH$_3$CN/H$_2$O/20 min, 100% CH$_3$CN/2 min, CH$_3$CN and H$_2$O containing 0.1% TFA, flow: 40 mL/min) to give the title compound (2S,4R)-4-fluoro-pyrrolidine-1,2-dicarboxylic acid 1-[(1-carbamoyl-1H-indol-3-yl)amide]2-[3-chloro-2-fluoro-5-(1H-tetrazol-5-yl)-benzylamide]: MS (LC/MS): 544.0 [M]+; t$_R$ (HPLC conditions c): 3.09 min.

Example 347

(2S,4R)-4-Fluoro-pyrrolidine-1,2-dicarboxylic acid 2-[5-(1-tert-butyl-1H-tetrazol-5-yl)-3-chloro-2-fluoro-benzylamide]1-[(1-carbamoyl-1H-indol-3-yl)-amide]

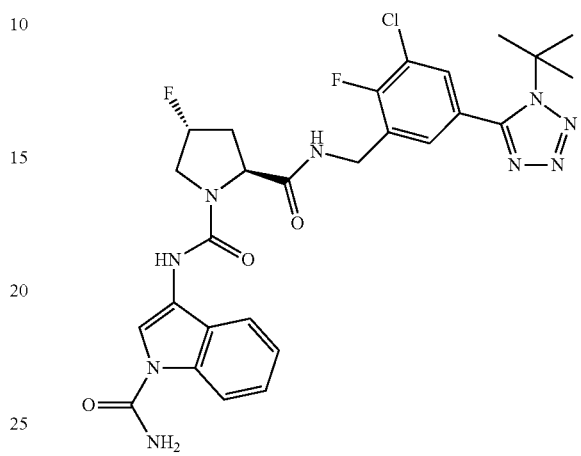

The title compound was prepared according to the general procedure described in Scheme D5 step C from a 2:1 mixture of (2S,4R)-4-fluoro-pyrrolidine-2-carboxylic acid 3-chloro-2-fluoro-5-(2H-tetrazol-5-yl)-benzylamide and (2S,4R)-4-fluoro-pyrrolidine-2-carboxylic acid 5-(1-tert-butyl-1H-tetrazol-5-yl)-3-chloro-2-fluoro-benzylamide (prepared as described in Part B). The crude products were purified without aqueous workup by RP-preparative HPLC (Waters Sunfire, C18-ODB, 5 μm, 30×100 mm, 5-80% CH$_3$CN/H$_2$O/20 min, 100% CH$_3$CN/2 min, CH$_3$CN and H$_2$O containing 0.1% TFA, flow: 40 mL/min) to give the title compound (2S,4R)-4-fluoro-pyrrolidine-1,2-dicarboxylic acid 2-[5-(1-tert-butyl-1H-tetrazol-5-yl)-3-chloro-2-fluoro-benzylamide]1-[(1-carbamoyl-1H-indol-3-yl)-amide]: MS (LC/MS): 600.2 [M]+; t$_R$ (HPLC conditions c): 3.63 min.

Example 348

2R,3S)-3-Fluoro-pyrrolidine-1,2-dicarboxylic acid 1-[(1-carbamoyl-1H-indol-3-yl)-amide]2-(3-chloro-benzylamide

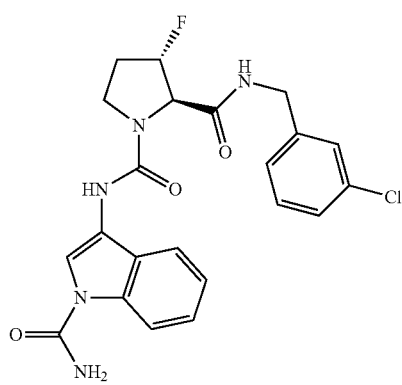 [SMILES: NC(=O)n1cc(NC(=O)N2CC[C@H](F)[C@H]2C(=O)NCc2cccc(Cl)c2)c2ccccc21]

The title compound was prepared according to the general procedure described in Scheme D5 (Steps B and C) starting from (2R,3S)-2-(3-chloro-benzylcarbamoyl)-3-fluoro-pyrrolidine-1-carboxylic acid tert-butyl ester (prepared by using similar protocols as described for the preparation of (2R,3S)-2-(3-chloro-2-fluoro-benzylcarbamoyl)-3-fluoro-pyrrolidine-1-carboxylic acid tert-butyl ester in Part B). White solid. MS (LC/MS): 458 [M+H]+; $t_R$ (HPLC conditions b): 3.56 min.

Example 349

2R,3R)-3-Fluoro-pyrrolidine-1,2-dicarboxylic acid 1-[(1-carbamoyl-1H-indol-3-yl)-amide]2-(3-chloro-benzylamide

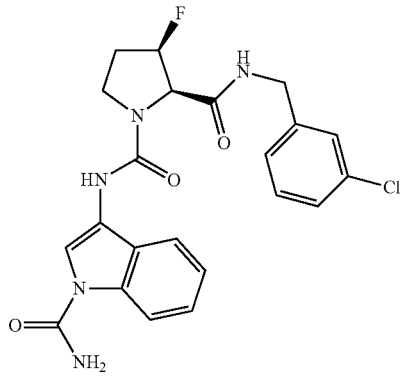 [SMILES: NC(=O)n1cc(NC(=O)N2CC[C@@H](F)[C@H]2C(=O)NCc2cccc(Cl)c2)c2ccccc21]

The title compound was prepared according to the general procedure described in Scheme D5 (Steps B and C) by starting from (2R,3R)-2-(3-chloro-benzylcarbamoyl)-3-fluoro-pyrrolidine-1-carboxylic acid tert-butyl ester (prepared by using similar protocols as described for the preparation of (2R,3R)-2-(3-chloro-2-fluoro-benzylcarbamoyl)-3-fluoro-pyrrolidine-1-carboxylic acid tert-butyl ester in Part B). White solid. MS (LC/MS): 458 [M+H]+; $t_R$ (HPLC conditions b): 3.42 min.

Example 350

2S,5R)-5-Methyl-pyrrolidine-1,2-dicarboxylic acid 1-[(1-carbamoyl-1H-indol-3-yl)-amide]2-(3-chloro-2-fluoro-benzylamide

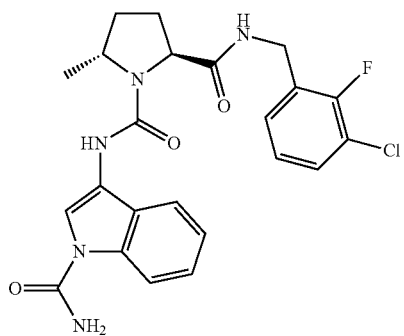 [SMILES: C[C@@H]1CC[C@@H](C(=O)NCc2cccc(Cl)c2F)N1C(=O)Nc1cn(C(N)=O)c2ccccc12]

The title compound (cis/trans ratio 1:11) was prepared according to the general procedure described in Scheme D5 except that CH$_2$Cl$_2$ was used instead of DMF in step A, and starting (2S,5R)-5-methyl-pyrrolidine-1,2-dicarboxylic acid 1-tert-butyl ester (prepared in cis/trans ratio of 1:11 as described in Scheme B1). White solid. TLC R$_f$ (EtOAc)=0.35; MS (LC/MS): 472 [M+H]+, 494 [M+Na]+; $t_R$ (HPLC conditions c): 4.52 min.

Example 351

2S,5R)-5-Ethyl-pyrrolidine-1,2-dicarboxylic acid 1-[(1-carbamoyl-1H-indol-3-yl)-amide]2-(3-chloro-2-fluoro-benzylamide

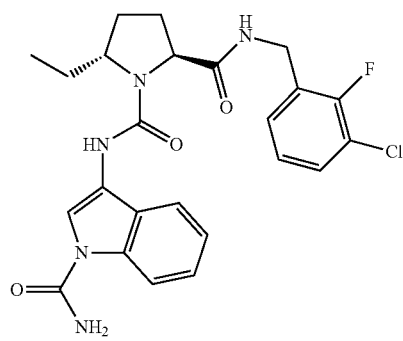 [SMILES: CC[C@@H]1CC[C@@H](C(=O)NCc2cccc(Cl)c2F)N1C(=O)Nc1cn(C(N)=O)c2ccccc12]

The title compound was prepared according to the general procedure described in Scheme D5 except that CH$_2$Cl$_2$ was used instead of DMF in step A, starting from a >9:1 diastereoisomeric mixture of (2S,5R)- and (2S,5S)-5-ethyl-pyrrolidine-1,2-diarboxylic acid 1-tert-butyl ester (prepared as described in Part B). The crude diastereoisomeric product mixture was purified by chiral preparative HPLC (Chiracel OJ, 10 μM, 250×4.6 mm, flow: 1.0 mL/min, mobile phase: heptane/EtOH 8:2; $t_R$=5.61 min (major) and 14.3 min (minor) in a peak ratio of 87:13) to give the title compound as single diastereomer. TLC, R$_f$(EtOAc/c-hexane 4:1)=0.31; MS (LC/MS): 486.1 [M+H]+; $t_R$ (HPLC conditions c): 4.76 min.

Example 352

2S,4R)-4-Hydroxymethyl-pyrrolidine-1,2-dicarboxylic acid 1-[(1-carbamoyl-1H-indol-3-yl)-amide]2-(3-chloro-2-fluoro-benzylamide

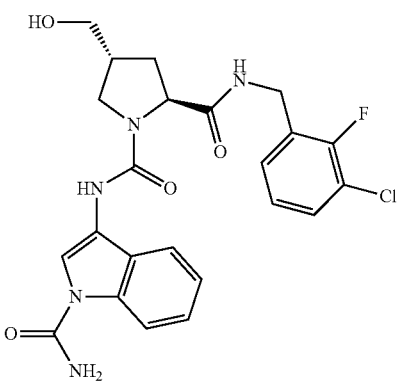 [SMILES: NC(=O)n1cc(NC(=O)N2C[C@H](CO)C[C@H]2C(=O)NCc2cccc(Cl)c2F)c2ccccc21]

The title compound was prepared according to Scheme D5 (steps B and C) from (2S,4R)-2-(3-chloro-2-fluoro-benzylcarbamoyl)-4-hydroxymethyl-pyrrolidine-1-carboxylic acid tert-butyl ester prepared using the same protocol as for the preparation of (2S,4S)-2-(3-chloro-2-fluoro-benzylcarbamoyl)-4-hydroxymethyl-pyrrolidine-1-carboxylic acid tert-butyl ester (prepared as described in Part B). TLC, R$_f$(EtOAc)=

0.05; MS (LC/MS): 488.1/490.1 [M+H]+, 510.1/512.1 [M+Na]+, 443.0/445.0 [M−CONH$_2$]−; $t_R$ (HPLC conditions a): 2.87 min.

Example 353

(3S,5S)-1-(1-Carbamoyl-1H-indol-3-ylcarbamoyl)-5-(3-chloro-2,6-difluoro-benzylcarbamoyl)-pyrrolidine-3-carboxylic acid methyl ester

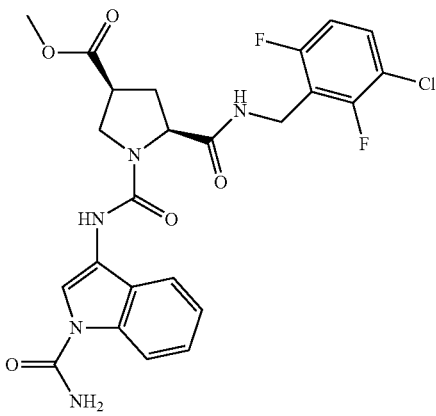 [SMILES: COC(=O)[C@H]1C[C@@H](C(=O)NCc2c(F)ccc(Cl)c2F)N(C(=O)Nc2cn(C(N)=O)c3ccccc23)C1]

The title compound was prepared according to Scheme D5 (steps B and C) from (3S,5S)-5-(3-chloro-2,6-difluoro-benzylcarbamoyl)-pyrrolidine-1,3-dicarboxylic acid 1-tert-butyl ester 3-methyl ester prepared using the protocols described for the preparation of (3S,5S)-5-(3-chloro-2-fluoro-benzylcarbamoyl)-pyrrolidine-1,3-dicarboxylic acid 1-tert-butyl ester 3-methyl ester in Part B. $R_f$ TLC (CH$_2$Cl$_2$/MeOH, 95:5)=0.2; MS (LC-MS): 534.3/536.2 [M+H]+, 532.2 [M−H]−; $t_R$ (HPLC conditions a): 2.96 min.

Example 354

(3S,5S)-1-(1-Carbamoyl-1H-indol-3-ylcarbamoyl)-5-(3-chloro-2,6-difluoro-benzylcarbamoyl)-pyrrolidine-3-carboxylic acid

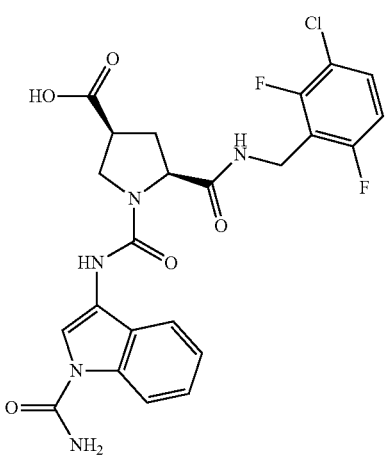 [SMILES: NC(=O)n1cc(NC(=O)N2C[C@@H](C(=O)O)C[C@H]2C(=O)NCc2c(F)ccc(Cl)c2F)c2ccccc21]

To a solution of (3S,5S)-1-(1-carbamoyl-1H-indol-3-ylcarbamoyl)-5-(3-chloro-2,6-difluoro-benzylcarbamoyl)-pyrrolidine-3-carboxylic acid methyl ester Example 353 (50 mg, 0.094 mmol) in THF (0.3 mL)/Et$_2$O (3 mL)/H$_2$O (0.3 mL) was added potassium trimethylsilanolate (19.5 mg, 0.2 mmol) and the resulting suspension was stirred at RT for 1.30 h. The reaction was diluted with EtOAc (15 mL) and H$_2$O (3 mL), and the biphasic mixture was vigorously stirred for 5 min. The layers were separated, and the aqueous one was extracted with EtOAc (×2). The aqueous layer was acidified by addition of 1N HCl and extracted with EtOAc, the combined organic layers were dried over Na$_2$SO$_4$, filtered and concentrated. The crude material was purified by preparative HPLC (Waters Sunfire, C18-ODB, 5 µm, 19×50 mm, eluent: 20% to 100% CH$_3$CN in H$_2$O in 25 min, CH$_3$CN and H$_2$O containing 0.1% HCOOH, flow: 20 mL/min) to give, after lyophilization of the purified fractions the title compound as a white solid. MS (LC-MS): 518.4 [M−H]−, 520.1 [M+H]+, 1039.3 [2M+H]+; $t_R$ (HPLC conditions f): 1.70 min.

Example 355

(2S,4S)-4-Hydroxymethyl-pyrrolidine-1,2-dicarboxylic acid 2-(3-bromo-2-fluoro-benzylamide) 1-[(1-carbamoyl-1H-indol-3-yl)-amide]

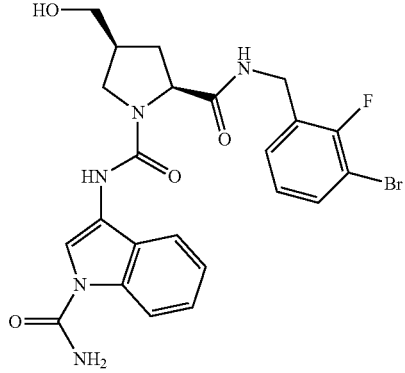 [SMILES: NC(=O)n1cc(NC(=O)N2C[C@@H](CO)C[C@H]2C(=O)NCc2cccc(Br)c2F)c2ccccc21]

To a solution of (3S,5S)-5-(3-bromo-2-fluoro-benzylcarbamoyl)-1-(1-carbamoyl-1H-indol-3-ylcarbamoyl)-pyrrolidine-3-carboxylic acid methyl ester (85 mg, 0.14 mmol) in THF (1.5 mL) under nitrogen atmosphere was added LiBH$_4$ (2 M in THF, 0.14 mL, 0.29 mmol). The reaction mixture was stirred at RT for 30 min, and then it was slowly poured into an aqueous saturated solution of NaHCO$_3$ and extracted twice with EtOAc. The combined organic layers were dried over Na$_2$SO$_4$, filtered and concentrated. The crude residue was purified by flash column chromatography on silica gel (eluent: 100% CH$_2$Cl$_2$ to CH$_2$Cl$_2$/MeOH 91-9) to give the desired material as white solid. $R_f$ TLC (EtOAc)=0.2; MS (UPLC-MS): 532.3/534.4 [M+H]+, 576.3/578.3 [M+HCOO]−, 530.4/532.5 [M−H]−; $t_R$ (HPLC conditions f): 1.69 min.

(3S,5S)-5-(3-Bromo-2-fluoro-benzylcarbamoyl)-1-(1-carbamoyl-1H-indol-3-ylcarbamoyl)-pyrrolidine-3-carboxylic acid methyl ester The title compound was prepared according to Scheme D5 (steps B and C) from (3S,5S)-5-(3-bromo-2-fluoro-benzylcarbamoyl)-pyrrolidine-1,3-dicarboxylic acid 1-tert-butyl ester 3-methyl ester prepared using the protocols as for the preparation of (3S,5S)-5-(3-chloro-2-fluoro-benzylcarbamoyl)-pyrrolidine-1,3-dicarboxylic acid 1-tert-butyl ester 3-methyl ester described in Part B. $R_f$, TLC (EtOAc)=0.45, MS (UPLC-MS): 560.5/562.4 [M+H]+, 577.3/579.4 [M+NH$_4$]+, 582.3/584.3 [M+Na]+, 604.4/606.3 [M+HCOO]−, 558.2/560.2 [M−H]−; $t_R$ (HPLC conditions f): 1.88 min.

Example 356

2S,4S)-4-Fluoro-4-hydroxymethyl-pyrrolidine-1,2-dicarboxylic acid 1-[(1-carbamoyl-1H-indol-3-yl)-amide]2-(3-chloro-2-fluoro-benzylamide

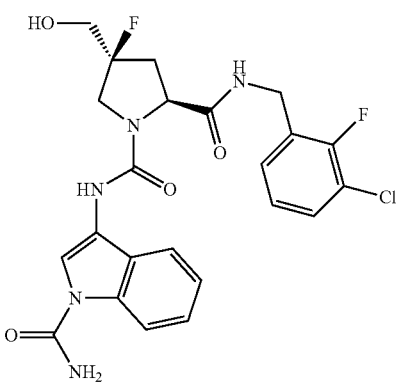 [SMILES: NC(=O)n1cc(NC(=O)N2C[C@](F)(CO)C[C@H]2C(=O)NCc2cccc(Cl)c2F)c2ccccc21]

The title compound was prepared according to Scheme D5 (steps B and C) from (2S,4S)-2-(3-chloro-2-fluoro-benzyl-carbamoyl)-4-fluoro-4-hydroxymethyl-pyrrolidine-1-carboxylic acid tert-butyl ester (prepared using similar protocols as described in Scheme B12). TLC, $R_f$ (EtOAc)=0.15; MS (LC-MS): 506.0/508.0 [M+H]+, 528.1/530.1 [M+Na]+, 504.1/506.1 [M−H], 461.0/463.0 [M−CONH$_2$]−; $t_R$ (HPLC conditions f): 1.71 min.

Example 357

1S,3S,5R)-5-Hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide

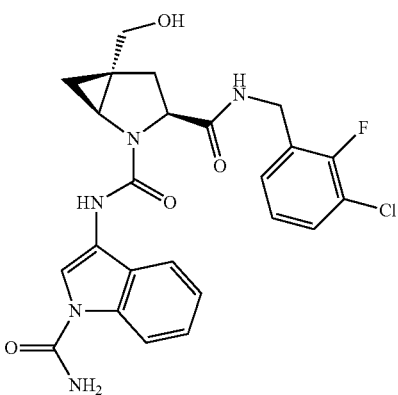 [SMILES: NC(=O)n1cc(NC(=O)N2[C@H]3C[C@@]3(CO)C[C@H]2C(=O)NCc2cccc(Cl)c2F)c2ccccc21]

The title compound was prepared according to Scheme D5 (steps B and C) using in step B HCl 4N in dioxane instead of TFA from a mixture of (1S,3S,5R) and (1R,3S,5S)-5-hydroxymethyl-2-aza-bicyclo[3.1.0]hexane-3-carboxylic acid 3-chloro-2-fluoro-benzylamide.HCl salt (prepared as described in Part B Scheme B28). The mixture of diastereoisomers was purified by flash column chromatography on silica gel (CH$_2$Cl$_2$ to CH$_2$Cl$_2$/MeOH:90:10) to give: (1R,3S,5S)-5-hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide) and (1S,3S,5R)-5-hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide) which was again purified by preparative HPLC (Waters Sunfire, C18-ODB, 5 μm, 19×50 mm, eluent: 20% to 100% (CH$_3$CN/MeOH 1:4)/H$_2$O in 30 min, (CH$_3$CN/MeOH 1:4) and H$_2$O containing 0.1% HCOOH, flow: 20 mL/min): UPLC-MS: 500 [M+H]+, 544.3/546.4 [M+HCOO−]−; $t_R$ (HPLC conditions f): 1.78 min. The absolute stereochemistry was tentatively assigned by NMR and based on the test results for the final compounds Example 357 and Example 358.

Example 358

1R,3S,5S)-5-Hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide

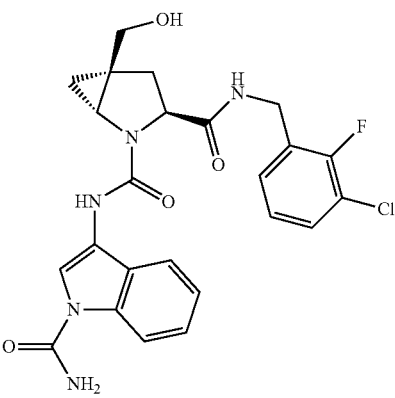 [SMILES: NC(=O)n1cc(NC(=O)N2[C@H](C(=O)NCc3cccc(Cl)c3F)C[C@@]3(CO)C[C@@H]23)c2ccccc21]

The title compound was prepared according to Scheme D5 (steps B and C) using in step B HCl 4N in dioxane instead of TFA from a mixture of (1S,3S,5R) and (1R,3S,5S)-5-hydroxymethyl-2-aza-bicyclo[3.1.0]hexane-3-carboxylic acid 3-chloro-2-fluoro-benzylamide.HCl salt (prepared as described in Part B Scheme B28). The mixture of diastereoisomers was purified by flash column chromatography on silica gel (CH$_2$Cl$_2$ to CH$_2$Cl$_2$/MeOH:90:10) to give: (1R,3S,5S)-5-hydroxymethyl-2-aza-bicyclo[3.1.0]hexane-2,3-dicarboxylic acid 2-[(1-carbamoyl-1H-indol-3-yl)-amide]3-(3-chloro-2-fluoro-benzylamide) which was again purified by preparative HPLC (Waters Sunfire, C18-ODB, 5 μm, 19×50 mm, eluent: 20% to 100% (CH$_3$CN/MeOH 1:4)/H$_2$O in 30 min, (CH$_3$CN/MeOH 1:4) and H$_2$O containing 0.1% HCOOH, flow: 20 mL/min) to give a white solid: 500.4/502.4 [M+H]+, 544.4/546.5 [M+HCOO−]−; $t_R$ (HPLC conditions f): 1.72 min. The absolute stereochemistry was tentatively assigned by NMR and based on the test results for the final compounds Example 357 and Example 358.

Example 359

(2S,4S)-4-Difluoromethyl-pyrrolidine-1,2-dicarboxylic acid 1-[(1-carbamoyl-1H-indol-3-yl)-amide]2-(3-chloro-2-fluoro-benzylamide)

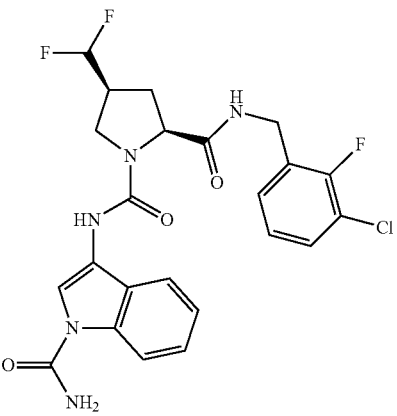 [SMILES: NC(=O)n1cc(NC(=O)N2C[C@@H](C(F)F)C[C@H]2C(=O)NCc2cccc(Cl)c2F)c2ccccc21]

The title compound was prepared according to Scheme D5 from (2S,4S)-4-difluoromethyl-pyrrolidine-1,2-dicarboxylic acid 1-tert-butyl ester (prepared following the procedure described in *J. Org. Chem.* 2002, 67, 7162). White solid. MS (LC/MS): 508 [M+H]+; $t_R$ (HPLC conditions b) 4.03 min.

Example 360

(2S,5R)-5-Hydroxymethyl-pyrrolidine-1,2-dicarboxylic acid 1-[(1-carbamoyl-1H-indol-3-yl)-amide] 2-[(3-trifluoromethoxy-phenyl)-amide]

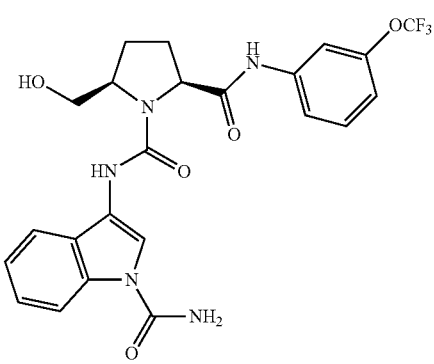 [SMILES: NC(=O)n1cc(NC(=O)N2[C@@H](CO)CC[C@H]2C(=O)Nc2cccc(OC(F)(F)F)c2)c2ccccc21]

was prepared according to Scheme D5 (step C) using (2S, 5R)-5-(tert-butyl-dimethyl-silanyloxymethyl)-pyrrolidine-2-carboxylic acid (3-trifluoromethoxy-phenyl)-amide (prepared as described in Part B). Except that after completion of the reaction, the mixture was poured into HCl 1N and EtOAc was added. The layers were separated and the aqueous one was back extracted twice with EtOAc. The combined organic layers were dried over Na$_2$SO$_4$, filtered and concentrated. The crude residue was purified by preparative HPLC (Waters SunFire C18-ODB, 5 µm, 19×50 mm, 20% CH$_3$CN/H$_2$O 2.5 min, 20-100% CH$_3$CN/H$_2$O in 10 min, CH$_3$CN/H$_2$O containing 0.1% HCOOH flow: 20 mL/min) to give after lyophilization of the purified HPLC fractions the title compound. MS (LC-MS): 506 [M+H]+; $t_R$ (HPLC conditions b) 4.13 min.

Example 361

4,5-Dihydro-pyrazole-1,5-dicarboxylic acid 1-[(1-carbamoyl-1H-indol-3-yl)-amide]5-(3-chloro-benzylamide)

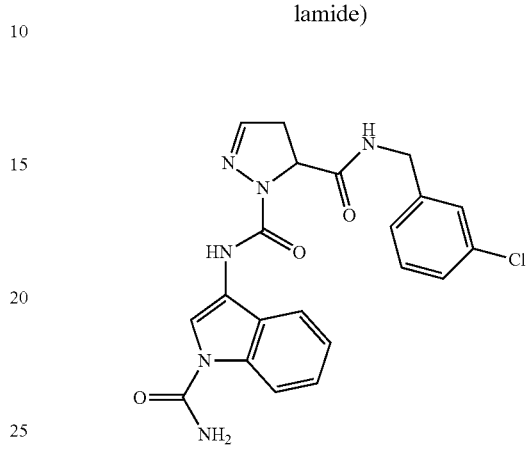

The title compound was prepared according to Scheme D5 (step C) from 3,4-dihydro-2H-pyrazole-3-carboxylic acid 3-chloro-benzylamide (prepared using similar protocols as described in Scheme B5). MS (LC-MS): 439.0 [M+H]; $t_R$ (HPLC conditions b): 3.55 min.

Example 362

S$^§$)-4,5-Dihydro-pyrazole-1,5-dicarboxylic acid 1-[(1-carbamoyl-1H-indol-3-yl)-amide]5-(3-chloro-2-fluoro-benzylamide

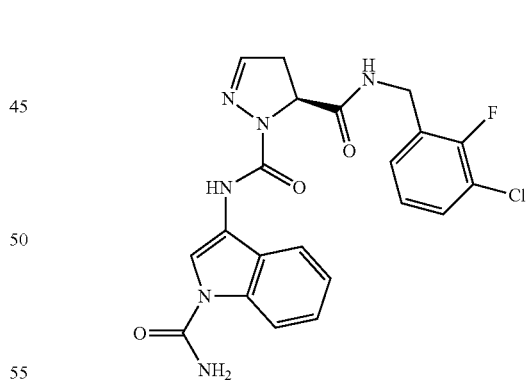

Obtained from racemic 4,5-dihydro-pyrazole-1,5-dicarboxylic acid 1-[(1-carbamoyl-1H-indol-3-yl)-amide]5-(3-chloro-2-fluoro-benzylamide) Example 201 by separation by chiral HPLC (Chiralpak ADi 5 µm, 1 mL/min, solvent: TBME/CH$_2$Cl$_2$/EtOH 50:30:20, $t_R$=9.08 min). MS (LC-MS): 457 [M+H]+; $t_R$ (HPLC conditions b): 3.73 min. The absolute stereochemistry has been assigned tentatively based on the test results for the final compounds Example 362 and Example 363 in the biological assay.

Example 363

R$^§$)-4,5-Dihydro-pyrazole-1,5-dicarboxylic acid 1-[(1-carbamoyl-1H-indol-3-yl)-amide]5-(3-chloro-2-fluoro-benzylamide

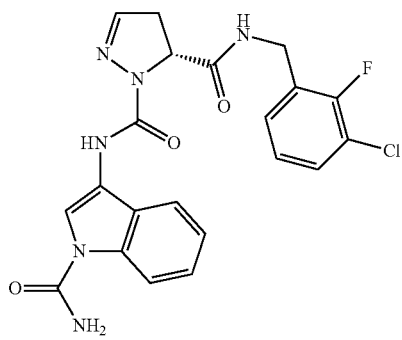 [SMILES: NC(=O)n1cc(NC(=O)N2N=CC[C@@H]2C(=O)NCc2cccc(Cl)c2F)c2ccccc21]

Obtained from racemic 4,5-dihydro-pyrazole-1,5-dicarboxylic acid 1-[(1-carbamoyl-1H-indol-3-yl)-amide]5-(3-chloro-2-fluoro-benzylamide) Example 201 by separation by chiral HPLC (Chiralpak ADi 5 µm, 1 mL/min, solvent: TBME/CH$_2$Cl$_2$/EtOH 50:30:20, t$_R$=6.49 min). MS (LC-MS): 457 [M+H]+; t$_R$ (HPLC conditions b): 3.73 min. The absolute stereochemistry has been assigned tentatively based on the test results for the final compounds Example 362 and Example 363 in the biological assay.

Example 364

(2S,3R)-3-Hydroxy-pyrrolidine-1,2-dicarboxylic acid 1-[(1-carbamoyl-1H-indol-3-yl)-amide]2-{[(R)-1-(3-chloro-2-fluoro-phenyl)-ethyl]-amide}

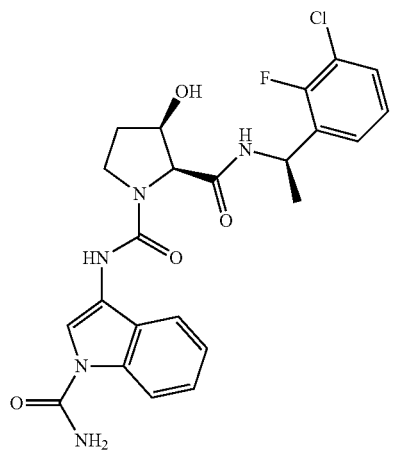 [SMILES: C[C@@H](NC(=O)[C@@H]1[C@H](O)CCN1C(=O)Nc1cn(C(N)=O)c2ccccc12)c1cccc(Cl)c1F]

The title compound was prepared according to the general procedure described in Scheme D5 (CH$_2$Cl$_2$ was used instead of DMF in step A) from a ca. (1:1)-mixture of diastereomers (2S,3R)-3-hydroxy-pyrrolidine-1,2-dicarboxylic acid 1-[(1-carbamoyl-1H-indol-3-yl)-amide]2-{[(R) and (S)-1-(3-chloro-2-fluoro-phenyl)-ethyl]-amide} and purification of the title compound by preparative chromatographic separation on a Chiralpak IA 5 µm stationary phase (column 250×10 mm) using heptane/TBME/MeOH/TFA 50:35:15:0.05 as the eluent (flow: 8 mL/min, detection 254 nm, 25° C.). White solid. MS (LC/MS): 488 [M+H]+; t$_R$ (HPLC conditions b): 3.28 min. t$_R$ (chiral HPLC conditions: Chiralpak IA 5 µm; column 250×4.6 mm; heptane/TBME/MeOH/TFA 50:35:15: 0.05; flow: 2.00 mL/min; detection 254 nm, 25° C.): 10.1 min. The absolute stereochemistry has been assigned tentatively based on the test results for the final compounds Example 364 and Example 365 in the biological assay.

Example 365

(2S,3R)-3-Hydroxy-pyrrolidine-1,2-dicarboxylic acid 1-[(1-carbamoyl-1H-indol-3-yl)-amide]2-{[(S)-1-(3-chloro-2-fluoro-phenyl)-ethyl]-amide}

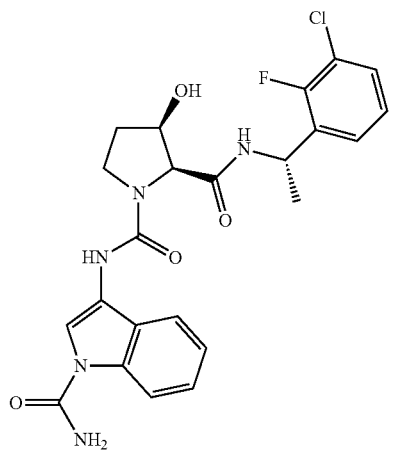 [SMILES: C[C@H](NC(=O)[C@@H]1[C@H](O)CCN1C(=O)Nc1cn(C(N)=O)c2ccccc12)c1cccc(Cl)c1F]

The title compound was prepared according to the general procedure described in Scheme D5 (CH$_2$Cl$_2$ was used instead of DMF in step A) from a ca. (1:1)-mixture of diastereomers (2S,3R)-3-hydroxy-pyrrolidine-1,2-dicarboxylic acid 1-[(1-carbamoyl-1H-indol-3-yl)-amide]2-{[(R) and (S)-1-(3-chloro-2-fluoro-phenyl)-ethyl]-amide} by preparative chromatographic separation on a Chiralpak IA 5 µm stationary phase (column 250×10 mm) using heptane/TBME/MeOH/TFA 50:35:15:0.05 as the eluent (flow: 8 mL/min, detection 254 nm, 25° C.). White solid. MS (LC/MS): 488 [M+H]+; t$_R$ (HPLC conditions b): 3.28 min. t$_R$ (chiral HPLC conditions: Chiralpak IA 5 µm; column 250×4.6 mm; heptane/TBME/MeOH/TFA 50:35:15:0.05; flow: 2.00 mL/min; detection 254 nm, 25° C.): 14.3 min. The absolute stereochemistry has been assigned tentatively based on the test results for the final compounds Example 364 and Example 365 in the biological assay.

Example 366

(S)-Pyrrolidine-1,2-dicarboxylic acid 1-{[1-(2-hydroxy-acetyl)-1H-indol-3-yl]-amide}2-[(3-trifluoromethoxy-phenyl)-amide]

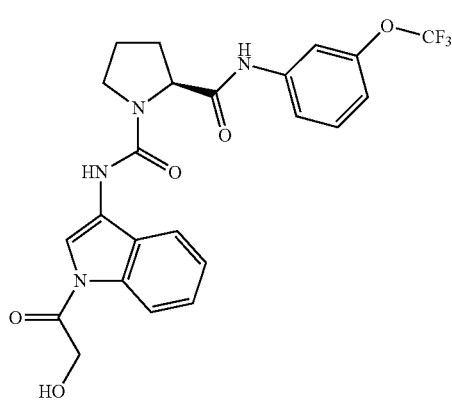 [SMILES: O=C(Nc1cccc(OC(F)(F)F)c1)[C@@H]1CCCN1C(=O)Nc1cn(C(=O)CO)c2ccccc12]

(S)-Pyrrolidine-1,2-dicarboxylic acid 1-{[1-(2-benzyloxy-acetyl)-1H-indol-3-yl]amide}2-[(3-trifluoromethoxy-phenyl)-amide] (55 mg, 0.095 mmol) was dissolved in MeOH (1 mL) and Pd/C 10% (12 mg) was added and the solution was degassed 3 times replacing air by nitrogen and finally nitrogen by hydrogen. The reaction mixture was further stirred under hydrogen atmosphere overnight and the catalyst was removed through a pad of Celite and washed with MeOH. Solvent was concentrated and the crude residue was purified by preparative HPLC (Waters SunFire C18-ODB, 5 μm, 19×50 mm, 20% CH$_3$CN/H$_2$O 2.5 min, 20-100% CH$_3$CN/H$_2$O in 10 min, CH$_3$CN/H$_2$O containing 0.1% HCOOH flow: 20 mL/min) to give after lyophilization of the pure fractions the desired compound. TLC, R$_f$ (CH$_2$Cl$_2$/MeOH 9:1)=0.49; MS (LC/MS): 491.1 [M+H]+, 513.2 [M+Na]+, 489.1 [M−H]−; t$_R$ (HPLC conditions a): 3.47 min.

(S)-Pyrrolidine-1,2-dicarboxylic acid 1-{[1-(2-benzyloxy-acetyl)-1H-indol-3-yl]-amide}2-[(3-trifluoromethoxy-phenyl)-amide]

To a solution of (S)-pyrrolidine-2-carboxylic acid (3-trifluoromethoxy-phenyl)-amide TFA salt (177 mg, 0.457 mmol) and Et$_3$N (191 μl, 1.37 mmol) in dry THF (3.5 mL) was added a solution of 2-benzyloxy-1-(3-isocyanato-indol-1-yl)-ethanone (140 mg, 0.457 mmol, prepared as described in Scheme A5) in dry THF (3.5 mL). The solution was stirred at RT under nitrogen for 15 min until completion. The mixture was poured into water, extracted twice with EtOAc. The combined organic layers were dried over Na$_2$SO$_4$, filtered and concentrated. The crude material was purified by flash column chromatography on silica gel (c-hexane to c-hexane/EtOAc 65:35) to afford the desired compound. TLC, R$_f$ (c-hexane/EtOAc 1:1)=0.3; MS (LC/MS): 581.2 [M+H]+, 579.1 [M−H]−; t$_R$ (HPLC conditions a): 4.18 min.

Example 367

(S)-Pyrrolidine-1,2-dicarboxylic acid 1-[(1-acetyl-6-cyano-1H-indol-3-yl)-amide]2-[(3-trifluoromethoxy-phenyl)-amide]

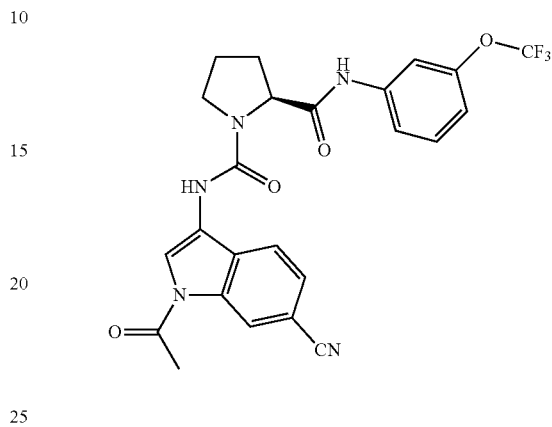

To a solution of (S)-Pyrrolidine-1,2-dicarboxylic acid 1-[(6-cyano-1H-indol-3-yl)-amide]2-[(3-trifluoromethoxy-phenyl)-amide] (60 mg, 0.131 mmol) in dry THF (1 mL) at 0° C. under nitrogen atmosphere was added potassium tert-butoxide (17.7 mg, 0.157 mmol). The suspension was stirred at 0° C. for 5 minutes before addition of acetyl chloride (0.011 mL, 0.157 mmol) and the resulting solution was stirred at RT under nitrogen overnight. The mixture was poured into an aqueous saturated solution of NaHCO$_3$ and extracted twice with CH$_2$Cl$_2$. The combined organic layers were dried over Na$_2$SO$_4$, filtered and concentrated. The crude material was successively purified by flash column chromatography on silica gel (CH$_2$Cl$_2$ to CH$_2$Cl$_2$/MeOH 95:5) and preparative HPLC (Waters Sunfire C18-ODB, 5 um, 19×50 mm, flow: 20 mL/min, gradient: 0-2.5 min 20% CH$_3$CN, 2.5-12.5 min 20 to 100% CH$_3$CN, 12.5-15 min 100% CH$_3$CN, H$_2$O and CH$_3$CN containing 0.1% HCOOH) to give after lyophilization of the purified fractions the desired compound. MS (LC/MS): 500 [M+H]+, 498.1 [M−H]−; t$_R$ (HPLC conditions a): 3.69 min.

(S)-Pyrrolidine-1,2-dicarboxylic acid 1-[(6-cyano-1H-indol-3-yl)-amide]2-[(3-trifluoromethoxy-phenyl)-amide]

A solution of (S)-pyrrolidine-2-carboxylic acid (3-trifluoromethoxy-phenyl)-amide TFA salt (315 mg, 0.81 mmol) in THF (10 mL) was added to a solution of 3-isocyanato-1H-indole-6-carbonitrile (270 mg, prepared as described in Part A, 70% purity as measured by NMR) in toluene (4 mL). Triethylamine (338 μl, 2.43 mmol) was added and the resulting solution was stirred at RT under nitrogen overnight. The mixture was poured into HCl 1N and extracted with EtOAc (×3). The combined organic layers were washed with a saturated aqueous NaHCO$_3$ solution, dried over Na$_2$SO$_4$, filtered and concentrated. The crude material was purified by flash column chromatography on silica gel (c-hexane to c-hexane/EtOAc 1:1) to give the title compound. TLC, R$_f$ (c-hexane/EtOAc 1:1)=0.5; MS (LC-MS): 554.0 [M+H]+, 556.0 [M−H]−; t$_R$ (HPLC conditions a): 3.74 min.

Example 368

2S,4R)-4-Fluoro-pyrrolidine-1,2-dicarboxylic acid 1-[(1-acetyl-6-difluoromethoxy-1H-indol-3-yl)-amide]2-(3-chloro-2-fluoro-benzylamide

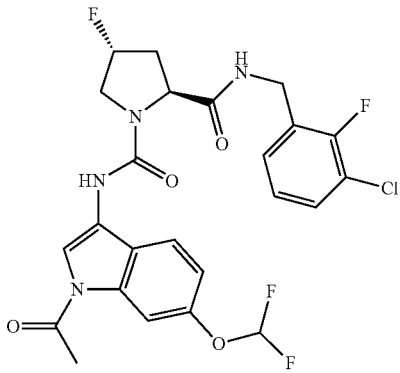 [SMILES: CC(=O)n1cc(NC(=O)N2C[C@H](F)C[C@H]2C(=O)NCc2cccc(Cl)c2F)c2ccc(OC(F)F)cc21]

To a solution of (2S,4R)-4-fluoro-pyrrolidine-1,2-dicarboxylic acid 2-(3-chloro-2-fluoro-benzylamide) 1-[(6-difluoromethoxy-1H-indol-3-yl)-amide] (105 mg, 0.210 mmol) in dry THF (5 mL) was added $Ac_2O$ (1 mL, 10.5 mmol) and DMAP (26 mg, 0.210 mmol). The reaction mixture was stirred at 60° C. for 18 h. The volatiles were evaporated under reduced pressure, and the residue was purified by preparative HPLC (Macherey-Nagel Nucleosil 100-10 C18, 5 µm, 40×250 mm, flow: 40 mL/min, eluent: 5-100% $CH_3CN/H_2O$/ 20 min, 100% $CH_3CN$/2 min, $CH_3CN$ and $H_2O$ containing 0.1% TFA) to afford after lyophilization of purified fractions the title compound as a white solid. MS (LC/MS): 541 [M+H]+, 563 [M+Na]+; $t_R$ (HPLC conditions k): 3.65 min.

(2S,4R)-4-fluoro-pyrrolidine-1,2-dicarboxylic acid 2-(3-chloro-2-fluoro-benzylamide) 1-[(6-difluoromethoxy-1H-indol-3-yl)-amide]

The title compound was prepared according to the general protocol described in Scheme D5. In Step C, 6-difluoromethoxy-3-isocyanato-1H-indole (prepared as described in Part A) was used and after completion of the reaction, the mixture was concentrated and directly purified by preparative HPLC (Waters Sunfire, C18-ODB, 5 µm, 30×100 mm, flow: 40 ml/min, eluent: 5-100% $CH_3CN/H_2O$/20 min, 100% CH3CN/2 min, $CH_3CN$ and $H_2O$ containing 0.1% TFA). White solid. MS (LC/MS): 499 [M+H]+, 521 [M+Na]+; $t_R$ (HPLC conditions k): 3.49 min).

Example 369

(S)-Pyrrolidine-1,2-dicarboxylic acid 1-[(1-carbamoyl-6-hydroxy-1H-indol-3-yl)-amide]2-[(3-trifluoromethoxy-phenyl)-amide]

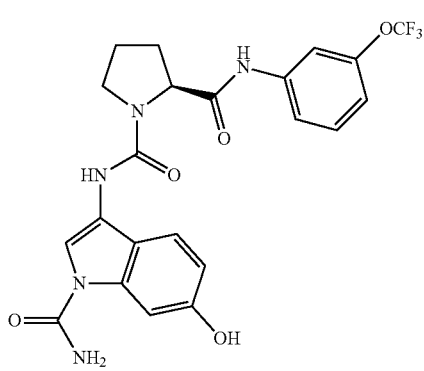 [SMILES: NC(=O)n1cc(NC(=O)N2CCC[C@H]2C(=O)Nc2cccc(OC(F)(F)F)c2)c2ccc(O)cc21]

(S)-Pyrrolidine-1,2-dicarboxylic acid 1-[(6-benzyloxy-1-carbamoyl-1H-indol-3-yl)amide]2-[(3-trifluoromethoxy-phenyl)-amide] Example 313 (75 mg, 0.129 mmol) was dissolved in a mixture of THF/DMF 1-1 (3 mL), Pd/C 10% (20 mg) was added to the solution and the solution was degassed 3 times replacing air by nitrogen and finally nitrogen by hydrogen. The reaction mixture was further stirred under hydrogen atmosphere for 3 h and the catalyst was removed through a pad of Celite and washed with THF. Solvents were concentrated and the resulting oil was poured into water and extracted with EtOAc (×3). The combined organic layers were washed twice with water, dried over $Na_2SO_4$, filtered and concentrated. The crude residue was purified by preparative HPLC (Waters SunFire C18-ODB, 5 µm, 19×50 mm, 20% to 100% $CH_3CN$ in $H_2O$ in 25 min, $CH_3CN/H_2O$ containing 0.1% HCOOH flow: 20 mL/min) to give after lyophilization of the purified fractions the desired compound. TLC, $R_f$(EtOAc)=0.39; MS (LC/MS): 492.1 [M+H]+, 490.1 [M−H]−; $t_R$ (HPLC conditions a): 3.22 min.

Example 370

(S)-Pyrrolidine-1,2-dicarboxylic acid 1-[(1-carbamoyl-5-hydroxy-1H-indol-3-yl)-amide]2-[(3-trifluoromethoxy-phenyl)-amide]

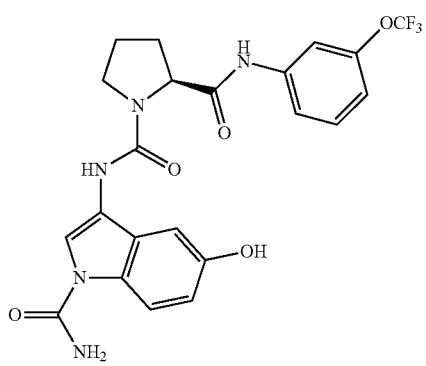 [SMILES: NC(=O)n1cc(NC(=O)N2CCC[C@H]2C(=O)Nc2cccc(OC(F)(F)F)c2)c2cc(O)ccc21]

A mixture of (S)-pyrrolidine-1,2-dicarboxylic acid 1-[(5-allyloxy-1-carbamoyl-1H-indol-3-yl)-amide]2-[(3-trifluoromethoxy-phenyl)-amide] Example 335 (30 mg, 0.056 mmol), palladium acetate (1.4 mg, 2.82 µmol) and triphenylphosphine (1.5 mg, 5.64 µmol) in formic acid (0.7 mL) was heated at 90° C. for 30 min under nitrogen. The mixture was poured into water and extracted twice with EtOAc. The combined organic layers were dried over $Na_2SO_4$, filtered and concentrated. The crude material was purified by flash column chromatography on silica gel (c-hexane/EtOAc 1:1 to EtOAc) to give the desired compound. TLC, $R_f$ (EtOAc)= 0.56; MS (LC/MS): 492 [M+H]+, 514.2 [M+Na]+, 490 [M−H]−, 447.1 [M−$CONH_2$]−; $t_R$ (HPLC conditions a): 3.13 min.

Example 371

1R,3S,5R)-2-Aza-bicyclo[3.1.0]hexane-2,3-dicarboxylic acid 2-[(1-carbamoyl-5-hydroxy-1H-indol-3-yl)-amide]3-(3-chloro-2-fluoro-benzylamide

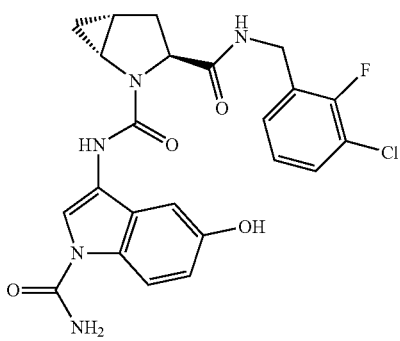 [SMILES: NC(=O)n1cc(NC(=O)N2[C@@H]3C[C@@H]3C[C@H]2C(=O)NCc2cccc(Cl)c2F)c2cc(O)ccc21]

Allyl palladium chloride dimer (4.9 mg, 0.013 mmol) and 2-di-tert-butylphosphino-2'-methylbiphenyl (16.6 mg, 0.053 mmol) were dissolved in DMF (0.4 mL) and the mixture was stirred for 5 min under nitrogen atmosphere. Formic acid (30 μL, 0.772 mmol), triethylamine (107 μL, 0.772 mmol) and (1R,3S,5R)-2-aza-bicyclo[3.1.0]hexane-2,3-dicarboxylic acid 2-[(5-allyloxy-1-carbamoyl-1H-indol-3-yl)-amide]3-(3-chloro-2-fluoro-benzylamide) Example 268 (70 mg, 0.133 mmol) in DMF (1 mL) were added in that order. The mixture was stirred at 10° C. for 1 h, then at RT for 2 days. The mixture was poured into water and extracted twice with EtOAc. The combined organic layers were dried over $Na_2SO_4$, filtered and concentrated. The crude material was purified by preparative HPLC (Waters Sunfire, C18-ODB, 5 μm, 19×50 mm, eluent: 20% to 100% $CH_3CN$ in $H_2O$ in 15 min, $CH_3CN$ and $H_2O$ containing 0.1% HCOOH, flow: 20 mL/min) to give the desired compound after lyophilization of the purified fractions. TLC, $R_f$(EtOAc)=0.4; MS (LC-MS): 486.0 [M+H]+, 441.1 [M−$CONH_2$]−; $t_R$ (HPLC conditions f): 1.65 min.

Example 372

1R,3S,5R)-2-Aza-bicyclo[3.1.0]hexane-2,3-dicarboxylic acid 2-[(1-carbamoyl-5-hydroxy-1H-indol-3-yl)-amide]3-(2-fluoro-benzylamide

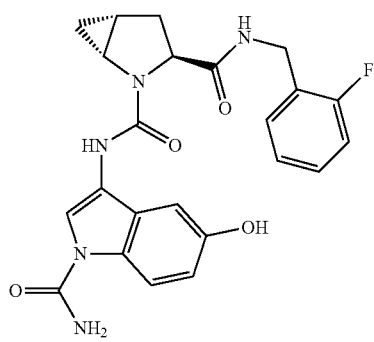 [SMILES: NC(=O)n1cc(NC(=O)N2[C@@H]3C[C@@H]3C[C@H]2C(=O)NCc2ccccc2F)c2cc(O)ccc21]

Allyl palladium chloride dimer (17.8 mg, 0.048 mmol) and 2-di-tert-butylphosphino-2'-methylbiphenyl (60.6 mg, 0.194 mmol) were dissolved in DMF (2 mL) and the mixture was stirred for 5 min. Formic acid (108 μL, 2.81 mmol), triethylamine (391 μL, 2.81 mmol) and (1R,3S,5R)-2-aza-bicyclo[3.1.0]hexane-2,3-dicarboxylic acid 2-[(5-allyloxy-1-carbamoyl-1H-indol-3-yl)-amide]3-(3-chloro-2-fluoro-benzylamide) Example 268 (255 mg, 0.485 mmol) in DMF (3 mL) were added in that order and the resulting solution was stirred at RT overnight under nitrogen. The mixture was poured into water and extracted twice with EtOAc. The combined organic layers were dried over $Na_2SO_4$, filtered and concentrated. The crude residue was purified by flash column chromatography on silica gel (c-hexane 100% to 100% EtOAc to $CH_2Cl_2$/MeOH 90-10) to give a mixture of the desired compound together with the dechlorinated analog. The mixture was purified by preparative HPLC (Interchrom, C18-ODB, 10 μm, 28×250 mm, eluent: 20% to 100% $CH_3CN$ in $H_2O$ in 40 min, $CH_3CN$ and $H_2O$ containing 0.1% HCOOH, flow: 40 mL/min) to give after extraction of the purified fractions with EtOAc (1R,3S,5R)-2-aza-bicyclo[3.1.0]hexane-2,3-dicarboxylic acid 2-[(1-carbamoyl-5-hydroxy-1H-indol-3-yl)-amide]3-(3-chloro-2-fluoro-benzylamide) and (1R,3S,5R)-2-aza-bicyclo[3.1.0]hexane-2,3-dicarboxylic acid 2-[(1-carbamoyl-5-hydroxy-1H-indol-3-yl)-amide]3-(2-fluoro-benzylamide). TLC, $R_f$(EtOAc)=0.3; MS (LC-MS): 452.1 [M+H]+, 474.1 [M+Na]+, 407 [M−$CONH_2$]−; $t_R$ (HPLC conditions f): 1.81 min.

Example 373

1R,3S,5R)-2-Aza-bicyclo[3.1.0]hexane-2,3-dicarboxylic acid 2-[(1-carbamoyl-5-cyanomethoxy-1H-indol-3-yl)-amide]3-(3-chloro-2-fluoro-benzylamide

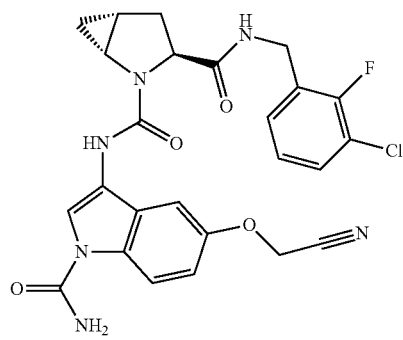 [SMILES: N#CCOc1ccc2c(c1)c(NC(=O)N1[C@@H]3C[C@@H]3C[C@H]1C(=O)NCc1cccc(Cl)c1F)cn2C(N)=O]

To a solution of Example 371 (1R,3S,5R)-2-aza-bicyclo[3.1.0]hexane-2,3-dicarboxylic acid 2-[(1-carbamoyl-5-hydroxy-1H-indol-3-yl)-amide]3-(3-chloro-2-fluoro-benzylamide) (50 mg, 0.103 mmol) in acetone (0.5 mL) were added cesium carbonate (36.9 mg, 0.11 mmol) and bromoacetonitrile (8.13 μL, 0.11 mmol) and the reaction mixture was stirred at RT under nitrogen for 4 h. Acetone was concentrated. The residue was dissolved in water and extracted twice with EtOAc. The combined organic extracts were dried over $Na_2SO_4$, filtered and concentrated. The crude material was purified by prep HPLC (Waters Sunfire, C18-ODB, 5 μm, 19×50 mm, eluent: 20% to 100% ($CH_3CN$/MeOH 1-4)/$H_2O$ in 15 min, ($CH_3CN$/MeOH 1-4) and $H_2O$ containing 0.1% HCOOH, flow: 20 mL/min). TLC, Rf (EtOAc)=0.45; MS (UPLC/MS): 525.4/527.2 [M+H]+, 542.4/544.7 [M+$NH_4$]+, 569.4/571.4 [M+HCOO]−; $t_R$ (HPLC conditions f): 1.89 min.

Example 374

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-acetic acid

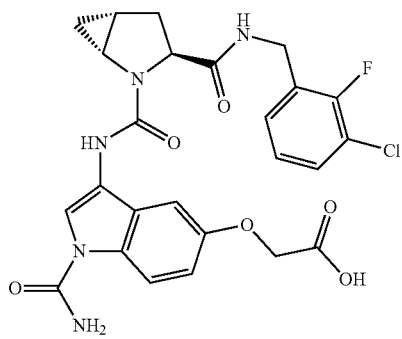 [SMILES: NC(=O)n1cc(NC(=O)N2[C@@H]3C[C@@H]3C[C@H]2C(=O)NCc2cccc(Cl)c2F)c2cc(OCC(=O)O)ccc21]

To a solution of (1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-acetic acid methyl ester Example 133 (85 mg, 0.145 mmol) in THF (1.2 mL) and H$_2$O (120 μL) was added NaOH 1N (290 μL, 0.29 mmol) and the reaction mixture was stirred at RT for 20 min. The crude was directly purified using trimethylaminopropyl cartridge (Mega Bond Elut-SAX, 1 g from Varian) pre-washed with CH$_3$CN (10 mL) and the compound was released with 10 mL of HCl 0.1N in CH$_3$CN. The resulting solution was concentrated and purified by preparative HPLC (Waters Sunfire, C18-ODB, 5 μm, 19×50 mm, eluent: 20% to 100% CH$_3$CN in H$_2$O in 15 min, CH$_3$CN and H$_2$O containing 0.1% HCOOH, flow: 20 mL/min) to give the desired material after lyophilization of the purified fractions. MS (UPLC-MS): 544.3/546.3 [M+H]+, 566.4/568.3 [M+Na]+, 542.3/544.4 [M−H]−; t$_R$ (HPLC conditions f): 1.72 min.

Example 375

(1-Carbamoyl-3-{[(2S,4R)-2-(3-chloro-2-fluoro-benzylcarbamoyl)-4-fluoro-4-methyl-pyrrolidine-1-carbonyl]-amino}-1H-indol-5-yloxy)-acetic acid

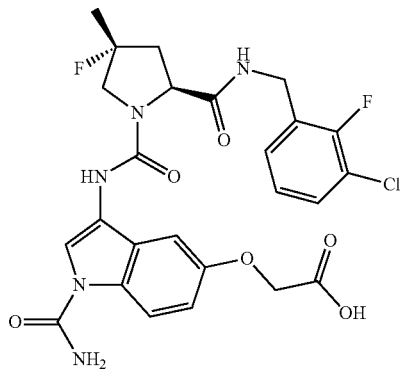 [SMILES: C[C@@]1(F)C[C@@H](C(=O)NCc2cccc(Cl)c2F)N(C(=O)Nc2cn(C(N)=O)c3ccc(OCC(=O)O)cc23)C1]

The title compound was prepared according to the protocol described for the preparation of Example 374 from (1-carbamoyl-3-{[(2S,4R)-2-(3-chloro-2-fluoro-benzylcarbam- oyl)-4-fluoro-4-methylpyrrolidine-1-carbonyl]-amino}-1H-indol-5-yloxy)-acetic acid methyl ester Example 318. MS (UPLC): 564.2 [M+H]+, 562.3 [M−H]−; t$_R$ (HPLC conditions f): 1.72 min.

Example 376

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yloxy)-acetic acid

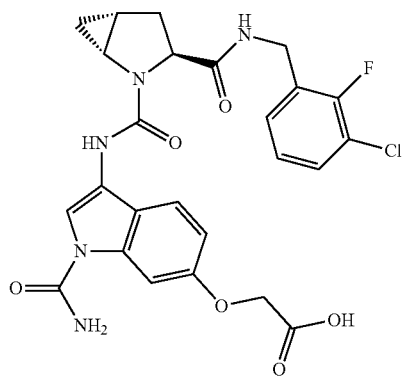 [SMILES: NC(=O)n1cc(NC(=O)N2[C@@H]3C[C@@H]3C[C@H]2C(=O)NCc2cccc(Cl)c2F)c2ccc(OCC(=O)O)cc21]

The title compound was prepared according to the protocol described for the preparation of Example 374 from (1-carbamoyl-3-{[(1R,3S,5R)-3-(3-chloro-2-fluoro-benzylcarbamoyl)-2-aza bicyclo[3.1.0]hexane-2-carbonyl]amino}-1H-indol-6-yloxy)-acetic acid methyl ester Example 394. MS (UPLC): 544.3/546.3 [M+H]+, 542.3/544.3 [M−H]−; t$_R$ (HPLC conditions f): 1.78 min.

Example 377

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yl)-acetic acid

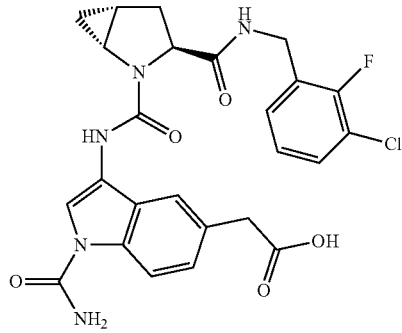 [SMILES: NC(=O)n1cc(NC(=O)N2[C@@H]3C[C@@H]3C[C@H]2C(=O)NCc2cccc(Cl)c2F)c2cc(CC(=O)O)ccc21]

The title compound was prepared according to the protocol described for the preparation of Example 374 from (1-carbamoyl-3-{[(1R,3S,5R)-3-(3-chloro-2-fluoro-benzylcarbamoyl)-2-3 Example 306. TLC, R$_f$ (EtOAc)=0.2; MS (UPLC): 528.3/530.2 [M+H]+, 526.3/528.6 [M−H]−, 483.3/485.3 [M−CONH₂]−; $t_R$ (HPLC conditions f): 1.74 min.

Example 378

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid

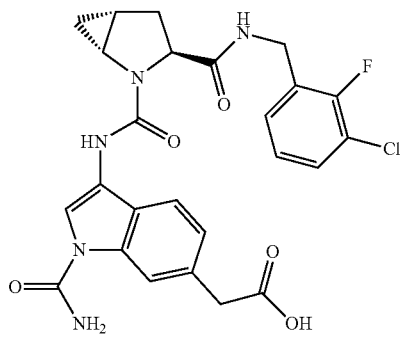 [SMILES: NC(=O)n1cc(NC(=O)N2[C@@H]3C[C@@H]3C[C@H]2C(=O)NCc2cccc(Cl)c2F)c2ccc(CC(=O)O)cc21]

to a solution of (1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid tert-butyl ester Example 127 (30 mg, 0.051 mmol) in CH₂Cl₂ (0.5 mL) was added TFA (157 µL, 2.05 mmol) and the mixture was stirred at RT for 1 h. Then concentrated and the crude residue was taken up in Et₂O and filtered-off to give the desired material. MS (UPLC): 528.2/530.3 [M+H]+, 1055.6/1057.2 [2M+H]+, 483.1/485.1 [M−CONH₂]−, 1053.6/1055.6 [2M−H]−; $t_R$ (HPLC conditions f): 1.75 min.

Example 379

1R,3S,5R)-2-Aza-bicyclo[3.1.0]hexane-2,3-dicarboxylic acid 2-{[1-carbamoyl-5-(2-hydroxy-ethoxy)-1H-indol-3-yl]-amide}3-(3-chloro-2-fluoro-benzylamide

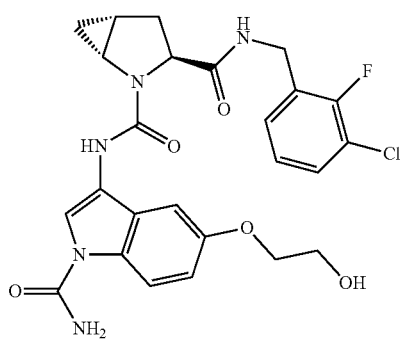 [SMILES: NC(=O)n1cc(NC(=O)N2[C@@H]3C[C@@H]3C[C@H]2C(=O)NCc2cccc(Cl)c2F)c2cc(OCCO)ccc21]

To a solution of (1-carbamoyl-3-{[(1R,3S,5R)-3-(3-chloro-2-fluoro-benzylcarbamoyl)-2-aza bicyclo[3.1.0]hexane-2-carbonyl]amino}-1H-indol-5-yloxy)-acetic acid methyl ester Example 133 (344 mg, 0.573 mmol) in THF (3 mL) under nitrogen was added LiBH₄ 2M in THF (573 µL, 1.15 mmol). The resulting solution was stirred at RT under nitrogen for 30 min, then slowly poured into an aqueous saturated solution of NaHCO₃ and extracted twice with EtOAc. The combined organic layers were dried over Na₂SO₄, filtered and concentrated. The crude residue was taken up in CH₂Cl₂ and filtered-off then purified by preparative HPLC (Waters Sunfire, C18-ODB, 5 µm, 19×50 mm, eluent: 20% to 100% CH₃CN in H₂O in 15 min, CH₃CN and H₂O containing 0.1% HCOOH, flow: 20 mL/min) to give the desired material after lyophilization of the purified fractions. $R_f$, TLC (EtOAc)=0.15; MS (LC-MS): 530/532 [M+H]+, 552.1/554.1 [M+Na]+, 528.1/530.1 [M−H]−, 485/487 [M−CONH₂]−; $t_R$ (HPLC conditions f): 1.64 min.

Example 380

S)-Thiazolidine-2,3-dicarboxylic acid 3-{[1-carbamoyl-5-(2-hydroxy-ethoxy)-1H-indol-3-yl]-amide}2-(3-chloro-2-fluoro-benzylamide

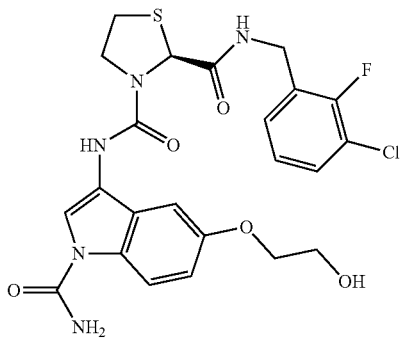 [SMILES: NC(=O)n1cc(NC(=O)N2CCS[C@H]2C(=O)NCc2cccc(Cl)c2F)c2cc(OCCO)ccc21]

The title compound was prepared according to the protocol described for the preparation of Example 379 from (1-carbamoyl-3-{[(S)-2-(3-chloro-2-fluoro-benzylcarbamoyl)-thiazolidine-3-carbonyl]-amino}-1H-indol-5-yloxy)-acetic acid methyl ester (prepared using similar protocols as for Example 133). TLC, $R_f$(EtOAc)=0.45; MS (UPLC): 564.2/566.2 [M+H]+, 581.2/583.2 [M+NH₄]+, 562.3/564.3 [M−H]−, 608.4/610.4 [M+HCOO]−; $t_R$ (HPLC conditions f): 1.82 min.

Example 381

(1R,3S,5R)-2-Aza-bicyclo[3.1.0]hexane-2,3-dicarboxylic acid 2-{[1-carbamoyl-5-(2-hydroxy-ethoxy)-1H-indol-3-yl]-amide}3-[(3-trifluoromethoxy-phenyl)-amide]

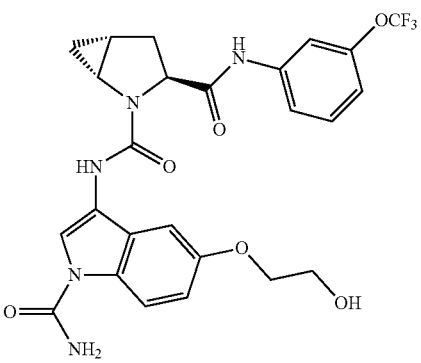 [SMILES: NC(=O)n1cc(NC(=O)N2[C@@H]3C[C@@H]3C[C@H]2C(=O)Nc2cccc(OC(F)(F)F)c2)c2cc(OCCO)ccc21]

The title compound was prepared according to the protocol described for the preparation of Example 379 from (1-carbamoyl-3-{[(1R,3S,5R)-3-(3-trifluoromethoxy-phenylcarbamoyl)-2-aza-bicyclo[3.1.0]hexane-2-carbonyl]amino}-

1H-indol-5-yloxy)-acetic acid methyl ester (prepared using similar protocols as for Example 133). MS (UPLC): 548.3 [M+H]+, 546.3 [M−H]−, 592.3 [M+HCOO]−; $t_R$ (HPLC conditions f): 1.80 min.

Example 382

1S*,2S*,5R*)-3-Aza-bicyclo[3.1.0]hexane-2,3-dicarboxylic acid 3-{[1-carbamoyl-5-(2-hydroxyethoxy)-1H-indol-3-yl]-amide}2-(3-chloro-2-fluoro-benzylamide

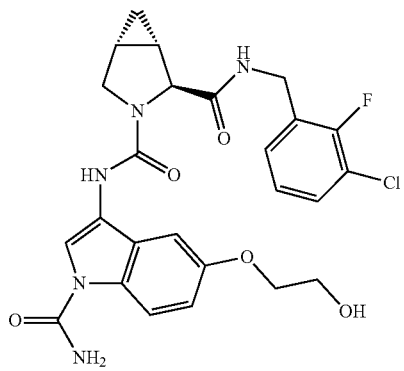 [SMILES: NC(=O)n1cc(NC(=O)N2C[C@@H]3C[C@@H]3[C@H]2C(=O)NCc2cccc(Cl)c2F)c2cc(OCCO)ccc21]

The title compound was prepared according to the protocol described for the preparation of Example 379 from (1-carbamoyl-3-{[(1S*,2S*,5R*)-2-(3-chloro-2-fluoro-benzylcarbamoyl)-3-aza-bicyclo[3.1.0]hexane-3-carbonyl]-amino}-1H-indol-5-yloxy)-acetic acid methyl ester ester (prepared using similar protocols as for Example 133). MS (UPLC): 530.3/532.2 [M+H]+, 528.2/530.4 [M−H]−, 574.3/576.3 [M+HCOO]−; $t_R$ (HPLC conditions f): 1.58 min.

Example 383

2S,4R)-4-Fluoro-4-methyl-pyrrolidine-1,2-dicarboxylic acid 1-{[1-carbamoyl-5-(2-hydroxy-ethoxy)-1H-indol-3-yl]-amide}2-(3-chloro-2-fluoro-benzylamide

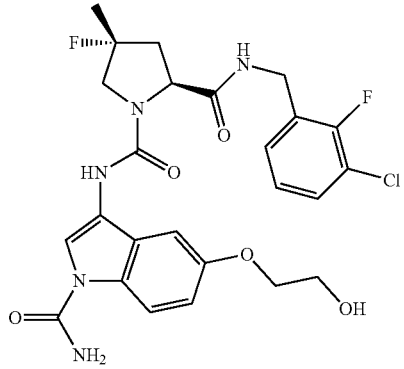 [SMILES: C[C@@]1(F)C[C@@H](C(=O)NCc2cccc(Cl)c2F)N(C(=O)Nc2cn(C(N)=O)c3ccc(OCCO)cc23)C1]

The title compound was prepared according to the protocol described for the preparation of Example 379 from (1-carbamoyl-3-{[(2S,4R)-2-(3-chloro-2-fluoro-benzylcarbamoyl)-4-fluoro-4-methyl-pyrrolidine-1-carbonyl]amino}-1H-indol-5-yloxy)-acetic acid methyl ester Example 318. TLC, $R_f$(EtOAc)=0.30; MS (UPLC): 550.3/552.5 [M+H]+, 505.7/507.1 [M−CONH$_2$]−; $t_R$ (HPLC conditions f): 1.72 min.

Example 384

1R,3S,5R)-2-Aza-bicyclo[3.1.0]hexane-2,3-dicarboxylic acid 2-{[1-carbamoyl-6-(2-hydroxy-ethyl)-1H-indol-3-yl]-amide}3-(3-chloro-2-fluoro-benzylamide

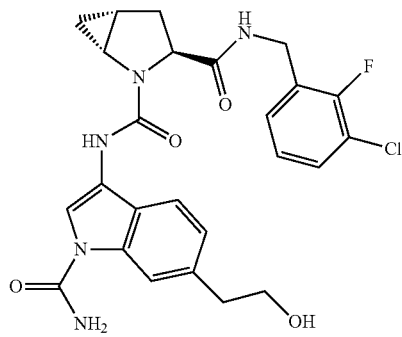 [SMILES: NC(=O)n1cc(NC(=O)N2[C@@H]3C[C@@H]3C[C@H]2C(=O)NCc2cccc(Cl)c2F)c2ccc(CCO)cc21]

The title compound was prepared according to the protocol described for the preparation of Example 379 from (1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yl)-acetic acid ethyl ester Example 315. MS (UPLC): 514.3/516.3 [M+H]+, 512.3/514.3 [M−H]−, 558.3/560.2 [M+HCOO]−; $t_R$ (HPLC conditions f): 1.75 min.

Example 385

1R,3S,5R)-2-Aza-bicyclo[3.1.0]hexane-2,3-dicarboxylic acid 2-{[1-carbamoyl-5-(2-hydroxy-ethyl)-1H-indol-3-yl]-amide}3-(3-chloro-2-fluoro-benzylamide

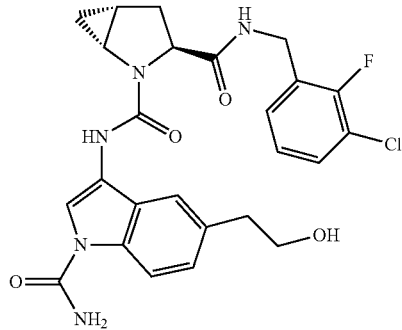 [SMILES: NC(=O)n1cc(NC(=O)N2[C@@H]3C[C@@H]3C[C@H]2C(=O)NCc2cccc(Cl)c2F)c2cc(CCO)ccc21]

The title compound was prepared according to the protocol described for the preparation of Example 379 from (1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yl)-acetic acid ethyl ester Example 306. TLC, $R_f$(EtOAc)=0.2; MS (UPLC): 514.2/516.3 [M+H]+, 512.3/

514.1 [M–H]–, 558.3/560.2 [M+HCOO]–, 469.2/471.4 [M–CONH₂]–; t_R (HPLC conditions f): 1.72 min.

Example 386

1R,3S,5R)-2-Aza-bicyclo[3.1.0]hexane-2,3-dicarboxylic acid 2-{[1-carbamoyl-5-(2-hydroxy-2-methyl-propoxy)-1H-indol-3-yl]-amide}3-(3-chloro-2-fluoro-benzylamide

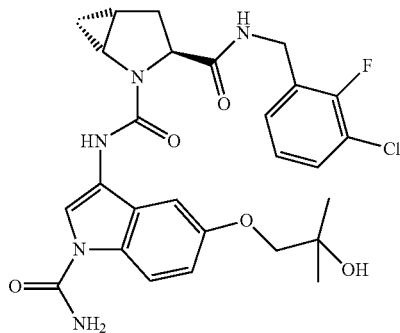

To a solution of (1-carbamoyl-3-{[(1R,3S,5R)-3-(3-chloro-2-fluoro-benzylcarbamoyl)-2-aza bicyclo[3.1.0]hexane-2-carbonyl]amino}-1H-indol-5-yloxy)-acetic acid methyl ester Example 133 (50 mg, 0.083 mmol) in dry THF (0.5 mL) at 0° C. was added methylmagnesium bromide (3M in Et₂O, 61 µL, 0.183 mmol). The mixture was stirred under nitrogen at 0° C. for 10 min, then allowed to reach RT and further stirred for 24 h. Water was added (2 mL) and the precipitate was filtered-out. The filtrate was extracted twice with EtOAc. The combined organic layers were dried over Na₂SO₄, filtered and concentrated. The crude residue was purified by preparative HPLC (Waters Sunfire, C18-ODB, 5 µm, 19×50 mm, eluent: 20% to 100% CH₃CN in H₂O in 15 min, CH₃CN and H₂O containing 0.1% HCOOH, flow: 20 mL/min) to give the desired material after lyophilization of the purified fractions. TLC, R_f (EtOAc)=0.25; MS (LC-MS): 558/560 [M+H]+, 513.1/515.2 [M–CONH₂]–; t_R (HPLC conditions f): 1.84 min.

Example 387

1R,3S,5R)-2-Aza-bicyclo[3.1.0]hexane-2,3-dicarboxylic acid 2-{[1-carbamoyl-5-(2-dimethylamino-ethoxy)-1H-indol-3-yl]-amide}3-(3-chloro-2-fluoro-benzylamide

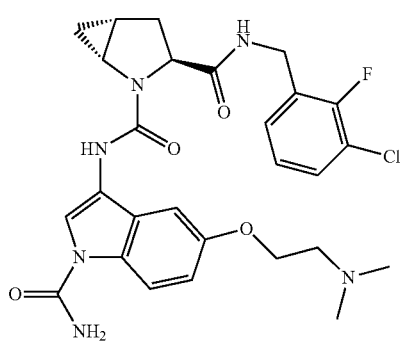 [SMILES: CN(C)CCOc1ccc2c(c1)c(NC(=O)N1[C@@H]3C[C@@H]3C[C@H]1C(=O)NCc1cccc(Cl)c1F)cn2C(N)=O]

A solution of methanesulfonic acid 2-(1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-ethyl ester (35 mg, 0.054 mmol) and dimethylamine 5.6 M in EtOH (0.5 mL) was heated at 70° C. for 4 h in a sealed tube. The reaction was poured into an aqueous saturated solution of NaHCO₃ and extracted twice with EtOAc. The combined organic layers were dried over Na₂SO₄, filtered and concentrated. The crude residue was purified by preparative HPLC (Nucleosil, C18-HD, 5 µm, 21×50 mm, eluent: 20% to 100% CH3CN in H₂O in 15 min, CH₃CN and H₂O containing 0.1% HCOOH, flow: 20 mL/min) to give after lyophilization of the purified fractions the desired material as a formic acid salt. MS (UPLC): 557.3/559.3 [M+H]+, 555.6/558.4 [M–H]–, 512.3/514.5 [M–CONH₂]–; t_R (HPLC conditions f): 1.47 min.

Methanesulfonic acid 2-(1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-ethyl ester To a solution of (1R,3S,5R)-2-aza-bicyclo[3.1.0]hexane-2,3-dicarboxylic acid 2-{[1-carbamoyl-5-(2-hydroxy-ethoxy)-1H-indol-3-yl]-amide}3-(3-chloro-2-fluoro-benzylamide) Example 379 (50 mg, 0.09 mmol) and Et₃N (62 µL, 0.448 mmol) in CH₂Cl₂ (1 mL) at 0° C. under nitrogen atmosphere, was added methanesulfonyl chloride (35 µL, 0.448 mmol). The resulting solution was stirred at RT overnight. Et₃N (31 µL, 0.224 mmol) and methanesulfonyl chloride (17 µL, 0.224 mmol) were added and the mixture was further stirred at RT for 1.5 h to complete the reaction. The reaction was poured into a saturated aqueous solution of NaHCO₃, extracted twice with CH₂Cl₂, dried over Na₂SO₄, filtered and concentrated. The crude residue was purified by flash column chromatography on silica gel (c-hexane/EtOAc 1-1 to 100% EtOAc) to give the desired material. TLC, R_f (EtOAc)=0.25; MS (UPLC): 608.5/610.2 [M+H]+, 563.4 [M–CONH₂]–, 606.4/608.0 [M–H]–; t_R (HPLC conditions f): 1.88 min.

Example 388

1R,3S,5R)-2-Aza-bicyclo[3.1.0]hexane-2,3-dicarboxylic acid 2-{[1-carbamoyl-5-(2-pyrrolidin-1-yl-ethoxy)-1H-indol-3-yl]-amide}3-(3-chloro-2-fluoro-benzylamide

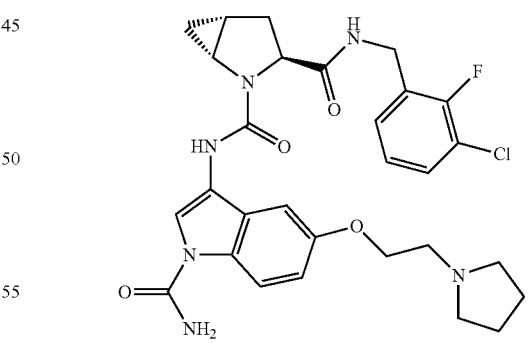

The title compound was prepared as a formic acid salt from methanesulfonic acid 2-(1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-ethyl ester and pyrrolidine according to the procedure described for the preparation of Example 387: (1R,3S,5R)-2-Aza-bicyclo[3.1.0]hexane-2,3-dicarboxylic acid 2-{[1-carbamoyl-5-(2-dimethylamino-ethoxy)-1H-indol-3-yl]-amide}3-(3-chloro-2-fluoro-benzylamide). TLC, R_f (CH₂Cl₂/MeOH 8-2)=0.3;

Example 389

1R,3S,5R)-2-Aza-bicyclo[3.1.0]hexane-2,3-dicarboxylic acid 2-{[1-carbamoyl-5-(2-imidazol-1-yl-ethoxy)-1H-indol-3-yl]-amide}3-(3-chloro-2-fluoro-benzylamide

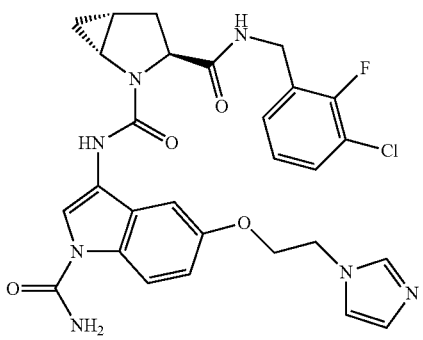 [SMILES: NC(=O)n1cc(NC(=O)N2[C@@H]3C[C@@H]3C[C@H]2C(=O)NCc2cccc(Cl)c2F)c2cc(OCCn3ccnc3)ccc21]

The title compound was prepared from methanesulfonic acid 2-(1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-5-yloxy)-ethyl ester and imidazole according to the procedure described for the preparation of Example 387: (1R,3S,5R)-2-Aza-bicyclo[3.1.0]hexane-2,3-dicarboxylic acid 2-{[1-carbamoyl-5-(2-dimethylamino-ethoxy)-1H-indol-3-yl]-amide}3-(3-chloro-2-fluoro-benzylamide). TLC, $R_f$(CH$_2$Cl$_2$/MeOH 8-2)=0.60; MS (UPLC/MS): 580.5/582.5 [M+H]+, 578.5/580.7 [M−H]−, 624.5/626.5 [M+HCOO]−; $t_R$ (HPLC conditions f): 1.49 min.

Example 390

(1-Carbamoyl-3-{[(1R,3S,5R)-3-(2-fluoro-benzyl-carbamoyl)-2-aza-bicyclo[3.1.0]hexane-2-carbonyl]-amino}-1H-indol-5-yloxy)-acetic acid tert-butyl ester

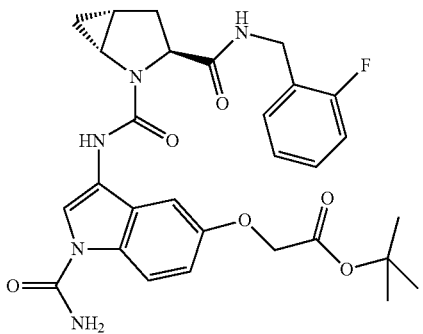 [SMILES: CC(C)(C)OC(=O)COc1ccc2c(c1)c(NC(=O)N1[C@@H]3C[C@@H]3C[C@H]1C(=O)NCc1ccccc1F)cn2C(N)=O]

To (1R,3S,5R)-2-Aza-bicyclo[3.1.0]hexane-2,3-dicarboxylic acid 2-[(1-carbamoyl-5-hydroxy-1H-indol-3-yl)-amide]3-(2-fluoro-benzylamide) Example 372 (38 mg, 0.084 mmol) in acetone (0.45 mL) was added cesium carbonate (30.2 mg, 0.093 mmol) and tert-butyl bromoacetate (14 μL, 0.093 mmol), and the resulting suspension was stirred at RT under nitrogen overnight. Acetone was concentrated and to the residue water was added and the mixture was extracted twice with EtOAc. The combined organic layers were dried (Na$_2$SO$_4$), filtered and concentrated. The crude residue was purified by preparative HPLC (Waters Sunfire, C18-ODB, 5 μm, 19×50 mm, eluent: 20% to 100% CH$_3$CN in H$_2$O in 15 min, CH$_3$CN and H$_2$O containing 0.1% HCOOH, flow: 20 mL/min) to give the desired material after lyophilization of the purified fractions. MS (LC-MS): 588.3 [M+Na]+, 510.1 [MH−tBu]+, 521.2 [M−CONH$_2$]−; $t_R$ (HPLC conditions f): 2.04 min.

Example 391

(1-Carbamoyl-3-{[(1R,3S,5R)-3-(2-fluoro-benzyl-carbamoyl)-2-aza-bicyclo[3.1.0]hexane-2-carbonyl]-amino}-1H-indol-5-yloxy)-acetic acid

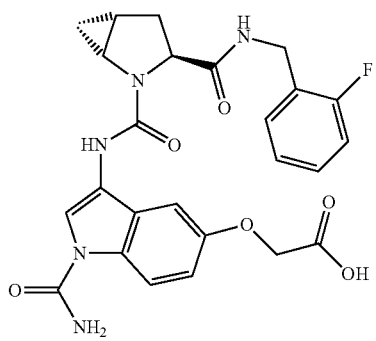

To (1-carbamoyl-3-{[(1R,3S,5R)-3-(2-fluoro-benzylcarbamoyl)-2-aza-bicyclo[3.1.0]hexane-2-carbonyl]-amino}-1H-indol-5-yloxy)-acetic acid tert-butyl ester Example 390 (18 mg, 0.032 mmol) in CH$_2$Cl$_2$ (0.5 mL) was added TFA (97 μL, 1.27 mmol) and the mixture was stirred at RT overnight. Then concentrated, taken up in CH$_2$Cl$_2$ and filtered-off to give the desired material which was further dried under high vacuum. MS (LC-MS): 510.1 [M+H]+, 532.2 [M+Na]+, 508.1 [M−H]−, 465.1 [M−CONH$_2$]−; $t_R$ (HPLC conditions f): 1.52 min.

Example 392

1R,3S,5R)-2-Aza-bicyclo[3.1.0]hexane-2,3-dicarboxylic acid 2-[(1-carbamoyl-6-hydroxy-1H-indol-3-yl)-amide]3-(3-chloro-2-fluoro-benzylamide

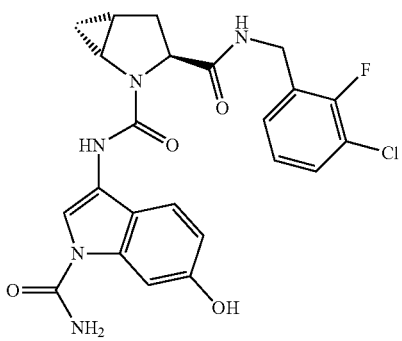

The title compound was prepared from (1R,3S,5R)-2-aza-bicyclo[3.1.0]hexane-2,3-dicarboxylic acid 2-[(6-allyloxy-1-carbamoyl-1H-indol-3-yl)-amide]-3-(3-chloro-2-fluoro-benzylamide) according to the procedure described for the preparation of (1R,3S,5R)-2-aza-bicyclo[3.1.0]hexane-2,3-dicarboxylic acid 2-[(1-carbamoyl-5-hydroxy-1H-indol-3- yl)-amide]3-(3-chloro-2-fluoro-benzylamide) Example 371. MS (LC-MS): 486.0 [M+H]+; $t_R$ (HPLC conditions b): 3.39 min.

Example 393

2S,4R)-4-Fluoro-pyrrolidine-1,2-dicarboxylic acid 1-[(1-carbamoyl-6-hydroxy-1H-indol-3-yl)-amide]2-(3-chloro-2-fluoro-benzylamide

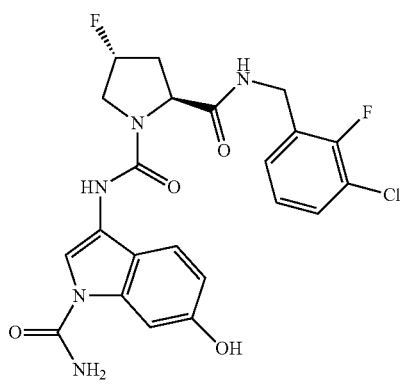 [SMILES: NC(=O)n1cc(NC(=O)N2C[C@H](F)C[C@H]2C(=O)NCc2cccc(Cl)c2F)c2ccc(O)cc21]

The title compound was prepared from (2S,4R)-4-fluoro-pyrrolidine-1,2-dicarboxylic acid 1-[(6-allyloxy-1-carbamoyl-1H-indol-3-yl)-amide]2-(3-chloro-2-fluoro-benzylamide) according to the procedure described for the preparation of (1R,3S,5R)-2-aza-bicyclo[3.1.0]hexane-2,3-dicarboxylic acid 2-[(1-carbamoyl-5-hydroxy-1H-indol-3-yl)amide]3-(3-chloro-2-fluoro-benzylamide) Example 371. MS (LC-MS): 492 [M+H]+; $t_R$ (HPLC conditions b): 3.12 min.

Example 394

(1-Carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yloxy)-acetic acid methyl ester

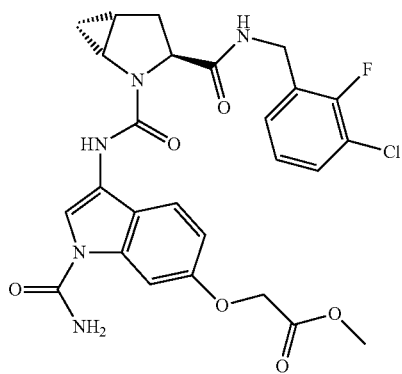

To (1R,3S,5R)-2-aza-bicyclo[3.1.0]hexane-2,3-dicarboxylic acid 2-[(1-carbamoyl-6-hydroxy-1H-indol-3-yl)-amide]3-(3-chloro-2-fluoro-benzylamide) Example 392 (70 mg, 0.144 mmol) in acetone (720 µL) were added $Cs_2CO_3$ (56.3 mg, 0.173 mmol) and methyl bromoacetate (16.4 µL, 0.173 mmol) and the reaction mixture was stirred at 23° C. overnight. 0.5 eq of methyl bromoacetate and 0.5 eq of $Cs_2CO_3$ were added and the reaction mixture was stirred at 23° C. for 4 hr to complete the reaction. The crude mixture was poured in water and extracted with EtOAc (×2). The combined organic layers were dried ($Na_2SO_4$), filtered and evaporated to dryness. The crude material was purified by preparative HPLC (Waters SunFire C180 DB, 5 µm, 30×100, eluent: 20% $CH_3CN$/80% $H_2O$ to 100% $CH_3CN$ in 20 min, $CH_3CN$ and $H_2O$ containing 0.1% of TFA, flow 40 mL/min) to give the desired material after lyophilization of the purified fractions. MS (LC-MS): 558 [M+H]+; $t_R$ (HPLC conditions b): 3.84 min.

Example 395

1R,3S,5R)-2-Aza-bicyclo[3.1.0]hexane-2,3-dicarboxylic acid 2-{[1-carbamoyl-6-(2-hydroxy-ethoxy)-1H-indol-3-yl]-amide}3-(3-chloro-2-fluoro-benzylamide

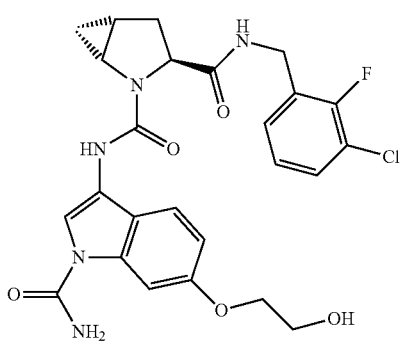

The title compound was prepared from (1-carbamoyl-3-{[(1R,3S,5R)-3-(3-chloro-2-fluoro-benzylcarbamoyl)-2-aza-bicyclo[3.1.0]hexane-2-carbonyl]-amino}-1H-indol-6-yloxy)-acetic acid methyl ester Example 394 according to the procedure described for the preparation of (1R,3S,5R)-2-aza-bicyclo[3.1.0]hexane-2,3-dicarboxylic acid 2-{[1-carbamoyl-5-(2-hydroxy-ethoxy)-1H-indol-3-yl]-amide}3-(3-chloro-2-fluoro-benzylamide) Example 379. TLC, Rf (EtOAc)=0.12; MS (UPLC): 530.3/532.3 [M+H]+, 528.2/530.5 [M−H]−, 574.2/576.4 [M+HCOO]−; $t_R$ (HPLC conditions f): 1.71 min.

Example 396

(2S,4S)-4-Amino-pyrrolidine-1,2-dicarboxylic acid 1-[(1-carbamoyl-1H-indol-3-yl)-amide]2-[(3-trifluoromethoxy-phenyl)-amide]

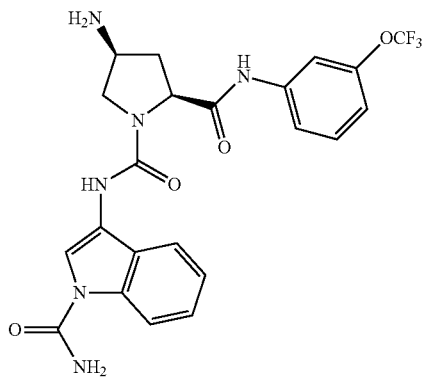 [SMILES: NC(=O)n1cc(NC(=O)N2C[C@@H](N)C[C@H]2C(=O)Nc2cccc(OC(F)(F)F)c2)c2ccccc21]

(2S,4S)-4-N-fmoc-Amino-pyrrolidine-1,2-dicarboxylic acid 1-[(1-carbamoyl-1H-indol-3-yl)-amide]2-[(3-trifluoromethoxy-phenyl)-amide] (380 mg, 0.533 mmol) was dissolved in a solution of piperidine 20% in DMF (2 mL). The mixture was stirred at RT for 1 h and directly purified by preparative HPLC (Interchrom C18-ODB, 10 μm, 28×250 mm, 5% CH₃CN in H₂O 2.5 min, then 5% to 100% CH₃CN in H₂O in 32.5 min, CH₃CN and H₂O containing 0.1% HCOOH; flow: 40 mL/min). To the purified HPLC fractions was added NaOH 1N and the compound was extracted with EtOAc (×3). The combined organic extracts were dried over Na₂SO₄, filtered and concentrated and this material was purified again by preparative HPLC (Water SunFire C18-ODB, 5 μm, 19×50 mm, eluent: 5% to 60% CH₃CN in H₂O in 18 min, CH₃CN and H₂O containing 0.1% HCOOH; flow: 20 mL/min) to give after lyophilization of the purified fractions the desired compound as a formate salt. MS (LC-MS): 491.2 [M+H]+, 489.1 [M−H]−.

(2S,4S)-4-N-fmoc-Amino-pyrrolidine-1,2-dicarboxylic acid 1-[(1-carbamoyl-1H-indol-3-yl)-amide]2-[(3-trifluoromethoxy-phenyl)-amide]

The title compound was prepared as described in Scheme D5 from (4S)-4-N-Fmoc-amino-1-Boc-L-proline. TLC, R$_f$ (CH₂Cl₂/MeOH 9:1)=0.45; t$_R$ (HPLC conditions a): 4.20 min.

Example 397

2S,3S,4R)-4-Amino-3-methoxy-pyrrolidine-1,2-dicarboxylicacid 1-[(1-carbamoyl-1H-indol-3-yl)-amide]2-(3-chloro-2-fluoro-benzylamide

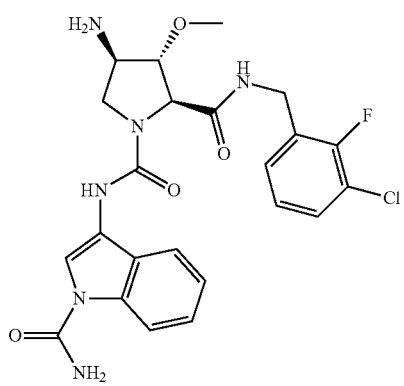 [SMILES: CO[C@H]1[C@H](N)CN(C(=O)Nc2cn(C(N)=O)c3ccccc23)[C@@H]1C(=O)NCc1cccc(Cl)c1F]

The title compound was prepared according to Scheme D5 (steps B and C) from (2S,3S,4R)-2-(3-chloro-2-fluoro-benzylcarbamoyl)-4-(9H-fluoren-9-ylmethoxycarbonylamino)-3-methoxy-pyrrolidine-1-carboxylic acid tert-butyl ester (described in Scheme B21) followed by Fmoc deprotection using the same protocol as described for Example 396. MS (UPLC-MS): 547 [M+H]+; t$_R$ (HPLC conditions f): 1.50 min; ¹⁹F NMR (100 MHz, DMSO-d₆) δ (ppm): −120.

Example 398

(2S,4S)-4-Amino-pyrrolidine-1,2-dicarboxylic acid 1-[(6-benzyloxy-1-carbamoyl-1H-indol-3-yl)-amide] 2-[(3-trifluoromethoxy-phenyl)-amide]

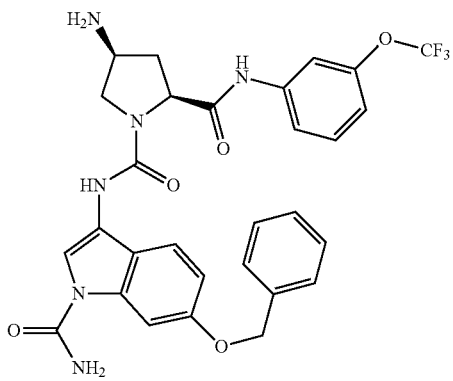 [SMILES: NC(=O)n1cc(NC(=O)N2C[C@@H](N)C[C@H]2C(=O)Nc2cccc(OC(F)(F)F)c2)c2ccc(OCc3ccccc3)cc21]

The title compound was prepared as described in Scheme D5 using (4S)-4-N-Fmoc-amino-1-Boc-L-proline in step A and 6-benzyloxy-3-isocyanato-indole-1-carboxylic acid amide (prepared as described in Part A4) in step C, followed by Fmoc deprotection as described in Scheme D2 step B. MS (LC/MS): 597.1 [M+H]+, 595.2 [M−H]; t$_R$ (HPLC conditions a): 3.16 min.

Example 399

S)-piperazine-1,2-dicarboxylic acid 1-[(1-carbamoyl-1H-indol-3-yl)-amide]2-(3-chloro-benzylamide

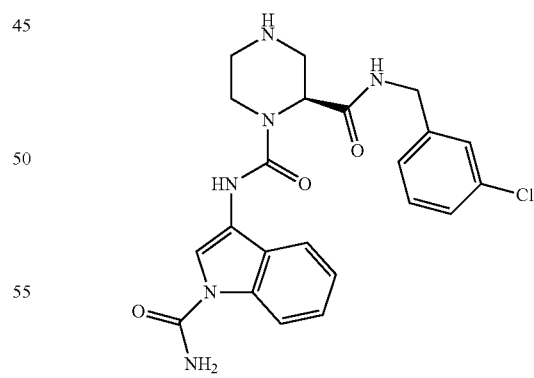

The title compound as a formate salt was prepared as described in Scheme D5 using (S)-1-N-Boc-4-N-Fmoc-piperazine-2-carboxylic acid and 1 equivalent of 3-chlorobenzylamine in step A followed by Fmoc deprotection as described in Scheme D2 step B. MS (LC/MS): 455.2/457.2 [M+H]+, 410/412 [M−CONH₂]−; t$_R$ (HPLC conditions a): 2.58 min.

Example 400

(S)-Pyrrolidine-1,2-dicarboxylic acid 2-[(4'-aminomethyl-biphenyl-3-yl)-amide]1-[(1-carbamoyl-1H-indol-3-yl)-amide]

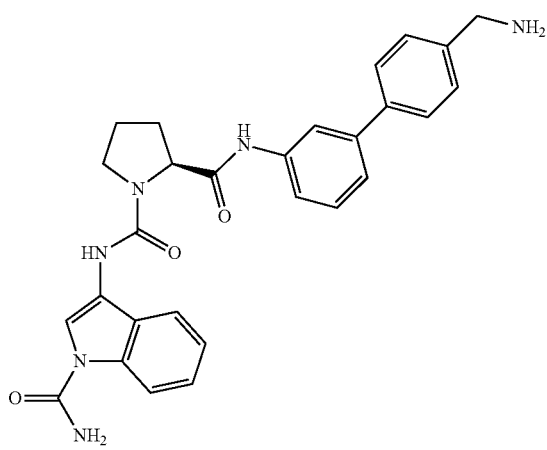 [SMILES: NCc1ccc(-c2cccc(NC(=O)[C@@H]3CCCN3C(=O)Nc3cn(C(N)=O)c4ccccc34)c2)cc1]

The solution of (S)-pyrrolidine-1,2-dicarboxylic acid 1-[(1-carbamoyl-1H-indol-3-yl)amide]2-[(4'-cyano-biphenyl-3-yl)-amide] Example 152 (25 mg, 0.051 mmol) in EtOH (1 mL) containing 5% of NH$_3$, was added a drop of Ni Raney dissolved in EtOH (0.5 mL). The resulting mixture was stirred at RT under hydrogen atmosphere for 26 h, then filtered through Celite, and concentrated. The crude residue was purified by preparative HPLC (Waters SunFire C180 DB, 5 μm, flow 20 mL/min, eluent: 5% CH$_3$CN/95% H$_2$O to 100% CH$_3$CN in 15 min, CH$_3$CN and H$_2$O containing 1% of HCOOH) to give after lyophilization of the purified fractions the desired compound as a formate salt. MS (LC/MS): 497 [M+H]+; $t_R$ (Waters Symmetry C18, 3.5 um, 2.1×50 mm, 5-95% CH$_3$CN/H$_2$O/3.5 min, 95% CH$_3$CN/2 min, CH$_3$CN and H$_2$O containing 0.1% TFA, flow: 0.6 mL/min) 3.04 min.

Example 401

(S)-Pyrrolidine-1,2-dicarboxylic acid 2-[(4'-aminomethyl-2'-fluoro-biphenyl-3-yl)-amide]1-[(1-carbamoyl-1H-indol-3-yl)-amide]

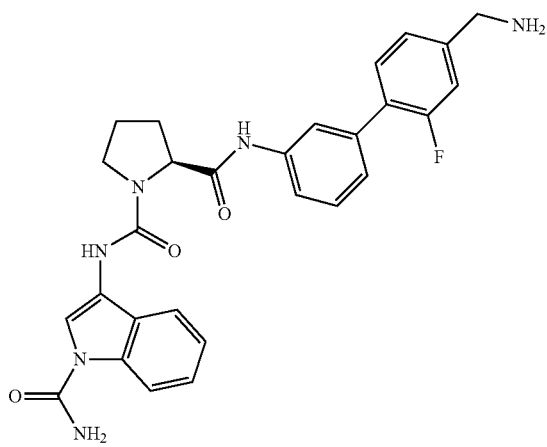 [SMILES: NCc1ccc(-c2cccc(NC(=O)[C@@H]3CCCN3C(=O)Nc3cn(C(N)=O)c4ccccc34)c2)c(F)c1]

To a solution of (S)-pyrrolidine-1,2-dicarboxylic acid 1-[(1-carbamoyl-1H-indol-3-yl)-amide]2-[(4'-cyano-2'-fluoro-biphenyl-3-yl)-amide] (140 mg, 0.274 mmol) (prepared according to the general procedure described in Scheme D5, using in step A 3'-Amino-2-fluoro-biphenyl-4-carbonitrile (prepared as described in Part C) in EtOH (15 mL) containing 4% of NH$_3$ was added Ra-nickel (70 mg) and the mixture was stirred under H$_2$ atmosphere for 18 h. The reaction mixture was filtered on Celite and concentrated. The crude residue was purified by preparative HPLC (Waters Sunfire (C18 ODB, 5 μm, 19×50, flow=20 mL/min, 20% CH$_3$CN/80% water to 100% CH$_3$CN) to give the desired compound. MS (LC/MS): 515 [M+H]+; $t_R$ (Waters Symmetry C18, 3.5 um, 2.1×50 mm, 5-95% CH$_3$CN/H$_2$O/3.5 min, 95% CH$_3$CN/2 min, CH$_3$CN and H$_2$O containing 0.1% TFA, flow: 0.6 mL/min) 3.1 min.

Example 402

(2S,5R)-5-Aminomethyl-pyrrolidine-1,2-dicarboxylic acid 1-[(1-carbamoyl-1H-indol-3-yl)-amide]2-[(3-trifluoromethoxy-phenyl)-amide]

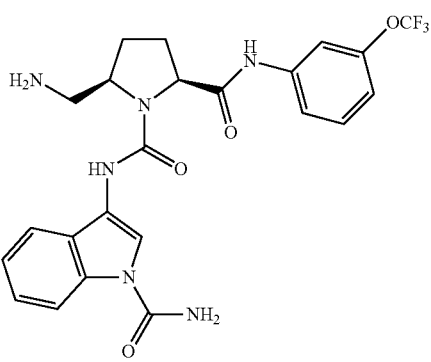 [SMILES: NC[C@H]1CC[C@@H](C(=O)Nc2cccc(OC(F)(F)F)c2)N1C(=O)Nc1cn(C(N)=O)c2ccccc12]

A mixture of (2S,5R)-5-azidomethyl-pyrrolidine-1,2-dicarboxylic acid 1-[(1-carbamoyl-1H-indol-3-yl)-amide]2-[(3-trifluoromethoxy-phenyl)-amide] Example 179 (50 mg, 0.094 mmol) and triphenylphosphine (29.7 mg, 0.113 mmol) in THF (1 mL) was stirred at RT overnight. After completion of the reaction MeOH (1 mL) and water (1 mL) were added and the solution was stirred for 1 h, then the crude reaction mixture was concentrated and purified by preparative HPLC (Waters SunFire C18-ODB 5 μm, 19×50, 5-100% CH$_3$CN/H$_2$O in 17 min, 100% CH$_3$CN for 3 min, CH$_3$CN and H$_2$O containing 0.1% TFA, flow: 20 mL/min) to give the title compound. MS: 505 [M+H]+; $t_R$ (HPLC conditions b): 3.24 min.

Example 403

(2S,4R)-4-Aminomethyl-pyrrolidine-1,2-dicarboxylic acid 1-[(1-carbamoyl-1H-indol-3-yl)-amide]2-[(3-trifluoromethoxy-phenyl)-amide]

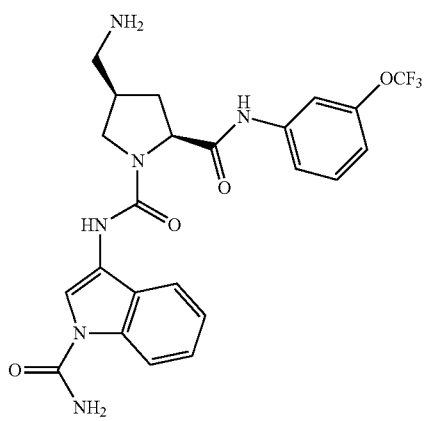 [SMILES: NC[C@H]1C[C@@H](C(=O)Nc2cccc(OC(F)(F)F)c2)N(C(=O)Nc2cn(C(N)=O)c3ccccc23)C1]

(2S,4S)-4-Cyano-pyrrolidine-1,2-dicarboxylic acid 1-[(1-carbamoyl-1H-indol-3-yl)-amide]2-[(3-trifluoromethoxy-phenyl)-amide] Example 125 (20 mg, 0.04 mmol) was dissolved in MeOH (0.2 mL). Ammonia (25% in water, 0.02 mL) and Raney Nickel (7.11 mg) were added. Air was removed from the flask and replaced with nitrogen three times. Finally the flask was again degassed and the mixture was placed under a hydrogen atmosphere, and stirred at RT overnight. The catalyst was removed through a pad of Celite and washed with MeOH. The filtrate was concentrated, and the residue purified by preparative HPLC (Waters SunFire C18-ODB, 5 μm, 19×50 mm, eluent: 5-100% $CH_3CN/H_2O$ in 17 min, $CH_3CN$ and $H_2O$ containing 0.1% TFA, flow: 20 mL/min) to give the title compound as a TFA salt. MS (LC-MS): 505 [M+H]+; $t_R$ (HPLC conditions b): 3.1 min.

Example 404

(2S,4S)-4-Aminomethyl-pyrrolidine-1,2-dicarboxylic acid 1-[(1-carbamoyl-1H-indol-3-yl)-amide]2-[(3-trifluoromethoxy-phenyl)-amide]

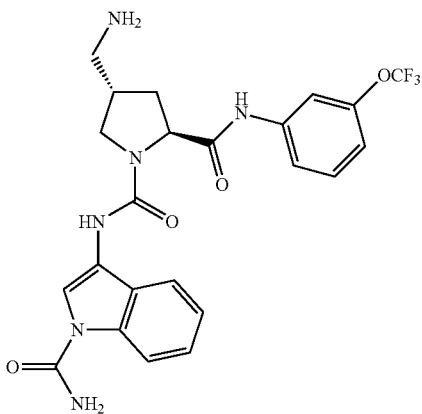 [SMILES: NC[C@@H]1C[C@@H](C(=O)Nc2cccc(OC(F)(F)F)c2)N(C(=O)Nc2cn(C(N)=O)c3ccccc23)C1]

The title compound was obtained from (2S,4R)-4-cyano-pyrrolidine-1,2-dicarboxylic acid 1-[(1-carbamoyl-1H-indol-3-yl)-amide]2-[(3-trifluoromethoxy-phenyl)-amide] Example 256 using the protocol described for the preparation of Example 403. MS (LC/MS): 505 [M+H]+; $t_R$ (HPLC conditions b): 3.1 min.

Example 405

2S,4R)-4-Aminomethyl-pyrrolidine-1,2-dicarboxylic acid 1-[(1-carbamoyl-1H-indol-3-yl)-amide]2-(3-chloro-2-fluoro-benzylamide

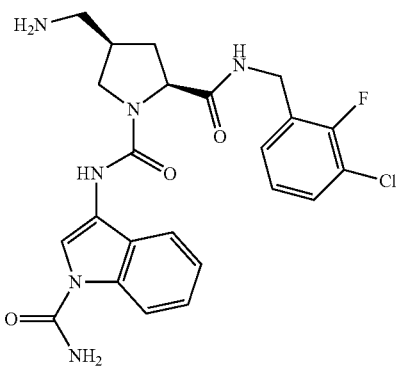 [SMILES: NC[C@H]1C[C@@H](C(=O)NCc2cccc(Cl)c2F)N(C(=O)Nc2cn(C(N)=O)c3ccccc23)C1]

The title compound was prepared analogously as described for the title compound Example 403 using (2S,4S)-4-cyano-pyrrolidine-1,2-dicarboxylic acid 1-[(1-carbamoyl-1H-indol-3-yl)-amide]2-(3-chloro-2-fluoro-benzylamide) pre- pared according to scheme D5. MS (LC/MS): 487 [M+H]+, 442 [M–$CONH_2$]–; $t_R$ (HPLC conditions f): 1.46 min.

Example 406

2S,4R)-4-Dimethylaminomethyl-pyrrolidine-1,2-dicarboxylic acid 1-[(1-carbamoyl-1H-indol-3-yl)-amide]2-(3-chloro-2-fluoro-benzylamide

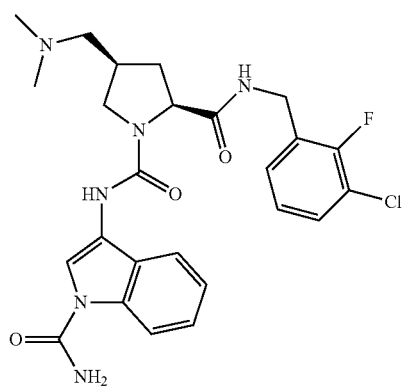 [SMILES: CN(C)C[C@H]1C[C@@H](C(=O)NCc2cccc(Cl)c2F)N(C(=O)Nc2cn(C(N)=O)c3ccccc23)C1]

To a solution of Example 405 (132 mg, 0.271 mmol) in MeOH (0.9 mL) was added formaldehyde 20% in MeOH (373 μL, 2.71 mmol), sodium cyanoborohydride (56 mg, 0.895 mmol) and acetic acid (31.5 μL, 0.542 mmol). The reaction mixture was stirred for 16 h at RT then concentrated. The crude material was purified by preparative HPLC (Waters SunFire C18-ODB, 5 μm, 19×50 mm, eluent: 10-100% $CH_3CN/H_2O$ in 30 min, $CH_3CN$ and $H_2O$ containing 0.1% TFA, flow: 20 mL/min) to give the desired material. TLC, $R_f$ (EtOAc)=0.02; MS (LC/MS): 515 [M+H]+, 470 [M–$CONH_2$]–; $t_R$ (HPLC conditions f): 1.47 min.

Example 407

2S,4S)-4-Aminomethyl-4-hydroxy-pyrrolidine-1,2-dicarboxylic acid 1-[(1-carbamoyl-1H-indol-3-yl)-amide]2-(3-chloro-2-fluoro-benzylamide

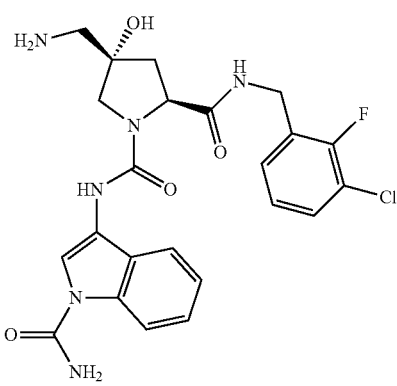

To a solution of (2S,4R)-4-azidomethyl-4-hydroxy-pyrrolidine-1,2-dicarboxylic acid 1-[(1-carbamoyl-1H-indol-3-yl)-amide]2-(3-chloro-2-fluoro-benzylamide) (300 mg, 0.567 mmol) (prepared according to Scheme D5 from (2S, 4R)-4-azidomethyl-2-(3-chloro-2-fluoro-benzylcarbamoyl)-4-hydroxy-pyrrolidine-1-carboxylic acid tert-butyl ester (described in Part B) in EtOAc (10 mL) was added Pd/C (10 mg). Air was removed from the flask and replaced with nitrogen three times. Finally the flask was again degassed and the mixture was placed under a hydrogen atmosphere, and stirred at RT overnight. The catalyst was removed through a pad of Celite and washed with EtOAc. The filtrate was concentrated, and the residue purified by preparative HPLC (Waters Sun-Fire C18-ODB, 5 μm, 19×50 mm, eluent: 5-100% CH$_3$CN/H$_2$O in 17 min, CH$_3$CN and H$_2$O containing 0.1% TFA, flow: 20 mL/min) to give the title compound as a TFA salt. MS (LC-MS): 503 [M+H]+; $t_R$ (HPLC conditions c): 3.57 min; $^{19}$F NMR (100 MHz, DMSO-d$_6$) δ (ppm): −122.

Example 408

2S,4R)-4-Aminomethyl-4-fluoro-pyrrolidine-1,2-dicarboxylic acid 1-[(1-carbamoyl-1H-indol-3-yl)-amide]2-(3-chloro-2-fluoro-benzylamide

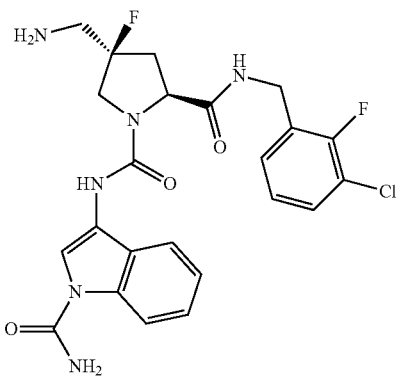 [SMILES: NC[C@]1(F)C[C@@H](C(=O)NCc2cccc(Cl)c2F)N(C(=O)Nc2cn(C(N)=O)c3ccccc23)C1]

The title compound was prepared analogously as described for Example 407 using (2S,4S)-4-azidomethyl-4-fluoro-pyrrolidine-1,2-dicarboxylic acid 1-[(1-carbamoyl-1H-indol-3-yl)amide]2-(3-chloro-2-fluoro-benzylamide) prepared according to scheme D5 from (2S,4S)-4-azidomethyl-2-(3-chloro-2-fluoro-benzylcarbamoyl)-4-fluoro-pyrrolidine-1-carboxylic acid tert-butyl ester (described in Part B). MS (LC-MS): 505/507 [M+H]+; $t_R$ (HPLC conditions f): 1.46 min; $^{19}$F NMR (100 MHz, DMSO-d$_6$) δ (ppm): −121, −150.

Example 409

2S,4S)-4-Aminomethyl-4-fluoro-pyrrolidine-1,2-dicarboxylic acid 1-[(1-carbamoyl-1H-indol-3-yl)-amide]2-(3-chloro-2-fluoro-benzylamide

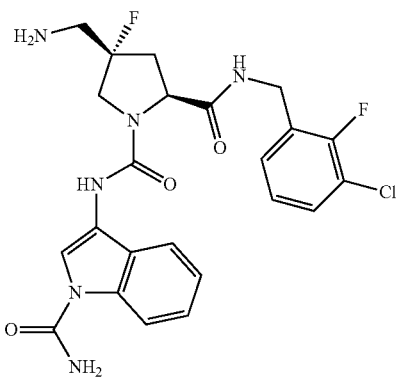 [SMILES: NC[C@@]1(F)C[C@@H](C(=O)NCc2cccc(Cl)c2F)N(C(=O)Nc2cn(C(N)=O)c3ccccc23)C1]

The title compound was prepared analogously as described for Example 407 using (2S,4R)-4-azidomethyl-4-fluoro-pyrrolidine-1,2-dicarboxylic acid 1-[(1-carbamoyl-1H-indol-3-yl)amide]2-(3-chloro-2-fluoro-benzylamide) prepared according to scheme D5 from (2S,4R)-4-azidomethyl-2-(3-chloro-2-fluoro-benzylcarbamoyl)-4-fluoro-pyrrolidine-1-carboxylic acid tert-butyl ester (described Scheme B15). MS (LC-MS): 505/507 [M+H]+; $t_R$ (HPLC conditions f): 1.47 min; $^{19}$F NMR (100 MHz, DMSO-d$_6$) δ (ppm): −121, −150.

Example 410

2S,4S)-4-Fluoro-4-formylaminomethyl-pyrrolidine-1,2-dicarboxylic acid 1-[(1-carbamoyl-1H-indol-3-yl)-amide]2-(3-chloro-2-fluoro-benzylamide

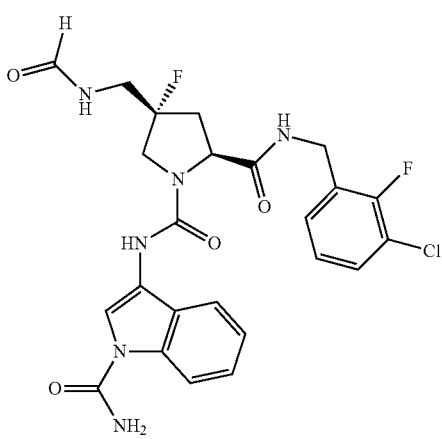 [SMILES: NC(=O)n1cc(NC(=O)N2C[C@@](F)(CNC=O)C[C@H]2C(=O)NCc2cccc(Cl)c2F)c2ccccc21]

The title compound was obtained from Example 409 (2S,4S)-4-aminomethyl-4-fluoro-pyrrolidine-1,2-dicarboxylic acid 1-[(1-carbamoyl-1H-indol-3-yl)-amide]2-(3-chloro-2-fluoro-benzylamide) as formylation occurred during the concentration of the purified Example 409 HPLC fractions from the preparative HPLC containing 1% HCOOH. MS (LC-MS): 531 [M−H]−, 533 [M+H]+; $t_R$ (HPLC conditions f): 0.56 min; $^{19}$F NMR (100 MHz, DMSO-d$_6$) δ (ppm): −121, −150.

Example 411

2S,4S)-4-Aminomethyl-4-fluoro-pyrrolidine-1,2-dicarboxylic acid 1-[(1-carbamoyl-1H-indol-3-yl)-amide]2-(3-chloro-2,6-difluoro-benzylamide

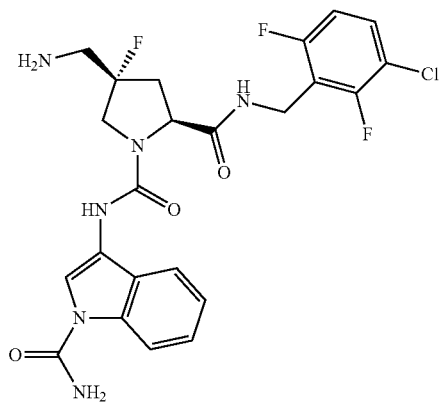 [SMILES: NC[C@@]1(F)C[C@@H](C(=O)NCc2c(F)ccc(Cl)c2F)N(C(=O)Nc2cn(C(N)=O)c3ccccc23)C1]

To a solution of (2S,4R)-4-azidomethyl-4-fluoro-pyrrolidine-1,2-dicarboxylic acid 1-[(1-carbamoyl-1H-indol-3-yl)- amide]2-(3-chloro-2,6-difluoro-benzylamide) (100 mg, 0.182 mmol) (prepared according to scheme D5 using (2S,4R)-4-azidomethyl-2-(3-chloro-2,6-difluoro-benzylcarbamoyl)-4-fluoro-pyrrolidine-1-carboxylic acid tert-butyl ester prepared analogously as described in Scheme B15) in THF (5 mL) and water (6.56 µL) under N₂ atmosphere at RT was added 1M PMe₃ in THF (0.219 mL, 0.219 mmol). The reaction mixture was stirred for 16 h then quenched with water and extracted twice with EtOAc. The combined organic layers were dried (Na₂SO₄), filtered and concentrated. The crude residue was purified preparative HPLC (Waters SunFire C18-ODB, 5 µm, 19×50 mm, 5% CH₃CN/H₂O 2.5 min, 5-100% CH₃CN/H₂O in 10 min, CH₃CN/H₂O containing 0.1% HCOOH flow: 20 mL/min) to give after lyophilization of the purified fractions the title compound (formic acid salt). MS (UPLC-MS): 523/525 [M+H]+, 521/523 [M−H]−; $t_R$ (HPLC conditions f): 1.42 min; ¹⁹F NMR (100 MHz, DMSO-d₆) δ (ppm): −115 (2F), −150.

Example 412

2S,4S)-4-Aminomethyl-4-fluoro-pyrrolidine-1,2-dicarboxylic acid 1-[(1-acetyl-1H-indol-3-yl)-amide] 2-(3-chloro-2-fluoro-benzylamide

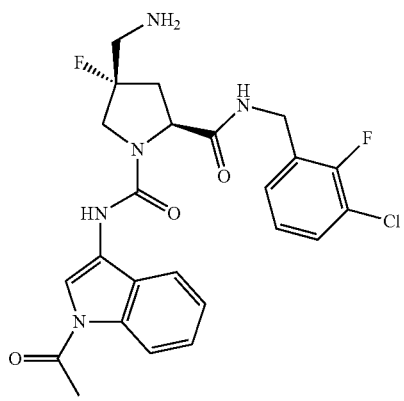 [SMILES: CC(=O)n1cc(NC(=O)N2C[C@@](F)(CN)C[C@H]2C(=O)NCc2cccc(Cl)c2F)c2ccccc21]

The title compound was prepared analogously as described for Example 411 using (2S,4R)-4-azidomethyl-4-fluoro-pyrrolidine-1,2-dicarboxylic acid 1-[(1-acetyl-1H-indol-3-yl)-amide]2-(3-chloro-2-fluoro-benzylamide) prepared according to scheme D5 from (2S,4R)-4-azidomethyl-2-(3-chloro-2-fluoro-benzylcarbamoyl)-4-fluoro-pyrrolidine-1-carboxylic acid tert-butyl ester (described Scheme B15) and 1-(3-isocyanato-indol-1-yl)ethanone (described in Scheme A1). MS (UPLC-MS): 504/506 [M+H]+, 502/504 [M−H]−; $t_R$ (HPLC conditions f): 1.62 min; ¹⁹F NMR (100 MHz, DMSO-d₆) δ (ppm): −121, −153.

Example 413

(2S,4S)-4-Aminomethyl-4-fluoro-pyrrolidine-1,2-dicarboxylic acid 2-{[(S)-1-(3-bromo-phenyl)-2-fluoro-ethyl]-amide}1-[(1-carbamoyl-1H-indol-3-yl)-amide]

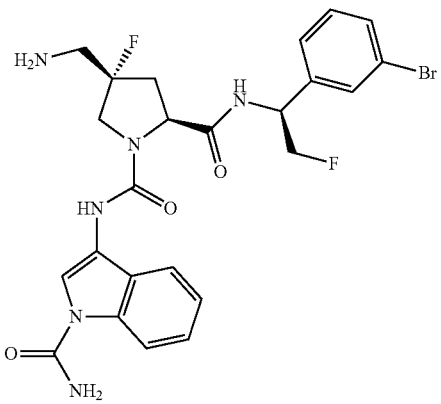 [SMILES: NC[C@@]1(F)C[C@@H](C(=O)N[C@H](CF)c2cccc(Br)c2)N(C(=O)Nc2cn(C(N)=O)c3ccccc23)C1]

The title compound was prepared analogously as described for Example 411 from (2S,4R)-4-azidomethyl-4-fluoro-pyrrolidine-1,2-dicarboxylic acid 2-{[(S)-1-(3-bromo-phenyl)-2-fluoro-ethyl]-amide}1-[(1-carbamoyl-1H-indol-3-yl)-amide] (82 mg, 0.115 mmol) (prepared according to scheme D5 step C using (2S,4R)-4-azidomethyl-2-[(S)-1-(3-bromo-phenyl)-2-fluoro-ethylcarbamoyl]-4-fluoro-pyrrolidine-1-carboxylic acid tert-butyl ester prepared as described in Scheme B16). Purification on preparative HPLC (Waters SunFire C18-ODB, 5 µm, 19×50 mm, 5% CH₃CN/H₂O 2.5 min, 5-100% CH₃CN/H₂O in 10 min, CH₃CN/H₂O containing 0.1% HCOOH flow: 20 mL/min) to give after lyophilization of the purified fractions the title compound (formic acid salt). MS (UPLC-MS): 561/563 [M+H]+, 561/563 [M−H]−; $t_R$ (HPLC conditions f): 1.42 min.

Example 414

(2S,4S)-4-Aminomethyl-4-fluoro-pyrrolidine-1,2-dicarboxylic acid 1-[(1-carbamoyl-1H-indol-3-yl)-amide]2-[(3-trifluoromethoxy-phenyl)-amide]

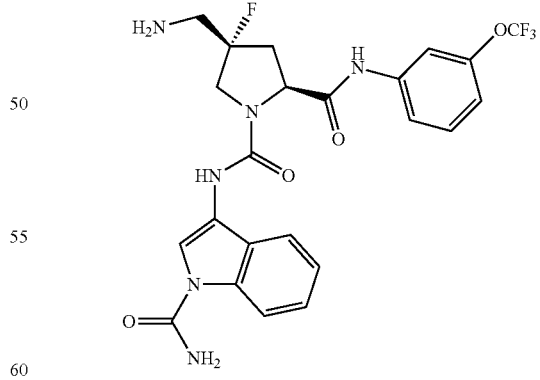

The title compound was prepared analogously as described for Example 411 from (2S,4R)-4-azidomethyl-4-fluoro-pyrrolidine-1,2-dicarboxylic acid 1-[(1-carbamoyl-1H-indol-3-yl)-amide]2-[(3-trifluoromethoxy-phenyl)-amide] (43 mg, 0.078 mmol) (prepared according to scheme D5 Step C using (2S,4R)-4-azidomethyl-4-fluoro-2-(3-trifluoromethoxy-phenylcarbamoyl)-pyrrolidine-1-carboxylic acid tert-butyl ester prepared as described Scheme B16 using 2-trifluoromethoxy-phenylamine in step G instead of 3(S)-1-(3-bromo-phenyl)-2-fluoro-ethylamine). Purification by preparative HPLC (Waters SunFire C18-ODB, 5 µm, 19×50 mm, 5% CH₃CN/H₂O 2.5 min, 5-100% CH₃CN/H₂O in 10 min, CH₃CN/H₂O containing 0.1% HCOOH flow: 20 mL/min) gave after lyophilization of the purified fractions the title compound (formic acid salt). MS (UPLC-MS): 523 [M+H]+, 521 [M−H]−; $t_R$ (HPLC conditions f): 1.59 min; 19F NMR (100 MHz, DMSO-$d_6$) δ (ppm): −57 (3F), −150.

Example 415

2S,3S,4S)-3-Amino-4-fluoro-pyrrolidine-1,2-dicarboxylic acid 1-[(1-acetyl-1H-indol-3-yl)-amide]2-(3-chloro-2-fluoro-benzylamide

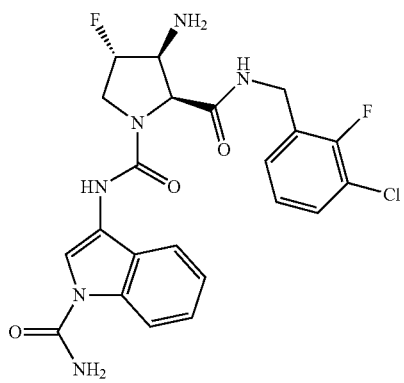 [SMILES: NC(=O)n1cc(NC(=O)N2C[C@H](F)[C@@H](N)[C@H]2C(=O)NCc2cccc(Cl)c2F)c2ccccc21]

The title compound was prepared according to Scheme D5 from (2S,3S,4S)-3-azido-2-(3-chloro-2-fluoro-benzylcarbamoyl)-4-fluoro-pyrrolidine-1-carboxylic acid tert-butyl ester (described in scheme B19) followed by reduction of the azide as described for the preparation of Example 411. TLC, $R_f$ (CH₂Cl₂/MeOH 95/5)=0.2; MS (LC-MS): 491 [M+H]+, 489 [M−H]−; $t_R$ (HPLC conditions f): 1.55 min.

Example 416

2S,3R,4S)-4-Amino-3-hydroxy-pyrrolidine-1,2-dicarboxylic acid 1-[(1-carbamoyl-1H-indol-3-yl)-amide]2-(3-chloro-2-fluoro-benzylamide

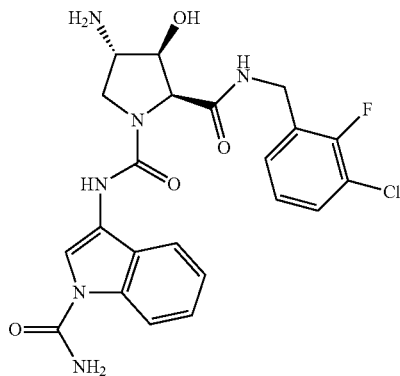 [SMILES: NC(=O)n1cc(NC(=O)N2C[C@H](N)[C@@H](O)[C@H]2C(=O)NCc2cccc(Cl)c2F)c2ccccc21]

The title compound was prepared according to Scheme D5 from (2S,3S,4S)-4-azido-2-(3-chloro-2-fluoro-benzylcarbamoyl)-3-hydroxy-pyrrolidine-1-carboxylic acid tert-butyl ester (described in scheme B19) followed by reduction of the azide as described for the preparation of Example 411. TLC, $R_f$ (CH₂Cl₂/MeOH 95/5)=0.2; MS (LC-MS): 489 [M+H]+, 487 [M−H]−; $t_R$ (HPLC conditions f): 1.34 min.

Example 417

2S,3R)-3-Amino-pyrrolidine-1,2-dicarboxylic acid 1-[(1-carbamoyl-1H-indol-3-yl)-amide]2-(3-chloro-2-fluoro-benzylamide

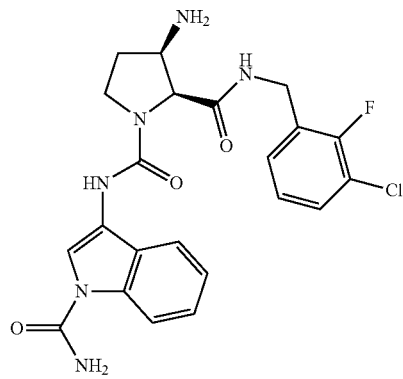 [SMILES: NC(=O)n1cc(NC(=O)N2CC[C@@H](N)[C@H]2C(=O)NCc2cccc(Cl)c2F)c2ccccc21]

A solution of (2S,3R)-3-azido-pyrrolidine-1,2-dicarboxylic acid 1-[(1-carbamoyl-1H-indol-3-yl)-amide]2-(3-chloro-2-fluoro-benzylamide) (prepared according to scheme D5 step C using (2S,3R)-3-azido-pyrrolidine-2-carboxylic acid 3-chloro-2-fluoro-benzylamide trifluoroacetate (prepared as described in Part B) (70 mg, 0.140 mmol) in MeOH (10 mL) was hydrogenated at RT (1 atm) over Pd/C 10% (14 mg, 20% w/w) for 4 h. The reaction mixture was filtered through a 0.45 microns filter and concentrated under reduced pressure. The crude product was purified by preparative HPLC (Waters Sunfire, C18-ODB, 5 µm, 30×100 mm; flow: 40 mL/min; eluent: 5-60% CH₃CN/H₂O for 20 min, 60% CH₃CN for 2 min, CH₃CN and H₂O containing 0.1% TFA) to afford the title compound as a white solid. MS (LC/MS): 473 [M+H]+; $t_R$ (HPLC conditions b): 2.75 min.

Example 418

2S,3R)-3-Amino-pyrrolidine-1,2-dicarboxylic acid 1-[(1-acetyl-1H-indol-3-yl)-amide]2-(3-chloro-2-fluoro-benzylamide

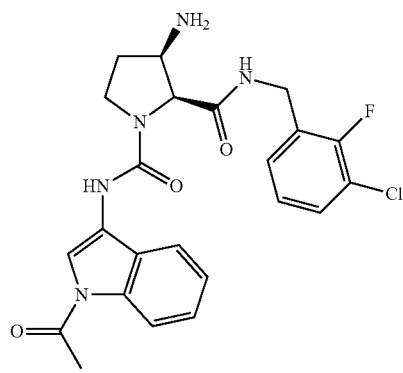 [SMILES: CC(=O)n1cc(NC(=O)N2CC[C@@H](N)[C@H]2C(=O)NCc2cccc(Cl)c2F)c2ccccc21]

Prepared as described for Example 417 from (2S,3R)-3-azido-pyrrolidine-1,2-dicarboxylic acid 1-[(1-acetyl-1H-indol-3-yl)-amide]2-(3-chloro-2-fluoro-benzylamide) prepared according to Scheme D5 by using (2S,3R)-3-azidopyrrolidine-2-carboxylic acid 3-chloro-2-fluoro-benzylamide trifluoroacetate (prepared as described in Part B) and 1-(3-isocyanato-indol-1-yl)-ethanone (prepared as described in Scheme A1). White solid. MS (LC/MS): 473 [M+H]+; $t_R$ (HPLC conditions b): 2.91 min.

Example 419

(2S,3R)-3-Amino-pyrrolidine-1,2-dicarboxylic acid 1-[(1-carbamoyl-1H-indol-3-yl)-amide]2-{[(S)-1-(3-chloro-2-fluoro-phenyl)-2,2,2-trifluoro-ethyl]-amide}

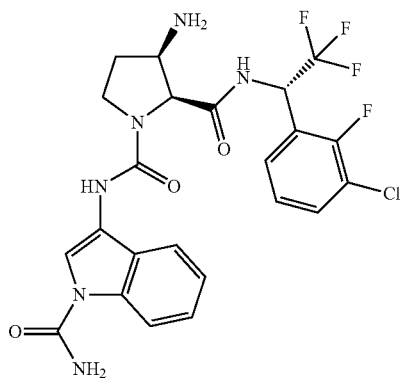 [SMILES: NC(=O)n1cc(NC(=O)N2CC[C@@H](N)[C@H]2C(=O)N[C@@H](c2cccc(Cl)c2F)C(F)(F)F)c2ccccc21]

The title compound was prepared as described for Example 417 starting from (2S,3R)-3-azido-pyrrolidine-1,2-dicarboxylic acid 1-[(1-carbamoyl-1H-indol-3-yl)-amide]2-{[(S)-1-(3-chloro-2-fluoro-phenyl)-2,2,2-trifluoro-ethyl]-amide} (prepared according to Scheme D5 (step C) from (2S,3R)-3-azido-pyrrolidine-2-carboxylic acid [(S)-1-(3-chloro-2-fluoro-phenyl)-2,2,2-trifluoro-ethyl]-amide (prepared in a similar manner as described in Part B for (2S,3R)-3-azido-pyrrolidine-2-carboxylic acid 3-chloro-2-fluoro-benzylamide trifluoroacetate starting from (S)-1-(3-chloro-2-fluorophenyl)-2,2,2-trifluoroethanamine. White solid. MS (LC/MS): 541.0 [M+H]+; $t_R$ (HPLC conditions c): 4.07 min.

Example 420

2S,3S)-3-Amino-pyrrolidine-1,2-dicarboxylic acid 1-[(1-carbamoyl-1H-indol-3-yl)-amide]2-(3-chloro-2-fluoro-benzylamide

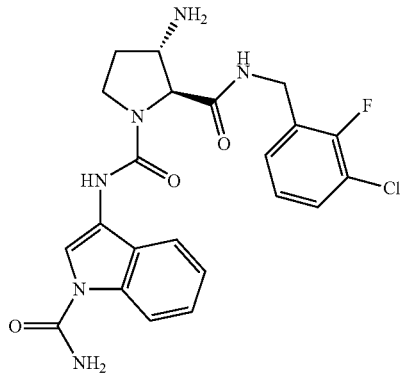 [SMILES: NC(=O)n1cc(NC(=O)N2CC[C@H](N)[C@H]2C(=O)NCc2cccc(Cl)c2F)c2ccccc21]

Prepared as described for Example 417 from (2S,3S)-3-azido-pyrrolidine-1,2-dicarboxylic acid 1-[(1-carbamoyl-1H-indol-3-yl)-amide]2-(3-chloro-2-fluoro-benzylamide) (prepared according to scheme D5 step C by using (2S,3S)-3-azido-pyrrolidine-2-carboxylic acid 3-chloro-2-fluoro-benzylamide (prepared as described in Part B). White solid. MS (LC/MS): 473 [M+H]+; $t_R$ (HPLC conditions b): 2.91 min.

Example 421

2S,3S)-3-Amino-pyrrolidine-1,2-dicarboxylic acid 1-[(1-carbamoyl-1H-indol-3-yl)-amide]2-(3-chloro-benzylamide

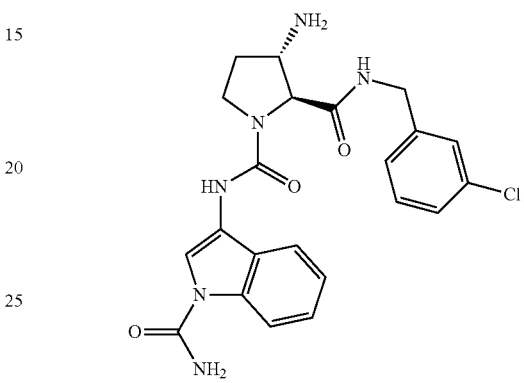

Prepared as described for Example 417 from (2S,3S)-3-azido-pyrrolidine-1,2-dicarboxylic acid 1-[(1-carbamoyl-1H-indol-3-yl)-amide]2-(3-chloro-benzylamide) (prepared according to scheme D5 step C by using (2S,3S)-3-azido-pyrrolidine-2-carboxylic acid 3-chloro-benzylamide (prepared using similar protocols as described in Part B for (2S,3S)-3-azido-pyrrolidine-2-carboxylic acid 3-chloro-2-fluoro-benzylamide). White solid. MS (LC/MS): 455 [M+H]+; $t_R$ (HPLC conditions b): 2.79 min.

Example 422

2S,3R)-3-Acetylamino-pyrrolidine-1,2-dicarboxylic acid 1-[(1-carbamoyl-1H-indol-3-yl)-amide]2-(3-chloro-2-fluoro-benzylamide

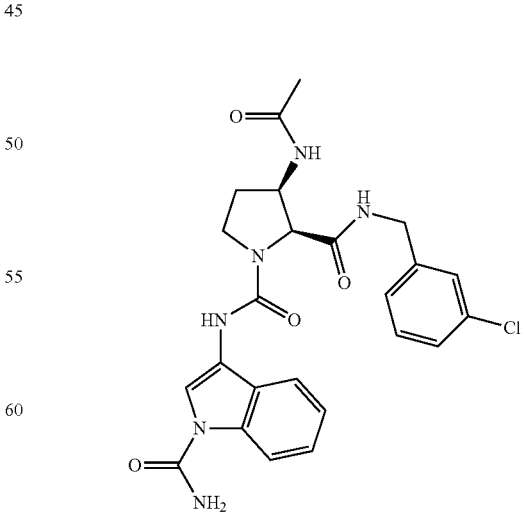

To an ice-cooled solution of (2S,3R)-3-amino-pyrrolidine-1,2-dicarboxylic acid 1-[(1-carbamoyl-1H-indol-3-yl)- amide]2-(3-chloro-2-fluoro-benzylamide) Example 417 (27.0 mg, 0.057 mmol) in dry $CH_2Cl_2$ (5 mL) and dry THF (2.5 mL) were added triethylamine (0.024 mL, 0.171 mmol) and acetic anhydride (0.108 mL, 1.14 mmol) under an argon atmosphere. The reaction mixture was stirred at RT for 16 h. Volatiles were removed under reduced pressure, and the residue was purified by preparative HPLC (Waters Sunfire, C18-ODB, 5 µm, 19×50 mm, eluent: 5-100% $CH_3CN/H_2O$/20 min, 100% $CH_3CN$/2 min, $CH_3CN$ and $H_2O$ containing 0.1% TFA, flow: 20 mL/min) to give after lyophilization the title compound as a white solid. MS (LC/MS): 515.0 [M+H]+; $t_R$ (HPLC conditions k): 2.96 min.

Example 423

2S,3R)-3-(2-Methoxy-ethylamino)-pyrrolidine-1,2-dicarboxylic acid 1-[(1-carbamoyl-1H-indol-3-yl)-amide]2-(3-chloro-2-fluoro-benzylamide

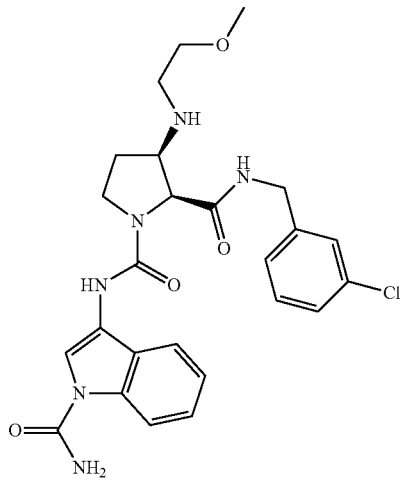 [SMILES: COCCN[C@@H]1CCN(C(=O)Nc2cn(C(N)=O)c3ccccc23)[C@@H]1C(=O)NCc1cccc(Cl)c1]

To a solution of (2S,3R)-3-amino-pyrrolidine-1,2-dicarboxylic acid 1-[(1-carbamoyl-1H-indol-3-yl)-amide]2-(3-chloro-2-fluoro-benzylamide) Example 417 (36 mg, 0.076 mmol) in dry DMF (1.5 mL) were added triethylamine (0.032 mL, 0.228 mmol) and 1-bromo-2-methoxyethane (0.014 mL, 0.144 mmol) under an argon atmosphere, followed by stirring at RT for 60 h. UPLC-MS showed formation of product and the presence of unreacted starting material (2S,3R)-3-amino-pyrrolidine-1,2-dicarboxylic acid 1-[(1-carbamoyl-1H-indol-3-yl)-amide]2-(3-chloro-2-fluoro-benzylamide). An excess of 1-bromo-2-methoxyethane (10 eq) and triethylamine (10 eq) were added to the reaction mixture, and stirring was continued at RT for 18 h, and then at 50° C. for 24 h. The crude material was directly purified by preparative HPLC (Waters Sunfire, C18-ODB, 5 µm, 19×50 mm, eluent: 5-100% $CH_3CN/H_2O$/20 min, 100% $CH_3CN$/2 min, $CH_3CN$ and $H_2O$ containing 0.1% TFA, flow: 20 mL/min) to give after lyophilization the title compound as a solid. MS (LC/MS): 531 [M+H]+; $t_R$ (HPLC conditions k): 2.97 min.

Example 424

2S,4S)-4-Fluoro-4-methylaminomethyl-pyrrolidine-1,2-dicarboxylic acid 1-[(1-carbamoyl-1H-indol-3-yl)-amide]2-(3-chloro-2-fluoro-benzylamide

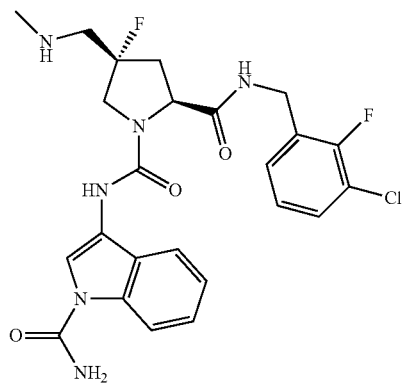 [SMILES: CNC[C@@]1(F)C[C@@H](C(=O)NCc2cccc(Cl)c2F)N(C(=O)Nc2cn(C(N)=O)c3ccccc23)C1]

[(3R,5S)-1-(1-carbamoyl-1H-indol-3-ylcarbamoyl)-5-(3-chloro-2-fluoro-benzylcarbamoyl)-3-fluoro-pyrrolidin-3-yl-methyl]-methyl-carbamic acid 2,2,2-trichloro-ethyl ester (prepared according to scheme D5 Steps B and C using (2S,4S)-4-fluoro-4-{[methyl-(2,2,2-trichloro-ethoxycarbonyl)-amino]-methyl}-pyrrolidine-1,2-dicarboxylic acid 2-benzyl ester 1-tert-butyl ester (prepared as described in Scheme B17) (56 mg, 0.08 mmol) was dissolved in MeOH (5 mL) under $N_2$ atmosphere at RT. Zinc dust was added (0.24 mg, 3.7 mmol), the pH was adjusted to pH 5-6 by adding some acetic acid. The reaction mixture was stirred for 1 h then filtered and concentrated. The crude residue was purified by preparative HPLC (Waters SunFire C18-ODB, 5 µm, 19×50 mm, 5% $CH_3CN/H_2O$ 2.5 min, 5-100% $CH_3CN/H_2O$ in 10 min, $CH_3CN/H_2O$ containing 0.1% HCOOH flow: 20 mL/min) to give after lyophilization of the purified fractions the title compound. MS (UPLC-MS): 519 [M+H]+; $t_R$ (HPLC conditions f): 1.32 min; $^{19}F$ NMR (100 MHz, DMSO-$d_6$) δ (ppm): −120, −150.

Example 425

2S,4S)-4-Methylamino-pyrrolidine-1,2-dicarboxylic acid 1-[(1-carbamoyl-1H-indol-3-yl)-amide]2-(3-chloro-2-fluoro-benzylamide

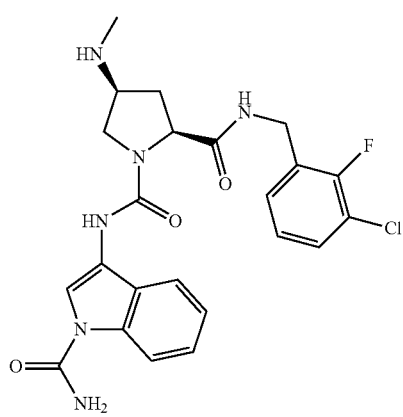 [SMILES: CN[C@H]1C[C@@H](C(=O)NCc2cccc(Cl)c2F)N(C(=O)Nc2cn(C(N)=O)c3ccccc23)C1]

The title compound was prepared according to Scheme D5 Steps B and C from (2S,4S)-2-(3-chloro-2-fluoro-benzylcarbamoyl)-4-[methyl-(2,2,2-trichloro-ethoxycarbonyl)-amino]-pyrrolidine-1-carboxylic acid tert-butyl ester (37 mg, 0.05 mmol) (prepared as described in Scheme B6) followed by the deprotection of the Troc protecting group as described for Example 424. Purification by preparative HPLC (Waters SunFire C18-ODB, 5 µm, 19×50 mm, 5% CH$_3$CN/H$_2$O 2.5 min, 5-100% CH$_3$CN/H$_2$O in 10 min, CH$_3$CN/H$_2$O containing 0.1% HCOOH flow: 20 mL/min) gave after lyophilization of the purified fractions the title compound (formic acid salt). MS (UPLC/MS): 489 [M+H]+; $t_R$ (HPLC conditions f): 1.48 min; $^{19}$F NMR (100 MHz, DMSO-d$_6$) δ (ppm): −120.

Example 426

2S,4S)-4-(2-Methoxy-ethylamino)-pyrrolidine-1,2-dicarboxylic acid 1-[(1-carbamoyl-1H-indol-3-yl)-amide]2-(3-chloro-2-fluoro-benzylamide

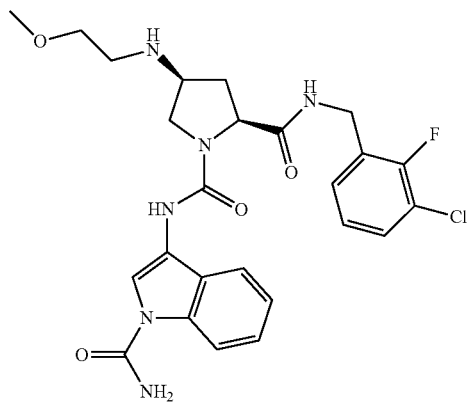 [SMILES: COCCN[C@H]1C[C@@H](C(=O)NCc2cccc(Cl)c2F)N(C(=O)Nc2cn(C(N)=O)c3ccccc23)C1]

To a solution of 2-methoxyethylamine (219 µL, 2.54 mmol) in MeOH (265 µL) was added HCl 1.25 N in MeOH (339 µL, 0.424 mmol) followed by (S)-4-oxo-pyrrolidine-1,2-dicarboxylic acid 1-[(1-carbamoyl-1H-indol-3-yl)-amide]2-(3-chloro-2-fluoro-benzylamide) (100 mg, 0.212 mmol) (prepared as described in scheme D5 from (S)-4-oxo-pyrrolidine-1,2-dicarboxylic acid 1-tert-butyl ester) and NaBH$_3$CN (16 mg, 0.254 mmol) and the reaction mixture was stirred at 23° C. during 1 week. 2-Methoxyethylamine (219 µL, 2.54 mmol) and NaBH$_3$CN (16 mg, 0.254 mmol) were added again and the reaction mixture was stirred at 23° C. for 2 days. The crude mixture was diluted in EtOAc and washed with NaHCO$_3$ saturated aqueous solution. The layers were separated and the aqueous one re-extracted with EtOAc. The combined organic layers were dried, filtered and concenrated to dryness. The crude residue was purified by flash column chromatography on silica gel (CH$_2$Cl$_2$/MeOH gradient 100:0 to 9:1) followed by preparative HPLC (Waters SunFire C180 DB, 5 µm, 30×100, eluent: 5% CH$_3$CN/95% H$_2$O to 100% CH$_3$CN in 20 min, CH$_3$CN and H$_2$O containing 0.1% of TFA, flow 40 mL/min) to give after lyophlisation of the purified fractions the desired material. MS: 531.1 [M+H]+; $t_R$ (HPLC conditions b): 3.1 min. The absolute stereochemistry has been assigned tentatively based on the test results for the final compound Example 426 in the biological assay.

Example 427

2S,4S)-4-Dimethylamino-pyrrolidine-1,2-dicarboxylic acid 1-[(1-carbamoyl-1H-indol-3-yl)-amide]2-(3-chloro-2-fluoro-benzylamide

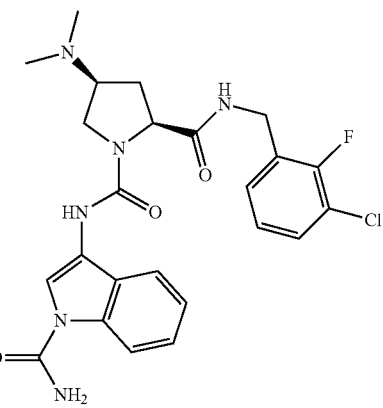

To a solution of (2S,4S)-4-amino-pyrrolidine-1,2-dicarboxylic acid 1-[(1-carbamoyl-1H-indol-3-yl)-amide]2-(3-chloro-2-fluoro-benzylamide) Example 26 (20 mg, 0.042 mmol) in MeOH (140 µl) was added formaldehyde (58.3 µl, 0.423 mmol), NaBH$_3$CN (8.77 mg, 0.140 mmol) and AcOH (4.84 µl, 0.085 mmol), and the reaction mixture was stirred at 23° C. under nitrogen for 16 h. After completion, the crude reaction mixture was purified by preparative HPLC (Waters SunFire C180 DB, 5 µm, 19×50, eluent: 5% CH$_3$CN/95% H$_2$O to 100% CH$_3$CN in 17 min, CH$_3$CN and H$_2$O containing 0.1% of TFA, flow 20 mL/min) to give after lyophilization of the purified fractions the desired material. MS (LC/MS): 501.1 [M+H]+; $t_R$ (HPLC conditions b): 2.75 min.

Example 428

S)-4,4-Dimethoxy-pyrrolidine-1,2-dicarboxylic acid 1-[(1-carbamoyl-1H-indol-3-yl)-amide]2-(3-chloro-2-fluoro-benzylamide

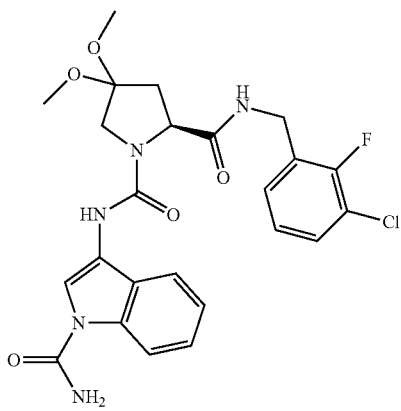 [SMILES: COC1(OC)C[C@@H](C(=O)NCc2cccc(Cl)c2F)N(C(=O)Nc2cn(C(N)=O)c3ccccc23)C1]

To a solution of methylamine hydrochloride (14.3 mg, 0.212 mmol) in MeOH (300 µL) was added HCl 1.25 N in MeOH (400 µl, 0.50 mmol), (S)-4-oxo-pyrrolidine-1,2-dicarboxylic acid 1-[(1-carbamoyl-1H-indol-3-yl)-amide]2-(3- chloro-2-fluoro-benzylamide) (100 mg, 0.212 mmol) (prepared as described in scheme D5 from (S)-4-oxo-pyrrolidine-1,2-dicarboxylic acid 1-tert-butyl ester) and NaBH₃CN (8 mg, 0.127 mmol) and the reaction mixture was stirred at 23° C. for 16 h. The crude reaction mixture was diluted with EtOAc and washed with aqueous saturated NaHCO₃ solution. The organic layer was dried, filtered and concentrated to dryness, finally purified by preparative HPLC (Waters SunFire C180 DB, 5 μm, 19×50, eluent: 20% CH₃CN/80% H₂O to 100% CH₃CN in 12.5 min, CH₃CN and H₂O containing 0.1% HCOOH, flow 20 mL/min) to give after lyophilization of the purified fractions the desired material. MS: 518 [M+H]+; $t_R$ (HPLC conditions b): 3.79 min.

Example 429

2S,3S,4R)-4-Amino-3-hydroxy-pyrrolidine-1,2-dicarboxylic acid 1-[(1-carbamoyl-1H-indol-3-yl)-amide]2-(3-chloro-2-fluoro-benzylamide

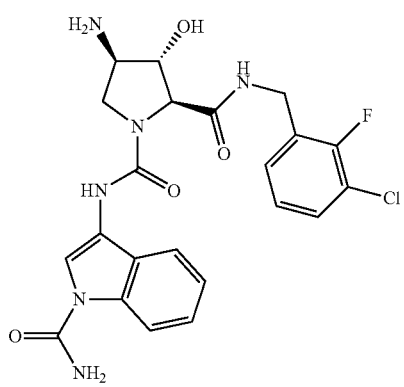 [SMILES: NC(=O)n1cc(NC(=O)N2C[C@@H](N)[C@H](O)[C@H]2C(=O)NCc2cccc(Cl)c2F)c2ccccc21]

The title compound was prepared as described for Example 411 using (2S,3R,4R)-4-azido-3-hydroxy-pyrrolidine-1,2-dicarboxylic acid 1-[(1-carbamoyl-1H-indol-3-yl)-amide]2-(3-chloro-2-fluoro-benzylamide). TLC, $R_f$ (EtOAc)=0.02; MS (LC-MS): 489 [M+H]+, 487 [M−H]−; $t_R$ (HPLC conditions g): 1.96 min.

2S,3R,4R)-4-azido-3-hydroxy-pyrrolidine-1,2-dicarboxylic acid 1-[(1-carbamoyl-1H-indol-3-yl)-amide] 2-(3-chloro-2-fluoro-benzylamide The title compound was prepared according to scheme D5 (steps B and C) from a mixture of (2S,3R,4R)-4-azido-2-(3-chloro-2-fluoro-benzylcarbamoyl)-3-hydroxy-pyrrolidine-1-carboxylic acid tert-butyl ester and (2S,3S,4S)-3-azido-4-hydroxy-pyrrolidine-1,2-dicarboxylic acid 1-[(1-carbamoyl-1H-indol-3-yl)-amide]2-(3-chloro-2-fluoro-benzylamide) in ratio 6:4 (described Scheme B19). The regioisomers were separated by flash column chromatography on silica gel (c-hexane 100% to EtOAc 100%) to give the title compound. TLC, $R_f$(EtOAc)=0.23; MS (LC-MS): 515/517 [M+H]+, 513 [M−H]−; $t_R$ (HPLC conditions f): 1.81 min.

Example 430

2R,3S,4R)-4-Amino-3-fluoro-pyrrolidine-1,2-dicarboxylic acid 1-[(1-carbamoyl-1H-indol-3-yl)-amide] 2-(3-chloro-2-fluoro-benzylamide

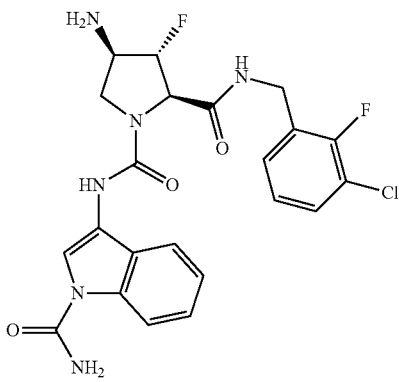 [SMILES: NC(=O)n1cc(NC(=O)N2C[C@@H](N)[C@H](F)[C@H]2C(=O)NCc2cccc(Cl)c2F)c2ccccc21]

The title compound was prepared according to Scheme D5 (steps B and C) from (2R,3R,4R)-4-azido-2-(3-chloro-2-fluoro-benzylcarbamoyl)-3-fluoro-pyrrolidine-1-carboxylic acid tert-butyl ester (described in scheme B19) followed by reduction of the azide as described for the preparation of Example 411. TLC, $R_f$ (EtOAc)=0.12; MS (LC-MS): 491 [M+H]+, 489 [M−H]−; $t_R$ (HPLC conditions f): 1.45 min.

Example 431

2S,3S,4S)-3-Amino-4-fluoro-pyrrolidine-1,2-dicarboxylic acid 1-[(1-carbamoyl-1H-indol-3-yl)-amide] 2-(3-chloro-2-fluorobenzylamide

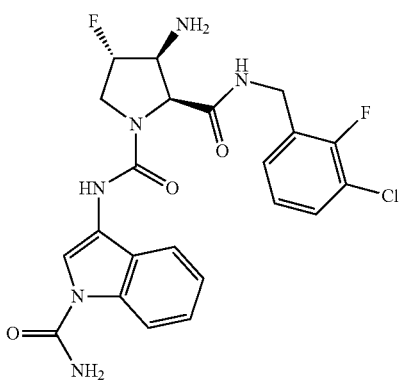 [SMILES: NC(=O)n1cc(NC(=O)N2C[C@H](F)[C@@H](N)[C@H]2C(=O)NCc2cccc(Cl)c2F)c2ccccc21]

The title compound was prepared according to Scheme D5 (steps B and C) from (2S,3S,4S)-3-azido-2-(3-chloro-2-fluoro-benzylcarbamoyl)-4-fluoro-pyrrolidine-1-carboxylic acid tert-butyl ester (described in scheme B19) followed by reduction of the azide as described for the preparation of Example 411. (Absolute stereochemistry tentatively assigned by NMR). TLC, $R_f$ (CH₂Cl₂/MeOH 95/5)=0.2; MS (LC-MS): 491 [M+H]+, 489 [M−H]−; $t_R$ (HPLC conditions f): 1.46 min.

Example 432

3-{2-[(S)-5-(3-Chloro-2-fluoro-benzylcarbamoyl)-pyrazolidin-1-yl]-2-oxo-ethyl}-indole-1-carboxylic acid amide

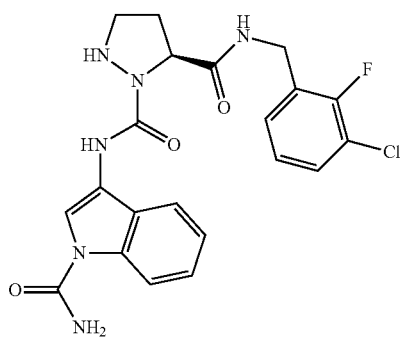 [SMILES: NC(=O)n1cc(NC(=O)N2NCC[C@H]2C(=O)NCc2cccc(Cl)c2F)c2ccccc21]

To a solution of (S)-2-(1-carbamoyl-1H-indol-3-ylcarbamoyl)-3-(3-chloro-2-fluoro-benzylcarbamoyl)-pyrazolidine-1-carboxylic acid tert-butyl ester (20 mg, 0.036 mmol) in CH$_2$Cl$_2$ (200 μL), TFA (27.6 μL, 0.358 mmol) was added, and the reaction mixture was stirred at 23° C. for 20 h. The solvents were concentrated and the crude residue was purified by preparative HPLC (Waters SunFire C18O DB, 5 μm, 19×50, eluent: 20% CH$_3$CN/80% H$_2$O to 100% CH$_3$CN in 12.5 min, CH$_3$CN and H$_2$O both containing 0.1% of HCOOH, flow 20 mL/min) to give the desired material after lyophilization of the purified fractions. MS (LC-MS): 459 [M+H]+; t$_R$ (HPLC conditions b): 3.72 min. (S)-2-(1-carbamoyl-1H-indol-3-ylcarbamoyl)-3-(3-chloro-2-fluoro-benzylcarbamoyl)-pyrazolidine-1-carboxylic acid tert-butyl ester was prepared as described in Scheme D5 step C using (S)-3-(3-chloro-2-fluoro-benzylcarbamoyl)-pyrazolidine-1-carboxylic acid tert-butyl ester (prepared as described in Scheme B5).

Example 433

3-{2-[(R)-5-(3-Chloro-2-fluoro-benzylcarbamoyl)-pyrazolidin-1-yl]-2-oxo-ethyl}-indole-1-carboxylic acid amide

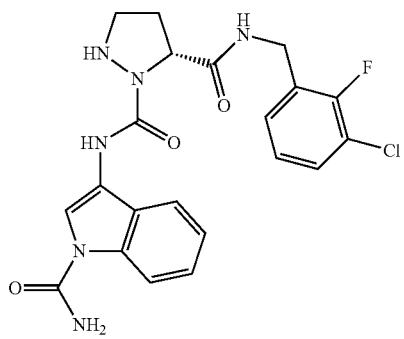 [SMILES: NC(=O)n1cc(NC(=O)N2NCC[C@@H]2C(=O)NCc2cccc(Cl)c2F)c2ccccc21]

The title compound was prepared from (R)-2-(1-carbamoyl-1H-indol-3-ylcarbamoyl)-3-(3-chloro-2-fluoro-benzylcarbamoyl)-pyrazolidine-1-carboxylic acid tert-butyl ester according to the procedure described for the preparation of Example 432 using 10 equivalents of TFA for the Boc deprotection. MS: 459 [M+H]+; t$_R$ (HPLC conditions b): 3.73 min. (R)-2-(1-Carbamoyl-1H-indol-3-ylcarbamoyl)-3-(3-chloro-2-fluoro-benzylcarbamoyl)-pyrazolidine-1-carboxylic acid tert-butyl ester was prepared as described in Scheme D5 step C using (R)-3-(3-chloro-2-fluoro-benzylcarbamoyl)-pyrazolidine-1-carboxylic acid tert-butyl ester (prepared as described in Scheme B5).

Example 434

Pyrazolidine-1,5-dicarboxylic acid 1-[(1-carbamoyl-1H-indol-3-yl)-amide]5-(3-chloro-benzylamide)

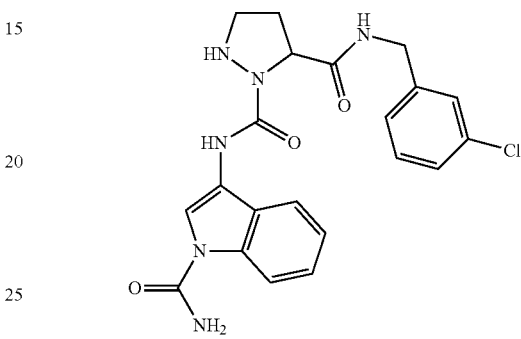

The title compound was prepared from 2-(1-carbamoyl-1H-indol-3-ylcarbamoyl)-3-(3-chloro-benzylcarbamoyl)-pyrazolidine-1-carboxylic acid tert-butyl ester according to the procedure described for the preparation of Example 432. MS (LC/MS) 441.1 [M+H]+; t$_R$ (HPLC conditions b): 3.67 min. 2-(1-Carbamoyl-1H-indol-3-ylcarbamoyl)-3-(3-chloro-benzylcarbamoyl)-pyrazolidine-1-carboxylic acid tert-butyl ester was prepared as described in Scheme D5 step C using 3-(3-chloro-benzylcarbamoyl)-pyrazolidine-1-carboxylic acid tert-butyl ester (prepared using similar protocols as described Scheme B5).

Example 435

(3S,5S)-1-(1-Carbamoyl-1H-indol-3-ylcarbamoyl)-5-(2-fluoro-3-trifluoromethoxy-phenylcarbamoyl)-pyrrolidine-3-carboxylic acid methyl ester

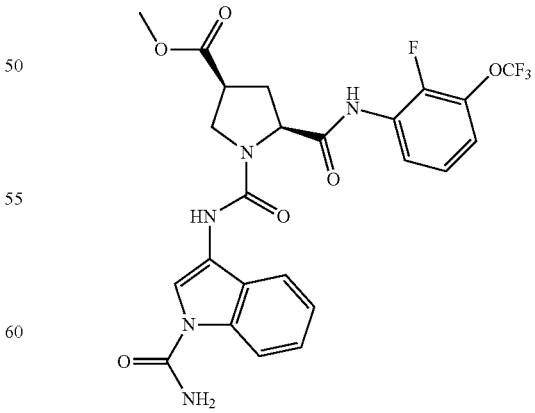

Chlorotrimethylsilane (537 μL, 4.24 mmol) was added dropwise to dry MeOH (700 μL) at 0° C., followed by a solution of (2S,4S)-4-cyano-pyrrolidine-1,2-dicarboxylic acid 1-[(1-carbamoyl-1H-indol-3-yl)-amide]2-[(2-fluoro-3-trifluoromethoxy-phenyl)-amide] Example 188 (110 mg, 0.212 mmol) in dry $CH_2Cl_2$ (600 µL). The reaction mixture was stirred at RT under $N_2$ overnight. Then cooled to 0° C., water and $CH_2Cl_2$ were added. The layers were separated and the aqueous one extracted back with $CH_2Cl_2$. The combined organic extracts were neutralized with an aqueous solution saturated with $NaHCO_3$ and brine, dried over $Na_2SO_4$, filtered and concentrated. The crude residue was purified by flash column chromatography on silica gel (c-hexane/EtOAc 1:1 to c-hexane/EtOAc 1:3 to EtOAc) to give the desired compound. $R_f$, TLC (EtOAc)=0.6; MS (LC-MS): 552.1 [M+H]+, 574.2 [M+Na]+, 550.2 [M−H]−; $t_R$ (HPLC conditions f): 1.98 min.

Example 436

2S,4S)-4-Hydroxymethyl-pyrrolidine-1,2-dicarboxylic acid 1-[(1-carbamoyl-1H-indol-3-yl)-amide]2-(3-chloro-2,6-difluoro-benzylamide

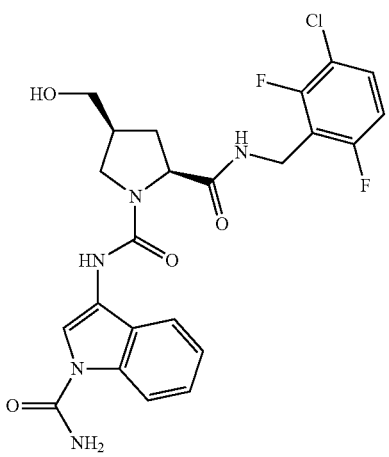 [SMILES: NC(=O)n1cc(NC(=O)N2C[C@@H](CO)C[C@H]2C(=O)NCc2c(F)ccc(Cl)c2F)c2ccccc21]

To a solution of (3S,5S)-1-(1-carbamoyl-1H-indol-3-yl-carbamoyl)-5-(3-chloro-2,6-difluoro-benzylcarbamoyl)-pyrrolidine-3-carboxylic acid methyl ester Example 353 (88 mg, 0.165 mmol) in THF (2 mL) was added Lithium borohydride 2 M in THF (0.18 mL, 0.36 mmol) and the reaction mixture was stirred at RT for 2 h under $N_2$ atmosphere. After completion, the mixture was quenched with brine and extracted twice with $CH_2Cl_2$. The combined organic layers were dried ($Na_2SO_4$), filtered and concentrated. The crude residue was purified by preparative HPLC (Waters Sunfire, C18-ODB, 5 µm, 19×50 mm, eluent: 20% to 100% $CH_3CN$ in $H_2O$ in 15 min, $CH_3CN$ and $H_2O$ containing 0.1% HCOOH, flow: 20 mL/min) to give after lyophilization of the purified fractions the desired material. $R_f$, TLC ($CH_2Cl_2$/MeOH 90:10)=0.65; MS (LC-MS): 506.2 [M+H]+, 1011.4 [2M+H]+, 504.2 [M−H]−; $t_R$ (HPLC conditions f): 1.62 min.

Example 437

(2S,4R)-4-Fluoro-pyrrolidine-1,2-dicarboxylic acid 2-[(3-bromo-5-carbamoyl-phenyl)-amide]1-[(1-carbamoyl-1H-indol-3-yl)-amide]

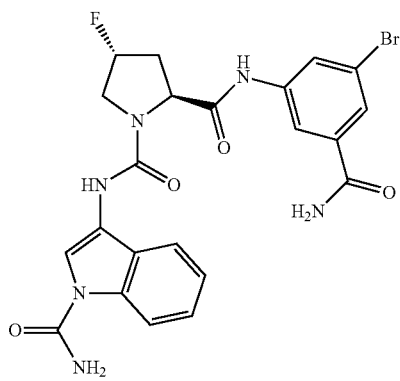 [SMILES: NC(=O)c1cc(Br)cc(NC(=O)[C@@H]2C[C@@H](F)CN2C(=O)Nc2cn(C(N)=O)c3ccccc23)c1]

To a solution of 3-bromo-5-{[(2S,4R)-1-(1-carbamoyl-1H-indol-3-ylcarbamoyl)-4-fluoro-pyrrolidine-2-carbonyl]-amino}-benzoic acid Example 159 (100 mg, 0.188 mmol), ammonium chloride (12 mg, 0.225 mmol) and HBTU (107 mg, 0.282 mmol) in DMF (3 mL) was added DIPEA (64 µl, 0.374 mmol) and the resulting solution was stirred at RT under nitrogen for 7 h. The reaction mixture was poured into water and extracted twice with EtOAc. The combined organic layers were washed water (×2), dried ($Na_2SO_4$), filtered and concentrated. The crude residue was purified by preparative HPLC (C18-ODB, 5 µm, 19×50 mm, waters, eluent: $CH_3CN$/$H_2O$+0.1% HCOOH flow: 20 mL/min, standard 20% method) to give the desired material after lyophilization of the purified fractions. TLC, $R_f$(EtOAc)=0.3; MS (LC-MS): 531/533 [M+H]+, 553/555 [M+Na]+, 529/531 [M−H]−; $t_R$ (HPLC conditions a): 2.79 min.

Example 438

(2S,4R)-4-Fluoro-pyrrolidine-1,2-dicarboxylic acid 1-[(1-carbamoyl-1H-indol-3-yl)-amide]2-[3-chloro-2-fluoro-5-(2-methoxy-ethylcarbamoyl)-benzylamide]

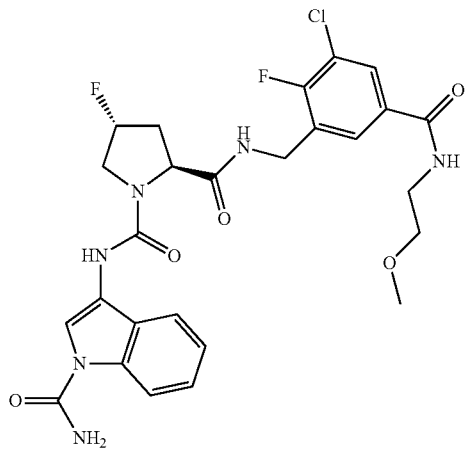 [SMILES: COCCNC(=O)c1cc(Cl)c(F)c(CNC(=O)[C@@H]2C[C@@H](F)CN2C(=O)Nc2cn(C(N)=O)c3ccccc23)c1]

559

To a mixture of 3-({[(2S,4R)-1-(1-carbamoyl-1H-indol-3-ylcarbamoyl)-4-fluoro-pyrrolidine-2-carbonyl]-amino}-methyl)-5-chloro-4-fluoro-benzoic acid Example 144 (30 mg, 0.06 mmol), 2-methoxyethylamine (5 mg, 0.07 mmol) and HATU (33 mg, 0.09 mmol) in DMF (1 mL) was added DIPEA (0.04 mL, 0.23 mmol) and the resulting solution was stirred at RT under nitrogen. The crude product was purified without aqueous workup by RP-preparative HPLC (Waters Sunfire, C18-ODB, 5 µm, 30×100 mm, 5-100% $CH_3CN/H_2O/20$ min, 100% $CH_3CN/2$ min, $CH_3CN$ and $H_2O$ containing 0.1% TFA, flow: 40 ml/min) to give the title compound. MS (LC-MS): 577.0 [M]+; $t_R$ (HPLC conditions c): 3.95 min.

Example 439

(S)-Pyrrolidine-1,2-dicarboxylic acid 1-[(1-carbamoyl-1H-indol-3-yl)-amide]2-[(3-isopropyl-isoxazol-5-yl)-amide]

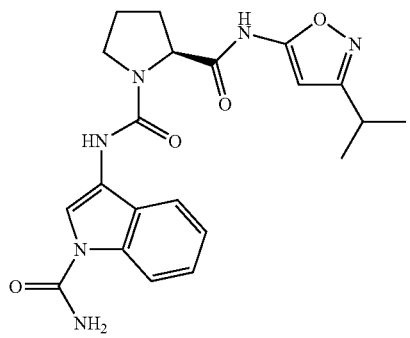 [SMILES: CC(C)c1cc(NC(=O)[C@@H]2CCCN2C(=O)Nc2cn(C(N)=O)c3ccccc23)on1]

The title compound was obtained as described in steps B and C Scheme D5 using (S)-2-(3-isopropyl-isoxazol-5-ylcarbamoyl)-pyrrolidine-1-carboxylic acid tert-butyl ester. MS (LC-MS): 425.2 [M+H]+, 447.1 [M+Na]+, 871.3 [2M+Na]+, 423.1 [M−H]−; $t_R$ (HPLC conditions a): 3.06 min.

(S)-2-(3-Isopropyl-isoxazol-5-ylcarbamoyl)-pyrrolidine-1-carboxylic acid tert-butyl ester To a mixture of Boc-L-proline (150 mg, 0.697 mmol), 3-isopropylisoxazol-5-amine (88 mg, 0.697 mmol) and HBTU (264 mg, 0.697 mmol) in DMF (7 mL) was added 2-tert-butylimino-2-diethylamino-1,3-dimethylperhydro-1,3,2-diazaphosphorine (BEMP) (201 µl, 0.697 mmol) and the reaction mixture was stirred at RT under nitrogen for 48 h. The mixture was poured into HCl 1N and extracted three times with EtOAc. The combined organic layers were washed with an aqueous saturated solution of $NaHCO_3$, with water, dried over $Na_2SO_4$, filtered and concentrated. The crude residue was purified by flash column chromatography on silica gel (c-hexane to c-hexane/EtOAc 7-3) to give the title compound. TLC, $R_f$ (c-hexane/EtOAc 1:1)=0.6; MS (LC-MS): 324.1 [M+H]+, 346.1 [M+Na]+, 669.2 [2M+Na]+, 322.1 [M−H]−; $t_R$ (HPLC conditions a): 3.42 min.

560

Example 440

(S)-Pyrrolidine-1,2-dicarboxylic acid 1-[(1-carbamoyl-1H-indol-3-yl)-amide]2-[(3-phenyl-isoxazol-5-yl)-amide]

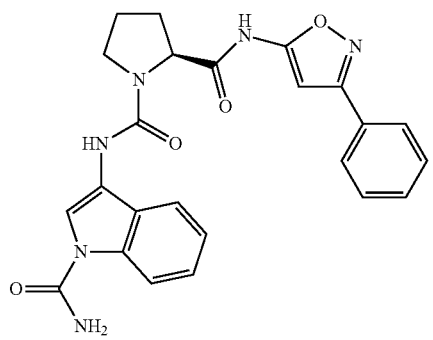 [SMILES: NC(=O)n1cc(NC(=O)N2CCC[C@H]2C(=O)Nc2cc(-c3ccccc3)no2)c2ccccc21]

The title compound was prepared in 3 steps as described for the preparation of Example 439. MS (LC/MS): 459.1 [M+H]+, 481.1 [M+Na]+, 918.3 [2M+H]+, 940.2 [2M+Na]+, 457.1 [M−H]−; $t_R$ (HPLC conditions a): 3.29 min.

Scheme D6: general protocol described for the preparation of Example 441: 3-{2-[(S)-2-(3-trifluoromethoxy-phenylcarbamoyl)-pyrrolidin-1-yl]-2-oxo-ethyl}-indole-1-carboxylic acid amide

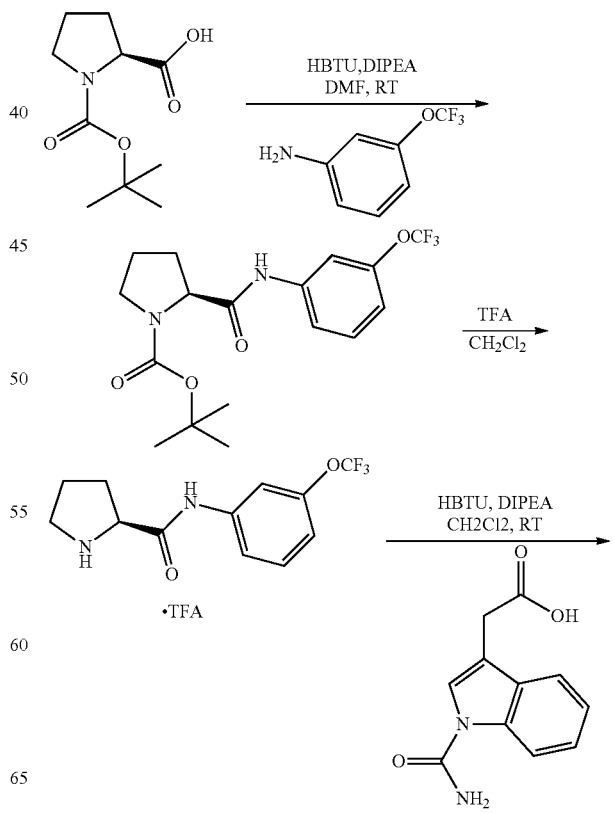

C. Example 441

3-{2-[(S)-2-(3-trifluoromethoxy-phenylcarbamoyl)-pyrrolidin-1-yl]-2-oxo-ethyl}-indole-1-carboxylic acid amide

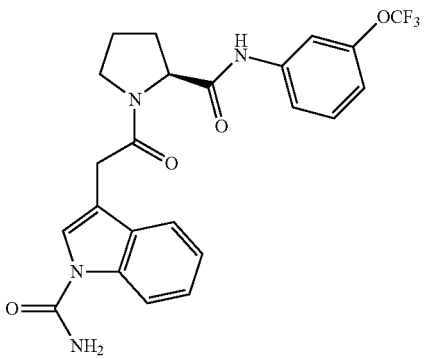

A. (S)-2-(3-Trifluoromethoxy-phenylcarbamoyl)-pyrrolidine-1-carboxylic acid tert-butyl ester The title compound was prepared according to the general procedures described in Scheme D5 Step A. TLC, $R_f$ (c-hexane/EtOAc 1:1)=0.57; MS (LC/MS): 397.1 [M+Na]+, 275.2 [MH−Boc]+, 373.3 [M−H]−; $t_R$ (HPLC conditions a) 3.81 min.

Dichloromethane can also be used instead of DMF.

B. (S)-Pyrrolidine-2-carboxylic acid (3-trifluoromethoxy-phenyl)-amide

The title compound as a TFA salt was prepared according to the general procedures described in Scheme D5 Step B. MS (LC/MS): 275.2 [M+H]+, 273.3 [M−H]−; $t_R$ (HPLC conditions a) 2.47 min.

(S)-Pyrrolidine-2-carboxylic acid (3-trifluoromethoxy-phenyl)-amide TFA salt (59.3 mg, 0.153 mmol, prepared as described in Sheme D5 steps A and B), (1-carbamoyl-1H-indol-3-yl)-acetic acid (40 mg, 0.183 mmol, prepared as described in Scheme A8) and HBTU (86.9 mg, 0.229 mmol) were dissolved in $CH_2Cl_2$ (4 mL) under nitrogen, DIPEA (52.3 µl, 0.306 mmol) was added and the reaction mixture was stirred at RT for 5 h. After completion of the reaction aqueous 1N HCl and EtOAc were added, the layers were separated and the aqueous one back-extracted twice with EtOAc. The combined organic extracts were washed with an aqueous saturated solution of $NaHCO_3$, dried over $Na_2SO_4$, filtered and concentrated. The crude residue was purified by preparative HPLC (Waters SunFire C18-ODB, 5 µm, 19×50 mm, 20% $CH_3CN/H_2O$ 2.5 min, 20-100% $CH_3CN/H_2O$ in 10 min, $CH_3CN/H_2O$ containing 0.1% HCOOH flow: 20 mL/min) to give after extraction of the pure fractions the desired compound. MS (LC/MS): 475 [M+H]+, 497 [M+Na]+; $t_R$ (HPLC conditions a) 3.47 min. DMF can also be used instead of Dichloromethane.

The examples below were prepared according to the general procedures described in Scheme D6 for the preparation of Example 441, from commercially available building blocks, if not otherwise stated (see notes at the end of table 5):

TABLE 5

| Example | Structure | Name | Characterization (end-table notes), TLC, $R_f$ (eluent); MS (LC/MS); $t_R$ (HPLC conditions); 19F NMR (100 MHz, solvent) δ (ppm) |
|---|---|---|---|
| 442 | ![structure] | 3-{2-[(2S,4R)-4-Fluoro-2-(2-fluoro-3-trifluoromethoxy-phenylcarbamoyl)-pyrrolidin-1-yl]-2-oxo-ethyl}-indole-1-carboxylic acid amide | (2,3) 511 [M + H]+, 533 [M + Na]+; $t_R$ (b): 3.88 min. |

TABLE 5-continued

| Example | Structure | Name | Characterization (end-table notes), TLC, R$_f$(eluent); MS (LC/MS); t$_R$ (HPLC conditions); 19F NMR (100 MHz, solvent) δ (ppm) |
|---|---|---|---|
| 443 | 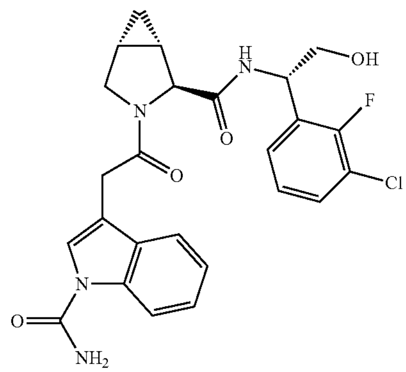 [SMILES: NC(=O)n1cc(CC(=O)N2C[C@@H]3C[C@@H]3[C@H]2C(=O)N[C@H](CO)c2cccc(Cl)c2F)c2ccccc21] | 3-(2-{(1S,2S,5R)-2-[(S)-1-(3-Chloro-2-fluoro-phenyl)-2-hydroxy-ethylcarbamoyl]-3-azabicyclo[3.1.0]hex-3-yl}-2-oxo-ethyl)-indole-1-carboxylic acid amide | (5[B9]) R$_f$(EtOAc) = 0.15; 499.3/501.3 [M + H]+, 543.3/545.3 [M + HCOO]−; t$_R$ (a): 3.0 min. |
| 444 | 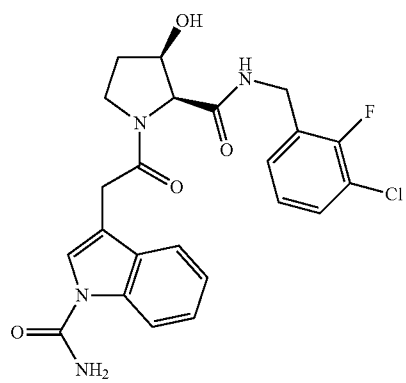 [SMILES: NC(=O)n1cc(CC(=O)N2CC[C@@H](O)[C@H]2C(=O)NCc2cccc(Cl)c2F)c2ccccc21] | 3-{2-[(2S,3R)-2-(3-Chloro-2-fluoro-benzylcarbamoyl)-3-hydroxy-pyrrolidin-1-yl]-2-oxo-ethyl}-indole-1-carboxylic acid amide | (2) 473 [M + H]+; t$_R$ (b): 3.20 min. |
| 445 | 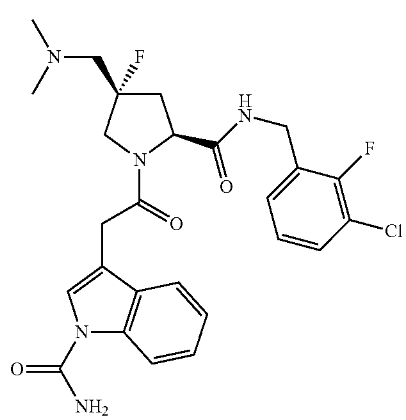 [SMILES: CN(C)C[C@@]1(F)C[C@@H](C(=O)NCc2cccc(Cl)c2F)N(C(=O)Cc2cn(C(N)=O)c3ccccc23)C1] | 3-{2-[(2S,4S)-2-(3-Chloro-2-fluoro-benzylcarbamoyl)-4-dimethylaminomethyl-4-fluoro-pyrrolidin-1-yl]-2-oxo-ethyl}-indole-1-carboxylic acid amide | (5[B15],6) 532/534 [M + H]+; t$_R$ (f): 1.53 min; 19F NMR (DMSO-d$_6$): −120, −149. |

TABLE 5-continued

| Example | Name | Characterization (end-table notes), TLC, $R_f$(eluent); MS (LC/MS); $t_R$ (HPLC conditions); 19F NMR (100 MHz, solvent) δ (ppm) |
|---|---|---|
| 446 | 3-{2-[(1R,3S,5R)-3-(3-Chloro-2-fluoro-benzylcarbamoyl)-2-aza-bicyclo[3.1.0]hex-2-yl]-2-oxo-ethyl}-indole-1-carboxylic acid amide | White solid. $R_f$(EtOAc/n-hexane 3:1) = 0.11; 469 [M + H]+; $t_R$ (b): 3.94 min. |
| 447 | 3-(2-{(2S,4R)-2-[(R)-1-(3-Chloro-2-fluoro-phenyl)-3-hydroxy-propylcarbamoyl]-4-fluoro-4-methyl-pyrrolidin-1-yl}-2-oxo-ethyl)-indole-1-carboxylic acid amide | (5[B9]) White solid, $R_f$ (CH$_2$Cl$_2$/MeOH 9:1) = 0.6; 519.3/521.3 [M + H]+, 563.3/565.3 [M + HCOO]−; $t_R$ (a): 3.1 min. |
| 448 | 3-{2-[(2S,4R)-2-(3-Chloro-2-fluoro-benzylcarbamoyl)-4-fluoro-pyrrolidin-1-yl]-2-oxo-ethyl}-indole-1-carboxylic acid amide | 475/477 [M + H]+; $t_R$ (b): 3.76 min. |
| 449 | 3-(2-{(1R,3S,5R)-3-[(S)-1-(3-Chloro-2-fluoro-phenyl)-2-hydroxy-ethyl carbamoyl]-2-aza-bicyclo[3.1.0]hex-2-yl}-2-oxo-ethyl)-indole-1-carboxylic acid amide | (5[B9]) 499.1 [M + H]+, 520.7/521.4 [M + Na]+, 543.2/545.2 [M + HCOO]−; $t_R$ (f): 1.79 min. |

TABLE 5-continued

| Example | Structure | Name | Characterization (end-table notes), TLC, R_f (eluent); MS (LC/MS); t_R (HPLC conditions); 19F NMR (100 MHz, solvent) δ (ppm) |
|---|---|---|---|
| 450 | 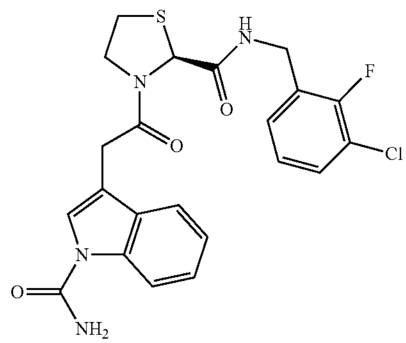 [SMILES: NC(=O)n1cc(CC(=O)N2CCS[C@H]2C(=O)NCc2cccc(Cl)c2F)c2ccccc21] | 3-{2-[(S)-2-(3-Chloro-2-fluoro-benzylcarbamoyl)-thiazolidin-3-yl]-2-oxo-ethyl}-indole-1-carboxylic acid amide | 475/477 [M + H]+; t_R (b): 3.95 min. |
| 451 | 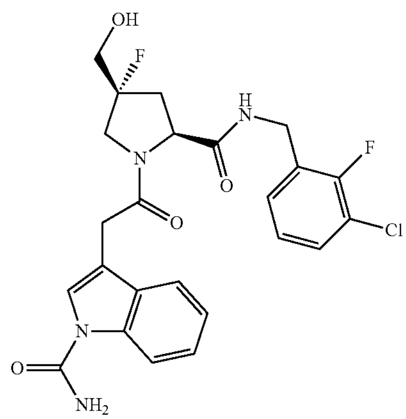 [SMILES: NC(=O)n1cc(CC(=O)N2C[C@@](F)(CO)C[C@H]2C(=O)NCc2cccc(Cl)c2F)c2ccccc21] | 3-{2-[(2S,4R)-2-(3-Chloro-2-fluoro-benzylcarbamoyl)-4-fluoro-4-hydroxymethyl-pyrrolidin-1-yl]-2-oxo-ethyl}-indole-1-carboxylic acid amide | (5[B12]). R_f (EtOAc) = 0.1; 505.1/507.2 [M + H]+, 527.0/529.2 [M + Na]+, 503/505 [M − H]−, 549.1/551 [M + HCOO]−; t_R (a): 2.96 min. |
| 452 | 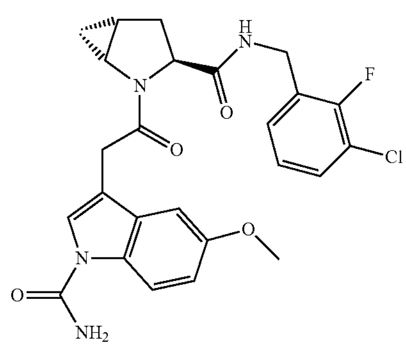 | 3-{2-[(1R,3S,5R)-3-(3-Chloro-2-fluoro-benzylcarbamoyl)-2-aza-bicylo[3.1.0]hex-2-yl]-2-oxo-ethyl}-5-methoxy-indole-1-carboxylic acid amide | (1[A4],6) R_f (EtOAc) = 0.3; 499.1/501.1 [M + H]+, 543.1/545 [M + HCOO]−, 454/456 [M − CONH_2]−; t_R (a): 2.25 min. |
| 453 | 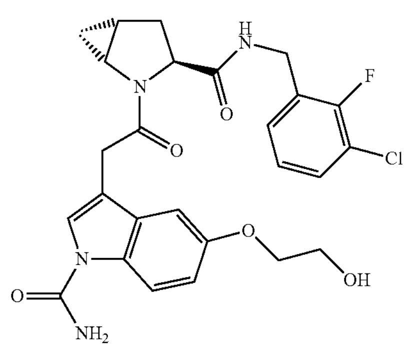 | 3-{2-[(1R,3S,5R)-3-(3-Chloro-2-fluoro-benzylcarbamoyl)-2-aza-bicylo[3.1.0]hex-2-yl]-2-oxo-ethyl}-5-(2-hydroxy-ethoxy)-indole-1-carboxylic acid amide | (1[A9]) 529.2/531.1 [M + H]+, 551/553.2 [M + Na]+, 573.1/575 [M + HCOO]−, 484.1/486.1 [M − CONH_2]−; t_R (a): 1.64 min. |

TABLE 5-continued

| Example | Name | Characterization (end-table notes), TLC, R$_f$ (eluent); MS (LC/MS); t$_R$ (HPLC conditions); 19F NMR (100 MHz, solvent) δ (ppm) |
|---|---|---|
| 454 | 3-{2-[(1R,3S,5S)-3-(3-Chloro-2-fluoro-benzylcarbamoyl)-5-methoxymethyl-2-aza-bicyclo[3.1.0]hex-2-yl]-2-oxo-ethyl}-indole-1-carboxylic acid amide | (4,5) White solid. R$_f$ (EtOAc) = 0.25; 513.3/515.3 [M + H]+, 557.4/559.4 [M + HCOO]−; t$_R$ (a): 3.23 min. |
| 455 | 5-(2-Hydroxy-ethoxy)-3-{2-oxo-2-[(1R,3S,5R)-3-(3-trifluoromethoxy-phenylcarbamoyl)-2-aza-bicyclo[3.1.0]hex-2-yl]-ethyl}-indole-1-carboxylic acid amide | (1[A9]) 547.2 [M + H]+, 564.3 [M + NH4]+, 545.2 [M − H]−, 591.2 [M + HCOO]−; t$_R$ (f): 1.85 min. |
| 456 | 3-(2-{(1R,3S,5R)-3-[(5-Chloro-thiophen-2-ylmethyl)-carbamoyl]-2-aza-bicyclo[3.1.0]hex-2-yl}-2-oxo-ethyl)-indole-1-carboxylic acid amide | R$_f$ (CH$_2$Cl$_2$/MeOH 9:1) = 0.43; 457 [M + H]+; t$_R$ (b): 3.84 min. |
| 457 | 3-(2-{(1R,3S,5R)-3-[(R)-1-(3-Chloro-2-fluoro-phenyl)-3-hydroxy-propylcarbamoyl]-2-azabicyclo[3.1.0]hex-2-yl}-2-oxo-ethyl)-indole-1-carboxylic acid amide | (5[B9]) Rf (EtOAc) = 0.2; 513.3 [M + H]+, 557.3/559.2 [M + HCOO]−; t$_R$ (f): 1.86 min. |

TABLE 5-continued

| Example | Structure | Name | Characterization (end-table notes), TLC, $R_f$ (eluent); MS (LC/MS); $t_R$ (HPLC conditions); 19F NMR (100 MHz, solvent) δ (ppm) |
|---|---|---|---|
| 458 | 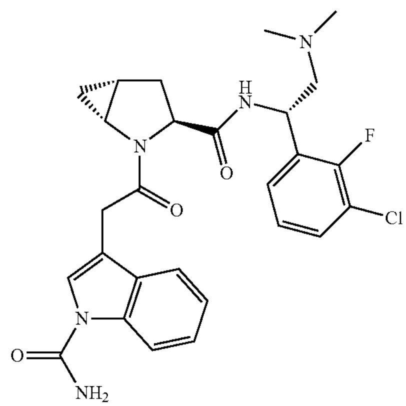 [SMILES: CN(C)C[C@@H](NC(=O)[C@@H]1C[C@H]2C[C@H]2N1C(=O)Cc1cn(C(N)=O)c2ccccc12)c1cccc(Cl)c1F] | 3-(2-{(1R,3S,5R)-3-[(S)-1-(3-Chloro-2-fluoro-phenyl)-2-dimethylamino-ethylcarbamoyl]-2-aza-bicyclo[3.1.0]hex-2-yl}-2-oxo-ethyl)-indole-1-carboxylic acid amide | (3[C4],4) White solid. $R_f$ (CH$_2$Cl$_2$/MeOH 9:1) = 0.45; 526.4/528.4 [M + H]+, 570.4/572.2 [M + HCOO]; $t_R$ (a): 2.80 min. |
| 459 | 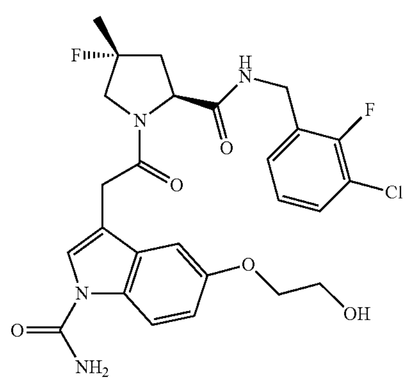 [SMILES: C[C@@]1(F)C[C@@H](C(=O)NCc2cccc(Cl)c2F)N(C(=O)Cc2cn(C(N)=O)c3ccc(OCCO)cc23)C1] | 3-{2-[(2S,4R)-2-(3-Chloro-2-fluoro-benzylcarbamoyl)-4-fluoro-4-methyl-pyrrolidin-1-yl]-2-oxo-ethyl)-5-(2-hydroxy-ethoxy)-indole-1-carboxylic acid amide | (1[A9],5[B13]) $R_f$ (EtOAc) = 0.2; 549.3/551.2 [M + H]+, 593.2/595.3 [M + HCOO]−; $t_R$ (f): 1.70 min. |
| 460 | 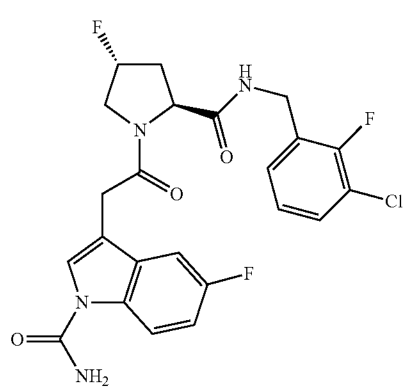 [SMILES: NC(=O)n1cc(CC(=O)N2C[C@H](F)C[C@H]2C(=O)NCc2cccc(Cl)c2F)c2cc(F)ccc21] | 3-{2-[(2S,4R)-2-(3-Chloro-2-fluoro-benzylcarbamoyl)-4-fluoro-pyrrolidin-1-yl]-2-oxo-ethyl}-5-fluoro-indole-1-carboxylic acid amide | (1[A4]) 493 [M + H]+; $t_R$ (b): 3.9 min. |

TABLE 5-continued

| Example | Name | Characterization (end-table notes), TLC, $R_f$ (eluent); MS (LC/MS); $t_R$ (HPLC conditions); 19F NMR (100 MHz, solvent) δ (ppm) |
|---|---|---|
| 461 | 3-{2-[(1R,3S,5R)-3-(3-Chloro-2-fluoro-benzylcarbamoyl)-2-aza-bicyclo[3.1.0]hex-2-yl]-2-oxo-ethyl}-2-methyl-indole-1-carboxylic acid amide | (1) 484 [M + H]+; $t_R$ (b): 3.93 min |
| 462 | 3-{2-[(S)-2-(3-Chloro-2-fluoro-benzylcarbamoyl)-thiazolidin-3-yl]-2-oxo-ethyl}-5-(2-hydroxy-ethoxy)-indole-1-carboxylic acid amide | (1[A9]) $R_f$ (EtOAc): 0.15; 535.2/537.3 [M + H]+, 579.3/581.1 [M + HCOO]−; $t_R$ (f): 1.70 min. |
| 463 | 3-(2-{(1R,2S,5S)-2-[(S)-1-(3-Chloro-2-fluoro-phenyl)-2-hydroxy-ethylcarbamoyl]-3-azabicyclo[3.1.0]hex-3-yl}-2-oxo-ethyl)-indole-1-carboxylic acid amide | (5[B9]) $R_f$ (CH$_2$Cl$_2$/MeOH 9:1) = 0.6; 499.3/501.3 [M + H]+, 543.3/545.3 [M + HCOO]−; $t_R$ (a): 3.02 min. |
| 464 | 3-(2-{(1R,3S,5R)-3-[(S)-1-(3-Chloro-2-fluoro-phenyl)-2-methoxy-ethylcarbamoyl]-2-aza-bicyclo[3.1.0]hex-2-yl}-2-oxo-ethyl)-indole-1-carboxylic acid amide | (5[B9]) White solid. $R_f$ (EtOAc) = 0.35; 513.0/515.0 [M + H]+, 557/559 [M + HCOO]−; tR (a): 3.33 min. |

TABLE 5-continued

| Example | Structure | Name | Characterization (end-table notes), TLC, $R_f$(eluent); MS (LC/MS); $t_R$ (HPLC conditions); 19F NMR (100 MHz, solvent) δ (ppm) |
|---|---|---|---|
| 465 | 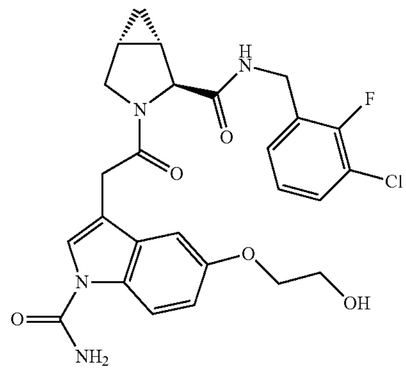 [SMILES: NC(=O)n1cc(CC(=O)N2C[C@@H]3C[C@@H]3[C@H]2C(=O)NCc2cccc(Cl)c2F)c2cc(OCCO)ccc21] | 3-{2-[(1S*,2S*,5R*)-2-(3-Chloro-2-fluoro-benzylcarbamoyl)-3-aza-bicyclo[3.1.0]hex-3-yl]-2-oxo-ethyl}-5-(2-hydroxy-ethoxy)-indole-1-carboxylic acid amide | (1[A9]) $R_f$(EtOAc) = 0.1, 529.3/531.3 [M + H]+, 573.2/575.4 [M + HCOO]–; $t_R$ (f): 1.61 min. |

(1) The (1-carbamoyl-1H-indol-3-yl)-acetic acid derivative used in step C was prepared as described in Part A; (2) $CH_2Cl_2$ was used instead of DMF in step A; (3) The substituted benzylamine or alinine derivative used in step A was prepared as described in Part C [Scheme]; (4) HCl (4M/dioxane) in dioxane was used instead of TFA in $CH_2Cl_2$ in step B; (5) The title compound was prepared according to the general procedure described in Scheme D6 steps B and C starting from the substituted proline derivative prepared as described in Part B [Scheme]; (6) DMF was used as solvent in step C.

Example 466

3-{2-[(2S,3S,4S)-3-Amino-2-(3-chloro-2-fluoro-benzylcarbamoyl)-4-fluoro-pyrrolidin-1-yl]-2-oxo-ethyl}-indole-1-carboxylic acid amide

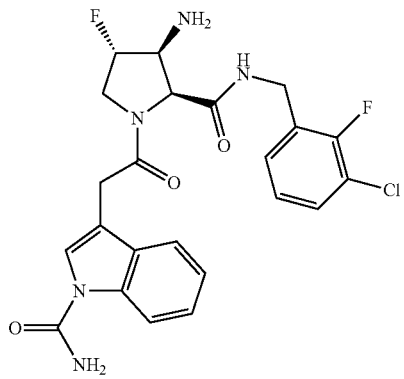 [SMILES: NC(=O)n1cc(CC(=O)N2C[C@H](F)[C@@H](N)[C@H]2C(=O)NCc2cccc(Cl)c2F)c2ccccc21]

The title compound was prepared according to Scheme D6 from (2S,3S,4S)-3-azido-2-(3-chloro-2-fluoro-benzylcarbamoyl)-4-fluoro-pyrrolidine-1-carboxylic acid tert-butyl ester (described in scheme B19) followed by reduction of the azide as described for the preparation of Example 411 (2S, 4S)-4-aminomethyl-4-fluoro-pyrrolidine-1,2-dicarboxylic acid 1-[(1-carbamoyl-1H-indol-3-yl)-amide]2-(3-chloro-2, 6-difluoro-benzylamide). TLC, $R_f$ ($CH_2Cl_2$/MeOH 95/5)= 0.3; MS (LC-MS): 490 [M+H]+, 488 [M–H]–; $t_R$ (HPLC conditions f): 1.42 min.

Example 467

3-{2-[(1R,3S,5S)-3-(3-Chloro-2-fluoro-benzylcarbamoyl)-5-hydroxymethyl-2-aza-bicyclo[3.1.0]hex-2-yl]-2-oxo-ethyl}-indole-1-carboxylic acid amide

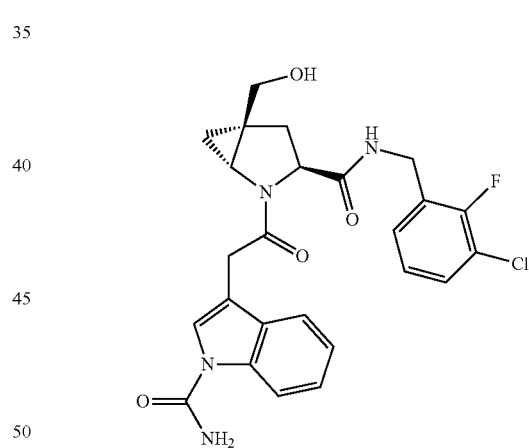

A solution of (1-carbamoyl-1H-indol-3-yl)-acetic acid (1R,3S,5S)-2-[2-(1-carbamoyl-1H-indol-3-yl)-acetyl]-3-(3-chloro-2-fluoro-benzylcarbamoyl)-2-aza-bicyclo[3.1.0]hex-5-ylmethyl ester (65 mg, 0.084 mmol) and NaOH 1N (0.5 mL, 0.5 mmol) in THF (0.4 mL)/water (40 µL) was stirred at RT for 1 h. Water and $CH_2Cl_2$ were added, the layers were separated and the aqueous one back-extracted with $CH_2Cl_2$ (×3). The combined organic extracts were dried ($Na_2SO_4$), filtered and concentrated. The crude material was purified by preparative HPLC (Waters Sunfire C18-ODB, 5 µm, 30×100 mm, eluent: 5% to 100% $CH_3CN$ in $H_2O$ in 25 min, $CH_3CN$ and $H_2O$ containing 0.1% TFA, flow: 40 mL/min). EtOAc and saturated aqueous $NaHCO_3$ were added to the combined purified fractions, the layers were separated and the aqueous one back-extracted with EtOAc (×3). The combined organic extracts were dried (Na$_2$SO$_4$), filtered and concentrated to give the desired material. TLC, R$_f$ (CH$_2$Cl$_2$/MeOH 4-1)= 0.35; MS (UPLC/MS): 499.4/501.4 [M+H]+, 521.3/523.3 [M+Na]+, 543.3/545.2; t$_R$ (HPLC conditions f): 1.75 min.

(1-Carbamoyl-1H-indol-3-yl)-acetic acid (1R,3S,5S)-2-[2-(1-carbamoyl-1H-indol-3-yl)-acetyl]-3-(3-chloro-2-fluoro-benzylcarbamoyl)-2-aza-bicyclo[3.1.0]hex-5-ylmethyl ester The title compound N,O bis-acylated was prepared according to Scheme D6 from (1R,3S,5S)-3-(3-chloro-2-fluoro-benzylcarbamoyl)-5-hydroxymethyl-2-aza-bicyclo[3.1.0]hexane-2-carboxylic acid tert-butyl ester (prepared as described in Part B Scheme B28) using HCl 4N in dioxane instead of TFA in Step B. (46.2 mg, 0.14 mmol) using (1-carbamoyl-1H-indol-3-yl)-acetic acid (60.2 mg, 0.28 mmol), HBTU (105 mg, 0.28 mmol) and DIPEA (94 µL, 0.55 mmol) in CH$_2$Cl$_2$ (1 mL). TLC, R$_f$(EtOAc)=0.25; MS (UPLC/MS): 699.4/701.3 [M+H]+, 721.3/723.3 [M+Na]+, 743.4/745.5 [M+HCOO]–; t$_R$ (HPLC conditions f): 2.05 min.

Example 468

3-{2-[(2S,4S)-4-Amino-2-(3-chloro-2-fluoro-benzylcarbamoyl)-pyrrolidin-1-yl]-2-oxo-ethyl}-indole-1-carboxylic acid amide

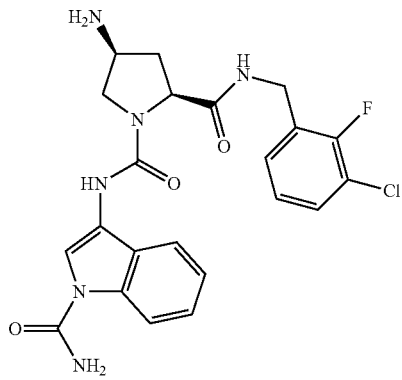

A solution of 3-{2-[(2S,4S)-4-azido-2-(3-chloro-2-fluoro-benzylcarbamoyl)-pyrrolidin-1-yl]-2-oxo-ethyl}-indole-1-carboxylic acid amide (80 mg, 0.161 mmol) in MeOH (8 mL) was hydrogenated over Pd/C 10% (8 mg, 10% w/w) at RT (1 atm). The reaction mixture was filtered through a 0.45 microns filter and concentrated under reduced pressure to give the title compound as colorless foam. MS (LC/MS): 472 [M+H]+; t$_R$ (HPLC conditions b) 2.94 min.

3-{2-[(2S,4S)-4-Azido-2-(3-chloro-2-fluoro-benzylcarbamoyl)-pyrrolidin-1-yl]-2-oxo-ethyl}-indole-1-carboxylic acid amide The title compound was prepared as described in Scheme D6 using (2S,4S)-4-azido-pyrrolidine-1,2-dicarboxylic acid 1-tert-butyl ester. TLC, Rf (EtOAc)=0.4; MS (UPLC/MS): 583.5/585.4 [M+H]+, 600.5/602.7 [M+NH$_4$]+, 605.5/607.4 [M+Na]+, 627.4/629.4 [M+HCOO]–; t$_R$ (HPLC conditions f) 2.20 min.

Example 469

3-{2-[5-(3-Chloro-benzylcarbamoyl)-pyrazolidin-1-yl]-2-oxo-ethyl}-indole-1-carboxylic acid amide

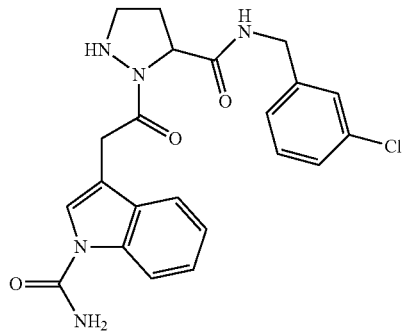 [SMILES: NC(=O)n1cc(CC(=O)N2NCCC2C(=O)NCc2cccc(Cl)c2)c2ccccc21]

A solution of 2-[2-(1-carbamoyl-1H-indol-3-yl)-acetyl]-3-(3-chloro-benzylcarbamoyl)-pyrazolidine-1-carboxylic acid tert-butyl ester (15 mg, 0.03 mmol) in HCl 4N in dioxane (69.4 µL, 0.278 mmol) was stirred at 23° C. for 1 h. The crude material was directly purified by preparative HPLC (waters SunFire C18 ODB 5 um, 19×50, 5-100% CH$_3$CN/H$_2$O/15 min, 100% CH$_3$CN/2.5 min, CH$_3$CN and H$_2$O containing 0.1% of TFA, flow: 20 mL/min) to give after lyophilization of the purified fractions the desired material. MS (LC-MS): 440 [M+H]+; t$_R$ (HPLC conditions b): 3.49 min.

2-[2-(1-carbamoyl-1H-indol-3-yl)-acetyl]-3-(3-chloro-benzylcarbamoyl)-pyrazolidine-1-carboxylic acid tert-butyl ester The title compound was prepared as described in Scheme D6 using 3-(3-chloro-benzylcarbamoyl)-pyrazolidine-1-carboxylic acid tert-butyl ester (prepared using a similar procedure as the one described in Scheme B5 for the preparation of 3-(3-chloro-2-fluoro-benzylcarbamoyl)-pyrazolidine-1-carboxylic acid tert-butyl ester).

Example 470

3-{2-[(2S,4S)-4-Aminomethyl-2-(3-chloro-2-fluoro-benzylcarbamoyl)-4-fluoro-pyrrolidin-1-yl]-2-oxo-ethyl}-indole-1-carboxylic acid amide

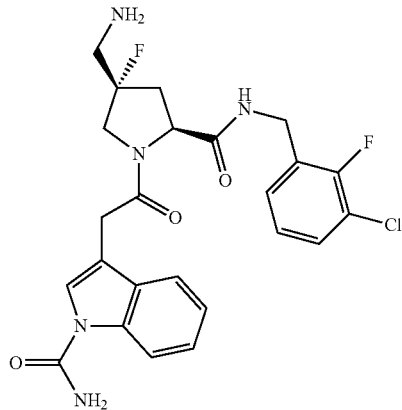 [SMILES: NC[C@@]1(F)C[C@@H](C(=O)NCc2cccc(Cl)c2F)N(C(=O)Cc2cn(C(N)=O)c3ccccc23)C1]

The title compound was prepared according to Scheme D6 from (2S,4R)-4-azidomethyl-2-(3-chloro-2-fluoro-benzylcarbamoyl)-4-fluoro-pyrrolidine-1-carboxylic acid tert-butyl ester (prepared as described scheme B15) using DMF as solvent followed by azide reduction as described for the preparation of Example 411. MS (LC-MS): 504/506 [M+H]+; $t_R$ (HPLC conditions f): 1.42 min; $^{19}$F NMR (100 MHz, DMSO-$d_6$) δ (ppm): −120, −152.

Example 471

3-{2-[(2S,4S)-4-Aminomethyl-2-(3-chloro-2,6-difluoro-benzylcarbamoyl)-4-fluoro-pyrrolidin-1-yl]-2-oxo-ethyl}-indole-1-carboxylic acid amide

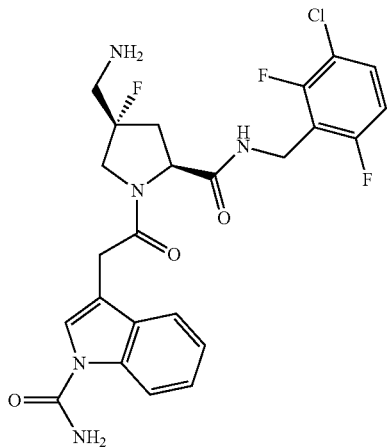 [SMILES: NC[C@@]1(F)C[C@@H](C(=O)NCc2c(F)ccc(Cl)c2F)N(C(=O)Cc2cn(C(N)=O)c3ccccc23)C1]

The title compound was prepared according to Scheme D6 from (2S,4R)-4-azidomethyl-2-(3-chloro-2,6-difluoro-benzylcarbamoyl)-4-fluoro-pyrrolidine-1-carboxylic acid tert-butyl ester (prepared using similar protocols as described for (2S,4R)-4-azidomethyl-2-(3-chloro-2-fluoro-benzylcarbamoyl)-4-fluoro-pyrrolidine-1-carboxylic acid tert-butyl ester scheme B15) using DMF as solvent followed by azide reduction as described for the preparation of Example 411. MS (UPLC-MS): 522/524 [M+H]+; $t_R$ (HPLC conditions f): 1.47 min; $^{19}$F NMR (100 MHz, DMSO-$d_6$) δ (ppm): −117 (2F), −150.

Example 472

3-{2-[(1R,3S,5R)-3-(3-Chloro-2-fluoro-benzylcarbamoyl)-2-aza-bicyclo[3.1.0]hex-2-yl]-2-oxo-ethyl}-5-(2-dimethylamino-ethoxy)-indole-1-carboxylic acid amide

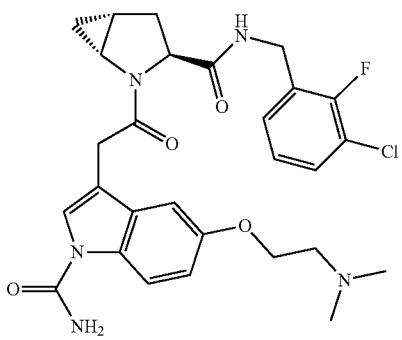 [SMILES: CN(C)CCOc1ccc2c(c1)c(CC(=O)N1[C@@H]3C[C@@H]3C[C@H]1C(=O)NCc1cccc(Cl)c1F)cn2C(N)=O]

Methanesulfonic acid 2-(1-carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-5-yloxy)-ethyl ester in a solution of dimethylamine 5.6 M in EtOH (1 mL) was sealed in a microwave vial and heated at 70° C. for 2 h (Emrys Optimizer; personal chemistry). The reaction mixture was quenched by addition of saturated aqueous NaHCO$_3$, extracted with EtOAc, dried (Na$_2$SO$_4$) and evaporated in vacuo. Then crude residue was purified by catch-release (SCX Tosic Acid-1 g from Silicycle; eluent MeOH (10 mL) to 2M ammonia in MeOH (10 mL)) to give the desired material which was precipitated in Et$_2$O. MS (UPLC/MS): 556.5/558.5 [M+H]+, 600.4/602.5 [M+HCOO]−; $t_R$ (HPLC conditions f): 1.46 min.

Methanesulfonic acid 2-(1-carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-5-yloxy)-ethyl ester To a solution of Example 453: 3-{2-[(1R,3S,5R)-3-(3-chloro-2-fluoro-benzylcarbamoyl)-2-aza-bicyclo[3.1.0]hex-2-yl]-2-oxo-ethyl}-5-(2-hydroxy-ethoxy)-indole-1-carboxylic acid amide (45 mg, 0.08 mmol) and Et$_3$N (56 μL, 0.41 mmol) in CH$_2$Cl$_2$ (1 mL) at 0° C. was added methanesulfonyl chloride (31 μL, 0.41 mmol) and the white suspension was stirred at RT under nitrogen overnight. Et3N (56 μL, 0.41 mmol) and methanesulfonyl chloride (31 μL, 0.41 mmol) were further added and the mixture was further stirred for 1.5 h to complete the reaction. The reaction mixture was quenched by addition of saturated aqueous NaHCO$_3$, extracted with CH$_2$Cl$_2$, dried (Na$_2$SO$_4$) and evaporated in vacuo. The crude residue was purified by column chromatography on silica gel (eluent: EtOAc to EtOAc/acetone 1-1). TLC, Rf (EtOAc)= 0.2; MS (UPLC/MS): 607.4/609.3 [M+H]+, 629.2/631.2 [M+Na]+, 562.2/564.1 [M−CONH$_2$]−, 651.3/653.3 [M+HCOO]−; $t_R$ (HPLC conditions f): 1.88 min.

Example 473

(1-Carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid

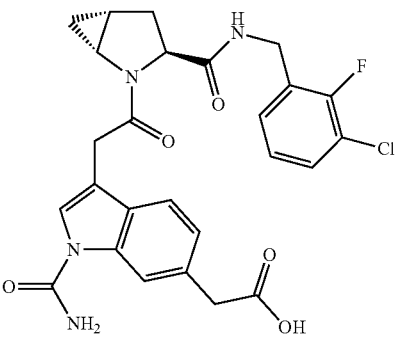 [SMILES: NC(=O)n1cc(CC(=O)N2[C@@H]3C[C@@H]3C[C@H]2C(=O)NCc2cccc(Cl)c2F)c2ccc(CC(=O)O)cc21]

A solution of (1-carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid tert-butyl ester (265 mg, 0.46 mmol) and TFA (1.05 mL, 23.5 mmol) in CH$_2$Cl$_2$ (4.8 mL) was stirred at RT for 3 h. The reaction mixture was concentrated taken up in EtOAC, c-hexane was added until a precipitate formed and was filtered. Further purification on trimethylaminopropyl cartridge (Mega Bond Elut-SAX, 1 g 6 mL, from Varian) (eluent: CH₃CN 10 mL then HCl 0.1N in CH₃CN 10 mL) gave a solid which was precipitated in Et₂O. MS (UPLC): 527.4/529.5 [M+H]+, 544.4/546.3 [M+NH₄]+, 571.3/573.4 [M+HCOO]−; $t_R$ (HPLC conditions f): 1.74 min.

(1-Carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid tert-butyl ester The title compound was prepared according to the protocol described in Scheme D6 using 6-tert-butoxycarbonylmethyl-1-carbamoyl-1H-indol-3-yl)-acetic acid (prepared as described in Part A) and (2S,4R)-2-(3-chloro-2-fluoro-benzylcarbamoyl)-4-fluoro-4-methyl-pyrrolidine-1-carboxylic acid tert-butyl ester (prepared as described in Scheme B13). TLC, $R_f$ (EtOAc)=0.2; MS (UPLC): 549.3/551.2 [M+H]+, 593.2/595.3 [M+HCOO]−; $t_R$ (HPLC conditions f): 1.70 min.

Example 474

3-{2-[(1R,3S,5R)-3-(3-Chloro-2-fluoro-benzylcarbamoyl)-2-aza-bicyclo[3.1.0]hex-2-yl]-2-oxo-ethyl}-6-(2-hydroxy-ethyl)-indole-1-carboxylic acid amide

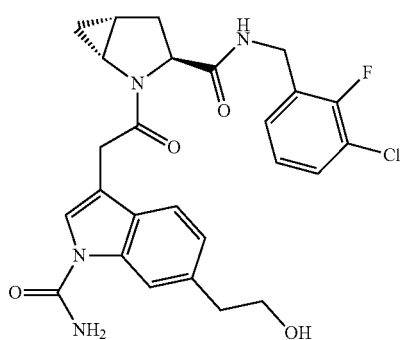 [SMILES: NC(=O)n1cc(CC(=O)N2[C@@H]3C[C@@H]3C[C@H]2C(=O)NCc2cccc(Cl)c2F)c2ccc(CCO)cc21]

To a solution of (1-carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid methyl ester (35 mg, 0.047 mmol) in THF (0.25 mL) was added LiBH₄ (2 M in THF, 47 μL, 0.094 mmol) under nitrogen atmosphere. And the reaction mixture was stirred at RT for 2 h. LiBH4 (2 M in THF, 47 μL, 0.094 mmol) was added again and the mixture was further stirred at RT for 2 h, then poured into aqueous NaHCO₃, extracted twice with EtOAc, dried (Na₂SO₄) and the solvent was removed in vacuo. The crude material was purified by prep HPLC (Waters Sunfire, C18-ODB, 5 μm, 19×50 mm, eluent: 20% to 100% (CH₃CN/MeOH 1-4)/H₂O in 15 min, (CH₃CN/MeOH 1-4) and H₂O containing 0.1% HCOOH, flow: 20 mL/min) to give after lyophilization of the purified fraction the desired material as a white powder. TLC, $R_f$ (EtOAc)=0.25; MS (UPLC/MS): 513.4/515.5 [M+H]+, 530.5/532.7 [M+NH₄]+, 557.4/559.4 [M+HCOO]−; $t_R$ (HPLC conditions f): 1.74 min.

(1-Carbamoyl-3-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid methyl ester To a suspension of Example 473: (1-carbamoyl-3-{2-[(1R, 3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid (98 mg, 0.18 mmol) in CH₂Cl₂ (1 mL) were added (40 mg, 0.195 mmol), DMAP (2.2 mg, 0.018 mmol) and MeOH (7.17 μL, 0.177 mmol) and the mixture was stirred at RT under nitrogen for 1.5 h. The mixture was poured into water and extracted twice with CH₂Cl₂. The combined organic layers were dried over Na₂SO₄, filtered and concentrated. The crude material was taken up in MeOH and filtered. The filtrate was concentrated and purified by prep HPLC (Waters Sunfire, C18-ODB, 5 μm, 19×50 mm, eluent: 20% to 100% (CH₃CN/MeOH 1-4)/H₂O in 22.5 min, (CH₃CN/MeOH 1-4) and H₂O containing 0.1% HCOOH, flow: 20 mL/min). TLC, $R_f$ (EtOAc)=0.35; MS (UPLC/MS): 541.4/543.4 [M+H]+, 558.5/560.5 [M+NH₄]+, 563.4/565.0 [M+Na]+, 585.3/587.3 [M+HCOO]−; $t_R$ (HPLC conditions f): 1.92 min.

Scheme D7: preparation of Example 475: 1-{2-[(1R,3S,5R)-3-(3-Chloro-2-fluoro-benzylcarbamoyl)-2-aza-bicyclo[3.1.0]hex-2-yl]-2-oxo-ethyl}-1H-indole-3-carboxylic acid amide

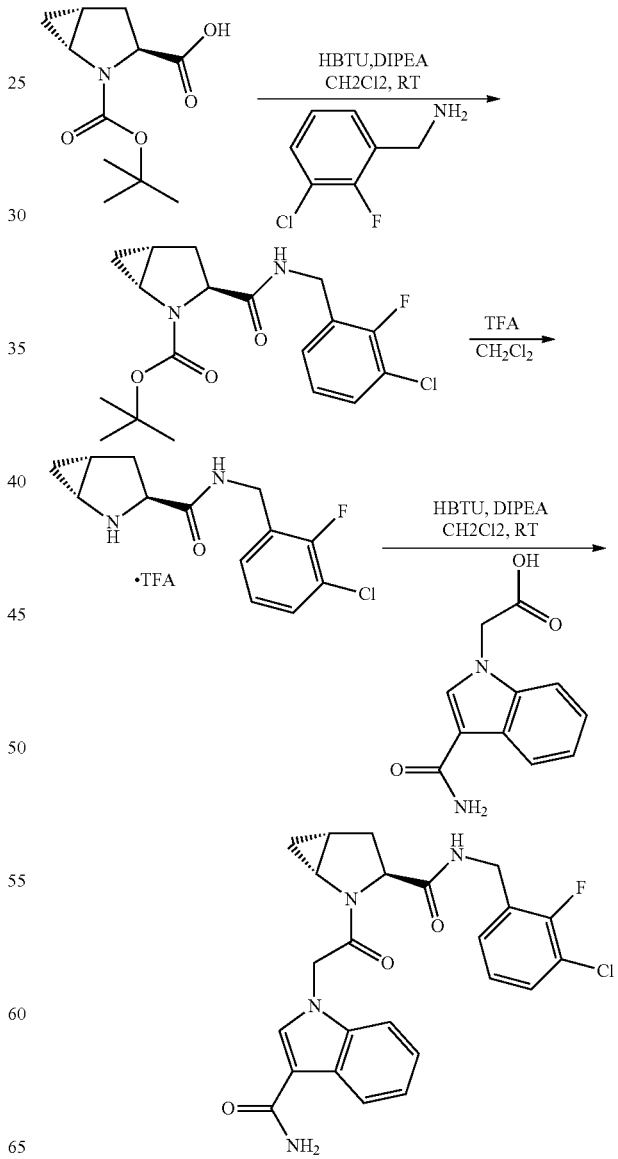

A. (1R,3S,5R)-3-(3-Chloro-2-fluoro-benzylcarbamoyl)-2-aza-bicyclo[3.1.0]hexane-2-carboxylic acid tert-butyl ester To a mixture of (1R,3S,5R)-2-aza-bicyclo[3.1.0]hexane-2,3-dicarboxylic acid 2-tert-butyl ester (4 g, 17.6 mmol), 3-chloro-2-fluorobenzylamine (3.09 g, 19.36 mmol) and HBTU (10.01 g, 26.4 mmol) in $CH_2Cl_2$ (88 mL) was added DIPEA (6.03 mL, 35.2 mmol) and the resulting yellow solution was stirred at RT under nitrogen. The reaction mixture was poured into HCl 1N and extracted twice with $CH_2Cl_2$. The combined organic layers were neutralized with sat. $NaHCO_3$, dried over $Na_2SO_4$, filtered and concentrated. The crude residue was purified by fish chromatography (c-hexane to c-hexane/EtOAc 1-9) to give the desired material as a white solid. TLC, $R_f$ (EtOAc)=0.75; MS (LC/MS): 391.1/393.1 [M+Na]+, 269.0/271.0 [MH−Boc]+, 413.0/415.1 [M+HCOO]−; $t_R$ (HPLC conditions f) 2.1 min.

DMF can also be used instead of Dichloromethane.

B. (1R,3S,5R)-2-Aza-bicyclo[3.1.0]hexane-3-carboxylic acid 3-chloro-2-fluoro-benzylamide To a solution of (1R,3S,5R)-3-(3-chloro-2-fluoro-benzylcarbamoyl)-2-aza-bicyclo[3.1.0]hexane-2-carboxylic acid tert-butyl ester (6.35 g, 17.22 mmol) in $CH_2Cl_2$ (60 mL) was added TFA (13.18 mL, 172 mmol) and the solution was stirred at RT for 3 h. The crude reaction mixture was concentrated under vacuum, $Et_2O$ was added and the white precipitate was filtered off to give the desired compound as a TFA salt. MS (LC/MS): 287.0 [M+H]+, 285.1 [M−H]−; $t_R$ (HPLC conditions f) 1.27 min.

C. Example 475

1-{2-[(1R,3S,5R)-3-(3-Chloro-2-fluoro-benzylcarbamoyl)-2-aza-bicyclo[3.1.0]hex-2-yl]-2-oxo-ethyl}-1H-indole-3-carboxylic acid amide The mixture of (1R,3S,5R)-2-aza-bicyclo[3.1.0]hexane-3-carboxylic acid 3-chloro-2-fluoro-benzylamide trifluoroacetate (70.2 mg, 0.183 mmol), (3-carbamoyl-indol-1-yl)acetic acid [1016689-54-5] (40.0 mg, 0.183 mmol), HBTU (104 mg, 0.275 mmol) and DIPEA (0.128 mL, 0.733 mmol) in $CH_2Cl_2$ (8 mL) was stirred at RT over 60 h. The reaction mixture was then diluted with $CH_2Cl_2$, and the solution was washed twice with 0.1N HCl. The precipitate formed in the aqueous layer was filtered off, washed with $CH_2Cl_2$ and dried in vacuo to afford the title product as a white solid. MS (LC/MS): 469 [M+H]+, 491 [M+Na]+; $t_R$ (HPLC conditions b): 3.56 min.

Alternatively, for final compounds containing a basic residue the pure HPLC fractions were neutralized with an aqueous saturated solution of $Na_2CO_3$, extracted with EtOAc, dried ($Na_2SO_4$), filtered and concentrated to give the desired material as a free base.

The examples below were prepared according to the general procedure described in Scheme D7 for the preparation of Example 475 commercially available building blocks if not otherwise mentioned (see notes at the end of table 6):

TABLE 6

| Example | Structure | Name | Characterization (end-table notes), TLC, $R_f$(eluent); MS (LC/MS); $t_R$ (HPLC conditions) |
|---|---|---|---|
| 476 | 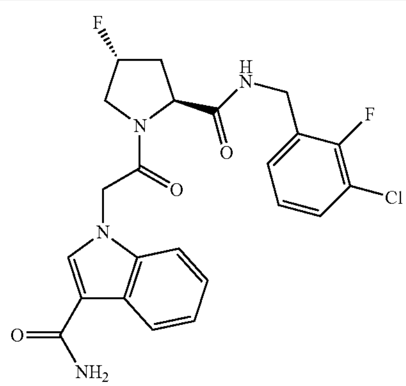 | 1-{2-[(2S,4R)-2-(3-Chloro-2-fluoro-benzylcarbamoyl)-4-fluoro-pyrrolidin-1-yl]-2-oxo-ethyl}-1H-indole-3-carboxylic acid amide | White solid. 475 [M + H]+, $t_R$ (b): 4.19 min. |
| 477 | 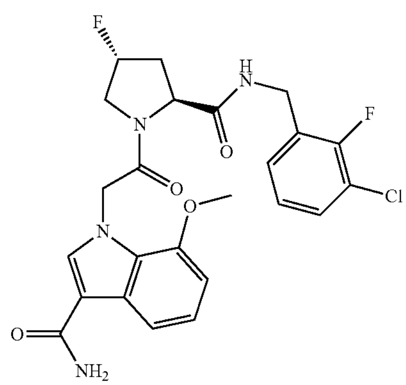 [SMILES: COc1cccc2c(C(N)=O)cn(CC(=O)N3C[C@H](F)C[C@H]3C(=O)NCc3cccc(Cl)c3F)c12] | 1-{2-[(2S,4R)-2-(3-Chloro-2-fluoro-benzylcarbamoyl)-4-fluoro-pyrrolidin-1-yl]-2-oxo-ethyl}-7-methoxy-1H-indole-3-carboxylic acid amide | (4[A11],5) Solid. 505 [M + H]+, 527 [M + Na]+; $t_R$ (c): 4.27 min |

TABLE 6-continued

| Example | Structure | Name | Characterization (end-table notes), TLC, R_f (eluent); MS (LC/MS); t_R (HPLC conditions) |
|---|---|---|---|
| 478 | 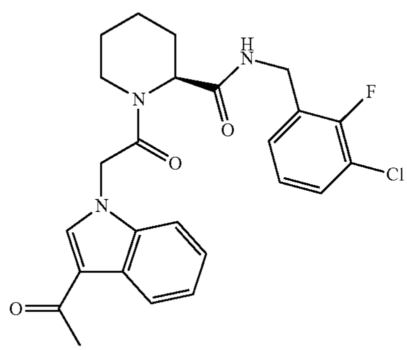 [SMILES: CC(=O)c1cn(CC(=O)N2CCCC[C@H]2C(=O)NCc2cccc(Cl)c2F)c2ccccc12] | (S)-1-[2-(3-Acetyl-indol-1-yl)-acetyl]-piperidine-2-carboxylic acid 3-chloro-2-fluoro-benzylamide | White solid. 470 [M + H]+, 492 [M + Na]+; t_R (c): 5.01 min. |
| 479 | 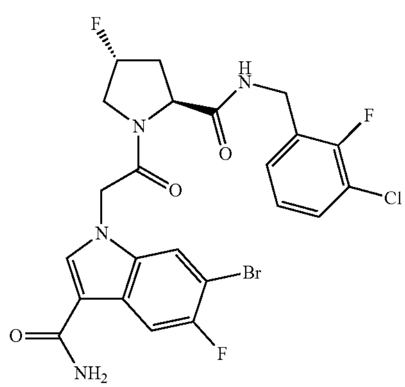 [SMILES: NC(=O)c1cn(CC(=O)N2C[C@H](F)C[C@H]2C(=O)NCc2cccc(Cl)c2F)c2cc(Br)c(F)cc12] | 6-Bromo-1-{2-[(2S,4R)-2-(3-chloro-2-fluoro-benzylcarbamoyl)-4-fluoro-pyrrolidin-1-yl]-2-oxo-ethyl}-5-fluoro-1H-indole-3-carboxylic acid amide | (4,5) Solid. 573.0 [M + H]+; t_R (k): 3.35 min. |
| 480 | 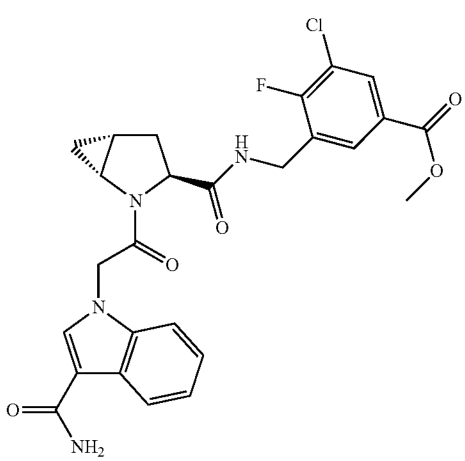 [SMILES: COC(=O)c1cc(Cl)c(F)c(CNC(=O)[C@@H]2C[C@H]3C[C@H]3N2C(=O)Cn2cc(C(N)=O)c3ccccc32)c1] | 3-[({(1R,3S,5R)-2-[2-(3-Acetyl-indol-1-yl)-acetyl]-2-aza-bicyclo[3.1.0]hexane-3-carbonyl}-amino)-methyl]-5-chloro-4-fluoro-benzoic acid methyl ester | (1) White solid. R_f (EtOAc 100) = 0.35; 526.0 [M + H]+, 548.0 [M + Na]+; t_R (c): 4.90 min. |

TABLE 6-continued

| Example | Structure | Name | Characterization (end-table notes), TLC, R_f (eluent); MS (LC/MS); t_R (HPLC conditions) |
|---|---|---|---|
| 481 | 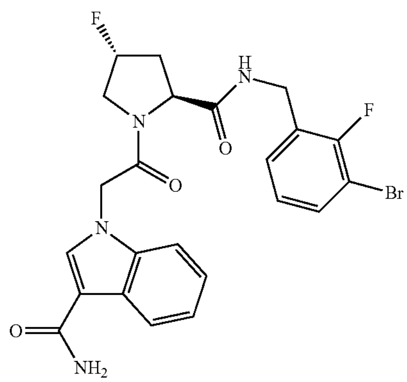 | 1-{2-[(2S,4R)-2-(3-Bromo-2-fluoro-benzylcarbamoyl)-4-fluoro-pyrrolidin-1-yl]-2-oxo-ethyl}-1H-indole-3-carboxylic acid amide | (1,5) R_f (CH_2Cl_2/MeOH 95:5) = 0.24; 521.0 [M + H]+; t_R (k): 3.10 min. |
| 482 | 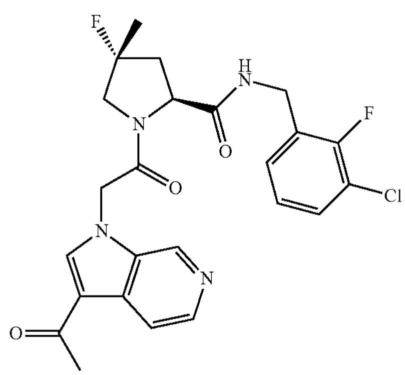 [SMILES: CC(=O)c1cn(CC(=O)N2C[C@](C)(F)C[C@H]2C(=O)NCc2cccc(Cl)c2F)c2cnccc12] | (2S,4R)-1-[2-(3-Acetyl-pyrrolo[2,3-c]pyridin-1-yl)-acetyl]-4-fluoro-4-methyl-pyrrolidine-2-carboxylic acid 3-chloro-2-fluoro-benzylamide | (3[B13], 4[A15]) R_f (CH_2Cl_2/MeOH 9:1) = 0.40; 489.2/491.2 [M + H]+, 533.3/535.2 [M + HCOO]−; t_R (f): 1.49 min. |
| 483 | 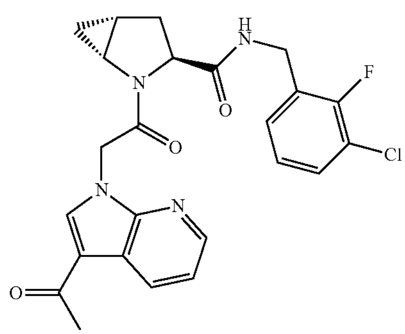 | (1R,3S,5R)-2-[2-(3-Acetyl-pyrrolo[2,3-b]pyridin-1-yl)-acetyl]-2-aza-bicyclo[3.1.0]hexane-3-carboxylic acid 3-chloro-2-fluoro-benzylamide | (4[A13]) R_f (EtOAc) = 0.10; 469.3/471.3 [M + H]+, 937.5/939.5 [2M + H]+, 513.3/515.3 [M + HCOO]−, 981.4/983.5 [2M + HCOO]−; t_R (f): 1.90 min. |
| 484 | 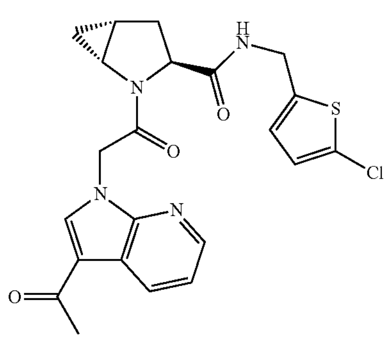 [SMILES: CC(=O)c1cn(CC(=O)N2[C@@H]3C[C@@H]3C[C@H]2C(=O)NCc2ccc(Cl)s2)c2ncccc12] | (1R,3S,5R)-2-[2-(3-Acetyl-pyrrolo[2,3-b]pyridin-1-yl)-acetyl]-2-aza-bicyclo[3.1.0]hexane-3-carboxylic acid (5-chloro-thiophen-2-ylmethyl)-amide | (4[A13]) R_f (CH_2Cl_2/MeOH 4:1) = 0.45; 457.3/459.2 [M + H]+, 479.2/481,1 [M + Na]+, 501.3/503.2 [M + HCOO]−; t_R (f): 1.86 min. |

| Example | Structure | Name | Characterization (end-table notes), TLC, $R_f$ (eluent); MS (LC/MS); $t_R$ (HPLC conditions) |
|---|---|---|---|
| 485 | 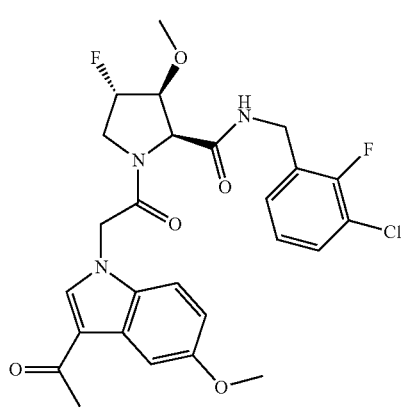 [SMILES: COc1ccc2c(c1)c(C(C)=O)cn2CC(=O)N1C[C@H](F)[C@@H](OC)[C@H]1C(=O)NCc1cccc(Cl)c1F] | (2S,3S,4S)-1-[2-(3-Acetyl-5-methoxy-indol-1-yl)-acetyl]-4-fluoro-3-methoxy-pyrrolidine-2-carboxylic acid 3-chloro-2-fluoro-benzylamide | (3[B24],4) 578 [M + HCOO]−, 534 [M + H]+; $t_R$ (f): 1.99 min. |
| 486 | 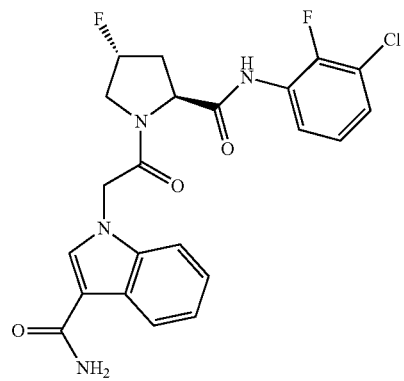 [SMILES: NC(=O)c1cn(CC(=O)N2C[C@H](F)C[C@H]2C(=O)Nc2cccc(Cl)c2F)c2ccccc12] | 1-{2-[(2S,4R)-2-(3-Chloro-2-fluoro-phenylcarbamoyl)-4-fluoro-pyrrolidin-1-yl]-2-oxo-ethyl}-1H-indole-3-carboxylic acid amide | 461 [M + H]+; $t_R$ (b): 4.25 min. |
| 487 | 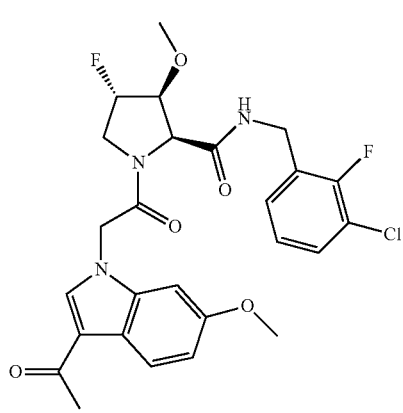 [SMILES: COc1ccc2c(C(C)=O)cn(CC(=O)N3C[C@H](F)[C@@H](OC)[C@H]3C(=O)NCc3cccc(Cl)c3F)c2c1] | (2S,3S,4S)-1-[2-(3-Acetyl-6-methoxy-indol-1-yl)-acetyl]-4-fluoro-3-methoxy-pyrrolidine-2-carboxylic acid 3-chloro-2-fluoro-benzylamide | (3[B24],4[A13]) and (3-acetyl-6-methoxy-indol-1-yl)-acetic acid (prepared as described in Part A). 578 [M + HCOO]−, 534 [M + H]+; $t_R$ (f): 2.03 min. |

| Example | Structure | Name | Characterization (end-table notes), TLC, R_f (eluent); MS (LC/MS); t_R (HPLC conditions) |
|---|---|---|---|
| 488 | 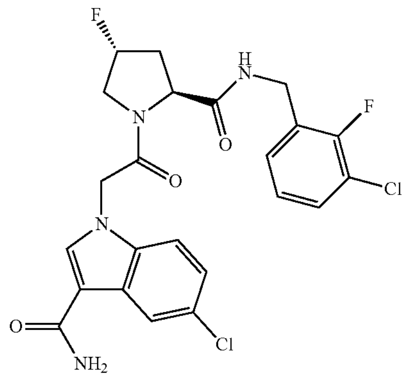 [SMILES: NC(=O)c1cn(CC(=O)N2C[C@H](F)C[C@H]2C(=O)NCc2cccc(Cl)c2F)c2ccc(Cl)cc12] | 5-Chloro-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide | (4[A11]) White solid. 509/510 [M + H]+, 532/533 [M + Na]+; t_R (b): 4.50 min. |
| 489 | 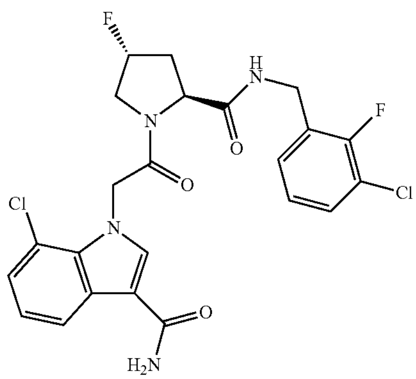 [SMILES: NC(=O)c1cn(CC(=O)N2C[C@H](F)C[C@H]2C(=O)NCc2cccc(Cl)c2F)c2c(Cl)cccc12] | 7-Chloro-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide | (4[A11]) White solid. 509/510 [M + H]+, 532/533 [M + Na]+; t_R (b): 4.42 min. |
| 490 | 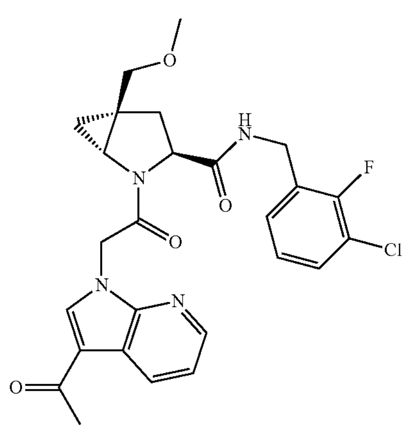 [SMILES: COC[C@@]12C[C@@H](C(=O)NCc3cccc(Cl)c3F)N(C(=O)Cn3cc(C(C)=O)c4cccnc43)[C@@H]1C2] | (1R,3S,5S)-2-[2-(3-Acetyl-pyrrolo[2,3-b]pyridin-1-yl)-acetyl]-5-methoxymethyl-2-aza-bicyclo[3.1.0]hexane-3-carboxylic acid 3-chloro-2-fluoro-benzylamide | (2,3,4[A13]) White solid. R_f (EtOAc) = 0.25; 513.3/515.3 [M + H]+, 557.4/559.4 [M + HCOO]−; t_R (a): 3.23 min. |

TABLE 6-continued

| Example | Structure | Name | Characterization (end-table notes), TLC, R_f (eluent); MS (LC/MS); t_R (HPLC conditions) |
|---|---|---|---|
| 491 | 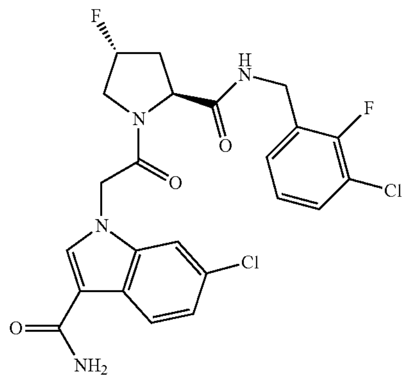 [SMILES: NC(=O)c1cn(CC(=O)N2C[C@H](F)C[C@H]2C(=O)NCc2cccc(Cl)c2F)c2cc(Cl)ccc12] | 6-Chloro-1-{2-[(2S,4R)-2-(3-chloro-2-fluoro-benzyl-carbamoyl)-4-fluoro-pyrrolidin-1-yl]-2-oxo-ethyl}-1H-indole-3-carboxylic acid amide | (4) White solid. 509/510 [M + H]+; 532/533 [M + Na]+; t_R (b): 4.52 min. |
| 492 | 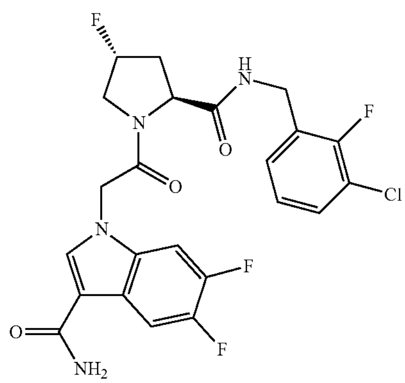 [SMILES: NC(=O)c1cn(CC(=O)N2C[C@H](F)C[C@H]2C(=O)NCc2cccc(Cl)c2F)c2cc(F)c(F)cc12] | 1-{2-[(2S,4R)-2-(3-Chloro-2-fluoro-benzylcarbamoyl)-4-fluoro-pyrrolidin-1-yl]-2-oxo-ethyl}-5,6-difluoro-1H-indole-3-carboxylic acid amide | (4,5) Solid. 511 [M + H]+; t_R (k): 3.28 min. |
| 493 | 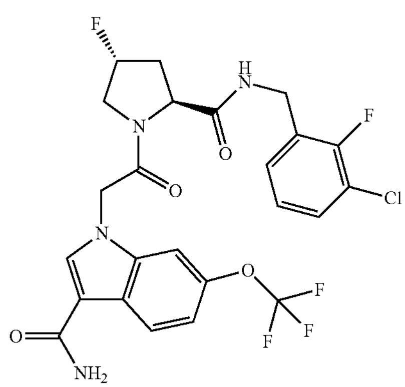 [SMILES: NC(=O)c1cn(CC(=O)N2C[C@H](F)C[C@H]2C(=O)NCc2cccc(Cl)c2F)c2cc(OC(F)(F)F)ccc12] | 1-{2-[(2S,4R)-2-(3-Chloro-2-fluoro-benzylcarbamoyl)-4-fluoro-pyrrolidin-1-yl]-2-oxo-ethyl}-6-trifluoromethoxy-1H-indole-3-carboxylic acid amide | (4,5) Solid. 560.0 [M + H]+; t_R (k): 3.45 min. |
| 494 | 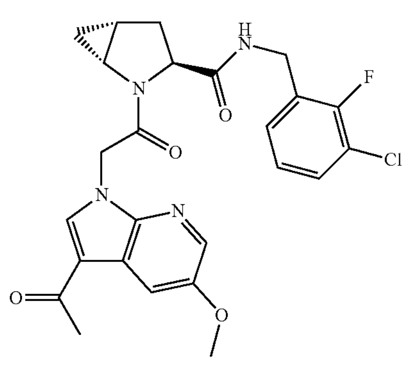 [SMILES: COc1cnc2c(c1)c(C(C)=O)cn2CC(=O)N1[C@@H]2C[C@@H]2C[C@H]1C(=O)NCc1cccc(Cl)c1F] | (1R,3S,5R)-2-[2-(3-Acetyl-5-methoxy-pyrrolo[2,3-b]pyridin-1-yl)-acetyl]-2-aza-bicyclo[3.1.0]hexane-3-carboxylic acid 3-chloro-2-fluoro-benzylamide | (4[A15]) R_f (CH_2Cl_2/MeOH 9:1) = 0.50; 499.3/501.3 [M + H]+, 543.3/545.3 [M + HCOO]−; t_R (f): 2.08 min. |

TABLE 6-continued

| Example | Structure | Name | Characterization (end-table notes), TLC, $R_f$ (eluent); MS (LC/MS); $t_R$ (HPLC conditions) |
|---|---|---|---|
| 495 | 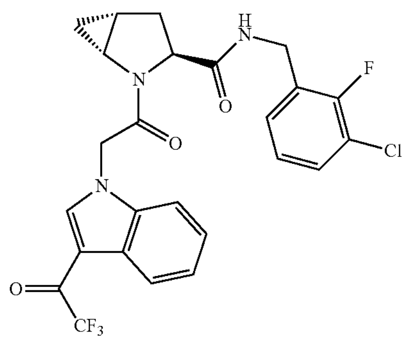 | (1R,3S,5R)-2-{2-[3-(2,2,2-Trifluoro-acetyl)-indol-1-yl]-acetyl}-2-aza-bicyclo[3.1.0] hexane-3-carboxylic acid 3-chloro-2-fluoro-benzylamide | (4[A13],5) White solid. 522.0 [M + H]+; $t_R$ (c): 5.53 min. |
| 496 | 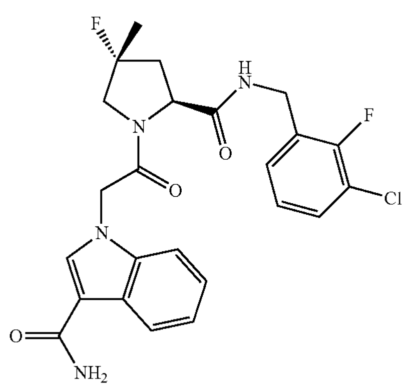 [SMILES: C[C@@]1(F)C[C@@H](C(=O)NCc2cccc(Cl)c2F)N(C(=O)Cn2cc(C(N)=O)c3ccccc32)C1] | 1-{2-[(2S,4R)-2-(3-Chloro-2-fluoro-benzylcarbamoyl)-4-fluoro-4-methyl-pyrrolidin-1-yl]-2-oxo-ethyl}-1H-indole-3-carboxylic acid amide | (3[B13],5) White solid. 489 [M + H]+; $t_R$ (c): 4.35 min. |
| 497 | 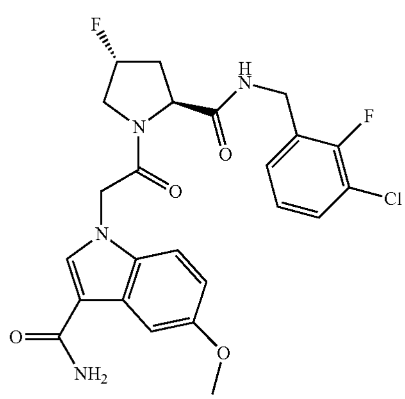 [SMILES: COc1ccc2c(c1)c(C(N)=O)cn2CC(=O)N1C[C@H](F)C[C@H]1C(=O)NCc1cccc(Cl)c1F] | 1-{2-[(2S,4R)-2-(3-Chloro-2-fluoro-benzylcarbamoyl)-4-fluoro-pyrrolidin-1-yl]-2-oxo-ethyl}-5-methoxy-1H-indole-3-carboxylic acid amide | (4[A12],5) White solid. 505 [M + H]+; $t_R$ (c): 4.17 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 498 | 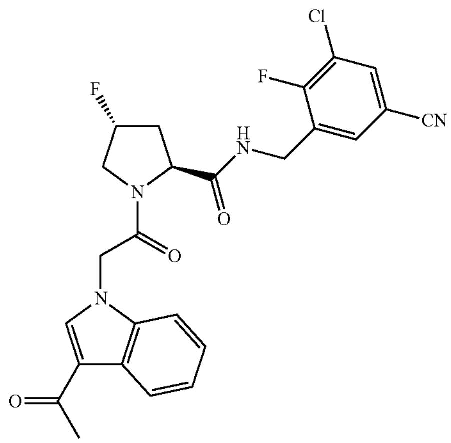 [SMILES: CC(=O)c1cn(CC(=O)N2C[C@H](F)C[C@H]2C(=O)NCc2cc(C#N)cc(Cl)c2F)c2ccccc12] | (2S,4R)-1-[2-(3-Acetyl-indol-1-yl)-acetyl]-4-fluoro-pyrrolidine-2-carboxylic acid 3-chloro-5-cyano-2-fluoro-benzylamide | (1) White solid. 499.0 [M + H]+, 497.0 [M − H]−; t$_R$ (c): 4.55 min. |
| 499 | 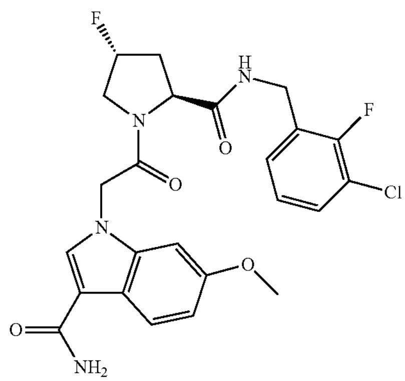 [SMILES: COc1ccc2c(C(N)=O)cn(CC(=O)N3C[C@H](F)C[C@H]3C(=O)NCc3cccc(Cl)c3F)c2c1] | 1-{2-[(2S,4R)-2-(3-Chloro-2-fluoro-benzylcarbamoyl)-4-fluoro-pyrrolidin-1-yl]-2-oxo-ethyl}-6-methoxy-1H-indole-3-carboxylic acid amide | (4[A10],5) White solid. 505 [M + H]+; t$_R$ (c): 4.19 min. |
| 500 | 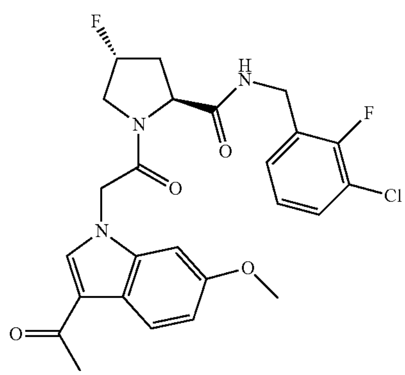 [SMILES: COc1ccc2c(C(C)=O)cn(CC(=O)N3C[C@H](F)C[C@H]3C(=O)NCc3cccc(Cl)c3F)c2c1] | (2S,4R)-1-[2-(3-Acetyl-6-methoxy-indol-1-yl)-acetyl]-4-fluoro-pyrrolidine-2-carboxylic acid 3-chloro-2-fluoro-benzylamide | (4[A13],5) Solid. 504 [M + H]+, 526 [M + Na]+; t$_R$ (k): 3.43 min. |
| 501 | 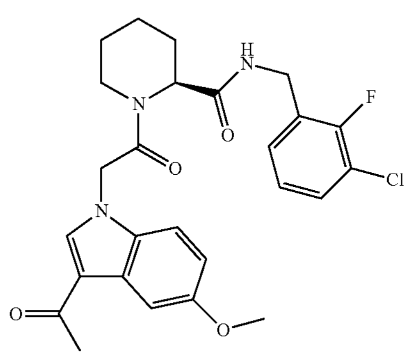 [SMILES: COc1ccc2c(c1)c(C(C)=O)cn2CC(=O)N1CCCC[C@H]1C(=O)NCc1cccc(Cl)c1F] | (S)-1-[2-(3-Acetyl-5-methoxy-indol-1-yl)-acetyl]-piperidine-2-carboxylic acid 3-chloro-2-fluoro-benzylamide | (4) White solid. 500 [M + H]+; t$_R$ (c): 4.96 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 502 | 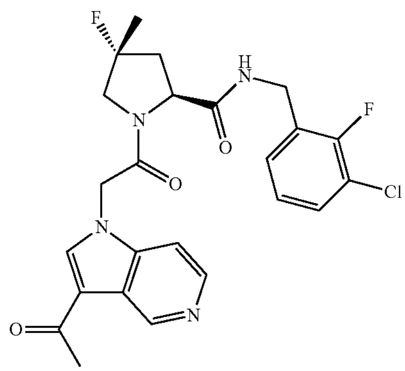 [SMILES: CC(=O)c1cn(CC(=O)N2C[C@](C)(F)C[C@H]2C(=O)NCc2cccc(Cl)c2F)c2ccncc12] | (2S,4R)-1-[2-(3-Acetyl-pyrrolo[3,2-c]pyridin-1-yl)-acetyl]-4-fluoro-4-methyl-pyrrolidine-2-carboxylic acid 3-chloro-2-fluoro-benzylamide | (3[B13], 4[A15]) R$_f$ (CH$_2$Cl$_2$/MeOH 9:1) = 0.40; 489.3/491.3 [M + H]+, 533.3/535.3 [M + HCOO]−; t$_R$ (f): 1.50 min. |
| 503 | 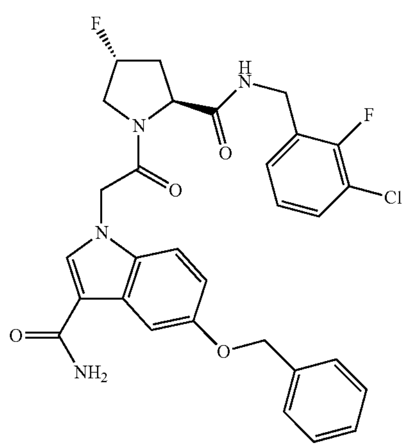 [SMILES: NC(=O)c1cn(CC(=O)N2C[C@H](F)C[C@H]2C(=O)NCc2cccc(Cl)c2F)c2ccc(OCc3ccccc3)cc12] | 5-Benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide | (4[A11]) White solid. R$_f$ (EtOAc/MeOH 95:5) = 0.27; 581/582 [M + H]+; t$_R$ (b): 4.90 min. |
| 504 | 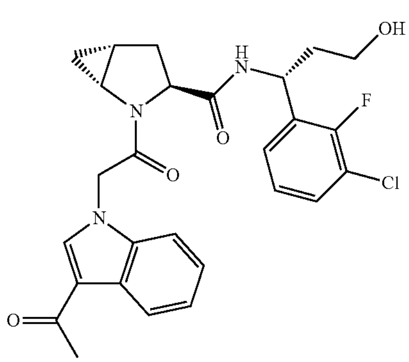 [SMILES: CC(=O)c1cn(CC(=O)N2[C@@H]3C[C@@H]3C[C@H]2C(=O)N[C@H](CCO)c2cccc(Cl)c2F)c2ccccc12] | (1R,3S,5R)-2-[2-(3-Acetyl-indol-1-yl)-acetyl]-2-aza-bicyclo[3.1.0]hexane-3-carboxylic acid [(R)-1-(3-chloro-2-fluoro-phenyl)-3-hydroxy-propyl]-amide | (3[B9]) R$_f$ (EtOAc) = 0.15; 512.3 [M + H]+, 556.3/558.4 [M + HCOO]−; t$_R$ (a): 3.22 min. |

TABLE 6-continued

| Example | Structure | Name | Characterization (end-table notes), TLC, R_f (eluent); MS (LC/MS); t_R (HPLC conditions) |
|---|---|---|---|
| 505 | 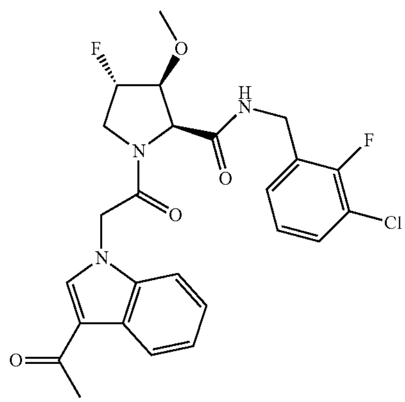 [SMILES: CO[C@H]1[C@@H](C(=O)NCc2cccc(Cl)c2F)N(C(=O)Cn2cc(C(C)=O)c3ccccc32)C[C@@H]1F] | (2S,3S,4S)-1-[2-(3-Acetyl-indol-1-yl)-acetyl]-4-fluoro-3-methoxy-pyrrolidine-2-carboxylic acid 3-chloro-2-fluoro-benzylamide | (3[B24]) 504 [M + H]+; t_R (f): 2.01 min. |
| 506 | 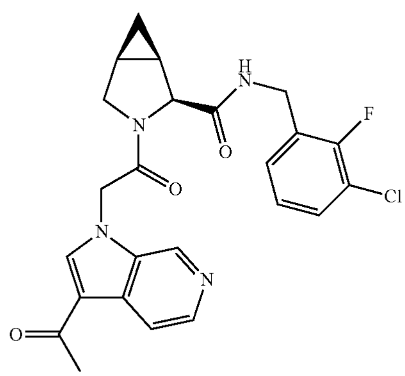 [SMILES: CC(=O)c1cn(CC(=O)N2C[C@H]3C[C@H]3[C@H]2C(=O)NCc2cccc(Cl)c2F)c2cnccc12] | (1R,2S,5S)-3-[2-(3-Acetyl-pyrrolo[2,3-c]pyridin-1-yl)-acetyl]-3-aza-bicyclo[3.1.0]hexane-2-carboxylic acid 3-chloro-2-fluoro-benzylamide | (4[A15]) R_f (CH_2Cl_2/MeOH 9:1) = 0.30; 469.3/471.3 [M + H]+, 513.2/515.2 [M + HCOO]−; t_R (f): 1.48 min. |
| 507 | 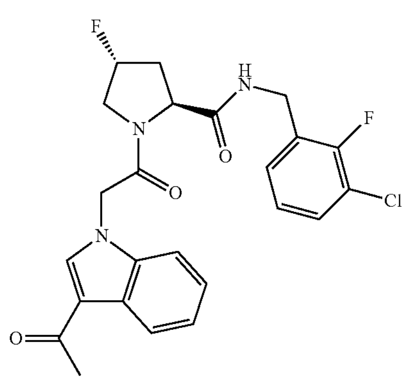 [SMILES: CC(=O)c1cn(CC(=O)N2C[C@H](F)C[C@H]2C(=O)NCc2cccc(Cl)c2F)c2ccccc12] | (2S,4R)-1-[2-(3-Acetyl-indol-1-yl)-acetyl]-4-fluoro-pyrrolidine-2-carboxylic acid 3-chloro-2-fluoro-benzylamide | White solid. 474 [M + H]+; t_R (b): 3.90 min. |

TABLE 6-continued

| Example | Structure | Name | Characterization (end-table notes), TLC, R_f (eluent); MS (LC/MS); t_R (HPLC conditions) |
|---|---|---|---|
| 508 | 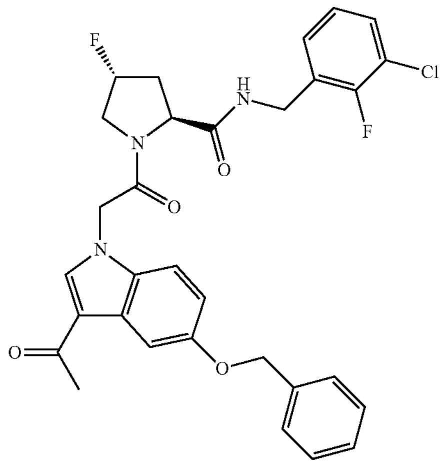 [SMILES: CC(=O)c1cn(CC(=O)N2C[C@H](F)C[C@H]2C(=O)NCc2cccc(Cl)c2F)c2ccc(OCc3ccccc3)cc12] | (2S,4R)-1-[2-(3-Acetyl-5-benzyloxy-indol-1-yl)-acetyl]-4-fluoro-pyrrolidine-2-carboxylic acid 3-chloro-2-fluoro-benzylamide | (4[A13],5) White solid. 580/582 [M + H]+; t_R (k): 3.81 min. |
| 509 | 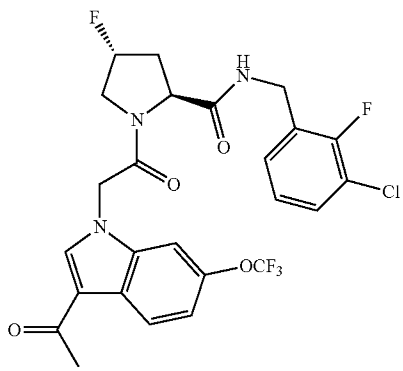 [SMILES: CC(=O)c1cn(CC(=O)N2C[C@H](F)C[C@H]2C(=O)NCc2cccc(Cl)c2F)c2cc(OC(F)(F)F)ccc12] | (2S,4R)-1-[2-(3-Acetyl-6-trifluoromethoxy-indol-1-yl)-acetyl]-4-fluoro-pyrrolidine-2-carboxylic acid 3-chloro-2-fluoro-benzylamide | (4,5) White solid. R_f (CH_2Cl_2/MeOH 95:5) = 0.31; 558.0 [M + H]+; t_R (c): 5.26 min. |
| 510 | 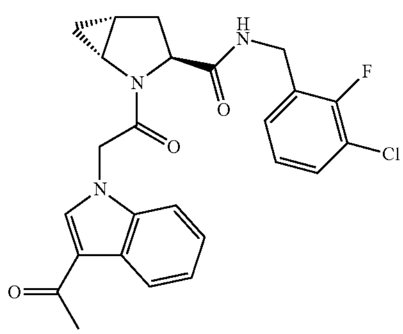 [SMILES: CC(=O)c1cn(CC(=O)N2[C@@H]3C[C@@H]3C[C@H]2C(=O)NCc2cccc(Cl)c2F)c2ccccc12] | (1R,3S,5R)-2-[2-(3-Acetyl-indol-1-yl)-acetyl]-2-aza-bicyclo[3.1.0]hexane-3-carboxylic acid 3-chloro-2-fluoro-benzylamide | (5) White solid. 468.0 [M + H]+; t_R (c): 4.77 min. |
| 511 | 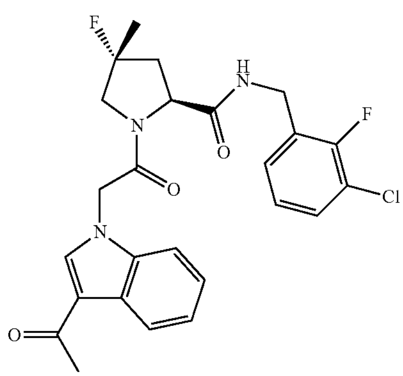 [SMILES: CC(=O)c1cn(CC(=O)N2C[C@](C)(F)C[C@H]2C(=O)NCc2cccc(Cl)c2F)c2ccccc12] | (2S,4R)-1-[2-(3-Acetyl-indol-1-yl)-acetyl]-4-fluoro-4-methyl-pyrrolidine-2-carboxylic acid 3-chloro-2-fluoro-benzylamide | (3[B13],5) White solid. R_f (CH_2Cl_2/MeOH 95:5) = 0.31; 488.0 [M + H]+; t_R(c): 4.82 min. |

TABLE 6-continued

| Example | Structure | Name | Characterization (end-table notes), TLC, R_f (eluent); MS (LC/MS); t_R (HPLC conditions) |
|---|---|---|---|
| 512 | 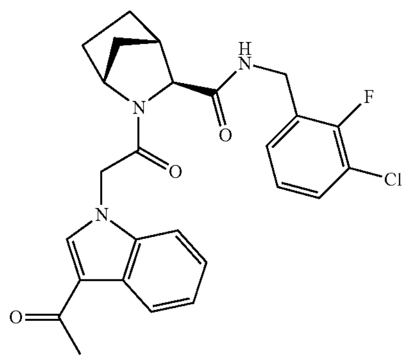 [SMILES: CC(=O)c1cn(CC(=O)N2[C@@H]3CC[C@@H](C3)[C@H]2C(=O)NCc2cccc(Cl)c2F)c2ccccc12] | (1R,3S,4S)-2-[2-(3-Acetyl-indol-1-yl)-acetyl]-2-aza-bicyclo[2.2.1]heptane-3-carboxylic acid 3-chloro-2-fluoro-benzylamide | 482 [M + H]+, 480 [M − H]−; t_R (f): 0.98 min. |
| 513 | 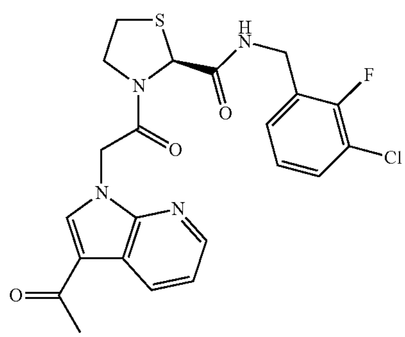 [SMILES: CC(=O)c1cn(CC(=O)N2CCS[C@H]2C(=O)NCc2cccc(Cl)c2F)c2ncccc12] | (S)-3-[2-(3-Acetyl-pyrrolo[2,3-b]pyridin-1-yl)-acetyl]-thiazolidine-2-carboxylic acid 3-chloro-2-fluoro-benzylamide | (4[A13]) R_f (EtOAc) = 0.80; 475.3/477.2 [M + H]+, 949.4/951.3 [2M + H]+, 519.2/521.2 [M + HCOO]−; t_R (f): 1.91 min. |
| 514 | 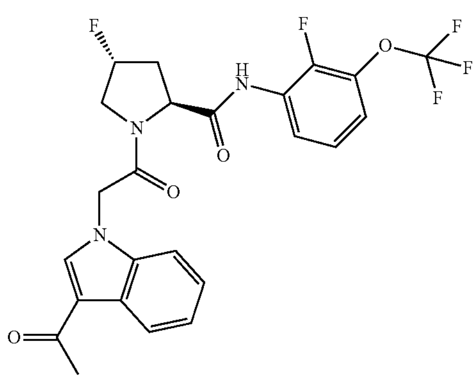 [SMILES: CC(=O)c1cn(CC(=O)N2C[C@H](F)C[C@H]2C(=O)Nc2cccc(OC(F)(F)F)c2F)c2ccccc12] | (2S,4R)-1-[2-(3-Actyl-indol-1-yl)-acetyl]-4-fluoro-pyrrolidine-2-carboxylic acid (2-fluoro-3-trifluoromethoxy-phenyl)-amide | (1,5) White solid. 510 [M + H]+, 532 [M + Na]+; t_R (k): 3.62 min. |
| 515 | 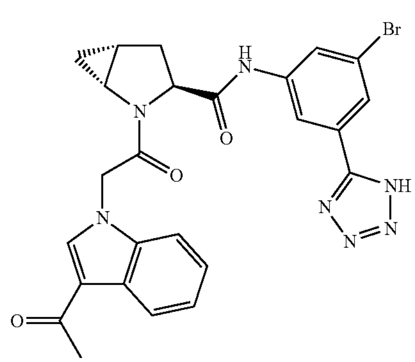 [SMILES: CC(=O)c1cn(CC(=O)N2[C@@H]3C[C@@H]3C[C@H]2C(=O)Nc2cc(Br)cc(-c3nnn[nH]3)c2)c2ccccc12] | (1R,3S,5R)-2-[2-(3-Acetyl-indol-1-yl)-acetyl]-2-aza-bicyclo[3.1.0]hexane-3-carboxylic acid [3-bromo-5-(2H-tetrazol-5-yl)-phenyl]-amide | (1,2) White solid. 548.0 [M + H]+; t_R (c): 4.51 min. |

TABLE 6-continued

| Example | Structure | Name | Characterization (end-table notes), TLC, $R_f$ (eluent); MS (LC/MS); $t_R$ (HPLC conditions) |
|---|---|---|---|
| 516 | 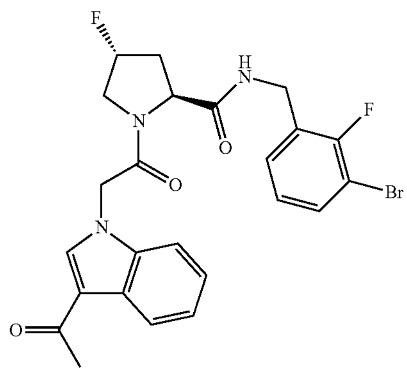 [SMILES: CC(=O)c1cn(CC(=O)N2C[C@H](F)C[C@H]2C(=O)NCc2cccc(Br)c2F)c2ccccc12] | (2S,4R)-1-[2-(3-Acetyl-indol-1-yl)-acetyl]-4-fluoro-pyrrolidine-2-carboxylic acid 3-bromo-2-fluoro-benzyl amide | (1,5) White solid. $R_f$ (CH$_2$Cl$_2$/MeOH 95:5) = 0.41; 518.0 [M + H]+; $t_R$ (k): 3.45 min |
| 517 | 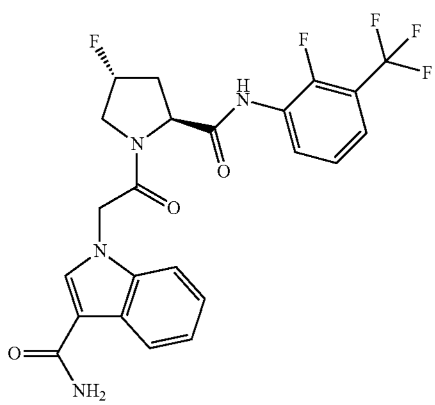 [SMILES: NC(=O)c1cn(CC(=O)N2C[C@H](F)C[C@H]2C(=O)Nc2cccc(C(F)(F)F)c2F)c2ccccc12] | 1-{2-[(2S,4R)-4-Fluoro-2-(2-fluoro-3-trifluoromethyl-phenylcarbamoyl)-pyrrolidin-1-yl]-2-oxo-ethyl}-1H-indole-3-carboxylic acid amide | (5,6) White solid. 495 [M + H]+, 989 [2M + 1]+; $t_R$ (c): 4.46 min. |
| 518 | 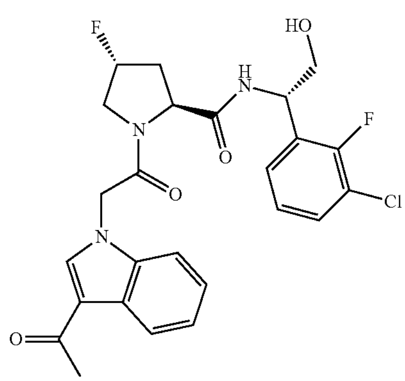 [SMILES: CC(=O)c1cn(CC(=O)N2C[C@H](F)C[C@H]2C(=O)N[C@H](CO)c2cccc(Cl)c2F)c2ccccc12] | (2S,4R)-1-[2-(3-Acetyl-indol-1-yl)-acetyl]-4-fluoro-pyrrolidine-2-carboxylic acid [(S)-1-(3-chloro-2-fluoro-phenyl)-2-hydroxy-ethyl]-amide | (5) White solid. $R_f$ (CH$_2$Cl$_2$/MeOH 95:5) = 0.32; 504.0 [M + H]+; $t_R$ (c): 4.21 min. |

TABLE 6-continued

| Example | Structure | Name | Characterization (end-table notes), TLC, R_f (eluent); MS (LC/MS); t_R (HPLC conditions) |
|---|---|---|---|
| 519 | 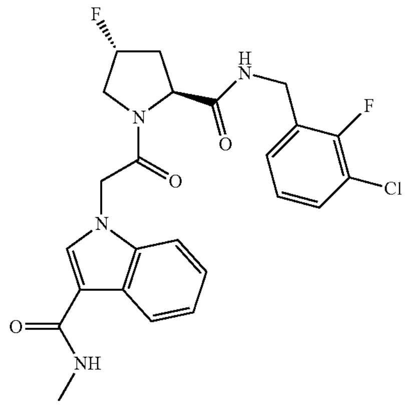 [SMILES: CNC(=O)c1cn(CC(=O)N2C[C@H](F)C[C@H]2C(=O)NCc2cccc(Cl)c2F)c2ccccc12] | 1-{2-[(2S,4R)-2-(3-Chloro-2-fluoro-benzylcarbamoyl)-4-fluoro-pyrrolidin-1-yl]-2-oxo-ethyl}-1H-indole-3-carboxylic acid methylamide | (4) 489 [M + H]+; t_R (b): 3.57 min. |
| 520 | 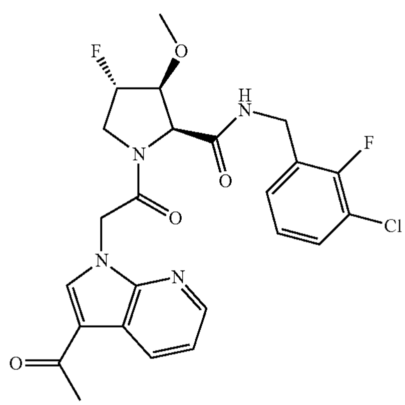 [SMILES: CO[C@H]1[C@@H](C(=O)NCc2cccc(Cl)c2F)N(C(=O)Cn2cc(C(C)=O)c3cccnc32)C[C@@H]1F] | (2S,3S,4S)-1-[2-(3-Acetyl-pyrrolo[2,3-b]pyridin-1-yl)-acetyl]-4-fluoro-3-methoxy-pyrrolidine-2-carboxylic acid 3-chloro-2-fluoro-benzylamide | (3[B24], 4[A13]) 549 [M + HCOO]−, 505 [M + H]+; t_R (f): 1.90 min. |
| 521 | 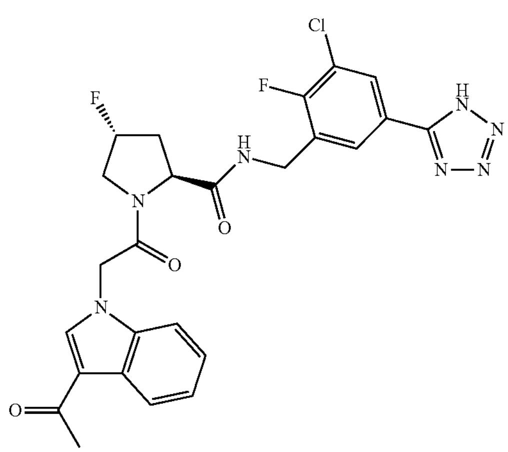 [SMILES: CC(=O)c1cn(CC(=O)N2C[C@H](F)C[C@H]2C(=O)NCc2cc(-c3nnn[nH]3)cc(Cl)c2F)c2ccccc12] | (2S,4R)-1-[2-(3-Acetyl-indol-1-yl)-acetyl]-4-fluoro-pyrrolidine-2-carboxylic acid 3-chloro-2-fluoro-5-(1H-tetrazol-5-yl)-benzylamide | (1,2) White solid. 542.3 [M + H]+, 540.3 [M − H]−; t_R (c): 4.27 min |

TABLE 6-continued

| Example | Structure | Name | Characterization (end-table notes), TLC, $R_f$ (eluent); MS (LC/MS); $t_R$ (HPLC conditions) |
|---|---|---|---|
| 522 | 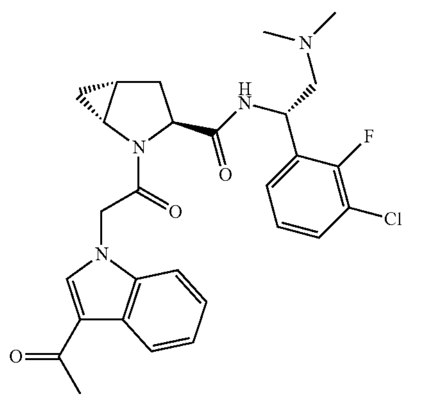 [SMILES: CC(=O)c1cn(CC(=O)N2[C@@H]3C[C@@H]3C[C@H]2C(=O)N[C@H](CN(C)C)c2cccc(Cl)c2F)c2ccccc12] | (1R,3S,5R)-2-[2-(3-Acetyl-indol-1-yl)-acetyl]-2-aza-bicyclo[3.1.0]hexane-3-carboxylic acid [(S)-1-(3-chloro-2-fluoro-phenyl)-2-dimethylamino-ethyl]-amide | (1[C4],2) $R_f$(EtOAc) = 0.1; 527/527 [M + H]+; $t_R$ (f): 1.66 min. |
| 523 | 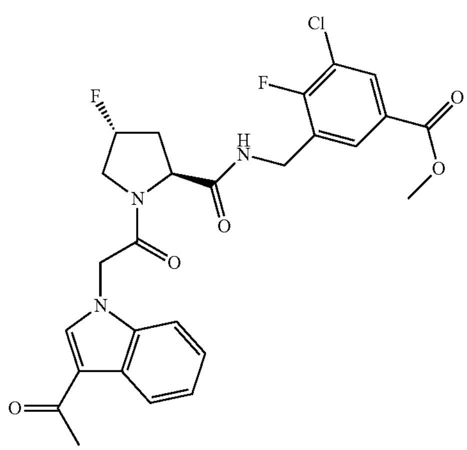 [SMILES: COC(=O)c1cc(Cl)c(F)c(CNC(=O)[C@@H]2C[C@@H](F)CN2C(=O)Cn2cc(C(C)=O)c3ccccc32)c1] | 3-[({(2S,4S)-1-[2-(3-Acetyl-indol-1-yl)-acetyl]-4-fluoro-pyrrolidine-2-carbonyl}-amino)-methyl]-5-chloro-4-fluoro-benzoic acid methyl ester | (1,5) White solid. 530.0 [M + H]+; $t_R$ (c): 4.73 min. |
| 524 | 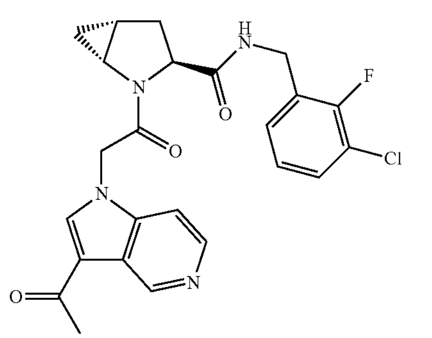 [SMILES: CC(=O)c1cn(CC(=O)N2[C@@H]3C[C@@H]3C[C@H]2C(=O)NCc2cccc(Cl)c2F)c2ccncc12] | (1R,3S,5R)-2-[2-(3-Acetyl-pyrrolo[3,2-c]pyridin-1-yl)-acetyl]-2-aza-bicyclo[3.1.0]hexane-3-carboxylic acid 3-chloro-2-fluoro-benzylamide | (4[A15]) $R_f$ (CH$_2$Cl$_2$/MeOH 4:1) = 0.35, 469.3/471.3 [M + H]+, 513.3/515.3 [M + HCOO]−; $t_R$ (f): 1.46 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 525 | 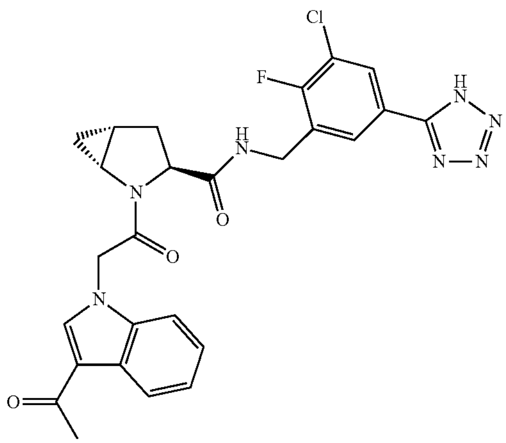 [SMILES: CC(=O)c1cn(CC(=O)N2[C@@H]3C[C@@H]3C[C@H]2C(=O)NCc2cc(-c3nnn[nH]3)cc(Cl)c2F)c2ccccc12] | (1R,3S,5R)-2-[2-(3-Acetyl-indol-1-yl)-acetyl]-2-aza-bicyclo[3.1.0]hexane-3-carboxylic acid 3-chloro-2-fluoro-5-(1H-tetrazol-5-yl)-benzylamide | (1,2) White solid. 536.3 [M + H]+, 534.3 [M − H]−; t$_R$ (c): 4.41 min. |
| 526 | 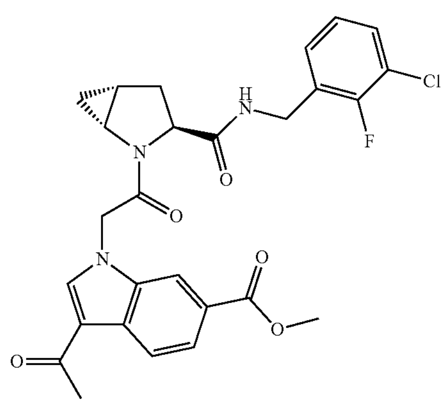 [SMILES: COC(=O)c1ccc2c(C(C)=O)cn(CC(=O)N3[C@@H]4C[C@@H]4C[C@H]3C(=O)NCc3cccc(Cl)c3F)c2c1] | 3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-6-carboxylic acid methyl ester | (4[A13],5) Solid. 526 [M + H]+, 1021 [2M + H]+; t$_R$ (k): 3.52 min. |
| 527 | 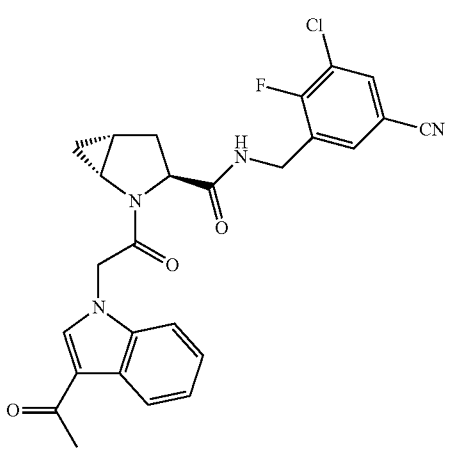 [SMILES: CC(=O)c1cn(CC(=O)N2[C@@H]3C[C@@H]3C[C@H]2C(=O)NCc2cc(C#N)cc(Cl)c2F)c2ccccc12] | (1R,3S,5R)-2-[2-(3-Acetyl-indol-1-yl)-acetyl]-2-aza-bicyclo[3.1.0]hexane-3-carboxylic acid 3-chloro-5-cyano-2-fluoro-benzylamide | (1) White solid. 493.0 [M + H]+; t$_R$ (c): 4.68 min |

TABLE 6-continued

| Example | Structure | Name | Characterization (end-table notes), TLC, R$_f$ (eluent); MS (LC/MS); t$_R$ (HPLC conditions) |
|---|---|---|---|
| 528 | 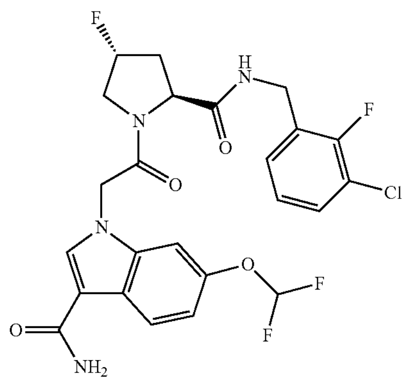 [SMILES: NC(=O)c1cn(CC(=O)N2C[C@H](F)C[C@H]2C(=O)NCc2cccc(Cl)c2F)c2cc(OC(F)F)ccc12] | 1-{2-[(2S,4R)-2-(3-Chloro-2-fluoro-benzylcarbamoyl)-4-fluoro-pyrrolidin-1-yl]-2-oxo-ethyl}-6-difluoromethoxy-1H-indole-3-carboxylic acid amide | (4,5) Solid. 541/543 [M + H]+; t$_R$ (k): 3.33 min. |
| 529 | 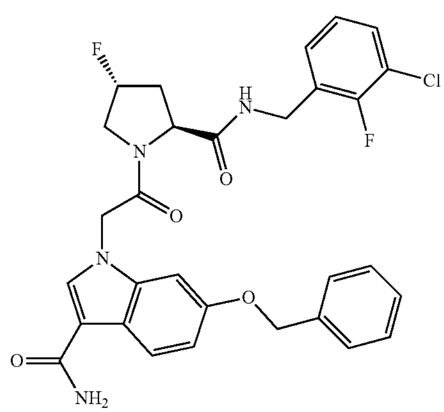 [SMILES: NC(=O)c1cn(CC(=O)N2C[C@H](F)C[C@H]2C(=O)NCc2cccc(Cl)c2F)c2cc(OCc3ccccc3)ccc12] | 6-Benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide | (4[A11]) White solid. 581/582 [M + H]+, 603/604 [M + Na]+; t$_R$ (b): 4.94 min. |
| 530 | 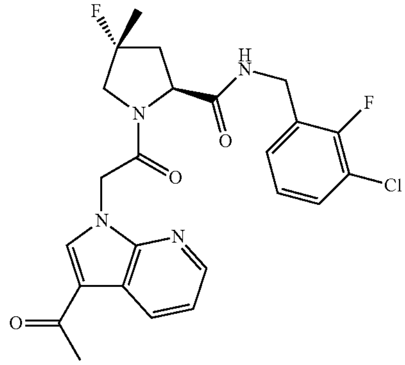 [SMILES: CC(=O)c1cn(CC(=O)N2C[C@](C)(F)C[C@H]2C(=O)NCc2cccc(Cl)c2F)c2ncccc12] | (2S,4R)-1-[2-(3-Acetyl-pyrrolo[2,3-b]pyridin-1-yl)-acetyl]-4-fluoro-4-methyl-pyrrolidine-2-carboxylic acid 3-chloro-2-fluoro-benzylamide | (3[B13], 4[A13]) R$_f$ (EtOAc) = 0.35; 489.3/491.2 [M + H]+, 533.3/535.2 [M + HCOO]−; t$_R$ (f): 1.93 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 531 | 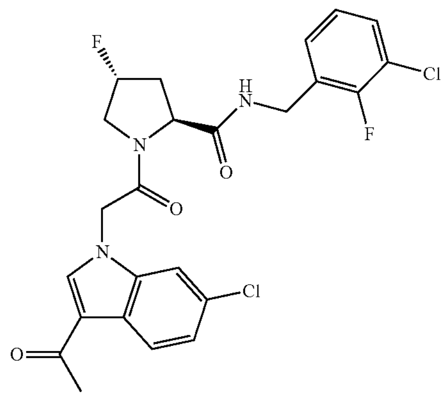 [SMILES: CC(=O)c1cn(CC(=O)N2C[C@H](F)C[C@H]2C(=O)NCc2cccc(Cl)c2F)c2cc(Cl)ccc12] | (2S,4R)-1-[2-(3-Acetyl-6-chloro-indol-1-yl)-acetyl]-4-fluoro-pyrrolidine-2-carboxylic acid 3-chloro-2-fluoro-benzylamide | (4[A13],5) Solid. 508/510 [M + H]+, 530 [M + Na]+; t$_R$ (k): 3.63 min. |
| 532 | 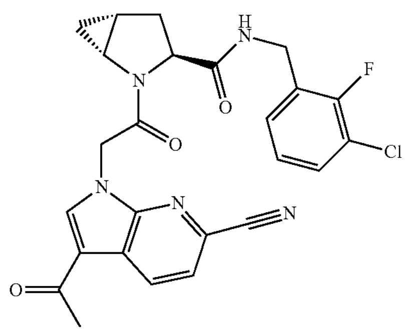 [SMILES: CC(=O)c1cn(CC(=O)N2[C@@H]3C[C@@H]3C[C@H]2C(=O)NCc2cccc(Cl)c2F)c2nc(C#N)ccc12] | (1R,3S,5R)-2-[2-(3-Acetyl-6-cyano-pyrrolo[2,3-b]pyridin-1-yl)-acetyl]-2-aza-bicyclo[3.1.0]hexane-3-carboxylic acid 3-chloro-2-fluoro-benzylamide | (4[A15]) R$_f$(EtOAc) = 0.25; 494.3/496.3 [M + H]+, 538.2/540.2 [M + HCOO]−; t$_R$ (f): 2.03 min. |
| 533 | 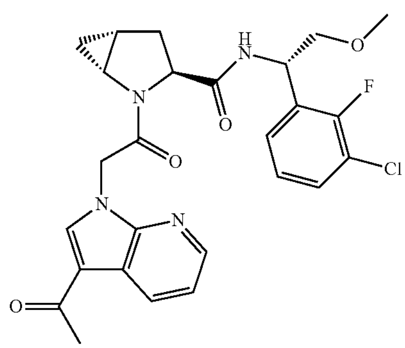 [SMILES: COC[C@@H](NC(=O)[C@@H]1C[C@H]2C[C@H]2N1C(=O)Cn1cc(C(C)=O)c2cccnc21)c1cccc(Cl)c1F] | (1R,3S,5R)-2-[2-(3-Acetyl-pyrrolo[2,3-b]pyridin-1-yl)-acetyl]-2-aza-bicyclo[3.1.0]hexane-3-carboxylic acid [(S)-1-(3-chloro-2-fluoro-phenyl)-2-methoxy-ethyl]-amide | (2,3[B9],4[A13]) White solid. R$_f$(EtOAc) = 0.50; 513.2/515.2 [M + H]+, 557.2/559.2 [M − H]−, [M + HCOO]−; t$_R$ (a): 3.26 min. |
| 534 | 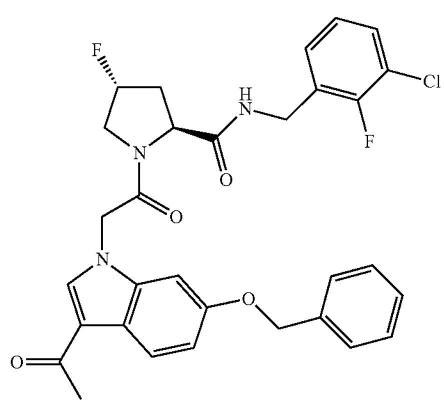 [SMILES: CC(=O)c1cn(CC(=O)N2C[C@H](F)C[C@H]2C(=O)NCc2cccc(Cl)c2F)c2cc(OCc3ccccc3)ccc12] | (2S,4R)-1-[2-(3-Acetyl-6-benzyloxy-indol-1-yl)-acetyl]-4-fluoro-pyrrolidine-2-carboxylic acid 3-chloro-2-fluoro-benzylamide | (4[A13],5) Solid. 580/581 [M + H]+; t$_R$ (k): 3.83 min. |

TABLE 6-continued

| Example | Structure | Name | Characterization (end-table notes), TLC, R_f (eluent); MS (LC/MS); t_R (HPLC conditions) |
|---|---|---|---|
| 535 | 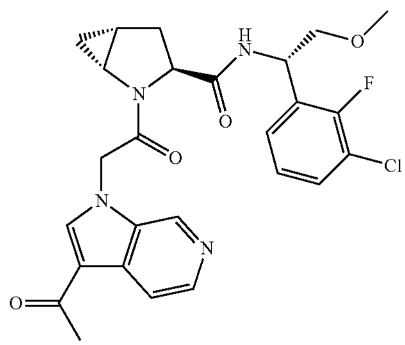 [SMILES: COC[C@@H](NC(=O)[C@@H]1C[C@H]2C[C@H]2N1C(=O)Cn1cc(C(C)=O)c2ccncc21)c1cccc(Cl)c1F] | (1R,3S,5R)-2-[2-(3-Acetyl-pyrrolo[2,3-c]pyridin-1-yl)-acetyl]-2-aza-bicyclo[3.1.0]hexane-3-carboxylic acid [(S)-1-(3-chloro-2-fluoro-phenyl)-2-methoxy-ethyl]-amide | (2,3[B9],4[A15]) R_f (CH$_2$Cl$_2$/MeOH 9:1) = 0.45; 513.3/515.3 [M + H]+, 557.2/559.2 [M + HCOO]–; t_R (f): 1.50. |
| 536 | 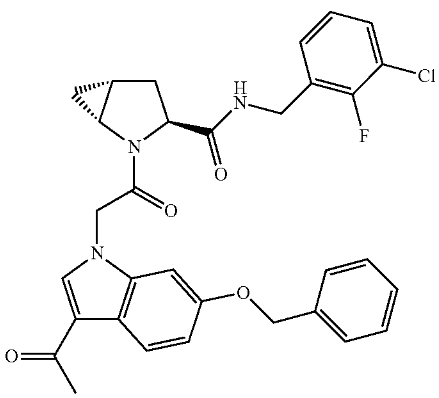 [SMILES: CC(=O)c1cn(CC(=O)N2[C@@H]3C[C@@H]3C[C@H]2C(=O)NCc2cccc(Cl)c2F)c2cc(OCc3ccccc3)ccc12] | (1R,3S,5R)-2-[2-(3-Acetyl-6-benzyloxy-indol-1-yl)-acetyl]-2-aza-bicyclo[3.1.0]hexane-3-carboxylic acid 3-chloro-2-fluoro-benzylamide | (4[A13],5) Solid. 574 [M + H]+; t_R (k): 3.89 min. |
| 537 | 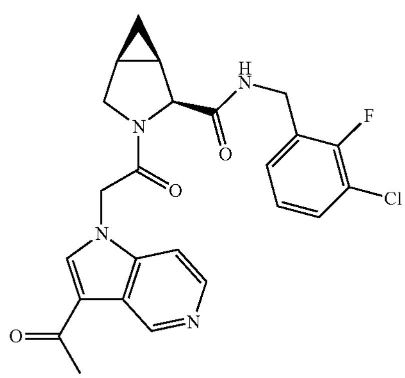 [SMILES: CC(=O)c1cn(CC(=O)N2C[C@H]3C[C@H]3[C@H]2C(=O)NCc2cccc(Cl)c2F)c2ccncc12] | (1R,2S,5S)-3-[2-(3-Acetyl-pyrrolo[3,2-c]pyridin-1-yl)-acetyl]-3-aza-bicyclo[3.1.0]hexane-2-carboxylic acid 3-chloro-2-fluoro-benzylamide | (4[A15]) R_f (CH$_2$Cl$_2$/MeOH 9:1) = 0.40, 469.3/471.3 [M + H]+, 513.3/515.3 [M + HCOO]–; t_R (f): 1.47 min. |
| 538 | 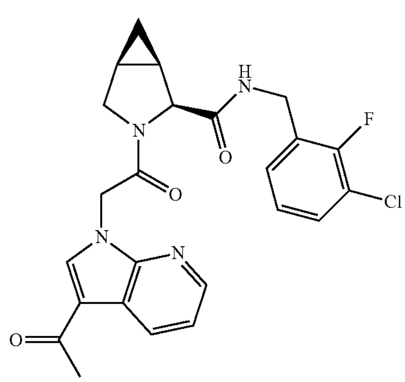 [SMILES: CC(=O)c1cn(CC(=O)N2C[C@H]3C[C@H]3[C@H]2C(=O)NCc2cccc(Cl)c2F)c2ncccc12] | (1R,2S,5S)-3-[2-(3-Acetyl-pyrrolo[2,3-b]pyridin-1-yl)-acetyl]-3-aza-bicyclo[3.1.0]hexane-2-carboxylic acid 3-chloro-2-fluoro-benzylamide | (4[A13]) R_f (CH$_2$Cl$_2$/MeOH 4:1) = 0.35; 469.3/471.3 [M + H]+, 513.3/515.2 M + HCOO]–; t_R (a): 3.15 min. |

TABLE 6-continued

| Example | Structure | Name | Characterization (end-table notes), TLC, $R_f$ (eluent); MS (LC/MS); $t_R$ (HPLC conditions) |
|---|---|---|---|
| 539 | 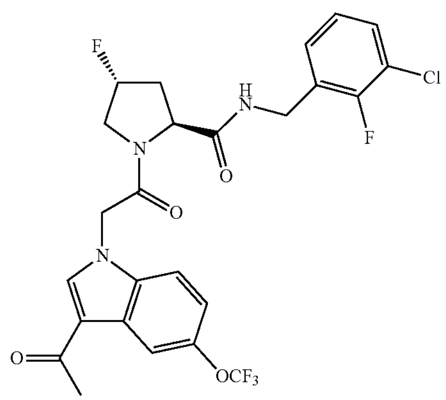 [SMILES: CC(=O)c1cn(CC(=O)N2C[C@H](F)C[C@H]2C(=O)NCc2cccc(Cl)c2F)c2ccc(OC(F)(F)F)cc12] | (2S,4R)-1-[2-(3-Acetyl-5-trifluoromethoxy-indol-1-yl)-acetyl]-4-fluoro-pyrrolidine-2-carboxylic acid 3-chloro-2-fluoro-benzylamide | (4[A13],5) White solid. 558.0 [M + H]+; $t_R$ (c): 5.25 min. |
| 540 | 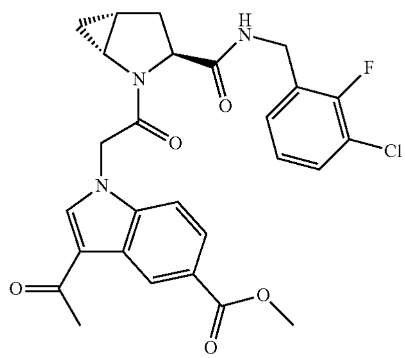 [SMILES: COC(=O)c1ccc2c(c1)c(C(C)=O)cn2CC(=O)N1[C@@H]2C[C@@H]2C[C@H]1C(=O)NCc1cccc(Cl)c1F] | 3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboxylic acid methyl ester | (4[A13],5) Solid. 526/528 [M + H]+, 548/550 [M + Na]+; $t_R$ (k): 3.54 min. |
| 541 | 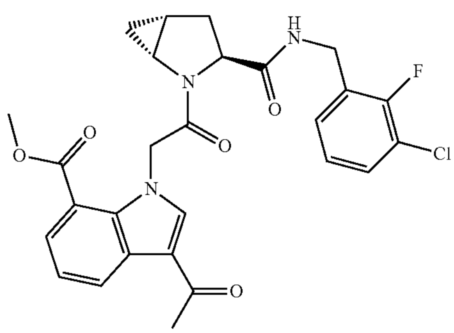 [SMILES: COC(=O)c1cccc2c(C(C)=O)cn(CC(=O)N3[C@@H]4C[C@@H]4C[C@H]3C(=O)NCc3cccc(Cl)c3F)c12] | 3-Acetyl-1-{2-[(1R,3S,5R)-3-(3-chloro-2-fluorobenzylcarbamoyl)-2-aza-bicyclo[3.1.0]hex-2-yl]-2-oxo-ethyl}-1H-indole-7-carboxylic acid methyl ester | (4[A13],5) Solid. MS (LC/MS): 526 [M + H]+, 1051 [2M + H]+; $t_R$ (k): 3.68 min. |
| 542 | 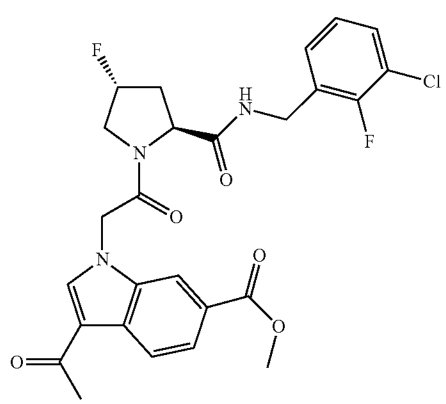 [SMILES: COC(=O)c1ccc2c(C(C)=O)cn(CC(=O)N3C[C@H](F)C[C@H]3C(=O)NCc3cccc(Cl)c3F)c2c1] | 3-Acetyl-1-{2-[(2S,4R)-2-(3-chloro-2-fluoro-benzylcarbamoyl)-4-fluoro-pyrrolidin-1-yl]-2-oxo-ethyl}-1H-indole-6-carboxylic acid methyl ester | (4[A13],5) Solid. 532 [M + H]+, 554 [M + Na]+; $t_R$ (k): 3.44 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 543 | 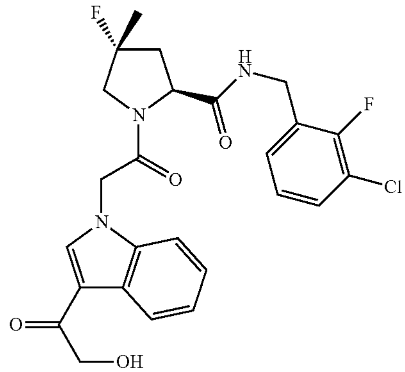 [SMILES: C[C@@]1(F)C[C@@H](C(=O)NCc2cccc(Cl)c2F)N(C(=O)Cn2cc(C(=O)CO)c3ccccc32)C1] | (2S,4R)-4-Fluoro-1-{2-[3-(2-hydroxy-acetyl)-indol-1-yl]-acetyl}-4-methyl-pyrrolidine-2-carboxylic acid 3-chloro-2-fluoro-benzylamide | (3[B13],4[A13],5) White solid. 504.0 [M + H]+; t$_R$ (c): 4.56 min. |
| 544 | 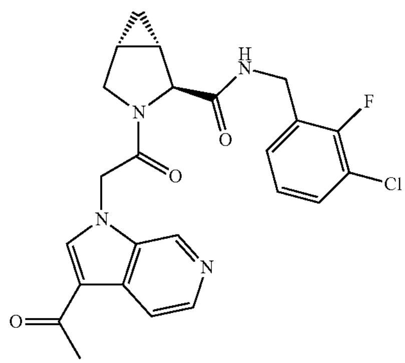 [SMILES: CC(=O)c1cn(CC(=O)N2C[C@@H]3C[C@@H]3[C@H]2C(=O)NCc2cccc(Cl)c2F)c2cnccc12] | (1S,2S,5R)-3-[2-(3-Acetyl-pyrrolo[2,3-c]pyridin-1-yl)-acetyl]-3-aza-bicyclo[3.1.0]hexane-2-carboxylic acid 3-chloro-2-fluoro-benzylamide | (4[A15]) R$_f$ (CH$_2$Cl$_2$/MeOH 9:1) = 0.45; 469.2/471.2 [M + H]+, 513.2/515.3 [M + HCOO]−; t$_R$ (f): 1.49 min. |
| 545 | 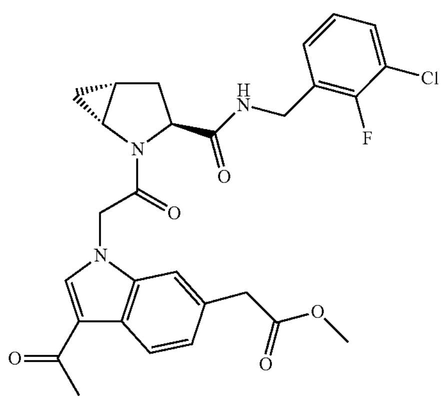 [SMILES: COC(=O)Cc1ccc2c(C(C)=O)cn(CC(=O)N3[C@@H]4C[C@@H]4C[C@H]3C(=O)NCc3cccc(Cl)c3F)c2c1] | (3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid methyl ester | (4,5) Solid. 540 [M + H]+, 562 [M + Na]+; t$_R$ (k): 3.51 min. |
| 546 | 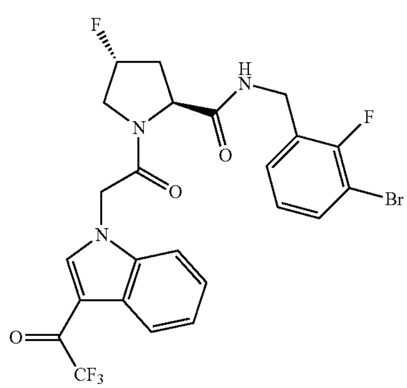 [SMILES: O=C(NCc1cccc(Br)c1F)[C@@H]1C[C@@H](F)CN1C(=O)Cn1cc(C(=O)C(F)(F)F)c2ccccc21] | (2S,4R)-4-Fluoro-1-{2-[3-(2,2,2-trifluoro-acetyl)-indol-1-yl]-acetyl}-pyrrolidine-2-carboxylic acid 3-bromo-2-fluoro-benzylamide | (1,4[A13],5) White solid. R$_f$ (CH$_2$Cl$_2$/Acetone 9:1) = 0.41; 573.0 [M + H]+; t$_R$ (k): 3.87 min |

TABLE 6-continued

| Example | Structure | Name | Characterization (end-table notes), TLC, $R_f$ (eluent); MS (LC/MS); $t_R$ (HPLC conditions) |
|---|---|---|---|
| 547 | 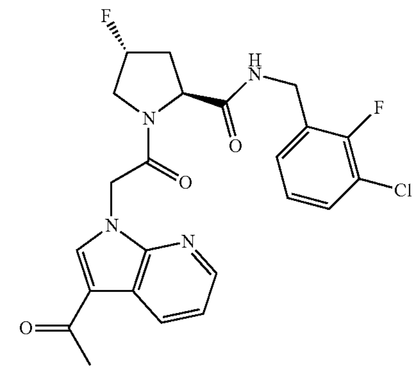 [SMILES: CC(=O)c1cn(CC(=O)N2C[C@H](F)C[C@H]2C(=O)NCc2cccc(Cl)c2F)c2ncccc12] | (2S,4R)-1-[2-(3-Acetyl-pyrrolo[2,3-b]pyridin-1-yl)-acetyl]-4-fluoro-pyrrolidine-2-carboxylic acid 3-chloro-2-fluoro-benzylamide | (4[A13]) $R_f$ (CH$_2$Cl$_2$/MeOH 4:1) = 0.80; 475.3/477.3 [M + H]+, 519.2/521.2 [M + HCOO]−; $t_R$ (f): 1.84 min. |
| 548 | 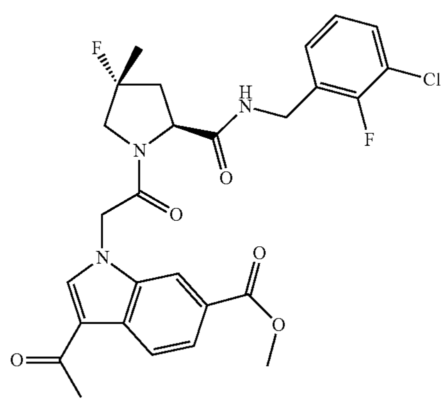 [SMILES: COC(=O)c1ccc2c(C(C)=O)cn(CC(=O)N3C[C@](C)(F)C[C@H]3C(=O)NCc3cccc(Cl)c3F)c2c1] | 3-Acetyl-1-{2-[(2S,4R)-2-(3-chloro-2-fluoro-benzylcarbamoyl)-4-fluoro-4-methyl-pyrrolidin-1-yl]-2-oxo-ethyl}-1H-indole-6-carboxylic acid methyl ester | (3[B13],4[A13],5) Solid. 546 [M + H]+, 568 [M + Na]+; $t_R$ (k): 3.58 min. |
| 549 | 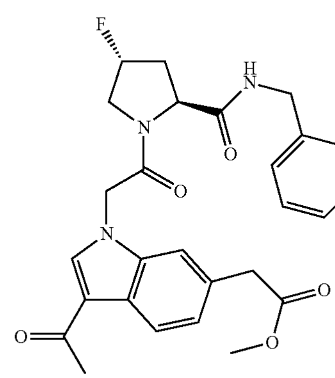 | (3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yl)-acetic acid methyl ester | (4,5) Solid. 546 [M + H]+, 568 [M + Na]+; $t_R$ (k): 3.46 min. |
| 550 | 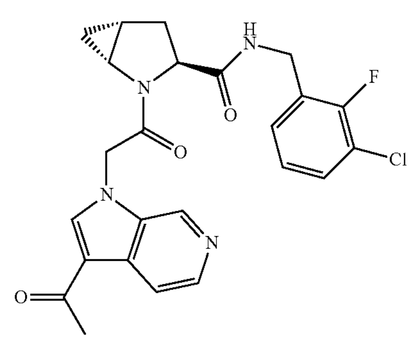 [SMILES: CC(=O)c1cn(CC(=O)N2[C@@H]3C[C@@H]3C[C@H]2C(=O)NCc2cccc(Cl)c2F)c2cnccc12] | (1R,3S,5R)-2-[2-(3-Acetyl-pyrrolo[2,3-c]pyridin-1-yl)-acetyl]-2-aza-bicyclo[3.1.0]hexane-3-carboxylic acid 3-chloro-2-fluorobenzylamide | (4[A15]) White solid. 469.3/471.3 [M + H]+, 513.2/515.2 [M + HCOO]−; $t_R$ (f): 1.48 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 551 | 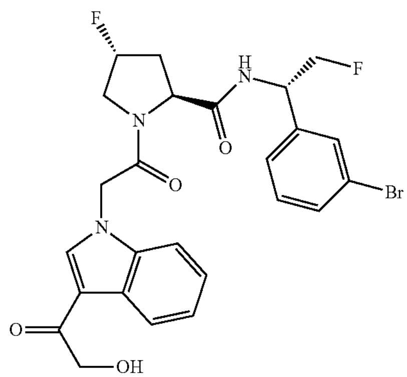 [SMILES: O=C(CO)c1cn(CC(=O)N2C[C@H](F)C[C@H]2C(=O)N[C@H](CF)c2cccc(Br)c2)c2ccccc12] | (2S,4R)-4-Fluoro-1-{2-[3-(2-hydroxy-acetyl)-indol-1-yl]-acetyl}-pyrrolidine-2-carboxylic acid [(S)-1-(3-bromo-phenyl)-2-fluoro-ethyl]-amide | (1,4[A13],5) White solid. 548.0 [M + H]+; t$_R$ (c): 4.47 min. |
| 552 | 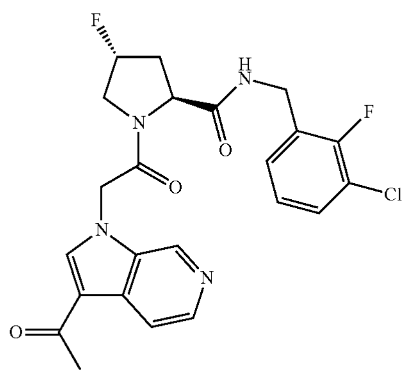 [SMILES: CC(=O)c1cn(CC(=O)N2C[C@H](F)C[C@H]2C(=O)NCc2cccc(Cl)c2F)c2cnccc12] | (2S,4R)-1-[2-(3-Acetyl-pyrrolo[2,3-c]pyridin-1-yl)-acetyl]-4-fluoro-pyrrolidine-2-carboxylic acid 3-chloro-2-fluoro-benzylamide | (4[A15]) R$_f$ (CH$_2$Cl$_2$/MeOH 9:1) = 0.40; 475.4/477.3 [M + H]+, 519.3/521.4 [M + HCOO]−; t$_R$ (f): 1.45 min. |
| 553 | 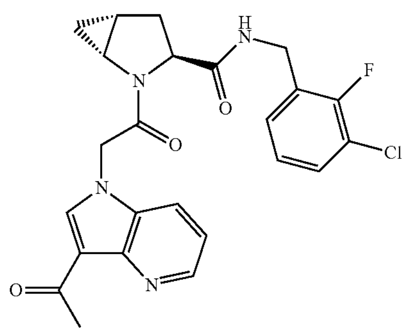 [SMILES: CC(=O)c1cn(CC(=O)N2[C@@H]3C[C@@H]3C[C@H]2C(=O)NCc2cccc(Cl)c2F)c2cccnc12] | (1R,3S,5R)-2-[2-(3-Acetyl-pyrrolo[3,2-b]pyridin-1-yl)-acetyl]-2-aza-bicyclo[3.1.0]hexane-3-carboxylic acid 3-chloro-2-fluoro-benzylamide | (4[A13]) R$_f$ (CH$_2$Cl$_2$/MeOH 4:1) = 0.35, 469.2/471.3 [M + H]+, 513.3/515.3 [M + HCOO]−; t$_R$ (f): 1.45 min. |
| 554 | 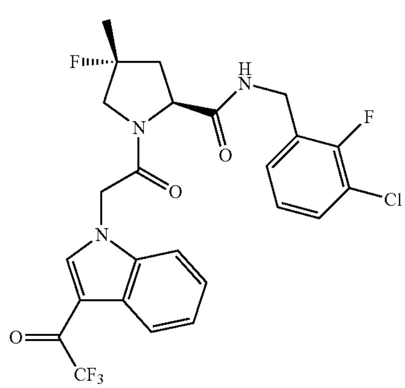 [SMILES: C[C@@]1(F)C[C@@H](C(=O)NCc2cccc(Cl)c2F)N(C(=O)Cn2cc(C(=O)C(F)(F)F)c3ccccc32)C1] | (2S,4R)-4-Fluoro-4-methyl-1-{2-[3-(2,2,2-trifluoro-acetyl)-indol-1-yl]-acetyl}-pyrrolidine-2-carboxylic acid 3-chloro-2-fluoro-benzylamide | (3[B13],4[A13],5) White solid. R$_f$ (CH$_2$Cl$_2$/MeOH 95:5) = 0.56; 542.0 [M + H]+; t$_R$ (c): 5.54 min. |

| Example | Structure | Name | Characterization (end-table notes), TLC, R$_f$ (eluent); MS (LC/MS); t$_R$ (HPLC conditions) |
|---|---|---|---|
| 555 | 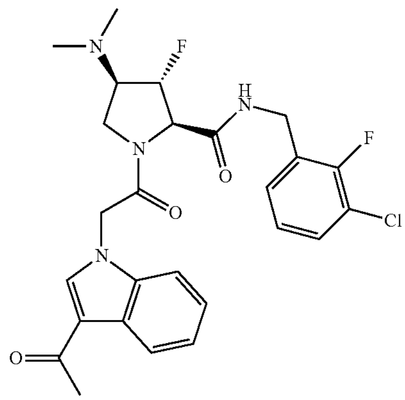 [SMILES: CC(=O)c1cn(CC(=O)N2C[C@@H](N(C)C)[C@H](F)[C@H]2C(=O)NCc2cccc(Cl)c2F)c2ccccc12] | (2R,3S,4R)-1-[2-(3-Acetyl-indol-1-yl)-acetyl]-4-dimethylamino-3-fluoro-pyrrolidine-2-carboxylic acid 3-chloro-2-fluoro-benzylamide | (3[B20]) R$_f$ (c-hexane/EtOAc 1/1) = 0.17; 517 [M + H]+, 561 [M − H]−; t$_R$ (f): 1.63 min. |
| 556 | 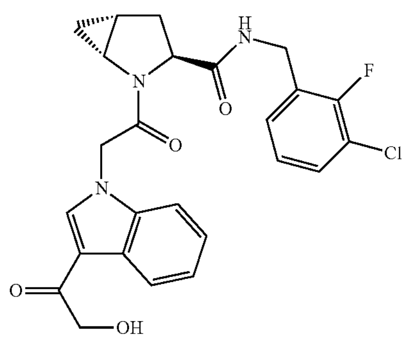 [SMILES: O=C(CO)c1cn(CC(=O)N2[C@@H]3C[C@@H]3C[C@H]2C(=O)NCc2cccc(Cl)c2F)c2ccccc12] | (1R,3S,5R)-2-{2-[3-(2-Hydroxy-acetyl)-indol-1-yl]-acetyl}-2-aza-bicyclo[3.1.0] hexane-3-carboxylic acid 3-chloro-2-fluoro-benzylamide | (4[A13],5) White solid. 484.0 [M + H]+; t$_R$ (c): 4.50 min. |
| 557 | 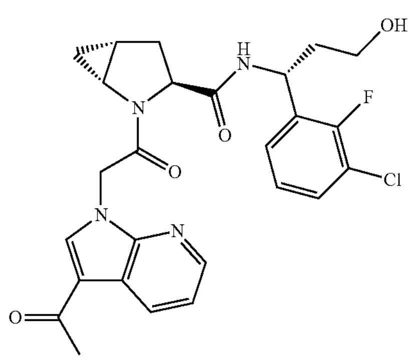 [SMILES: CC(=O)c1cn(CC(=O)N2[C@@H]3C[C@@H]3C[C@H]2C(=O)N[C@H](CCO)c2cccc(Cl)c2F)c2ncccc12] | (1R,3S,5R)-2-[2-(3-Acetyl-pyrrolo[2,3-b]pyridin-1-yl)-acetyl]-2-aza-bicyclo[3.1.0] hexane-3-carboxylic acid [(R)-1-(3-chloro-2-fluoro-phenyl)-3-hydroxy-propyl]-amide | (3[B9],4[A13]) R$_f$ (CH$_2$Cl$_2$/MeOH 9:1) = 0.7; 513.3/515.3 [M + H]+, 557.2 [M + HCOO]−; t$_R$ (a): 3.02 min. |
| 558 | 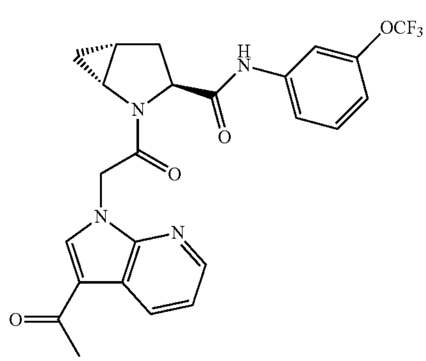 [SMILES: CC(=O)c1cn(CC(=O)N2[C@@H]3C[C@@H]3C[C@H]2C(=O)Nc2cccc(OC(F)(F)F)c2)c2ncccc12] | (1R,3S,5R)-2-[2-(3-Acetyl-pyrrolo[2,3-b]pyridin-1-yl)-acetyl]-2-aza-bicyclo[3.1.0] hexane-3-carboxylic acid (3-trifluoromethoxy-phenyl)-amide | (4[A13]) R$_f$ (EtOAc) = 0.30; 487.3 [M + H]+, 973.5 [2M + H]+, 485.3 [M − H]−, 531.3 [M + HCOO]−, 1017.5 [2M + HCOO]−; t$_R$ (f): 2.08 min. |

TABLE 6-continued

| Example | Name | Characterization (end-table notes), TLC, R_f (eluent); MS (LC/MS); t_R (HPLC conditions) |
|---|---|---|
| 559 | (S)-1-[2-(3-Formyl-indol-1-yl)-acetyl]-pyrrolidine-2-carboxylic acid (3-trifluoro-methoxy-phenyl)-amide | R_f (c-hexane/EtOAc 1:2) =0.04; 460.1 [M + H]+, 482 [M + Na]+, 941.2 [2M + Na]+, 458.2 [M − H]−; t_R (a): 3.58 min. |
| 560 | (2S,4R)-4-Fluoro-1-[2-(3-formyl-5-methoxy-indol-1-yl)-acetyl]-pyrrolidine-2-carboxylic acid 3-chloro-2-fluoro-benzylamide | MS (LC/MS): 490.0 [M + H]+; t_R (l): 1.77 min. |
| 561 | (2S,4R)-4-Fluoro-1-{2-[3-(2,2,2-trifluoro-acetyl)-indol-1-yl]-acetyl}-pyrrolidine-2-carboxylic acid 3-chloro-2-fluoro-benzylamide | (4[A13],5) White solid. R_f (c-hexane/EtOAc 1:1) = 0.18; 528.0 [M + H]+; t_R (c): 5.44 min. |
| 562 | (1R,3S,5R)-2-[2-(3-Acetyl-pyrrolo[2,3-b]pyridin-1-yl)-acetyl]-2-aza-bicyclo[3.1.0]hexane-3-carboxylic acid (2-fluoro-3-trifluoromethoxy-phenyl)-amide | (1,4[A13]) R_f (EtOAc) = 0.45; 505.4 [M + H]+, 1009.6 [2M + H]+, 503.3 [M − H]−, 549.3 [M + HCOO]−, 1007.7 [2M + HCOO]−; t_R (f) 2.08 min. |

TABLE 6-continued

| Example | Structure | Name | Characterization (end-table notes), TLC, R$_f$ (eluent); MS (LC/MS); t$_R$ (HPLC conditions) |
|---|---|---|---|
| 563 | 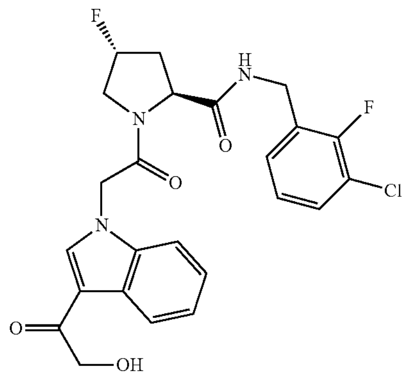 [SMILES: O=C(CO)c1cn(CC(=O)N2C[C@H](F)C[C@H]2C(=O)NCc2cccc(Cl)c2F)c2ccccc12] | (2S,4R)-4-Fluoro-1-{2-[3-(2-hydroxy-acetyl)-indol-1-yl]-acetyl}-pyrrolidine-2-carboxylic acid 3-chloro-2-fluoro-benzylamide | (4[A13],5) White solid. 490.1 [M + H]+, 485.5 [M − H]−; t$_R$ (c): 4.39 min. |
| 564 | 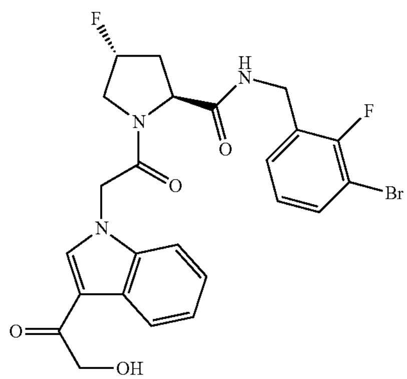 [SMILES: O=C(CO)c1cn(CC(=O)N2C[C@H](F)C[C@H]2C(=O)NCc2cccc(Br)c2F)c2ccccc12] | (2S,4R)-4-Fluoro-1-{2-[3-(2-hydroxy-acetyl)-indol-1-yl]-acetyl}-pyrrolidine-2-carboxylic acid 3-bromo-2-fluoro-benzylamide | (1,4[A13],5) Solid. R$_f$ (CH$_2$Cl$_2$/MeOH 9:1) = 0.50; 534.0 [M + H]+; t$_R$ (k): 3.25 min. |
| 565 | 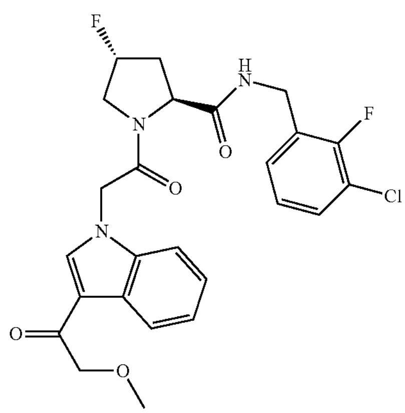 [SMILES: COCC(=O)c1cn(CC(=O)N2C[C@H](F)C[C@H]2C(=O)NCc2cccc(Cl)c2F)c2ccccc12] | (2S,4R)-4-Fluoro-1-{2-[3-(2-methoxy-acetyl)-indol-1-yl]-acetyl}-pyrrolidine-2-carboxylic acid 3-chloro-2-fluoro-benzylamide | (4[A13],5) White solid. 504.0 [M + H]+; t$_R$ (c): 4.63 min. |
| 566 | 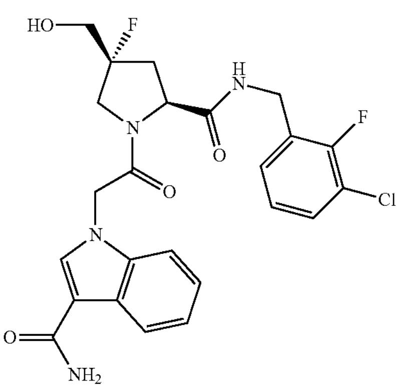 [SMILES: NC(=O)c1cn(CC(=O)N2C[C@@](F)(CO)C[C@H]2C(=O)NCc2cccc(Cl)c2F)c2ccccc12] | 1-{2-[(2S,4R)-2-(3-Chloro-2-fluoro-benzylcarbamoyl)-4-fluoro-4-hydroxymethyl-pyrrolidin-1-yl]-2-oxo-ethyl}-1H-indole-3-carboxylic acid amide | (3[B12]) 503 [M − H], 505 [M + H]+; t$_R$ (f): 1.66 min. |

TABLE 6-continued

| Example | Structure | Name | Characterization (end-table notes), TLC, $R_f$ (eluent); MS (LC/MS); $t_R$ (HPLC conditions) |
|---|---|---|---|
| 567 | 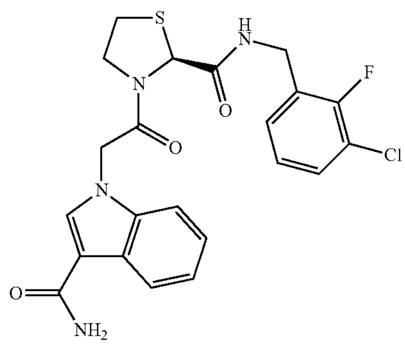 [SMILES: NC(=O)c1cn(CC(=O)N2CCS[C@H]2C(=O)NCc2cccc(Cl)c2F)c2ccccc12] | 1-{2-[(S)-2-(3-Chloro-2-fluoro-benzylcarbamoyl)-thiazolidin-3-yl]-2-oxo-ethyl}-1H-indole-3-carboxylic acid amide | White solid. 475 [M + H]+; $t_R$ (c): 4.32 min. |
| 568 | 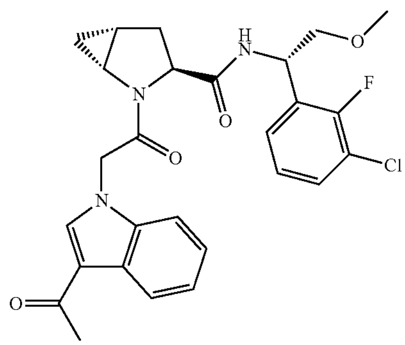 [SMILES: COC[C@@H](NC(=O)[C@@H]1C[C@H]2C[C@H]2N1C(=O)Cn1cc(C(C)=O)c2ccccc21)c1cccc(Cl)c1F] | (1R,3S,5R)-2-[2-(3-Acetyl-indol-1-yl)-acetyl]-2-azabicyclo[3.1.0]hexane-3-carboxylic acid [(S)-1-(3-chloro-2-fluoro-phenyl)-2-methoxy-ethyl]-amide | (2,3[B9]). White solid. $R_f$ (EtOAc) = 0.35; 511.9 [M + H]+, 510.1 [M − H]−, 556.2 [M + HCOO]−; $t_R$ (a): 3.43 min. |

(1) The substituted benzylamide or aniline derivative used in step A was prepared as described in Part C; (2) HCl (4M in dioxane) was used instead of TFA in step B; (3) The title compound was prepared according to the general procedure described in Scheme D6 steps B and C starting from the substituted proline derivative prepared as described in Part B [Scheme]; (4) Compound was prepared as described in Scheme D7 using (3-carbamoyl-indol-1-yl)-acetic acid derivative or (3-acetyl-indol-1-yl)-acetyl acid derivative (prepared as described in Part A); (5) DMF was used instead of $CH_2Cl_2$ in step C; (6) HATU was used as the coupling reagent in step C.

Example 569

(2S,3S,4S)-1-[2-(3-Acetyl-indol-1-yl)-acetyl]-4-fluoro-3-ethoxy-pyrrolidine-2-carboxylic acid 3-chloro-2-fluoro-benzylamide

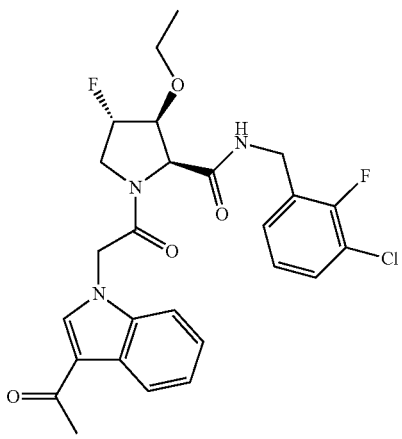 [SMILES: CCO[C@H]1[C@@H](C(=O)NCc2cccc(Cl)c2F)N(C(=O)Cn2cc(C(C)=O)c3ccccc32)C[C@@H]1F]

The title compound was prepared according to Scheme D7 from (2S,3S,4S)-4-fluoro-3-ethoxy-pyrrolidine-2-carboxylic acid 3-chloro-2-fluoro-benzylamide (prepared as described in Scheme B24 using ethyl iodide instead of methyl iodide in Step B). MS (UPLC-MS): 518 [M+H]+, 562 [M+HCOO]−; $t_R$ (HPLC conditions f): 2.11 min.

Example 570

(2S,3S,4S)-1-[2-(3-Acetyl-indol-1-yl)-acetyl]-4-fluoro-3-methoxy-pyrrolidine-2-carboxylic acid [(R)-1-(3-chloro-2-fluoro-phenyl)-ethyl]-amide

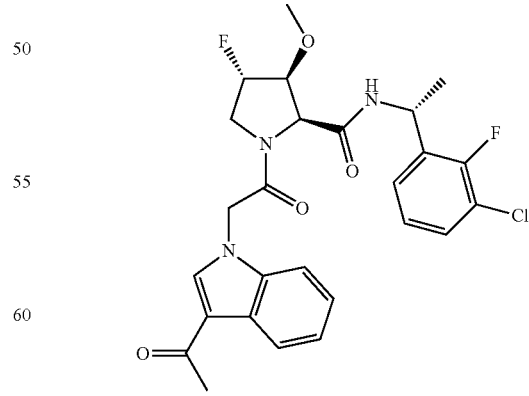

The title compound was prepared according to Scheme D7 from (2S,3S,4S)-4-fluoro-3-methoxy-pyrrolidine-2-carboxylic acid (R)-1-(3-chloro-2-fluoro-phenyl)-ethyl]-amide prepared as described in Scheme B24 using (R)-1-(3-chloro- 2-fluorophenyl)ethanamine in Step D. MS (UPLC-MS): 562 [M+HCOO]−, 518 [M+H]+; t$_R$ (HPLC conditions f): 2.11 min.

Example 571

(2S,3S,4S)-1-[2-(3-Acetyl-indol-1-yl)-acetyl]-4-fluoro-3-methoxy-pyrrolidine-2-carboxylic acid [(S)-1-(3-chloro-2-fluoro-phenyl)-ethyl]-amide

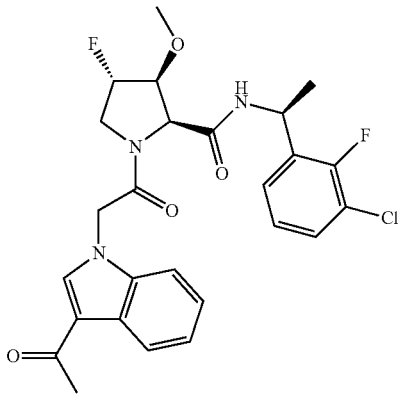 [SMILES: CO[C@H]1[C@@H](C(=O)N[C@@H](C)c2cccc(Cl)c2F)N(C(=O)Cn2cc(C(C)=O)c3ccccc32)C[C@@H]1F]

The title compound was prepared according to Scheme D7 from (2S,3S,4S)-4-fluoro-3-methoxy-pyrrolidine-2-carboxylic acid (S)-1-(3-chloro-2-fluoro-phenyl)-ethyl]-amide prepared as described in Scheme B24 using (S)-1-(3-chloro-2-fluorophenyl)ethanamine in Step D. MS (UPLC-MS): 562 [M+HCOO]−, 518 [M+H]+; t$_R$ (HPLC conditions f): 2.09 min.

Example 572

(2S,3S,4S)-1-[2-(3-Acetyl-indol-1-yl)-acetyl]-4-fluoro-3-methoxy-pyrrolidine-2-carboxylic acid [1-(3-chloro-phenyl)-cyclopropyl]-amide

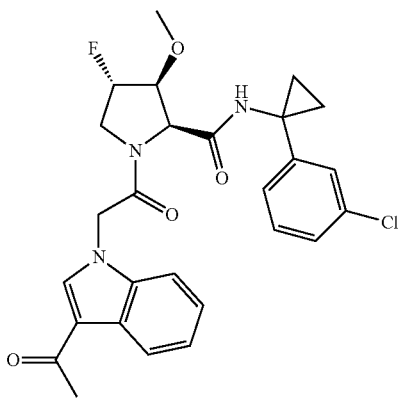 [SMILES: CO[C@H]1[C@@H](C(=O)NC2(c3cccc(Cl)c3)CC2)N(C(=O)Cn2cc(C(C)=O)c3ccccc32)C[C@@H]1F]

The title compound was prepared according to Scheme D7 from (2S,3S,4S)-2-[1-(3-chloro-phenyl)-cyclopropylcarbamoyl]-4-fluoro-3-methoxy-pyrrolidine-1-carboxylic acid tert-butyl ester (prepared using the same protocols as described in Scheme B24 using 1-(3-chloro-phenyl)-cyclopropylamine in Step D). Preparation of 1-(3-chloro-phenyl)-cyclopropylamine was described in Part C. MS (UPLC-MS): 556 [M+HCOO]−, 512 [M+H]+; t$_R$ (HPLC conditions f): 2.05 min.

Example 573

(2S,3S,4S)-1-[2-(3-Acetyl-indol-1-yl)-acetyl]-4-fluoro-3-methoxy-pyrrolidine-2-carboxylic acid [1-(4-chloro-phenyl)-cyclopropyl]-amide

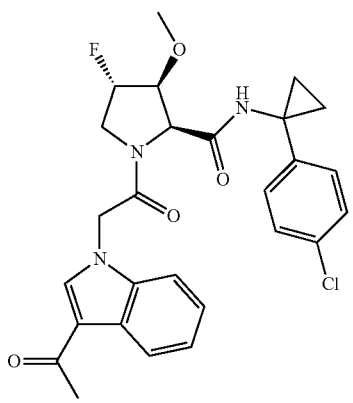 [SMILES: CO[C@H]1[C@@H](C(=O)NC2(c3ccc(Cl)cc3)CC2)N(C(=O)Cn2cc(C(C)=O)c3ccccc32)C[C@@H]1F]

The title compound was prepared according to Scheme D7 from (2S,3S,4S)-2-[1-(3-chloro-phenyl)-cyclopropylcarbamoyl]-4-fluoro-3-methoxy-pyrrolidine-1-carboxylic acid tert-butyl ester (prepared using the same protocols as described in Scheme B24 using 1-(4-chloro-phenyl)-cyclopropylamine in Step D). Preparation of 1-(4-chloro-phenyl)-cyclopropylamine was described in Part C. MS (UPLC-MS): 556 [M+HCOO]−, 512 [M+H]+; t$_R$ (HPLC conditions f): 2.05 min.

Example 574

1-{2-[(2S,3S,4S)-3-Amino-2-(3-chloro-2-fluoro-benzylcarbamoyl)-4-fluoro-pyrrolidin-1-yl]-2-oxo-ethyl}-1H-indole-3-carboxylic acid amide

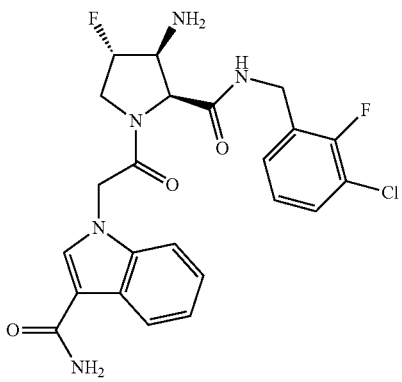 [SMILES: NC(=O)c1cn(CC(=O)N2C[C@H](F)[C@@H](N)[C@H]2C(=O)NCc2cccc(Cl)c2F)c2ccccc12]

The title compound was prepared according to Scheme D7 from (2S,3S,4S)-3-azido-2-(3-chloro-2-fluoro-benzylcarbamoyl)-4-fluoro-pyrrolidine-1-carboxylic acid tert-butyl ester (described in scheme B19) followed by reduction of the azide as described for the preparation of Example 411 (2S,4S)-4-aminomethyl-4-fluoro-pyrrolidine-1,2-dicarboxylic acid 1-[(1-carbamoyl-1H-indol-3-yl)-amide]2-(3-chloro-2,6-difluoro-benzylamide). TLC, $R_f$ (CH$_2$Cl$_2$/MeOH 95/5)= 0.2; MS (LC-MS): 490 [M+H]+, 488 [M–H]–; $t_R$ (HPLC conditions f): 1.46 min.

Example 575

(2S,3S,4S)-1-[2-(3-Acetyl-indol-1-yl)-acetyl]-3-amino-4-fluoro-pyrrolidine-2-carboxylic acid 3-chloro-2-fluoro-benzylamide

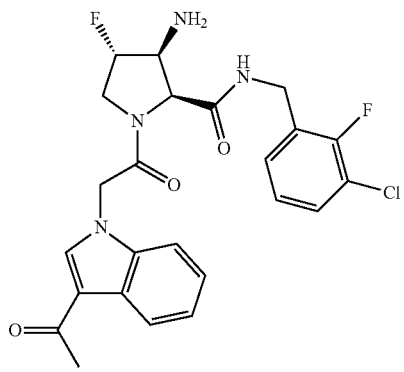 [SMILES: CC(=O)c1cn(CC(=O)N2C[C@H](F)[C@@H](N)[C@H]2C(=O)NCc2cccc(Cl)c2F)c2ccccc12]

The title compound was prepared according to Scheme D7 starting from a mixture of (2R,3S,4R) and (2S,3S,4S)-2-(3-chloro-2-fluoro-benzylcarbamoyl)-4-(9H-fluoren-9-yl-methoxycarbonylamino)-3-fluoro-pyrrolidine-1-carboxylic acid tert-butyl ester in a 2:1 ratio (prepared as described in Scheme B22) followed by Fmoc deprotection using the protocol described for the preparation of Example 396. The regioisomers were separated by preparative HPLC to give the title compound: MS (UPLC-MS): 489 [M+H]+, 533 [M–H]–; $t_R$ (HPLC conditions f): 1.62 min.

Example 576

(2R,3S,4R)-1-[2-(3-Acetyl-indol-1-yl)-acetyl]-4-amino-3-fluoro-pyrrolidine-2-carboxylic acid 3-chloro-2-fluoro-benzylamide

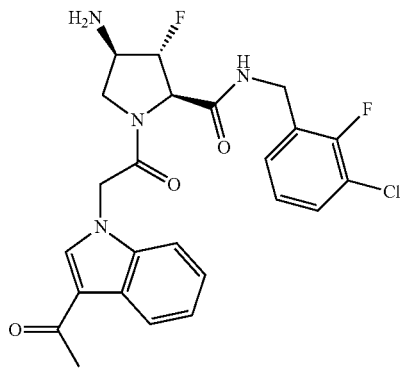 [SMILES: CC(=O)c1cn(CC(=O)N2C[C@@H](N)[C@H](F)[C@H]2C(=O)NCc2cccc(Cl)c2F)c2ccccc12]

The title compound was prepared according to Scheme D7 starting from a mixture of (2R,3S,4R) and (2S,3S,4S)-2-(3-chloro-2-fluoro-benzylcarbamoyl)-4-(9H-fluoren-9-yl-methoxycarbonylamino)-3-fluoro-pyrrolidine-1-carboxylic acid tert-butyl ester in a 2:1 ratio (prepared as described in Scheme B22) followed by Fmoc deprotection using the protocols described for the preparation of Example 396. TLC, $R_f$ (CH$_2$Cl$_2$/MeOH 95/5)=0.26; MS (UPLC-MS): 489 [M+H]+, 533 [M+HCOO]–; $t_R$ (HPLC conditions f): 1.63 min.

Example 577

1-{2-[(2S,4R)-2-(3-Chloro-2-fluoro-benzylcarbamoyl)-4-fluoro-pyrrolidin-1-yl]-2-oxo-ethyl}-5-hydroxy-1H-indole-3-carboxylic acid amide

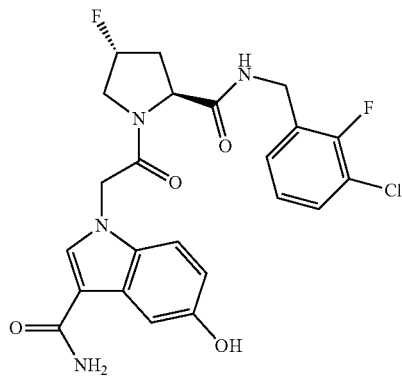 [SMILES: NC(=O)c1cn(CC(=O)N2C[C@H](F)C[C@H]2C(=O)NCc2cccc(Cl)c2F)c2ccc(O)cc12]

To a suspension of 5-benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide Example 503 (148 mg, 0.255 mmol) in TFA (2.5 mL), cooled to 0° C., was added thioanisole (0.301 mL, 2.55 mmol), and the reaction mixture was stirred at RT for 3 h. Volatiles were evaporated under reduced pressure, and the residue was suspended in a saturated aqueous NaHCO$_3$ solution, followed by freeze-drying in vacuo. The residue was suspended in a small amount of methanol and the solid was filtered off. The filtrate was purified by preparative HPLC (Sunfire, C18-ODB, 5 µm, 30×100 mm, flow: 40 mL/min, 20-100% CH$_3$CN/H$_2$O/20 min, 100% CH$_3$CN/2 min, CH$_3$CN and H$_2$O containing 0.1% TFA). The title compound was obtained as a white solid. MS (LC/MS): 491 [M+H]+; 983 [2M+H]+; $t_R$ (HPLC, conditions b): 3.75 min.

Example 578

1-{2-[(2S,4R)-2-(3-Chloro-2-fluoro-benzylcarbamoyl)-4-fluoro-pyrrolidin-1-yl]-2-oxo-ethyl}-6-hydroxy-1H-indole-3-carboxylic acid amide

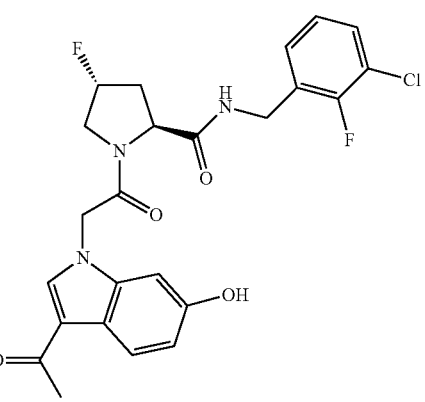

The title compound was prepared in a similar manner as described above for Example 577 from (6-benzyloxy-1-{2-[(2S,4R)-2-(3-chloro-2-fluoro-benzylcarbamoyl)-4-fluoro-pyrrolidin-1-yl]-2-oxo-ethyl}-1H-indole-3-carboxylic acid amide Example 529 (220 mg, 0.379 mmol). White solid. MS (LC/MS): 491 [M+H]+; $t_R$ (HPLC conditions b): 3.76 min.

Example 579

(2S,4R)-1-[2-(3-Acetyl-5-hydroxy-indol-1-yl)-acetyl]-4-fluoro-pyrrolidine-2-carboxylic acid 3-chloro-2-fluoro-benzylamide

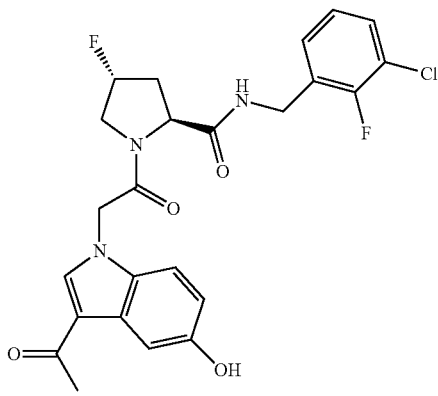 [SMILES: CC(=O)c1cn(CC(=O)N2C[C@H](F)C[C@H]2C(=O)NCc2cccc(Cl)c2F)c2ccc(O)cc12]

The title compound was prepared in a similar manner as described for Example 577 from (2S,4R)-1-[2-(3-acetyl-5-benzyloxy-indol-1-yl)-acetyl]-4-fluoro-pyrrolidine-2-carboxylic acid 3-chloro-2-fluoro-benzylamide Example 508 (167 mg, 0.288 mmol). White solid. MS (LC/MS): 490 [M+H]+; $t_R$ (HPLC conditions k): 3.03 min.

Example 580

(2S,4R)-1-[2-(3-Acetyl-5-hydroxy-indol-1-yl)-acetyl]-4-fluoro-4-methyl-pyrrolidine-2-carboxylic acid 3-chloro-2-fluoro-benzylamide

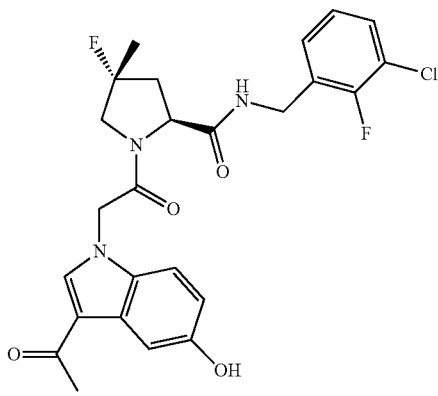 [SMILES: CC(=O)c1cn(CC(=O)N2C[C@](C)(F)C[C@H]2C(=O)NCc2cccc(Cl)c2F)c2ccc(O)cc12]

The title compound was prepared in a similar manner as described above for Example 577 from (2S,4R)-1-[2-(3-acetyl-5-benzyloxy-indol-1-yl)-acetyl]-4-fluoro-4-methyl-pyrrolidine-2-carboxylic acid 3-chloro-2-fluoro-benzylamide (57.0 mg, 0.096 mmol), TFA (3 mL), and thioanisole (0.114 mL, 0.960 mmol). Solid. MS (LC/MS): 504 [M+H]+; $t_R$ (HPLC, conditions k): 3.22 min.

(2S,4R)-1-[2-(3-acetyl-5-benzyloxy-indol-1-yl)-acetyl]-4-fluoro-4-methyl-pyrrolidine-2-carboxylic acid 3-chloro-2-fluoro-benzylamide was prepared as described in Scheme D7 from (3-acetyl-5-benzyloxy-indol-1-yl)-acetic acid (prepared as described in Part A) using DMF instead of $CH_2Cl_2$ in Step C. White solid. MS (LC/MS): 594 [M+H]+; $t_R$ (HPLC conditions k): 3.89 min.

Example 581

(1R,3S,5R)-2-[2-(3-Acetyl-5-hydroxy-indol-1-yl)-acetyl]-2-aza-bicyclo[3.1.0]hexane-3-carboxylic acid 3-chloro-2-fluoro-benzylamide

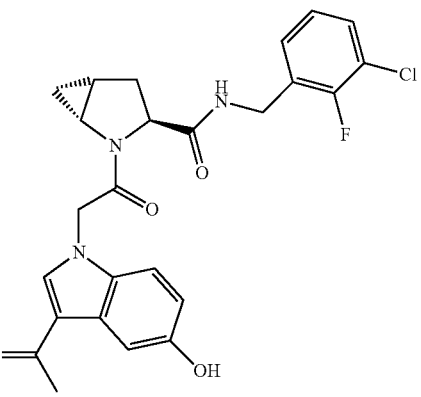

The title compound was prepared in a similar manner as described above for Example 577 from (1R,3S,5R)-2-[2-(3-acetyl-5-benzyloxy-indol-1-yl)-acetyl]-2-aza-bicyclo[3.1.0]hexane-3-carboxylic acid 3-chloro-2-fluoro-benzylamide (79.0 mg, 0.138 mmol), TFA (3 mL) and thioanisole (0.163 mL, 1.38 mmol). Solid. MS (LC/MS): 484 [M+H]+; $t_R$ (HPLC, conditions k): 3.18 min.

(1R,3S,5R)-2-[2-(3-acetyl-5-benzyloxy-indol-1-yl)-acetyl]-2-aza-bicyclo[3.1.0]hexane-3-carboxylic acid 3-chloro-2-fluoro-benzylamide was prepared as described in Scheme D7 from (3-acetyl-5-benzyloxy-indol-1-yl)-acetic acid (prepared as described in Part A) using DMF instead of $CH_2Cl_2$ in Step C. White solid. MS (LC/MS): 574 [M+H]+; $t_R$ (HPLC conditions k): 3.88 min.

Example 582

(2S,4R)-1-[2-(3-Acetyl-6-hydroxy-indol-1-yl)-acetyl]-4-fluoro-4-methyl-pyrrolidine-2-carboxylic acid 3-chloro-2-fluoro-benzylamide

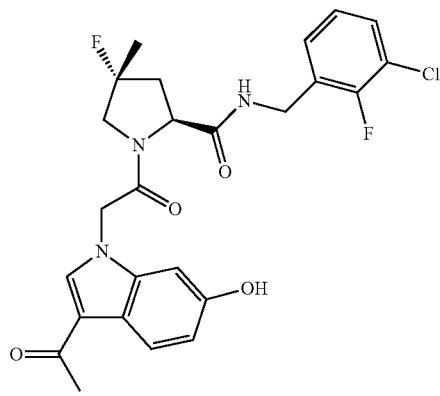 [SMILES: CC(=O)c1cn(CC(=O)N2C[C@](C)(F)C[C@H]2C(=O)NCc2cccc(Cl)c2F)c2cc(O)ccc12]

The title compound was prepared in a similar manner as described above for Example 577 from (2S,4R)-1-[2-(3- acetyl-6-benzyloxy-indol-1-yl)-acetyl]-4-fluoro-4-methyl-pyrrolidine-2-carboxylic acid 3-chloro-2-fluoro-benzylamide (96.0 mg, 0.137 mmol), TFA (2 mL) and thioanisole (0.162 mL, 1.374 mmol). Solid. MS (LC/MS): 504 [M+H]+; $t_R$ (HPLC, conditions k): 3.26 min.

(2S,4R)-1-[2-(3-acetyl-6-benzyloxy-indol-1-yl)-acetyl]-4-fluoro-4-methyl-pyrrolidine-2-carboxylic acid 3-chloro-2-fluoro-benzylamide was prepared as described in Scheme D7 from (3-acetyl-6-benzyloxy-indol-1-yl)-acetic acid (prepared as described in Part A) using DMF instead of $CH_2Cl_2$ in Step C. Solid. MS (LC/MS): 594 [M+H]+; $t_R$ (HPLC conditions k): 3.94 min.

Example 583

(2S,4R)-1-[2-(3-Acetyl-6-hydroxy-indol-1-yl)-acetyl]-4-fluoro-pyrrolidine-2-carboxylic acid 3-chloro-2-fluoro-benzylamide

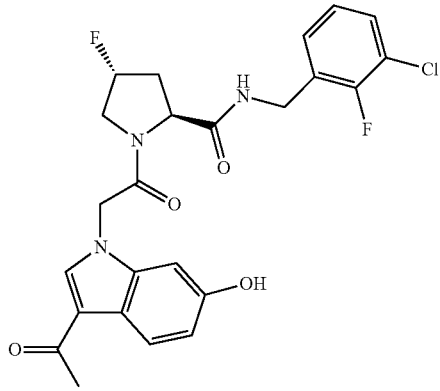

The title compound was prepared in a similar manner as described for Example 577 from (2S,4R)-1-[2-(3-acetyl-6-benzyloxy-indol-1-yl)-acetyl]-4-fluoro-pyrrolidine-2-carboxylic acid 3-chloro-2-fluoro-benzylamide Example 534 (100 mg, 0.172 mmol). White solid. MS (LC/MS): 490 [M+H]+, 512 [M+Na]+; $t_R$ (HPLC conditions k): 3.15 min.

Example 584

(1R,3S,5R)-2-[2-(3-Acetyl-6-hydroxy-indol-1-yl)-acetyl]-2-aza-bicyclo[3.1.0]hexane-3-carboxylic acid 3-chloro-2-fluoro-benzylamide

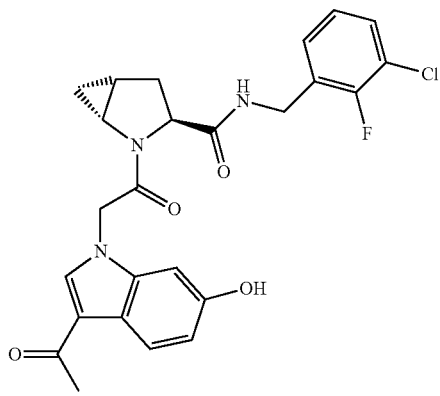

The title compound was prepared in a similar manner as described for Example 577 from (1R,3S,5R)-2-[2-(3-acetyl-6-benzyloxy-indol-1-yl)-acetyl]-2-aza-bicyclo[3.1.0]hexane-3-carboxylic acid 3-chloro-2-fluoro-benzylamide Example 536 (360 mg, 0.527 mmol). Solid. MS (LC/MS): 484 [M+H]+; $t_R$ (HPLC conditions k): 3.21 min.

Example 585

1-{2-[(2S,4R)-2-(3-Chloro-2-fluoro-benzylcarbamoyl)-4-fluoro-pyrrolidin-1-yl]-2-oxo-ethyl}-6-(1H-tetrazol-5-ylmethoxy)-1H-indole-3-carboxylic acid amide

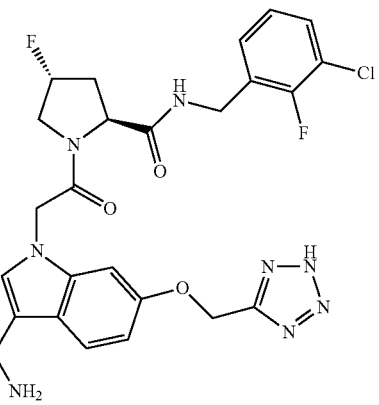

A solution of 1-{2-[(2S,4R)-2-(3-chloro-2-fluoro-benzylcarbamoyl)-4-fluoro-pyrrolidin-1-yl]-2-oxo-ethyl}-6-hydroxy-1H-indole-3-carboxylic acid amide Example 578 (148 mg, 0.283 mmol) in DMSO (3 mL) was treated with $Cs_2CO_3$ (0.28 g, 0.85 mmol). The mixture was stirred at RT for 5 min, followed by addition of 5-(chloromethyl)-1H-tetrazole (35 mg, 0.098 mmol) and stirring at RT for 36 h. The reaction mixture was neutralised by addition of 1N HCl. Water was then added to the mixture to form a precipitate. The solid material was filtered off, washed with water, and dried in vacuo to afford the title compound as a solid. MS (LC/MS): 573 [M+H]+; $t_R$ (HPLC conditions k): 2.92 min.

Example 586

(2S,4R)-1-{2-[3-Acetyl-6-(1H-tetrazol-5-yl-methoxy)-indol-1-yl]-acetyl}-4-fluoro-pyrrolidine-2-carboxylic acid 3-chloro-2-fluoro-benzylamide

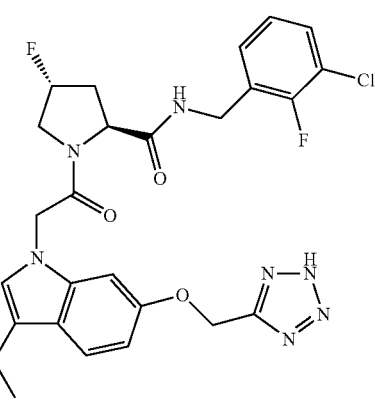

The title compound was prepared in a similar manner as described above for Example 585 from (2S,4R)-1-[2-(3-acetyl-6-hydroxy-indol-1-yl)-acetyl]-4-fluoro-pyrrolidine-2-carboxylic acid 3-chloro-2-fluoro-benzylamide Example 583 (60.0 mg, 0.122 mmol), cesium carbonate (120 mg, 0.367 mmol) and 5-(chloromethyl)-1H-tetrazole (44.0 mg, 0.366 mmol) in DMSO (2.5 mL). Solid. MS (LC/MS): 572 [M+H]+; $t_R$ (HPLC conditions k): 3.23 min.

Example 587

(1R,3S,5R)-2-{2-[3-Acetyl-6-(1H-tetrazol-5-yl-methoxy)-indol-1-yl]-acetyl}-2-aza-bicyclo[3.1.0]hexane-3-carboxylic acid 3-chloro-2-fluoro-benzylamide

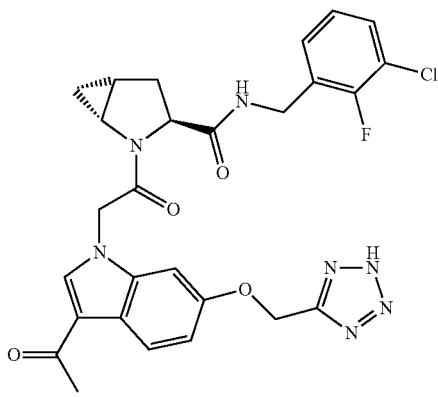

A solution of (1R,3S,5R)-2-[2-(3-Acetyl-6-hydroxy-indol-1-yl)-acetyl]-2-aza-bicyclo[3.1.0]-hexane-3-carboxylic acid 3-chloro-2-fluoro-benzylamide Example 584 (80.0 mg, 0.165 mmol) in DMSO (2 mL) was treated with cesium carbonate (162 mg, 0.496 mmol). After stirring at RT for 5 min, 5-(chloromethyl)-1H-tetrazole (21.0 mg, 0.174 mmol) was added and stirring was continued at RT for 36 h. The mixture was neutralised by addition of 1N HCl, diluted with water extracted with EtOAc (2×). The combined organic layers were washed with water (2×) and brine. The resulting suspension was filtered over phase separator and concentrated. The filtered solid was triturated with methanol, decanted and dried in vacuo to give the title compound. The filtrate was purified by preparative HPLC (Macherey-Nagel Nucleosil 100-10 C18, 5 μm, 40×250 mm, flow: 40 mL/min, eluent: 20-100% CH₃CN/H₂O/20 min, 100% CH₃CN/2 min, CH₃CN and H₂O containing 0.1% TFA) to afford after lyophilization of the purified fractions a second batch of the title compound as a white solid. MS (LC/MS): 566 [M+H]+; $t_R$ (HPLC conditions k): 3.22 min.

Example 588

(2S,4R)-1-[2-(3-Acetyl-5-methoxy-indol-1-yl)-acetyl]-4-fluoro-pyrrolidine-2-carboxylic acid 3-chloro-2-fluoro-benzylamide

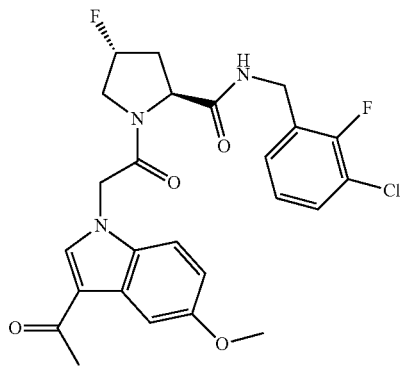 [SMILES: COc1ccc2c(c1)c(C(C)=O)cn2CC(=O)N1C[C@H](F)C[C@H]1C(=O)NCc1cccc(Cl)c1F]

A solution of (2S,4R)-1-[2-(3-acetyl-5-hydroxy-indol-1-yl)-acetyl]-4-fluoro-pyrrolidine-2-carboxylic acid 3-chloro-2-fluoro-benzylamide Example 579 (28.0 mg, 0.057 mmol) in DMSO (2 mL) was treated with potassium hydroxide (15.0 mg, 0.257 mmol). The mixture was stirred at RT for 5 min, followed by addition of iodomethane (0.006 mL, 0.089 mmol) and stirring at RT for 60 h. The reaction mixture was partitioned between water and CH₂Cl₂ and the aqueous layer was extracted with CH₂Cl₂ (2×). The combined organics were washed with brine (3×), dried (phase separator) and concentrated under reduced pressure. The crude product was purified by preparative HPLC (Waters Sunfire, C18-ODB, 5 μm, 19×50 mm, flow: 20 mL/min, eluent: 5-100% CH₃CN/H₂O/20 min, 100% CH₃CN/2 min, CH₃CN and H₂O containing 0.1% TFA) to afford after lyophilization of the purified fractions the title compound as a solid. MS (LC/MS): 504 [M+H]+, 526 [M+Na]+; $t_R$ (HPLC conditions k): 3.38 min.

Example 589

(2S,4R)-1-{2-[3-Acetyl-5-(pyridin-2-ylmethoxy)-indol-1-yl]-acetyl}-4-fluoro-pyrrolidine-2-carboxylic acid 3-chloro-2-fluoro-benzylamide

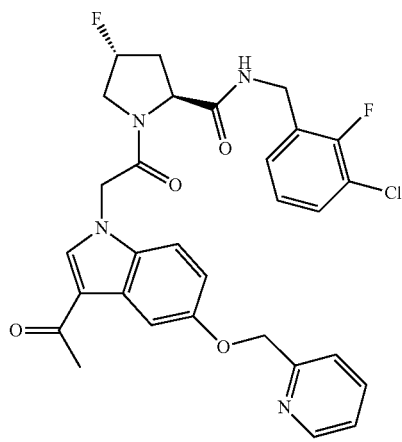 [SMILES: CC(=O)c1cn(CC(=O)N2C[C@H](F)C[C@H]2C(=O)NCc2cccc(Cl)c2F)c2ccc(OCc3ccccn3)cc12]

A solution of (2S,4R)-1-[2-(3-acetyl-5-hydroxy-indol-1-yl)-acetyl]-4-fluoro-pyrrolidine-2-carboxylic acid 3-chloro-2-fluoro-benzylamide Example 579 (60.0 mg, 0.122 mmol) in DMSO (2.5 mL) was treated with cesium carbonate (160 mg, 0.490 mmol). After stirring at RT for 5 min, 2-(bromomethyl)pyridine (31.0 mg, 0.122 mmol) was added to the reaction mixture and stirring was continued at RT for 16 h. Water was then added to the mixture to form a solid precipitate which was filtered off, washed with water and dried in vacuo. Purification by preparative HPLC (Waters Sunfire, C18-ODB, 5 μm, 30×100 mm, flow: 40 mL/min, eluent: 20-100% CH₃CN/H₂O/20 min, 100% CH₃CN/2 min, CH₃CN and H₂O containing 0.1% TFA) afforded after lyophilization of the purified fractions the title compound as a white solid. MS (LC/MS): 580/581 [M+H]+; $t_R$ (HPLC conditions k): 3.00 min.

Example 590

(2S,4R)-1-{2-[3-Acetyl-5-(pyrimidin-2-ylmethoxy)-indol-1-yl]-acetyl}-4-fluoro-pyrrolidine-2-carboxylic acid 3-chloro-2-fluoro-benzylamide

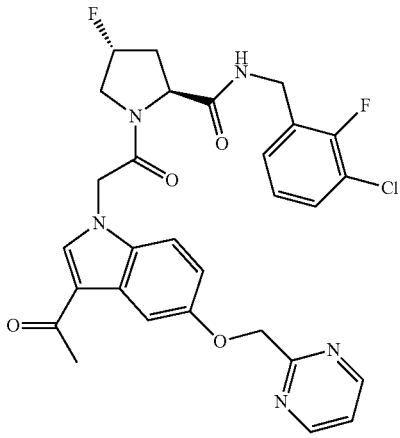 [SMILES: CC(=O)c1cn(CC(=O)N2C[C@H](F)C[C@H]2C(=O)NCc2cccc(Cl)c2F)c2ccc(OCc3ncccn3)cc12]

The title compound was prepared according to procedure described for the preparation of Example 589 (2S,4R)-1-{2-[3-acetyl-5-(pyridin-2-ylmethoxy)-indol-1-yl]-acetyl}-4-fluoro-pyrrolidine-2-carboxylic acid 3-chloro-2-fluoro-benzylamide from (2S,4R)-1-[2-(3-acetyl-5-hydroxy-indol-1-yl)-acetyl]-4-fluoro-pyrrolidine-2-carboxylic acid 3-chloro-2-fluoro-benzylamide Example 579 (23.0 mg, 0.047 mmol), cesium carbonate (61 mg, 0.188 mmol) and 2-(chloromethyl)pyrimidine (0.012 mg, 0.070 mmol) in DMSO (2 mL). White solid. MS (LC/MS): 582/583 [M+H]+; $t_R$ (HPLC conditions k): 3.19 min.

Example 591

1-{2-[(2S,4R)-2-(3-Chloro-2-fluoro-benzylcarbamoyl)-4-fluoro-pyrrolidin-1-yl]-2-oxo-ethyl}-6-(2-methoxy-ethoxy)-1H-indole-3-carboxylic acid amide

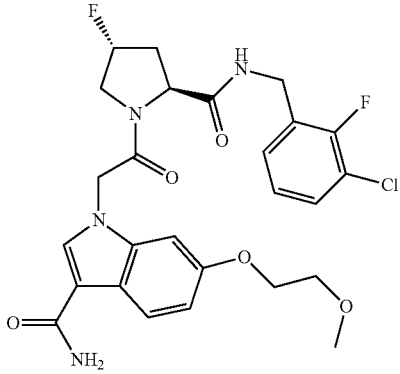 [SMILES: COCCOc1ccc2c(C(N)=O)cn(CC(=O)N3C[C@H](F)C[C@H]3C(=O)NCc3cccc(Cl)c3F)c2c1]

A solution of 1-{2-[(2S,4R)-2-(3-chloro-2-fluoro-benzylcarbamoyl)-4-fluoro-pyrrolidin-1-yl]-2-oxo-ethyl}-6-hydroxy-1H-indole-3-carboxylic acid amide Example 578 (50 mg, 0.102 mmol) in DMSO (1 mL) was treated with KOH (26.0 mg, 0.458 mmol). The mixture was stirred at RT for 5 min, followed by addition of (2-bromoethyl)methyl ether (0.015 mL, 0.158 mmol) and stirring at RT for 2 h. The mixture was partitioned between water and CH$_2$Cl$_2$, and the aqueous phase was extracted twice with CH$_2$Cl$_2$. The combined organics were washed with brine (3×), dried (phase separator) and concentrated under reduced pressure. Purification by preparative HPLC (SunFire C18-ODB, 5 μm, 30×100 mm, eluent: 20-100% CH$_3$CN/H$_2$O/20 min, 100% CH$_3$CN/2 min, CH$_3$CN and H$_2$O containing 0.1% TFA, flow: 40 mL/min) afforded after lyophilization of the purified fractions the title compound as a white solid. MS: 549 [M+H]+; $t_R$ (HPLC conditions c): 4.17 min.

Example 592

(3-Carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid methyl ester

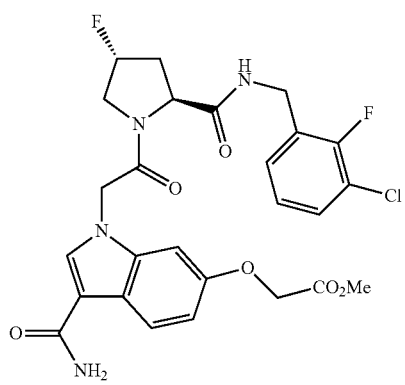 [SMILES: COC(=O)COc1ccc2c(C(N)=O)cn(CC(=O)N3C[C@H](F)C[C@H]3C(=O)NCc3cccc(Cl)c3F)c2c1]

A solution of 1-{2-[(2S,4R)-2-(3-chloro-2-fluoro-benzylcarbamoyl)-4-fluoro-pyrrolidin-1-yl]-2-oxo-ethyl}-6-hydroxy-1H-indole-3-carboxylic acid amide Example 578 (140 mg, 0.285 mmol) in DMSO (3 mL) was treated with Cs$_2$CO$_3$ (0.28 g, 0.85 mmol). The mixture was stirred at RT for 5 min, followed by addition of methyl 2-bromoacetate (0.039 mL, 0.428 mmol) and stirring at RT for 4 h. The mixture was partitioned between water and CH$_2$Cl$_2$, and the organic phase was washed twice with brine (the combined aqueous washings were filtered and the solid thus obtained was dried in vacuo to give an aliquot of the title compound), dried (phase separator) and concentrated under reduced pressure. Purification by preparative HPLC (SunFire C18-ODB, 5 μm, 30×100 mm, eluent: 20-100% CH$_3$CN/H$_2$O/20 min, 100% CH$_3$CN/2 min, CH$_3$CN and H$_2$O containing 0.1% TFA, flow: 40 mL/min) afforded after lyophilization of the purified fractions the title compound as a white solid. MS: 563 [M+H]+; $t_R$ (HPLC conditions c): 4.17 min.

Example 593

(3-Carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid

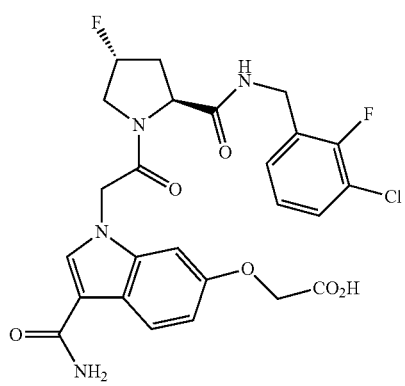 [SMILES: NC(=O)c1cn(CC(=O)N2C[C@H](F)C[C@H]2C(=O)NCc2cccc(Cl)c2F)c2cc(OCC(=O)O)ccc12]

To a solution of (3-carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid methyl ester Example 592 (18 mg, 0.032 mmol) in a mixture of THF (2 mL) and water (0.2 mL) was added 1N NaOH (0.064 mL), followed by stirring at RT for 4 h. The reaction mixture was partitioned between CH$_2$Cl$_2$ and water. The aqueous phase was adjusted to pH=2 by addition of 1N HCl, followed by extraction with CH$_2$Cl$_2$ (3×). The combined organics were dried (phase separator) and concentrated under reduced pressure to afford the title compound as a white solid. MS: 549 [M+H]+; t$_R$ (HPLC conditions c): 3.74 min.

Example 594

1-{2-[(2S,4R)-2-(3-Chloro-2-fluoro-benzylcarbamoyl)-4-fluoro-pyrrolidin-1-yl]-2-oxo-ethyl}-6-(2-hydroxy-ethoxy)-1H-indole-3-carboxylic acid amide

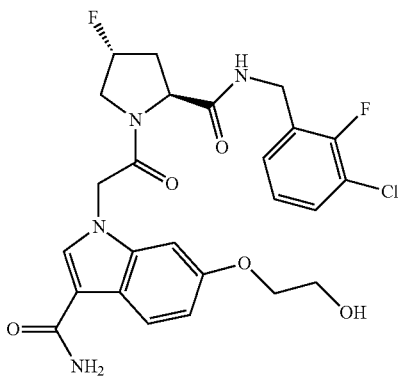 [SMILES: NC(=O)c1cn(CC(=O)N2C[C@H](F)C[C@H]2C(=O)NCc2cccc(Cl)c2F)c2cc(OCCO)ccc12]

To a solution of (3-carbamoyl-1-{2-[(2S,4R)-2-(3-chloro-2-fluoro-benzylcarbamoyl)-4-fluoro-pyrrolidin-1-yl]-2-oxo-ethyl}-1H-indol-6-yloxy)-acetic acid methyl ester Example 592 (30.0 mg, 0.049 mmol) in THF (1 mL) was added LiBH$_4$ (2M in THF; 0.049 mL, 0.098 mmol) and stirring was continued at RT for 2 h. The reaction mixture was partitioned between CH$_2$Cl$_2$ and water, and the aqueous layer was extracted with CH$_2$Cl$_2$ (3×). The combined organics were dried (phase separator) and concentrated under reduced pressure. Purification by preparative HPLC (SunFire C18-ODB, 5 μm, 19×50 mm, eluent: 5-100% CH$_3$CN/H$_2$O/20 min, 100% CH$_3$CN/2 min, CH$_3$CN and H$_2$O containing 0.1% TFA, flow: 20 mL/min) afforded after lyophilization of the purified fractions the desired compound as a white solid. MS: 535 [M+H]+; t$_R$ (HPLC conditions c): 3.72 min.

Example 595

(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yl)-acetic acid

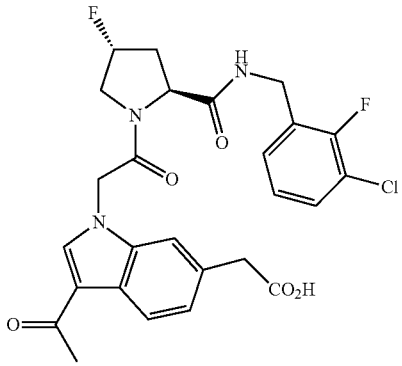 [SMILES: CC(=O)c1cn(CC(=O)N2C[C@H](F)C[C@H]2C(=O)NCc2cccc(Cl)c2F)c2cc(CC(=O)O)ccc12]

To a solution of (3-acetyl-1-{2-[(2S,4R)-2-(3-chloro-2-fluoro-benzylcarbamoyl)-4-fluoro-pyrrolidin-1-yl]-2-oxo-ethyl}-1H-indol-6-yl)-acetic acid methyl ester Example 549 (200 mg, 0.366 mmol) in THF (5 mL) and water (0.5 mL) was added 1N NaOH (1.46 mL, 1.46 mmol) and the reaction was stirred at RT for 60 h. The mixture was partitioned between diethylether and water. The layers were separated and the aqueous phase was adjusted to pH=2 by addition of a 1N HCl solution to form a precipitate. The solid was filtered off, washed with water diethylether and dried in vacuo to afford the title compound as a solid. MS (LC/MS): 532 [M+H]+; t$_R$ (HPLC conditions k): 3.19 min.

Example 596

(3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid

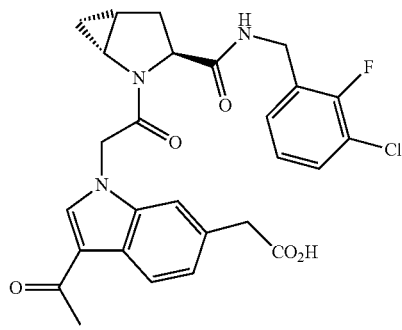

The title compound was prepared in a similar manner as described for Example 595 from (3-acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indol-6-yl)-acetic acid methyl ester Example 545 (200 mg, 0.370 mmol). Solid. MS (LC/MS): 526 [M+H]+; t$_R$ (HPLC conditions k): 3.24 min.

Example 597

3-Acetyl-1-{2-[(2S,4R)-2-(3-chloro-2-fluoro-benzylcarbamoyl)-4-fluoro-pyrrolidin-1-yl]-2-oxo-ethyl}-1H-indole-6-carboxylic acid

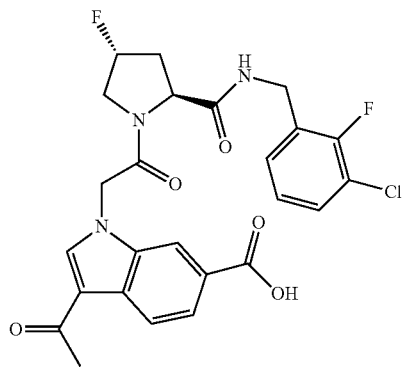 [SMILES: CC(=O)c1cn(CC(=O)N2C[C@H](F)C[C@H]2C(=O)NCc2cccc(Cl)c2F)c2cc(C(=O)O)ccc12]

The title compound was prepared in a similar manner as described for Example 595 from 3-acetyl-1-{2-[(2S,4R)-2-(3-chloro-2-fluoro-benzylcarbamoyl)-4-fluoro-pyrrolidin-1- yl]-2-oxo-ethyl}-1H-indole-6-carboxylic acid methyl ester Example 542 (200 mg, 0.370 mmol). Solid. MS (LC/MS): 518 [M+H]+; $t_R$ (HPLC conditions k): 3.14 min.

Example 598

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-6-carboxylic acid

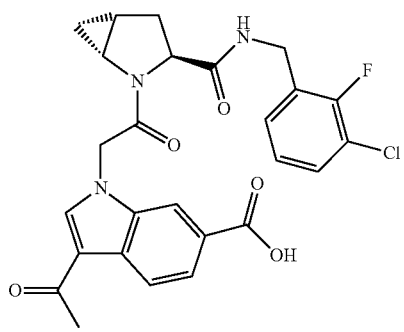

Example 599

3-Acetyl-1-{2-[(2S,4R)-2-(3-chloro-2-fluoro-benzyl-carbamoyl)-4-fluoro-4-methyl-pyrrolidin-1-yl]-2-oxo-ethyl}-1H-indole-6-carboxylic acid

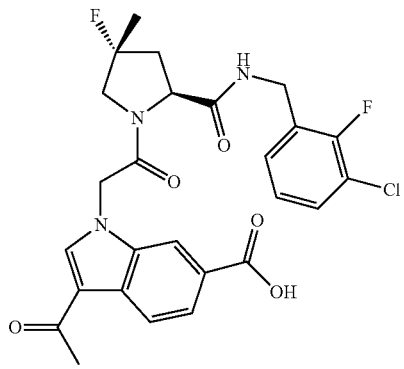 [SMILES: CC(=O)c1cn(CC(=O)N2C[C@](C)(F)C[C@H]2C(=O)NCc2cccc(Cl)c2F)c2cc(C(=O)O)ccc12]

The title compound was prepared in a similar manner as described for Example 595 from 3-acetyl-1-{2-[(2S,4R)-2-(3-chloro-2-fluoro-benzylcarbamoyl)-4-fluoro-4-methyl-pyrrolidin-1-yl]-2-oxo-ethyl}-1H-indole-6-carboxylic acid methyl ester Example 548 (70 mg, 0.128 mmol). Solid. MS (LC/MS): 532 [M+H]+; $t_R$ (HPLC conditions c): 4.34 min.

Example 600

2S,3S,4S)-4-Fluoro-3-methoxy-pyrrolidine-1,2-dicarboxylic acid 1-[(1-carbamoyl-1H-indol-3-yl)-amide]2-(3-chloro-2-fluoro-benzylamide

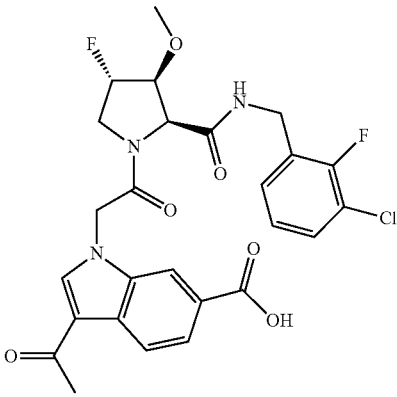 [SMILES: CO[C@H]1[C@@H](C(=O)NCc2cccc(Cl)c2F)N(C(=O)Cn2cc(C(C)=O)c3ccc(C(=O)O)cc32)C[C@@H]1F]

The title compound was prepared in a similar manner as described for Example 595 starting from (2S,3S,4S)-4-fluoro-3-methoxy-pyrrolidine-2-carboxylic acid 3-chloro-2-fluoro-benzylamide (prepared as described in Scheme D7 from 3-acetyl-1-carboxymethyl-1H-indole-6-carboxylic acid methyl ester (described in Part C) and (2S,3S,4S)-4-fluoro-3-methoxy-pyrrolidine-2-carboxylic acid 3-chloro-2-fluoro-benzylamide (described Scheme B24). MS (UPLC-MS): 548 [M+H]+, 592 [M+HCOO]−; $t_R$ (HPLC conditions f): 1.84 min.

Example 601

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-7-carboxylic acid

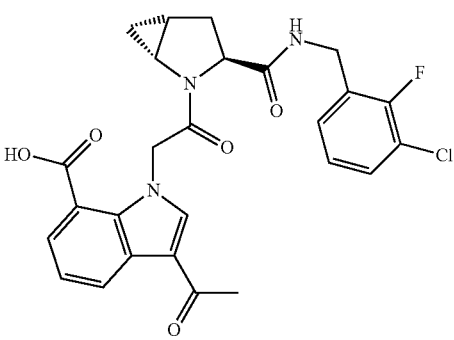

To a solution of 3-acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-7-carboxylic acid methyl ester Example 541 (110 mg, 0.209 mmol) in THF (3 mL) and water (0.3 mL) was added 2N LiOH (1.05 mL, 2.09 mmol). Stirring of the reaction mixture was continued at RT for 18 h. A 1N HCl solution was added to adjust to pH=2-3 and the resulting aqueous suspension was filtered. The solid was washed with water then dried in vacuo. The residue was purified by preparative HPLC (Waters Sunfire, C18-ODB, 5 µm, 30×100 mm, flow: 40 mL/min, eluent: 20-100% CH₃CN/H₂O/20 min, 100% CH₃CN/2 min, CH₃CN and H₂O containing 0.1% TFA) to afford after lyophilization of the purified fractions the title compound as a white solid. MS (LC/MS): 512 [M+H]+; $t_R$ (HPLC conditions k): 3.34 min.

Example 602

4-(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yloxymethyl)-benzoic acid

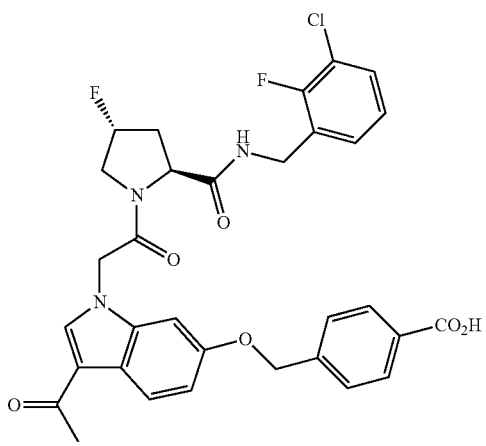 [SMILES: CC(=O)c1cn(CC(=O)N2C[C@H](F)C[C@H]2C(=O)NCc2cccc(Cl)c2F)c2cc(OCc3ccc(C(=O)O)cc3)ccc12]

The title compound was prepared in a similar manner as described for Example 595 from 4-(3-acetyl-1-{2-[(2S,4R)-2-(3-chloro-2-fluoro-benzylcarbamoyl)-4-fluoro-pyrrolidin-1-yl]-2-oxo-ethyl}-1H-indol-6-yloxymethyl)-benzoic acid methyl ester (37.0 mg, 0.058 mmol) and 1N NaOH (0.928 mL, 0.928 mmol) in THF (5 mL) and water (0.5 mL). Solid. MS (LC/MS): 624/626 [M+H]+; $t_R$ (HPLC conditions k): 3.48 min.

4-(3-Acetyl-1-{2-[(2S,4R)-2-(3-chloro-2-fluoro-benzylcarbamoyl)-4-fluoro-pyrrolidin-1-yl]-2-oxo-ethyl}-1H-indol-6-yloxymethyl)-benzoic acid methyl ester A solution of (2S,4R)-1-[2-(3-acetyl-6-hydroxy-indol-1-yl)-acetyl]-4-fluoro-pyrrolidine-2-carboxylic acid 3-chloro-2-fluoro-benzylamide Example 583 (60.0 mg, 0.122 mmol) in DMSO (2.5 mL) was treated with cesium carbonate (160 mg, 0.490 mmol). After stirring at RT for 5 min, methyl 4-(bromomethyl)benzoate (28.0 mg, 0.122 mmol) was added and the reaction was stirred at RT for 1 h. The mixture was neutralised with 1N HCl and diluted with water to form a precipitate. The solid was filtered off, washed with water and dried in vacuo. The crude product was purified by preparative HPLC (Waters Sunfire, C18-ODB, 5 µm, 30×100 mm, flow: 40 mL/min, eluent: 20-100% CH₃CN/H₂O/20 min, 100% CH₃CN/2 min, CH₃CN and H₂O containing 0.1% TFA) to afford after lyophilization the title compound as a white solid. MS (LC/MS): 639 [M+H]+; $t_R$ (HPLC conditions k): 3.82 min.

Example 603

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboxylic acid

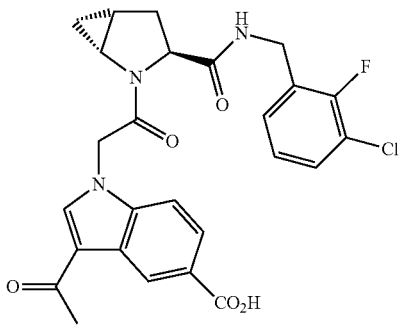

To a solution of 3-acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboxylic acid methyl ester (141 mg, 0.268 mmol) in THF (3 mL) and water (0.3 mL) was added 2N LiOH (1.07 mL, 2.14 mmol). Stirring of the reaction mixture was continued at 50° C. for 60 h. After cooling to RT, a 1N HCl solution was added to adjust to pH=2-3, and the resulting aqueous suspension was extracted with CH₂Cl₂ (3×). The combined organics were dried (phase separator) and concentrated under reduced pressure. The residue was purified by preparative HPLC (Waters Sunfire, C18-ODB, 5 µm, 30×100 mm, flow: 40 mL/min, eluent: 20-100% CH₃CN/H₂O/20 min, 100% CH₃CN/2 min, CH₃CN and H₂O containing 0.1% TFA) to afford after lyophilization of the purified fractions the title compound as a white solid. MS (LC/MS): 512 [M+H]+; $t_R$ (HPLC conditions c): 4.33 min.

3-Acetyl-1-[2-[(1R,3S,5R)-3-(3-chloro-2-fluoro-benzylcarbamoyl)-2-aza-bicyclo[3.1.0]hex-2-yl]-2-oxo-ethyl]-1H-indole-5-carboxylic acid methyl ester The title compound was prepared as described in Scheme D7 from 3-acetyl-1-carboxymethyl-1H-indole-5-carboxylic acid methyl ester (prepared as described in Part A) and by using DMF instead of CH₂Cl₂. Solid. MS (LC/MS): 526 [M+H]+, 548 [M+Na]+; $t_R$ (HPLC conditions k): 3.54 min.

Example 604

(2S,4R)-1-[2-(3-Acetyl-6-hydroxymethyl-indol-1-yl)-acetyl]-4-fluoro-pyrrolidine-2-carboxylic acid 3-chloro-2-fluoro-benzylamide

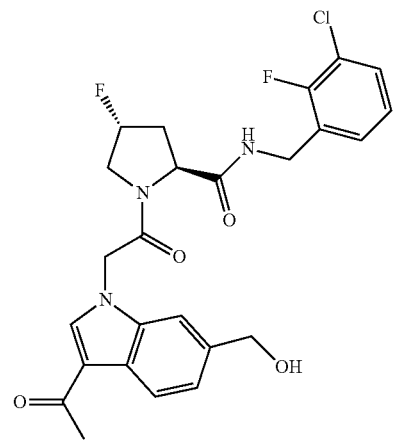 [SMILES: CC(=O)c1cn(CC(=O)N2C[C@H](F)C[C@H]2C(=O)NCc2cccc(Cl)c2F)c2cc(CO)ccc12]

655

To a solution of (2S,4R)-1-[2-(3-acetyl-6-triisopropylsilanyloxymethyl-indol-1-yl)-acetyl]-4-fluoro-pyrrolidine-2-carboxylic acid 3-chloro-2-fluoro-benzylamide (50.0 mg, 0.057 mmol) in THF (5 mL), cooled to at 0° C., was added TBAF (1M in THF, 0.057 mL, 0.057 mmol), and stirring was continued for 3 h. The reaction was quenched with saturated aqueous NaHCO$_3$ followed by addition of EtOAc. The layers were separated and the aqueous phase was extracted with EtOAc. The combined organics were washed with water (1×) and brine, dried (phase separator) and concentrated in vacuo. Purification by preparative HPLC (Waters Sunfire, C18-ODB, 5 µm, 30×100 mm, flow: 40 mL/min, eluent: 20% CH$_3$CN/H$_2$O/20 min, 100% CH$_3$CN/2 min, CH$_3$CN and H$_2$O containing 0.1% TFA) afforded after lyophilization of the purified fractions the title compound as a white solid. MS (LC/MS): 504 [M+H]+; $t_R$ (HPLC conditions k): 3.10 min.

(2S,4R)-1-[2-(3-Acetyl-6-triisopropylsilanyloxymethyl-indol-1-yl)-acetyl]-4-fluoro-Pyrrolidine-2-carboxylic acid 3-chloro-2-fluoro-benzylamide The title compound was prepared as described in Scheme D7 from (3-acetyl-5-triisopropylsilanyloxymethyl-indol-1-yl)-acetic acid (prepared as described in Scheme A14) and by using DMF instead of CH$_2$Cl$_2$. Yellow wax. MS (LC/MS): 683 [M+Na]+; $t_R$ (HPLC conditions k): 4.72 min.

Example 605

3-[({(2S,4R)-1-[2-(3-Acetyl-indol-1-yl)-acetyl]-4-fluoro-pyrrolidine-2-carbonyl}-amino)-methyl]-5-chloro-4-fluoro-benzoic acid

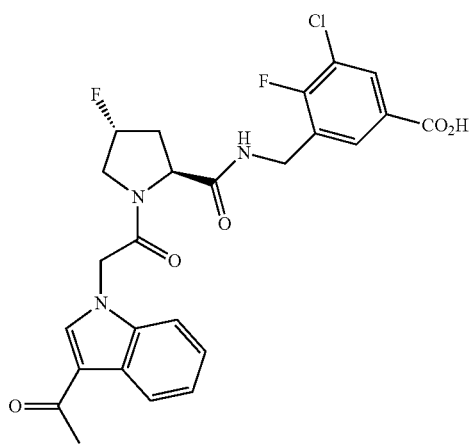 [SMILES: CC(=O)c1cn(CC(=O)N2C[C@H](F)C[C@H]2C(=O)NCc2cc(C(=O)O)cc(Cl)c2F)c2ccccc12]

To 3-[({(2S,4R)-1-[2-(3-acetyl-indol-1-yl)-acetyl]-4-fluoro-pyrrolidine-2-carbonyl}-amino)-methyl]-5-chloro-4-fluoro-benzoic acid methyl ester Example 523 (35.0 mg, 0.066 mmol) in THF-MeOH—H$_2$O (ratio 2:1:1; 1 mL) was added LiOH.H$_2$O (2.76 mg, 0.066 mmol). The reaction mixture was stirred at RT for 4 h. Volatiles were evaporated and the residue was taken up in water, Acidification to pH=1 by addition of a 6M HCl solution formed a precipitate which was filtered and dried at 50° C. in vacuo for 1 h to afford the title compound as a solid. MS: 518.0 [M+H]+; $t_R$ (HPLC conditions c): 4.26 min.

656

Example 606

3-[({(1R,3S,5R)-2-[2-(3-Acetyl-indol-1-yl)-acetyl]-2-aza-bicyclo[3.1.0]hexane-3-carbonyl}-amino)-methyl]-5-chloro-4-fluoro-benzoic acid

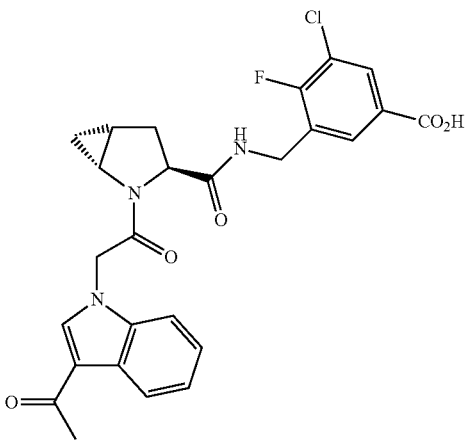

The title compound was prepared according to procedure described for the preparation of 3-[({(2S,4R)-1-[2-(3-acetyl-indol-1-yl)-acetyl]-4-fluoro-pyrrolidine-2-carbonyl}-amino)-methyl]-5-chloro-4-fluoro-benzoic acid Example 605 starting from 3-[({(1R,3S,5R)-2-[2-(3-acetyl-indol-1-yl)-acetyl]-2-aza-bicyclo[3.1.0]hexane-3-carbonyl}-amino)-methyl]-5-chloro-4-fluoro-benzoic acid methyl ester Example 480. MS: 512.0 [M+H]+; $t_R$ (HPLC conditions c): 4.41 min.

Example 607

(2S,4S)-1-[2-(3-Acetyl-indol-1-yl)-acetyl]-4-aminomethyl-4-fluoro-pyrrolidine-2-carboxylic acid 3-chloro-2-fluoro-benzylamide

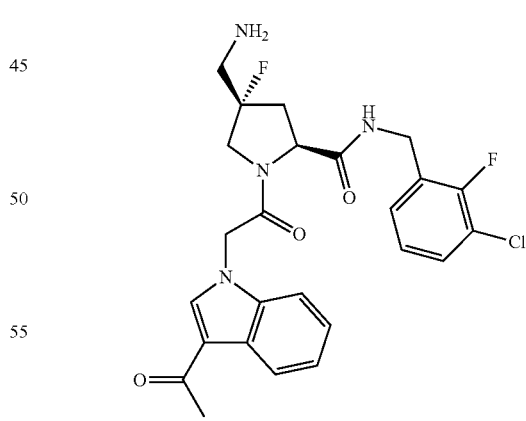

The title compound was prepared according to Scheme D7 from (2S,4R)-4-azidomethyl-2-(3-chloro-2-fluoro-benzylcarbamoyl)-4-fluoro-pyrrolidine-1-carboxylic acid tert-butyl ester (described in scheme B15) using DMF as solvent in step C, followed by azide reduction as described for the preparation of Example 411 (2S,4S)-4-aminomethyl-4-fluoro-pyrrolidine-1,2-dicarboxylic acid 1-[(1-carbamoyl-1H-indol-3-yl)-amide]2-(3-chloro-2,6-difluoro-benzylamide). MS (UPLC-MS): 503 [M+H]+; $t_R$ (HPLC conditions f): 1.60 min; $^{19}$F NMR (100 MHz, DMSO-$d_6$) δ (ppm): −117, −150.

Example 608

(2S,4S)-1-[2-(3-Acetyl-indol-1-yl)-acetyl]-4-methylamino-pyrrolidine-2-carboxylic acid 3-chloro-2-fluoro-benzylamide

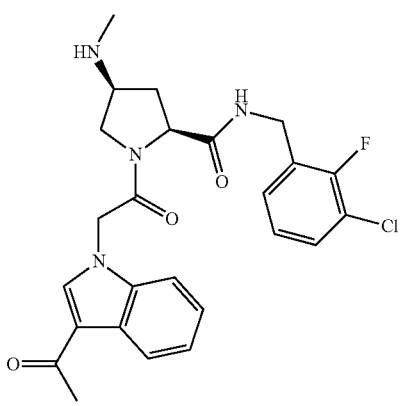 [SMILES: CN[C@H]1C[C@@H](C(=O)NCc2cccc(Cl)c2F)N(C(=O)Cn2cc(C(C)=O)c3ccccc32)C1]

The title compound was prepared according to Scheme D7 from (2S,4S)-2-(3-chloro-2-fluoro-benzylcarbamoyl)-4-[methyl-(2,2,2-trichloro-ethoxycarbonyl)-amino]-pyrrolidine-1-carboxylic acid tert-butyl ester (prepared as described in Scheme B6) followed by the deprotection of the Troc protecting group as described for Example 424. Purification by preparative HPLC (Waters SunFire C18-ODB, 5 µm, 19×50 mm, 5% CH$_3$CN/H$_2$O 2.5 min, 5-100% CH$_3$CN/H$_2$O in 10 min, CH$_3$CN/H$_2$O containing 0.1% HCOOH flow: 20 mL/min) gave after lyophilization of the purified fractions the title compound (formic acid salt). MS (UPLC-MS): 487 [M+H]+; $t_R$ (HPLC conditions f): 1.60 min; $^{19}$F NMR (100 MHz, DMSO-$d_6$) δ (ppm): −120.

Example 609

(2S,4S)-1-[2-(3-Acetyl-indol-1-yl)-acetyl]-4-(2-methoxy-ethylamino)-pyrrolidine-2-carboxylic acid 3-chloro-2-fluoro-benzylamide

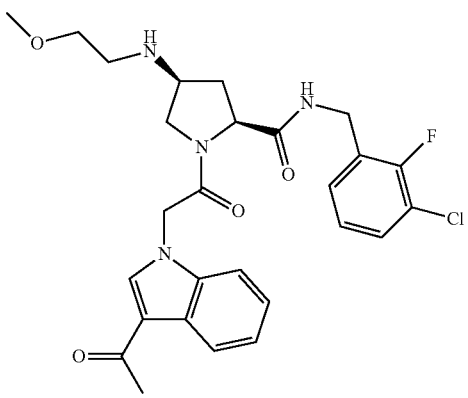 [SMILES: COCCN[C@H]1C[C@@H](C(=O)NCc2cccc(Cl)c2F)N(C(=O)Cn2cc(C(C)=O)c3ccccc32)C1]

The title compound was prepared according to Scheme D7 from (2S,4S)-2-(3-chloro-2-fluoro-benzylcarbamoyl)-4-[(2-methoxy-ethyl)-(2,2,2-trichloro-ethoxycarbonyl)-amino]-pyrrolidine-1-carboxylic acid tert-butyl ester (prepared as described in Scheme B6 using 1-bromo-2-methoxyethane instead of methyl iodide in step B) followed by deprotection of the Troc protecting group as described for Example 424. Purification on preparative HPLC (Waters SunFire C18-ODB, 5 µm, 19×50 mm, 5% CH$_3$CN/H$_2$O 2.5 min, 5-100% CH$_3$CN/H$_2$O in 10 min, CH$_3$CN/H$_2$O containing 0.1% HCOOH flow: 20 mL/min) gave after lyophilization of the purified fractions the title compound (formic acid salt). MS (UPLC/MS): 531 [M+H]+; $t_R$ (HPLC conditions f): 1.66 min; $^{19}$F NMR (100 MHz, DMSO-$d_6$) δ (ppm): −120.

Example 610

(1R,3S,5S)-2-[2-(3-Acetyl-pyrrolo[2,3-b]pyridin-1-yl)-acetyl]-5-hydroxy methyl-2-aza-bicyclo[3.1.0]hexane-3-carboxylic acid 3-chloro-2-fluoro-benzylamide

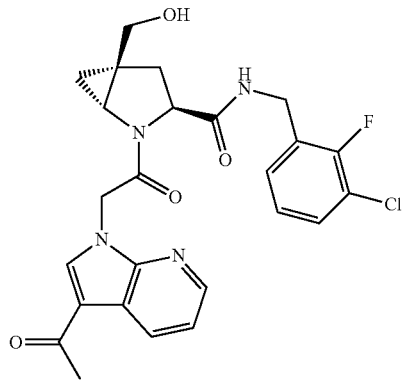

A solution of (3-acetyl-pyrrolo[2,3-b]pyridin-1-yl)-acetic acid (1R,3S,5S)-2-[2-(3-acetyl-pyrrolo[2,3-b]pyridin-1-yl)-acetyl]-3-(3-chloro-2-fluoro-benzylcarbamoyl)-2-aza-bicyclo[3.1.0]hex-5-ylmethyl ester (90 mg, 0.115 mmol) and NaOH 1N (0.58 mL, 0.58 mmol) in THF (0.55 mL)/water (55 µL) was stirred at RT for 1 h. Water and CH$_2$Cl$_2$ were added, the layers were separated and the aqueous one back-extracted with CH$_2$Cl$_2$ (×3). The combined organic extracts were dried (Na$_2$SO$_4$), filtered and concentrated. The crude material was purified by preparative HPLC (Waters Sunfire C18-ODB, 5 µm, 30×100 mm, eluent: 5% to 100% CH$_3$CN in H$_2$O in 25 min, CH$_3$CN and H$_2$O containing 0.1% TFA, flow: 40 mL/min). EtOAc and saturated aqueous NaHCO$_3$ were added to the combined purified fractions, the layers were separated and the aqueous one back-extracted with EtOAc (×3). The combined organic extracts were dried (Na$_2$SO$_4$), filtered and concentrated to give the desired material. TLC, $R_f$ (CH$_2$Cl$_2$/MeOH 9-1)=0.45; MS (UPLC/MS): 499.3/501.3 [M+H]+, 521.1/523.2 [M+Na]+; $t_R$ (HPLC conditions f): 1.73 min.

(3-Acetyl-pyrrolo[2,3-b]pyridin-1-yl)-acetic acid (1R,3S,5S)-2-[2-(3-acetyl-pyrrolo[2,3-b]pyridin-1-yl)-acetyl]-3-(3-chloro-2-fluoro-benzylcarbamoyl)-2-aza-bicyclo[3.1.0]hex-5-ylmethyl ester The title compound N,O bis-acylated was prepared according to Scheme D7 Steps B and C from (1R,3S,5S)-3-(3-chloro-2-fluoro-benzylcarbamoyl)-5-hydroxymethyl-2-aza-bicyclo[3.1.0]hexane-2-carboxylic acid tert-butyl ester (prepared as described in Part B Scheme B28) using HCl 4N in dioxane instead of TFA in Step B and 2 equivalents of (3-acetyl-pyrrolo[2,3-b]pyridin-1-yl)-acetic acid (described in Part A) in Step C. Purification by flash column chromatography on silica gel (CH₂Cl₂ to CH₂Cl₂/MeOH 94-6). TLC, R_f (CH₂Cl₂/MeOH 9-1)=0.48; MS (UPLC/MS): 699.4/701.3 [M+H]+, 743.4/745.4 [M+HCOO]–; t_R (HPLC conditions f): 2.05 min.

Example 611

(1R,3S,5S)-2-[2-(3-Acetyl-indol-1-yl)-acetyl]-5-hydroxymethyl-2-aza-bicyclo[3.1.0]hexane-3-carboxylic acid 3-chloro-2-fluoro-benzylamide

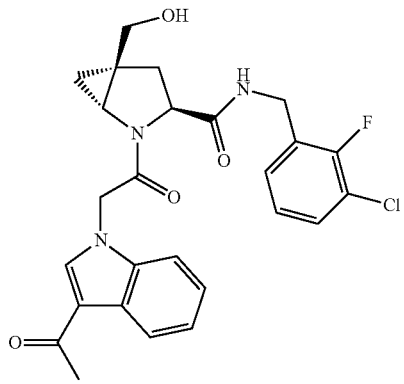 [SMILES: CC(=O)c1cn(CC(=O)N2[C@H](C(=O)NCc3cccc(Cl)c3F)C[C@@]3(CO)C[C@@H]23)c2ncccc12]

The title compound was prepared in 2 steps according to the procedure described for the preparation of Example 610 (1R,3S,5S)-2-[2-(3-acetyl-pyrrolo[2,3-b]pyridin-1-yl)-acetyl]-5-hydroxymethyl-2-aza-bicyclo[3.1.0]hexane-3-carboxylic acid 3-chloro-2-fluoro-benzylamide using (3-acetyl-indol-1-yl)-acetic acid instead of (3-acetyl-pyrrolo[2,3-b]pyridin-1-yl)-acetic acid. White powder. TLC, R_f (EtOAc)=0.05; MS (LC/MS): 498/500 [M+H]+, 520/522 [M+Na]+; t_R (HPLC conditions f): 1.84 min.

Example 612

(1S,2S,5R)-3-[2-(3-Acetyl-indol-1-yl)-acetyl]-3-aza-bicyclo[3.1.0]hexane-2-carboxylic acid [(S)-1-(3-chloro-2-fluoro-phenyl)-2hydroxy-ethyl]-amide

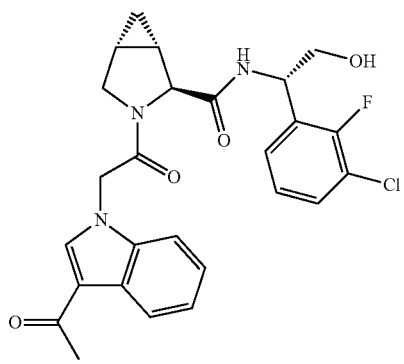 [SMILES: CC(=O)c1cn(CC(=O)N2C[C@@H]3C[C@@H]3[C@H]2C(=O)N[C@H](CO)c2cccc(Cl)c2F)c2ccccc12]

The title compound was prepared in 2 steps according to the procedure described for the preparation of Example 610 (1R,3S,5S)-2-[2-(3-acetyl-pyrrolo[2,3-b]pyridin-1-yl)-acetyl]-5-hydroxymethyl-2-aza-bicyclo[3.1.0]hexane-3-carboxylic acid 3-chloro-2-fluoro-benzylamide from (1S,2S,5R)-2-[(S)-1-(3-chloro-2-fluoro-phenyl)-2-hydroxy-ethylcarbamoyl]-3-aza-bicyclo[3.1.0]hexane-3-carboxylic acid tert-butyl ester (prepared using similar protocols as described in Scheme B9) and (3-acetyl-indol-1-yl)-acetic acid. White powder. TLC, R_f (EtOAc)=0.10; MS (UPLC/MS): 498.3/500.4 [M+H]+, 542.4/544.3 [M+HCOO]–; t_R (HPLC conditions a): 3.10 min.

Example 613

(1R,3S,5R)-2-[2-(3-Acetyl-pyrrolo[2,3-b]pyridin-1-yl)-acetyl]-2-aza-bicyclo[3.1.0]hexane-3-carboxylic acid [(S)-1-(3-chloro-2-fluoro-phenyl)-2-hydroxy-ethyl]-amide

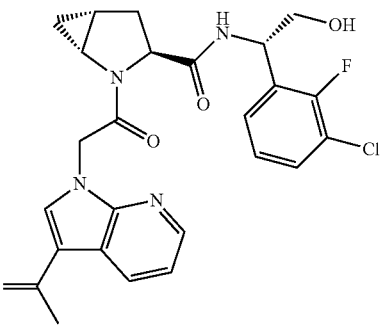

The title compound was prepared in 2 steps according to the procedure described for the preparation of Example 610 (1R,3S,5S)-2-[2-(3-acetyl-pyrrolo[2,3-b]pyridin-1-yl)-acetyl]-5-hydroxymethyl-2-aza-bicyclo[3.1.0]hexane-3-carboxylic acid 3-chloro-2-fluoro-benzylamide from (1R,3S,5R)-3-[(S)-1-(3-chloro-2-fluoro-phenyl)-2-hydroxy-ethylcarbamoyl]-2-aza-bicyclo[3.1.0]hexane-2-carboxylic acid tert-butyl ester (prepared as described in Scheme B9). White powder. TLC, R_f (CH₂/Cl₂/EtOAc 9:1)=0.70; MS (UPLC/MS): 499.3/501.3 [M+H]+, 543.2/545.3 [M+HCOO]–; t_R (HPLC conditions a): 3.02 min.

Example 614

(2S,4R)-1-[2-(3-Acetyl-pyrrolo[2,3-b]pyridin-1-yl)-acetyl]-4-fluoro-4-methyl-pyrrolidine-2-carboxylic acid [(S)-1-(3-chloro-2-fluoro-phenyl)-2-hydroxy-ethyl]-amide

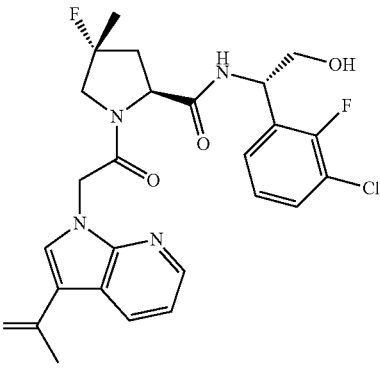

The title compound was prepared in 2 steps according to the procedure described for the preparation of Example 610

(1R,3S,5S)-2-[2-(3-acetyl-pyrrolo[2,3-b]pyridin-1-yl)-acetyl]-5-hydroxymethyl-2-aza-bicyclo[3.1.0]hexane-3-carboxylic acid 3-chloro-2-fluoro-benzylamide from (2S,4R)-2-[(S)-1-(3-chloro-2-fluoro-phenyl)-2-hydroxy-ethylcarbamoyl]-4-fluoro-4-methyl-pyrrolidine-1-carboxylic acid tert-butyl ester (prepared using similar protocols as described in Scheme B9). White powder. TLC, $R_f$(CH$_2$/Cl$_2$/EtOAc 9:1)=0.60; MS (UPLC/MS): 519.3/521.3 [M+H]+, 563.3/565.3 [M+HCOO]–; $t_R$ (HPLC conditions a): 2.96 min.

Example 615

(1R,3S,5R)-2-{2-[3-Acetyl-5-(N,N-dimethyl-carbamimidoyl)-indol-1-yl]-acetyl}-2-aza-bicyclo[3.1.0]hexane-3-carboxylic acid 3-chloro-2-fluoro-benzylamide

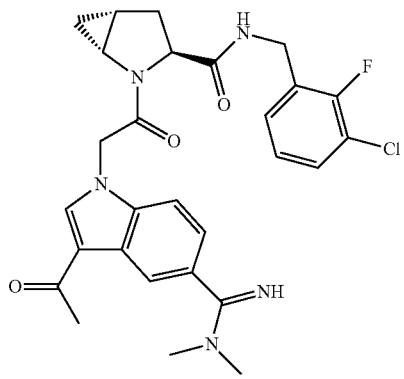 [SMILES: CC(=O)c1cn(CC(=O)N2[C@@H]3C[C@@H]3C[C@H]2C(=O)NCc2cccc(Cl)c2F)c2ccc(C(=N)N(C)C)cc12]

HCl (gaz) was slowly bubbled for 3 h in a suspension of (1R,3S,5R)-2-[2-(3-acetyl-5-cyano-indol-1-yl)-acetyl]-2-aza-bicyclo[3.1.0]hexane-3-carboxylic acid 3-chloro-2-fluoro-benzylamide (50 mg, 0.1 mmol) in MeOH (3 mL) cooled at 0° C. The reaction mixture was allowed to reach RT and further stirred for 1 h. After completion argon was bubbled to remove the excess of HCl and the reaction mixture was concentrated. Crude 3-acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indole-5-carboximidic acid methyl ester (MS (UPLC/MS): 525.3/527.3 [M+H]+) was diluted in MeOH (2 mL), dimethylamine (2 M in MeOH, 0.26 mL, 0.524 mmol) was added and the mixture refluxed overnight. The reaction mixture was concentrated and the crude material was purified by preparative HPLC (Waters Sunfire C18-ODB, 5 μm, 30×100 mm, 5-95% CH$_3$CN/H$_2$O, CH$_3$CN and H$_2$O containing 0.1% TFA flow: 40 ml/min) to give after lyophilization of the purified fractions the desired material as a TFA salt. TLC, $R_f$(CH$_2$Cl$_2$/MeOH 9:1): 0.65; MS (UPLC/MS): 539.3/541.3 [M+H]+, 583.3/585.4 [M+HCOO]–; $t_R$ (HPLC conditions a): 3.05 min.

(1R,3S,5R)-2-[2-(3-Acetyl-5-cyano-indol-1-yl)-acetyl]-2-aza-bicyclo[3.1.0]hexane-3-carboxylic acid 3-chloro-2-fluoro-benzylamide The title compound was prepared according to Scheme D7 from (3-acetyl-5-cyano-indol-1-yl)-acetic acid (prepared as described in Part C). TLC, $R_f$(CH$_2$Cl$_2$/MeOH 9:1)=0.40; MS (UPLC/MS): 493.3/495.3 [M+H]+, 537.3/539.3 [M+HCOO]–; $t_R$ (HPLC conditions a): 3.42 min.

Example 616

(1R,3S,5R)-2-{2-[3-Acetyl-6-(N,N-dimethyl-carbamimidoyl)-indol-1-yl]-acetyl}-2-aza-bicyclo[3.1.0]hexane-3-carboxylic acid 3-chloro-2-fluoro-benzylamide

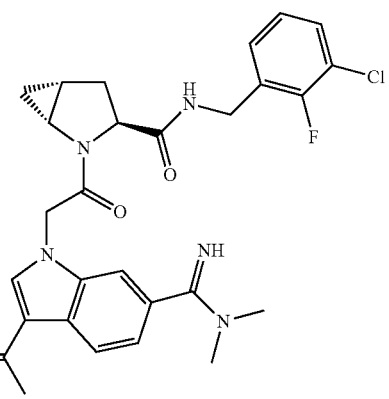

The title compound was prepared in a similar manner as described above for Example 615 from (3-acetyl-6-cyano-indol-1-yl)-acetic acid (prepared as described in Part C). TLC, $R_f$(CH$_2$Cl$_2$/MeOH 9:1): 0.65; MS (UPLC/MS): 539.3/541.3 [M+H]+ 583.3/585.3 [M+HCOO]–; $t_R$ (HPLC conditions a): 3.13 min.

(2S,4R)-1-[2-(3-acetyl-6-cyano-indol-1-yl)-acetyl]-4-fluoro-pyrrolidine-2-carboxylic acid 3-chloro-2-fluoro-benzylamide The title compound was prepared according to Scheme D7 from (3-acetyl-6-cyano-indol-1-yl)-acetic acid (prepared as described in Part C). Powder. TLC, $R_f$(CH$_2$Cl$_2$/MeOH 9-1)= 0.40; MS (UPLC/MS): 493.3/495.3 [M+H]+, 537.3/539.3 [M+HCOO]–; $t_R$ (HPLC conditions a): 3.46 min.

Example 617

(2S,4R)-1-{2-[3-Acetyl-6-(1H-tetrazol-5-yl)-indol-1-yl]-acetyl}-4-fluoro-pyrrolidine-2-carboxylic acid 3-chloro-2-fluoro-benzylamide

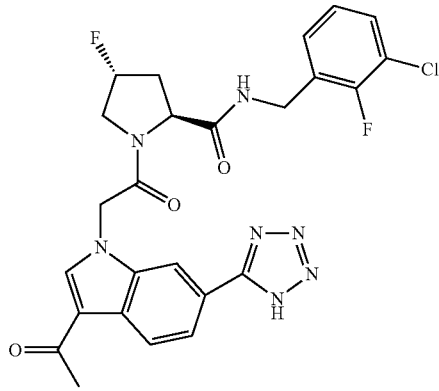 [SMILES: CC(=O)c1cn(CC(=O)N2C[C@H](F)C[C@H]2C(=O)NCc2cccc(Cl)c2F)c2cc(-c3nnn[nH]3)ccc12]

To a suspension of (2S,4R)-1-[2-(3-acetyl-6-cyano-indol-1-yl)-acetyl]-4-fluoro-pyrrolidine-2-carboxylic acid 3-chloro-2-fluoro-benzylamide (prepared as described in Example 616 (45.0 mg, 0.09 mmol) in water (2 mL) and isopropanol (1 mL) at RT were added sodium azide (24.0 mg, 0.360 mmol) and zinc bromide (40.0 mg, 0.180 mmol). The mixture was heated to 130° C. for 10 h in a microwave apparatus (Personnal Chemistry, Biotage). After cooling to RT, a 6N HCl solution was added to the mixture, followed by extraction with EtOAc (3×). The combined organics were washed with brine, dried (phase separator) and concentrated in vacuo. Purification of the residue by preparative HPLC (Waters Sunfire, C18-ODB, 5 µm, 30×100 mm, eluent: 20-100% CH$_3$CN/H$_2$O/20 min, 100% CH$_3$CN/2 min, CH$_3$CN and H$_2$O containing 0.1% TFA, flow: 40 mL/min) afforded after lyophilization the title compound as solid. MS (LC/MS): 542.0 [M+H]+; t$_R$ (HPLC conditions k): 3.15 min.

Example 618

(1R,3S,5R)-2-{2-[3-Acetyl-6-(1H-tetrazol-5-yl)-indol-1-yl]-acetyl}-2-aza-bicyclo[3.1.0]hexane-3-carboxylic acid 3-chloro-2-fluoro-benzylamide

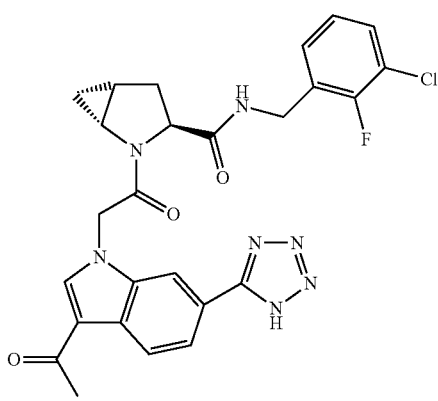

The title compound was prepared in a similar manner as described above for Example 617 from (1R,3S,5R)-2-[2-(3-acetyl-6-cyano-indol-1-yl)-acetyl]-2-aza-bicyclo[3.1.0]hexane-3-carboxylic acid 3-chloro-2-fluoro-benzylamide (prepared as described in Example 616 (100.0 mg, 0.203 mmol), sodium azide (66.0 mg, 1.014 mmol) and zinc bromide (228.0 mg, 1.014 mmol) in water (2 mL) and isopropanol (1 mL). White solid. MS (LC/MS): 536.0 [M+H]+; t$_R$ (HPLC conditions k): 3.21 min.

Example 619

(2S,3S,4S)-1-[2-(3-Acetyl-d3-indol-1-yl)-acetyl]-4-fluoro-3-methoxy-pyrrolidine-2-carboxylic acid 3-chloro-2-fluoro-benzylamide

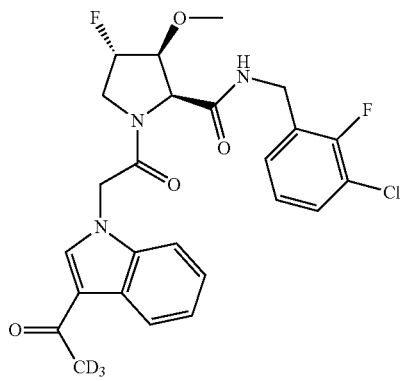

The title compound was prepared according to Scheme D7 from (2S,3S,4S)-4-fluoro-3-methoxy-pyrrolidine-2-carboxylic acid 3-chloro-2-fluoro-benzylamide (prepared as described in Scheme B24) and (3-acetyl-d3-indol-1-yl)-acetic acid (prepared in a similar manner as described in Scheme A13 using acetyl-d3-chloride in step A) using DMF as solvent in step C. MS (UPLC-MS): 507/509 [M+H]+, 551/553 [M+HCOO]−; t$_R$ (HPLC conditions f): 2.01 min.

Example 620

(2S,3S,4S)-1-[2-(3-Acetyl-indol-1-yl)-acetyl]-4-fluoro-3-methoxy-d3-pyrrolidine-2-carboxylic acid 3-chloro-2-fluoro-benzylamide

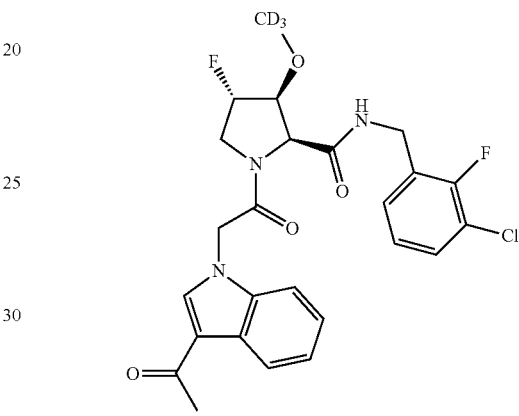

The title compound was prepared according to Scheme D7 from (2S,3S,4S)-4-fluoro-3-methoxy-d3-pyrrolidine-2-carboxylic acid 3-chloro-2-fluoro-benzylamide (prepared as described in Scheme B24 using methyl-d3-iodide instead of methyl iodide in Step B). MS (UPLC-MS): 507/509 [M+H]+, 551/553 [M+HCOO]−; t$_R$ (HPLC conditions f): 2.01 min.

Example 621

(1R,3S,5R)-2-[2-(1-Acetyl-imidazo[1,5-a]pyridin-3-yl)-acetyl]-2-aza-bicyclo[3.1.0]hexane-3-carboxylic acid 3-chloro-2-fluoro-benzylamide

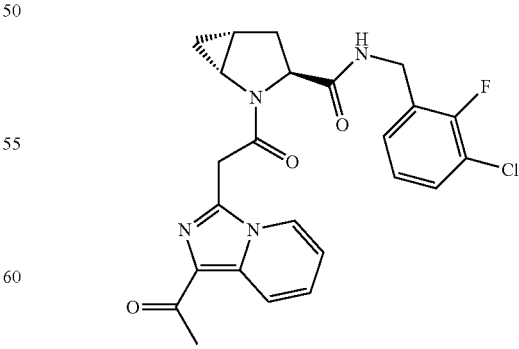

The title compound was prepared according to Scheme D7 using in Step C (1-acetyl-imidazo[1,5-a]pyridin-3-yl)-acetic acid (prepared as described in Scheme A19) and DMF as solvent. MS (UPLC-MS): 469.3/471.4 [M+H]+, 513.4/515.5 [M+HCOO]−; $t_R$ (HPLC conditions a): 3.08 min.

Example 622

{(1R,3S,5R)-2-[2-(3-Acetyl-indol-1-yl)-acetyl]-2-aza-bicyclo[3.1.0]hex-3-ylmethyl}-carbamic acid 3-chloro-2-fluoro-phenyl ester

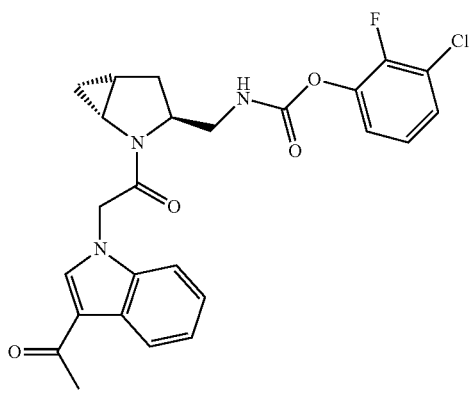

To a solution of [(1R,3S,5R)-1-(2-aza-bicyclo[3.1.0]hex-3-yl)methyl]-carbamic acid 3-chloro-2-fluoro-phenyl ester, trifluoroacetate (prepared as described in Example 115) (60.0 mg, 0.211 mmol) in THF (3 mL) was added HBTU (120 mg, 0.316 mmol), DIPEA (0.147 mL, 0.843 mmol) and (3-acetyl-indol-1-yl)-acetic acid (50 mg, 0.232 mmol). The reaction mixture was stirred at RT for 60 h. Volatiles were removed under reduced pressure and the residue was purified by preparative HPLC (Waters Sunfire, C18-ODB, 5 μm, 30×100 mm, eluent: 20-100% CH₃CN/H₂O/20 min, 100% CH₃CN/2 min, CH₃CN and H₂O containing 0.1% TFA, flow: 40 mL/min) to give after lyophilization of the purified HPLC fractions the title compound. MS (LC/MS): 484.0 [M+H]+; $t_R$ (HPLC conditions k): 3.69 min.

Scheme D8: preparation of Example 623: (2S,4R)-1-[2-(3-Acetyl-pyrazolo[3,4-c]pyridin-1-yl)-acetyl]-4-fluoro-pyrrolidine-2-carboxylic acid 3-chloro-2-fluoro-benzylamide formate

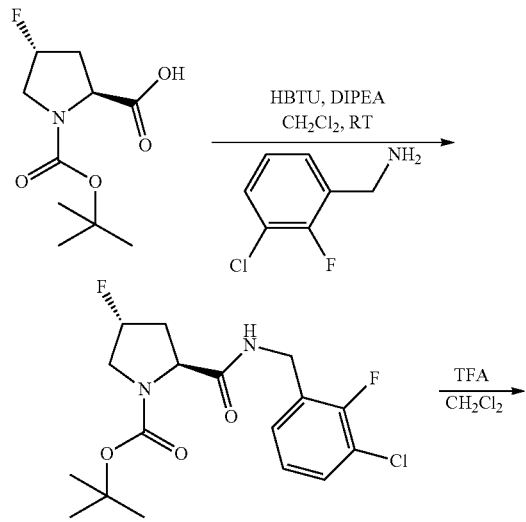

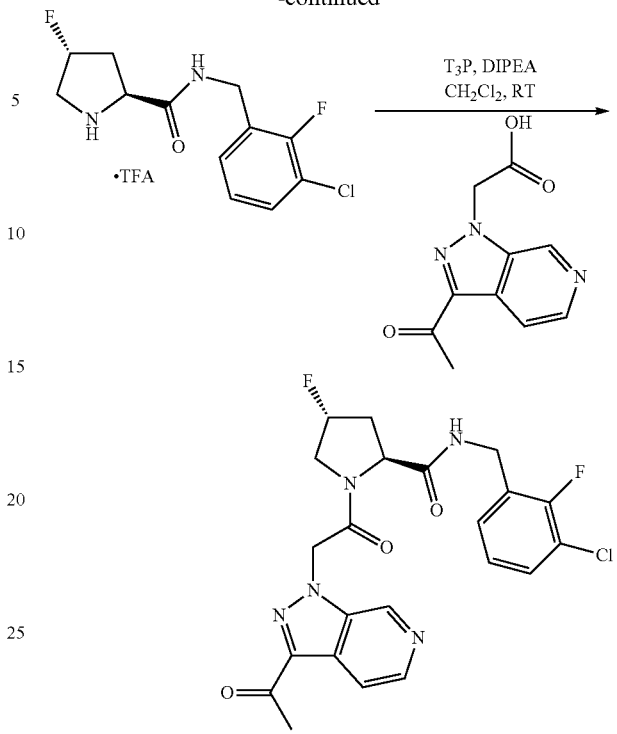

A. (2S,4R)-2-(3-Chloro-2-fluoro-benzylcarbamoyl)-4-fluoro-pyrrolidine-1-carboxylic acid tert-butyl ester To a solution of (2S,4R)-4-fluoro-pyrrolidine-1,2-dicarboxylic acid 1-tert-butyl ester (3.97 g, 17.02 mmol) in CH₂Cl₂ (34 mL) were successively added 3-chloro-2-fluoro-benzylamine (2.35 mL, 18.72 mmol), HBTU (9.68 g, 25.5 mmol) and DIPEA (8.92 mL, 51.1 mmol). The reaction mixture was stirred at RT for 16 h. Water was added and the phases were separated. The organic layer was washed successively with 0.1N HCl (2×), sat. aq. NaHCO₃ (2×) and brine, then dried (phase separator) and concentrated in vacuo. The residual oil was purified via flash column chromatography on silica gel (c-hexane/EtOAc 9-1 to 1-1). MS (LC/MS): 397 [M+Na]+, 319 [MH−tBu]+; 275 [MH−Boc]+; $t_R$ (HPLC conditions k): 3.52 min.

DMF can also be used instead of Dichloromethane.

B. (2S,4R)-4-fluoro-pyrrolidine-2-carboxylic acid 3-chloro-2-fluoro-benzylamide trifluoroacetate To a solution of (2S,4R)-2-(3-chloro-2-fluoro-benzylcarbamoyl)-4-fluoro-pyrrolidine-1-carboxylic acid tert-butyl ester (7.94 g, 21.18 mmol) in CH₂Cl₂ (70.5 mL) was added TFA (16.32 mL, 212 mmol) and the solution was stirred at RT for 16 h. The crude reaction mixture was concentrated under vacuum and the material this obtained was used without further purification in the next step. MS (LC/MS): 274.9 [M+H]+; $t_R$ (HPLC conditions b): 2.13 min.

C. Example 623

(2S,4R)-1-[2-(3-Acetyl-pyrazolo[3,4-c]pyridin-1-yl)-acetyl]-4-fluoro-pyrrolidine-2-carboxylic acid 3-chloro-2-fluoro-benzylamide formate To a solution of (2S,4R)-4-fluoro-pyrrolidine-2-carboxylic acid 3-chloro-2-fluoro-benzylamide trifluoroacetate (50 mg, 0.13 mmol), propylphosphonic anhydride (50% in EtOAc, 0.057 ml, 0.19 mmol) and (3-acetyl-pyrazolo[3,4-c]pyridin-1-yl)acetic acid trifluoroacetate (prepared as described in Scheme A20, 42.9 mg, 0.13 mmol) in CH$_2$Cl$_2$ (5 mL) was added DIPEA (0.067 ml, 0.386 mmol) under nitrogen atmosphere. The reaction mixture was stirred 2 h at RT and quenched by addition of a saturated aqueous solution of NaHCO$_3$. The layers were separated, the aqueous layer was extracted with CH$_2$Cl$_2$ (×2), the combined organic extracts were dried (Na$_2$SO$_4$), filtered and concentrated. The crude residue was purified by preparative HPLC (Waters Sunfire (C18 ODB, 5 μm, 19×50, flow=20 mL/min, 5% CH$_3$CN in water for 2.5 min, 5 to 100% CH$_3$CN in water in 10 min to 100% CH$_3$CN for 2.5 min, both CH$_3$CN and water containing 0.1% HCOOH) and the pure HPLC fractions were concentrated and lyophilized. MS (LC/MS): 476/478 [M+H]+, t$_R$ (HPLC conditions f): 1.51 min.

Alternatively, the pure HPLC fractions were neutralized with an aqueous saturated solution of Na$_2$CO$_3$, extracted with EtOAc, dried (Na$_2$SO$_4$), filtered and concentrated to give the desired material as a free base.

The examples below were prepared according to the general procedures described in Scheme D8 for the preparation of Example 623 from commercially available building blocks if not otherwise mentioned (see notes at the end of table 7):

TABLE 7

| Example | Structure | Name | Characterization (end-table notes), TLC, R$_f$(eluent); MS (LC/MS); t$_R$ (HPLC conditions) |
| --- | --- | --- | --- |
| 624 | 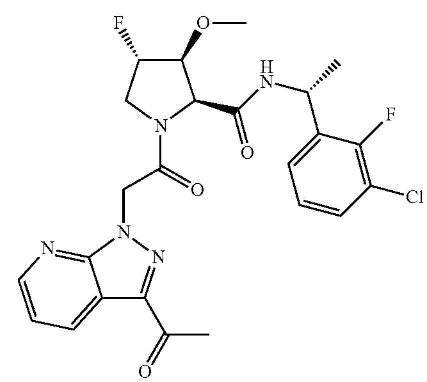 [SMILES: CO[C@H]1[C@@H](C(=O)N[C@H](C)c2cccc(Cl)c2F)N(C(=O)Cn2nc(C(C)=O)c3cccnc32)C[C@@H]1F] | (2S,3S,4S)-1-[2-(3-Acetyl-pyrazolo[3,4-b]pyridin-1-yl)-acetyl]-4-fluoro-3-methoxy-pyrrolidine-2-carboxylic acid [(R)-1-(3-chloro-2-fluoro-phenyl)-ethyl]-amide | (1,2) 520 [M + H]+, 564 [M + HCOO]−; t$_R$ (f): 2.04 min. |
| 625 | 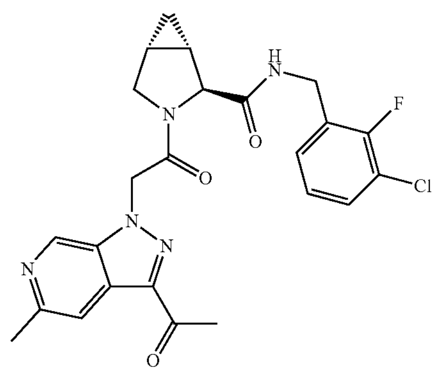 [SMILES: CC(=O)c1nn(CC(=O)N2C[C@@H]3C[C@@H]3[C@H]2C(=O)NCc2cccc(Cl)c2F)c2cnc(C)cc12] | (1S,2S,5R)-3-[2-(3-Acetyl-5-methyl-pyrazolo[3,4-c]pyridin-1-yl)-acetyl]-3-aza-bicyclo[3.1.0]hexane-2-carboxylic acid 3-chloro-2-fluoro-benzylamide | (2) 484 [M + H]+, 528 [M + HCOO]−; t$_R$ (f): 1.59 min. |
| 626 | 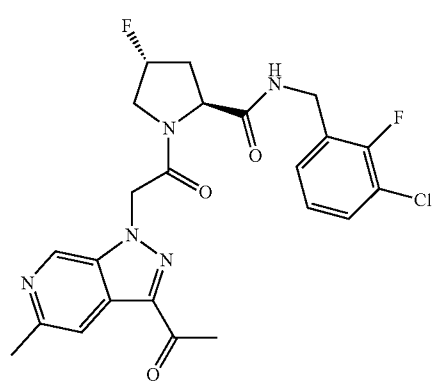 [SMILES: CC(=O)c1nn(CC(=O)N2C[C@H](F)C[C@H]2C(=O)NCc2cccc(Cl)c2F)c2cnc(C)cc12] | (2S,4R)-1-[2-(3-Acetyl-5-methyl-pyrazolo[3,4-c]pyridin-1-yl)-acetyl]-4-fluoro-pyrrolidine-2-carboxylic acid 3-chloro-2-fluoro-benzylamide | (2) 490 [M + H]+, 534 [M + HCOO]−; t$_R$ (f): 1.54 min. |

TABLE 7-continued

| Example | Structure | Name | Characterization (end-table notes), TLC, R_f (eluent); MS (LC/MS); t_R (HPLC conditions) |
|---|---|---|---|
| 627 | 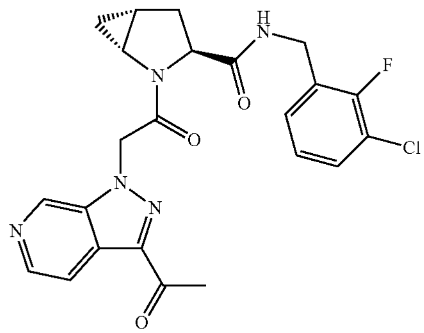 [SMILES: CC(=O)c1nn(CC(=O)N2[C@@H]3C[C@@H]3C[C@H]2C(=O)NCc2cccc(Cl)c2F)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid 3-chloro-2-fluoro-benzylamide | (2) 470/472 [M + H]+; t_R (f): 1.58 min. |
| 628 | 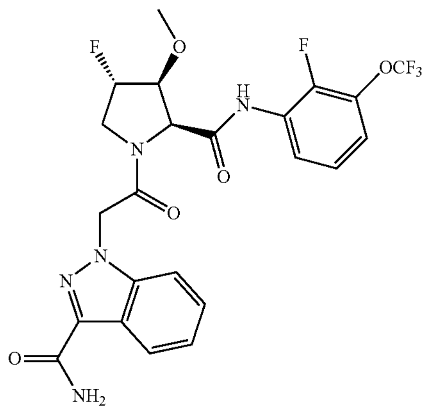 [SMILES: CO[C@H]1[C@@H](C(=O)Nc2cccc(OC(F)(F)F)c2F)N(C(=O)Cn2nc(C(N)=O)c3ccccc32)C[C@@H]1F] | 1-{2-[(2S,3S,4S)-4-Fluoro-2-(2-fluoro-3-trifluoromethoxy-phenylcarbamoyl)-3-methoxy-pyrrolidin-1-yl]-2-oxo-ethyl}-1H-indazole-3-carboxylic acid amide | (1,2) 542.3 [M + H]+, 559.3 [M + NH_4]+, 440.3 [M − H]−; t_R (f): 1.97 min |
| 629 | 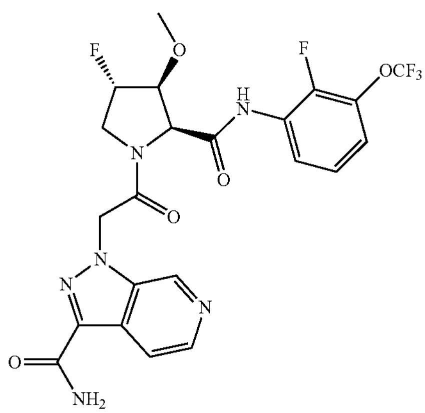 | 1-{2-[(2S,3S,4S)-4-Fluoro-2-(2-fluoro-3-trifluoromethoxy-phenylcarbamoyl)-3-methoxy-pyrrolidin-1-yl]-2-oxo-ethyl}-1H-pyrazolo[3,4-c]pyridine-3-carboxylic acid amide trifluoroacetate | (1,2) 543.2 [M + H]+, 541.2 [M − H]−; t_R (f): 1.52 min |
| 630 | 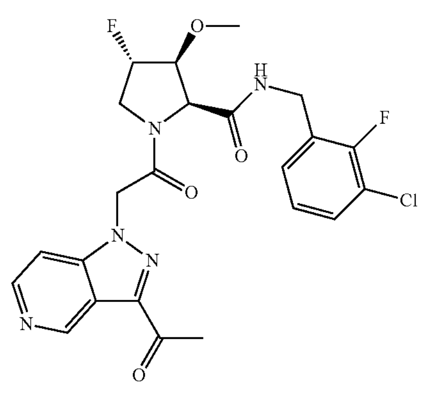 [SMILES: CO[C@H]1[C@@H](C(=O)NCc2cccc(Cl)c2F)N(C(=O)Cn2nc(C(C)=O)c3cnccc32)C[C@@H]1F] | (2S,3S,4S)-1-[2-(3-Acetyl-pyrazolo[4,3-c]pyridin-1-yl)-acetyl]-4-fluoro-3-methoxy-pyrrolidine-2-carboxylic acid 3-chloro-2-fluoro-benzylamide | (1,2) 506.2/508.2 [M + H]+, 504.2 [M − H]−, 550.2/552.2 [M + HCOO]−; t_R (f): 1.49 min. |

TABLE 7-continued

| Example | Name | Characterization (end-table notes), TLC, $R_f$ (eluent); MS (LC/MS); $t_R$ (HPLC conditions) |
|---|---|---|
| 631 | (2S,3S,4S)-1-[2-(3-Acetyl-pyrazolo[3,4-c]pyridin-1-yl)-acetyl]-4-fluoro-3-methoxy-pyrrolidine-2-carboxylic acid [1-(3-chloro-2-fluoro-phenyl)-cyclopropyl]-amide | (1,2) 532.4/534.5 [M + H]+, 576.6/578.5 [M + HCOO]−; $t_R$ (f): 1.64 min. |
| 632 | 3-Acetyl-1-{2-[(1R,3S,5R)-3-(3-chloro-2-fluoro-benzyl carbamoyl)-2-aza-bicyclo[3.1.0]hex-2-yl]-2-oxo-ethyl}-1H-indazole-6-carboxylic acid methyl ester | (2) 544.1/546.1 [M + NH₄]+, 571.2/573.2 [M + HCOO]−; $t_R$ (m): 1.08 min. |
| 633 | (1R,3S,5R)-2-[2-(3-Acetyl-pyrazolo[3,4-b]pyridin-1-yl)-acetyl]-2-aza-bicyclo[3.1.0]hexane-3-carboxylic acid [3-(3-chloro-2-fluoro-phenyl)-oxetan-3-yl]-amide | (1,2) 512.1/514.1 [M + H]+, 534.1/536.1 [M + Na]+; $t_R$ (f): 1.89 min. |
| 634 | (2S,3S,4S)-1-[2-(3-Acetyl-indol-1-yl)-acetyl]-3-(2-dimethylamino-ethoxy)-4-fluoro-pyrrolidine-2-carboxylic acid 3-chloro-2-fluoro-benzylamide formate | (1) 561.4/563.4 [M + H]+, 605.5/607.5 [M + HCOO]−; $t_R$ (f): 1.62 min. |

TABLE 7-continued

| Example | Structure | Name | Characterization (end-table notes), TLC, R$_f$ (eluent); MS (LC/MS); t$_R$ (HPLC conditions) |
|---|---|---|---|
| 635 | 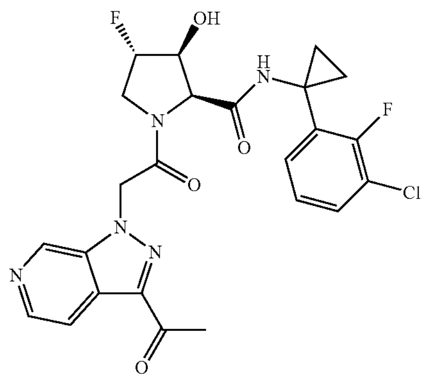 [SMILES: CC(=O)c1nn(CC(=O)N2C[C@H](F)[C@@H](O)[C@H]2C(=O)NC2(c3cccc(Cl)c3F)CC2)c2cnccc12] | (2S,3S,4S)-1-[2-(3-Acetyl-pyrazolo[3,4-c]pyridin-1-yl)-acetyl]-4-fluoro-3-hydroxy-pyrrolidine-2-carboxylic acid [1-(3-chloro-2-fluoro-phenyl)-cyclopropyl]-amide formate | (1,2) 518.4/520.4 [M + H]+, 562.5 [M + HCOO]−; t$_R$ (f): 1.51 min. |
| 636 | 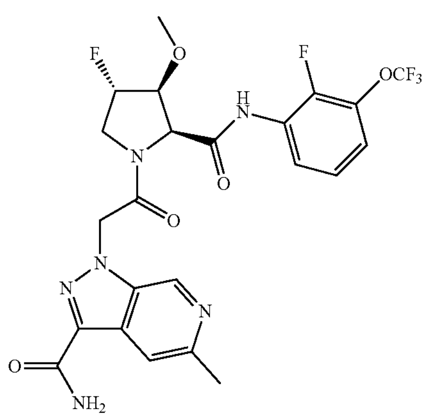 [SMILES: CO[C@H]1[C@@H](C(=O)Nc2cccc(OC(F)(F)F)c2F)N(C(=O)Cn2nc(C(N)=O)c3cc(C)ncc32)C[C@@H]1F] | 1-{2-[(2S,3S,4S)-4-Fluoro-2-(2-fluoro-3-trifluoromethoxy-phenylcarbamoyl)-3-methoxy-pyrrolidin-1-yl]-2-oxo-ethyl}-5-methyl-1H-pyrazolo[3,4-c]pyridine-3-carboxylic acid amide triflate | (1,2) 557.2 [M + H]+, 555.2 [M − H]−; t$_R$ (f): 1.50 min |
| 637 | 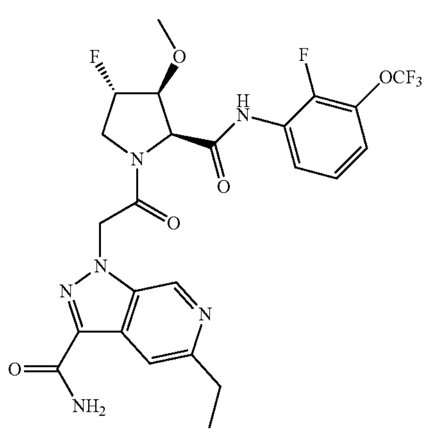 [SMILES: CCc1cc2c(C(N)=O)nn(CC(=O)N3C[C@H](F)[C@@H](OC)[C@H]3C(=O)Nc3cccc(OC(F)(F)F)c3F)c2cn1] | 5-Ethyl-1-{2-[(2S,3S,4S)-4-fluoro-2-(2-fluoro-3-trifluoromethoxy-phenyl carbamoyl)-3-methoxy-pyrrolidin-1-yl]-2-oxo-ethyl}-1H-pyrazolo[3,4-c]pyridine-3-carboxylic acid amide triflate | (1,2) 571.3 [M + H]+, 569.3 [M − H]−; t$_R$ (f): 1.55 min |

TABLE 7-continued

| Example | Structure | Name | Characterization (end-table notes), TLC, $R_f$ (eluent); MS (LC/MS); $t_R$ (HPLC conditions) |
|---|---|---|---|
| 638 | 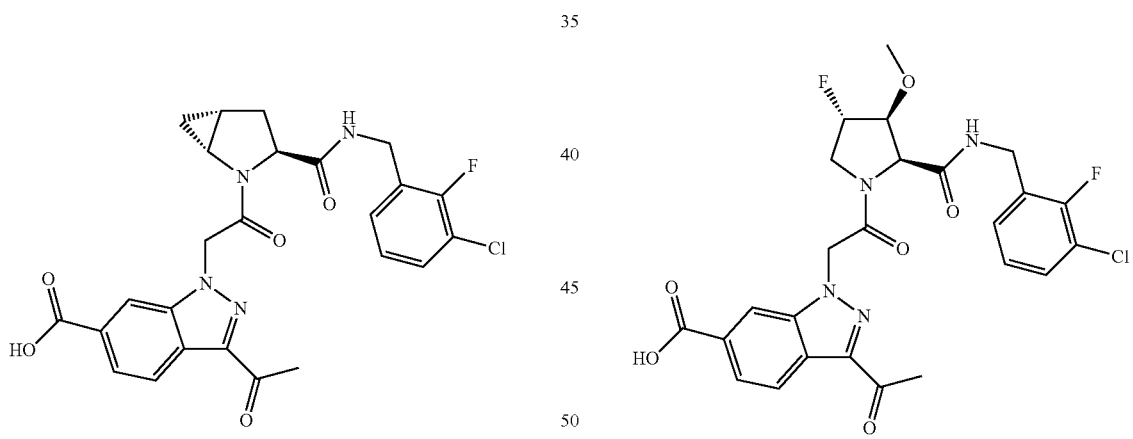 | (2S,3S,4S)-1-{2-[3-Acetyl-5-(pyrimidin-2-ylmethoxy)-indazol-1-yl]-acetyl}-4-fluoro-3-methoxy-pyrrolidine-2-carboxylic acid (2-fluoro-3-trifluoromethoxy-phenyl)-amide | (1,2) 649.3 [M + H]+, 647.3 [M − H]−; $t_R$ (f): 1.99 min |

(1) The title compound was prepared according to the general procedure described in Scheme D8 steps B and C starting from the substituted proline derivative prepared as described in Part B; (2) The acid reagent used in step C was prepared as described in Part A.

Example 639

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-indazole-6-carboxylic acid A solution of Example 632 (65 mg, 0.123 mmol) in MeOH (5 mL) and sodium hydroxide (d=1 g/mL, 0.247 mL, 0.617 mmol) was stirred for 16 h at RT. The reaction was quenched by addition of HCl (1N, until pH=1) and concentrated under reduced pressure. The aqueous residue was extracted with $CH_2Cl_2$ (×3) and concentrated. The crude material was purified by preparative HPLC (Waters Sunfire C18-ODB, 5 μm, 30×100 mm, eluent: 5% to 100% $CH_3CN$ in $H_2O$ in 25 min, $CH_3CN$ and $H_2O$ containing 0.1% TFA, flow: 40 mL/min). MS (LC/MS): 530.2/532.2 [M+H]+; 511.1/513.1 [M−H]−, 557.2/559.2 [M+HCOO]−; $t_R$ (UPLC conditions m): 0.91 min.

Example 640

3-Acetyl-1-{2-[(2S,3S,4S)-2-(3-chloro-2-fluoro-benzylcarbamoyl)-4-fluoro-3-methoxy-pyrrolidin-1-yl]-2-oxo-ethyl}-1H-indazole-6-carboxylic acid 3-Acetyl-1-{2-[(2S,3S,4S)-2-(3-chloro-2-fluoro-benzyl-carbamoyl)-4-fluoro-3-methoxy-pyrrolidin-1-yl]-2-oxo-ethyl}-1H-indazole-6-carboxylic acid benzyl ester (47 mg, 0.063 mmol) was dissolved in MeOH (5 mL), Pd/C (10%, 5 mg) was added and the solution was degassed 3 times replacing air by nitrogen and finally nitrogen by hydrogen. The reaction mixture was further stirred under hydrogen atmosphere for 1 h. The catalyst was removed through a pad of Celite and washed with MeOH. The solvent was concentrated under reduced pressure and the crude residue was purified by preparative HPLC (Waters Sunfire C18-ODB, 5 μm, 30×100 mm, eluent: 5% to 100% $CH_3CN$ in $H_2O$ in 25 min, $CH_3CN$ and $H_2O$ containing 0.1% TFA, flow: 40 mL/min). MS (LC/MS): 549.5 [M+H]+; 547.5 [M−H]−; $t_R$ (HPLC conditions f): 1.93 min.

3-Acetyl-1-{2-[(2S,3S,4S)-2-(3-chloro-2-fluoro-benzylcarbamoyl)-4-fluoro-3-methoxy-pyrrolidin-1-yl]-2-oxo-ethyl}-1H-indazole-6-carboxylic acid benzyl ester was prepared using similar protocols as described in Scheme D8 Step C for the preparation of Example 623 from 3-acetyl-1-carboxymethyl-1H-indazole-6-carboxylic acid benzyl ester (prepared as described in Part A) and (2S,3S,4S)-4-fluoro-3-methoxy-pyrrolidine-2-carboxylic acid 3-chloro-2-fluoro-benzylamide trifluoroacetate (prepared as described in Scheme B24). White solid. MS (UPLC/MS): 683.6/685.7 [M+HCOO]−; $t_R$ (HPLC conditions f): 2.43 min.

Scheme D9: preparation of Example 641: (1R,3S,5R)-2-[2-(3-Acetyl-pyrrolo[2,3-c]pyridin-1-yl)-acetyl]-2-aza-bicyclo[3.1.0]hexane-3-carboxylic acid [(R)-1-(3-chloro-2-fluoro-phenyl)-ethyl]-amide

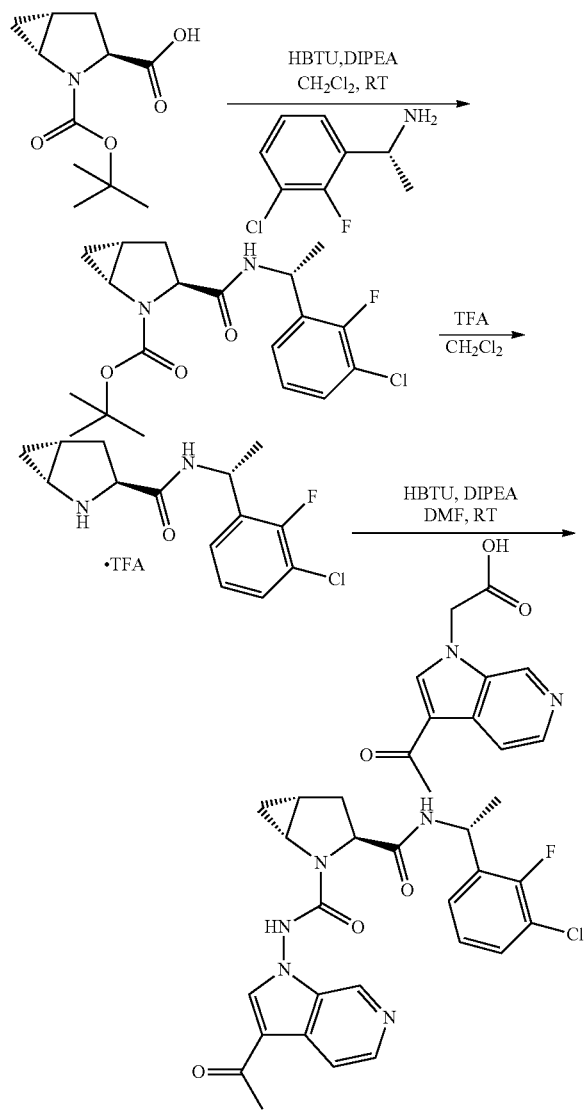

A. (1R,3S,5R)-3-[(R)-1-(3-Chloro-2-fluoro-phenyl)-ethylcarbamoyl]-2-aza-bicyclo[3.1.0]hexane-2-carboxylic acid tert-butyl ester To a solution of (R)-1-(3-chloro-2-fluoro-phenyl)-ethylamine (1.85 g, 8.80 mmol) in CH$_2$Cl$_2$ (44 mL) were successively added (1R,3S,5R)-2-aza-bicyclo[3.1.0]hexane-2,3-dicarboxylic acid 2-tert-butyl ester (2 g, 8.80 mmol), DIPEA (4.61 mL, 26.4 mmol) and HBTU (4.01 g, 10.56 mmol). The reaction mixture was stirred at RT for 16 h. Water was added and the phases were separated. The organic layer was washed successively with 1N HCl (2×), sat. aq. NaHCO$_3$ (2×) and brine, then dried (phase separator) and concentrated in vacuo. The residual oil was purified via flash column chromatography on silica gel (c-hexane/EtOAc 9-1 to 9-4). MS (LC/MS): 405 [M+Na]+, 283 [MH−Boc]+; $t_R$ (HPLC conditions c): 4.93 min.

DMF can also be used instead of Dichloromethane.

B. (1R,3S,5R)-2-Aza-bicyclo[3.1.0]hexane-3-carboxylic acid [(R)-1-(3-chloro-2-fluoro-phenyl)-ethyl]-amide trifluoroacetate To a solution of (1R,3S,5R)-3-[(R)-1-(3-chloro-2-fluoro-phenyl)-ethylcarbamoyl]-2-aza-bicyclo[3.1.0]hexane-2-carboxylic acid tert-butyl ester (3.2 g, 8.36 mmol) in CH$_2$Cl$_2$ (30 mL) was added TFA (15 mL, 195 mmol) and the solution was stirred at RT for 1 h. The crude reaction mixture was concentrated under vacuum, the residue was suspended in MeOH and concentrated again under vacuum. The crude product was used without further purification in the next step. MS (LC/MS): 283.0 [M+H]+; $t_R$ (HPLC conditions c): 3.41 min.

C. Example 641

(1R,3S,5R)-2-[2-(3-Acetyl-pyrrolo[2,3-c]pyridin-1-yl)-acetyl]-2-aza-bicyclo[3.1.0]hexane-3-carboxylic acid [(R)-1-(3-chloro-2-fluoro-phenyl)-ethyl]-amide To a solution of (3-acetyl-pyrrolo[2,3-c]pyridin-1-yl)-acetic acid trifluoroacetate (prepared as described Scheme [A15], 52 mg, 0.157 mmol) in DMF (1.5 mL) were added successively (1R,3S,5R)-2-aza-bicyclo[3.1.0]hexane-3-carboxylic acid [(R)-1-(3-chloro-2-fluoro-phenyl)-ethyl]-amide trifluoroacetate (62.3 mg, 1.57 mmol), HBTU (89 mg, 0.235 mmol) and DIPEA (107 µL, 0.626 mmol). The reaction mixture was stirred at RT for 16 h and poured into water. The layers were separated and the aqueous layer extracted with CH$_2$Cl$_2$ (×2). The combined organic extracts were dried (Na$_2$SO$_4$), filtered and concentrated in vacuo. The residual oil was purified by preparative HPLC (Waters Sunfire C18-ODB, 5 µm, 30×100 mm, eluent: 5% to 100% CH$_3$CN in H$_2$O in 25 min, CH$_3$CN and H$_2$O containing 0.1% TFA, flow: 40 mL/min). The pure fractions were combined, neutralized by filtration through a Varian VariPure HCO$_3$-MP cartridge and lyophilized to give the desired material as a white powder. TLC, R$_f$ (CH$_2$Cl$_2$/MeOH 9:1)=0.42; MS (LC/MS): 483.4/485.3 [M+H]+, 527.4/529.4 [M+HCOO]−; $t_R$ (HPLC conditions a): 2.74 min.

Alternatively, the pure HPLC fractions were neutralized with an aqueous saturated solution of Na$_2$CO$_3$, extracted with EtOAc (×2), dried (Na$_2$SO$_4$), filtered and concentrated to give the desired material.

Alternatively, the crude residue was purified by preparative HPLC (Waters Sunfire (C18 ODB, 5 µm, 19×50, flow=20 mL/min, 5% CH$_3$CN in H$_2$O for 2.5 min, 5 to 100% CH$_3$CN in H$_2$O in 10 min to 100% CH$_3$CN for 2.5 min, CH$_3$CN and H$_2$O both containing 0.1% HCOOH) and the pure HPLC fractions were concentrated and lyophilized to give the desired compound as a formate salt.

The examples below were prepared according to the general procedures described in Scheme D9 for the preparation of Example 641 from commercially available building blocks if not otherwise mentioned (see notes at the end of table 8):

TABLE 8

| Example | Structure | Name | Characterization (end-table notes), TLC, R$_f$(eluent); MS (LC/MS); t$_R$ (HPLC conditions) |
|---|---|---|---|
| 642 | 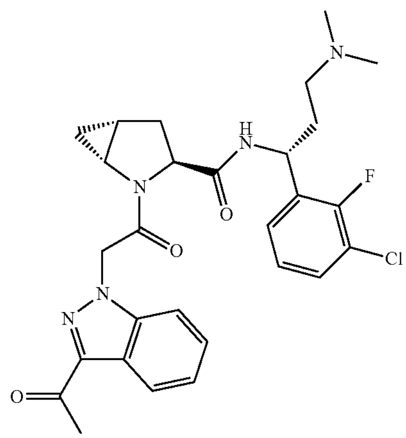 [SMILES: CC(=O)c1nn(CC(=O)N2[C@@H]3C[C@@H]3C[C@H]2C(=O)N[C@H](CCN(C)C)c2cccc(Cl)c2F)c2ccccc12] | (1R,3S,5R)-2-[2-(3-Acetyl-indazol-1-yl)-acetyl]-2-aza-bicyclo[3.1.0]hexane-3-carboxylic acid [(R)-1-(3-chloro-2-fluoro-phenyl)-3-dimethylamino-propyl]-amide | (1,2,4) White solid. R$_f$(CH$_2$Cl$_2$/MeOH 9:1) = 0.55; 540.5/542.5 [M + H]+, 584.5/586.5 [M + HCOO]−; t$_R$ (a): 2.93 min. |
| 643 | 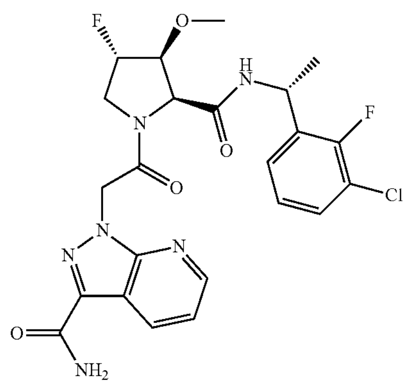 [SMILES: CO[C@H]1[C@@H](C(=O)N[C@H](C)c2cccc(Cl)c2F)N(C(=O)Cn2nc(C(N)=O)c3cccnc32)C[C@@H]1F] | 1-(2-{(2S,3S,4S)-2-[(R)-1-(3-Chloro-2-fluoro-phenyl)-ethylcarbamoyl]-4-fluoro-3-methoxy-pyrrolidin-1-yl}-2-oxo-ethyl)-1H-pyrazolo[3,4-b]pyridine-3-carboxylic acid amide | (3,4) 521 [M + H]+, 543 [M + Na]+; t$_R$ (k): 3.10 min. |
| 644 | 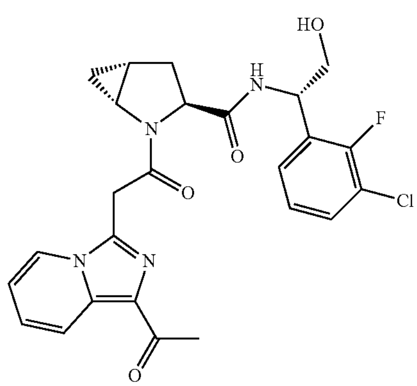 [SMILES: CC(=O)c1nc(CC(=O)N2[C@@H]3C[C@@H]3C[C@H]2C(=O)N[C@H](CO)c2cccc(Cl)c2F)n2ccccc12] | (1R,3S,5R)-2-[2-(1-Acetyl-imidazo[1,5-a]pyridin-3-yl)-acetyl]-2-aza-bicyclo[3.1.0]hexane-3-carboxylic acid [(S)-1-(3-chloro-2-fluoro-phenyl)-2-hydroxy-ethyl]-amide | (2,3,4) Rf (CH$_2$Cl$_2$/MeOH 9:1) = 0.75; 499.1/501.1 [M + H]+, 543.2/544.3 [M + HCOO]−; t$_R$ (a): 2.74 min. |

TABLE 8-continued

| Example | Structure | Name | Characterization (end-table notes), TLC, R_f (eluent); MS (LC/MS); t_R (HPLC conditions) |
|---|---|---|---|
| 645 | 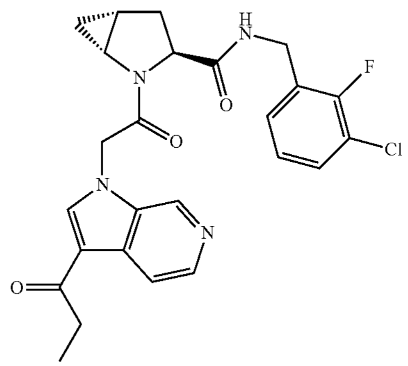 [SMILES: CCC(=O)c1cn(CC(=O)N2[C@@H]3C[C@@H]3C[C@H]2C(=O)NCc2cccc(Cl)c2F)c2cnccc12] | (1R,3S,5R)-2-[2-(3-Propionyl-pyrrolo[2,3-c]pyridin-1-yl)-acetyl]-2-aza-bicyclo[3.1.0]hexane-3-carboxylic acid 3-chloro-2-fluoro-benzylamide | (4) White solid. 483.4/485.4 [M + H]+, 527.3/529.4 [M + HCOO]−; t_R (f): 1.56 min. |
| 646 | 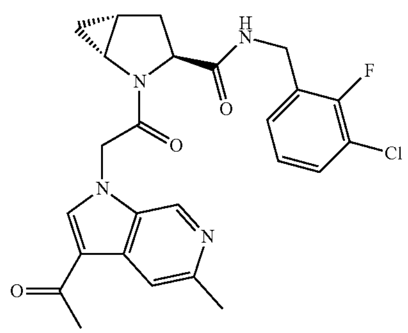 [SMILES: CC(=O)c1cn(CC(=O)N2[C@@H]3C[C@@H]3C[C@H]2C(=O)NCc2cccc(Cl)c2F)c2cnc(C)cc12] | (1R,3S,5R)-2-[2-(3-Acetyl-5-methyl-pyrrolo[2,3-c]pyridin-1-yl)-acetyl]-2-aza-bicyclo[3.1.0]hexane-3-carboxylic acid 3-chloro-2-fluoro-benzylamide | (4) White solid. R_f (CH_2Cl_2/MeOH 9:1) = 0.4; 483.4/485.4 [M + H]+, 527.5/529.4 [M + HCOO]−; t_R (f): 1.52 min. |
| 647 | 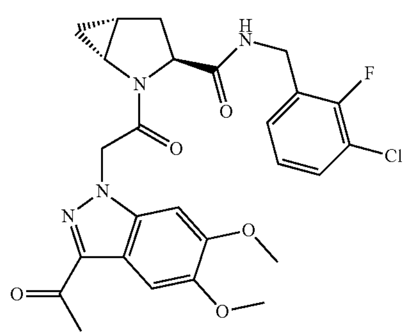 [SMILES: COc1cc2c(C(C)=O)nn(CC(=O)N3[C@@H]4C[C@@H]4C[C@H]3C(=O)NCc3cccc(Cl)c3F)c2cc1OC] | (1R,3S,5R)-2-[2-(3-Acetyl-5,6-dimethoxy-indazol-1-yl)-acetyl]-2-aza-bicyclo[3.1.0]hexane-3-carboxylic acid 3-chloro-2-fluoro-benzylamide | (4) 529 [M + H]+; t_R (k): 3.46 min. |
| 648 | 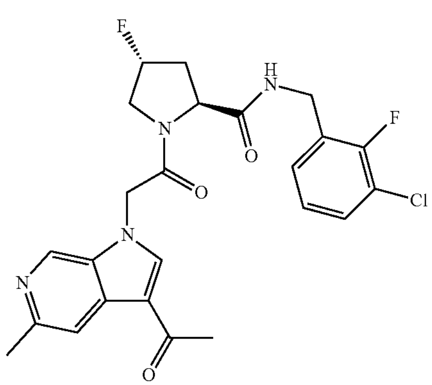 | (2S,4R)-1-[2-(3-Acetyl-5-methyl-pyrrolo[2,3-c]pyridin-1-yl)-acetyl]-4-fluoro-pyrrolidine-2-carboxylic acid 3-chloro-2-fluoro-benzylamide | (4,5) White solid. 587.1 [M − H]−; t_R (c): 3.71 min. |

TABLE 8-continued

| Example | Name | Characterization (end-table notes), TLC, R$_f$(eluent); MS (LC/MS); t$_R$ (HPLC conditions) |
|---|---|---|
| 649 | (1R,3S,5R)-2-[2-(5-Acetyl-pyrrolo[2,3-d]pyrimidin-7-yl)-acetyl]-2-aza-bicyclo[3.1.0]hexane-3-carboxylic acid 3-chloro-2-fluoro-benzylamide | (4) White solid. R$_f$ (CH$_2$Cl$_2$/MeOH 9:1) = 0.4; 470.4/472.4 [M + H]+, 514.4/516.5 [M + HCOO]−; t$_R$ (f): 1.54 min. |
| 650 | 1-{2-[(1R,3S,5R)-3-(3-Chloro-2-fluoro-benzylcarbamoyl)-2-aza-bicyclo[3.1.0]hex-2-yl]-2-oxo-ethyl}-1H-pyrazolo[4,3-c]pyridine-3-carboxylic acid amide | (4) 471 [M + H]+; t$_R$ (k): 2.69 min. |
| 651 | 1-{2-[(1R,3S,5R)-3-(3-Chloro-2-fluoro-benzylcarbamoyl)-2-aza-bicyclo[3.1.0]hex-2-yl]-2-oxo-ethyl}-5-methyl-1H-pyrazolo[3,4-c]pyridine-3-carboxylic acid amide | (4) 485 [M + H]+; t$_R$ (k): 2.71 min. |
| 652 | (1R,3S,5R)-2-{2-[3-(2-Hydroxy-acetyl)-indazol-1-yl]-acetyl}-2-aza-bicyclo[3.1.0]hexane-3-carboxylic acid 3-chloro-2-fluoro-benzylamide | (4) 485 [M + H]+, 507 [M + Na]+; t$_R$ (k): 3.24 min. |

TABLE 8-continued

| Example | Structure | Name | Characterization (end-table notes), TLC, R_f (eluent); MS (LC/MS); t_R (HPLC conditions) |
|---|---|---|---|
| 653 | 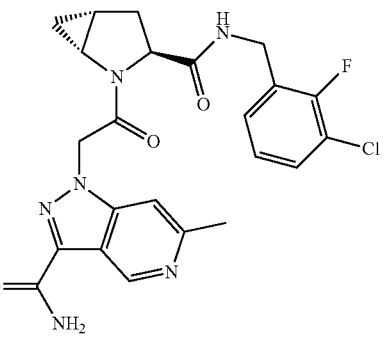 | 1-{2-[(1R,3S,5R)-3-(3-Chloro-2-fluoro-benzylcarbamoyl)-2-aza-bicyclo[3.1.0]hex-2-yl]-2-oxo-ethyl}-6-methyl-1H-pyrazolo[4,3-c]pyridine-3-carboxylic acid amide | (4) 485 [M + H]+; t_R (k): 2.73 min. |
| 654 | 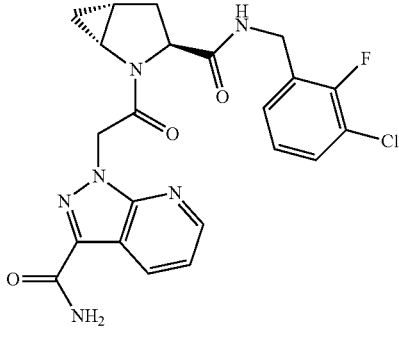 [SMILES: NC(=O)c1nn(CC(=O)N2[C@@H]3C[C@@H]3C[C@H]2C(=O)NCc2cccc(Cl)c2F)c2ncccc12] | 1-{2-[(1R,3S,5R)-3-(3-Chloro-2-fluoro-benzylcarbamoyl)-2-aza-bicyclo[3.1.0]hex-2-yl]-2-oxo-ethyl}-1H-pyrazolo[3,4-b]pyridine-3-carboxylic acid amide | (4) 471 [M + H]+; t_R (k): 2.99 min. |
| 655 | 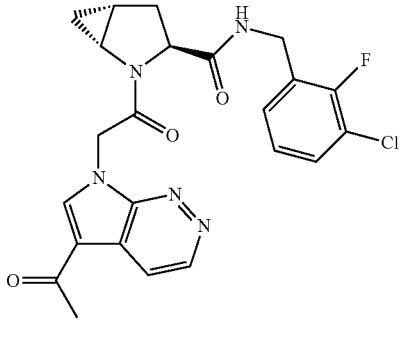 [SMILES: CC(=O)c1cn(CC(=O)N2[C@@H]3C[C@@H]3C[C@H]2C(=O)NCc2cccc(Cl)c2F)c2nnccc12] | (1R,3S,5R)-2-[2-(5-Acetyl-pyrrolo[2,3-c]pyridazin-7-yl)-acetyl]-2-aza-bicyclo[3.1.0]hexane-3-carboxylic acid 3-chloro-2-fluoro-benzylamide | (4) R_f (CH_2Cl_2/MeOH 9:1) = 0.4; 470.1/472.2 [M + H]+, 514.2/516.2 [M + HCOO]−; t_R (f): 1.51 min. |
| 656 | 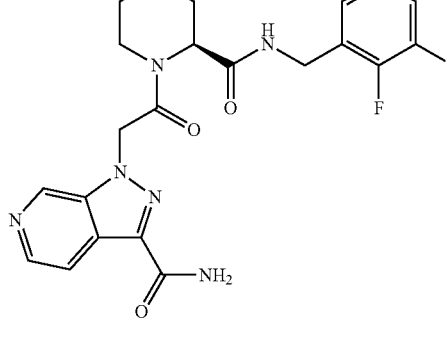 | 1-{2-[(S)-2-(3-Chloro-2-fluoro-benzylcarbamoyl)-piperidin-1-yl]-2-oxo-ethyl}-1H-pyrazolo[3,4-c]pyridine-3-carboxylic acid amide | (4) White solid. 473.0 [M + H]+, 495.0 [M + Na]+; t_R (c): 3.63 min. |

TABLE 8-continued

| Example | Structure | Name | Characterization (end-table notes), TLC, R$_f$ (eluent); MS (LC/MS); t$_R$ (HPLC conditions) |
|---|---|---|---|
| 657 | 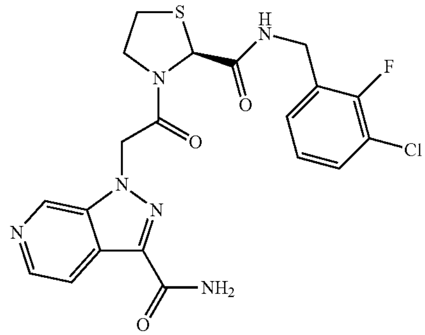 [SMILES: NC(=O)c1nn(CC(=O)N2CCS[C@H]2C(=O)NCc2cccc(Cl)c2F)c2cnccc12] | 1-{2-[(S)-2-(3-Chloro-2-fluoro-benzylcarbamoyl)-thiazolidin-3-yl]-2-oxo-ethyl}-1H-pyrazolo[3,4-c]pyridine-3-carboxylic acid amide | (4) White solid. 477.0 [M + H]+, 498.9 [M + Na]+; t$_R$ (c): 3.50 min. |
| 658 | 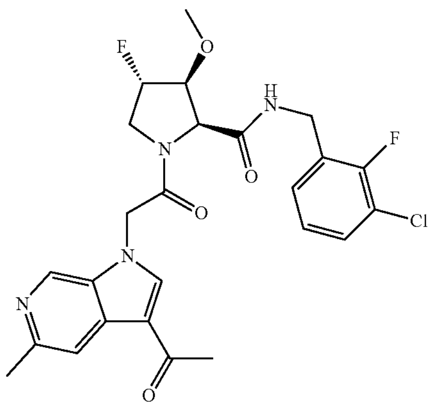 [SMILES: CO[C@H]1[C@@H](C(=O)NCc2cccc(Cl)c2F)N(C(=O)Cn2cc(C(C)=O)c3cc(C)ncc32)C[C@@H]1F] | (2S,3S,4S)-1-[2-(3-Acetyl-5-methyl-pyrrolo[2,3-c]pyridin-1-yl)-acetyl]-4-fluoro-3-methoxy-pyrrolidine-2-carboxylic acid 3-chloro-2-fluoro-benzylamide formate | (3,4) 519/521 [M + H]+; t$_R$ (f): 1.51 min. |
| 659 | 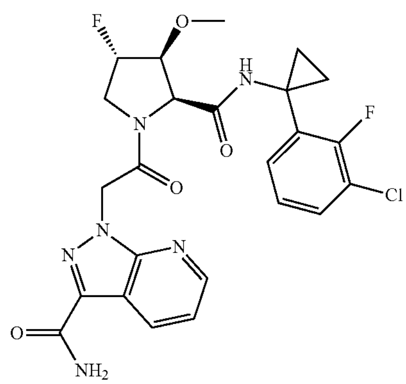 [SMILES: CO[C@H]1[C@@H](C(=O)NC2(c3cccc(Cl)c3F)CC2)N(C(=O)Cn2nc(C(N)=O)c3cccnc32)C[C@@H]1F] | 1-(2-{(2S,3S,4S)-2-[1-(3-Chloro-2-fluoro-phenyl)-cyclopropyl carbamoyl]-4-fluoro-3-methoxy-pyrrolidin-1-yl}-2-oxo-ethyl)-1H-pyrazolo[3,4-b]pyridine-3-carboxylic acid amide | (3,4) 533 [M + H]+; t$_R$ (k): 3.16 min. |
| 660 | 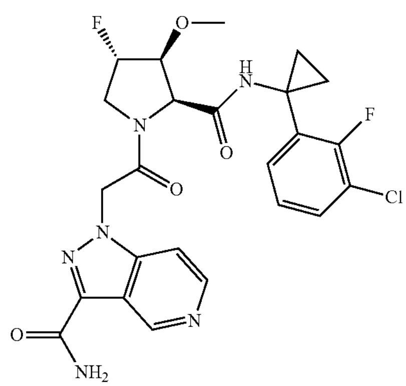 [SMILES: CO[C@H]1[C@@H](C(=O)NC2(c3cccc(Cl)c3F)CC2)N(C(=O)Cn2nc(C(N)=O)c3cnccc32)C[C@@H]1F] | 1-(2-{(2S,3S,4S)-2-[1-(3-Chloro-2-fluoro-phenyl)-cyclopropyl carbamoyl]-4-fluoro-3-methoxy-pyrrolidin-1-yl}-2-oxo-ethyl)-1H-pyrazolo[4,3-c]pyridine-3-carboxylic acid amide | (3,4) 533 [M + H]+; t$_R$ (k): 2.84 min. |

TABLE 8-continued

| Example | Structure | Name | Characterization (end-table notes), TLC, R_f (eluent); MS (LC/MS); t_R (HPLC conditions) |
|---|---|---|---|
| 661 | 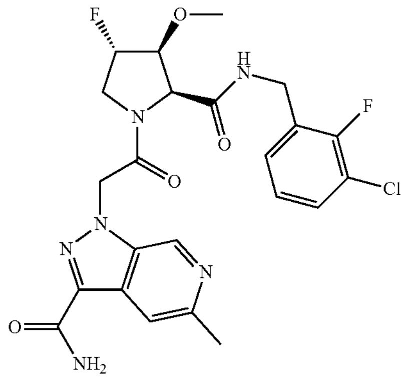 [SMILES: CO[C@H]1[C@@H](C(=O)NCc2cccc(Cl)c2F)N(C(=O)Cn2nc(C(N)=O)c3cc(C)ncc32)C[C@@H]1F] | 1-{2-[(2S,3S,4S)-2-(3-Chloro-2-fluoro-benzylcarbamoyl)-4-fluoro-3-methoxy-pyrrolidin-1-yl]-2-oxo-ethyl}-5-methyl-1H-pyrazolo[3,4-c]pyridine-3-carboxylic acid amide | (3,4) 521 [M + H]+; t_R (k): 2.73 min. |
| 662 | 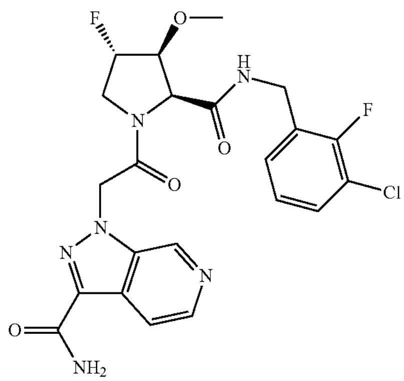 [SMILES: CO[C@H]1[C@@H](C(=O)NCc2cccc(Cl)c2F)N(C(=O)Cn2nc(C(N)=O)c3ccncc32)C[C@@H]1F] | 1-{2-[(2S,3S,4S)-2-(3-Chloro-2-fluoro-benzylcarbamoyl)-4-fluoro-3-methoxy-pyrrolidin-1-yl]-2-oxo-ethyl}-1H-pyrazolo[3,4-c]pyridine-3-carboxylic acid amide | (3,4) 507 [M + H]+; t_R (k): 2.71 min. |
| 663 | 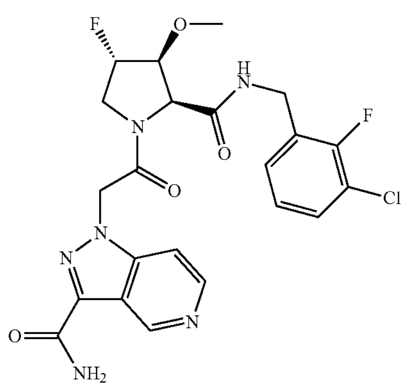 [SMILES: CO[C@H]1[C@@H](C(=O)NCc2cccc(Cl)c2F)N(C(=O)Cn2nc(C(N)=O)c3cnccc32)C[C@@H]1F] | 1-{2-[(2S,3S,4S)-2-(3-Chloro-2-fluoro-benzylcarbamoyl)-4-fluoro-3-methoxy-pyrrolidin-1-yl]-2-oxo-ethyl}-1H-pyrazolo[4,3-c]pyridine-3-carboxylic acid amide | (3,4) 507 [M + H]+; t_R (k): 2.71 min. |
| 664 | 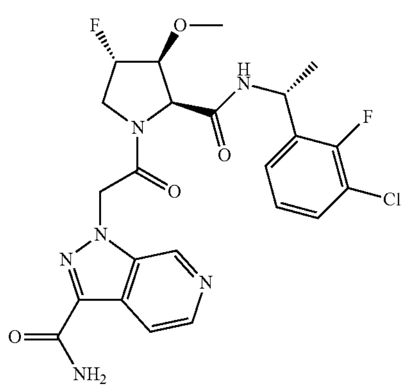 [SMILES: CO[C@H]1[C@@H](C(=O)N[C@H](C)c2cccc(Cl)c2F)N(C(=O)Cn2nc(C(N)=O)c3ccncc32)C[C@@H]1F] | 1-(2-{(2S,3S,4S)-2-[(R)-1-(3-Chloro-2-fluoro-phenyl)-ethylcarbamoyl]-4-fluoro-3-methoxy-pyrrolidin-1-yl}-2-oxo-ethyl)-1H-pyrazolo[3,4-c]pyridine-3-carboxylic acid amide | (3,4) 521 [M + H]+; t_R (k): 2.78 min. |

TABLE 8-continued

| Example | Structure | Name | Characterization (end-table notes), TLC, R*f* (eluent); MS (LC/MS); t*R* (HPLC conditions) |
|---|---|---|---|
| 665 | 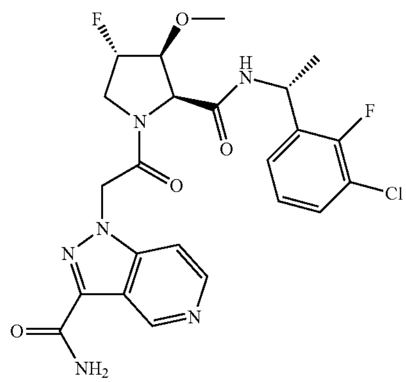 [SMILES: CO[C@H]1[C@@H](C(=O)N[C@H](C)c2cccc(Cl)c2F)N(C(=O)Cn2nc(C(N)=O)c3cnccc32)C[C@@H]1F] | 1-(2-{(2S,3S,4S)-2-[(R)-1-(3-Chloro-2-fluoro-phenyl)-ethylcarbamoyl]-4-fluoro-3-methoxy-pyrrolidin-1-yl}-2-oxo-ethyl)-1H-pyrazolo[4,3-c]pyridine-3-carboxylic acid amide | (3,4) 521 [M + H]+; t*R* (k): 2.79 min. |
| 666 | 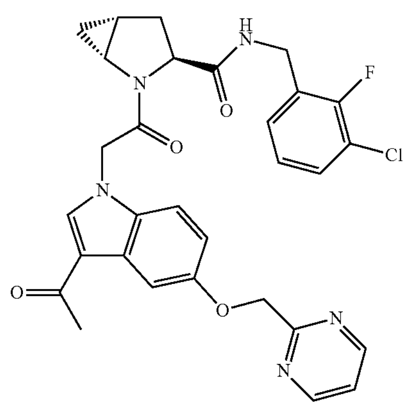 [SMILES: CC(=O)c1cn(CC(=O)N2[C@@H]3C[C@@H]3C[C@H]2C(=O)NCc2cccc(Cl)c2F)c2ccc(OCc3ncccn3)cc12] | (1R,3S,5R)-2-{2-[3-Acetyl-5-(pyrimidin-2-ylmethoxy)-indol-1-yl]-acetyl}-2-aza-bicyclo[3.1.0]hexane-3-carboxylic acid 3-chloro-2-fluoro-benzylamide | (4) 576/578 [M + H]+; t*R* (k): 3.48 min. |
| 667 | 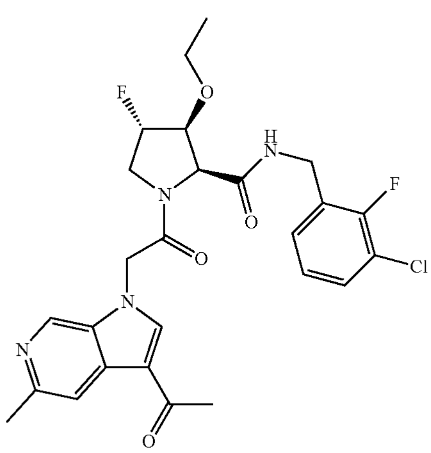 [SMILES: CCO[C@H]1[C@@H](C(=O)NCc2cccc(Cl)c2F)N(C(=O)Cn2cc(C(C)=O)c3cc(C)ncc32)C[C@@H]1F] | (2S,3S,4S)-1-[2-(3-Acetyl-5-methyl-pyrrolo[2,3-c]pyridin-1-yl)-acetyl]-3-ethoxy-4-fluoro-pyrrolidine-2-carboxylic acid 3-chloro-2-fluoro-benzylamide formate | (3,4) 533/535 [M + H]+; t*R* (f): 1.61 min. |

TABLE 8-continued

| Example | Structure | Name | Characterization (end-table notes), TLC, R_f (eluent); MS (LC/MS); t_R (HPLC conditions) |
|---|---|---|---|
| 668 | 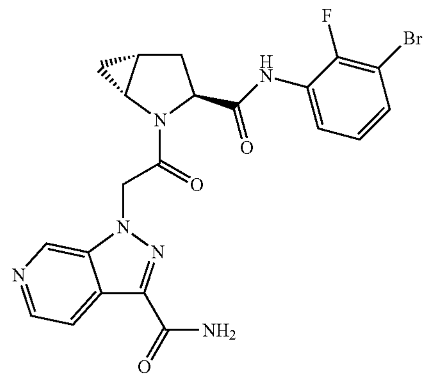 [SMILES: NC(=O)c1nn(CC(=O)N2[C@@H]3C[C@@H]3C[C@H]2C(=O)Nc2cccc(Br)c2F)c2cnccc12] | 1-{2-[(1R,3S,5R)-3-(3-Bromo-2-fluoro-phenylcarbamoyl)-2-aza-bicyclo[3.1.0]hex-2-yl]-2-oxo-ethyl}-1H-pyrazolo[3,4-c]pyridine-3-carboxylic acid amide | (4) R_f (EtOAc) = 0.1; 501.1/503.0 [M + H]+, 499.0/501.2 [M − H]−, 545.1/548.3 [M + HCOO]− ; t_R (a): 2.42 min. |
| 669 | 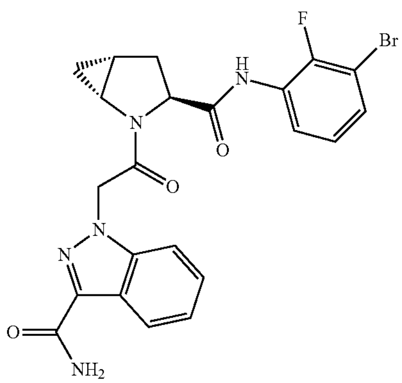 [SMILES: NC(=O)c1nn(CC(=O)N2[C@@H]3C[C@@H]3C[C@H]2C(=O)Nc2cccc(Br)c2F)c2ccccc12] | 1-{2-[(1R,3S,5R)-3-(3-Bromo-2-fluoro-phenylcarbamoyl)-2-aza-bicyclo[3.1.0]hex-2-yl]-2-oxo-ethyl}-1H-indazole-3-carboxylic acid amide | (4) R_f (EtOAc) = 0.6; 517.1/519.1 [M + NH_4]+, 498.2/500.1 [M − H]− ; t_R (a): 3.18 min. |
| 670 | 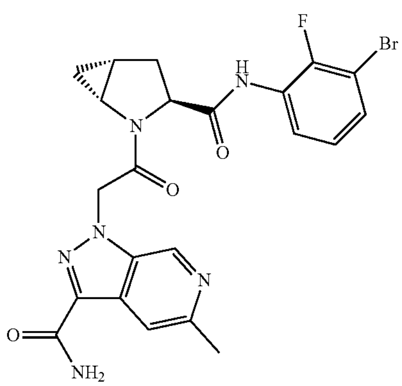 [SMILES: Cc1cc2c(C(N)=O)nn(CC(=O)N3[C@@H]4C[C@@H]4C[C@H]3C(=O)Nc3cccc(Br)c3F)c2cn1] | 1-{2-[(1R,3S,5R)-3-(3-Bromo-2-fluoro-phenylcarbamoyl)-2-aza-bicyclo[3.1.0]hex-2-yl]-2-oxo-ethyl}-5-methyl-1H-pyrazolo[3,4-c]pyridine-3-carboxylic acid amide | (4) R_f (EtOAc) = 0.1; 515.2/517.1 [M + H]+, 513.2/515.1 [M − H]−, 561.2 [M + HCOO]− ; t_R (a): 2.48 min. |
| 671 | 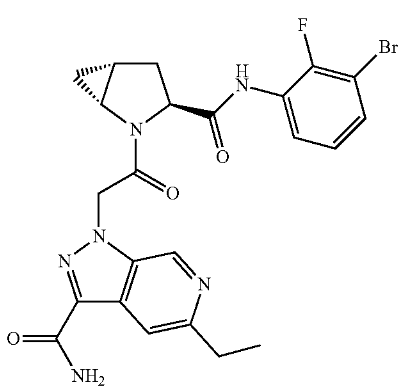 [SMILES: CCc1cc2c(C(N)=O)nn(CC(=O)N3[C@@H]4C[C@@H]4C[C@H]3C(=O)Nc3cccc(Br)c3F)c2cn1] | 1-{2-[(1R,3S,5R)-3-(3-Bromo-2-fluoro-phenylcarbamoyl)-2-aza-bicyclo[3.1.0]hex-2-yl]-2-oxo-ethyl}-5-ethyl-1H-pyrazolo[3,4-c]pyridine-3-carboxylic acid amide | (4) R_f (EtOAc) = 0.15; 529.1/531.1 [M + H]+, 527.2/529.1 [M − H]−, 573.2/575.3 [M + HCOO]− ; t_R (a): 2.55 min. |

TABLE 8-continued

| Example | Structure | Name | Characterization (end-table notes), TLC, R_f (eluent); MS (LC/MS); t_R (HPLC conditions) |
|---------|-----------|------|------------------------------------------------------------------------------------------|
| 672 | 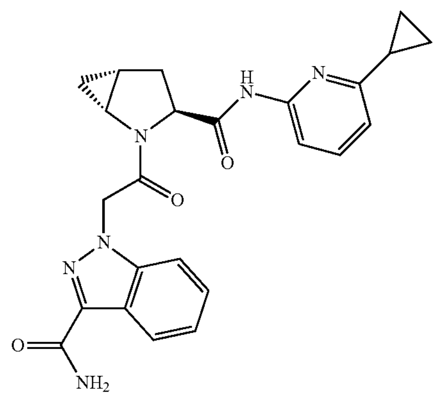 [SMILES: NC(=O)c1nn(CC(=O)N2[C@@H]3C[C@@H]3C[C@H]2C(=O)Nc2cccc(C3CC3)n2)c2ccccc12] | 1-{2-[(1R,3S,5R)-3-(6-Cyclopropyl-pyridin-2-ylcarbamoyl)-2-aza-bicyclo[3.1.0]hex-2-yl]-2-oxo-ethyl}-1H-indazole-3-carboxylic acid amide | (4,5) R_f (EtOAc) = 0.4; 445.3/446.3 [M + H]+, 489.4/491.4 [M + HCOO]− ; t_R (a): 2.53 min. |
| 673 | 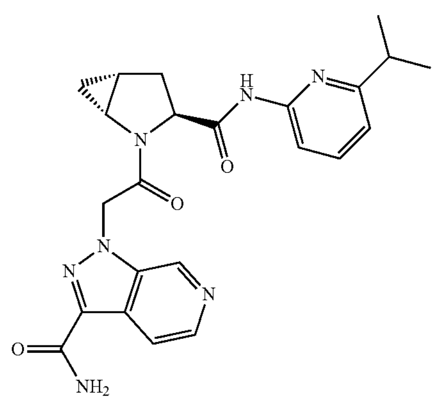 [SMILES: CC(C)c1cccc(NC(=O)[C@@H]2C[C@H]3C[C@H]3N2C(=O)Cn2nc(C(N)=O)c3ccncc32)n1] | 1-{2-[(1R,3S,5R)-3-(6-Isopropyl-pyridin-2-ylcarbamoyl)-2-aza-bicyclo[3.1.0]hex-2-yl]-2-oxo-ethyl}-1H-pyrazolo[3,4-c]pyridine-3-carboxylic acid amide | (4,5) R_f (EtOAc) = 0.1; 448.3 [M + H]+, 446.0 [M − H]−, 492.3 [M + HCOO]− ; t_R (a): 1.31 min. |
| 674 | 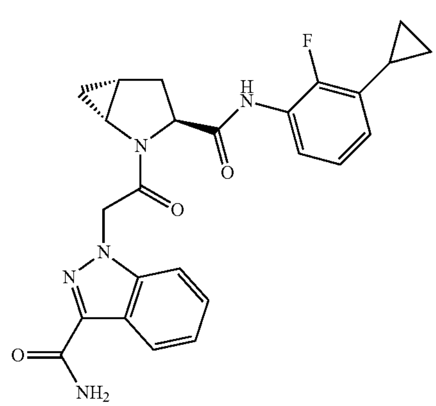 [SMILES: NC(=O)c1nn(CC(=O)N2[C@@H]3C[C@@H]3C[C@H]2C(=O)Nc2cccc(C3CC3)c2F)c2ccccc12] | 1-{2-[(1R,3S,5R)-3-(3-Cyclopropyl-2-fluoro-phenylcarbamoyl)-2-aza-bicyclo[3.2.1]hex-2-yl]-2-oxo-ethyl}-1H-indazole-3-carboxylic acid amide | (1,4) R_f (c-hexane/EtOAc 2:1) = 0.6; 361.2 [M + H]+, 738.4 [2M + Na]+; t_R (f): 2.29 min. |

TABLE 8-continued

| Example | Structure | Name | Characterization (end-table notes), TLC, R_f (eluent); MS (LC/MS); t_R (HPLC conditions) |
|---|---|---|---|
| 675 | 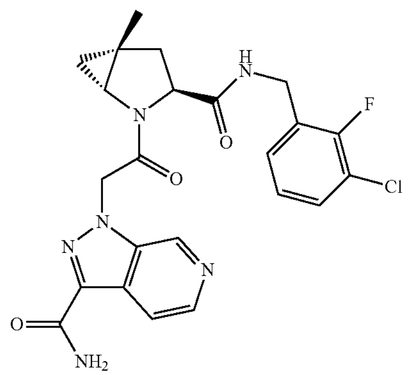 [SMILES: C[C@@]12C[C@@H](C(=O)NCc3cccc(Cl)c3F)N(C(=O)Cn3nc(C(N)=O)c4ccncc43)[C@@H]1C2] | 1-{2-[(1R,3S,5R)-3-(3-Chloro-2-fluoro-benzylcarbamoyl)-5-methyl-2-aza-bicyclo[3.1.0]hex-2-yl]-2-oxo-ethyl}-1H-pyrazolo[3,4-c]pyridine-3-carboxylic acid amide | (2,3,4) R_f (CH$_2$Cl$_2$/MeOH 9:1) = 0.4; 485.3/487.3 [M + H]+, 507.2/509.2 [M + Na]+, 529.3/531.3 [M + HCOO]−; t_R (f): 1.47 min. |
| 676 | 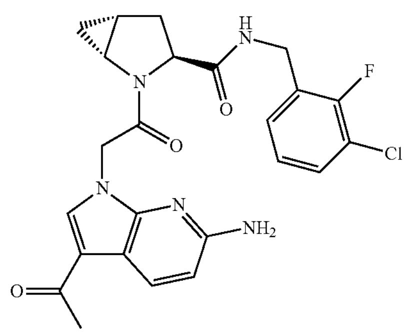 | (1R,3S,5R)-2-[2-(3-Acetyl-6-amino-pyrrolo[2,3-b]pyridin-1-yl)-acetyl]-2-aza-bicyclo[3.1.0]hexane-3-carboxylic acid 3-chloro-2-fluoro-benzylamide | (4) R_f (CH$_2$Cl$_2$/MeOH 9:1) = 0.5; 503.1/505.1 [M + H]+, 547.1/549.1 [M + HCOO]−; t_R (f): 2.11 min. |
| 677 | 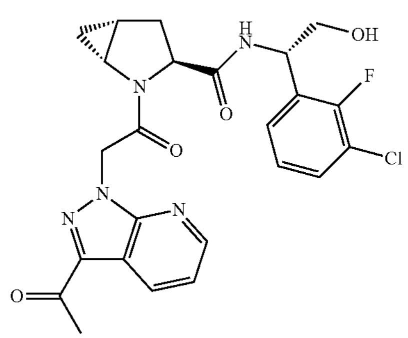 [SMILES: CC(=O)c1nn(CC(=O)N2[C@@H]3C[C@@H]3C[C@H]2C(=O)N[C@H](CO)c2cccc(Cl)c2F)c2ncccc12] | (1R,3S,5R)-2-[2-(3-Acetyl-pyrazolo[3,4-b]pyridin-1-yl)-acetyl]-2-aza-bicyclo[3.1.0]hexane-3-carboxylic acid [(S)-1-(3-chloro-2-fluoro-phenyl)-2-hydroxy-ethyl]-amide | (2,3,4) R_f (CH$_2$Cl$_2$/MeOH 9:1) = 0.55; 500.1/502.1 [M + H]+, 1000.3/1001.3 [2M + H]+, 544.1/546.1; t_R (f): 1.81 min. |
| 678 | 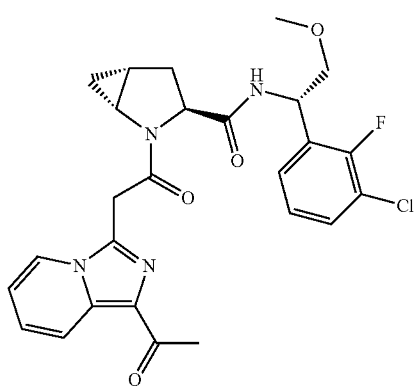 [SMILES: COC[C@@H](NC(=O)[C@@H]1C[C@H]2C[C@H]2N1C(=O)Cc1nc(C(C)=O)c2ccccn12)c1cccc(Cl)c1F] | (1R,3S,5R)-2-[2-(1-Acetyl-imidazo[1,5-a]pyridin-3-yl)-acetyl]-2-aza-bicyclo[3.1.0]hexane-3-carboxylic acid [(S)-1-(3-chloro-2-fluoro-phenyl)-2-methoxy-ethyl]-amide | (2,3,4) R_f (CH$_2$Cl$_2$/MeOH 9:1) = 0.7; 513.2/515.2 [M + H]+, 557.2/558.3 [M + HCOO]−; t_R (a): 3.15 min. |

TABLE 8-continued

| Example | Structure | Name | Characterization (end-table notes), TLC, R$_f$ (eluent); MS (LC/MS); t$_R$ (HPLC conditions) |
|---|---|---|---|
| 679 | 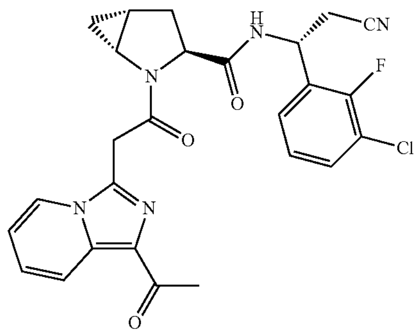 [SMILES: CC(=O)c1nc(CC(=O)N2[C@@H]3C[C@@H]3C[C@H]2C(=O)N[C@H](CC#N)c2cccc(Cl)c2F)n2ccccc12] | (1R,3S,5R)-2-[2-(1-Acetyl-imidazo[1,5-a]pyridin-3-yl)-acetyl]-2-aza-bicyclo[3.1.0]hexane-3-carboxylic acid [(R)-1-(3-chloro-2-fluoro-phenyl)-2-cyano-ethyl]-amide | (4) Rf (EtOAc) = 0.2; 508.3 [M + H]+, 506.2 [M − H]−; t$_R$ (a): 3.05 min. |
| 680 | 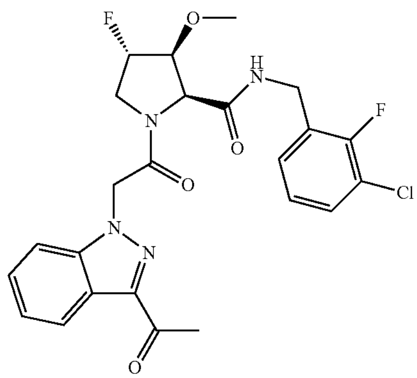 [SMILES: CO[C@H]1[C@@H](C(=O)NCc2cccc(Cl)c2F)N(C(=O)Cn2nc(C(C)=O)c3ccccc32)C[C@@H]1F] | (2S,3S,4S)-1-[2-(3-Acetyl-indazol-1-yl)-acetyl]-4-fluoro-3-methoxy-pyrrolidine-2-carboxylic acid 3-chloro-2-fluoro-benzylamide | (3) 505.2/507.2 [M + H]+, 549.3/551.4 [M + HCOO]−; t$_R$ (f): 2.09 min. |
| 681 | 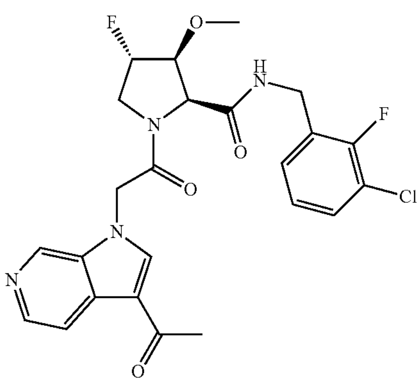 [SMILES: CO[C@H]1[C@@H](C(=O)NCc2cccc(Cl)c2F)N(C(=O)Cn2cc(C(C)=O)c3ccncc32)C[C@@H]1F] | (2S,3S,4S)-1-[2-(3-Acetyl-pyrrolo[2,3-c]pyridin-1-yl)-acetyl]-4-fluoro-3-methoxy-pyrrolidine-2-carboxylic acid 3-chloro-2-fluoro-benzylamide | (3,4) 505.2/507.2 [M + H]+, 549.2/551.2 [M + HCOO]−; t$_R$ (f): 1.49 min. |
| 682 | 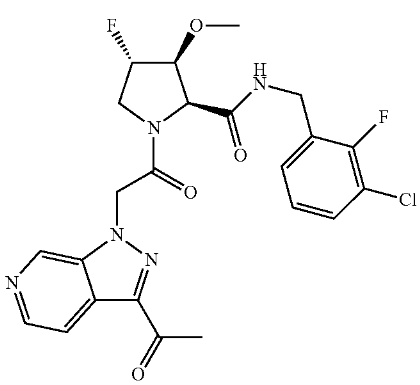 [SMILES: CO[C@H]1[C@@H](C(=O)NCc2cccc(Cl)c2F)N(C(=O)Cn2nc(C(C)=O)c3ccncc32)C[C@@H]1F] | (2S,3S,4S)-1-[2-(3-Acetyl-pyrazolo[3,4-c]pyridin-1-yl)-acetyl]-4-fluoro-3-methoxy-pyrrolidine-2-carboxylic acid 3-chloro-2-fluoro-benzylamide | (3,4) 506.4/508.4 [M + H]+, 550.5/552.6 [M + HCOO]−; t$_R$ (f): 1.59 min. |

TABLE 8-continued

| Example | Structure | Name | Characterization (end-table notes), TLC, R_f (eluent); MS (LC/MS); t_R (HPLC conditions) |
|---|---|---|---|
| 683 | 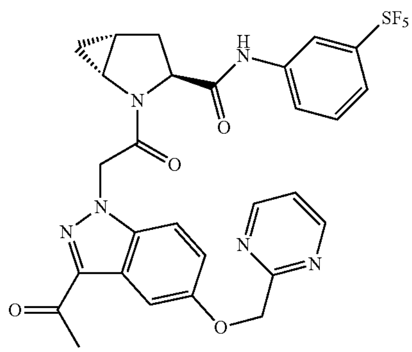 | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (3-sulfur pentafluoride-phenyl)-amide | (4,7) 451.0 [M + Na]+, 328.9 [M − tBu]+, 427.1 [M − H]−; t_R (c): 5.29 min. |
| 684 | 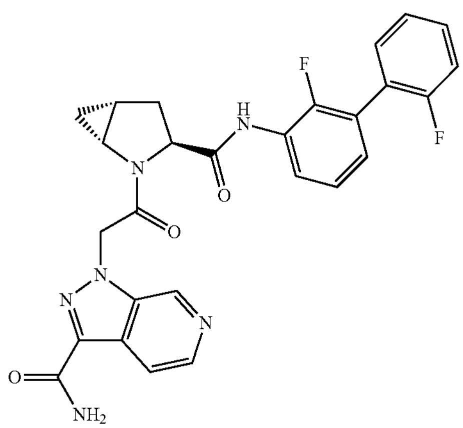 [SMILES: NC(=O)c1nn(CC(=O)N2[C@@H]3C[C@@H]3C[C@H]2C(=O)Nc2cccc(-c3ccccc3F)c2F)c2cnccc12] | 1-{2-[(1R,3S,5R)-3-(2,2'-Difluoro-biphenyl-3-ylcarbamoyl)-2-aza-bicyclo[3.1.0]hex-2-yl]-2-oxo-ethyl}-1H-pyrazolo[3,4-c]pyridine-3-carboxylic acid amide | (1,4,7) 517 [M + H]+; t_R (k): 3.01 min. |
| 685 | 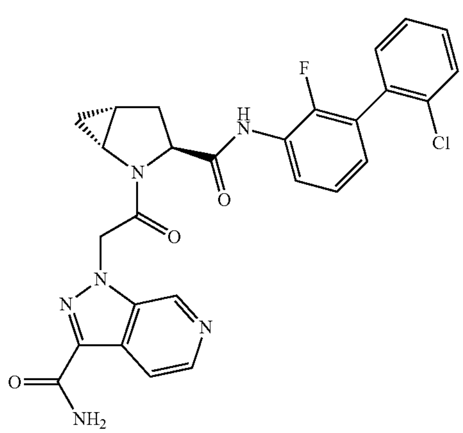 [SMILES: NC(=O)c1nn(CC(=O)N2[C@@H]3C[C@@H]3C[C@H]2C(=O)Nc2cccc(-c3ccccc3Cl)c2F)c2cnccc12] | 1-{2-[(1R,3S,5R)-3-(2'-Chloro-2-fluoro-biphenyl-3-ylcarbamoyl)-2-aza-bicyclo[3.1.0]hex-2-yl]-2-oxo-ethyl}-1H-pyrazolo[3,4-c]pyridine-3-carboxylic acid amide | (1,4,7) 533 [M + H]+; t_R (k): 3.05 min. |

| Example | Structure | Name | Characterization (end-table notes), TLC, R_f (eluent); MS (LC/MS); t_R (HPLC conditions) |
|---|---|---|---|
| 686 | 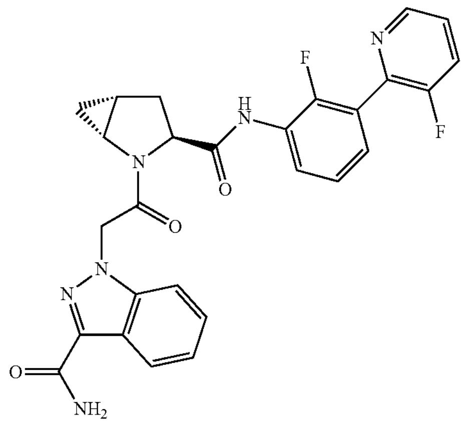 [SMILES: NC(=O)c1nn(CC(=O)N2[C@@H]3C[C@@H]3C[C@H]2C(=O)Nc2cccc(-c3ncccc3F)c2F)c2ccccc12] | 1-(2-{(1R,3S,5R)-3-[2-Fluoro-3-(3-fluoro-pyridin-2-yl)-phenylcarbamoyl]-2-aza-bicyclo[3.1.0]hex-2-yl}-2-oxo-ethyl)-1H-indazole-3-carboxylic acid amide | (1,4,7) 517 [M + H]+; t_R (k): 3.10 min. |
| 687 | 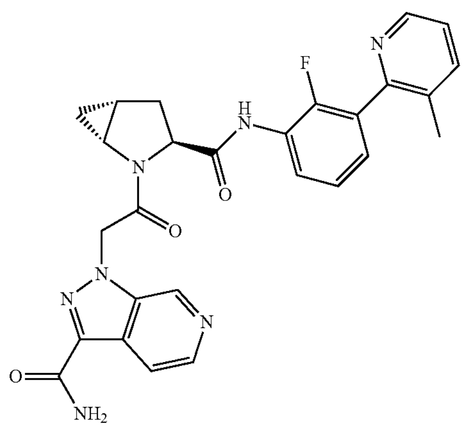 [SMILES: Cc1cccnc1-c1cccc(NC(=O)[C@@H]2C[C@H]3C[C@H]3N2C(=O)Cn2nc(C(N)=O)c3ccncc32)c1F] | 1-(2-{(1R,3S,5R)-3-[2-Fluoro-3-(3-methyl-pyridin-2-yl)-phenylcarbamoyl]-2-aza-bicyclo[3.1.0]hex-2-yl}-2-oxo-ethyl)-1H-pyrazolo[3,4-c]pyridine-3-carboxylic acid amide | (1,4,7) 514 [M + H]+; t_R (k): 2.32 min. |
| 688 | 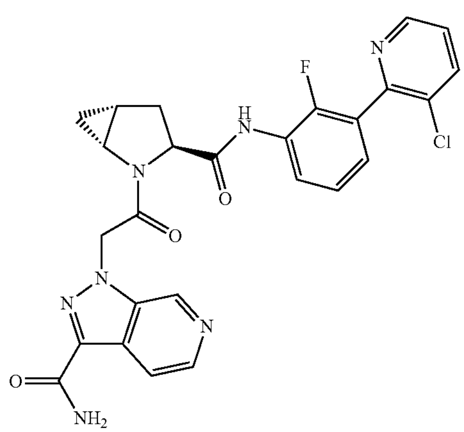 [SMILES: NC(=O)c1nn(CC(=O)N2[C@@H]3C[C@@H]3C[C@H]2C(=O)Nc2cccc(-c3ncccc3Cl)c2F)c2cnccc12] | 1-(2-{(1R,3S,5R)-3-[3-(3-Chloro-pyridin-2-yl)-2-fluoro-phenylcarbamoyl]-2-aza-bicyclo[3.1.0]hex-2-yl}-2-oxo-ethyl)-1H-pyrazolo[3,4-c]pyridine-3-carboxylic acid amide | (1,4,7) 534 [M + H]+; t_R (k): 2.72 min. |

TABLE 8-continued

| Example | Structure | Name | Characterization (end-table notes), TLC, $R_f$ (eluent); MS (LC/MS); $t_R$ (HPLC conditions) |
|---|---|---|---|
| 689 | 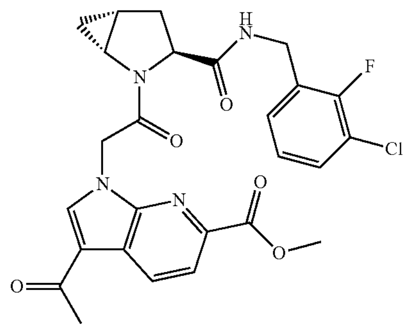 [SMILES: COC(=O)c1ccc2c(C(C)=O)cn(CC(=O)N3[C@@H]4C[C@@H]4C[C@H]3C(=O)NCc3cccc(Cl)c3F)c2n1] | 3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-pyrrolo[2,3-b]pyridine-6-carboxylic acid methyl ester | (4) 527 [M + H]+, 549 [M + Na]+; $t_R$ (k): 3.43 min. |
| 690 | 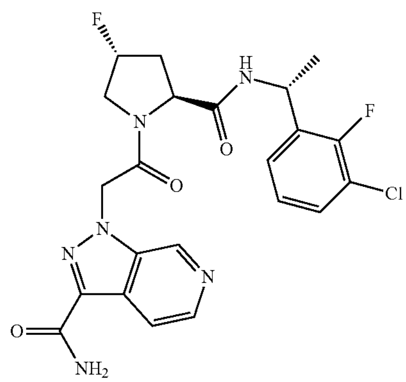 [SMILES: C[C@@H](NC(=O)[C@@H]1C[C@@H](F)CN1C(=O)Cn1nc(C(N)=O)c2ccncc21)c1cccc(Cl)c1F] | 1-(2-{(2S,4R)-2-[(R)-1-(3-Chloro-2-fluoro-phenyl)-ethylcarbamoyl]-4-fluoro-pyrrolidin-1-yl}-2-oxo-ethyl)-1H-pyrazolo[3,4-c]pyridine-3-carboxylic acid amide | (4) 489/491 [M + H]+, 513 [M + Na]+; $t_R$ (c): 3.43 min. |
| 691 | 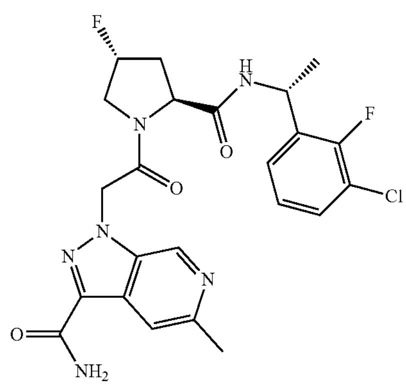 [SMILES: Cc1cc2c(C(N)=O)nn(CC(=O)N3C[C@H](F)C[C@H]3C(=O)N[C@H](C)c3cccc(Cl)c3F)c2cn1] | 1-(2-{(2S,4R)-2-[(R)-1-(3-Chloro-2-fluoro-phenyl)-ethylcarbamoyl]-4-fluoro-pyrrolidin-1-yl}-2-oxo-ethyl)-5-methyl-1H-pyrazolo[3,4-c]pyridine-3-carboxylic acid amide | (4) 505 [M + H]+; $t_R$ (k): 2.74 min. |
| 692 | 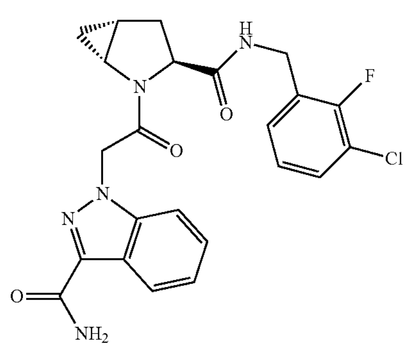 | 1-{2-[(1R,3S,5R)-3-(3-Chloro-2-fluoro-benzylcarbamoyl)-2-aza-bicyclo[3.1.0]hex-2-yl]-2-oxo-ethyl}-1H-indazole-3-carboxylic acid amide | (4) 470 [M + H]+, 492 [M + Na]+; $t_R$ (c): 4.17 min. |

TABLE 8-continued

| Example | Structure | Name | Characterization (end-table notes), TLC, R_f (eluent); MS (LC/MS); $t_R$ (HPLC conditions) |
|---|---|---|---|
| 693 | 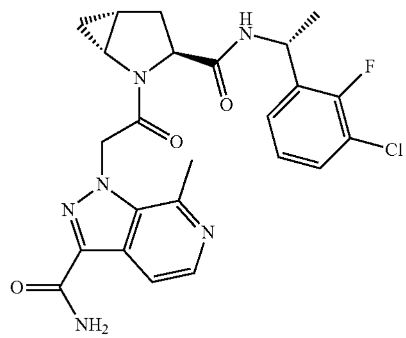 [SMILES: Cc1nccc2c(C(N)=O)nn(CC(=O)N3[C@@H]4C[C@@H]4C[C@H]3C(=O)N[C@H](C)c3cccc(Cl)c3F)c12] | 1-(2-{(1R,3S,5R)-3-[(R)-1-(3-Chloro-2-fluoro-phenyl)-ethylcarbamoyl]-2-aza-bicyclo[3.1.0]hex-2-yl}-2-oxo-ethyl)-7-methyl-1H-pyrazolo[3,4-c]pyridine-3-carboxylic acid amide | (4) 499 [M + H]+; $t_R$ (c): 3.51 min. |
| 694 | 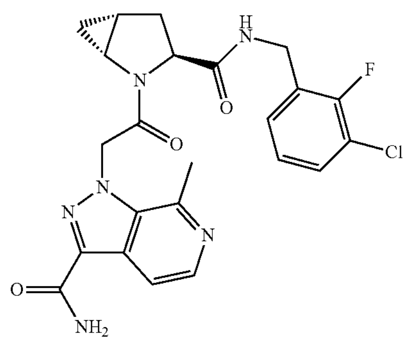 [SMILES: Cc1nccc2c(C(N)=O)nn(CC(=O)N3[C@@H]4C[C@@H]4C[C@H]3C(=O)NCc3cccc(Cl)c3F)c12] | 1-{2-[(1R,3S,5R)-3-(3-Chloro-2-fluoro-benzylcarbamoyl)-2-aza-bicyclo[3.1.0]hex-2-yl]-2-oxo-ethyl}-7-methyl-1H-pyrazolo[3,4-c]pyridine-3-carboxylic acid amide | (4) 485 [M + H]+; $t_R$ (c): 3.39 min. |
| 695 | 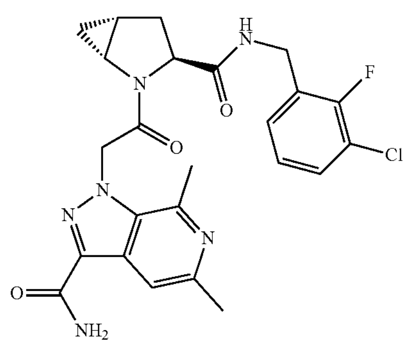 [SMILES: Cc1cc2c(C(N)=O)nn(CC(=O)N3[C@@H]4C[C@@H]4C[C@H]3C(=O)NCc3cccc(Cl)c3F)c2c(C)n1] | 1-{2-[(1R,3S,5R)-3-(3-Chloro-2-fluoro-benzylcarbamoyl)-2-aza-bicyclo[3.1.0]hex-2-yl]-2-oxo-ethyl}-5,7-dimethyl-1H-pyrazolo[3,4-c]pyridine-3-carboxylic acid amide | (4) 499 [M + H]+; $t_R$ (c): 3.46 min. |
| 696 | 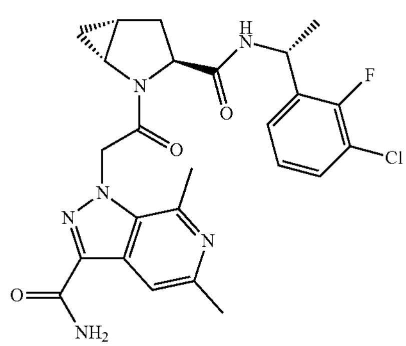 [SMILES: Cc1cc2c(C(N)=O)nn(CC(=O)N3[C@@H]4C[C@@H]4C[C@H]3C(=O)N[C@H](C)c3cccc(Cl)c3F)c2c(C)n1] | 1-(2-{(1R,3S,5R)-3-[(R)-1-(3-Chloro-2-fluoro-phenyl)-ethylcarbamoyl]-2-aza-bicyclo[3.1.0]hex-2-yl}-2-oxo-ethyl)-5,7-dimethyl-1H-pyrazolo[3,4-c]pyridine-3-carboxylic acid amide | (4) 513 [M + H]+, 511 [M + H]+; $t_R$ (c): 3.58 min. |

TABLE 8-continued

| Example | Structure | Name | Characterization (end-table notes), TLC, R$_f$(eluent); MS (LC/MS); t$_R$ (HPLC conditions) |
|---|---|---|---|
| 697 | 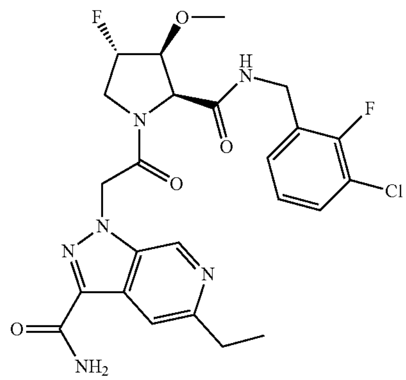 [SMILES: CCc1cc2c(C(N)=O)nn(CC(=O)N3C[C@H](F)[C@@H](OC)[C@H]3C(=O)NCc3cccc(Cl)c3F)c2cn1] | 1-{2-[(2S,3S,4S)-2-(3-Chloro-2-fluoro-benzylcarbamoyl)-4-fluoro-3-methoxy-pyrrolidin-1-yl]-2-oxo-ethyl}-5-ethyl-1H-pyrazolo[3,4-c]pyridine-3-carboxylic acid amide | (3,4) 535 [M + H]+; t$_R$ (c): 2.82 min. |
| 698 | 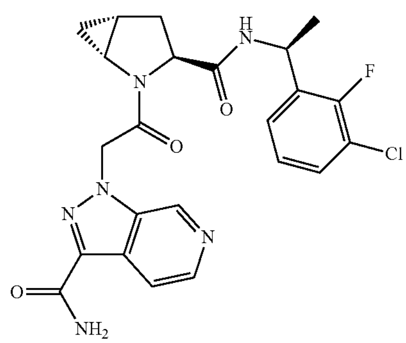 [SMILES: C[C@H](NC(=O)[C@@H]1C[C@H]2C[C@H]2N1C(=O)Cn1nc(C(N)=O)c2ccncc21)c1cccc(Cl)c1F] | 1-(2-{(1R,3S,5R)-3-[(S)-1-(3-Chloro-2-fluoro-phenyl)-ethylcarbamoyl]-2-aza-bicyclo[3.1.0]hex-2-yl}-2-oxo-ethyl)-1H-pyrazolo[3,4-c]pyridine-3-carboxylic acid amide | (4) 485 [M + H]+; t$_R$ (c): 3.59 min. |
| 699 | 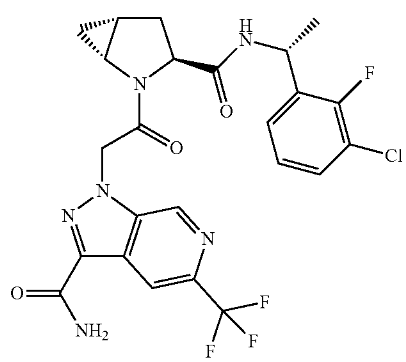 [SMILES: C[C@@H](NC(=O)[C@@H]1C[C@H]2C[C@H]2N1C(=O)Cn1nc(C(N)=O)c2cc(C(F)(F)F)ncc21)c1cccc(Cl)c1F] | 1-(2-{(1R,3S,5R)-3-[(R)-1-(3-Chloro-2-fluoro-phenyl)-ethylcarbamoyl]-2-aza-bicyclo[3.1.0]hex-2-yl}-2-oxo-ethyl)-5-trifluoromethyl-1H-pyrazolo[3,4-c]pyridine-3-carboxylic acid amide | (4) 553 [M + H]+; t$_R$ (c): 4.48 min. |
| 700 | 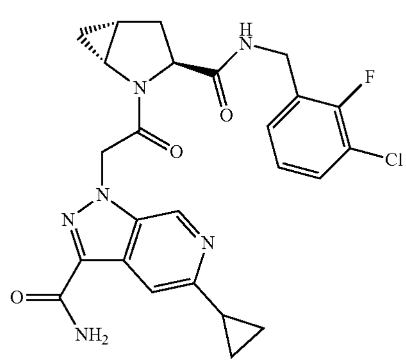 [SMILES: NC(=O)c1nn(CC(=O)N2[C@@H]3C[C@@H]3C[C@H]2C(=O)NCc2cccc(Cl)c2F)c2cnc(C3CC3)cc12] | 1-{2-[(1R,3S,5R)-3-(3-Chloro-2-fluoro-benzylcarbamoyl)-2-aza-bicyclo[3.1.0]hex-2-yl]-2-oxo-ethyl}-5-cyclopropyl-1H-pyrazolo[3,4-c]pyridine-3-carboxylic acid amide | (4) 511 [M + H]+; t$_R$ (c): 3.62 min. |

TABLE 8-continued

| Example | Structure | Name | Characterization (end-table notes), TLC, R$_f$(eluent); MS (LC/MS); t$_R$ (HPLC conditions) |
|---|---|---|---|
| 701 | 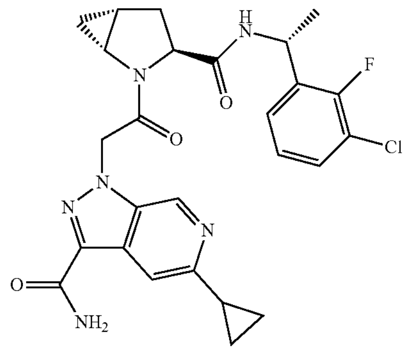 [SMILES: C[C@@H](NC(=O)[C@@H]1C[C@H]2C[C@H]2N1C(=O)Cn1nc(C(N)=O)c2cc(C3CC3)ncc21)c1cccc(Cl)c1F] | 1-(2-{(1R,3S,5R)-3-[(R)-1-(3-Chloro-2-fluoro-phenyl)-ethylcarbamoyl]-2-aza-bicyclo[3.1.0]hex-2-yl}-2-oxo-ethyl)-5-cyclopropyl-1H-pyrazolo[3,4-c]pyridine-3-carboxylic acid amide | (4) 525 [M + H]+; t$_R$ (c): 3.75 min. |

(1) The amine reagent used in step A was prepared as described in Part C; (2) HCl (4M in dioxane) was used instead of TFA in step B; (3) The title compound was prepared according to the general procedure described in Scheme D9 steps B and C starting from the substituted proline derivative prepared as described in Part B; (4) The acid reagent used in step C was prepared as described in Part A; (5) CH$_2$Cl$_2$ was used instead of DMF in step C; (6) T$_3$P was used instead of HBTU in step C and the reaction was performed in CH$_2$Cl$_2$; (7) In step A, DMF was used instead of CH$_2$Cl$_2$ and the reaction was performed at 50-70° C.

Example 702

1-(2-{(1R,3S,5R)-3-[(R)-1-(3-Chloro-2-fluoro-phenyl)-ethylcarbamoyl]-2-aza-bicyclo[3.1.0]hex-2-yl}-2-oxo-ethyl)-1H-pyrazolo[3,4-c]pyridine-3-carboxylic acid amide

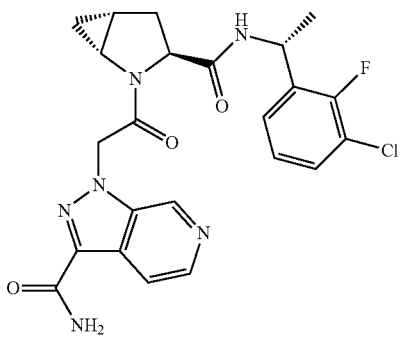 [SMILES: C[C@@H](NC(=O)[C@@H]1C[C@H]2C[C@H]2N1C(=O)Cn1nc(C(N)=O)c2ccncc21)c1cccc(Cl)c1F]

To a solution of (3-carbamoyl-pyrazolo[3,4-c]pyridin-1-yl)-acetic acid trifluoroacetate salt (2.65 g, 7.94 mmol, prepared as described in Scheme A26) in DMF (30 mL) were added successively (1R,3S,5R)-2-aza-bicyclo[3.1.0]hexane-3-carboxylic acid, [(R)-1-(3-chloro-2-fluoro-phenyl)-ethyl]-amide trifluoroacetate salt (3.00 g, 7.56 mmol), HBTU (3.44 g, 9.07 mmol) and DIPEA (5.28 mL, 30.2 mmol). The reaction mixture was stirred at RT for 16 h and then was concentrated under vacuum. The residual oil was partitioned between CH$_2$Cl$_2$ and a sat. aq. NaHCO$_3$ solution. A solid precipitated from the resulting emulsion and was filtered off, washed with water and dried under vacuum. The solid was suspended in a mixture of water (150 mL) and MeOH (3 mL), stirred for 1 h at RT, filtered, washed with water and finally dried under vacuum to give the title material as a white powder. MS (LC/MS): 485 [M+H]+; t$_R$ (HPLC conditions c): 3.54 min.

Example 703

1-(2-((1R,3S,5R)-3-((3-Chloro-2-fluorobenzyl)carbamoyl)-2-azabicyclo[3.1.0]hexan-2-yl)-2-oxoethyl)-1H-pyrazolo[3,4-c]pyridine-3-carboxamide

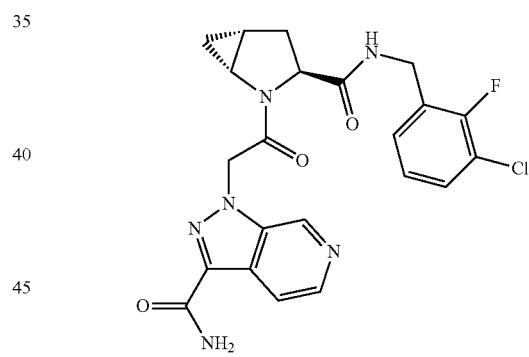

To a solution of (3-carbamoyl-pyrazolo[3,4-c]pyridin-1-yl)-acetic acid trifluoroacetate salt (2.12 g, 6.35 mmol, prepared as described in Scheme A26) in DMF (32 mL) were successively added (1R,3S,5R)—N-(3-chloro-2-fluorobenzyl)-2-azabicyclo[3.1.0]hexane-3-carboxamide trifluoroacetate salt (2.70 g, 6.35 mmol), HBTU (3.37 g, 8.89 mmol) and DIPEA (4.44 mL, 25.4 mmol). The reaction mixture was stirred at RT for 16 h, and then was concentrated under vacuum. The residual oil was partitioned between CH$_2$Cl$_2$ and a sat. aq. NaHCO$_3$ solution. A solid precipitated from the resulting emulsion and was filtered off, washed with water and dried under vacuum. The solid was suspended in a mixture of water (150 mL) and MeOH (3 mL), stirred for 1 h at RT, filtered, washed with water and finally dried under vacuum to give the title material as a white powder. MS (LC/MS): 471 [M+H]+; t$_R$ (HPLC conditions c): 3.41 min.

Example 704

3-Acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-pyrrolo[2,3-b]pyridine-6-carboxylic acid

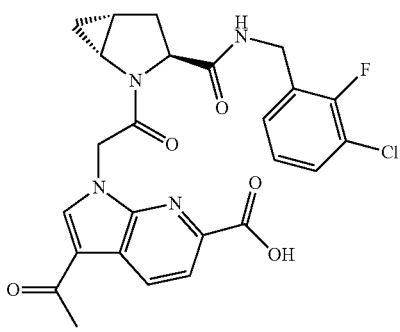 [SMILES: CC(=O)c1cn(CC(=O)N2[C@@H]3C[C@@H]3C[C@H]2C(=O)NCc2cccc(Cl)c2F)c2nc(C(=O)O)ccc12]

To a solution of 3-acetyl-1-{2-[(1R,3S,5R)-3-(3-chloro-2-fluoro-benzylcarbamoyl)-2-aza-bicyclo[3.1.0]hex-2-yl]-2-oxo-ethyl}-1H-pyrrolo[2,3-b]pyridine-6-carboxylic acid methyl ester (Example 689, 70 mg, 0.133 mmol) in THF (3 mL) and water (0.3 mL) was added a 2N aqueous LiOH solution (0.664 mL, 1.33 mmol). The reaction mixture was stirred at 25° C. for 16 h, then a 1N HCl aqueous solution was added to acidify the reaction mixture to pH=2 to 3. The resulting aqueous suspension was filtered, the solid was washed with water and then dried in vacuo. The crude solid was purified by preparative HPLC (Waters Sunfire C18-OBD, 5 µm, 30×100 mm, flow: 40 mL/min, eluent: 20% to 100% $CH_3CN$ in $H_2O$ in 20 min, 100% $CH_3CN$ 2 min, $CH_3CN$ and $H_2O$ containing 0.1% TFA). The pure fractions were combined, $CH_3CN$ was evaporated under reduced pressure and the resulting aqueous solution was lyophilized to give the title compound as a white solid. MS: 513 [M+H]+, 535 [M+Na]+; $t_R$ (HPLC conditions k): 3.14 min.

Example 705

3-Carbamoyl-1-(2-((1R,3S,5R)-3-(3-chloro-2-fluorobenzylcarbamoyl)-2-azabicyclo[3.1.0]hexan-2-yl)-2-oxoethyl)-1H-pyrazolo[3,4-c]pyridine 6-oxide

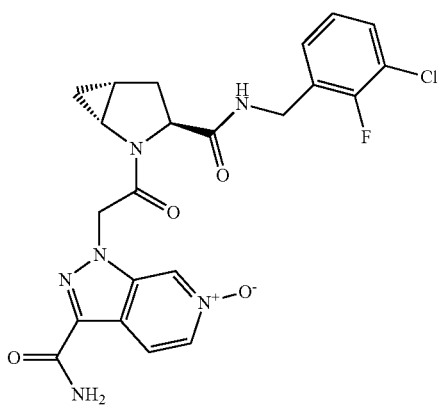 [SMILES: NC(=O)c1nn(CC(=O)N2[C@@H]3C[C@@H]3C[C@H]2C(=O)NCc2cccc(Cl)c2F)c2c[n+]([O-])ccc12]

To a solution of 1-(2-((1R,3S,5R)-3-(3-chloro-2-fluorobenzylcarbamoyl)-2-azabicyclo[3.1.0]hexan-2-yl)-2-oxoethyl)-1H-pyrazolo[3,4-c]pyridine-3-carboxamide (Example 703, 100 mg, 0.21 mmol) in acetic acid (4 mL) was added 3-chlorobenzoperoxoic acid (58 mg, 0.34 mmol) at 55° C. The reaction mixture was stirred at 55° C. for 18 h and then cooled to RT. Volatiles were evaporated and the residue was purified by preparative HPLC (Waters Sunfire, C18-ODB, 5 µm, 30×100 mm, flow: 40 mL/min, eluent: 5-100% $CH_3CN$/$H_2O$/20 min, 100% $CH_3CN$/2 min, $CH_3CN$ and $H_2O$ containing 0.1% TFA) to afford the title compound as a white solid. MS: 487 [M+H]+; $t_R$ (HPLC conditions c): 3.44 min.

Example 706

3-Carbamoyl-1-(2-((1R,3S,5R)-3-((R)-1-(3-chloro-2-fluorophenyl)ethyl-carbamoyl)-2-azabicyclo[3.1.0]hexan-2-yl)-2-oxoethyl)-1H-pyrazolo[3,4-c]pyridine 6-oxide

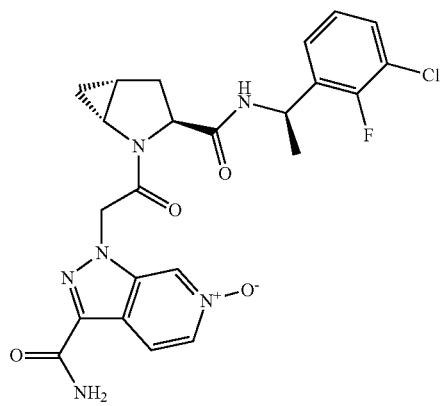 [SMILES: C[C@@H](NC(=O)[C@@H]1C[C@H]2C[C@H]2N1C(=O)Cn1nc(C(N)=O)c2cc[n+]([O-])cc21)c1cccc(Cl)c1F]

To a solution of 1-(2-((1R,3S,5R)-3-((R)-1-(3-chloro-2-fluorophenyl)ethylcarbamoyl)-2-azabicyclo[3.1.0]hexan-2-yl)-2-oxoethyl)-1H-pyrazolo[3,4-c]pyridine-3-carboxamide (Example 702, 150 mg, 0.31 mmol) in acetic acid (4 mL) was added 3-chlorobenzoperoxoic acid (85 mg, 0.50 mmol) at 55° C. The reaction mixture was stirred at 55° C. for 18 h and then cooled to RT. Volatiles were evaporated and the residue was purified by preparative HPLC (Waters Sunfire, C18-ODB, 5 µm, 30×100 mm, flow: 40 mL/min, eluent: 5-100% $CH_3CN$/$H_2O$/20 min, 100% $CH_3CN$/2 min, $CH_3CN$ and $H_2O$ containing 0.1% TFA) to afford the title compound as a white solid. MS: 501 [M+H]+; $t_R$ (HPLC conditions c): 3.64 min.

Scheme D10: general protocol described for the preparation of Example 707: 1-{2-[(1R,3S,5R)-3-(2-Fluoro-3-trifluoromethoxy-phenylcarbamoyl)-2-aza-bicyclo[3.1.0] hex-2-yl]-2-oxo-ethyl}-1H-indazole-3-carboxylic acid amide

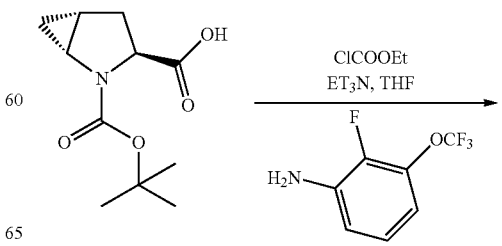

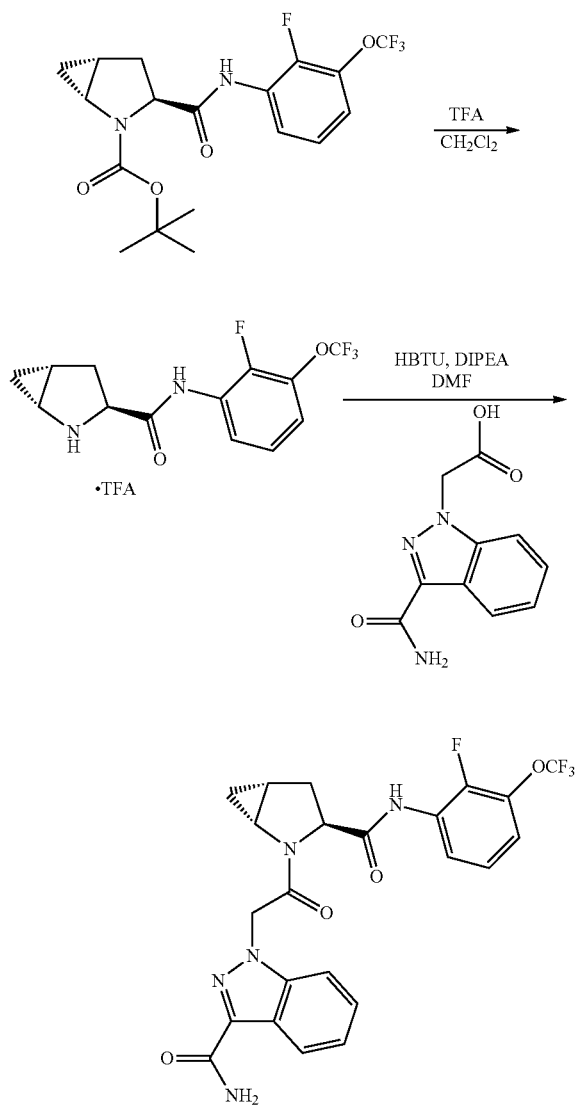

A. (1R,3S,5R)-3-(2-Fluoro-3-trifluoromethoxy-phenylcarbamoyl)-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (1.83 g, 8.07 mmol) in dry THF (45 mL) at −20° C. under nitrogen atmosphere was added triethylamine (3.32 mL, 23.8 mmol) followed by ethylchloroformate (0.775 mL, 8.07 mmol) dropwise. The reaction mixture was stirred at −20° C. for 90 min and a solution of 2-fluoro-3-(trifluoromethoxy)aniline (prepared as described in Part C, 1.5 g, 7.69 mmol) in dry THF (5 mL) was added. The reaction mixture was further stirred at −20° C. for 1 h, warmed up to RT and stirred at 65° C. for 16 h until completion of the reaction. The reaction mixture was diluted with EtOAC, washed with a saturated aqueous solution of NaHCO₃ (×3) and brine, dried (phase separator) and concentrated under reduced pressure. The crude residue was purified via flash column chromatography on silica gel (EtOAc/c-hexane 1:1) to give the desired material as a colorless oil. MS: 427 [M+Na]+, 304.9 [MH−Boc]+; $t_R$ (HPLC conditions c): 5.23 min.

B. (1R,3S,5R)-2-Aza-bicyclo[3.1.0]hexane-3-carboxylic acid (2-fluoro-3-trifluoro methoxy-phenyl)-amide trifluoroacetate To a solution of ((1R,3S,5R)-3-(2-fluoro-3-trifluoromethoxy-phenylcarbamoyl)-2-aza-bicyclo[3.1.0]hexane-2-carboxylic acid tert-butyl ester (2.56 g, 6.33 mmol) in CH₂Cl₂ (20 mL) was added TFA (10 mL, 130 mmol) and the solution was stirred at RT for 16 h. CH₂Cl₂ was concentrated, the residue was suspended in MeOH, concentrated again and dried under high vacuum to give the desired material which was used without further purification in the next step. MS: 305 [M+H]+; $t_R$ (HPLC conditions c): 3.55 min.

C. Example 707

1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-1H-indazole-3-carboxylic acid amide To a solution of (3-carbamoyl-indazol-1-yl)-acetic acid (73.4 mg, 0.335 mmol, prepared as described in Scheme A25) in DMF (2 mL) were successively added (1R,3S,5R)-2-aza-bicyclo[3.1.0]hexane-3-carboxylic acid (2-fluoro-3-trifluoromethoxy-phenyl)-amide trifluoroacetate (140 mg, 0.335 mmol), DIPEA (0.234 mL, 1.34 mmol) and HBTU (152 mg, 0.402 mmol). The reaction mixture was stirred at 25° C. for 2 h, concentrated and the residue was purified by preparative HPLC (Waters Sunfire C18-OBD, 5 μm, 30×100 mm, flow: 40 mL/min, eluent: 5% to 100% CH₃CN in H₂O in 20 min, 100% CH₃CN 2 min, CH₃CN and H₂O containing 0.1% TFA). The pure fractions were combined, CH₃CN was evaporated under reduced pressure and the resulting aqueous solution was lyophilized. White powder: MS: 506 [M+H]+; $t_R$ (HPLC conditions k): 3.40 min.

Alternatively, for final compounds containing a basic residue: the pure HPLC fractions were combined, CH₃CN was evaporated under reduced pressure, the resulting aqueous solution was adjusted to pH 8-9 by addition of an aqueous saturated solution of NaHCO₃, extracted with CH₂Cl₂ (×3), the combined organic extracts were dried (phase separator) and concentrated under vacuum.

The examples below were prepared according to the general procedures described in Scheme D10 for Example 707 using commercially available building blocks if not otherwise stated (see note at the end of table 9):

TABLE 9

| Example | Structure | Name | Characterization (end-table notes), TLC, R$_f$ (eluent); MS (LC/MS); t$_R$ (HPLC conditions) |
|---|---|---|---|
| 708 | 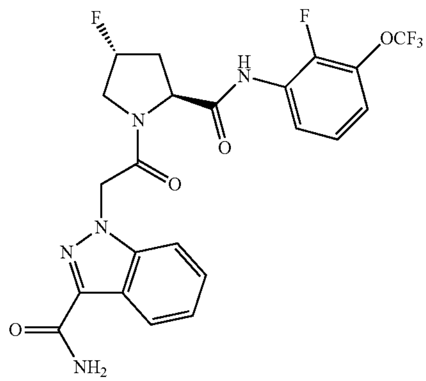 [SMILES: NC(=O)c1nn(CC(=O)N2C[C@H](F)C[C@H]2C(=O)Nc2cccc(OC(F)(F)F)c2F)c2ccccc12] | 1-(2-((2S,4R)-4-fluoro-2-(2-fluoro-3-(trifluoromethoxy)phenylcarbamoyl) pyrrolidin-1-yl)-2-oxoethyl)-1H-indazole-2-carboxamide | (1) 512 [M + H]+; t$_R$ (k): 3.31 min. |
| 709 | 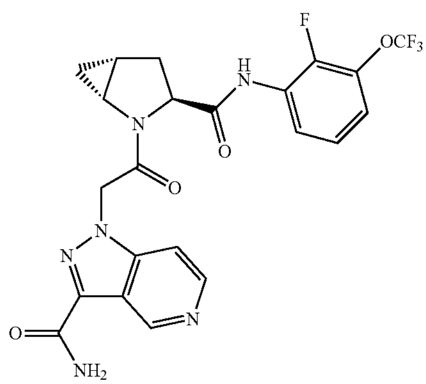 [SMILES: NC(=O)c1nn(CC(=O)N2[C@@H]3C[C@@H]3C[C@H]2C(=O)Nc2cccc(OC(F)(F)F)c2F)c2ccncc12] | 1-(2-((1R,3S,5R)-3-(2-fluoro-3-(trifluoromethoxy)phenylcarbamoyl)-2-azabicyclo[3.1.0]hexan-2-yl)-2-oxoethyl)-1H-pyrazolo[4,3-c]pyridine-3-carboxamide | (1) 507 [M + H]+; t$_R$ (k): 2.90 min. |
| 710 | 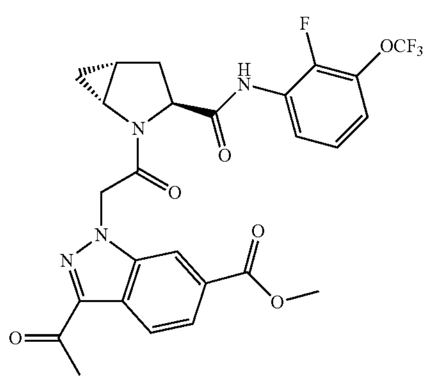 [SMILES: COC(=O)c1ccc2c(C(C)=O)nn(CC(=O)N3[C@@H]4C[C@@H]4C[C@H]3C(=O)Nc3cccc(OC(F)(F)F)c3F)c2c1] | Methyl 3-acetyl-1-(2-((1R,3S,5R)-3-(2-fluoro-3-(trifluoromethoxy) phenylcarbamoyl)-2-azabicyclo [3.1.0]hexan-2-yl)-2-oxoethyl)-1H-indazole-6-carboxylate | (1) 563 [M + H]+, 585 [M + Na]+; t$_R$ (k): 3.89 min. |
| 711 | 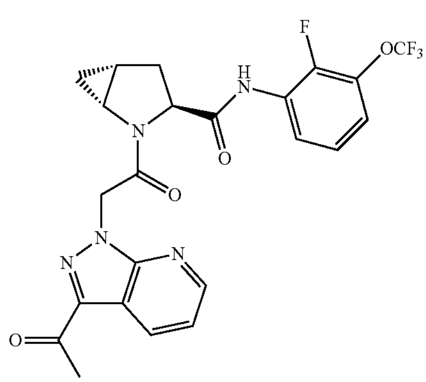 | (1R,3S,5R)-2-[2-(3-Acetyl-pyrazolo[3,4-b]pyridin-1-yl)-acetyl]-2-aza-bicyclo[3.1.0]hexane-3-carboxylic acid (2-fluoro-3-trifluoromethoxy-phenyl)-amide | (1) 506 [M + H]+; t$_R$ (k): 3.67 min. |

| Example | Structure | Name | Characterization (end-table notes), TLC, $R_f$ (eluent); MS (LC/MS); $t_R$ (HPLC conditions) |
|---|---|---|---|
| 712 | 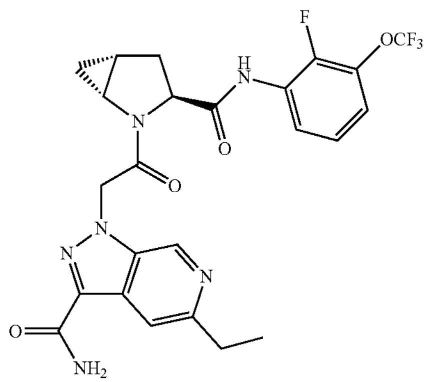 [SMILES: CCc1cc2c(C(N)=O)nn(CC(=O)N3[C@@H]4C[C@@H]4C[C@H]3C(=O)Nc3cccc(OC(F)(F)F)c3F)c2cn1] | 5-Ethyl-1-{2-[(1R,3S,5R)-3-(2-fluoro-3-trifluoromethoxy-phenylcarbamoyl)-2-aza-bicyclo[3.1.0]hex-2-yl]-2-oxo-ethyl}-1H-pyrazolo[3,4-c]pyridine-3-carboxylic acid amide | (1) 535 [M + H]+; $t_R$ (k): 2.97 min. |
| 713 | 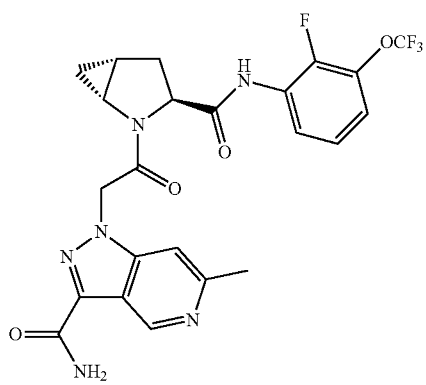 [SMILES: Cc1cc2c(cn1)c(C(N)=O)nn2CC(=O)N1[C@@H]2C[C@@H]2C[C@H]1C(=O)Nc1cccc(OC(F)(F)F)c1F] | 1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-6-methyl-1H-pyrazolo[4,3-c]pyridine-3-carboxylic acid amide | (1) 521 [M + H]+; $t_R$ (k): 2.92 min. |
| 714 | 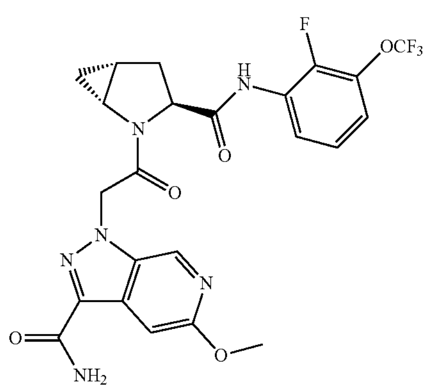 [SMILES: COc1cc2c(C(N)=O)nn(CC(=O)N3[C@@H]4C[C@@H]4C[C@H]3C(=O)Nc3cccc(OC(F)(F)F)c3F)c2cn1] | 1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-5-methoxy-1H-pyrazolo[3,4-c]pyridine-3-carboxylic acid amide | (1) 537 [M + H]+; $t_R$ (k): 3.24 min. |
| 715 | 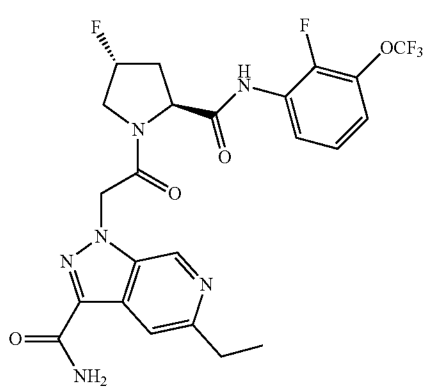 [SMILES: CCc1cc2c(C(N)=O)nn(CC(=O)N3C[C@H](F)C[C@H]3C(=O)Nc3cccc(OC(F)(F)F)c3F)c2cn1] | 5-Ethyl-1-{2-[(2S,4R)-4-fluoro-2-(2-fluoro-3-trifluoromethoxy-phenyl carbamoyl)-pyrrolidin-1-yl]-2-oxo-ethyl}-1H-pyrazolo[3,4-c]pyridine-3-carboxylic acid amide | (1) 541 [M + H]+; $t_R$ (k): 2.95 min. |

TABLE 9-continued

| Example | Structure | Name | Characterization (end-table notes), TLC, R_f (eluent); MS (LC/MS); t_R (HPLC conditions) |
|---------|-----------|------|------------------------------------------------------------------------------------------|
| 716 | 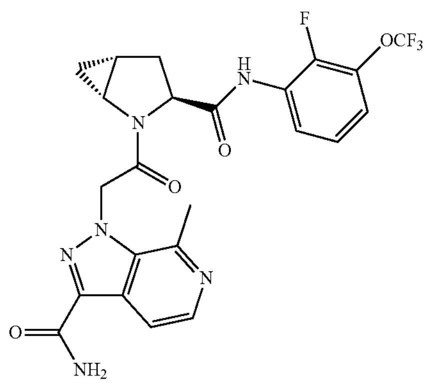 [SMILES: Cc1nccc2c(C(N)=O)nn(CC(=O)N3[C@@H]4C[C@@H]4C[C@H]3C(=O)Nc3cccc(OC(F)(F)F)c3F)c12] | 1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-7-methyl-1H-pyrazolo[3,4-c]pyridine-3-carboxylic acid amide | (1) 521 [M + H]+; t_R (k): 2.90 min. |
| 717 | 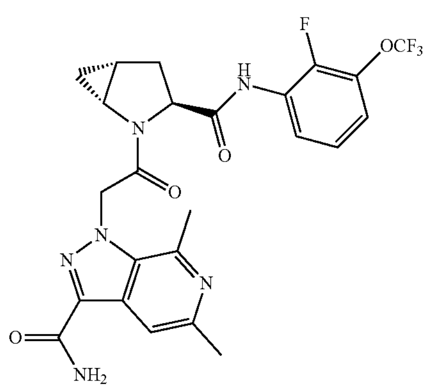 [SMILES: Cc1cc2c(C(N)=O)nn(CC(=O)N3[C@@H]4C[C@@H]4C[C@H]3C(=O)Nc3cccc(OC(F)(F)F)c3F)c2c(C)n1] | 1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-5,7-dimethyl-1H-pyrazolo[3,4-c]pyridine-3-carboxylic acid amide | (1) 535 [M + H]+; t_R (c): 3.84 min. |
| 718 | 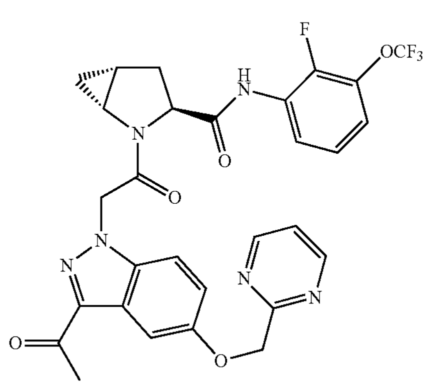 [SMILES: CC(=O)c1nn(CC(=O)N2[C@@H]3C[C@@H]3C[C@H]2C(=O)Nc2cccc(OC(F)(F)F)c2F)c2ccc(OCc3ncccn3)cc12] | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (2-fluoro-3-trifluoromethoxy-phenyl)-amide | (1) 613 [M + H]+, 635 [M + Na]+; t_R (c): 4.81 min. |

TABLE 9-continued

| Example | Structure | Name | Characterization (end-table notes), TLC, R_f (eluent); MS (LC/MS); t_R (HPLC conditions) |
|---|---|---|---|
| 719 | 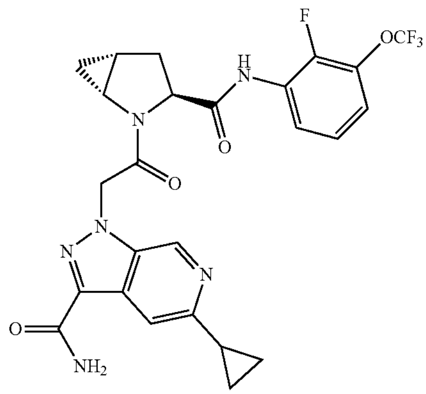 [SMILES: NC(=O)c1nn(CC(=O)N2[C@@H]3C[C@@H]3C[C@H]2C(=O)Nc2cccc(OC(F)(F)F)c2F)c2cnc(C3CC3)cc12] | 5-Cyclopropyl-1-(2-((1R,3S,5R)-3-((2-fluoro-3-(trifluoromethoxy)phenyl)carbamoyl)-2-azabicyclo[3.1.0]hexan-2-yl)-2-oxoethyl)-1H-pyrazolo[3,4-c]pyridine-3-carboxamide | (1) 547 [M + H]+; t_R (c): 3.97 min. |
| 720 | 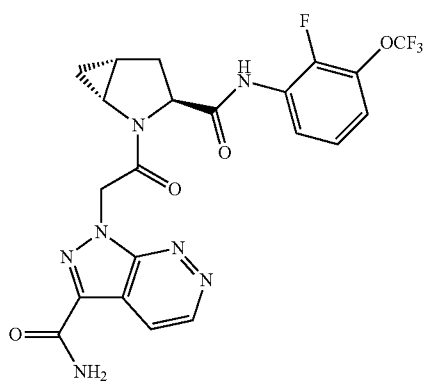 [SMILES: NC(=O)c1nn(CC(=O)N2[C@@H]3C[C@@H]3C[C@H]2C(=O)Nc2cccc(OC(F)(F)F)c2F)c2nnccc12] | 1-(2-((1R,3S,5R)-3-((2-Fluoro-3-(trifluoromethoxy)phenyl)carbamoyl)-2-azabicyclo[3.1.0]hexan-2-yl)-2-oxoethyl)-1H-pyrazolo[3,4-c]pyridazine-3-carboxamide | (1) 508.0 [M + H]+, 529.9 [M + Na]+; t_R (c): 4.08 min. |
| 721 | 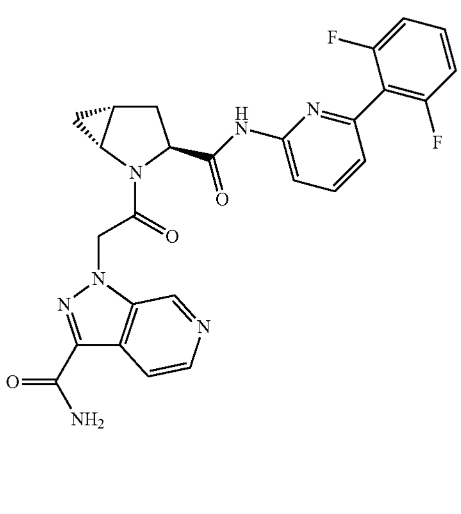 [SMILES: NC(=O)c1nn(CC(=O)N2[C@@H]3C[C@@H]3C[C@H]2C(=O)Nc2cccc(-c3c(F)cccc3F)n2)c2cnccc12] | 1-(2-{(1R,3S,5R)-3-[6-(2,6-Difluoro-phenyl)-pyridin-2-ylcarbamoyl]-2-aza-bicyclo[3.1.0]hex-2-yl}-2-oxo-ethyl)-1H-pyrazolo[3,4-c]pyridine-3-carboxamide | (1,2) 518 [M + H]+; t_R (k): 2.90 min. |

TABLE 9-continued

| Example | Structure | Name | Characterization (end-table notes), TLC, $R_f$ (eluent); MS (LC/MS); $t_R$ (HPLC conditions) |
|---|---|---|---|
| 722 | 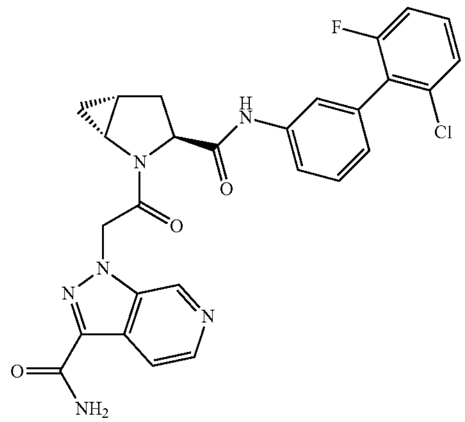 [SMILES: NC(=O)c1nn(CC(=O)N2[C@@H]3C[C@@H]3C[C@H]2C(=O)Nc2cccc(-c3c(F)cccc3Cl)c2)c2cnccc12] | 1-(2-((1R,3S,5R)-3-(2'-Chloro-6'-fluorobiphenyl-3-ylcarbamoyl)-2-azabicyclo[3.1.0]hexan-2-yl)-2-oxoethyl)-1H-pyrazolo[3,4-c]pyridine-3-carboxamide | (1,2) 533 [M + H]+; $t_R$ (c): 4.12 min. |

(1) The acid derivative used in step C was prepared as described in Part A; (2) The amine derivative used in step A was prepared as described in Part C.

Example 723

1-{2-[(1R,3S,5R)-3-(2-Fluoro-3-trifluoromethoxy-phenylcarbamoyl)-2-aza-bicyclo[3.1.0]hex-2-yl]-2-oxo-ethyl}-5-methyl-1H-pyrazolo[3,4-c]pyridine-3-carboxylic acid amide

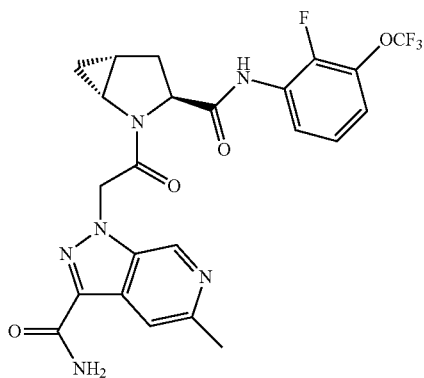 [SMILES: Cc1cc2c(C(N)=O)nn(CC(=O)N3[C@@H]4C[C@@H]4C[C@H]3C(=O)Nc3cccc(OC(F)(F)F)c3F)c2cn1]

To a solution of (3-carbamoyl-5-methyl-pyrazolo[3,4-c]pyridin-1-yl)acetic acid trifluoroacetate salt (3.87 g, 11.1 mmol; prepared as described in Scheme A27) in DMF (45 mL) were successively added (1R,3S,5R)-2-aza-bicyclo[3.1.0]hexane-3-carboxylic acid (2-fluoro-3-trifluoro methoxy-phenyl)-amide trifluoroacetate salt (5.00 g, 11.1 mmol), DIPEA (7.77 mL, 44.5 mmol) and HBTU (5.06 g, 13.3 mmol). The reaction mixture was stirred at 25° C. for 2 h and was then concentrated in vacuo. The residue was purified by preparative HPLC (Waters Sunfire C18-OBD, 5 µm, 30×100 mm, flow: 50 mL/min, eluent: 5% to 100% CH₃CN in H₂O in 20 min, 100% CH₃CN 2 min, CH₃CN and H₂O containing 0.1% TFA). The pure fractions were combined and volatiles were evaporated under reduced pressure. The resulting aqueous solution was adjusted to pH 8 to 9 by addition of an aqueous saturated solution of NaHCO₃, and then was extracted with CH₂Cl₂ (×3). The combined organic extracts were dried (phase separator) and concentrated under vacuum to afford the title compound as a white solid. MS: 521 [M+H]+; $t_R$ (HPLC conditions c): 3.81 min.

Example 724

1-(2-((1R,3S,5R)-3-(2-Fluoro-3-(trifluoromethoxy)phenyl)carbamoyl)-2-azabicyclo[3.1.0]hexan-2-yl)-2-oxoethyl)-1H-pyrazolo[3,4-c]pyridine-3-carboxamide

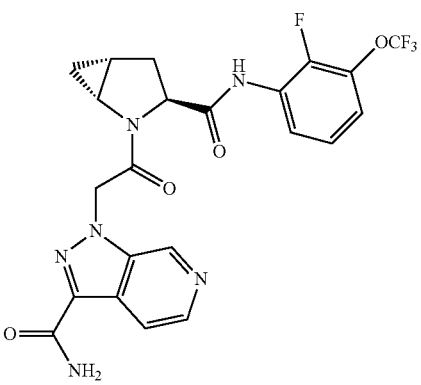

To a solution of (3-carbamoyl-pyrazolo[3,4-c]pyridin-1-yl)-acetic acid trifluoroacetate salt (1.60 g, 4.78 mmol; prepared as described in Scheme A26) in DMF (40 mL) were successively added (1R,3S,5R)-2-aza-bicyclo[3.1.0]hexane-3-carboxylic acid (2-fluoro-3-trifluoro methoxy-phenyl)-amide trifluoroacetate salt (2.50 g, 4.78 mmol), DIPEA (3.34 mL, 19.1 mmol) and HBTU (2.17 g, 5.74 mmol). The reaction mixture was stirred at 25° C. for 2 h and then was concentrated. The residue was purified by preparative HPLC (Waters Sunfire C18-OBD, 5 µm, 30×100 mm, flow: 50 mL/min, eluent: 5% to 100% CH₃CN in H₂O in 20 min, 100% CH₃CN 2 min, CH₃CN and H₂O containing 0.1% TFA). The pure fractions were combined and volatiles were removed under reduced pressure. The resulting aqueous solution was adjusted to pH 8 to 9 by addition of an aqueous saturated solution of NaHCO₃ and was then extracted with CH₂Cl₂ (×3). The combined organic extracts were dried (phase separator) and concentrated under vacuum. The residual solid was suspended in Et₂O and stirred at RT for 16 h. The solid was filtered and dried under vacuum to afford the title compound as a white solid. MS: 507 [M+H]+; $t_R$ (HPLC conditions c): 3.77 min.

Example 725

3-Acetyl-1-{2-[(1R,3S,5R)-3-(2-fluoro-3-trifluoromethoxy)phenyl-carbamoyl)-2-aza-bicyclo[3.1.0]hex-2-yl]-2-oxo-ethyl}-1H-indazole-6-carboxylic acid

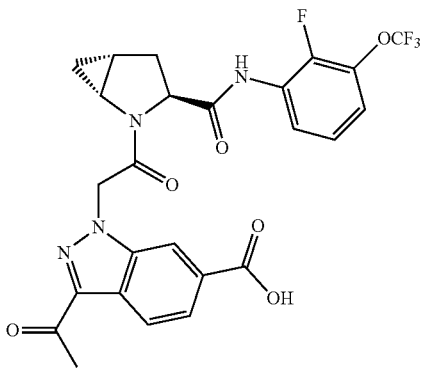 [SMILES: CC(=O)c1nn(CC(=O)N2[C@@H]3C[C@@H]3C[C@H]2C(=O)Nc2cccc(OC(F)(F)F)c2F)c2cc(C(=O)O)ccc12]

To a solution of methyl 3-acetyl-1-(2-((1R,3S,5R)-3-(2-fluoro-3-trifluoromethoxy)phenyl-carbamoyl)-2-azabicyclo[3.1.0]hexan-2-yl)-2-oxo-ethyl)-1H-indazole-6-carboxylate (Example 710, 25 mg, 0.044 mmol) in THF (2 mL) and water (0.2 mL) was added a 2N aqueous LiOH solution (0.089 mL, 0.178 mmol). The reaction mixture was stirred at 25° C. for 4 h, then a 1N HCl aqueous solution was added to acidify the reaction mixture to pH=2 to 3. The resulting aqueous solution was extracted with $CH_2Cl_2$ (×3), the combined organic extracts were dried (Phase separator) and then concentrated under reduced pressure. The residue was purified by preparative HPLC (Waters Sunfire C18-OBD, 5 μm, 30×100 mm, flow: 40 mL/min, eluent: 5% to 100% $CH_3CN$ in $H_2O$ in 20 min, 100% $CH_3CN$ 2 min, $CH_3CN$ and $H_2O$ containing 0.1% TFA). The pure fractions were combined, volatiles were removed under reduced pressure and the resulting aqueous solution was lyophilized to afford the title compound as a white solid. MS: 549 [M+H]+; $t_R$ (HPLC conditions c): 4.76 min.

Example 726

3-Carbamoyl-1-(2-((1R,3S,5R)-3-(2-fluoro-3-hydroxyphenyl)carbamoyl)-2-azabicyclo[3.1.0]hexan-2-yl)-2-oxoethyl)-5-methyl-1H-pyrazolo[3,4-c]pyridine 6-oxide

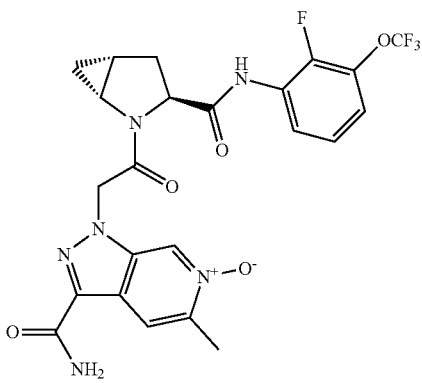 [SMILES: Cc1cc2c(C(N)=O)nn(CC(=O)N3[C@@H]4C[C@@H]4C[C@H]3C(=O)Nc3cccc(OC(F)(F)F)c3F)c2c[n+]1[O-]]

To a solution of 1-{2-[(1R,3S,5R)-3-(2-fluoro-3-trifluoromethoxy-phenylcarbamoyl)-2-aza-bicyclo[3.1.0]hex-2-yl]-2-oxo-ethyl}-5-methyl-1H-pyrazolo[3,4-c]pyridine-3-carboxylic acid amide (Example 723, 50 mg, 0.096 mmol) in acetic acid (3 mL) was added 3-chlorobenzoperoxoic acid (38 mg, 0.154 mmol) at 55° C. The reaction mixture was stirred at 55° C. for 18 h and then cooled to RT. Volatiles were evaporated, the residue was then dissolved in EtOAc and washed with a sat. aq. $NaHCO_3$ solution (×3) and brine, dried (Phase separator) and concentrated under reduced pressure to afford the title compound as a white solid. MS: 537 [M+H]+; $t_R$ (HPLC conditions k): 3.00 min.

Scheme D11: general protocol described for the preparation of Example 727: 1-{2-[(1R,3S,5R)-3-(6-Bromo-pyridin-2-ylcarbamoyl)-2-aza-bicyclo[3.1.0]hex-2-yl]-2-oxo-ethyl}-1H-indazole-3-carboxylic acid amide

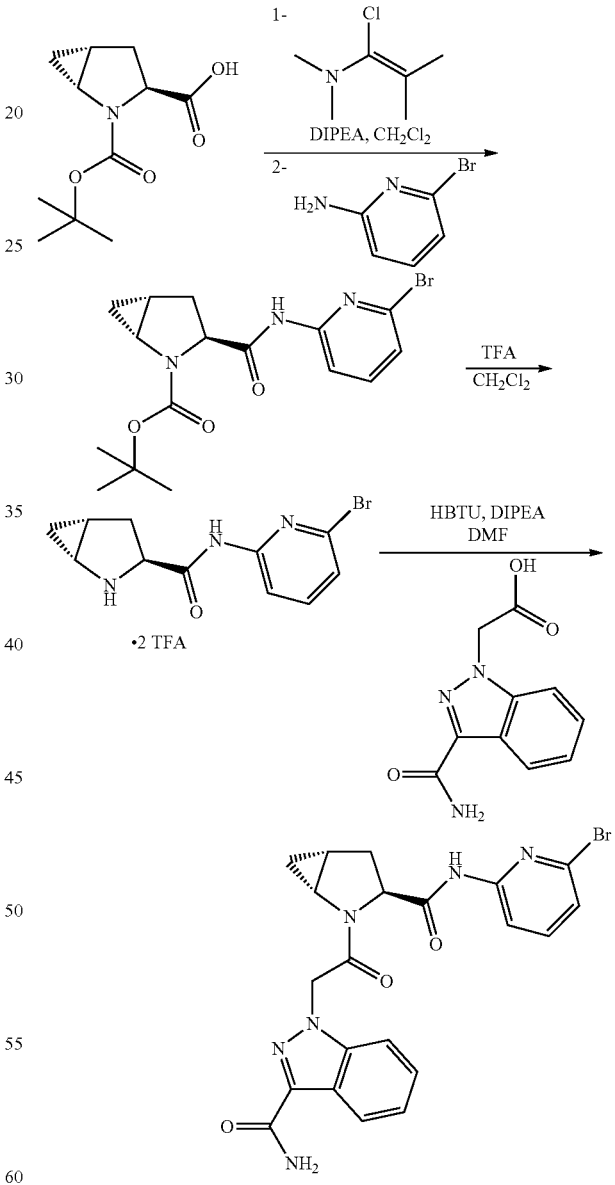

A. (1R,3S,5R)-3-(6-Bromo-pyridin-2-ylcarbamoyl)-2-aza-bicyclo[3.1.0]hexane-2-carboxylic acid tert-butyl ester To a solution of (1R,3S,5R)-2-aza-bicyclo[3.1.0]hexane-2,3-dicarboxylic acid 2-tert-butyl ester (500 mg, 2.2 mmol) in dry CH$_2$Cl$_2$ (2 mL) was added 1-chloro-N,N,2-trimethylpropenylamine (349 µL, 2.64 mmol) at 0° C. under nitrogen atmosphere. Formation of the acyl chlorid intermediate was monitored by TLC after quenching of an aliquot with MeOH. After completion (1-1.5 h), 2-amino-6-bromopyridine (457 mg, 2.64 mmol) was added at 0° C., followed by DIPEA (1.13 mL, 6.60 mmol) and the reaction mixture further stirred 2 h at RT. The reaction mixture was poured into water and extracted twice with CH$_2$Cl$_2$. The combined organic extracts were dried (Na$_2$SO$_4$), filtered and concentrated. CH$_2$Cl$_2$ was added to the crude residue and the precipitate filtered to give the desired material as a white solid. TLC, R$_f$(EtOAc)=0.85; MS: 382.1/384.1 [M+H]+, 380.2/382.3 [M−H]−, 426.7/428.3 [M+HCOO]−; t$_R$ (HPLC conditions h): 2.19 min.

B. (1R,3S,5R)-2-Aza-bicyclo[3.1.0]hexane-3-carboxylic acid (6-bromo-pyridin-2-yl)-amide di(trifluoroacetate) salt To a solution of (1R,3S,5R)-3-(6-bromo-pyridin-2-ylcarbamoyl)-2-aza-bicyclo[3.1.0]hexane-2-carboxylic acid tert-butyl ester (561 mg, 1.47 mmol) in CH$_2$Cl$_2$ (11 mL) was added TFA (1.13 mL, 14.7 mmol) and the solution was stirred at RT overnight. CH$_2$Cl$_2$ was concentrated and the crude residue was dried under high vacuum to give the desired material which was used without further purification in the next step. MS: 282.1/284.1 [M+H]+, 304.0/306.1 [M+Na]+, 563.1/565.2 [2M+H]+; t$_R$ (HPLC conditions f): 0.96 min.

C. Example 727

1-{2-[(1R,3S,5R)-3-(6-Bromo-pyridin-2-ylcarbamoyl)-2-aza-bicyclo[3.1.0]hex-2-yl]-2-oxo-ethyl}-1H-indazole-3-carboxylic acid amide (3-Carbamoyl-indazol-1-yl)-acetic acid (130 mg, 0.59 mmol, prepared as described in Scheme A25), (1R,3S,5R)-2-aza-bicyclo[3.1.0]hexane-3-carboxylic acid (6-bromo-pyridin-2-yl)-amide (2 TFA salt, 303 mg, 0.59 mmol) and HBTU (337 mg, 0.89 mmol) were dissolved in DMF (3 mL). DIPEA (406 µL, 2.37 mmol) was added and the reaction mixture was stirred at 25° C. for 1 h. The crude reaction mixture was purified by preparative HPLC (Waters Sunfire C18-OBD, 5 µm, 30×100 mm, flow: 40 mL/min, eluent: 20% to 100% CH$_3$CN in H$_2$O in 25 min, CH$_3$CN and H$_2$O containing 0.1% TFA). The pure fractions were combined, neutralized with an aqueous saturated solution of NaHCO$_3$ and extracted with CH$_2$Cl$_2$ to give the desired compound. TLC, R$_f$ (CH$_2$Cl$_2$/MeOH 9:1)=0.55; MS: 483.1/485.1 [M+H]+, 965.4/967.4 [2M+H]+, 982.4/984.3 [2M+NH$_4$]+, 481.1/483.2 [M−H]−, 527.2/529.1 [M+HCOO]−; t$_R$ (HPLC conditions a): 2.79 min. Alternatively, for final compounds containing a basic residue: the pure HPLC fractions were combined, CH$_3$CN was evaporated under reduced pressure, the resulting aqueous solution was adjusted to pH 8-9 by addition of an aqueous saturated solution of NaHCO$_3$, extracted with CH$_2$Cl$_2$ (×3), the combined organic extracts were dried (Na$_2$SO$_4$) and concentrated under vacuum.

The examples below were prepared according to the general procedures described in Scheme D11 for Example 727 using commercially available building blocks if not otherwise stated (see notes at the end of table 10):

TABLE 10

| Example | Structure | Name | Characterization (end-table notes), TLC, R$_f$(eluent); MS (LC/MS); t$_R$ (HPLC conditions) |
|---|---|---|---|
| 728 | 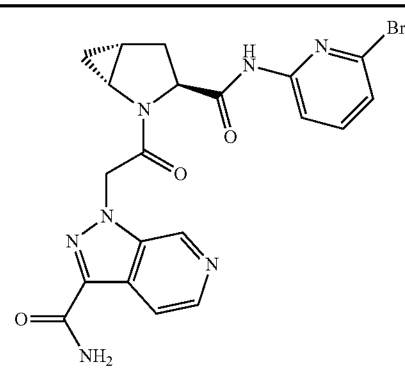 | 1-{2-[(1R,3S,5R)-3-(6-bromo-pyridin-2-ylcarbamoyl)-2-aza-bicyclo[3.1.0]hex-2-yl]-2-oxo-ethyl}-1H-pyrazolo[3,4-c]pyridine-3-carboxylic acid amide | (1) 484.1/486.1 [M + H]+, 482.0/484.1 [M − H]−, 528.2/530.1 [M + HCOO]−; t$_R$ (a): 2.22 min. |
| 729 | 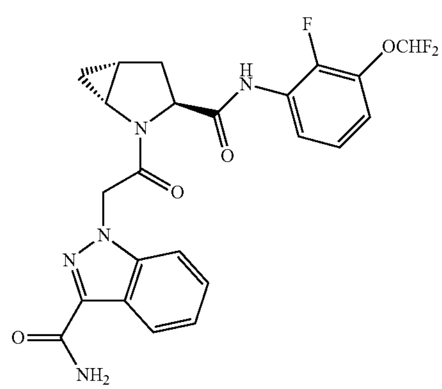 [SMILES: NC(=O)c1nn(CC(=O)N2[C@@H]3C[C@@H]3C[C@H]2C(=O)Nc2cccc(OC(F)F)c2F)c2ccccc12] | 1-{2-[(1R,3S,5R)-3-(3-Difluoromethoxy-2-fluoro-phenylcarbamoyl)-2-aza-bicyclo[3.1.0]hex-2-yl]-2-oxo-ethyl}-1H-indazole-3-carboxylic acid amide | (1,2,3) 488.2 [M + H]+, 505.2 [M + NH$_4$]+, 486.2 [M − H]−; t$_R$ (f): 1.90 min |

TABLE 10-continued

| Example | Structure | Name | Characterization (end-table notes), TLC, R$_f$(eluent); MS (LC/MS); t$_R$ (HPLC conditions) |
|---|---|---|---|
| 730 | 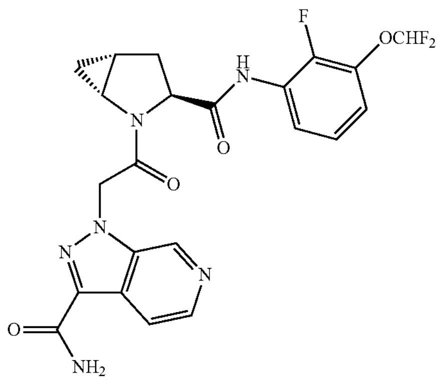 [SMILES: NC(=O)c1nn(CC(=O)N2[C@@H]3C[C@@H]3C[C@H]2C(=O)Nc2cccc(OC(F)F)c2F)c2cnccc12] | 1-{2-[(1R,3S,5R)-3-(3-Difluoromethoxy-2-fluoro-phenylcarbamoyl)-2-aza-bicyclo[3.1.0]hex-2-yl]-2-oxo-ethyl}-1H-pyrazolo[3,4-c]pyridine-3-carboxylic acid amide | (1,2,3) 489.2 [M + H]+, 487.2 [M − H]−, 533.2 [M + HCOO]−; t$_R$ (f): 1.41 min |
| 731 | 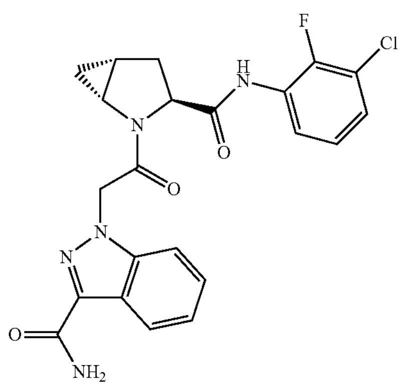 | 1-{2-[(1R,3S,5R)-3-(3-Chloro-2-fluoro-phenylcarbamoyl)-2-aza-bicyclo[3.1.0]hex-2-yl]-2-oxo-ethyl}-1H-indazole-3-carboxylic acid amide | (1) R$_f$(CH$_2$Cl$_2$/MeOH 9:1) = 0.55; 473.2/475.2 [M + NH$_4$]+, 478.2/480.2 [M + Na]+, 454.3/456.2 [M − H]−, 500.2/502.2 [M + HCOO]−; t$_R$ (a): 1.86 min. |
| 732 | 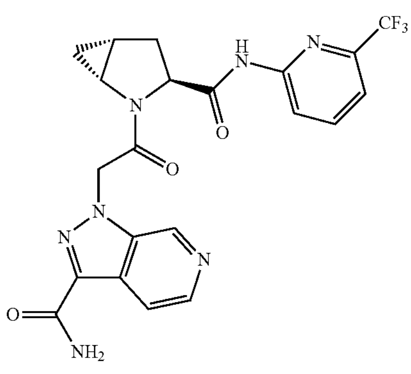 [SMILES: NC(=O)c1nn(CC(=O)N2[C@@H]3C[C@@H]3C[C@H]2C(=O)Nc2cccc(C(F)(F)F)n2)c2cnccc12] | 1-{2-Oxo-2-[(1R,3S,5R)-3-(6-trifluoromethyl-pyridin-2-ylcarbamoyl)-2-aza-bicyclo[3.1.0]hex-2-yl]-ethyl}-1H-pyrazolo[3,4-c]pyridine-3-carboxylic acid amide | (1) R$_f$(EtOAc) = 0.1; 474.2 [M + H]+, 472.2 [M − H]−, 518.3 [M + HCOO]−; t$_R$ (a): 2.09 min. |
| 733 | 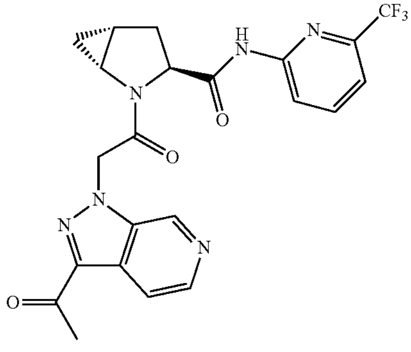 [SMILES: CC(=O)c1nn(CC(=O)N2[C@@H]3C[C@@H]3C[C@H]2C(=O)Nc2cccc(C(F)(F)F)n2)c2cnccc12] | (1R,3S,5R)-2-[2-(3-Acetyl-pyrazolo[3,4-c]pyridin-1-yl)-acetyl]-2-aza-bicyclo[3.1.0] hexane-3-carboxylic acid (6-trifluoromethyl-pyridin-2-yl)-amide | (1) R$_f$(EtOAc) = 0.25; 473.2 [M + H]+, 471.2 [M − H]−, 517.2 [M + HCOO]−; t$_R$ (a): 2.30 min. |

TABLE 10-continued

| Example | Structure | Name | Characterization (end-table notes), TLC, R*f* (eluent); MS (LC/MS); t*R* (HPLC conditions) |
|---|---|---|---|
| 734 | 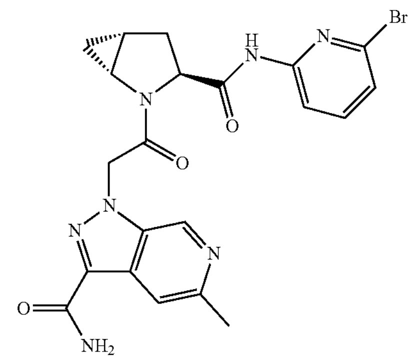 [SMILES: Cc1cc2c(C(N)=O)nn(CC(=O)N3[C@@H]4C[C@@H]4C[C@H]3C(=O)Nc3cccc(Br)n3)c2cn1] | 1-{2-[(1R,3S,5R)-3-(6-Bromo-pyridin-2-ylcarbamoyl)-2-aza-bicyclo[3.1.0]hex-2-yl]-2-oxo-ethyl}-5-methyl-1H-pyrazolo[3,4-c]pyridine-3-carboxylic acid amide | (1) R*f* (EtOAc) = 0.1; 498.1/500.1 [M + H]+, 496.2/498.1 [M − H]−, 542.3/544.1 [M + HCOO]−; t*R* (a): 2.27 min. |
| 735 | 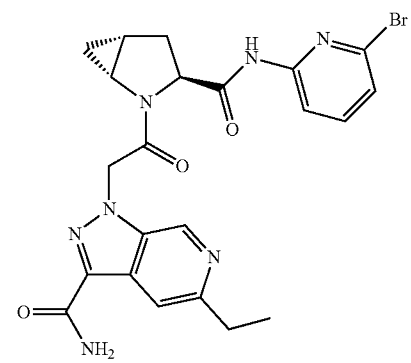 [SMILES: CCc1cc2c(C(N)=O)nn(CC(=O)N3[C@@H]4C[C@@H]4C[C@H]3C(=O)Nc3cccc(Br)n3)c2cn1] | 1-{2-[(1R,3S,5R)-3-(6-Bromo-pyridin-2-ylcarbamoyl)-2-aza-bicyclo[3.1.0]hex-2-yl]-2-oxo-ethyl}-5-ethyl-1H-pyrazolo[3,4-c]pyridine-3-carboxylic acid amide | (1) R*f* (EtOAc) = 0.26; 12.2/514.2 [M + H]+, 510.2/512.2 [M − H]−, 556.2/558.2 [M + HCOO]−; t*R* (a): 2.35 min. |
| 736 | 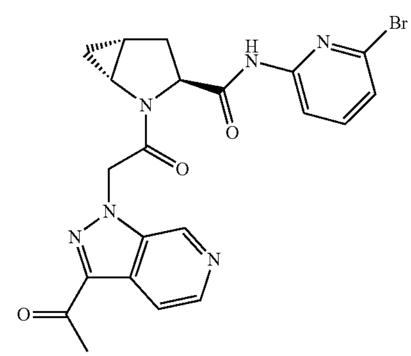 [SMILES: CC(=O)c1nn(CC(=O)N2[C@@H]3C[C@@H]3C[C@H]2C(=O)Nc2cccc(Br)n2)c2cnccc12] | (1R,3S,5R)-2-[2-(3-Acetyl-pyrazolo[3,4-c]pyridin-1-yl)-acetyl]-2-aza-bicyclo[3.1.0]hexane-3-carboxylic acid (6-bromo-pyridin-2-yl)-amide | (1) R*f* (CH$_2$Cl$_2$/MeOH 9:1) = 0.5; 483.1/485.1 [M + H]+, 481.1/483.1 [M − H]−; t*R* (f): 1.38 min. |
| 737 | 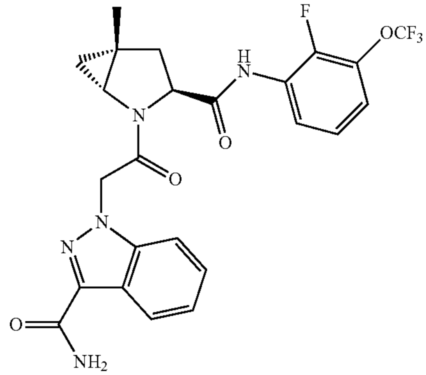 | 1-{2-[(1R,3S,5R)-3-(2-Fluoro-3-trifluoromethoxy-phenylcarbamoyl)-5-methyl-2-aza-bicyclo[3.1.0]hex-2-yl]-2-oxo-ethyl}-1H-indazole-3-carboxylic acid amide | (1,4) 419.2 [M + H]+, 436.2 [M + NH$_4$]+, 417.2 [M − H]−, 463.2 [M + HCOO]−; t*R* (f): 2.46 min. |

TABLE 10-continued

| Example | Structure | Name | Characterization (end-table notes), TLC, R$_f$ (eluent); MS (LC/MS); t$_R$ (HPLC conditions) |
|---|---|---|---|
| 738 | 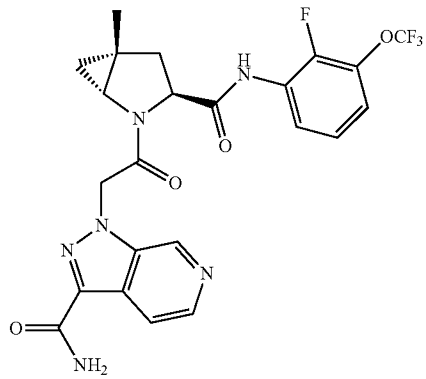 [SMILES: C[C@@]12C[C@@H](C(=O)Nc3cccc(OC(F)(F)F)c3F)N(C(=O)Cn3nc(C(N)=O)c4ccncc43)[C@@H]1C2] | 1-{2-[(1R,3S,5R)-3-(2-Fluoro-3-trifluoromethoxy-phenyl carbamoyl)-5-methyl-2-aza-bicyclo[3.1.0]hex-2-yl]-2-oxo-ethyl}-1H-pyrazolo[3,4-c]pyridine-3-carboxylic acid amide | (1,4) R$_f$ (CH$_2$Cl$_2$/MeOH 9:1) = 0.5; 521.2 [M + H]+, 1041.5 [2M + H]+, 519.2 [M − H]−; 1039.5 [2M − H]−; t$_R$ (f): 1.49 min. |
| 739 | 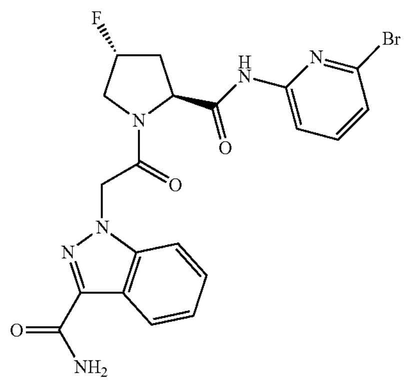 [SMILES: NC(=O)c1nn(CC(=O)N2C[C@H](F)C[C@H]2C(=O)Nc2cccc(Br)n2)c2ccccc12] | 1-{2-[(2S,4R)-2-(6-Bromo-pyridin-2-ylcarbamoyl)-4-fluoro-pyrrolidin-1-yl]-2-oxo-ethyl}-1H-indazole-3-carboxylic acid amide | (1) R$_f$ (CH$_2$Cl$_2$/MeOH 9:1) = 0.5; 489.2/491.1 [M + H]+, 487.1/489.3 [M − H]−; t$_R$ (f): 1.56 min. |
| 740 | 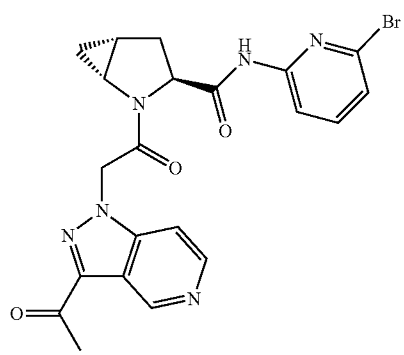 [SMILES: CC(=O)c1nn(CC(=O)N2[C@@H]3C[C@@H]3C[C@H]2C(=O)Nc2cccc(Br)n2)c2ccncc12] | (1R,3S,5R)-2-[2-(3-Acetyl-pyrazolo[4,3-c]pyridin-1-yl)-acetyl]-2-aza-bicyclo[3.1.0]hexane-3-carboxylic acid (6-bromo-pyridin-2-yl)-amide | (1) R$_f$ (CH$_2$Cl$_2$/MeOH 9:1) = 0.6; 483.1/485.2 [M + H]+, 965.3/697.3 [2M + H]+, 481.1/483.2 [M − H]−; t$_R$ (f): 1.34 min. |
| 741 | 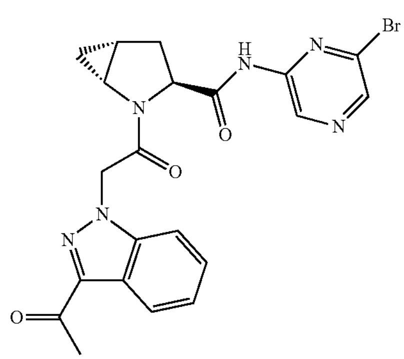 [SMILES: CC(=O)c1nn(CC(=O)N2[C@@H]3C[C@@H]3C[C@H]2C(=O)Nc2cncc(Br)n2)c2ccccc12] | 1-{2-[(1R,3S,5R)-3-(6-Bromo-pyrazin-2-ylcarbamoyl)-2-aza-bicyclo[3.1.0]hex-2-yl]-2-oxo-ethyl}-1H-indazole-3-carboxylic acid | (1) R$_f$ (CH$_2$Cl$_2$/MeOH 9:1) = 0.6; 501.2/503.2 [M + NH$_4$]+, 482.1/484.1 [M − H]−; t$_R$ (f): 1.51 min. |

| Example | Name | Characterization (end-table notes), TLC, R$_f$ (eluent); MS (LC/MS); t$_R$ (HPLC conditions) |
|---|---|---|
| 742 | 1-{2-[(1R,3S,5R)-3-(4-Bromo-thiazol-2-ylcarbamoyl)-2-aza-bicyclo[3.1.0]hex-2-yl]-2-oxo-ethyl}-1H-indazole-3-carboxylic acid amide | (1) R$_f$ (CH$_2$Cl$_2$/MeOH 9:1) = 0.5; 489.1/491.1 [M + H]+, 511.1/513.1 [M + Na]+, 487.1/489.1 [M − H]−; t$_R$ (f): 1.59 min. |
| 743 | 1-{2-[(1R,3S,5R)-3-(6-Bromo-pyridin-2-ylcarbamoyl)-2-aza-bicyclo[3.1.0]hex-2-yl]-2-oxo-ethyl}-5,7-dimethyl-1H-pyrazolo[3,4-c]pyridine-3-carboxylic acid amide | (1) R$_f$ (CH$_2$Cl$_2$/MeOH 9:1) = 0.45; 512.2/514.2 [M + H]+, 510.2/512.2 [M − H]−; t$_R$ (f): 1.25 min. |
| 744 | 1-{2-[(1R,3S,5R)-3-(6-Bromo-pyridin-2-ylcarbamoyl)-5-methyl-2-aza-bicyclo[3.1.0]hex-2-yl]-2-oxo-ethyl}-1H-indazole-3-carboxylic acid amide | (1,4) R$_f$ (CH$_2$Cl$_2$/MeOH 9:1) = 0.4; 497.2/499.2 [M + H]+, 495.2/497.2 [M − H]−; t$_R$ (f): 1.82 min. |
| 745 | 1-{2-[(1R,3S,5R)-3-(6-Bromo-pyridin-2-ylcarbamoyl)-5-methyl-2-aza-bicyclo[3.1.0]hex-2-yl]-2-oxo-ethyl}-5-methyl-1H-pyrazolo[3,4-c]pyridine-3-carboxylic acid amide | (1,4) R$_f$ (CH$_2$Cl$_2$/MeOH 9:1) = 0.4; 512.2/514.2 [M + H]+, 510.1/512.2 [M − H]−, 556.3/558.2 [M + HCOO]−; t$_R$ (f): 1.37 min. |

TABLE 10-continued

| Example | Name | Characterization (end-table notes), TLC, R*f* (eluent); MS (LC/MS); t*R* (HPLC conditions) |
|---------|------|---------------------------------------------------------------------------------------------|
| 746 | 1-{2-[(1R,2S,5S)-2-(6-Bromo-pyridin-2-ylcarbamoyl)-3-aza-bicyclo[3.1.0]hex-3-yl]-2-oxo-ethyl}-1H-indazole-3-carboxylic acid amide | (1) R*f* (CH$_2$Cl$_2$/MeOH 9:1) = 0.55; 483.1/485.1 [M + H]+, 481.1/483.1 [M − H]−, 527.3/529.1 [M + HCOO]−; t*R* (f): 1.74 min. |
| 747 | 1-{2-[(1R,3S,5R)-3-(6-Bromo-pyridin-2-ylcarbamoyl)-2-aza-bicyclo[3.1.0]hex-2-yl]-2-oxo-ethyl}-7-methyl-1H-pyrazolo[3,4-c]pyridine-3-carboxylic acid amide | (1) R*f* (CH$_2$Cl$_2$/MeOH 9:1) = 0.4; 498.2/500.2 [M + H]+, 496.7/498.4 [M − H]−; t*R* (f): 1.26 min. |
| 748 | (1R,3S,5R)-2-{2-[3-Acetyl-5-(pyrimidin-2-ylmethoxy)-indazol-1-yl]-acetyl}-2-aza-bicyclo[3.1.0]hexane-3-carboxylic acid (6-bromo-pyridin-2-yl)-amide | (1) R*f* (CH$_2$Cl$_2$/MeOH 9:1) = 0.75; 590.2/592.2 [M + H]+, 1179.5/1181.4 [2M + H]+, 588.3/590.4 [M − H]−; t*R* (f): 1.80 min. |
| 749 | 1-{2-[(1R,3S,5R)-3-(6-Bromo-pyridin-2-ylcarbamoyl)-2-aza-bicyclo[3.1.0]hex-2-yl]-2-oxo-ethyl}-6-chloro-1H-indazole-3-carboxylic acid amide | (1) R*f* (CH$_2$Cl$_2$/MeOH 9:1) = 0.55; 517.1/519.1 [M + H]+, 515.1/517.1 [M − H]−, 561.1/563.2 [M + HCOO]−; t*R* (f): 1.88 min. |

TABLE 10-continued

| Example | Structure | Name | Characterization (end-table notes), TLC, R$_f$(eluent); MS (LC/MS); t$_R$ (HPLC conditions) |
|---|---|---|---|
| 750 | 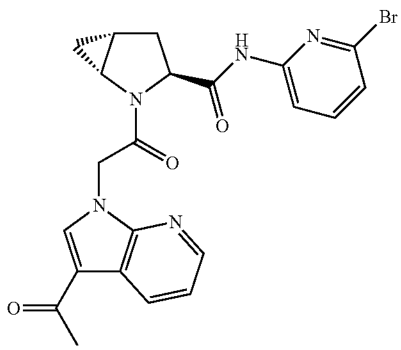 [SMILES: CC(=O)c1cn(CC(=O)N2[C@@H]3C[C@@H]3C[C@H]2C(=O)Nc2cccc(Br)n2)c2ncccc12] | (1R,3S,5R)-2-[2-(3-Acetyl-pyrrolo[2,3-b]pyridin-1-yl)-acetyl]-2-aza-bicyclo[3.1.0]hexane-3-carboxylic acid (6-bromo-pyridin-2-yl)-amide | (1) R$_f$(CH$_2$Cl$_2$/MeOH 9:1) = 0.75; 482.1/484.2 [M + H]+, 480.1/482.1 [M − H]−, 526.0/528.1 [M + HCOO]−; t$_R$ (f): 1.75 min. |
| 751 | 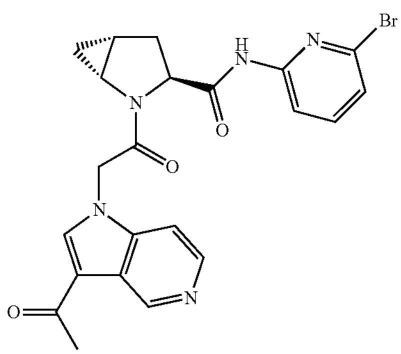 [SMILES: CC(=O)c1cn(CC(=O)N2[C@@H]3C[C@@H]3C[C@H]2C(=O)Nc2cccc(Br)n2)c2ccncc12] | (1R,3S,5R)-2-[2-(3-Acetyl-pyrrolo[3,2-c]pyridin-1-yl)-acetyl]-2-aza-bicyclo[3.1.0]hexane-3-carboxylic acid (6-bromo-pyridin-2-yl)-amide | (1) R$_f$(CH$_2$Cl$_2$/MeOH 9:1) = 0.5; 482.1/484.2 [M + H]+, 480.0/482.1 [M − H]−, 526.1/528.2 [M + HCOO]−; t$_R$ (f): 1.27 min. |
| 752 | 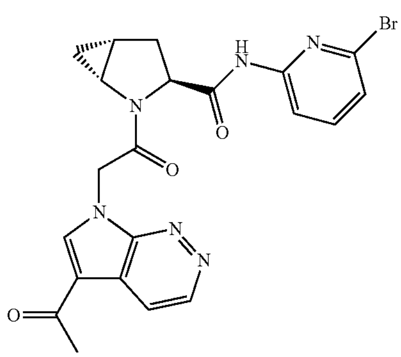 [SMILES: CC(=O)c1cn(CC(=O)N2[C@@H]3C[C@@H]3C[C@H]2C(=O)Nc2cccc(Br)n2)c2nnccc12] | (1R,3S,5R)-2-[2-(5-Acetyl-pyrrolo[2,3-c]pyridazin-7-yl)-acetyl]-2-aza-bicyclo[3.1.0]hexane-3-carboxylic acid (6-bromo-pyridin-2-yl)-amide | (1) R$_f$(CH$_2$Cl$_2$/MeOH 9:1) = 0.55; 483.2/485.1 [M + H]+, 481.1/483.1 [M − H]−; t$_R$ (f): 1.29 min. |
| 753 | 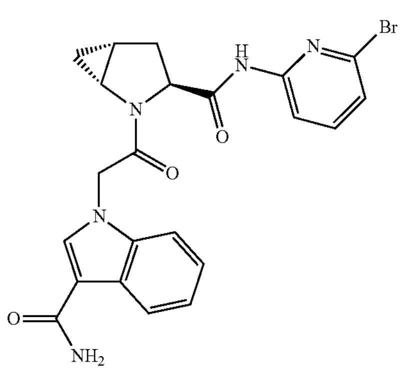 [SMILES: NC(=O)c1cn(CC(=O)N2[C@@H]3C[C@@H]3C[C@H]2C(=O)Nc2cccc(Br)n2)c2ccccc12] | 1-{2-[(1R,3S,5R)-3-(6-Bromo-pyridin-2-ylcarbamoyl)-2-aza-bicyclo[3.1.0]hex-2-yl]-2-oxo-ethyl}-1H-indole-3-carboxylic acid amide | (1) R$_f$(CH$_2$Cl$_2$/MeOH 9:1) = 0.45; 482.1/484.1 [M + H]+, 499.2/501.2 [M + NH$_4$]+, 480.1/482.1 [M − H]−; t$_R$ (f): 1.64 min. |

TABLE 10-continued

| Example | Structure | Name | Characterization (end-table notes), TLC, $R_f$(eluent); MS (LC/MS); $t_R$ (HPLC conditions) |
|---|---|---|---|
| 754 | 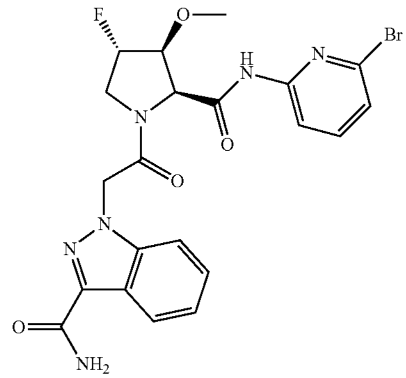 [SMILES: CO[C@H]1[C@@H](C(=O)Nc2cccc(Br)n2)N(C(=O)Cn2nc(C(N)=O)c3ccccc32)C[C@@H]1F] | 1-{2-[(2S,3S,4S)-2-(6-Bromo-pyridin-2-ylcarbamoyl)-4-fluoro-3-methoxy-pyrrolidin-1-yl]-2-oxo-ethyl}-1H-indazole-3-carboxylic acid amide | (1,5) 519.1/521.1 [M + H]+, 517.1/519.1 [M − H]−; $t_R$ (f): 1.64 min. |
| 755 | 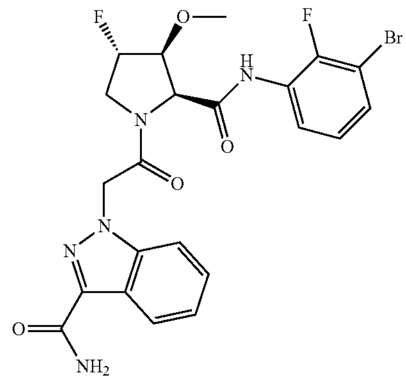 [SMILES: CO[C@H]1[C@@H](C(=O)Nc2cccc(Br)c2F)N(C(=O)Cn2nc(C(N)=O)c3ccccc32)C[C@@H]1F] | 1-{2-[(2S,3S,4S)-2-(3-Bromo-2-fluoro-phenylcarbamoyl)-4-fluoro-3-methoxy-pyrrolidin-1-yl]-2-oxo-ethyl}-1H-indazole-3-carboxylic acid amide | (1,5) $R_f$(AcOEt) = 0.5; 553.2/555.2 [M + NH$_4$]+, 534.2/536.1 [M − H]−, 580.1/582.2 [M + HCOO]−; $t_R$ (f): 1.76 min. |
| 756 | 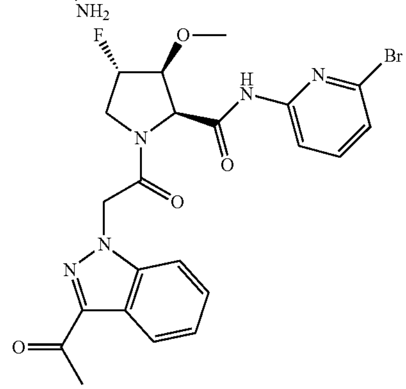 | (2S,3S,4S)-1-[2-(3-Acetyl-indazole-1-yl)-acetyl]-4-fluoro-3-methoxy-pyrrolidine-2-carboxylic acid (6-bromo-pyridin-2-yl)-amide | (1,5) $R_f$(AcOEt) = 0.9; 518.2/520.1 [M + H]+ 516.1/518.1 [M − H]− 562.2/564.2 [M + HCOO]−; $t_R$ (f): 1.92 min. |
| 757 | 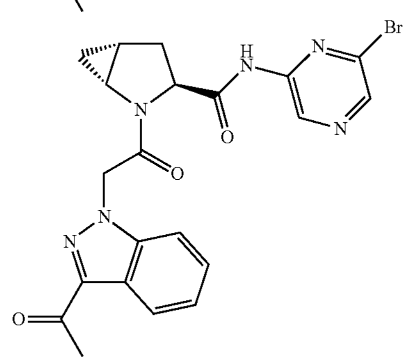 | (1R,3S,5R)-2-[2-(3-Acetyl-indazol-1-yl)-acetyl]-2-aza-bicyclo[3.1.0]hexane-3-carboxylic acid (6-bromo-pyrazin-2-yl)-amide | (1) $R_f$(CH$_2$Cl$_2$/MeOH 9:1) = 0.85; 483.1/485.1 [M + H]+, 500.2/502.2 [M + NH$_4$]+, 481.1/483.1 [M − H]−; $t_R$ (f): 1.91 min. |

(1) The acid derivative used in step C was prepared as described in Part A; (2) The amine derivative used in step A was prepared as described in Part C; (3) Step C was performed using T$_3$P and DIPEA as described in Scheme D8 Step C; (4) The acid derivative used in step A was prepared as described in Part B; (5) The title compound was prepared according to the general procedure described in Scheme D11 steps B and C starting from the substituted proline derivative prepared as described in Part B.

Example 758

1-{2-[(1R,3S,5S)-3-(2-Fluoro-3-trifluoromethoxy-phenylcarbamoyl)-5-hydroxymethyl-2-aza-bicyclo[3.1.0]hex-2-yl]-2-oxo-ethyl}-1H-indazole-3-carboxylic acid amide

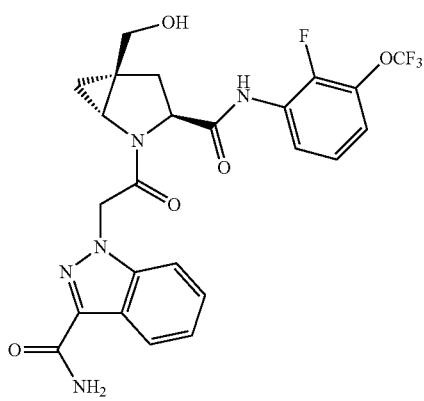 [SMILES: NC(=O)c1nn(CC(=O)N2[C@H](C(=O)Nc3cccc(OC(F)(F)F)c3F)C[C@@]3(CO)C[C@@H]23)c2ccccc12]

A solution of (3-carbamoyl-indazol-1-yl)-acetic acid (1R,3S,5S)-2-[2-(3-carbamoyl-indazol-1-yl)-acetyl]-3-(2-fluoro-3-trifluoromethoxy-phenylcarbamoyl)-2-aza-bicyclo[3.1.0]hex-5-ylmethyl ester (69.2 mg, 0.085 mmol) and NaOH (1N, 188 µL, 0.19 mmol) in THF (0.45 mL) and water (43 µL) was stirred at RT 1 h. Water and EtOAc were added, the layers were separated and the aqueous one extracted with EtOAc (×2). The combined organic extracts were dried (Na$_2$SO$_4$), filtered and concentrated. The crude residue was purified by preparative HPLC (Waters Sunfire C18-OBD, 5 µm, 30×100 mm, eluent: 20% to 100% CH$_3$CN in H$_2$O in 25 min, CH$_3$CN and H$_2$O containing 0.1% TFA, flow: 40 mL/min). R$_f$, TLC (CH$_2$Cl$_2$/MeOH 9:1)=0.45; MS (UPLC/MS): 536.4 [M+H]+, 553.3 [M+NH$_4$]+, 558.2 [M+Na]+, 534.3 [M−H]−, 580.3 [M+HCOO]−; t$_R$ (HPLC conditions f): 1.82 min.

(3-Carbamoyl-indazol-1-yl)-acetic acid (1R,3S,5S)-2-[2-(3-carbamoyl-indazol-1-yl)-acetyl]-3-(2-fluoro-3-trifluoromethoxy-phenylcarbamoyl)-2-aza-bicyclo[3.1.0]hex-5-ylmethyl ester To a mixture of (3-carbamoyl-indazol-1-yl)-acetic acid (prepared as described in Scheme A25, mg, 0.18 mmol, 2 eq.), (1R,3S,5S)-5-hydroxymethyl-2-aza-bicyclo[3.1.0]hexane-3-carboxylic acid (2-fluoro-3-trifluoromethoxy-phenyl)-amide hydrochloride (prepared as described in Scheme B29, 51 mg, 0.09 mmol, 1 eq.), and HBTU (106 mg, 0.28 mmol) in DMF (0.45 mL) was added DIPEA (64 µL, 0.37 mmol). The reaction mixture was stirred at RT for 30 min, then poured into water and extracted with EtOAc (×2). The combined organic extracts were washed with brine, dried (Na$_2$SO$_4$), filtered and concentrated. The material thus obtained was used in the next step without further purification. MS (UPLC/MS): 737.3 [M+H]+, 759.3 [M+Na]+, 735.2 [M−H]−; t$_R$ (HPLC conditions f): 2.03 min.

Example 759

1-{2-[(1R,3S,5S)-3-(3-Bromo-2-fluoro-phenylcarbamoyl)-5-hydroxymethyl-2-aza-bicyclo[3.1.0]hex-2-yl]-2-oxo-ethyl}-1H-indazole-3-carboxylic acid amide

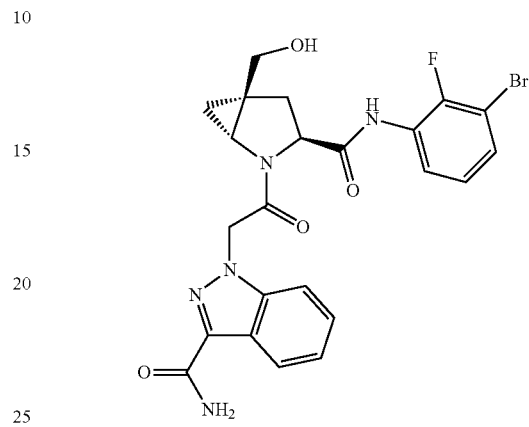

was prepared using the protocols described for the preparation of Example 758 using 3-bromo-2-fluoro-phenylamine instead of 2-fluoro-3-trifluoromethoxy-phenylamine. R$_f$, TLC (CH$_2$Cl$_2$/MeOH 9:1)=0.45; MS (UPLC/MS): 547.2/549.2 [M+NH$_4$]+, 552.2/554.1 [M+Na]+, 1081.3/1083.3 [2M+Na]+, 574.3/576.0 [M+HCOO]−, 1057.3/1059.3 [2M−H]−; t$_R$ (HPLC conditions f): 1.62 min.

Example 760

1-{2-[(1R,3S,5S)-3-(6-Bromo-pyridin-2-ylcarbamoyl)-5-hydroxymethyl-2-aza-bicyclo[3.1.0]hex-2-yl]-2-oxo-ethyl}-1H-indazole-3-carboxylic acid amide

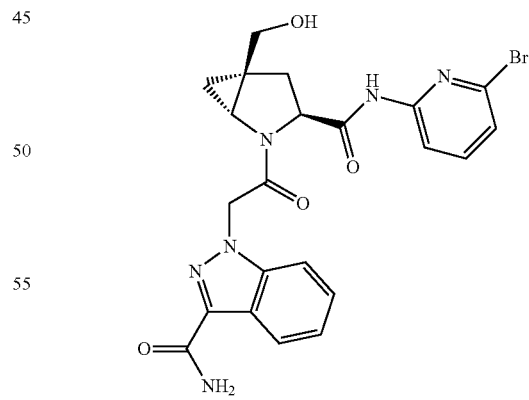

was prepared using the protocols described for the preparation of Example 758 using 6-bromo-pyridin-2-ylamine instead of 2-fluoro-3-trifluoromethoxy-phenylamine. R$_f$, TLC (CH$_2$Cl$_2$/MeOH 9:1)=0.4; MS (UPLC/MS): 513.2/515.2 [M+H]+, 530.3/532.2 [M+NH$_4$]+, 535.3/537.2 [M+Na]+; t$_R$ (HPLC conditions f): 1.47 min.

Example 761

(1R,3S,5S)-2-[2-(1-Acetyl-imidazo[1,5-a]pyridin-3-yl)-acetyl]-5-hydroxy methyl-2-aza-bicyclo[3.1.0]hexane-3-carboxylic acid 3-chloro-2-fluoro-benzylamide

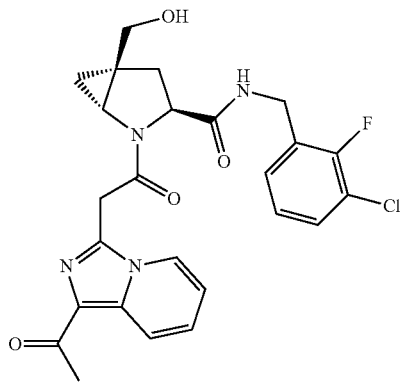 [SMILES: CC(=O)c1nc(CC(=O)N2[C@H](C(=O)NCc3cccc(Cl)c3F)C[C@@]3(CO)C[C@@H]23)n2ccccc12]

was prepared using the protocols described for the preparation of Example 758 from (1R,3S,5S)-3-(3-chloro-2-fluoro-benzylcarbamoyl)-5-hydroxymethyl-2-aza-bicyclo[3.1.0]-hexane-2-carboxylic acid tert-butyl ester (prepared as described in Scheme B28) and (1-acetyl-imidazo[1,5-a]pyridin-3-yl)-acetic acid (prepared as described in Scheme A19). $R_f$ TLC (CH$_2$Cl$_2$/MeOH 9:1)=0.40; MS (UPLC/MS): 499.4/501.4 [M+H]+, 521.4/523.4 [M+Na]+, 543.5/545.5 [M+HCOO]−; $t_R$ (HPLC conditions f): 1.66 min.

Example 762

(1R,3S,5R)-2-Aza-bicyclo[3.1.0]hexane-2,3-dicarboxylic acid 3-[(6-bromo-pyridin-2-yl)-amide]2-[(1-carbamoyl-1H-indol-3-yl)-amide]

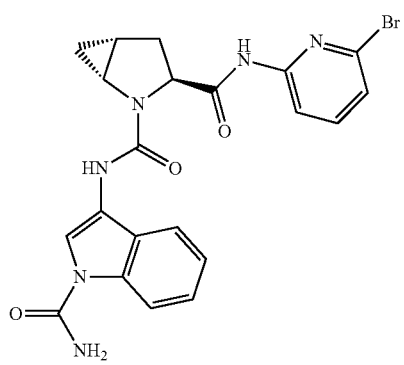 [SMILES: NC(=O)n1cc(NC(=O)N2[C@@H]3C[C@@H]3C[C@H]2C(=O)Nc2cccc(Br)n2)c2ccccc21]

To a solution of ((1R,3S,5R)-2-aza-bicyclo[3.1.0]hexane-3-carboxylic acid (6-bromo-pyridin-2-yl)-amide (2 TFA salt, 40 mg, 0.08 mmol) and Et$_3$N (44 µl, 0.31 mmol) in THF (0.4 mL) was added a suspension of 3-isocyanato-indole-1-carboxylic acid amide (25 mg, 0.08 mmol, prepared as described in Scheme A1) in THF (0.8 mL). The resulting solution was stirred at RT under nitrogen for 45 min, concentrated and purified by preparative HPLC (Waters SunFire C18-ODB, 5 µm, 19×50 mm, 20-100% CH$_3$CN/H$_2$O in 25 min, CH$_3$CN and H$_2$O both containing 0.1% TFA flow: 40 mL/min) to give the desired material after neutralization (saturated aqueous solution of NaHCO$_3$) and extraction of the purified fractions (CH$_2$Cl$_2$). TLC, R$_f$(CH$_2$Cl$_2$/MeOH 9:1)=0.45; MS (LC/MS): 483.1/485.2 [M+H]+, 965.3/967.3 [2M+H]+, 481.1/483.1 [M−H]−; $t_R$ (HPLC conditions f): 1.83 min.

Example 763

(1R,2S,5S)-3-Aza-bicyclo[3.1.0]hexane-2,3-dicarboxylic acid 2-[(6-bromo-pyridin-2-yl)-amide]3-[(1-carbamoyl-1H-indol-3-yl)-amide]

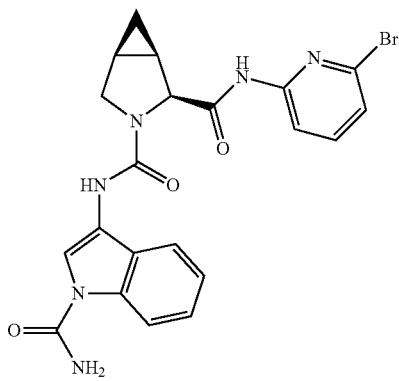 [SMILES: NC(=O)n1cc(NC(=O)N2C[C@H]3C[C@H]3[C@H]2C(=O)Nc2cccc(Br)n2)c2ccccc21]

was prepared using the protocol described for the synthesis of Example 762; TLC, R$_f$ (CH$_2$Cl$_2$/MeOH 9:1)=0.55; 483.1/485.1 [M+H]+, 965.3/967.3 [2M+H]+, 481.1/483.2 [M−H]−; $t_R$ (HPLC conditions f): 1.72 min.

Example 764

(2S,4R)-4-Fluoro-pyrrolidine-1,2-dicarboxylic acid 2-[(6-bromo-pyridin-2-yl)-amide]1-[(1-carbamoyl-1H-indol-3-yl)-amide]

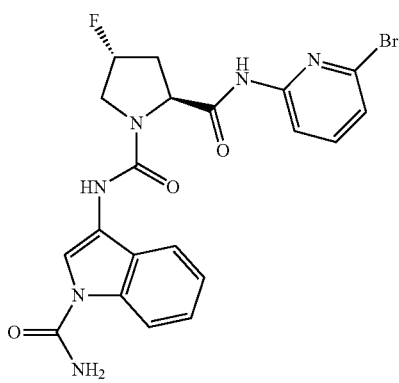

was prepared using the protocol described for the synthesis of Example 762; TLC, R$_f$ (CH$_2$Cl$_2$/MeOH 9:1)=0.45; 489.1/491.1 [M+H]+, 506.1/508.2 [M+NH$_4$]+, 487.1/489.1 [M−H]−; $t_R$ (HPLC conditions f): 1.70 min.

Scheme D12: general protocol described for the preparation of Example 765: (S)-2-({(1R,3S,5R)-2-[2-(3-Acetyl-pyrazolo[3,4-b]pyridin-1-yl)-acetyl]-2-aza-bicyclo[3.1.0]hexane-3-carbonyl}-amino)-3-cyclohexyl-propionic acid ethyl ester

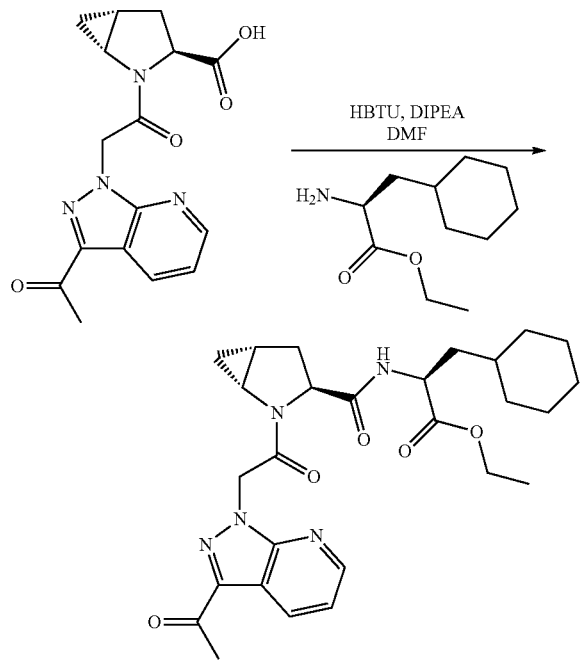

(1R,3S,5R)-2-[2-(3-Acetyl-pyrazolo[3,4-b]pyridin-1-yl)-acetyl]-2-aza-bicyclo[3.1.0]hexane-3-carboxylic acid (20 mg, 0.061 mmol, prepared as described in Scheme B30), (S)-2-amino-3-cyclohexyl-propanoic acid ethyl ester (17.3 mg, 0.073 mmol) and HBTU (34.7 mg, 0.091 mmol) were dissolved in DMF (0.2 mL). DIPEA (32 μl, 0.18 mmol) was added and the reaction mixture was stirred at 25° C. for 20 h. The crude material was purified by preparative HPLC (XBridge C180 DB, 5 μm, 30×100, eluent: 20% $CH_3CN$/80% $H_2O$ to 100% $CH_3CN$ in 12 min, $CH_3CN$ and $H_2O$ containing 7.3 mM of $NH_3$, flow 45 mL/min). The pure fractions were combined and lyophilized to give the desired material as a white powder. MS: 510.1 [M+H]+, 532.0 [M+Na]+; $t_R$ (HPLC conditions I): 3.42 min.

The examples below were prepared according to the general procedures described in Scheme D12 for Example 765 using commercially available building blocks, if not otherwise stated:

TABLE 11

| Example | Structure | Name | Characterization MS (LC/MS); $t_R$ (HPLC conditions) |
|---|---|---|---|
| 766 | 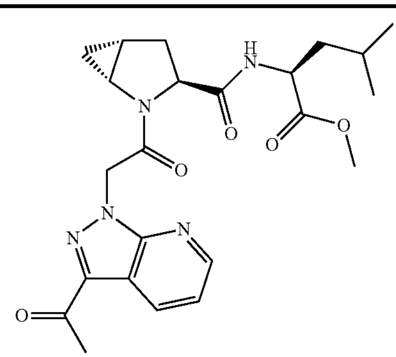 | (S)-2-({(1R,3S,5R)-2-[2-(3-Acetyl-pyrazolo[3,4-b]pyridin-1-yl)-acetyl]-2-aza-bicyclo[3.1.0] hexane-3-carbonyl}-amino)-4-methyl-pentanoic acid methyl ester | 456.0 [M + H]+, 478.0 [M + Na]+; $t_R$ (I): 2.812 min. |
| 767 | 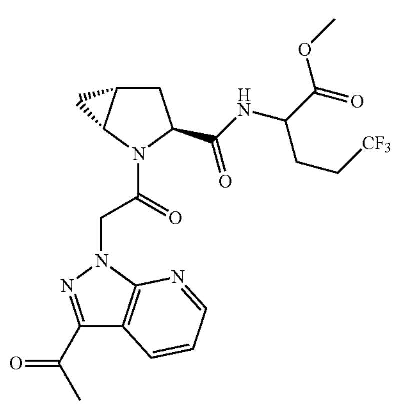 [SMILES: COC(=O)C(CCC(F)(F)F)NC(=O)[C@@H]1C[C@H]2C[C@H]2N1C(=O)Cn1nc(C(C)=O)c2cccnc21] | 2-({(1R,3S,5R)-2-[2-(3-Acetyl-pyrazolo[3,4-b]pyridin-1-yl)-acetyl]-2-aza-bicyclo[3.1.0] hexane-3-carbonyl}-amino)-5,5,5-trifluoro-pentanoic acid methyl ester | 496.0 [M + H]+, 518.0 [M + Na]+; $t_R$ (I): 2.813 min. |

TABLE 11-continued

| Example | Structure | Name | Characterization MS (LC/MS); $t_R$ (HPLC conditions) |
|---|---|---|---|
| 768 | 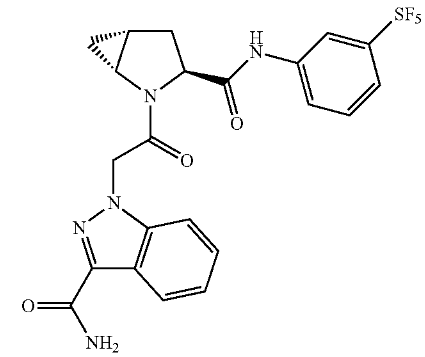 | 1-{2-[(1R,3S,5R)-3-(3-Sulfur-pentafluoride-phenyl-phenylcarbamoyl)-2-aza-bicyclo[3.1.0]hex-2-yl]-2-oxo-ethyl}-1H-indazole-3-carboxylic acid amide | (1,2) 530 [M + H]+; $t_R$ (k): 3.45 min. |

(1) The reaction was performed at 40° C., (2) The acid derivative used as starting material was prepared according to Scheme B31.

Example 769

(1R,3S,5R)-2-[2-(3-Acetyl-pyrazolo[3,4-b]pyridin-1-yl)-acetyl]-2-aza-bicyclo[3.1.0]hexane-3-carboxylic acid (4-trifluoromethyl-pyrimidin-2-yl)-amide

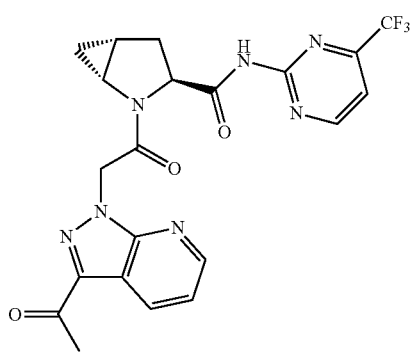 [SMILES: CC(=O)c1nn(CC(=O)N2[C@@H]3C[C@@H]3C[C@H]2C(=O)Nc2nccc(C(F)(F)F)n2)c2ncccc12]

Scheme D13: general protocol described for the preparation of Example 770: (1R,3S,5R)-2-{2-[3-Acetyl-5-(2-methoxy-ethoxy)-indazol-1-yl]-acetyl}-2-aza-bicyclo[3.1.0]hexane-3-carboxylic acid (2-fluoro-3-trifluoromethoxy-phenyl)-amide

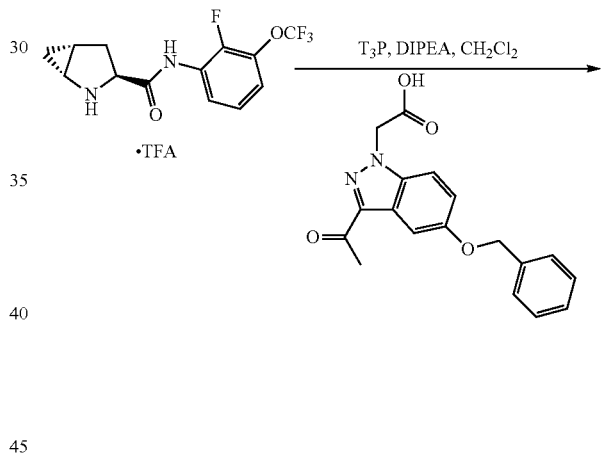

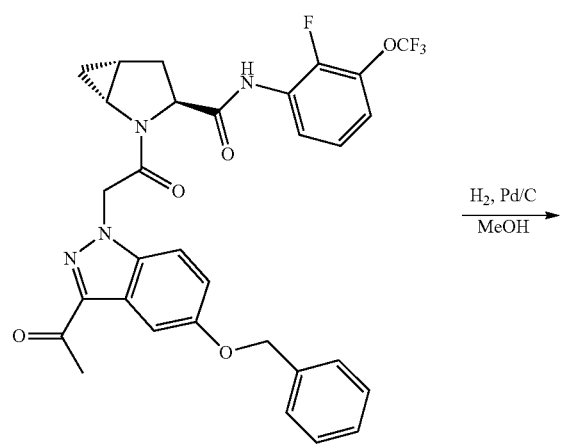

To a solution of (1R,3S,5R)-2-[2-(3-acetyl-pyrazolo[3,4-b]pyridin-1-yl)-acetyl]-2-aza-bicyclo[3.1.0]hexane-3-carboxylic acid (50 mg, 0.15 mmol, prepared as described in part B) in CH$_2$Cl$_2$ (3 mL) was added 1-chloro-N,N,2-trimethyl-prop-1-en-1-amine (81 mg, 0.609 mmol) at 0° C. under nitrogen atmosphere. After stirring at 0° C. for 1 h, 4-(trifluoromethyl)pyrimidin-2-amine (27.3 mg, 0.17 mmol) followed by DIPEA (0.053 ml, 0.305 mmol) were added and the mixture was stirred at RT for 16 h. The mixture was concentrated and the residue was purified by preparative HPLC (Waters Sunfire C18-ODB, 5 um, 30×100 mm, flow: 40 mL/min, gradient: 0-18.5 min 5% to 100% CH$_3$CN, 18.5-20 min 100% CH$_3$CN, H$_2$O and CH$_3$CN containing 0.1% TFA). The pure fractions were combined, neutralized with an aqueous saturated solution of Na$_2$CO$_3$, extracted with EtOAc, dried (Na$_2$SO$_4$), filtered and concentrated. MS (UPLC-MS): 474.3 [M+H]+, 472.3 [M−H]−; $t_R$ (HPLC conditions f): 1.81 min.

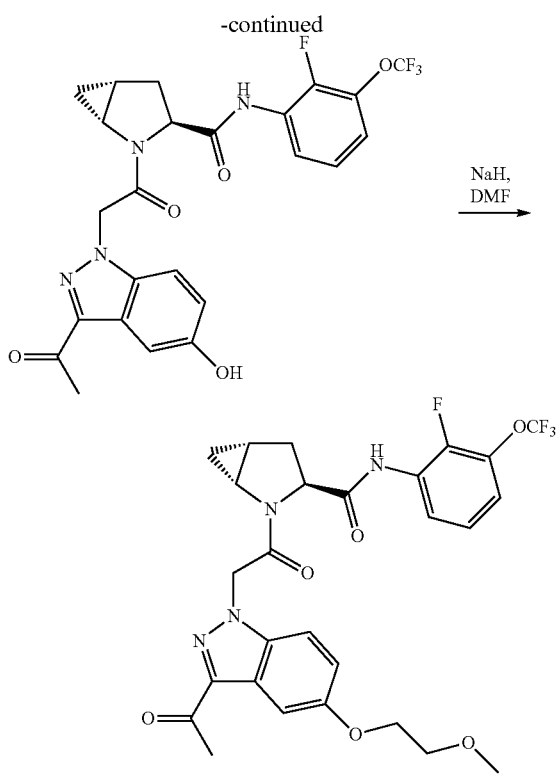

A. (1R,3S,5R)-2-[2-(3-Acetyl-5-benzyloxy-indazol-1-yl)-acetyl]-2-aza-bicyclo[3.1.0]hexane-3-carboxylic acid (2-fluoro-3-trifluoromethoxy-phenyl)-amide To a solution of (3-acetyl-5-benzyloxy-indazol-1-yl)-acetic acid (1.38 g, 4.30 mmol, prepared as described in Part A), (1R,3S,5R)-2-aza-bicyclo[3.1.0]hexane-3-carboxylic acid (2-fluoro-3-trifluoro methoxy-phenyl)-amide trifluoroacetate (1.80 g, 4.30 mmol) and propylphosphonic anhydride (50% in EtOAc, 3.80 ml, 6.46 mmol) in CH$_2$Cl$_2$ (40 ml) was added DIPEA (2.25 mL, 12.91 mmol) and the resulting mixture was stirred at RT for 2 h. The mixture was concentrated and the crude residue was purified by flash column chromatography on silica gel (c-hexane/EtOAc 1:0 to 0:1). MS (UPLC-MS): 611 [M+H]+; t$_R$ (HPLC conditions f): 2.40 min.

B. (1R,3S,5R)-2-[2-(3-Acetyl-5-hydroxy-indazol-1-yl)-acetyl]-2-aza-bicyclo[3.1.0]hexane-3-carboxylic acid (2-fluoro-3-trifluoromethoxy-phenyl)-amide A mixture of (1R,3S,5R)-2-[2-(3-acetyl-5-benzyloxy-indazol-1-yl)-acetyl]-2-aza-bicyclo[3.1.0]hexane-3-carboxylic acid (2-fluoro-3-trifluoromethoxy-phenyl)-amide (2.0 g, 3.28 mmol) and Pd/C (10%, 165 mg) in MeOH (40 mL) was stirred under a H$_2$ atmosphere for 1 h. The mixture was filtered through a celite pad and concentrated. The product was used in the next step without further purification. MS (UPLC-MS): 521 [M+H]+; t$_R$ (HPLC conditions f): 2.02 min.

C. Example 770

(1R,3S,5R)-2-{2-[3-Acetyl-5-(2-methoxy-ethoxy)-indazol-1-yl]-acetyl}-2-aza-bicyclo[3.1.0]hexane-3-carboxylic acid (2-fluoro-3-trifluoromethoxy-phenyl)-amide To a suspension of sodium hydride (60% in Mineral oil, 4.8 mg, 0.121 mmol) in DMF (5 mL) at 0° C. was added 1R,3S,5R)-2-[2-(3-acetyl-5-hydroxy-indazol-1-yl)-acetyl]-2-aza-bicyclo[3.1.0]hexane-3-carboxylic acid (2-fluoro-3-trifluoromethoxy-phenyl)-amide (60 mg, 0.115 mmol). After stirring for 5 min, 1-bromo-2-methoxyethane (0.016 mL, 0.173 mmol) was added and the reaction mixture was stirred at RT for 16 h. The reaction mixture was quenched with water and extracted with EtOAc. The organic layer was dried over Na$_2$SO$_4$, filtered and concentrated. The crude residue was purified by preparative HPLC (Waters Sunfire C18-ODB, 5 um, 30×100 mm, flow: 40 mL/min, gradient: 0-18.5 min 5% to 100% CH$_3$CN, 18.5-20 min 100% CH$_3$CN, H$_2$O and CH$_3$CN containing 0.1% TFA). Further purification by flash chromatography on silica gel (c-hexane/EtOAc 1:0 to 0:1) afforded the title compound. MS (UPLC-MS): 579.3. t$_R$ (HPLC conditions f): 2.07 min.

Example 771

(1R,3S,5R)-2-{2-[3-Acetyl-5-(cyano-methyl-methoxy)-indazol-1-yl]-acetyl}-2-aza-bicyclo[3.1.0]hexane-3-carboxylic acid (2-fluoro-3-trifluoromethoxy-phenyl)-amide

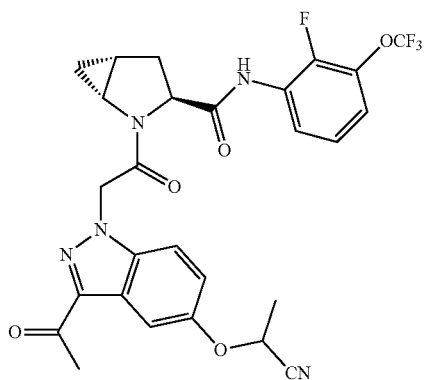 [SMILES: CC(=O)c1nn(CC(=O)N2[C@@H]3C[C@@H]3C[C@H]2C(=O)Nc2cccc(OC(F)(F)F)c2F)c2ccc(OC(C)C#N)cc12]

was prepared using the protocol described for the synthesis of Example 770 in Scheme A13. The crude residue was purified by flash column chromatography on silica gel (c-hexane/EtOAc 1:0 to 0:1). MS (UPLC-MS): 572.2 [M−H]−; t$_R$ (HPLC conditions f): 2.15 min.

Example 772

(1R,3S,5R)-2-{2-[3-Acetyl-5-(tetrahydro-furan-2-ylmethoxy)-indazol-1-yl]-acetyl}-2-aza-bicyclo[3.1.0]hexane-3-carboxylic acid (2-fluoro-3-trifluoromethoxy-phenyl)-amide

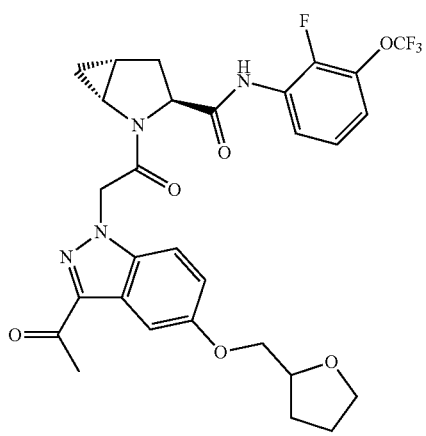 [SMILES: CC(=O)c1nn(CC(=O)N2[C@@H]3C[C@@H]3C[C@H]2C(=O)Nc2cccc(OC(F)(F)F)c2F)c2ccc(OCC3CCCO3)cc12]

was prepared using the protocol described for the synthesis of Example 770 in Scheme D13 with the following procedure for Step C. To a suspension of sodium hydride (60% in Mineral oil, 4.8 mg, 0.121 mmol) in DMF (5 mL) at 0° C. was added 1R,3S,5R)-2-[2-(3-acetyl-5-hydroxy-indazol-1-yl)-acetyl]-2-aza-bicyclo[3.1.0]hexane-3-carboxylic acid (2-fluoro-3-trifluoromethoxy-phenyl)-amide (60 mg, 0.115 mmol). After stirring for 5 min, 2-(bromomethyl)tetrahydrofuran (28.5 mg, 0.173 mmol) was added and the reaction mixture was stirred at RT for 16 h. Additional portions of NaH (60% in Mineral oil, 4.6 mg, 0.115 mmol) and 2-(bromomethyl)tetrahydrofurane (19.0 mg, 0.115 mmol) were added and the resulting mixture was stirred at RT for 16 h. The reaction mixture was quenched with water and extracted with EtOAc. The organic layer was dried over $Na_2SO_4$, filtered and concentrated. The crude residue was purified by preparative HPLC (Waters Sunfire C18-ODB, 5 um, 30×100 mm, flow: 40 mL/min, gradient: 0-18.5 min 5% to 100% $CH_3CN$, 18.5-20 min 100% $CH_3CN$, $H_2O$ and $CH_3CN$ containing 0.1% TFA). MS (UPLC-MS): 605.4. $t_R$ (HPLC conditions f): 2.20 min.

Scheme D14: general protocol described for the preparation of Example 773: (2R,3S,4S)-1-[2-(3-Acetyl-indol-1-yl)-acetyl]-3,4-difluoro-pyrrolidine-2-carboxylic acid 3-chloro-2-fluoro-benzylamide

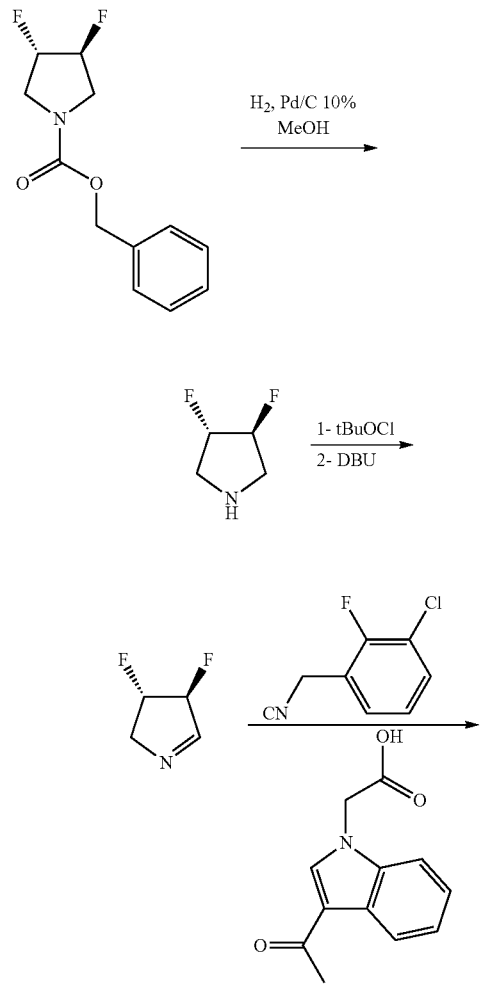

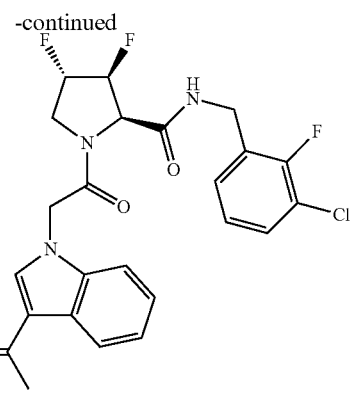

A. (3S,4S)-3,4-Difluoro-pyrrolidine

To a solution of (3S,4S)-3,4-Difluoro-pyrrolidine-1-carboxylic acid benzyl ester (ACS Scientific Inc., cat #6-0511, 3 g, 12.44 mmol) in MeOH (41 mL) was added Pd/C 10% (500 mg) and the solution was degassed 3 times replacing air by nitrogen and finally nitrogen by hydrogen. The reaction mixture was further stirred under hydrogen atmosphere for 3 days. After completion, the solution was degassed 3 times replacing hydrogen by nitrogen and the catalyst was removed through a pad of Celite. The resulting solution of volatile (3S,4S)-3,4-difluoro-pyrrolidine in MeOH (approx. 0.209 mol/L) was stored in the fridge and used without further treatment in the next step. $R_f$(EtOAc): 0.1.

B. (3S,4S)-3,4-difluoro-3,4-dihydro-2H-pyrrole

To a solution of (3S,4S)-3,4-difluoro-pyrrolidine (0.209 M in MeOH, 2.5 mL, 0.52 mmol) in a flask protected with an aluminium sheet at 0° C. under argon was added tBuOCl (73 μL, 0.52 mmol). The reaction mixture was stirred at 0° C. for 1 h; until TLC ($CH_2Cl_2$/MeOH 9:1) indicated consumption of the starting material. DBU (79 μL, 0.52 mmol) was then added at 0° C. to the resulting solution of (3S,4S)-1-chloro-3,4-difluoro-pyrrolidine and the mixture was allowed to reach RT and further stirred for 3 h. The solution thus obtained was used in the next step.

C. Example 773

(2R,3S,4S)-1-[2-(3-Acetyl-indol-1-yl)-acetyl]-3,4-difluoro-pyrrolidine-2-carboxylic acid 3-chloro-2-fluoro-benzylamide To the crude solution of (3S,4S)-3,4-difluoro-3,4-dihydro-2H-pyrrole (0.52 mmol) in MeOH under argon were successively added (3-acetyl-indol-1-yl)-acetic acid (57 mg, 0.26 mmol) and 1-chloro-2-fluoro-3-(isocyanomethyl)benzene (44 mg, 0.26 mmol) in MeOH (0.2 mL). The reaction mixture was stirred at RT for 60 h and poured into a saturated aqueous solution of $NaHCO_3$ and extracted with $CH_2Cl_2$ (×2). The combined organic extracts were dried ($Na_2SO_4$), filtered and concentrated. The crude residue was purified by flash column chromatography on silica gel (Gold RediSep column, 24 g, $CH_2Cl_2$ to $CH_2Cl_2$/MeOH 95-5), the fractions containing the desired material as a mixture of 2 diastereoisomers were concentrated and the residue was purified again by preparative HPLC (Waters Sunfire C18-OBD, 5 μm, 30×100 mm, eluent: 5% to 100% $CH_3CN$ in $H_2O$ in 25 min, $CH_3CN$ and $H_2O$ containing 0.1% TFA, flow: 40 mL/min) to give (2S,3S, 4S)-1-[2-(3-acetyl-indol-1-yl)-acetyl]-3,4-difluoro-pyrrolidine-2-carboxylic acid 3-chloro-2-fluoro-benzylamide: $R_f$ (EtOAc): 0.60; MS (UPLC): 492.2/494.2 [M+H]+, 536.2/538.2 [M+HCOO]– and (2R,3S,4S)-1-[2-(3-acetyl-indol-1-yl)-acetyl]-3,4-difluoro-pyrrolidine-2-carboxylic acid 3-chloro-2-fluoro-benzylamide; $R_f$ (EtOAc): 0.50; MS (UPLC): 492.2/494.2 [M+H]+, 536.2/538.2 [M+HCOO]–; $t_R$ (HPLC conditions a): 3.37 min. The absolute stereochemistry has been assigned tentatively based on comparison of 1H-NMR spectra and test results in the biological assay measured for both diastereoisomers.

1H NMR and HRMS Data for Selected Compounds:

$^1$H NMR spectra were recorded using a Bruker Avance DPX 400 and II 600 Spectrometers.

Example 1

$^1$H NMR (400 MHz, DMSO-$d_6$) δ (ppm): 8.65 (t, 1H), 8.35 (s, 1H), 8.27 (d, 1H), 8.00 (s, 1H), 7.74 (d, 1H), 7.34-7.54 (m, 4H), 7.26 (m, 1H), 7.08-7.21 (m, 2H), 5.51-5.38 (m, 1H), 4.55 (t, 1H), 4.27-4.46 (m, 2H), 3.92-4.07 (m, 1H), 3.89-3.96 (m, 1H), 2.5 (m, 1H), 1.97-2.19 (m, 1H).

Example 26

$^1$H NMR (400 MHz, DMSO-$d_6$) δ (ppm): 8.28 (m, 2H), 8.20 (s, 1H), 7.98 (s, 1H), 7.72 (d, 1H), 7.34-7.57 (m, 4H), 7.26 (t, 1H), 7.06-7.23 (m, 2H), 4.24-4.52 (m, 3H), 3.82 (dd, 1H), 3.69 (m, 1H), 3.53 (dd, 1H), 2.4 (m, 1H), 1.78 (m, 1H).

Example 73

HRMS: 497.2294 [M+H]+ (calcd 497.2296 for $C_{28}H_{28}N_6O_3$).

Example 107

$^1$H NMR (400 MHz, DMSO-$d_6$) δ (ppm): 8.19-8.34 (m, 2H), 7.98 (s, 2H), 7.69-7.86 (m, 4H), 7.64 (t, 1H), 7.41 (br.s, 2H), 7.26 (t, 1H), 7.18 (t, 1H), 5.44-5.30 (m, 1H), 4.16 (m, 1H), 3.93 (m, 1H), 3.49-3.76 (m, 1H), 3.18 (m, 1H), 3.03 (m, 1H), 2.29 (m, 1H), 1.94-2.20 (m, 1H).

Example 124

HRMS: 476.1539 [M+H]$^+$ (calcd 476.1540 for $C_{22}H_{20}F_3N_5O_4$), 498.1358 [M+Na]+ (calcd 498.1360 for $C_{22}H_{20}F_3N_5O_4Na$), 493.1805 [M+NH$_4$]+ (calcd 493.1806 for $C_{22}H_{20}F_3N_5O_4NH_4$); $t_R$ (HPLC conditions a) 3.46 min.

Example 133

$^1$H NMR (400 MHz, DMSO-$d_6$) δ (ppm): 8.42-8.56 (m, 2H), 8.18 (d, 1H), 8.01 (s, 1H), 7.29-7.53 (m, 5H), 7.16 (t, 1H), 6.93 (dd, 1H), 4.75 (dd, 2H), 4.23-4.46 (m, 1H), 4.16 (dd, 1H), 3.81 (m, 1H), 3.71 (s, 3H), 2.34 (m, 1H), 2.10 (m, 1H), 1.80 (m, 1H), 0.84 (m, 1H), 0.56 (m, 1H).

Example 134

HRMS: 488.1539 [M+H]$^+$ (calcd 488.1540 for $C_{23}H_{20}F_3N_5O_4$), 510.1358 [M+Na]+ (calcd 510.1360 for $C_{23}H_{20}F_3N_5O_4Na$), 505.1805 [M+NH$_4$]+ (calcd 505.1806 for $C_{23}H_{20}F_3N_5O_4NH_4$).

Example 136

$^1$H NMR (400 MHz, DMSO-$d_6$) δ (ppm): 8.38-8.54 (m, 2H), 8.17 (d, 1H), 7.99 (s, 1H), 7.46 (t, 1H), 7.25-7.42 (m, 4H), 7.16 (t, 1H), 6.89 (dd, 1H), 4.23-4.46 (m, 2H), 4.16 (dd, 1H), 3.83 (m, 1H), 3.78 (s, 3H), 2.33 (dd, 1H), 2.09 (m, 1H), 1.78 (m, 1H), 0.84 (m, 1H), 0.56 (m, 1H).

Example 141

HRMS: 488.1539 [M+H]+ (calcd 488.1540 for $C_{23}H_{20}F_3N_5O_4$), 510.1358 [M+Na]+ (calcd 510.1360 for $C_{23}H_{21}N_4O_4F_3Na$).

Example 148

$^1$H NMR (400 MHz, DMSO-$d_6$) δ (ppm): 10.07 (s, 1H), 8.64 (s, 1H), 8.27 (d, 1H), 8.00 (s, 2H), 7.80 (d, 1H), 7.49-7.59 (m, 1H), 7.38 (br.s, 2H), 7.11-7.30 (m, 4H), 4.18 (t, 1H), 3.88-3.97 (m, 1H), 2.29-2.41 (m, 1H), 2.08-2.21 (m, 1H), 1.74-1.88 (m, 1H), 0.77-0.89 (m, 1H), 0.50-0.65 (m, 1H).

Example 155

$^1$H NMR (400 MHz, DMSO-$d_6$) δ (ppm): 8.55 (m, 2H), 8.28 (d, 1H), 8.00 (s, 1H), 7.79 (d, 1H), 7.43 (br.s, 2H), 7.27 (t, 1H), 7.19 (t, 1H), 6.94 (d, 1H), 6.84 (d, 1H), 4.35 (m, 1H), 4.14 (dd, 1H), 3.80 (m, 1H), 2.30 (dd, 1H), 2.09 (m, 1H), 1.77 (m, 1H), 0.84 (m, 1H), 0.54 (m, 1H).

Example 158

$^1$H NMR (400 MHz, DMSO-$d_6$) δ (ppm): 10.16 (s, 1H), 8.68 (s, 1H), 8.29 (d, 1H), 8.01 (s, 1H), 7.92 (d, 1H), 7.80 (d, 1H), 7.70 (t, 1H), 7.40 (br.s, 2H), 7.23-7.32 (m, 1H), 7.20 (t, 1H), 6.99 (d, 1H), 4.38 (t, 1H), 3.93 (m, 1H), 2.68 (q, 2H), 2.39 (m, 1H), 2.19 (m, 1H), 1.80 (m, 1H), 1.22 (t, 3H), 0.84 (m, 1H), 0.54 (m, 1H).

Example 166

$^1$H NMR (400 MHz, DMSO-$d_6$) δ (ppm): 8.57 (s, 1H), 8.46 (t, 1H), 8.29 (d, 1H), 8.01 (s, 1H), 7.79 (d, 1H), 7.39-7.55 (m, 3H), 7.35 (t, 1H), 7.27 (m, 1H), 7.18 (m, 2H), 4.25-4.48 (m, 2H), 4.17 (dd, 1H), 3.83 (m, 1H), 2.33 (dd, 1H), 2.11 (m, 1H), 1.79 (m, 1H), 0.85 (m, 1H), 0.56 (m, 1H).

Example 170

$^1$H NMR (400 MHz, DMSO-$d_6$) δ (ppm): 8.49 (t, 1H), 8.25 (d, 1H), 8.10 (s, 1H), 7.97 (s, 1H), 7.72 (d, 1H), 7.36-7.54 (m, 3H), 7.33 (t, 1H), 7.23 (t, 1H), 7.12 (m, 2H), 4.20-4.49 (m, 3H), 3.69 (m, 1H), 3.53 (m, 1H), 2.13 (m, 1H), 1.73-2.02 (m, 3H).

Example 175

$^1$H NMR (400 MHz, DMSO-$d_6$) δ (ppm): 9.98 (s, 1H), 8.68 (s, 1H), 8.29 (d, 1H), 7.91-8.04 (m, 2H), 7.80 (d, 1H), 7.43 (br.s, 2H), 7.24-7.36 (m, 3H), 7.20 (t, 1H), 4.40 (dd, 1H), 3.84-3.96 (m, 1H), 2.31-2.43 (m, 1H), 2.17-2.27 (m, 1H), 1.77-1.88 (m, 1H), 0.81-0.92 (m, 1H), 0.53-0.64 (m, 1H).

Example 176

$^1$H NMR (400 MHz, DMSO-$d_6$) δ (ppm): 9.88 (s, 1H), 8.68 (s, 1H), 8.29 (d, 1H), 8.01 (s, 1H), 7.88 (t, 1H), 7.80 (d, 1H), 7.43 (br.s, 2H), 7.16-7.37 (m, 4H), 4.35-4.44 (m, 1H), 3.87-3.95 (m, 1H), 2.32-2.43 (m, 1H), 2.16-2.27 (m, 1H), 1.78-1.87 (m, 1H), 0.82-0.91 (m, 1H), 0.55-0.63 (m, 1H).

Example 178

¹H NMR (400 MHz, DMSO-d₆) δ (ppm): 8.65 (br.s, 1H), 8.50 (br.s, 1H), 8.26 (d, 1H), 7.97 (br.s, 1H), 7.71 (d, 1H), 6.99-7.57 (m, 7H), 5.54 (br.s, 1H), 4.17-4.50 (m, 2H), 4.00 (br.s, 2H), 3.20 (br.s, 2H).

Example 181

¹H NMR (400 MHz, DMSO-d₆) δ (ppm): 8.65 (t, 1H), 8.34 (br.s, 1H), 8.27 (d, 1H), 8.00 (s, 1H), 7.76 (d, 1H), 7.41-7.55 (m, 3H), 7.37 (t, 1H), 7.26 (t, 1H), 7.04-7.21 (m, 2H), 5.36 (t, 1H), 4.59 (t, 1H), 4.37-4.49 (m, 1H), 4.21-4.37 (m, 1H), 3.81-3.94 (m, 1H), 3.53-3.81 (m, 3H), 2.34-2.40 (m, 1H), 1.97-2.18 (m, 1H).

Example 183

¹H NMR (400 MHz, DMSO-d₆) δ (ppm): 8.56 (s, 1H), 8.45 (t, 1H), 8.28 (d, 1H), 8.02 (s, 1H), 7.80 (d, 1H), 7.44 (m, 2H), 7.22-7.38 (m, 5H), 7.18 (t, 1H), 4.30 (m, 1H), 4.17 (dd, 1H), 3.82 (m, 1H), 2.33 (dd, 1H), 2.12 (m, 1H), 1.78 (br.s, 1H), 0.86 (m, 1H), 0.56 (dt, 1H).

Example 184

¹H NMR (400 MHz, DMSO-d₆): 8.54 (s, 1H), 8.47 (m, 1H), 8.28 (d, 1H), 8.01 (s, 1H), 7.81 (d, 1H), 7.47 (t, 1H), 7.44 (m, 2H), 7.36 (t, 1H), 7.27 (t, 1H), 7.18 (t, 2H), 4.36 (m, 2H), 4.23 (m, 1H), 3.77 (m, 1H), 3.45 (d, 1H), 3.36 (d, 1H), 3.29 (s, 3H), 2.39 (dd, 1H), 2.10 (dd, 1H), 0.95 (m, 1H), 0.82 (m, 1H).

Example 186

¹H NMR (400 MHz, DMSO-d₆) δ (ppm): 8.47 (t, 1H), 8.27 (d, 1H), 8.12 (s, 1H), 7.99 (s, 1H), 7.73 (d, 1H), 7.34-7.52 (m, 4H), 7.26 (t, 1H), 7.09-7.20 (m, 2H), 4.59 (d, 1H), 4.27-4.47 (m, 2H), 4.11-4.19 (m, 1H), 3.72-3.82 (m, 1H), 3.50-3.61 (m, 1H), 3.34 (s, 3H), 2.03-2.23 (m, 2H).

Example 190

¹H NMR (400 MHz, DMSO-d₆) δ (ppm): 8.56 (t, 1H), 8.37 (s, 1H), 8.28 (d, 1H), 8.02 (s, 1H), 7.80 (d, 1H), 7.33-7.52 (m, 4H), 7.26 (t, 1H), 7.10-7.20 (m, 2H), 5.32-5.58 (m, 1H), 4.59-4.71 (m, 1H), 4.30-4.48 (m, 2H), 3.81-3.91 (m, 1H), 3.69-3.79 (m, 1H), 2.15-2.32 (m, 2H).

Example 194

¹H NMR (400 MHz, DMSO-d₆) δ (ppm): 10.63 (s, 1H), 8.68 (d, 1H), 8.45 (s, 1H), 8.39-8.43 (m, 2H), 8.26 (d, 1H), 7.97 (s, 1H), 7.76 (d, 1H), 7.41 (br.s, 2H), 7.25 (t, 1H), 7.17 (t, 1H), 5.51 (d, 1H), 4.55-4.68 (m, 1H), 3.74-4.14 (m, 2H), 2.53-2.64 (m, 1H), 2.04-2.28 (m, 1H).

Example 195

¹H NMR (400 MHz, DMSO-d₆) δ (ppm): 8.56 (s, 1H), 8.45 (t, 1H), 8.29 (d, 1H), 8.01 (s, 1H), 7.79 (d, 1H), 7.44 (br.s, 2H), 7.23-7.36 (m, 2H), 7.11-7.23 (m, 3H), 4.27-4.48 (m, 2H), 4.18 (dd, 1H), 3.81 (m, 1H), 2.33 (dd, 1H), 2.12 (m, 1H), 1.78 (m, 1H), 0.87 (m, 1H), 0.56 (m, 1H).

Example 200

¹H NMR (400 MHz, DMSO-d₆) δ (ppm): 8.52 (m, 1H), 8.23 (m, 2H), 7.97 (s, 1H), 7.75 (d, 1H), 7.28-7.51 (m, 4H), 7.22 (t, 1H), 7.04-7.18 (m, 2H), 4.32-4.50 (m, 2H), 4.18-4.32 (m, 1H), 3.96 (t, 1H), 3.80 (t, 1H), 3.61 (s, 3H), 3.31 (m, 2H), 2.08 (m, 1H).

Example 203

¹H NMR (400 MHz, DMSO-d₆) δ (ppm): 8.53 (s, 1H), 8.19-8.33 (m, 2H), 7.95 (s, 1H), 7.74 (d, 1H), 7.34-7.52 (m, 4H), 7.27 (t, 1H), 6.96-7.23 (m, 2H), 5.12 (m, 1H), 5.02 (t, 1H), 4.24 (dd, 1H), 3.79 (m, 1H), 3.58 (m, 2H), 2.21-2.31 (m, 1H), 2.07-2.17 (m, 1H), 1.77 (m, 1H), 0.85 (m, 1H), 0.53 (m, 1H).

Example 205

¹H NMR (400 MHz, DMSO-d₆) δ (ppm): 8.65 (t, 1H), 8.32 (s, 1H), 8.27 (d, 1H), 8.00 (s, 1H), 7.75 (d, 1H), 7.32-7.57 (m, 4H), 7.26 (t, 1H), 7.06-7.21 (m, 2H), 4.57 (t, 1H), 4.38-4.50 (m, 1H), 4.23-4.38 (m, 1H), 3.97 (dd, 1H), 3.61-3.80 (m, 1H), 2.4 (m, 1H), 1.86-2.14 (m, 1H), 1.57 (d, 3H).

Example 208

¹H NMR (400 MHz, DMSO-d₆) δ (ppm): 8.87 (t, 1H), 8.24-8.32 (m, 2H), 7.99 (s, 1H), 7.73 (d, 1H), 7.38-7.52 (m, 3H), 7.31-7.37 (m, 1H), 7.23-7.30 (m, 1H), 7.11-7.20 (m, 2H), 5.13-5.36 (m, 1H), 4.62-4.74 (m, 1H), 4.29-4.45 (m, 2H), 3.87-3.97 (m, 1H), 3.60-3.72 (m, 1H), 2.07-2.36 (m, 2H).

Example 210

¹H NMR (400 MHz, DMSO-d₆) δ (ppm): 8.41 (t, 1H), 8.27 (d, 1H), 8.14 (s, 1H), 7.98 (s, 1H), 7.74 (d, 1H), 7.45 (m, 4H), 7.25 (t, 1H), 7.15 (m, 2H), 4.37-4.49 (m, 2H), 4.25-4.37 (m, 1H), 3.93 (d, 1H), 3.64 (dd, 1H), 1.91 (m, 1H), 1.78 (m, 1H), 0.73 (q, 1H), 0.63 (m, 1H).

Example 213

¹H NMR (400 MHz, DMSO-d₆) δ (ppm): 8.24-8.33 (m, 2H), 8.08 (s, 1H), 7.99 (s, 1H), 7.73 (d, 1H), 7.53 (t, 1H), 7.37-7.48 (m, 3H), 7.26 (t, 1H), 7.16 (t, 1H), 7.08 (t, 1H), 5.35 (d, 1H), 4.30-4.52 (m, 4H), 3.74-3.84 (m, 1H), 3.50-3.60 (m, 1H), 1.96-2.16 (m, 2H).

Example 216

¹H NMR (400 MHz, DMSO-d₆) δ (ppm): 8.53 (s, 1H), 8.46 (t, 1H), 7.88 (m, 2H), 7.68 (d, 1H), 7.27-7.57 (m, 4H), 7.18 (t, 1H), 6.83 (dd, 1H), 4.22-4.47 (m, 2H), 4.16 (dd, 1H), 3.79 (m, 4H), 2.32 (m, 1H), 2.02-2.17 (m, 1H), 1.77 (m, 1H), 0.84 (m, 1H), 0.54 (m, 1H).

Example 218

¹H NMR (400 MHz, DMSO-d₆) δ (ppm): 10.00 (s, 1H), 8.68 (s, 1H), 8.29 (d, 1H), 8.17-8.25 (m, 1H), 8.00 (s, 1H), 7.80 (d, 1H), 7.34-7.57 (m, 4H), 7.23-7.31 (m, 1H), 7.16-7.23 (m, 1H), 4.34-4.46 (m, 1H), 3.85-3.95 (m, 1H), 2.31-2.43 (m, 1H), 2.19-2.29 (m, 1H), 1.77-1.88 (m, 1H), 0.81-0.92 (m, 1H), 0.55-0.64 (m, 1H).

Example 223

¹H NMR (400 MHz, DMSO-d₆): δ (ppm): 8.52 (s, 1H), 8.34 (d, 1H), 8.27 (d, 1H), 7.95 (s, 1H), 7.74 (d, 1H), 7.48-

7.41 (m, 4H), 7.27 (t, 1H), 7.22-7.16 (m, 2H), 5.19 (m, 1H), 4.18 (dd, 1H), 3.79 (m, 1H), 3.40 (2H under H₂O signal), 2.28 (dd, 1H), 2.10-2.04 (m, 1H), 1.92-1.73 (m, 3H), 0.85 (m, 1H), 0.53 (m, 1H).

Example 237

¹H NMR (400 MHz, DMSO-d₆) δ (ppm): 8.71 (br.s, 1H), 8.48 (s, 2H), 8.35 (s, 1H), 8.26 (d, 1H), 8.02 (s, 1H), 7.88 (br.s, 1H), 7.75 (d, 1H), 7.42 (br.s, 2H), 7.26 (t, 1H), 7.16 (t, 1H), 5.27-5.66 (m, 1H), 4.53 (m, 1H), 4.37 (m, 2H), 4.01 (m, 1H), 3.73-3.93 (m, 1H), 2.08-2.24 (m, 1H), 1.94-2.08 (m, 1H).

Example 258

¹H NMR (400 MHz, DMSO-d₆) δ (ppm): 8.53 (s, 1H), 8.37 (t, 1H), 8.29 (d, 1H), 8.01 (s, 1H), 7.79 (d, 1H), 7.44 (br.s, 2H), 7.15-7.34 (m, 5H), 4.22-4.39 (m, 2H), 4.20 (dd, 1H), 3.81 (m, 1H), 2.31 (m, 1H), 2.13 (m, 1H), 1.77 (m, 1H), 0.85 (m, 1H), 0.54 (td, 1H).

Example 274

¹H NMR (400 MHz, DMSO-d₆) δ (ppm): 10.22 (br.s, 1H), 8.43 (br.s, 1H), 8.27 (d, 1H), 7.94-8.06 (m, 2H), 7.77 (d, 1H), 7.41 (br.s, 2H), 7.13-7.34 (m, 4H), 5.39-5.62 (m, 1H), 4.83 (t, 1H), 3.79-4.14 (m, 2H), 2.58-2.65 (m, 1H), 2.06-2.30 (m, 1H).

Example 285

HRMS: 446.2186 [M+H]+ (calcd 446.2187 for $C_{26}H_{27}N_6O_3F_3$), 468.2005 [M+Na]+ (calcd 468.2006 for $C_{25}H_{27}N_5O_3Na$); ¹H NMR (400 MHz, DMSO-d₆) δ (ppm): 9.83 (s, 1H), 8.62 (s, 1H), 8.29 (d, 1H), 8.02 (s, 1H), 7.81 (d, 1H), 7.53 (br. s, 1H), 7.47 (d, 1H), 7.38 (br. s, 2H), 7.12-7.31 (m, 3H), 6.93 (d, 1H), 4.23 (t, 1H), 3.93 (br. s, 1H), 2.85 (m, 1H), 2.35 (m, 1H), 2.20 (m, 1H), 1.82 (br. s, 1H), 1.20 (d, 6H), 0.86 (br. s, 1H), 0.58 (br. s, 1H).

Example 294

¹H NMR (400 MHz, DMSO-d₆) δ (ppm): 8.56 (s, 1H), 8.47 (t, 1H), 8.26-8.32 (m, 1H), 8.09 (s, 1H), 7.61-7.66 (m, 1H), 7.42-7.58 (m, 3H), 7.35 (t, 1H), 7.08-7.20 (m, 2H), 4.26-4.45 (m, 2H), 4.13-4.20 (m, 1H), 3.75-3.82 (m, 1H), 2.28-2.37 (m, 1H), 2.06-2.15 (m, 1H), 1.74-1.84 (m, 1H), 0.82-0.90 (m, 1H), 0.52-0.60 (m, 1H).

Example 298

¹H NMR (400 MHz, DMSO-d₆): δ (ppm): 10.22 (s, 1H), 8.33 (s, 1H), 8.15 (d, 1H), 7.93-8.05 (m, 2H), 7.22-7.41 (m, 5H), 6.83-6.91 (m, 1H), 5.39-5.62 (m, 1H), 4.83 (t, 1H), 3.80-4.13 (m, 2H), 3.78 (s, 3H), 2.54-2.66 (m, 1H), 2.07-2.29 (m, 1H).

Example 300

¹H NMR (400 MHz, DMSO-d₆) δ (ppm): 8.41-8.49 (m, 2H), 8.16 (d, 1H), 8.00 (s, 1H), 7.46 (m, 1H), 7.27-7.42 (m, 4H), 7.16 (t, 1H), 6.90 (dd, 1H), 4.24-4.45 (m, 2H), 4.16 (dd, 1H), 3.98-4.13 (m, 2H), 3.84 (m, 1H), 3.67 (t, 2H), 3.32 (s, 3H), 2.35 (m, 1H), 2.05-2.17 (m, 1H), 1.71-1.86 (m, 1H), 0.86 (m, 1H), 0.55 (m, 1H).

Example 302

¹H NMR (400 MHz, DMSO-d₆) δ (ppm): 8.49 (t, 1H), 8.27 (d, 1H), 7.99 (s, 1H), 7.58 (s, 1H), 7.34-7.52 (m, 4H), 7.19-7.32 (m, 2H), 7.11 (t, 1H), 6.85 (t, 1H), 4.67-4.85 (m, 1H), 4.28-4.50 (m, 2H), 2.14-2.32 (m, 1H), 1.83-1.98 (m, 2H), 1.70-1.82 (m, 1H), 1.58 (s, 3H), 1.44 (s, 3H).

Example 306

¹H NMR (400 MHz, DMSO-d₆) δ (ppm): 8.56 (s, 1H), 8.45 (t, 1H), 8.21 (d, 1H), 8.01 (s, 1H), 7.69 (s, 1H), 7.40-7.54 (m, 3H), 7.34 (t, 1H), 7.11-7.21 (m, 2H), 4.27-4.45 (m, 2H), 4.18 (dd, 1H), 4.09 (q, 2H), 3.82 (m, 1H), 3.70 (s, 2H), 2.35 (m, 1H), 2.12 (m, 1H), 1.80 (m, 1H), 1.19 (t, 3H), 0.85 (m, 1H), 0.56 (m, 1H).

Example 312

¹H NMR (400 MHz, DMSO-d₆) δ (ppm): 8.50 (t, 1H), 8.27 (d, 1H), 8.18 (s, 1H), 7.99 (s, 1H), 7.77 (d, 1H), 7.31-7.53 (m, 4H), 7.25 (t, 1H), 7.14 (m, 2H), 4.76 (t, 1H), 4.35-4.49 (m, 2H), 4.30 (dd, 1H), 3.83 (t, 1H), 3.37-3.52 (m, 3H), 2.41 (m, 1H), 2.30 (m, 1H), 1.62 (m, 1H).

Example 315

¹H NMR (400 MHz, DMSO-d₆) δ (ppm): 8.55 (s, 1H), 8.46 (t, 1H), 8.22 (s, 1H), 7.98 (s, 1H), 7.72 (d, 1H), 7.41-7.55 (m, 3H), 7.35 (m, 1H), 7.17 (t, 1H), 7.08 (dd, 1H), 4.26-4.46 (m, 2H), 4.17 (dd, 1H), 4.09 (q, 2H), 3.80 (m, 1H), 3.75 (s, 2H), 2.28-2.34 (m, 1H), 2.10 (m, 1H), 1.78 (m, 1H), 1.19 (t, 3H), 0.85 (m, 1H), 0.56 (m, 1H).

Example 331

¹H NMR (400 MHz, DMSO-d₆) δ (ppm): 8.57 (t, 1H), 8.27 (d, 1H), 8.19 (s, 1H), 7.99 (s, 1H), 7.76 (d, 1H), 7.31-7.56 (m, 4H), 7.26 (t, 1H), 7.07-7.21 (m, 2H), 5.33 (d, 1H), 4.44 (dd, 1H), 4.26-4.40 (m, 3H), 3.76 (dd, 1H), 3.57 (dd, 1H), 2.30-2.42 (m, 1H), 1.82-1.94 (m, 1H).

Example 332

HRMS: 512.1350 [M+H]⁺ (calcd 512.1352 for $C_{22}H_{18}F_5N_5O_4$), 534.1169 [M+Na]+ (calcd 534.1171 for $C_{22}H_{18}F_5N_5O_4Na$), 529.1617 [M+NH₄]+ (calcd 529.1617 for $C_{22}H_{18}F_5N_5O_4NH_4$).

Example 333

¹H NMR (400 MHz, DMSO-d₆) δ (ppm): 10.31 (s, 1H), 8.59-8.69 (m, 1H), 8.43 (s, 1H), 8.26 (d, 1H), 7.98 (s, 1H), 7.90-7.96 (m, 1H), 7.76 (d, 1H), 7.30-7.51 (m, 2H), 7.25 (t, 1H), 7.17 (t, 1H), 5.50 (d, 1H), 4.83 (t, 1H), 4.31 (q, 2H), 3.77-4.12 (m, 2H), 2.53-2.66 (m, 1H), 2.09-2.30 (m, 1H), 1.30 (t, 3H).

Example 334

HRMS: 488.1539 [M+H]+ (calcd 488.1540 for $C_{23}H_{20}F_3N_5O_4$), 510.1358 [M+Na]+ (calcd 510.1360 for $C_{23}H_{20}F_3N_5O_4Na$). 1H NMR (400 MHz, DMSO-d₆) δ (ppm): 10.22 (s, 1H), 8.66 (s, 1H), 8.27 (d, 1H), 8.00 (s, 1H), 7.83 (s, 1H), 7.80 (d, 1H), 7.54 (d, 1H), 7.43 (t, 1H), 7.40 (m, 2H), 7.26 (t, 1H), 7.19 (t, 1H), 7.03 (d, 1H), 4.18 (t, 1H), 3.95 (m, 1H), 2.30 (m, 1H), 2.10 (m, 1H), 1.80 (m, 1H), 0.83 (m, 1H), 0.59 (m, 1H).

Example 340

¹H NMR (400 MHz, DMSO-d₆) δ (ppm): 10.27 (s, 1H), 8.68 (s, 1H), 8.29 (d, 1H), 8.15-8.24 (m, 2H), 8.01 (s, 1H), 7.82 (d, 1H), 7.71 (s, 1H), 7.39 (br.s, 2H), 7.28 (t, 1H), 7.21 (t, 1H), 4.18 (t, 1H), 3.86-4.00 (m, 1H), 2.30-2.44 (m, 2H), 2.10-2.24 (m, 1H), 1.74-1.89 (m, 1H), 0.77-0.92 (m, 1H), 0.54-0.68 (m, 1H).

Example 343

$^1$H NMR (400 MHz, DMSO-$d_6$) δ (ppm): 10.32-10.48 (m, 1H), 8.51-8.59 (m, 1H), 8.48 (s, 1H), 8.25 (d, 1H), 7.97 (s, 1H), 7.86-7.92 (m, 1H), 7.77 (d, 2H), 7.40 (br.s, 2H), 7.23 (t, 1H), 7.15 (t, 1H), 5.48 (d, 1H), 4.87 (t, 1H), 3.76-4.12 (m, 2H), 2.54-2.65 (m, 1H), 2.03-2.29 (m, 1H).

Example 344

$^1$H NMR (400 MHz, DMSO-$d_6$) δ ppm 10.37 (s, 1H), 8.69 (s, 1H), 8.40 (s, 1H), 8.28 (d, 1H), 8.15 (s, 1H), 8.01 (s, 1H), 7.88 (s, 1H), 7.82 (d, 1H), 7.40 (br. s, 2H), 7.27 (t, 1H), 7.20 (t, 1H), 4.21 (t, 1H), 3.90-4.01 (m, 1H), 2.41 (dd, 1H), 2.19 (dt, 1H), 1.78-1.91 (m, 1H), 0.86 (dt, 1H), 0.58-0.68 (m, 1H).

Example 350

$^1$H NMR (400 MHz, DMSO-$d_6$) δ (ppm): 8.45 (t, 1H), 8.27 (d, 1H), 8.01 (s, 1H), 7.97 (s, 1H), 7.68 (d, 1H), 7.37-7.48 (m, 3H), 7.21-7.33 (m, 2H), 7.14 (t, 1H), 6.99 (br.s, 1H), 4.27-4.57 (m, 4H), 2.26-2.42 (m, 1H), 2.08-2.23 (m, 1H), 1.77-1.89 (m, 1H), 1.55-1.66 (m, 1H), 1.22 (d, 2H).

Example 358

$^1$H NMR (400 MHz, DMSO-$d_6$) δ (ppm): 8.53 (s, 1H), 8.39-8.45 (m, 1H), 8.28 (d, 1H), 8.00 (s, 1H), 7.81 (d, 1H), 7.31-7.54 (m, 4H), 7.27 (t, 1H), 7.17 (t, 2H), 4.29-4.44 (m, 2H), 4.17-4.26 (m, 1H), 3.69 (m, 1H), 3.49-3.44 (m, 2H under DMSO signal), 2.30-2.37 (m, 1H), 2.04-2.16 (m, 1H), 0.97 (m, 1H), 0.75 (m, 1H).

Example 359

$^1$H NMR (400 MHz, DMSO-$d_6$) δ (ppm): 8.6 (t, 1H), 8.26 (m, 2H), 7.97 (s, 1H), 7.75 (d, 1H), 7.45-7.34 (m, 4H), 7.24 (t, 1H), 7.14 (m, 2H), 6.28-6.05 (tt, 1H), 4.46-4.27 (m, 3H), 3.89 (m, 1H), 3.65 (m, 1H), 2.88 (m, 1H), 2.39 (m, 1H), 1.8 (m, 1H).

Example 362

$^1$H NMR (400 MHz, DMSO-$d_6$) δ (ppm): 8.80 (s, 1H), 8.75 (m, 1H), 8.27 (d, 1H), 7.98 (s, 1H), 7.66 (d, 1H), 7.41-7.56 (m, 3H), 7.37 (t, 1H), 7.25 (t, 1H), 7.03-7.22 (m, 3H), 4.72 (dd, 1H), 4.21-4.47 (m, 2H), 3.30 (m, 1H), 2.88 (dd, 1H).

Example 371

$^1$H NMR (400 MHz, DMSO-$d_6$) δ (ppm): 9.09 (br.s, 1H), 8.44 (m, 2H), 8.06 (d, 1H), 7.92 (s, 1H), 7.46 (t, 1H), 7.24-7.40 (m, 3H), 7.19 (t, 1H), 7.11 (d, 1H), 6.75 (dd, 1H), 4.24-4.47 (m, 2H), 4.16 (dd, 1H), 3.80 (m, 1H), 2.31 (dd, 1H), 2.00-2.20 (m, 1H), 1.77 (m, 1H), 0.85 (m, 1H), 0.54 (m, 1H).

Example 374

$^1$H NMR (400 MHz, DMSO-$d_6$) δ (ppm): 12.95 (br.s, 1H), 8.46 (m, 2H), 8.17 (d, 1H), 8.01 (s, 1H), 7.25-7.55 (m, 5H), 7.17 (t, 1H), 6.92 (dd, 1H), 4.66 (m, 2H), 4.27-4.43 (m, 2H), 4.17 (dd, 1H), 3.82 (m, 1H), 2.33 (dd, 1H), 2.10 (m, 1H), 1.78 (m, 1H), 0.86 (m, 1H), 0.55 (d, 1H).

Example 377

$^1$H NMR (400 MHz, DMSO-$d_6$) δ (ppm): 8.56 (s, 1H), 8.45 (t, 1H), 8.21 (d, 1H), 8.01 (s, 1H), 7.69 (s, 1H), 7.27-7.57 (m, 4H), 7.17 (m, 2H), 4.26-4.45 (m, 2H), 4.18 (dd, 1H), 3.83 (m, 1H), 3.62 (s, 2H), 2.31-2.37 (m, 1H), 2.04-2.17 (m, 1H), 1.78 (m, 1H), 0.85 (m, 1H), 0.55 (m, 1H).

Example 378

$^1$H NMR (400 MHz, DMSO-$d_6$) δ (ppm): 12.28 (br.s, 1H), 8.54 (s, 1H), 8.45 (t, 1H), 8.21 (s, 1H), 7.98 (s, 1H), 7.71 (d, 1H), 7.41-7.54 (m, 3H), 7.35 (t, 1H), 7.17 (t, 1H), 7.08 (dd, 1H), 4.27-4.45 (m, 2H), 4.17 (dd, 1H), 3.81 (m, 1H), 3.66 (s, 2H), 2.24-2.33 (m, 1H), 2.12 (m, 1H), 1.77 (m, 1H), 0.84 (m, 1H), 0.55 (m, 1H).

Example 379

$^1$H NMR (400 MHz, DMSO-$d_6$) δ (ppm): 8.48 (m, 2H), 8.16 (d, 1H), 8.00 (s, 1H), 7.46 (m, 1H), 7.24-7.42 (m, 4H), 7.17 (t, 1H), 6.90 (dd, 1H), 4.89 (t, 1H), 4.22-4.46 (m, 2H), 4.16 (dd, 1H), 3.99 (m, 2H), 3.84 (m, 1H), 3.74 (q, 2H), 2.34 (m, 1H), 2.10 (m, 1H), 1.73 (m, 1H), 0.85 (m, 1H), 0.55 (m, 1H).

Example 384

$^1$H NMR (400 MHz, DMSO-$d_6$) δ (ppm): 8.51 (s, 1H), 8.45 (t, 1H), 8.14 (s, 1H), 7.93 (s, 1H), 7.68 (d, 1H), 7.27-7.55 (m, 4H), 7.18 (t, 1H), 7.05 (dd, 1H), 4.65 (t, 1H), 4.25-4.46 (m, 2H), 4.17 (dd, 1H), 3.81 (m, 1H), 3.63 (m, 2H), 2.83 (t, 2H), 2.26-2.33 (m, 1H), 2.10 (m, 1H), 1.77 (m, 1H), 0.84 (m, 1H), 0.54 (m, 1H).

Example 385

$^1$H NMR (400 MHz, DMSO-$d_6$) δ (ppm): 8.39-8.53 (m, 2H), 8.17 (d, 1H), 7.98 (s, 1H), 7.63 (s, 1H), 7.46 (t, 1H), 7.27-7.40 (m, 3H), 7.09-7.21 (m, 2H), 4.65 (t, 1H), 4.26-4.45 (m, 2H), 4.17 (dd, 1H), 3.83 (m, 1H), 3.64 (m, 2H), 2.81 (t, 2H), 2.27-2.34 (m, 1H), 2.12 (m, 1H), 1.77 (m, 1H), 0.87 (m, 1H), 0.55 (m, 1H).

Example 387

$^1$H NMR (400 MHz, DMSO-$d_6$) δ (ppm): 8.46 (m, 2H), 8.16 (m, 2H), 7.99 (s, 1H), 7.46 (m, 1H), 7.25-7.41 (m, 3H), 7.15 (t, 1H), 6.89 (dd, 1H), 4.25-4.45 (m, 2H), 4.16 (dd, 1H), 3.96-4.12 (m, 2H), 3.84 (m, 1H), 2.59-2.72 (m, 2H), 2.34 (m, 1H), 2.24 (s, 6H), 2.11 (m, 1H), 1.71-1.83 (m, 1H), 0.84 (m, 1H), 0.55 (m, 1H).

Example 388

$^1$H NMR (400 MHz, DMSO-$d_6$) δ (ppm): 8.47 (m, 2H), 8.17 (s, 2H), 7.98 (s, 1H), 7.45 (t, 1H), 7.34 (m, 4H), 7.14 (t, 1H), 6.90 (dd, 1H), 4.36 (m, 3H), 4.16 (m, 1H), 4.24 (dd, 1H), 4.06 (m, 3H), 3.82 (m, 1H), 2.82 (m, 2H), 2.34 (m, 1H), 2.10 (m, 1H), 1.78 (m, 1H), 1.70 (m, 4H), 0.85 (m, 1H), 0.56 (m, 1H).

Example 392

$^1$H NMR (400 MHz, DMSO-$d_6$) δ (ppm): 9.28 (s, 1H), 8.43 (m, 2H), 7.78 (m, 2H), 7.56 (d, 1H), 7.47 (t, 1H), 7.35 (t, 1H), 7.30 (br.s, 2H), 7.18 (t, 1H), 6.66 (dd, 1H), 4.25-4.48 (m, 2H), 4.16 (m, 1H), 3.79 (m, 1H), 2.31 (dd, 1H), 2.03-2.13 (m, 1H), 1.70-1.83 (m, 1H), 0.85 (m, 1H), 0.52 (m, 1H).

Example 394

$^1$H NMR (400 MHz, DMSO-$d_6$) δ (ppm): 8.53 (s, 1H), 8.44 (t, 1H), 7.88 (s, 1H), 7.82 (d, 1H), 7.68 (d, 1H), 7.27-7.49 (m, 4H), 7.16 (t, 1H), 6.85 (dd, 1H), 4.79 (s, 2H), 4.22-4.45 (m, 2H), 4.14 (dd, 1H), 3.78 (m, 1H), 3.70 (s, 3H), 2.32 (m, 1H), 1.98-2.15 (m, 1H), 1.77 (m, 1H), 0.83 (m, 1H), 0.54 (m, 1H).

Example 395

$^1$H NMR (400 MHz, DMSO-$d_6$) δ (ppm): 8.52 (s, 1H), 8.45 (t, 1H), 7.88 (m, 2H), 7.68 (d, 1H), 7.26-7.55 (m, 4H), 7.18 (t, 1H), 6.84 (dd, 1H), 4.88 (br.s, 1H), 4.26-4.46 (m, 2H), 4.16 (dd, 1H), 4.00 (t, 2H), 3.70-3.85 (m, 3H), 2.32 (dd, 1H), 2.02-2.18 (m, 1H), 1.77 (m, 1H), 0.85 (m, 1H), 0.55 (m, 1H).

Example 396

HRMS: 494.1648 [M+H]+ (calcd 491.1649 for $C_{22}H_{21}F_3N_6O_4$).

Example 409

$^1$H NMR (400 MHz, DMSO-$d_6$) δ (ppm): 8.57 (t, 1H), 8.28 (m, 3H), 8.02 (s, 1H), 7.8 (d, 1H), 7.4 (t, 2H), 7.3 (t, 1H), 7.2 (t, 1H), 7.15 (m, 2H), 4.7 (d, 1H), 4.4 (d, 2H), 3.94 (m, 2H), 3.0 (d, 2H), 2.4 (t, 1H), 2.3 (t, 1H).

Example 412

$^1$H NMR (400 MHz, DMSO-$d_6$) δ (ppm): 8.7 (t, 1H), 8.53 (s, 1H), 8.35 (d, 1H), 7.87 (m, 2H), 7.47 (t, 1H), 7.41 (t, 1H), 7.36 (t, 1H), 7.28 (t, 1H), 7.12 (t, 1H), 4.60 (t, 1H), 4.37 (m, 2H), 3.97 (dd, 1H), 3.80 (dd, 1H), 3.0 (dd, 2H), 2.61 (s, 3H), 2.45 (m, 1H), 2.07 (m, 1H).

Example 415

$^1$H NMR (400 MHz, DMSO-$d_6$) δ ppm 7.81-7.92 (m, 3H), 7.41-7.57 (m, 2H), 7.33-7.41 (m, 1H), 7.23-7.33 (m, 1H), 7.04-7.17 (m, 1H), 4.54-4.64 (m, 2H), 4.40 (dd, 2H), 4.09-4.17 (m, 1H), 3.94-3.66 (m, 2H), 2.61 (s, 3H).

Example 417

$^1$H NMR (400 MHz, DMSO-$d_6$) δ (ppm): 8.80 (t, 1H), 8.26-8.32 (m, 2H), 8.16 (br.s, 2H), 7.95 (s, 1H), 7.72 (d, 1H), 7.41-7.51 (m, 4H), 7.22-7.30 (m, 1H), 7.10-7.17 (m, 2H), 4.49-4.62 (m, 2H), 4.31-4.42 (m, 1H), 3.84-3.99 (m, 2H), 3.56-3.67 (m, 1H), 2.28-2.37 (m, 1H), 2.01-2.14 (m, 1H).

Example 430

$^1$H NMR (400 MHz, DMSO-$d_6$) δ (ppm): 8.88 (br. s, 1H), 8.23-8.32 (m, 1H), 8.15 (s, 1H), 7.97 (s, 1H), 7.73 (d, 1H), 7.37-7.51 (m, 2H), 7.24 (t, 1H), 7.09-7.18 (m, 2H), 4.90 (d, 1H), 4.57 (d, 1H), 4.29-4.47 (m, 2H), 3.81-3.88 (m, 1H), 3.51-3.64 (m, 1H).

Example 431

$^1$H NMR (400 MHz, DMSO-$d_6$) δ (ppm): 8.78 (br. s, 1H), 8.42 (s, 1H), 8.25 (d, 1H), 7.93 (s, 1H), 7.67 (d, 1H), 7.38-7.56 (m, 2H), 7.25 (t, 1H), 7.06-7.19 (m, 2H), 5.18-5.40 (m, 1H), 4.69 (d, 1H), 4.25-4.48 (m, 2H), 4.02-4.25 (m, 2H), 3.77-3.92 (m, 1H).

Example 432

$^1$H NMR (400 MHz, DMSO-$d_6$) δ (ppm): 8.80 (s, 1H), 8.54 (t, 1H), 8.27 (d, 1H), 8.03 (s, 1H), 7.60 (d, 1H), 7.37-7.54 (m, 3H), 7.34 (t, 1H), 7.27 (t, 1H), 7.06-7.23 (m, 2H), 5.43 (dd, 1H), 4.48 (t, 1H), 4.24-4.44 (m, 2H), 3.22 (m, 1H), 2.63-2.80 (m, 1H), 1.95 (m, 1H).

Example 446

$^1$H NMR (400 MHz, DMSO-$d_6$) δ (ppm): 8.44 (t, 1H), 8.22-8.28 (m, 1H), 7.77 (s, 1H), 7.55-7.60 (m, 1H), 7.42-7.54 (m, 3H), 7.21-7.31 (m, 2H), 7.09-7.20 (m, 2H), 4.28-4.47 (m, 2H), 4.22-4.28 (m, 1H), 3.94 (s, 2H), 3.64-3.72 (m, 1H), 2.08-2.29 (m, 2H), 1.75-1.85 (m, 1H), 0.75-0.92 (m, 1H), 0.51-0.57 (m, 1H).

Example 452

$^1$H NMR (400 MHz, DMSO-$d_6$) δ (ppm): 8.46 (t, 1H), 8.13 (d, 1H), 7.74 (s, 1H), 7.33-7.54 (m, 3H), 7.28 (t, 1H), 7.03-7.19 (m, 2H), 6.87 (dd, 1H), 4.29-4.42 (m, 2H), 4.25 (dd, 1H), 3.90 (s, 2H), 3.75 (s, 3H), 3.68 (m, 1H), 2.19-2.31 (m, 1H), 2.04-2.19 (m, 1H), 1.78 (m, 1H), 0.94 (m, 1H), 0.54 (m, 1H).

Example 466

$^1$H NMR (400 MHz, DMSO-$d_6$) δ (ppm): 8.40-8.82 (m, 1H), 8.11-8.37 (dd, 1H), 7.73 (s, 1H), 7.54-7.55 (dd, 1H), 7.07-7.46 (m, 8H), 4.90-5.04 (m, 1H), 4.34-4.47 (m, 3H), 4.08-4.16 (m, 1H), 3.61-3.87 (m, 4H)

Example 476

$^1$H NMR (400 MHz, DMSO-$d_6$) δ (ppm): 4:1 mixture of rotamers δ (ppm): 9.02 (t, 0.2H), 8.63 (t, 0.8H), 8.11-8.21 (m, 1H), 7.89-7.96 (m, 1H), 7.36-7.51 (m, 2H), 6.96-7.29 (m, 4H), 5.41-5.61 (m, 1H), 5.08-5.40 (m, 2H), 4.88 (t, 0.2H), 4.13-4.56 (m, 3.8H), 3.81-4.11 (m, 1H), 2.43-2.49 (m, 1H), 1.97-2.18 (m, 1H).

Example 483

$^1$H NMR (400 MHz, DMSO-$d_6$): 8.51-8.46 (m, 3H), 8.35 (m, 1H), 7.46 (m, 1H), 7.31 (dd, 1H), 7.21 (m, 1H), 7.09 (t, 1H), 5.53 (d, 1H), 5.37 (d, 1H), 4.41-4.27 (m, 3H), 3.72 (m, 1H), 2.47 (s, 3H), 2.26 (m, 1H), 2.19-2.13 (m, 1H), 1.89 (m, 1H), 1.08 (m, 1H), 0.75 (m, 1H).

Example 491

$^1$H NMR (400 MHz, DMSO-$d_6$) δ (ppm): 4:1 mixture of rotamers δ (ppm): 9.03 (t, 0.2H), 8.64 (t, 0.8H), 8.11-8.19 (m, 1H), 7.91-7.99 (m, 1H), 7.61 (m, 0.8H), 7.48-7.58 (br s, 1H), 7.34-7.48 (m, 1.2H), 7.11-7.28 (m, 2H), 6.97 (t, 1H), 5.43-5.63 (m, 1H), 5.09-5.43 (m, 2H), 4.89 (t, 0.2H), 4.10-4.59 (m, 3.8H), 3.83-4.05 (m, 0.8H), 3.42-3.59 (m, 0.2H), 2.71-2.85 (m, 0.2H), 2.42-2.47 (m, 0.8H), 1.98-2.27 (m, 1H).

Example 496

$^1$H NMR (400 MHz, DMSO-$d_6$): 4:1 mixture of rotamers δ (ppm): 9.01 (t, 0.2H), 8.63 (t, 0.8H), 8.12-8.19 (m, 1H), 7.89-7.94 (m, 1H), 7.36-7.49 (m, 2H), 7.20-7.27 (m, 0.8H), 7.09-7.19 (m, 3H), 6.90-7.04 (m, 0.8H), 6.74-6.81 (m, 0.2H), 6.54-6.61 (m, 0.2H), 5.33 (d, 0.8H), 5.22 (d, 0.2H), 5.07 (d, 0.8H), 4.88 (t, 0.2H), 4.56 (d, 0.2H), 4.33-4.52 (m, 2H), 4.11-4.31 (m, 1.8H), 3.90-4.03 (m, 0.2H), 3.70-3.87 (m, 0.8H), 2.46-2.54 (m, 1H, overlapped by DMSO residual signal) 1.90-2.27 (m, 1H), 1.47-1.66 (m, 3H).

Example 497

$^1$H NMR (400 MHz, DMSO-d$_6$): 4:1 mixture of rotamers δ (ppm): 9.02 (t, 0.2H), 8.82 (br. s, NH2) 8.63 (t, 0.8H), 7.83-7.90 (m, 1H), 7.66 (s, 1H), 7.12-7.51 (m, 3H), 7.02 (t, 1H), 6.72-6.80 (m, 1H), 5.39-5.58 (m, 0.8H), 5.00-5.37 (m, 2H), 4.86 (t, 0.2H), 4.23-4.62 (m, 3.4H), 4.09-4.22 (m, 0.8H), 3.81-4.05 (m, 0.8H), 3.78 (s, 3H), 2.71-2.85 (m, 0.2H), 1.97-2.26 (m, 0.8H), (NH$_2$ protons partially exchanged with deuterium).

Example 499

$^1$H NMR (400 MHz, DMSO-d$_6$): 4:1 mixture of rotamers δ (ppm): 9.03 (t, 0.2H), 8.65 (t, 0.8H), 8.00 (d, 1H), 7.72-7.84 (m, 1H), 7.33-7.48 (m, 1H), 7.24 (t, 0.8H), 7.14 (t, 0.2H), 6.88-7.01 (m, 1.6H), 6.69-6.82 (m, 1.4H), 5.40-5.61 (m, 1H), 5.30 (d, 0.8H), 5.14-5.22 (m, 0.2H), 5.05 (d, 0.8H), 4.88 (t, 0.2H), 4.23-4.57 (m, 3.2H), 4.09-4.23 (m, 0.8H), 3.80-4.06 (m, 1H), 3.68-3.77 (m, 3H), 3.42-3.61 (m, 1H), 2.71-2.84 (m, 0.2H), 1.98-2.28 (m, 0.8H), (NH$_2$ protons exchanged with deuterium).

Example 500

$^1$H NMR (400 MHz, DMSO-d$_6$): 4:1 mixture of rotamers δ (ppm): 9.05 (t, 0.2H), 8.65 (t, 0.8H), 8.06-8.12 (m, 1H), 8.01-8.05 (m, 1H), 7.35-7.47 (m, 1.2H), 7.11-7.27 (m, 1H), 6.98 (d, 0.8H), 6.92 (t, 0.8H), 6.80-6.88 (m, 1.2H), 5.40-5.61 (m, 1H), 5.28-5.39 (m, 0.8H), 5.08-5.24 (m, 1H), 4.88 (t, 0.2H), 4.59 (d, 0.2H), 4.24-4.53 (m, 2.8H), 4.08-4.20 (m, 1H), 3.83-4.05 (m, 1H), 3.68-3.77 (m, 3H), 2.70-2.84 (m, 0.2H), 2.40 (s, 3H), 1.99-2.27 (m, 0.8H).

Example 505

$^1$H NMR (400 MHz, DMSO-d$_6$) δ (ppm): 8.72 (t, 1H), 8.23 (s, 1H), 8.20 (m, 1H), 7.45 (m, 2H), 7.27 (t, 1H), 7.21 (m, 2H), 7.03 (t, 1H), 5.37 (d, 1H), 5.2 (m, 2H), 4.65 (d, 1H), 4.4 (dd, 1H), 4.3 (m, 3H), 4.1 (m, 2H), 3.4 (s, 3H), 2.42 (s, 3H).

Example 507

$^1$H NMR (400 MHz, DMSO-d$_6$) δ (ppm): 4:1 mixture of rotamers δ (ppm): 9.03 (t, 0.2H), 8.63 (t, 0.8H), 8.15-8.29 (m, 2H), 7.38-7.51 (m, 2H), 7.13-7.31 (m, 3.2H), 6.97 (t, 0.8H), 5.43-5.61 (m, 1H), 5.14-5.43 (m, 1.8H), 4.87 (t, 0.2H), 4.64 (d, 0.2H), 4.10-4.54 (m, 3.8H), 3.84-4.05 (m, 0.8H), 3.43-3.61 (m, 0.2H), 2.44 (s, 3H and m, 1H), 1.96-2.30 (m, 1H).

Example 508

$^1$H NMR (400 MHz, DMSO-d$_6$): 4:1 mixture of rotamers δ (ppm): 9.02 (t, 0.2H), 8.62 (t, 0.8H), 8.12-8.22 (m, 1H), 7.75-7.83 (m, 1H), 7.30-7.53 (m, 7H), 7.24 (t, 0.8H), 7.16 (t, 0.2H), 7.10 (d, 0.2H), 6.96-7.03 (m, 0.8H), 6.88-6.96 (m, 1H), 5.41-5.61 (m, 0.8H), 5.27-5.41 (m, 1H), 5.19-5.26 (m, 0.2H), 5.09-5.19 (m, 2.8H), 4.85 (t, 0.2H), 4.59 (d, 0.2H), 4.22-4.51 (m, 2.8H), 4.07-4.21 (m, 0.8H), 3.80-4.05 (m, 1H), 3.43-3.60 (m, 0.2H), 3.35 (m, 1H, overlapping with H$_2$O residual signal) 2.68-2.84 (m, 0.2H), 2.41 (s, 3H), 1.98-2.19 (m, 0.8H).

Example 510

$^1$H NMR (400 MHz, DMSO-d$_6$) 5 ppm 8.49 (t, 1H), 8.31 (s, 1H), 8.16-8.24 (m, 1H), 7.41-7.55 (m, 2H), 7.15-7.28 (m, 3H), 7.04 (t, 1H), 5.39 (dd, 2H), 4.37-4.46 (m, 1H), 4.21-4.35 (m, 2H), 3.68-3.80 (m, 1H), 2.45 (s, 3H), 2.23-2.33 (m, 1H), 2.11-2.22 (m, 1H), 1.80-1.95 (m, 1H), 1.00-1.13 (m, 1H), 0.70-0.82 (m, 1H).

Example 514

1H NMR (400 MHz, DMSO-d$_6$): 4:1 mixture of rotamers δ (ppm): 10.54 (s, 0.2H), 10.20 (s, 0.8H), 8.23-8.31 (m, 1H), 8.15-8.21 (m, 1H), 7.84-8.00 (m, 1H), 7.39-7.49 (m, 1H), 7.18-7.39 (m, 4H), 5.33-5.66 (m, 2H), 5.13-5.28 (m, 1H), 4.69-4.89 (m, 1H), 4.15-4.28 (m, 1H), 3.89-4.14 (m, 1H), 2.56-2.66 (m, 1H), 2.44 (s, 3H), 2.08-2.30 (m, 1H).

Example 515

$^1$H NMR (400 MHz, DMSO-d$_6$) 5 ppm 10.31 (s, 1H), 8.27-8.41 (m, 2H), 8.18 (d, 1H), 8.04-8.11 (m, 1H), 7.88 (s, 1H), 7.52 (d, 1H), 7.10-7.32 (m, 2H), 5.45 (dd, 2H), 4.31 (dd, 1H), 3.86 (t, 1H), 2.44 (s, 3H), 2.32-2.40 (m, 1H), 2.21-2.32 (m, 1H), 1.83-2.02 (m, 1H), 0.98-1.13 (m, 1H), 0.73-0.89 (m, 1H).

Example 521

$^1$H NMR (400 MHz, DMSO-d$_6$) δ (ppm): 3:1 mixture of rotamers 9.23 (t, 0.25H), 8.75 (t, 0.75H), 8.24 (s, 0.75H), 8.05-8.18 (m, 2.25H), 7.97 (m, 1H), 7.41 (m, 0.75H), 7.01-7.21 (m, 2.25H), 5.13-5.63 (m, 2.75H), 4.91 (t, 0.25H), 3.83-4.64 (m, 5H), 2.37-2.46 (m, 3H), 1.96-2.20 (m, 1H).

Example 524

$^1$H NMR (400 MHz, DMSO-d$_6$): 9.35 (s, 1H), 8.50 (t, 1H), 8.40 (s, 1H), 8.32 (d, 1H), 7.54 (d, 1H), 7.46 (m, 1H), 7.19 (t, 1H), 7.03 (t, 1H), 5.53 (d, 1H), 5.33 (d, 1H), 4.43 (dd, 1H), 4.31-4.26 (m, 2H), 3.71 (m, 1H), 2.49 (s, 3H), 2.34-2.26 (m, 1H), 2.20-2.14 (m, 1H), 1.90 (m, 1H), 1.06 (m, 1H), 0.78 (m, 1H).

Example 525

$^1$H NMR (400 MHz, DMSO-d$_6$) 5 ppm 8.61 (t, 1H), 8.30 (s, 1H), 8.14-8.20 (m, 1H), 8.11 (dd, 1H), 7.97-8.02 (m, 1H), 7.41-7.51 (m, 1H), 7.18 (dd, 2H), 5.39 (dd, 2H), 4.39-4.46 (m, 2H), 4.33 (dd, 1H), 3.71-3.79 (m, 1H), 2.44 (s, 3H), 2.13-2.37 (m, 2H), 1.86-1.98 (m, 1H), 1.02-1.15 (m, 1H), 0.74-0.84 (m, 1H).

Example 526

$^1$H NMR (400 MHz, DMSO-d$_6$): δ (ppm): 8.51-8.61 (m, 2H), 8.26-8.33 (m, 1H), 8.22 (s, 1H), 7.85 (dd, 1H), 7.37-7.44 (m, 1H), 7.16 (t, 1H), 6.91 (t, 1H), 5.63 (d, 1H), 5.40 (d, 1H), 4.38-4.47 (m, 1H), 4.24-4.33 (m, 2H), 3.67-3.91 (m, 4H), 2.47 (s, 3H), 2.26-2.35 (m, 1H), 2.13-2.22 (m, 1H), 1.85-1.96 (m, 1H), 1.04-1.13 (m, 1H), 0.73-0.80 (m, 1H).

Example 534

$^1$H NMR (400 MHz, DMSO-d$_6$): 4:1 mixture of rotamers δ (ppm): 9.05 (t, 0.2H), 8.67 (t, 0.8H), 8.13 (s, 0.8H), 8.05 (m, 1.2H), 7.29-7.50 (m, 6.2H), 7.22 (t, 0.8H), 7.08-7.15 (m, 1H), 6.83-6.98 (m, 2H), 5.41-5.63 (m, 0.8H), 5.28-5.40 (m, 1H), 4.87-5.25 (m, 3.2H), 4.23-4.67 (m, 3H), 3.83-4.21 (m, 1.8H), 3.43-3.61 (m, 0.2H), 2.54-2.60 (m, 1H), 2.41 (s, 3H), 1.99-2.21 (m, 1H).

Example 536

$^1$H NMR (400 MHz, DMSO-d$_6$): δ (ppm): 8.53 (t, 1H), 8.21 (s, 1H), 8.00-8.09 (m, 1H), 7.30-7.42 (m, 6H), 7.14-7.21 (m, 2H), 6.88-6.97 (m, 2H), 5.20-5.48 (m, 2H), 4.89-5.07 (m, 2H), 4.38-4.50 (m, 1H), 4.23-4.33 (m, 2H), 3.70-3.78 (m, 1H), 2.42 (s, 3H), 2.26-2.36 (m, 1H), 2.12-2.22 (m, 1H), 1.84-1.94 (m, 1H), 1.01-1.09 (m, 1H), 0.70-0.79 (m, 1H).

Example 542

$^1$H NMR (400 MHz, DMSO-d$_6$): 4:1 mixture of rotamers δ (ppm): 9.05 (t, 0.2H), 8.66 (t, 0.8H), 8.38-8.46 (m, 1H), 8.28 (d, 1H), 7.95-8.20 (m, 1H), 7.84 (dd, 1H), 7.34-7.48 (m, 1.2H), 7.10-7.22 (m, 1H), 6.85 (t, 0.8H), 5.28-5.63 (m, 2.8H), 4.92 (t, 0.2H), 4.72 (d, 0.2H), 4.11-4.55 (m, 3.8H), 3.88-4.06 (m, 1H), 3.78-3.88 (m, 3H), 3.35 (m, 1H, overlapping with H$_2$O residual signal) 2.56-2.61 (m, 0.2H), 2.46 (s, 3H), 2.02-2.23 (m, 0.8H).

Example 545

$^1$H NMR (400 MHz, DMSO-d$_6$): δ (ppm): 8.51 (t, 1H), 8.27-8.33 (m, 1H), 8.12 (d, 1H), 7.40-7.50 (m, 2H), 7.10-7.23 (m, 2H), 6.96-7.09 (m, 1H), 5.46 (d, 1H), 5.29 (s, 1H), 4.36-4.50 (m, 1H), 4.22-4.36 (m, 2H), 3.56-3.78 (m, 5H), 2.44 (s, 3H), 2.24-2.37 (m, 1H), 2.12-2.22 (m, 1H), 1.84-1.95 (m, 1H), 1.26 (d, 1H), 1.02-1.10 (m, 1H), 0.73-0.80 (m, 1H).

Example 548

$^1$H NMR (400 MHz, DMSO-d$_6$): 4:1 mixture of rotamers δ (ppm): 9.04 (t, 0.2H), 8.67 (t, 0.8H), 8.38-8.46 (m, 1H), 8.25-8.31 (m, 1H), 8.16 (s, 0.8H), 7.95 (s, 0.2H), 7.84 (d, 1H), 7.34-7.46 (m, 1.2H), 7.11-7.22 (m, 1H), 6.84 (t, 0.8H), 5.47-5.58 (m, 0.8H), 5.35-5.44 (m, 0.2H), 5.28 (d, 0.8H), 4.89-4.99 (m, 0.2H), 4.70 (d, 0.2H), 4.35-4.58 (m, 2H), 4.09-4.29 (m, 1.6H), 3.92-4.04 (m, 0.2H), 3.84-3.91 (m, 1H), 3.72-3.84 (m, 3H), 3.35 (m, 1H, overlapping with H$_2$O residual signal) 2.55-2.60 (m, 0.2H), 2.46 (s, 3H), 1.93-2.18 (m, 0.8H), 1.47-1.69 (m, 3H).

Example 549

$^1$H NMR (400 MHz, DMSO-d$_6$): 4:1 mixture of rotamers δ (ppm): 8.99-9.09 (m, 0.2H), 8.64 (t, 0.8H), 8.15-8.24 (m, 1H), 8.12 (d, 1H), 7.35-7.50 (m, 2H), 7.22 (t, 0.8H), 7.04-7.19 (m, 1.4H), 6.95 (t, 0.8H), 5.28-5.61 (m, 1.8H), 5.11-5.28 (m, 1H), 4.88 (t, 0.2H), 4.62 (d, 0.2H), 4.23-4.54 (m, 3H), 4.09-4.23 (m, 0.8H), 3.81-4.05 (m, 1H), 3.56-3.75 (m, 6H), 2.54-2.60 (m, 0.2H), 2.39-2.45 (m, 3H), 1.97-2.29 (m, 0.8H).

Example 550

$^1$H NMR (400 MHz, DMSO-d$_6$): 8.90 (m, 1H), 8.51 (t, 1H), 8.49 (s, 1H), 8.33 (d, 1H), 8.06 (m, 1H), 7.45 (m, 1H), 7.20 (m, 1H), 7.06 (t, 1H), 5.63 (d, 1H), 5.42 (d, 1H), 4.42 (dd, 1H), 4.32-4.28 (m, 2H), 3.72 (m, 1H), 2.48 (s, 3H), 2.34-2.26 (m, 1H), 2.21-2.14 (m, 1H), 1.90 (m, 1H), 1.08 (m, 1H), 0.81 (m, 1H).

Example 551

$^1$H NMR (400 MHz, DMSO-d$_6$) δ (ppm): 3:1 mixture of rotamers 9.24 (d, 0.25H), 8.78 (d, 0.75H), 8.31 (s, 0.75H), 8.23 (s, 0.25H), 8.13-8.21 (m, 1H), 7.69 (s, 0.25H), 7.62 (s, 0.75H), 7.32-7.50 (m, 3H), 7.10-7.27 (m, 3.25H), 7.04 (d, 0.25H), 5.43-5.63 (m, 1H), 5.06-5.43 (m, 3H), 4.94 (t, 0.25H), 4.74 (d, 0.25H), 4.40-4.67 (m, 5H), 4.09-4.24 (m, 0.75H), 3.81-4.06 (m, 1.25H), 2.00-2.21 (m, 1H).

Example 556

$^1$H NMR (400 MHz, DMSO-d$_6$) δ ppm 8.49 (t, 1H), 8.39 (s, 1H), 8.15-8.26 (m, 1H), 7.40-7.55 (m, 2H), 7.13-7.30 (m, 3H), 7.05 (t, 1H), 5.40 (dd, 2H), 4.55 (s, 2H), 4.36-4.45 (m, 1H), 4.20-4.35 (m, 2H), 3.67-3.78 (m, 1H), 2.23-2.32 (m, 1H), 2.12-2.21 (m, 1H), 1.81-1.95 (m, 1H), 1.06 (ddd, 1H), 0.71-0.82 (m, 1H).

Example 561

$^1$H NMR (400 MHz, DMSO-d$_6$) δ ppm: 4:1 mixture of rotamers 9.04 (t, 0.2H), 8.63 (t, 0.8H), 8.42-8.57 (m, 1H), 8.11-8.29 (m, 1H), 7.59 (d, 0.8H), 7.29-7.50 (m, 3.4H), 7.09-7.27 (m, 1H), 6.94 (t, 0.8H), 5.23-5.68 (m, 2.8H), 4.86 (t, 0.2H), 4.78 (d, 0.2H), 3.82-4.57 (m, 4.4H), 3.43-3.63 (m, 0.2H), 2.57 (d, 0.2H), 1.97-2.24 (m, 1H).

Example 563

$^1$H NMR (400 MHz, DMSO-d$_6$) δ ppm 4:1 mixture of rotamers 9.03 (t, 0.2H), 8.63 (t, 0.8H), 8.34 (s, 0.8H), 8.29 (s, 0.2H), 8.20 (d, 1H), 7.34-7.51 (m, 2H), 7.11-7.30 (m, 3.2H), 6.98 (t, 0.8H), 5.14-5.63 (m, 2.8H), 4.87 (t, 0.2H), 4.64 (d, 0.2H), 4.54 (s, 2H), 3.79-4.52 (m, 4.8H), 1.97-2.20 (m, 1H).

Example 564

$^1$H NMR (400 MHz, DMSO-d$_6$) δ ppm 4:1 mixture of rotamers 9.02 (t, 0.2H), 8.62 (t, 0.8H), 8.34 (s, 0.8H), 8.29 (s, 0.2H), 8.14-8.25 (m, 1H), 7.51-7.62 (m, 1H), 7.38-7.50 (m, 1H), 7.17-7.31 (m, 3H), 7.10 (t, 0.2H), 6.91 (t, 0.8H), 5.11-5.65 (m, 2.8H), 4.87 (t, 0.2H), 4.63 (d, 0.2H), 4.54 (s, 2H), 3.82-4.51 (m, 4.8H), 1.97-2.21 (m, 1H).

Example 565

$^1$H NMR (400 MHz, DMSO-d$_6$) δ (ppm): 4:1 mixture of rotamers 9.04 (t, 0.2H), 8.63 (t, 0.8H), 8.33 (s, 0.8H), 8.29 (s, 0.2H), 8.15-8.25 (m, 1H), 7.37-7.50 (m, 2H), 7.19-7.28 (m, 3H), 7.16 (t, 0.2H), 6.97 (t, 0.8H), 5.15-5.63 (m, 2.8H), 4.87 (t, 0.2H), 4.64 (d, 0.2H), 3.78-4.54 (m, 6.8H), 3.39 (s, 3H), 1.98-2.20 (m, 1H).

Example 568

$^1$H NMR (400 MHz, DMSO-d$_6$): δ (ppm): 8.41 (d, 1H), 8.29 (s, 1H), 8.19 (m, 1H), 7.48-7.42 (m, 2H), 7.30 (t, 1H), 7.26-7.20 (m, 2H), 7.10 (t, 1H), 5.47 (d, 1H), 5.28-4.21 (m, 2H), 4.33 (dd, 1H), 3.72 (m, 1H), 3.48 (d, 1H), 3.33 (d, 1H), 3.22 (s, 3H), 2.43 (s, 3H), 2.27-2.22 (m, 1H), 2.18-2.12 (m, 1H), 1.87 (m, 1H), 1.05 (m, 1H), 0.73 (m, 1H).

Example 577

$^1$H NMR (400 MHz, DMSO-d$_6$) δ (ppm): 4:1 mixture of rotamers δ (ppm): 8.99 (t, 0.2H), 8.62 (t, 0.8H), 7.78-7.85 (m, 1H), 7.56 (m, 1H), 7.35-7.51 (m, 1.2H), 7.25 (t, 0.8H), 7.14-7.20 (m, 1H), 7.04 (t, 0.8H), 6.93 (d, 0.2H), 6.59-6.66 (m, 1H), 5.38-5.59 (m, 1H), 4.96-5.31 (m, 1.8H), 4.85 (t, 0.2H), 4.09-4.52 (m, 4H), 3.96-4.04 (m, 0.2H), 3.78-3.95 (m, 0.8H), 2.40-2.49 (m, 1H, under DMSO residual peak), 1.96-2.25 (m, 1H).

Example 578

$^1$H NMR (400 MHz, DMSO-d$_6$) δ (ppm): 4:1 mixture of rotamers δ (ppm): 8.93-9.19 (m, 1H), 8.63 (t, 1H), 7.90 (d, 1H), 7.67-7.74 (m, 1H), 7.22-7.53 (m, 2H), 7.01-7.22 (m, 1H), 6.55-6.75 (m, 2H), 5.27-5.62 (m, 1H), 4.79-5.26 (m, 2H), 4.10-4.54 (m, 3.8H), 3.96-4.05 (m, 0.2H), 3.78-3.95 (m, 0.8H), 3.42-3.58 (m, 0.2H), 2.70-2.84 (m, 0.2H), 2.40-2.49 (m, 0.8H), 1.97-2.31 (m, 1H).

Example 579

$^1$H NMR (400 MHz, DMSO-d$_6$): 4:1 mixture of rotamers δ (ppm): 8.96-9.10 (m, 1.2H), 8.63 (t, 0.8H), 8.05-8.14 (m, 1H), 7.57-7.64 (m, 1H), 7.36-7.51 (m, 1.2H), 7.11-7.29 (m, 1.8H), 6.95-7.05 (m, 1H), 6.67 (dd, 1H), 5.40-5.60 (m, 0.8H), 5.04-5.35 (m, 2H), 4.84 (t, 0.2H), 4.23-4.62 (m, 3H), 3.96-4.22 (m, 1H), 3.79-3.96 (m, 0.8H), 3.42-3.59 (m, 0.2H), 3.35 (m, 1H, overlapping with H$_2$O residual signal) 2.70-2.83 (m, 0.2H), 2.38 (s, 3H), 1.97-2.17 (m, 0.8H).

Example 580

$^1$H NMR (400 MHz, DMSO-d$_6$): 4:1 mixture of rotamers δ (ppm): 8.59-9.06 (m, 1H), 8.06-8.15 (m, 1H), 7.57-7.64 (m, 1H), 7.33-7.51 (m, 1.2H), 7.13-7.30 (m, 1.8H), 6.94-7.07 (m, 1H), 6.67 (dd, 1H), 4.95-5.31 (m, 2H), 4.85 (t, 0.2H), 4.39-4.58 (m, 1.8H), 4.06-4.39 (m, 2H), 3.90-4.03 (m, 0.2H), 3.68-3.84 (m, 0.8H), 3.35 (m, 1H, overlapping with H$_2$O residual signal) 2.70-2.84 (m, 0.2H), 2.38 (s, 3H), 1.90-2.27 (m, 0.8H), 1.48-1.65 (m, 3H), (OH proton exchanged with deuterium).

Example 581

$^1$H NMR (400 MHz, DMSO-d$_6$): δ (ppm): 8.48 (t, 1H), 8.18 (s, 1H), 7.61 (d, 1H), 7.43-7.51 (m, 1H), 7.17-7.30 (m, 2H), 7.07 (t, 1H), 6.69 (dd, 1H), 5.15-5.44 (m, 2H), 4.23-4.50 (m, 3H), 3.65-3.74 (m, 1H), 2.39 (s, 3H), 2.21-2.32 (m, 1H), 2.10-2.21 (m, 1H), 1.81-1.94 (m, 1H), 0.99-1.10 (m, 1H), 0.70-0.79 (m, 1H), (OH proton exchanged with deuterium).

Example 582

$^1$H NMR (400 MHz, DMSO-d$_6$): 4:1 mixture of rotamers δ (ppm): 8.60-9.04 (m, 1H), 7.98-8.07 (m, 0.8H), 7.90-7.98 (m, 1H), 7.84-7.90 (m, 0.2H), 7.37-7.52 (m, 1.2H), 7.14-7.29 (m, 1H), 7.03 (t, 0.8H), 6.70-6.79 (m, 1.8H), 6.59 (d, 0.2H), 4.93-5.30 (m, 1.8H), 4.85 (t, 0.2H), 4.40-4.57 (m, 1.8H), 4.09-4.40 (m, 2H), 3.91-4.05 (m, 0.2H), 3.66-3.85 (m, 1H), 3.35 (m, 1H, overlapping with H$_2$O residual signal) 2.71-2.85 (m, 0.2H), 2.32-2.42 (m, 3H), 1.88-2.25 (m, 0.8H), 1.47-1.66 (m, 3H), (OH proton exchanged with deuterium).

Example 583

$^1$H NMR (400 MHz, DMSO-d$_6$): 4:1 mixture of rotamers δ (ppm): 9.18-9.36 (m, 1H), 9.00 (t, 0.2H), 8.63 (t, 0.8H), 7.89-8.17 (m, 2H), 7.37-7.53 (m, 1.2H), 7.22-7.31 (m, 0.8H), 6.99-7.21 (m, 1H), 6.58-6.82 (m, 2H), 5.40-5.61 (m, 0.8H), 5.27 (d, 1H), 4.98-5.20 (m, 1H), 4.85 (t, 0.2H), 4.23-4.58 (m, 3.2H), 4.09-4.23 (m, 0.8H), 3.78-4.07 (m, 1H), 3.35 (m, 1H, overlapping with H$_2$O residual signal) 2.69-2.83 (m, 0.2H), 2.38 (s, 3H), 1.95-2.25 (m, 0.8H).

Example 584

$^1$H NMR (400 MHz, DMSO-d$_6$): δ (ppm): 8.51 (t, 1H), 8.10 (s, 1H), 7.87-8.00 (m, 1H), 7.45 (t, 1H), 7.23 (t, 1H), 7.10 (t, 1H), 6.69-6.85 (m, 2H), 5.08-5.42 (m, 2H), 4.23-4.53 (m, 3H), 3.64-3.78 (m, 1H), 2.39 (s, 3H), 2.21-2.31 (m, 1H), 2.11-2.21 (m, 1H), 1.83-1.94 (m, 1H), 1.01-1.11 (m, 1H), 0.69-0.77 (m, 1H), (OH proton exchanged with deuterium).

Example 585

$^1$H NMR (400 MHz, DMSO-d$_6$): 4:1 mixture of rotamers δ (ppm): 9.04 (t, 0.2H), 8.66 (t, 0.8H), 8.03-8.11 (m, 1H), 7.80-7.88 (m, 1H), 7.34-7.49 (m, 1.2H), 7.23 (t, 0.8H), 7.11-7.19 (m, 1H), 6.88-7.04 (m, 2H), 5.27-5.60 (m, 3.8H), 5.21 (d, 0.2H), 5.08 (d, 0.8H), 4.88 (t, 0.2H), 4.23-4.60 (m, 3.2H), 4.09-4.23 (m, 0.8H), 3.82-4.06 (m, 1H), 3.51-3.60 (m, 1H), 2.70-2.87 (m, 0.2H), 1.95-2.31 (m, 0.8H), (NH$_2$ protons exchanged with deuterium).

Example 586

$^1$H NMR (400 MHz, DMSO-d$_6$): 4:1 mixture of rotamers δ (ppm): 9.22-9.34 (m, 1H), 8.95-9.10 (m, 0.2H), 8.59-8.79 (m, 0.8H), 7.90-8.24 (m, 2H), 7.34-7.51 (m, 1.2H), 7.14-7.29 (m, 1.6H), 6.95-7.14 (m, 1.2H), 6.70-6.95 (m, 1H), 5.28-5.62 (m, 3H), 5.01-5.27 (m, 1H), 4.82-4.92 (m, 0.2H), 4.53-4.65 (m, 0.2H), 4.23-4.53 (m, 2.8H), 4.07-4.23 (m, 0.8H), 3.76-4.07 (m, 1H), 3.35 (m, 1H, overlapping with H$_2$O residual signal) 2.37-2.44 (m, 3H), 1.94-2.28 (m, 1H).

Example 587

$^1$H NMR (400 MHz, DMSO-d$_6$): δ (ppm): 8.51 (t, 1H), 8.23 (s, 1H), 8.02-8.14 (m, 1H), 7.33-7.46 (m, 1H), 7.10-7.25 (m, 2H), 6.89-7.05 (m, 2H), 5.37-5.53 (m, 2H), 5.20-5.35 (m, 2H), 4.34-4.54 (m, 1H), 4.21-4.34 (m, 2H), 3.67-3.78 (m, 1H), 2.40-2.45 (m, 3H), 2.26-2.37 (m, 1H), 2.11-2.23 (m, 1H), 1.90 (d, 1H), 1.00-1.15 (m, 1H), 0.73-0.86 (m, 1H).

Example 588

$^1$H NMR (400 MHz, DMSO-d$_6$): 4:1 mixture of rotamers δ (ppm): 9.02 (t, 0.2H), 8.63 (t, 0.8H), 8.11-8.22 (m, 1H), 7.67-7.73 (m, 1H), 7.30-7.53 (m, 2H), 7.12-7.28 (m, 1H), 6.96-7.11 (m, 1H), 6.80-6.87 (m, 1H), 5.40-5.61 (m, 0.8H), 5.08-5.39 (m, 2H), 4.85 (t, 0.2H), 4.59 (d, 0.2H), 4.22-4.52 (m, 2.8H), 4.08-4.21 (m, 0.8H), 3.81-4.05 (m, 1H), 3.79 (s, 3H), 3.53-3.62 (m, 0.2H), 3.35 (m, 1H, overlapping with H$_2$O residual signal) 2.70-2.85 (m, 0.2H), 2.41 (s, 3H), 1.98-2.19 (m, 0.8H).

Example 589

$^1$H NMR (400 MHz, DMSO-d$_6$): 4:1 mixture of rotamers δ (ppm): 8.58-9.07 (m, 2H), 8.14-8.24 (m, 1H), 7.98 (t, 1H), 7.76-7.82 (m, 1H), 7.66 (d, 1H), 7.35-7.51 (m, 3H), 7.09-7.28 (m, 1.2H), 6.92-7.03 (m, 1.8H), 5.41-5.63 (m, 1H), 5.10-5.40 (m, 3.8H), 4.85 (t, 0.2H), 4.59 (d, 0.2H), 4.22-4.52 (m, 2.8H), 4.08-4.20 (m, 1H), 3.80-4.05 (m, 1H), 2.40 (s, 3H), 1.96-2.27 (m, 1H).

Example 590

¹H NMR (400 MHz, DMSO-d₆): 4:1 mixture of rotamers δ (ppm): 8.58-9.05 (m, 3H), 8.11-8.19 (m, 1H), 7.68-7.72 (m, 1H), 7.41-7.49 (m, 2H), 7.32-7.40 (m, 1H), 7.13-7.27 (m, 1H), 6.95-7.11 (m, 1H), 6.91 (dd, 1H), 5.40-5.59 (m, 1H), 5.27-5.39 (m, 3H), 5.09-5.25 (m, 1H), 4.85 (t, 0.2H), 4.58 (d, 0.2H), 4.42-4.51 (m, 1H), 4.23-4.42 (m, 1.8H), 4.07-4.20 (m, 0.8H), 3.80-4.04 (m, 1H), 3.35 (m, 1H, overlapping with H₂O residual signal) 2.38 (s, 3H), 1.97-2.19 (m, 1H).

Example 592

¹H NMR (400 MHz, DMSO-d₆): 4:1 mixture of rotamers δ (ppm): 9.02 (t, 0.2H), 8.65 (t, 0.8H), 8.02 (d, 1H), 7.78-7.84 (m, 1H), 7.34-7.49 (m, 1H), 7.11-7.27 (m, 1H), 6.91-7.02 (m, 1.8H), 6.81 (m, 1.2H), 5.25-5.60 (m, 1.8H), 5.18 (d, 0.2H), 5.04 (d, 0.8H), 4.87 (t, 0.2H), 4.53-4.76 (m, 2H), 4.24-4.52 (m, 3H), 4.08-4.23 (m, 0.8H), 3.81-4.06 (m, 1H), 3.69 (s, 3H), 3.42-3.59 (m, 0.2H), 2.71-2.85 (m, 0.2H), 1.97-2.18 (m, 0.8H). (NH₂ protons partially exchanged with deuterium).

Example 593

¹H NMR (400 MHz, DMSO-d₆): 4:1 mixture of rotamers δ (ppm): 12.90 (br. s, 1H), 9.01 (t, 0.2H), 8.64 (t, 0.8H), 8.02 (d, 1H), 7.77-7.85 (m, 1H), 7.36-7.50 (m, 1H), 7.24 (t, 0.8H), 7.16 (t, 0.2H), 6.94-7.04 (m, 1.6H), 6.76-6.90 (m, 1.4H), 5.39-5.61 (m, 0.8H), 5.24-5.35 (m, 1H), 5.19 (d, 0.2H), 5.05 (d, 0.8H), 4.87 (t, 0.2H), 4.24-4.68 (m, 5H), 4.09-4.22 (m, 1H), 3.81-4.05 (m, 1H), 3.43-3.64 (m, 0.8H), 3.35 (m, 0.2H, overlapping with H₂O residual signal) 2.71-2.85 (m, 0.2H), 1.98-2.17 (m, 0.8H). (NH₂ protons exchanged with deuterium).

Example 595

¹H NMR (400 MHz, DMSO-d₆): 4:1 mixture of rotamers δ (ppm): 12.29 (br. s, 1H), 9.05 (t, 0.2H), 8.64 (t, 0.8H), 8.15-8.22 (m, 1H), 8.11 (d, 1H), 7.35-7.49 (m, 2H), 7.23 (t, 0.8H), 7.09-7.19 (m, 1.4H), 6.95 (t, 0.8H), 5.41-5.63 (m, 1H), 5.38 (d, 0.8H), 5.22-5.33 (m, 0.2H), 5.16 (d, 0.8H), 4.88 (t, 0.2H), 4.61 (d, 0.2H), 4.23-4.53 (m, 3H), 4.10-4.22 (m, 0.8H), 3.81-4.06 (m, 1H), 3.48-3.64 (m, 2H), 3.35 (m, 1H, overlapping with H₂O residual signal) 2.70-2.84 (m, 0.2H), 2.42 (s, 3H), 1.98-2.27 (m, 0.8H).

Example 596

¹H NMR (400 MHz, DMSO-d₆): δ (ppm): 12.29 (br. s, 1H), 8.52 (t, 1H), 8.28 (s, 1H), 8.11 (d, 1H), 7.36-7.50 (m, 2H), 7.10-7.23 (m, 2H), 7.01 (t, 1H), 5.45 (d, 1H), 5.27 (d, 1H), 4.35-4.51 (m, 1H), 4.23-4.35 (m, 2H), 3.70-3.79 (m, 1H), 3.50-3.67 (m, 2H), 2.44 (s, 3H), 2.24-2.36 (m, 1H), 2.11-2.22 (m, 1H), 1.90 (q, 1H), 1.01-1.13 (m, 1H), 0.73-0.81 (m, 1H).

Example 597

¹H NMR (400 MHz, DMSO-d₆): 85:15 mixture of rotamers δ (ppm): 12.77 (br. s, 1H), 9.06 (t, 0.15H), 8.68 (t, 0.85H), 8.36-8.46 (m, 1H), 8.26 (d, 1H), 8.18 (s, 0.85H), 7.98 (s, 0.15H), 7.83 (d, 1H), 7.36-7.49 (m, 1.15H), 7.10-7.27 (m, 1H), 6.92 (t, 0.85H), 5.24-5.64 (m, 2.85H), 4.92 (t, 0.15H), 4.72 (d, 0.15H), 4.11-4.55 (m, 3.85H), 3.86-4.06 (m, 1H), 3.35 (m, 1H, overlapping with H₂O residual signal) 2.55-2.60 (m, 0.15H), 2.46 (s, 3H), 2.00-2.20 (m, 0.85H).

Example 598

¹H NMR (400 MHz, DMSO-d₆): δ (ppm): 8.46-8.60 (m, 2H), 8.18-8.31 (m, 2H), 7.84 (dd, 1H), 7.42 (t, 1H), 7.19 (t, 1H), 6.98 (t, 1H), 5.61 (d, 1H), 5.38 (d, 1H), 4.35-4.45 (m, 1H), 4.23-4.35 (m, 2H), 3.74-3.82 (m, 1H), 2.47 (s, 3H), 2.24-2.35 (m, 1H), 2.11-2.22 (m, 1H), 1.85-1.94 (m, 1H), 1.04-1.13 (m, 1H), 0.73-0.81 (m, 1H).

Example 599

¹H NMR (400 MHz, DMSO-d₆): 4:1 mixture of rotamers δ (ppm): 9.03 (t, 0.2H), 8.66 (t, 0.8H), 8.35-8.44 (m, 1H), 8.21-8.29 (m, 1H), 8.16 (s, 0.8H), 7.96 (s, 0.2H), 7.83 (d, 1H), 7.36-7.49 (m, 1.2H), 7.13-7.25 (m, 1H), 6.92 (t, 0.8H), 5.46-5.57 (m, 0.8H), 5.34-5.43 (m, 0.2H), 5.27 (d, 0.8H), 4.88-5.00 (m, 0.2H), 4.71 (d, 0.2H), 4.34-4.57 (m, 2H), 4.09-4.29 (m, 1.8H), 3.98 (dd, 1H), 3.73-3.91 (m, 0.8H), 3.40-3.48 (m, 0.2H), 2.55-2.60 (m, 0.2H), 2.46 (s, 3H), 1.93-2.27 (m, 0.8H), 1.47-1.67 (m, 3H), (COOH proton exchanged with deuterium).

Example 604

¹H NMR (400 MHz, DMSO-d₆): 4:1 mixture of rotamers δ (ppm): 9.04 (t, 0.2H), 8.65 (t, 0.8H), 8.14-8.21 (m, 1H), 8.10-8.14 (m, 1H), 7.38-7.47 (m, 2H), 7.14-7.26 (m, 2.2H), 6.97 (t, 0.8H), 5.43-5.61 (m, 0.8H), 5.39 (d, 0.8H), 5.12-5.32 (m, 1H), 4.88 (t, 0.2H), 4.63 (d, 0.2H), 4.52-4.59 (m, 2H), 4.34-4.52 (m, 2H), 4.11-4.32 (m, 2H), 3.83-4.06 (m, 1H), 3.35 (m, 1H, overlapping with H₂O residual signal) 2.42 (s, 3H), 1.98-2.27 (m, 1H).

Example 605

¹H NMR (400 MHz, DMSO-d₆) δ (ppm): 3:1 mixture of rotamers 9.14 (t, 0.25H), 8.69 (t, 0.75H), 8.24 (s, 1H), 8.18 (d, 1.75H), 7.92-8.02 (m, 1.25H), 7.87 (m, 1H), 7.44 (m, 1H), 7.08-7.27 (m, 3H), 5.17-5.60 (m, 3.75H), 4.85-4.95 (t, 0.25H), 4.59 (d, 0.25H), 3.78-4.55 (m, 5.75H), 2.70-2.85 (m, 0.25H), 1.90-2.16 (m, 0.75H).

Example 615

¹H NMR (400 MHz, DMSO-d₆): δ (ppm): 9.27 (s, 1H), 8.86 (s, 1H), 8.52 (d, 1H), 8.50 (m, 1H), 8.41 (d, 1H), 7.74 (d, 1H), 7.47-7.40 (m, 2H), 7.20 (t, 1H), 7.05 (t, 1H), 5.60 (d, 1H), 5.37 (d, 1H), 4.40 (dd, 1H), 3.32-4.26 (m, 2H), 3.73 (m, 1H), 3.25 (s, 3H), 3.02 (s, 3H), 2.49 (s, 3H), 2.34-2.26 (m, 1H), 2.20-2.14 (m, 1H), 1.90 (m, 1H), 1.08 (m, 1H), 0.78 (m, 1H).

Example 617

¹H NMR (400 MHz, DMSO-d₆): 85:15 mixture of rotamers δ (ppm): 9.06 (t, 0.15H), 8.70 (t, 0.85H), 8.33-8.44 (m, 2H), 8.25 (s, 0.85H), 8.09 (s, 0.15H), 7.85 (d, 1H), 7.38-7.49 (m, 0.15H), 7.28-7.35 (m, 0.85H), 7.11-7.22 (m, 1H), 6.81 (t, 1H), 5.42-5.65 (m, 1.85H), 5.27-5.42 (m, 1H), 4.93 (t, 0.15H), 4.75 (d, 0.15H), 4.11-4.58 (m, 3.85H), 3.89-4.09 (m, 1H), 2.54-2.62 (m, 0.15H), 2.48 (s, 3H), 2.00-2.29 (m, 0.85H).

Example 621

¹H NMR (400 MHz, DMSO-d₆): δ (ppm): 8.51 (t, 1H), 8.34 (d, 1H), 8.18 (br. d, 1H), 7.46 (m, 1H), 7.35 (m, 1H), 7.22

(m, 1H), 7.08 (t, 1H), 6.95 (dt, 1H), 4.63 (d, 1H), 4.24-4.45 (m, 4H), 3.69 (m, 1H), 2.51 (s, 3H), 2.29 (m, 1H), 2.18 (m, 1H), 1.84 (m, 1H), 1.02 (m, 1H), 0.79 (m, 1H).

Example 628

$^1$H NMR (400 MHz, DMSO-d$_6$): 4:1 mixture of rotamers δ (ppm): 10.51 (s, 0.2H), 10.16 (s, 0.8H), 8.18 (m, 1H), 7.91 (m, 0.2H), 7.83 (m, 0.8H), 7.65 (m, 1H), 7.62 (d, 0.8H), 7.56 (d, 0.2H), 7.46-7.22 (m, 5H), 5.66-5.24 (m, 3H), 5.08 (d, 0.2H), 4.95 (d, 0.8H), 4.56 (m, 0.2H), 4.33 (ddd, 0.8H), 4.24-4.00 (m, 1.6H), 3.87-3.60 (m, 0.4H), 3.47 (s, 0.6H), 3.43 (s, 2.4H).

Example 652

$^1$H NMR (400 MHz, DMSO-d$_6$): δ (ppm): 8.48 (br. s, 1H), 8.22 (d, 1H), 7.71 (d, 1H), 7.36-7.52 (m, 4H), 7.20 (t, 1H), 7.05 (t, 1H), 5.84 (d, 1H), 5.55 (d, 1H), 4.85 (s, 2H), 4.37-4.47 (m, 2H), 4.25-4.33 (m, 2H), 3.68-3.76 (m, 1H), 2.24-2.36 (m, 1H), 2.10-2.21 (m, 1H), 1.83-1.94 (m, 1H), 0.99-1.08 (m, 1H), 0.83 (m, 1H).

Example 657

$^1$H NMR (400 MHz, DMSO-d$_6$): δ (ppm): 9.17 (br. s, 1H), 8.65 (br. s, 1H), 8.38 (t, 1H), 8.07 (d, 1H), 7.85 (br. s, 1H), 7.56 (br. s, 1H), 7.46 (t, 1H), 7.22 (t, 1H), 6.99-7.15 (m, 1H), 5.76 (br. s, 2H), 5.45 (d, 1H), 4.38 (d, 1H), 4.28 (d, 1H), 4.15-4.24 (m, 1H), 4.02-4.12 (m, 1H).

Example 661

$^1$H NMR (400 MHz, DMSO-d$_6$): 4:1 mixture of rotamers δ (ppm): 8.99 (d, 0.8H), 8.92 (s, 0.2H), 8.63 (t, 1H), 7.90 (s, 1H), 7.77 (br. s, 1H), 7.48-7.55 (m, 1H), 7.40-7.48 (m, 1H), 7.17-7.29 (m, 1H), 7.04 (t, 1H), 5.53-5.80 (m, 1.8H), 5.43-5.50 (m, 0.2H), 5.30-5.41 (m, 0.4H), 5.19-5.27 (m, 0.2H), 5.01-5.13 (m, 0.4H), 4.66 (d, 0.8H), 4.51-4.60 (m, 0.2H), 4.34-4.49 (m, 1.2H), 4.09-4.32 (m, 2.6H), 3.95-4.09 (m, 0.8H), 3.56-3.86 (m, 0.4H), 3.39 (s, 3H), 2.61 (s, 3H).

Example 662

$^1$H NMR (400 MHz, DMSO-d$_6$): 4:1 mixture of rotamers δ (ppm): 9.12 (d, 0.8H), 8.97-9.07 (m, 0.4H), 8.64 (br. s, 0.8H), 8.37 (d, 1H), 8.07 (dd, 1H), 7.84 (br. s, 1H), 7.56 (br. s, 1H), 7.40-7.52 (m, 1.2H), 7.18-7.30 (m, 1H), 7.05 (t, 0.8H), 5.57-5.81 (m, 1.6H), 5.47 (m, 0.4H), 5.34 (m, 0.4H), 5.17-5.28 (m, 0.2H), 5.05-5.17 (m, 0.4H), 4.67 (d, 0.8H), 4.50-4.62 (m, 0.2H), 4.35-4.49 (m, 1.2H), 4.11-4.32 (m, 2.8H), 3.99-4.10 (m, 0.8H), 3.64-3.83 (m, 0.2H), 3.40 (s, 3H).

Example 663

$^1$H NMR (400 MHz, DMSO-d$_6$): 4:1 mixture of rotamers δ (ppm): 9.43 (d, 0.8H), 8.99 (m, 0.2H), 8.62 (m, 1H), 8.39-8.48 (m, 1H), 7.89 (br. s, 1H), 7.63 (m, 1.8H), 7.40-7.55 (m, 1.2H), 7.17-7.30 (m, 1.2H), 7.04 (t, 0.8H), 5.55-5.71 (m, 1H), 5.43-5.54 (m, 1H), 5.20-5.41 (m, 0.6H), 4.90-5.13 (m, 0.4H), 4.65 (d, 0.8H), 4.50-4.60 (m, 0.2H), 4.35-4.48 (m, 1.2H), 4.08-4.32 (m, 2.8H), 3.96-4.08 (m, 0.8H), 3.61-3.85 (m, 0.2H), 3.39 (s, 3H).

Example 664

$^1$H NMR (400 MHz, DMSO-d$_6$): 4:1 mixture of rotamers δ (ppm): 9.12 (s, 0.8H), 8.96-9.03 (m, 0.2H), 8.93 (s, 0.2H), 8.55-8.66 (m, 0.8H), 8.34-8.41 (m, 1H), 8.05-8.11 (m, 1H), 7.84 (br. s, 0.8H), 7.78 (br. s, 0.2H), 7.50-7.60 (m, 1H), 7.35-7.50 (m, 1.2H), 7.30 (t, 0.8H), 7.04-7.19 (m, 1H), 5.55-5.79 (m, 1.8H), 5.47 (m, 0.2H), 5.20-5.39 (m, 0.8H), 5.00-5.13 (m, 1.2H), 4.95 (d, 0.2H), 4.67 (d, 0.8H), 4.12-4.30 (m, 1.8H), 3.93-4.08 (m, 0.8H), 3.57-3.85 (m, 0.4H), 3.41-3.48 (m, 3H), 1.48 (d, 0.6H), 1.34 (d, 2.4H).

Example 668

$^1$H NMR (400 MHz, DMSO-d$_6$): δ (ppm): 9.86 (s, 1H), 9.18 (s, 1H), 8.37 (d, 1H), 8.07 (d, 1H), 7.84 (m, 1H), 7.76 (t, 1H), 7.55 (m, 1H), 7.46 (t, 1H), 7.12 (t, 1H), 5.97 (d, 1H), 5.67 (d, 1H), 4.52 (m, 1H), 3.80 (m, 1H), 2.40-2.20 (m, 2H), 1.93 (m, 1H), 1.05 (m, 1H), 0.83 (m, 1H).

Example 675

$^1$H NMR (400 MHz, DMSO-d$_6$): δ (ppm): 9.14 (s, 1H), 8.50 (m, 1H), 8.38 (d, 1H), 8.08 (d, 1H), 7.84 (m, 1H), 7.55 (m, 1H), 7.45 (t, 1H), 7.21 (t, 1H), 7.07 (t, 1H), 5.88 (d, 1H), 5.57 (d, 1H), 4.41-4.24 (m, 3H), 3.48 (m, 1H), 2.44 (dd, 3H), 1.93 (dd, 1H), 1.28 (s, 3H), 1.01-0.96 (m, 2H).

Example 684

$^1$H NMR (400 MHz, DMSO-d$_6$): δ (ppm): 9.79 (br. s, 1H), 9.19 (s, 1H), 8.37 (d, 1H), 8.08 (dd, 1H), 7.81-8.01 (m, 2H), 7.37-7.66 (m, 3H), 7.11-7.37 (m, 4H), 5.98 (d, 1H), 5.67 (d, 1H), 4.55 (dd, 1H), 3.75-3.89 (m, 1H), 2.21-2.41 (m, 2H), 1.87-2.01 (m, 1H), 0.98-1.13 (m, 1H), 0.82 (m, 1H).

Example 685

$^1$H NMR (400 MHz, DMSO-d$_6$): δ (ppm): 9.79 (br. s, 1H), 9.28 (s, 1H), 8.40 (d, 1H), 8.15 (d, 1H), 7.91 (t, 2H), 7.53-7.70 (m, 2H), 7.32-7.53 (m, 3H), 7.24 (t, 1H), 6.97-7.14 (m, 1H), 6.00 (d, 1H), 5.69 (d, 1H), 4.56 (dd, 1H), 3.75-3.86 (m, 1H), 2.23-2.40 (m, 2H), 1.85-2.01 (m, 1H), 0.94-1.13 (m, 1H), 0.82 (td, 1H).

Example 686

$^1$H NMR (400 MHz, DMSO-d$_6$): δ (ppm): 9.81 (br. s, 1H), 8.58 (m, 1H), 8.19 (d, 1H), 7.81-8.03 (m, 2H), 7.48-7.73 (m, 3H), 7.23-7.47 (m, 4H), 5.82 (d, 1H), 5.51 (d, 1H), 4.54 (dd, 1H), 3.76-3.84 (m, 1H), 2.32 (m, 2H), 1.86-1.98 (m, 1H), 1.00-1.10 (m, 1H), 0.71-0.81 (m, 1H).

Example 688

$^1$H NMR (400 MHz, DMSO-d$_6$): δ (ppm): 9.81 (br. s, 1H), 9.22 (s, 1H), 8.64 (dd, 1H), 8.38 (d, 1H), 8.02-8.19 (m, 2H), 7.82-8.02 (m, 2H), 7.46-7.63 (m, 2H), 7.27 (t, 1H), 7.18-7.23 (m, 1H), 5.99 (d, 1H), 5.68 (d, 1H), 4.55 (dd, 1H), 3.75-3.91 (m, 1H), 2.19-2.41 (m, 2H), 1.84-2.03 (m, 1H), 0.96-1.17 (m, 1H), 0.75-0.90 (m, 1H).

Example 690

$^1$H NMR (400 MHz, DMSO-d$_6$): δ (ppm): 8.42-8.51 (m, 1H), 7.52 (br. s, 2H), 7.46 (t, 1H), 7.28 (br. s, 1H), 7.20 (t, 1H), 7.11 (s, 1H), 7.06 (t, 1H), 5.62 (d, 1H), 5.35 (d, 1H), 4.37-4.47 (m, 1H), 4.22-4.35 (m, 3H), 3.63-3.71 (m, 1H), 2.21-2.32 (m, 1H), 2.09-2.20 (m, 1H), 1.81-1.92 (m, 1H), 0.97-1.06 (m, 1H), 0.67-0.76 (m, 1H).

Example 693

$^1$H NMR (400 MHz, DMSO-d$_6$): δ (ppm): 8.40-8.48 (m, 1H), 8.24 (d, 1H), 8.08 (d, 1H), 7.89-7.98 (m, 1H), 7.58 (br. s, 1H), 7.37-7.44 (m, 1H), 7.27 (t, 1H), 6.98 (t, 1H), 6.00 (d, 1H), 5.72 (d, 1H), 5.04 (m, 1H), 4.29 (dd, 1H), 3.74-3.81 (m, 1H), 2.78 (s, 3H), 2.29 (dd, 1H), 2.09-2.20 (m, 1H), 1.84-1.97 (m, 1H), 1.33 (d, 3H), 1.01-1.11 (m, 1H), 0.68 (m, 1H).

Example 694

$^1$H NMR (400 MHz, DMSO-d$_6$): δ (ppm): 8.48 (t, 1H), 8.24 (d, 1H), 8.08 (d, 1H), 7.90 (br. s, 1H), 7.61 (br. s, 1H), 7.45 (t, 1H), 7.21 (t, 1H), 7.06 (t, 1H), 6.02 (d, 1H), 5.75 (d, 1H), 4.20-4.40 (m, 3H), 3.71-3.85 (m, 1H), 2.84 (s, 3H), 2.31 (dd, 1H), 2.14 (m, 1H), 1.83-2.01 (m, 1H), 0.99-1.16 (m, 1H), 0.62-0.80 (m, 1H).

Example 695

$^1$H NMR (400 MHz, DMSO-d$_6$): δ (ppm): 8.47 (br. s, 1H), 8.00 (br. s, 1H), 7.88 (br. s, 1H), 7.61 (br. s, 1H), 7.45 (t, 1H), 7.21 (t, 1H), 7.02-7.12 (m, 1H), 6.01 (d, 1H), 5.73 (d, 1H), 4.22-4.40 (m, 3H), 3.73-3.82 (m, 1H), 2.85 (s, 3H), 2.62 (s, 3H), 2.31 (dd, 1H), 2.07-2.19 (m, 1H), 1.85-1.96 (m, 1H), 1.00-1.12 (m, 1H), 0.64-0.76 (m, 1H).

Example 696

$^1$H NMR (400 MHz, DMSO-d$_6$): δ (ppm): 8.36-8.50 (m, 1H), 7.96 (m, 1H), 7.63 (br. s, 1H), 7.40 (t, 1H), 7.27 (t, 1H), 6.98 (t, 1H), 6.02 (d, 1H), 5.71 (d, 1H), 4.97-5.13 (m, 1H), 4.28 (dd, 1H), 3.72-3.83 (m, 1H), 2.82 (s, 3H), 2.60-2.72 (m, 3H), 2.21-2.39 (m, 1H), 2.07-2.19 (m, 1H), 1.83-1.97 (m, 1H), 1.33 (d, 3H), 1.01-1.13 (m, 1H), 0.62-0.76 (m, 1H).

Example 697

$^1$H NMR (400 MHz, DMSO-d$_6$): 4:1 mixture of rotamers δ (ppm): 9.09 (s, 0.8H), 9.01 (br. s, 0.2H), 8.59-8.69 (m, 1H), 7.89-8.00 (m, 1H), 7.81 (br. s, 1H), 7.48-7.59 (m, 1.2H), 7.38-7.48 (m, 1H), 7.18-7.30 (m, 1H), 7.04 (t, 0.8H), 5.56-5.80 (m, 1.8H), 5.20-5.52 (m, 0.8H), 5.10 (m, 0.4H), 4.66 (d, 0.8H), 4.50-4.61 (m, 0.2H), 4.33-4.49 (m, 1.4H), 3.97-4.33 (m, 3.4H), 3.60-3.86 (m, 0.2H), 3.39 (s, 3H), 2.92 (m, 2H), 1.20-1.40 (m, 3H).

Example 702

$^1$H NMR (400 MHz, DMSO-d$_6$): δ (ppm): 9.14 (s, 1H), 8.30-8.47 (m, 2H), 8.07 (m, 1H), 7.88 (br. s, 1H), 7.53 (br. s, 1H), 7.35-7.46 (m, 1H), 7.28 (t, 1H), 6.94-7.16 (m, 1H), 5.90 (d, 1H), 5.62 (d, 1H), 5.06 (quin, 1H), 4.30 (dd, 1H), 3.57-3.78 (m, 1H), 2.20-2.36 (m, 1H), 2.06-2.20 (m, 1H), 1.76-1.99 (m, 1H), 1.33 (d, 3H), 0.94-1.10 (m, 1H), 0.70-0.84 (m, 1H).

Example 703

$^1$H NMR (400 MHz, DMSO-d$_6$): δ (ppm): 9.16 (s, 1H), 8.45-8.54 (m, 1H), 8.38 (d, 1H), 8.08 (dd, 1H), 7.85 (br. s, 1H), 7.55 (br. s, 1H), 7.45 (t, 1H), 7.20 (t, 1H), 7.07 (t, 1H), 5.92 (d, 1H), 5.63 (d, 1H), 4.36-4.51 (m, 1H), 4.25-4.33 (m, 2H), 3.68-3.75 (m, 1H), 2.24-2.37 (m, 1H), 2.10-2.22 (m, 1H), 1.84-1.95 (m, 1H), 1.00-1.10 (m, 1H), 0.80 (m, 1H).

Example 705

$^1$H NMR (400 MHz, DMSO-d$_6$): δ (ppm): 8.99 (br. s, 1H), 8.40-8.54 (m, 1H), 8.02 (s, 2H), 7.88 (br. s, 1H), 7.61 (br. s, 1H), 7.36-7.53 (m, 1H), 7.17-7.28 (m, 1H), 7.04-7.17 (m, 1H), 5.75 (d, 1H), 5.45 (d, 1H), 4.24-4.48 (m, 3H), 3.58-3.71 (m, 1H), 2.21-2.32 (m, 1H), 2.10-2.21 (m, 1H), 1.82-1.93 (m, 1H), 0.97-1.07 (m, 1H), 0.82 (m, 1H).

Example 706

$^1$H NMR (400 MHz, DMSO-d$_6$): δ (ppm): 8.98 (s, 1H), 8.39 (m, 1H), 8.01 (d, 2H), 7.90 (br. s, 1H), 7.58 (br. s, 1H), 7.36-7.49 (m, 1H), 7.29 (t, 1H), 7.06-7.19 (m, 1H), 5.73 (d, 1H), 5.43 (d, 1H), 5.06 (quin, 1H), 4.28 (dd, 1H), 3.60-3.69 (m, 1H), 2.24 (m, 1H), 2.12 (m, 1H), 1.80-1.92 (m, 1H), 1.34 (d, 3H), 0.95-1.05 (m, 1H), 0.76-0.86 (m, 1H).

Example 707

$^1$H NMR (400 MHz, DMSO-d$_6$): δ (ppm): 9.96 (br. s, 1H), 8.19 (d, 1H), 7.78-7.88 (m, 1H), 7.65 (d, 2H), 7.21-7.49 (m, 5H), 5.81 (d, 1H), 5.51 (d, 1H), 4.50 (dd, 1H), 3.78-3.85 (m, 1H), 2.22-2.39 (m, 2H), 1.92 (m, 1H), 1.04 (dt, 1H), 0.77 (m, 1H).

Example 708

$^1$H NMR (400 MHz, DMSO-d$_6$): 4:1 mixture of rotamers δ (ppm): 10.52 (s, 0.1H), 10.19 (s, 0.9H), 8.12-8.25 (m, 1H), 7.84-7.98 (m, 1H), 7.63 (d, 2H), 7.34-7.47 (m, 2H), 7.20-7.34 (m, 3H), 5.54-5.75 (m, 2H), 5.38-5.54 (m, 0.9H), 4.96-5.27 (m, 0.2H), 4.73 (t, 0.9H), 4.16-4.33 (m, 1H), 4.00 (dd, 1H), 3.91 (m, 1H), 2.56-2.65 (m, 1H), 2.04-2.31 (m, 1H).

Example 709

$^1$H NMR (400 MHz, DMSO-d$_6$): δ (ppm): 9.97 (d, 1H), 9.49 (s, 1H), 8.50 (d, 1H), 7.99 (br. s, 1H), 7.79-7.86 (m, 2H), 7.69 (br. s, 1H), 7.22-7.37 (m, 2H), 5.90 (d, 1H), 5.59 (d, 1H), 4.51 (dd, 1H), 3.76-3.83 (m, 1H), 2.21-2.39 (m, 2H), 1.89-1.98 (m, 1H), 0.99-1.09 (m, 1H), 0.79 (m, 1H).

Example 712

$^1$H NMR (400 MHz, DMSO-d$_6$): δ (ppm): 9.97 (br. s, 1H), 9.17 (br. s, 1H), 7.99 (s, 1H), 7.79-7.89 (m, 2H), 7.57 (br. s, 1H), 7.23-7.38 (m, 2H), 5.97 (d, 1H), 5.65 (d, 1H), 4.51 (dd, 1H), 3.76-3.86 (m, 1H), 2.93 (q, 2H), 2.23-2.41 (m, 2H), 1.87-1.99 (m, 1H), 1.30 (t, 3H), 1.01-1.11 (m, 1H), 0.82 (td, 1H).

Example 716

$^1$H NMR (400 MHz, DMSO-d$_6$): δ (ppm): 10.01 (br. s, 1H), 8.24 (d, 1H), 8.09 (d, 1H), 7.80-7.99 (m, 2H), 7.61 (br. s, 1H), 7.21-7.36 (m, 2H), 6.11 (d, 1H), 5.76 (d, 1H), 4.52 (dd, 1H), 3.81-3.93 (m, 1H), 2.90 (s, 3H), 2.39 (m, 1H), 2.21-2.33 (m, 1H), 1.90-2.03

Example 717

$^1$H NMR (400 MHz, DMSO-d$_6$): δ (ppm): 10.01 (br. s, 1H), 7.96 (m, 1H), 7.69-7.91 (m, 2H), 7.59 (br. s, 1H), 7.16-7.39 (m, 2H), 6.09 (d, 1H), 5.72 (d, 1H), 4.51 (dd, 1H), 3.73-3.98 (m, 1H), 2.88 (s, 3H), 2.59 (s, 3H), 2.31-2.45 (m, 1H), 2.20-2.31 (m, 1H), 1.95 (dt, 1H), 1.02-1.13 (m, 1H), 0.68-0.78 (m, 1H).

Example 718

$^1$H NMR (400 MHz, DMSO-d$_6$): δ (ppm): 9.95 (br. s, 1H), 8.85 (d, 2H), 7.78-7.87 (m, 1H), 7.64 (d, 1H), 7.57 (s, 1H), 7.47 (t, 1H), 7.17-7.37 (m, 3H), 5.88 (d, 1H), 5.55 (d, 1H), 5.36 (s, 2H), 4.51 (dd, 1H), 3.77-3.86 (m, 1H), 2.58 (s, 3H), 2.23-2.37 (m, 2H), 1.84-1.97 (m, 1H), 0.95-1.09 (m, 1H), 0.74-0.89 (m, 1H).

Example 719

$^1$H NMR (400 MHz, DMSO-$d_6$): δ (ppm): 9.96 (br. s, 1H), 8.93-9.08 (m, 1H), 7.92 (d, 1H), 7.70-7.86 (m, 2H), 7.49 (br. s, 1H), 7.19-7.39 (m, 2H), 5.90 (d, 1H), 5.60 (d, 1H), 4.50 (dd, 1H), 3.74-3.85 (m, 1H), 2.15-2.42 (m, 3H), 1.84-2.03 (m, 1H), 0.99-1.09 (m, 1H), 0.89-0.99 (m, 4H), 0.76-0.84 (m, 1H).

Example 721

$^1$H NMR (400 MHz, DMSO-$d_6$): δ (ppm): 10.63 (br. s, 1H), 9.29 (s, 1H), 8.40 (d, 1H), 8.05-8.23 (m, 2H), 7.82-8.02 (m, 2H), 7.44-7.71 (m, 2H), 7.15-7.33 (m, 3H), 6.02 (d, 1H), 5.69 (d, 1H), 4.43-4.60 (m, 1H), 3.72-3.93 (m, 1H), 2.20-2.38 (m, 2H), 1.87-1.97 (m, 1H), 1.00-1.08 (m, 1H), 0.75-0.84 (m, 1H).

Example 723

$^1$H NMR (400 MHz, DMSO-$d_6$): δ (ppm): 9.98 (br. s, 1H), 9.25 (br. s, 1H), 8.09 (br. s, 1H), 7.90 (br. s, 1H), 7.78-7.87 (m, 1H), 7.61 (br. s, 1H), 7.22-7.39 (m, 2H), 5.99 (d, 1H), 5.67 (d, 1H), 4.51 (dd, 1H), 3.76-3.86 (m, 1H), 2.67 (s, 3H), 2.21-2.41 (m, 2H), 1.88-1.99 (m, 1H), 1.05 (dt, 1H), 0.82 (m, 1H).

Example 724

$^1$H NMR (400 MHz, DMSO-$d_6$): δ (ppm): 9.98 (br. s, 1H), 9.22 (s, 1H), 8.39 (d, 1H), 8.11 (d, 1H), 7.77-7.93 (m, 2H), 7.47-7.67 (m, 1H), 7.22-7.36 (m, 2H), 5.99 (d, 1H), 5.68 (d, 1H), 4.52 (dd, 1H), 3.76-3.86 (m, 1H), 2.21-2.40 (m, 2H), 1.87-1.99 (m, 1H), 1.01-1.10 (m, 1H), 0.83 (m, 1H).

Example 726

$^1$H NMR (400 MHz, DMSO-$d_6$): δ (ppm): 9.98 (br. s, 1H), 9.08 (s, 1H), 8.10 (s, 1H), 7.78-7.90 (m, 2H), 7.57 (br. s, 1H), 7.22-7.36 (m, 2H), 5.79 (d, 1H), 5.47 (d, 1H), 4.50 (m, 1H), 3.60-3.83 (m, 1H), 2.44 (s, 3H), 2.21-2.38 (m, 2H), 1.91 (m, 1H), 0.97-1.07 (m, 1H), 0.80-0.90 (m, 1H).

Example 727

$^1$H NMR (400 MHz, DMSO-$d_6$): δ (ppm): 10.77 (m, 1H), 8.18 (d, 1H), 8.03 (d, 1H), 7.72 (t, 1H), 7.70 (m, 1H), 7.65 (d, 1H), 7.43 (t, 1H), 7.40 (m, 1H), 7.33 (d, 1H), 7.27 (t, 1H), 5.82 (d, 1H), 5.50 (d, 1H), 4.45 (m, 1H), 3.80 (m, 1H), 2.32 (m, 1H), 2.21 (m, 1H), 1.90 (m, 1H), 1.01 (m, 1H), 0.75 (m, 1H).

Example 731

$^1$H NMR (400 MHz, DMSO-$d_6$): δ (ppm): 9.86 (m, 1H), 8.19 (d, 1H), 7.74 (br. t, 1H), 7.67 (m, 1H), 7.66 (d, 1H), 7.45 (br. t, 1H), 7.39 (m, 1H), 7.34 (br. t, 1H), 7.28 (td, 1H), 5.81 (d, 1H), 5.51 (d, 1H), 4.50 (dd, 1H), 3.80 (m, 1H), 2.30 (m, 2H), 1.92 (m, 1H), 1.04 (m, 1H), 0.77 (m, 1H).

Example 741

$^1$H NMR (400 MHz, DMSO-$d_6$): δ (ppm): 11.14 (br.s, 1H), 9.27 (s, 1H), 8.55 (s, 1H), 8.18 (d, 1H), 7.68 (m, 1H), 7.66 (d, 1H), 7.45 (t, 1H), 7.38 (m, 1H), 7.27 (t, 1H), 5.83 (d, 1H), 5.51 (d, 1H), 4.47 (m, 1H), 3.83 (m, 1H), 2.32-2.37 (m, 1H), 2.22-2.28 (m, 1H), 1.91 (m, 1H), 1.01 (m, 1H), 0.77 (m, 1H).

Example 744

$^1$H NMR (400 MHz, DMSO-$d_6$): δ (ppm): 10.77 (m, 1H), 8.18 (d, 1H), 8.04 (d, 1H), 7.72 (t, 1H), 7.67 (m, 1H), 7.64 (d, 1H), 7.44 (t, 1H), 7.37 (m, 1H), 7.33 (d, 1H), 7.26 (t, 1H), 5.78 (d, 1H), 5.44 (d, 1H), 4.40 (m, 1H), 3.59 (m, 1H), 2.46 (dd, 1H), 1.98 (dd, 1H), 1.90 (m, 1H), 1.30 (s, 3H), 0.96 (br. t, 1H), 0.90 (dd, 1H).

Example 746

$^1$H NMR (400 MHz, DMSO-$d_6$) δ (ppm): 90:10 mixture of rotamers, only the major rotamer is described: δ (ppm): 10.85 (s, 1H), 8.16 (d, 1H), 8.01 (d, 1H), 7.70 (t, 1H), 7.64 (d, 1H), 7.62 (m, 1H), 7.43 (t, 1H), 7.37 (m, 1H), 7.31 (d, 1H), 7.25 (t, 1H), 5.44 (s, 2H), 4.62 (br. d, 1H), 4.00 (dd, 1H), 3.87 (d, 1H), 1.99 (m, 1H), 1.87 (m, 1H), 0.78 (m, 1H), 0.73 (m, 1H).

Example 754

$^1$H NMR (400 MHz, DMSO-$d_6$) δ (ppm): 85:15 mixture of rotamers, only the major rotamer is described: δ (ppm): 10.98 (m, 1H), 8.17 (d, 1H), 8.03 (d, 1H), 7.72 (t, 1H), 7.64 (d, 1H), 7.63 (m, 1H), 7.44 (t, 1H), 7.38 (m, 1H), 7.34 (d, 1H), 7.26 (t, 1H), 5.63 (d, 1H), 5.51 (d, 1H), 5.50-5.34 (m, 1H), 4.90 (m, 1H), 4.33 (m, 1H), 4.23-4.03 (m, 2H), 3.41 (s, 3H).

Example 762

$^1$H NMR (400 MHz, DMSO-$d_6$): δ (ppm): 10.68 (m, 1H), 8.65 (m, 1H), 8.28 (d, 1H), 8.10 (d, 1H), 8.00 (s, 1H), 7.80 (d, 1H), 7.75 (t, 1H), 7.38 (m, 2H), 7.35 (d, 1H), 7.27 (t, 1H), 7.20 (t, 1H), 4.35 (t, 1H), 3.93 (m, 1H), 2.38 (dd, 1H), 2.17 (m, 1H), 1.80 (m, 1H), 0.85 (m, 1H), 0.55 (m, 1H).

Example 770

$^1$H NMR (400 MHz, DMSO-$d_6$): 4:1 mixture of rotamers δ (ppm): 9.95 (s, 1H), 7.81 (m, 1H), 7.63 (d, 1H), 7.56 (d, 1H), 7.30 (m, 1H), 7.27 (m, 1H), 7.14 (dd, 1H), 5.89-5.52 (AB system, 2H), 4.50 (dd, 1H), 4.14 (m, 2H), 3.80 (m, 1H), 3.70 (m, 2H), 3.32 (s, 3H), 2.59 (s, 3H), 2.29 (m, 2H), 1.91 (m, 1H), 1.02 (m, 1H), 0.81 (m, 1H).

Example 773

$^1$H NMR (600 MHz, DMSO-$d_6$) δ (ppm): 85:15 mixture of rotamers δ (ppm): 9.15 (t, 0.15H), 8.72 (t, 0.85H), 8.32 (s, 0.15H), 8.23 (s, 0.85H), 8.19-8.20 (m, 1H), 7.48-7.49 (m, 1H), 7.44 (m, 0.85H), 7.41 (m, 0.15H), 7.20-7.23 (m, 2H), 7.18 (t, 0.15H), 7.01 (t, 0.85H), 5.75 (m, 0.15H), 5.67 (m, 0.15H), 5.61 (m, 0.85H), 5.52 (m, 1H), 5.45 (d, 0.85H), 5.28 (d, 0.15H), 5.22 (d, 0.85H), 4.72 (m, 1H), 4.54 (m, 0.3H), 4.43 (dd, 0.85H), 4.31 (dd, 0.85H), 4.08-4.25 (m, 1.70H), 4.01 (m, 0.15H), 3.70 (m, 0.15H), 2.43 (s, 3H).

Factor D Inhibition Data Using Method 1 to Determine the $IC_{50}$s.

| Example | $IC_{50}$ (nM) |
| --- | --- |
| 1 | 7 |
| 2 | 25 |
| 3 | 450 |
| 4 | 3980 |
| 5 | 30 |

-continued

| Example | IC$_{50}$ (nM) |
|---|---|
| 6 | 2100 |
| 7 | 32 |
| 8 | 9 |
| 9 | 250 |
| 10 | 604 |
| 11 | 7 |
| 12 | 11135 |
| 13 | 139 |
| 14 | 55 |
| 15 | 1100 |
| 16 | 94 |
| 17 | 4048 |
| 18 | 815 |
| 19 | 10 |
| 20 | 1126 |
| 21 | 31 |
| 22 | 191 |
| 23 | 1850 |
| 24 | 1700 |
| 25 | 6750 |
| 26 | 25 |
| 27 | 8300 |
| 28 | 2525 |
| 29 | 588 |
| 30 | 2700 |
| 31 | 12150 |
| 32 | 3350 |
| 33 | 24050 |
| 34 | 90 |
| 35 | 2850 |
| 36 | 3250 |
| 37 | 22000 |
| 38 | 6300 |
| 39 | 1050 |
| 40 | 11150 |
| 41 | 3200 |
| 42 | 2850 |
| 43 | 7750 |
| 44 | 2600 |
| 45 | 22500 |
| 46 | 22800 |
| 47 | 8950 |
| 48 | 7500 |
| 49 | 900 |
| 50 | 21600 |
| 51 | 8500 |
| 52 | 400 |
| 53 | 1750 |
| 54 | 1850 |
| 55 | 125 |
| 56 | 1950 |
| 57 | 1350 |
| 58 | 350 |
| 59 | 6400 |
| 60 | 800 |
| 61 | 7100 |
| 62 | 85 |
| 63 | 11400 |
| 64 | 22450 |
| 65 | 13100 |
| 66 | 65 |
| 67 | 22200 |
| 68 | 15100 |
| 69 | 1050 |
| 70 | 2575 |
| 71 | 2900 |
| 72 | 7000 |
| 73 | 325 |
| 74 | 3650 |
| 75 | 12550 |
| 76 | 15650 |
| 77 | 14550 |
| 78 | 10400 |
| 79 | 6000 |
| 80 | 14950 |
| 81 | 4750 |
| 82 | 24750 |

-continued

| Example | IC$_{50}$ (nM) |
|---|---|
| 83 | 2250 |
| 84 | 6000 |
| 85 | 11350 |
| 86 | 14300 |
| 87 | 4650 |
| 88 | 6800 |
| 89 | 7700 |
| 90 | 1150 |
| 91 | 2950 |
| 92 | 8650 |
| 93 | 4000 |
| 94 | 10950 |
| 95 | 1350 |
| 96 | 8050 |
| 97 | 900 |
| 98 | 1850 |
| 99 | 23250 |
| 100 | 17550 |
| 101 | 15200 |
| 102 | 567 |
| 103 | 550 |
| 104 | 1487 |
| 105 | 800 |
| 106 | 700 |
| 107 | 75 |
| 108 | 55 |
| 109 | 2700 |
| 110 | 20 |
| 111 | 60 |
| 112 | 550 |
| 113 | 1150 |
| 114 | 500 |
| 115 | 1536 |
| 116 | 1150 |
| 117 | 11850 |
| 118 | 17500 |
| 119 | 4800 |
| 120 | 3200 |
| 121 | 1250 |
| 122 | 150 |
| 123 | 2930 |
| 124 | 500 |
| 125 | 5100 |
| 126 | 100 |
| 127 | 3 |
| 128 | 2000 |
| 129 | 4 |
| 130 | 54 |
| 131 | 4600 |
| 132 | 18 |
| 133 | 6 |
| 134 | 500 |
| 135 | 59 |
| 136 | 17900 |
| 137 | 300 |
| 138 | 9 |
| 139 | 1500 |
| 140 | 18300 |
| 141 | 650 |
| 142 | 19 |
| 143 | 350 |
| 144 | 15 |
| 145 | 300 |
| 146 | 9 |
| 147 | 120 |
| 148 | 45 |
| 149 | 10800 |
| 150 | 25 |
| 151 | 9323 |
| 152 | 4400 |
| 153 | 55 |
| 154 | 1367 |
| 155 | 20 |
| 156 | 150 |
| 157 | 850 |
| 158 | 80 |
| 159 | 55 |

-continued

| Example | IC$_{50}$ (nM) |
|---|---|
| 160 | 1400 |
| 161 | 987 |
| 162 | 5 |
| 163 | 100 |
| 164 | 400 |
| 165 | 140 |
| 166 | 3 |
| 167 | 108 |
| 168 | 250 |
| 169 | 268 |
| 170 | 30 |
| 171 | 200 |
| 172 | 1050 |
| 173 | 111 |
| 174 | 35 |
| 175 | 10 |
| 176 | 30 |
| 177 | 85 |
| 178 | 6 |
| 179 | 400 |
| 180 | 650 |
| 181 | 20 |
| 182 | 63 |
| 183 | 20 |
| 184 | 9 |
| 185 | 550 |
| 186 | 20 |
| 187 | 22200 |
| 188 | 1067 |
| 189 | 942 |
| 190 | 20 |
| 191 | 48 |
| 192 | 17750 |
| 193 | 160 |
| 194 | 93 |
| 195 | 14 |
| 196 | 700 |
| 197 | 100 |
| 198 | 357 |
| 199 | 8650 |
| 200 | 25 |
| 201 | 20 |
| 202 | 450 |
| 203 | 6 |
| 204 | 7 |
| 205 | 14 |
| 206 | 187 |
| 207 | 321 |
| 208 | 29 |
| 209 | 1900 |
| 210 | 22 |
| 211 | 1319 |
| 212 | 10 |
| 213 | 12 |
| 214 | 1572 |
| 215 | 386 |
| 216 | 65 |
| 217 | 41 |
| 218 | 24 |
| 219 | 1850 |
| 220 | 233 |
| 221 | 23 |
| 222 | 137 |
| 223 | 12 |
| 224 | 700 |
| 225 | 350 |
| 226 | 417 |
| 227 | 800 |
| 228 | 100 |
| 229 | 29 |
| 230 | 2550 |
| 231 | 103 |
| 232 | 989 |
| 233 | 850 |
| 234 | 150 |
| 235 | 80 |
| 236 | 8 |

-continued

| Example | IC$_{50}$ (nM) |
|---|---|
| 237 | 70 |
| 238 | 650 |
| 239 | 52 |
| 240 | 141 |
| 241 | 250 |
| 242 | 200 |
| 243 | 200 |
| 244 | 17 |
| 245 | 1046 |
| 246 | 2000 |
| 247 | 400 |
| 248 | 119 |
| 249 | 1425 |
| 250 | 549 |
| 251 | 325 |
| 252 | 114 |
| 253 | 1068 |
| 254 | 150 |
| 255 | 434 |
| 256 | 4000 |
| 257 | 3950 |
| 258 | 78 |
| 259 | 25 |
| 260 | 200 |
| 261 | 75 |
| 262 | 200 |
| 263 | 400 |
| 264 | 10 |
| 265 | 83 |
| 266 | 1625 |
| 267 | 83 |
| 268 | 8 |
| 269 | 1600 |
| 270 | 54 |
| 271 | 629 |
| 272 | 271 |
| 273 | 2263 |
| 274 | 14 |
| 275 | 30 |
| 276 | 1310 |
| 277 | 627 |
| 278 | 350 |
| 279 | 2900 |
| 280 | 250 |
| 281 | 18 |
| 282 | 3675 |
| 283 | 900 |
| 284 | 286 |
| 285 | 55 |
| 286 | 2650 |
| 287 | 112 |
| 288 | 1100 |
| 289 | 555 |
| 290 | 15783 |
| 291 | 3250 |
| 292 | 3 |
| 293 | 35 |
| 294 | 5 |
| 295 | 150 |
| 296 | 218 |
| 297 | 350 |
| 298 | 7 |
| 299 | 1800 |
| 300 | 4 |
| 301 | 95 |
| 302 | 75 |
| 303 | 8 |
| 304 | 653 |
| 305 | 1354 |
| 306 | 4 |
| 307 | 13300 |
| 308 | 127 |
| 309 | 550 |
| 310 | 475 |
| 311 | 70 |
| 312 | 115 |
| 313 | 1300 |

| Example | IC$_{50}$ (nM) | | Example | IC$_{50}$ (nM) |
|---|---|---|---|---|
| 314 | 20 | | 391 | 30 |
| 315 | 13 | | 392 | 7 |
| 316 | 3100 | | 393 | 7 |
| 317 | 2800 | | 394 | 70 |
| 318 | 3 | | 395 | 25 |
| 319 | 548 | | 396 | 667 |
| 320 | 7 | | 397 | 3161 |
| 321 | 85 | | 398 | 3050 |
| 322 | 348 | | 399 | 1600 |
| 323 | 902 | | 400 | 3950 |
| 324 | 4250 | | 401 | 1050 |
| 325 | 2250 | | 402 | 300 |
| 326 | 7151 | | 403 | 1000 |
| 327 | 1700 | | 404 | 1000 |
| 328 | 102 | | 405 | 295 |
| 329 | 181 | | 406 | 150 |
| 330 | 250 | | 407 | 1050 |
| 331 | 35 | | 408 | 1400 |
| 332 | 450 | | 409 | 25 |
| 333 | 47 | | 410 | 15 |
| 334 | 53 | | 411 | 26 |
| 335 | 550 | | 412 | 14 |
| 336 | 750 | | 413 | 101 |
| 337 | 250 | | 414 | 311 |
| 338 | 18900 | | 415 | 48 |
| 339 | 65 | | 416 | 315 |
| 340 | 29 | | 417 | 40 |
| 341 | 95 | | 418 | 168 |
| 342 | 55 | | 419 | 476 |
| 343 | 30 | | 420 | 1150 |
| 344 | 68 | | 421 | 9300 |
| 345 | 800 | | 422 | 888 |
| 346 | 69 | | 423 | 780 |
| 347 | 677 | | 424 | 68 |
| 348 | 200 | | 425 | 1232 |
| 349 | 150 | | 426 | 436 |
| 350 | 85 | | 427 | 665 |
| 351 | 600 | | 428 | 478 |
| 352 | 200 | | 429 | 1036 |
| 353 | 252 | | 430 | 58 |
| 354 | 1664 | | 431 | 31 |
| 355 | 104 | | 432 | 7 |
| 356 | 480 | | 433 | 1789 |
| 357 | 389 | | 434 | 35 |
| 358 | 8 | | 435 | 250 |
| 359 | 250 | | 436 | 150 |
| 360 | 1000 | | 437 | 107 |
| 361 | 25 | | 438 | 924 |
| 362 | 5 | | 439 | 1250 |
| 363 | 9250 | | 440 | 1050 |
| 364 | 900 | | 441 | 5625 |
| 365 | 45 | | 442 | 850 |
| 366 | 3250 | | 443 | 4468 |
| 367 | 7950 | | 444 | 243 |
| 368 | 66 | | 445 | 580 |
| 369 | 850 | | 446 | 16 |
| 370 | 95 | | 447 | 739 |
| 371 | 3 | | 448 | 26 |
| 372 | 45 | | 449 | 51 |
| 373 | 1 | | 450 | 25 |
| 374 | 3 | | 451 | 90 |
| 375 | 2 | | 452 | 15 |
| 376 | 247 | | 453 | 13 |
| 377 | 20 | | 454 | 103 |
| 378 | 24 | | 455 | 767 |
| 379 | 5 | | 456 | 85 |
| 380 | 17 | | 457 | 107 |
| 381 | 57 | | 458 | 169 |
| 382 | 184 | | 459 | 211 |
| 383 | 4 | | 460 | 20 |
| 384 | 32 | | 461 | 6250 |
| 385 | 7 | | 462 | 75 |
| 386 | 8 | | 463 | 3114 |
| 387 | 57 | | 464 | 254 |
| 388 | 28 | | 465 | 1589 |
| 389 | 30 | | 466 | 43 |
| 390 | 38 | | 467 | 47 |

| Example | IC$_{50}$ (nM) |
|---|---|
| 468 | 350 |
| 469 | 3350 |
| 470 | 250 |
| 471 | 89 |
| 472 | 255 |
| 473 | 463 |
| 474 | 95 |
| 475 | 350 |
| 476 | 33 |
| 477 | 628 |
| 478 | 258 |
| 479 | 89 |
| 480 | 33 |
| 481 | 22 |
| 482 | 188 |
| 483 | 60 |
| 484 | 358 |
| 485 | 15 |
| 486 | 2450 |
| 487 | 13 |
| 488 | 250 |
| 489 | 124 |
| 490 | 214 |
| 491 | 28 |
| 492 | 237 |
| 493 | 108 |
| 494 | 50 |
| 495 | 19 |
| 496 | 176 |
| 497 | 128 |
| 498 | 692 |
| 499 | 36 |
| 500 | 36 |
| 501 | 471 |
| 502 | 449 |
| 503 | 115 |
| 504 | 57 |
| 505 | 14 |
| 506 | 331 |
| 507 | 16 |
| 508 | 12 |
| 509 | 58 |
| 510 | 16 |
| 511 | 71 |
| 512 | 411 |
| 513 | 193 |
| 514 | 95 |
| 515 | 268 |
| 516 | 8 |
| 517 | 1456 |
| 518 | 41 |
| 519 | 722 |
| 520 | 22 |
| 521 | 37 |
| 522 | 415 |
| 523 | 51 |
| 524 | 64 |
| 525 | 36 |
| 526 | 54 |
| 527 | 483 |
| 528 | 75 |
| 529 | 186 |
| 530 | 72 |
| 531 | 11 |
| 532 | 223 |
| 533 | 34 |
| 534 | 51 |
| 535 | 62 |
| 536 | 121 |
| 537 | 609 |
| 538 | 911 |
| 539 | 31 |
| 540 | 236 |
| 541 | 91 |
| 542 | 19 |
| 543 | 245 |
| 544 | 1110 |

| Example | IC$_{50}$ (nM) |
|---|---|
| 545 | 113 |
| 546 | 10 |
| 547 | 38 |
| 548 | 363 |
| 549 | 69 |
| 550 | 33 |
| 551 | 899 |
| 552 | 40 |
| 553 | 5297 |
| 554 | 44 |
| 555 | 2272 |
| 556 | 25 |
| 557 | 134 |
| 558 | 1986 |
| 559 | 15700 |
| 560 | 141 |
| 561 | 14 |
| 562 | 804 |
| 563 | 42 |
| 564 | 13 |
| 565 | 369 |
| 566 | 436 |
| 567 | 293 |
| 568 | 121 |
| 569 | 13 |
| 570 | 27 |
| 571 | 99 |
| 572 | 284 |
| 573 | 865 |
| 574 | 217 |
| 575 | 843 |
| 576 | 400 |
| 577 | 71 |
| 578 | 50 |
| 579 | 39 |
| 580 | 252 |
| 581 | 60 |
| 582 | 134 |
| 583 | 25 |
| 584 | 38 |
| 585 | 17 |
| 586 | 132 |
| 587 | 79 |
| 588 | 31 |
| 589 | 237 |
| 590 | 10 |
| 591 | 109 |
| 592 | 115 |
| 593 | 56 |
| 594 | 85 |
| 595 | 41 |
| 596 | 95 |
| 597 | 14 |
| 598 | 14 |
| 599 | 46 |
| 600 | 14 |
| 601 | 110 |
| 602 | 227 |
| 603 | 1613 |
| 604 | 37 |
| 605 | 54 |
| 606 | 14 |
| 607 | 28 |
| 608 | 1835 |
| 609 | 1559 |
| 610 | 45 |
| 611 | 141 |
| 612 | 3433 |
| 613 | 215 |
| 614 | 245 |
| 615 | 42 |
| 616 | 123 |
| 617 | 28 |
| 618 | 39 |
| 619 | 14 |
| 620 | 17 |
| 621 | 19 |

| Example | IC$_{50}$ (nM) |
|---|---|
| 622 | 5595 |
| 623 | 24 |
| 624 | 26 |
| 625 | 19 |
| 626 | 36 |
| 627 | 16 |
| 628 | 38 |
| 629 | 17 |
| 630 | 36 |
| 631 | 11 |
| 632 | 18 |
| 633 | 55 |
| 634 | 53 |
| 635 | 18 |
| 636 | 13 |
| 637 | 9 |
| 638 | 5 |
| 639 | 62 |
| 640 | 8 |
| 641 | 32 |
| 642 | 15 |
| 643 | 25 |
| 644 | 79 |
| 645 | 132 |
| 646 | 12 |
| 647 | 16 |
| 648 | 17 |
| 649 | 441 |
| 650 | 22 |
| 651 | 21 |
| 652 | 19 |
| 653 | 47 |
| 654 | 18 |
| 655 | 91 |
| 656 | 358 |
| 657 | 78 |
| 658 | 24 |
| 659 | 25 |
| 660 | 16 |
| 661 | 10 |
| 662 | 13 |
| 663 | 36 |
| 664 | 24 |
| 665 | 58 |
| 666 | 6 |
| 667 | 16 |
| 668 | 19 |
| 669 | 10 |
| 670 | 90 |
| 671 | 77 |
| 672 | 178 |
| 673 | 157 |
| 674 | 75 |
| 675 | 23 |
| 676 | 11 |
| 677 | 10 |
| 678 | 40 |
| 679 | 134 |
| 680 | 16 |
| 681 | 19 |
| 682 | 12 |
| 683 | 48 |
| 684 | 27 |
| 685 | 5 |
| 686 | 30 |
| 687 | 98 |
| 688 | 10 |
| 689 | 156 |
| 690 | 34 |
| 691 | 68 |
| 692 | 3 |
| 693 | 6 |
| 694 | 17 |
| 695 | 15 |
| 696 | 101 |
| 697 | 3 |
| 698 | 29 |
| 699 | 118 |
| 700 | 6 |
| 701 | 15 |
| 702 | 10 |
| 703 | 10 |
| 704 | 23 |
| 705 | 21 |
| 706 | 45 |
| 707 | 88 |
| 708 | 54 |
| 709 | 144 |
| 710 | 52 |
| 711 | 71 |
| 712 | 38 |
| 713 | 260 |
| 714 | 300 |
| 715 | 27 |
| 716 | 46 |
| 717 | 31 |
| 718 | 24 |
| 719 | 13 |
| 720 | 140 |
| 721 | 98 |
| 722 | 20 |
| 723 | 90 |
| 724 | 61 |
| 725 | 18 |
| 726 | 169 |
| 727 | 9 |
| 728 | 8 |
| 729 | 62 |
| 730 | 143 |
| 731 | 53 |
| 732 | 44 |
| 733 | 25 |
| 734 | 4 |
| 735 | 3 |
| 736 | 18 |
| 737 | 36 |
| 738 | 93 |
| 739 | 23 |
| 740 | 13 |
| 741 | 5 |
| 742 | 37 |
| 743 | 5 |
| 744 | 4 |
| 745 | 5 |
| 746 | 7 |
| 747 | 13 |
| 748 | 4 |
| 749 | 4 |
| 750 | 34 |
| 751 | 81 |
| 752 | 95 |
| 753 | 66 |
| 754 | 5 |
| 755 | 17 |
| 756 | 7 |
| 757 | 3 |
| 758 | 64 |
| 759 | 9 |
| 760 | 12 |
| 761 | 70 |
| 762 | 5 |
| 763 | 14 |
| 764 | 4 |
| 765 | 211 |
| 766 | 216 |
| 767 | 346 |
| 768 | 146 |
| 769 | 378 |
| 770 | 9 |
| 771 | 8 |
| 772 | 7 |
| 773 | 28 |

What is claimed is:

1. A compound or salt thereof represented by one of the formulae (IIIb) or (IVb):

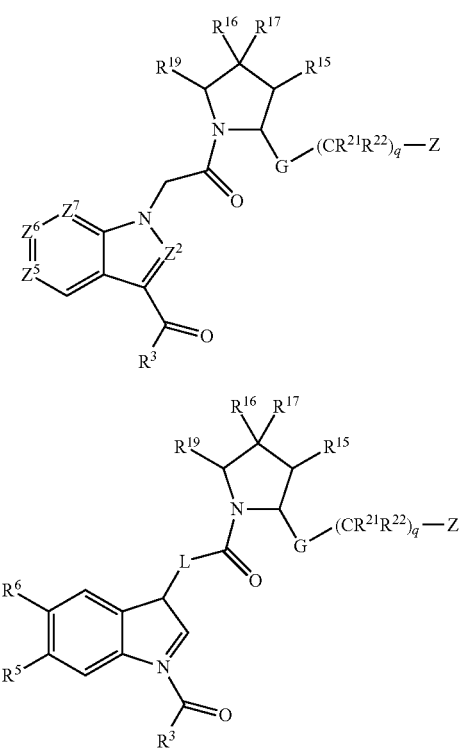

wherein $Z^2$ is CH or N;

$Z^5$ is $CR^5$ or N;

$Z^6$ is $CR^6$ or N; or an N-oxide thereof $Z^7$ is CH, C(CH$_3$) or N, wherein 0 or 1 or 2 of $Z^5$, $Z^6$ and $Z^7$ is N;

$R^3$ is hydrogen, methyl, ethyl, iPr, amino, hydroxymethyl, CH2OMe, or mono-, di- and tri-fluoromethyl, NHMe;

$R^5$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, tetrazole, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, cyano, tetrazole, $C_1$-$C_4$alkoxy, $CO_2H$, $C_1$-$C_4$alkoxycarbonyl, tetrahydrofuranyl, optionally substituted phenyl, pyridyl and pyrimidinyl, and wherein the phenyl is unsubstituted or substituted with 1 or 2 substituents independently selected from halogen, hydroxy, methyl, methoxy and $CO_2H$;

$R^6$ is hydrogen, halogen, $C_1$-$C_4$alkyl, $C_1$-$C_4$alkoxy, $C_2$-$C_4$alkenyl, $C_2$-$C_4$alkenyloxy, hydroxy, $CO_2H$, $C_1$-$C_4$alkoxycarbonyl, cyano, wherein each alkyl or alkoxy group is unsubstituted or substituted with up to 5 halogen atoms and with 0 or 1 additional substituents selected from the group consisting of hydroxy, $NR^{10}R^{11}$, tetrazole, cyano, imidazolyl, $C_1$-$C_4$alkoxy, $CO_2H$, $C_1$-$C_4$alkoxycarbonyl, optionally substituted phenyl, pyrrolyl, morpholino, piperidino, piperazino, and pyridyl, and wherein the phenyl is unsubstituted or substituted with 1 or 2 substituents independently selected from halogen, hydroxy, methyl, methoxy, mono- and dimethyl amino, and $CO_2H$;

L is $CH_2$ or NH;

$R^{15}$ is hydrogen, fluoro, methyl, hydroxy, methoxy, ethoxy and $OCH_2CH_2OMe$, $OCH_2CH_2N(CH_3)_2$, amino or $OCH_2CH_2$pyrrolyl;

$R^{16}$ is hydrogen, fluoro, methyl, amino, hydroxymethyl, methoxymethyl, or aminomethyl;

$R^{17}$ is hydrogen, fluoro or methyl;

$R^{19}$ is hydrogen or $R^{19}$ and $R^{17}$, taken in combination, form a cyclopropyl ring; or $R^{15}$ and $R^{16}$, taken in combination, form a cyclopropyl ring;

G is —C(O)N(H)—; and q is 0 or 1;

$R^{21}$ is hydrogen, methyl, or ethyl, which methyl and ethyl are unsubstituted or substituted with hydroxy, methoxy, cyano, amino, mono- or di-methyl amino, morpholinomethyl, optionally substituted azetidinomethyl, which azetidino ring is substituted with 0 or 1 fluoro or methoxy; or $R^{22}$ is hydrogen;

$CR^{21}R^{22}$, taken in combination, from a cyclopropane ring;

Z is phenyl, pyridyl, pyrazinyl or thienyl, each of which is unsubstituted or substituted with 1, 2, or 3 residues independently selected at each occurrence from the group consisting of halogen, methyl, ethyl, isopropyl, cyclopropyl, methoxy, hydroxy, trifluoromethyl, di or trifluoromethoxy, $SF_5$, $CO_2H$, tetrazole, and $NR^{23}R^{24}$, unsubstituted or substituted phenyl and unsubstituted or substituted pyridinyl, which substituted phenyl and pyridinyl has 1 or 2 substituents independently selected from the group consisting of halogen and methyl.

2. The compound of claim 1, wherein the compound is represented by formula:

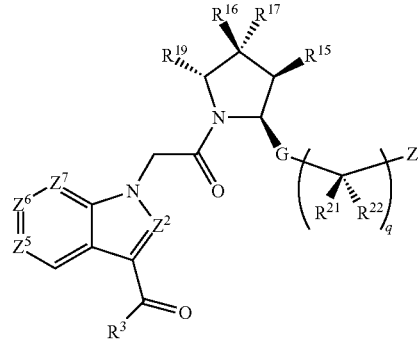

or a pharmaceutically acceptable salt thereof.

3. A pharmaceutical composition comprising one or more pharmaceutically acceptable carriers and a therapeutically effective amount of a compound of claim 1.

4. The compound of claim 1, wherein the compound is represented by formula:

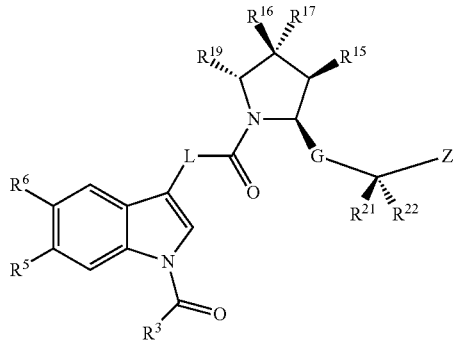

or a pharmaceutically acceptable salt thereof.

5. 1-(2-((1R,3S,5R)-3-((2-fluoro-3-(trifluoromethoxy)phenyl)carbamoyl)-2-azabicyclo[3.1.0]hexan-2-yl)-2-oxo-ethyl)-5-methyl-1H-pyrazolo[3,4-c]pyridine-3-carboxamide or a pharmaceutically acceptable salt thereof.

6. The pharmaceutical composition according to claim 3, wherein the compound is a compound of claim 2.

7. The pharmaceutical composition according to claim 3, wherein the compound is a compound of claim 4.

8. The pharmaceutical composition according to claim 3, wherein the compound is a compound of claim 5.

* * * * *